(12) United States Patent
Takahashi et al.

(10) Patent No.: US 11,552,251 B2
(45) Date of Patent: Jan. 10, 2023

(54) ORGANIC ELECTROLUMINESCENT ELEMENT AND ELECTRONIC DEVICE

(71) Applicant: IDEMITSU KOSAN CO., LTD., Chiyoda-ku (JP)

(72) Inventors: Ryota Takahashi, Ichihara (JP); Tomoki Kato, Ichihara (JP); Hirokatsu Ito, Ichihara (JP); Masahiro Kawamura, Basel (CH); Masakazu Funahashi, Chiba (JP); Hiroyuki Saito, Goyang-si (KR); Yuichiro Kawamura, Chiba (JP); Yoshiaki Takahashi, Chiba (JP); Tetsuya Masuda, Chiba (JP); Hitoshi Kuma, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 538 days.

(21) Appl. No.: 16/077,966

(22) PCT Filed: Feb. 13, 2017

(86) PCT No.: PCT/JP2017/005168
§ 371 (c)(1),
(2) Date: Aug. 14, 2018

(87) PCT Pub. No.: WO2017/141876
PCT Pub. Date: Aug. 24, 2017

(65) Prior Publication Data
US 2019/0051835 A1    Feb. 14, 2019

(30) Foreign Application Priority Data

Feb. 18, 2016 (JP) .............................. JP2016-029057

(51) Int. Cl.
*H01L 51/50* (2006.01)
*H01L 51/00* (2006.01)
(Continued)

(52) U.S. Cl.
CPC ........ *H01L 51/0056* (2013.01); *C07C 211/61* (2013.01); *C07D 209/86* (2013.01);
(Continued)

(58) Field of Classification Search
None
See application file for complete search history.

(56) References Cited

U.S. PATENT DOCUMENTS

| 7,838,130 B2 | 11/2010 | Takashima et al. |
| 2004/0164292 A1* | 8/2004 | Tung ................. G02F 1/133603 257/40 |

(Continued)

FOREIGN PATENT DOCUMENTS

| CN | 101104676 A | 1/2008 |
| CN | 105440004 A | 3/2016 |

(Continued)

OTHER PUBLICATIONS

International Search Report dated Apr. 4, 2017, in PCT/JP2017/005168 filed Feb. 13, 2017.

(Continued)

*Primary Examiner* — Gregory D Clark
(74) *Attorney, Agent, or Firm* — Oblon, McClelland, Maier & Neustadt, L.L.P.

(57) ABSTRACT

The compound represented by formula (1):

(1)

(Continued)

wherein A, B, R¹, and R² are as defined in the description, provides organic electroluminescence (EL) devices having a high emission efficiency when operated at low voltage and a long lifetime and electronic devices including such organic EL devices.

10 Claims, 1 Drawing Sheet

(51) Int. Cl.
| | |
|---|---|
| C07C 211/61 | (2006.01) |
| C07D 251/24 | (2006.01) |
| C09K 11/06 | (2006.01) |
| C07D 239/26 | (2006.01) |
| C07D 239/74 | (2006.01) |
| C07D 213/16 | (2006.01) |
| C07D 241/12 | (2006.01) |
| C07D 333/76 | (2006.01) |
| C07D 307/92 | (2006.01) |
| C07D 231/56 | (2006.01) |
| C07D 333/74 | (2006.01) |
| C07D 213/22 | (2006.01) |
| C07D 237/08 | (2006.01) |
| C07D 209/86 | (2006.01) |
| C07D 471/04 | (2006.01) |
| C07D 235/18 | (2006.01) |
| H01L 51/56 | (2006.01) |

(52) U.S. Cl.
CPC ......... *C07D 213/16* (2013.01); *C07D 213/22* (2013.01); *C07D 231/56* (2013.01); *C07D 235/18* (2013.01); *C07D 237/08* (2013.01); *C07D 239/26* (2013.01); *C07D 239/74* (2013.01); *C07D 241/12* (2013.01); *C07D 251/24* (2013.01); *C07D 307/92* (2013.01); *C07D 333/74* (2013.01); *C07D 333/76* (2013.01); *C07D 471/04* (2013.01); *C09K 11/06* (2013.01); *H01L 51/006* (2013.01); *H01L 51/0055* (2013.01); *H01L 51/0067* (2013.01); *C07C 2603/18* (2017.05); *C07C 2603/52* (2017.05); *C07C 2603/94* (2017.05); *C07C 2603/97* (2017.05); *C09K 2211/1018* (2013.01); *H01L 51/001* (2013.01); *H01L 51/508* (2013.01); *H01L 51/5012* (2013.01); *H01L 51/5016* (2013.01); *H01L 51/5056* (2013.01); *H01L 51/5064* (2013.01); *H01L 51/5076* (2013.01); *H01L 51/5096* (2013.01); *H01L 51/56* (2013.01); *H01L 2251/5376* (2013.01); *H01L 2251/558* (2013.01)

(56) References Cited

U.S. PATENT DOCUMENTS

| | | |
|---|---|---|
| 2012/0181520 A1 | 7/2012 | Kim et al. |
| 2016/0351817 A1 | 12/2016 | Kim et al. |

FOREIGN PATENT DOCUMENTS

| | | | | |
|---|---|---|---|---|
| CN | 106206964 A | | 12/2016 | |
| KR | 10-2014-0115636 A | | 10/2014 | |
| KR | 2014115636 | * | 10/2014 | ............ H01L 51/50 |
| KR | 2015-35780 | * | 5/2015 | ............ H01L 51/50 |
| KR | 20150073935 | * | 5/2015 | ............ C09K 11/06 |
| KR | 10-2016-0111559 A | | 9/2016 | |
| WO | WO 2015/041358 A1 | | 3/2015 | |

OTHER PUBLICATIONS

Combined Chinese Office Action and Search Report dated Jul. 6, 2021 in Patent Application No. 201780011490.7 (with English language translation and English translation of Category of Cited Documents), 14 pages.

Office Action as received in the corresponding CN Application No. 201780011490.7, dated Jan. 5, 2022 w/English Translation, 10 pages

* cited by examiner

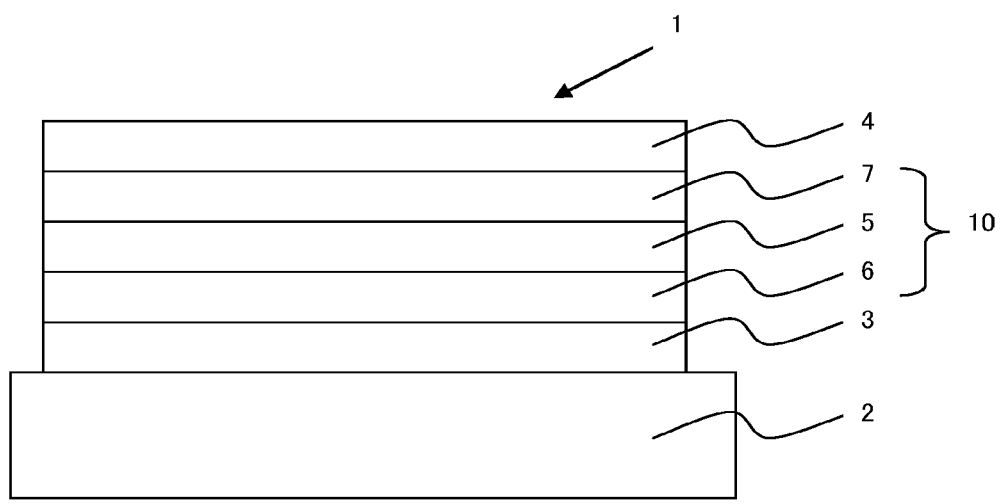

ORGANIC ELECTROLUMINESCENT ELEMENT AND ELECTRONIC DEVICE

TECHNICAL FIELD

The present invention relates to organic electroluminescence devices and electronic devices comprising the organic electroluminescence devices. Further, the present invention relates to compounds usable as materials for organic electroluminescence devices.

BACKGROUND ART

An organic electroluminescence (EL) device is generally composed of an anode, a cathode, and one or more organic thin film layers sandwiched between the anode and the cathode. When a voltage is applied between the electrodes, electrons are injected from the cathode and holes are injected from the anode into a light emitting region. The injected electrons recombine with the injected holes in the light emitting region to form excited states. When the excited states return to the ground state, the energy is released as light.

Many researches have been made on the applications of organic EL device to display, etc. because of its wide selection of emission colors by using various emitting materials in a light emitting layer. Particularly, the research on the materials each emitting three primary red, green, and blue colors has been made most actively, and the intensive research has been made to improve their properties.

One of the most important problems involved in organic EL devices is to achieve a high emission efficiency. To obtain an organic EL device with high emission efficiency, it has been known to form a light emitting layer by doping a host material with a several percent of a dopant material. For example, the compounds described in Patent Literatures 1 to 5 have been known as such materials for organic electroluminescence devices.

CITATION LIST

Patent Literature

Patent Literature 1: KR 10-2014-0115636A
Patent Literature 2: CN 101104676A
Patent Literature 3: US 2012/0181520A
Patent Literature 4: WO 2015/041358
Patent Literature 5: U.S. Pat. No. 7,838,130

SUMMARY OF INVENTION

Technical Problem

The inventors have studied the compounds disclosed in Patent Literatures 1 to 4 and have found that there is room for further improvement on the compounds in view of the emission efficiency and the lifetime.

Thus, an object of the present invention is to provide an organic EL device having a high emission efficiency at low voltage and a long lifetime, an electronic device comprising the organic EL device, and a compound which provides the organic EL device.

Solution to Problem

As a result of extensive study for solving the above problem, the inventors have found that the problem is solved by using a compound of formula (1), wherein a specific substituent is introduced into a dibenzofluorene skeleton having a spiro atom, as a material for organic EL devices.

In an aspect of the invention, the following (1) to (4) are provided:

(1) a compound represented by formula (1):

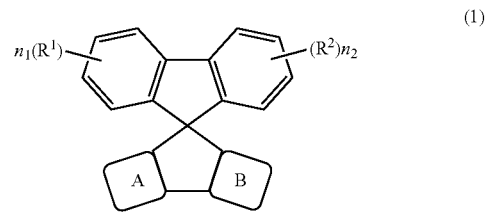

wherein:

each of A and B is a substituted or unsubstituted naphthalene ring or a substituted or unsubstituted phenanthrene ring;

a substituent on the naphthalene ring or the phenanthrene ring is a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a group represented by —Si($R_{101}$)($R_{102}$)($R_{103}$), or a group represented by —Z—$R^a$;

the substituents, if present on the naphthalene ring and the phenanthrene ring represented by A and B, may be bonded to each other to form a ring structure;

each of $R^1$ and $R^2$ is independently a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a substituted or unsubstituted aryl group having 6 to 30 ring carbon atoms, a substituted or unsubstituted heteroaryl group having 5 to 30 ring carbon atoms, or a group represented by —Si($R_{101}$)($R_{102}$)($R_{103}$);

$R^1$'s and $R^2$'s, if present, may be the same or different, and $R^1$'s and $R^2$'s may be bonded to each other to form a ring structure, respectively;

Z is a single bond, a substituted or unsubstituted arylene group having 6 to 30 ring carbon atoms, a substituted or unsubstituted heteroarylene group having 5 to 30 ring atoms, or a divalent linking group wherein two to four groups selected from the arylene group and the heteroarylene group are linked together;

Zs, if present, may be the same or different;

$R^a$ is a group represented by —$N(R_{104})(R_{105})$, a substituted or unsubstituted aryl group having 6 to 30 ring carbon atoms, or a substituted or unsubstituted heteroaryl group having 5 to 30 ring atoms;

$R^a$'s, if present, may be the same or different;

each of $R_{101}$ to $R_{105}$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms;

provided that at least one substituent on A and B is a group represented by —Z—$R^a$;

two or more groups represented by —Z—$R^a$, if present, may be the same or different; and each of n1 and n2 is an integer of 0 to 4;

(2) a material for organic electroluminescence devices comprising the compound described in item (1);

(3) an organic electroluminescence device comprising an organic thin film layer which comprises one or more layers and is disposed between a cathode and an anode, wherein the organic thin film layer comprises a light emitting layer and at least one layer of the organic thin film layer comprises the compound described in item (1); and (4) an electronic device comprising the organic electroluminescence device described in item (3).

Advantageous Effects of Invention

The organic EL device of the invention has a high emission efficiency at low voltage and a long lifetime. Since the compound of the invention for use as a material for organic EL devices has a high carrier mobility, the compound is useful as a host material of a light emitting layer and also useful as an electron transporting material and a hole transporting material. Particularly, an organic EL device comprising the compound of the invention in a light emitting layer as a dopant material has a high emission efficiency at low voltage and a long lifetime.

DESCRIPTION OF EMBODIMENTS

FIG. 1 is a schematic view showing the structure of an example of the organic EL device in an aspect of the invention.

DESCRIPTION OF EMBODIMENTS

The term of "XX to YY carbon atoms" referred to by "a substituted or unsubstituted group ZZ having XX to YY carbon atoms" used herein is the number of carbon atoms of an unsubstituted group ZZ and does not include any carbon atom in the substituent of a substituted group ZZ.

The term of "XX to YY atoms" referred to by "a substituted or unsubstituted group ZZ having XX to YY atoms" used herein is the number of atoms of an unsubstituted group ZZ and does not include any atom in the substituent of a substituted group ZZ.

The number of ring carbon atoms referred to herein means the number of the carbon atoms included in the atoms which are members forming the ring itself of a compound in which a series of atoms is bonded to form a ring (for example, a monocyclic compound, a fused ring compound, a cross-linked compound, a carbocyclic compound, and a heterocyclic compound). If the ring has a substituent, the carbon atom in the substituent is not included in the ring carbon atom. Unless otherwise noted, the same applies to "the number of ring carbon atoms" described below. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of ring atoms referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring and the atom in a substituent, if the ring is substituted, are not counted as the ring atom. Unless otherwise noted, the same applies to "the number of ring atoms" described below. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

The definition of "hydrogen atom" used herein includes isotopes different in the neutron numbers, i.e., light hydrogen (protium), heavy hydrogen (deuterium), and tritium.

The terms of "heteroaryl group", "heteroarylene group" and "heterocyclic group" used herein means a group having at least one hetero atom as a ring atom. The hetero atom is preferably at least one selected from a nitrogen atom, an oxygen atom, a sulfur atom, a silicon atom, and a selenium atom.

A "substituted or unsubstituted carbazolyl group" referred to herein includes the following carbazolyl groups:

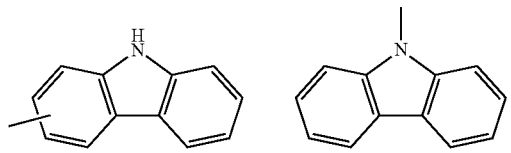

and a substituted carbazolyl group, wherein each of the above carbazolyl groups has an optional substituent.

The optional substituents may be bonded to each other to form a fused ring structure, may include a hetero atom, such as a nitrogen atom, an oxygen atom, a silicon atom, and selenium atom, and may be bonded to any of 1- to 9-positions. Examples of such substituted carbazolyl groups are shown below.

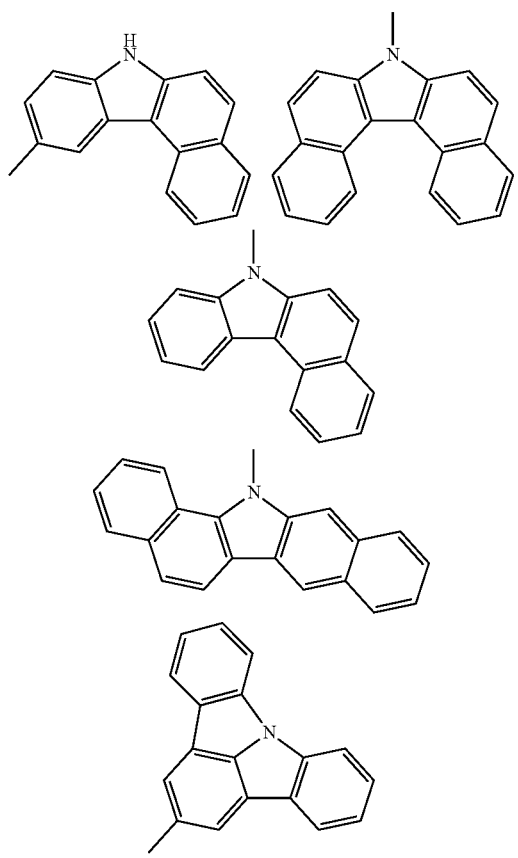

A "substituted or unsubstituted dibenzofuranyl group" and a "substituted or unsubstituted dibenzothiophenyl group" referred to herein include the following dibenzofuranyl group and the following dibenzothiophenyl group:

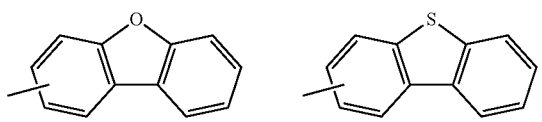

and a substituted dibenzofuranyl group and a substituted dibenzothiophenyl group, wherein each of the above groups has an optional substituent.

The optional substituents may be bonded to each other to form a fused ring structure, may include a hetero atom, such as a nitrogen atom, an oxygen atom, a silicon atom, and selenium atom, and may be bonded to any of 1- to 8-positions.

Examples of such substituted dibenzofuranyl groups and substituted dibenzothiophenyl groups are shown below:

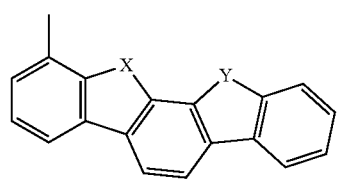

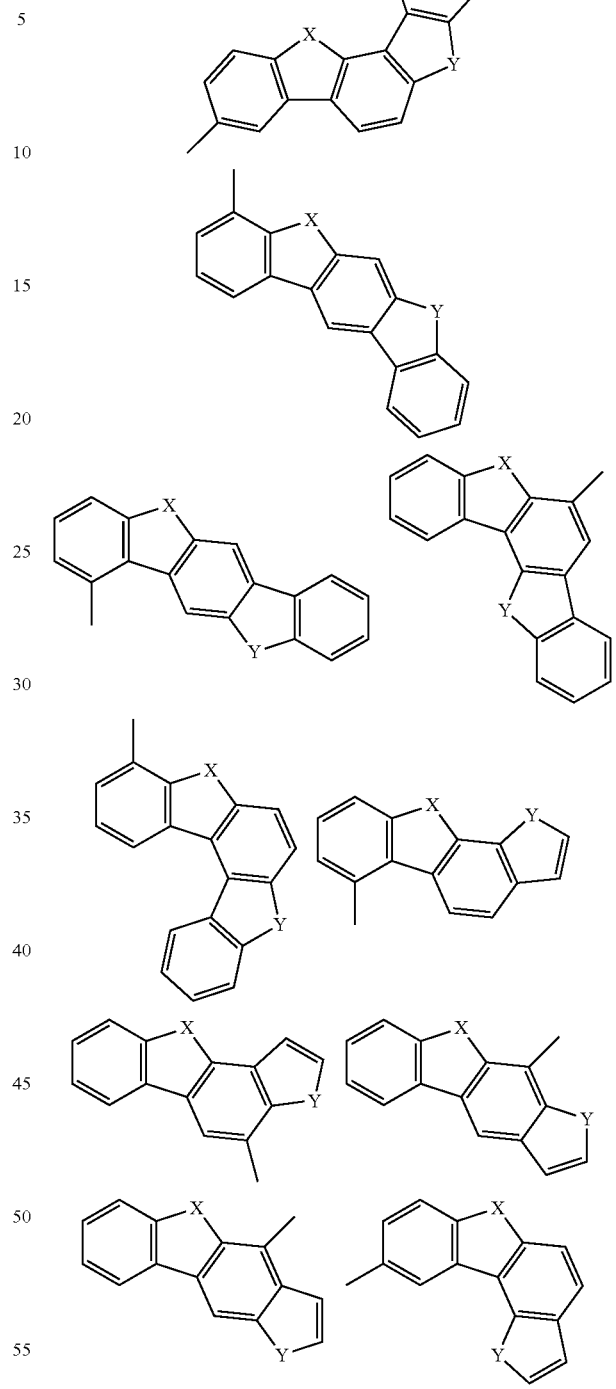

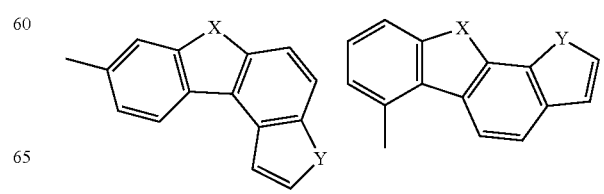

-continued

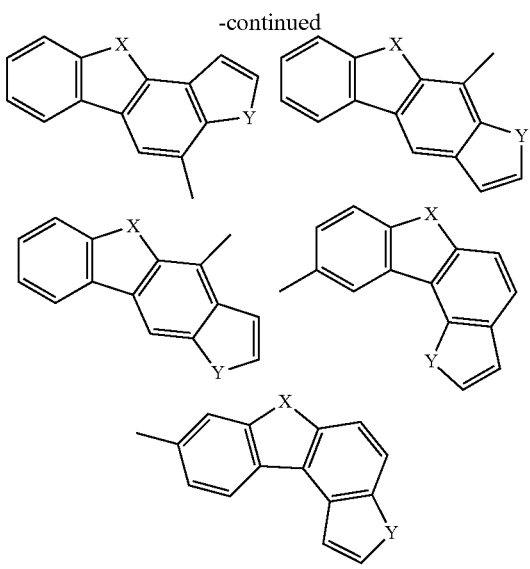

wherein X represents an oxygen atom or a sulfur atom and Y represents an oxygen atom, a sulfur atom, NH, $NR^a$ wherein $R^a$ represents an alkyl group or an aryl group, $CH_2$, or $CR^b_2$ wherein $R^b$ represents an alkyl group or an aryl group.

The "substituent" and the optional substituent referred to by "substituted or unsubstituted" used herein is preferably at least one selected from, but not limited to, the group consisting of an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; an aralkyl group having 7 to 51, preferably 7 to 30, more preferably 7 to 20 carbon atoms which includes an aryl group having 6 to 50, preferably 6 to 25, more preferably 6 to 18 ring carbon atoms; an amino group; a mono- or disubstituted amino group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkoxy group having an alkyl group having 1 to 50, preferably 1 to 18, more preferably 1 to 8 carbon atoms; an aryloxy group having an aryl group having 6 to 50, preferably 6 to 25, more preferably 6 to 18 ring carbon atoms; a mono-, di- or tri-substituted silyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms; a haloalkyl group having 1 to 50, preferably 1 to 18, more preferably 1 to 8 carbon atoms; a halogen atom selected from a fluorine atom, a chlorine atom, a bromine atom and an iodine atom; a cyano group; a nitro group; a substituted sulfonyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a di-substituted phosphoryl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl-substituted or aryl-substituted carbonyl group; a carboxyl group; a vinyl group; a (meth) acryloyl group; an epoxy group; and an oxetanyl group.

The above substituent may further has the substituent mentioned above. The substituents may be bonded to each other to form a ring.

The term of "unsubstituted" referred to by "substituted or unsubstituted" used herein means that no hydrogen atom in the group is substituted by a substituent.

Of the above substituents, more preferred are a substituted or unsubstituted alkyl group having 1 to 50, preferably 1 to 18, more preferably 1 to 8 carbon atoms; a substituted or unsubstituted cycloalkyl group having 3 to 50, preferably 3 to 10, more preferably 3 to 8, still more preferably 5 or 6 ring carbon atoms; a substituted or unsubstituted aryl group having 6 to 50, preferably 6 to 25, more preferably 6 to 18 ring carbon atoms; a mono- or disubstituted amino group, wherein the substituent is selected from a substituted or unsubstituted alkyl group having 1 to 50, preferably 1 to 18, more preferably 1 to 8 carbon atoms and a substituted or unsubstituted aryl group having 6 to 50, preferably 6 to 25, more preferably 6 to 18 ring carbon atoms; a substituted or unsubstituted heteroaryl group having 5 to 50, preferably 5 to 24, more preferably 5 to 13 ring atoms; a halogen atom; and a cyano group.

A preferred embodiment, for example, for the compounds, the groups, and the numerical ranges described herein may be combined with any of other preferred embodiments, for example, for the compounds, the groups, and the numerical ranges. A combination of preferred embodiments (inclusive of more preferred embodiments, still more preferred embodiments, and particularly preferred embodiments) is a more preferred embodiment.

The compound of the invention is represented by formula (1):

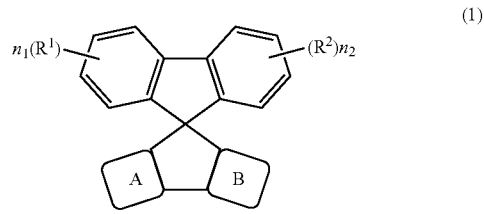

(1)

wherein:
each of A and B is a substituted or unsubstituted naphthalene ring or a substituted or unsubstituted phenanthrene ring;
a substituent on the naphthalene ring or the phenanthrene ring is a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a group represented by —Si($R_{101}$)($R_{102}$)($R_{103}$), or a group represented by —Z—$R^a$;

the substituents, if present on the naphthalene ring and the phenanthrene ring represented by A and B, may be bonded to each other to form a ring structure;

each of $R^1$ and $R^2$ is independently a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a substituted or unsubstituted aryl group having 6 to 30 ring carbon atoms, a substituted or unsubstituted heteroaryl group having 5 to 30 ring carbon atoms, or a group represented by —Si($R_{101}$)($R_{102}$)($R_{103}$);

$R^1$'s and $R^2$'s, if present, may be the same or different, and $R^1$'s and $R^2$'s may be bonded to each other to form a ring structure, respectively;

Z is a single bond, a substituted or unsubstituted arylene group having 6 to 30 ring carbon atoms, a substituted or unsubstituted heteroarylene group having 5 to 30 ring atoms, or a divalent linking group wherein two to four groups selected from the arylene group and the heteroarylene group are linked together;

Zs, if present, may be the same or different;

$R^a$ is a group represented by —N($R_{104}$)($R_{105}$), a substituted or unsubstituted aryl group having 6 to 30 ring carbon atoms, or a substituted or unsubstituted heteroaryl group having 5 to 30 ring atoms;

$R^a$'s, if present, may be the same or different;

each of $R_{101}$ to $R_{105}$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms;

provided that at least one substituent on A and B is a group represented by —Z—$R^a$;

two or more groups represented by —Z—$R^a$, if present, may be the same or different; and each of n1 and n2 is an integer of 0 to 4.

In formula (1), examples of the alkyl group having 1 to 20, preferably 1 to 10, more preferably 1 to 6 carbon atoms for $R^1$, $R^2$, the substituent of A and B, and $R_{101}$ to $R_{105}$ include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups). Preferred are a methyl group, an ethyl group, a n-propyl group, an isopropyl group, a n-butyl group, an isobutyl group, a s-butyl group, a t-butyl group, and a pentyl group (inclusive of isomeric groups), with a methyl group, an ethyl group, a n-propyl group, an isopropyl group, a n-butyl group, an isobutyl group, a s-butyl group, and a t-butyl group being more preferred, and a methyl group, an ethyl group, an isopropyl group, and a t-butyl group being particularly preferred.

Examples of the cycloalkyl group having 3 to 20, preferably 3 to 6, more preferably 5 or 6 ring carbon atoms for $R^1$, $R^2$, the substituent of A and B, and $R_{101}$ to $R_{105}$ include a cyclopropyl group, a cyclobutyl group, a cyclopentyl group, a cyclohexyl group, a cycloheptyl group, a cyclooctyl group, and an adamantyl group, with a cyclopentyl group and a cyclohexyl group being preferred.

Examples of the alkoxy group having 1 to 20, preferably 1 to 10, more preferably 1 to 6 carbon atoms for $R^1$, $R^2$, and the substituent of A and B include those having an alkyl portion selected from the alkyl group having 1 to 20 carbon atoms mentioned above. Preferred examples of the alkoxy group are those having an alkyl portion selected from the preferred alkyl group mentioned above.

The fluoroalkyl group having 1 to 20, preferably 1 to 10, more preferably 1 to 6 carbon atoms for $R^1$, $R^2$, and the substituent of A and B is a group derived from the above alkyl group, preferably the preferred alkyl group mentioned above by substituting a fluorine atom for a hydrogen atom.

The fluoroalkoxy group having 1 to 20, preferably 1 to 10, more preferably 1 to 6 carbon atoms for $R^1$, $R^2$, and the substituent of A and B is a group derived from the above alkoxy group, preferably the preferred alkoxy group mentioned above by substituting a fluorine atom for a hydrogen atom.

Examples of the aryloxy group having 6 to 30, preferably 6 to 24, more preferably 6 to 18, still more preferably 6 to 10 ring carbon atoms for $R^1$, $R^2$, and the substituent of A and B include those having an aryl portion selected from the aryl group having 6 to 30 ring carbon atoms mentioned below with respect to $R^1$, $R^2$, and $R_{101}$ to $R_{105}$. Preferred examples of the aryloxy group are those having an aryl portion selected from the preferred aryl group mentioned below.

Examples of the alkylthio group having 1 to 20, preferably 1 to 10, more preferably 1 to 6 carbon atoms for $R^1$, $R^2$, and the substituent of A and B include those having an alkyl portion selected from the alkyl group having 1 to 20 carbon atoms mentioned above. Preferred examples of the alkoxy group are those having an alkyl portion selected from the preferred alkyl group mentioned above.

Examples of the arylthio group having 6 to 30, preferably 6 to 24, more preferably 6 to 18, still more preferably 6 to 10 ring carbon atoms for $R^1$, $R^2$, and the substituent of A and B include those having an aryl portion selected from the aryl group having 6 to 30 ring carbon atoms mentioned below with respect to $R^1$, $R^2$, and $R_{101}$ to $R_{105}$. Preferred examples of the arylthio group are those having an aryl portion selected from the preferred aryl group mentioned below.

Examples of the "group represented by —Si($R_{101}$)($R_{102}$)($R_{103}$)" for $R^1$, $R^2$, and the substituent of A and B include a monoalkylsilyl group, a dialkylsilyl group, a trialkylsilyl group, a monoarylsilyl group, a diarylsilyl group, a triarylsilyl group, a monoalkyldiarylsilyl group, and a dialkylmonoarylsilyl group.

The alkyl portion of these substituted silyl groups has preferably 1 to 20, more preferably 1 to 10, and still more preferably 1 to 6 carbon atoms. The aryl portion has preferably 6 to 30, more preferably 6 to 24, still more preferably 6 to 18, and particularly preferably 6 to 10 ring carbon atoms.

Preferred are a trialkylsilyl group and a trialkylsilyl group, with a trimethylsilyl group, a triethylsilyl group, a triisopropylsilyl group, a t-butyldimethylsilyl group, a triphenylsilyl group, and a tritolylsilyl group being more preferred.

Examples of the "group represented by —N(R$_{104}$)(R$_{105}$)" for R$^a$ in formula (1) include a monoalkylamino group, a dialkylamino group, a monoarylamino group, a diarylamino group, a monoheteroarylamino group, a diheteroarylamino group, a monoalkylmonoarylamino group, a monoalkylmonoheteroarylamino group, and a monoarylmonoheteroarylamino group. The aryl portion of these substituted amino groups may have a substituent, for example, an alkyl group having 1 to 20, preferably 1 to 10, more preferably 1 to 6 carbon atoms.

The alkyl portion of these substituted amino groups has preferably 1 to 20, more preferably 1 to 10, still more preferably 1 to 6 carbon atoms. The aryl portion has preferably 6 to 30, more preferably 6 to 24, still more preferably 6 to 18, particularly preferably 6 to 10 ring carbon atoms. The heteroaryl portion has preferably 5 to 30, more preferably 5 to 24, still more preferably 5 to 12 ring atoms.

Preferred are a dialkyl amino group, a diarylamino group, a diheteroarylamino group, and a monoarylmonoheteroarylamino group, with a dimethylamino group, a diethylamino group, a diisopropylamino group, a diphenylamino group, a bis(alkyl-substituted phenyl)amino group, and a bis(aryl-substituted phenyl)amino group being more preferred.

Two or more groups represented by —Si(R$_{101}$)(R$_{102}$)(R$_{103}$), if present in formula (1), may be the same or different. Two or more groups represented by —N(R$_{104}$)(R$_{105}$), if present in formula (1), may be the same or different.

The aryl group having 6 to 30, preferably 6 to 24, more preferably 6 to 18, still more preferably 6 to 10 ring carbon atoms for R$^1$, R$^2$, and R$_{101}$ to R$_{105}$ may be either a fused ring or a non-fused ring. Examples of the aryl group include a phenyl group, a biphenylyl group, a terphenylyl group, a naphthyl group, an acenaphthylenyl group, an anthryl group, a benzanthryl group, an aceanthryl group, a phenanthryl group, a benzo[c]phenanthryl group, a phenalenyl group, a fluorenyl group, a picenyl group, a pentaphenyl group, a pyrenyl group, a chrysenyl group, a benzo[g]chrysenyl group, a s-indacenyl group, an as-indacenyl group, a fluoranthenyl group, a benzo[k]fluoranthenyl group, a triphenylenyl group, a benzo[b]triphenylenyl group, and a perylenyl group. Preferred are a phenyl group, a biphenylyl group, a terphenylyl group, a naphthyl group, an anthryl group, a pyrenyl group, and a fluoranthenyl group, with a phenyl group, a biphenylyl group, and a terphenylyl group being more preferred, and a phenyl group being still more preferred.

The heteroaryl group having 5 to 30, preferably 5 to 24, more preferably 5 to 12 ring atoms for R$^1$, R$^2$, and R$_{101}$ to R$_{105}$ includes at least one, preferably 1 to 5, more preferably 1 to 4, and still more preferably 1 to 3 hetero atoms, which is selected from, for example, a nitrogen atom, a sulfur atom and an oxygen atom and preferably a nitrogen atom and an oxygen atom.

Examples of the heteroaryl group include a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a 9-phenylcarbazolyl group, a phenanthridinyl group, an acridinyl group, a phenanthrolinyl group, a phenazinyl group, a phenothiazinyl group, a phenoxazinyl group, and a xanthenyl group. Preferred are a pyridyl group, an imidazopyridyl group, a pyridazinyl group, a pyrimidinyl group, a pyrazinyl group, a triazinyl group, a benzimidazolyl group, a dibenzofuranyl group, a dibenzothiophenyl group, a carbazolyl group, a 9-phenylcarbazolyl group, a phenanthrolinyl group, and a quinazolinyl group.

Examples of the arylene group having 6 to 30, preferably 6 to 24, more preferably 6 to 18, and still more preferably 6 to 10 ring carbon atoms for Z of formula (1), include divalent groups derived from the aryl group mentioned above by removing one hydrogen atom. Preferred are a phenylene group, a naphthylene group, an anthrylene group, a phenanthrylene group, a pyrenylene group, and a fluorenylene group having two substituents at 9-position, with a 1,4-phenylene group, a 1,3-phenylene group, a 1,2-phenylene group, a 1,4-naphthylene group, a 2,6-naphthylene group, a 9,9-dimethyl-2,7-fluorenylene group, and a 9,9-diphenyl-2,7-fluorenylene group being more preferred.

Examples of the heteroaryl group having 5 to 30, preferably 5 to 24, and more preferably 5 to 12 ring atoms for Z include divalent groups derived from the heteroaryl group mentioned above by removing one hydrogen atom. Preferred are a pyridinylene group, a pyrimidinylene group, a pyrazinylene group, a pyridazinylene group, a triazinylene group, a phenanthrolinylene group, a dibenzofuranylene group, and a dibenzothiophenylene group, with a pyridinylene group, a pyrimidinylene group, a triazinylene group, a dibenzofuranylene group, and a dibenzothiophenylene group being more preferred. Of the substituents mentioned above, the substituent of the heteroarylene group is preferably an aryl group having 6 to 30 ring carbon atoms, more preferably an aryl group having 6 to 24 ring carbon atoms, still more preferably an aryl group having 6 to 12 ring carbon atoms, and particularly preferably a phenyl group.

Z may be a divalent group wherein two to four groups selected from the arylene group and the heteroarylene group are linked together. Examples of such a divalent group include -arylene group-heteroarylene group-, -heteroarylene group-arylene group-, -arylene group-heteroarylene group-arylene group-, -heteroarylene group-arylene group-heteroarylene group-, -arylene group-heteroarylene group-arylene group-heteroarylene group-, and -heteroarylene group-arylene group-heteroarylene group-arylene group-.

Examples and preferred examples of the aryl group and the heteroaryl group for R$^a$ of formula (1) include those mentioned above with respect to R$^1$ and R$^2$, respectively.

The compound represented by formula (1) is preferably represented by any of formulae (2-1) to (2-10):
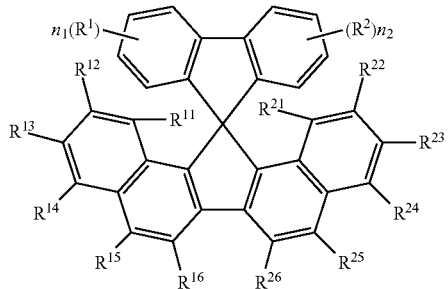
(2-1)
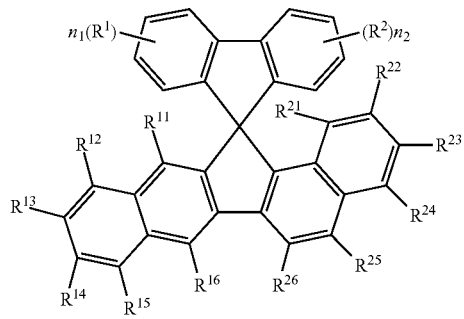
(2-2)
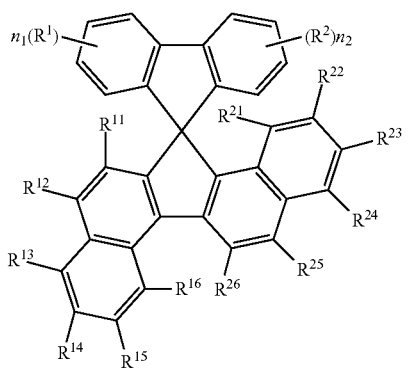
(2-3)
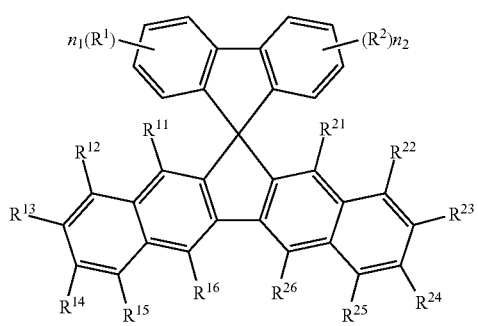
(2-4)
-continued
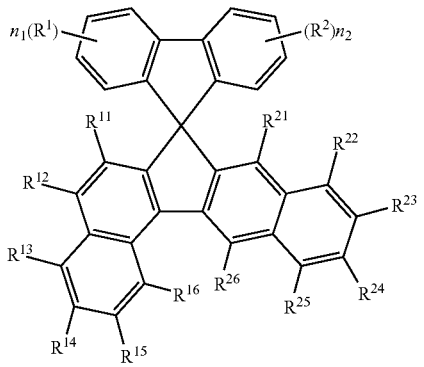
(2-5)
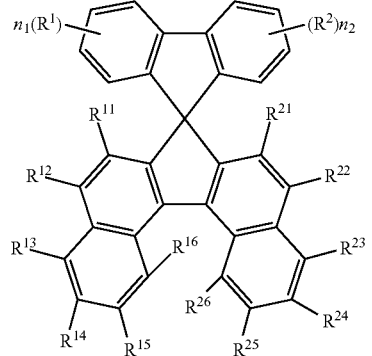
(2-6)
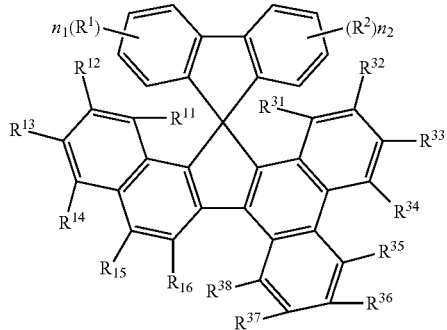
(2-7)
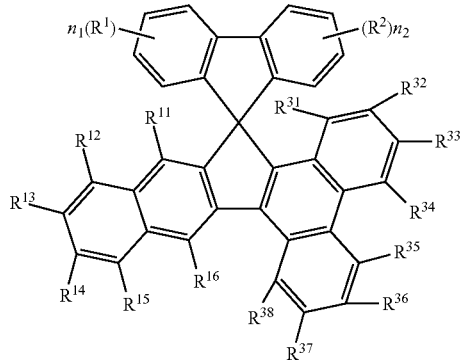
(2-8)

-continued

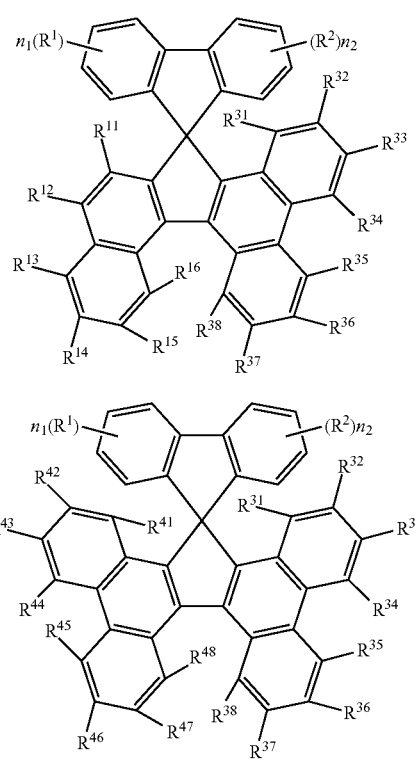

(2-9)

(2-10)

wherein:

R¹, R², n1, and n2 are as defined in formula (1);

each of $R^{11}$ to $R^{16}$, $R^{21}$ to $R^{26}$, $R^{31}$ to $R^{38}$, and $R^{41}$ to $R^{48}$ is independently a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a group represented by —Si($R_{101}$)($R_{102}$)($R_{103}$), or a group represented by —Z—$R^a$;

$R_{101}$ to $R_{103}$, Z, and $R^a$ are as defined above;

provided that at least one of $R^{11}$ to $R^{16}$ and $R^{21}$ to $R^{26}$ of each of formulae (2-1), (2-2), (2-3), (2-4), (2-5), and (2-6) is a group represented by —Z—$R^a$, at least one of $R^{11}$ to $R^{16}$ and $R^{31}$ to $R^{38}$ of each of formulae (2-7), (2-8), and (2-9) is a group represented by —Z—$R^a$, and at least one of $R^{41}$ to $R^{48}$ and $R^{31}$ to $R^{38}$ of formula (2-10) is a group represented by —Z—$R^a$;

R¹'s and R²'s, if present, may be the same or different, and R¹'s and R²'s may be bonded to each other to form a ring structure, respectively; and adjacent two selected from $R^{11}$ to $R^{16}$, $R^{21}$ to $R^{26}$, $R^{31}$ to $R^{38}$, and $R^{41}$ to $R^{48}$ may be bonded to each other to form a ring structure.

In formulae (2-1), (2-2), (2-3), (2-4), (2-5), and (2-6), one of $R^{11}$ to $R^{16}$ is preferably a group represented by —Z—$R^a$, or one of $R^{21}$ to $R^{26}$ is preferably a group represented by —Z—$R^a$.

In formulae (2-7), (2-8), and (2-9), one of $R^{11}$ to $R^{16}$ is preferably a group represented by —Z—$R^a$, or one of $R^{31}$ to $R^{38}$ is preferably a group represented by —Z—$R^a$.

In formula (2-10), one of $R^{41}$ to $R^{48}$ is preferably a group represented by —Z—$R^a$, or one of $R^{31}$ to $R^{38}$ is preferably a group represented by —Z—$R^a$.

In formulae (2-1), (2-2), (2-3), (2-4), (2-5), and (2-6), one of $R^{11}$ to $R^{16}$ is preferably a group represented by —Z—$R^a$, and one of $R^{21}$ to $R^{26}$ is preferably a group represented by —Z—$R^a$.

In formulae (2-7), (2-8), and (2-9), one of $R^{11}$ to $R^{16}$ is preferably a group represented by —Z—$R^a$, and one of $R^{31}$ to $R^{38}$ is preferably a group represented by —Z—$R^a$.

In formula (2-10), one of $R^{41}$ to $R^{48}$ is preferably a group represented by —Z—$R^a$, and one of $R^{31}$ to $R^{38}$ is preferably a group represented by —Z—$R^a$.

Examples and preferred examples of R¹ and R² of formulae (2-1) to (2-10) are the same as those described above with respect to formula (1).

Examples and preferred examples of each group for $R^{11}$ to $R^{16}$, $R^{21}$ to $R^{26}$, $R^{31}$ to $R^{38}$, and $R^{41}$ to $R^{48}$ are the same as those described above with respect to the substituent of A and B.

The group represented by —Z—$R^a$ is preferably represented by any of formulae (a) to (c):

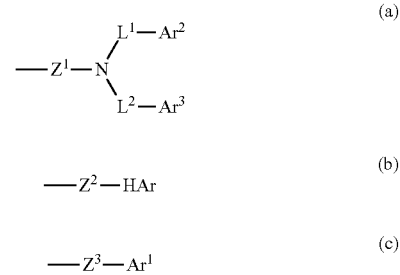

wherein:

each of $Z^1$ to $Z^3$ is independently a single bond, a substituted or unsubstituted arylene group having 6 to 30 ring carbon atoms, a substituted or unsubstituted heteroarylene group having 5 to 30 ring atoms, or a divalent linking group wherein two to four groups selected from the arylene group and the heteroarylene group are linked together;

each of $L^1$ and $L^2$ is independently a single bond, a substituted or unsubstituted arylene group having 6 to 30 ring carbon atoms, a substituted or unsubstituted heteroarylene group having 5 to 30 ring atoms, or a divalent linking group wherein two to four groups selected from the arylene group and the heteroarylene group are linked together;

each of Ar² and Ar³ is independently a substituted or unsubstituted aryl group having 6 to 30 ring carbon atoms or a substituted or unsubstituted heteroaryl group having 5 to 30 ring atoms;

HAr is a substituted or unsubstituted heteroaryl group having 5 to 30 ring atoms; and $Ar^1$ is a substituted or unsubstituted aryl group having 14 to 30 ring carbon atoms.

Examples and preferred examples of $Z^1$ to $Z^3$ in formulae (a) to (c) are the same as those described above with respect to Z in formula (1), respectively. Particularly, in formula (a), $Z^1$ is preferably a single bond or an arylene group having 6 to 30 ring carbon atoms and more preferably a single bond; in formula (b), $Z^2$ is preferably a single bond or an arylene group having 6 to 30 ring carbon atoms; and in formula (c), $Z^3$ is preferably a single bond or an arylene group having 6 to 30 ring carbon atoms and more preferably an arylene group having 6 to 30 ring carbon atoms.

Examples and preferred examples of the arylene group having 6 to 30, preferably 6 to 24, more preferably 6 to 18, and still more preferably 6 to 10 ring carbon atoms and the heteroarylene group having 5 to 30, preferably 5 to 24, and more preferably 5 to 12 ring atoms each for $L^1$ and $L^2$ in formula (a) are the same as those described above with respect to the arylene group and the heteroarylene group for Z in formula (1), respectively. Examples of the "divalent group wherein two to four groups selected from the arylene group and the heteroarylene group are linked together" for $L^1$ and $L^2$ include -arylene group-heteroarylene group-, -heteroarylene group-arylene group-, -arylene group-heteroarylene group-arylene group-, -heteroarylene group-arylene group-heteroarylene group-, -arylene group-heteroarylene group-arylene group-heteroarylene group-, and -heteroarylene group-arylene group-heteroarylene group-arylene group-.

Examples of the aryl group having 6 to 30, preferably 6 to 20, and more preferably 6 to 14 ring carbon atoms for $Ar^2$ and $Ar^3$ in formula (a) include a phenyl group, a biphenylyl group (2-biphenylyl group, 4-biphenylyl group), a terphenylyl group, a naphthyl group, an acenaphthylenyl group, an anthryl group, a benzanthryl group, an aceanthryl group, a phenanthryl group, a benzo[c]phenanthryl group, a phenalenyl group, a fluorenyl group, a picenyl group, a pentaphenyl group, a pyrenyl group, a chrysenyl group, a benzo[g]chrysenyl group, a s-indacenyl group, an as-indacenyl group, a fluoranthenyl group, a benzo[k]fluoranthenyl group, a triphenylenyl group, a benzo[b]triphenylenyl group, and a perylenyl group. In view of the emission efficiency, the device lifetime, and the driving voltage, a phenyl group, a biphenylyl group (2-biphenylyl group, 4-biphenylyl group), a terphenylyl group, a naphthyl group, and an anthryl group are preferred; a phenyl group and a biphenylyl group (2-biphenylyl group, 4-biphenylyl group) are more preferred; a biphenylyl group (2-biphenylyl group, 4-biphenylyl group) is still more preferred; and a 4-biphenylyl group is particularly preferred.

Particularly, in view of the device lifetime, the aryl group preferably has a substituent. When the aryl group is a phenyl group, the device lifetime tends to be largely improved by the presence of a substituent, for example, an alkyl group having 1 to 20 carbon atoms, a cycloalkyl group having 3 to 20 ring carbon atoms, or an alkoxy group having 1 to 30 carbon atoms.

Examples and preferred examples of the heteroaryl group having 5 to 30, preferably 5 to 20, and more preferably 5 to 14 ring atoms for $Ar^2$ and $Ar^3$ are the same as those described above with respect to the heteroaryl group for $R^1$ in formula (1).

In formula (a), each of $Ar^2$ and $Ar^3$ is preferably a substituted or unsubstituted aryl group having 6 to 30 ring carbon atoms.

Also preferred is a formula (a), wherein each of $L^1$ and $L^2$ is a single bond and each of $Ar^2$ and $Ar^3$ is independently a substituted or unsubstituted phenyl group, a substituted or unsubstituted naphthyl group, a substituted or unsubstituted phenanthryl group, a substituted or unsubstituted fluorenyl group, a substituted or unsubstituted dibenzofuranyl group, or a substituted or unsubstituted dibenzothiophenyl group.

Formula (a) is preferably represented by formula (a'), wherein each of $L^1$ and $L^2$ is a single bond:

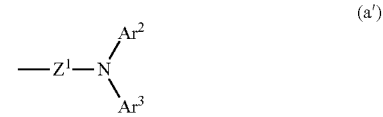

wherein $Z^1$, $Ar^2$, and $Ar^3$ are as defined in formula (a).

Examples and preferred examples of the heteroaryl group having 5 to 30 ring atoms for HAr in formula (b) are the same as those described above with respect to the heteroaryl group for $R^1$ and $R^2$ in formula (1). HAr is more preferably a pyridinyl group, a pyrimidinyl group, a triazinyl group, a dibenzofuranyl group, or a dibenzothiophenyl group.

Examples of the aryl group having 14 to 30 ring carbon atoms for $Ar^1$ in formula (c) are those having 14 to 30 ring carbon atoms selected from the aryl group described above with respect to $R^1$ and $R^2$ in formula (1). Preferred is an aryl group having 14 to 25 ring carbon atoms and more preferred is an aryl group having 14 to 20 ring carbon atoms. Examples thereof include an anthryl group, a phenanthryl group, a pyrenyl group, a fluoranthenyl group, and a benzo[k]fluoranthenyl group, with an anthryl group being more preferred. Although not particularly limited, $Ar^1$ preferably has a substituent, particularly when $Z^3$ is a single bond. The substituent is preferably an aryl group having 6 to 25 ring carbon atoms and more preferably an aryl group having 6 to 12 ring carbon atoms, such as a phenyl group, a naphthyl group, and a biphenylyl group.

—HAr in formula (b) is preferably a group selected from the following groups:

-continued

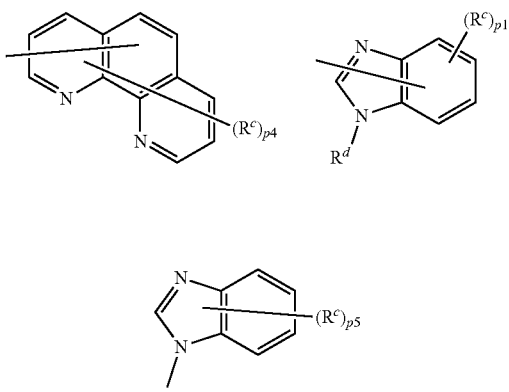

wherein:

each $R^c$ is independently a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, a substituted or unsubstituted aralkyl group having 7 to 30 carbon atoms which includes an aryl group having 6 to 30 ring carbon atoms, an amino group, a mono- or dialkylamino group having an alkyl group having 1 to 20 carbon atoms, a mono- or diarylamino group having an aryl group having 6 to 30 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a mono-, or tri-substituted silyl group having a substituent selected from an alkyl group having 1 to 20 carbon atoms and an aryl group having 6 to 30 ring carbon atoms, a substituted or unsubstituted heteroaryl group having 5 to 30 ring atoms, a halogen atom, a cyano group, or a nitro group;

$R^c$s, if present in each group, may be the same or different;

$R^d$ is a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, or a substituted or unsubstituted heteroaryl group having 5 to 30 ring atoms; and each p1 is independently an integer of 0 to 4, each p2 is independently an integer of 0 to 3, p3 is an integer of 0 to 2, p4 is an integer of 0 to 7, and p5 is an integer of 0 to 5.

The free bond "—" in the above groups is bonded to an atom constituting $Z^2$. $R^c$ in each group may be bonded to any of the ring carbon atoms.

Examples and preferred examples of each group for $R^c$ and $R^d$ are the same as those described above with respect to $R^1$ and $R^2$ in formula (1), respectively.

Preferably, each of p1 to p5 is an integer of 0 to 2.

Of the above, —HAr in formula (b) is preferably the following group:

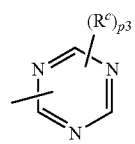

wherein $R^c$ and p3 are as defined above.

In formulae (2-1), (2-2), (2-3), (2-4), (2-5), and (2-6), one of $R^{11}$ to $R^{16}$ is preferably a group represented by any of formulae (a) to (c), or one of $R^{21}$ to $R^{26}$ is preferably a group represented by any of formulae (a) to (c).

In formulae (2-7), (2-8), and (2-9), one of $R^{11}$ to $R^{16}$ is preferably a group represented by any of formulae (a) to (c), or one of $R^{31}$ to $R^{38}$ is preferably a group represented by any of formulae (a) to (c).

In formula (2-10), one of $R^{41}$ to $R^{48}$ is preferably a group represented by any of formulae (a) to (c), or one of $R^{31}$ to $R^{38}$ is preferably a group represented by any of formulae (a) to (c).

In formulae (2-1), (2-2), (2-3), (2-4), (2-5), and (2-6), one of $R^{11}$ to $R^{16}$ is preferably a group represented by any of formulae (a) to (c), and one of $R^{21}$ to $R^{26}$ is preferably a group represented by any of formulae (a) to (c).

In formulae (2-7), (2-8), and (2-9), one of $R^{11}$ to $R^{16}$ is preferably a group represented by any of formulae (a) to (c), and one of $R^{31}$ to $R^{38}$ is preferably a group represented by any of formulae (a) to (c).

In formula (2-10), one of $R^{41}$ to $R^{48}$ is preferably a group represented by any of formulae (a) to (c), and one of $R^{31}$ to $R^{38}$ is preferably a group represented by any of formulae (a) to (c).

Examples of the compound of the invention are described below, although not particularly limited thereto.

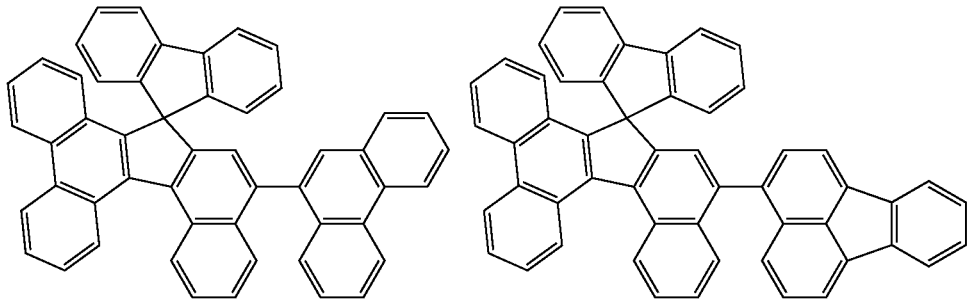

-continued
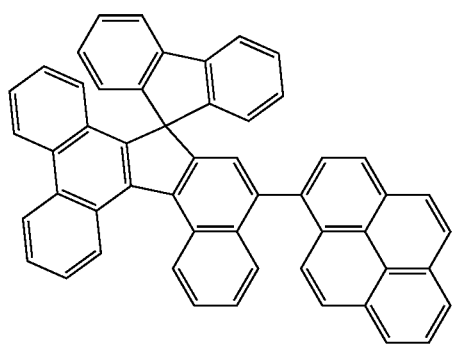
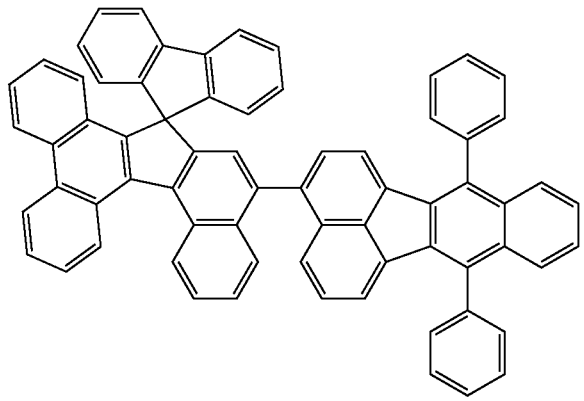
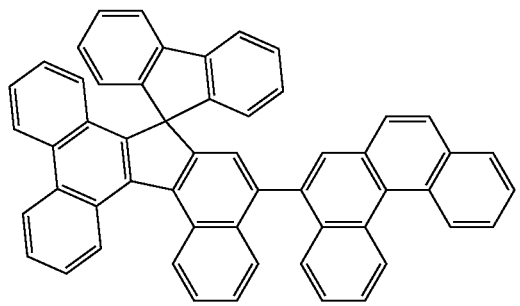
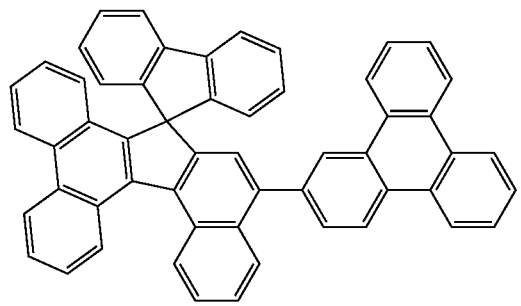
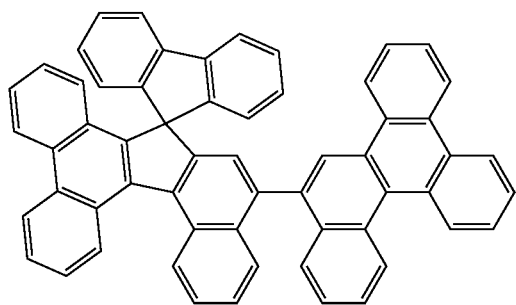
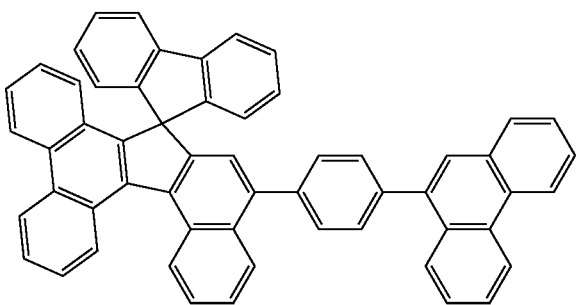
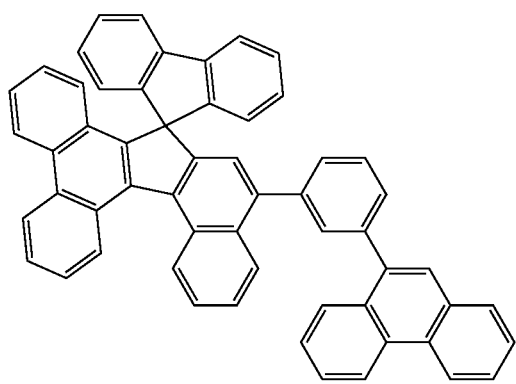
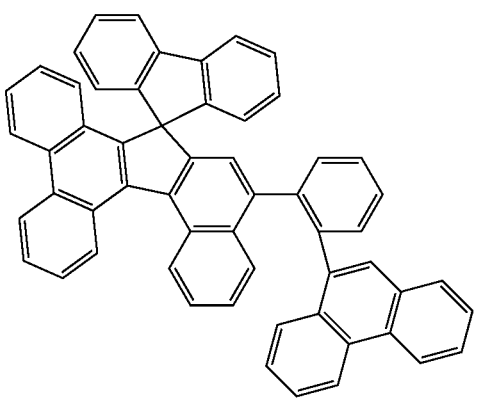

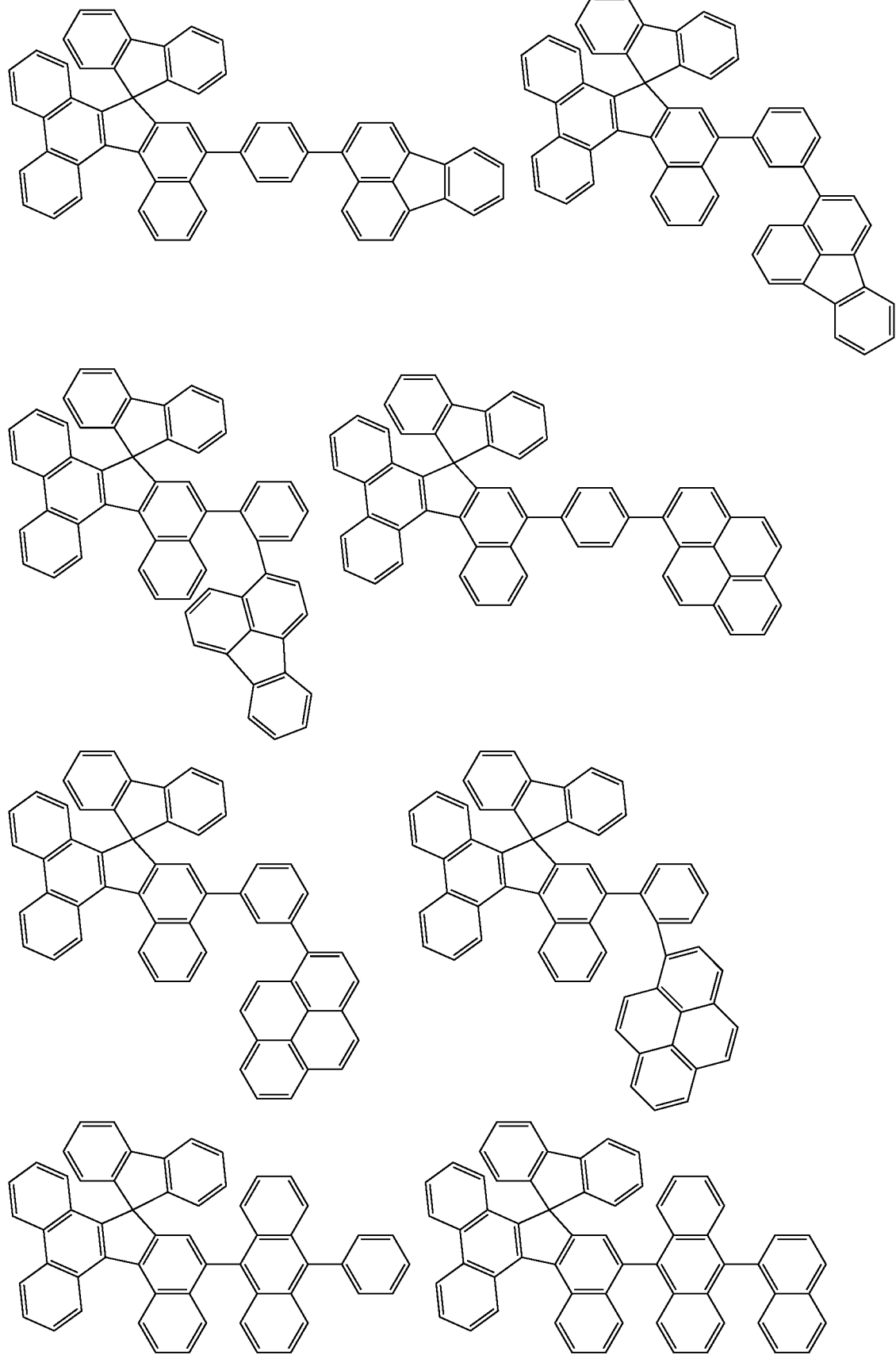

-continued
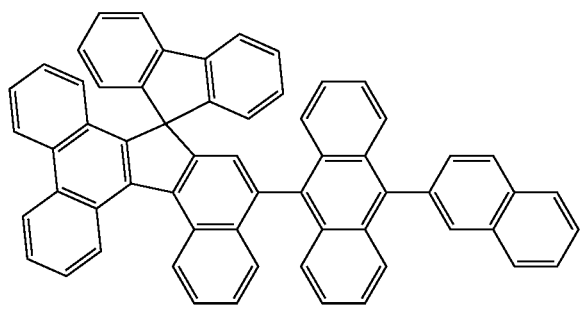
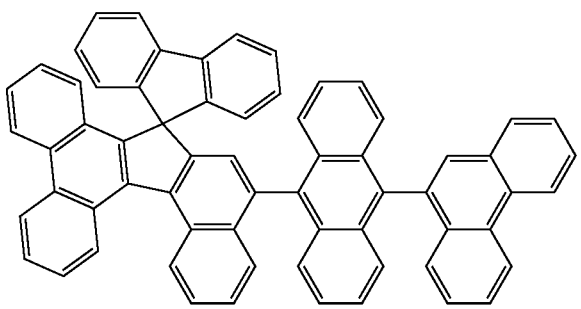
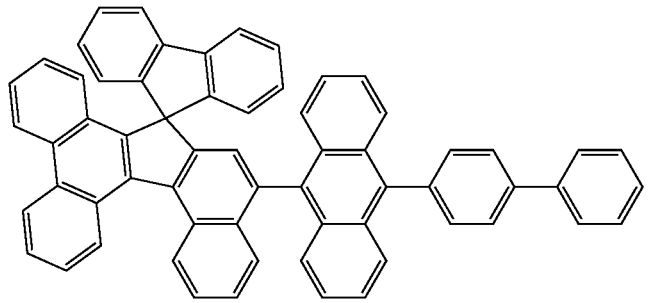
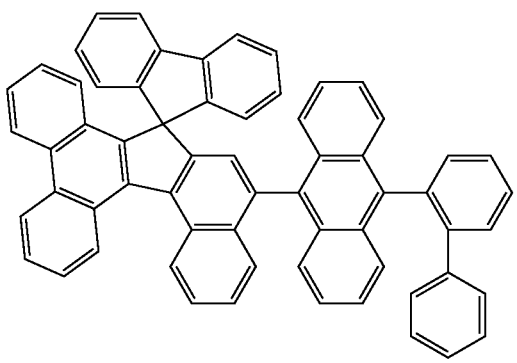
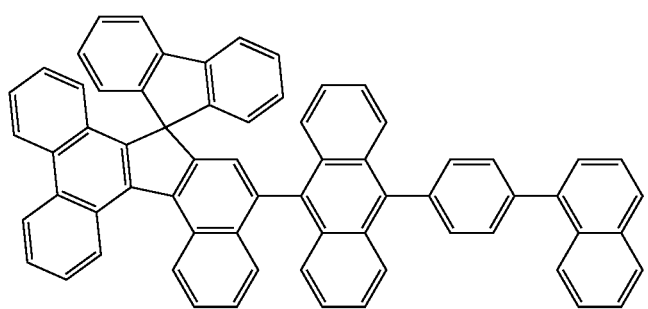
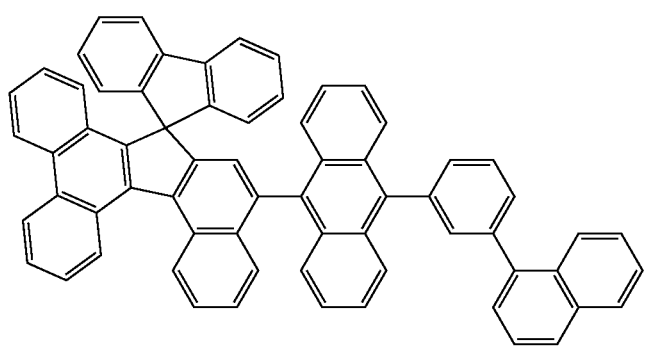

-continued
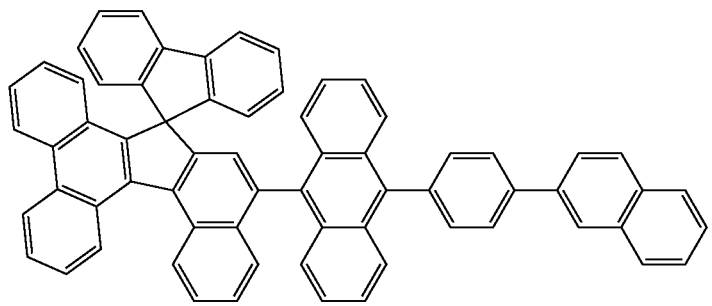
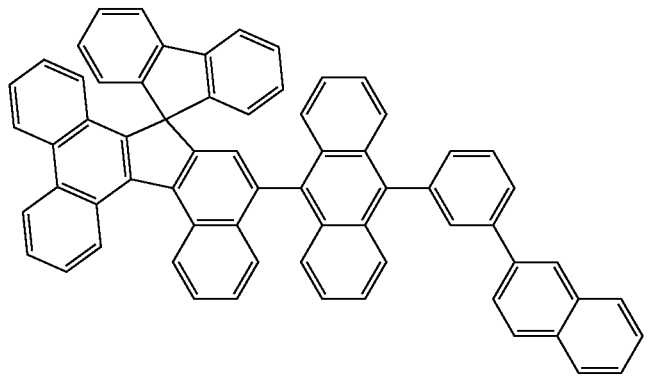
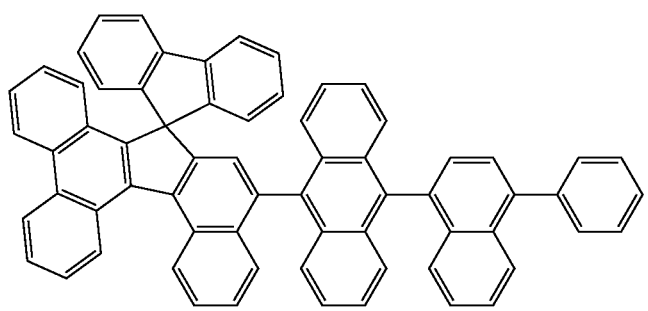
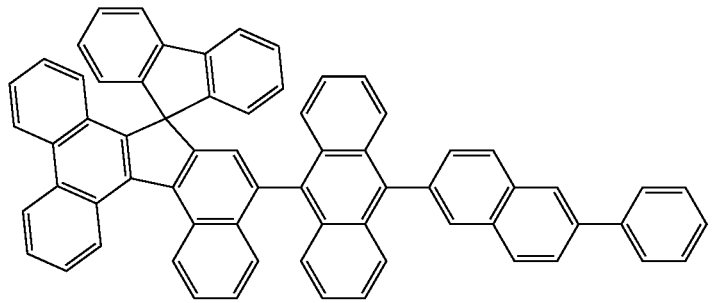
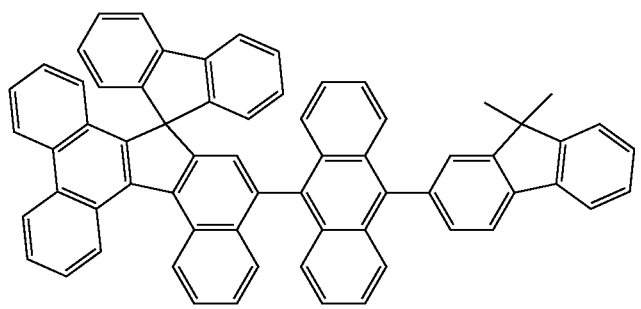

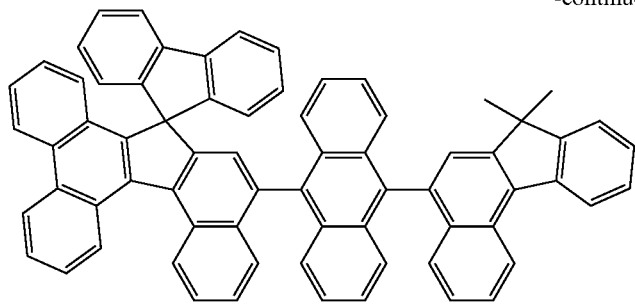

-continued
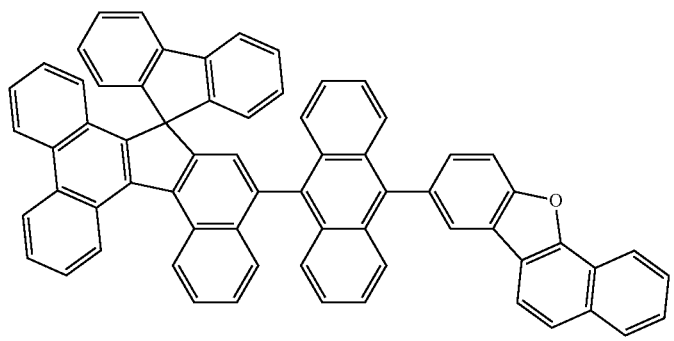
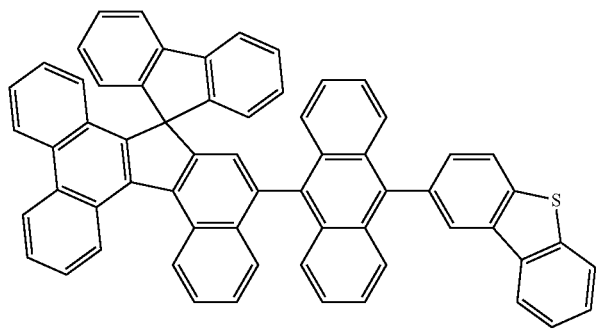
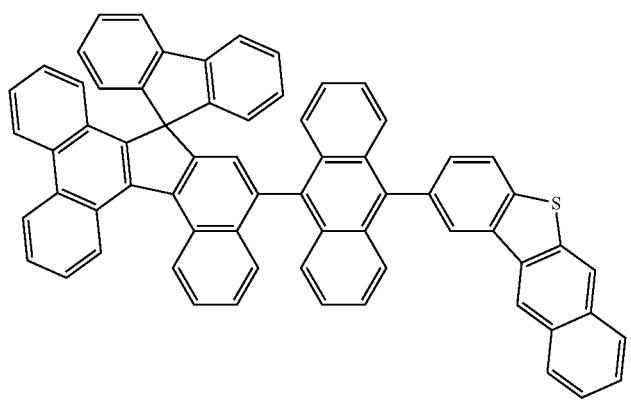
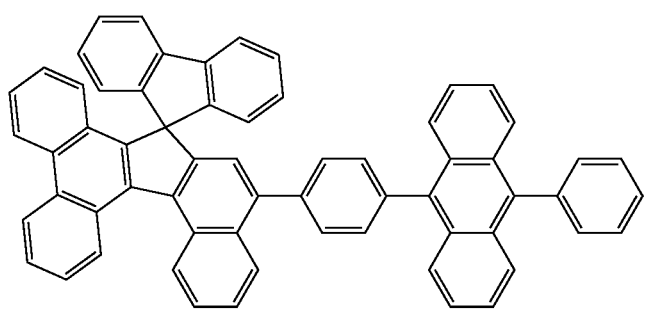
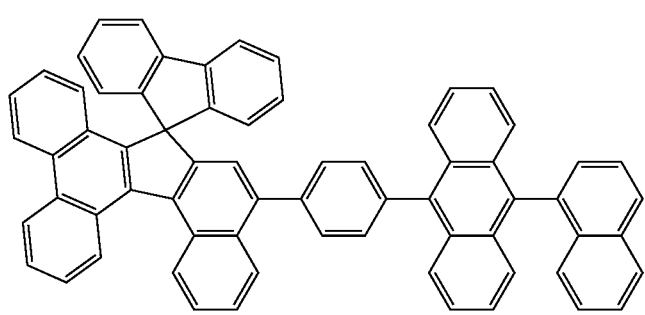

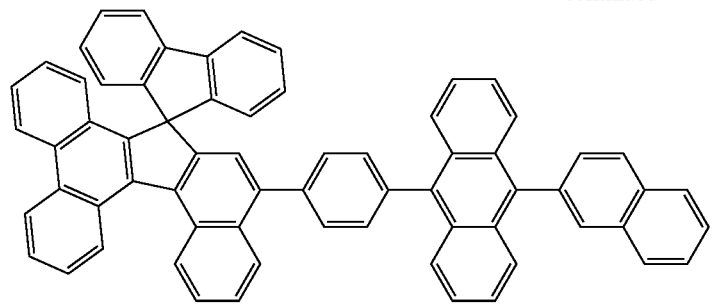
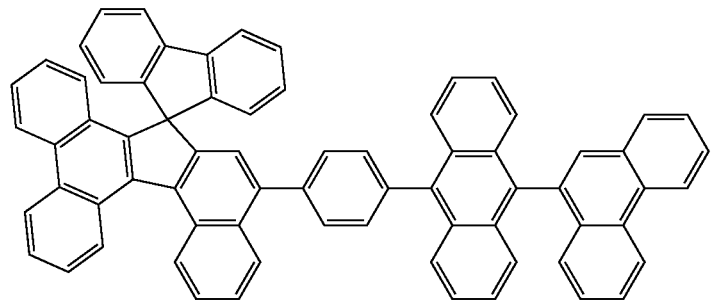
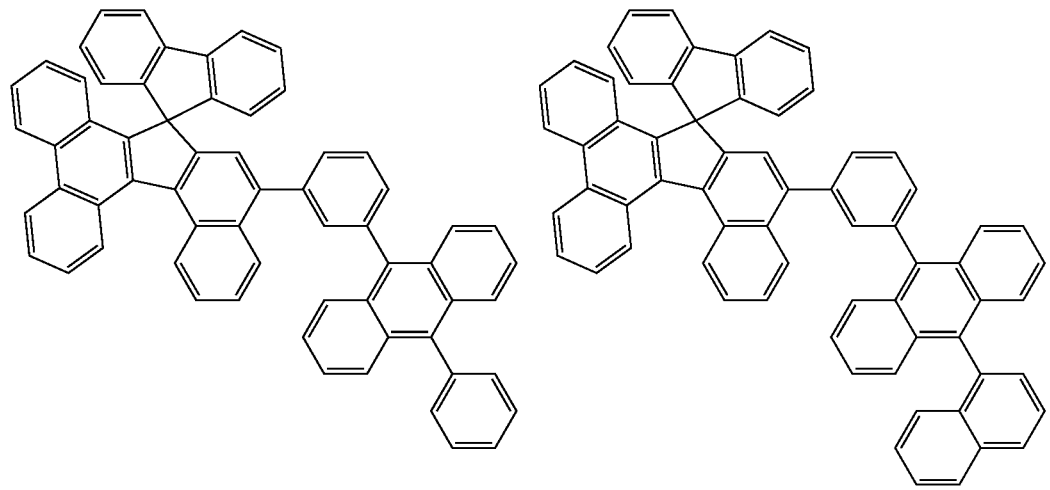
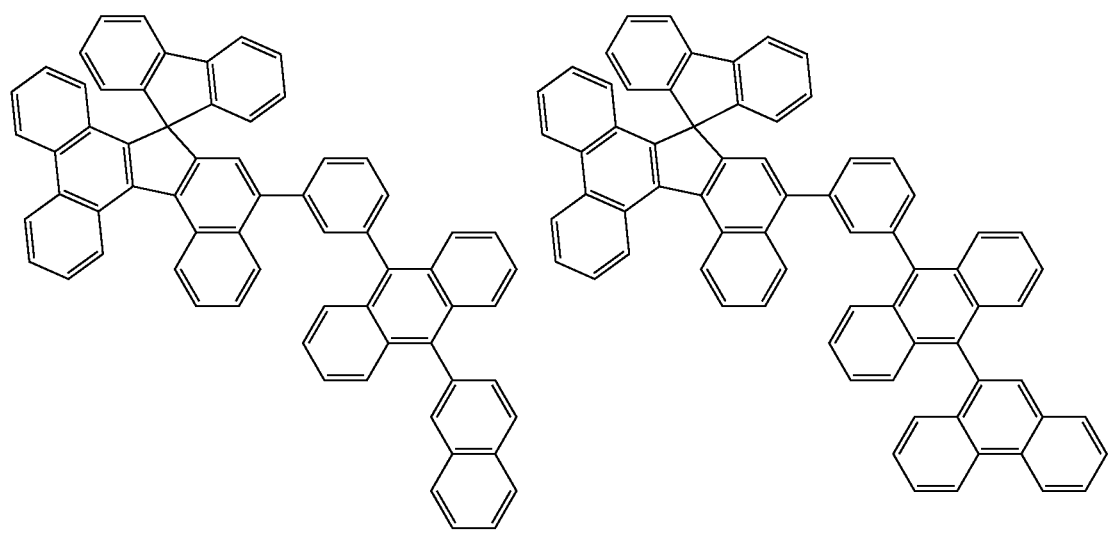

-continued
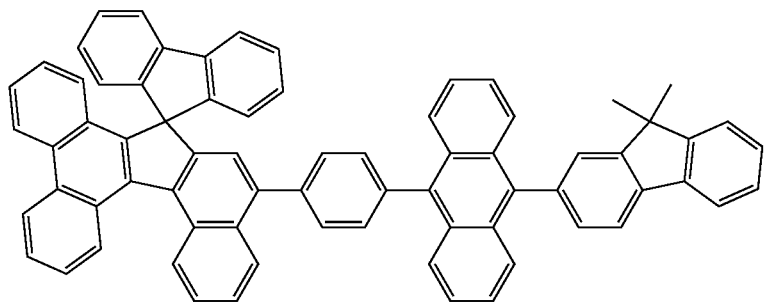
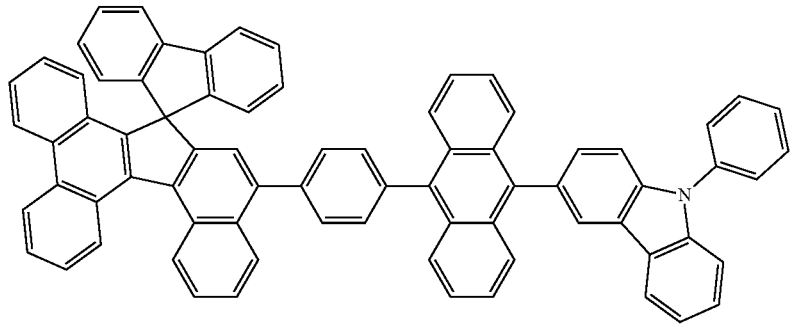
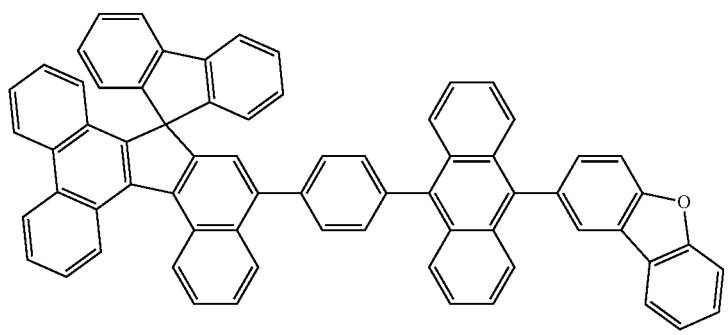
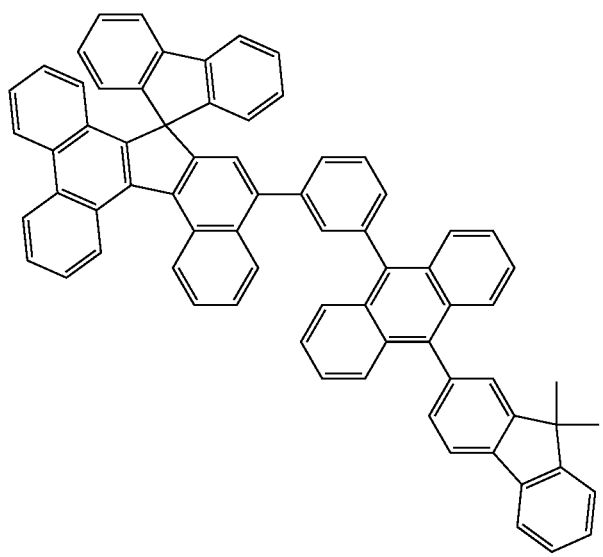

-continued
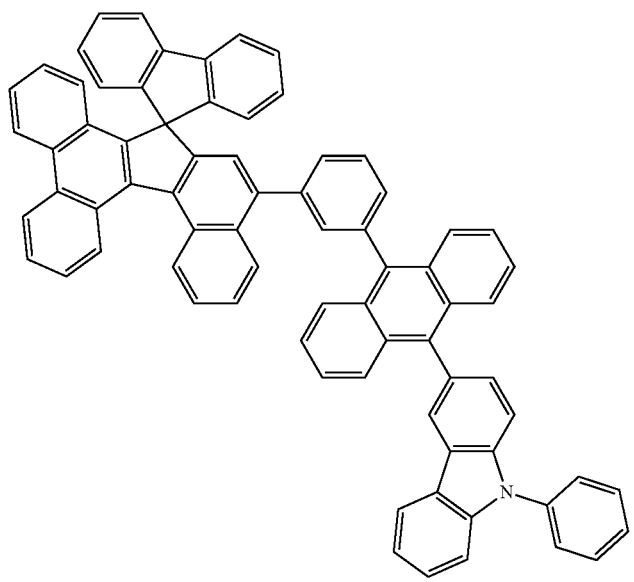
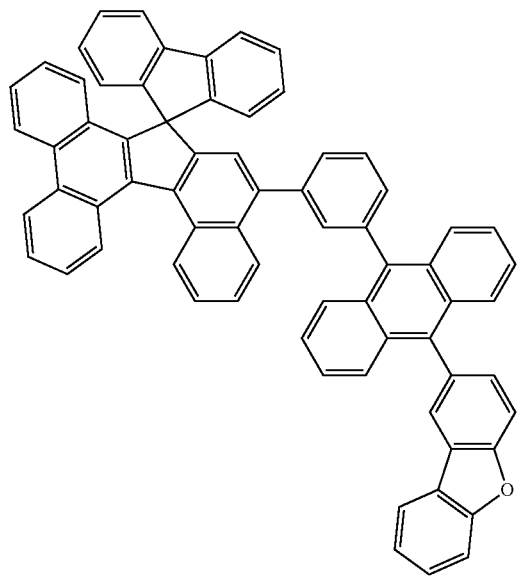
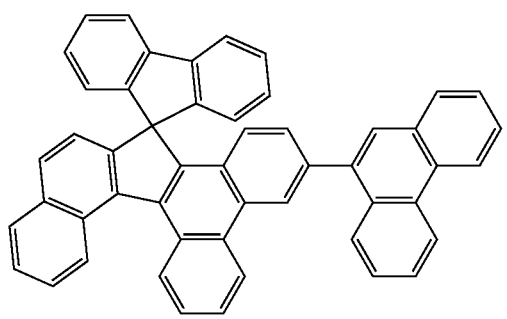
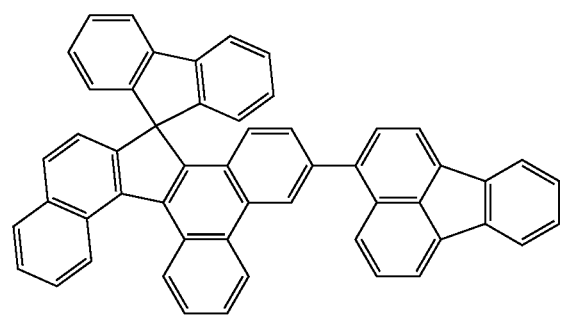
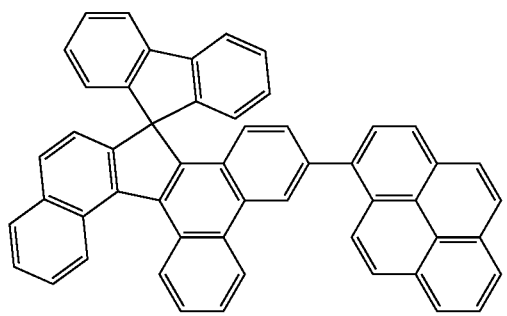
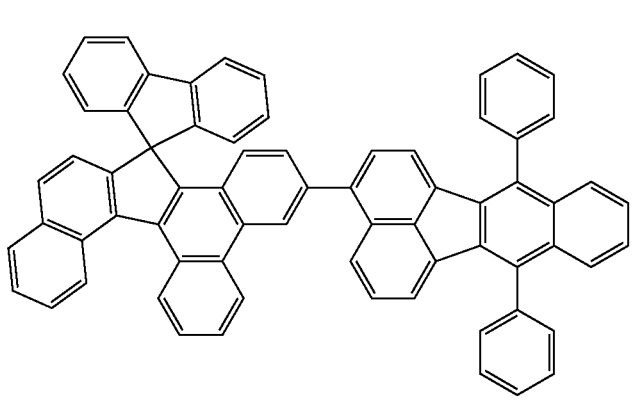
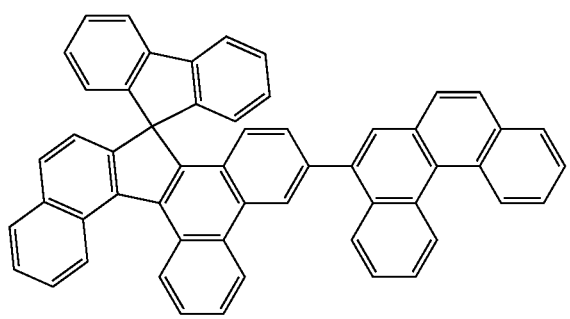
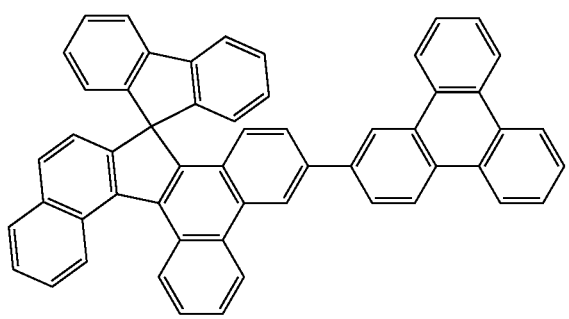

-continued
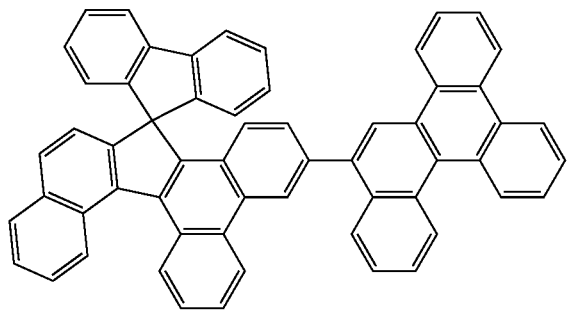
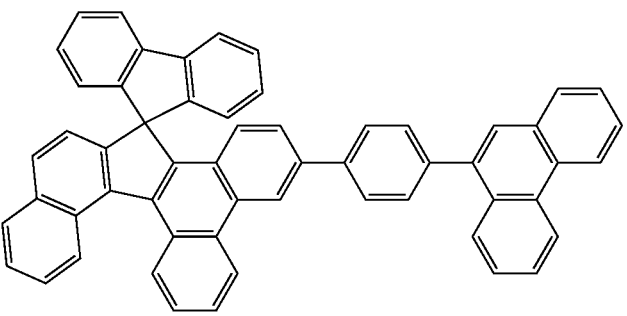
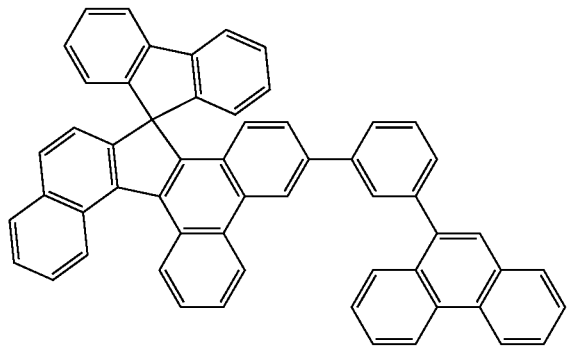
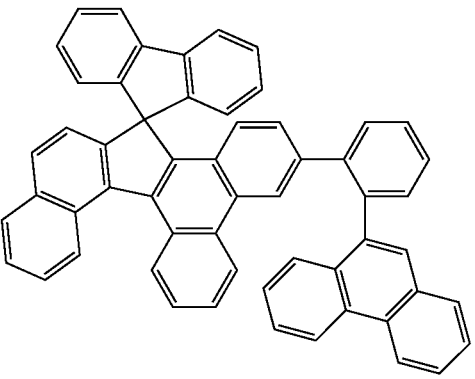
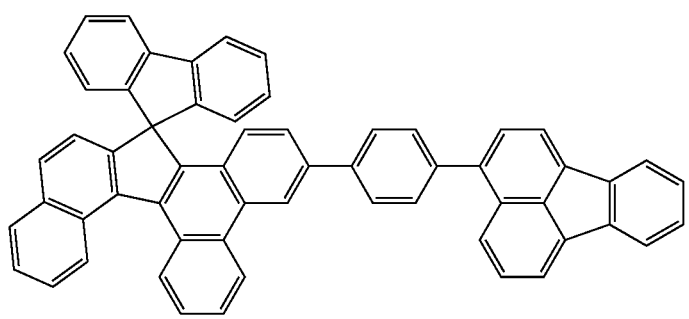
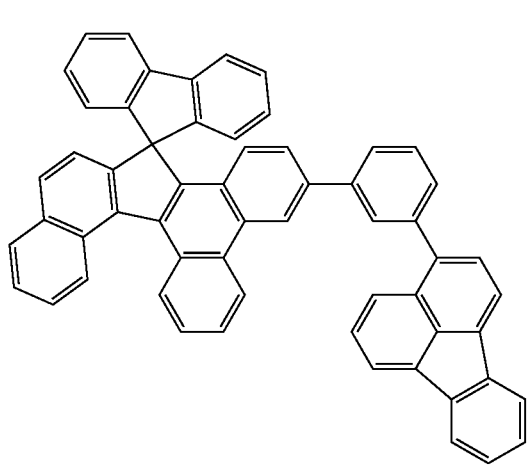
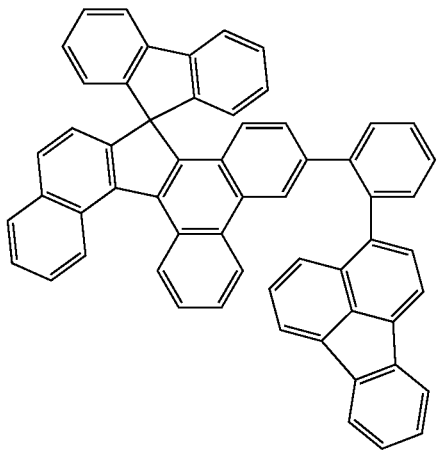

-continued
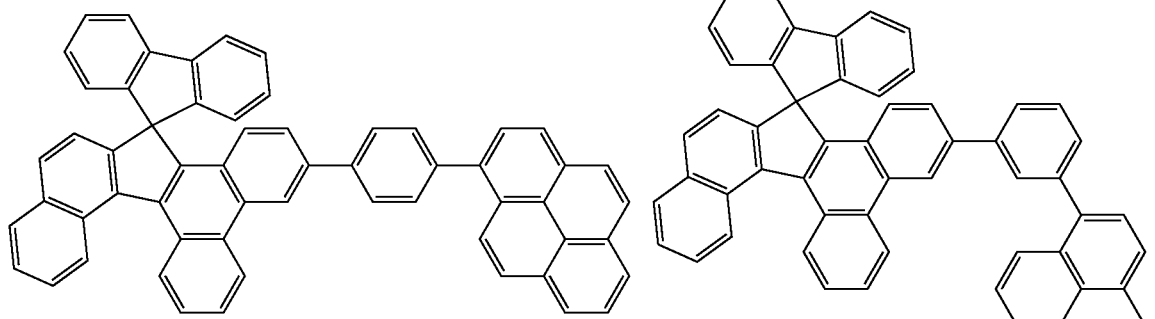
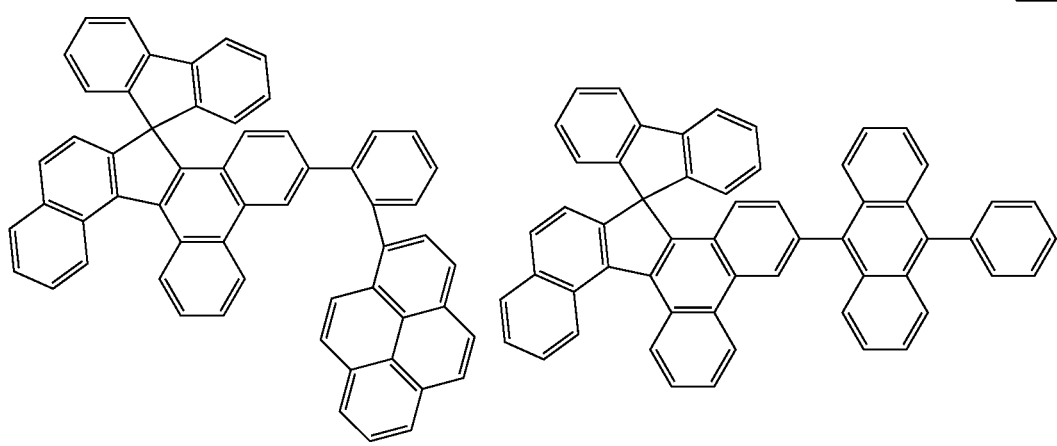
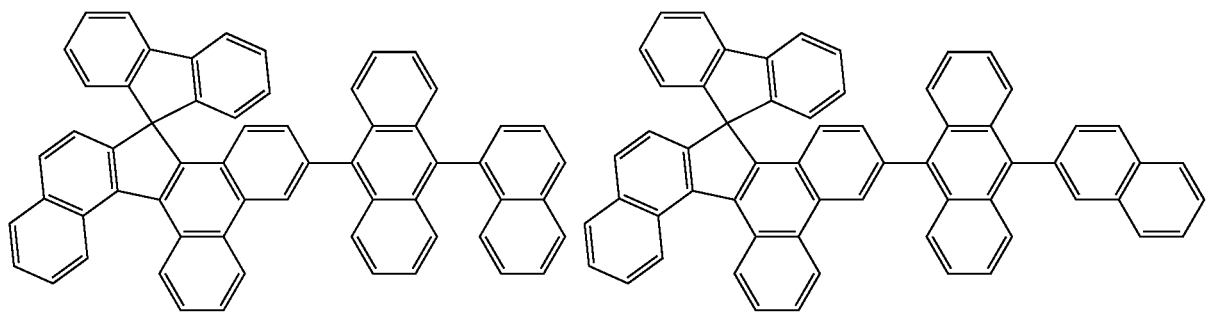
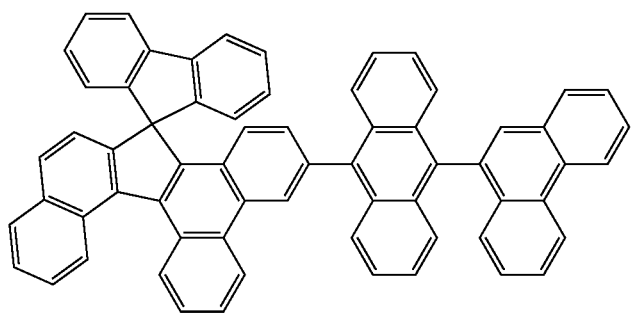

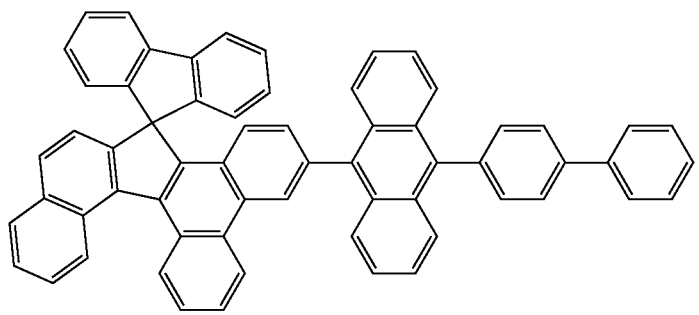

-continued
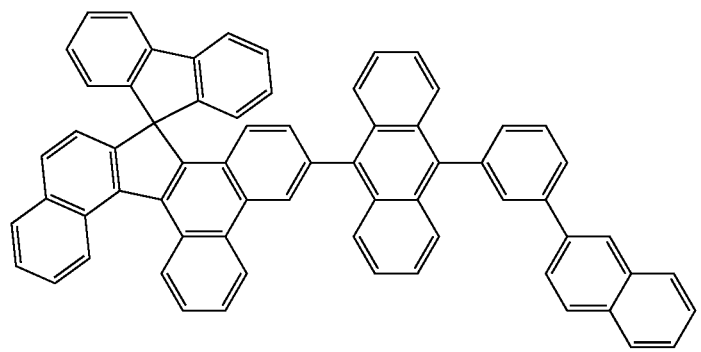
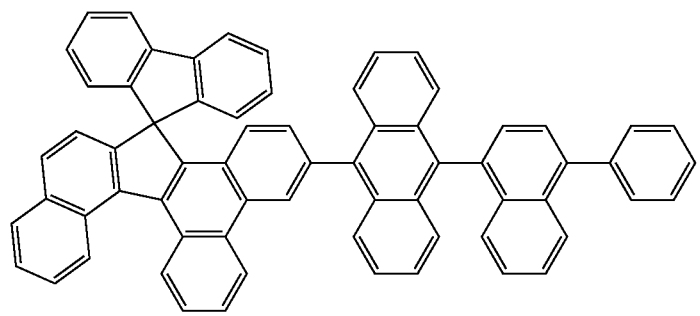
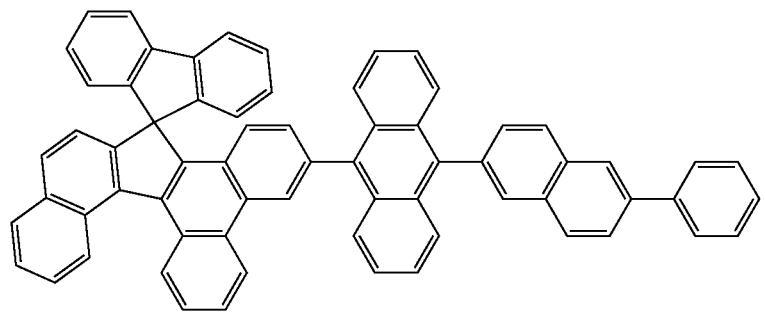
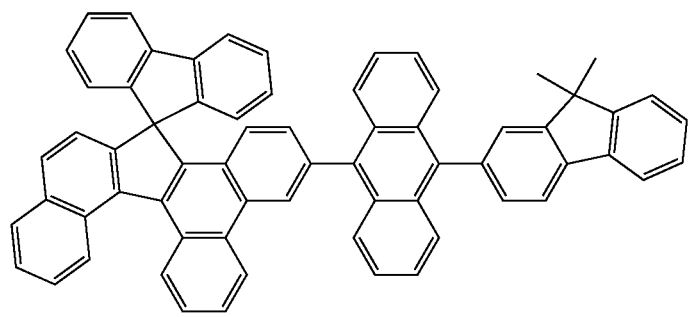
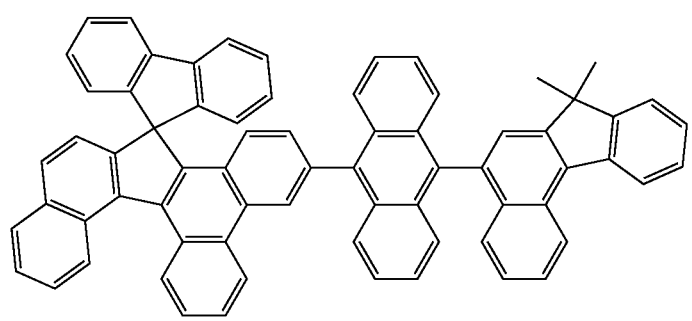

-continued
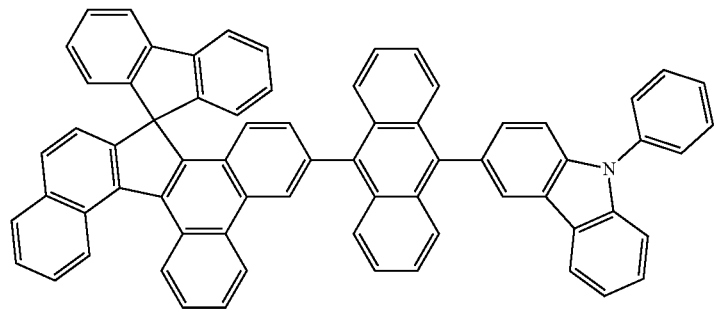
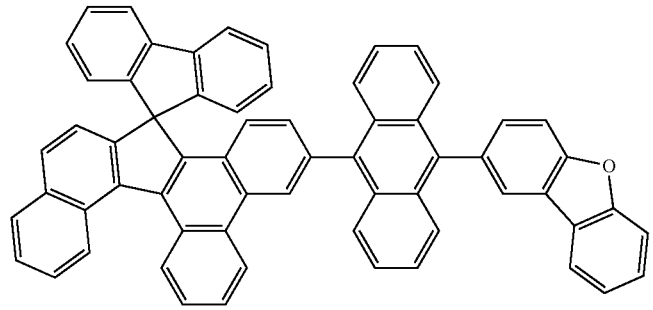
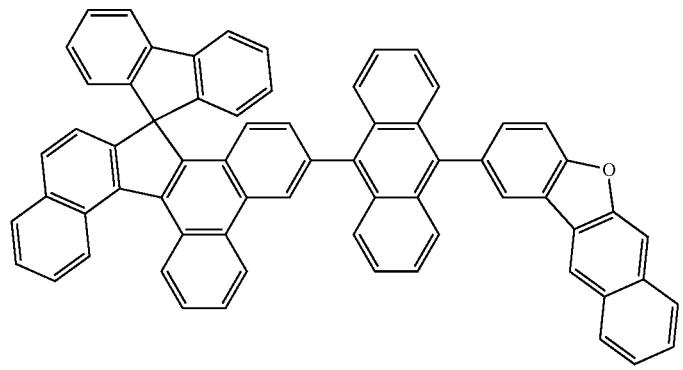
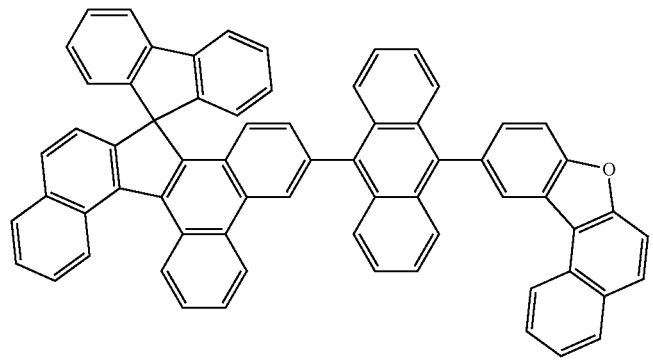
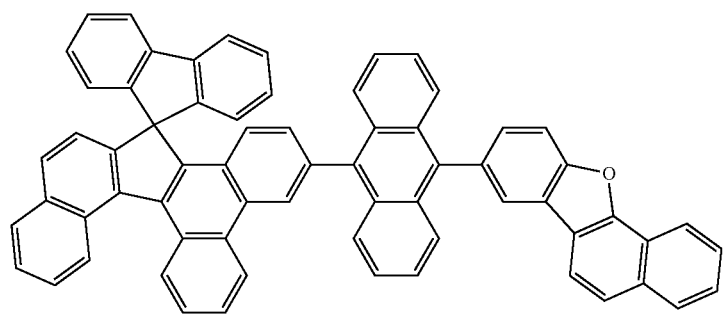

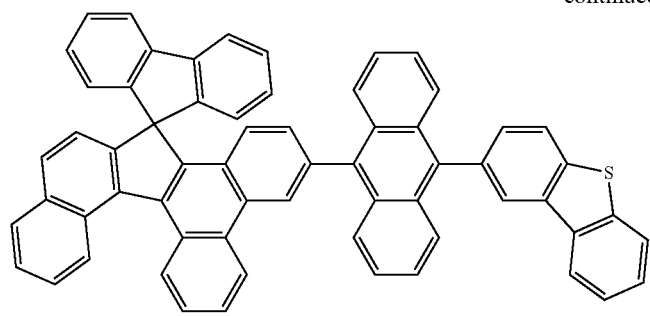
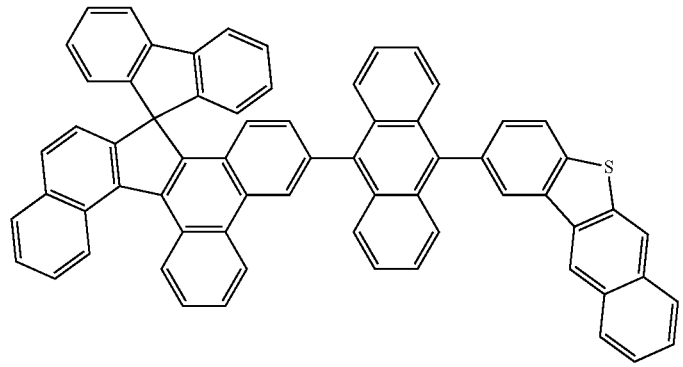
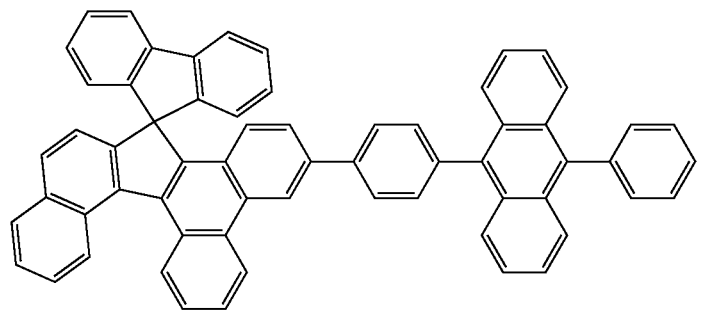
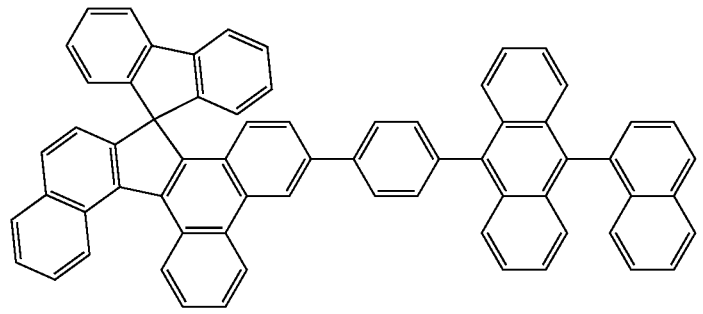
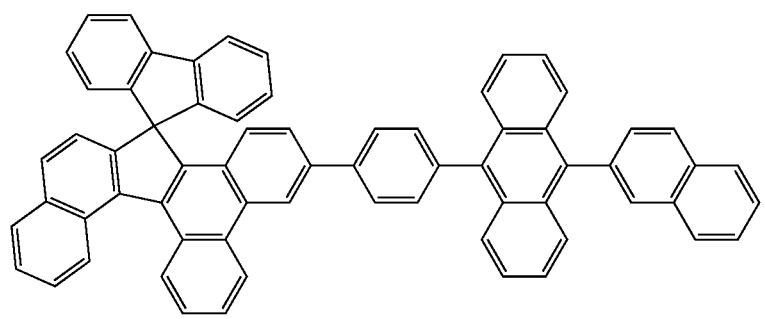

-continued
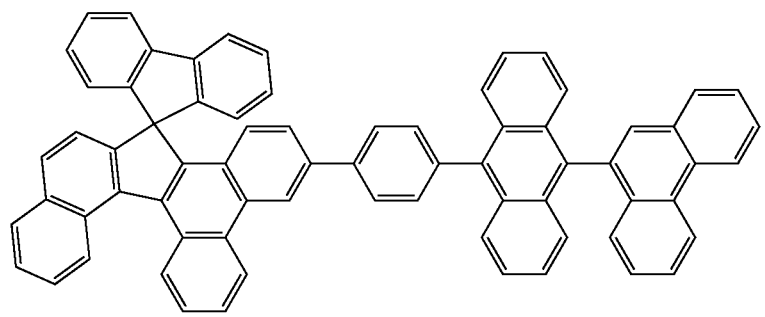
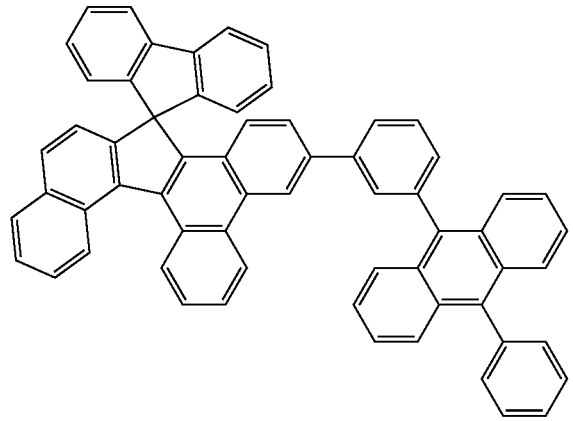
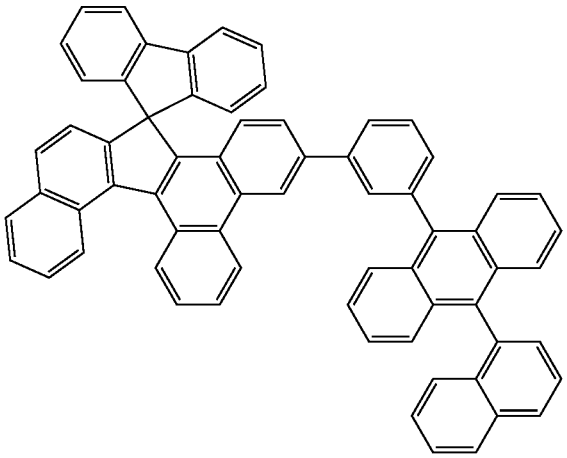
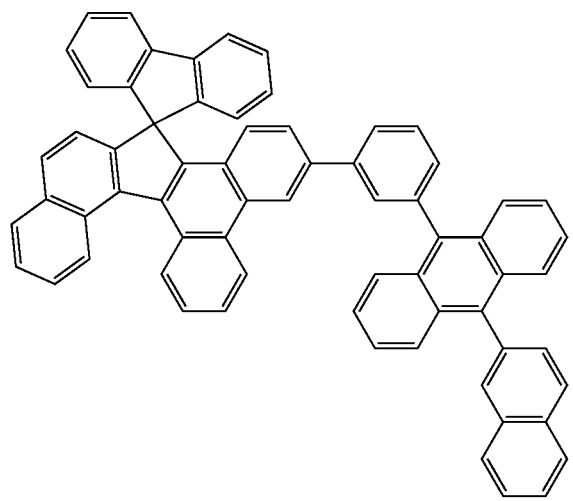
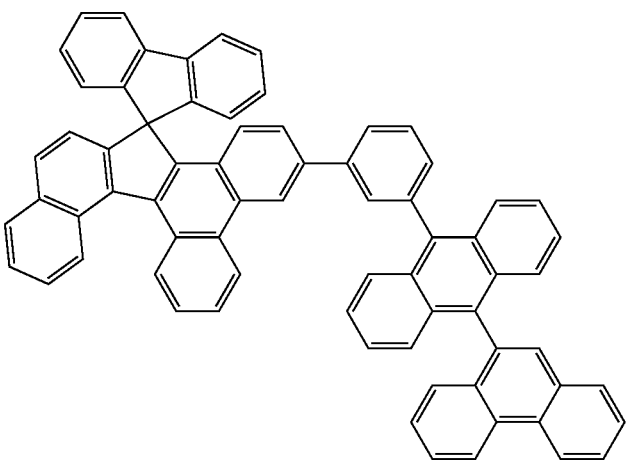
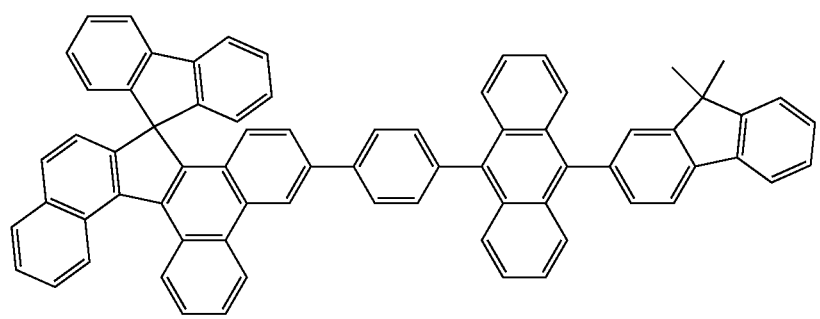

-continued
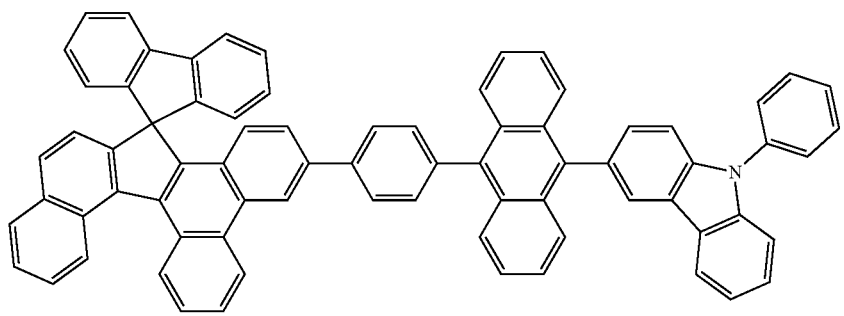
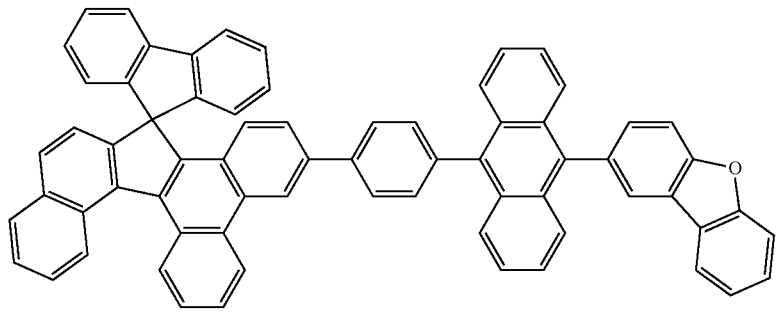
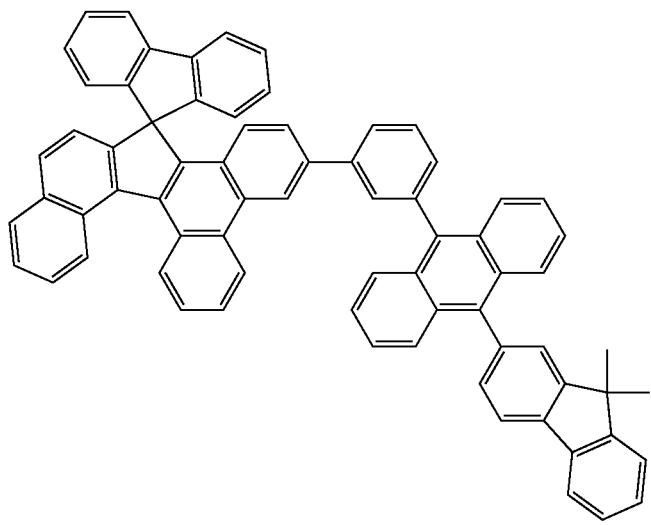
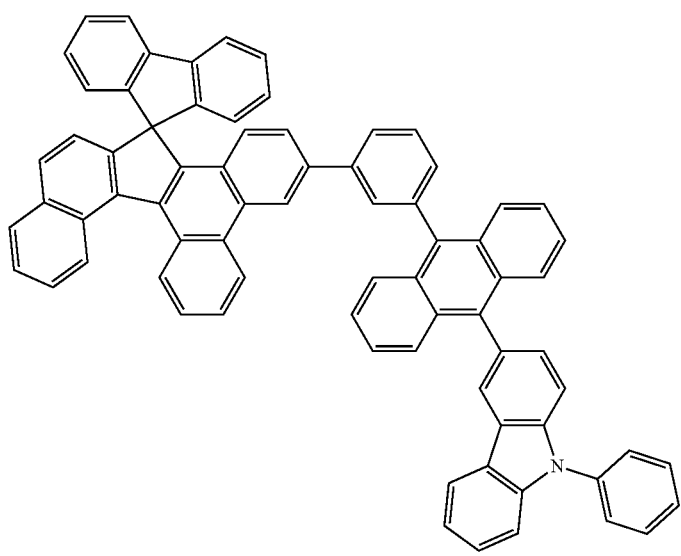

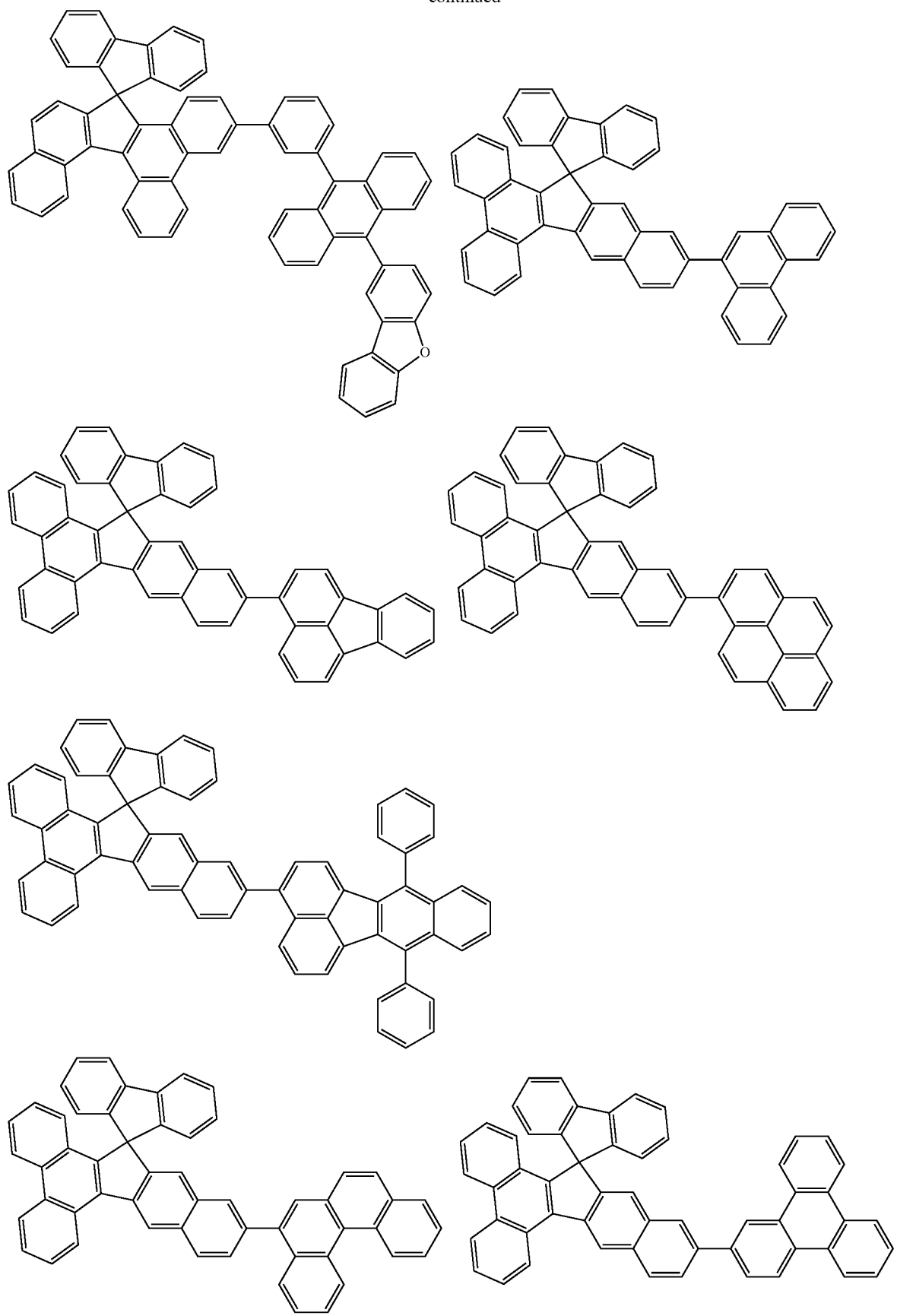

-continued
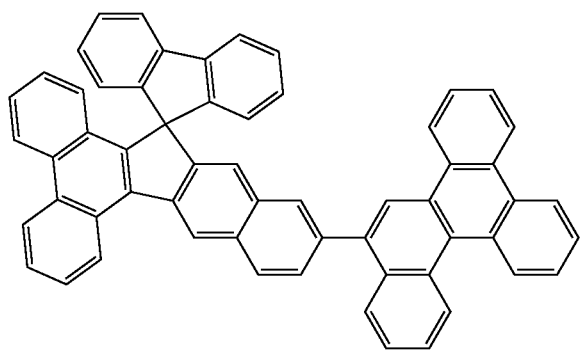
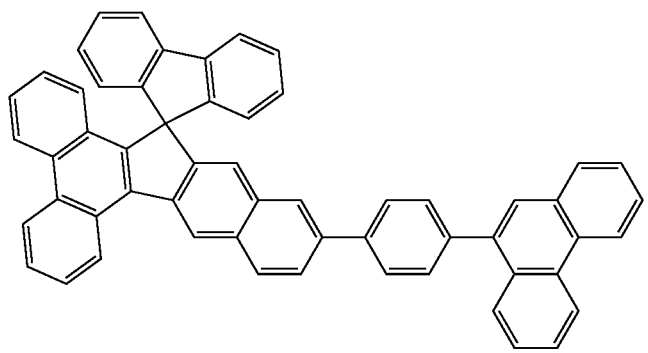
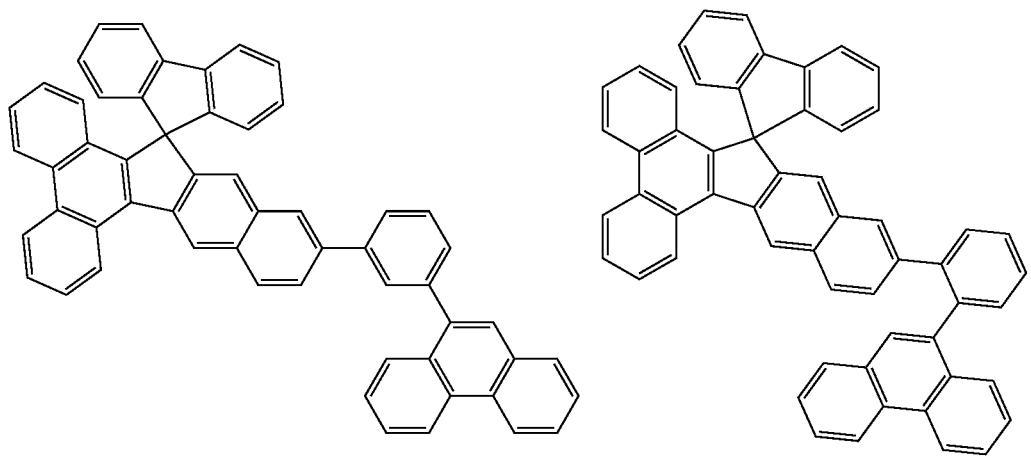
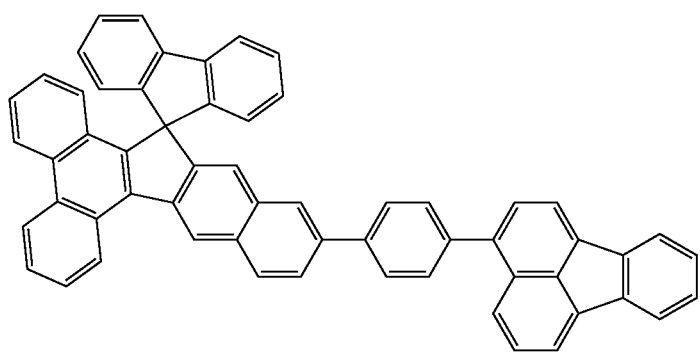

-continued
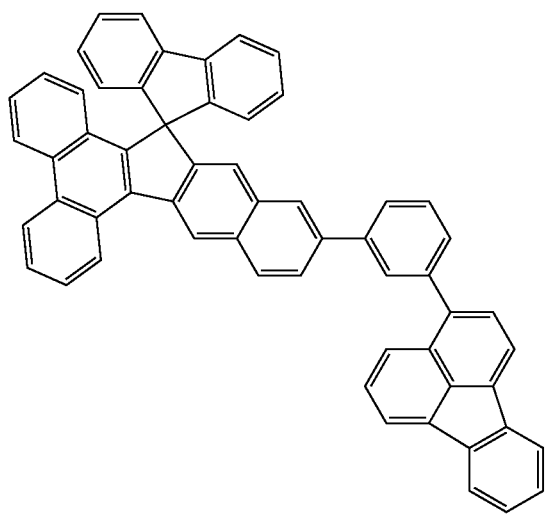
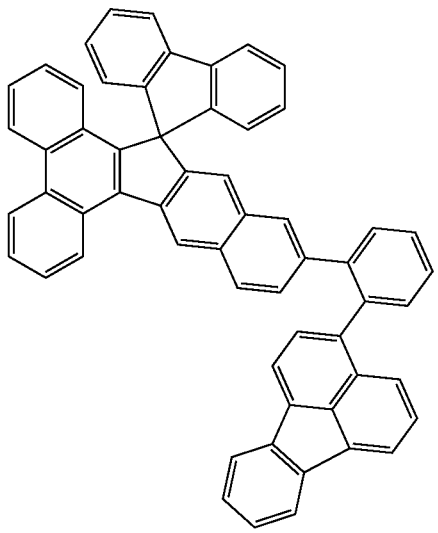
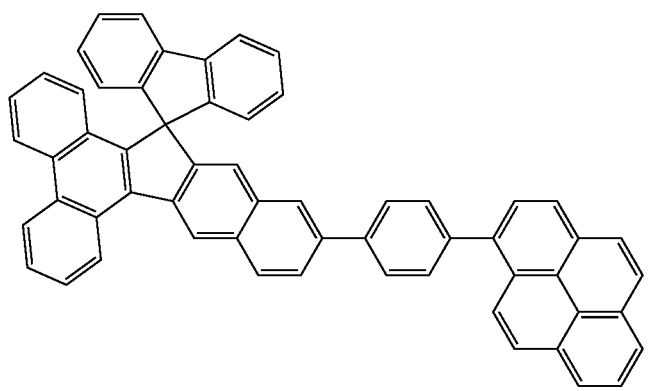
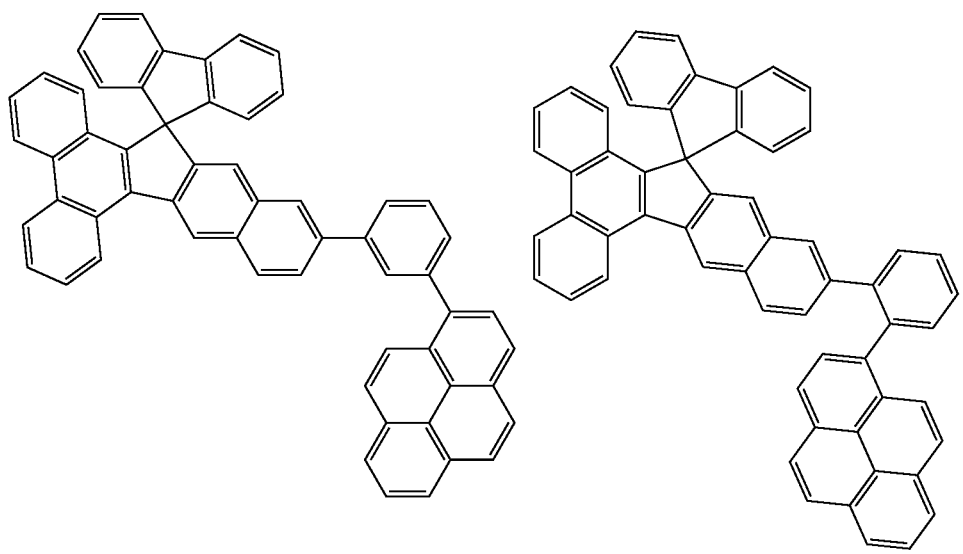

-continued
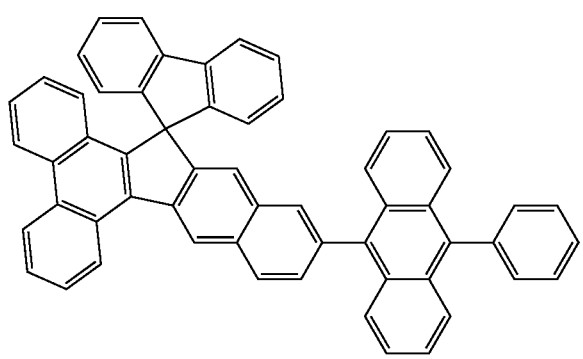

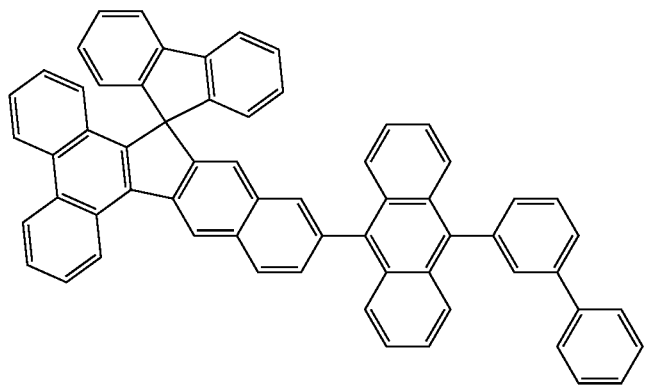
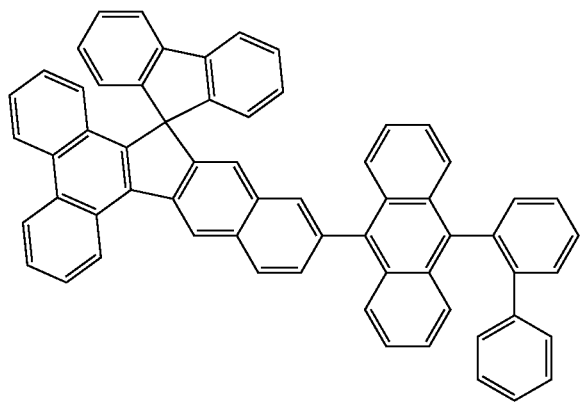
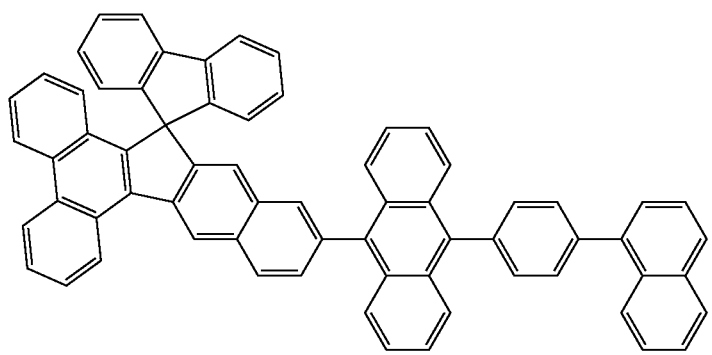
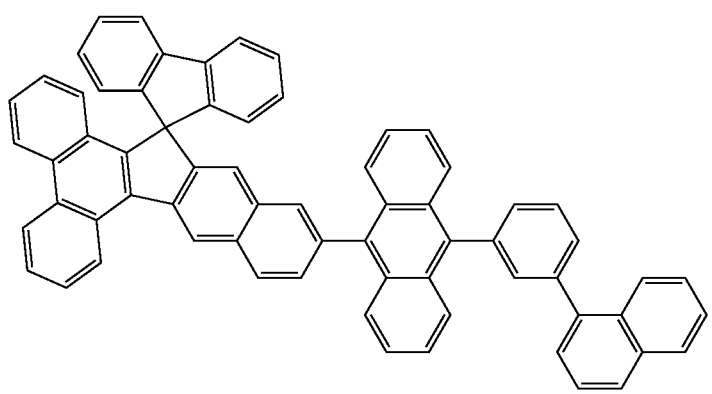

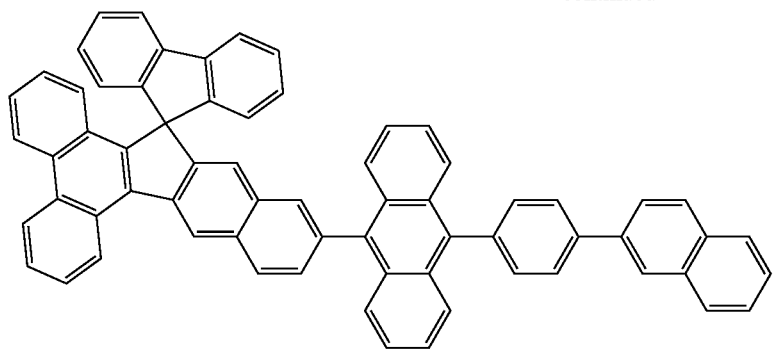

-continued
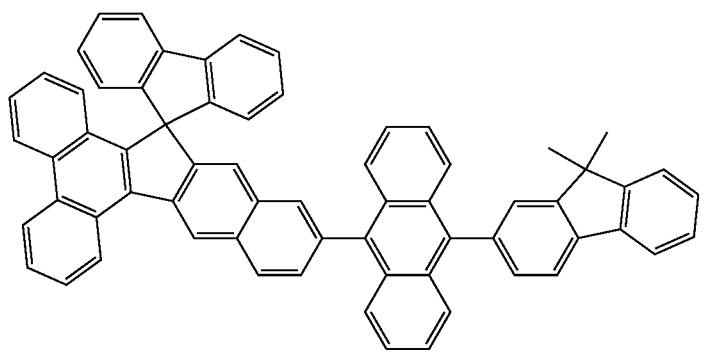
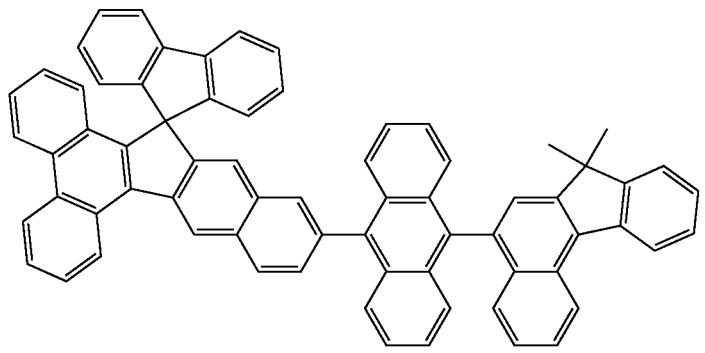
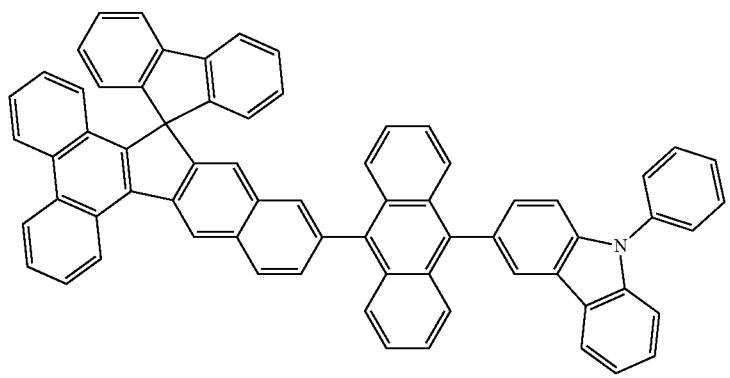
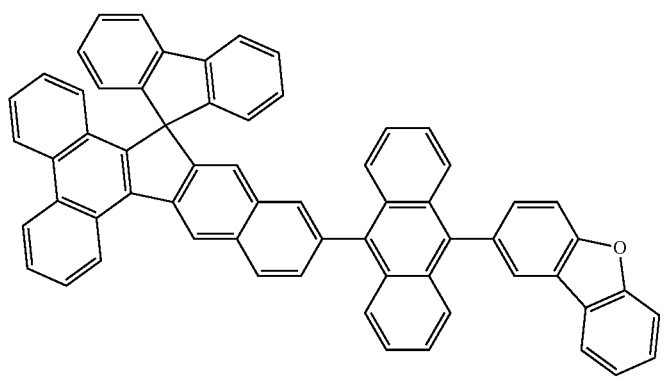

-continued
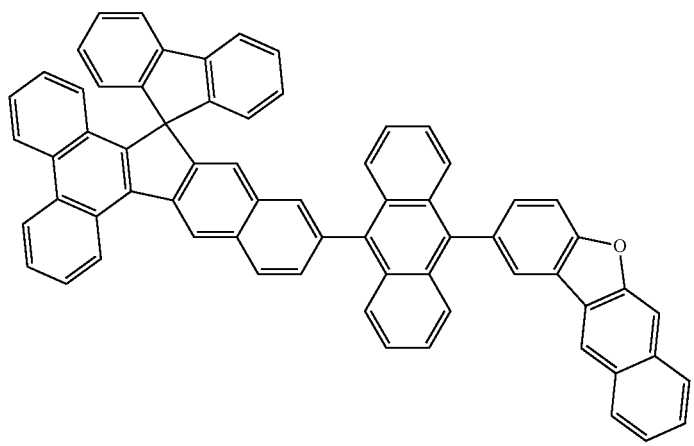
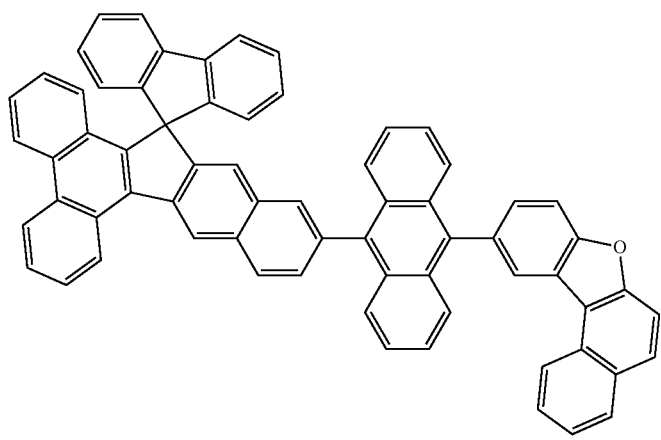
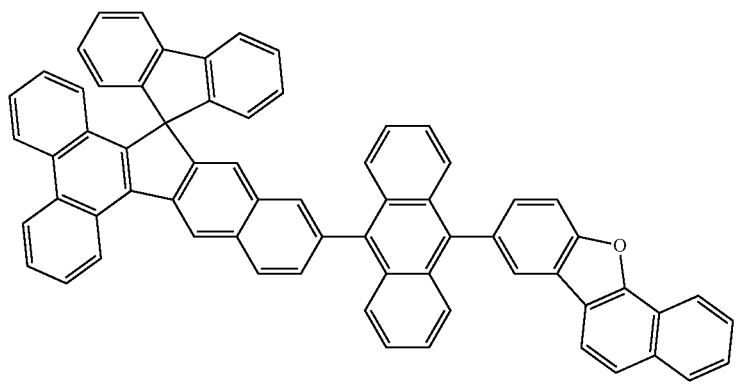
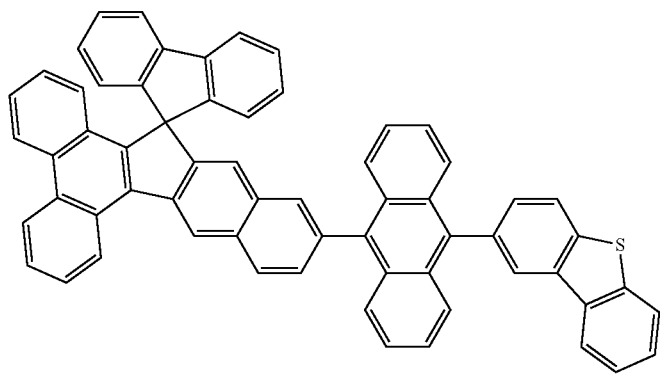

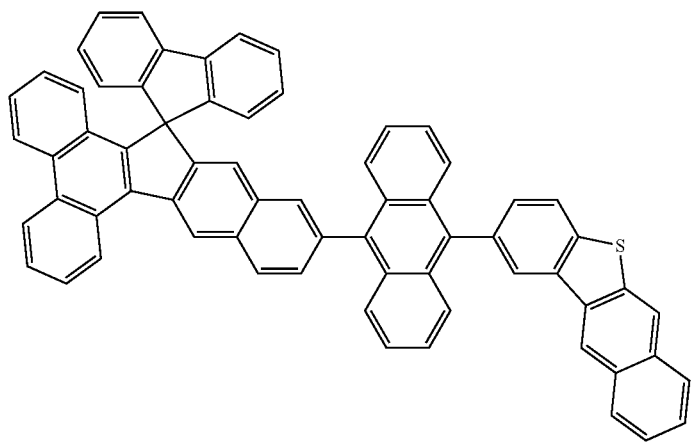
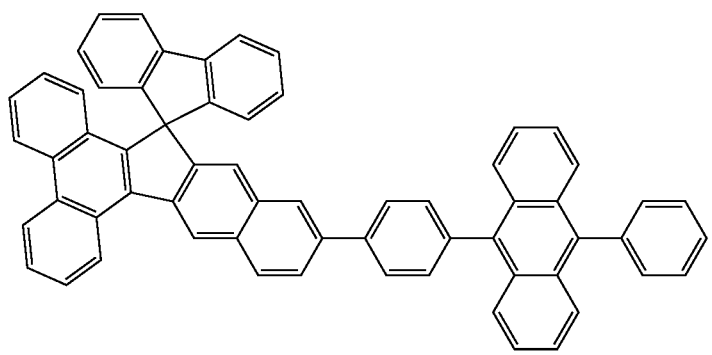
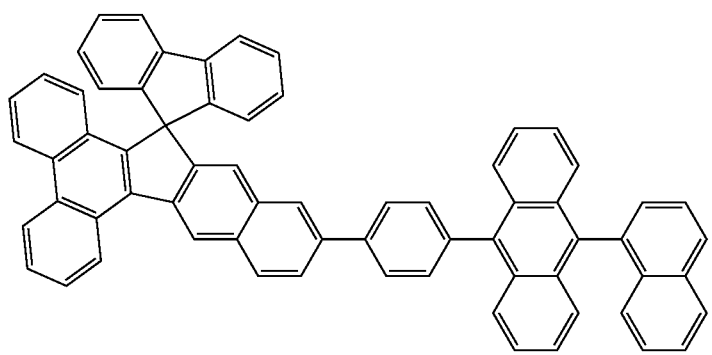
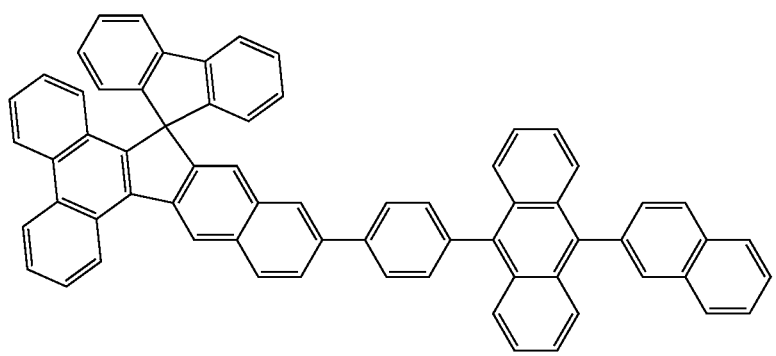

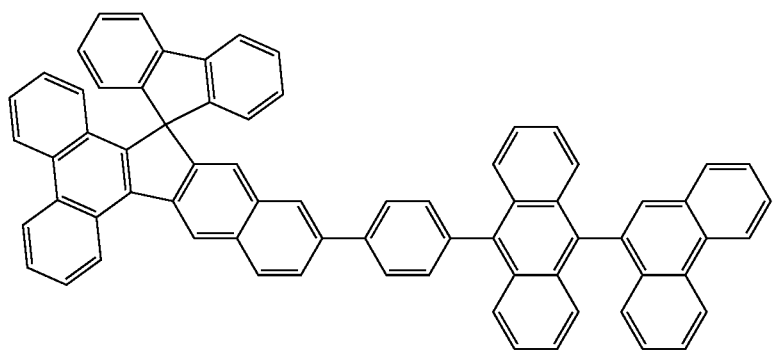

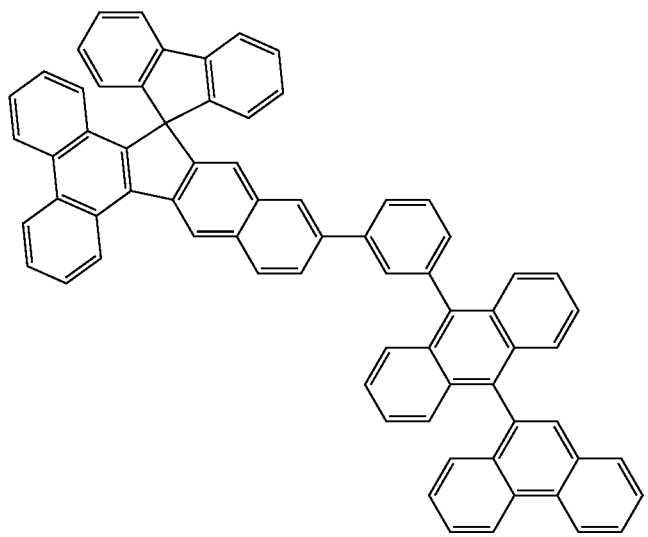

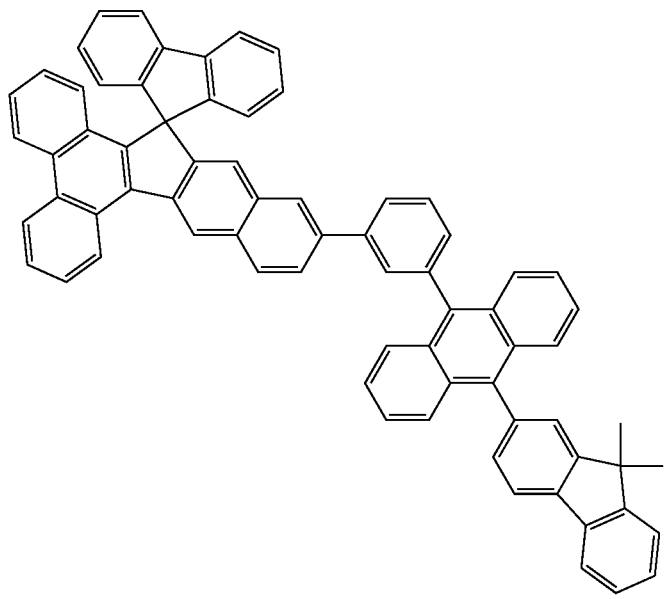
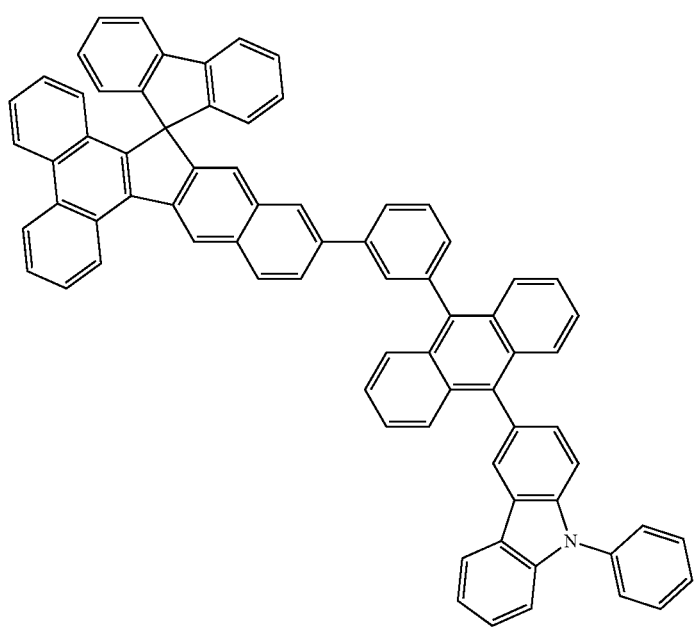

-continued
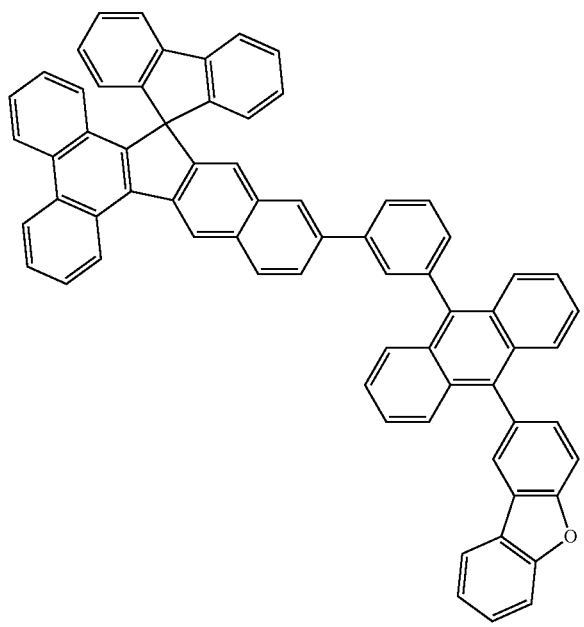
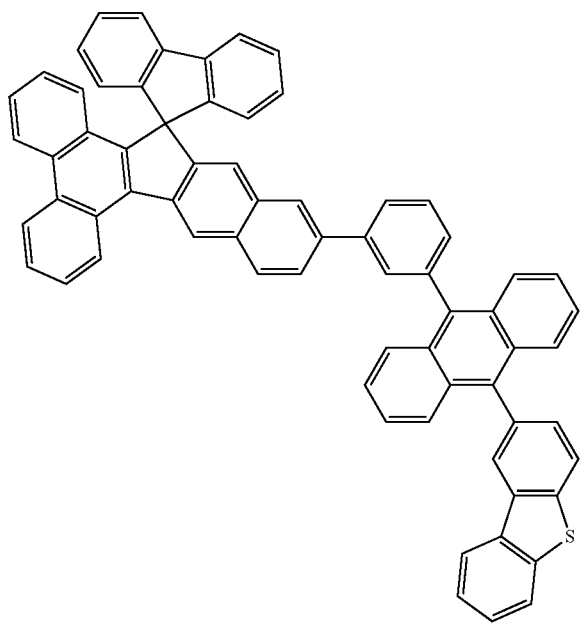
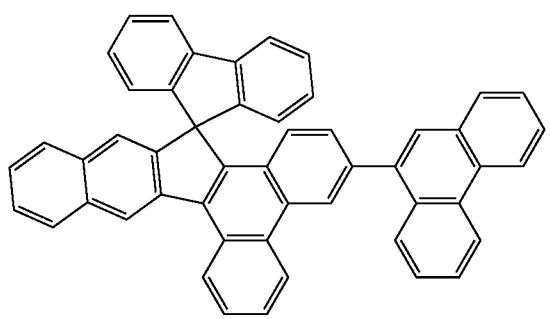
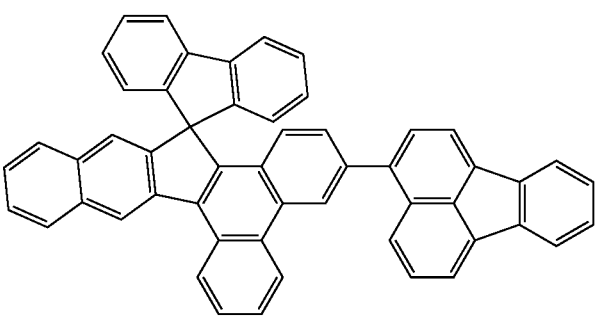
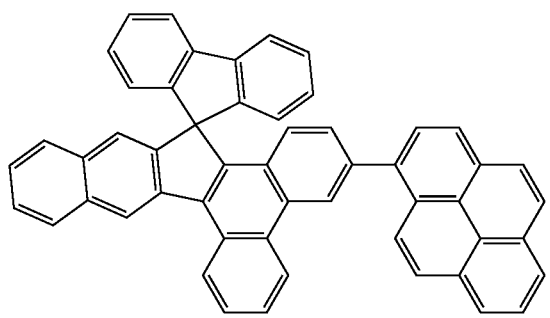
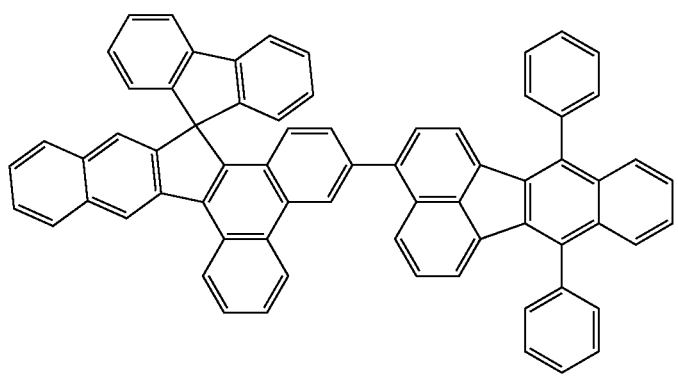

-continued
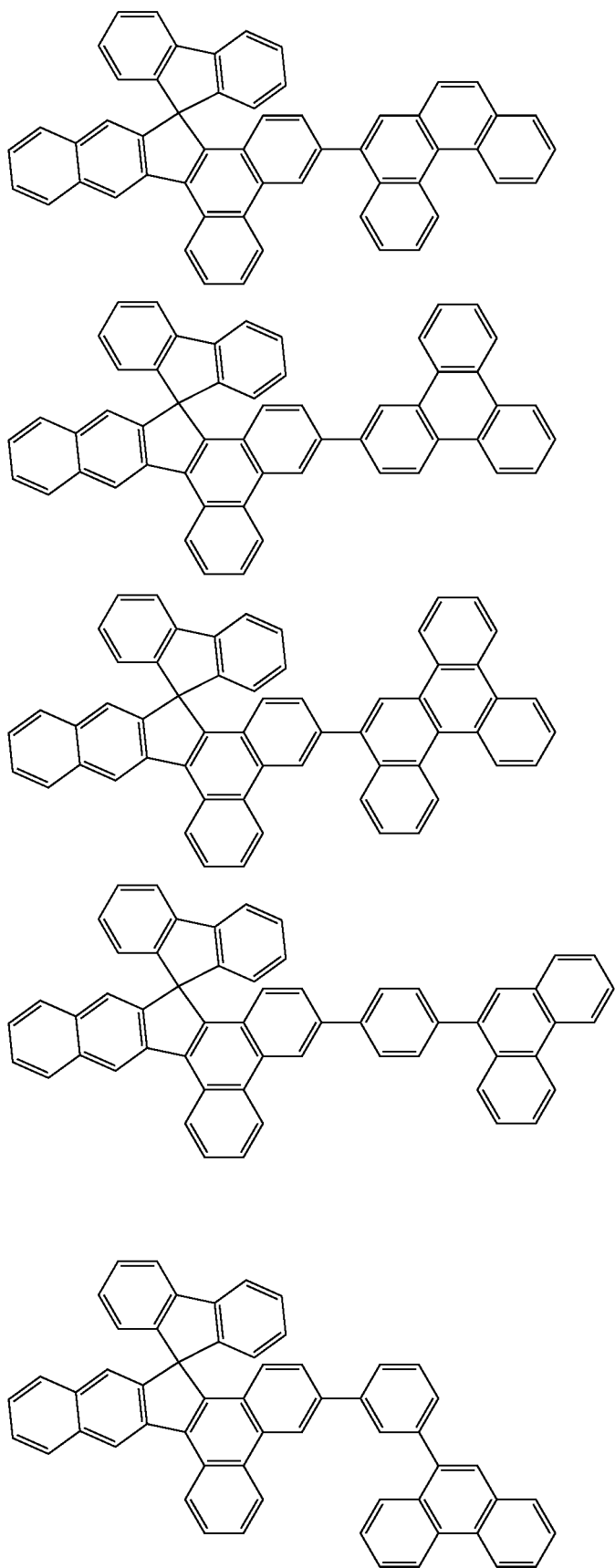

-continued
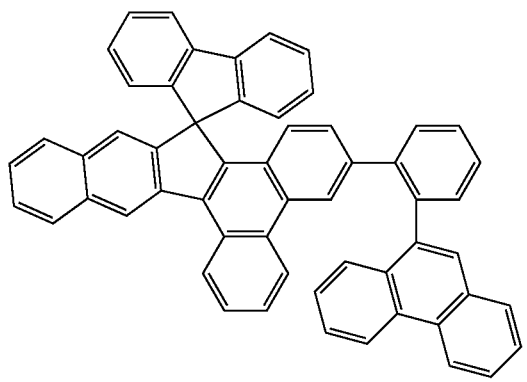
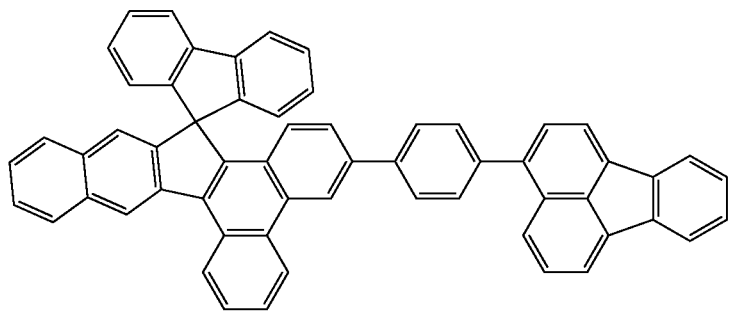
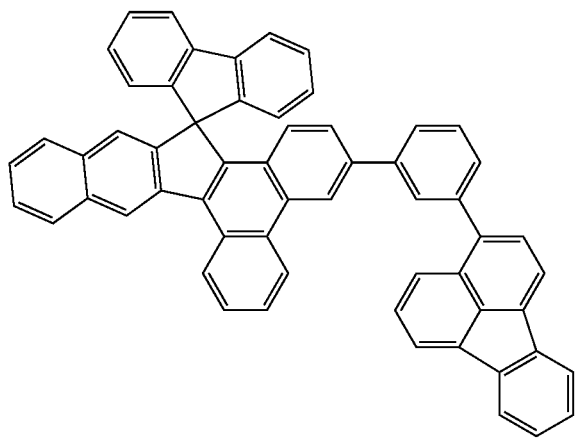
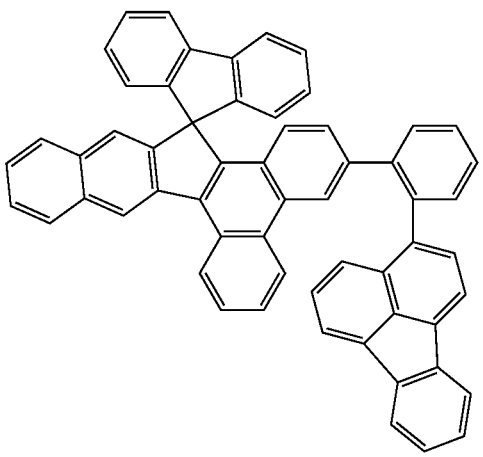
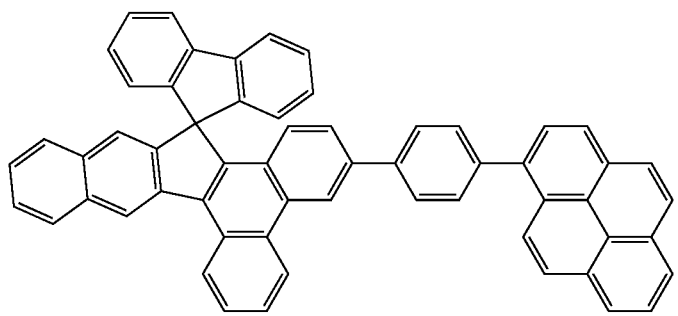

-continued
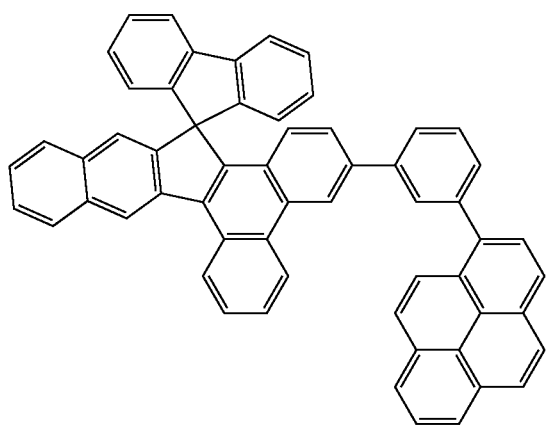
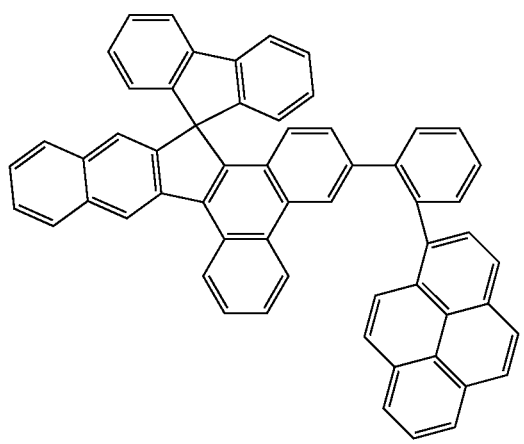
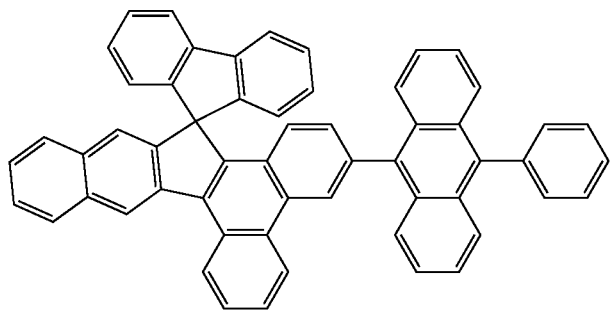
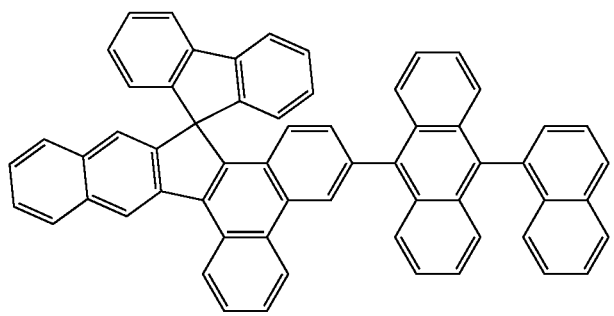
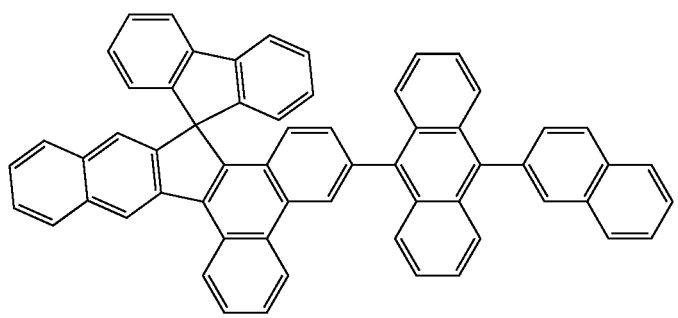
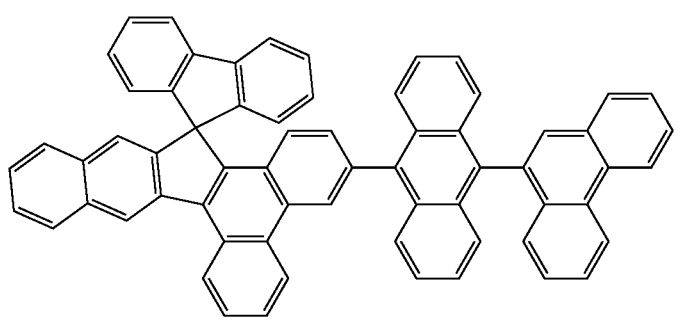

-continued
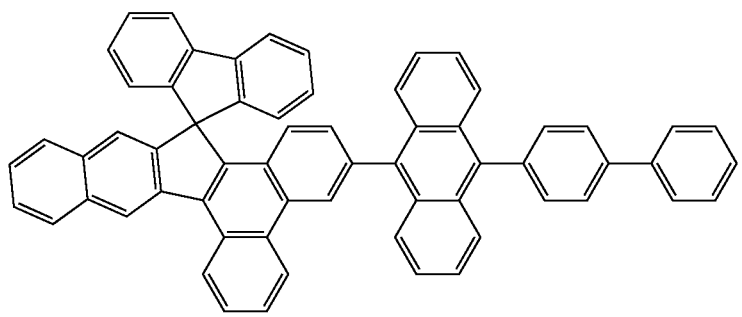
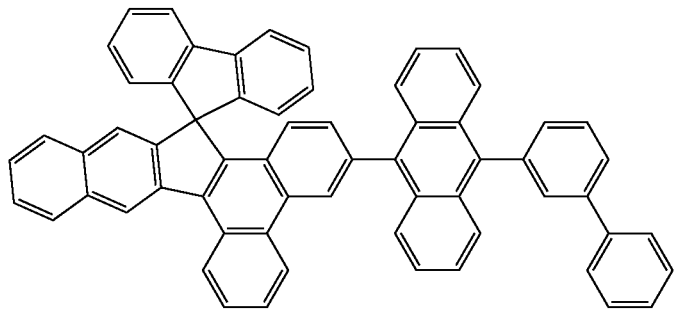
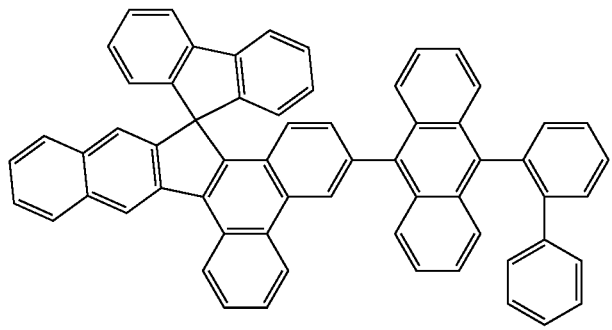
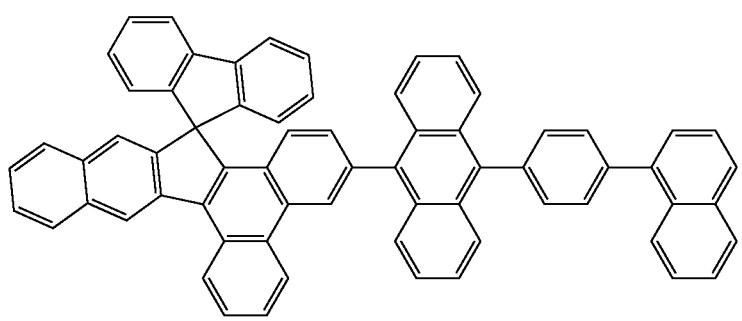
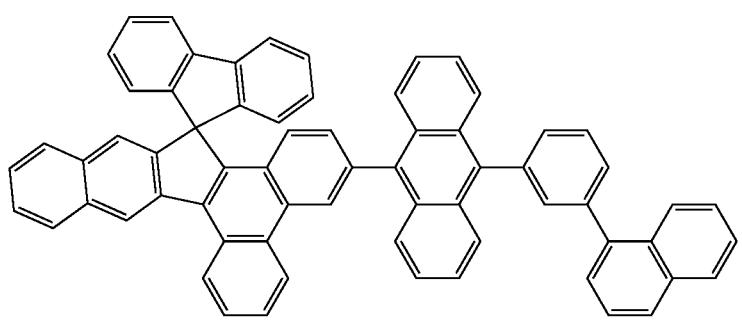

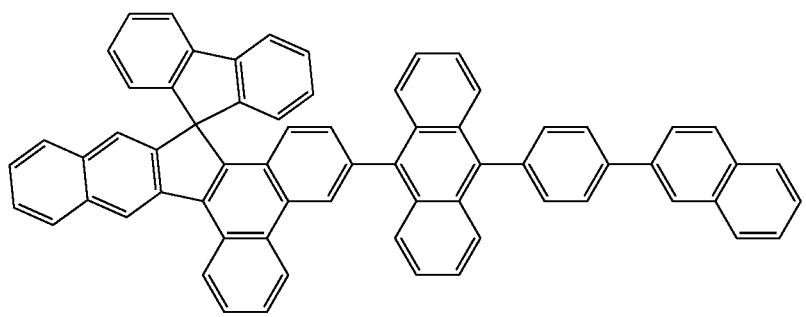
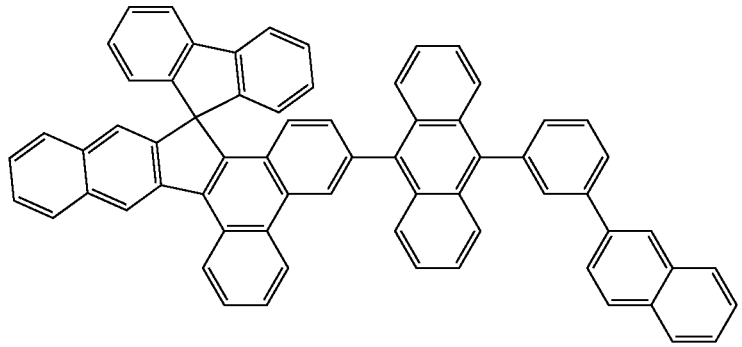
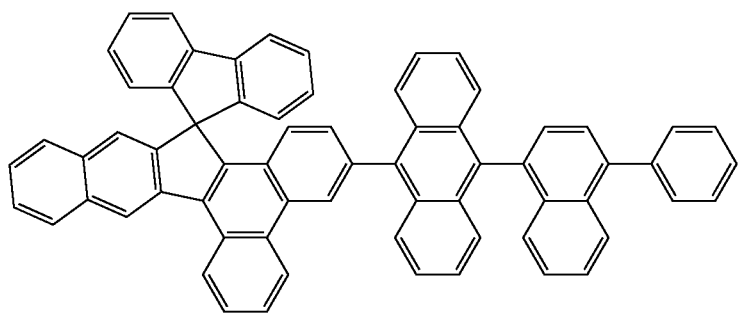
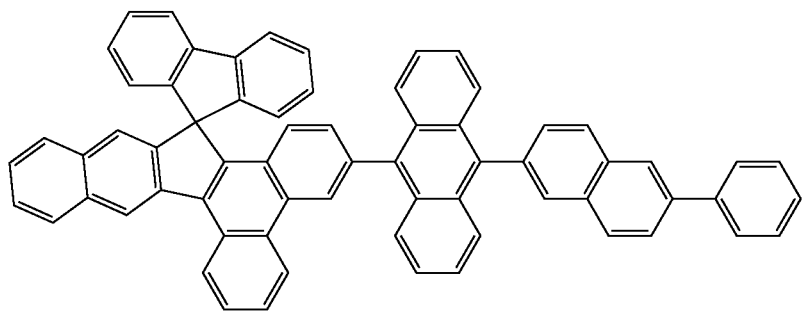
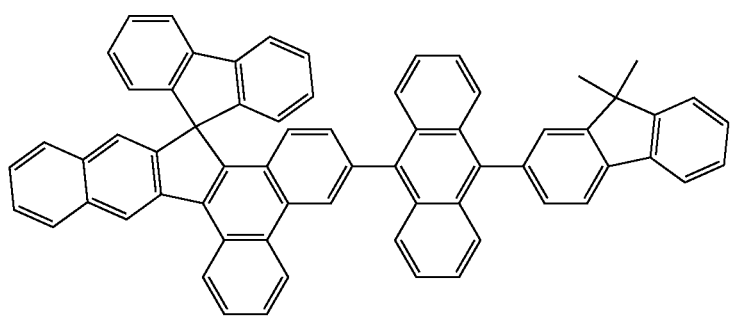

-continued
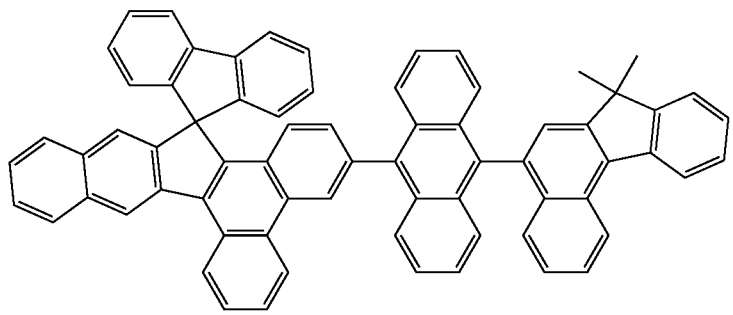
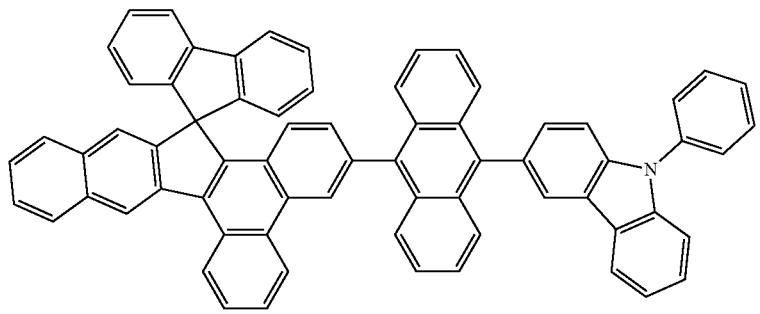
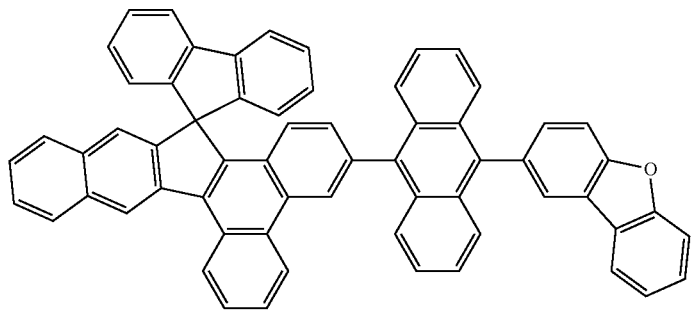
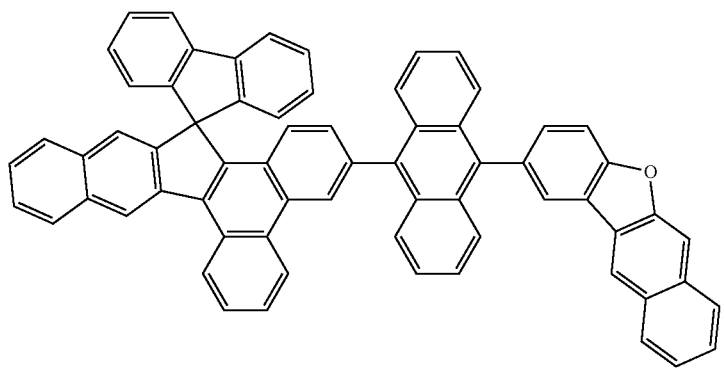
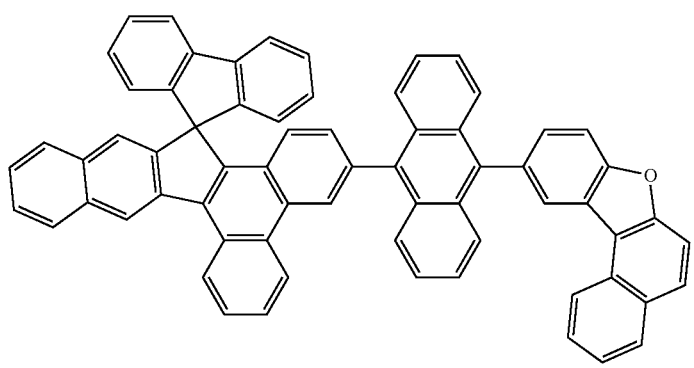

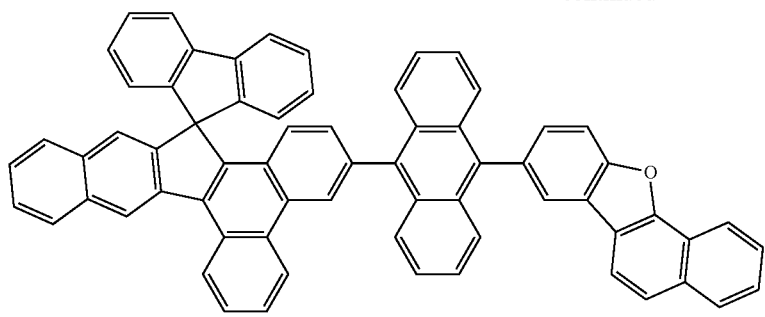
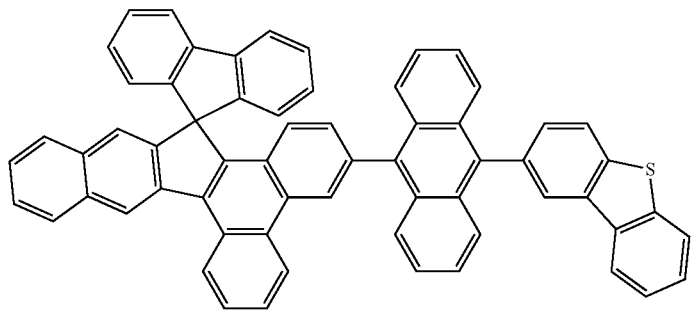
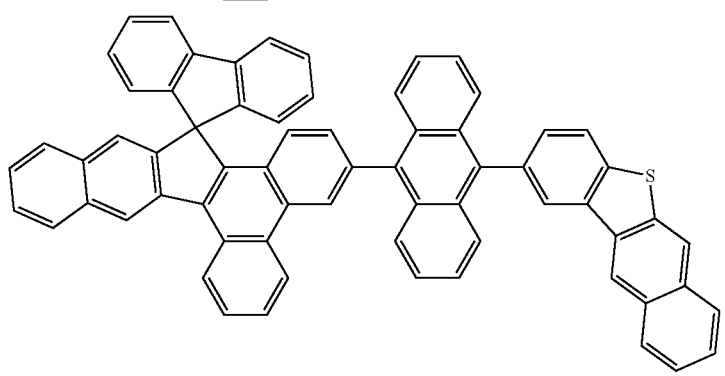
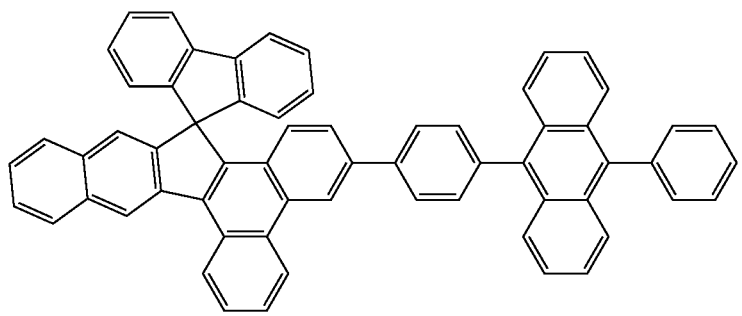
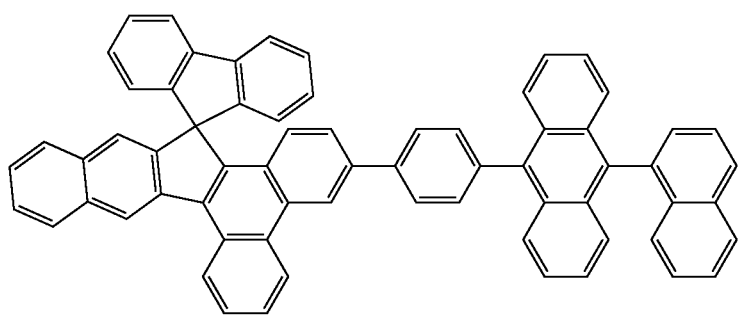

-continued
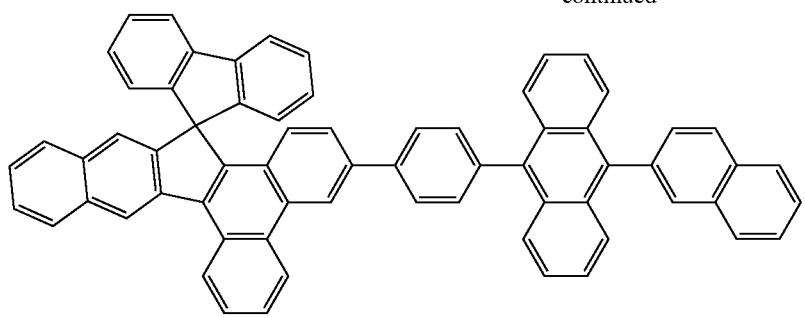
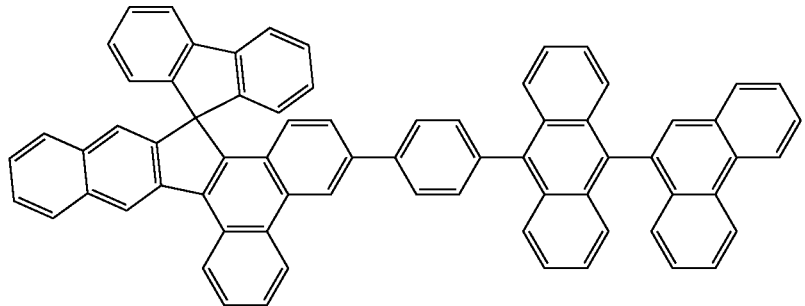
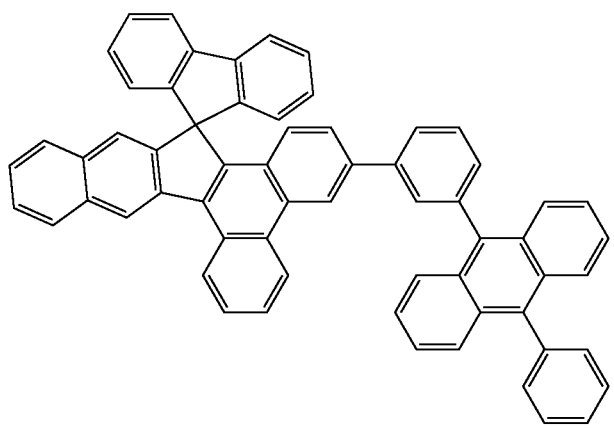
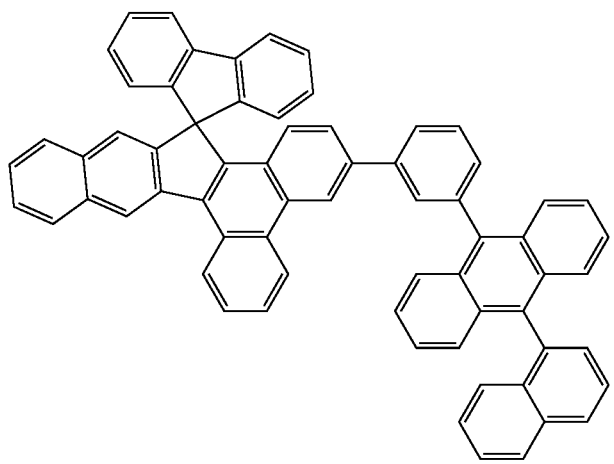

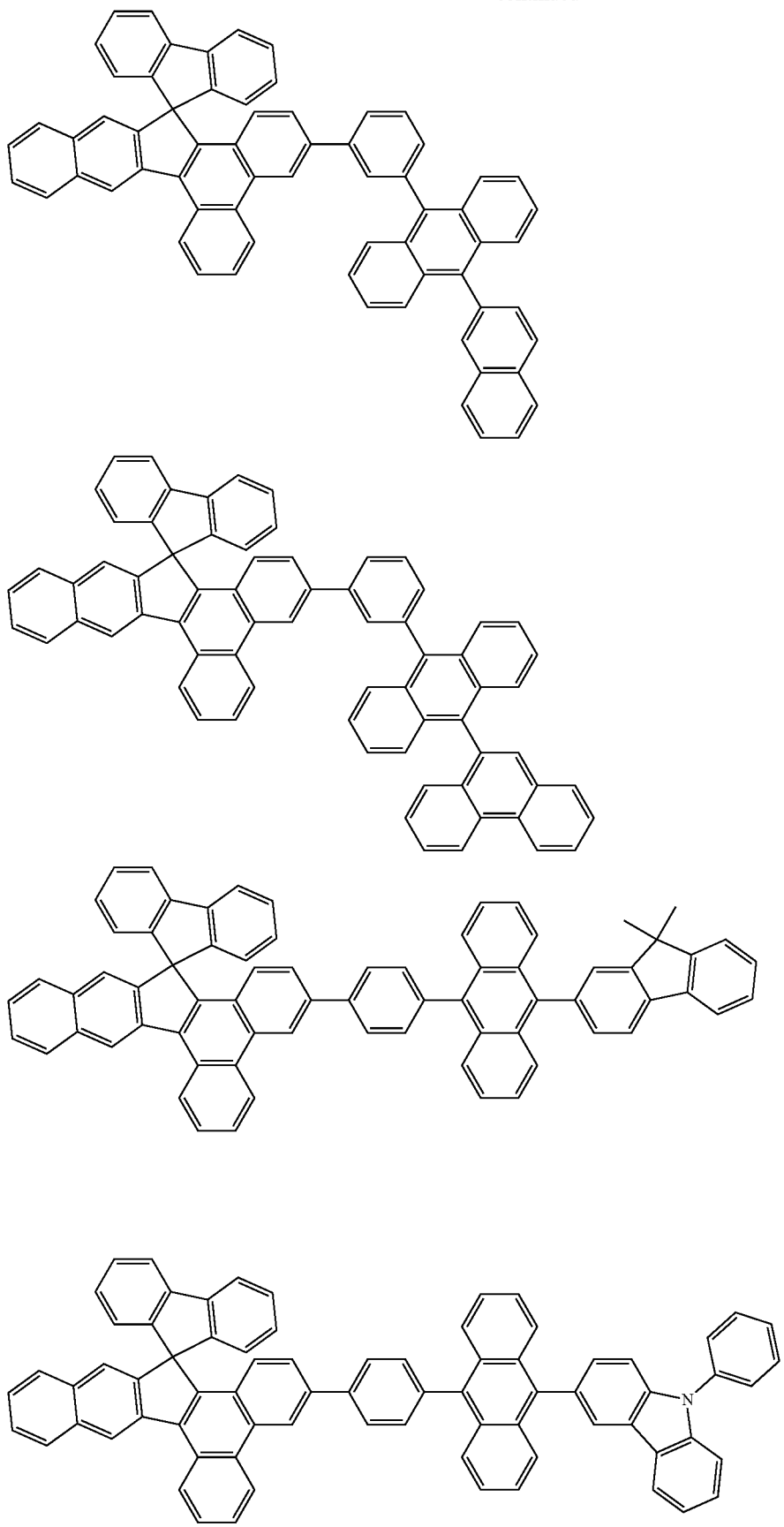

-continued
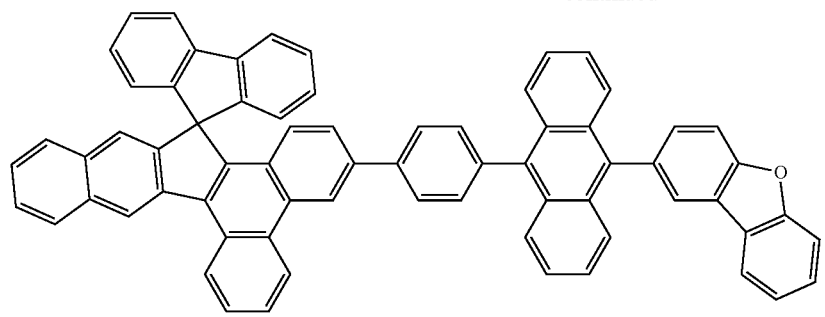
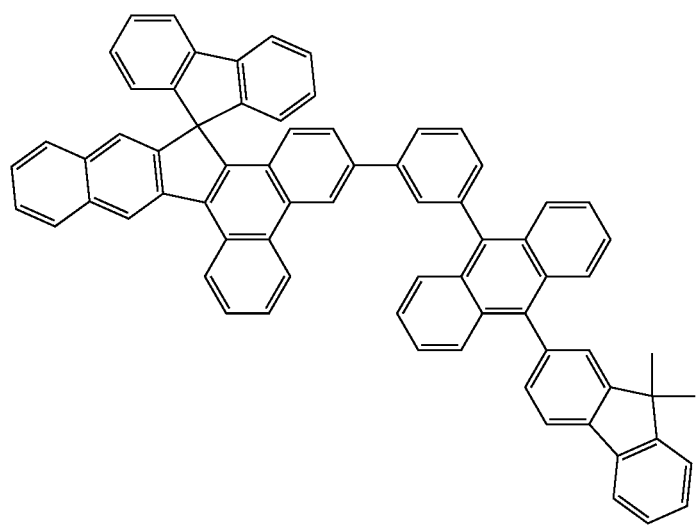
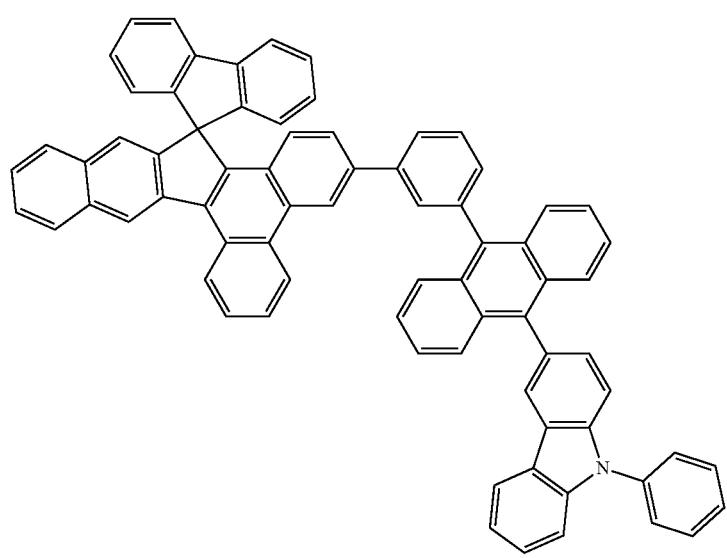

101
102
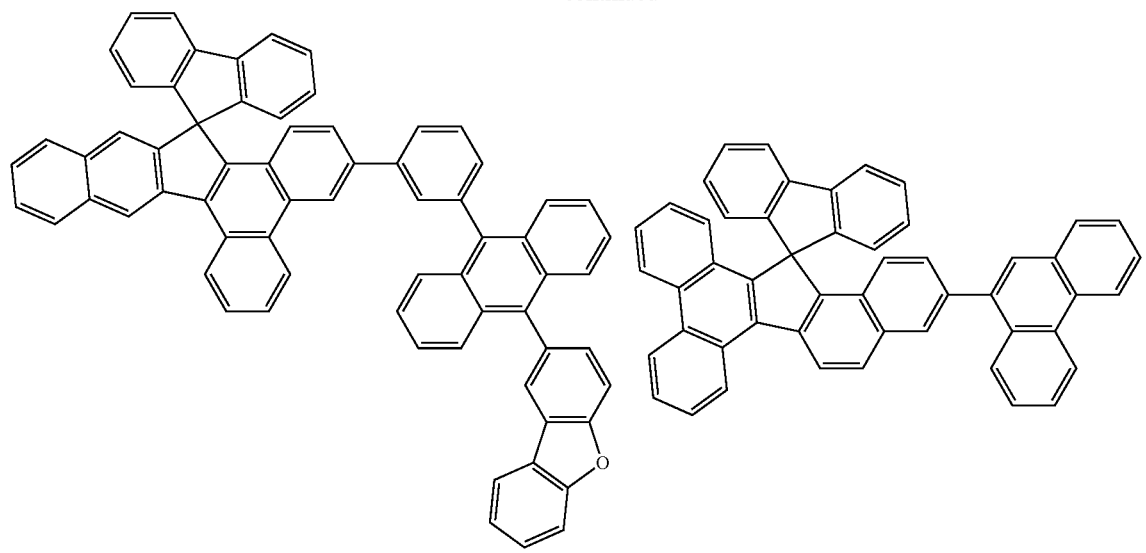
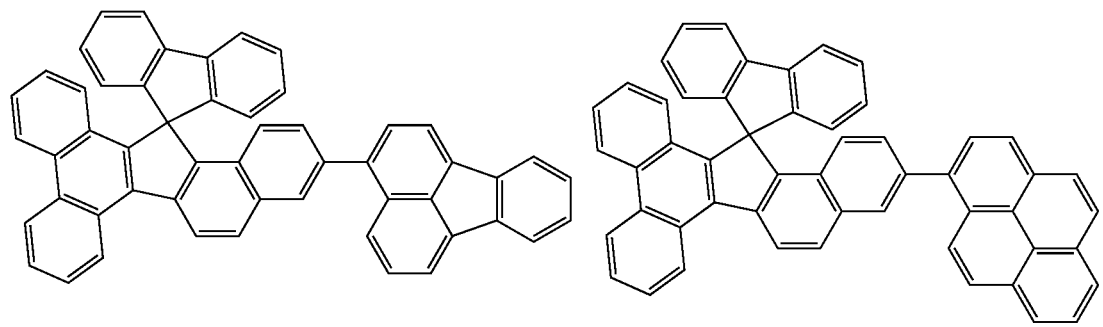
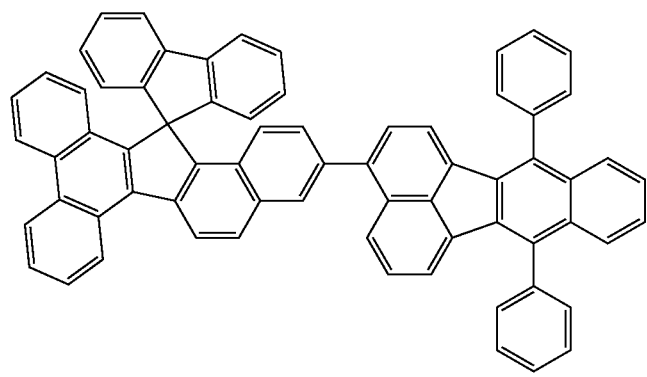
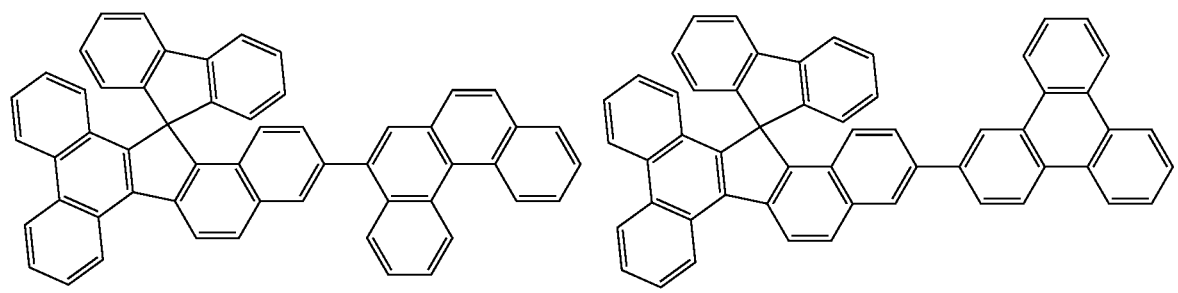

-continued
103
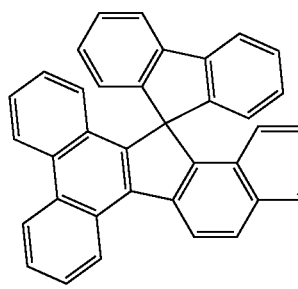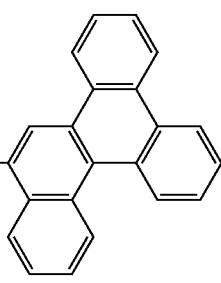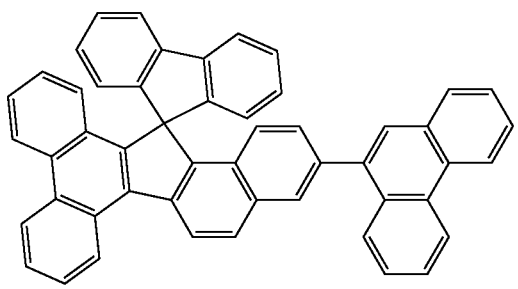
104
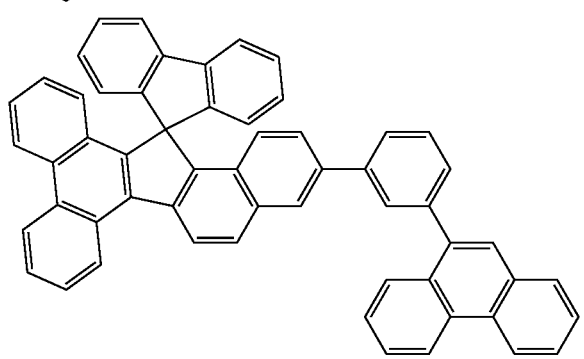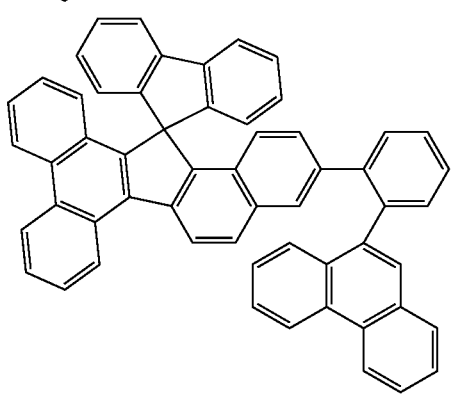
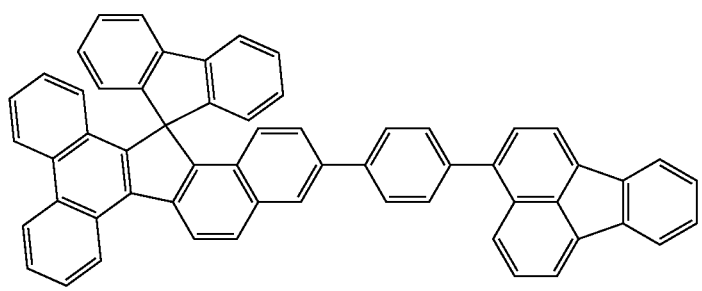
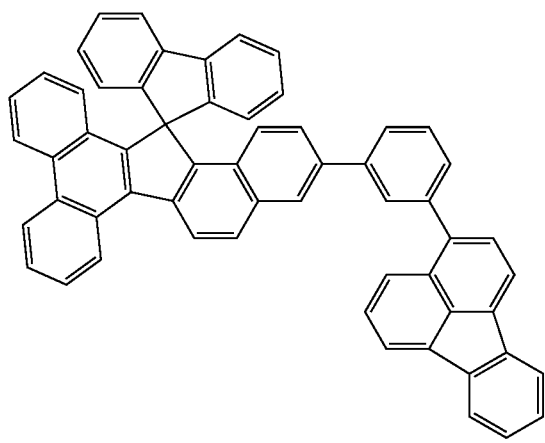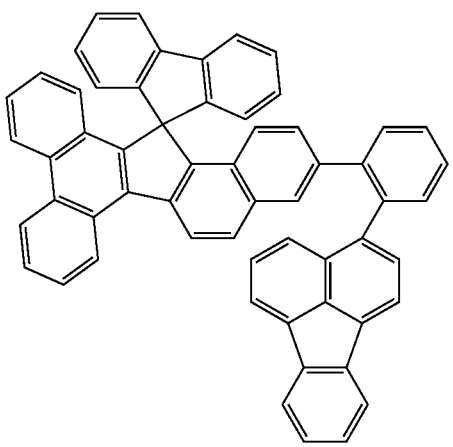

105 106
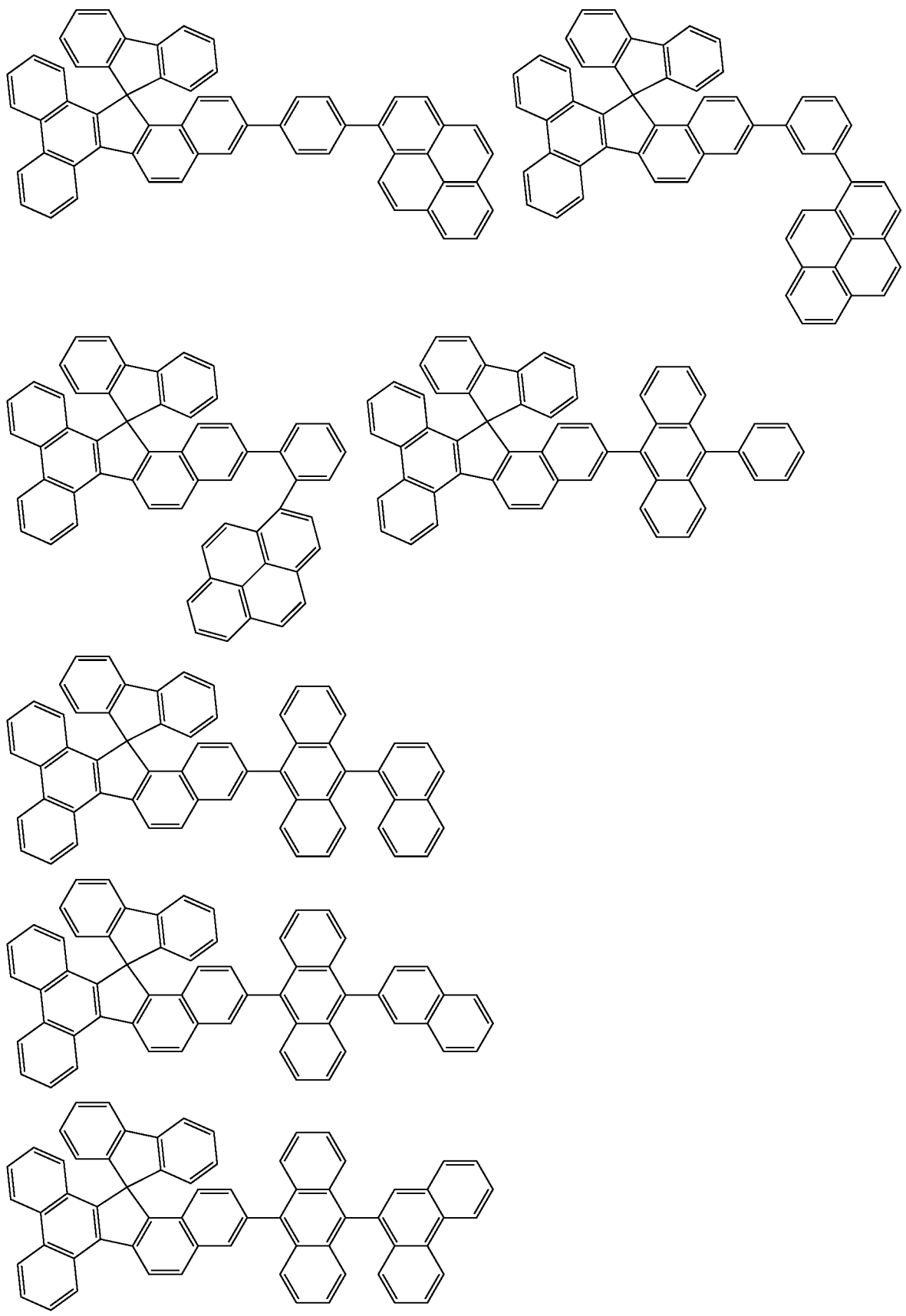

-continued
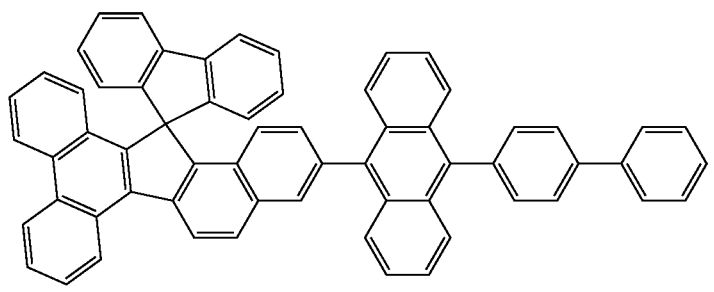

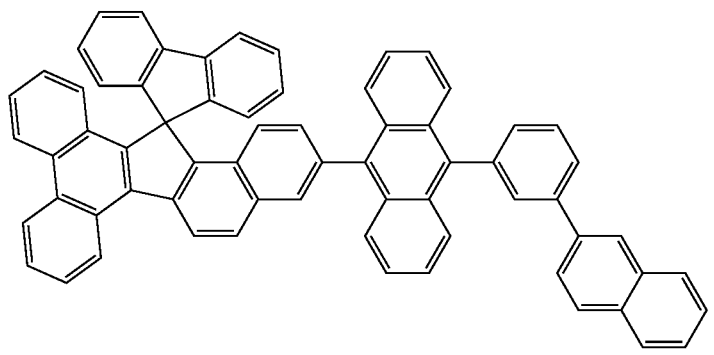
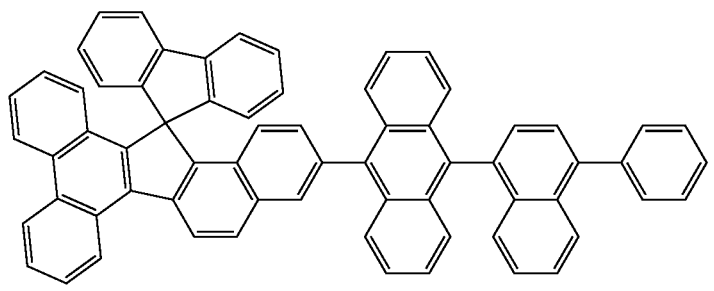
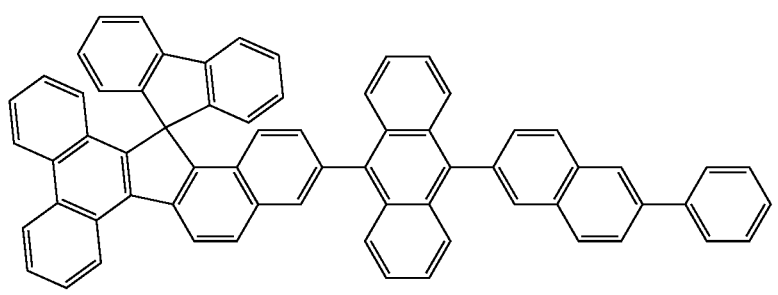

-continued
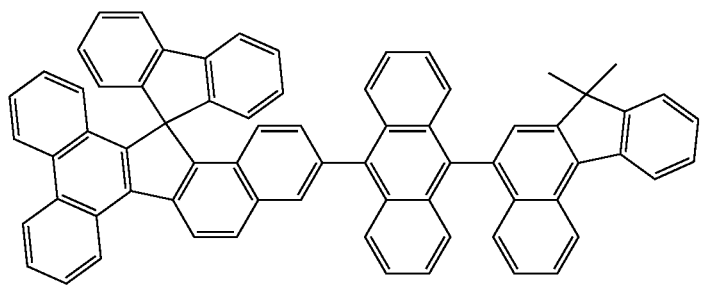
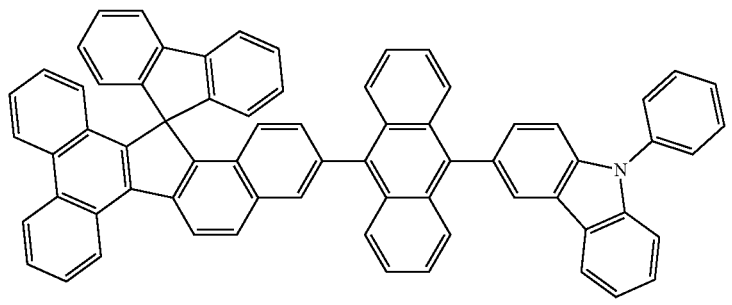
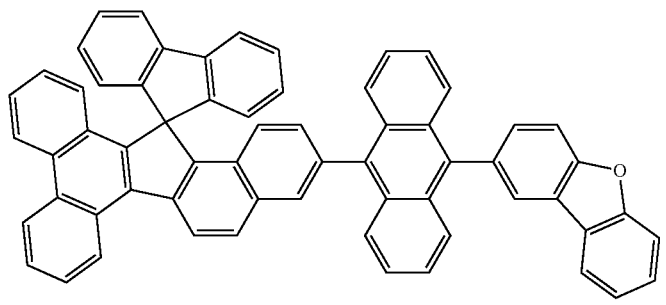
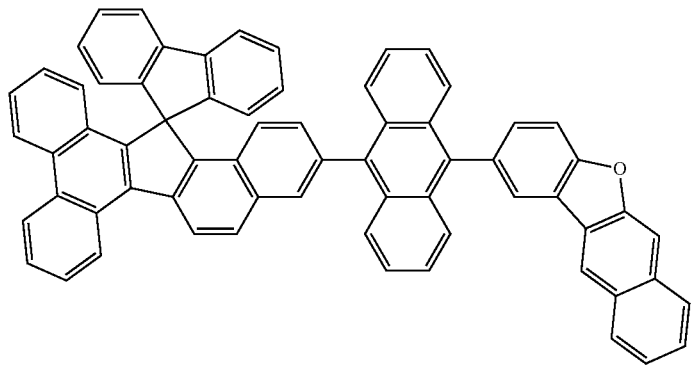

-continued
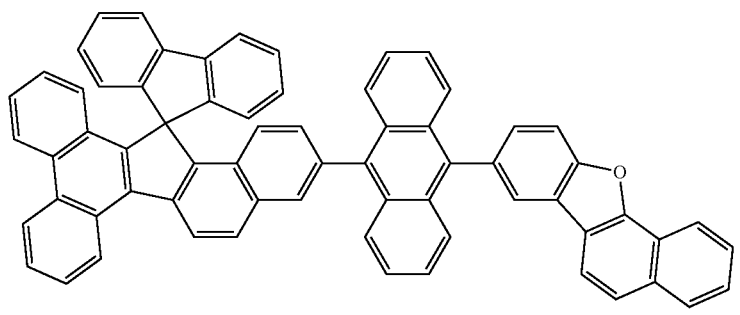
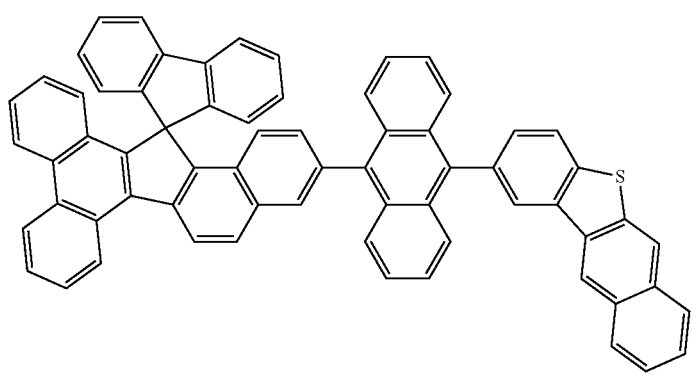
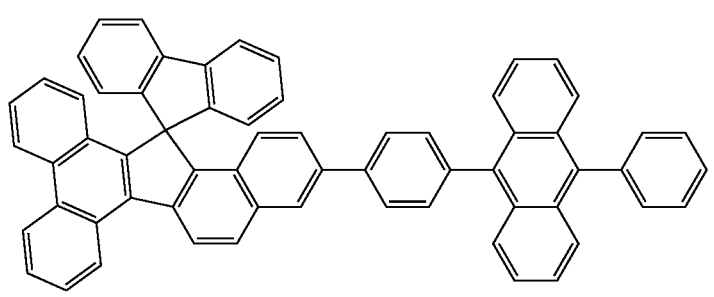
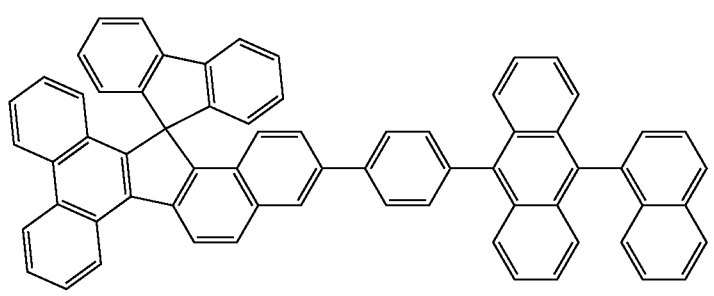

-continued
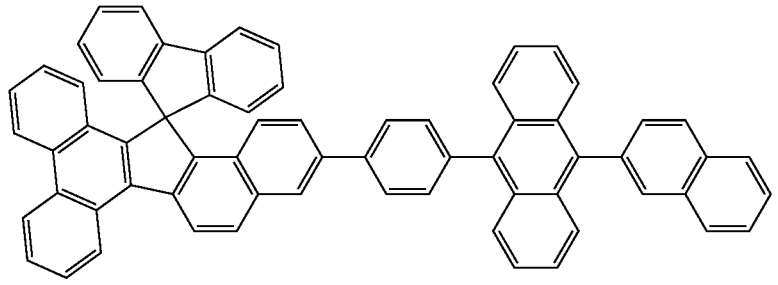

-continued
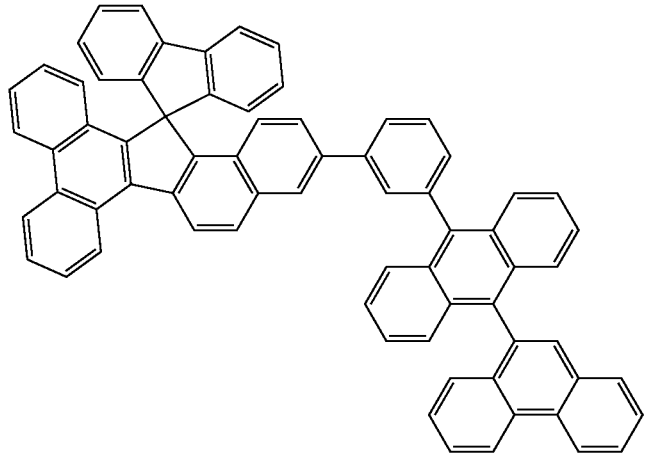
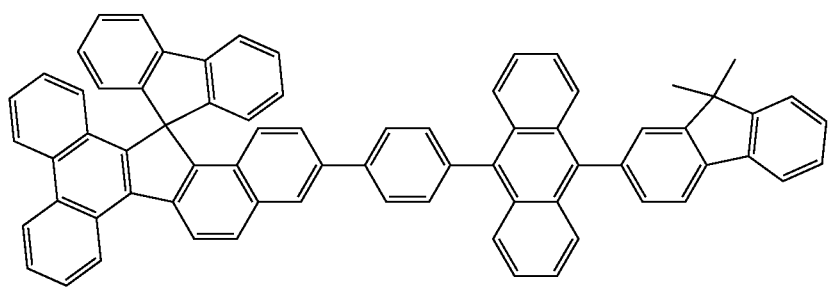
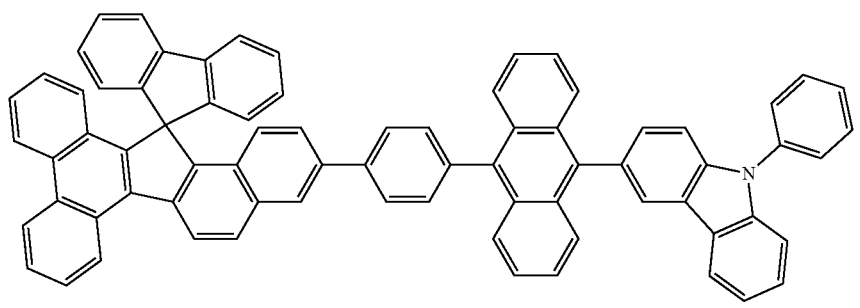
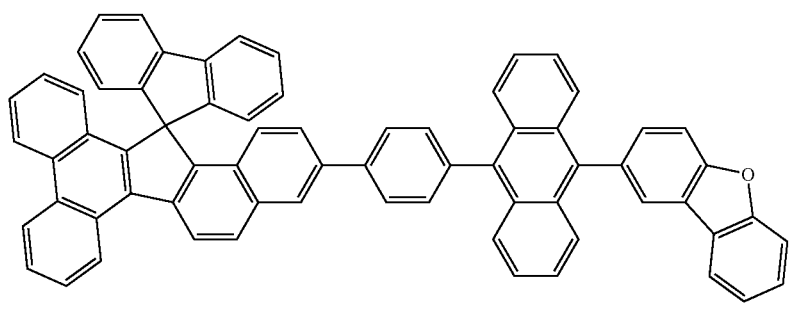

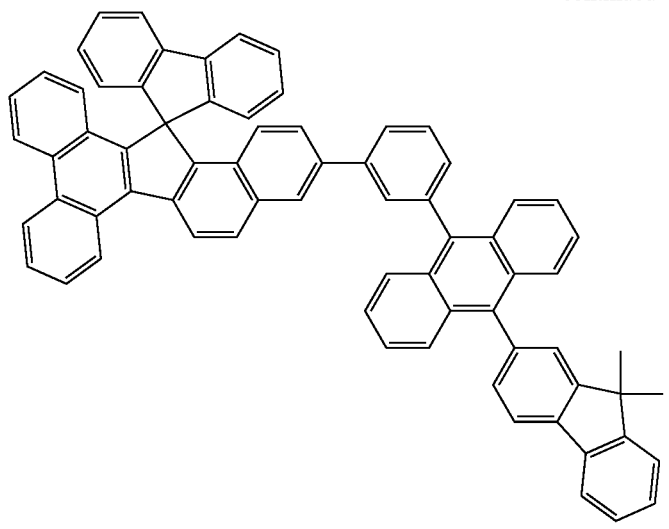
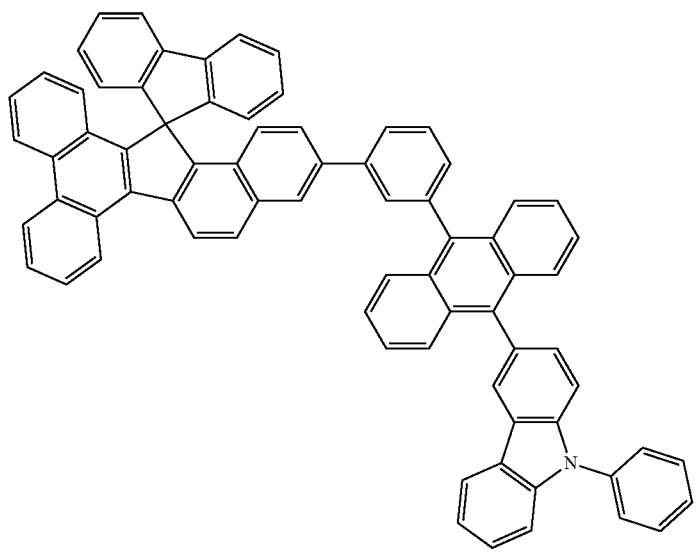
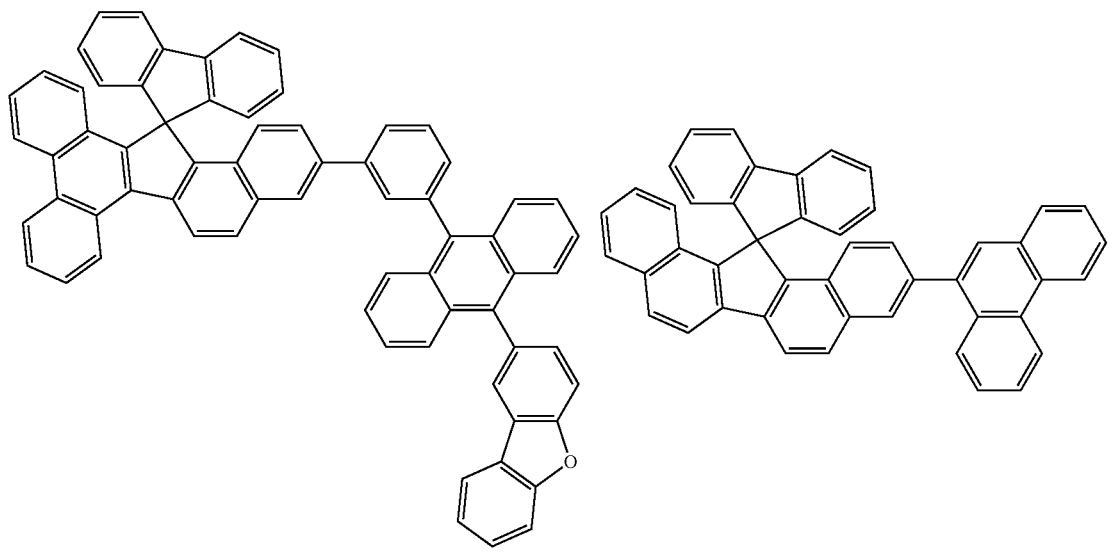

-continued
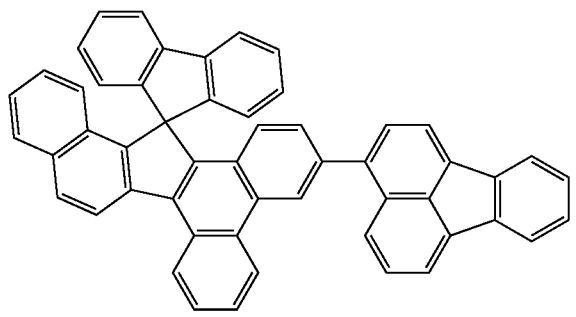
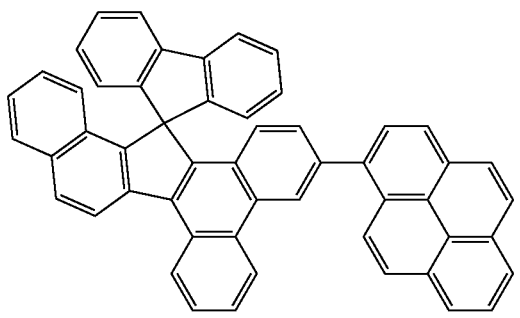
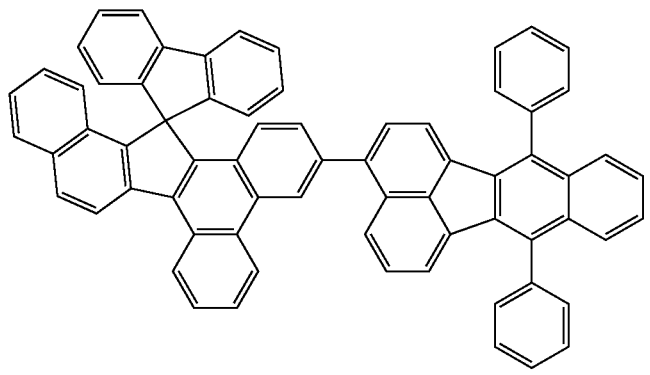
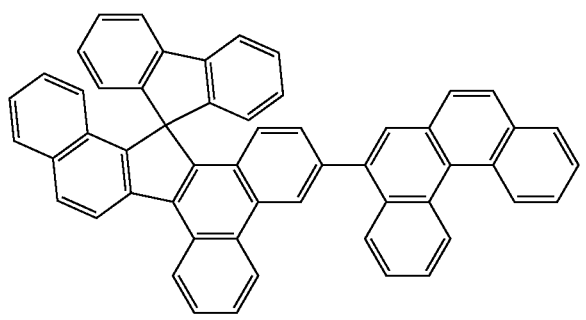
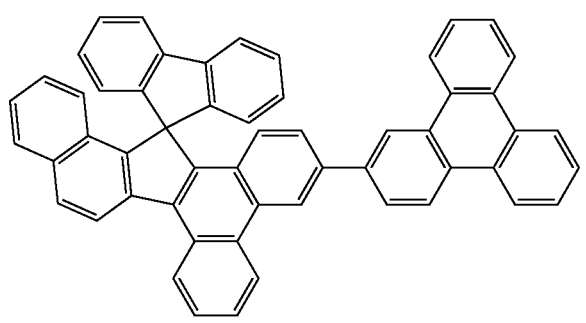
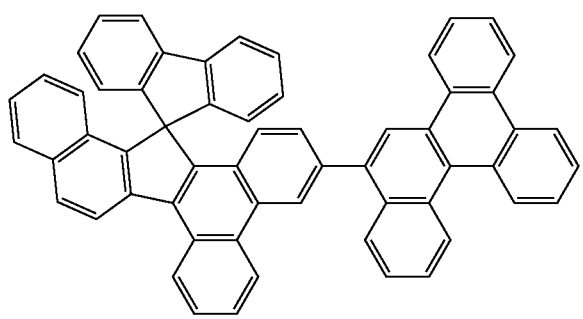
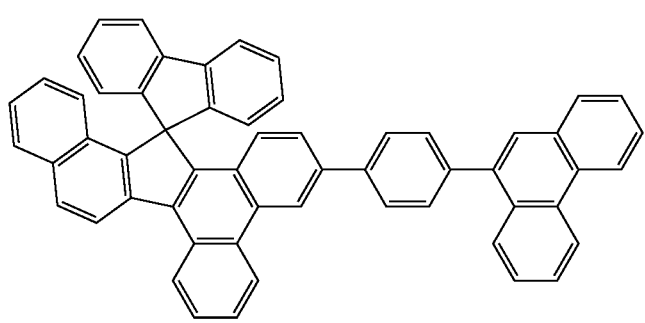

123
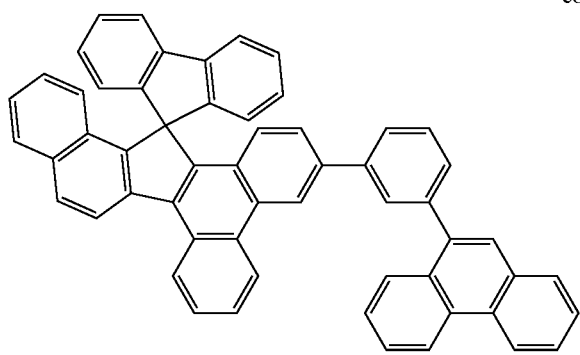
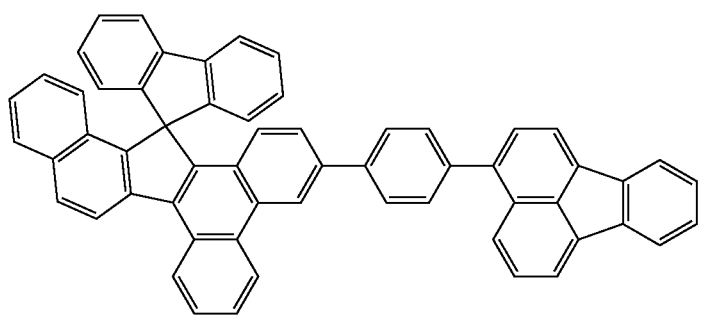
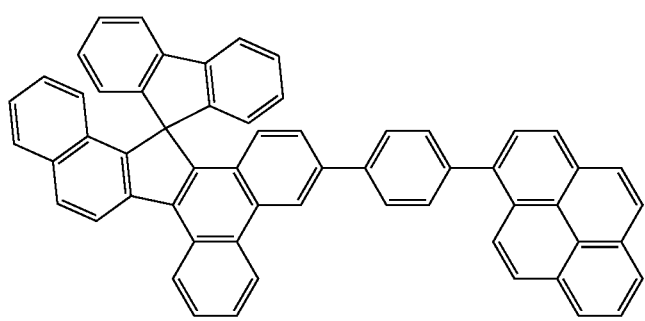
124
-continued
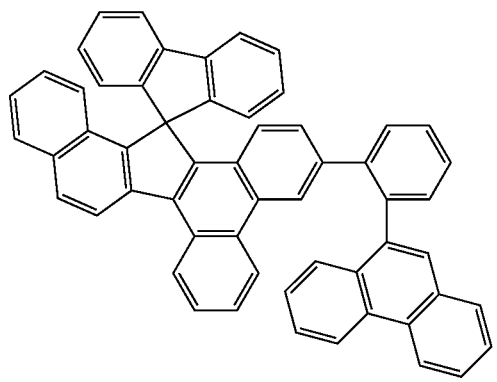
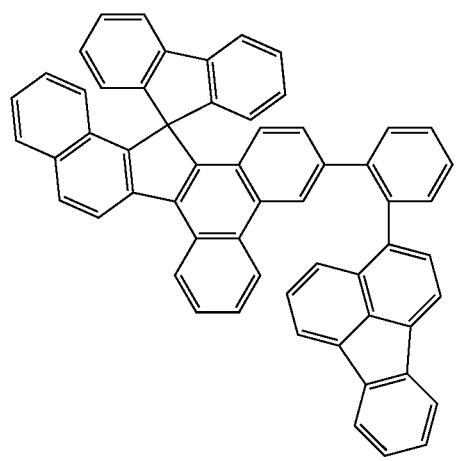
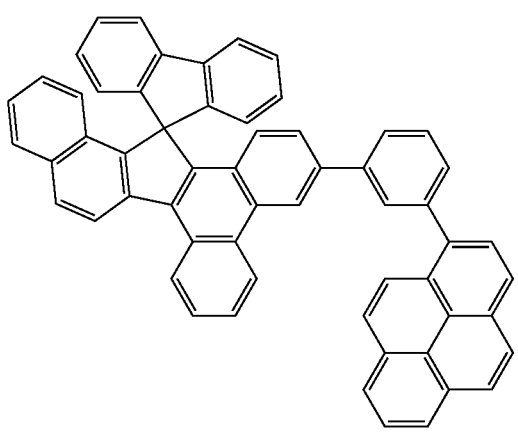

125
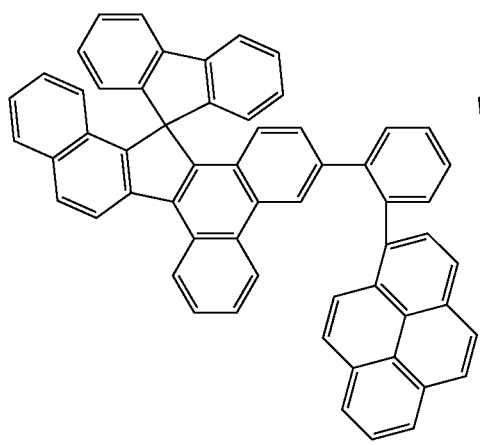
126
-continued
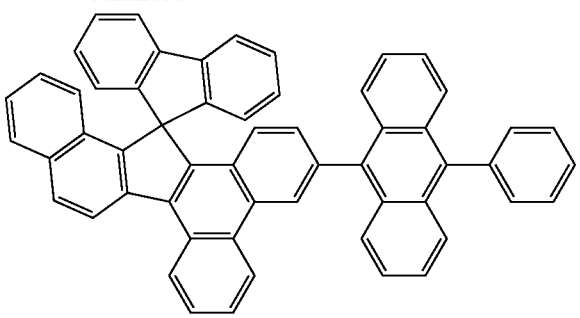
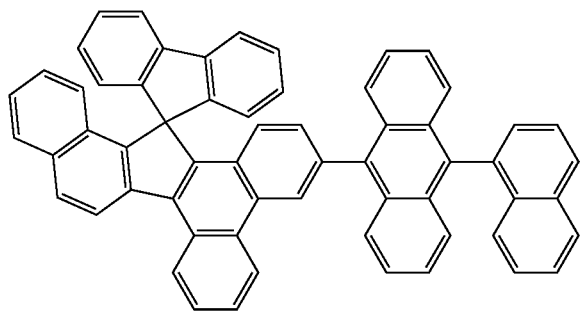
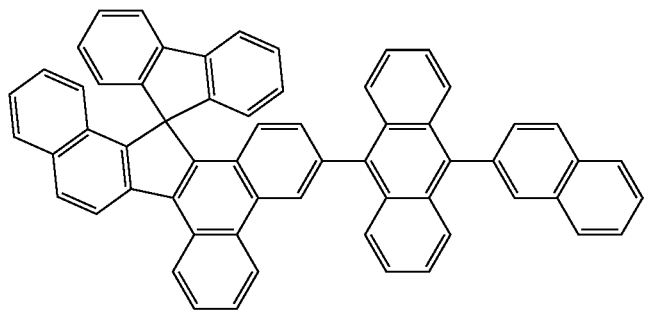
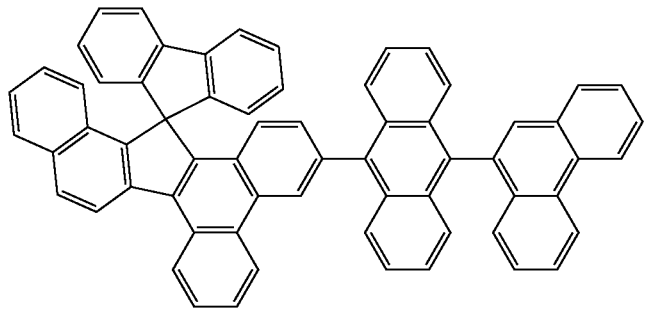
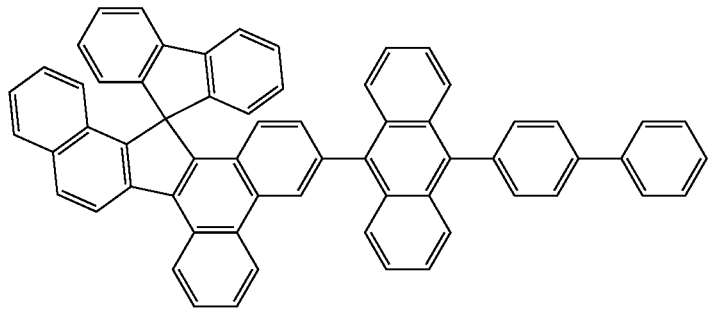

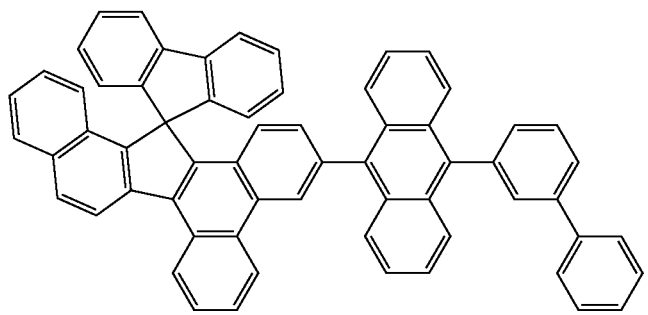
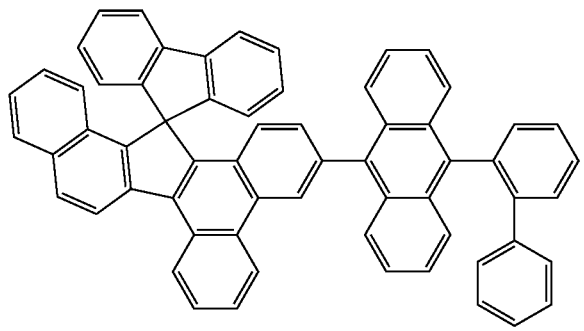
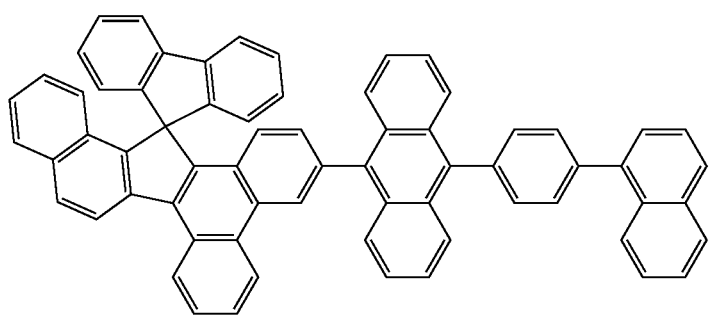
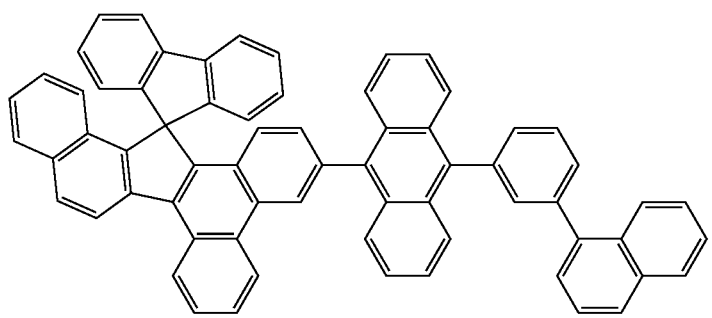
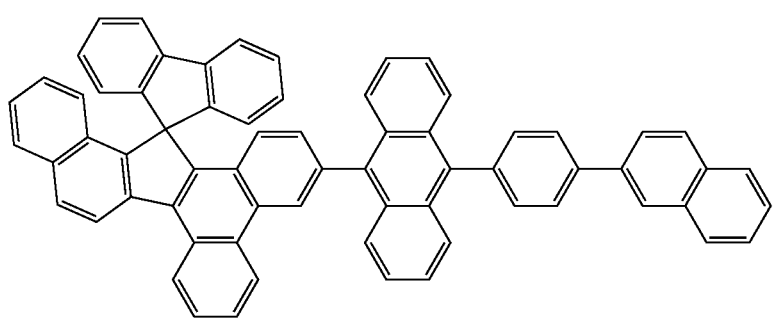

-continued
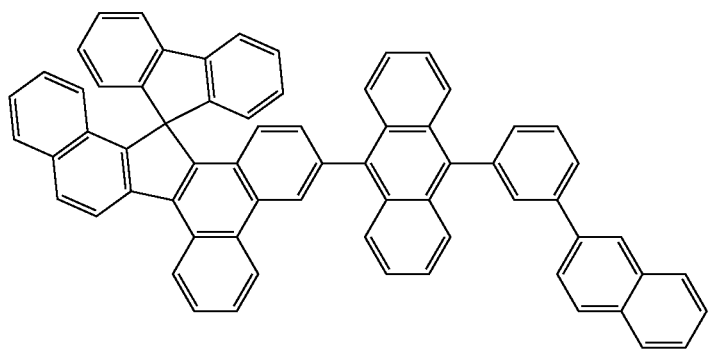
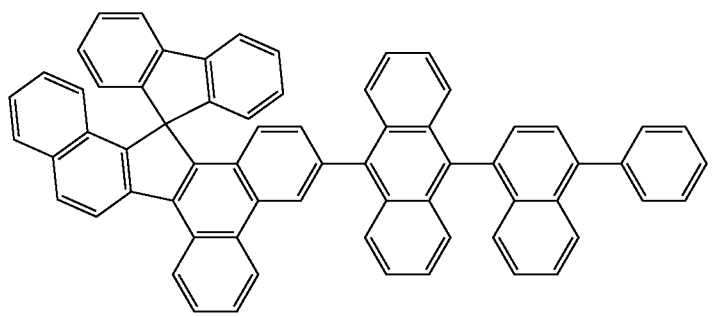
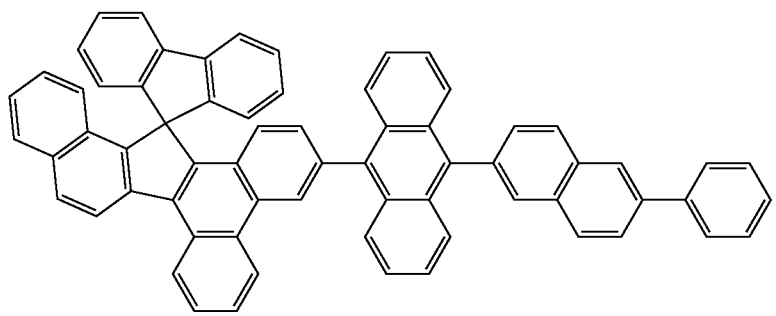
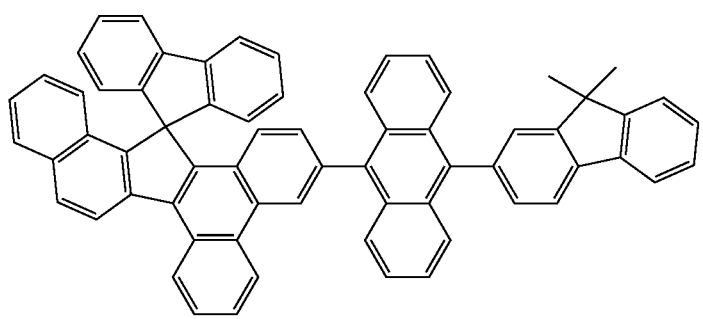
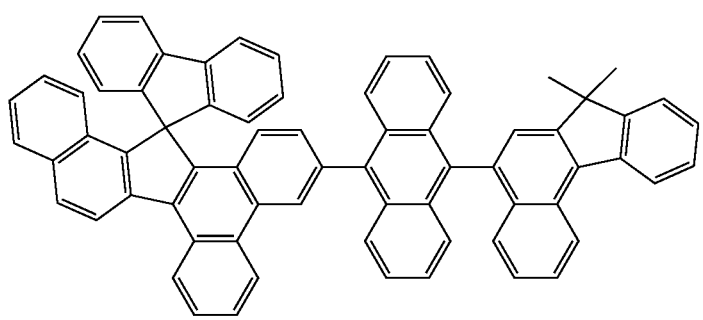

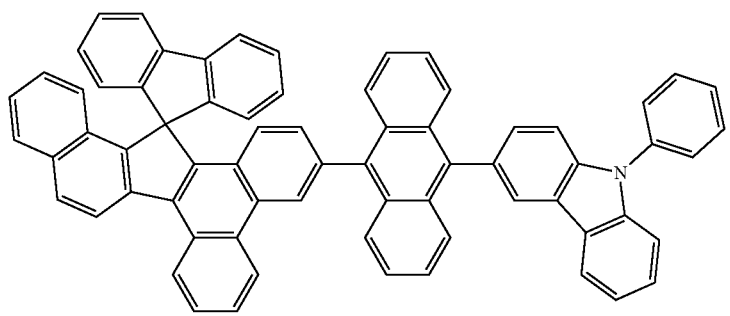
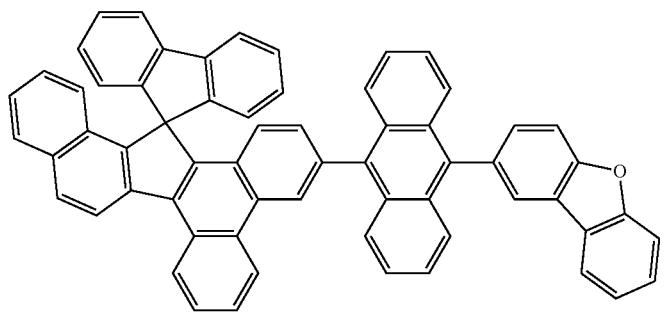
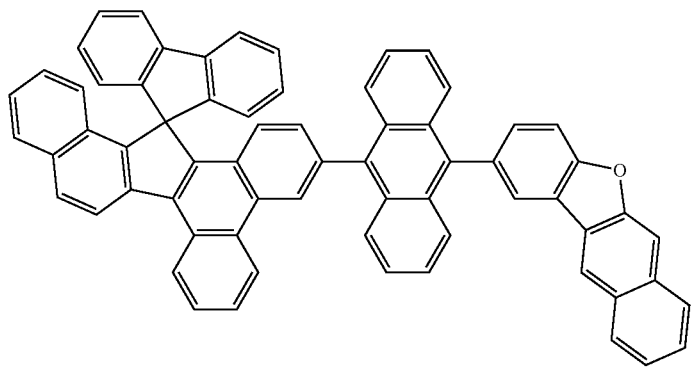
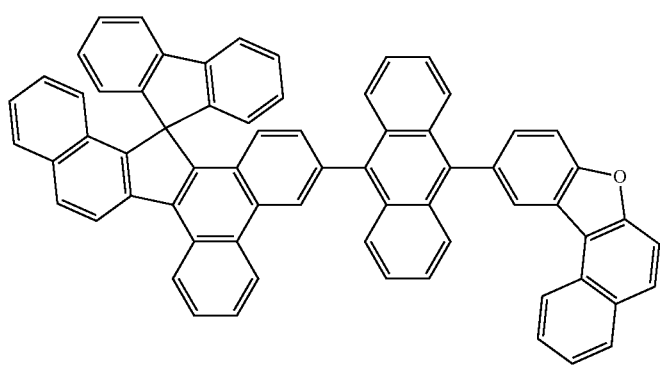
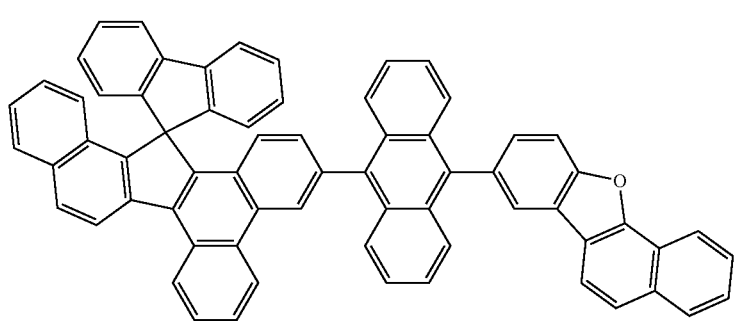

-continued
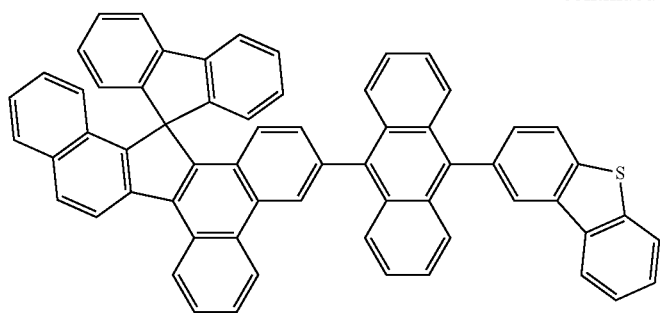
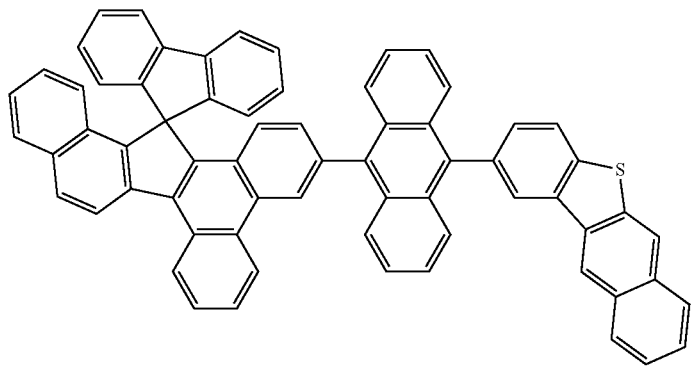
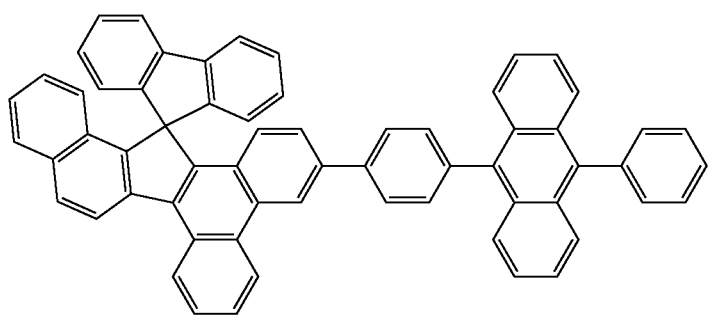
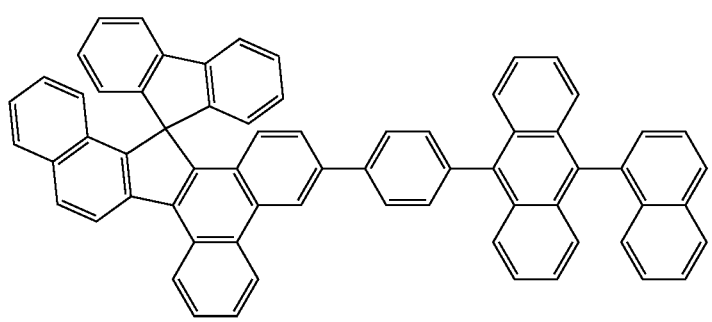
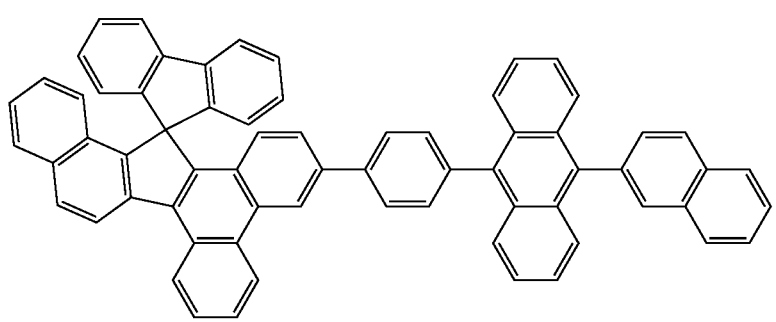

-continued
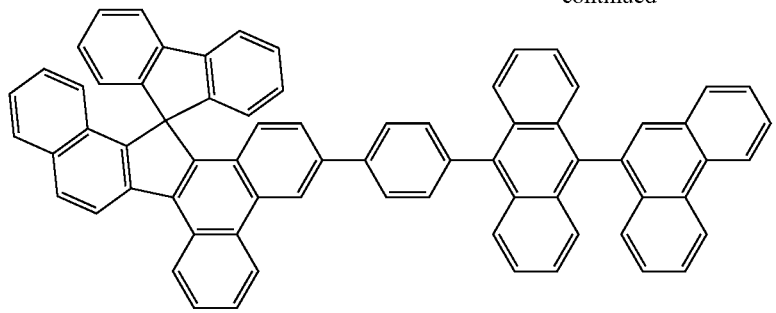

-continued
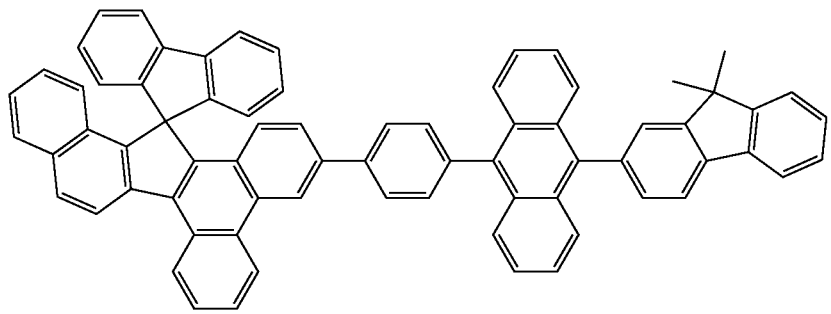

-continued
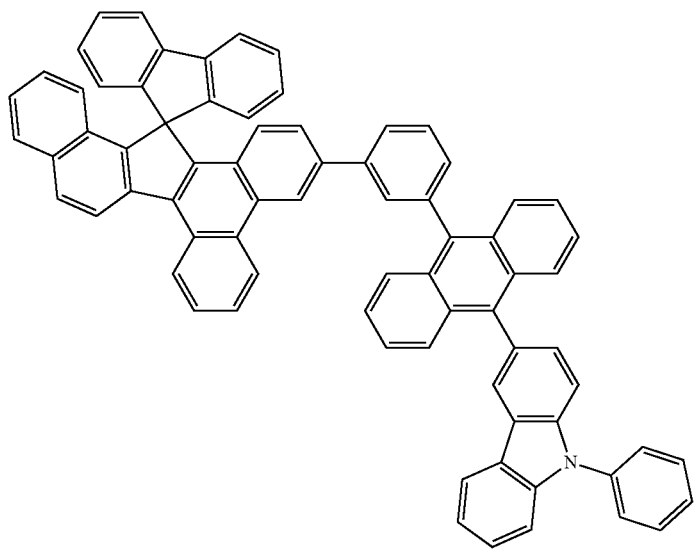
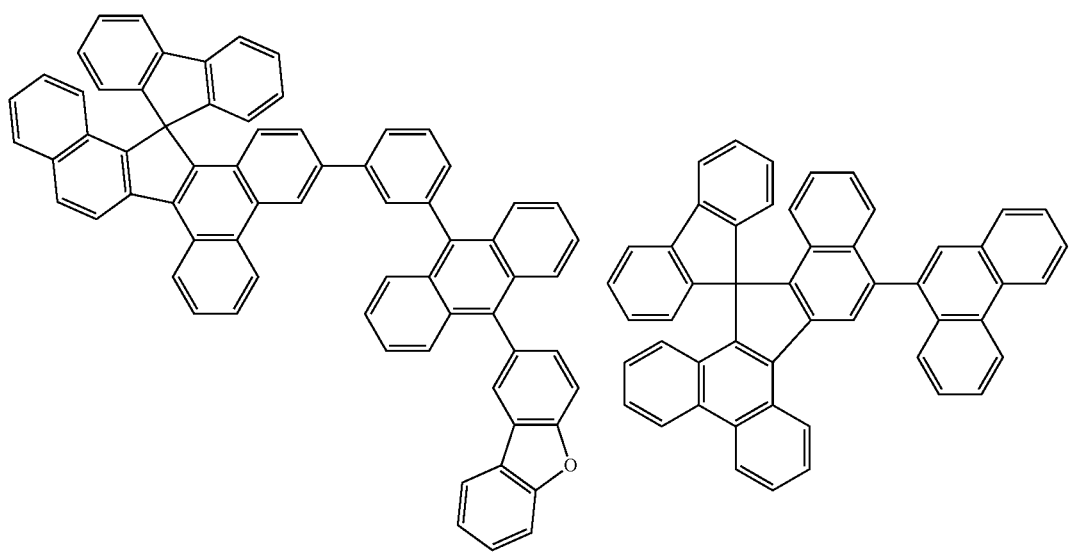
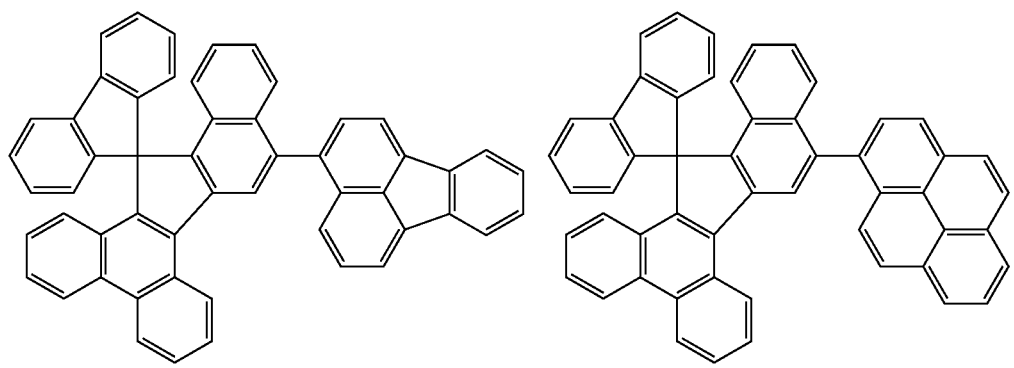

-continued
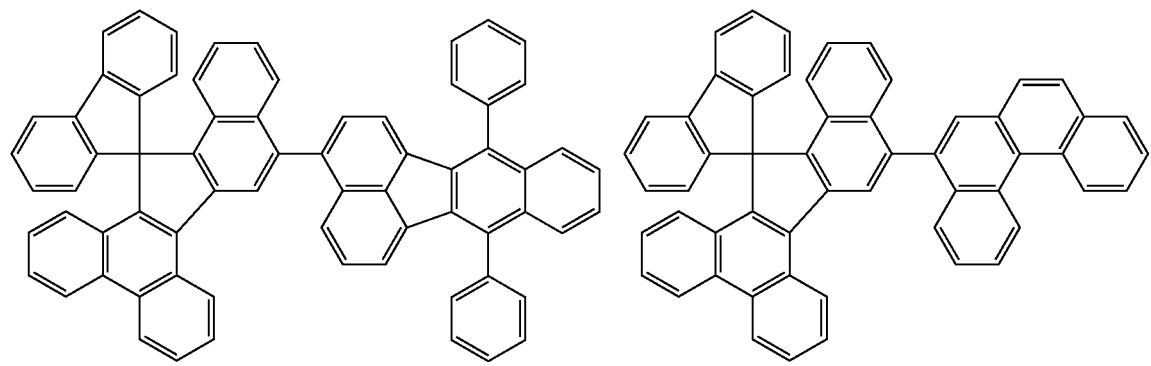
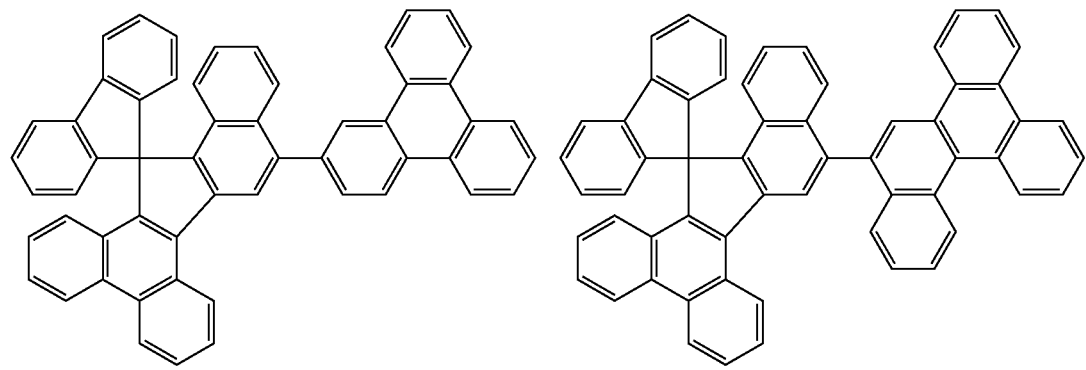
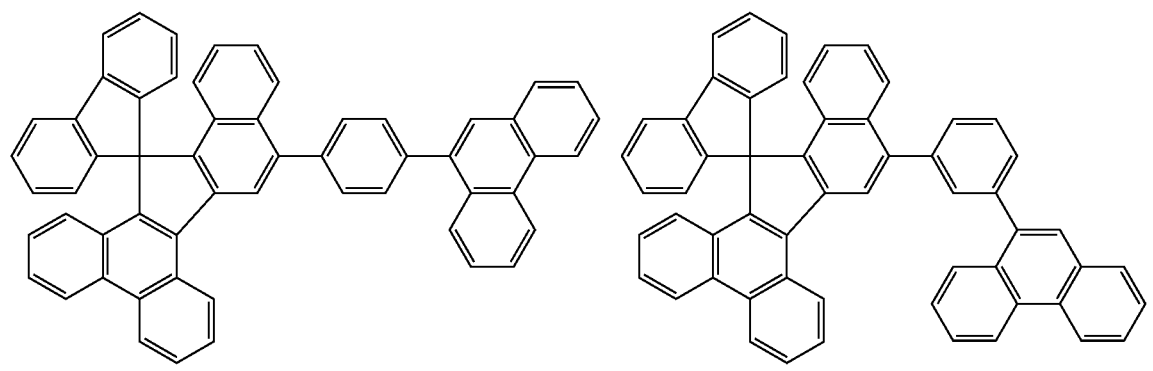
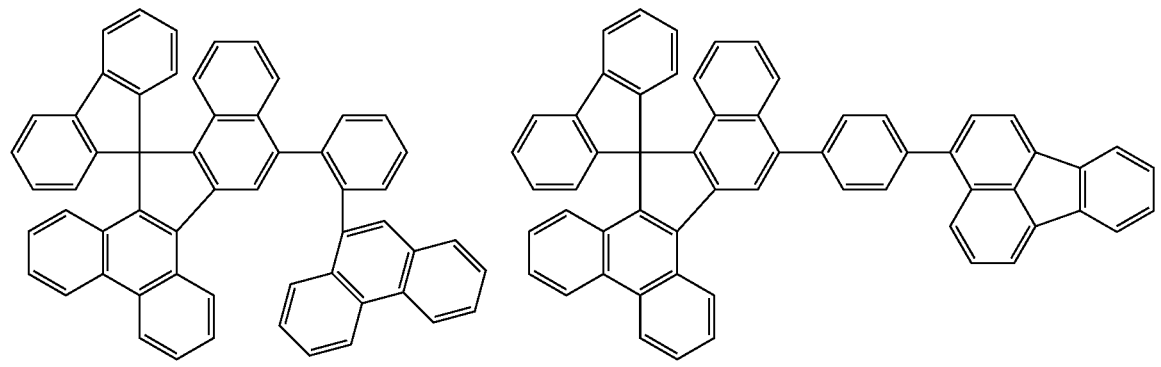

-continued
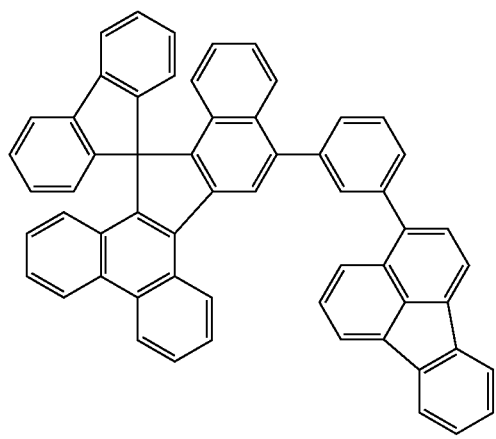
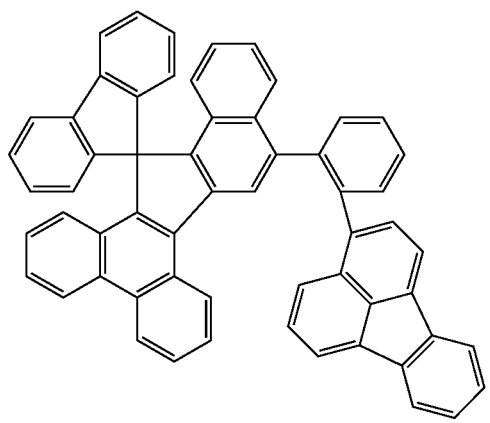
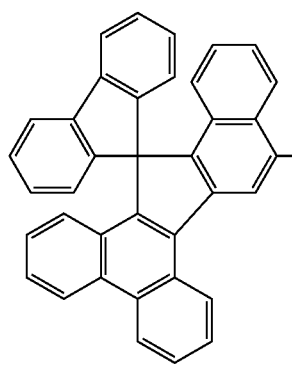
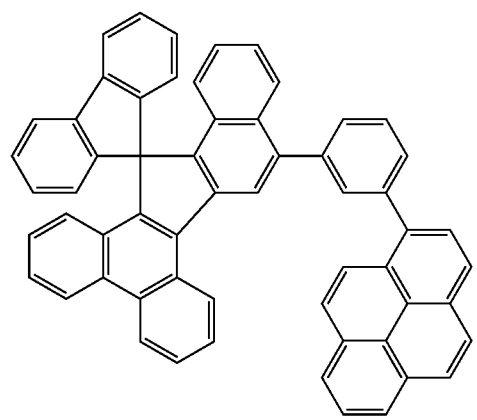
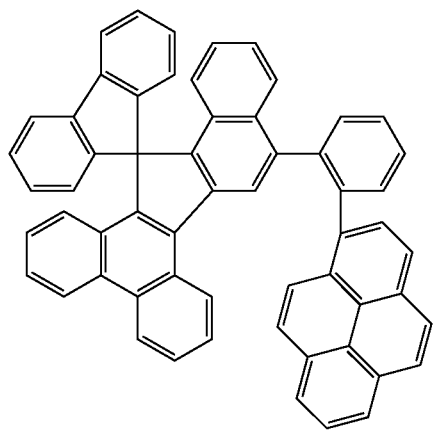
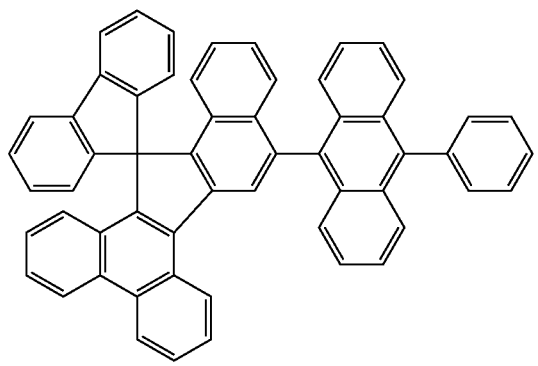
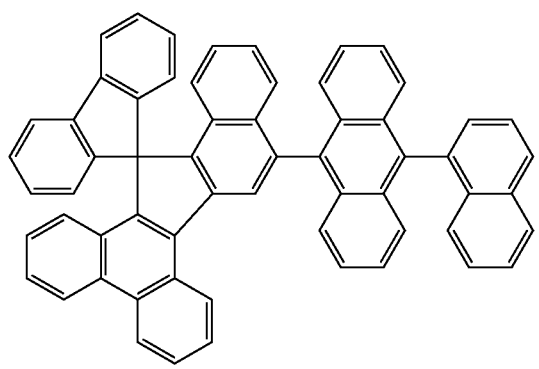
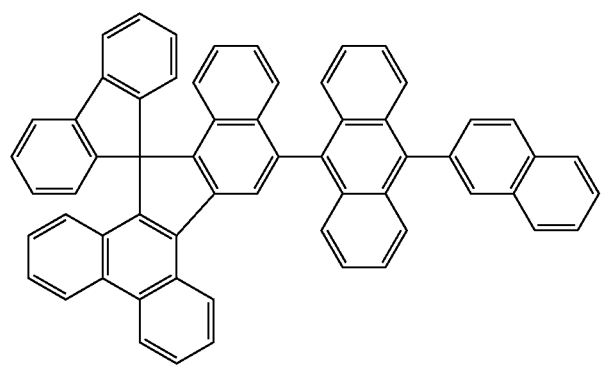

-continued
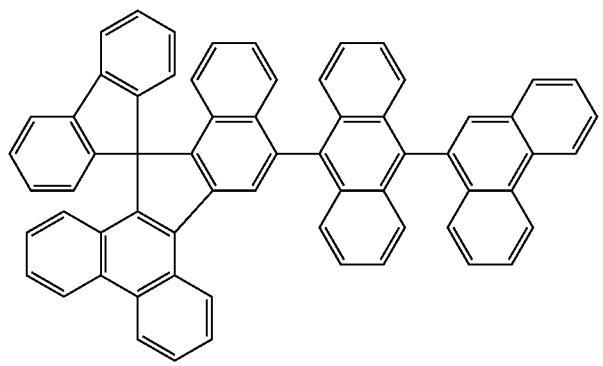
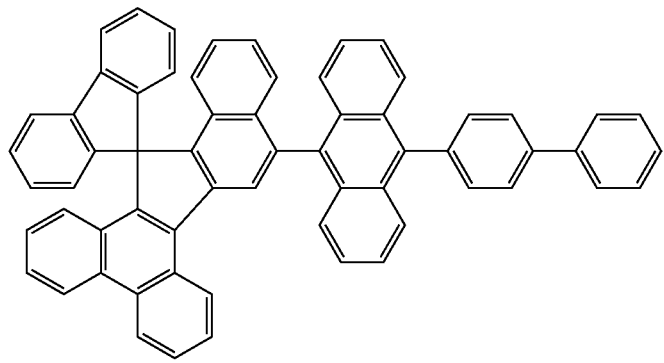
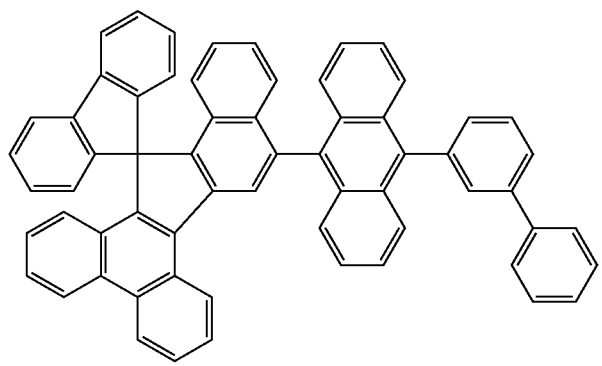
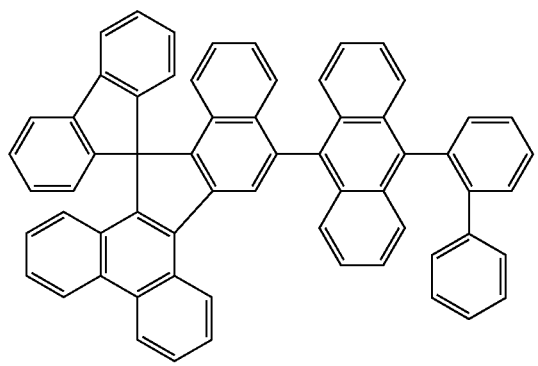
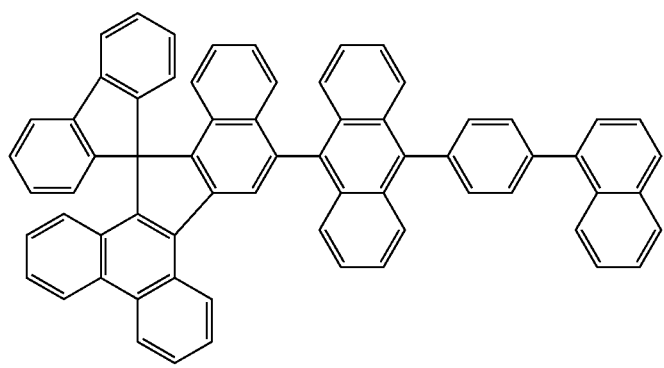

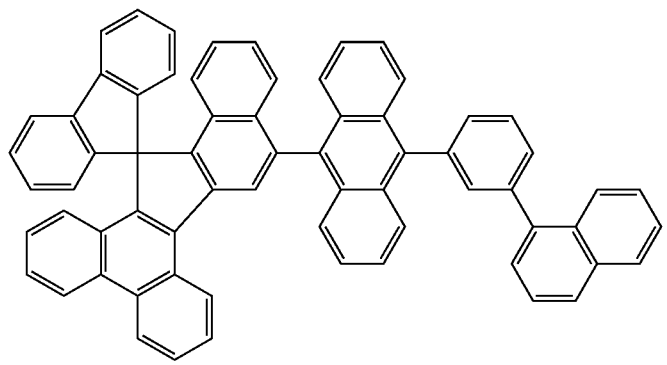

-continued
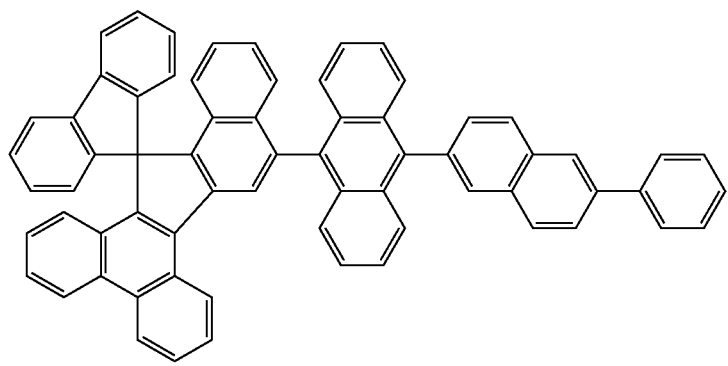
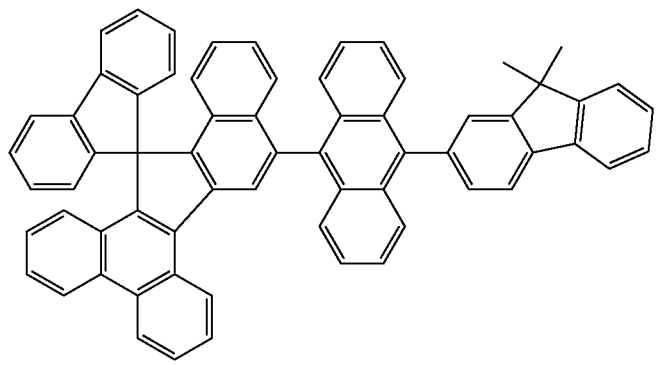
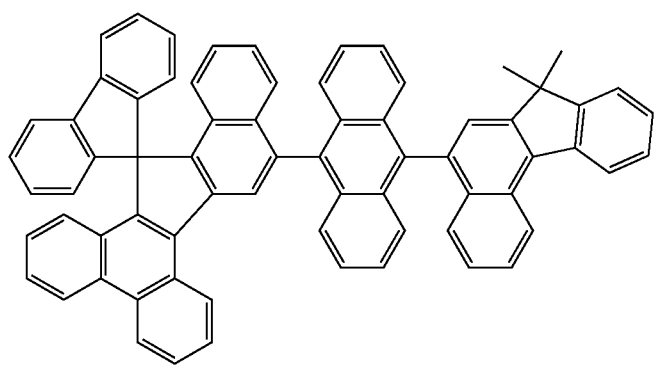
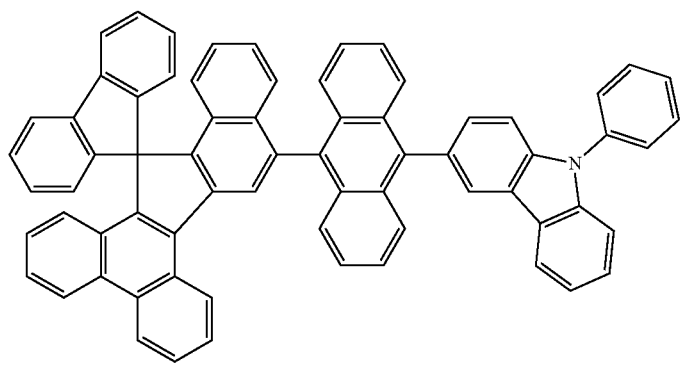

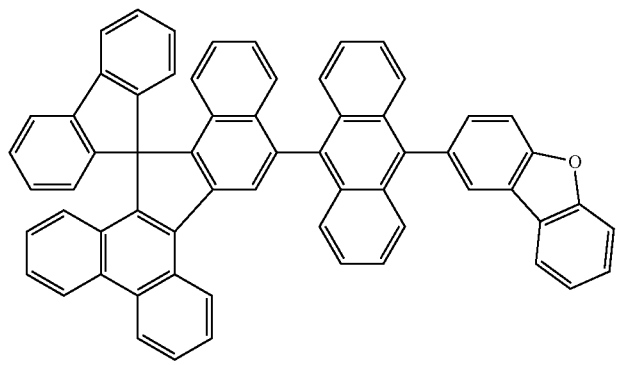
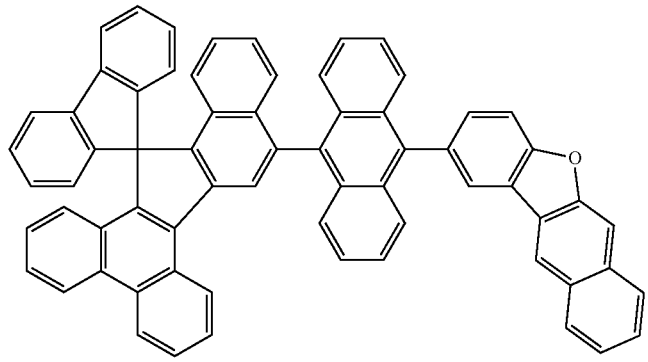
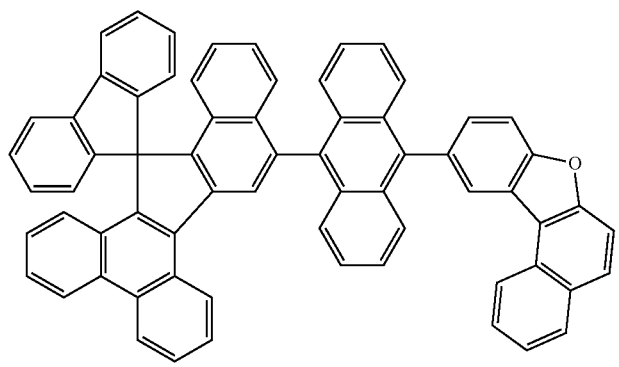
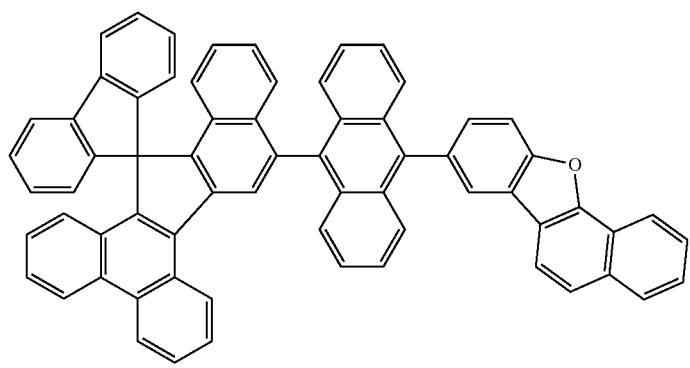

-continued
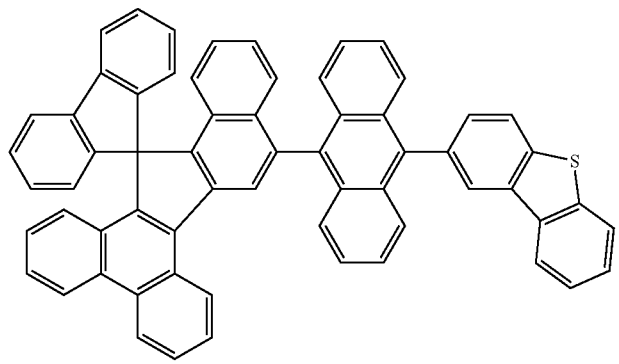
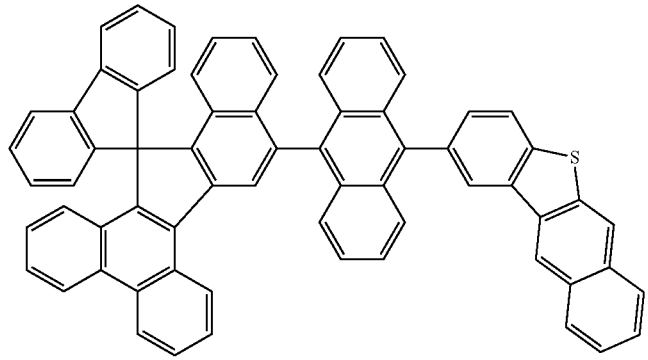
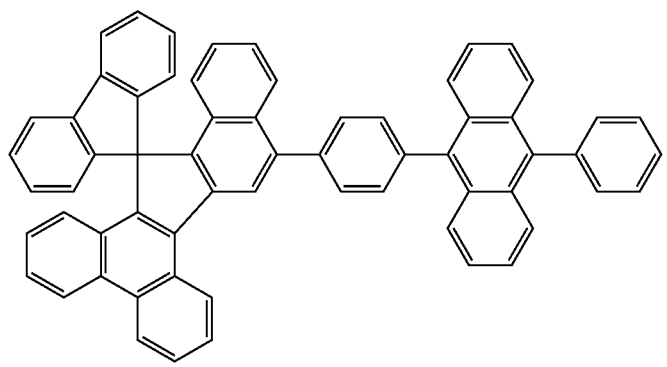
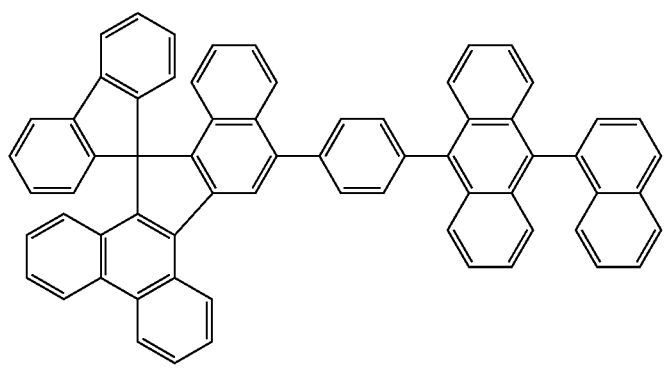

-continued
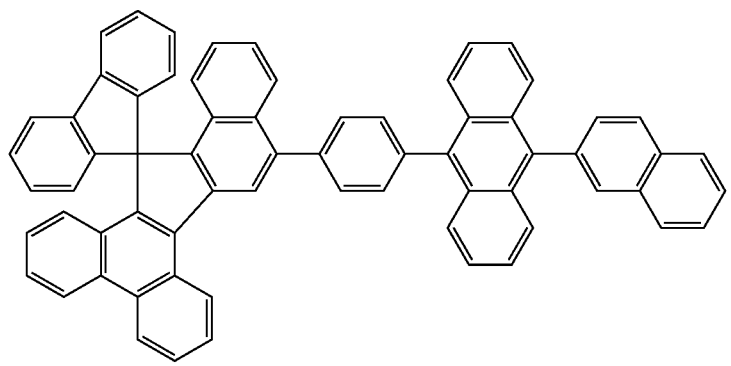
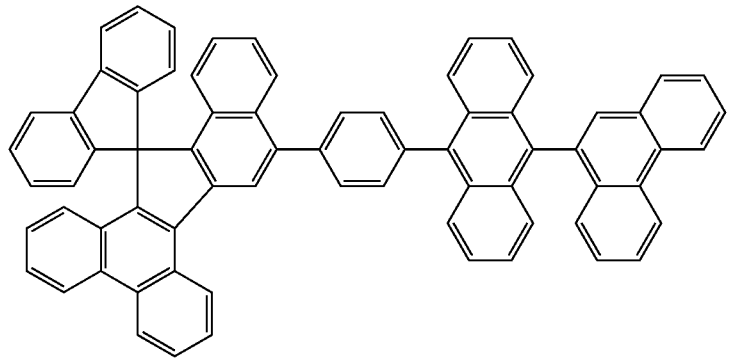
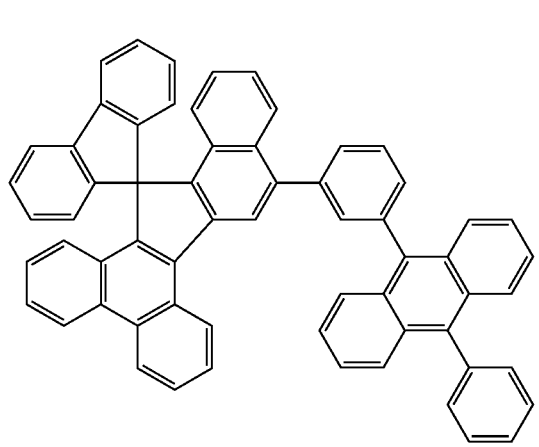
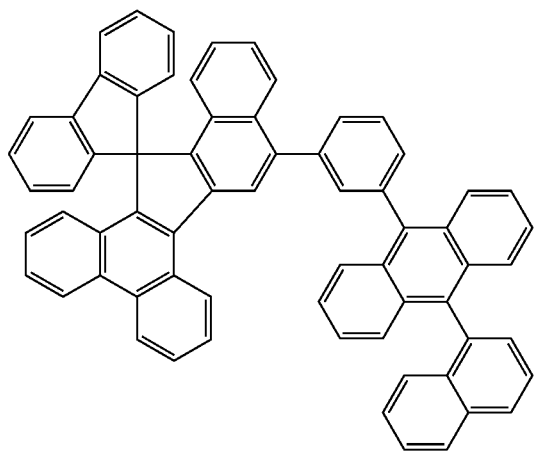
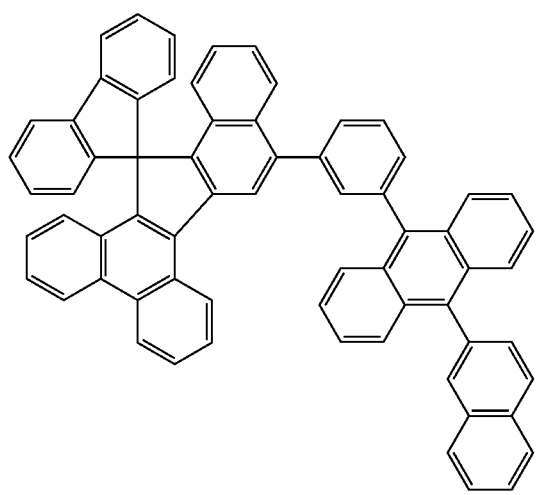
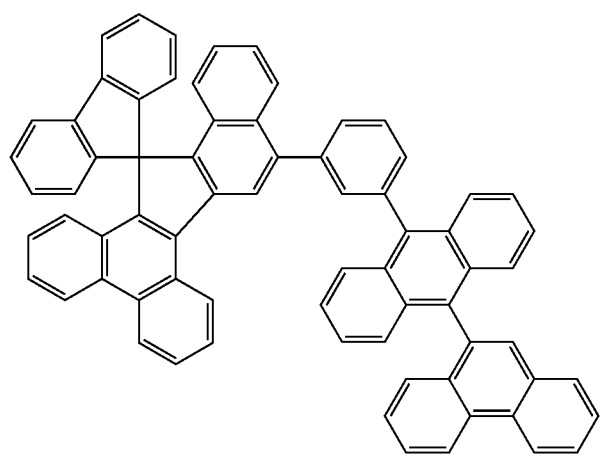

-continued
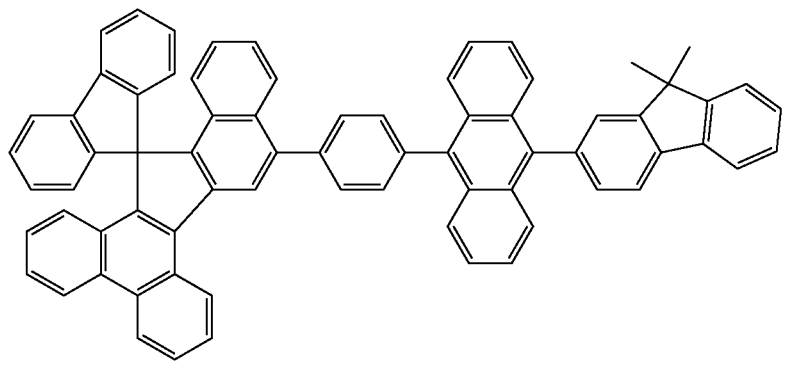
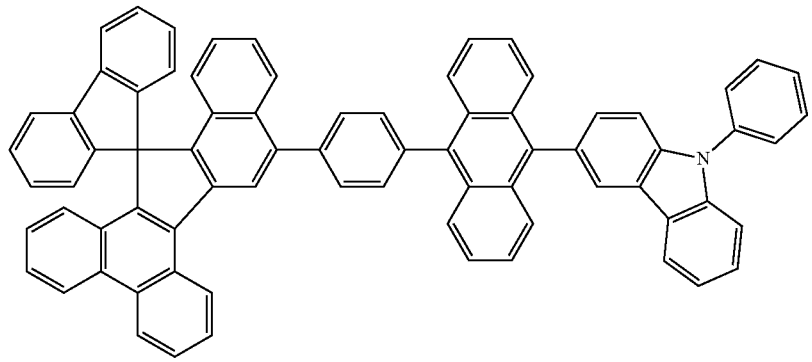
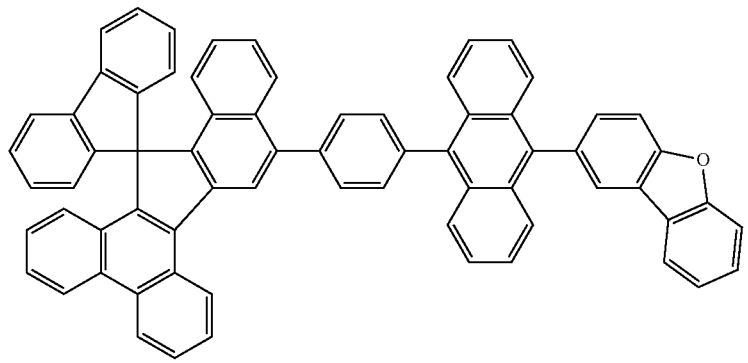
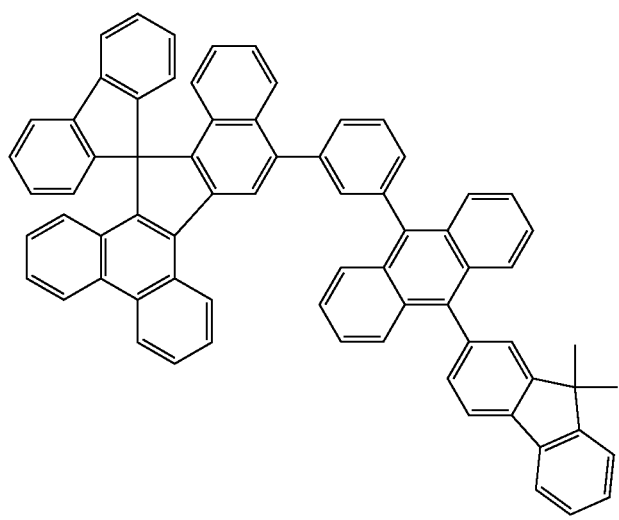

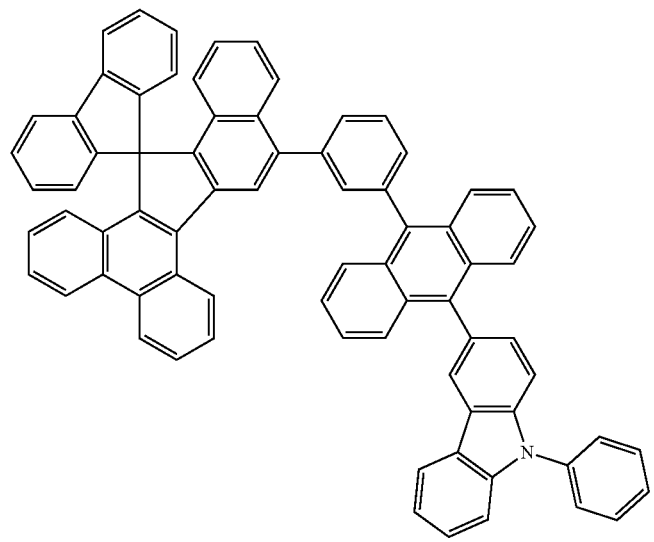
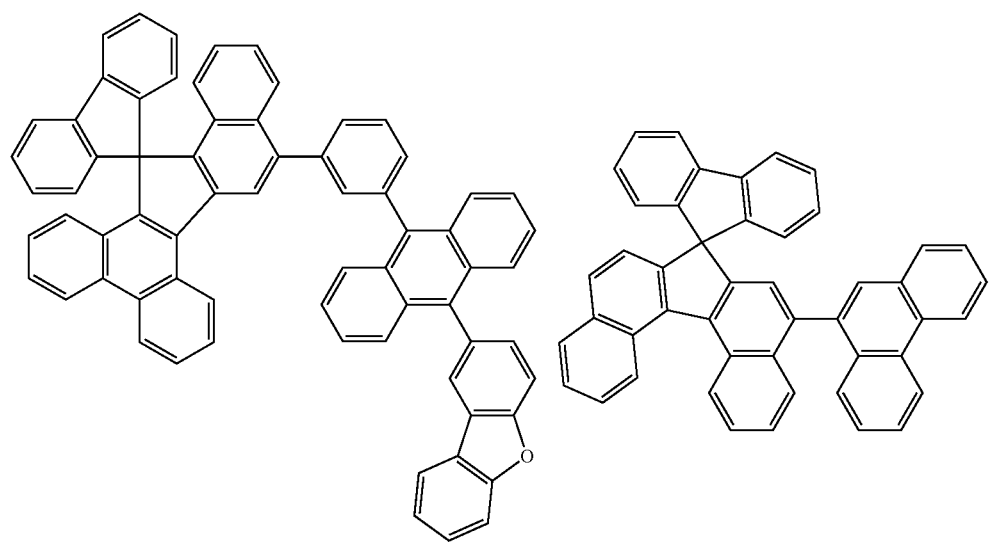
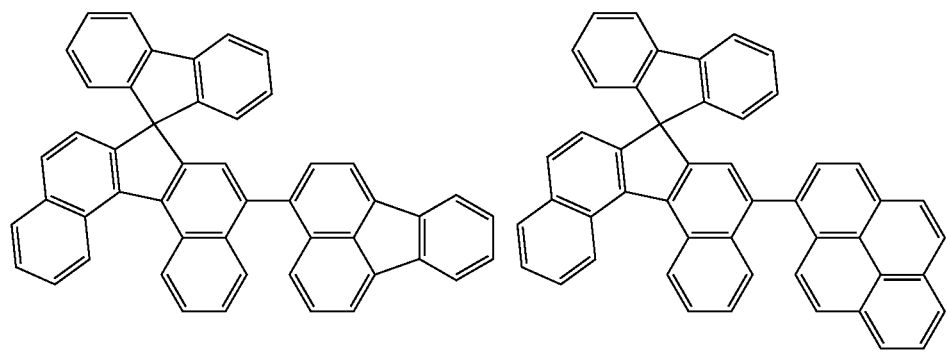

-continued
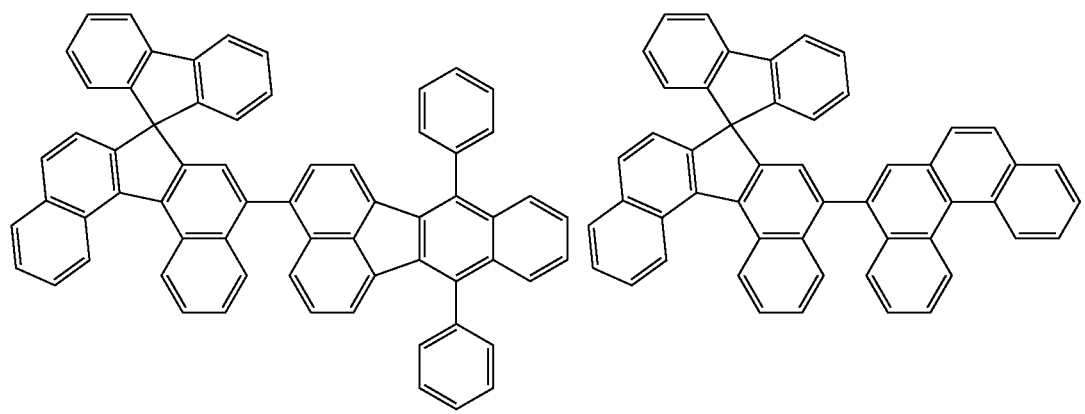
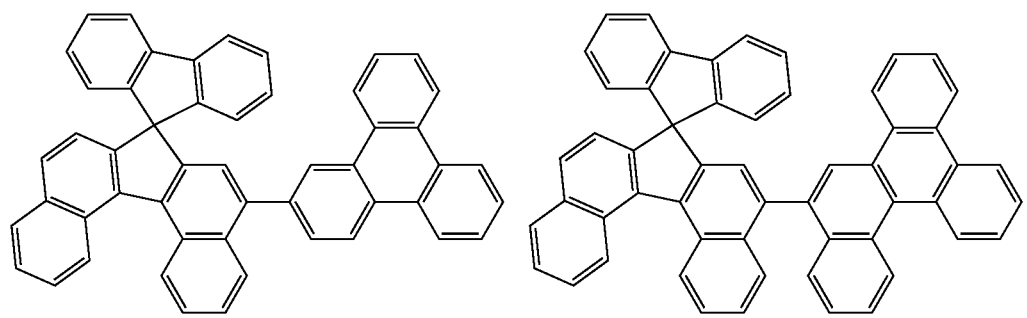
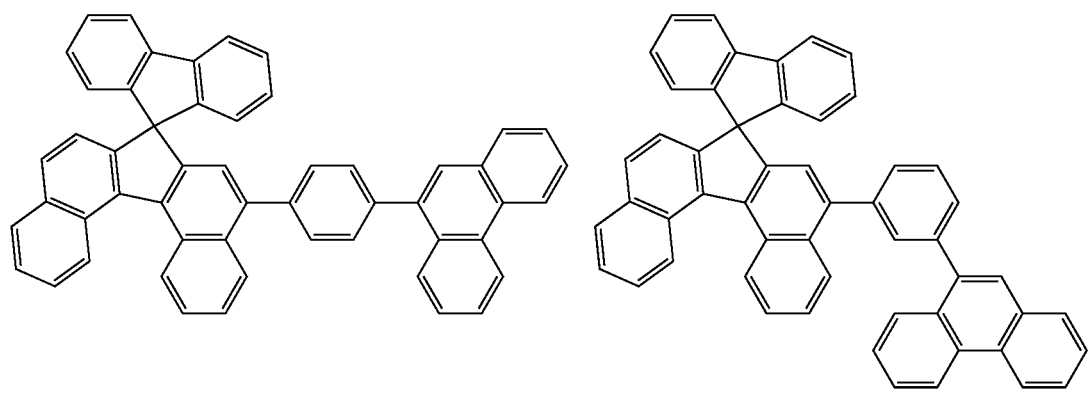
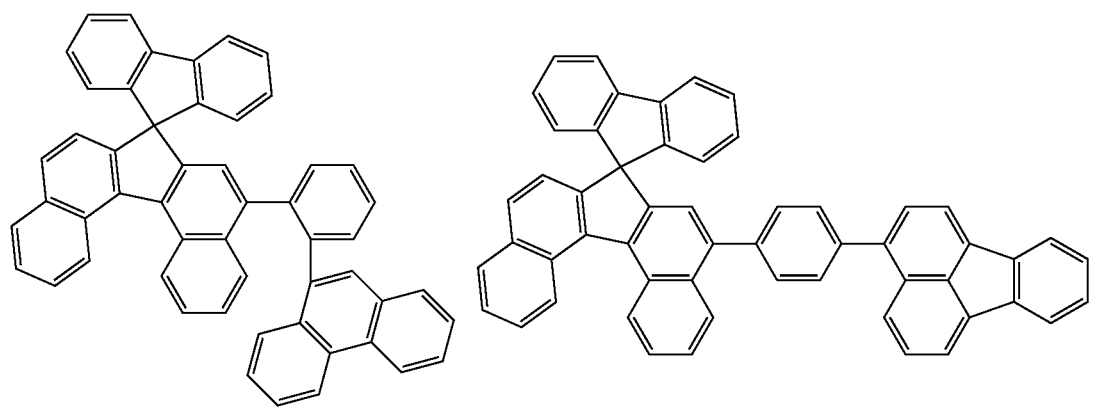

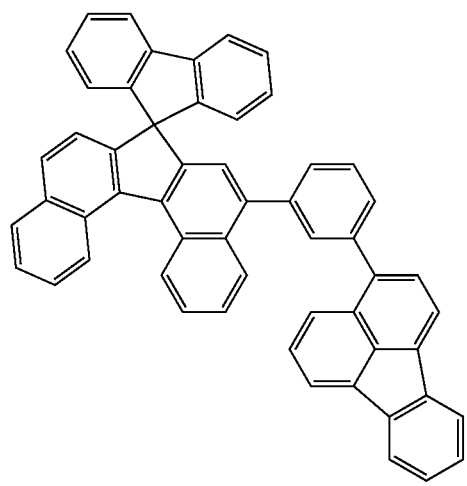
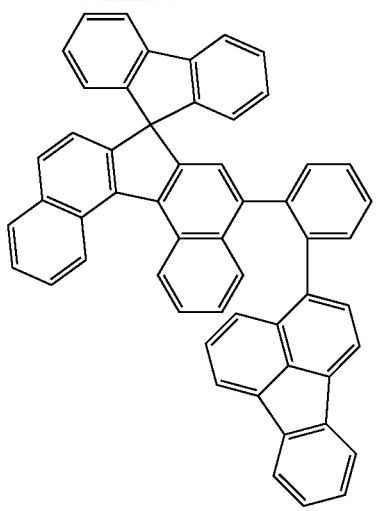
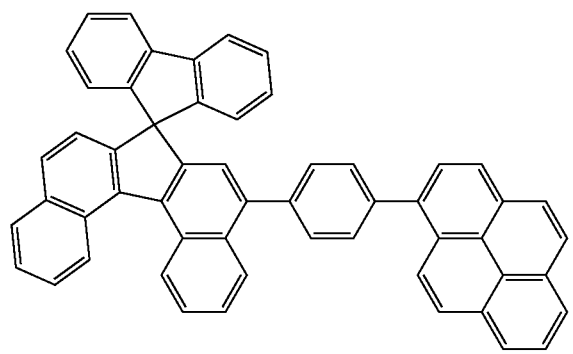
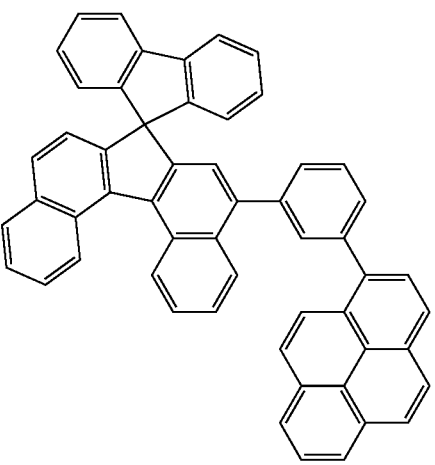
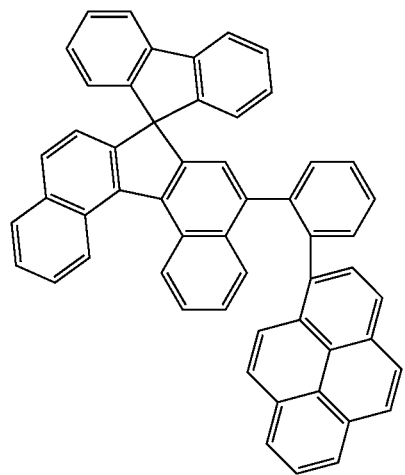
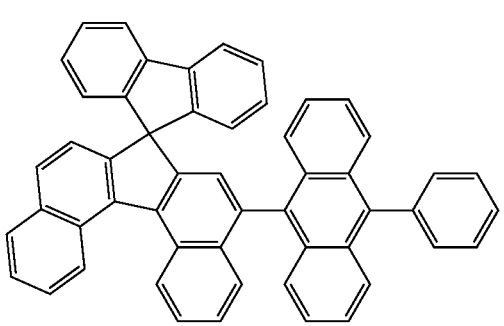

-continued
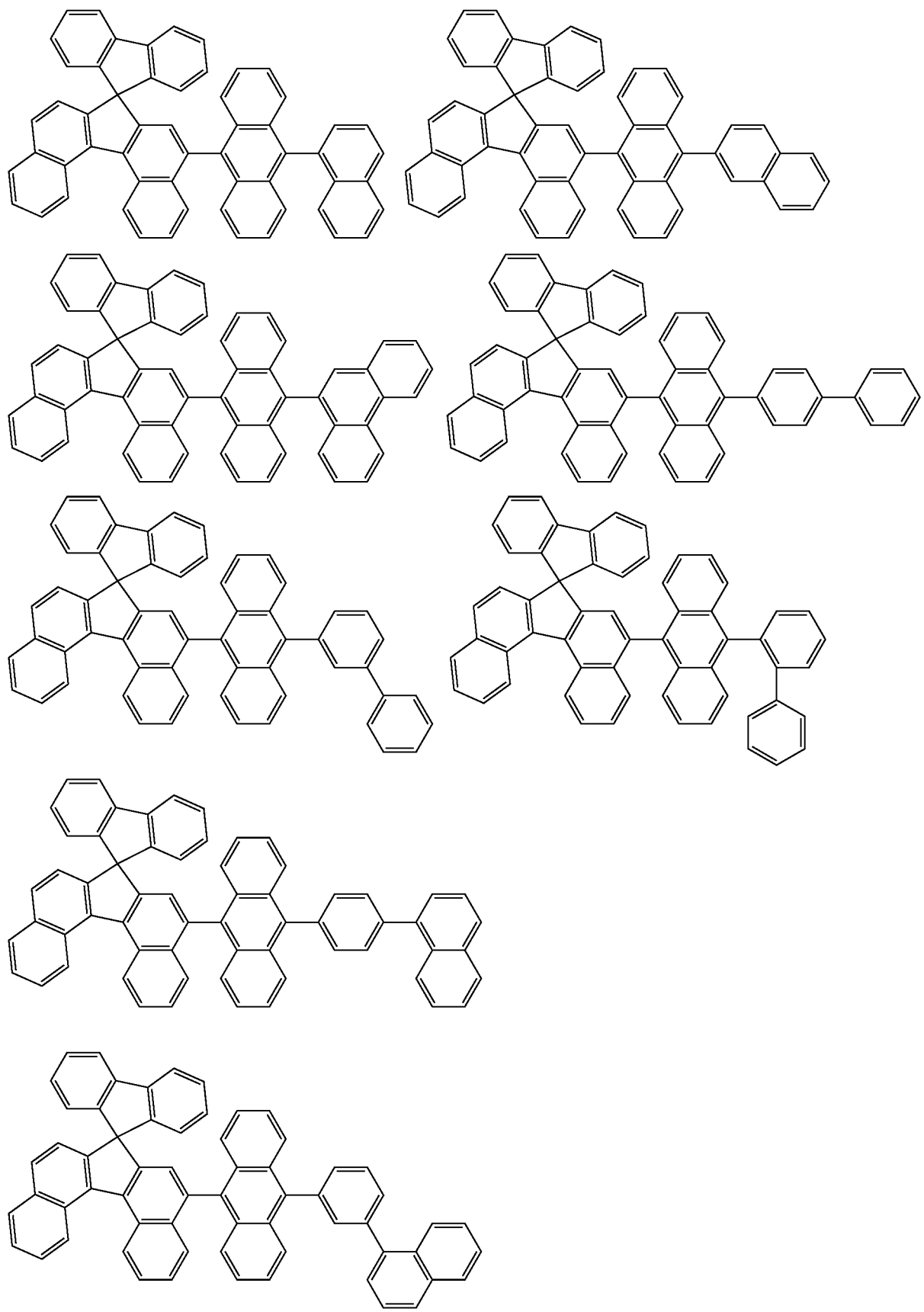

-continued
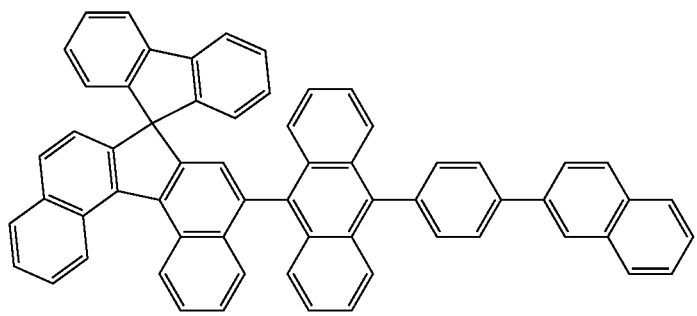
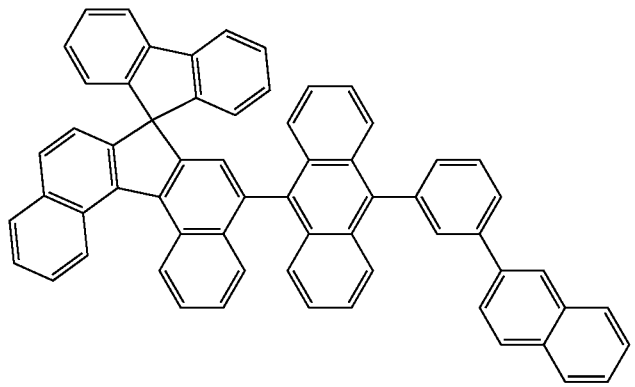
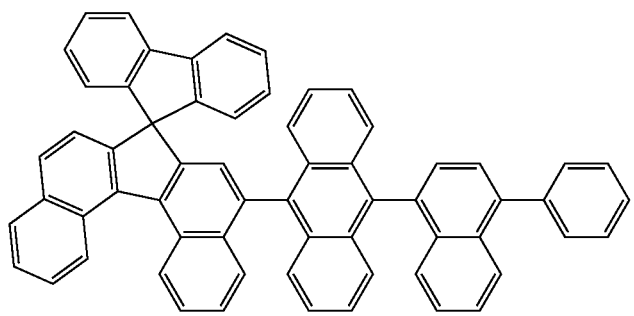
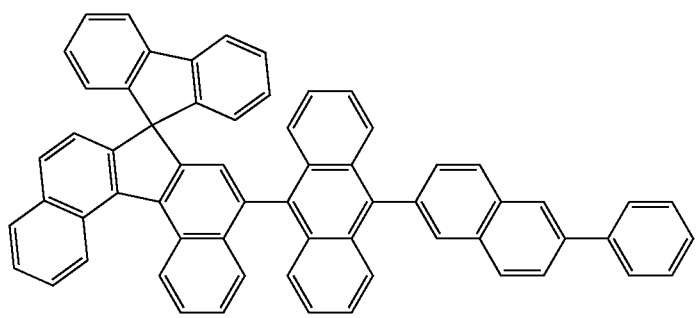
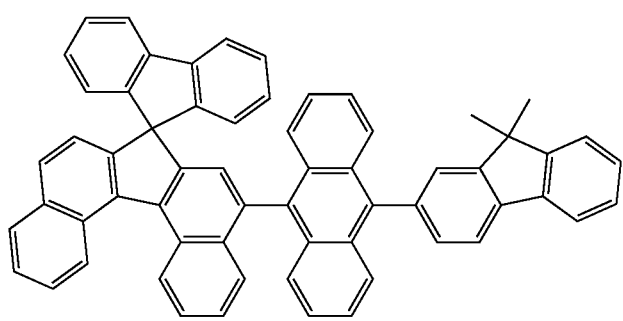

-continued
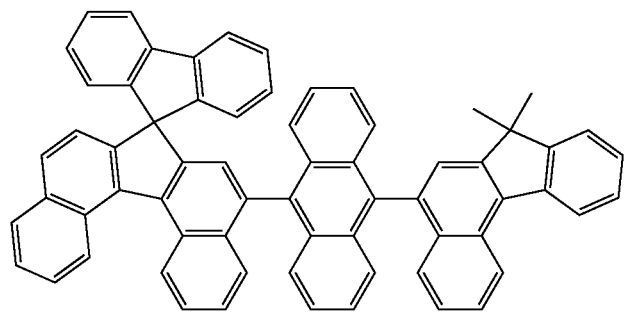
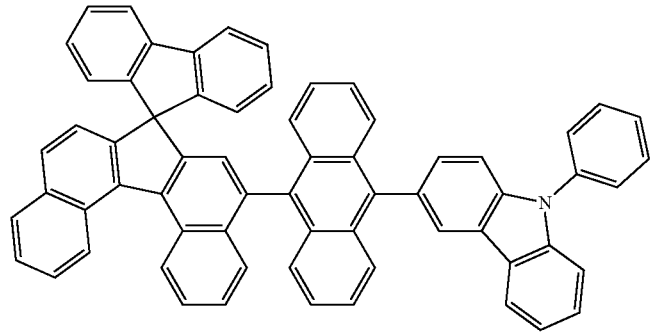
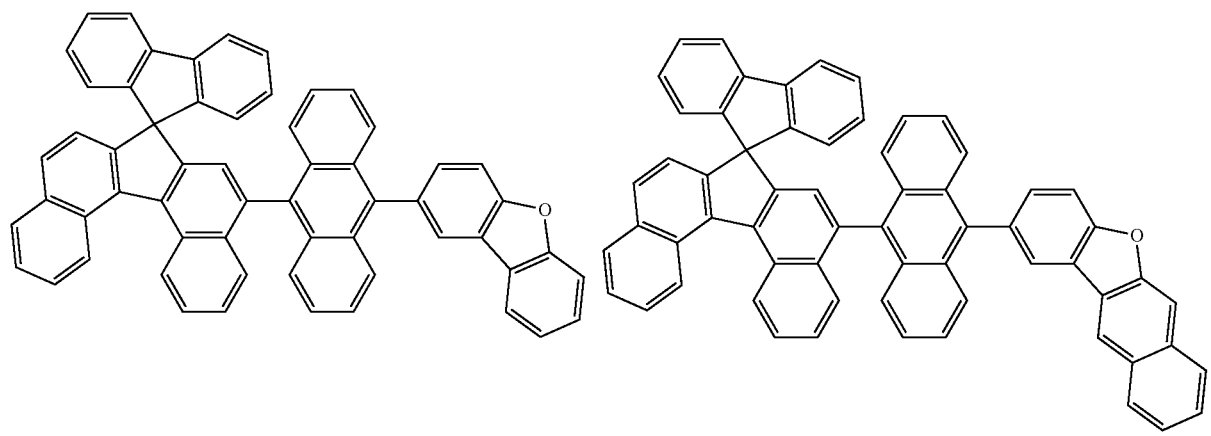
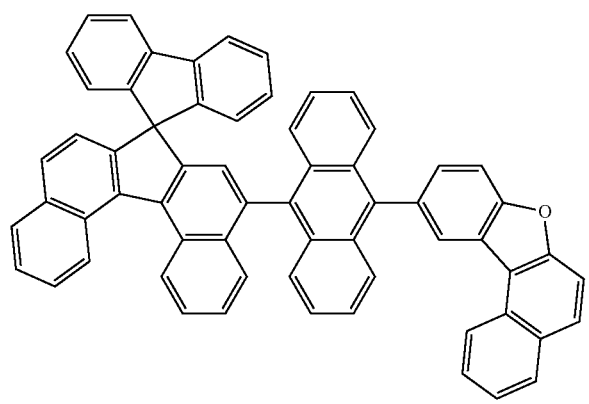

-continued
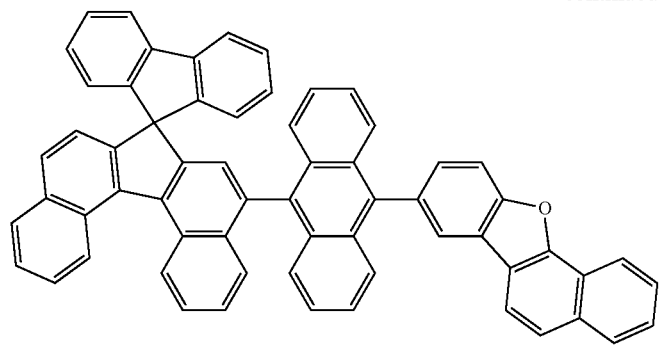
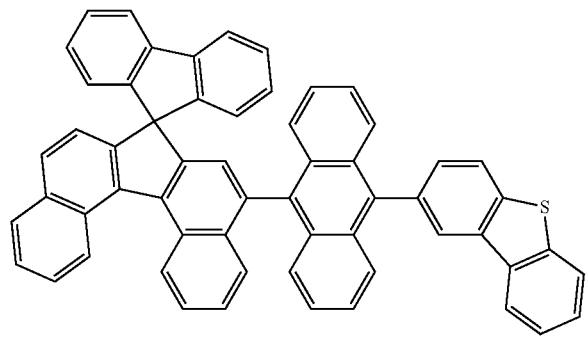
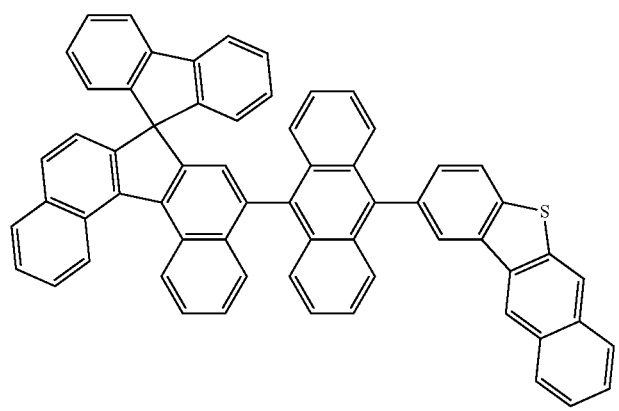
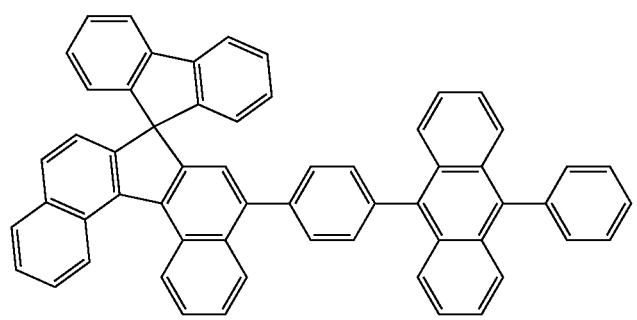
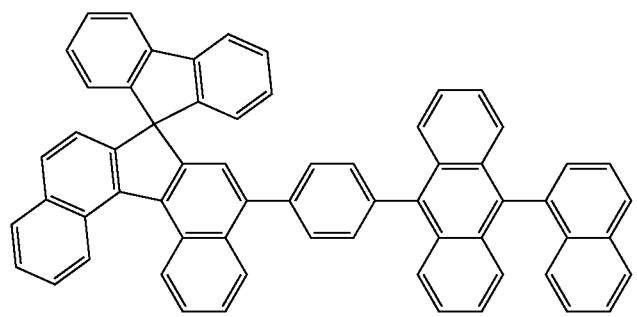

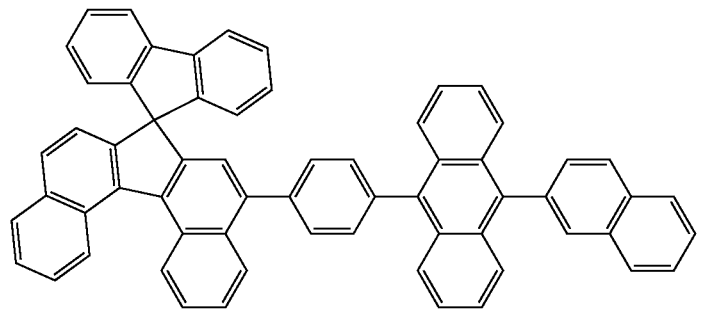
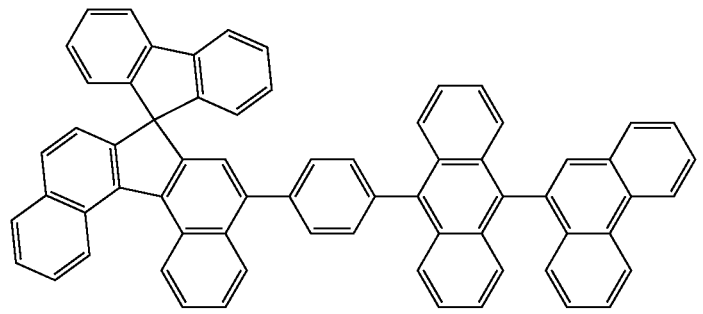
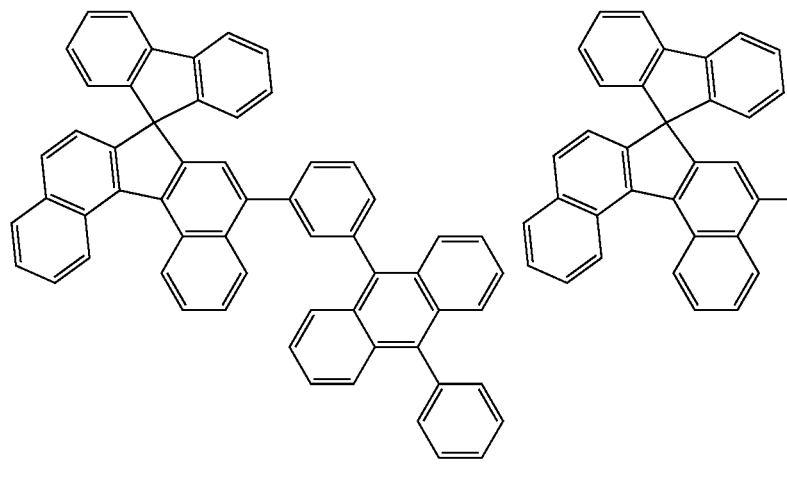
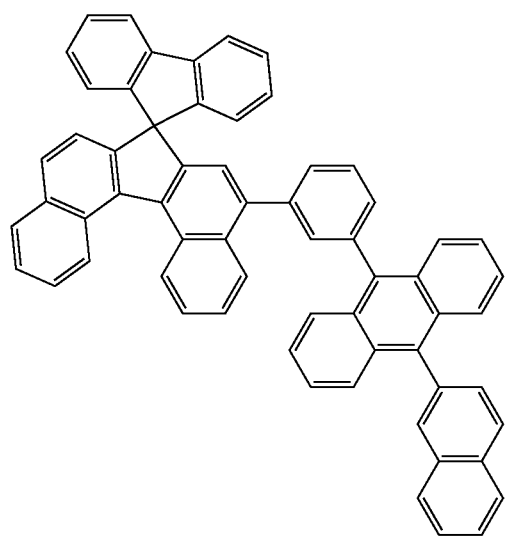
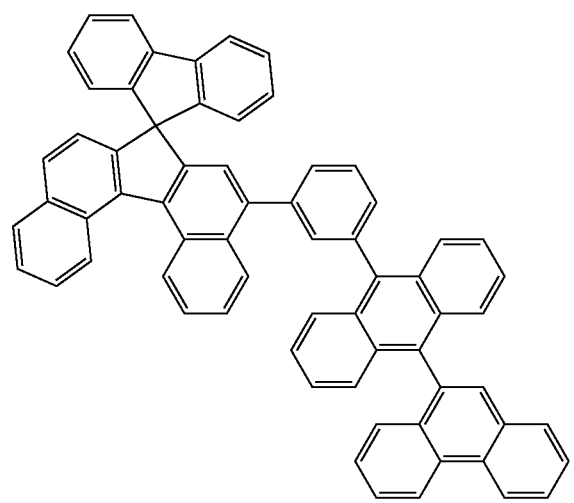

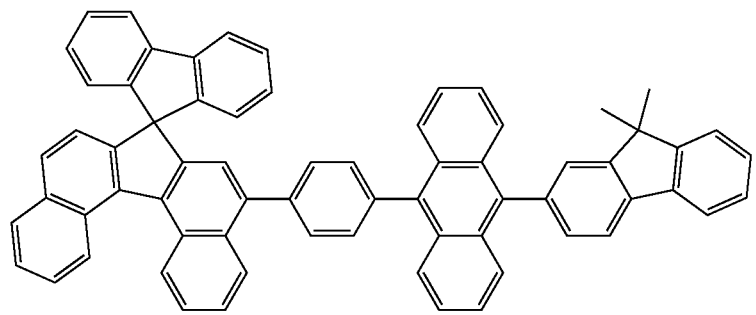

-continued
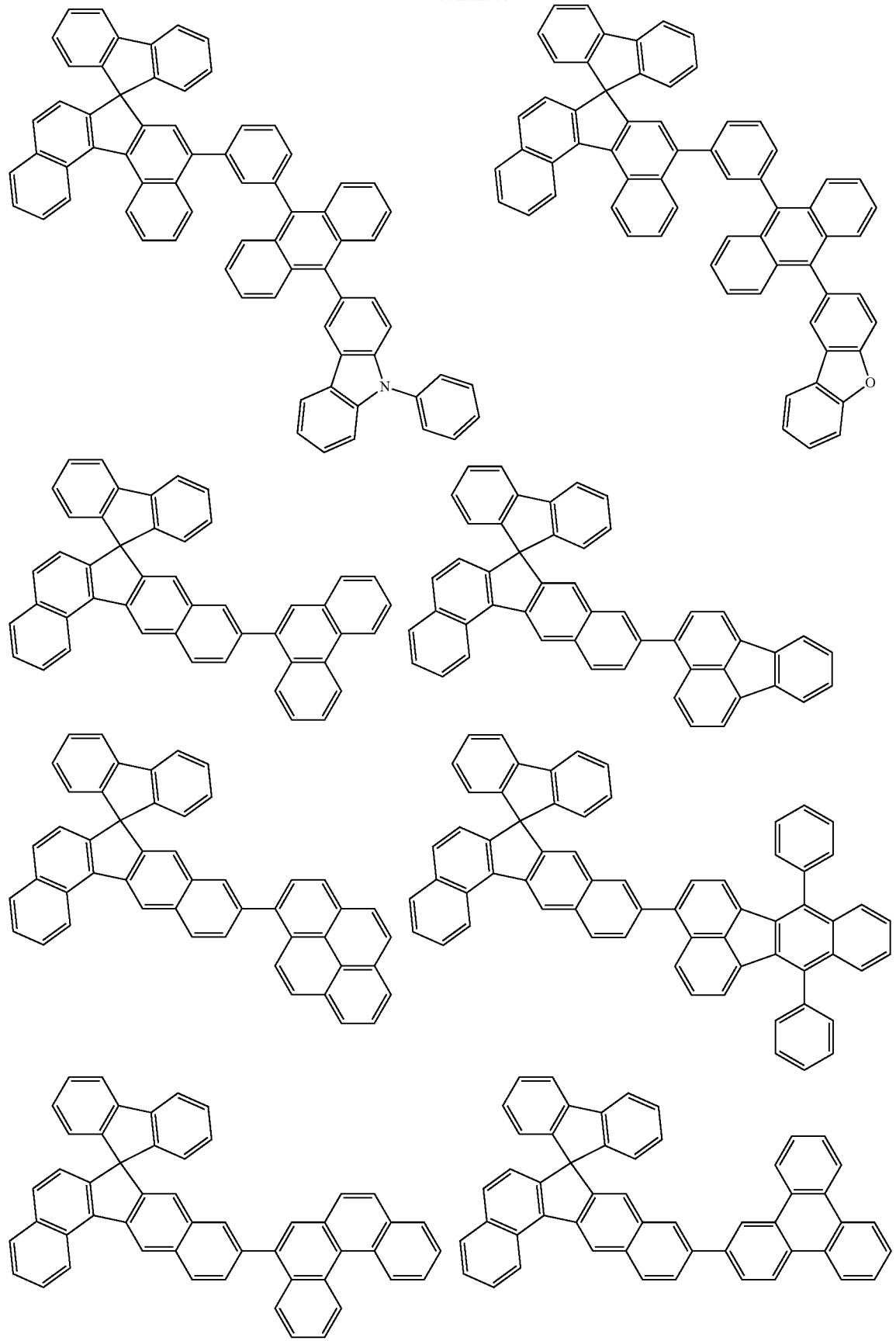

-continued
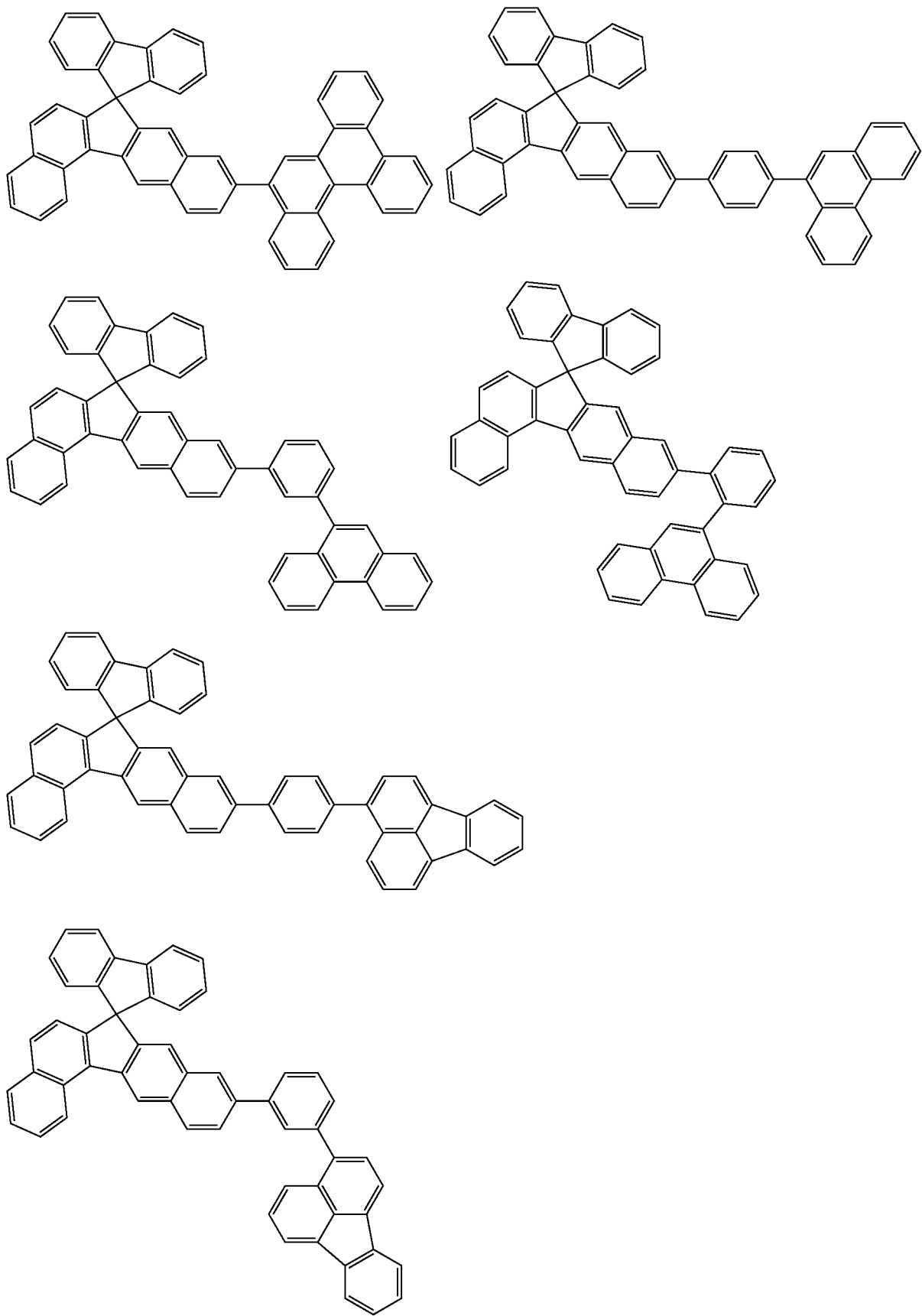

181
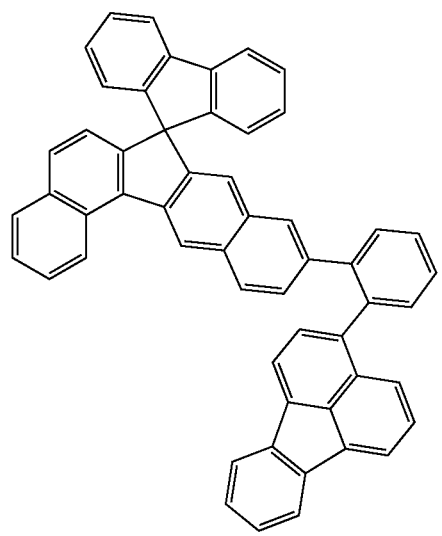
182
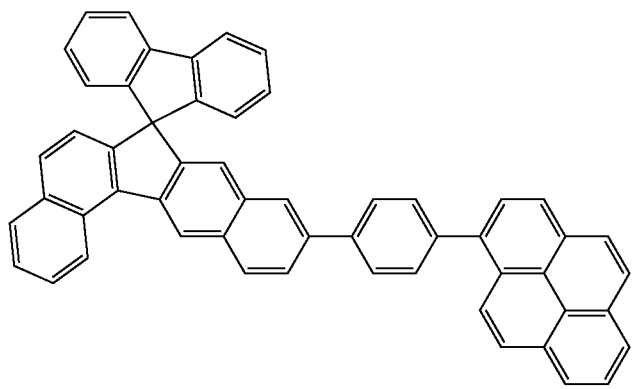
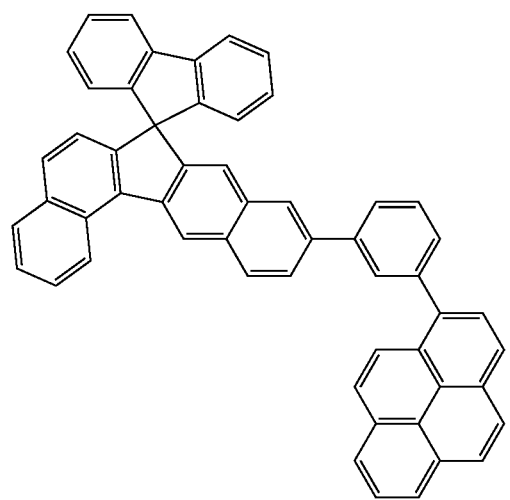
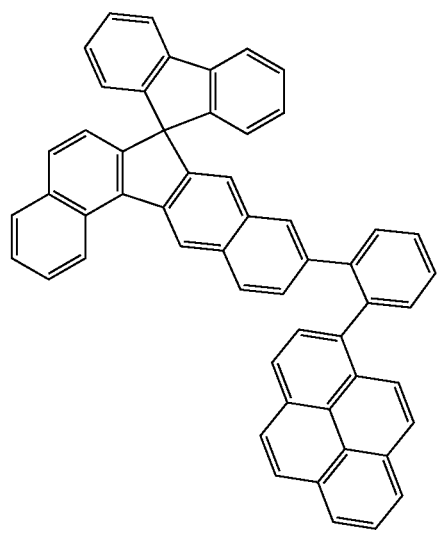
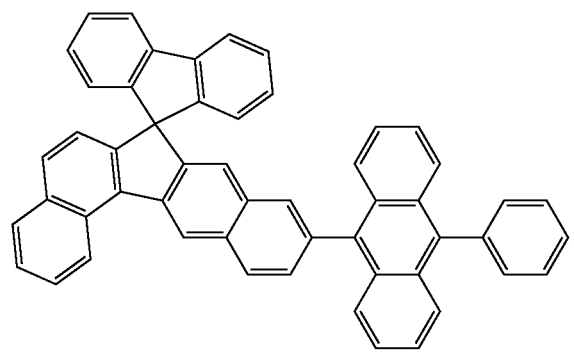
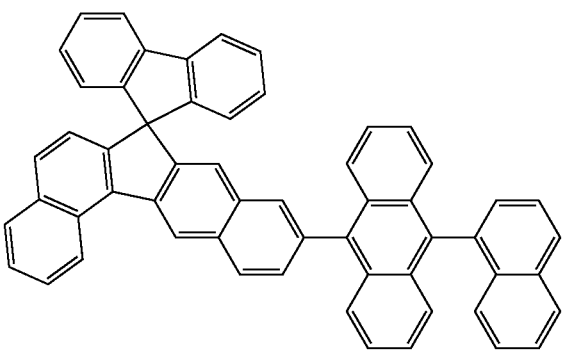

183
-continued
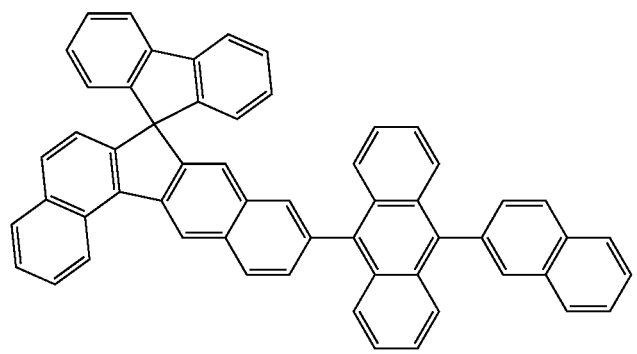
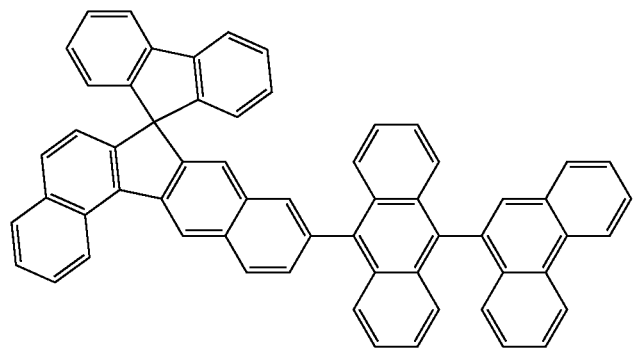
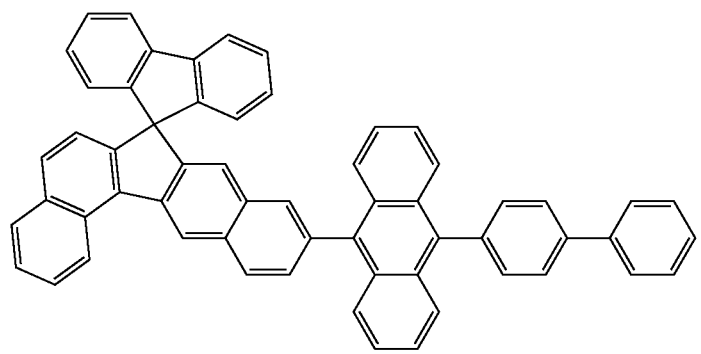
184
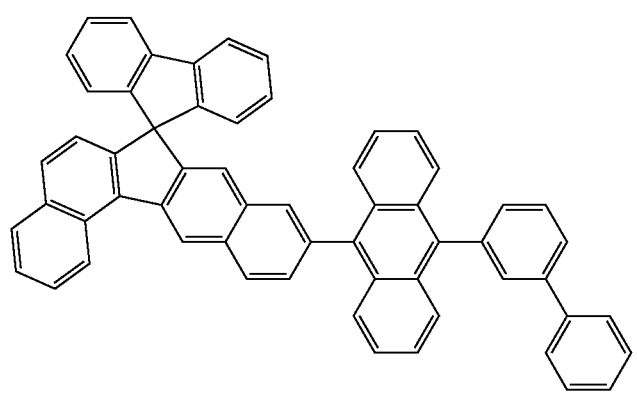
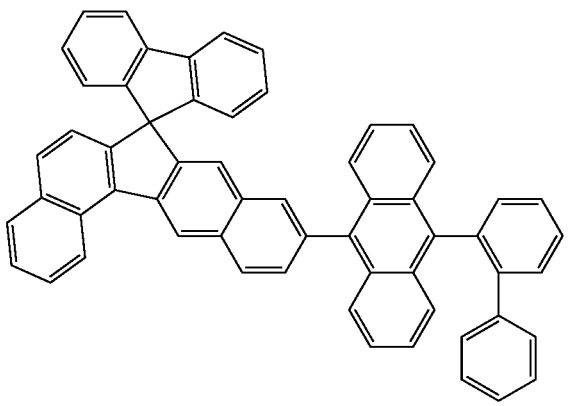

-continued
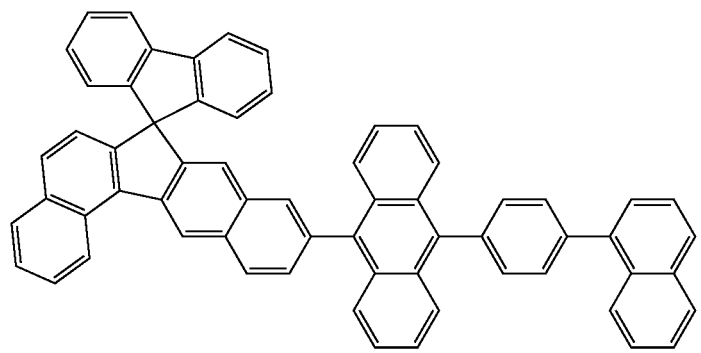
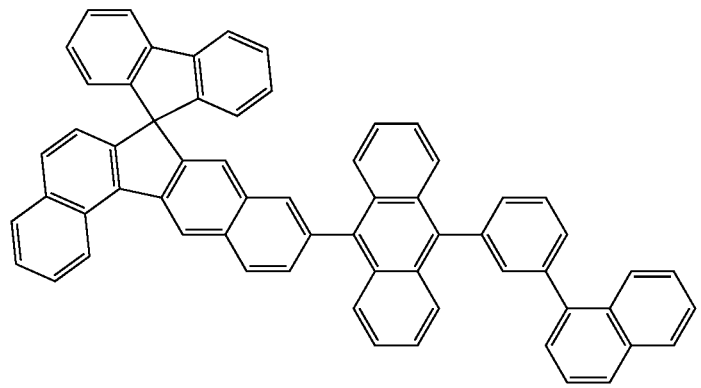
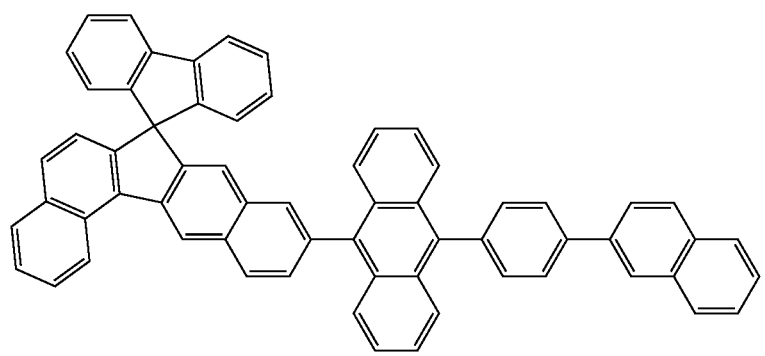
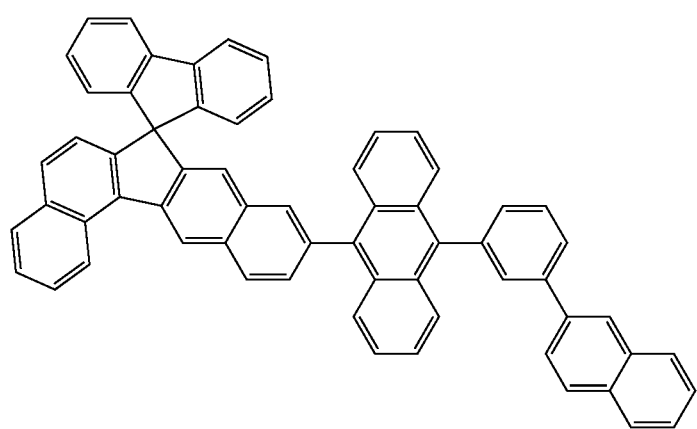

-continued
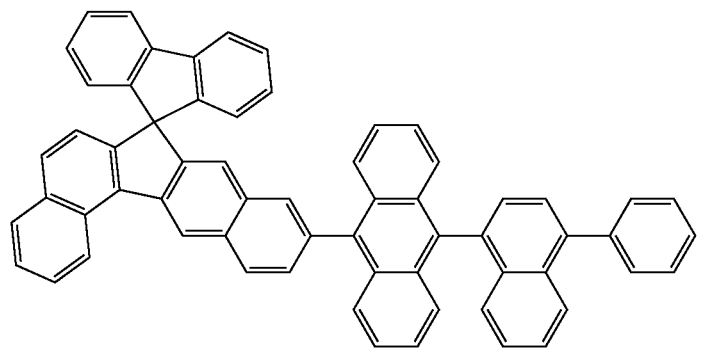
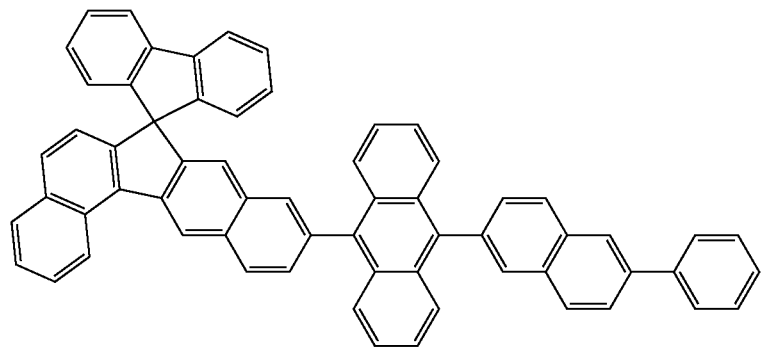
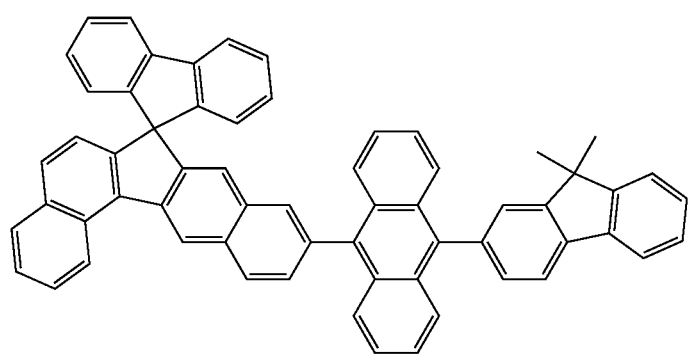
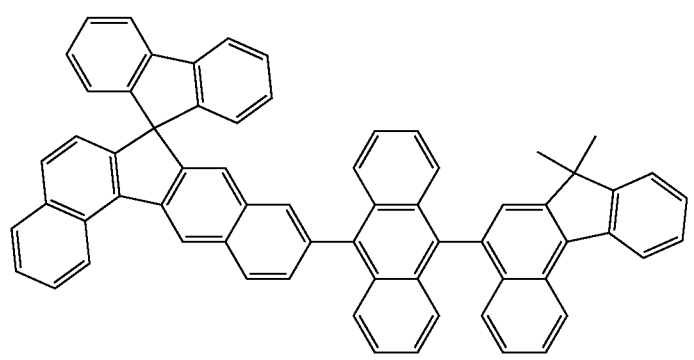

-continued
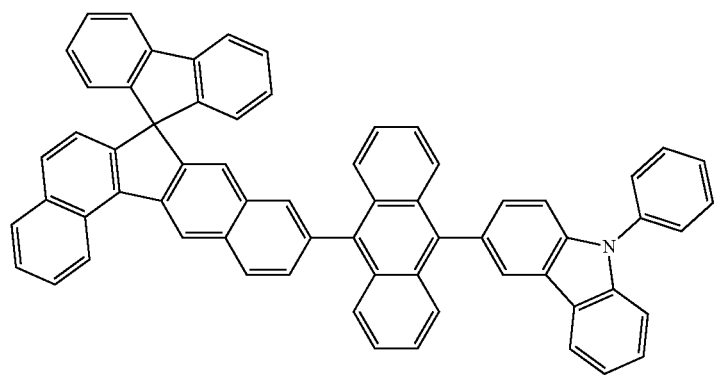
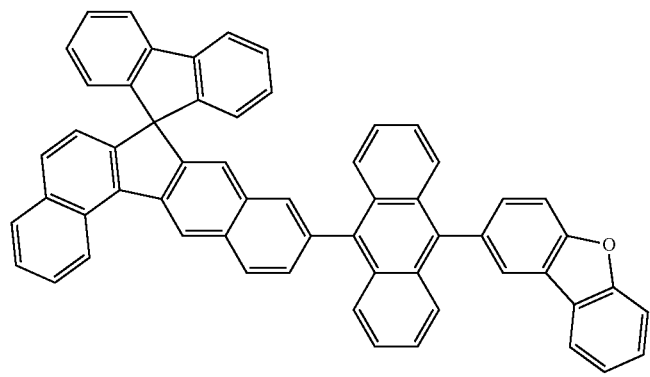
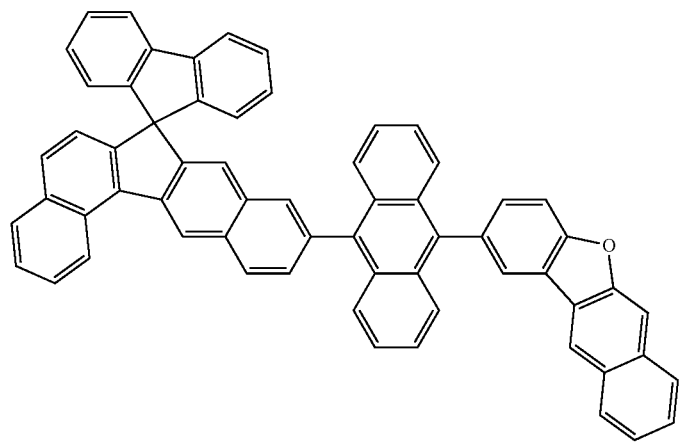
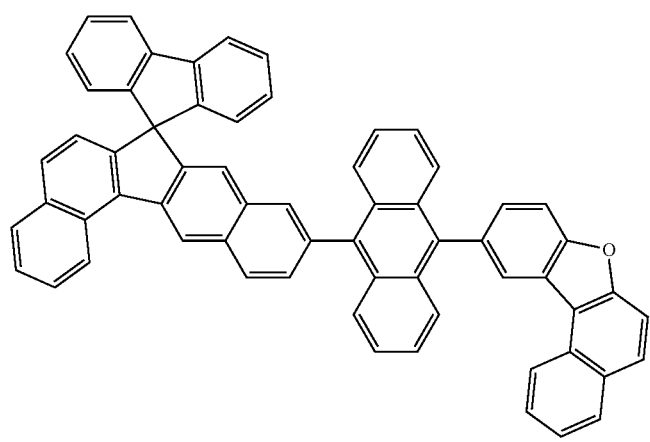

-continued
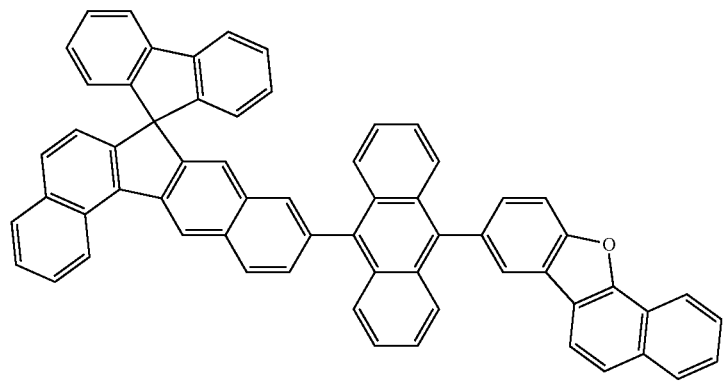
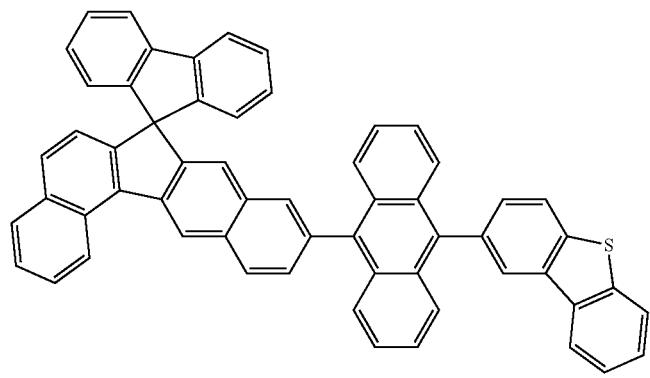
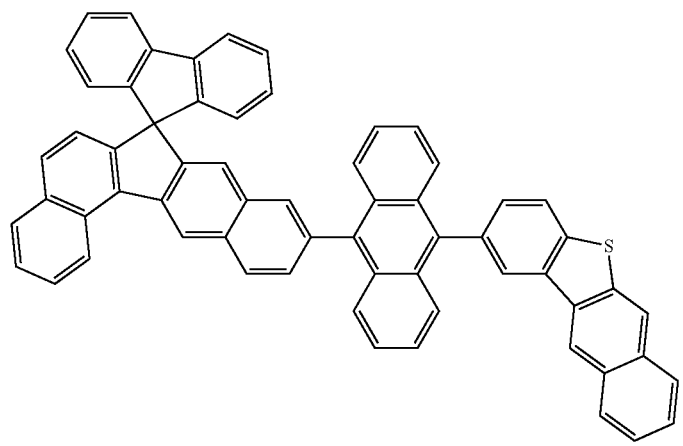
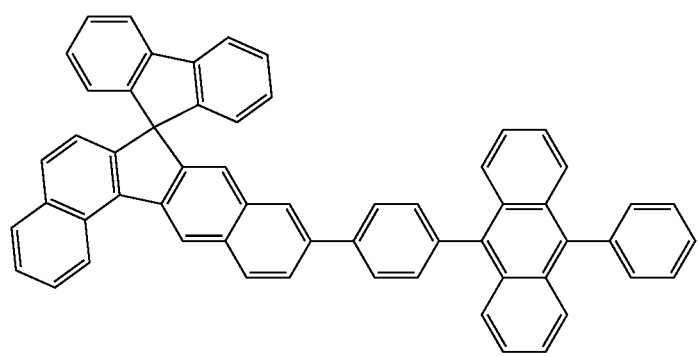

-continued
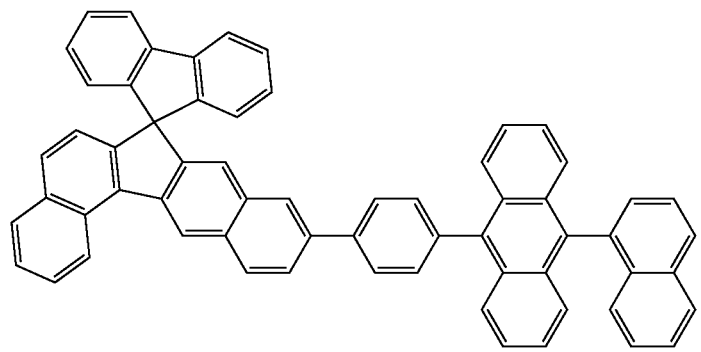
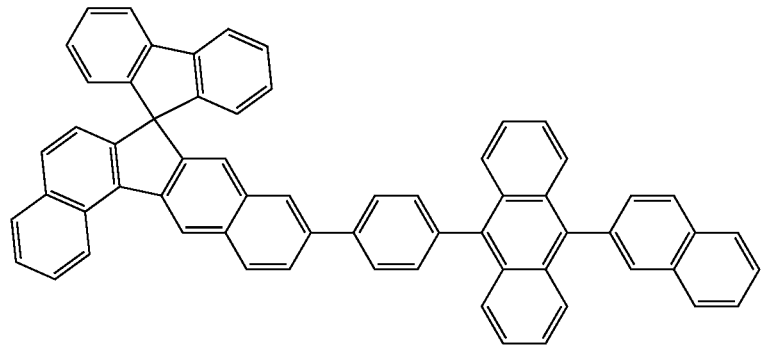
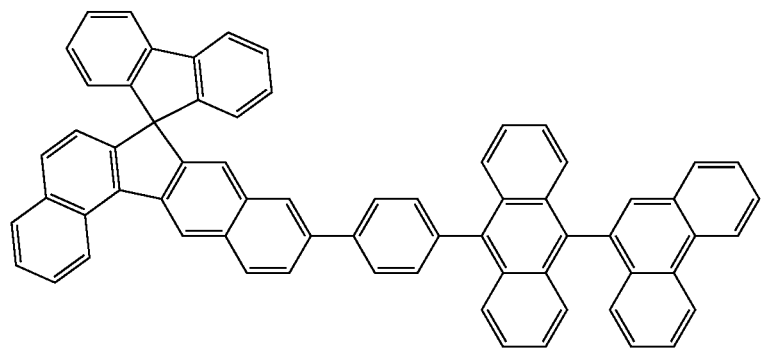
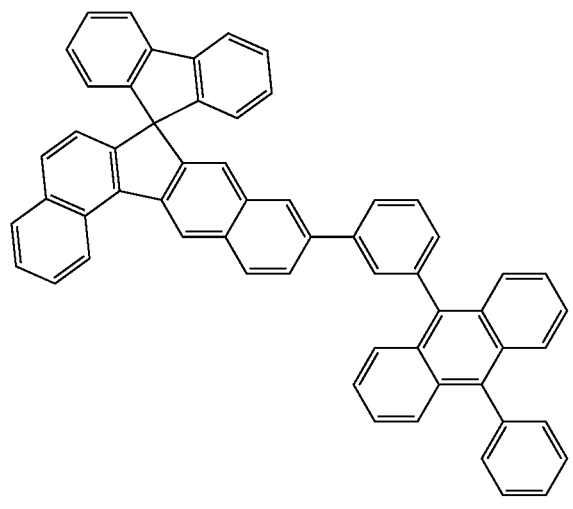
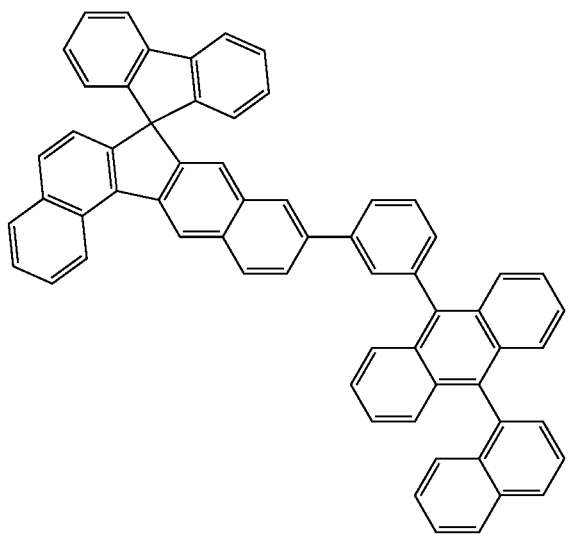

-continued
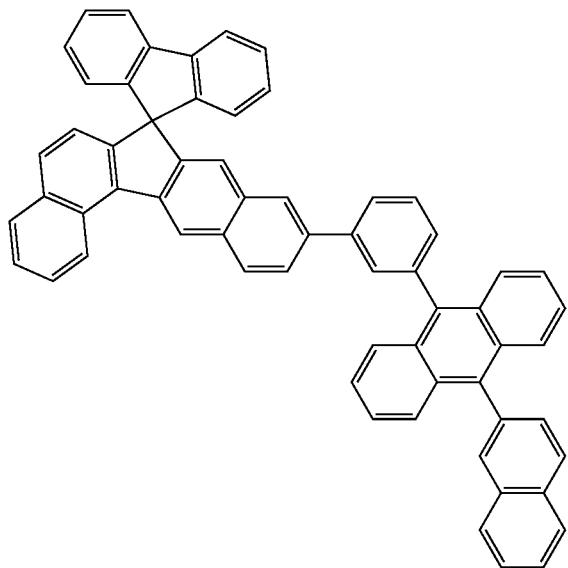
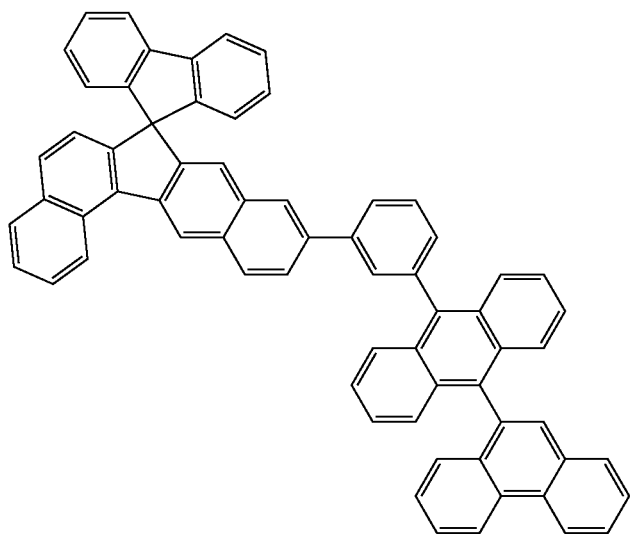
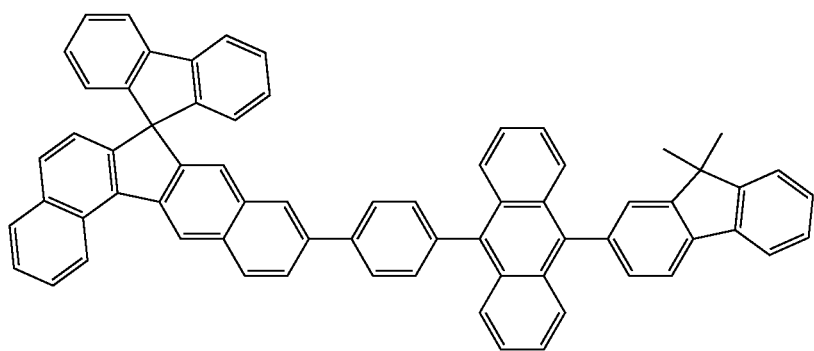

-continued
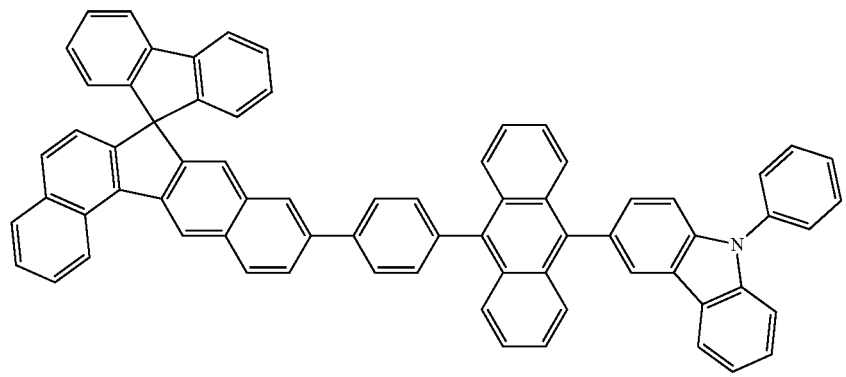
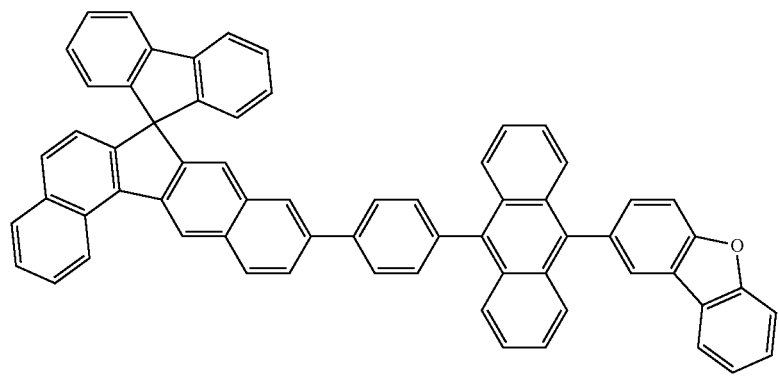
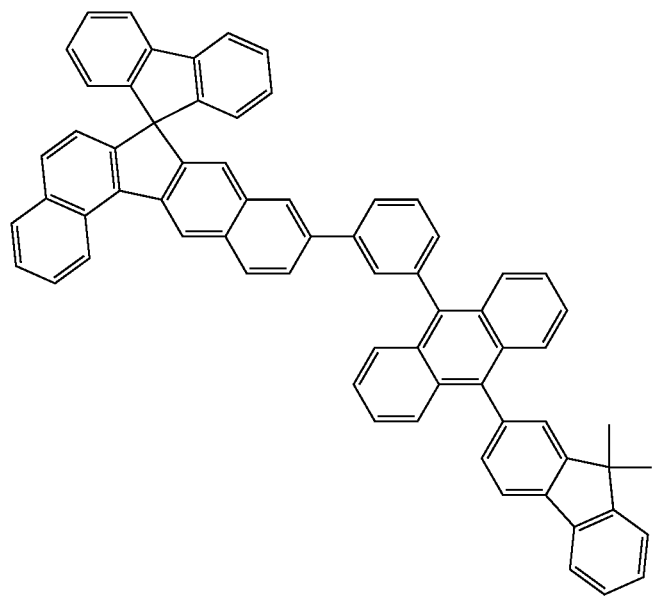

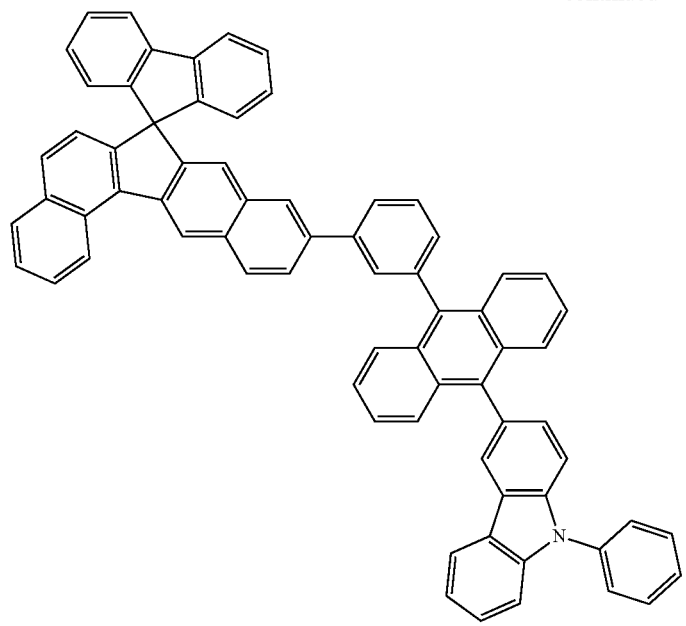
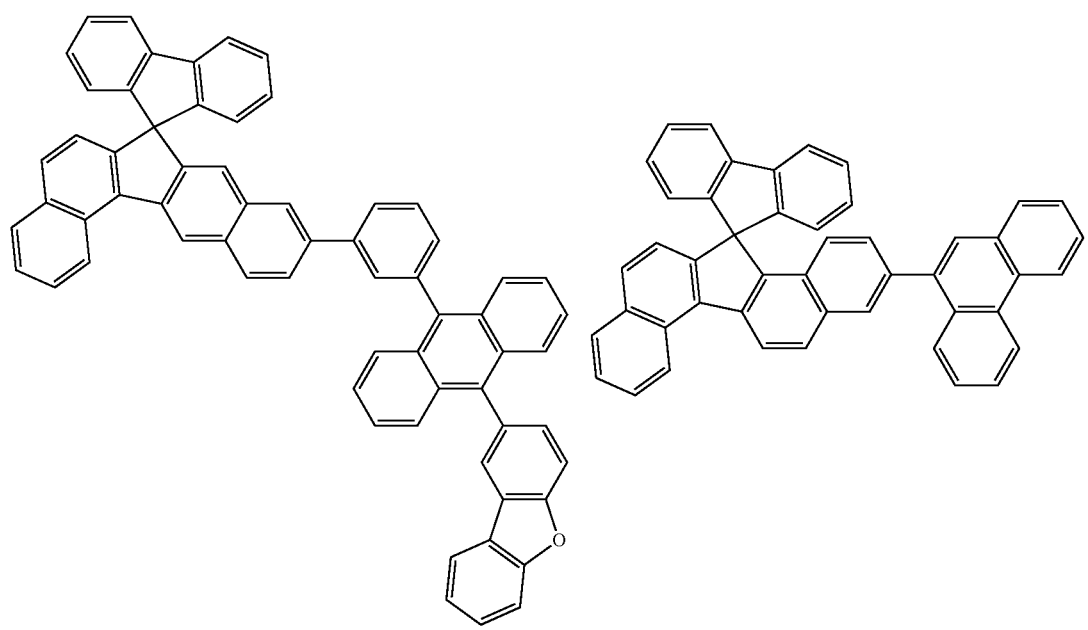
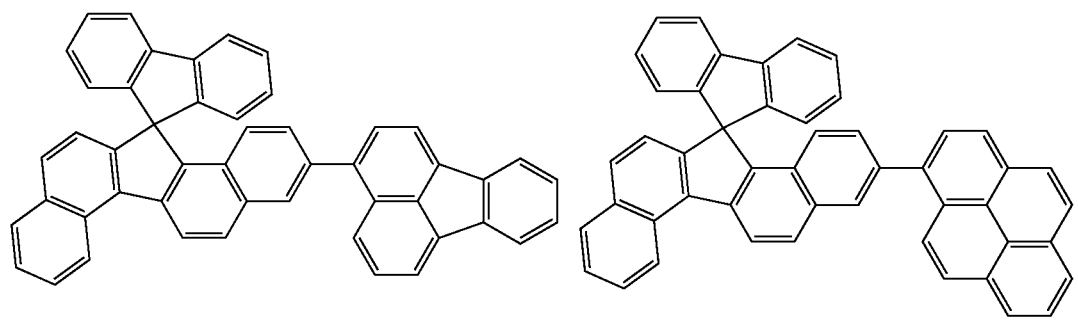

-continued
201   202
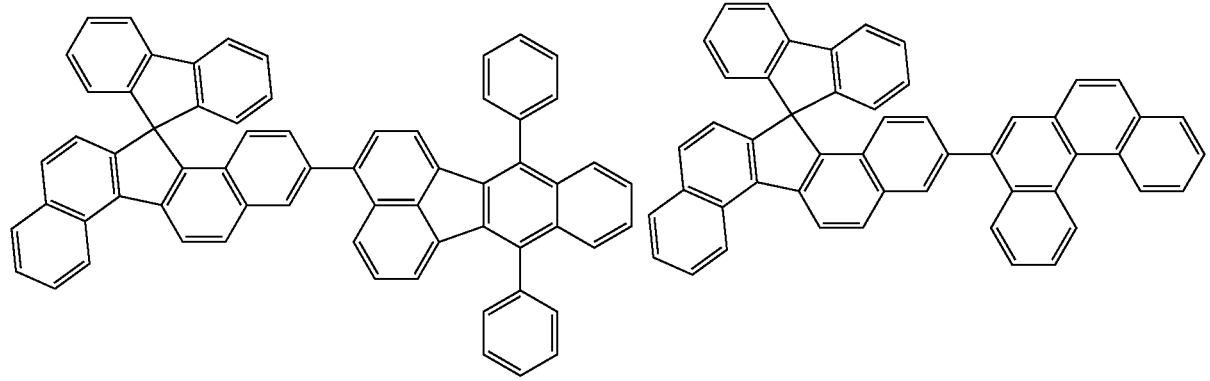
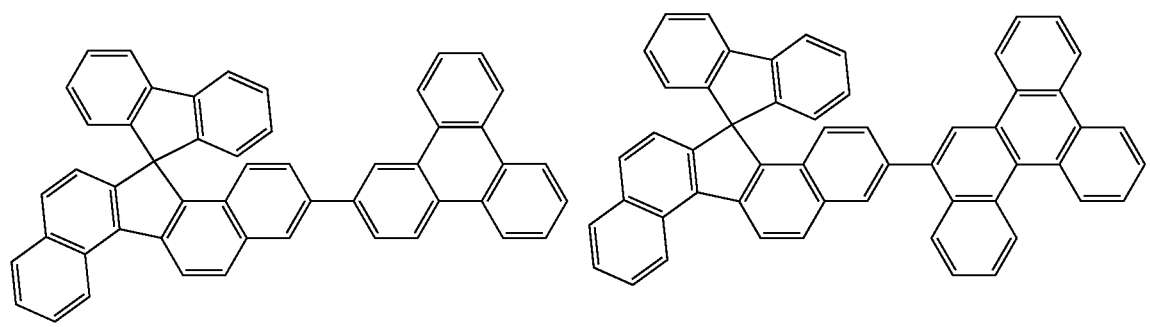
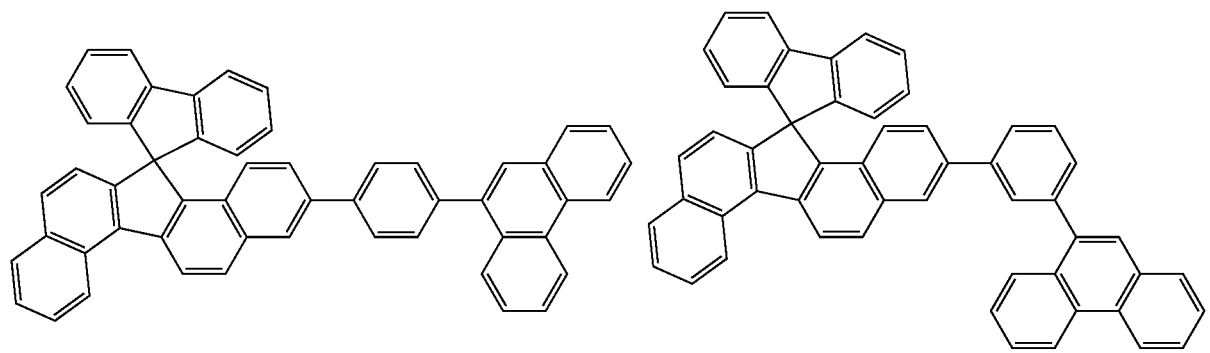
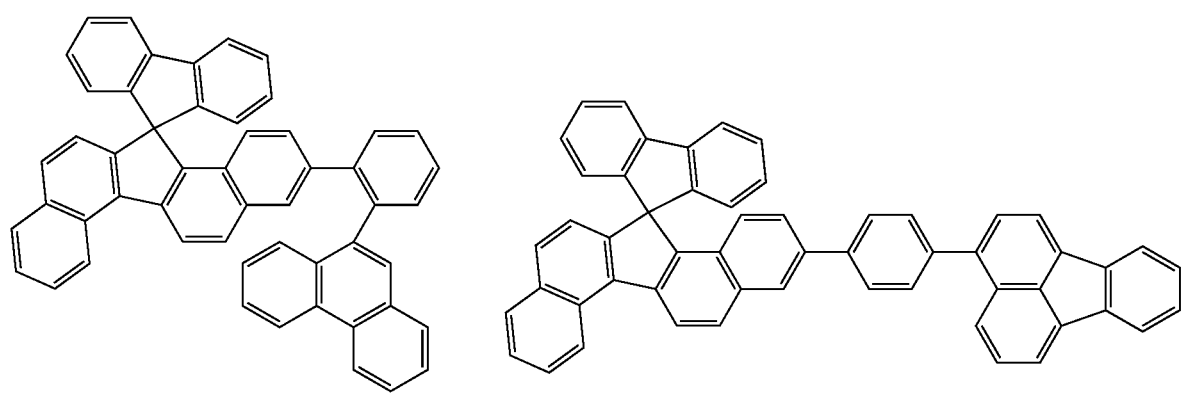

-continued
| 203 | 204 |
|---|---|
| 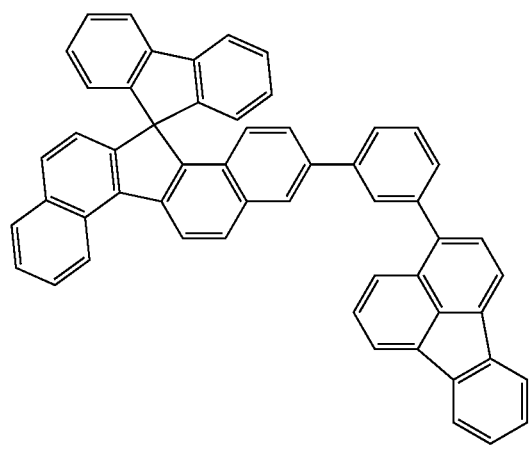 | 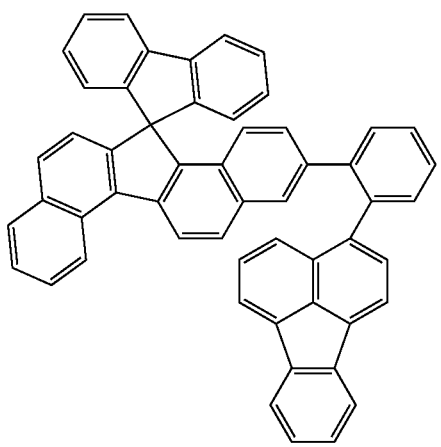 |
| 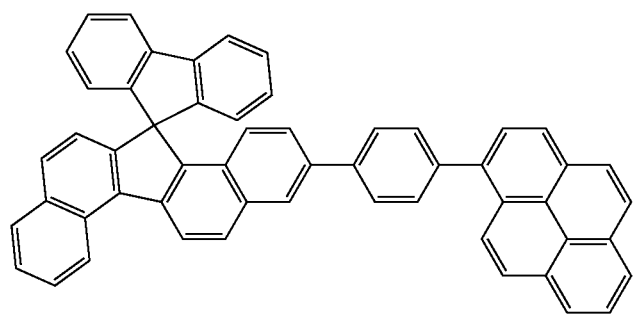 | 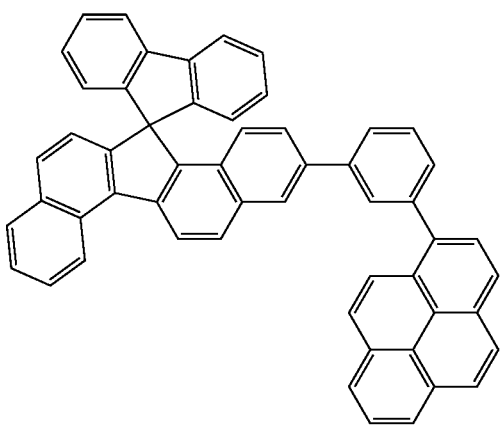 |
| 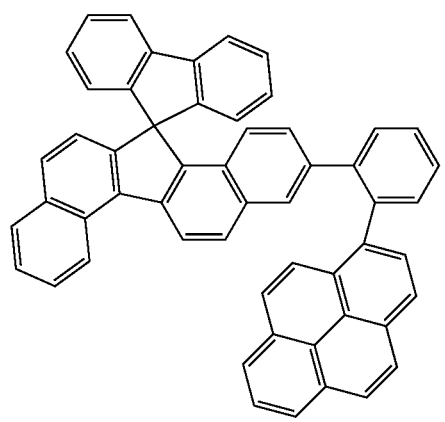 | 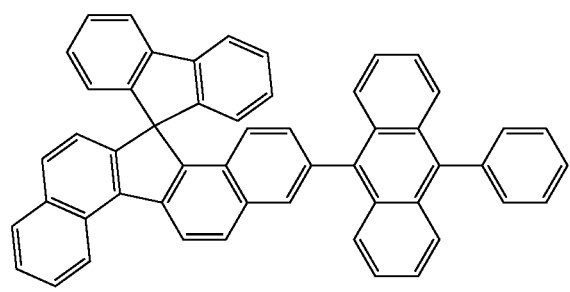 |
| 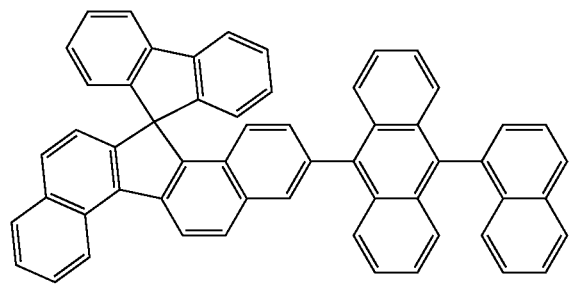 | 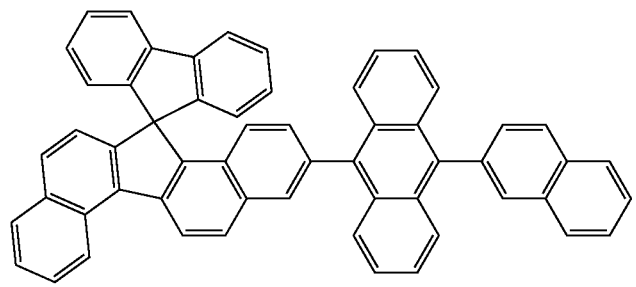 |

-continued
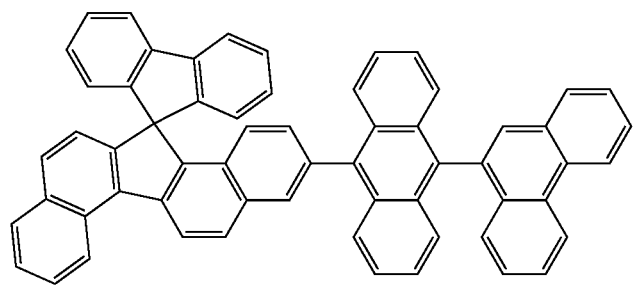
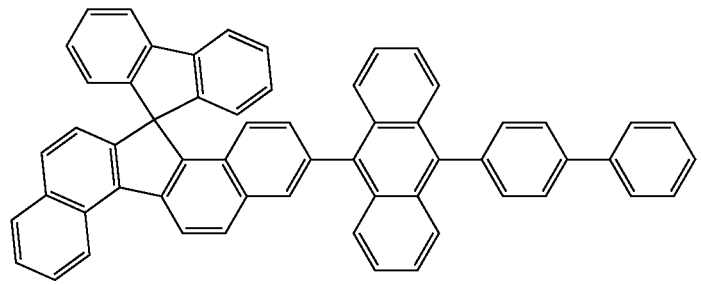
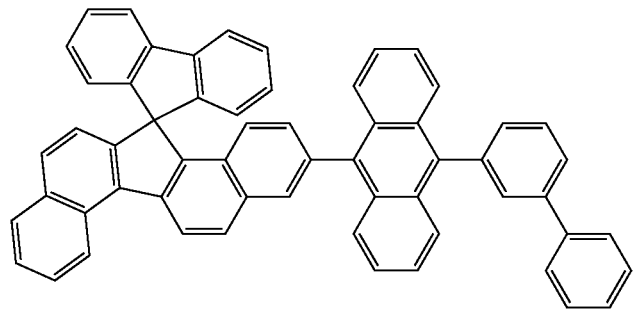
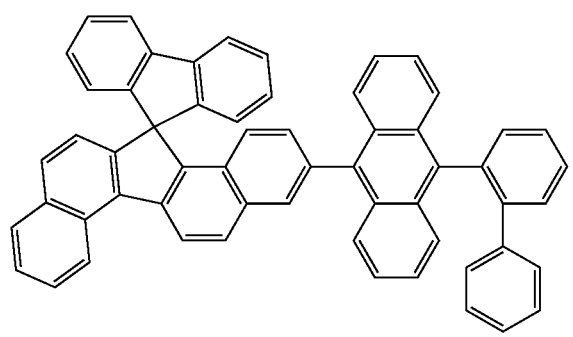
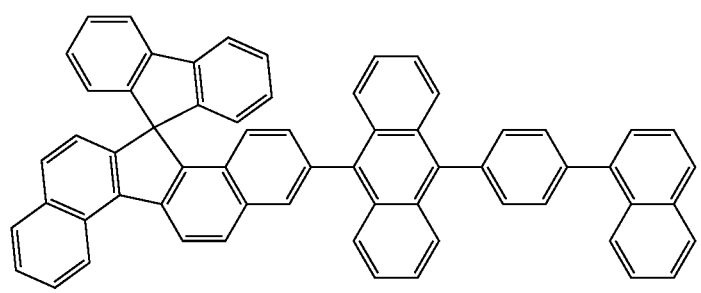

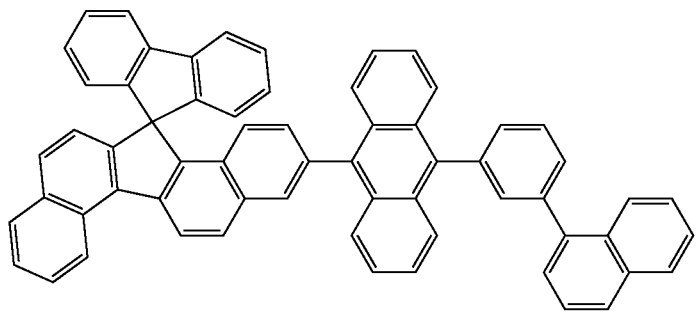
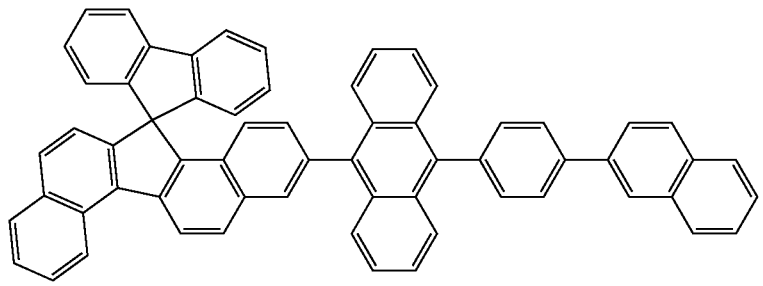
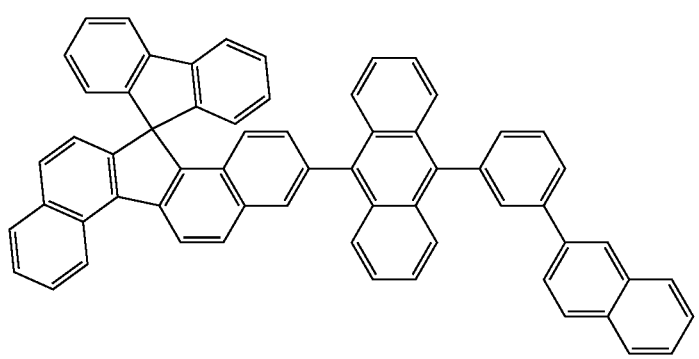
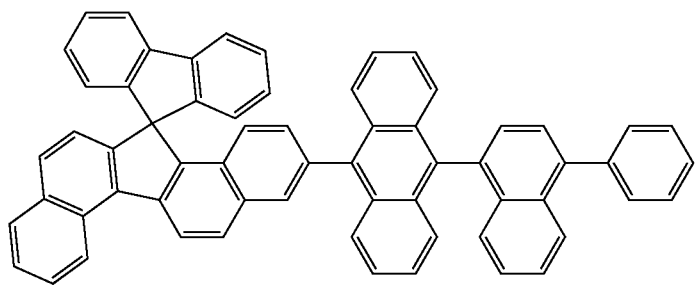
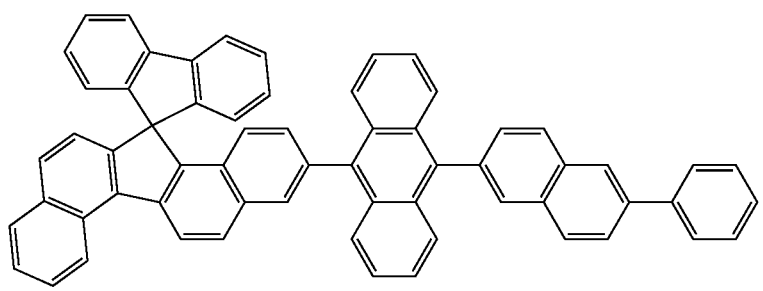

-continued
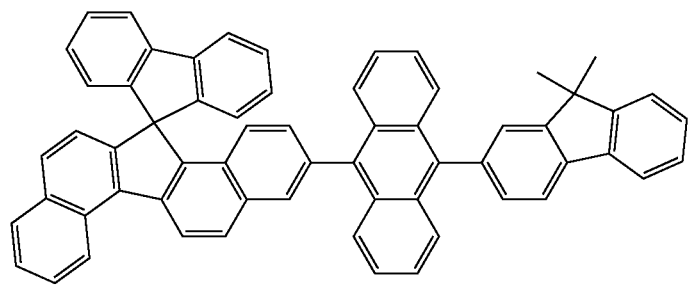
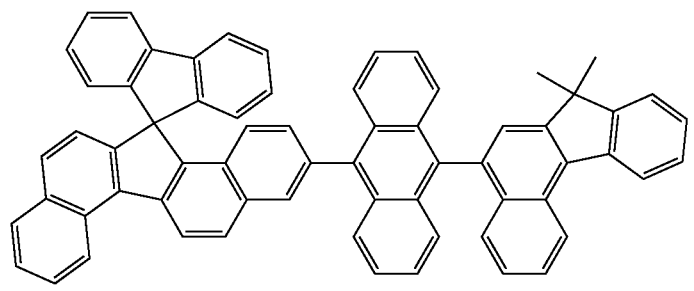
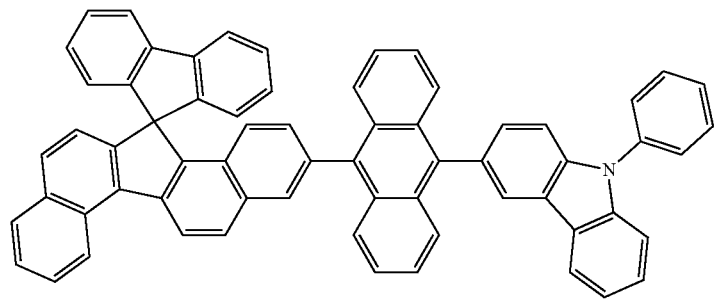
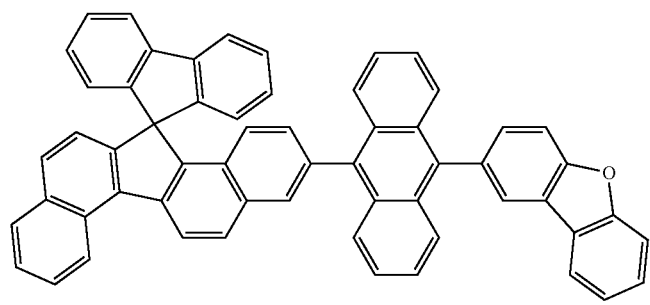
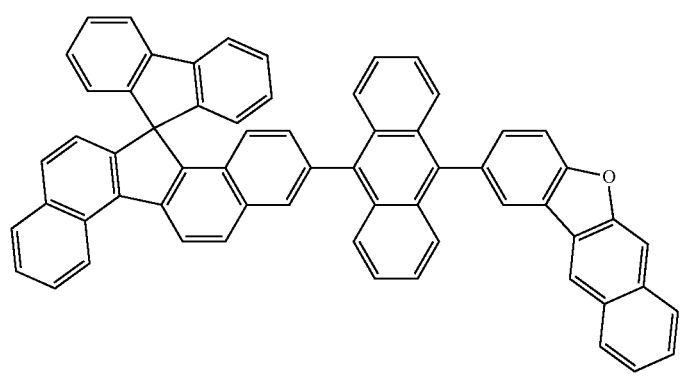

-continued
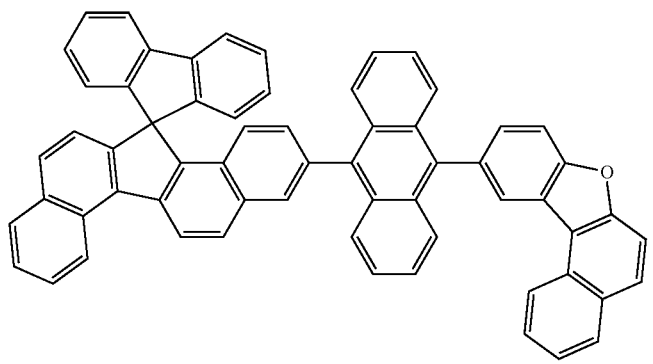
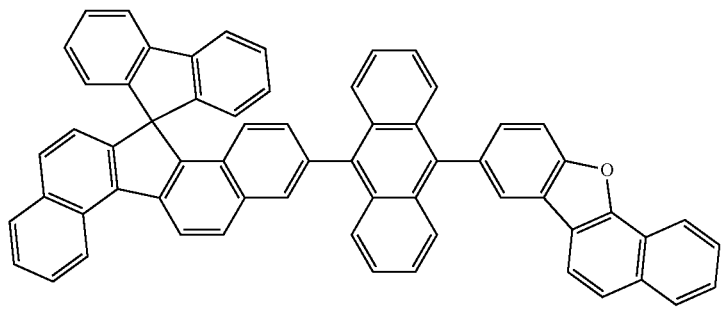
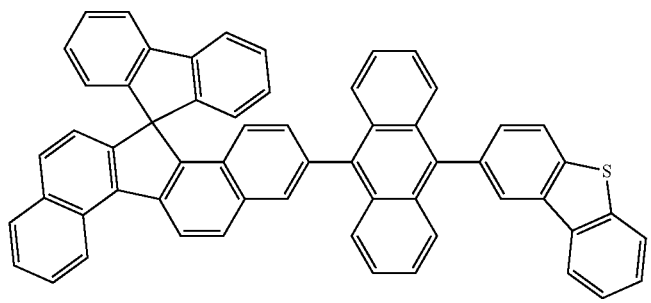
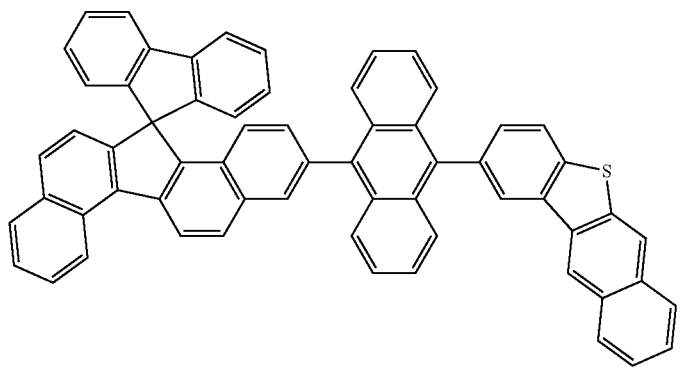
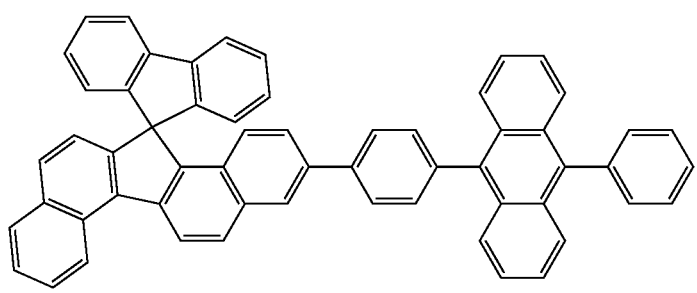

-continued
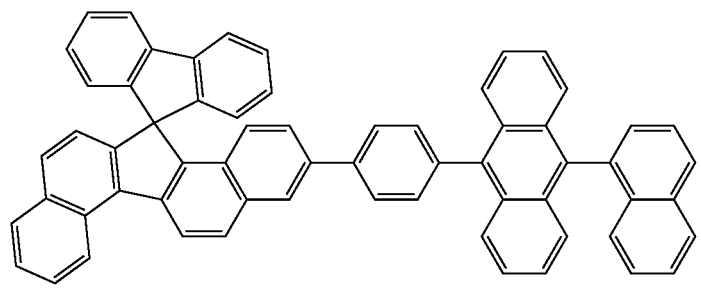
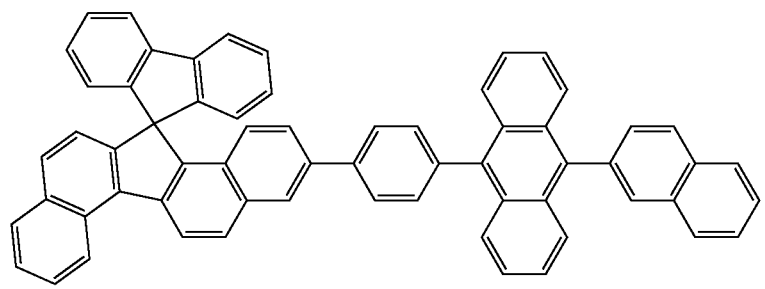
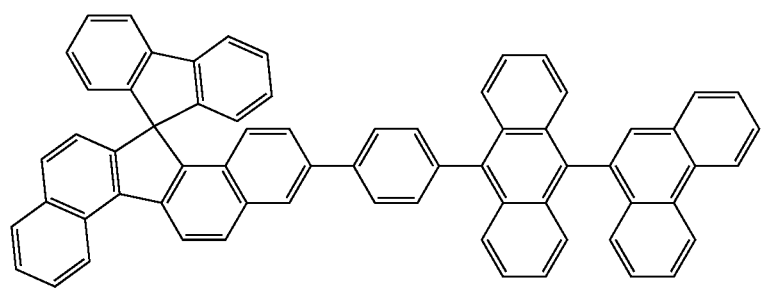
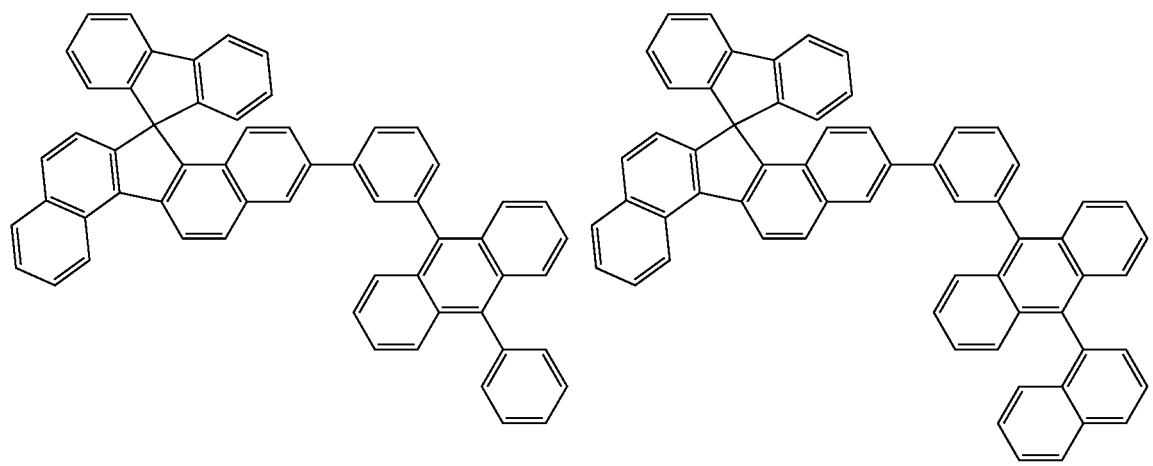

215
216
-continued
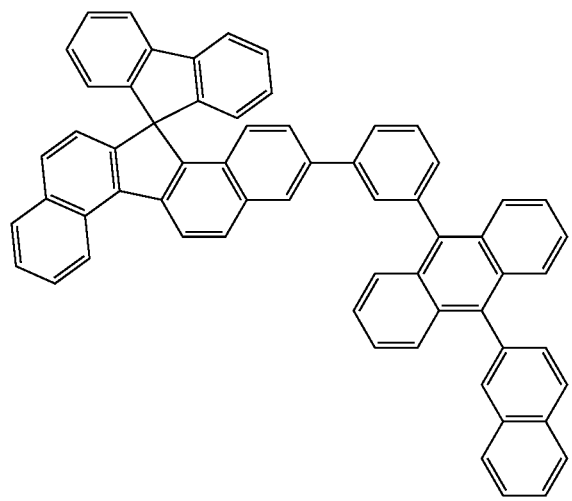
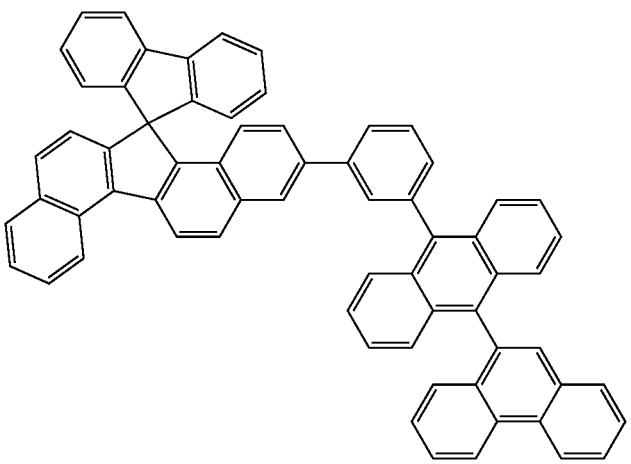
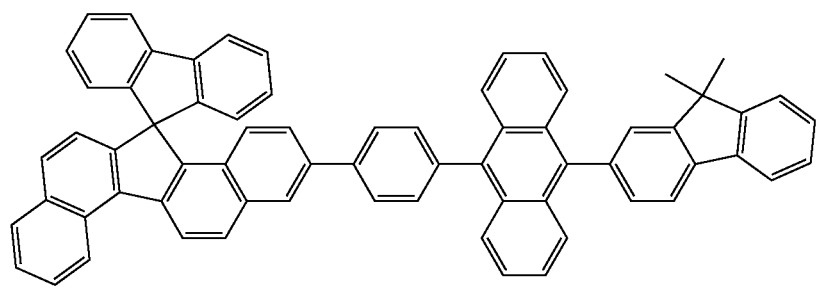
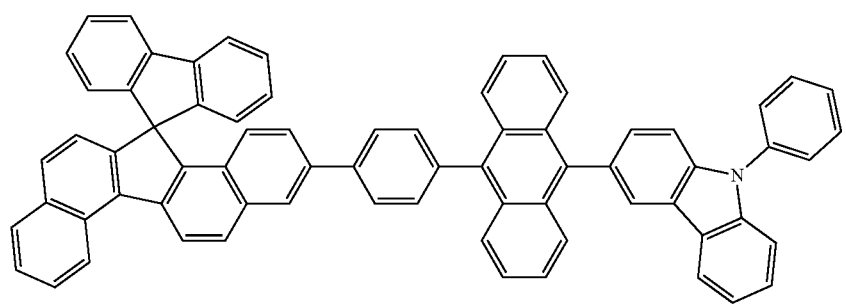
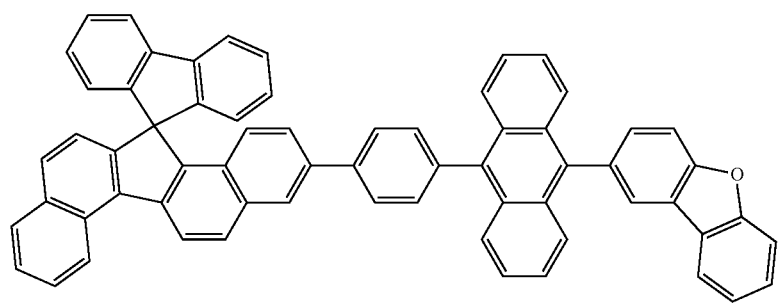

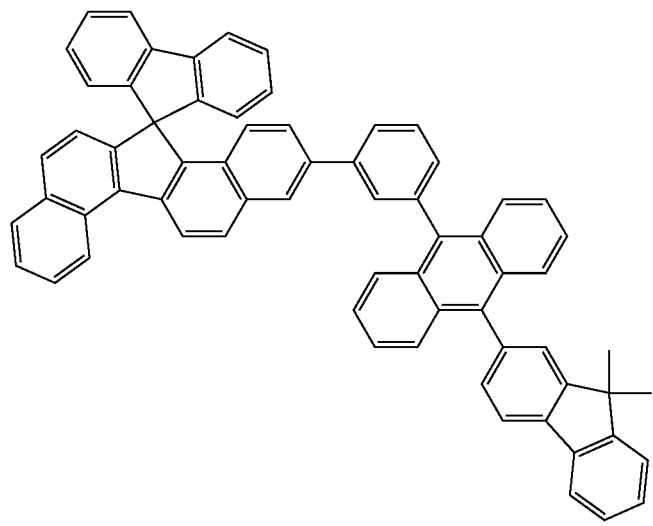
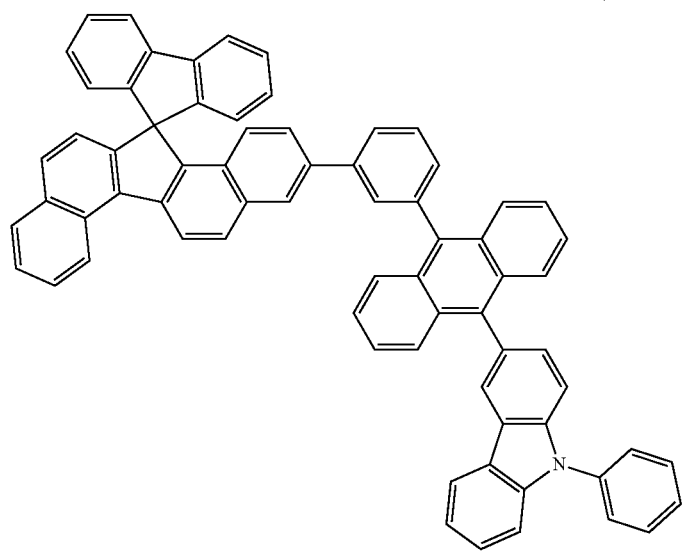
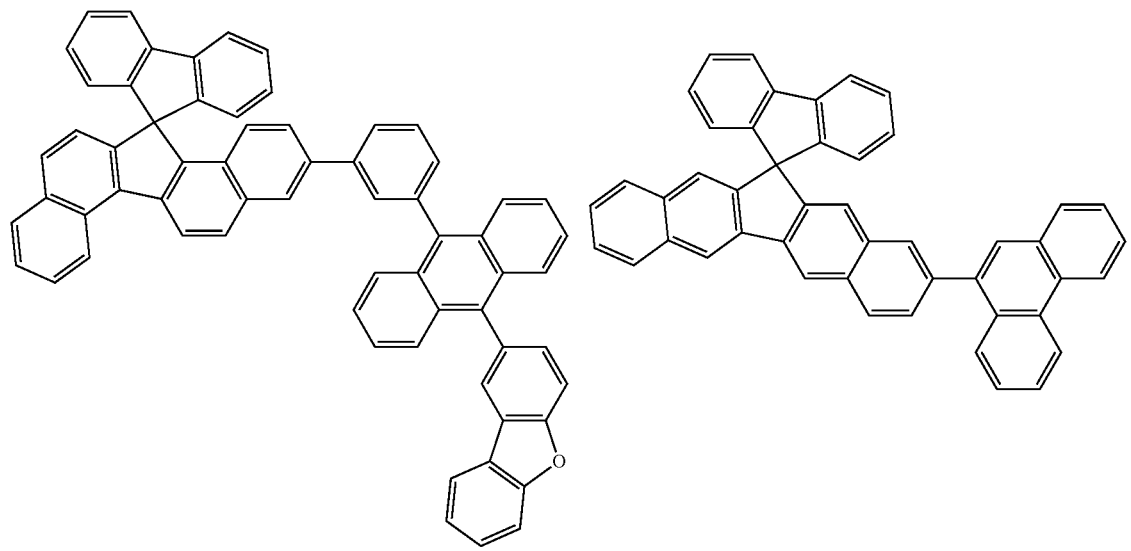

219 220
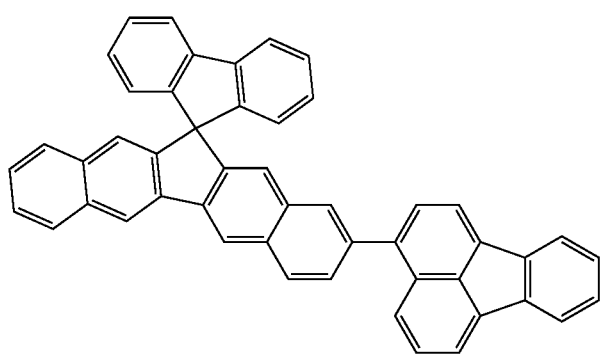
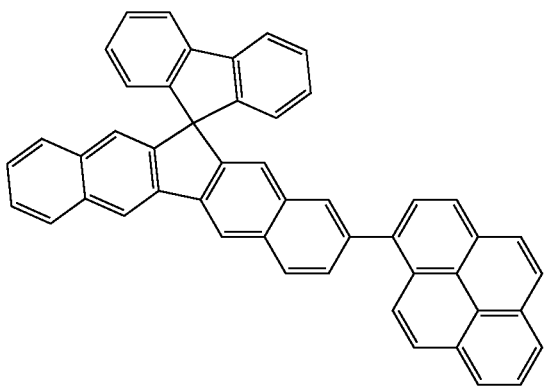
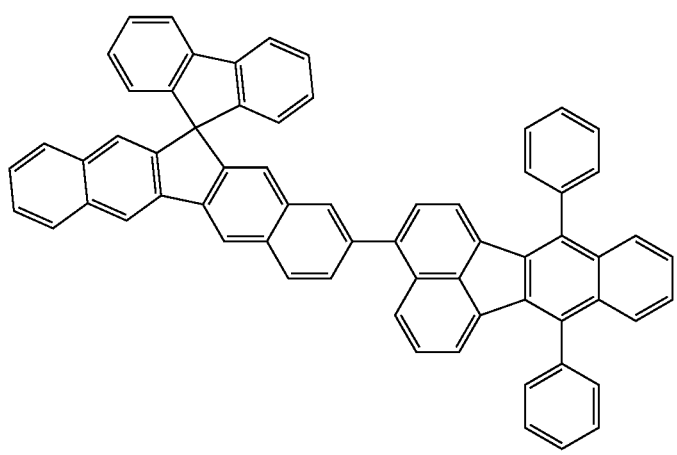
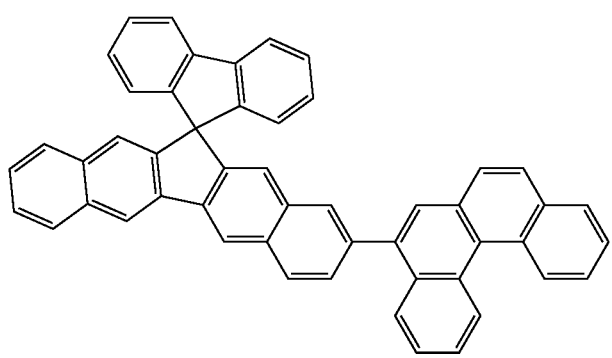
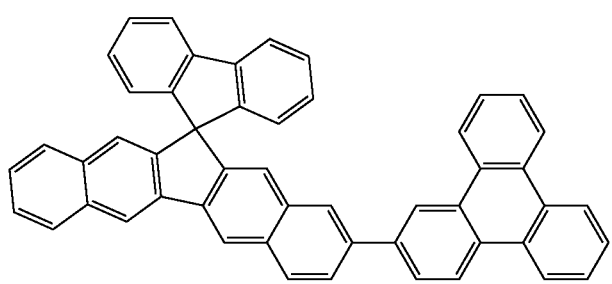

-continued
221
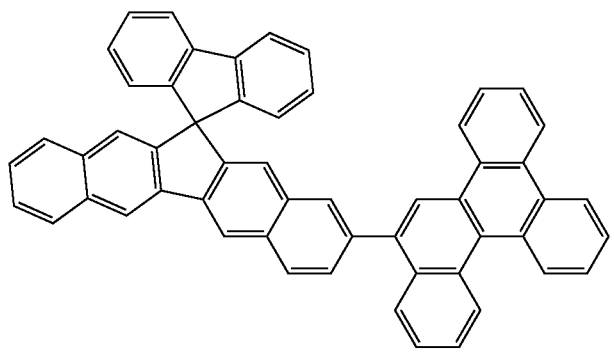
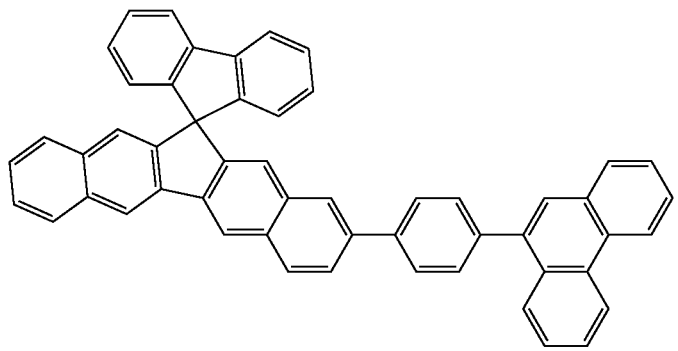
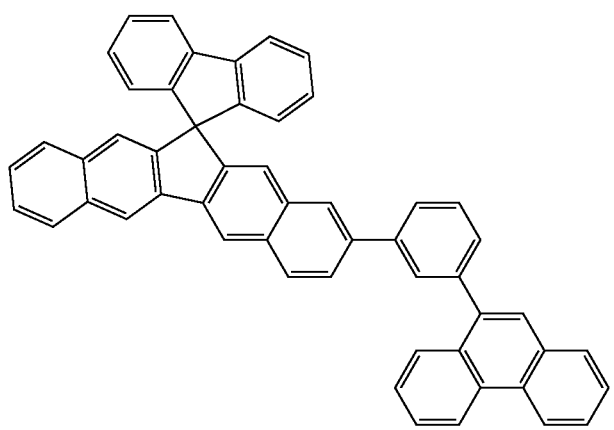
222
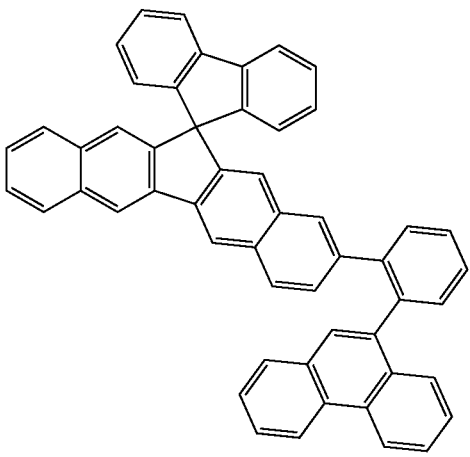
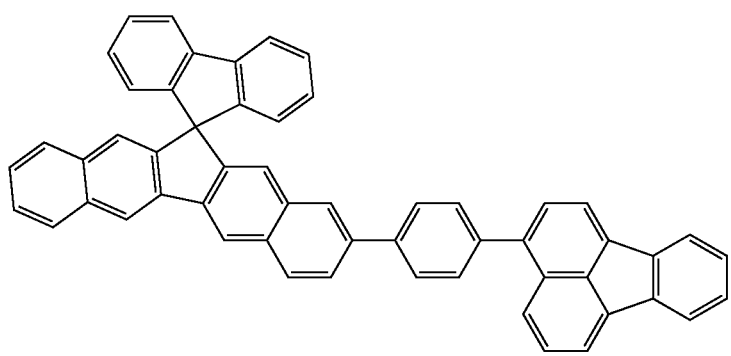

-continued
| 223 | 224 |
|---|---|
| 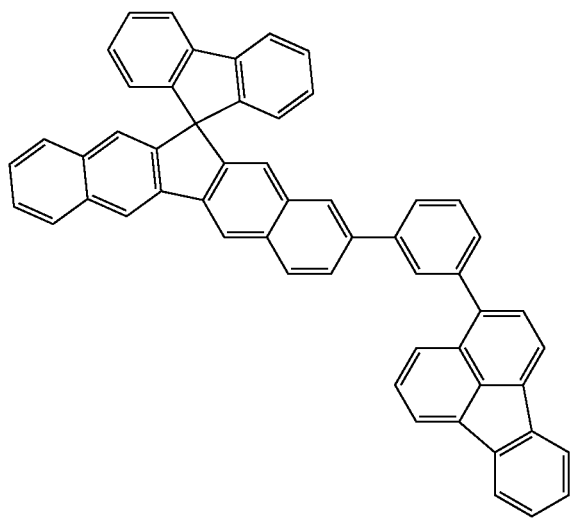 | 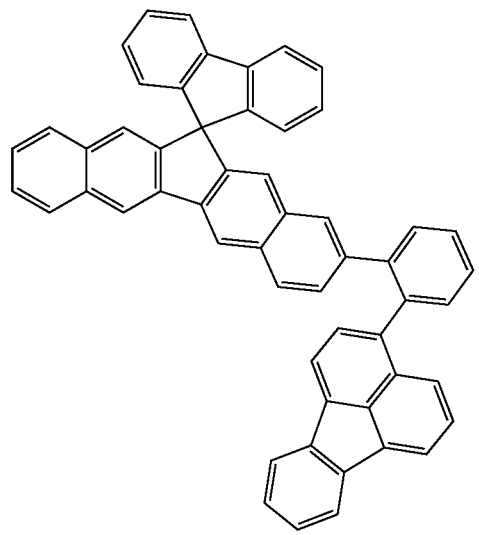 |
| 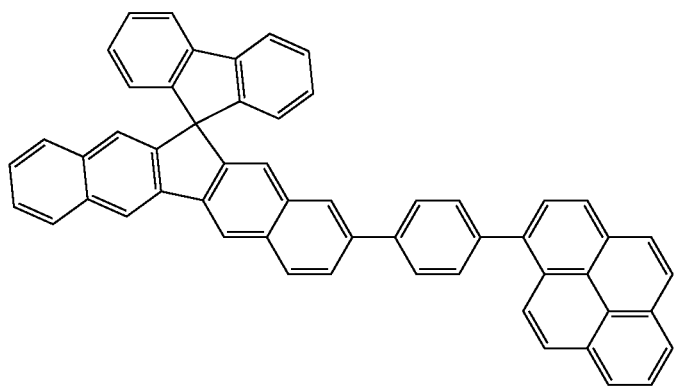 | |
| 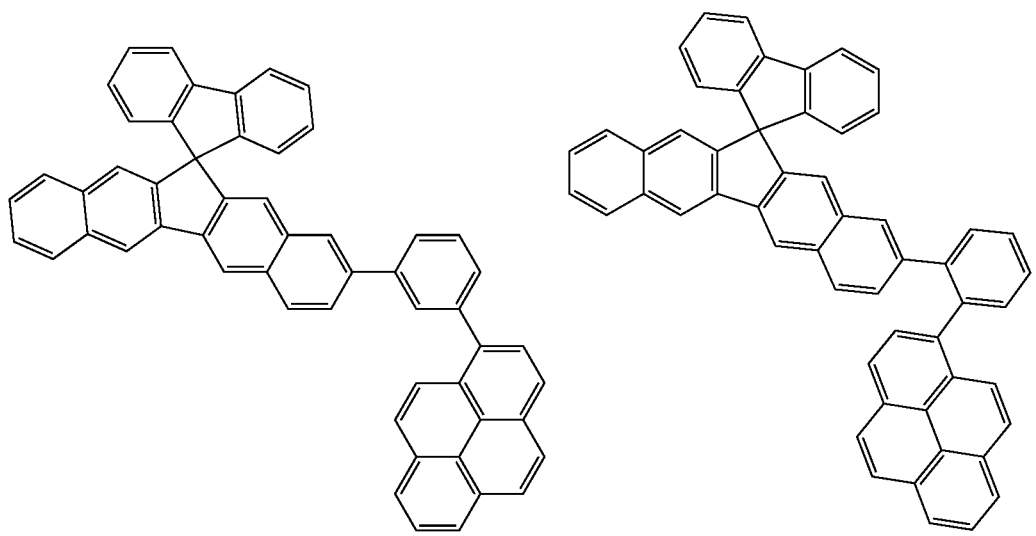 | |

-continued
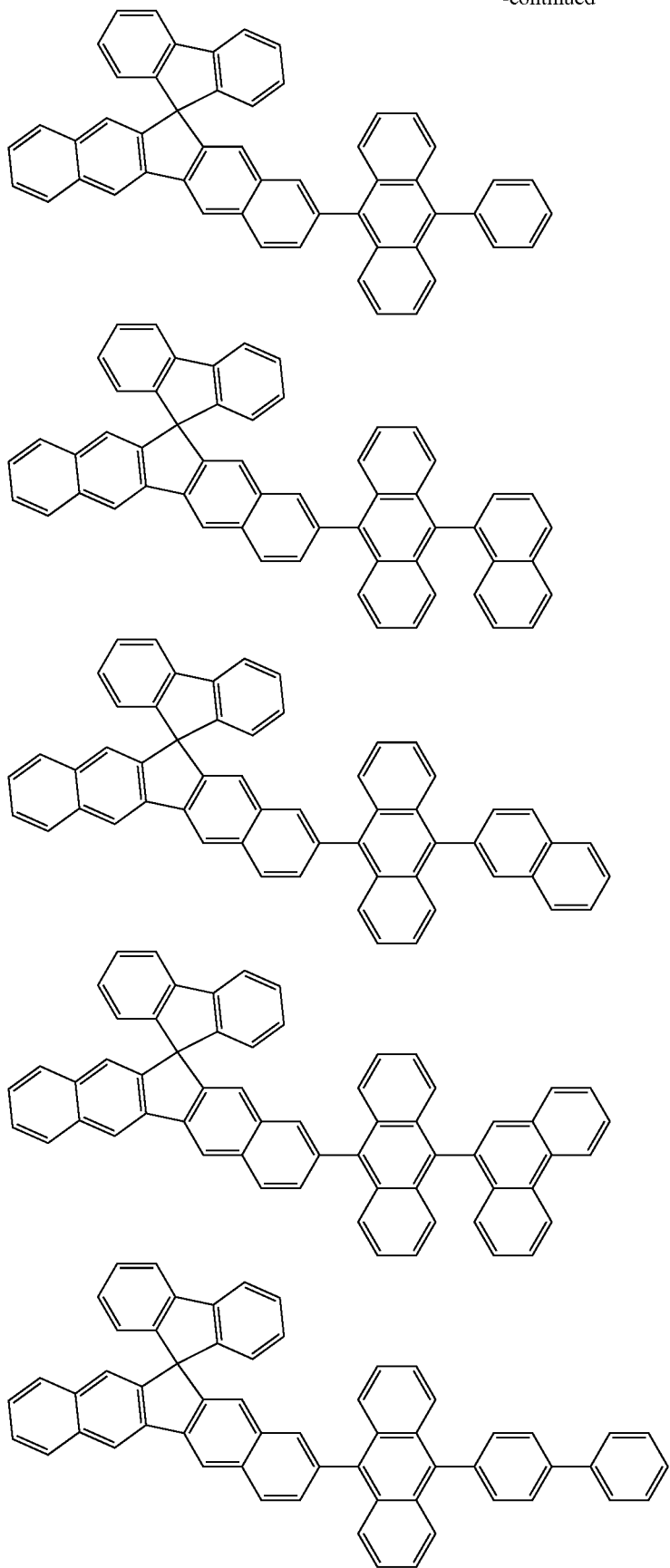

-continued
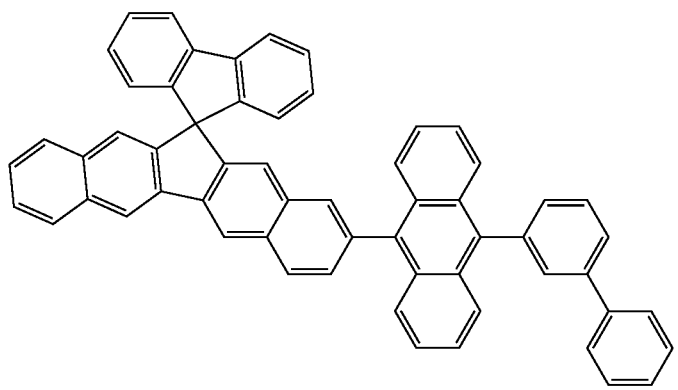

-continued
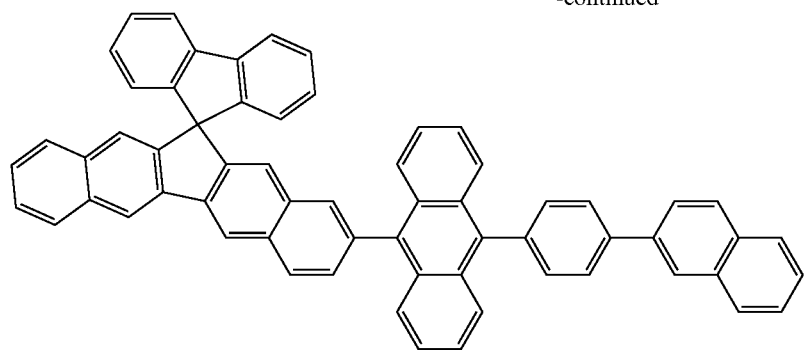
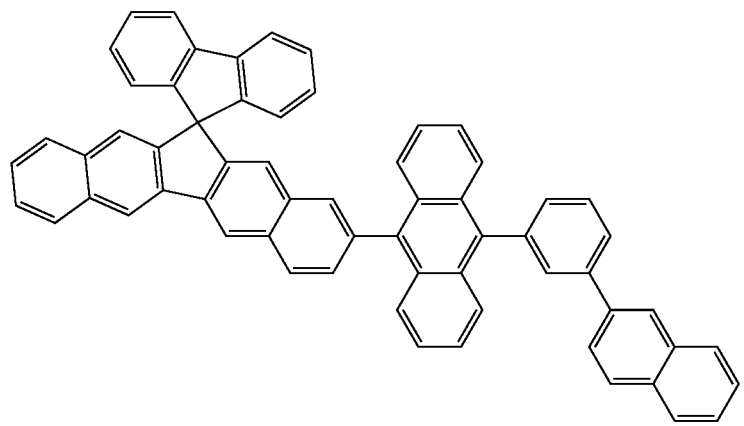
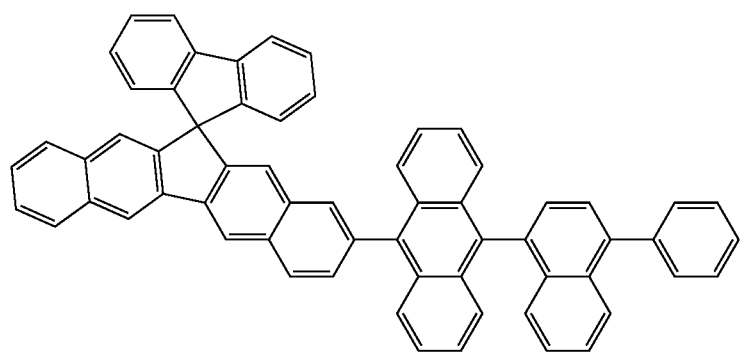
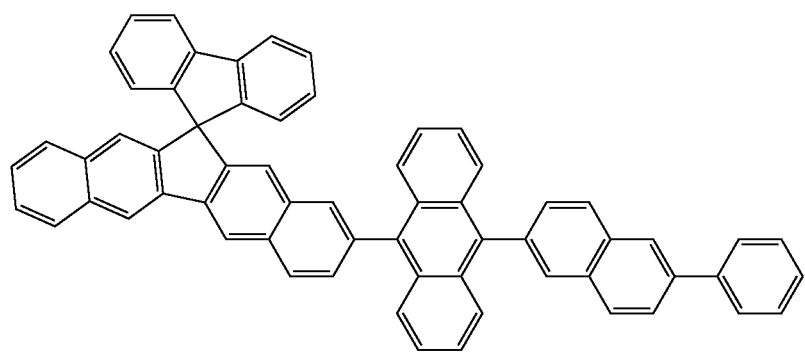

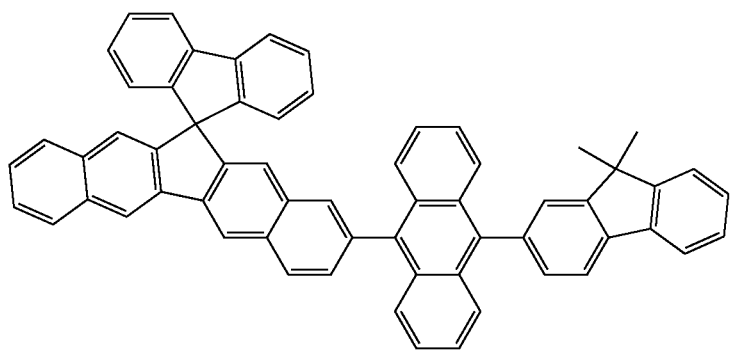
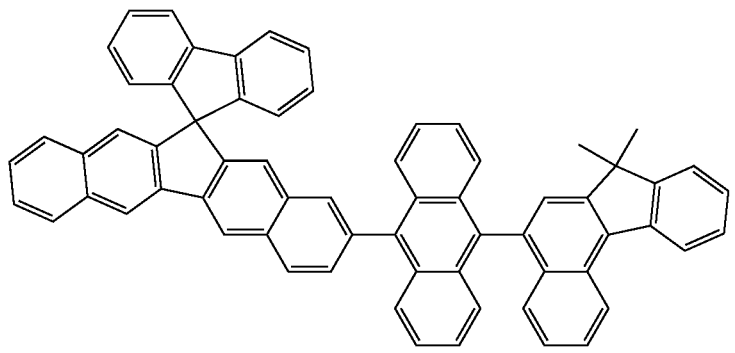
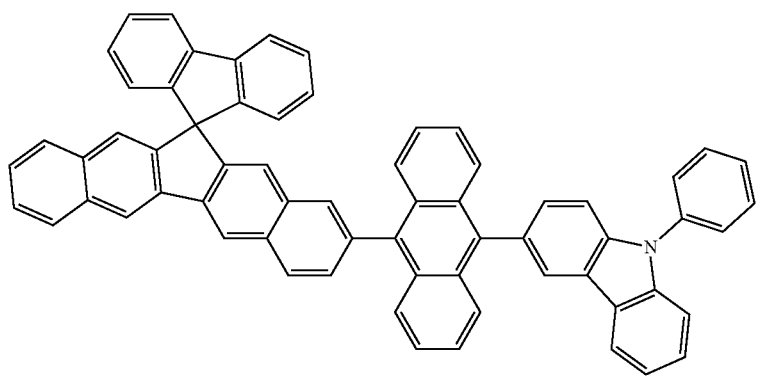
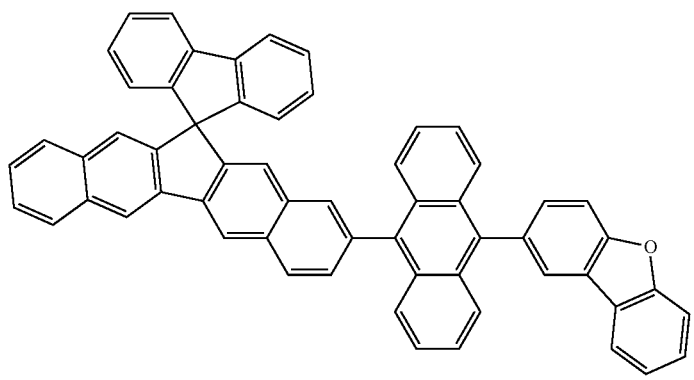

-continued
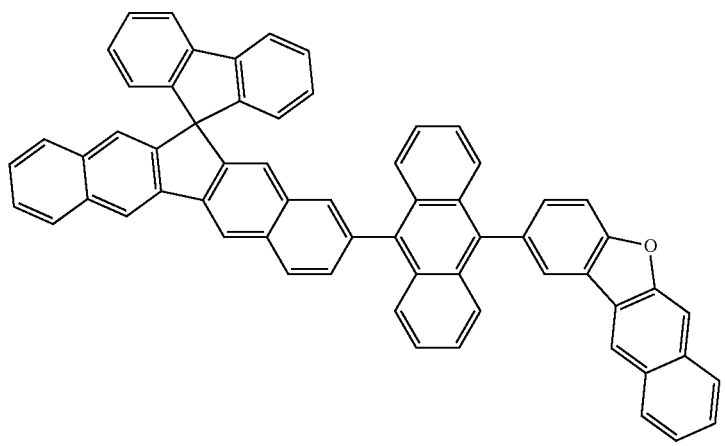
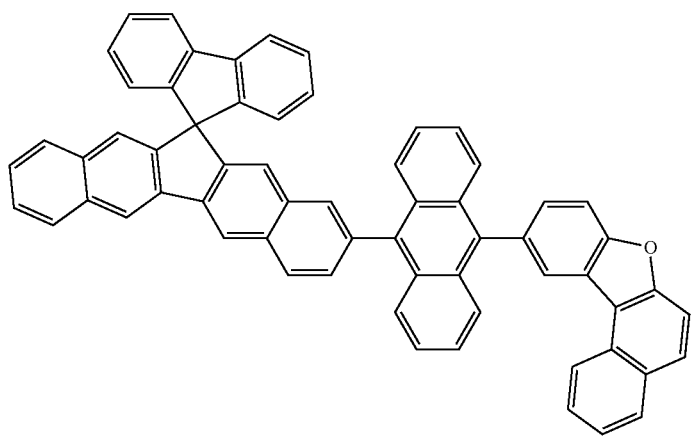
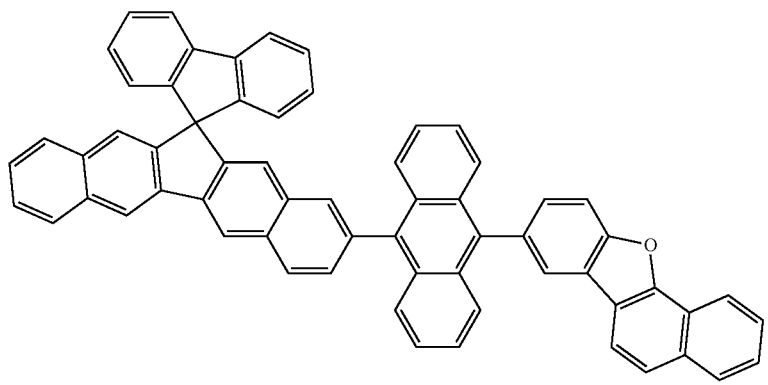
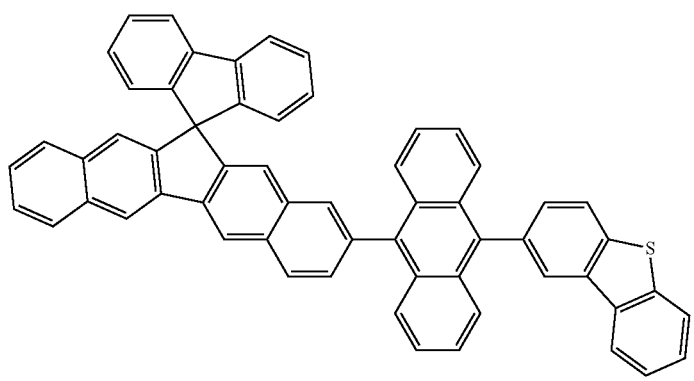

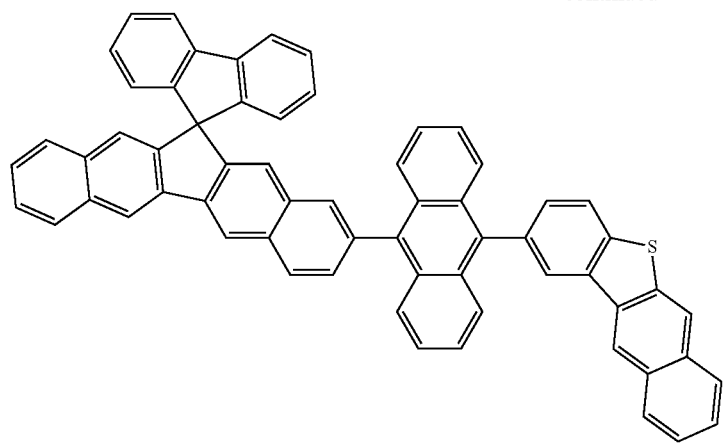
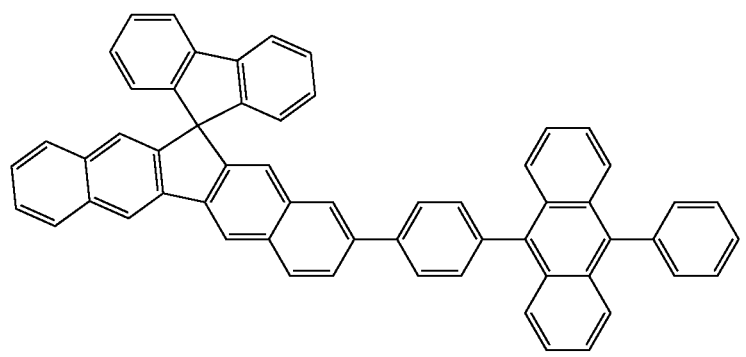
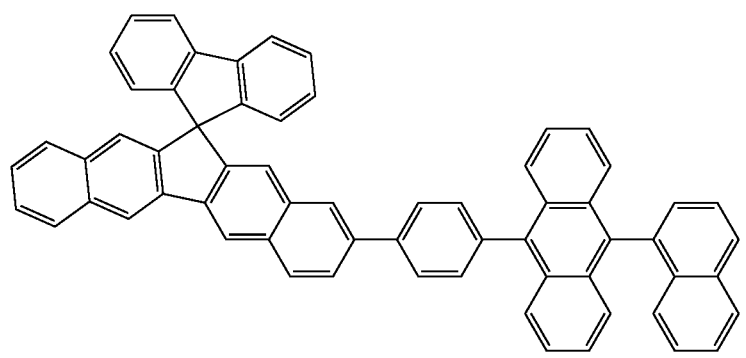
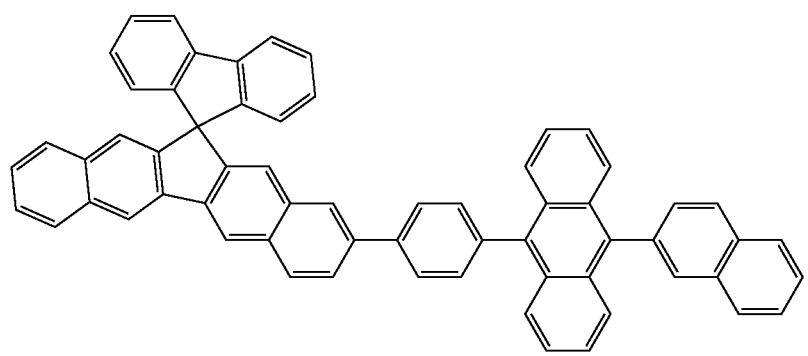

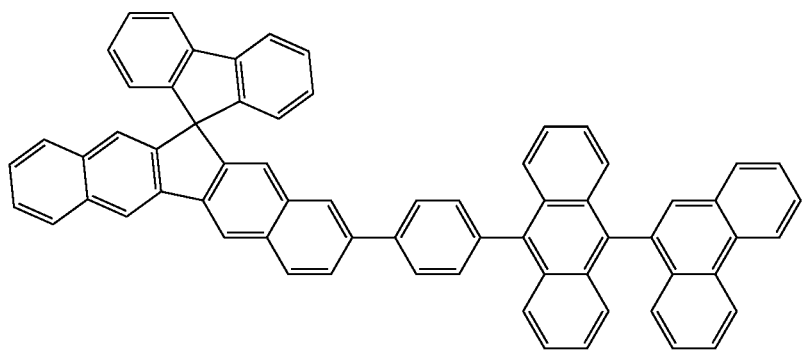
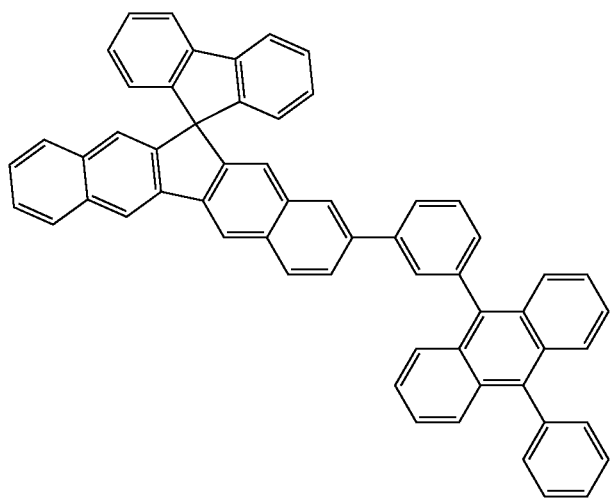
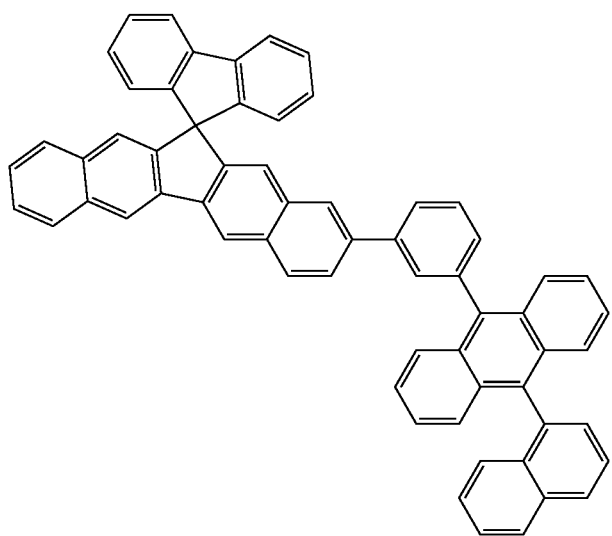

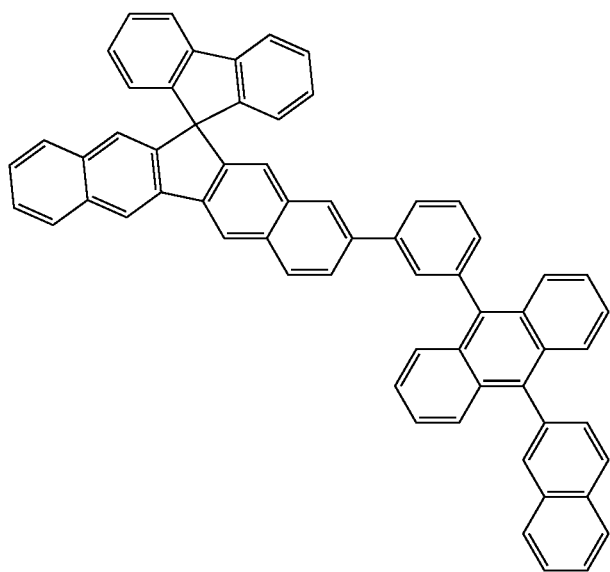
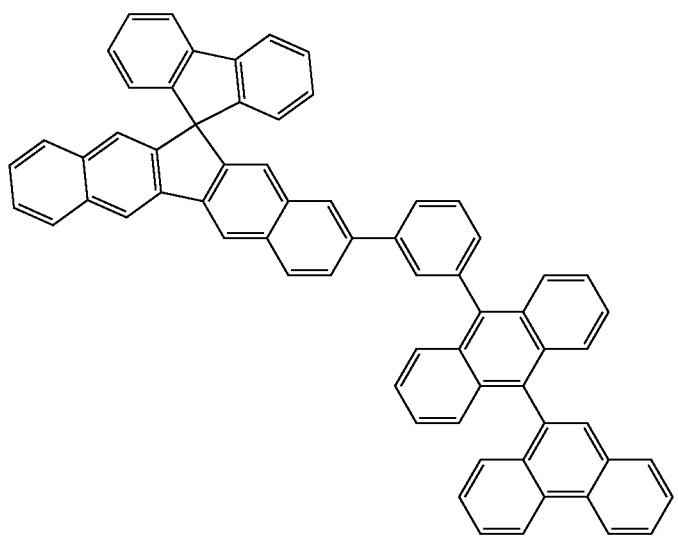
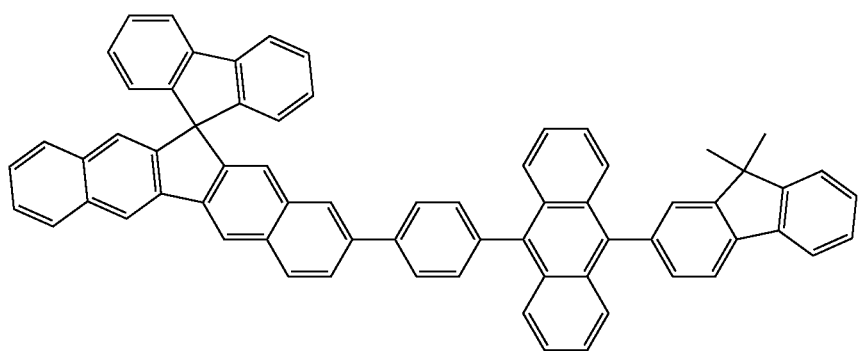

-continued
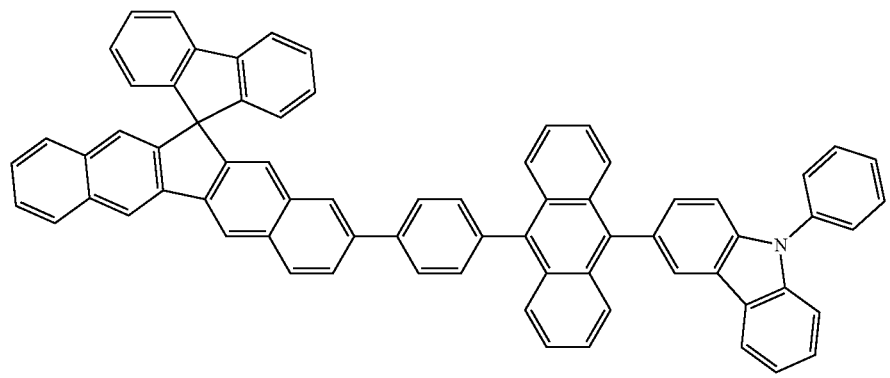
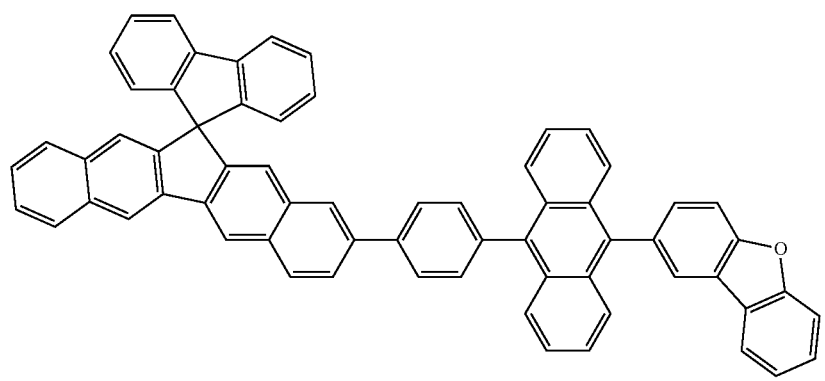
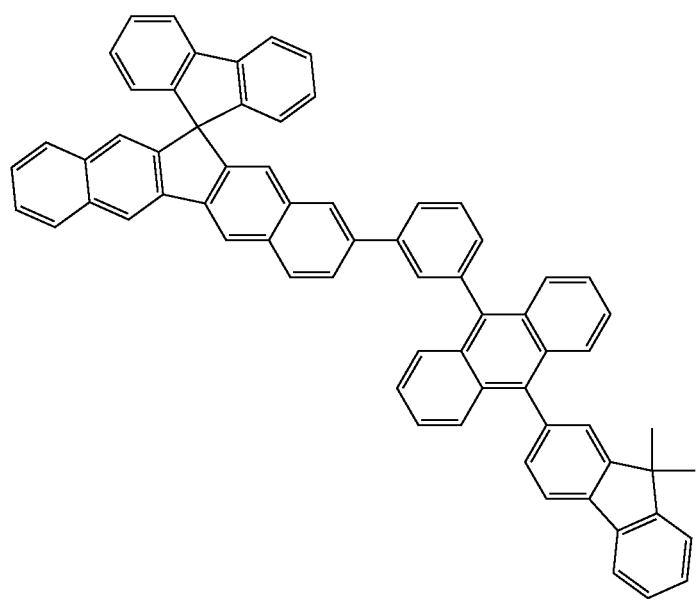

-continued
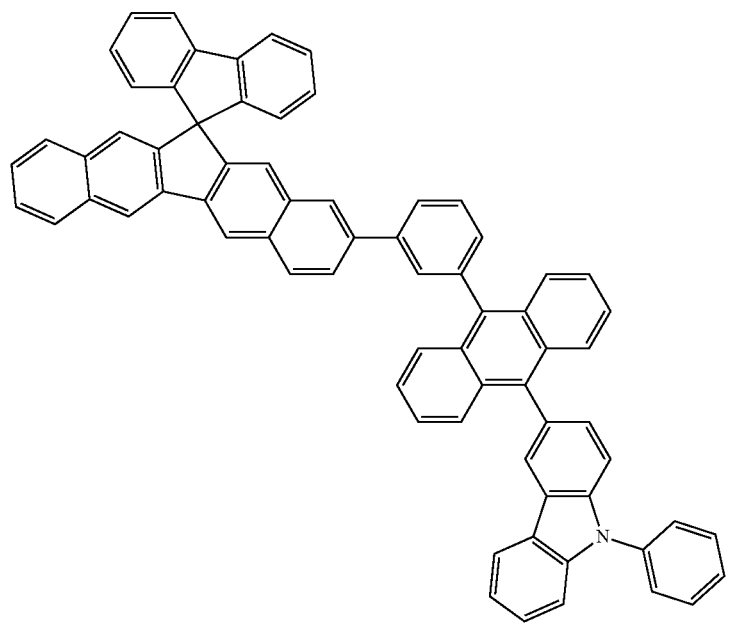
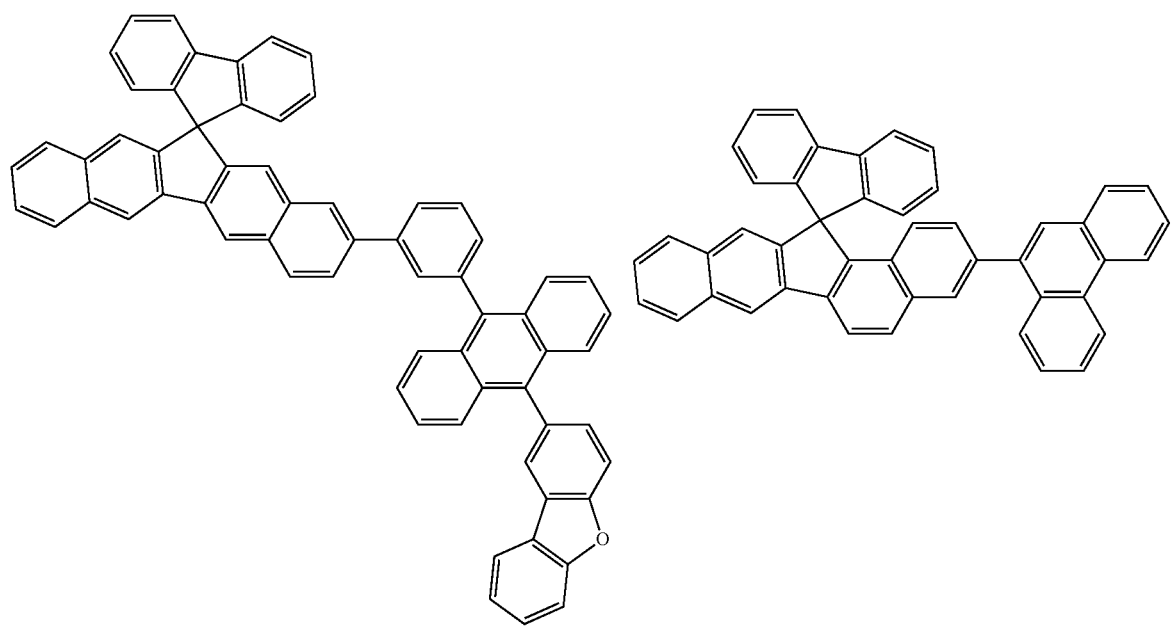
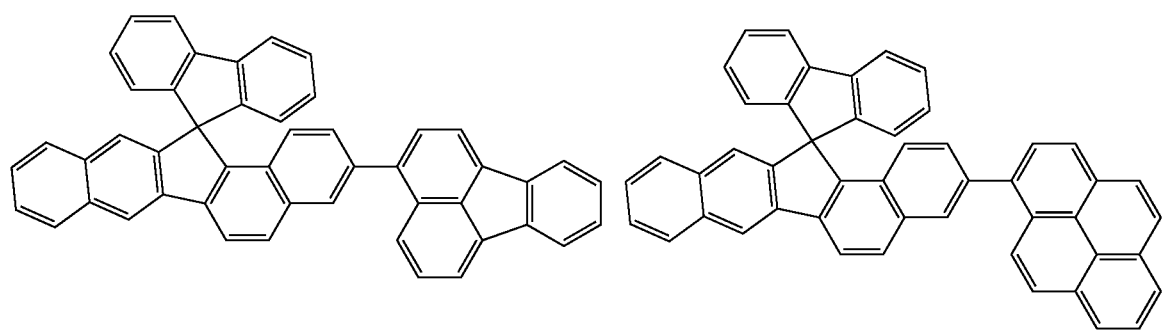

-continued
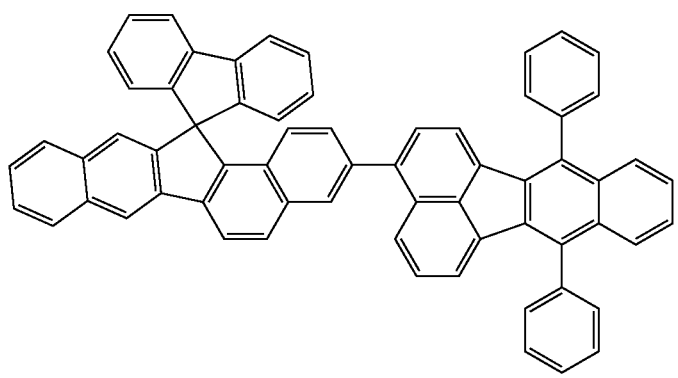

-continued
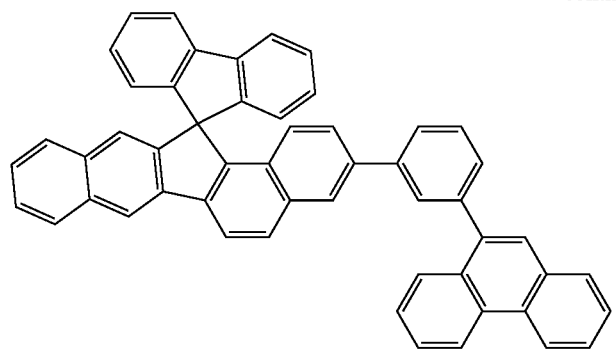
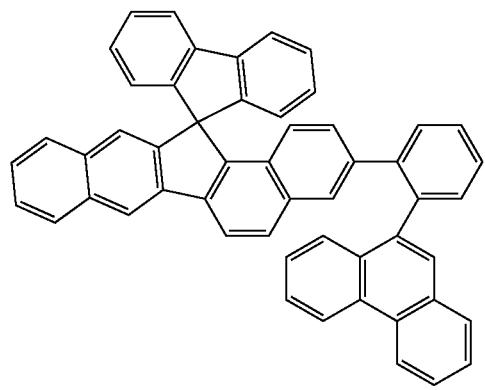
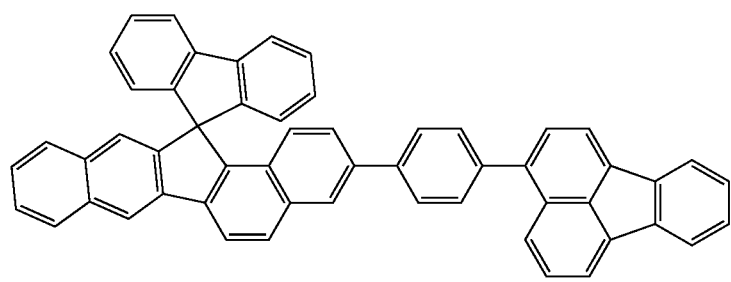
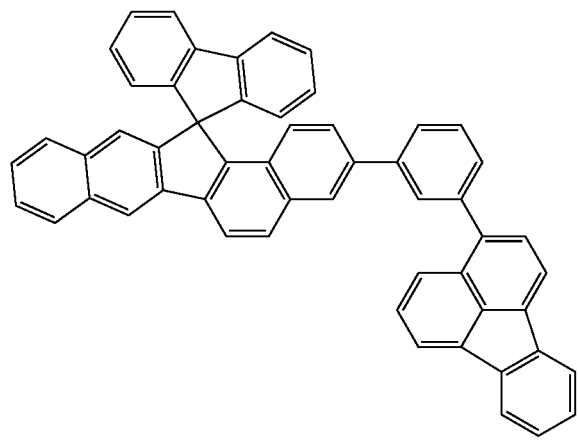
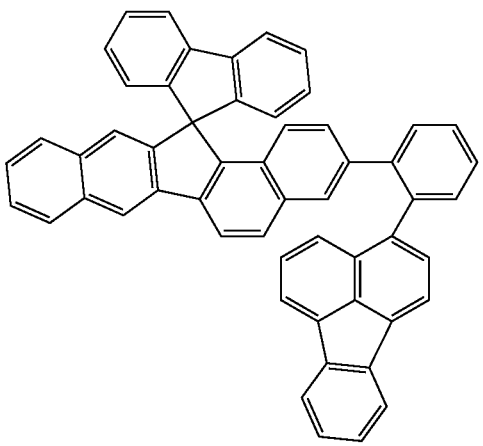

-continued
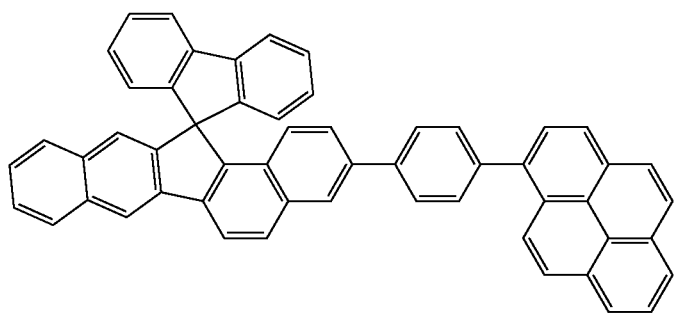

-continued
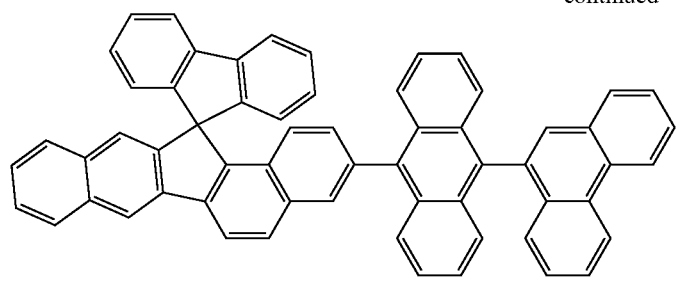
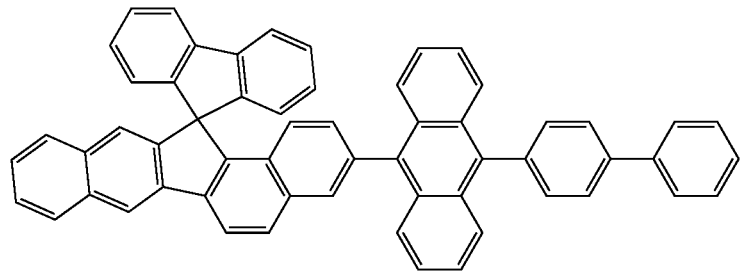
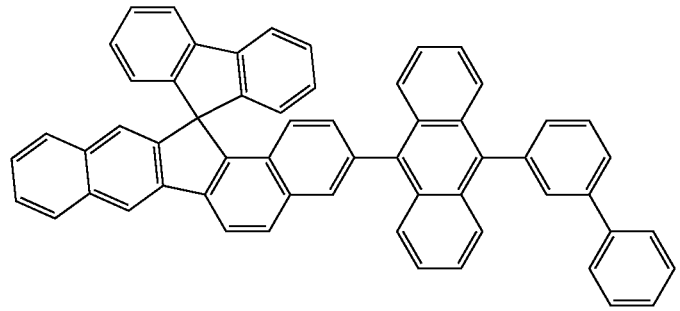
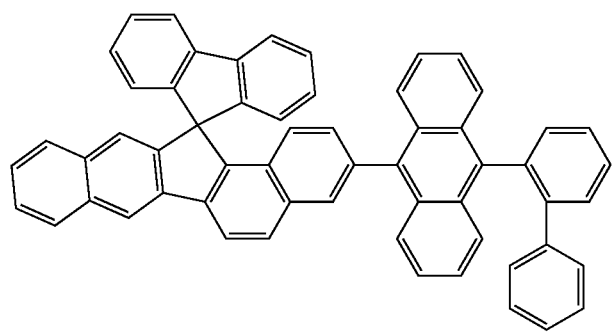
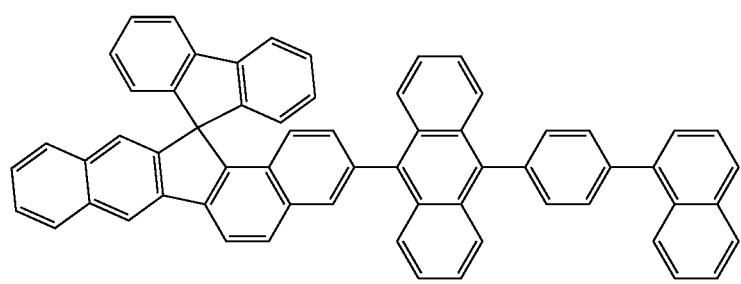

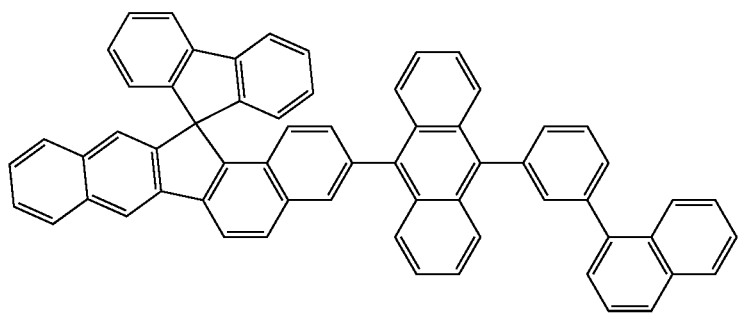
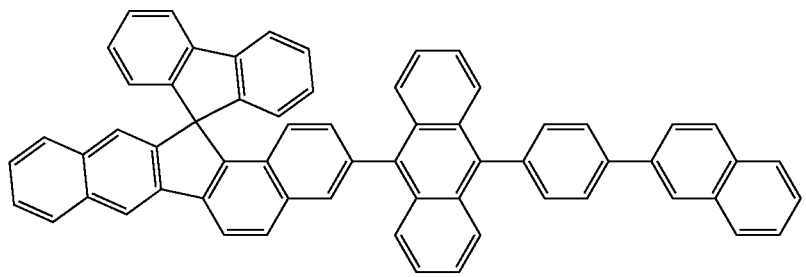
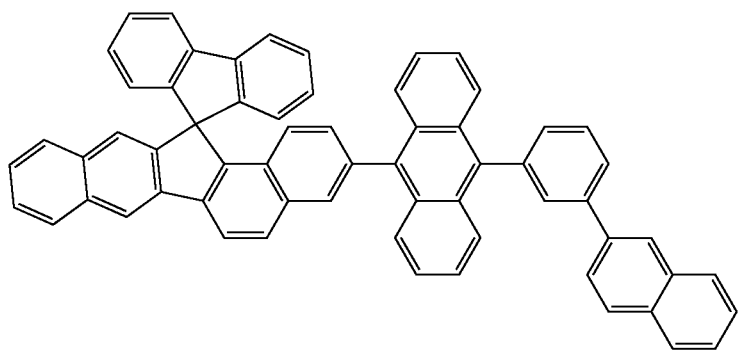
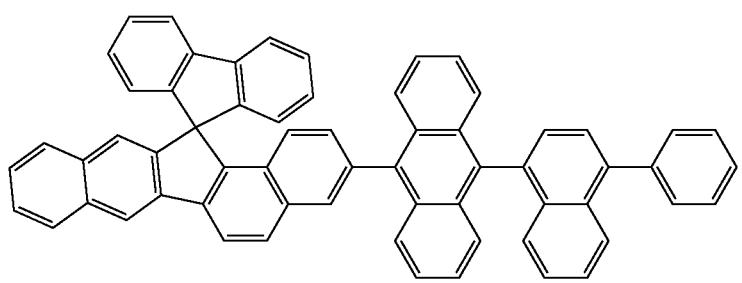
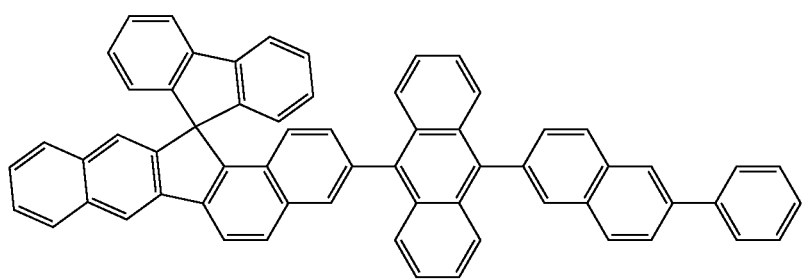

-continued
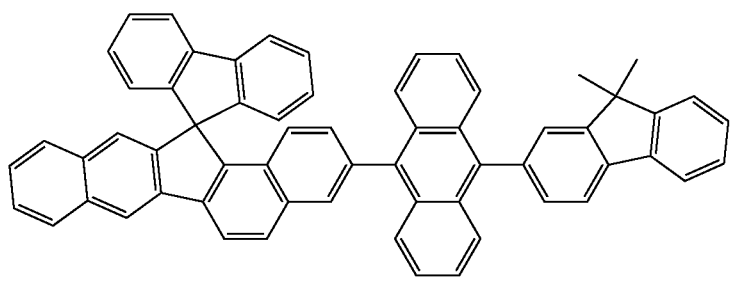
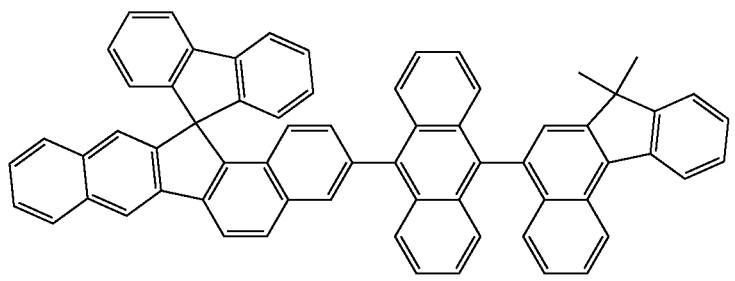
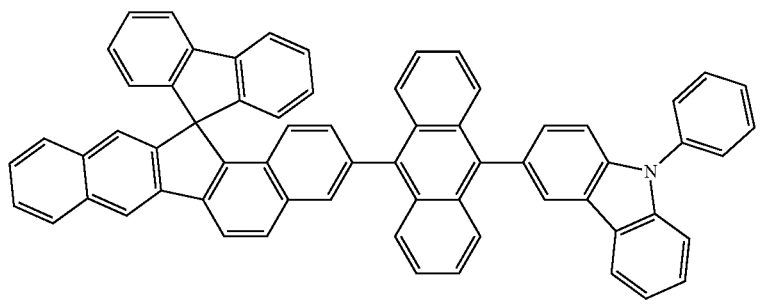
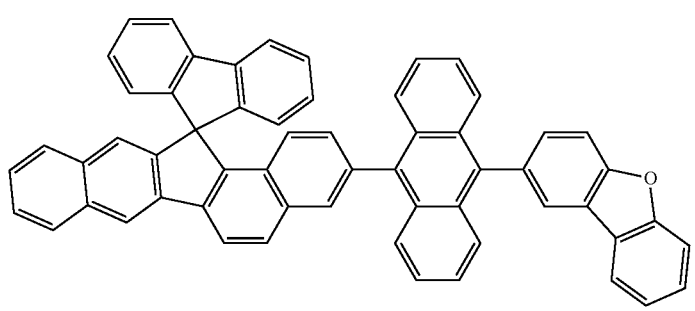
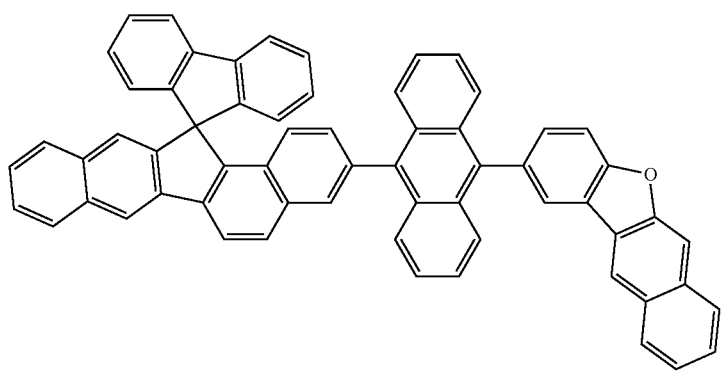

-continued
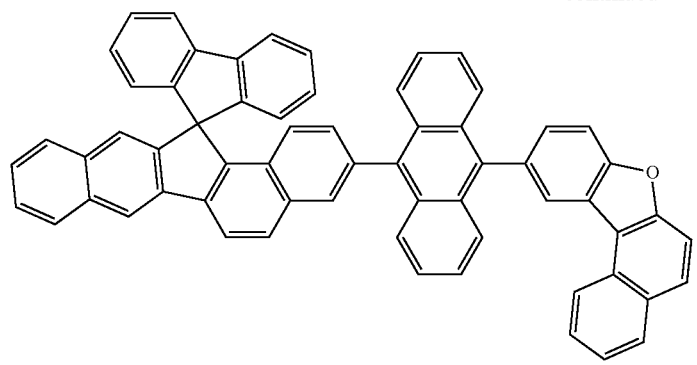
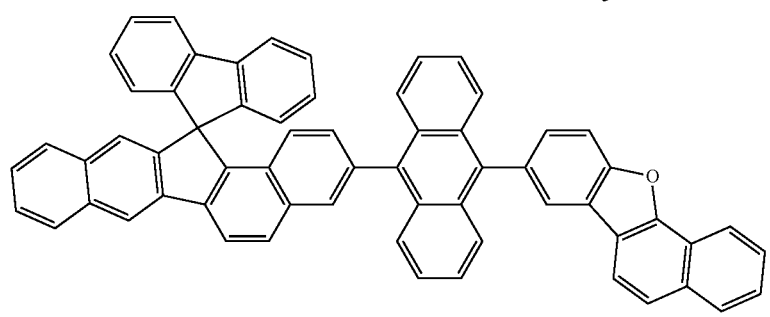
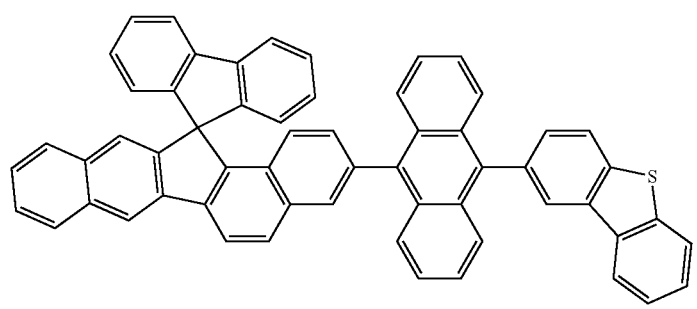
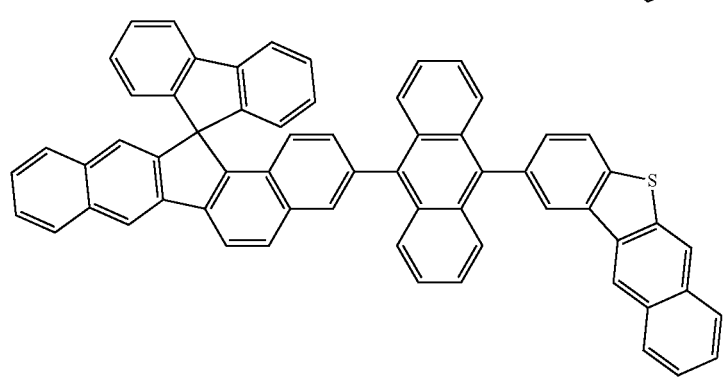
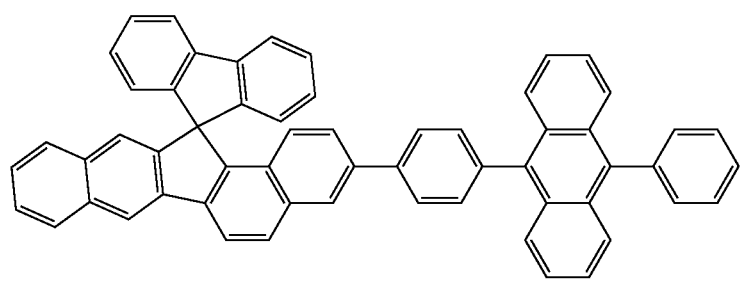

-continued
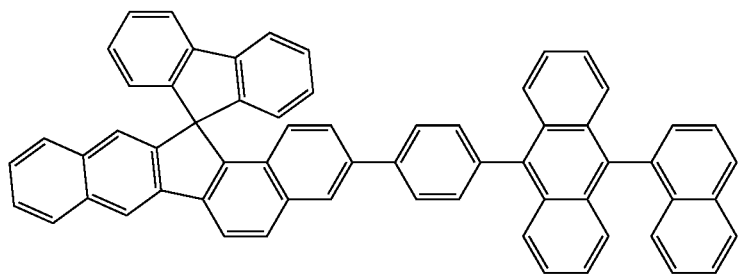
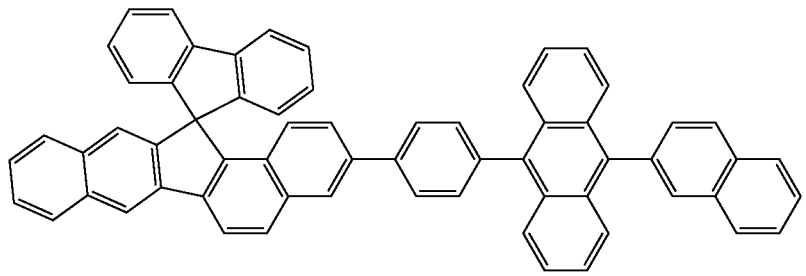
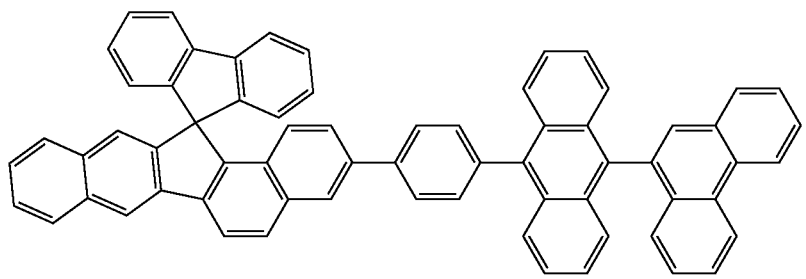
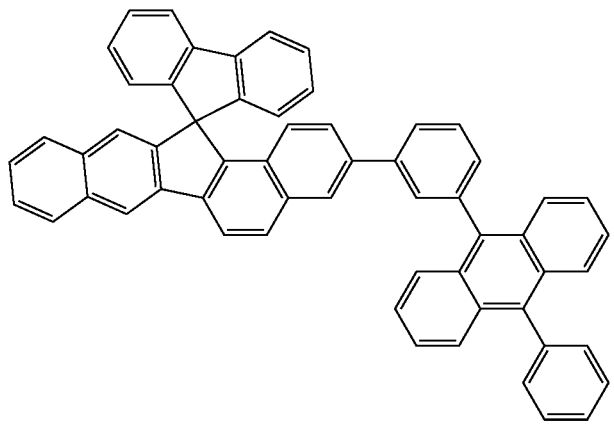
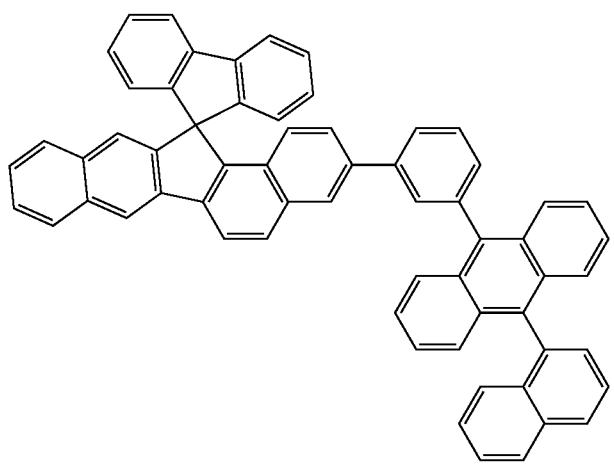

-continued
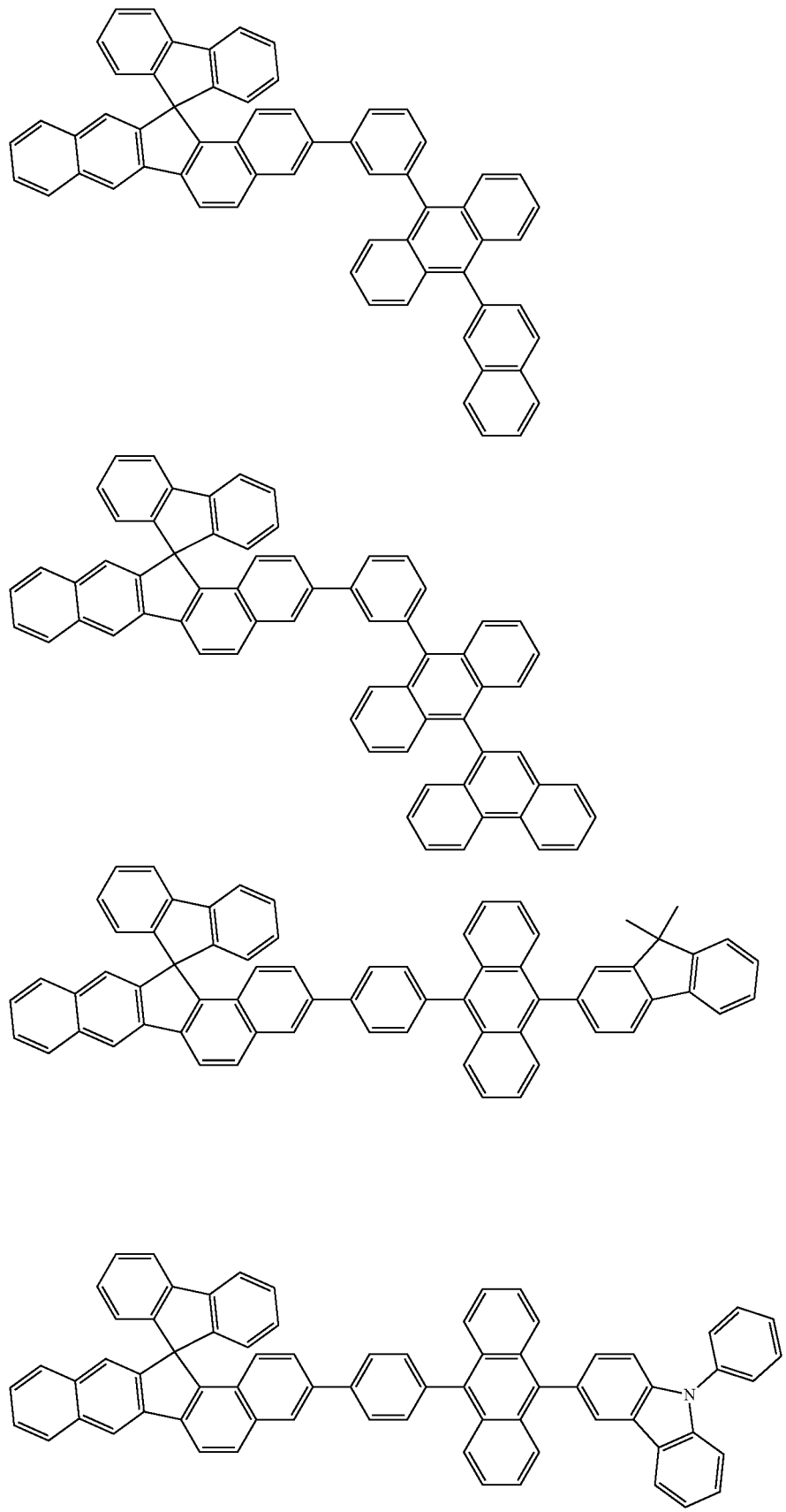

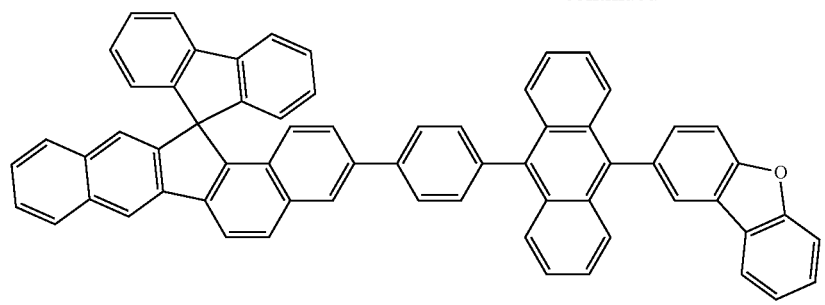
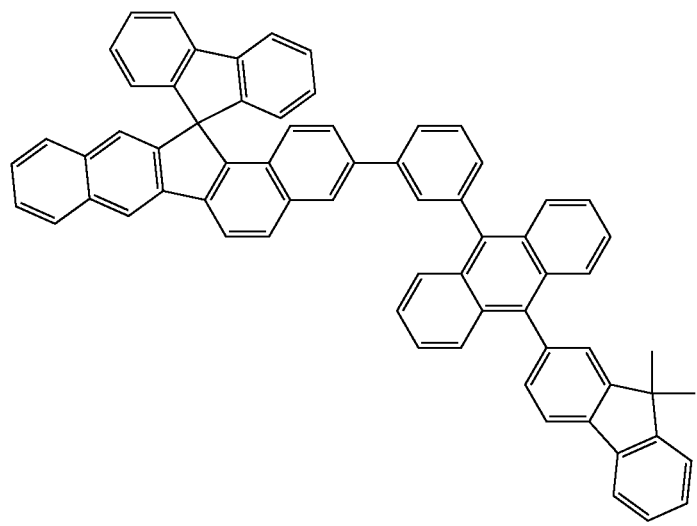
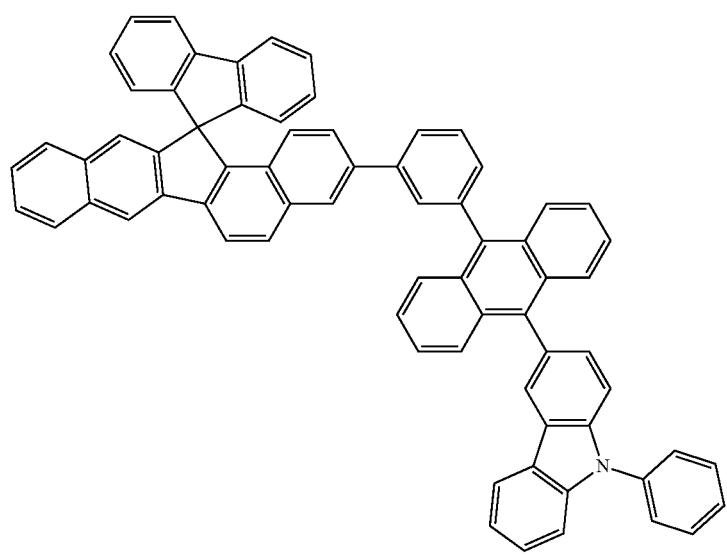

265 266
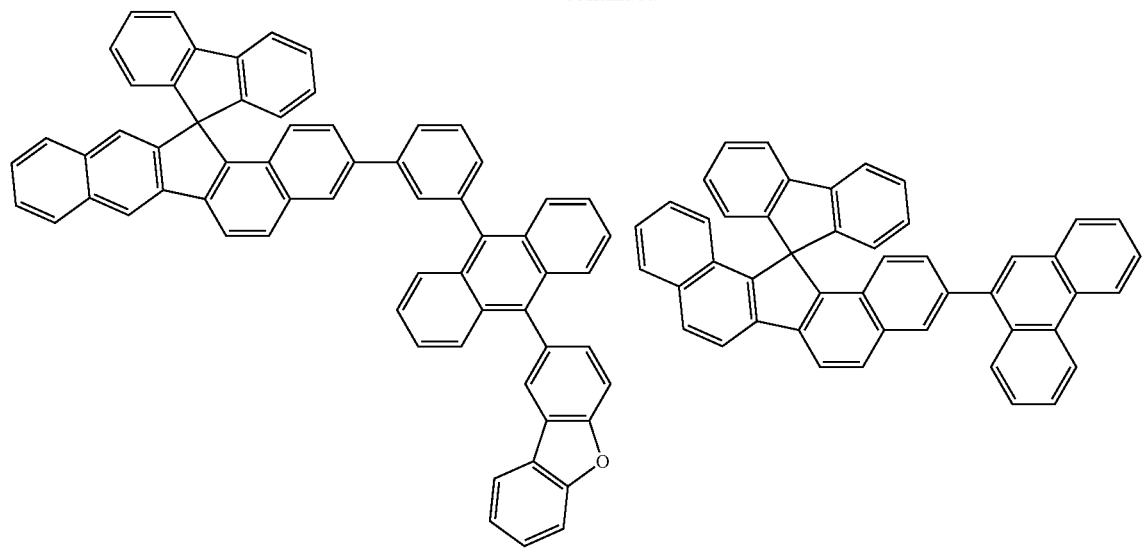
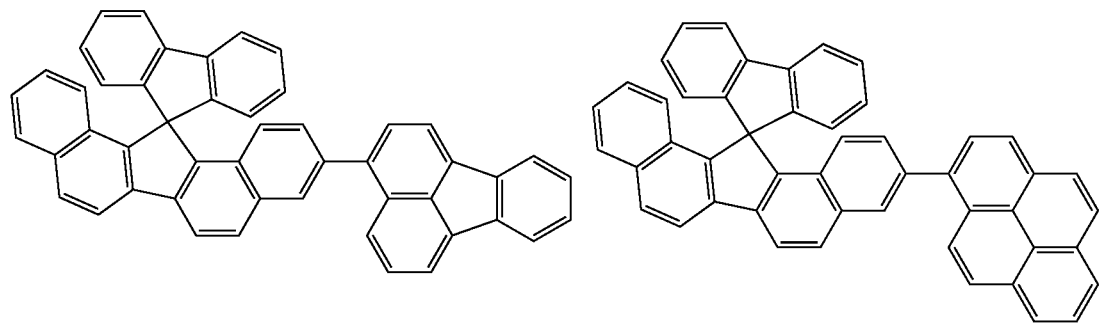
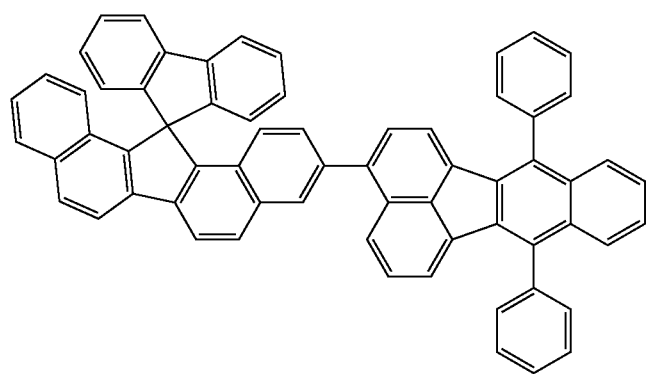
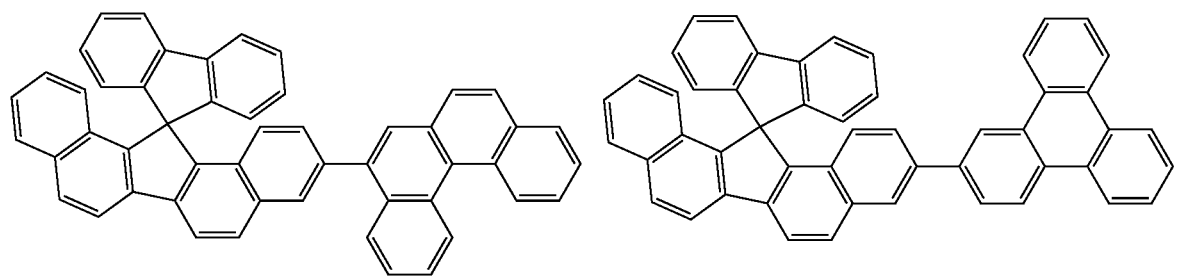

-continued
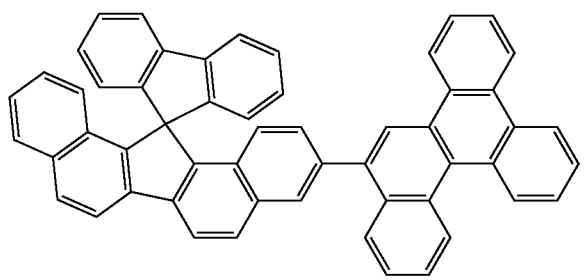
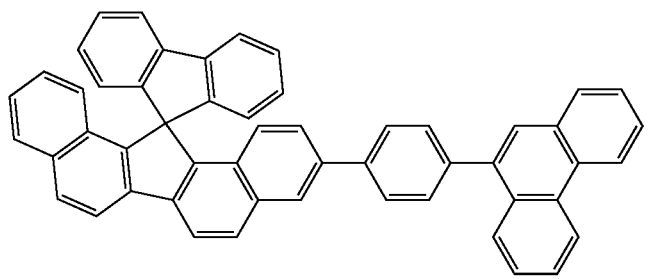
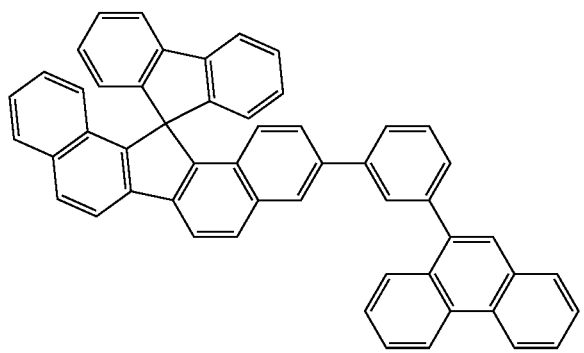
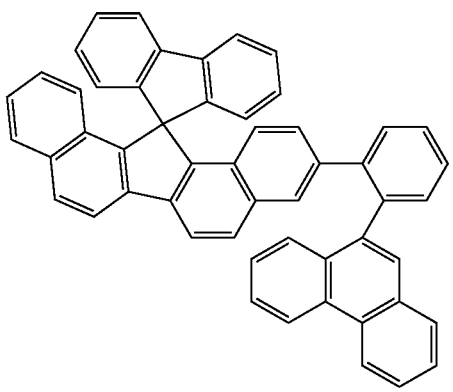
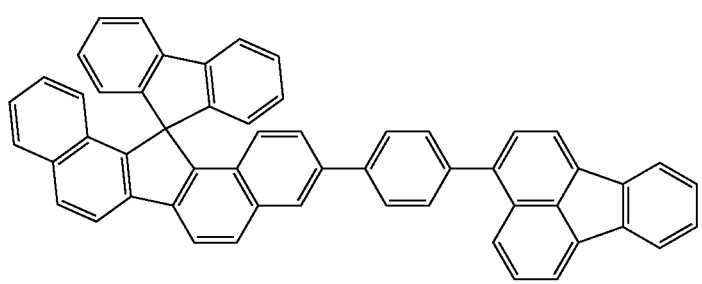
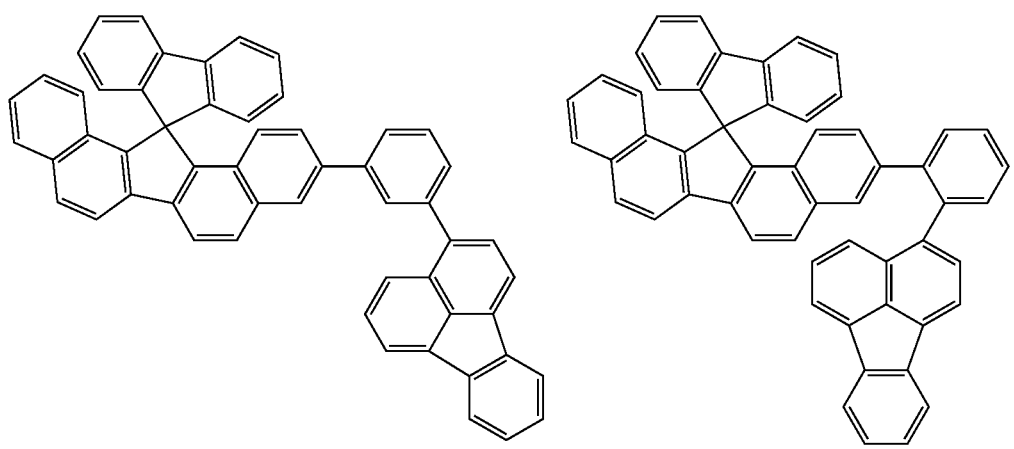

269 270
-continued
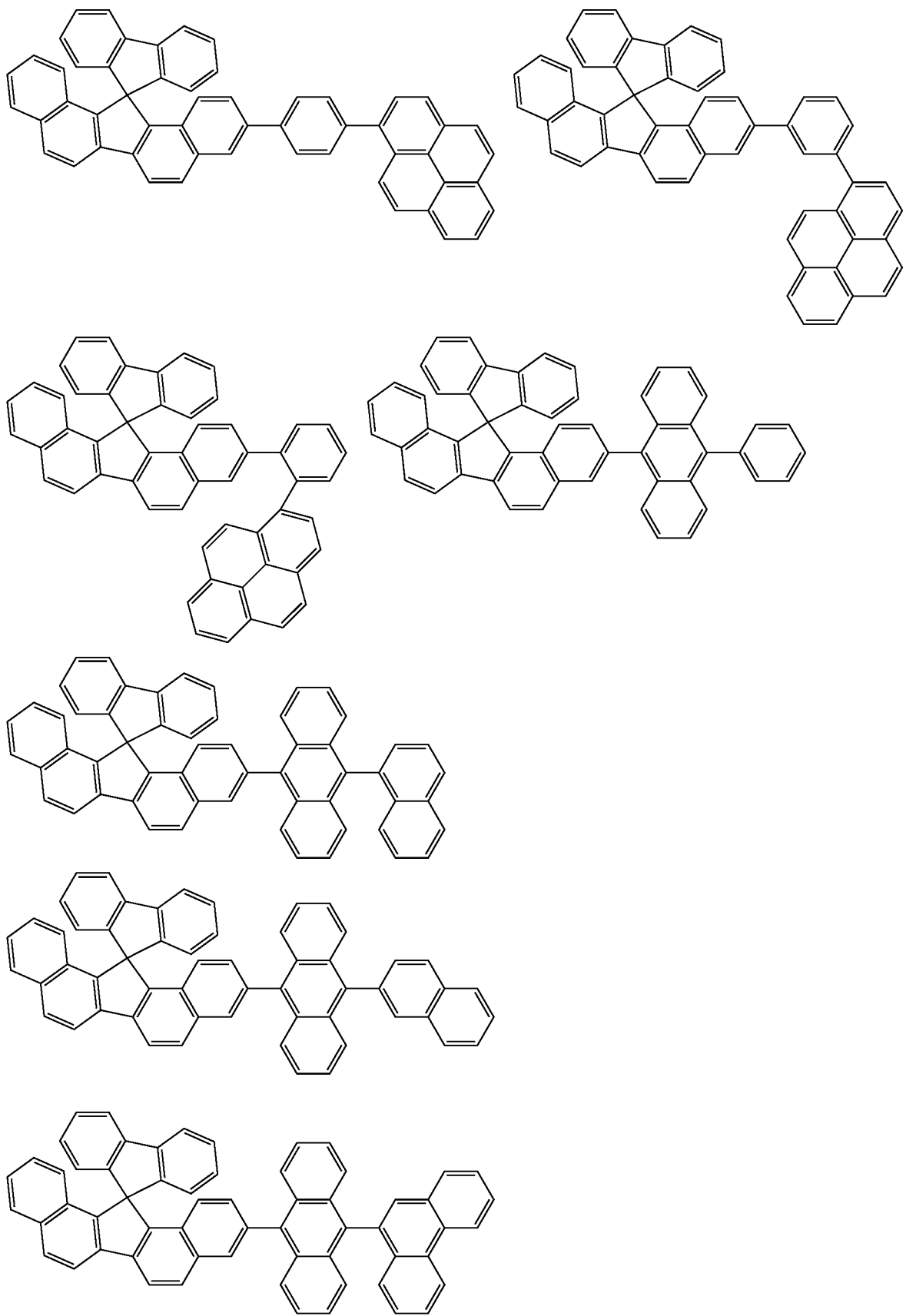

-continued
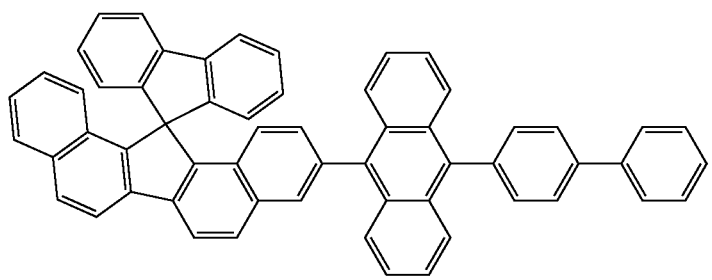
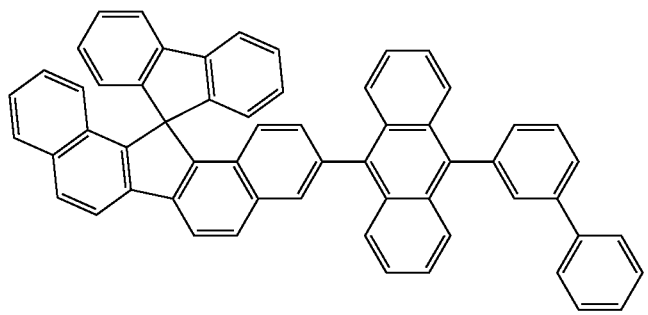
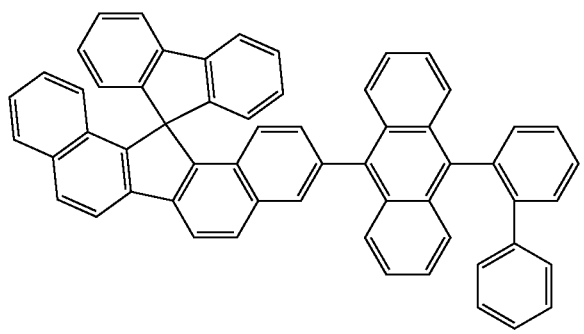
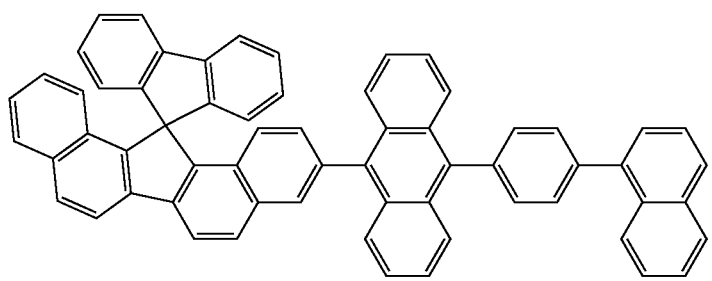
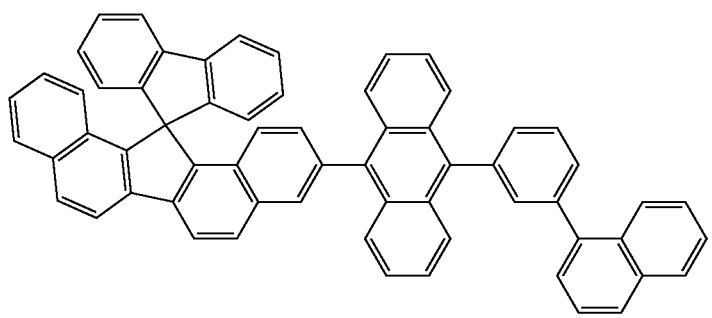

-continued
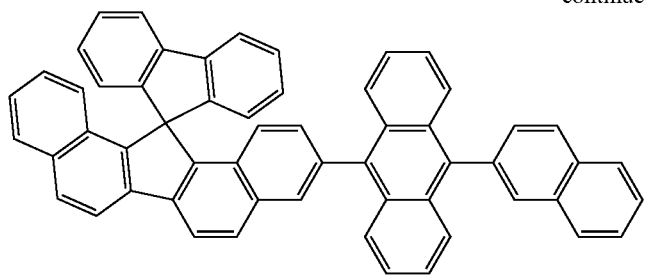
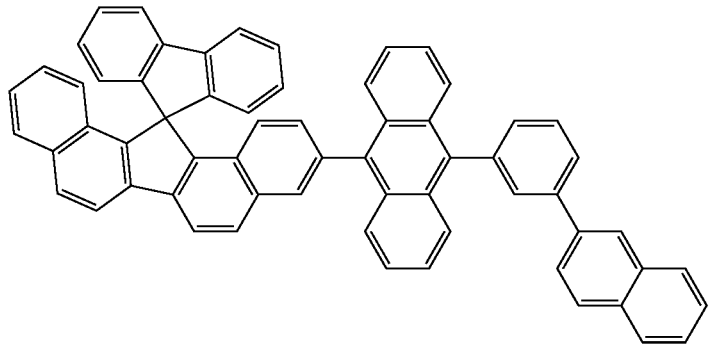
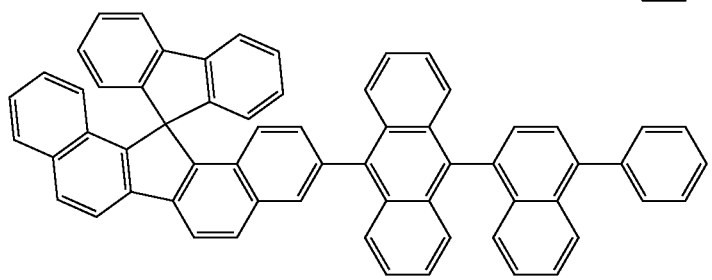
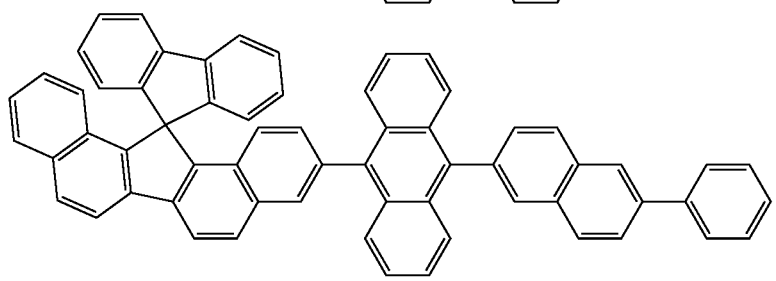
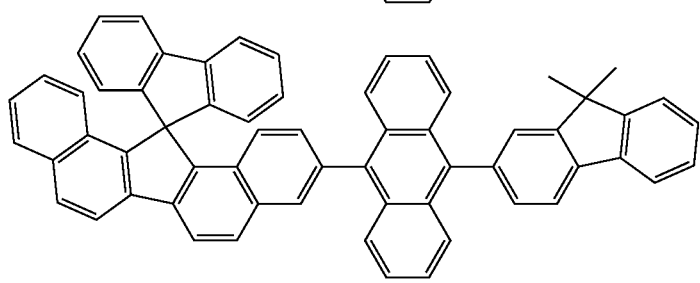
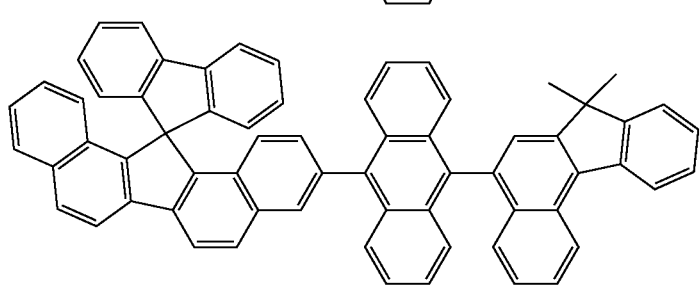

-continued
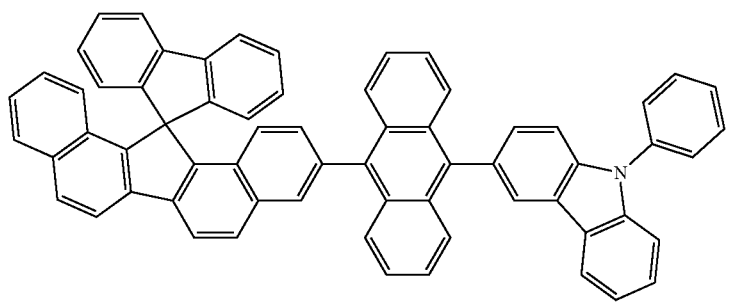
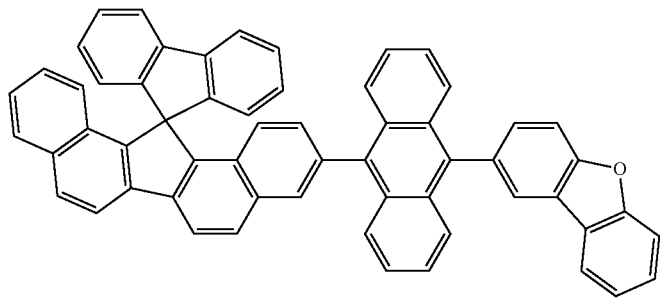
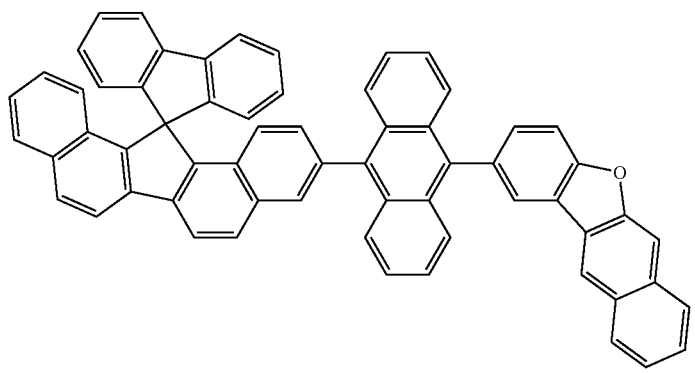
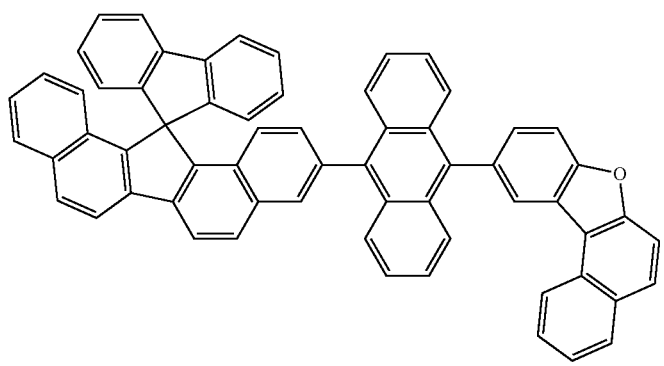
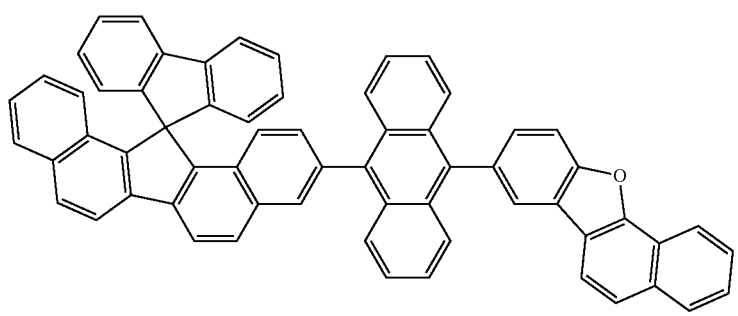

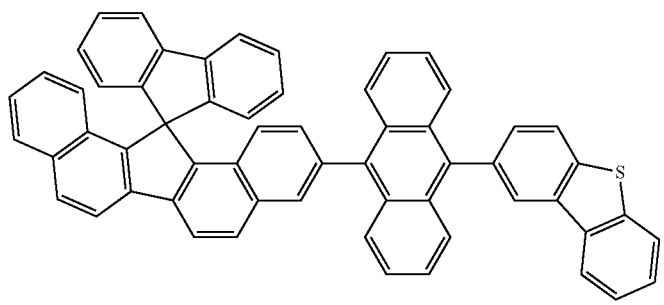
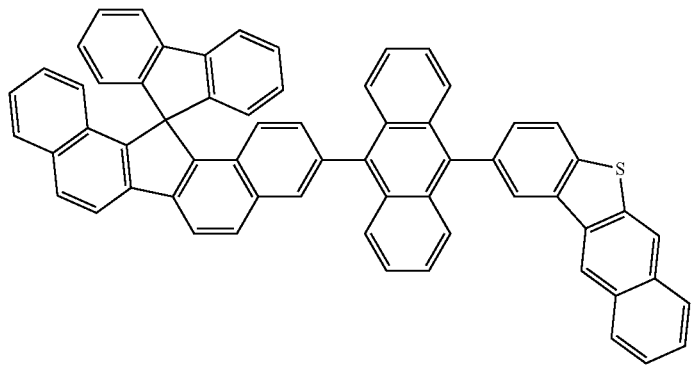
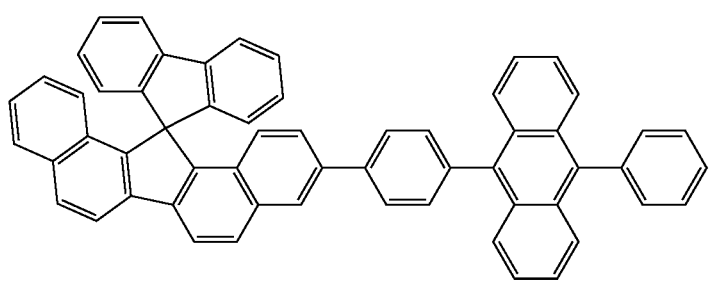
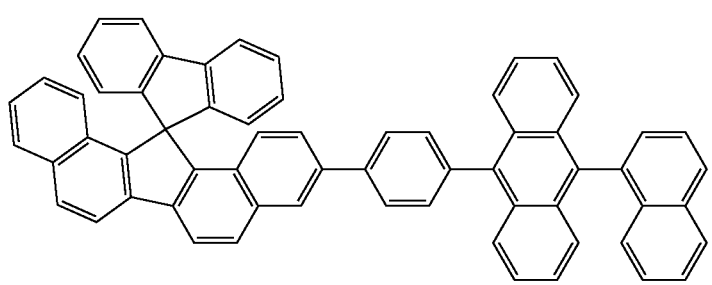
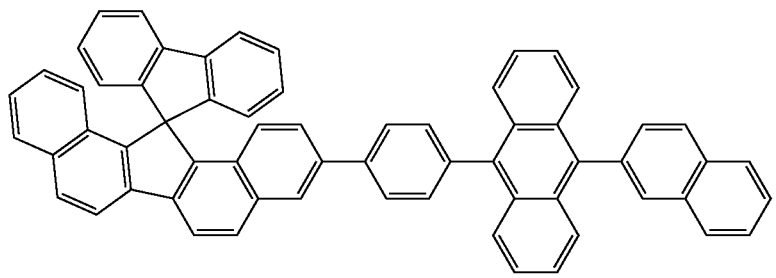

-continued
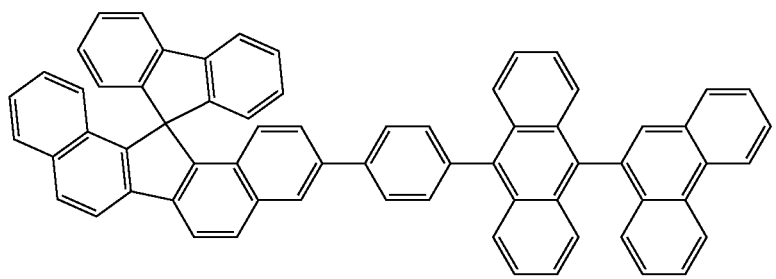
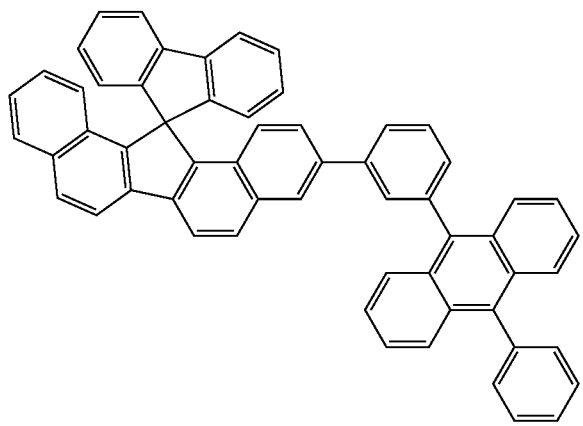
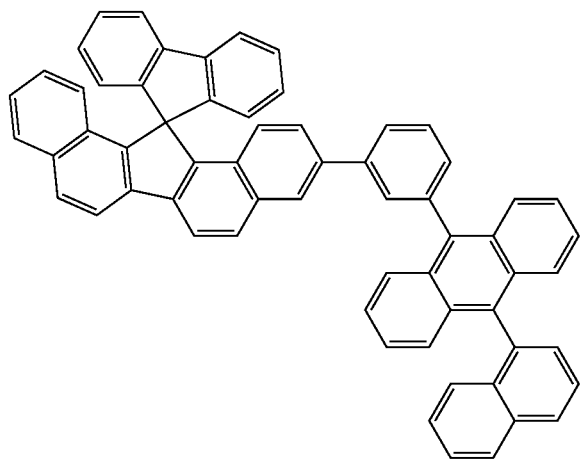
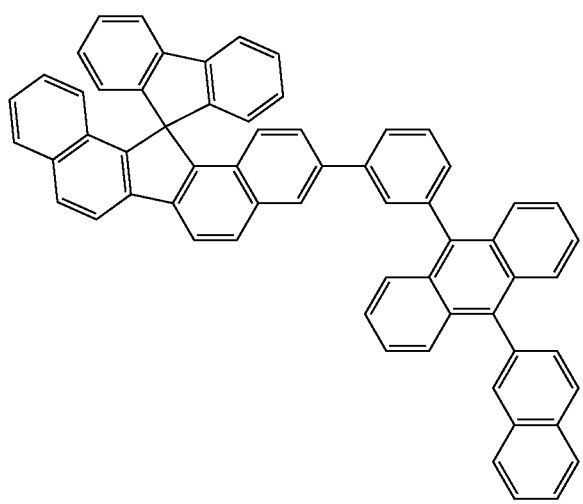
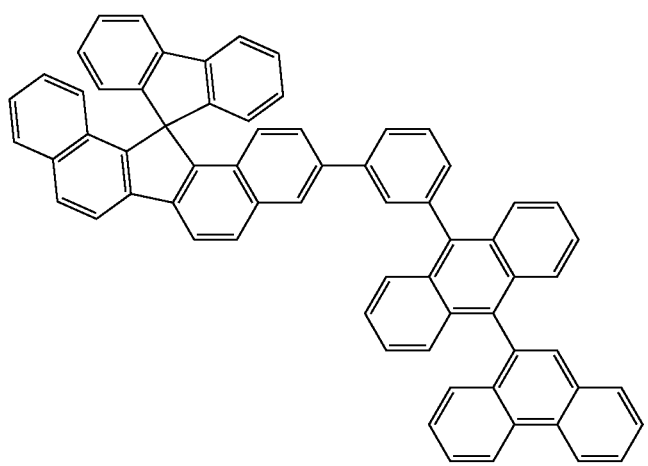

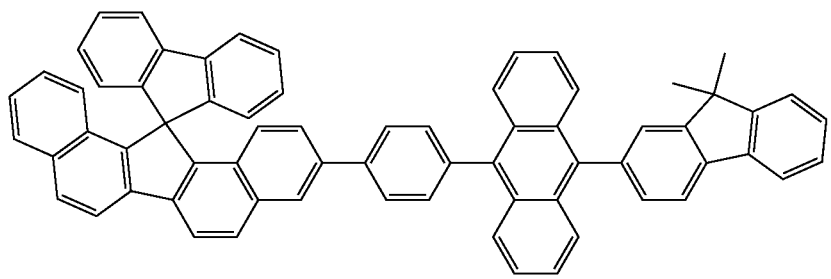
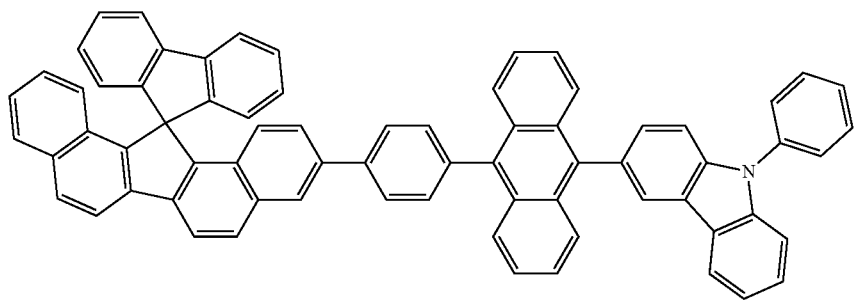
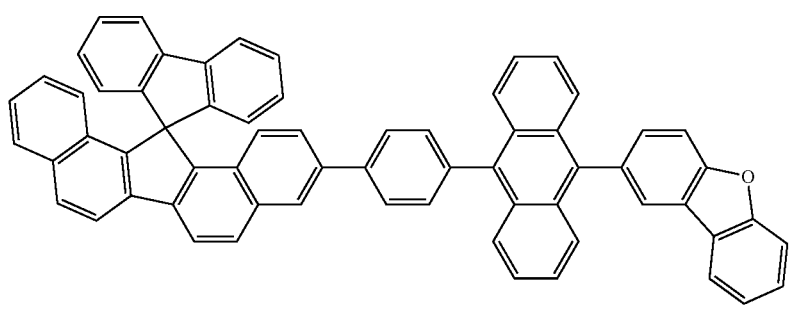
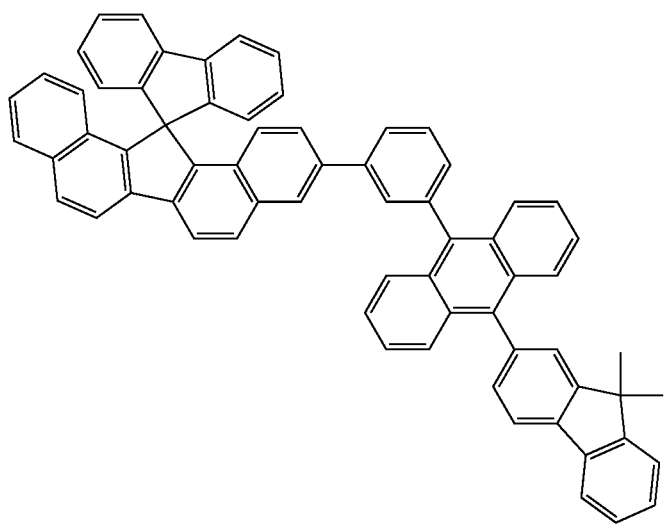

-continued
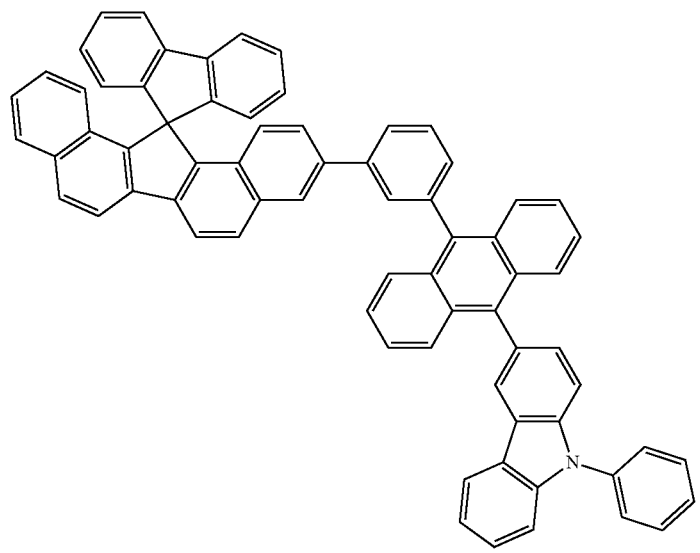
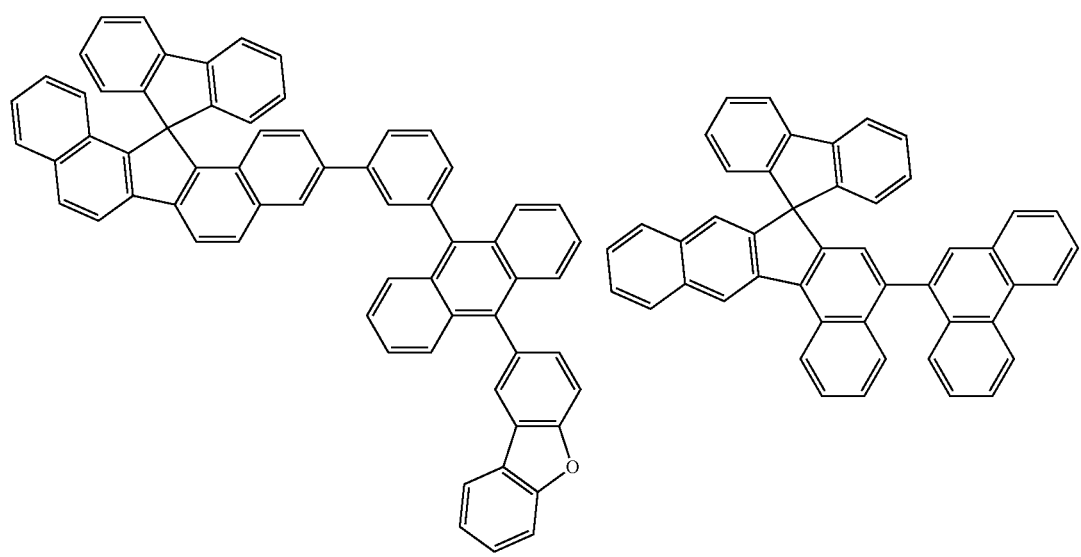
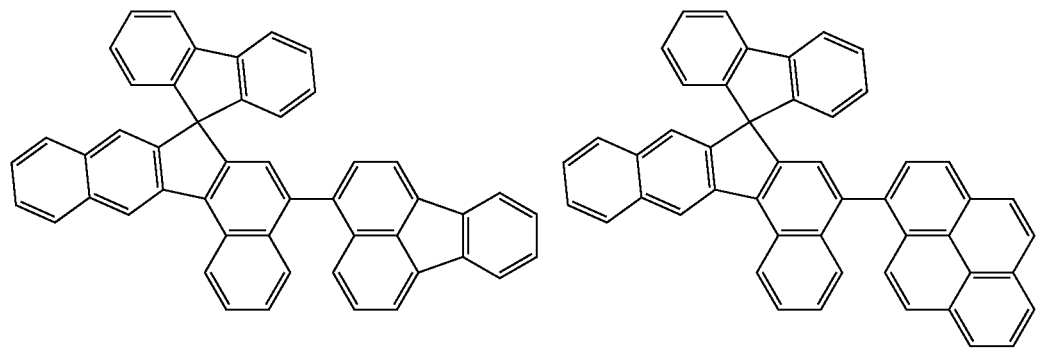

285
286
-continued
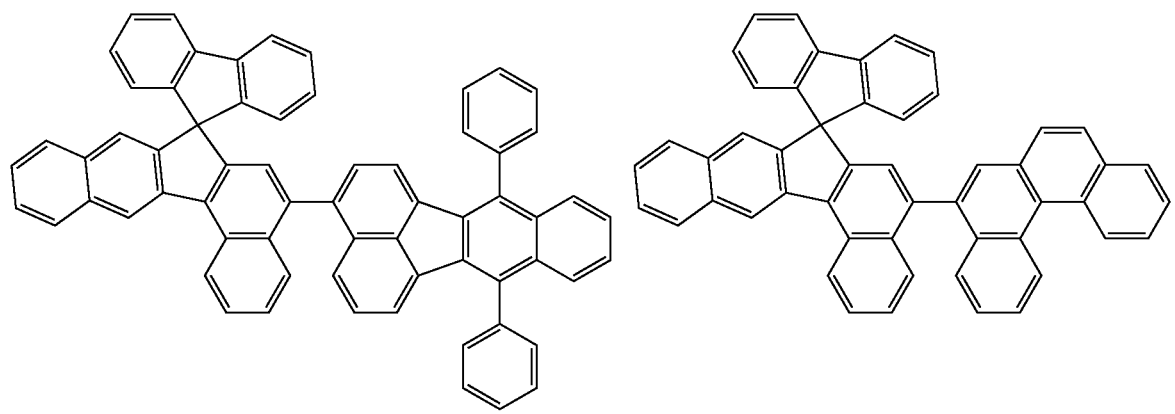
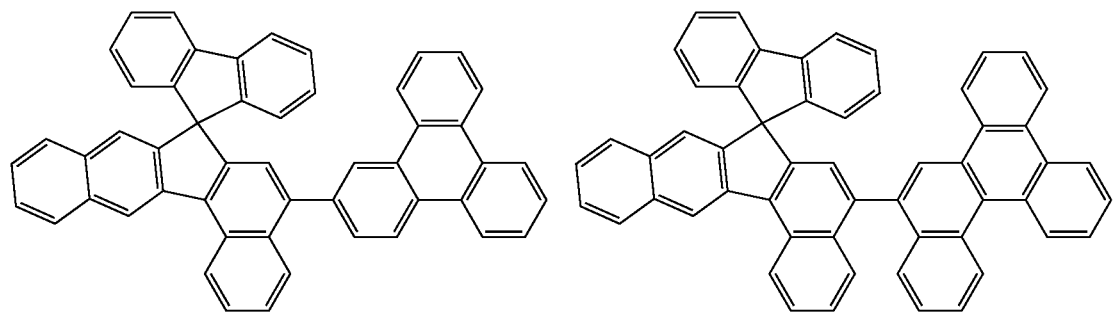
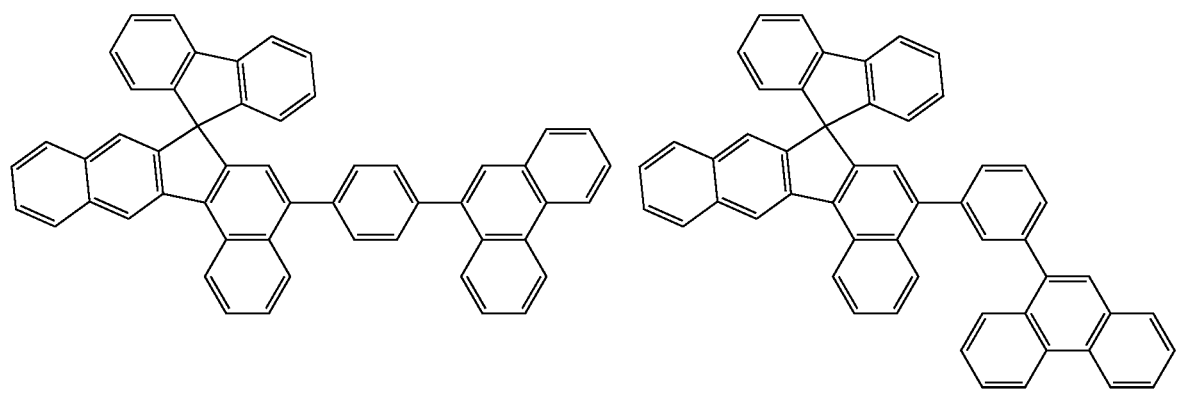
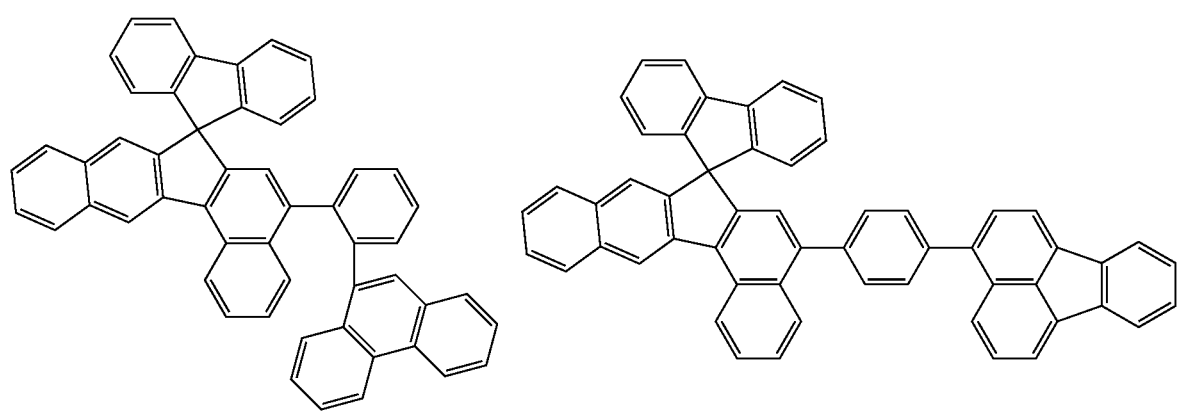

287
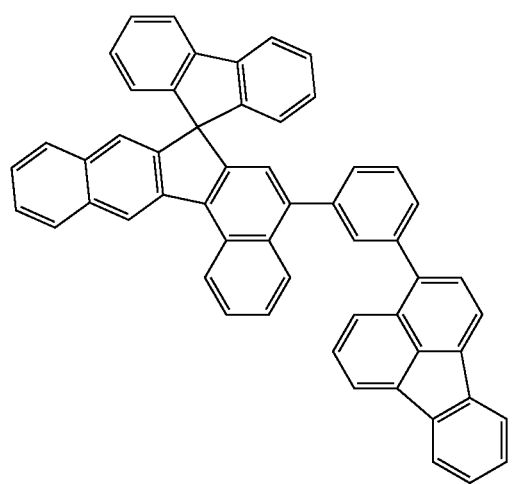
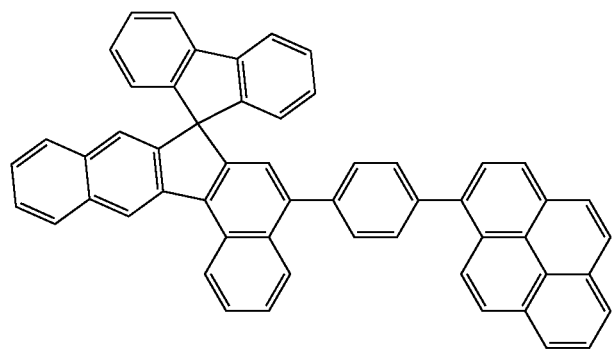
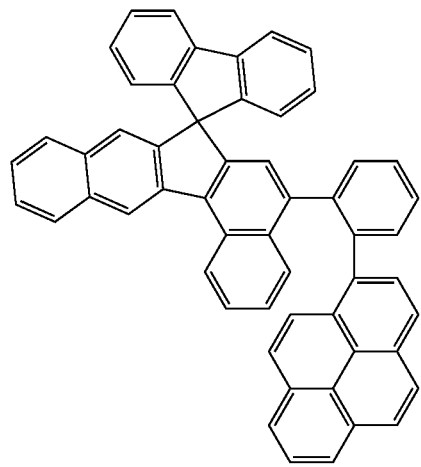
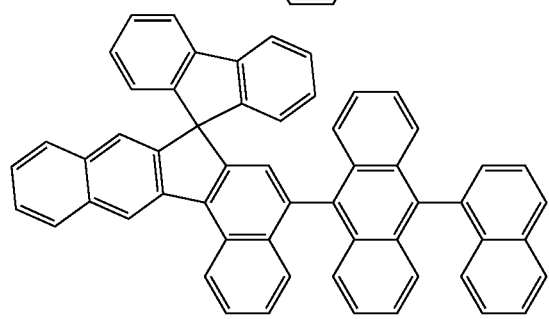
288
-continued
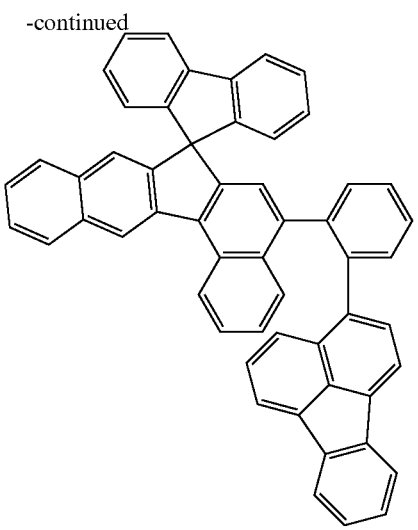
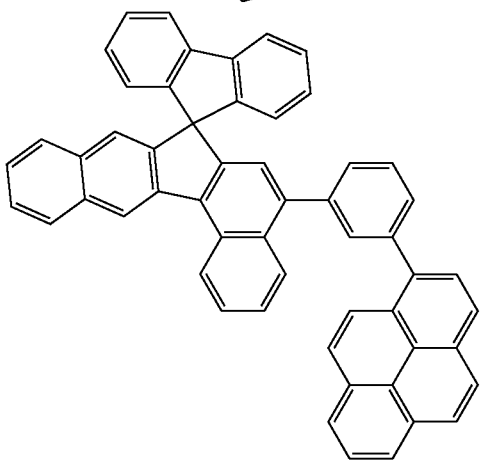
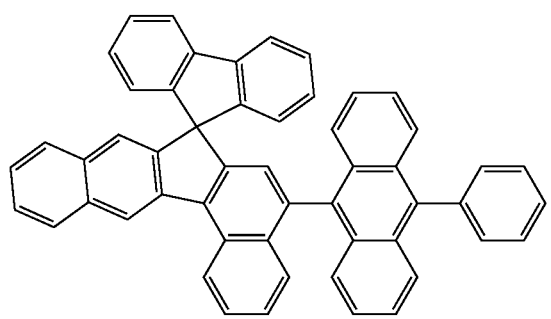
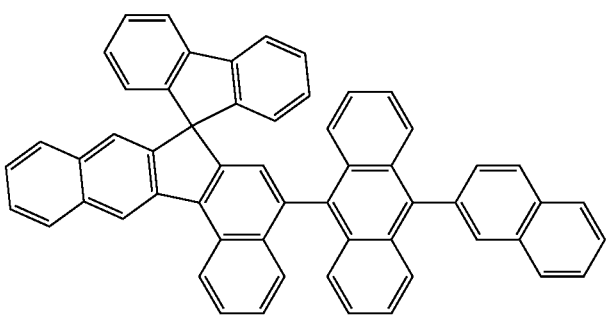

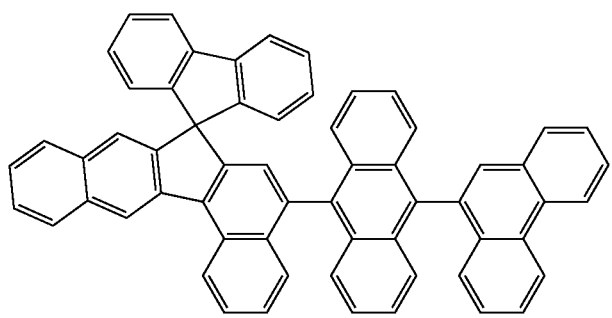 [SMILES: c1ccc2c(c1)-c1ccccc1C21c2cc3ccccc3cc2-c2c1cc(-c1c3ccccc3c(-c3cc4ccccc4c4ccccc34)c3ccccc13)c1ccccc21]
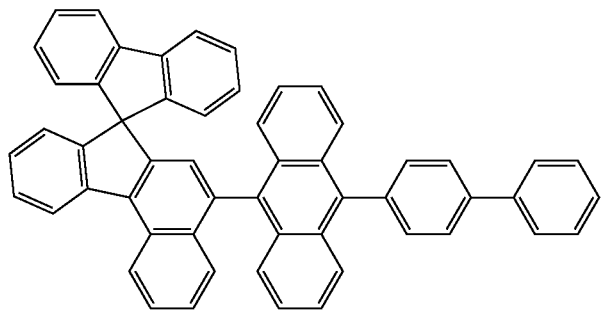
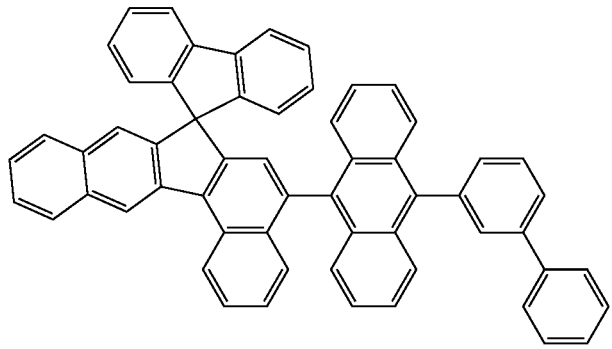
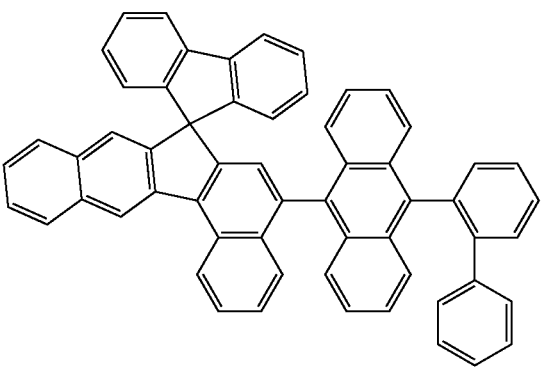
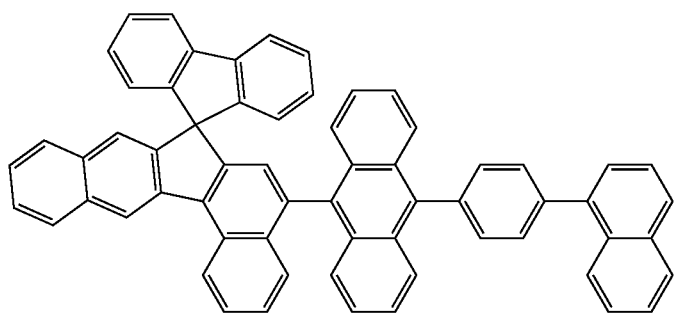
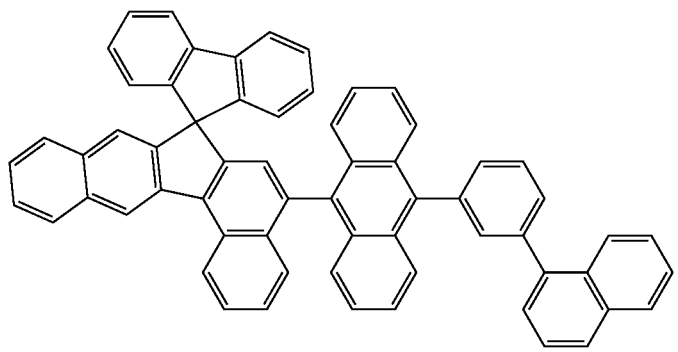

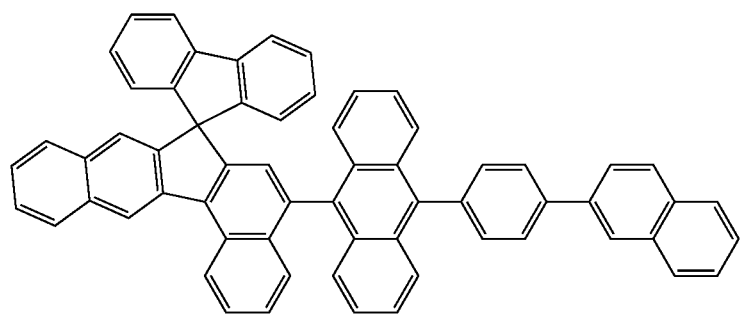
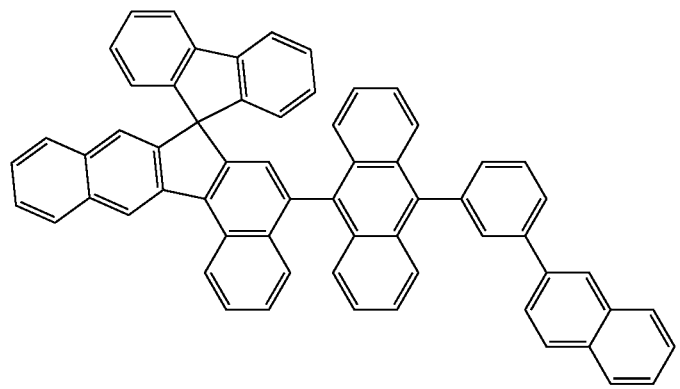
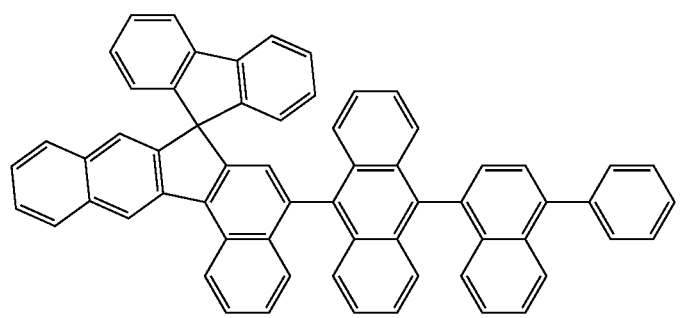
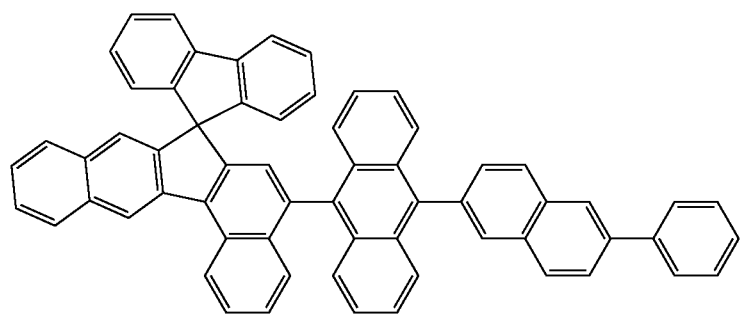
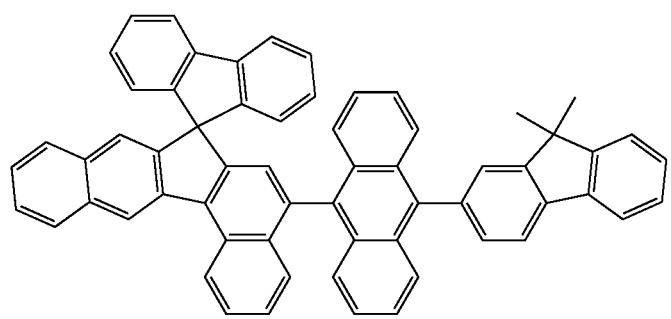

-continued
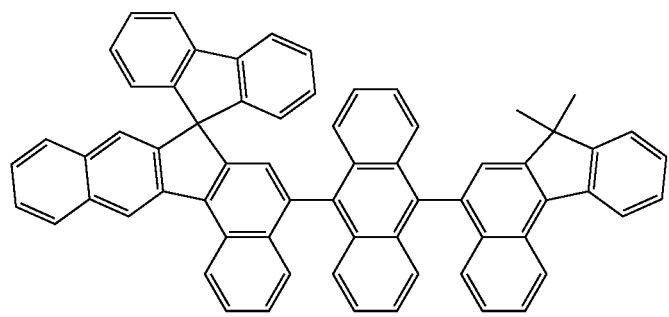
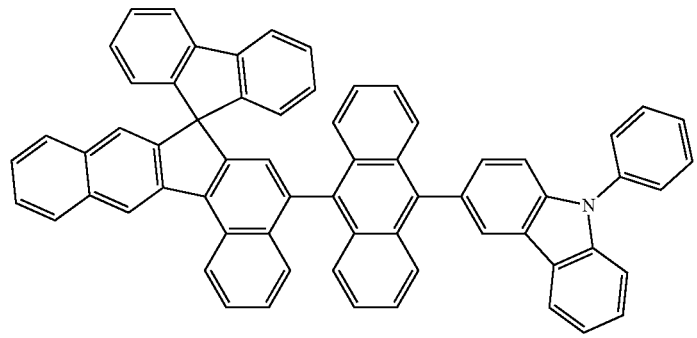
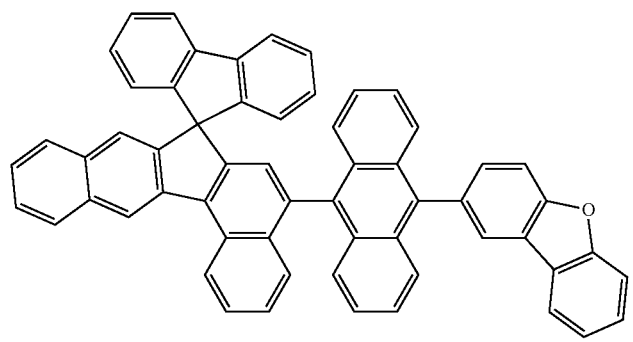
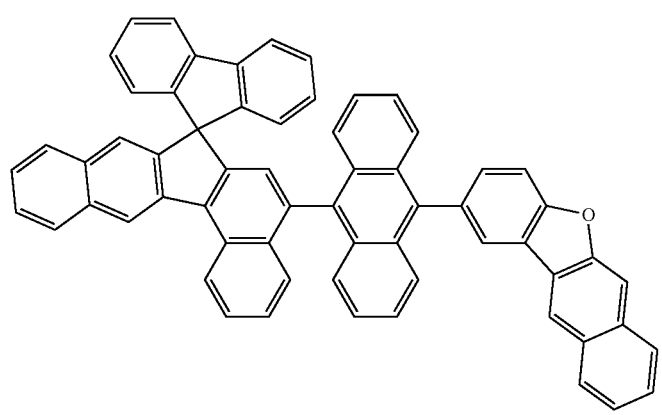

-continued
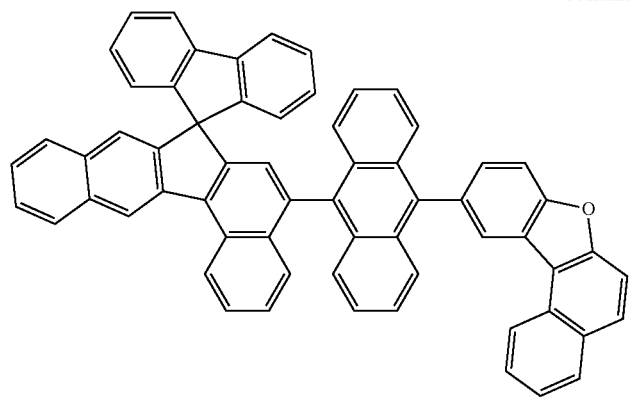
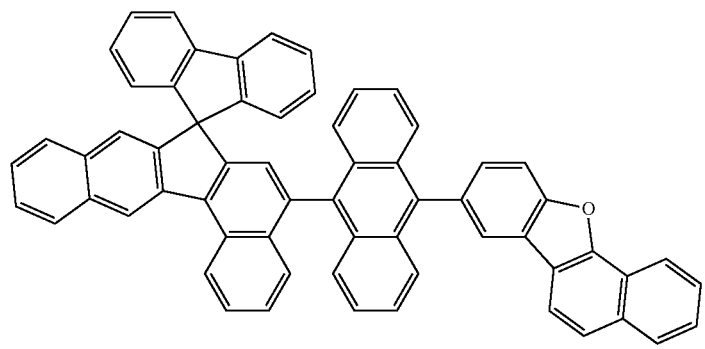
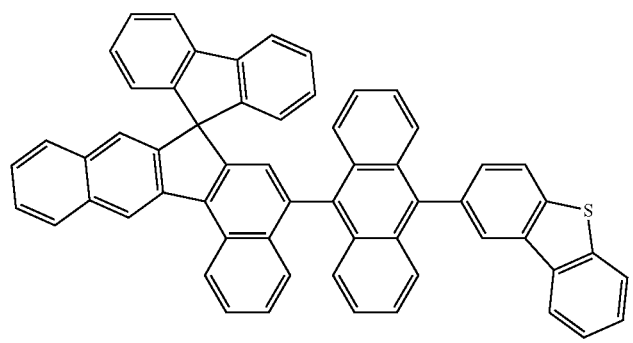
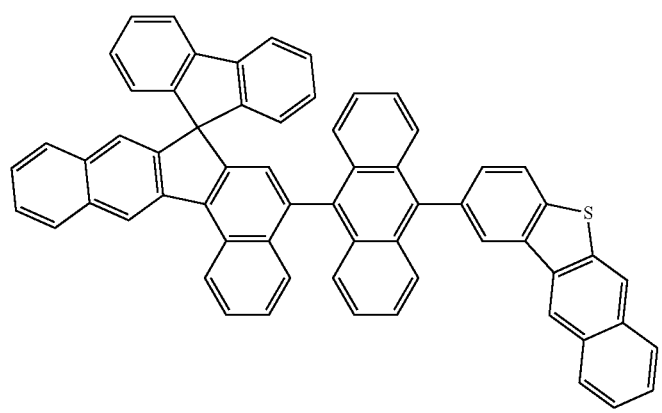

-continued
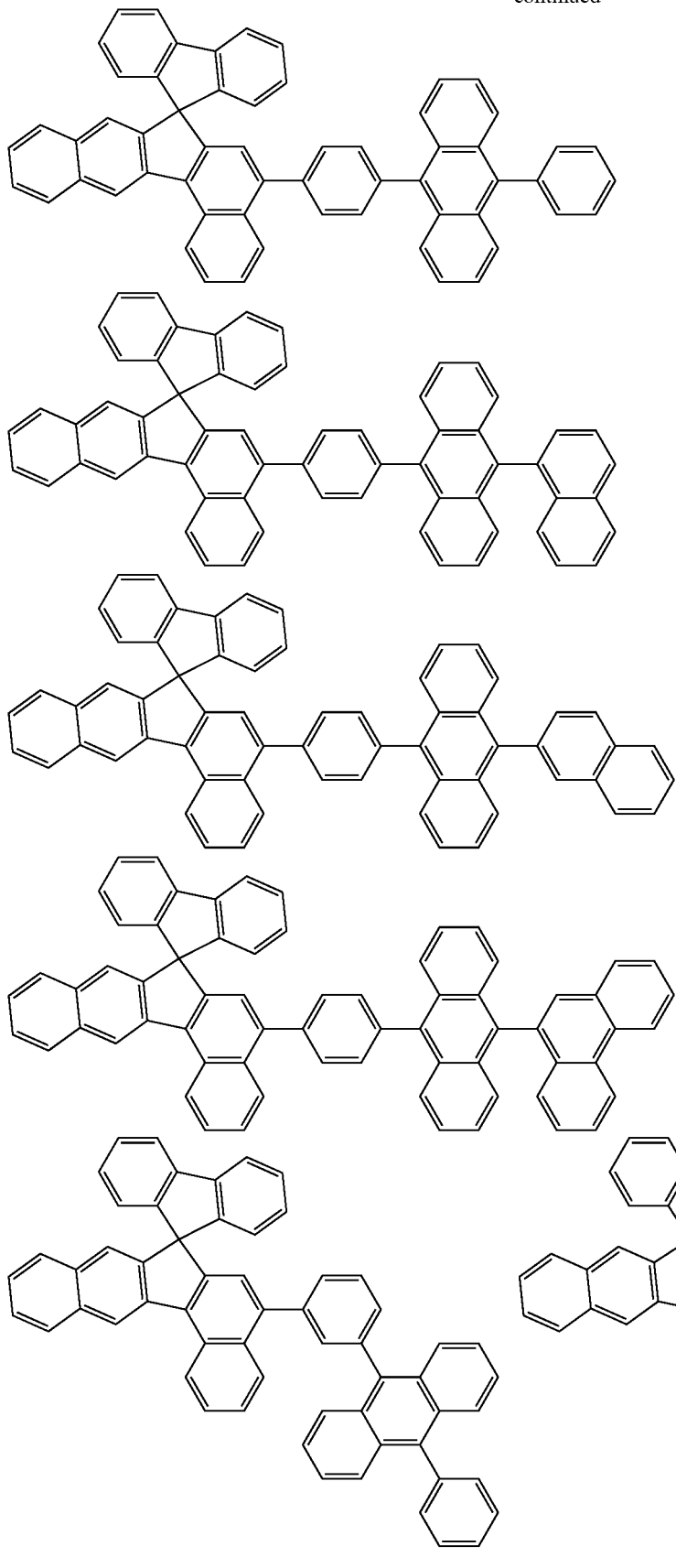

299
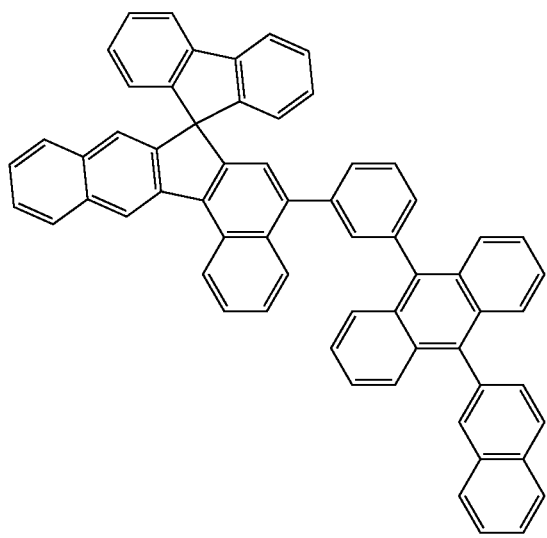
300
-continued
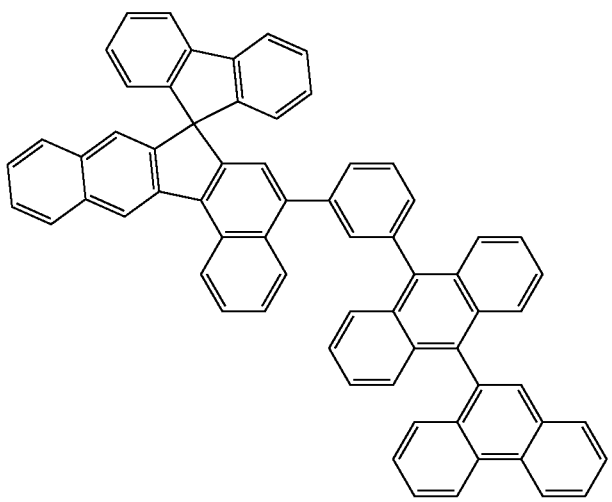
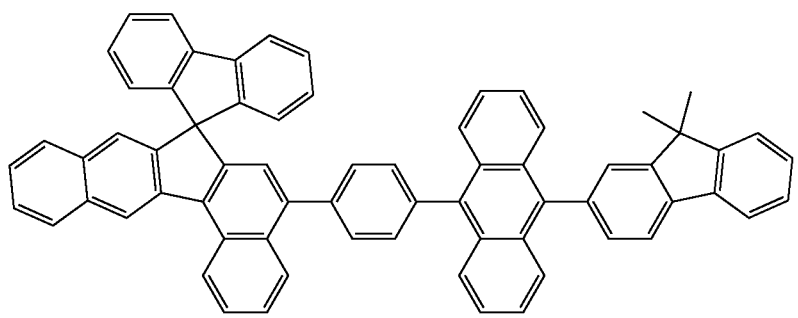
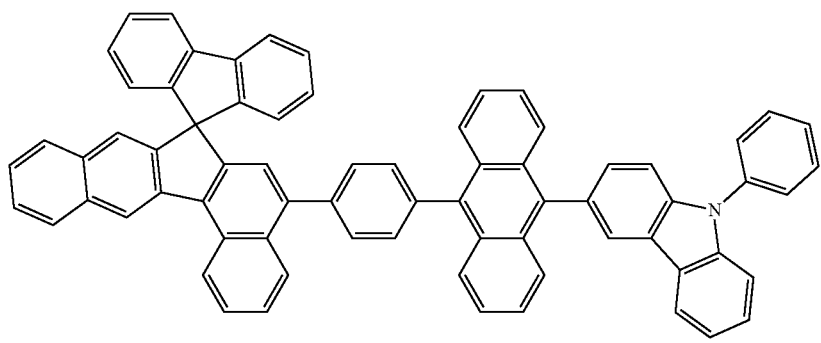
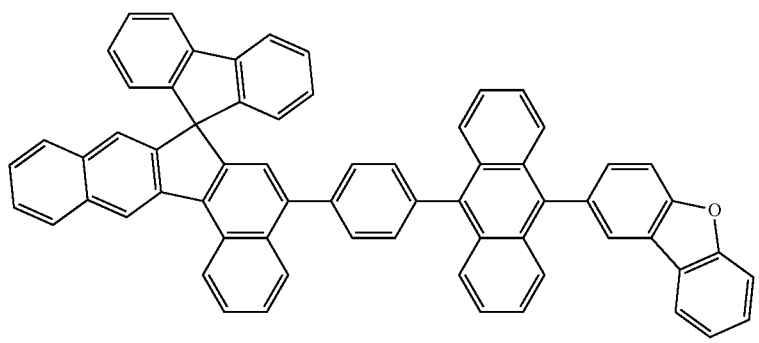

-continued
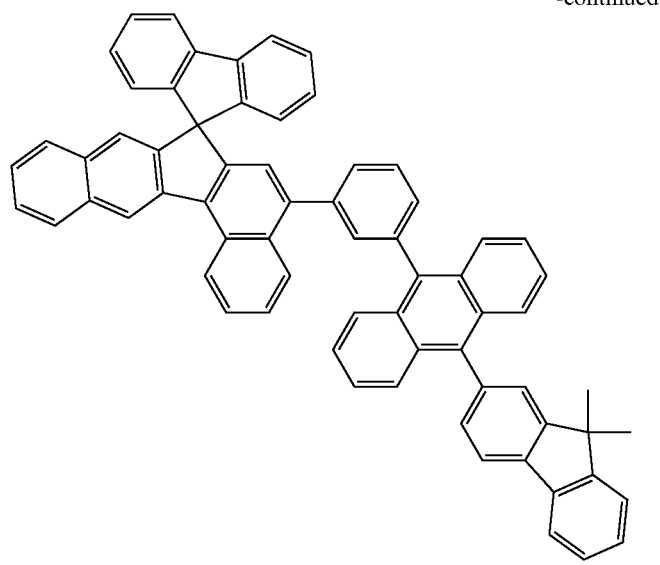
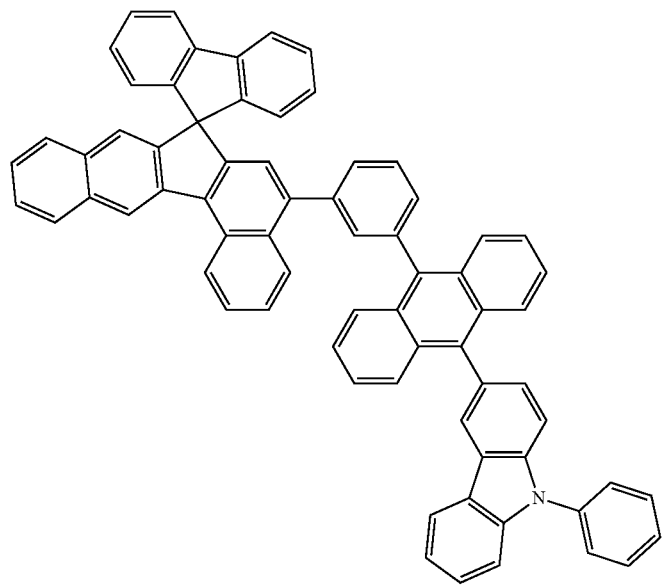
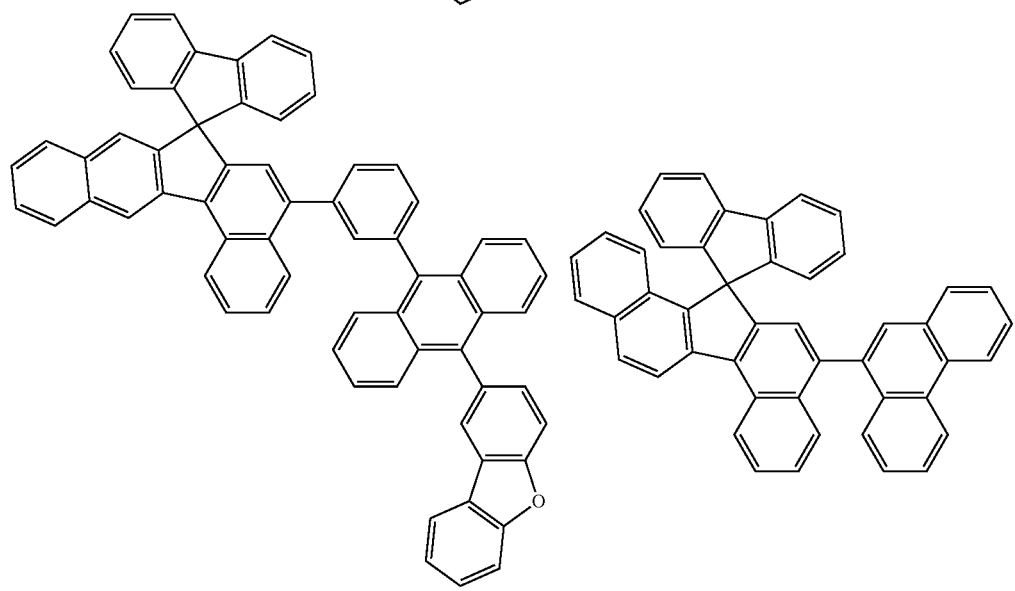

303
304
-continued
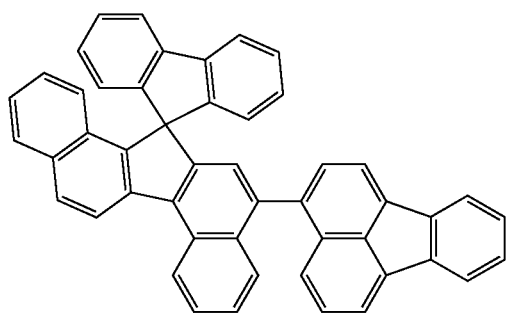

305
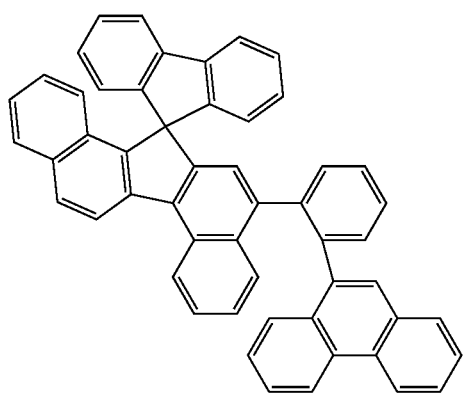
306
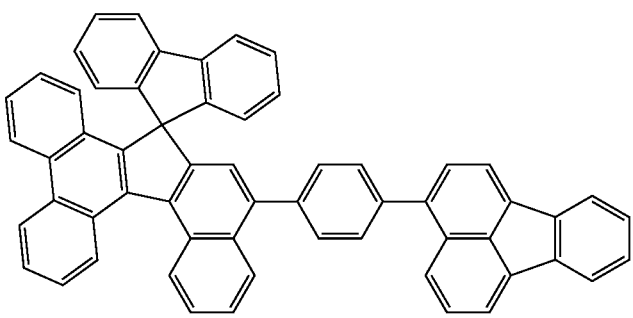
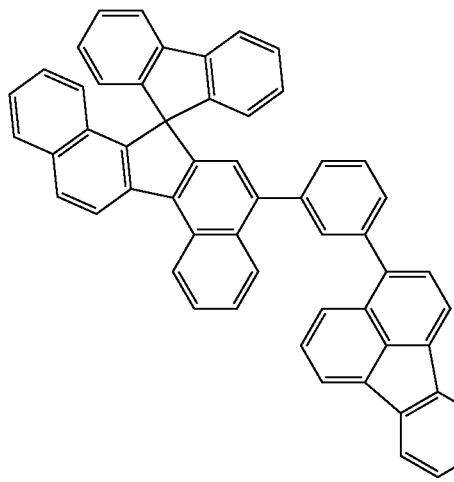
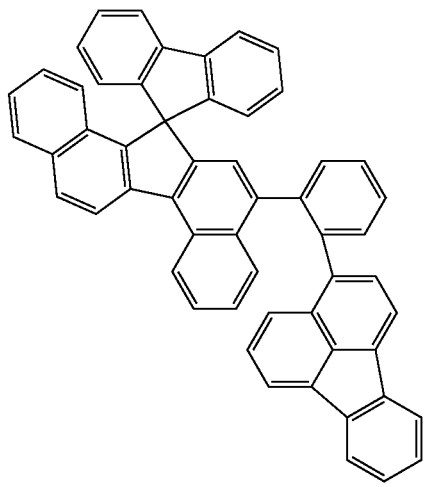
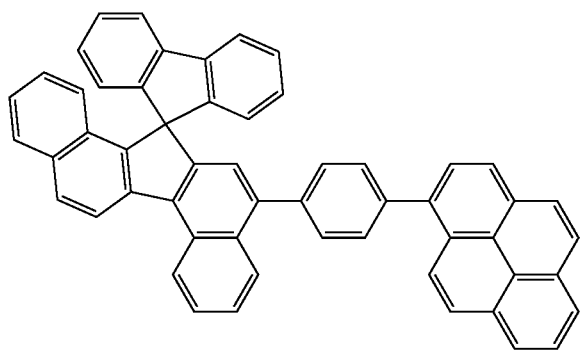
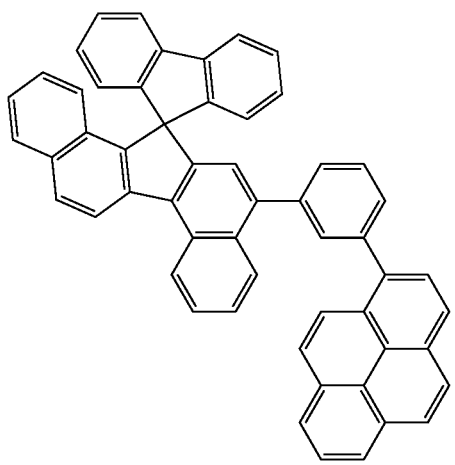

-continued
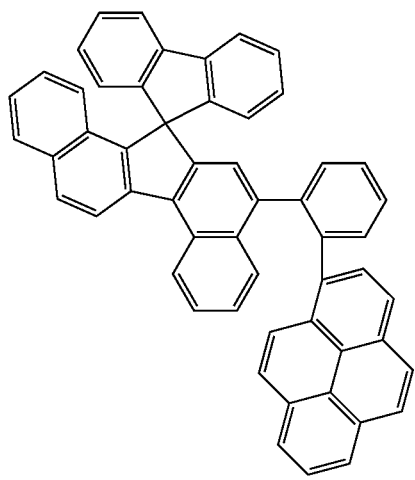
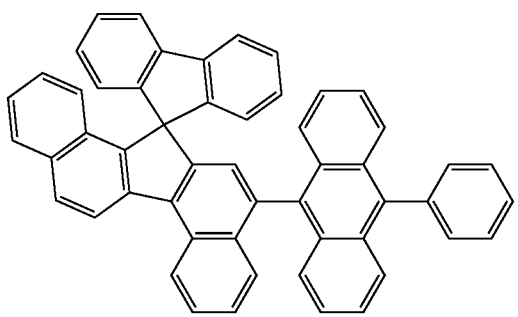
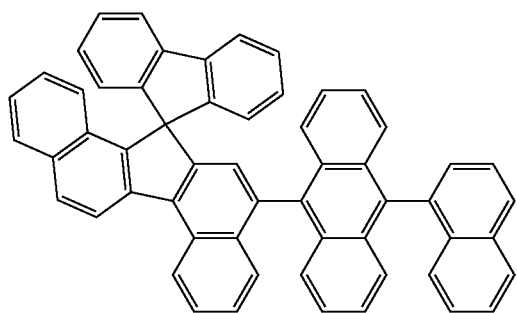
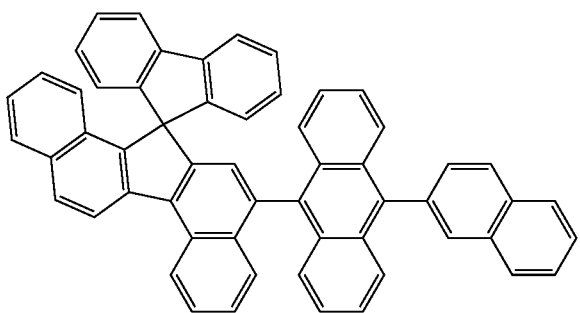
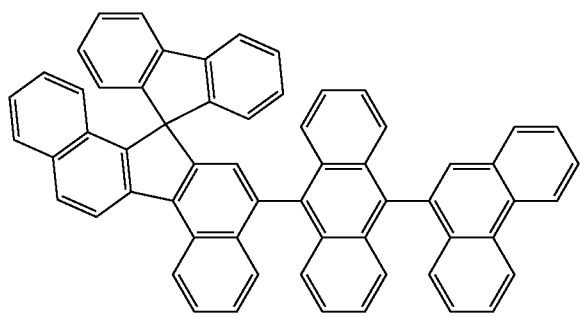
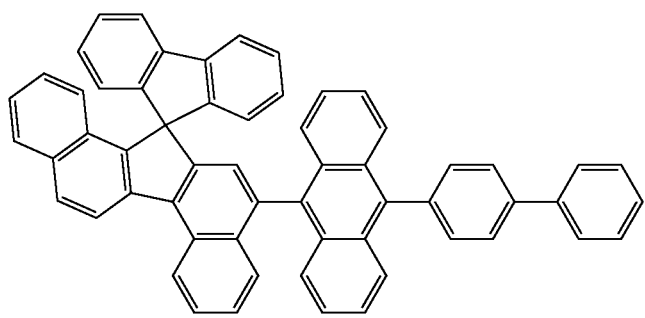

309 310
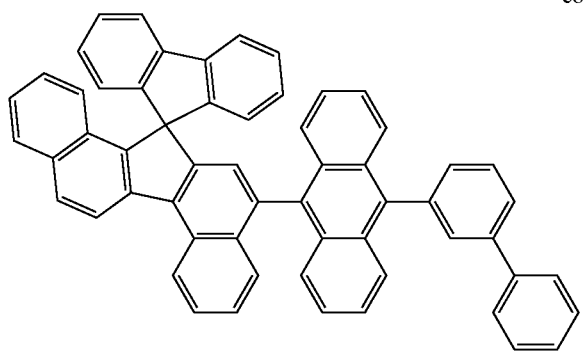
-continued

-continued
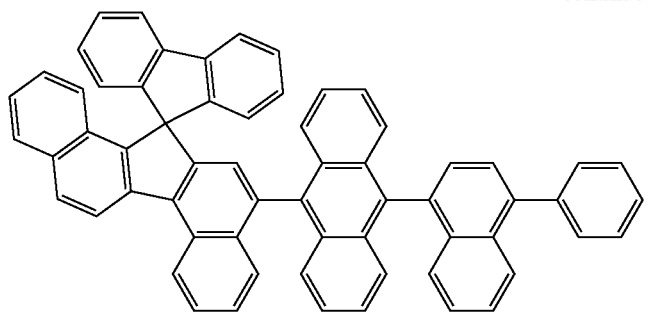
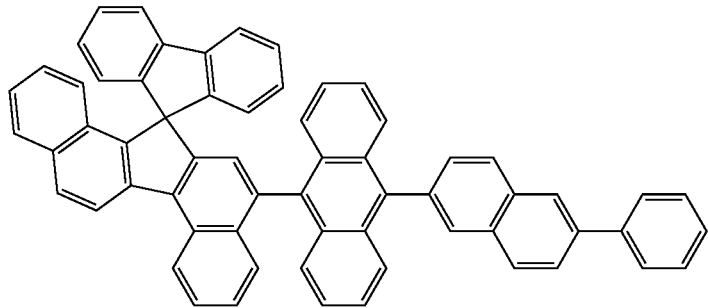
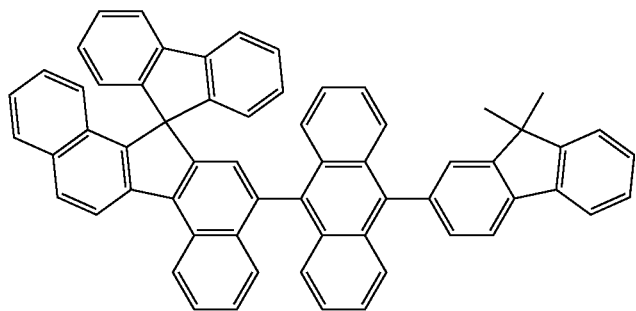
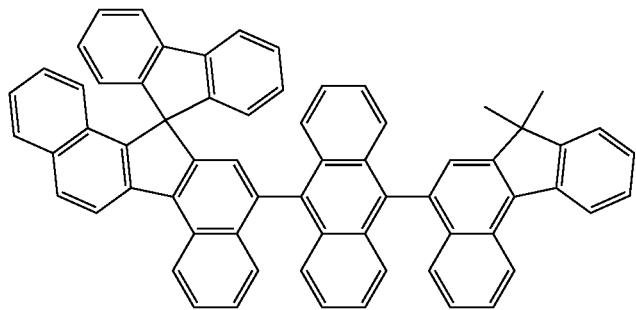
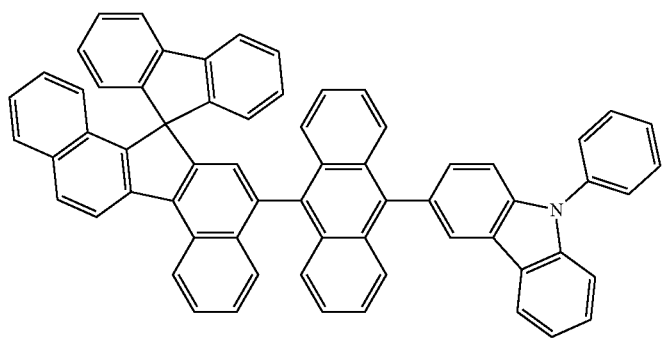

-continued
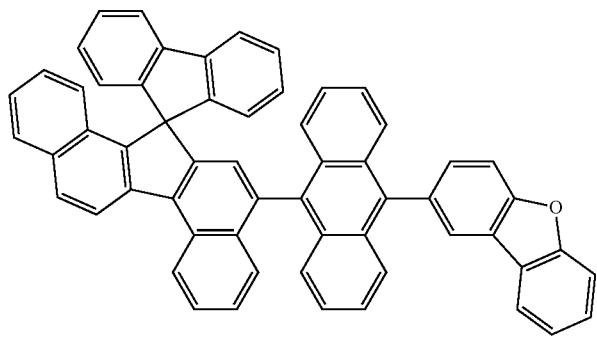
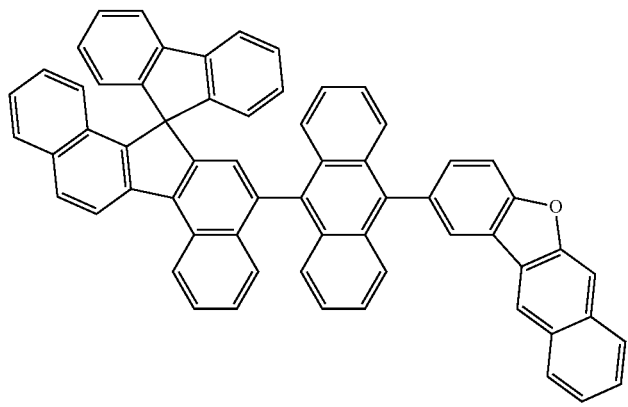
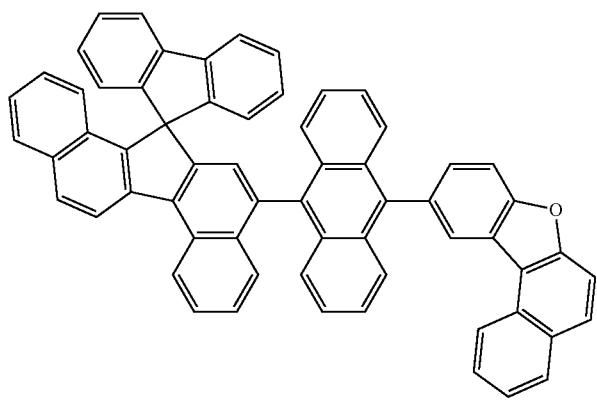
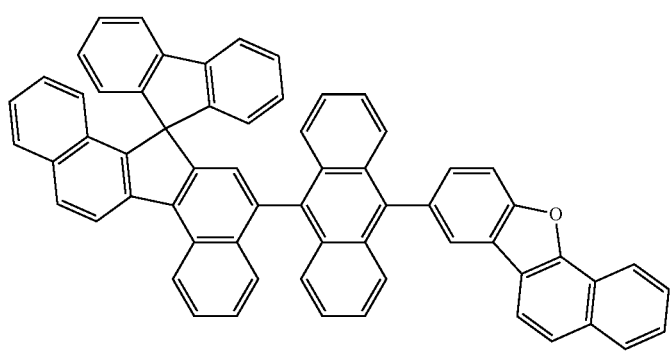

-continued
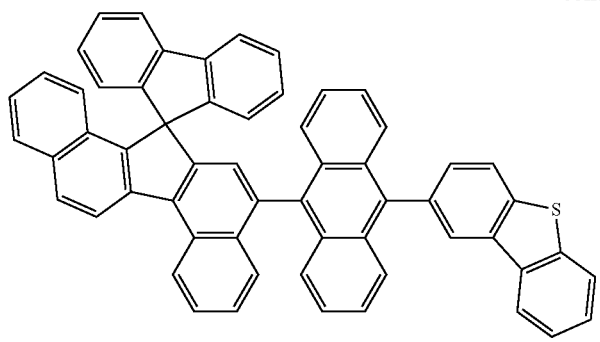
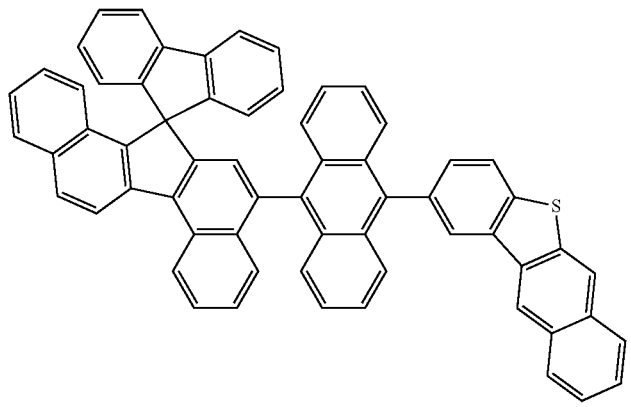
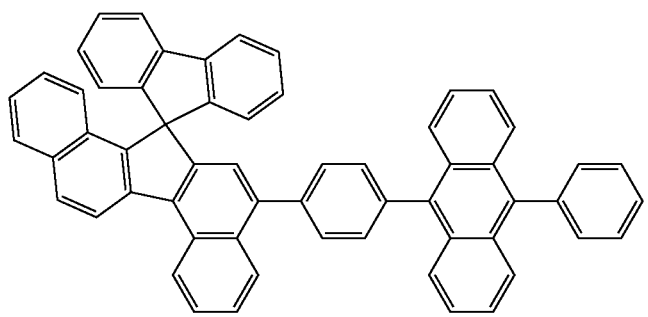
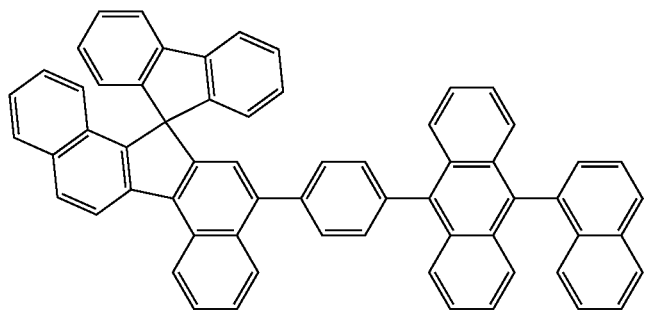
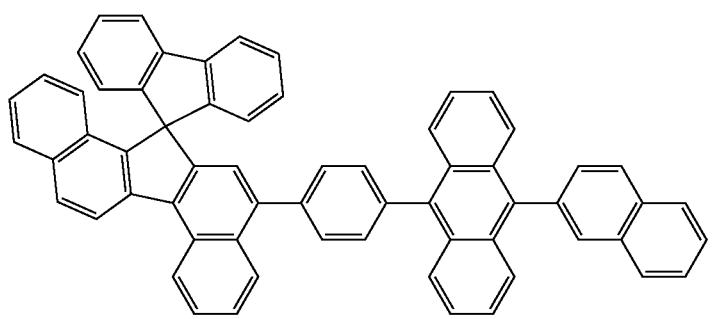

-continued
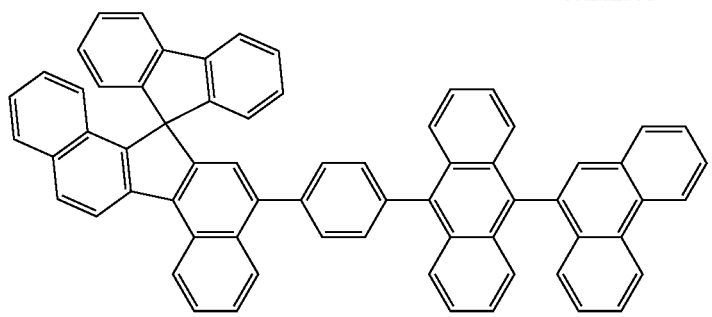
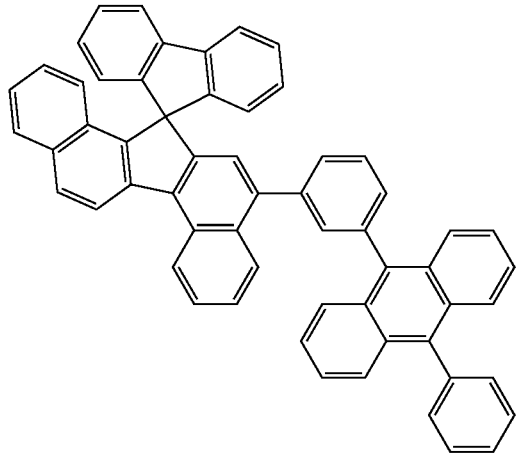
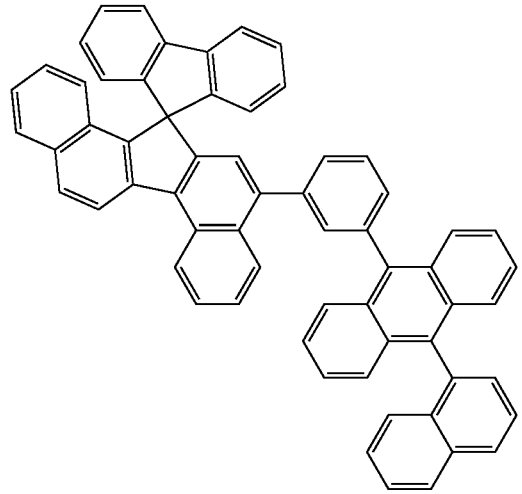
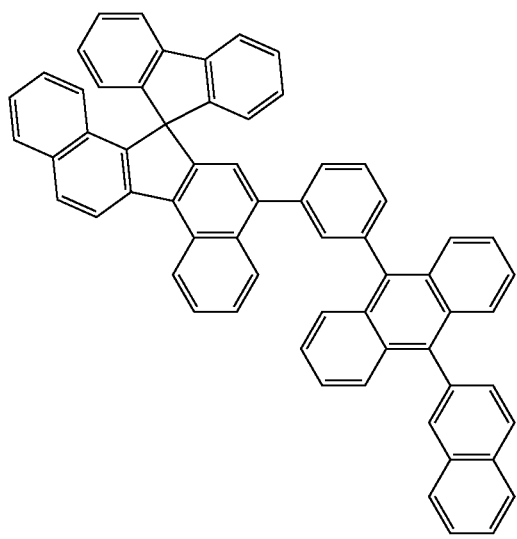
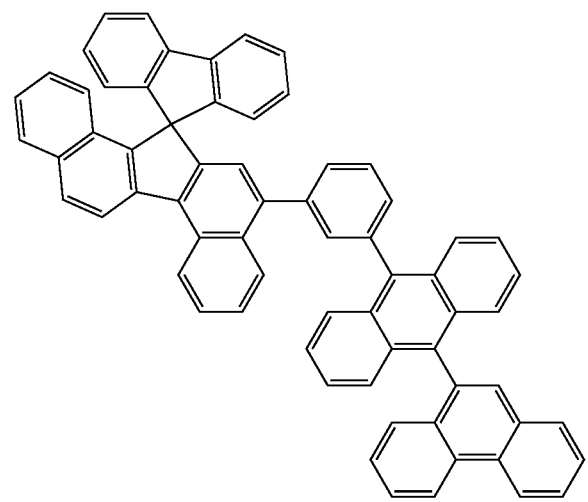
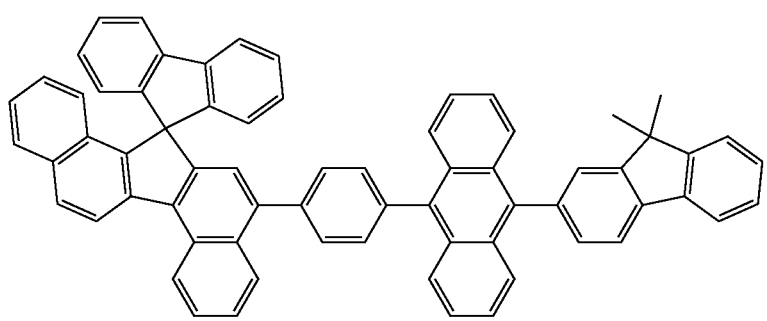

-continued
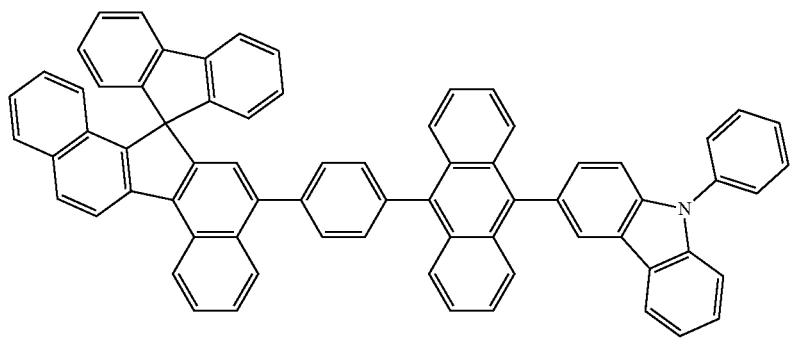
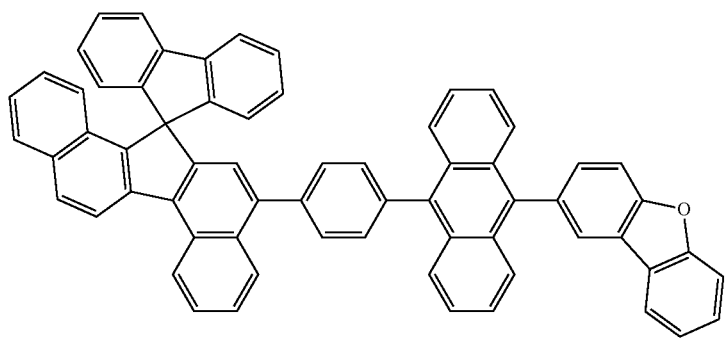
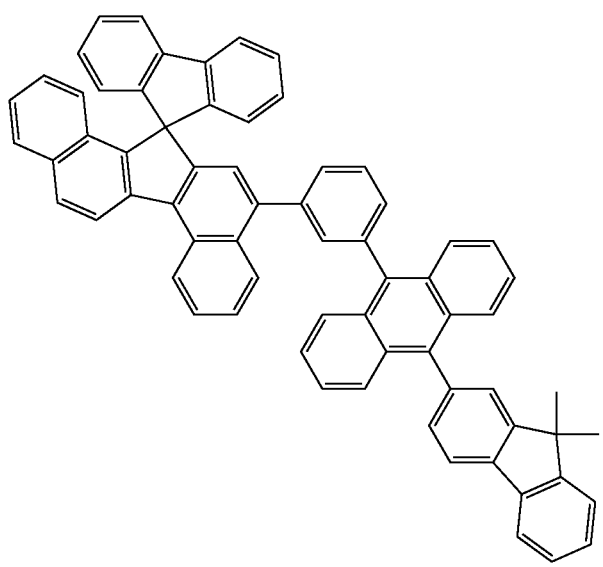

-continued
| 321 | 322 |
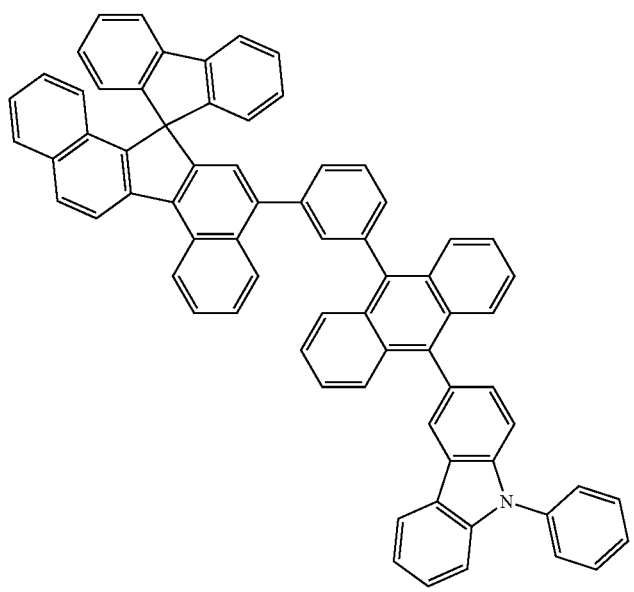
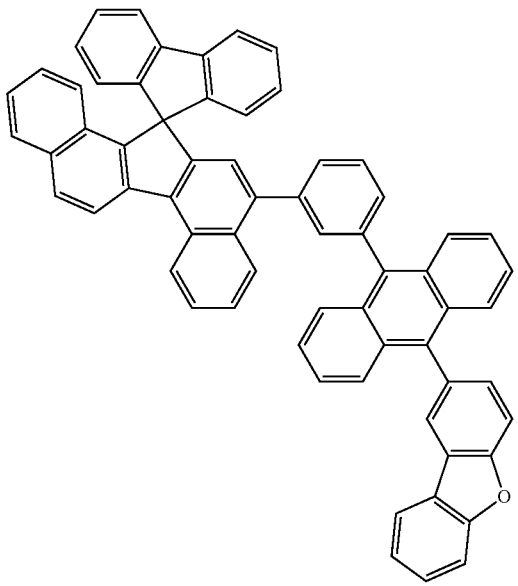
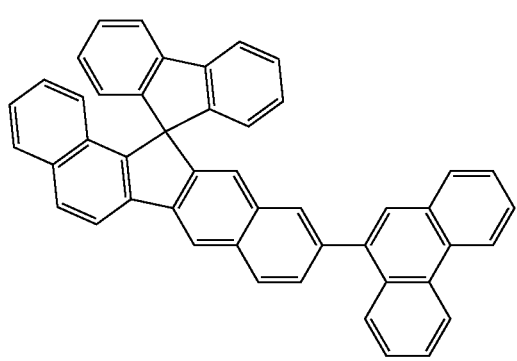
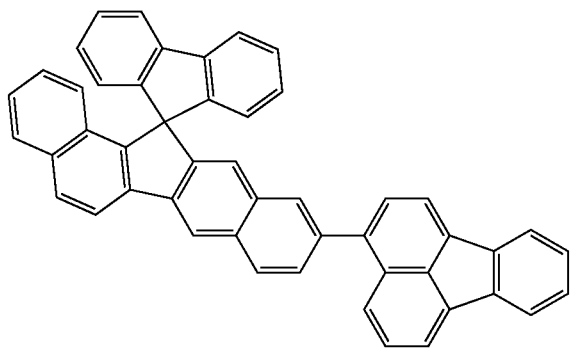
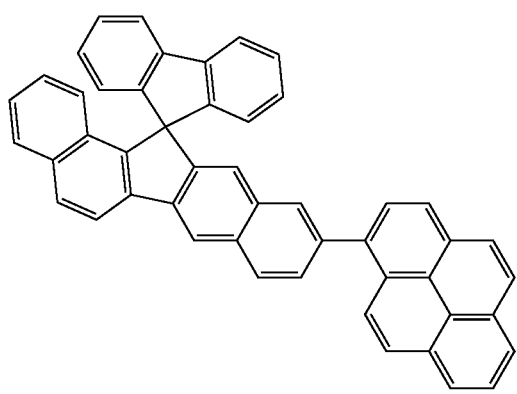
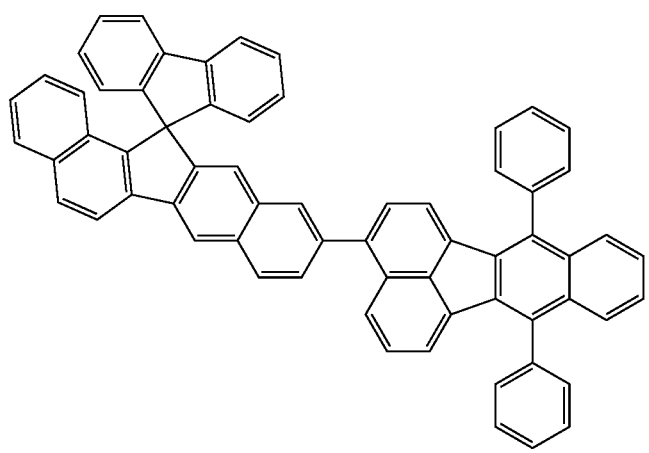

323
324
-continued
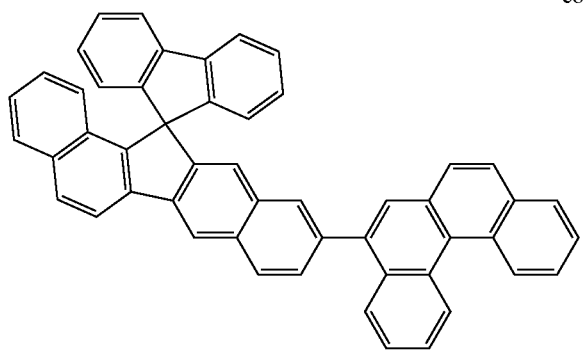

325 326
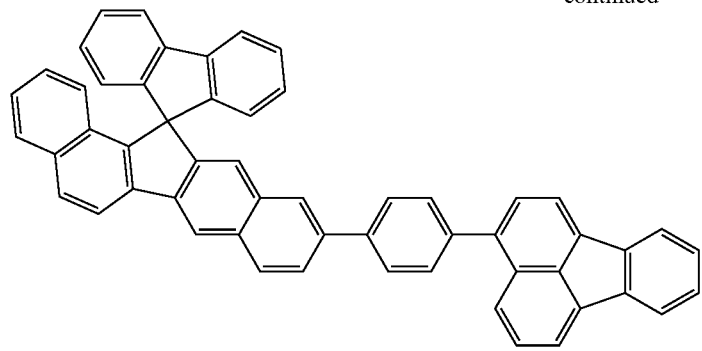
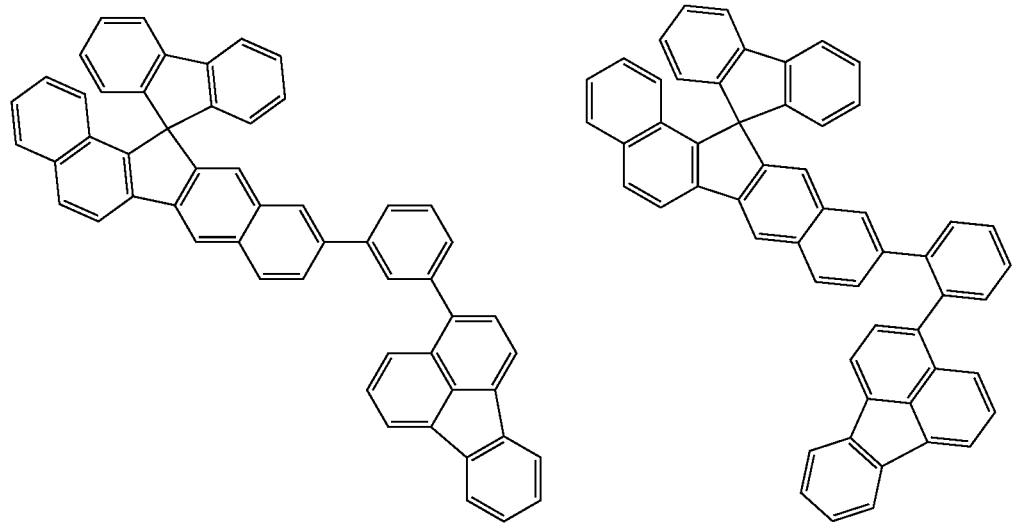
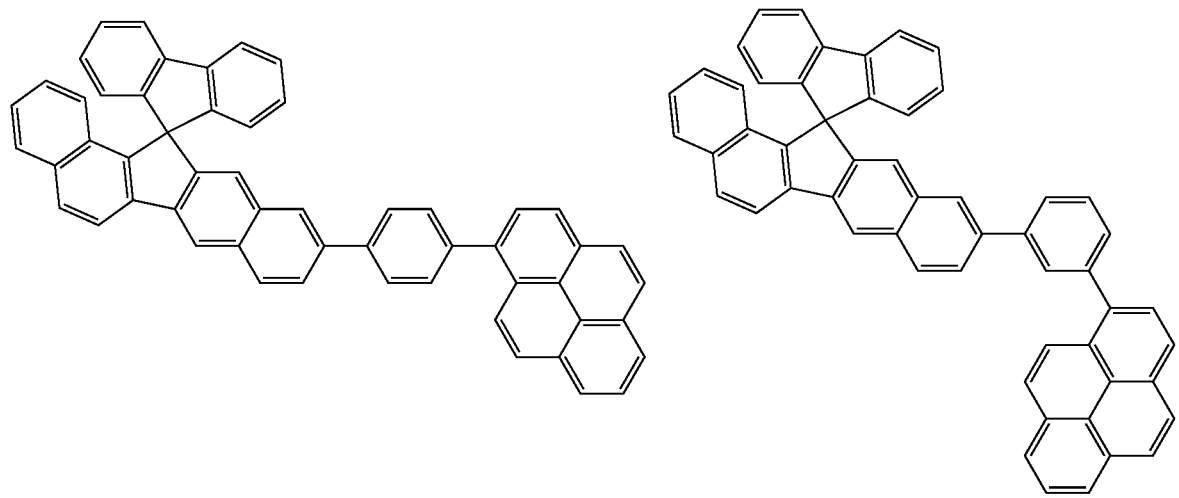

-continued
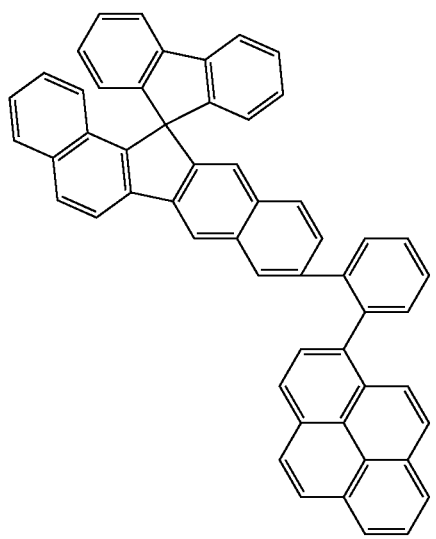
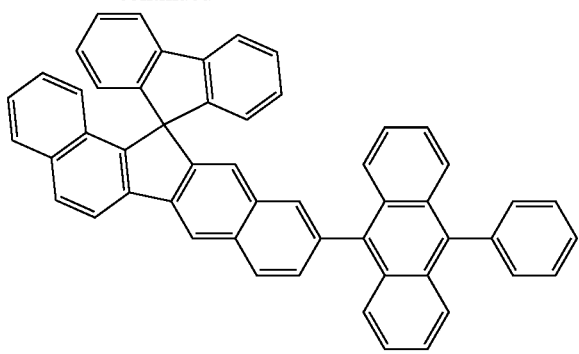
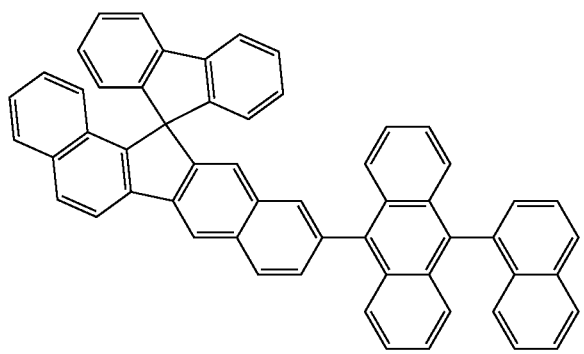
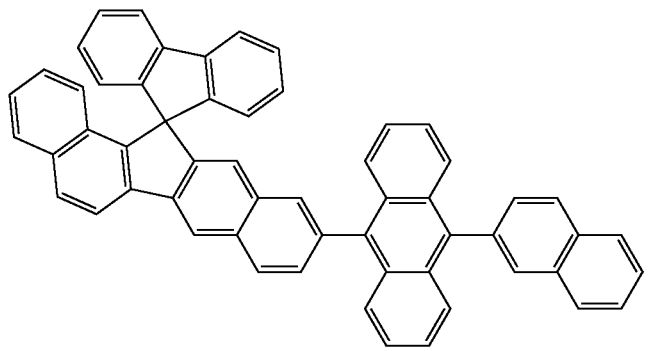
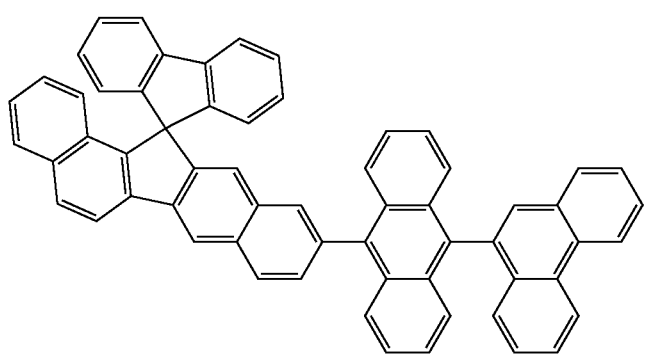

-continued
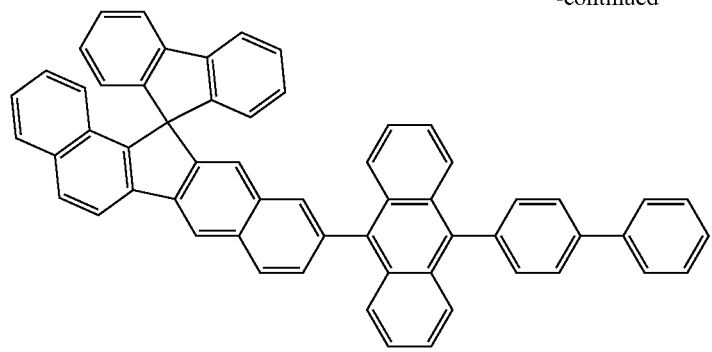

-continued
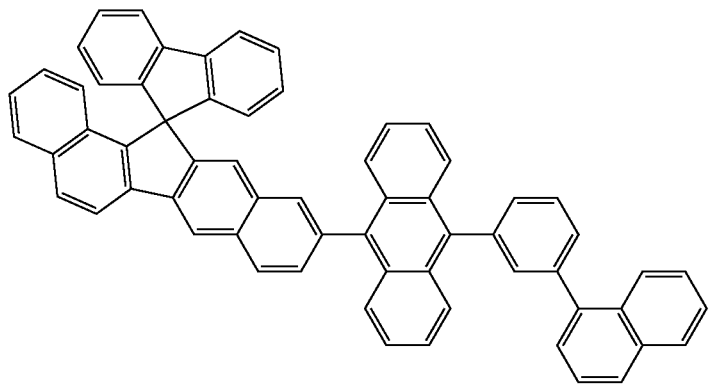

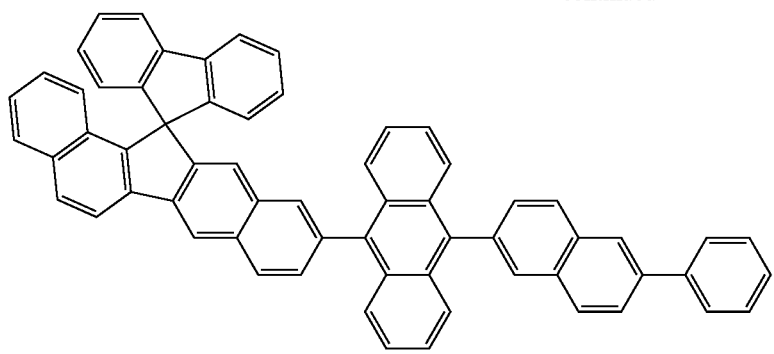

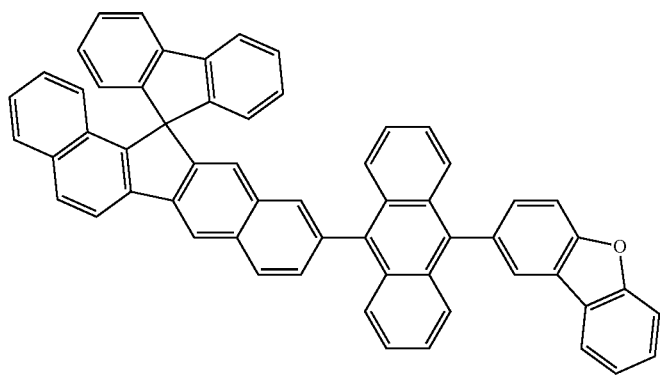

-continued
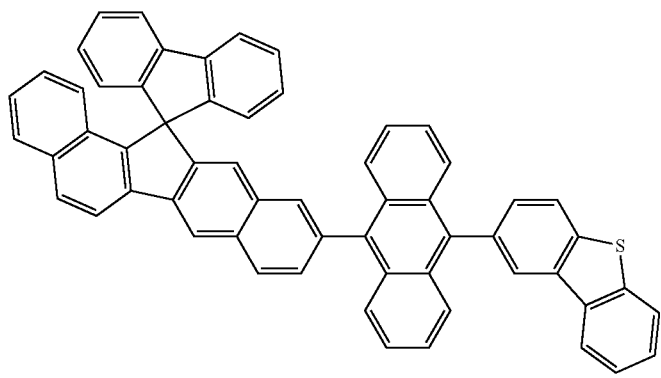

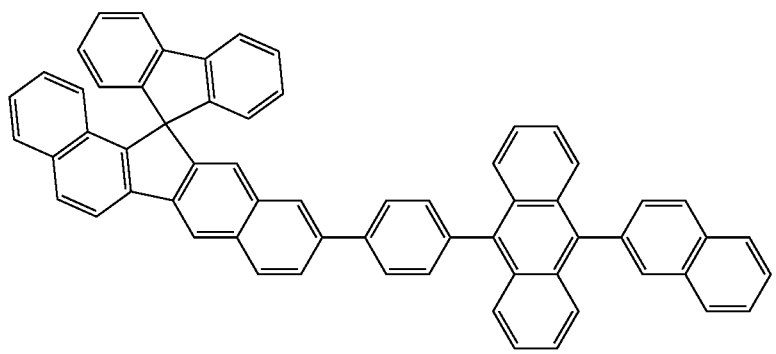

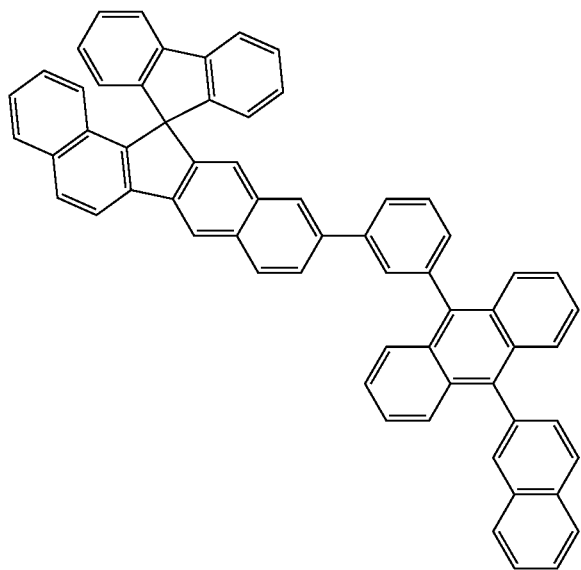
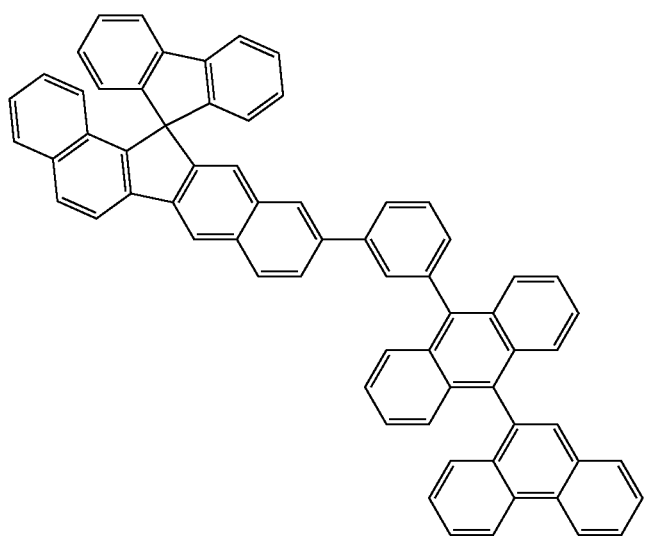 [SMILES: c1cc(-c2ccc3cc4c(cc3c2)C2(c3ccccc3-c3ccccc32)c2c-4ccc3ccccc23)cc(-c2c3ccccc3c(-c3cc4ccccc4c4ccccc34)c3ccccc23)c1]
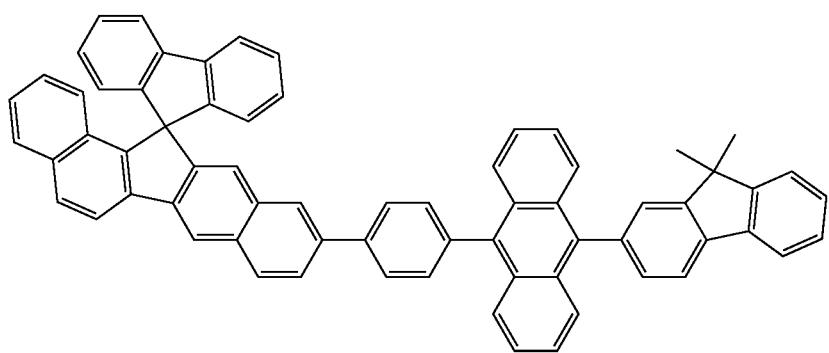

-continued
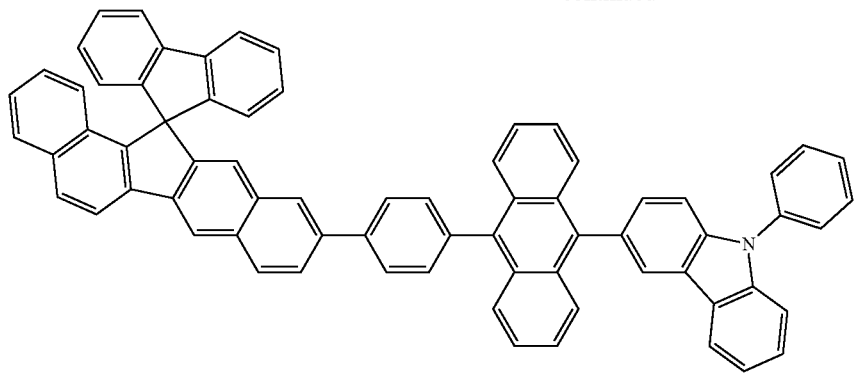
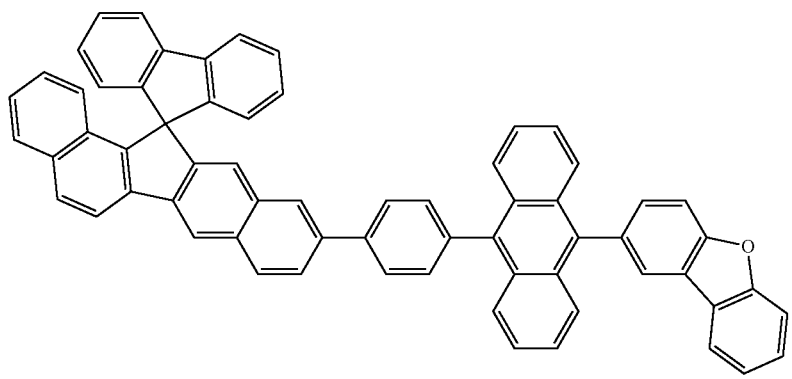
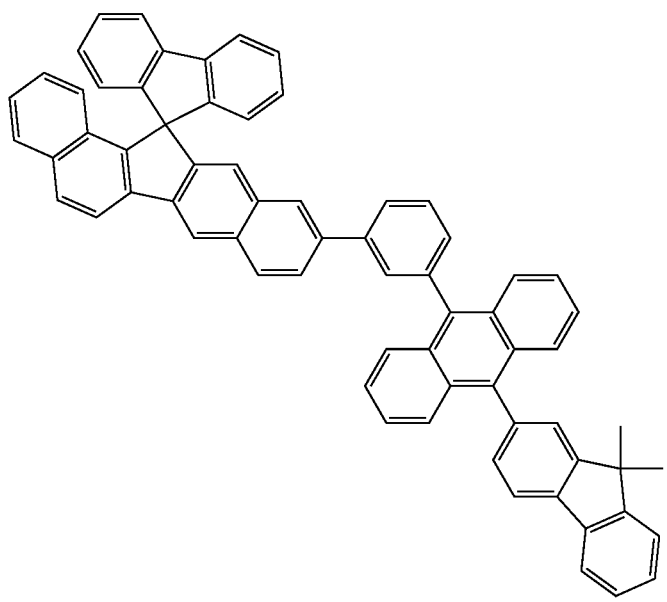

-continued
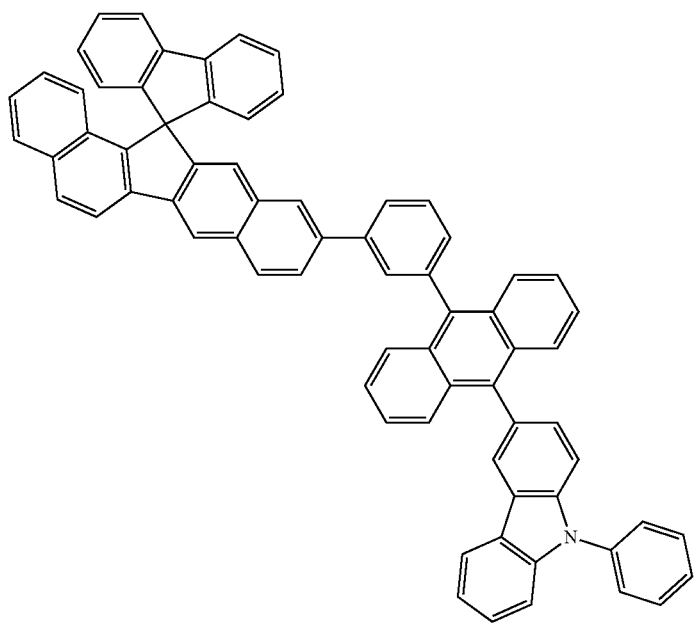
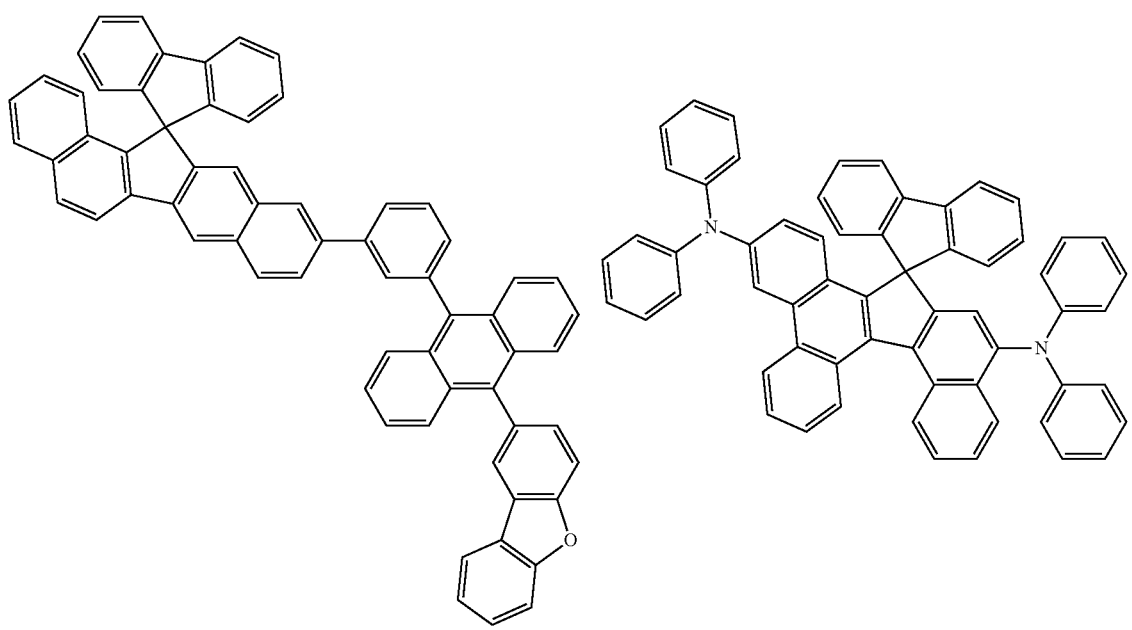
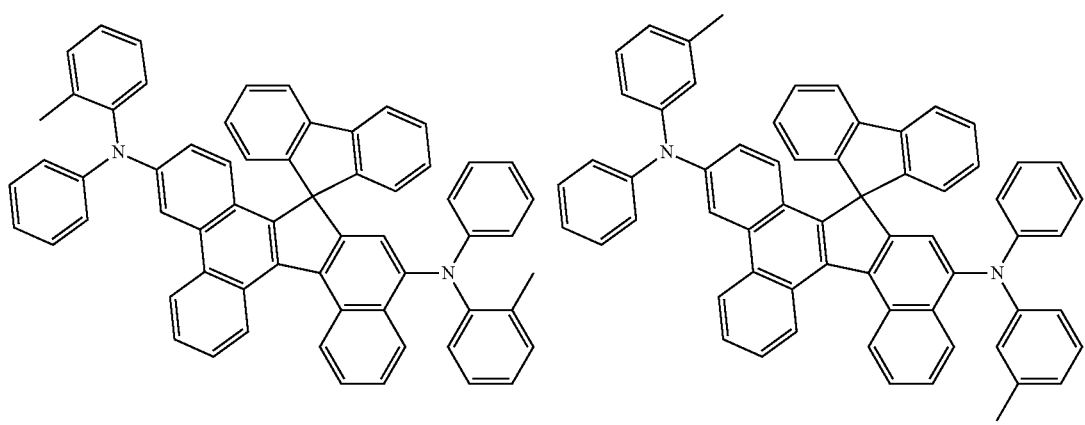

347
348
-continued
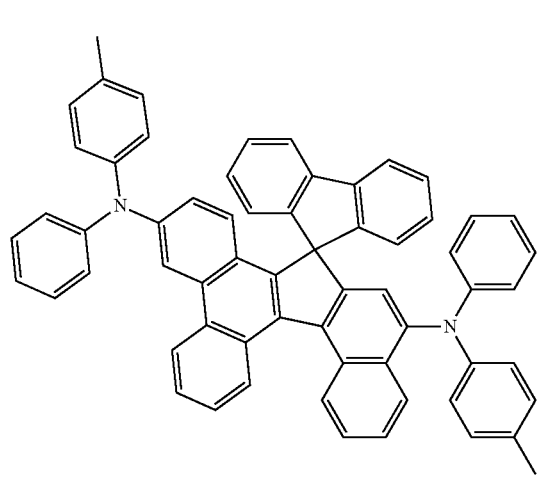
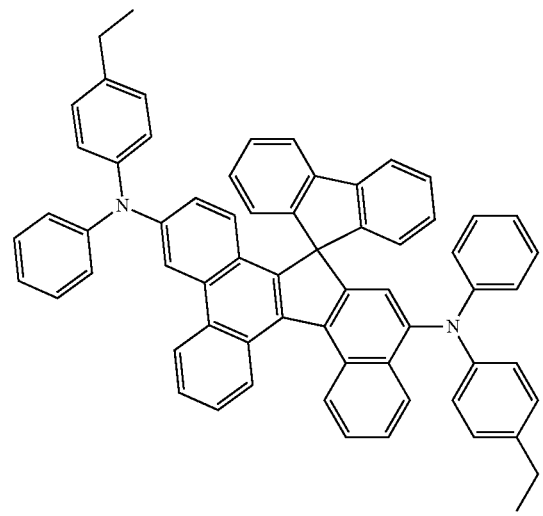
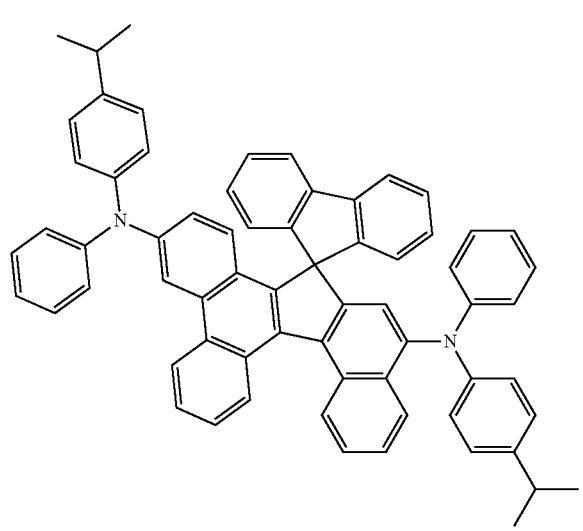
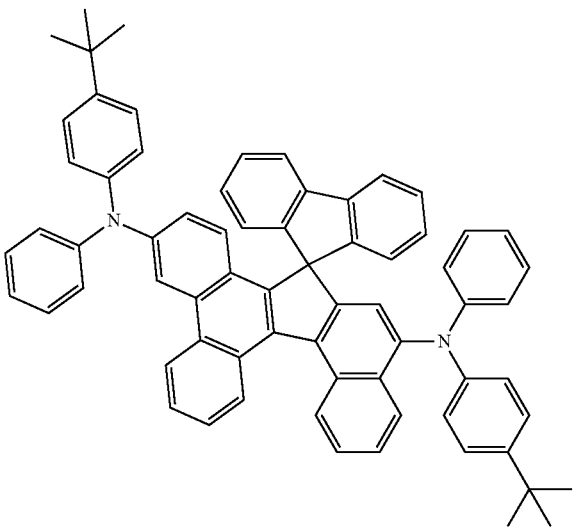
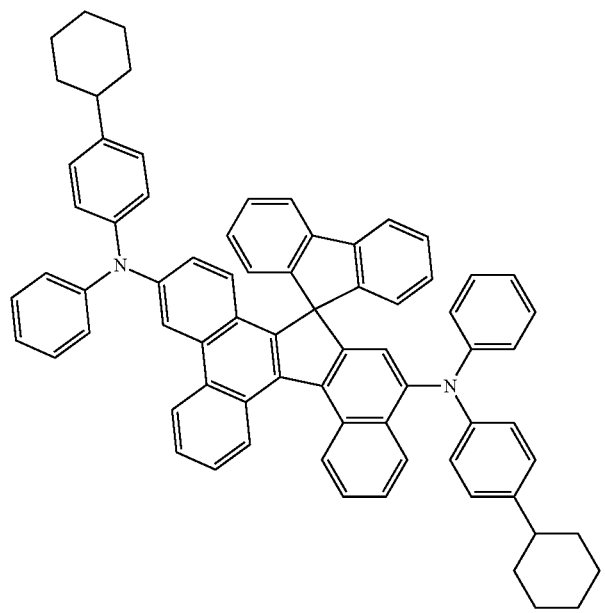
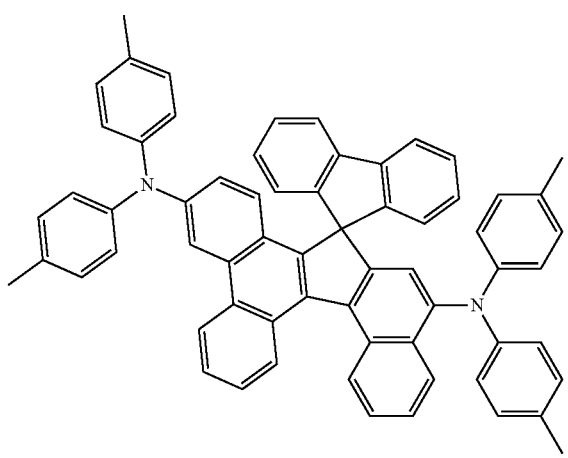

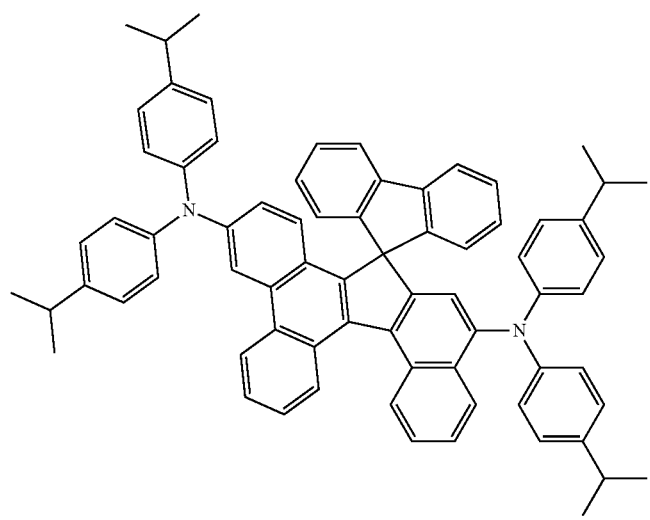
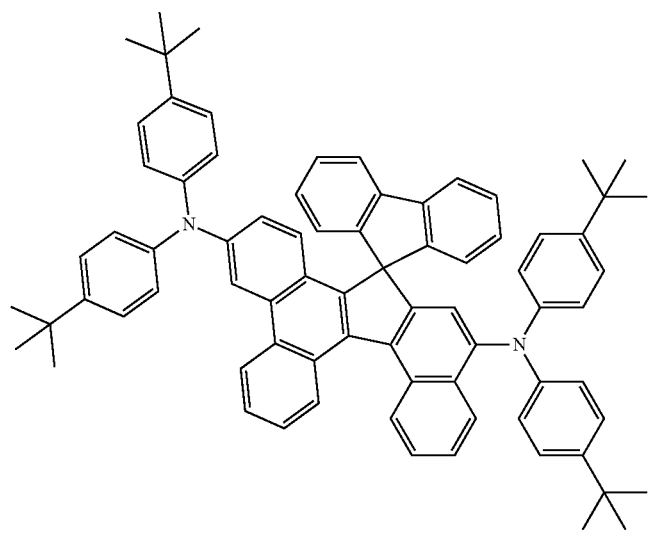
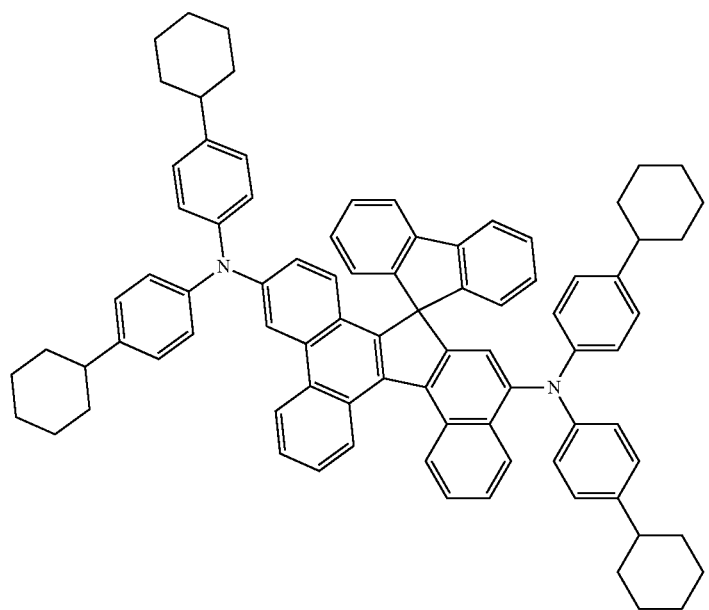

-continued
| 351 | 352 |
|---|---|
| 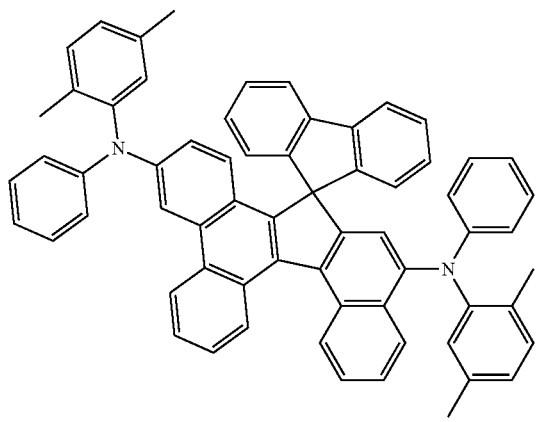 | 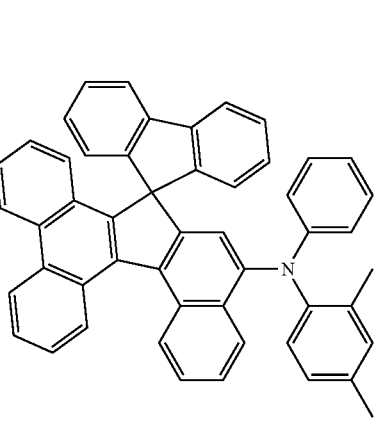 |
| 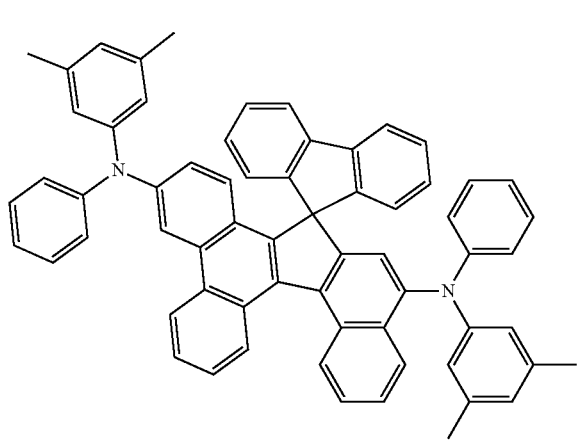 | 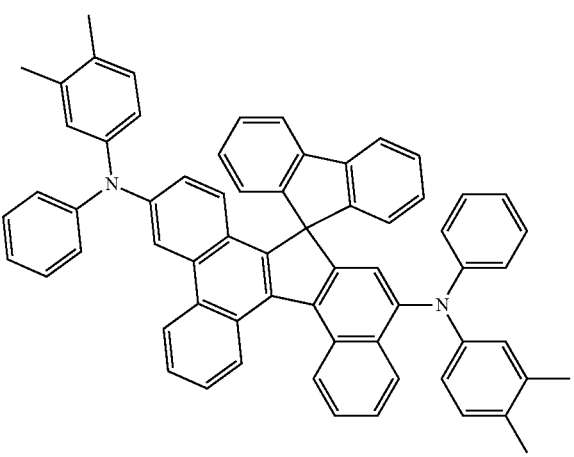 |
| 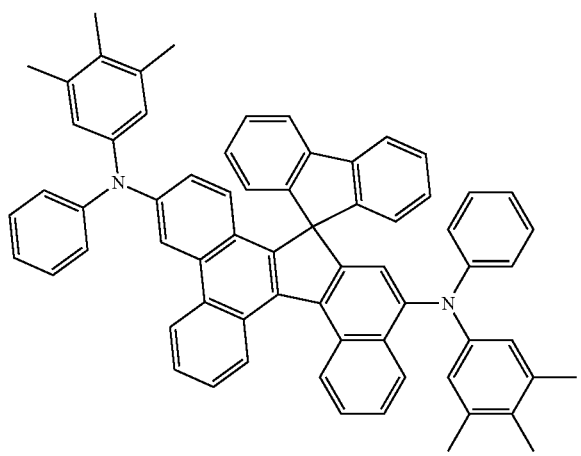 | 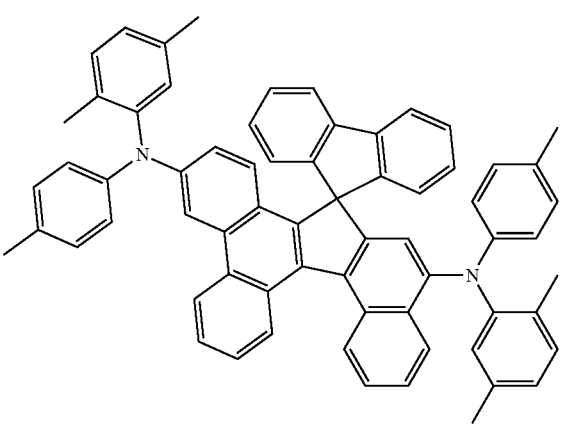 |

-continued
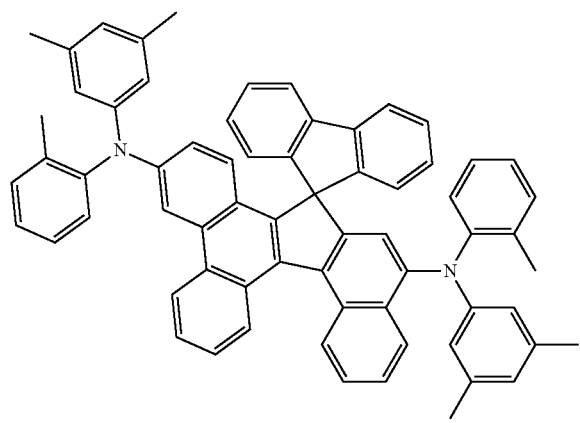
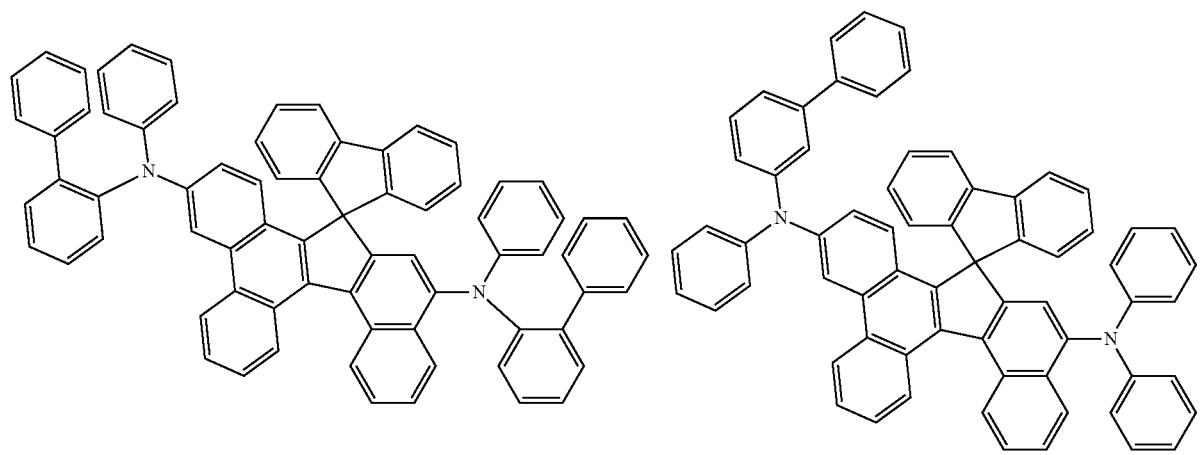
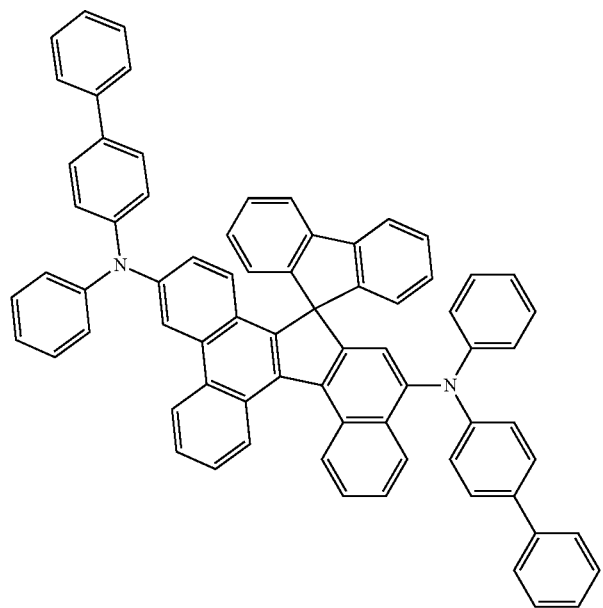

-continued
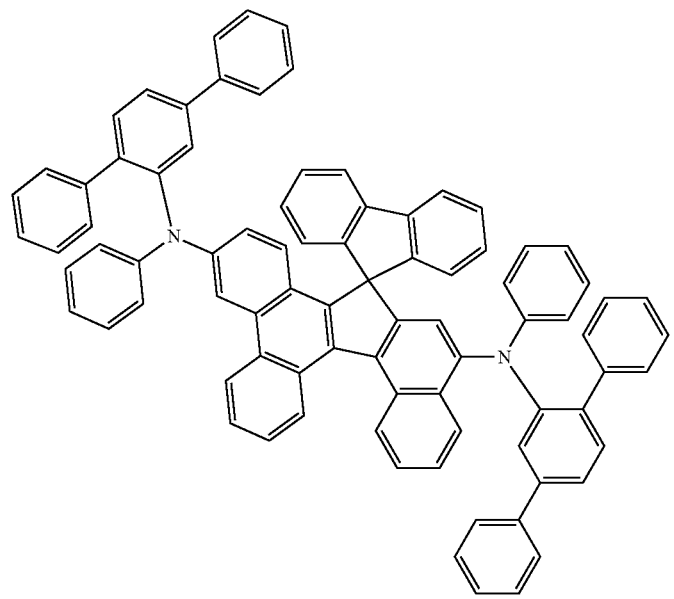
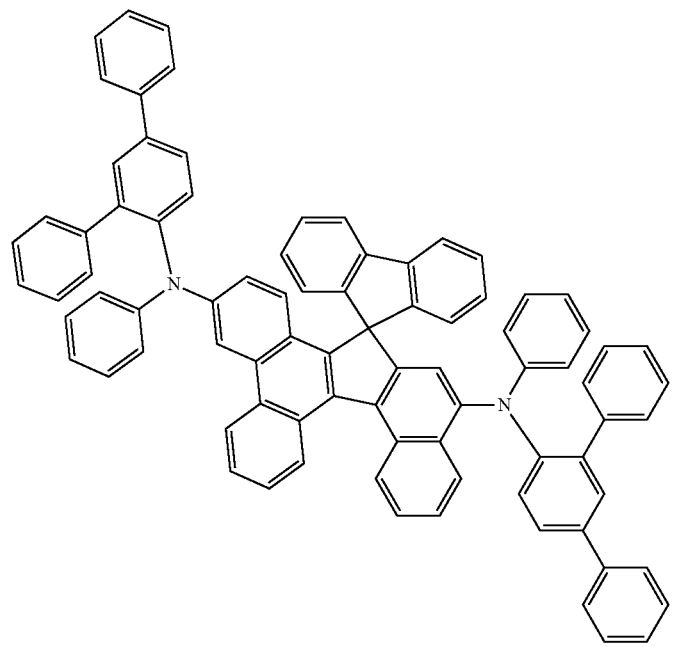
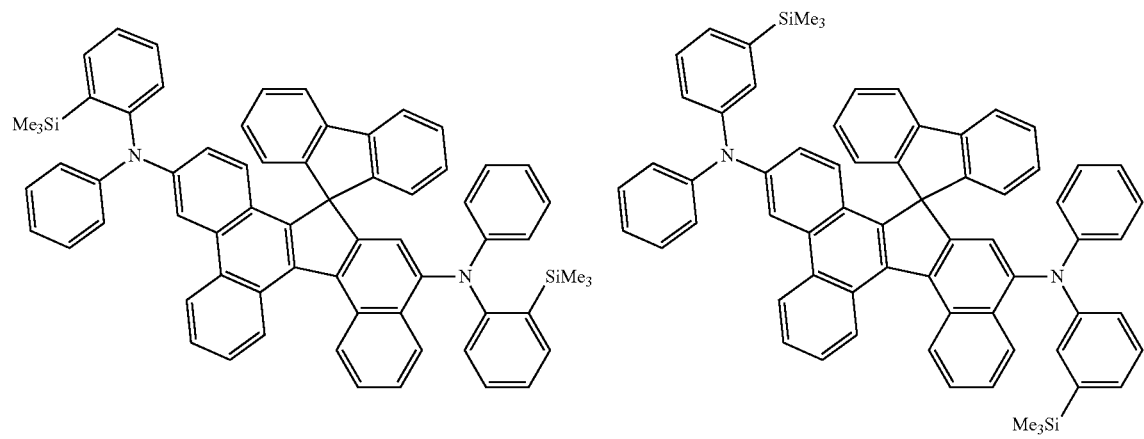

-continued
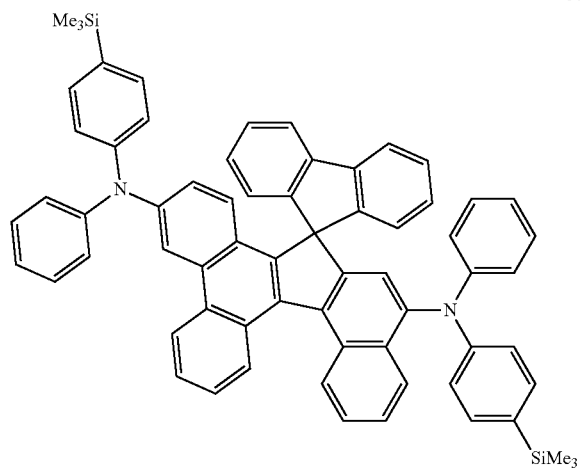
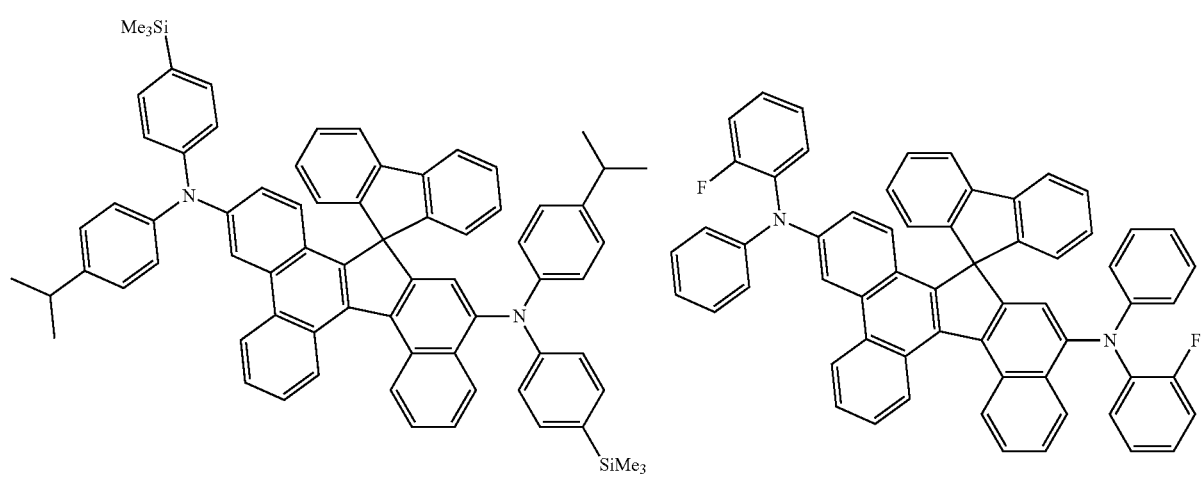
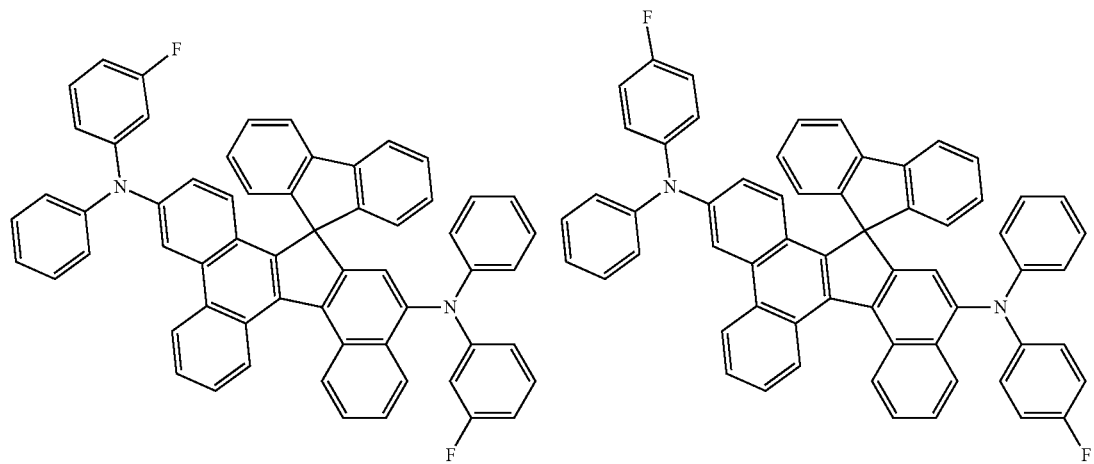

-continued
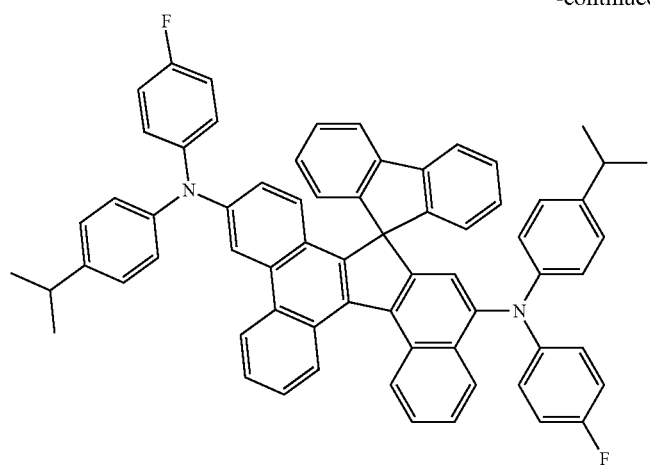
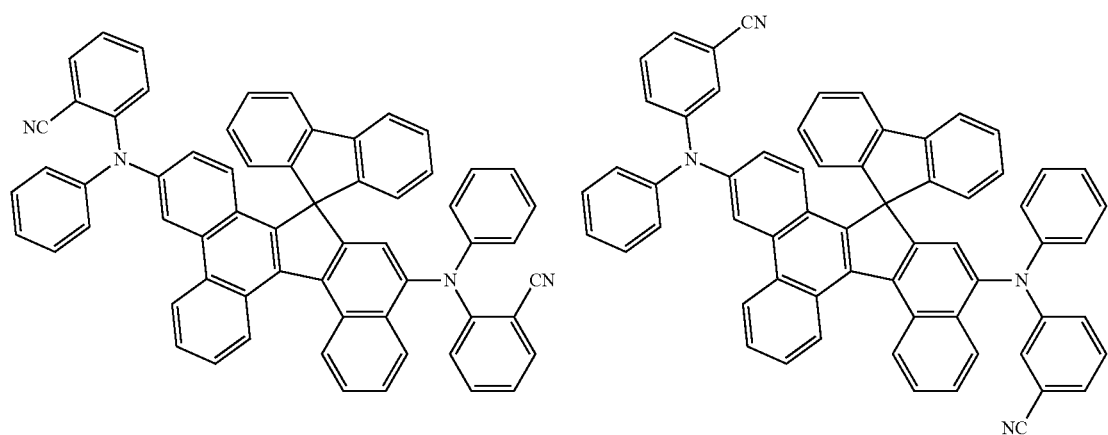
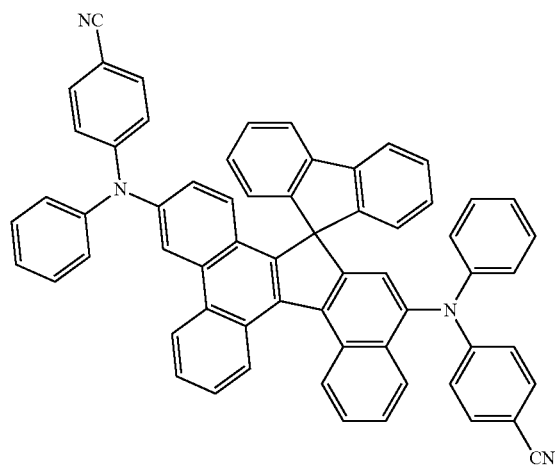

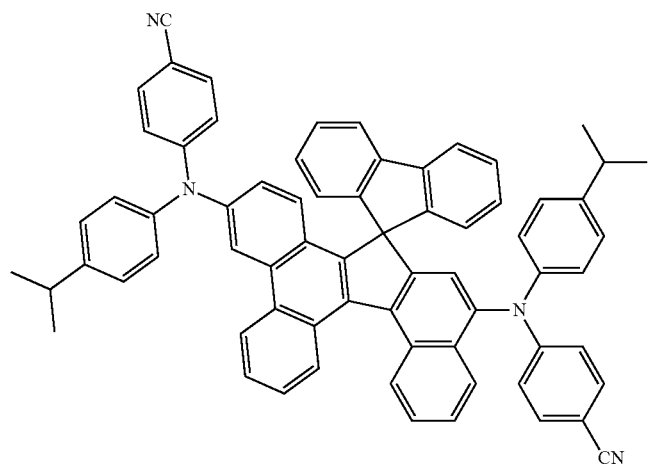
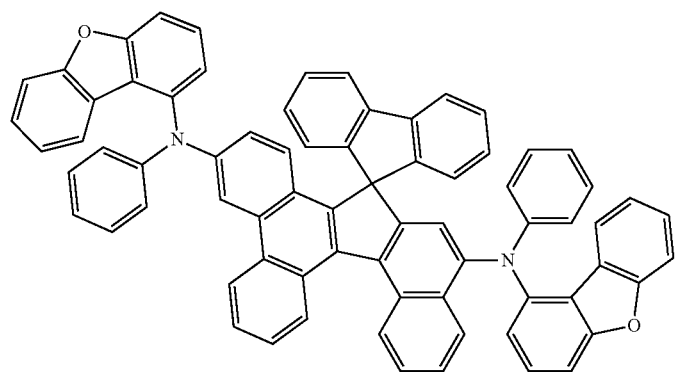
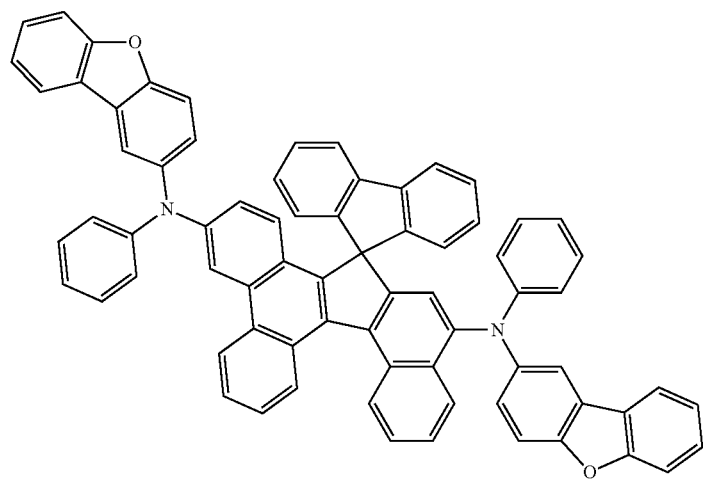

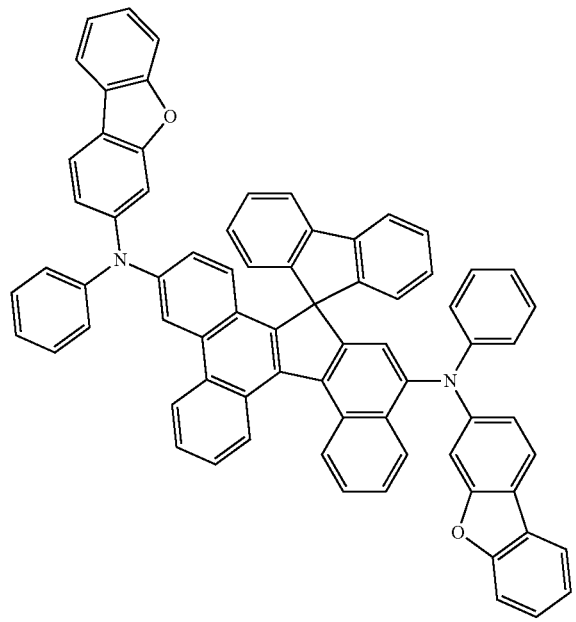
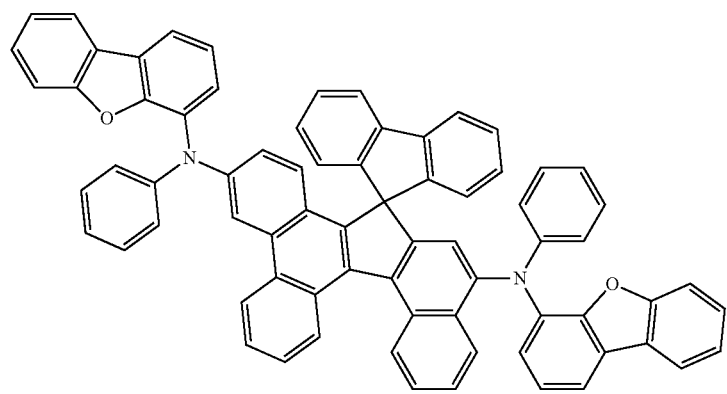
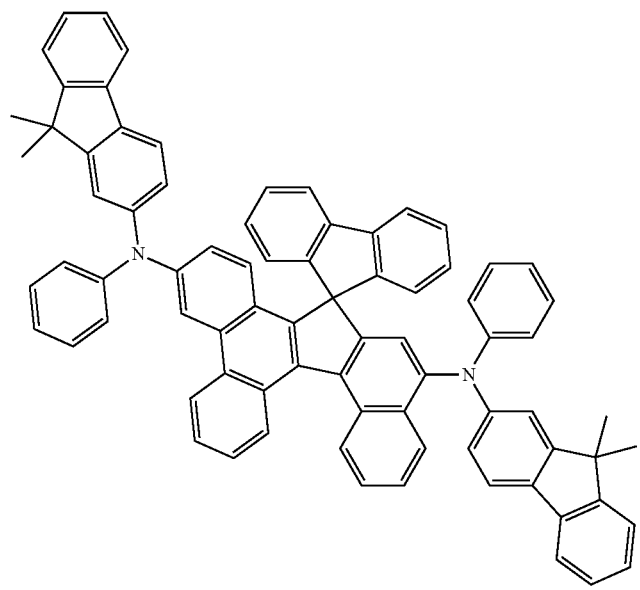

-continued
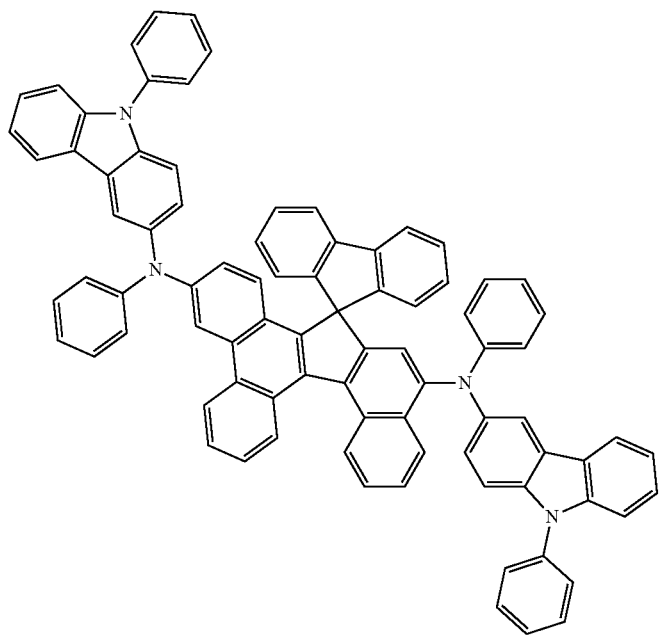
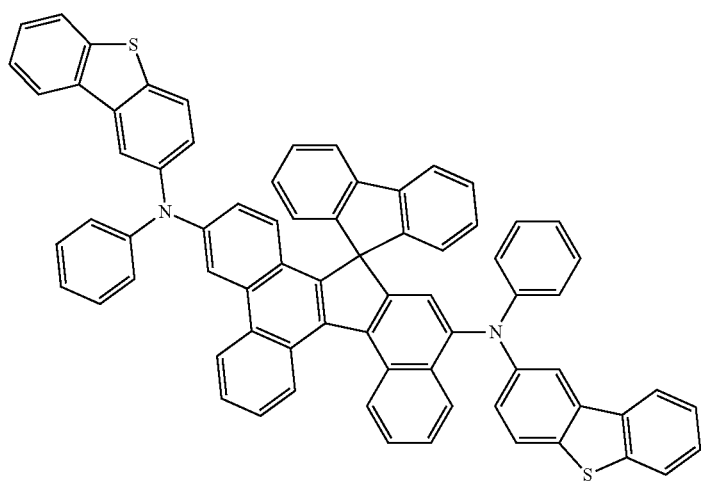
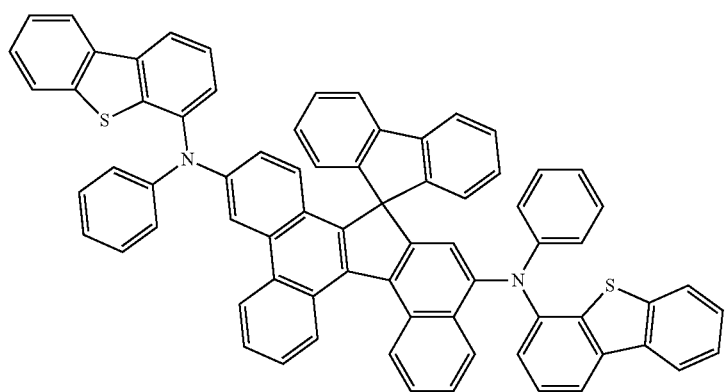

-continued
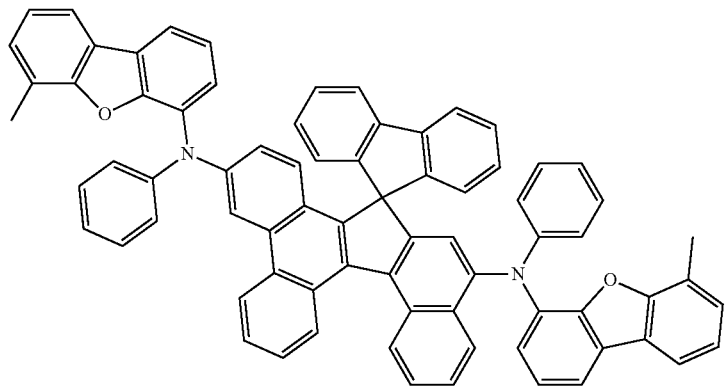
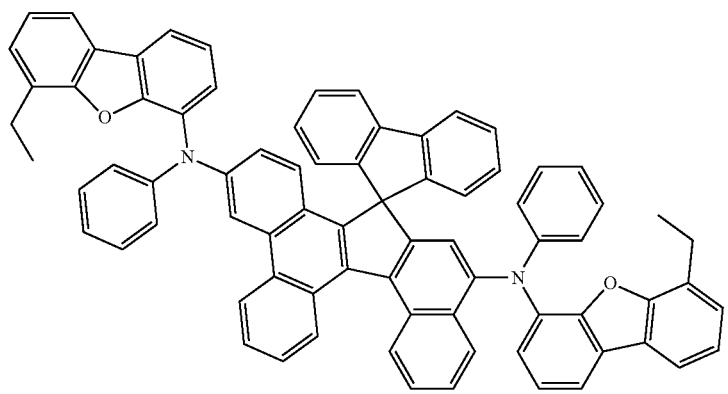
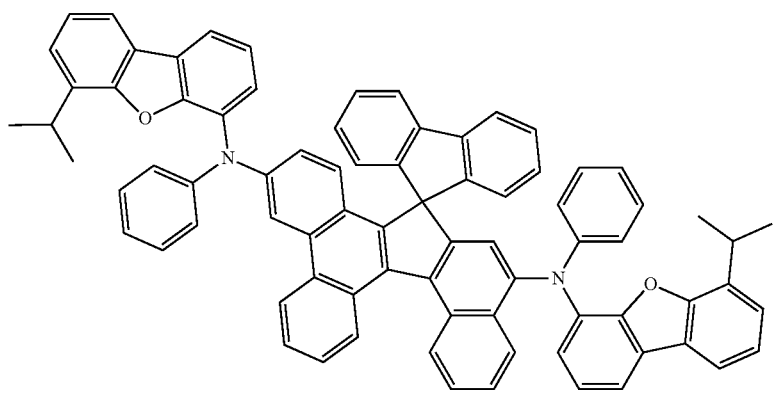
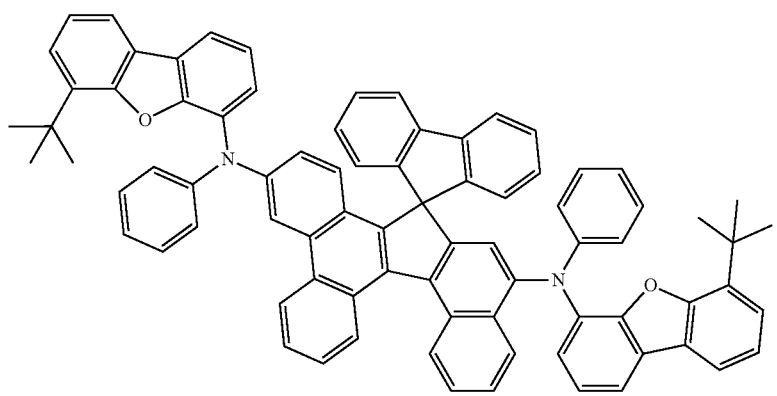

-continued
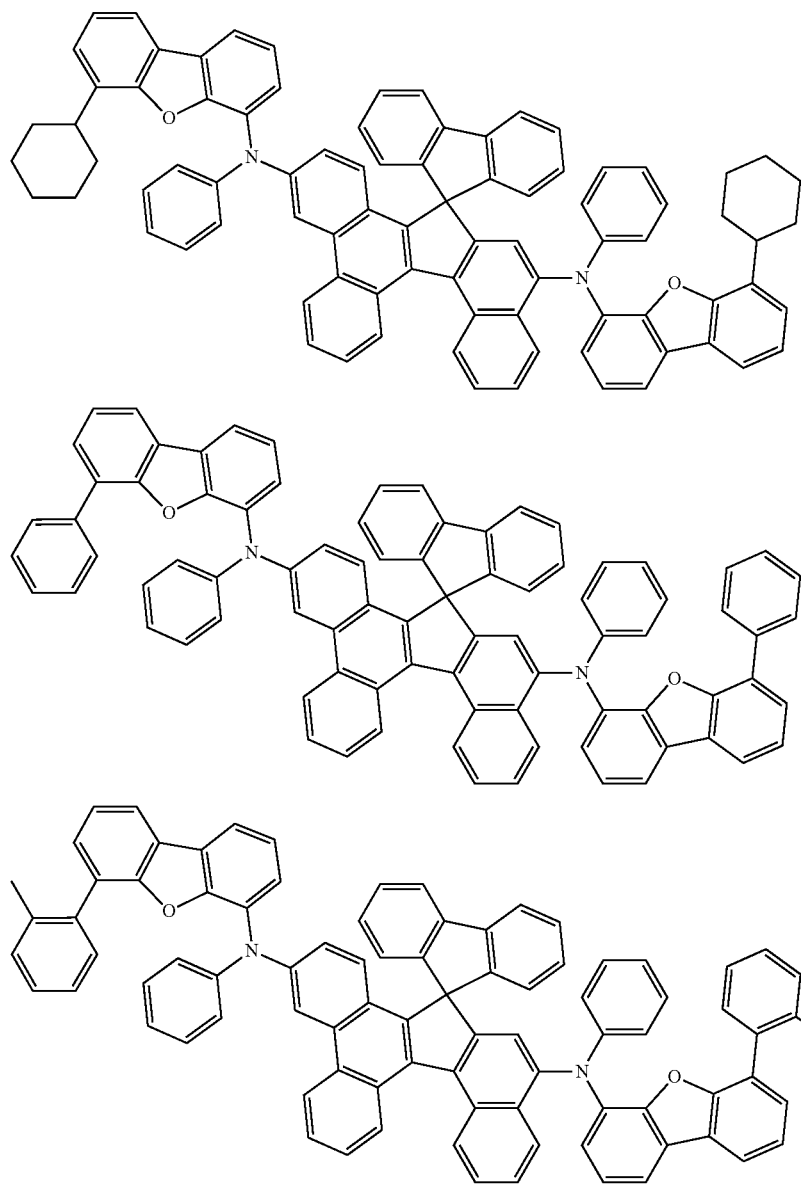
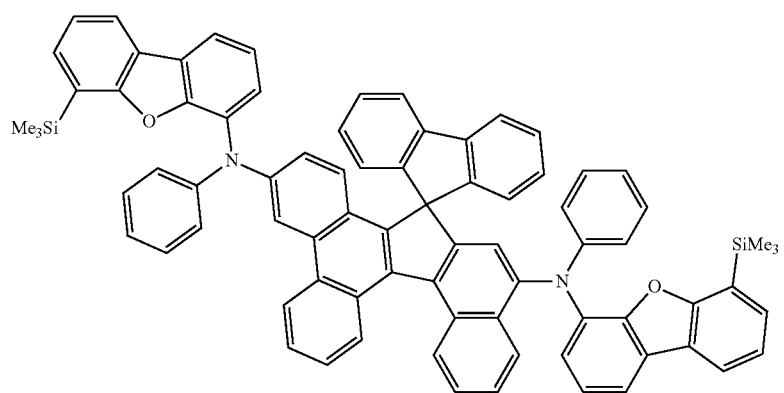

-continued
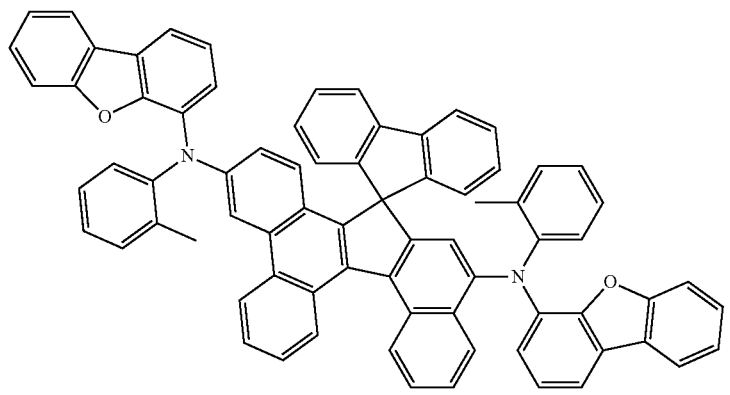
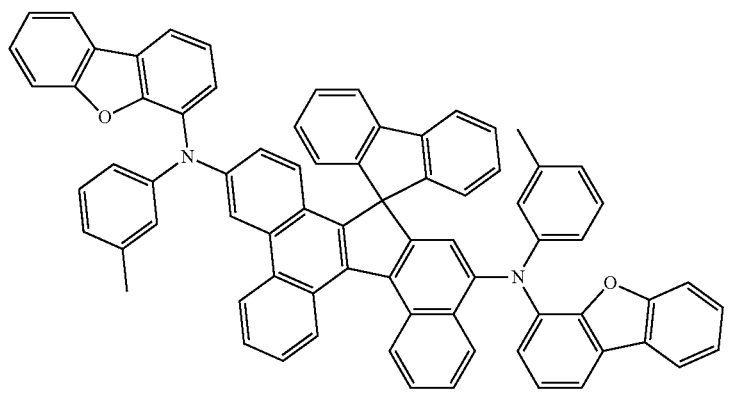
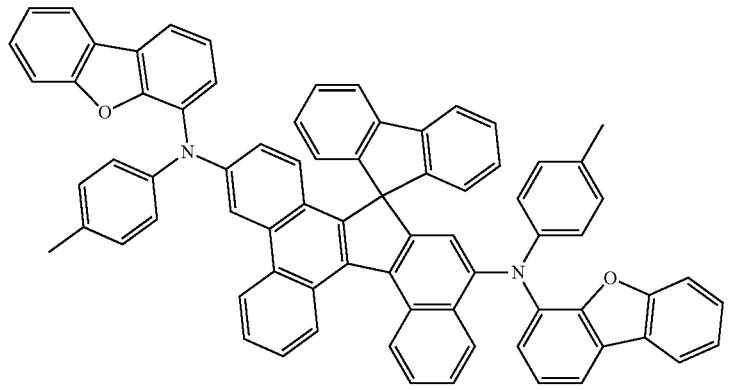
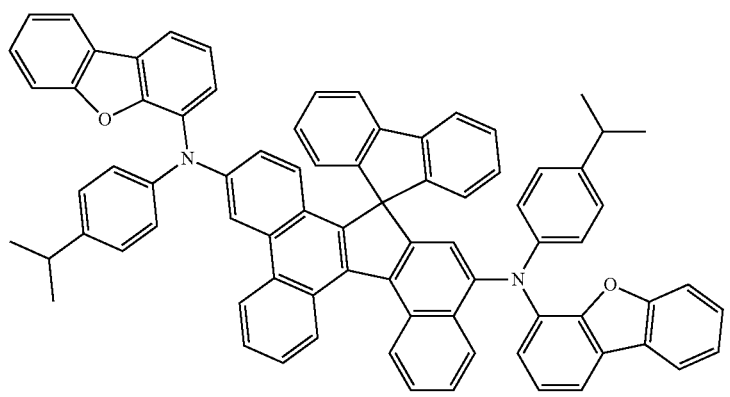

-continued
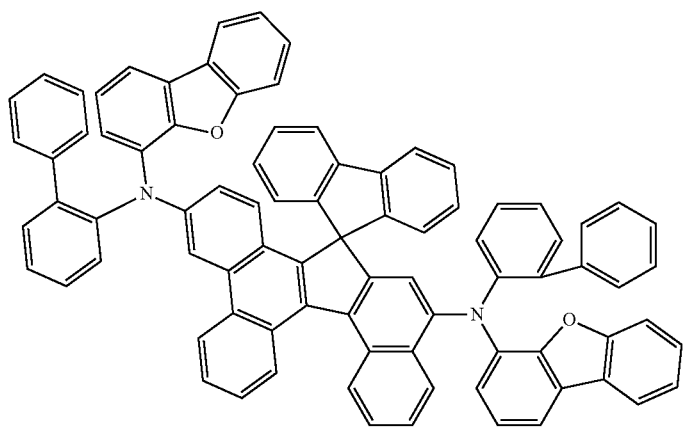
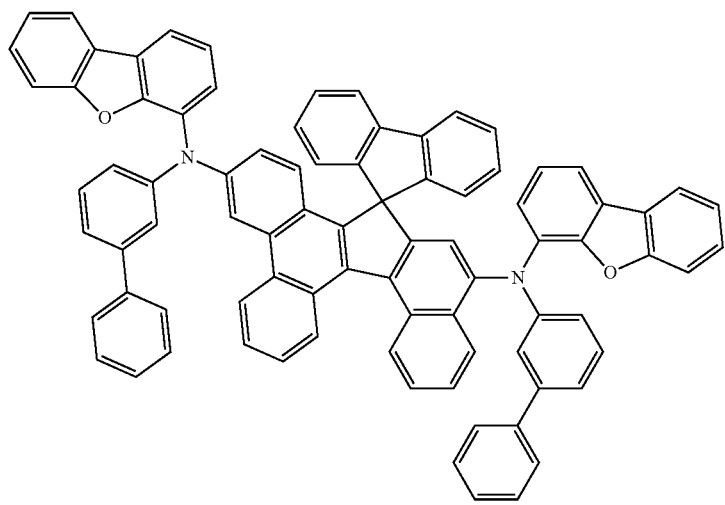
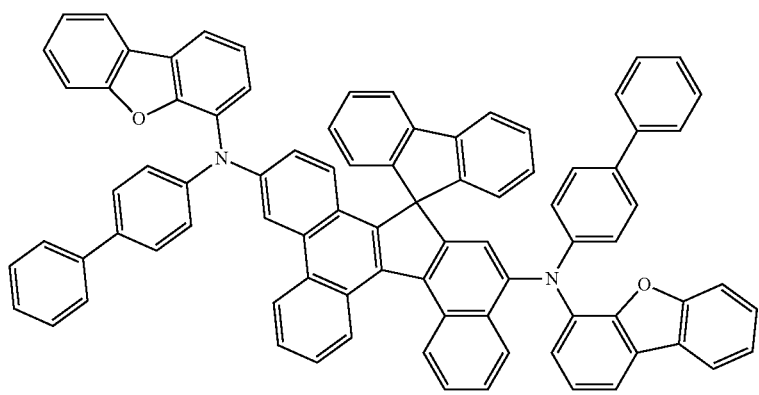
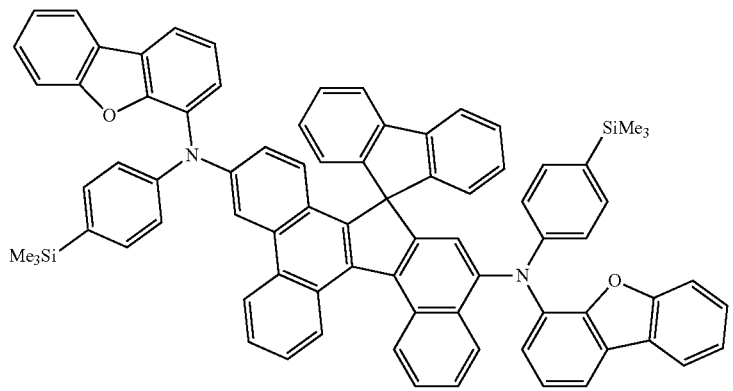

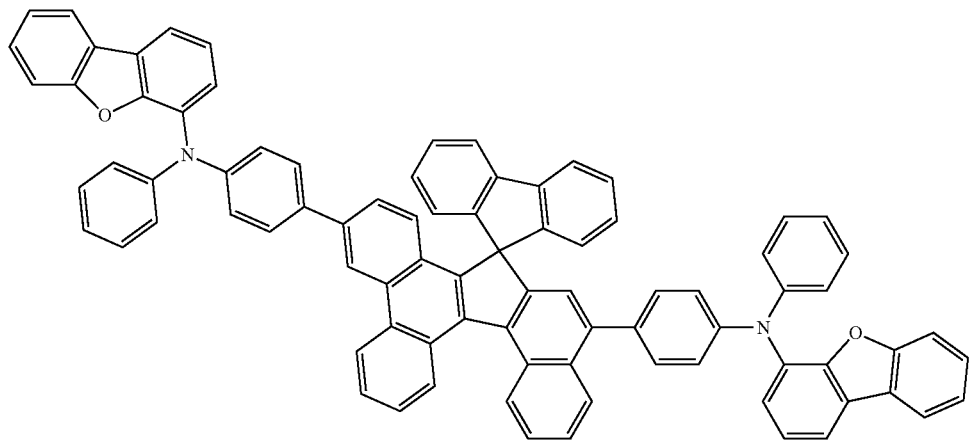
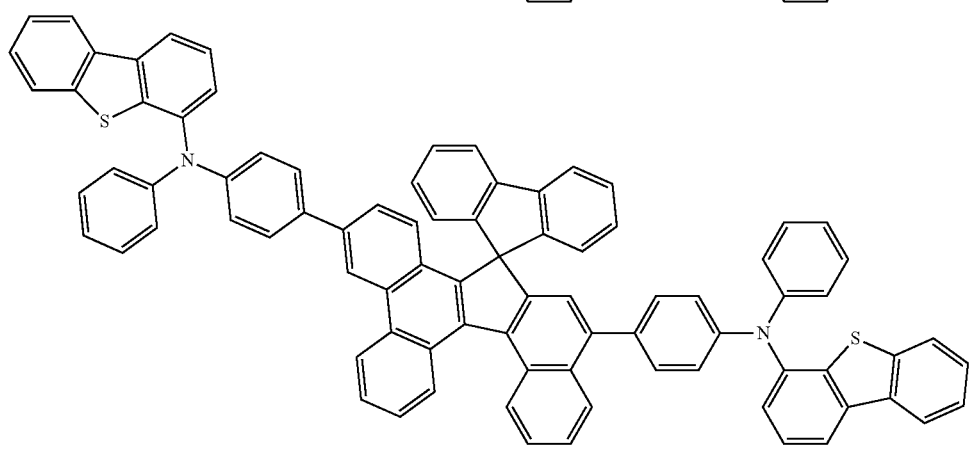
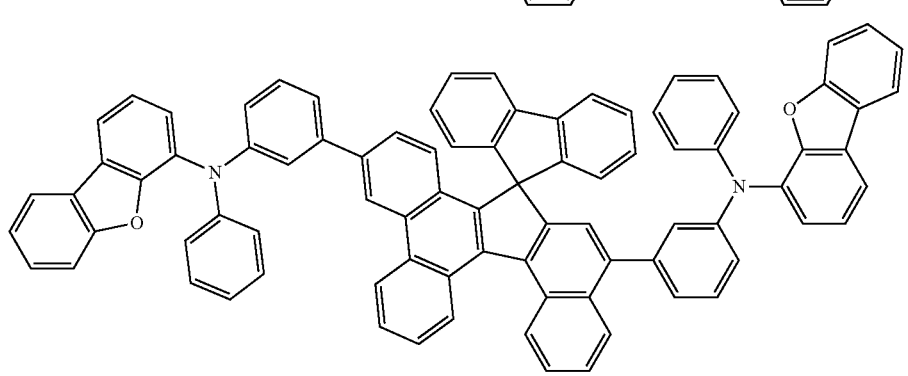
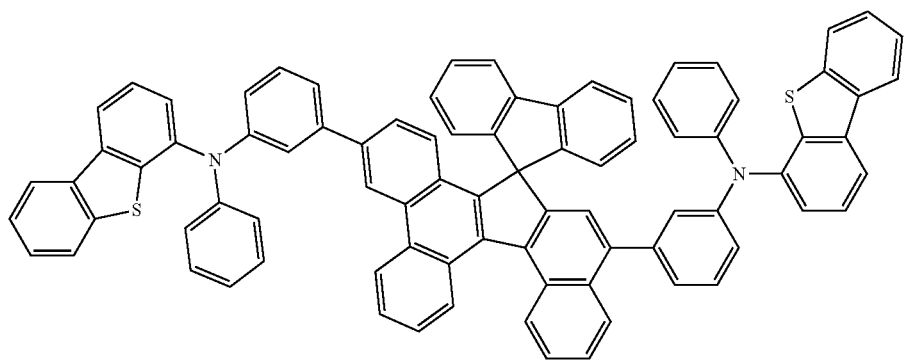

-continued
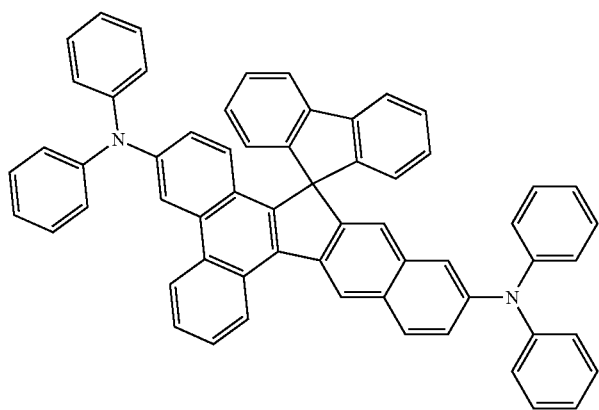
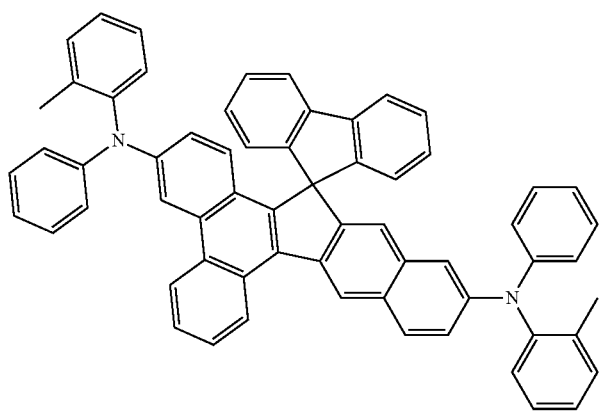
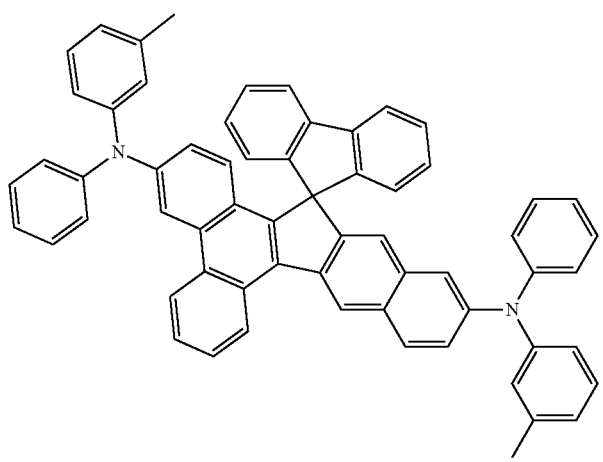

-continued
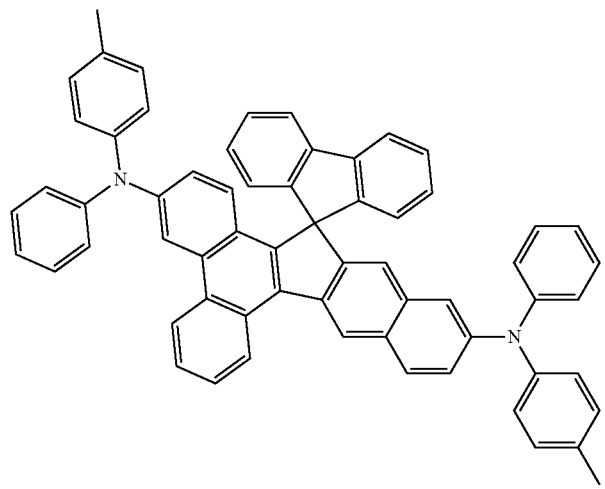
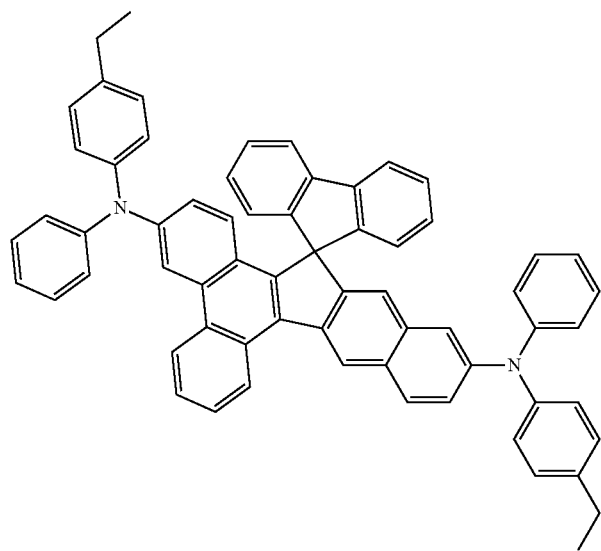
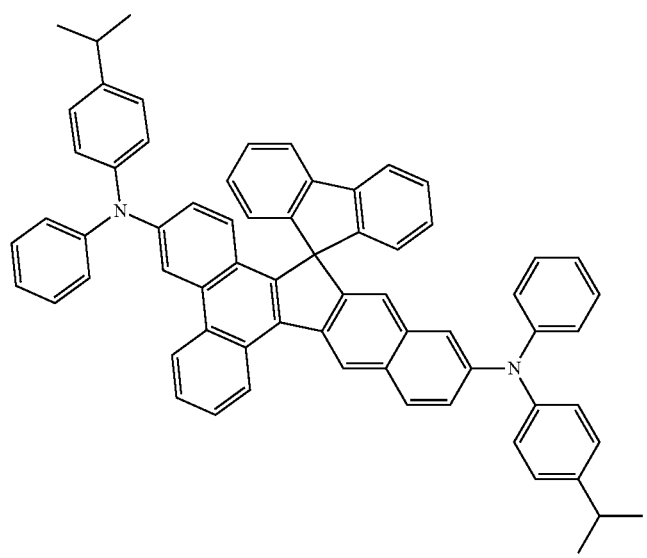

-continued
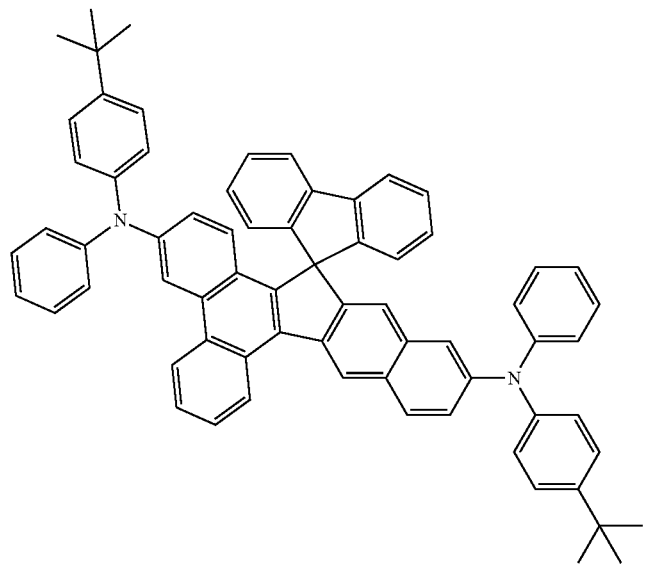
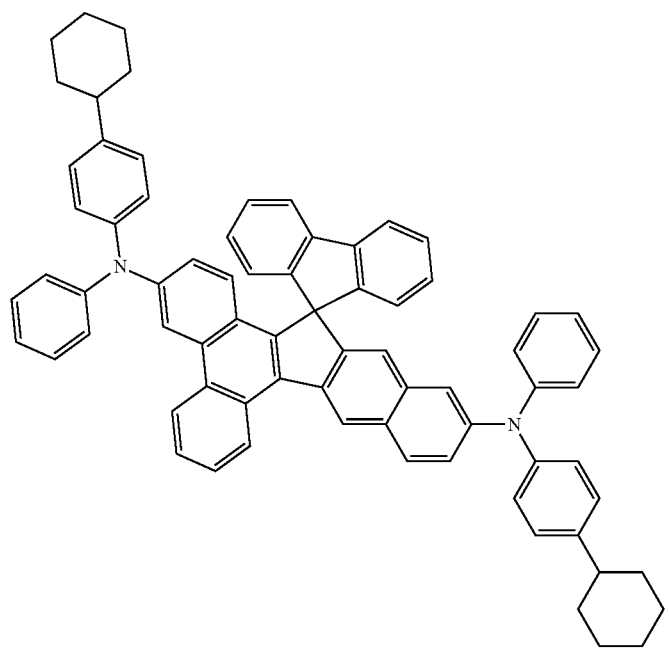
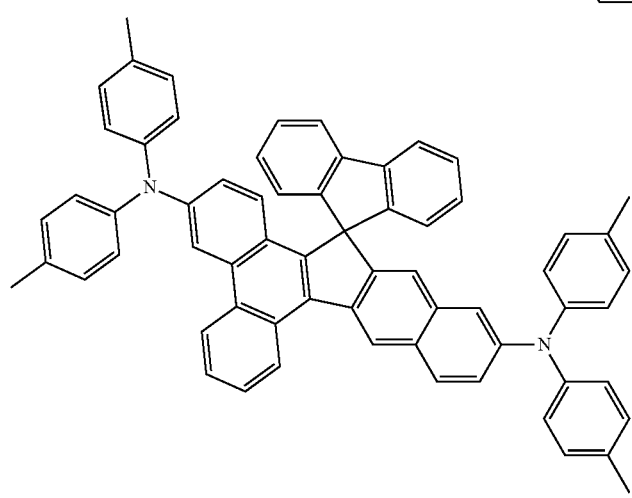

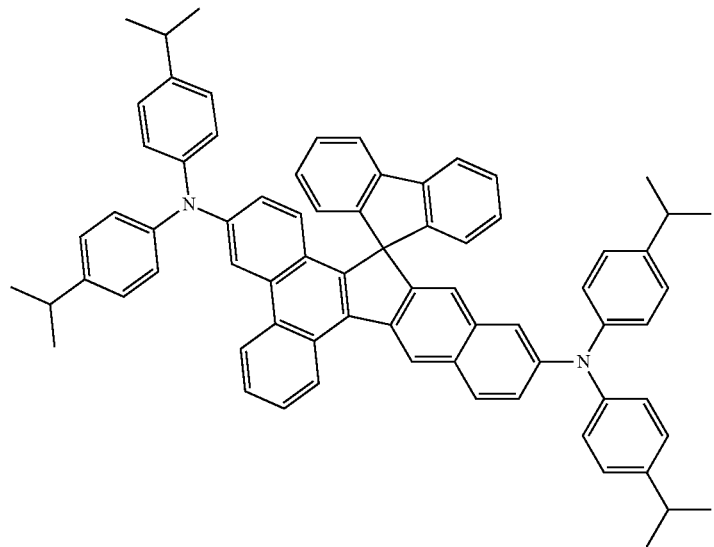
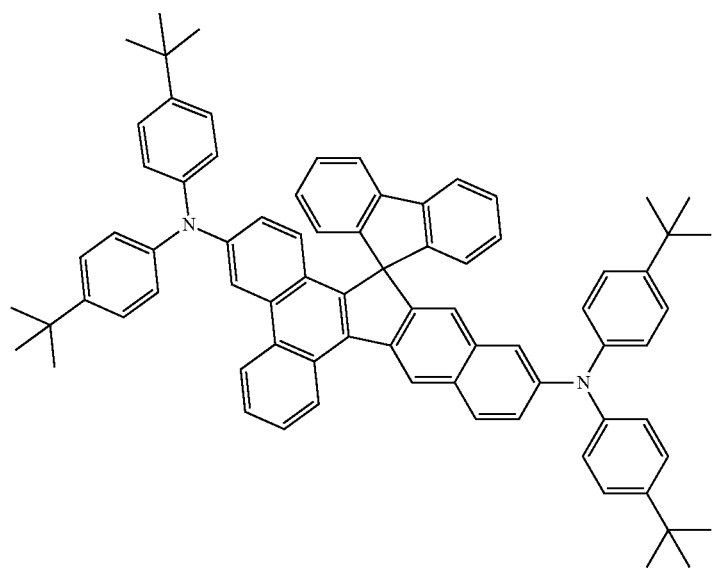

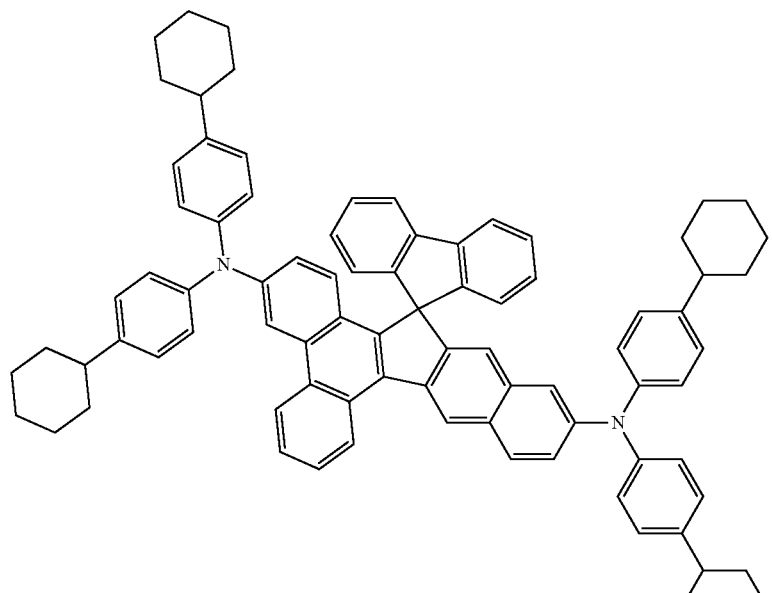
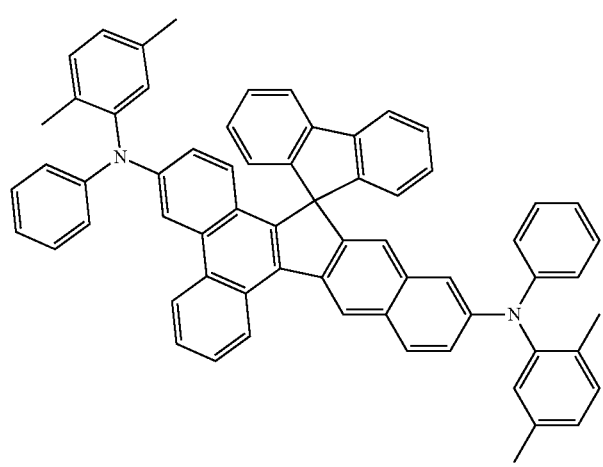
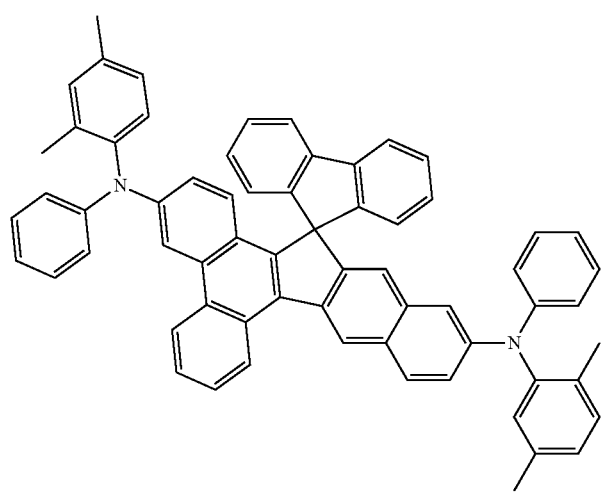

-continued
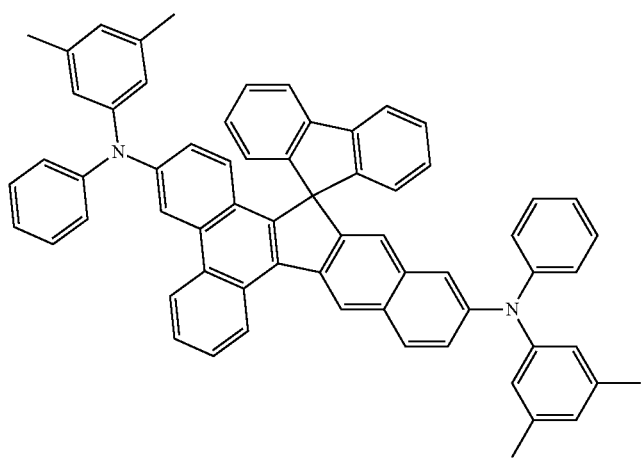
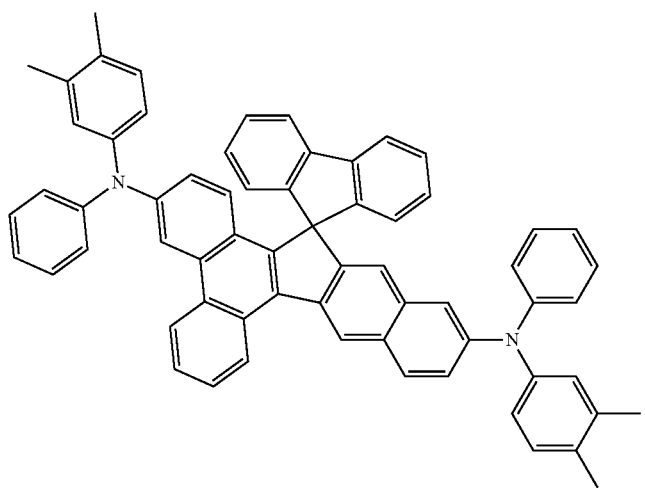
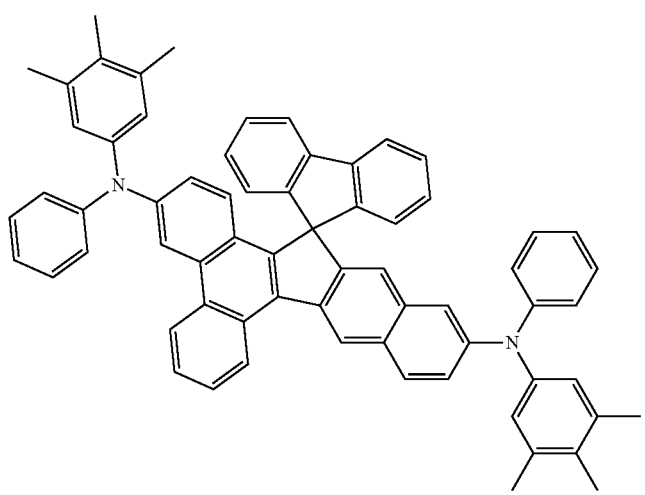

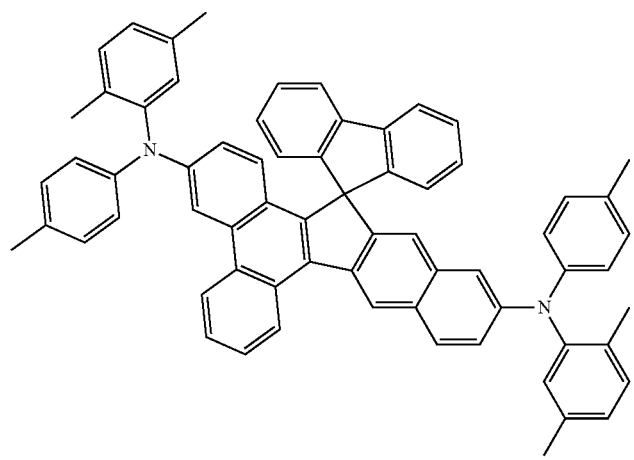
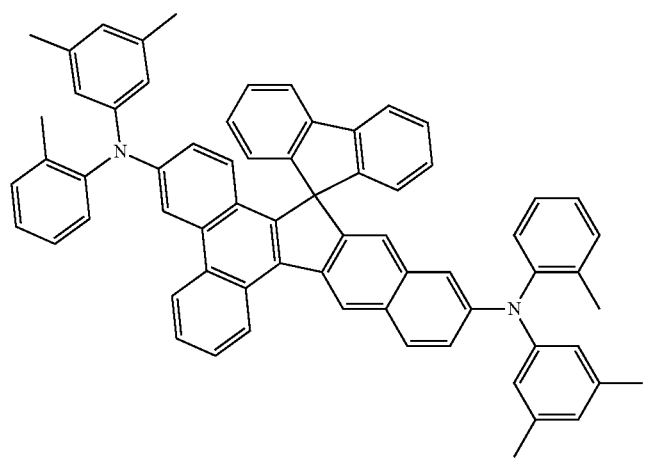
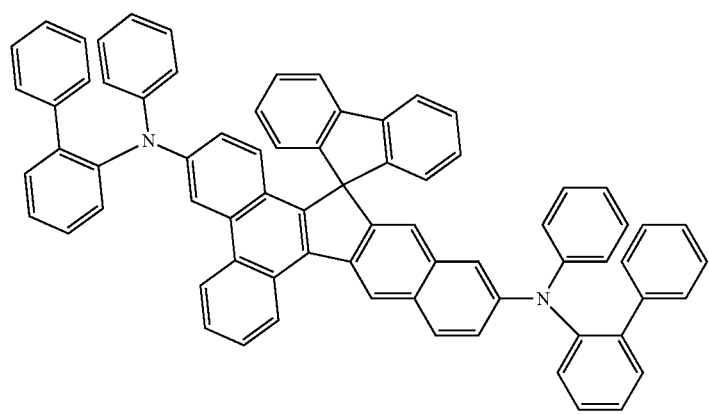

-continued
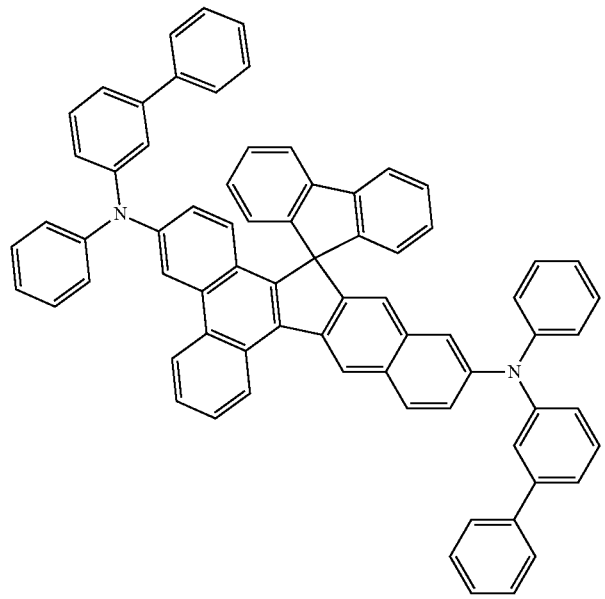
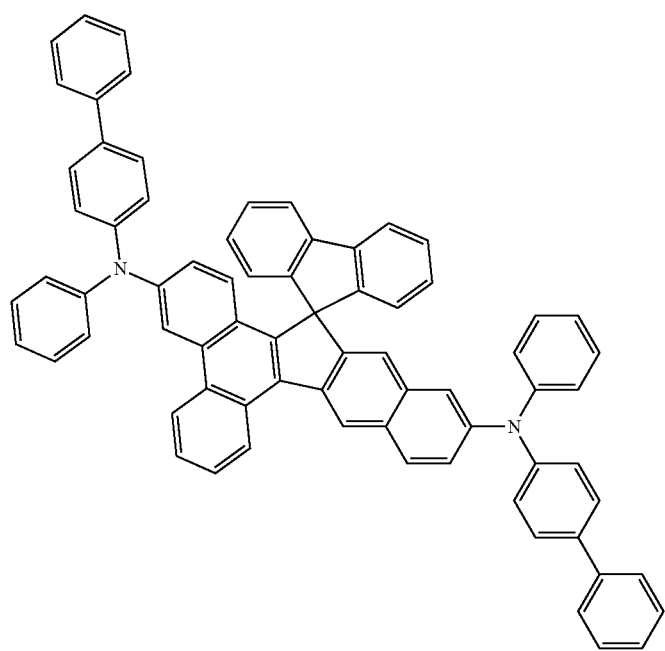

-continued
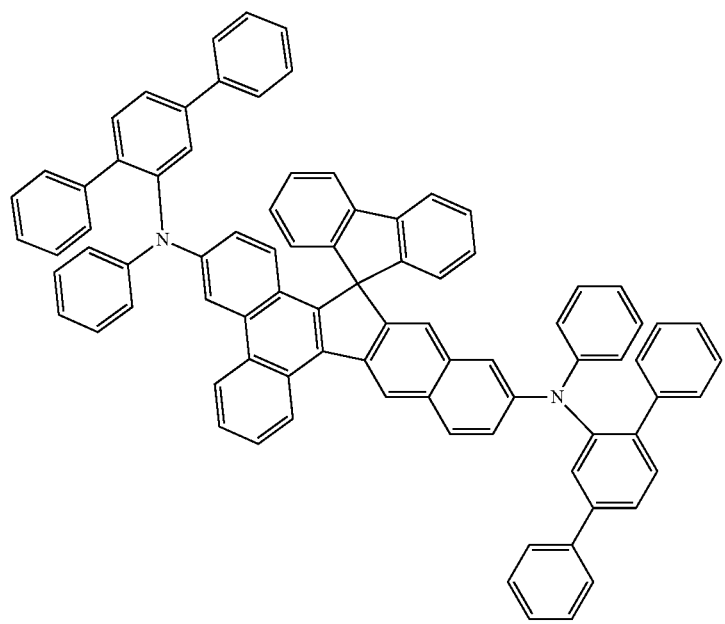
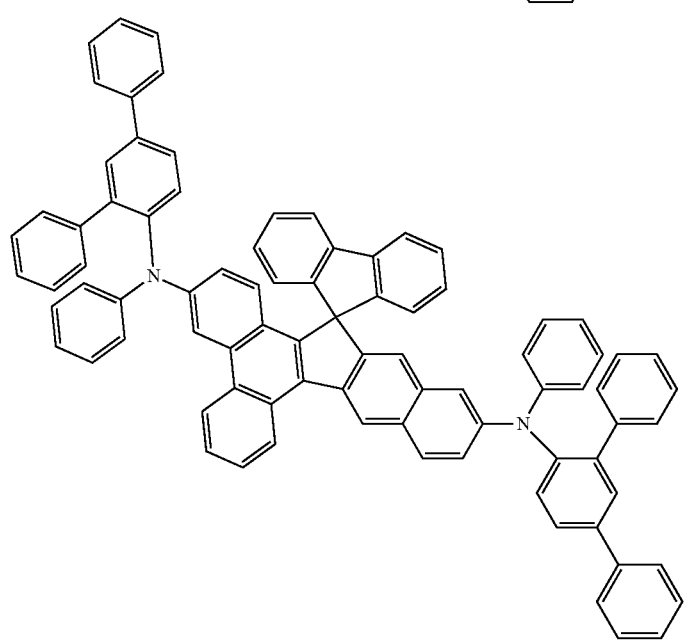
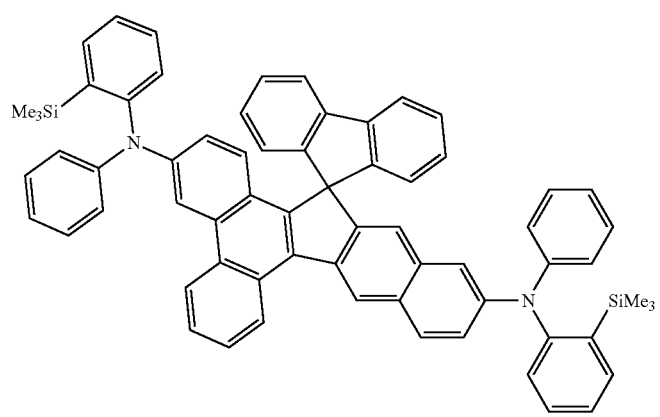

-continued
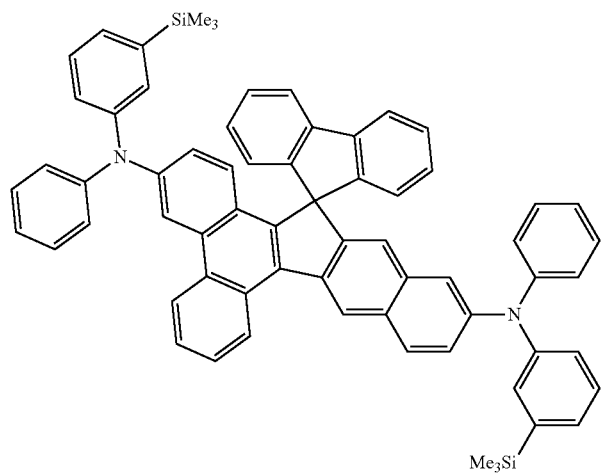
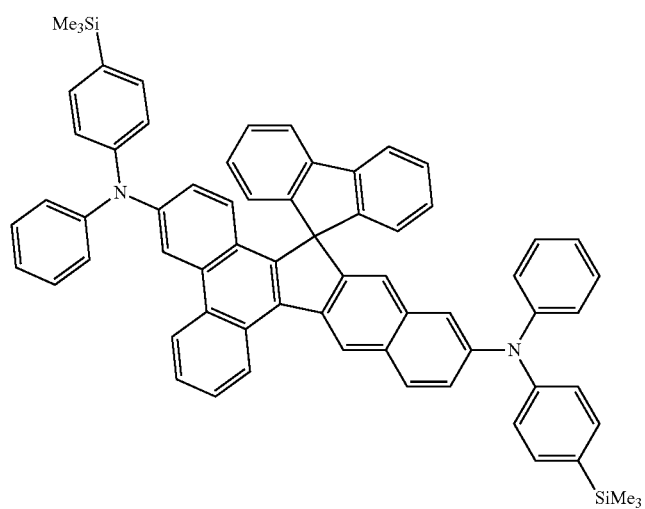
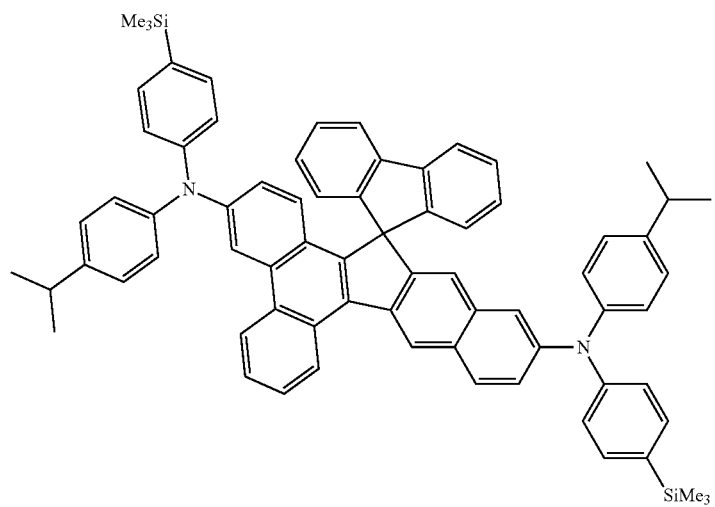

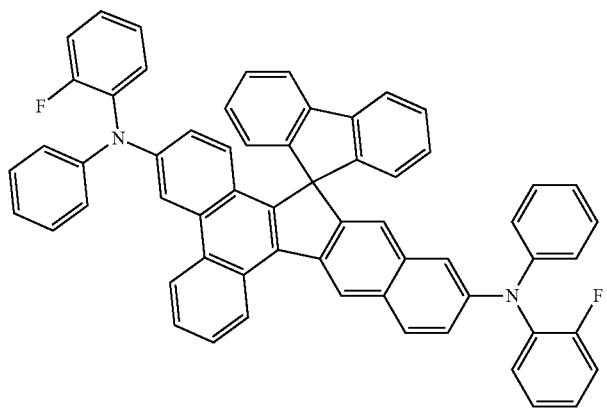
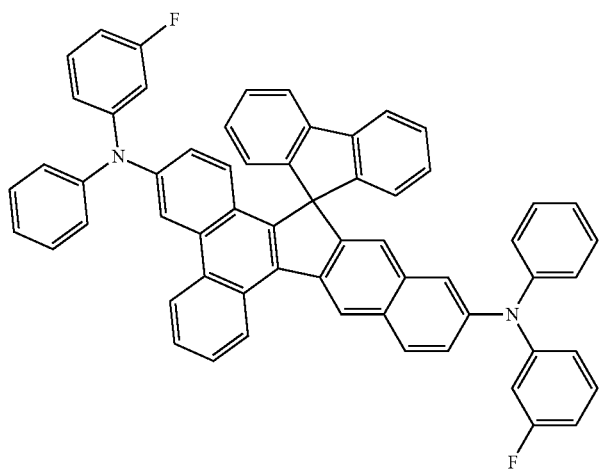
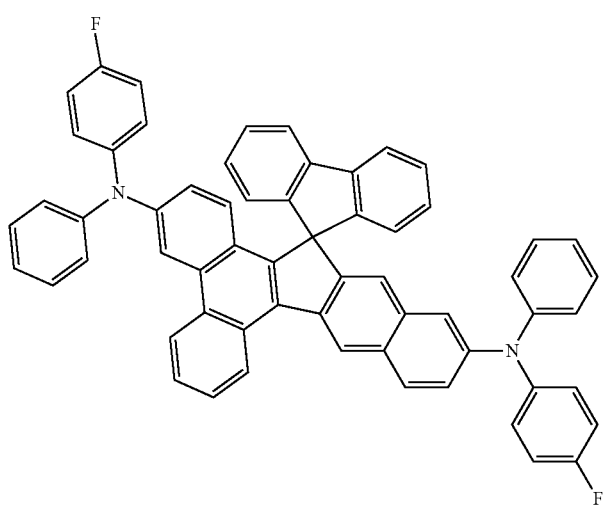

-continued
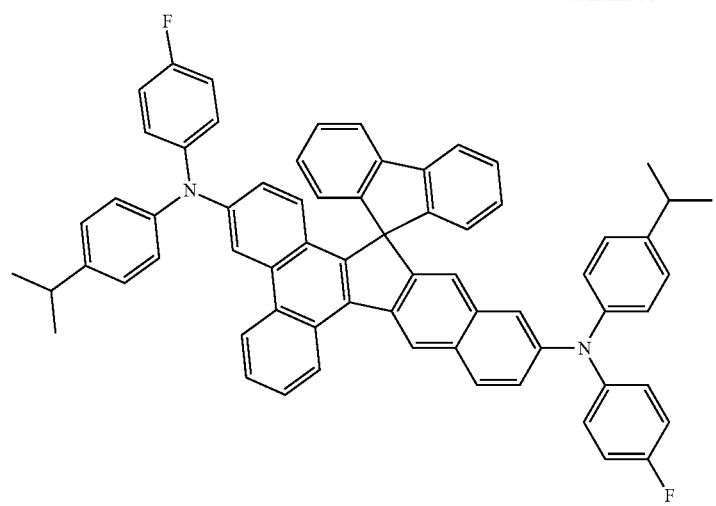
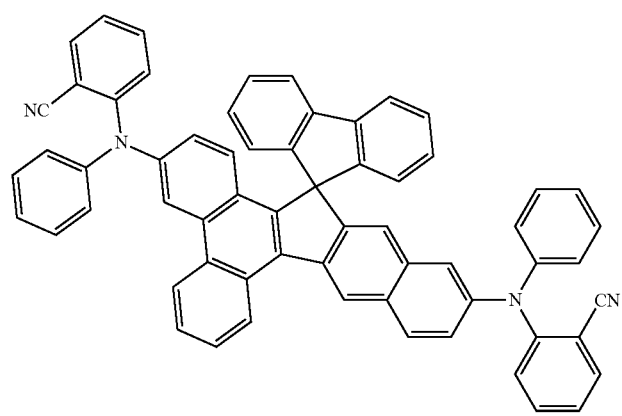
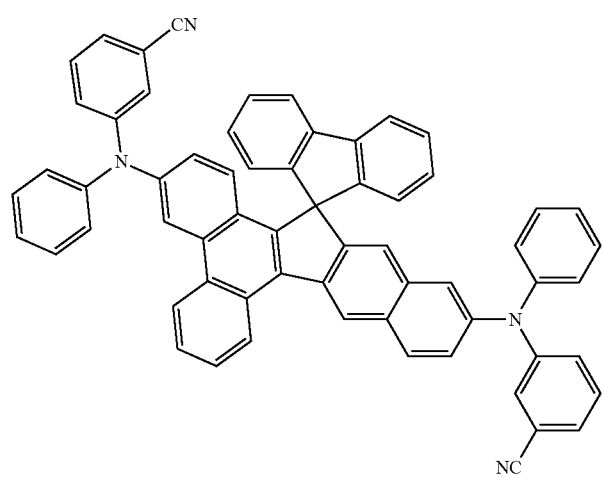

-continued
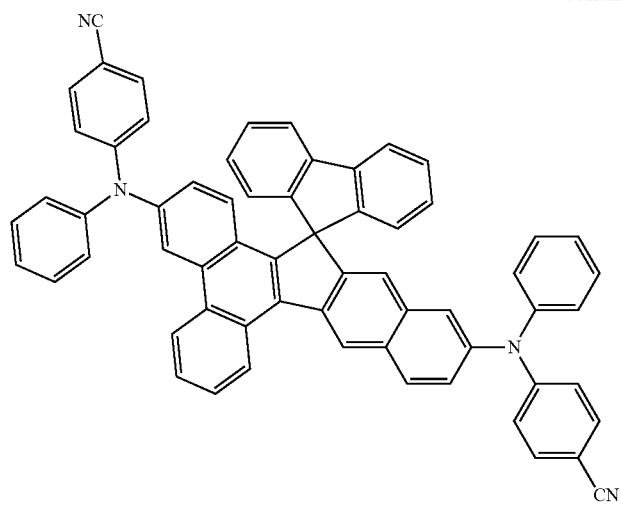
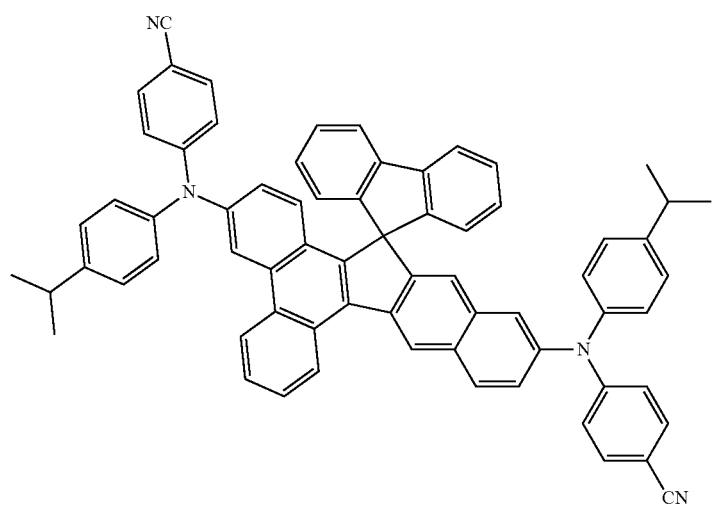
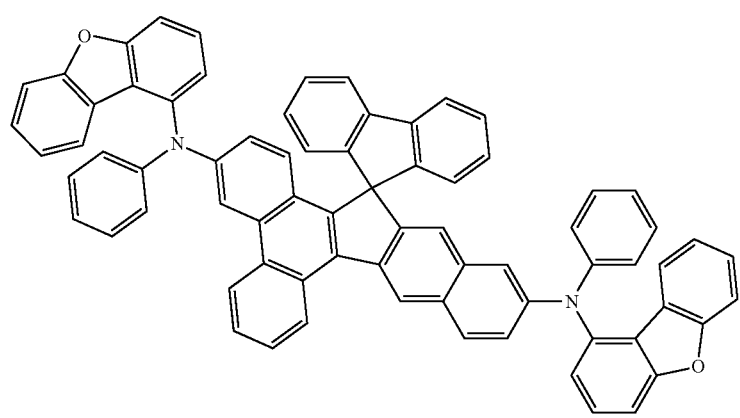

-continued
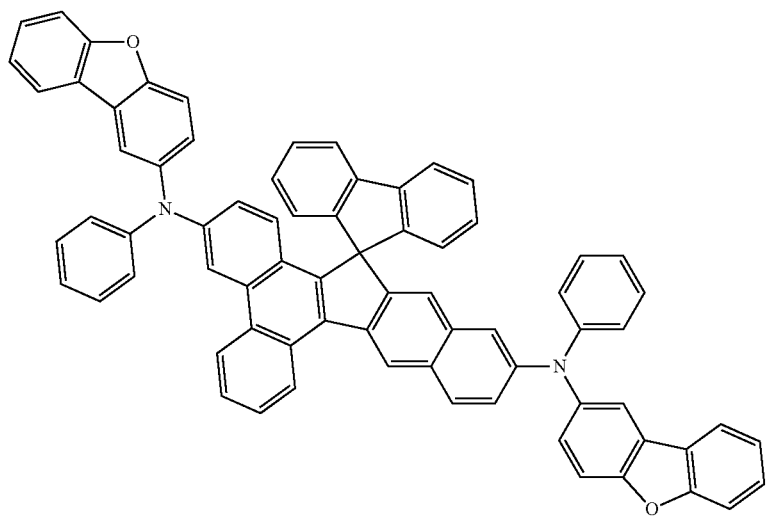
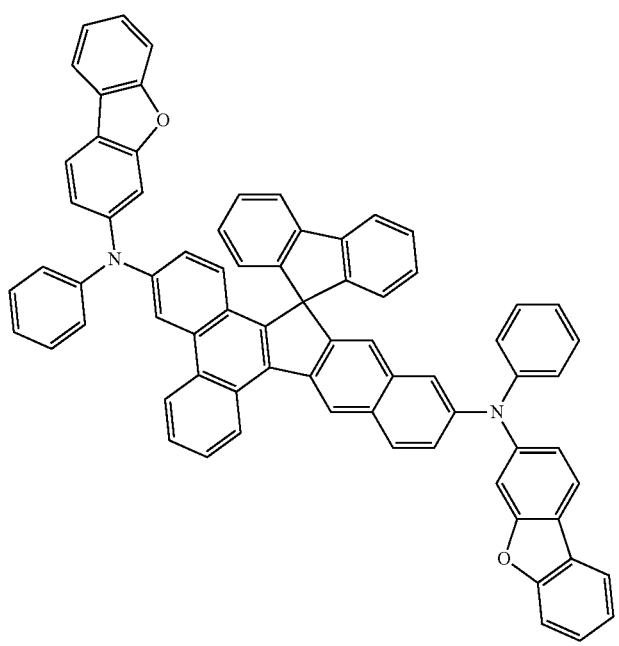
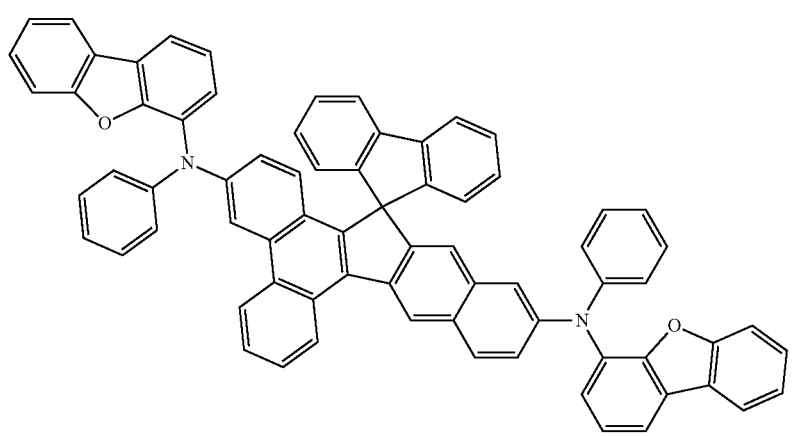

-continued
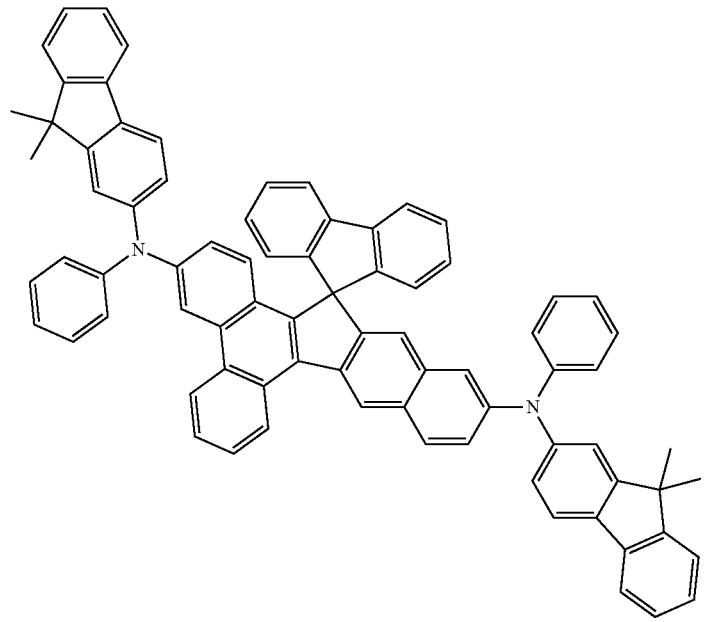
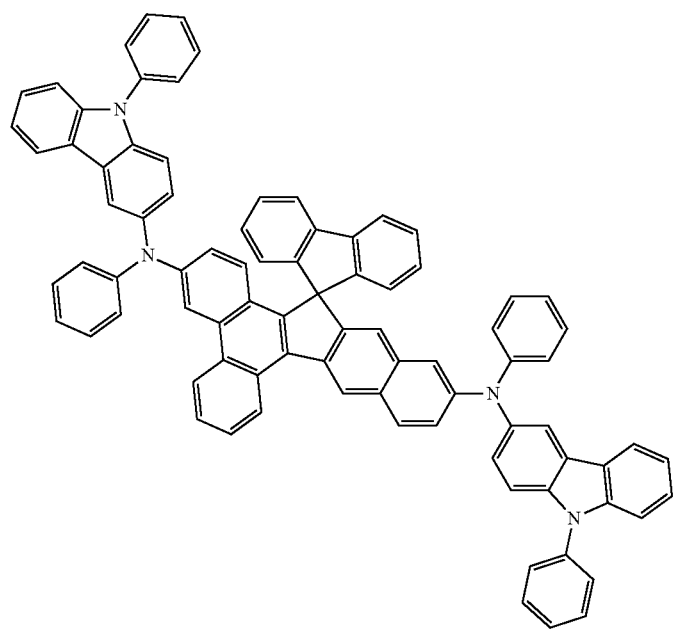

-continued
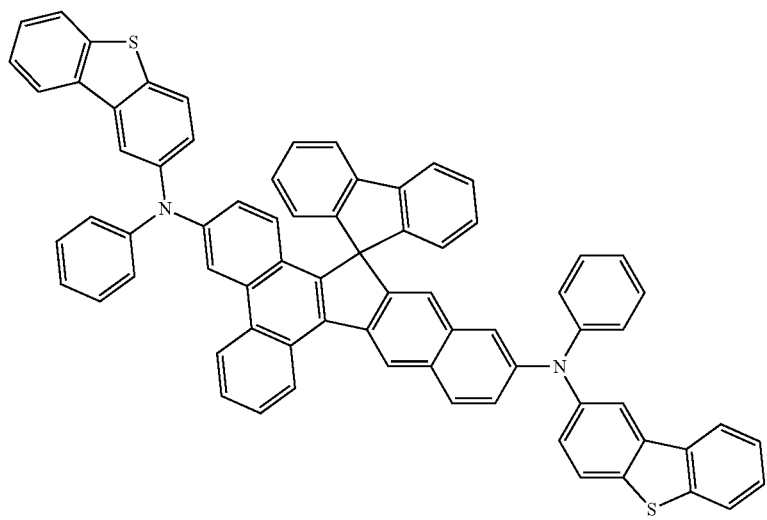
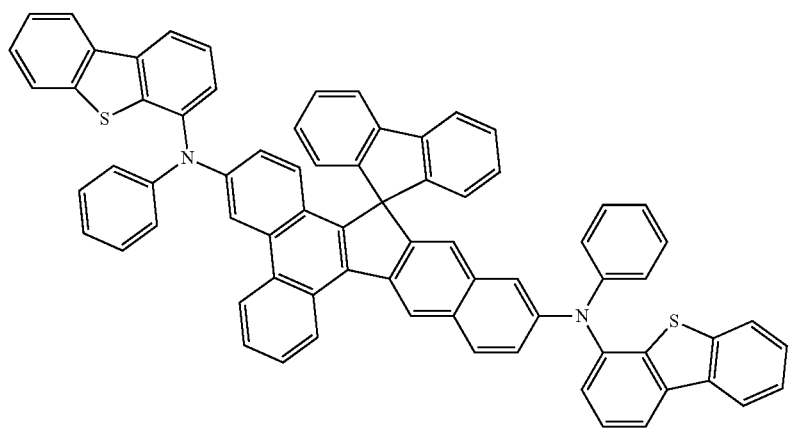
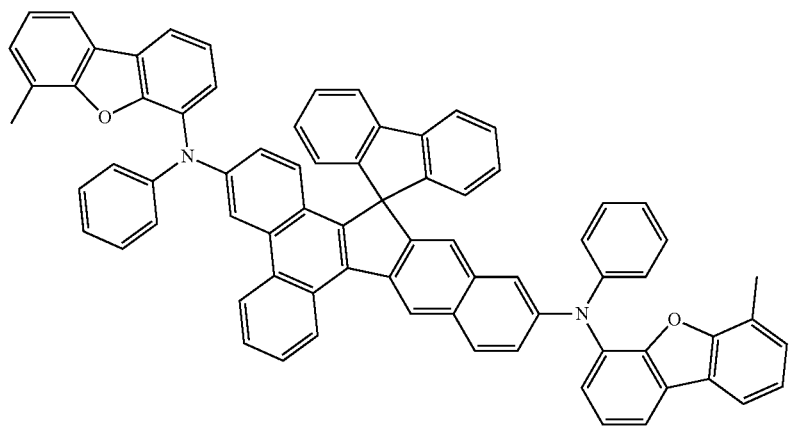

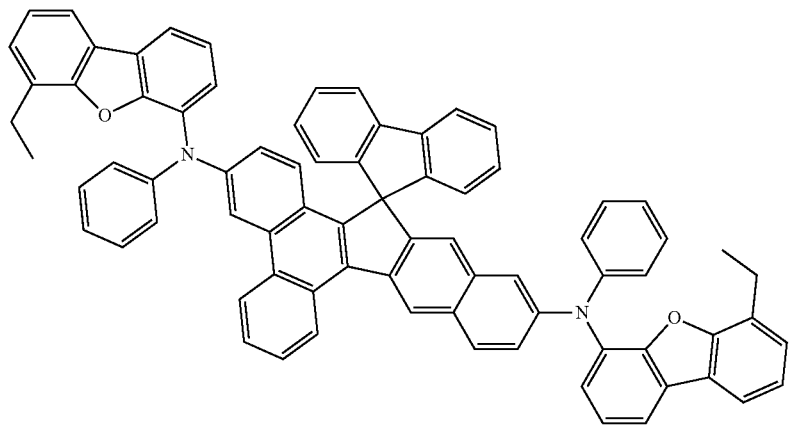
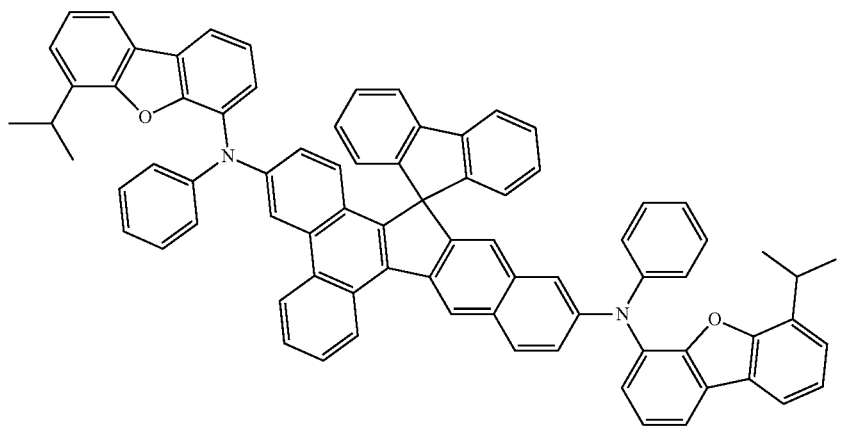
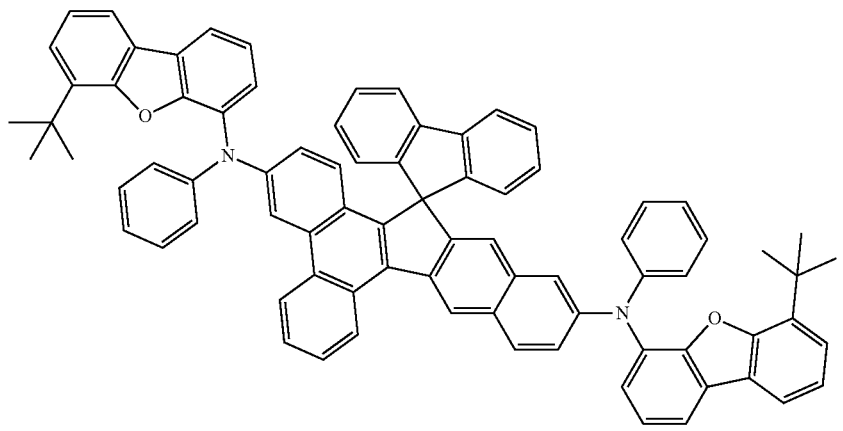
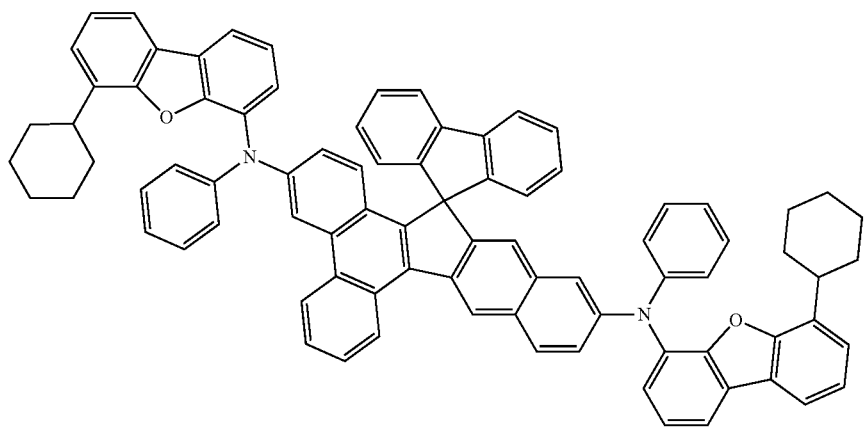

-continued
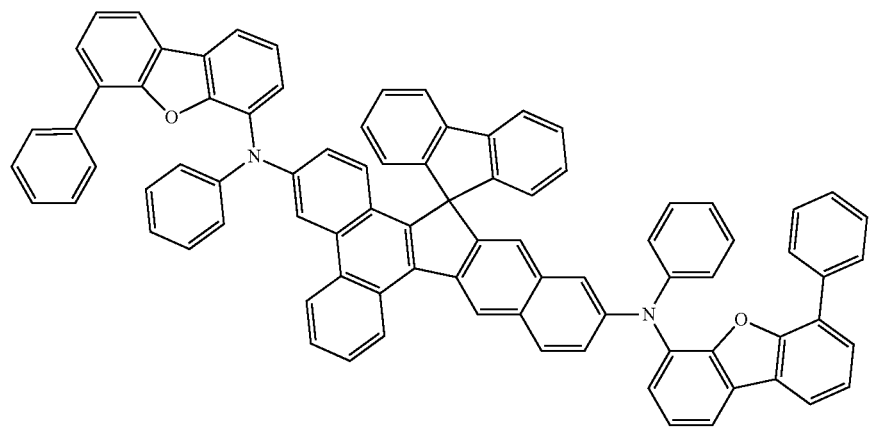
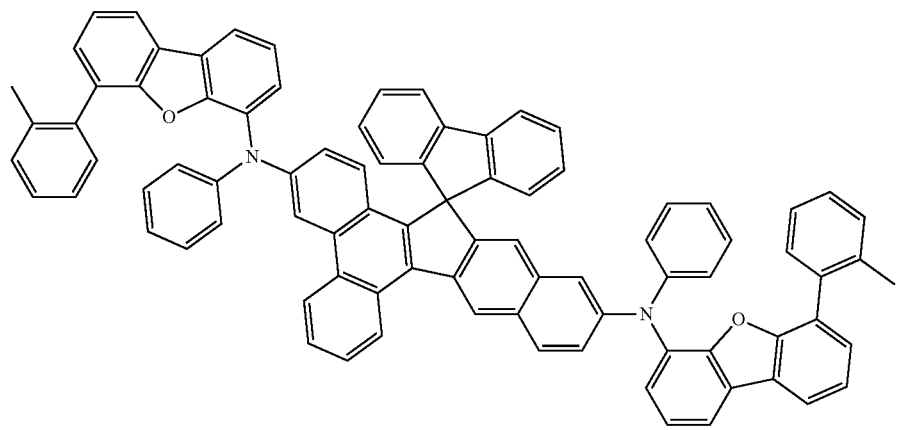
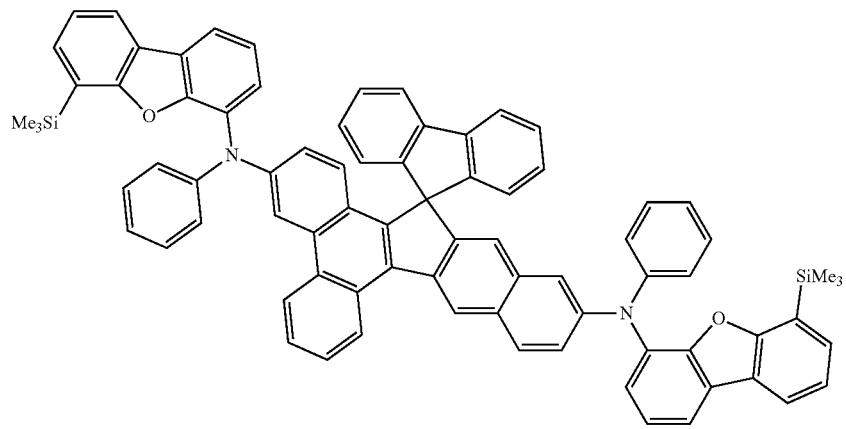
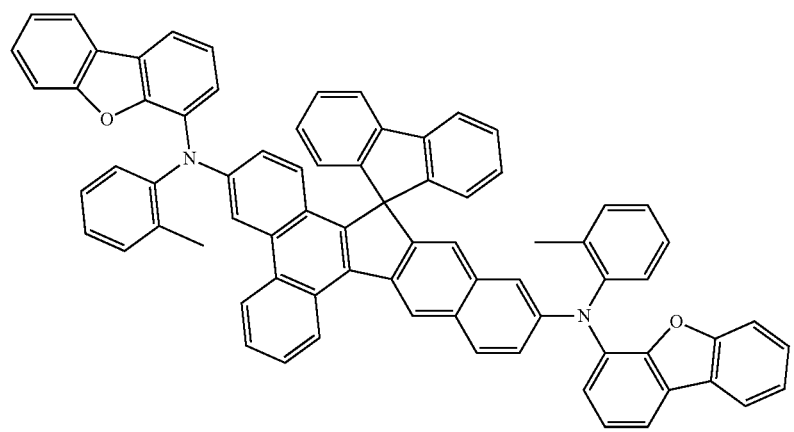

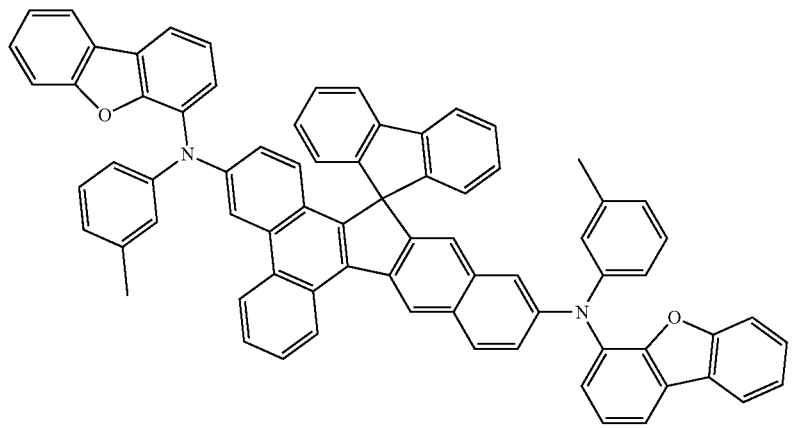
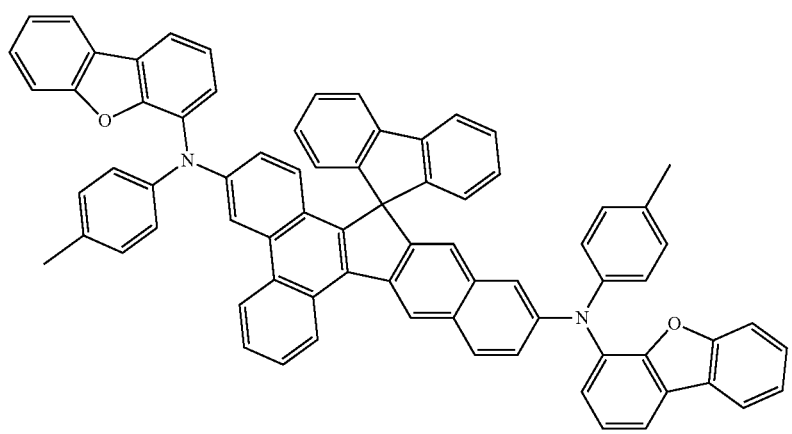
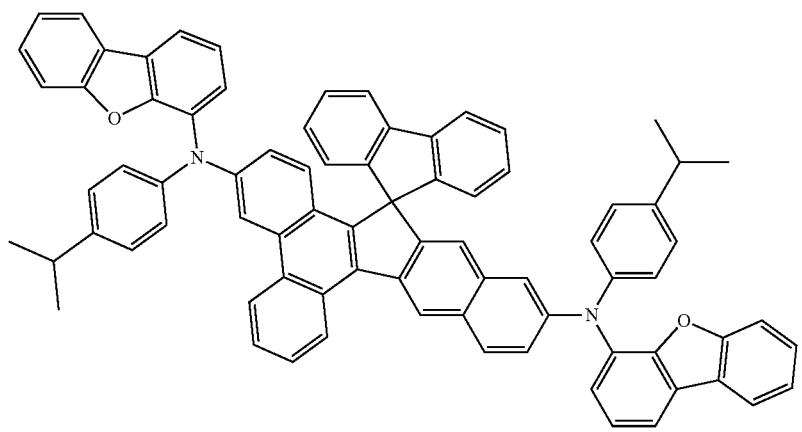

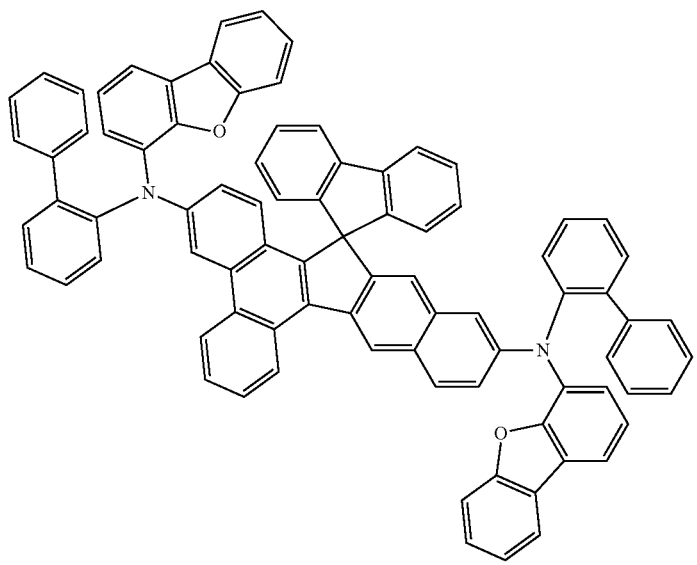
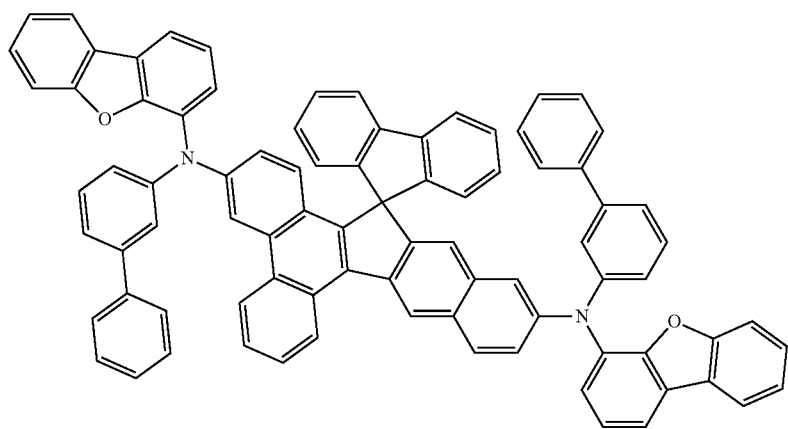
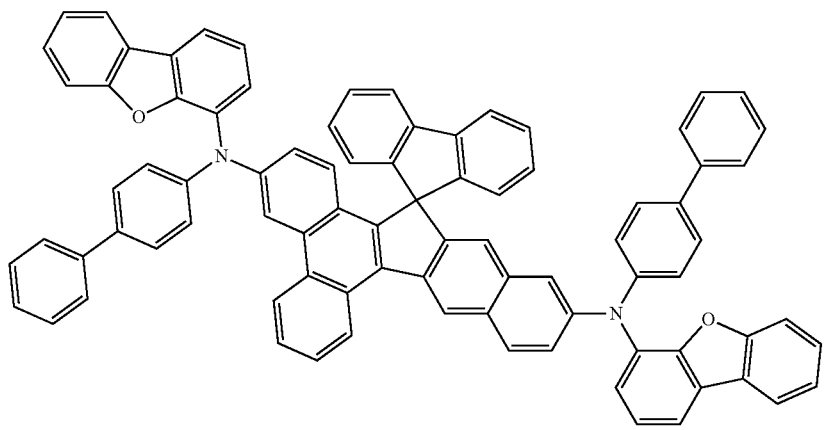

-continued
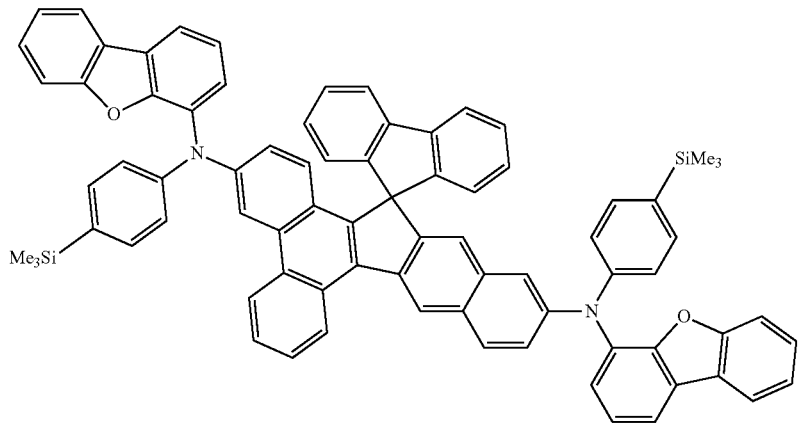
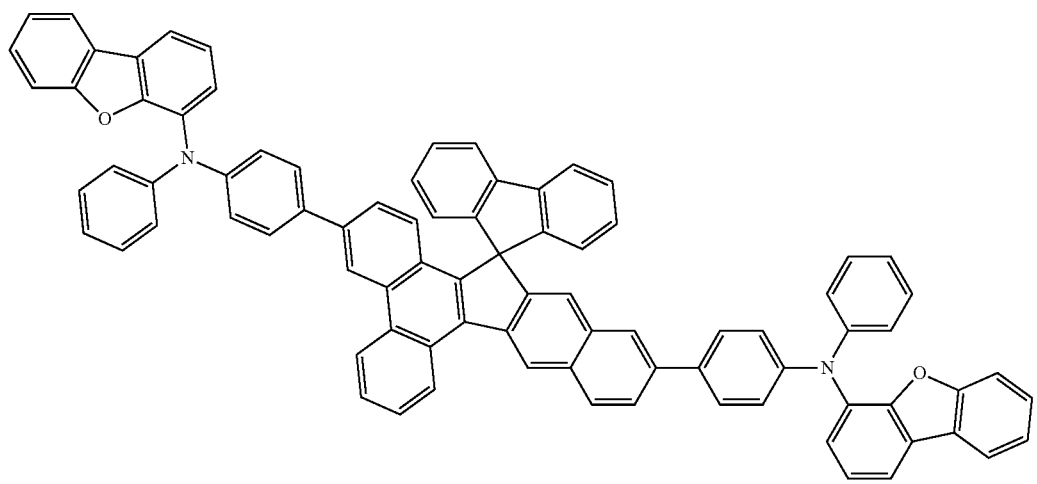
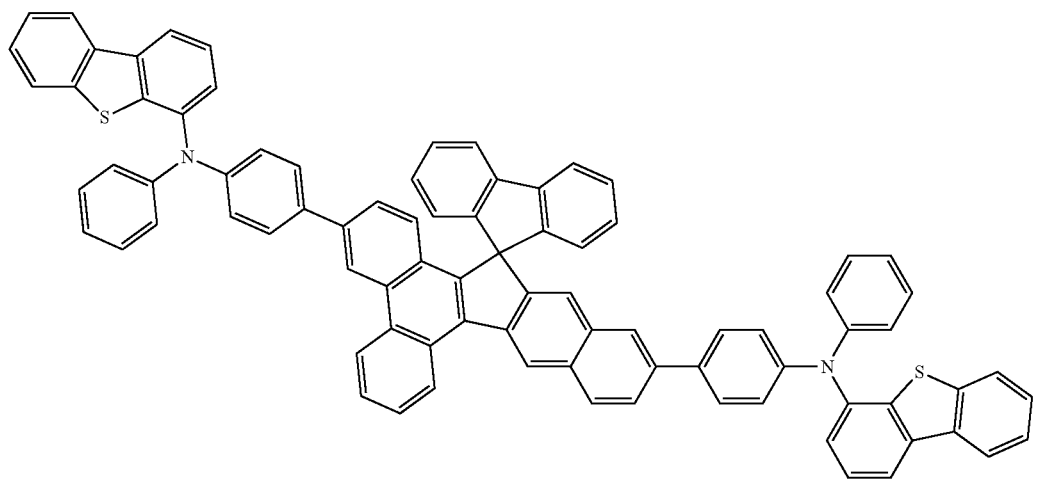
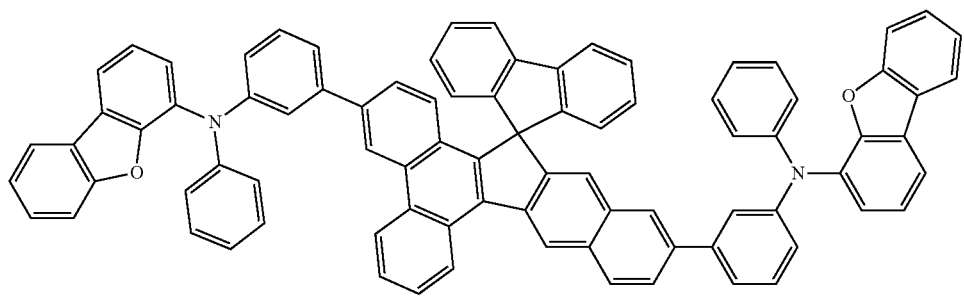

419 420
-continued
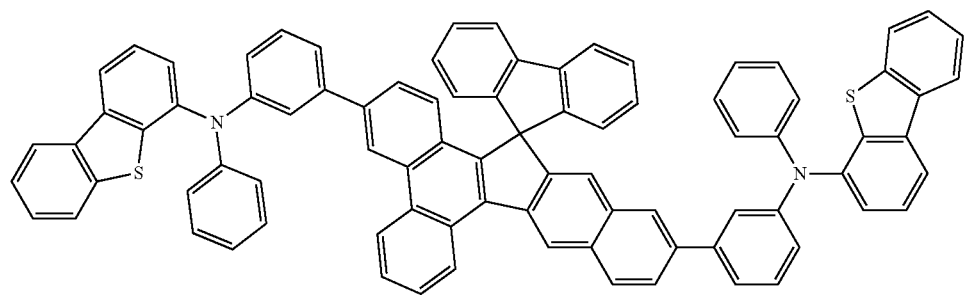
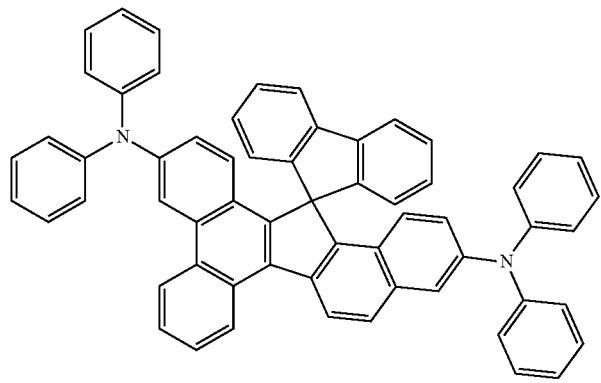
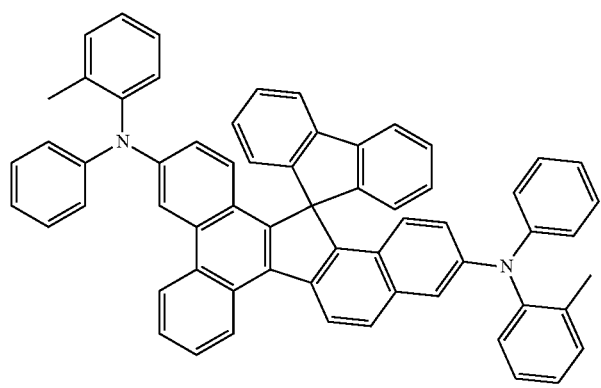
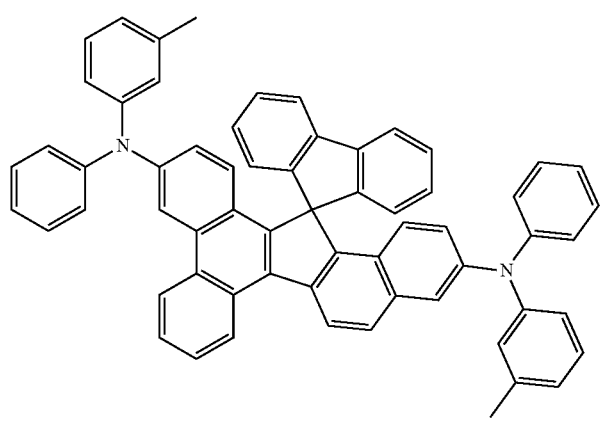

-continued
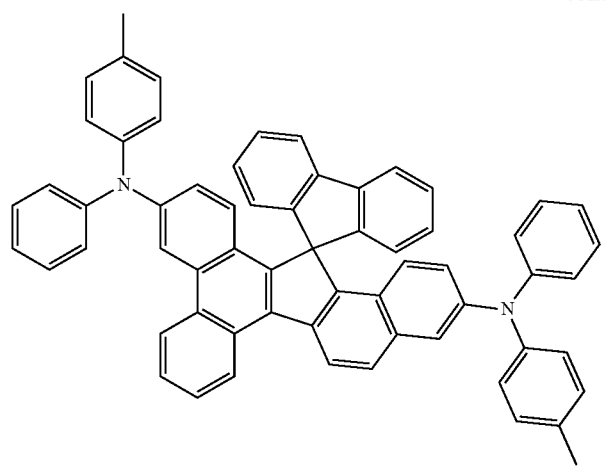
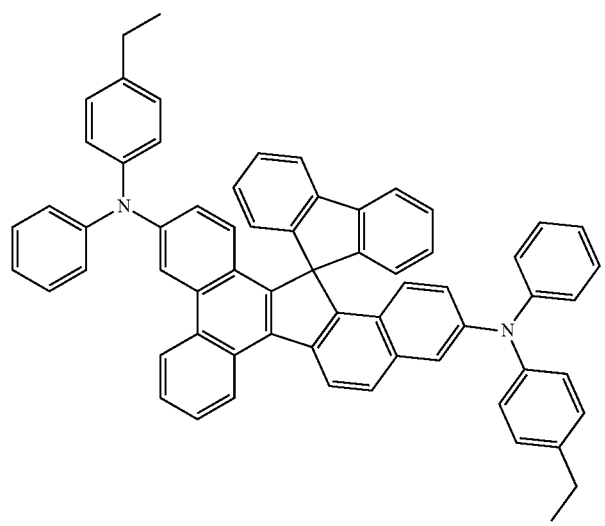
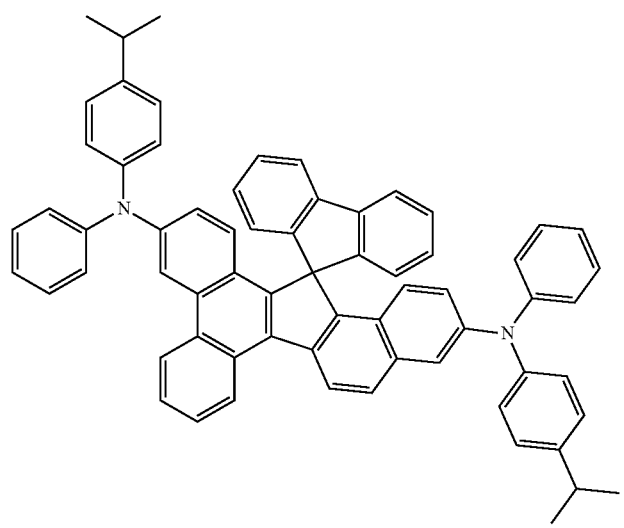

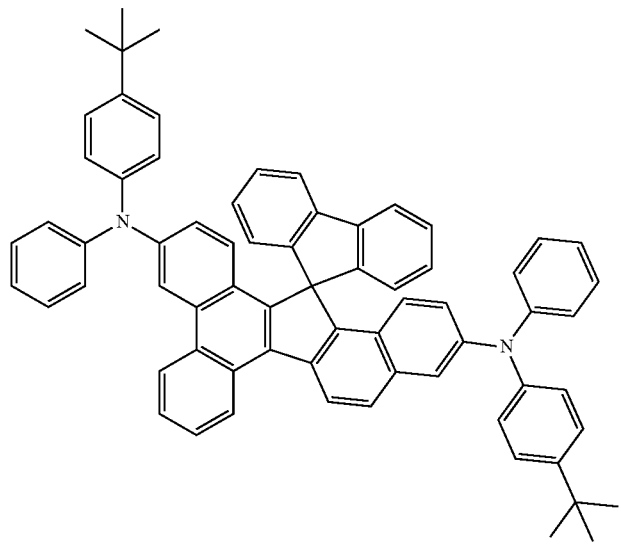
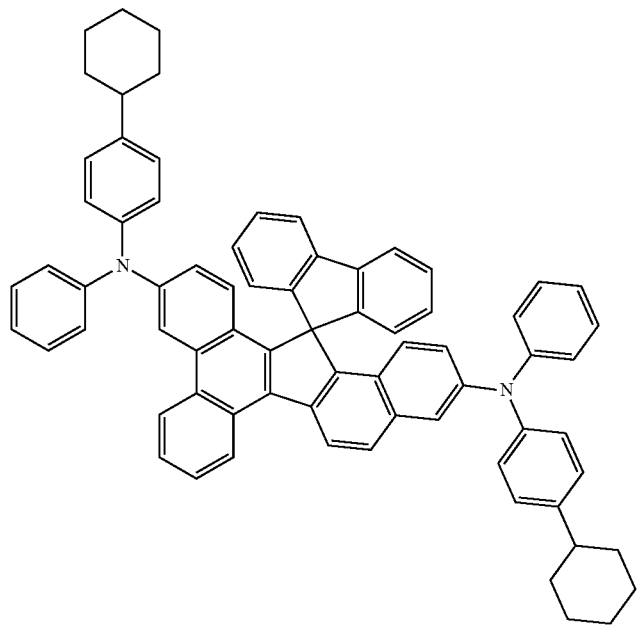
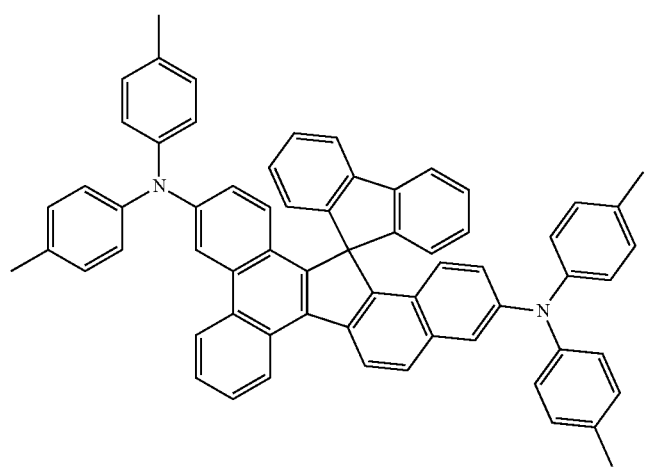

-continued
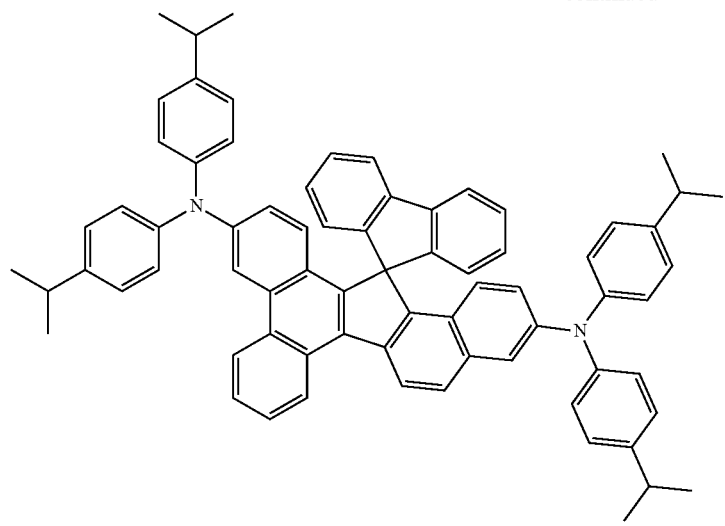
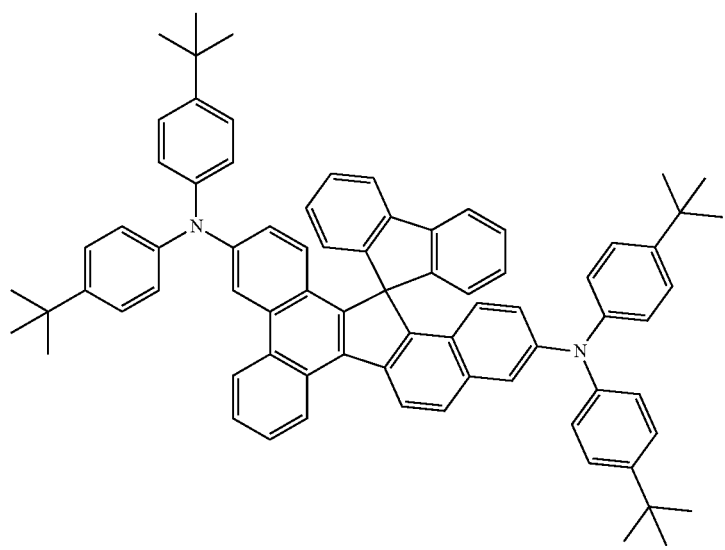
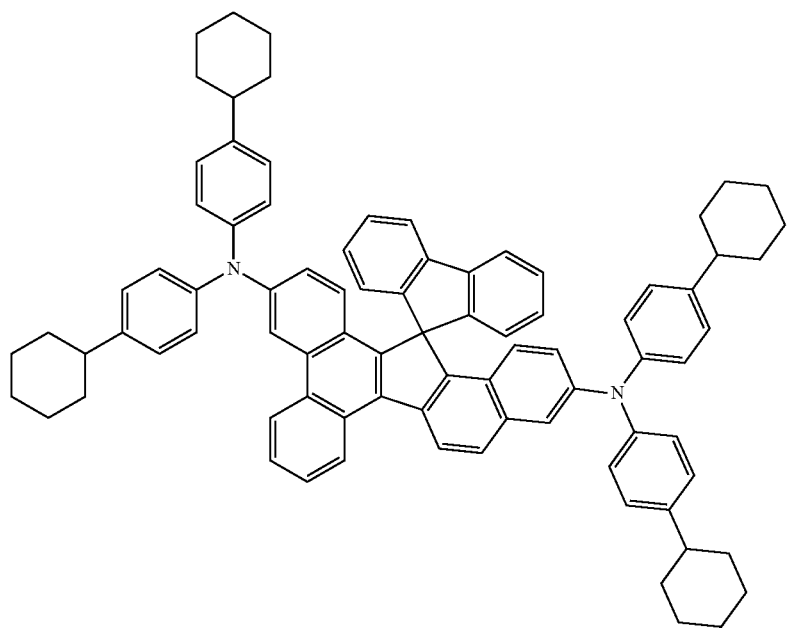

-continued
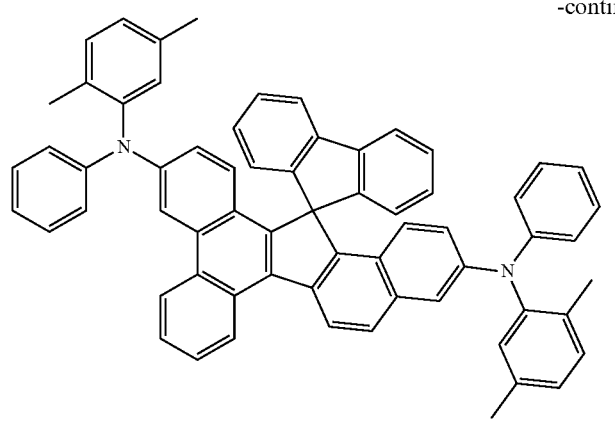
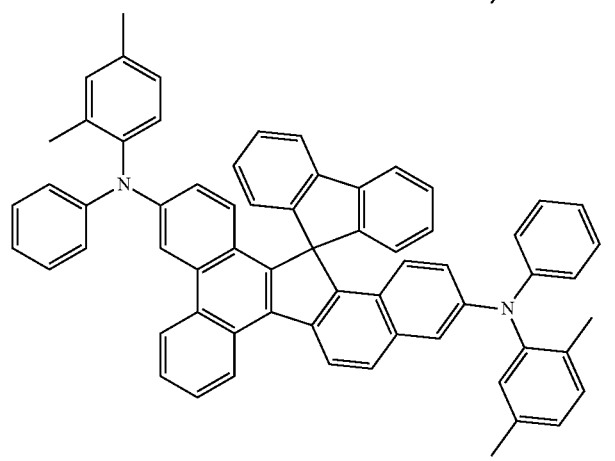
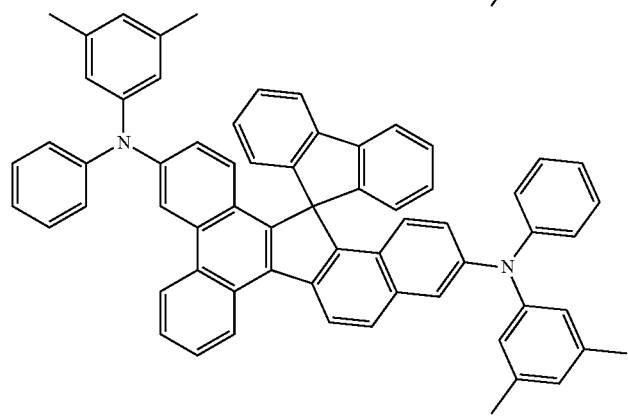
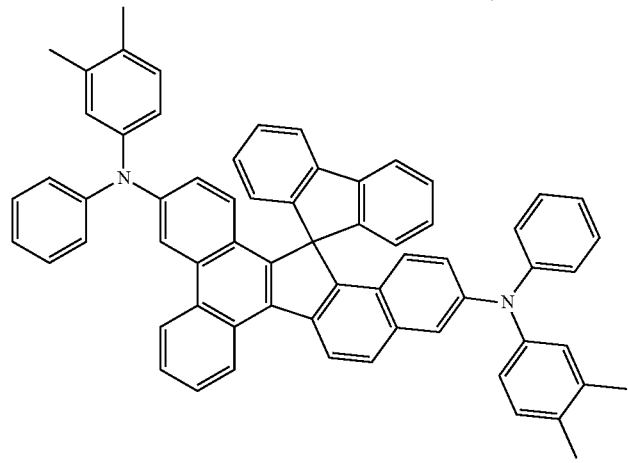

-continued
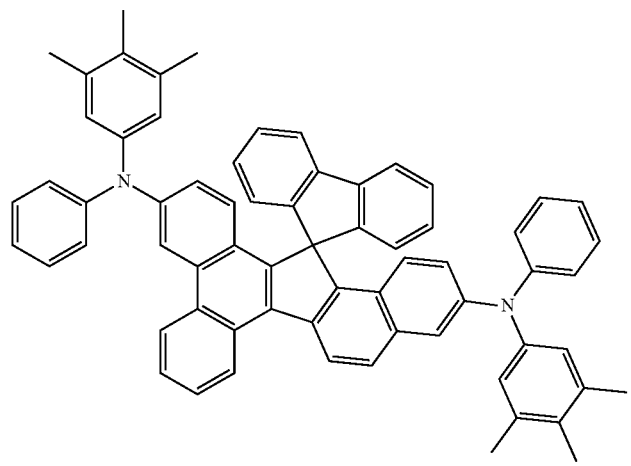
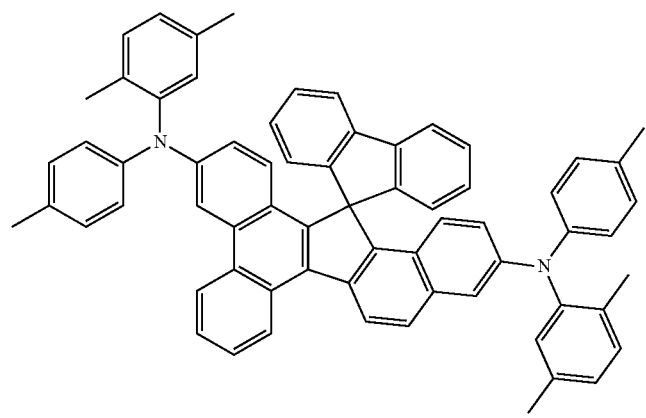
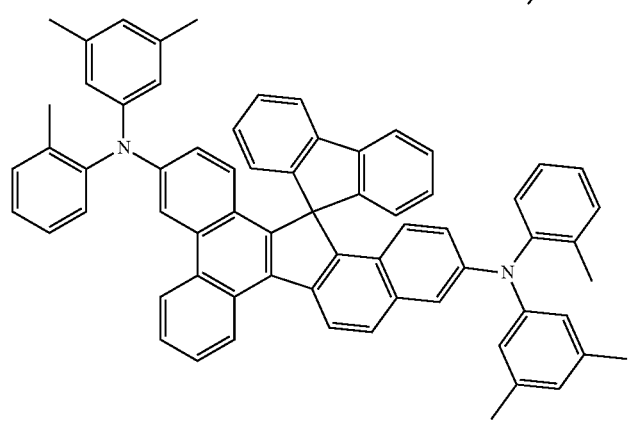
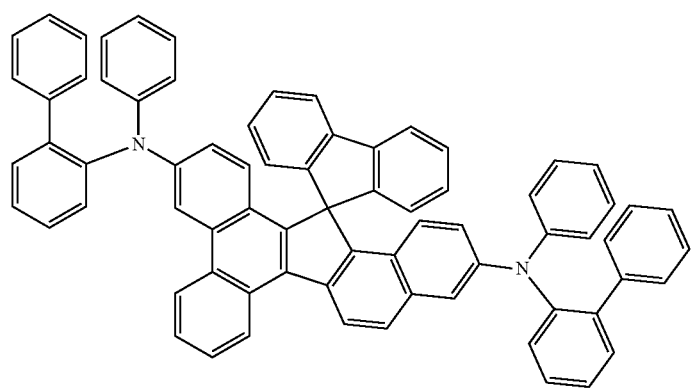

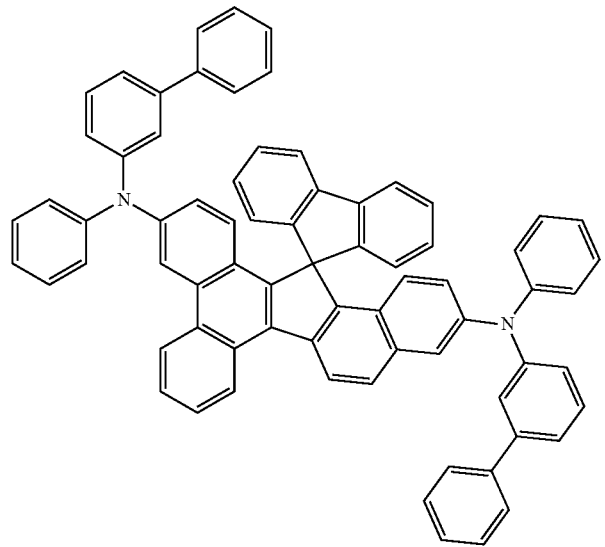
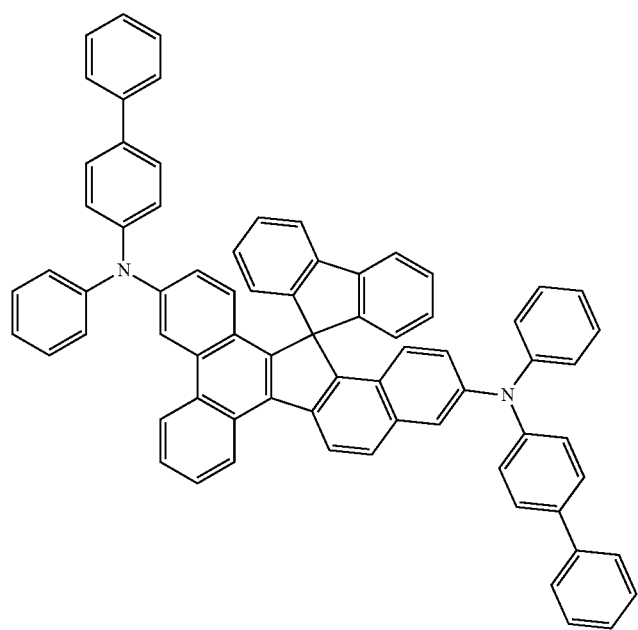

-continued
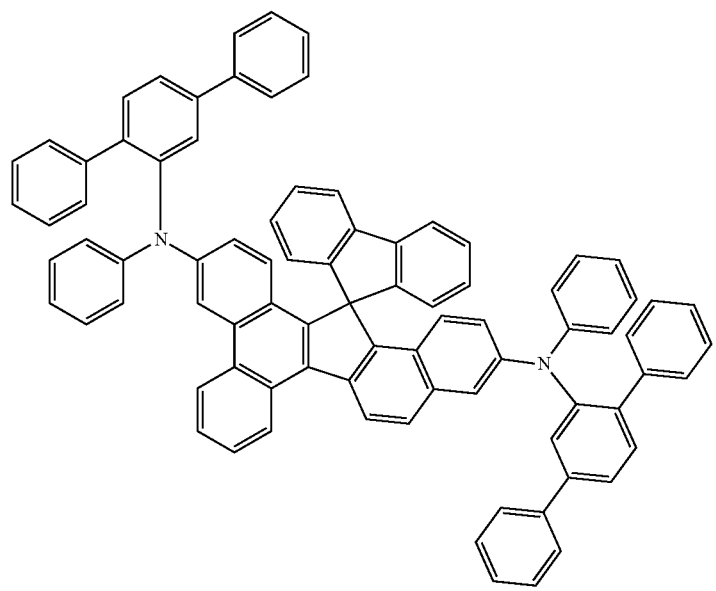
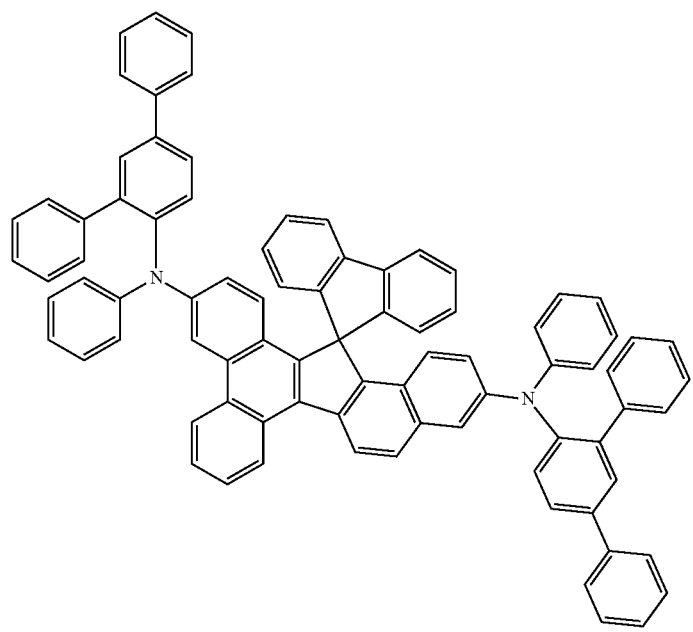
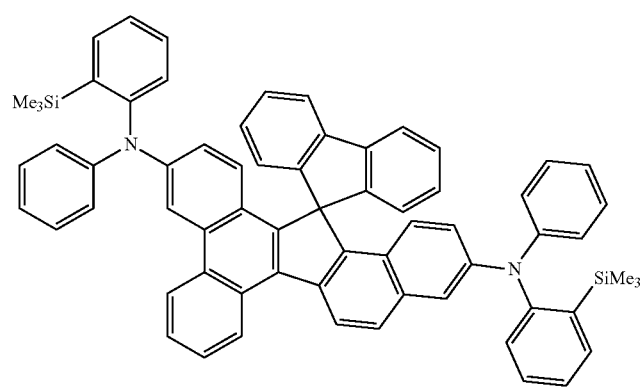

-continued
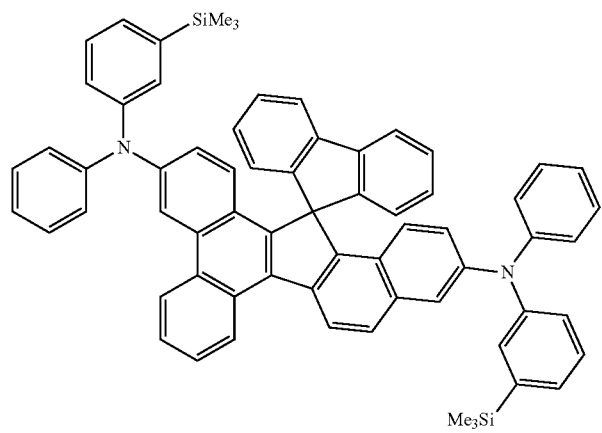
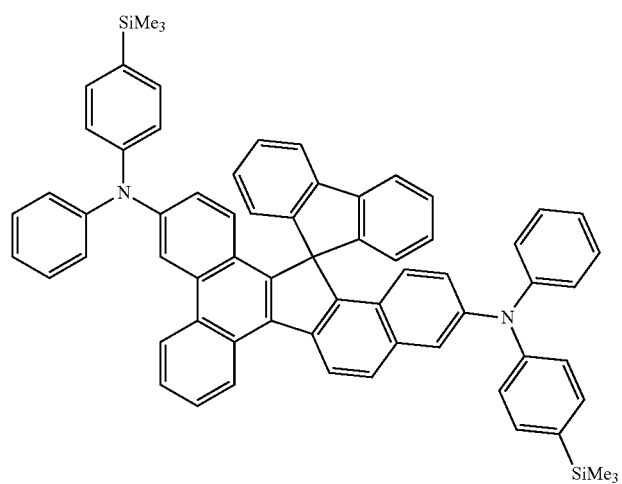
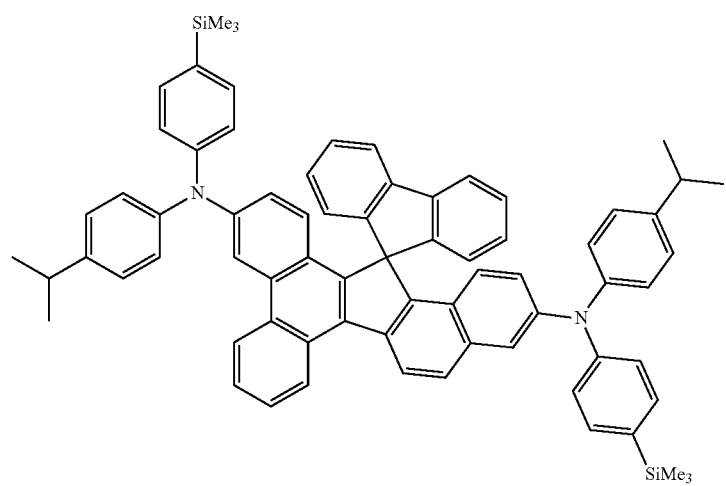

-continued
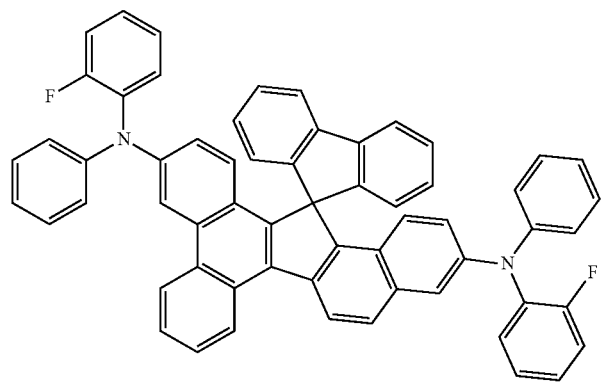
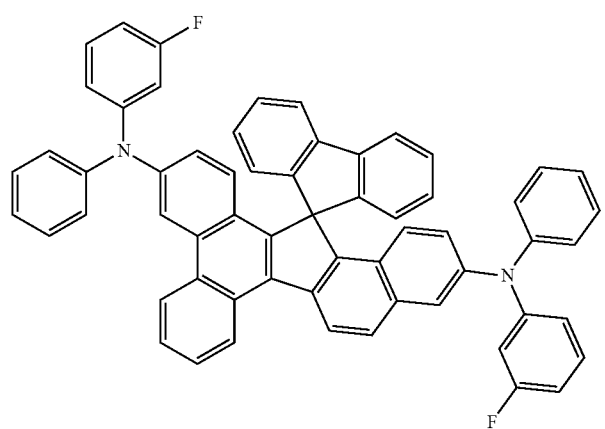
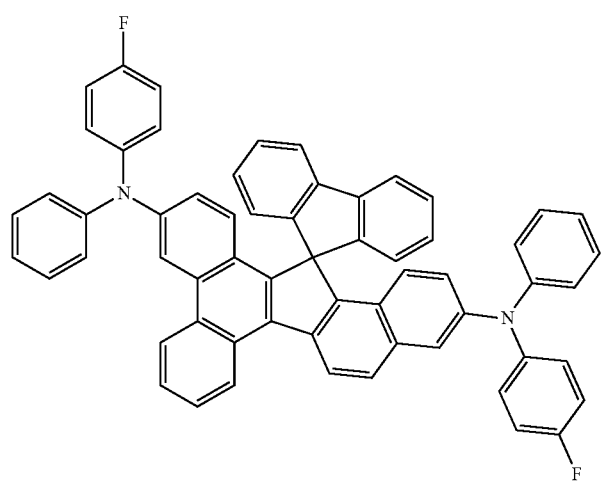

-continued
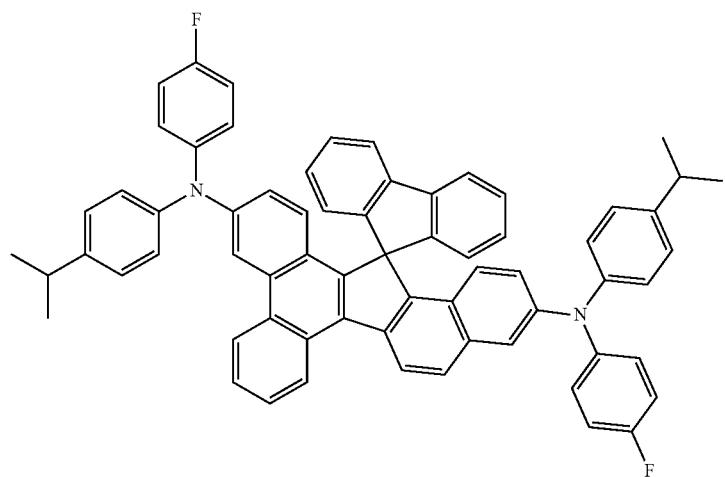
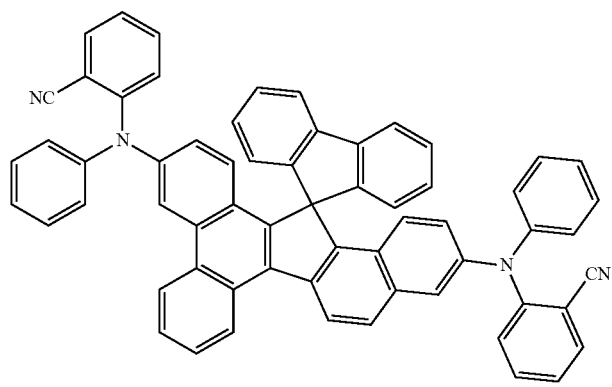
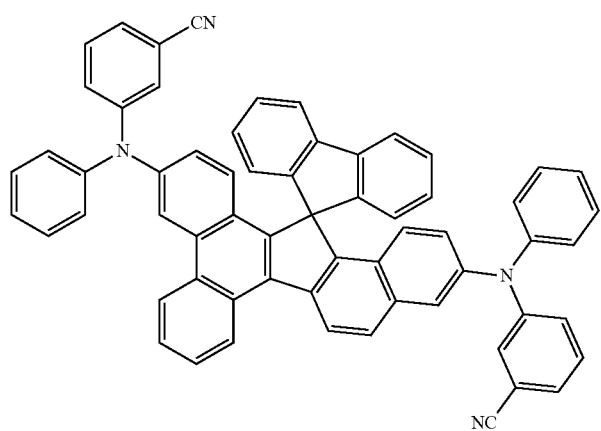

441 442
-continued
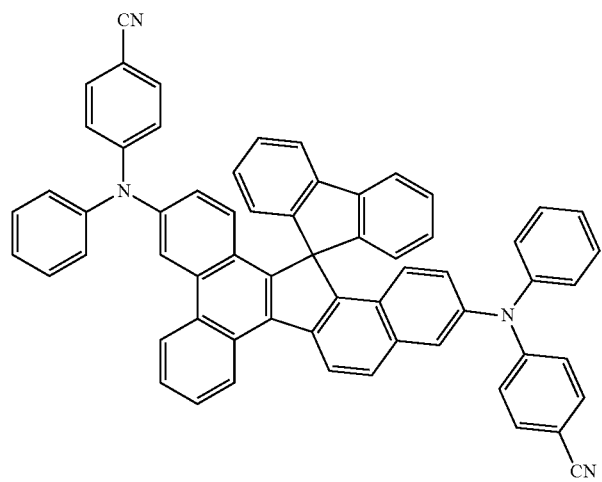
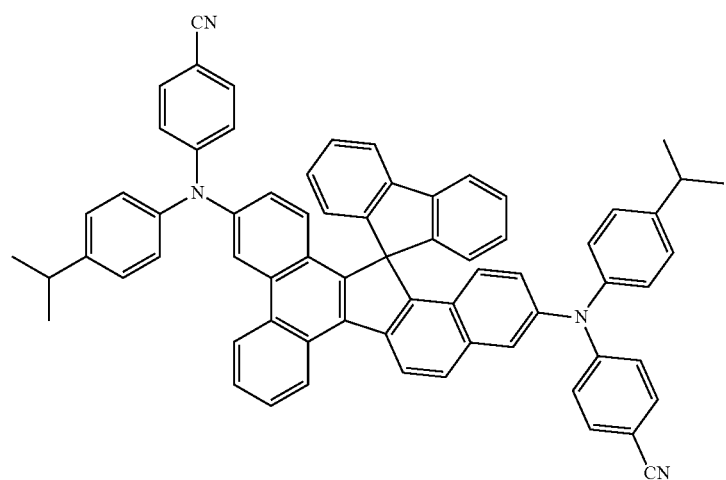
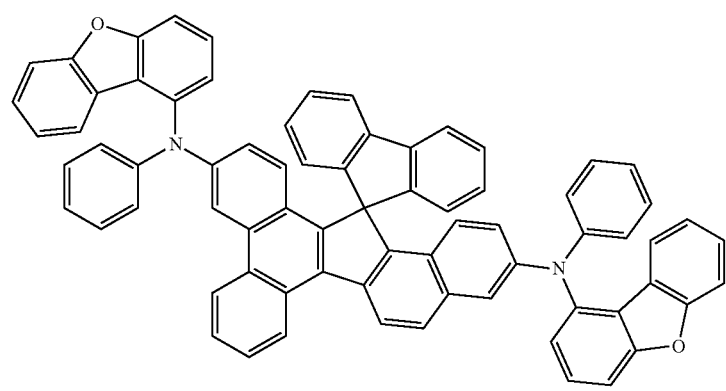

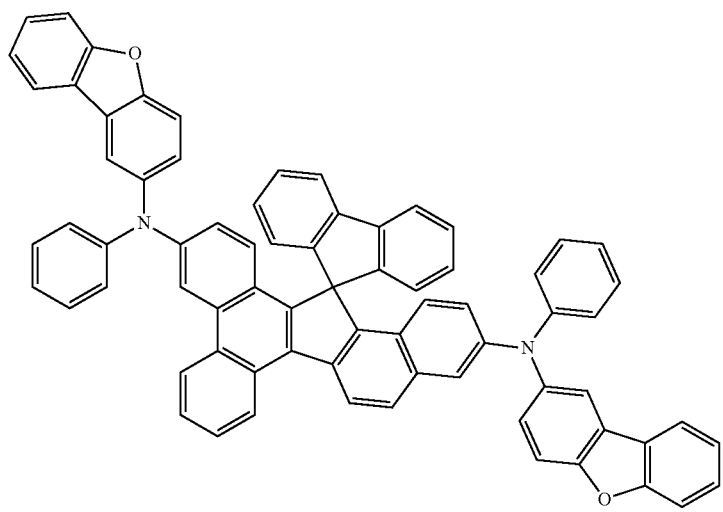
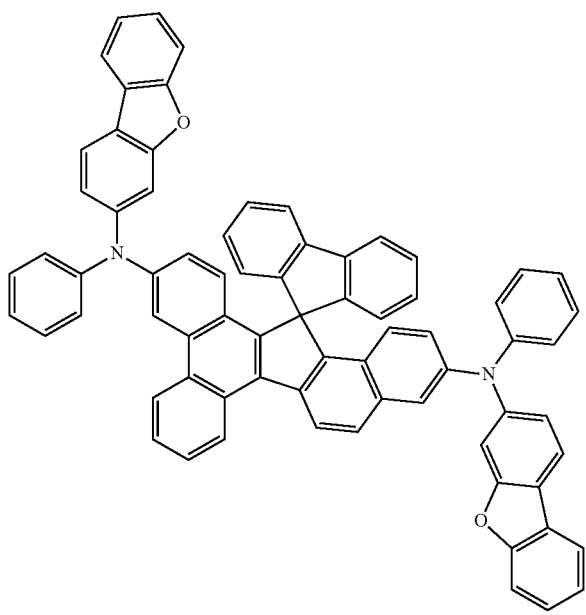
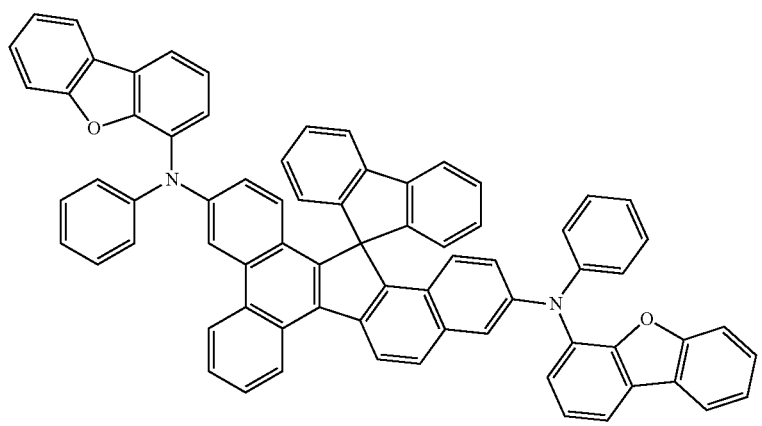

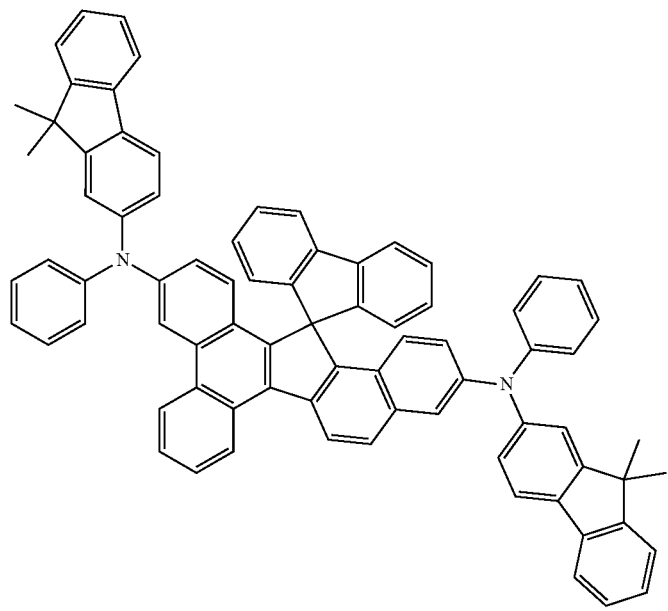
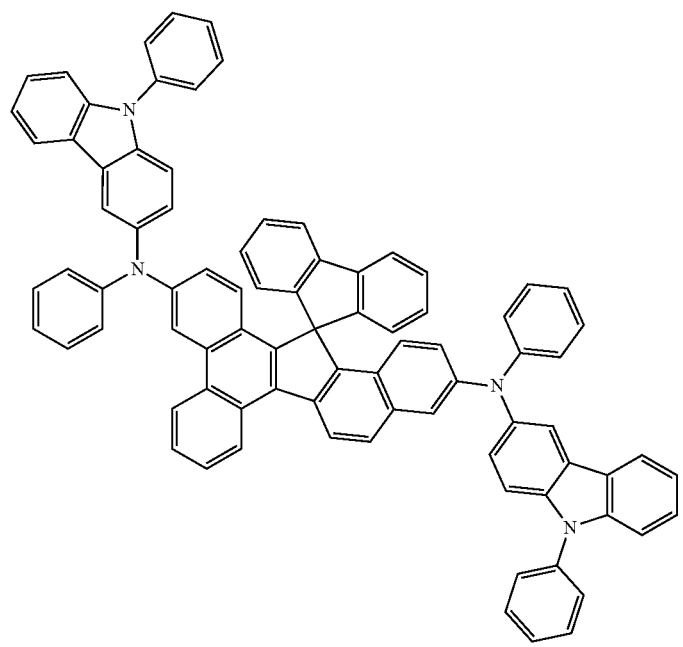

-continued
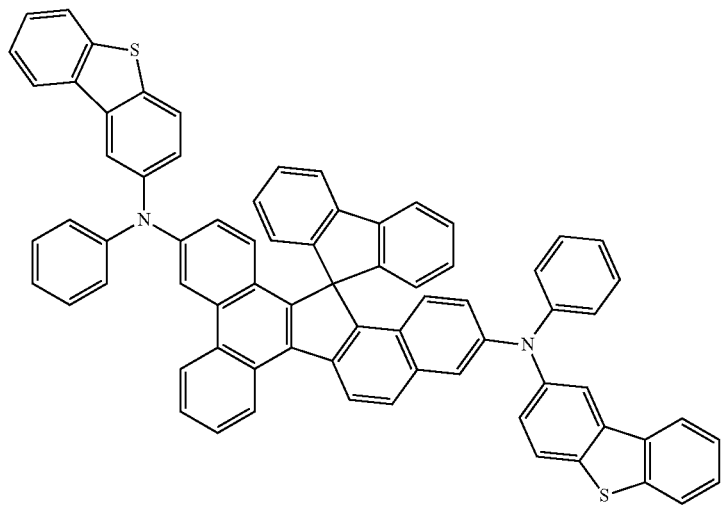
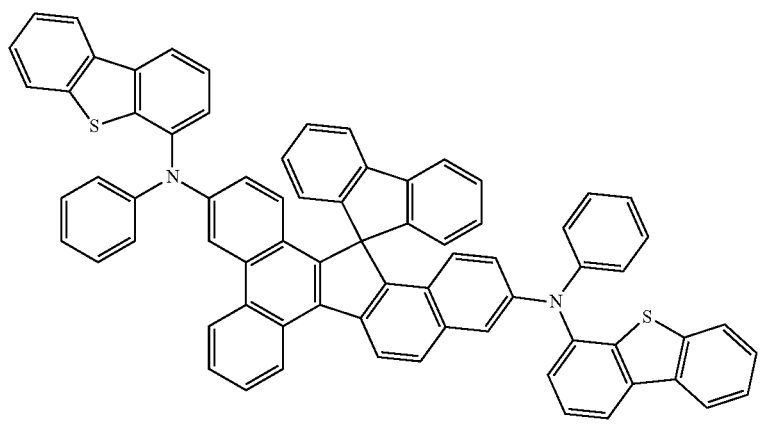
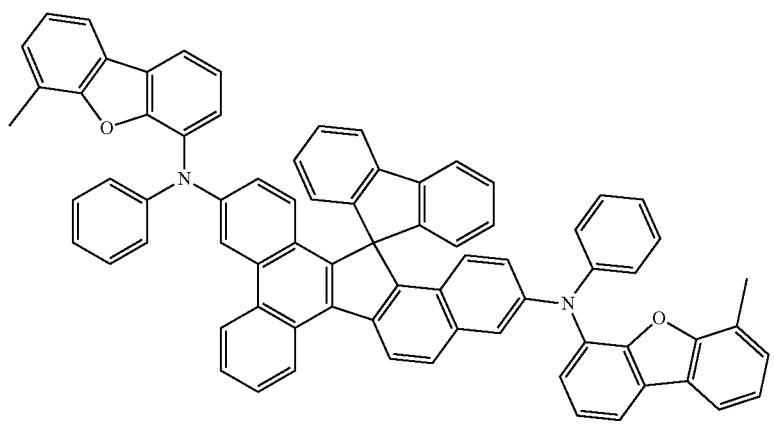

-continued
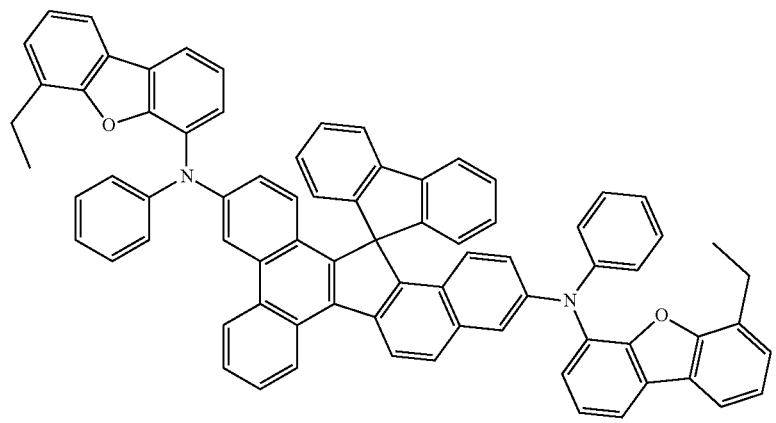
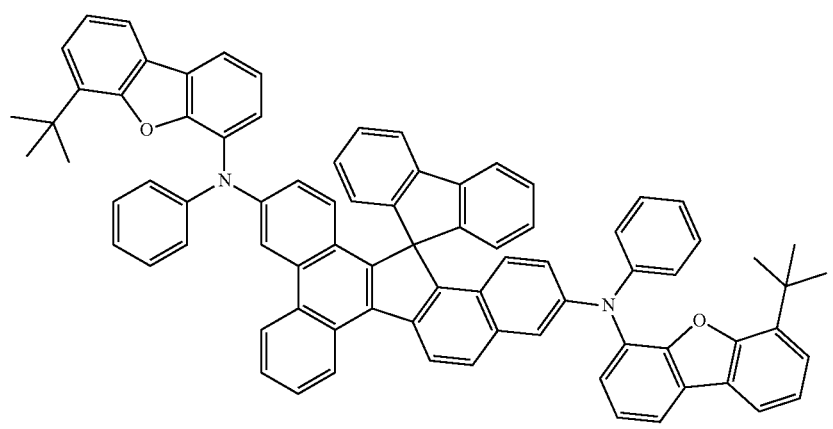
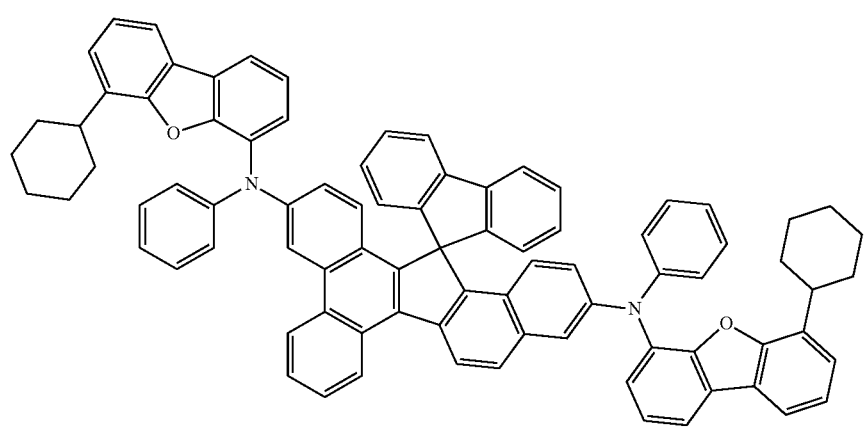

-continued
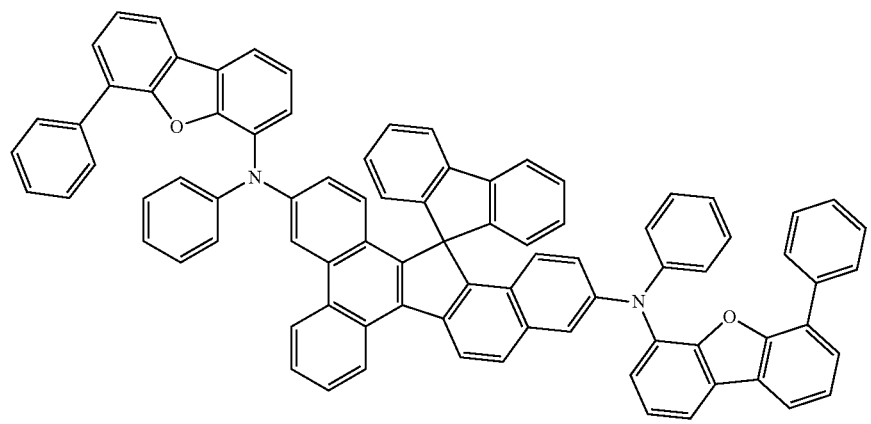
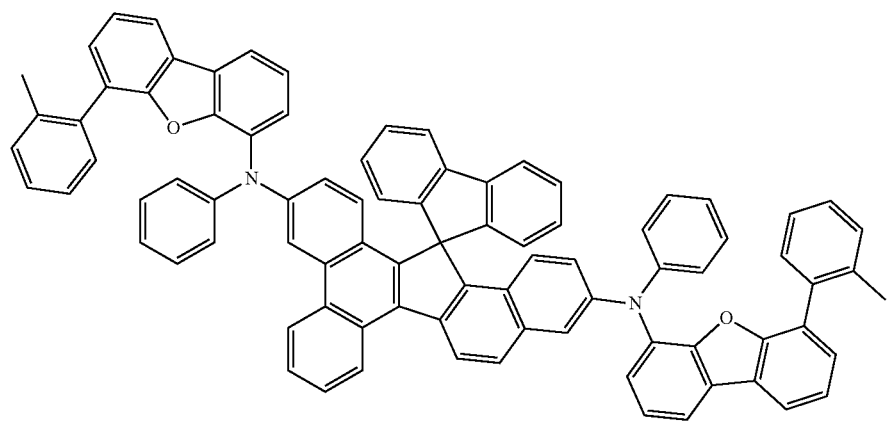
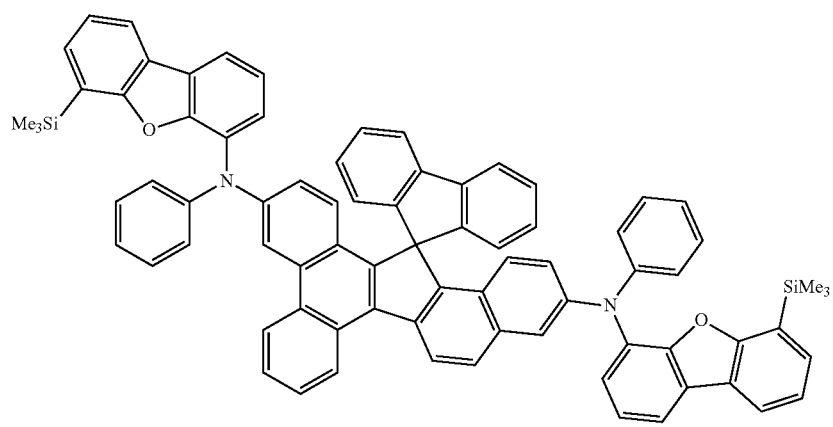
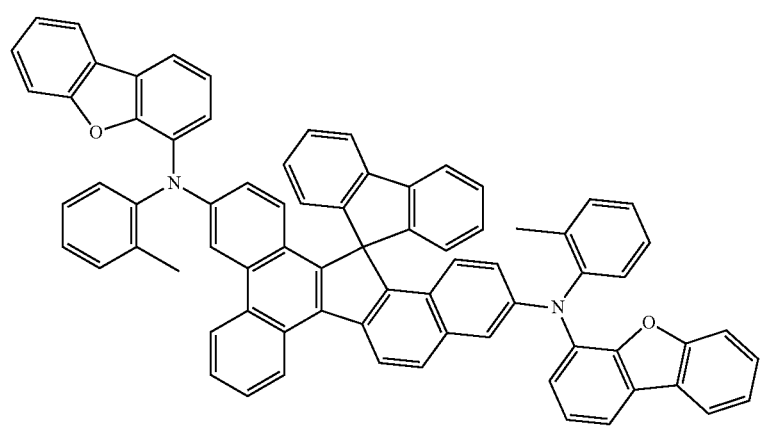

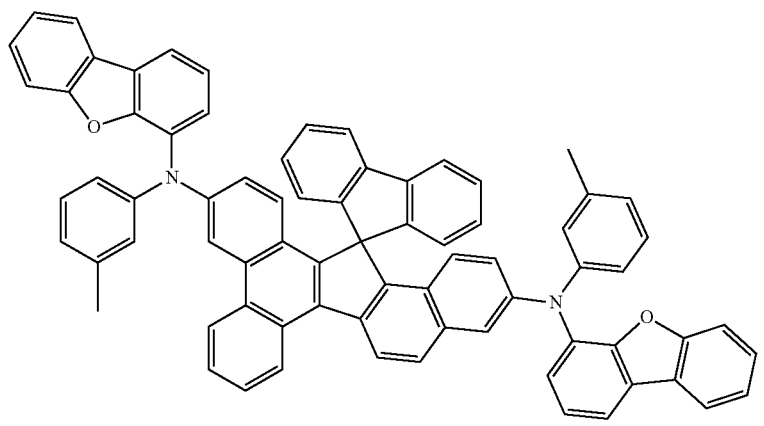
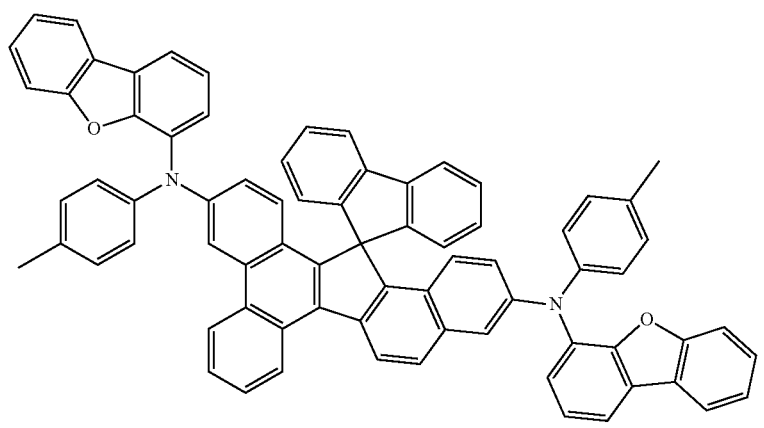
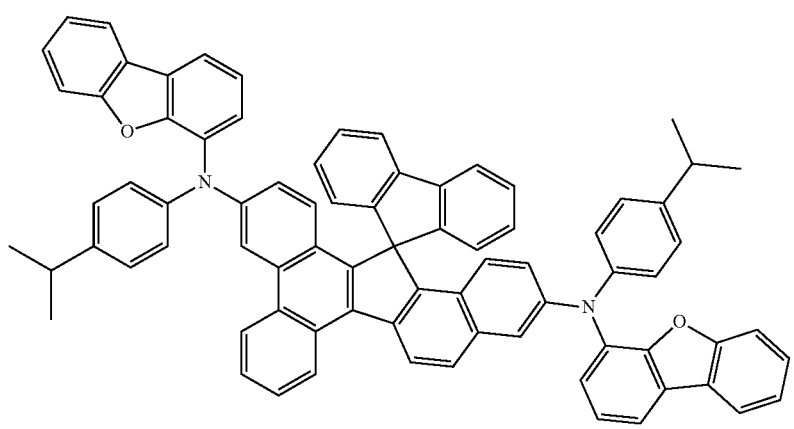

-continued
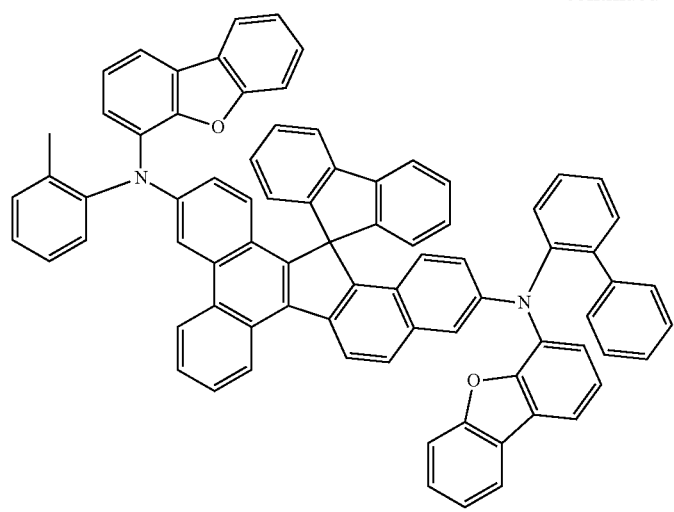
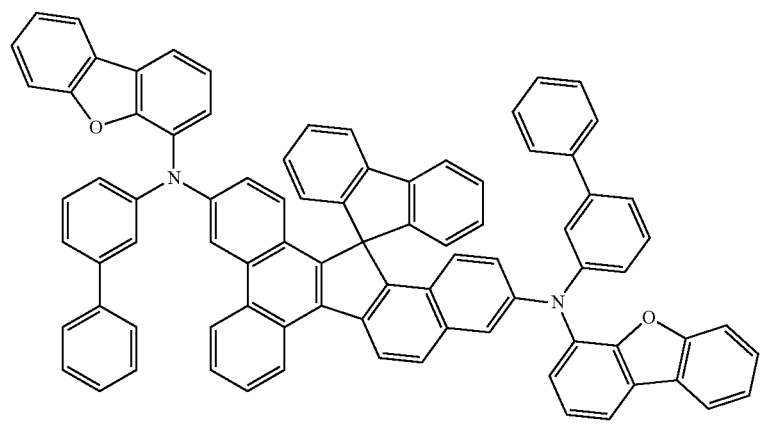
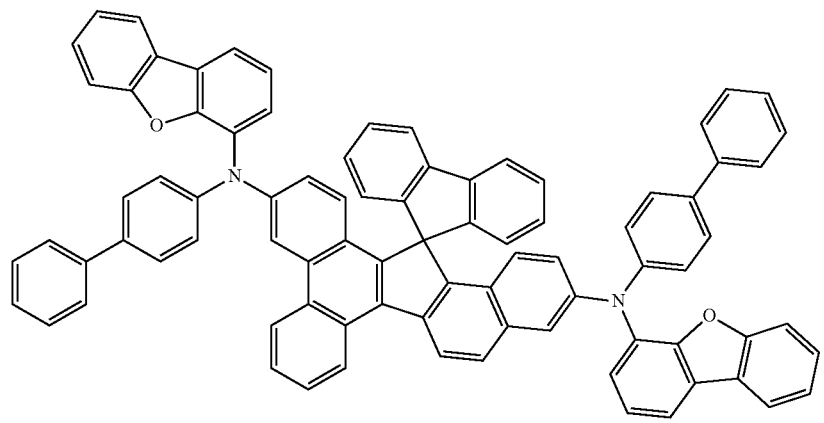

-continued
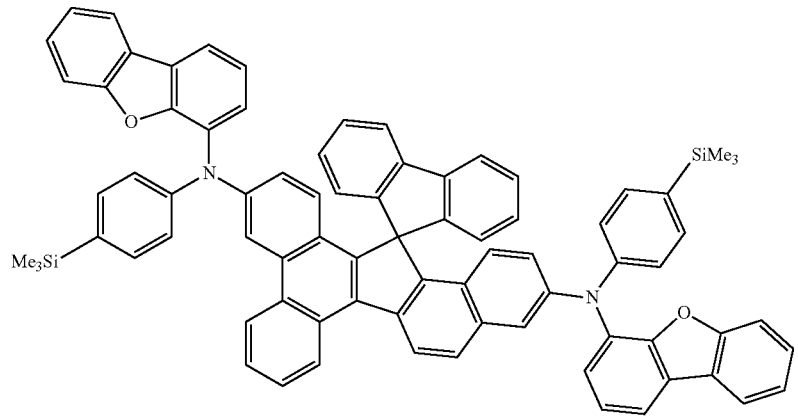
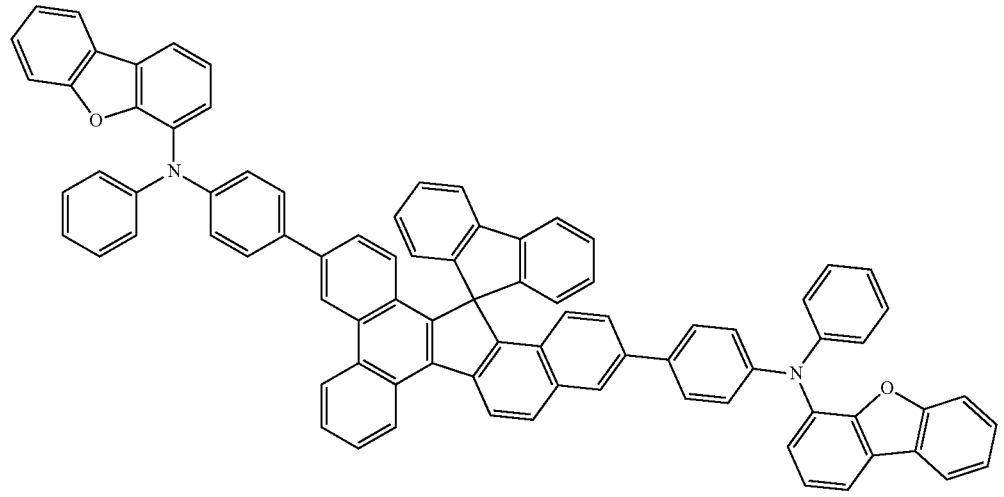
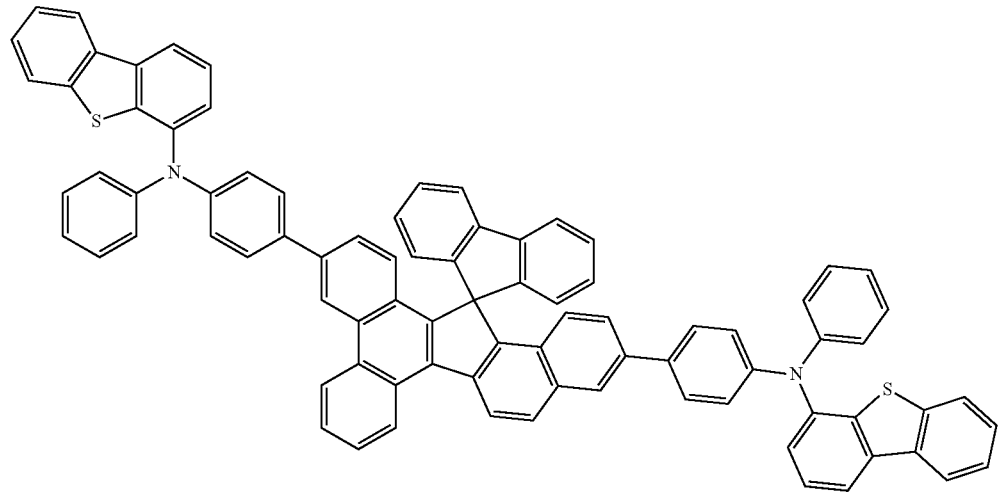
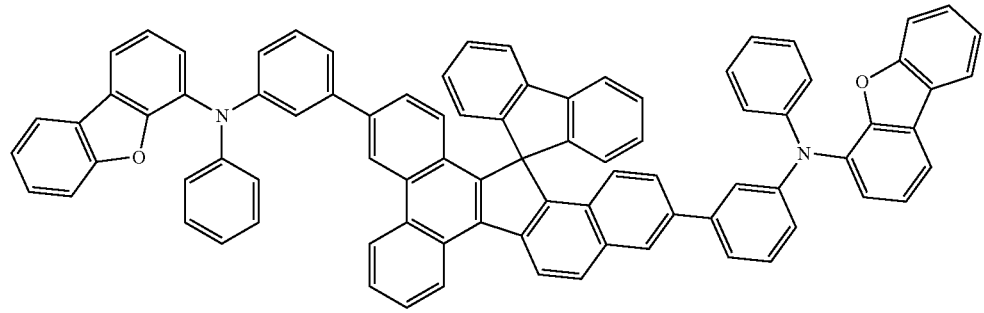

-continued
| 459 | 460 |
|---|---|
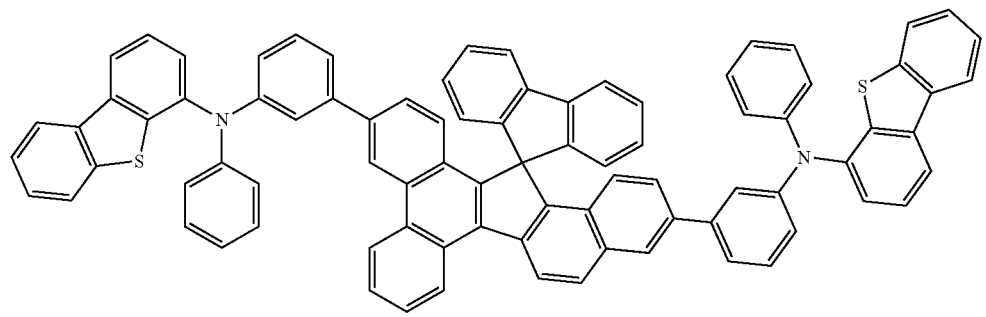
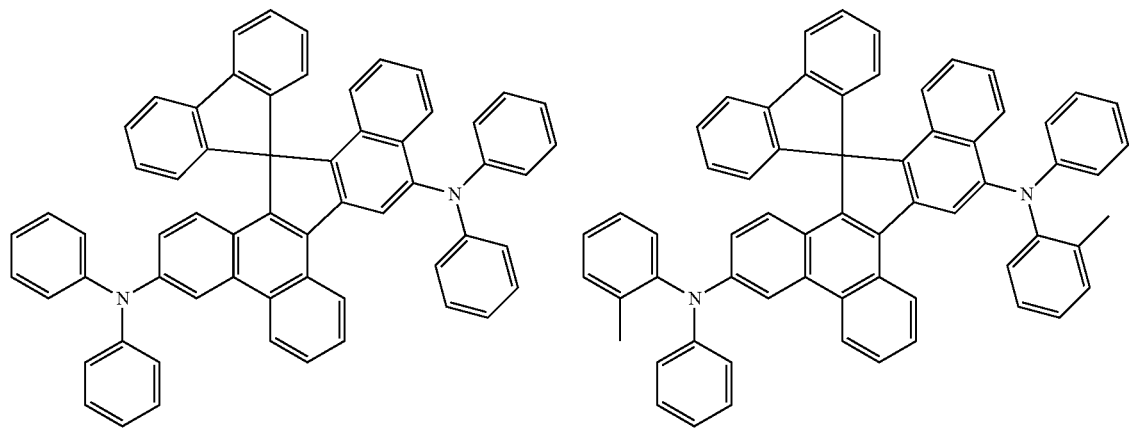
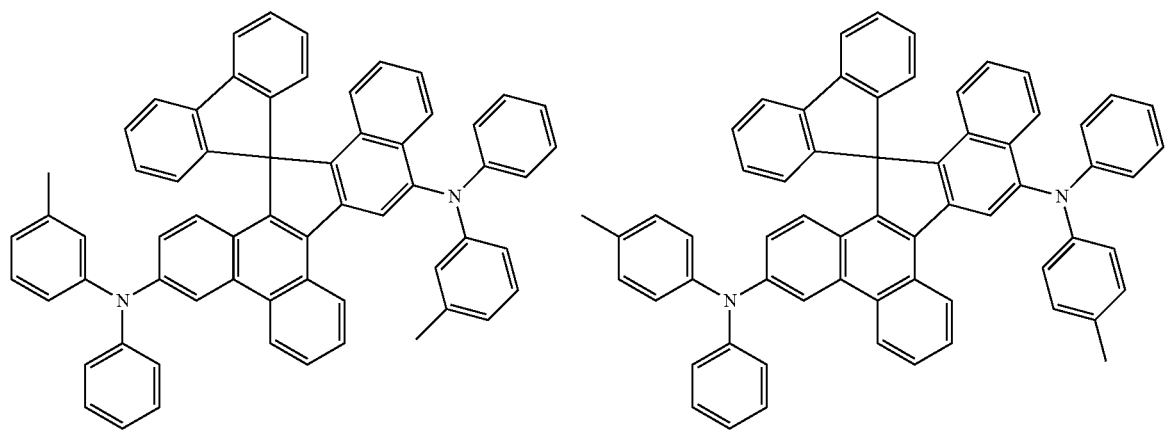
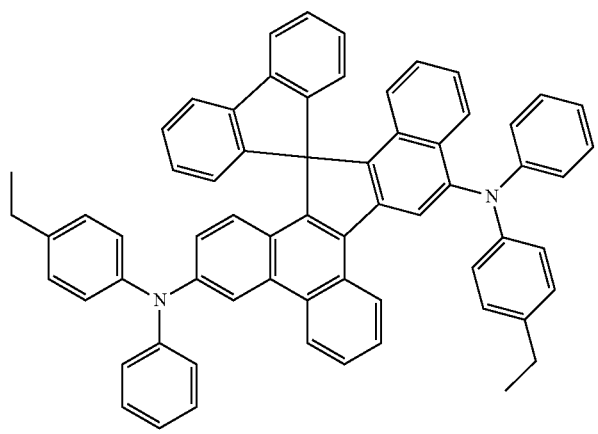

461
462
-continued
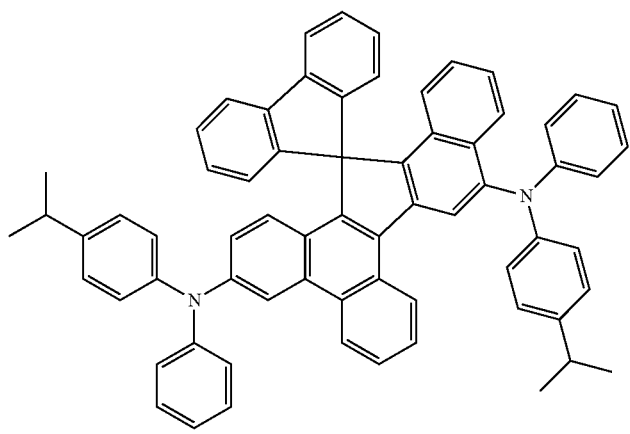
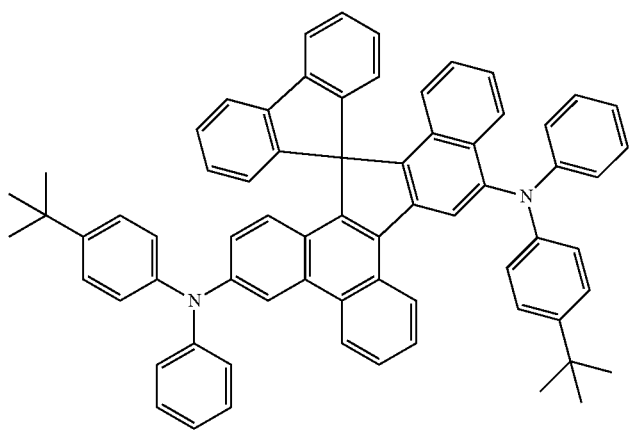
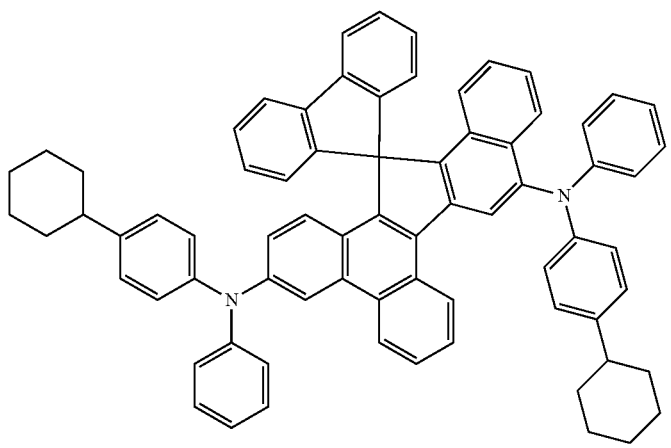

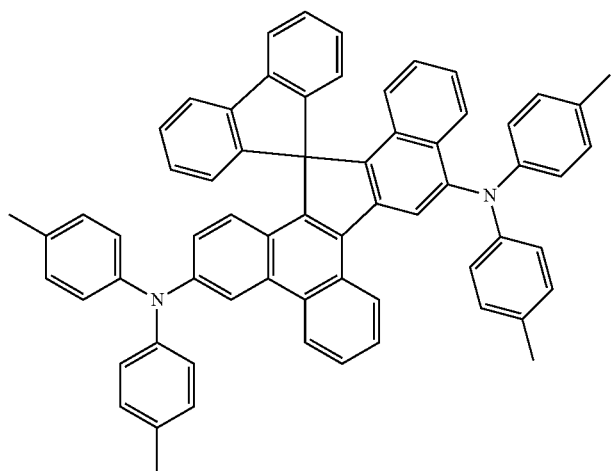
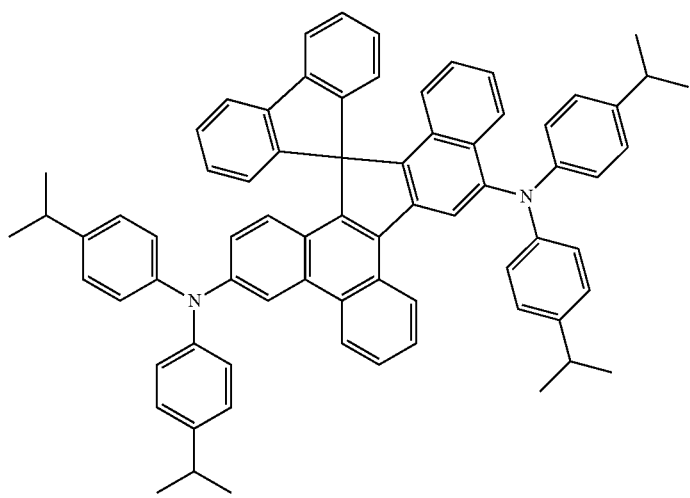
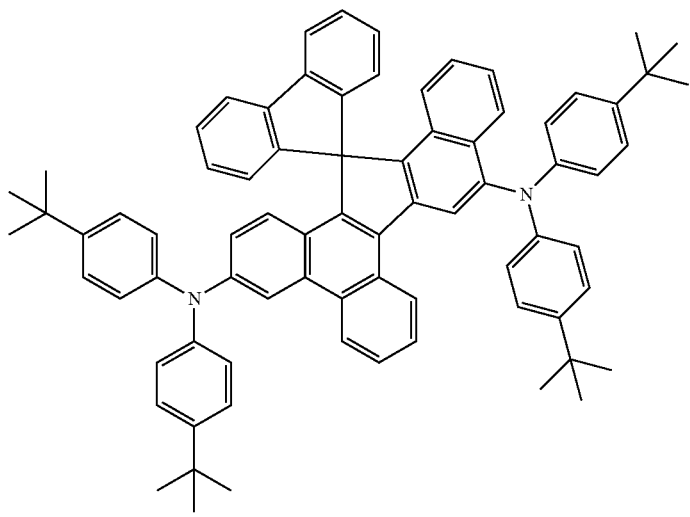

-continued
465
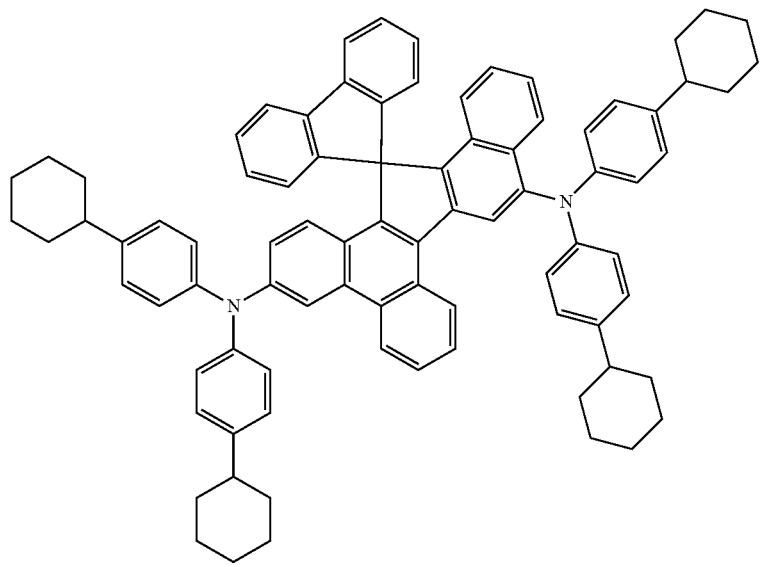
466
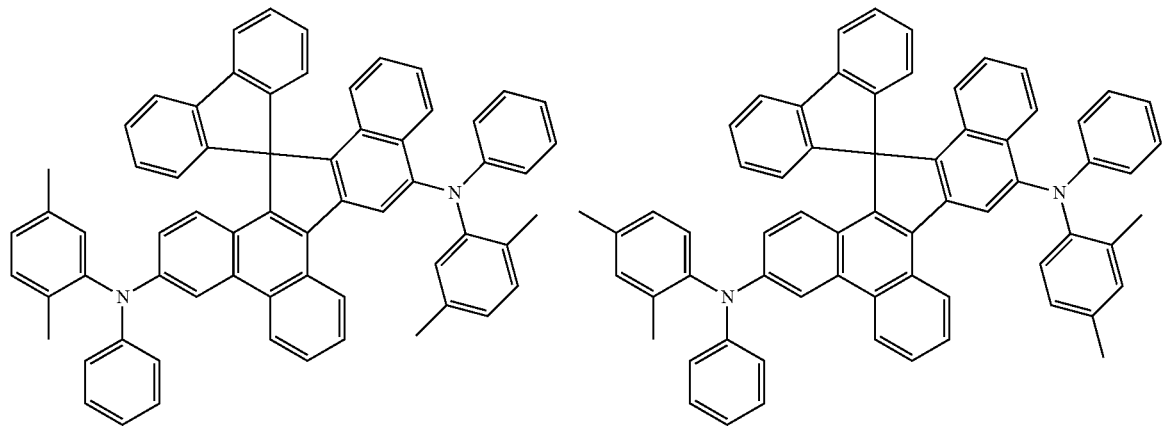
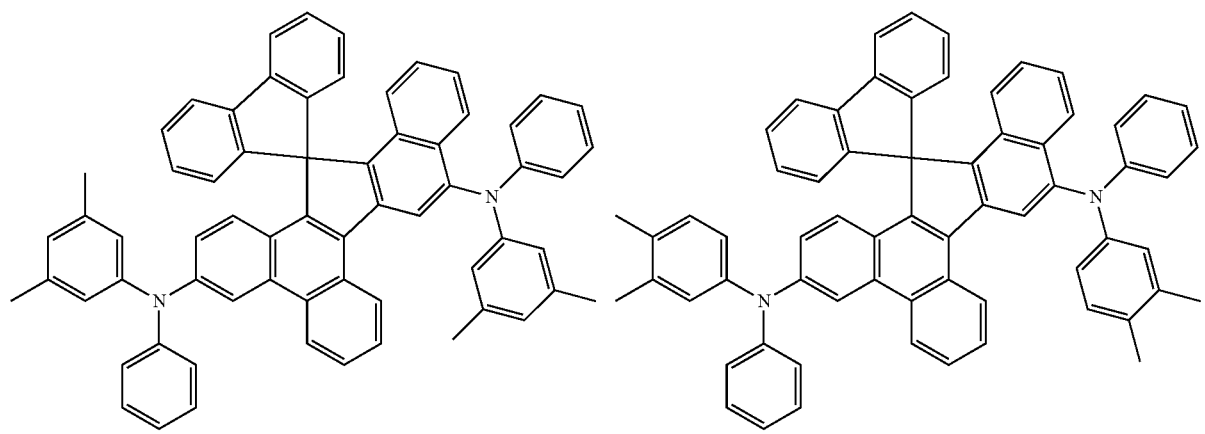

467 468
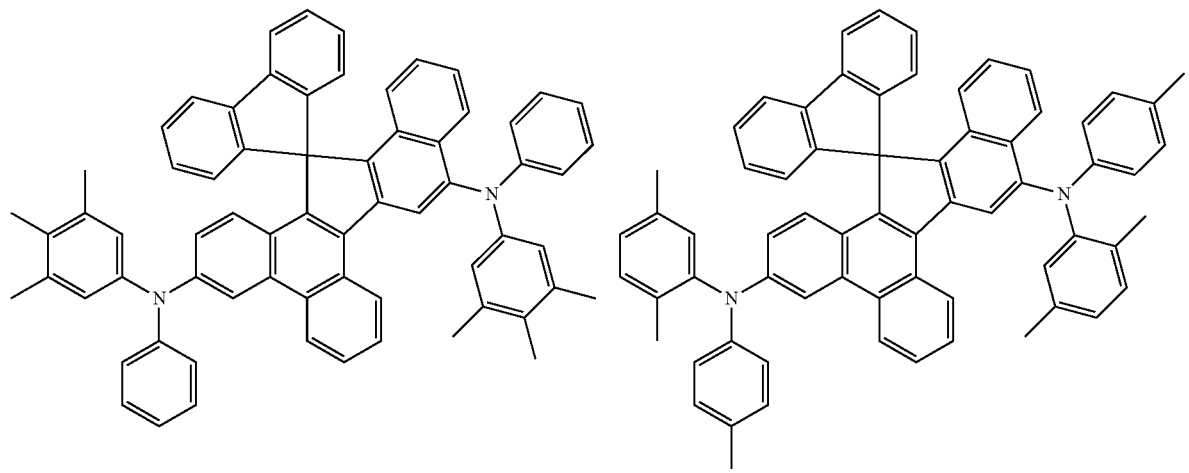
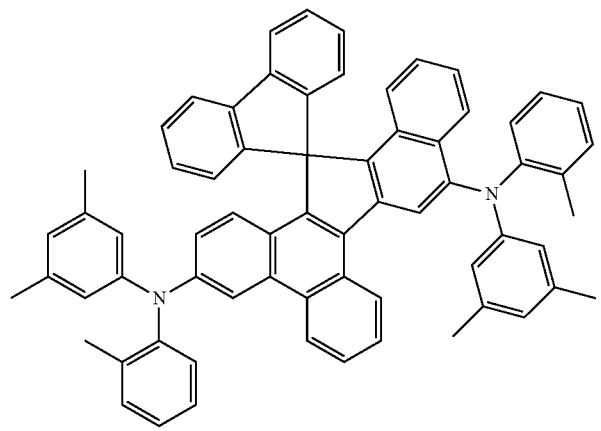
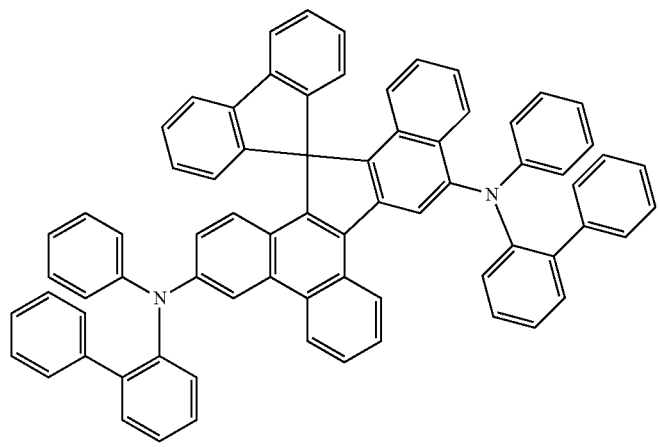

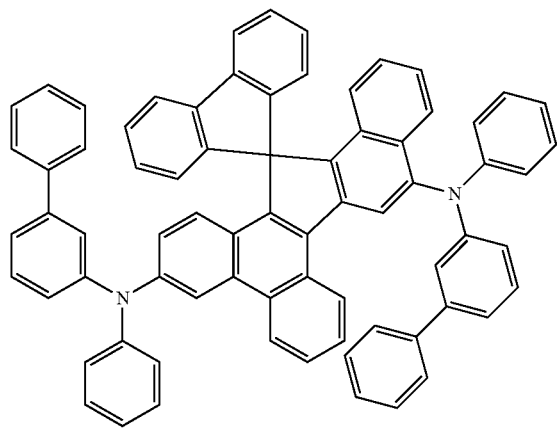
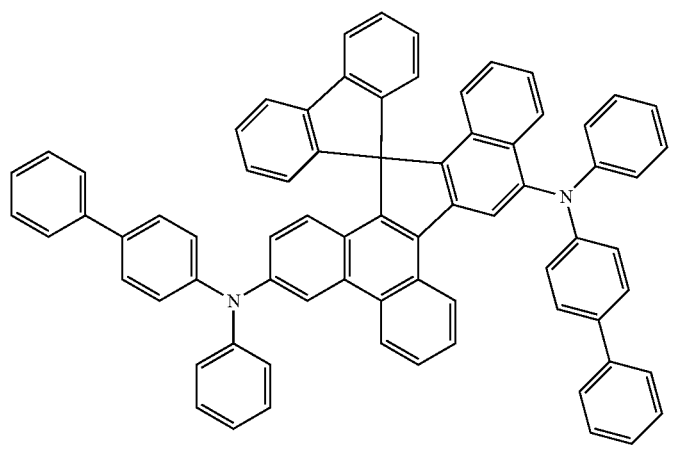
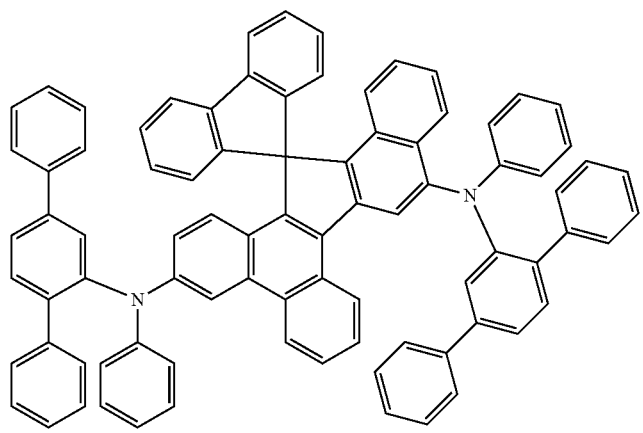

471
472
-continued
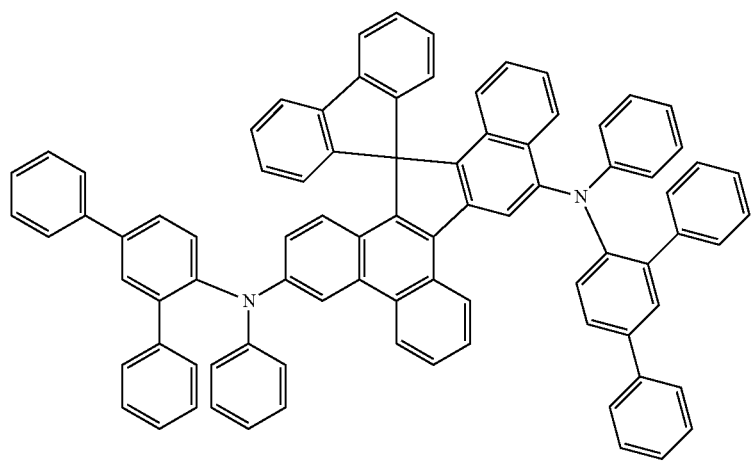
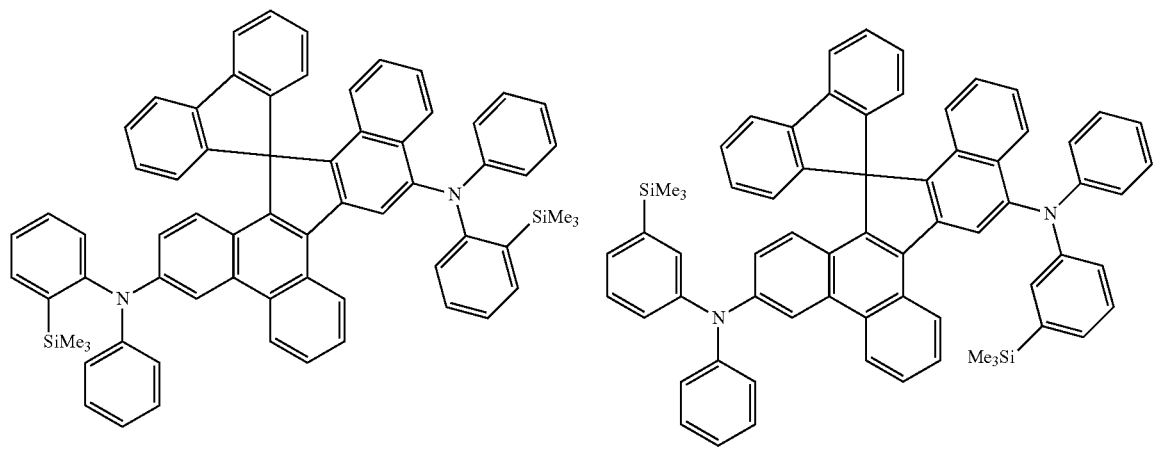
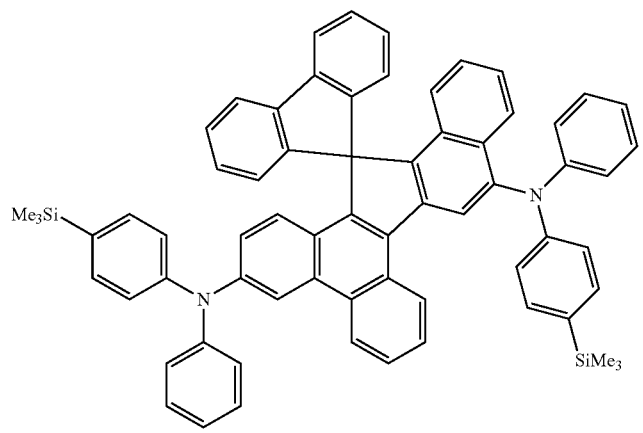

473
-continued
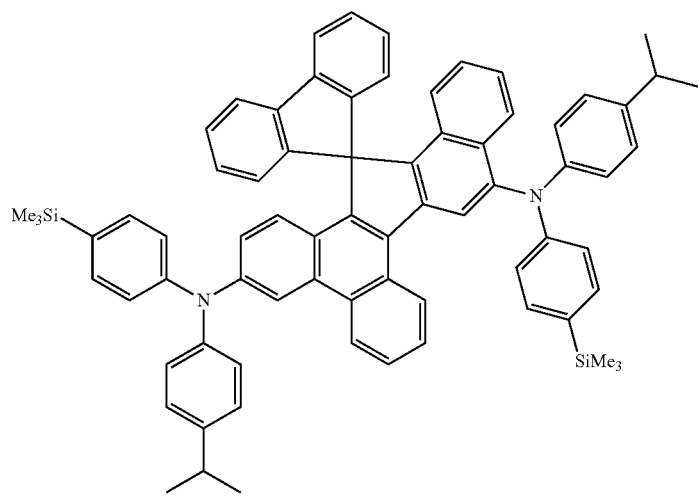
474
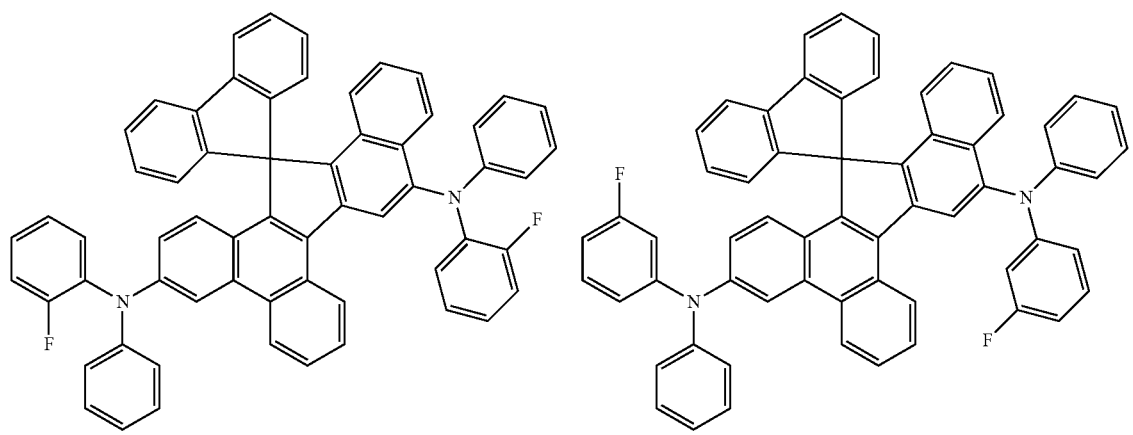
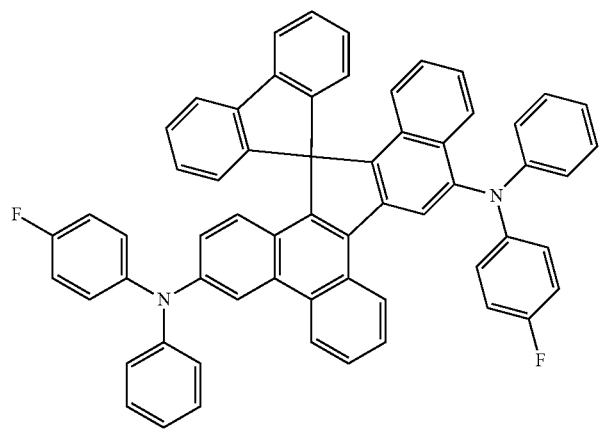

475
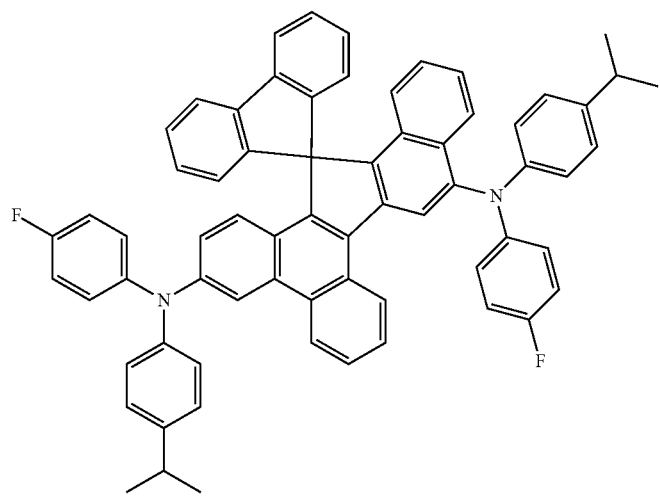
-continued
476
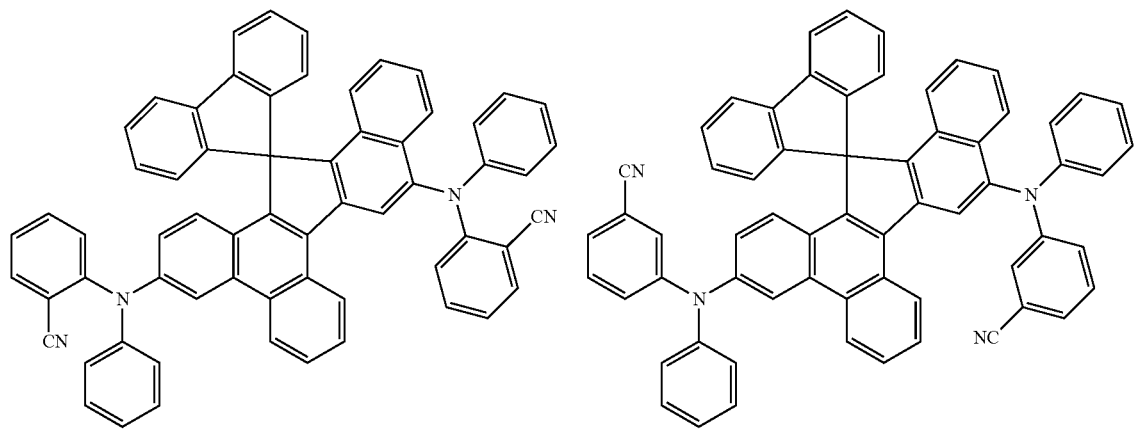
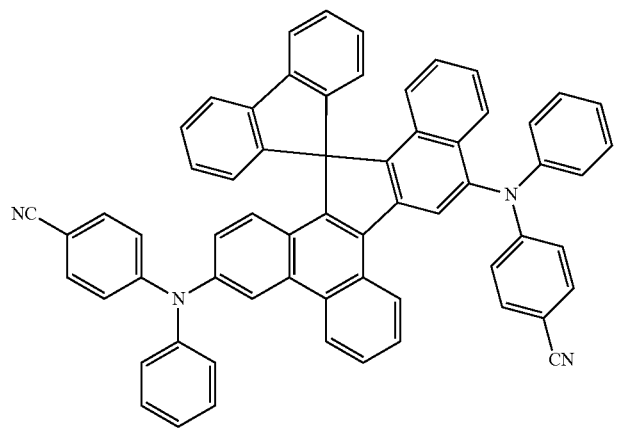

-continued
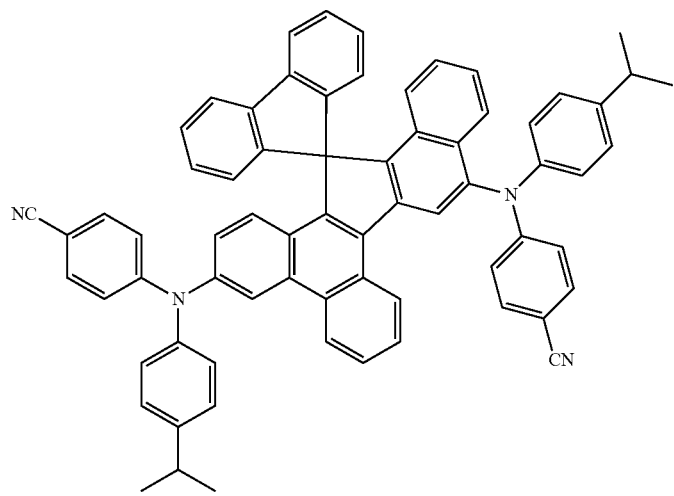
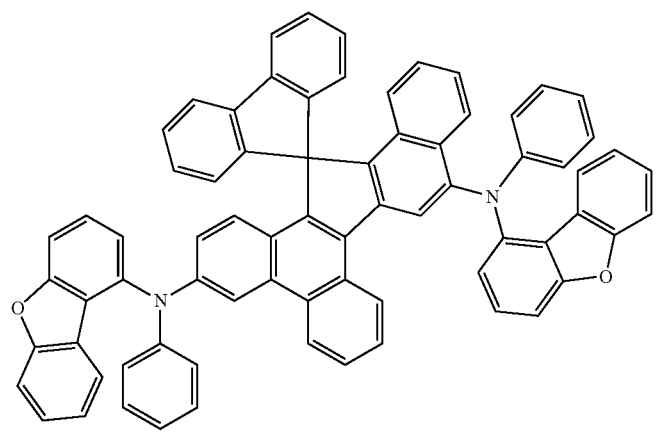
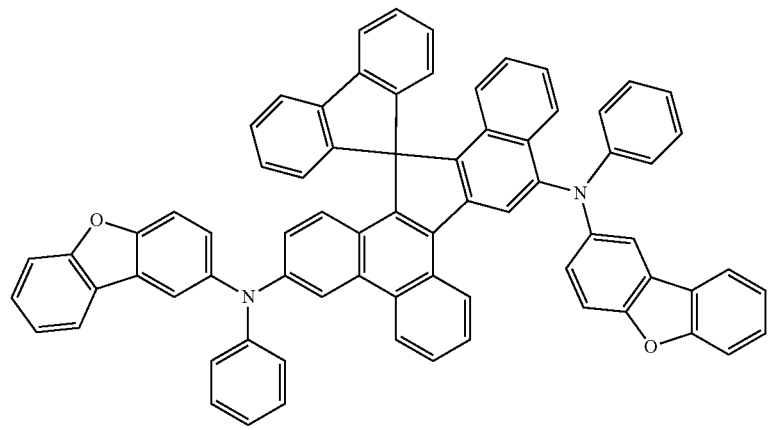

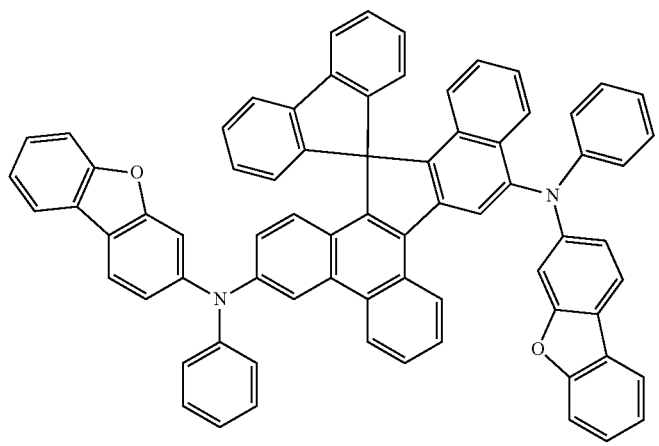
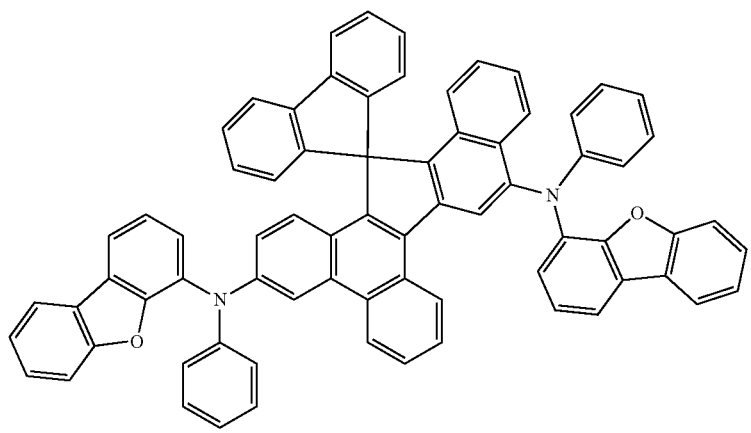
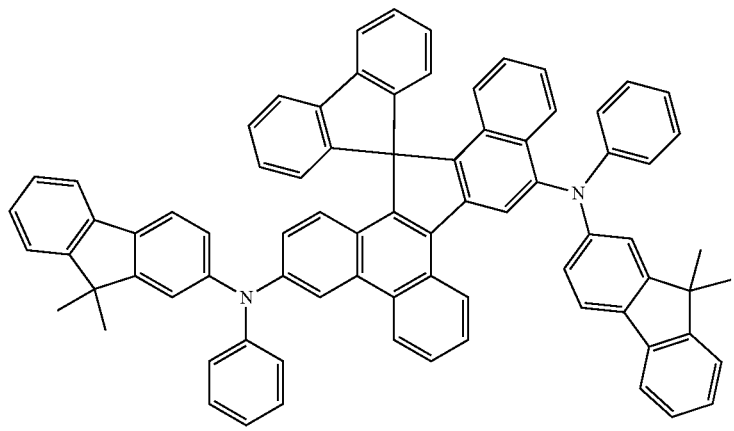

-continued
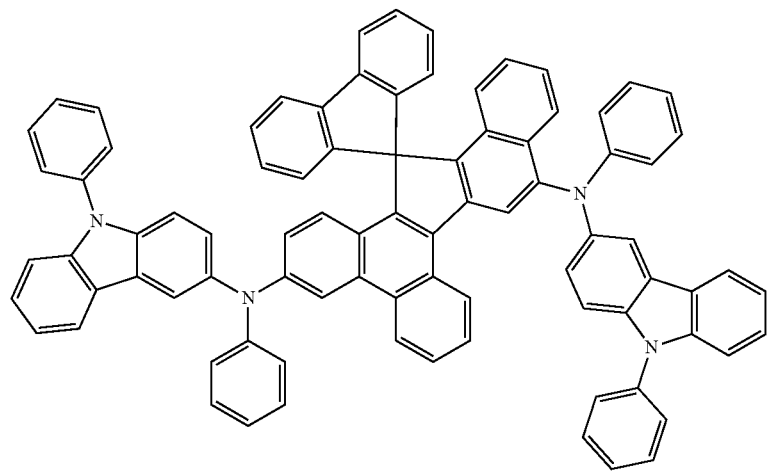
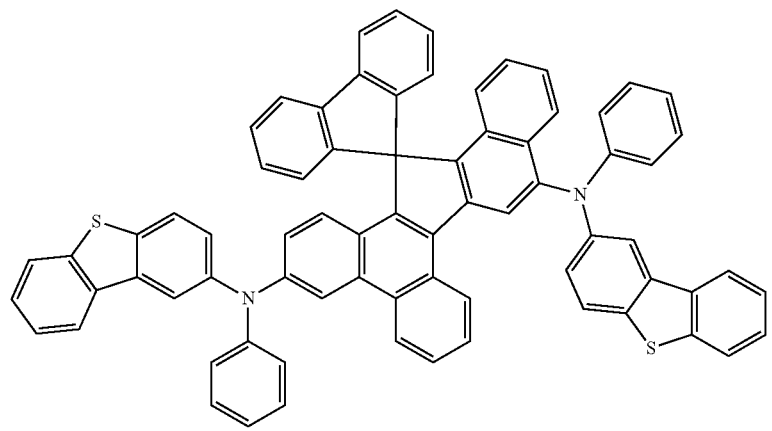
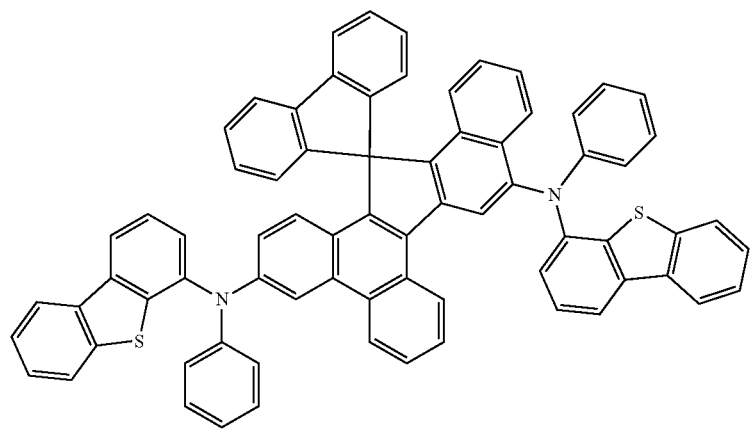

-continued
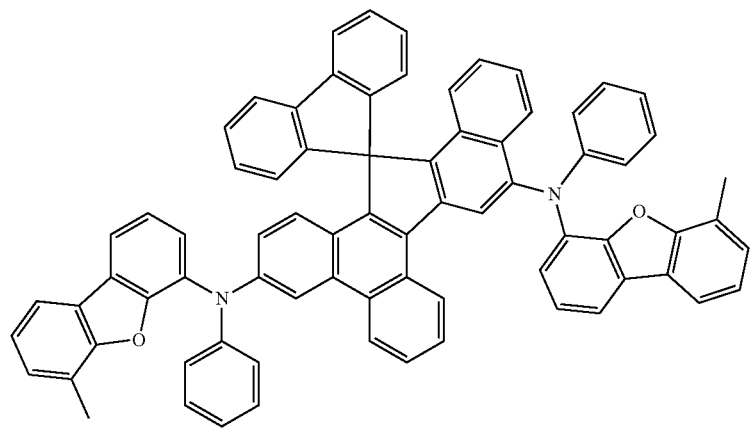
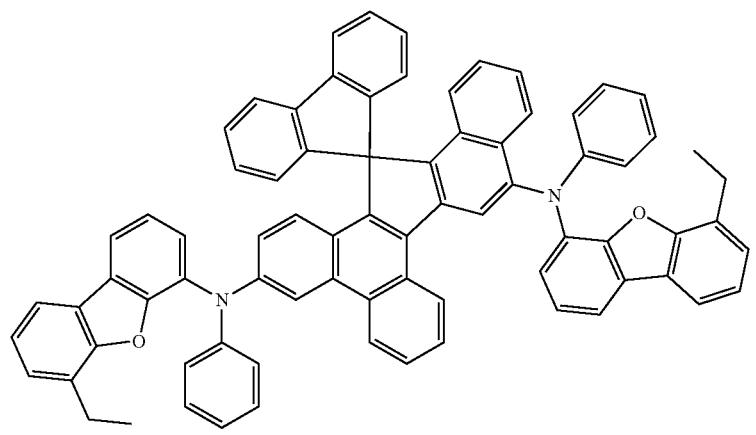
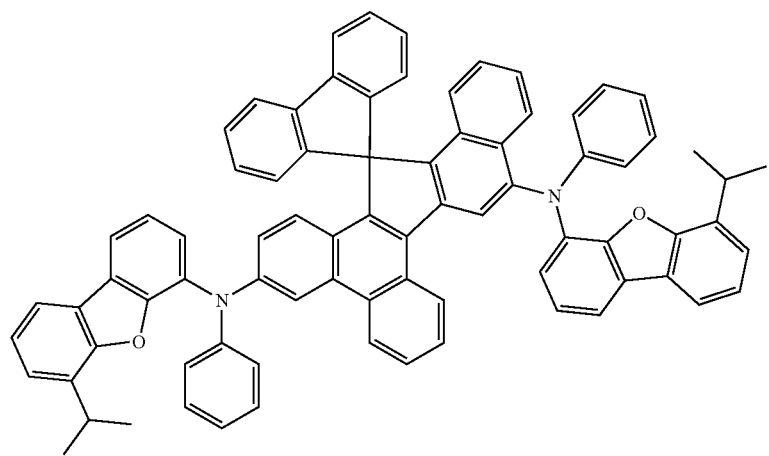

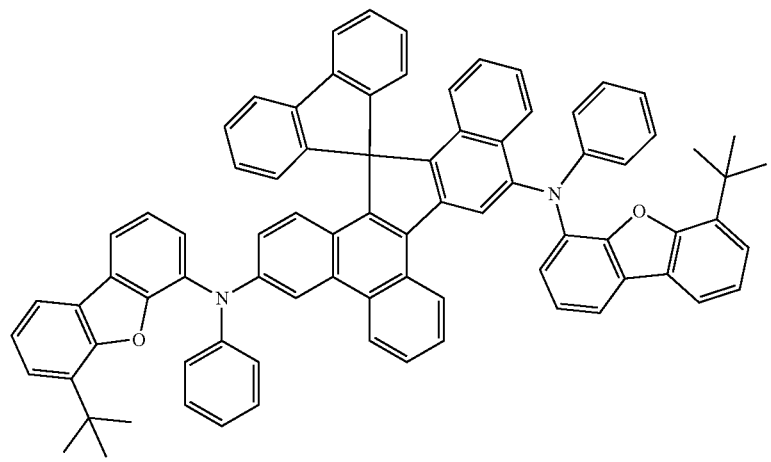
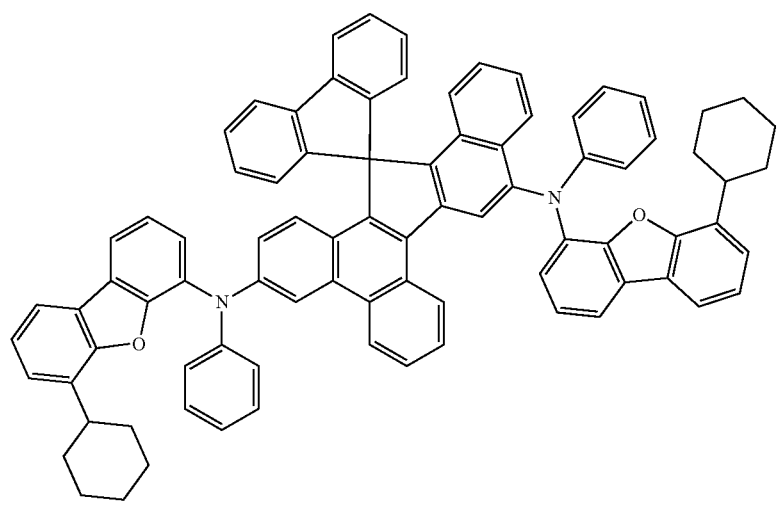
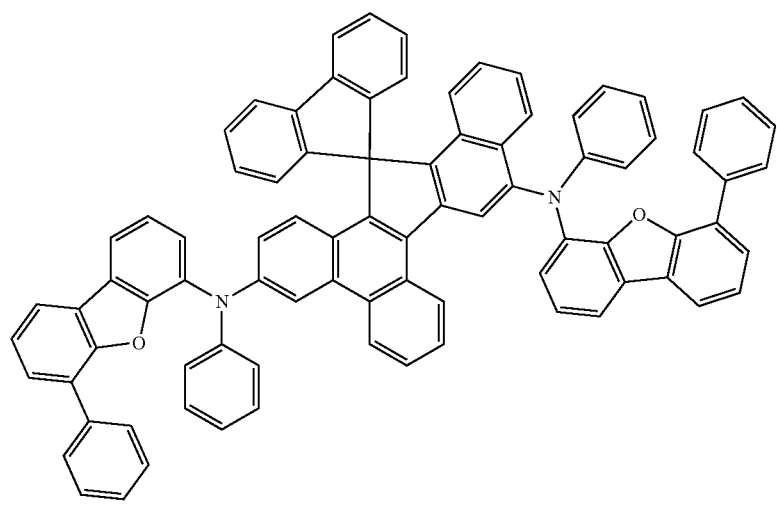

-continued
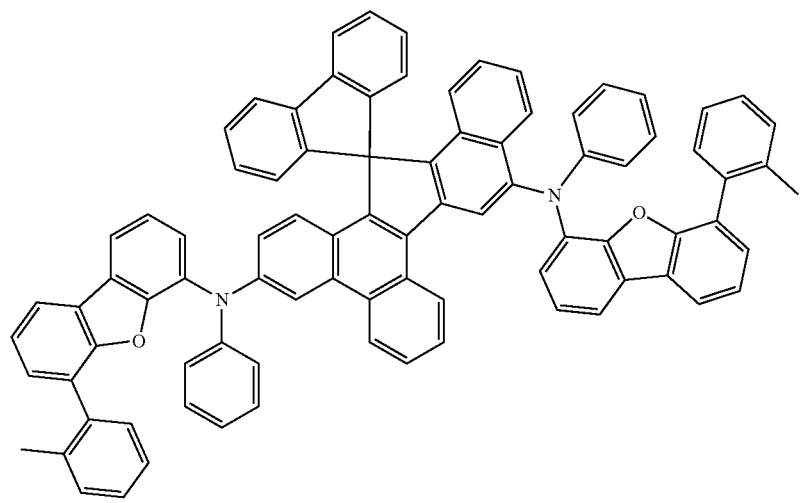
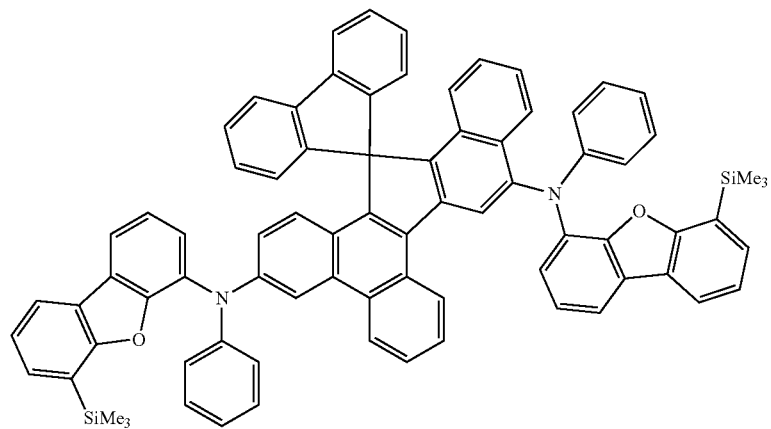
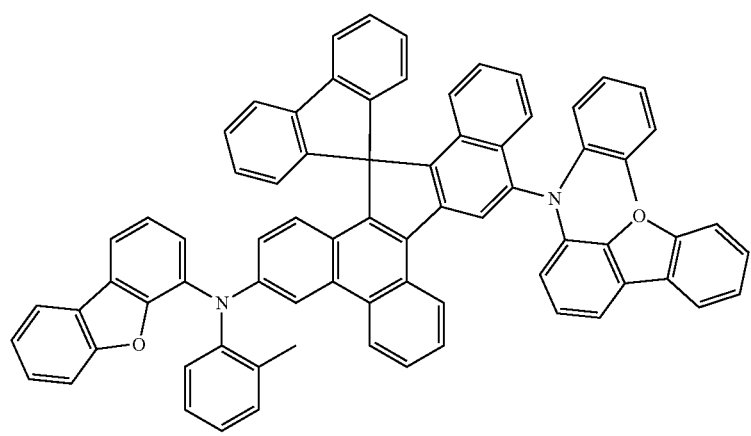

-continued
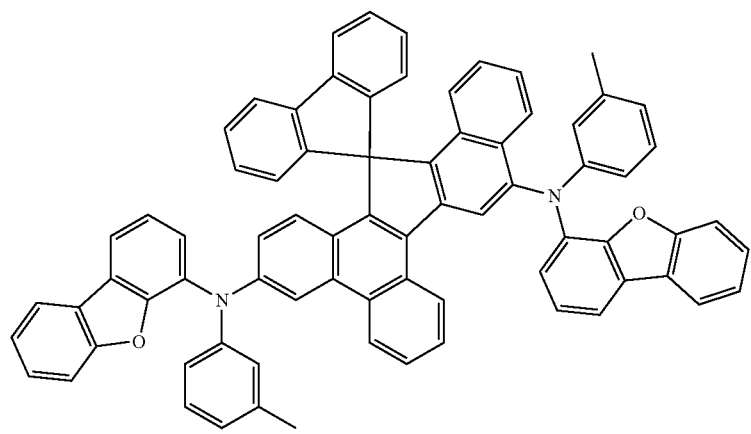
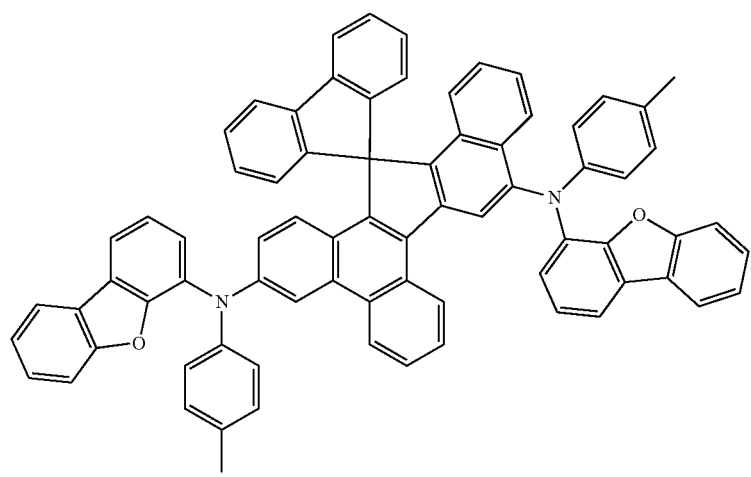
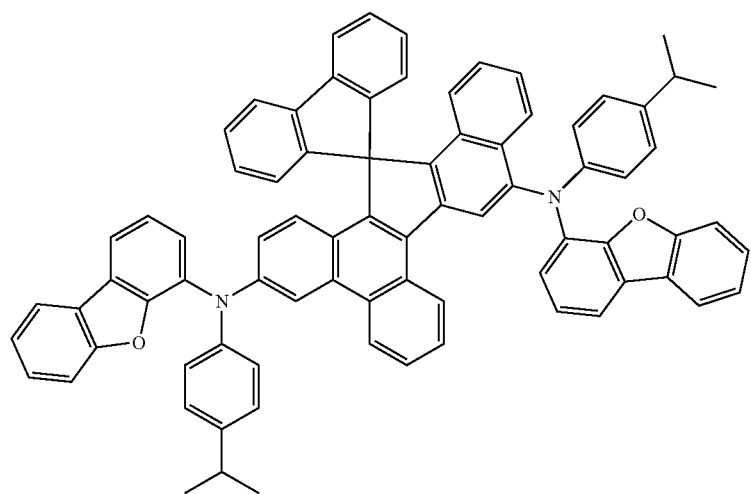

491
492
-continued
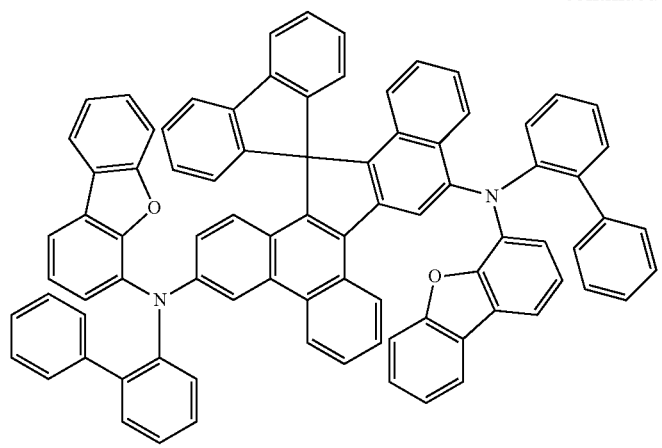
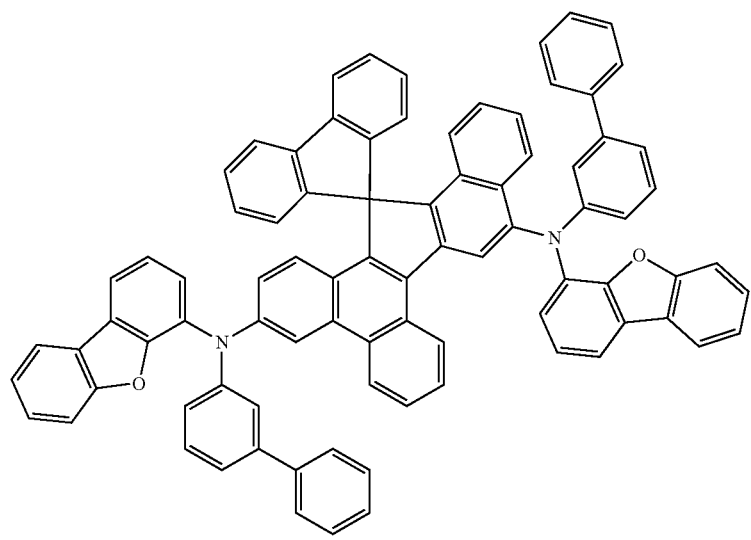
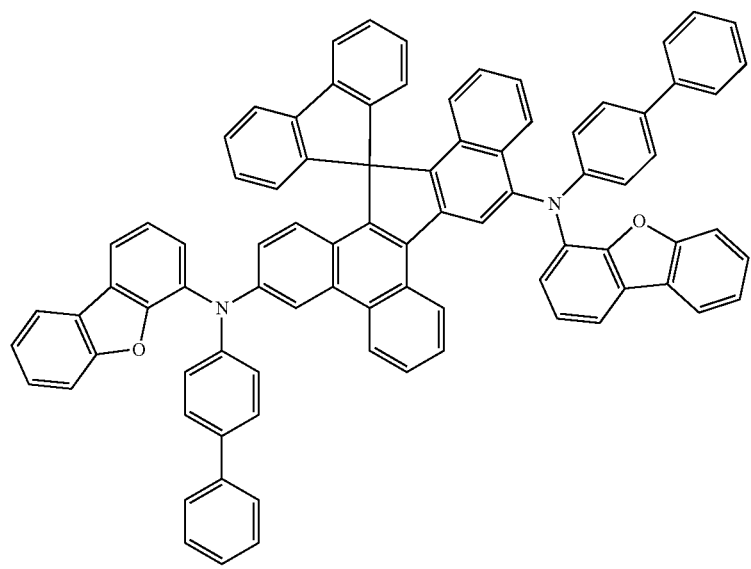

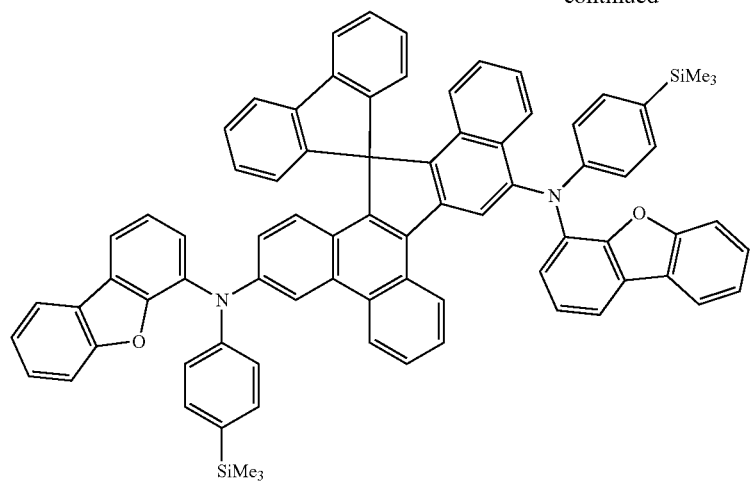
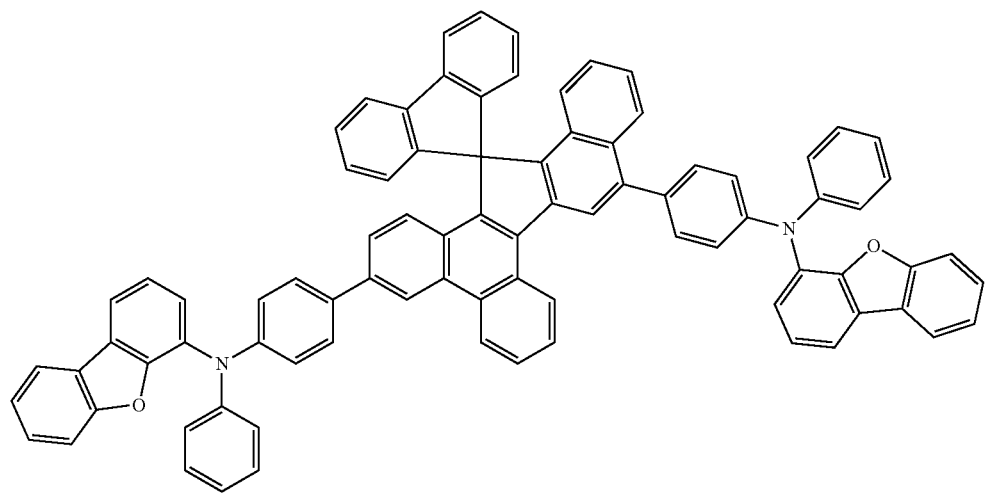
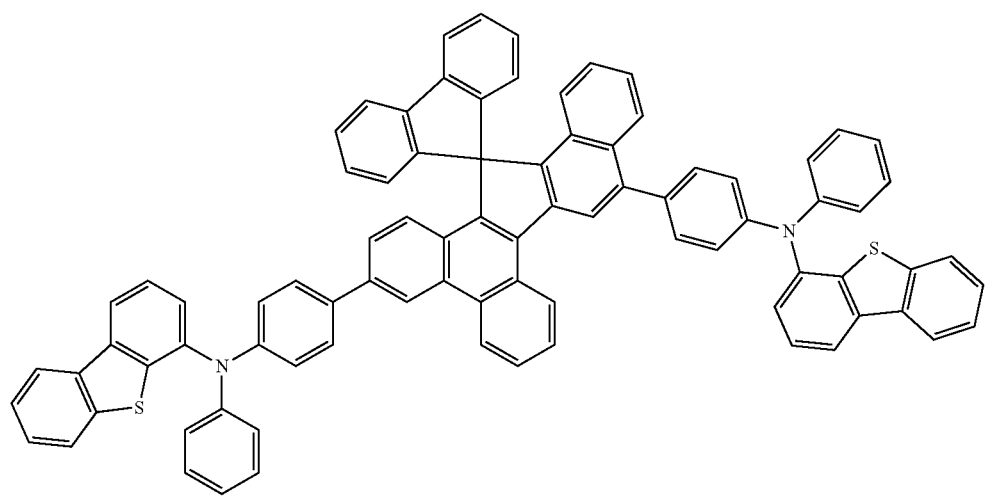

495
496
-continued
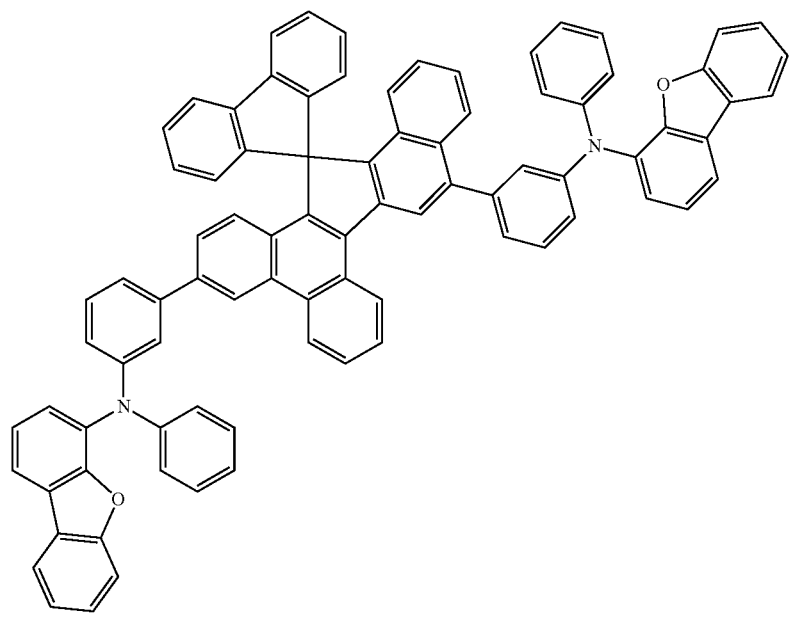
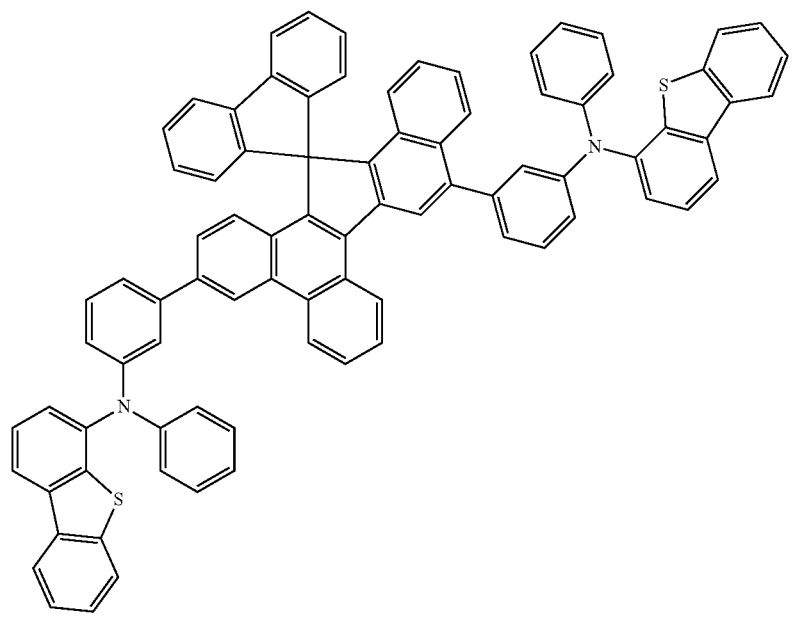
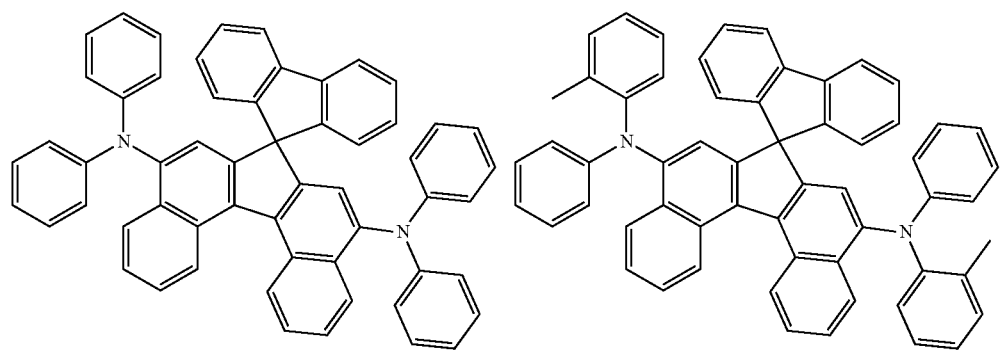

-continued
497
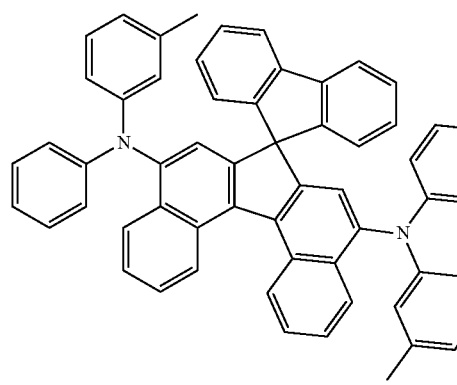
498
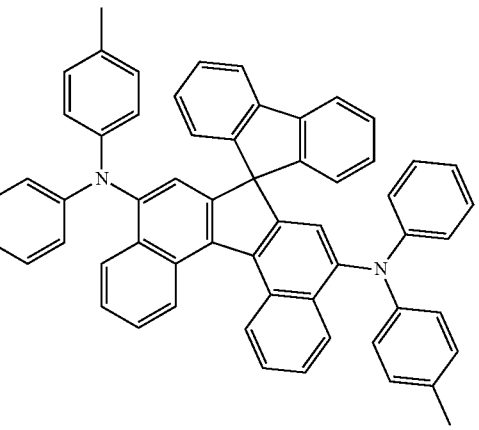
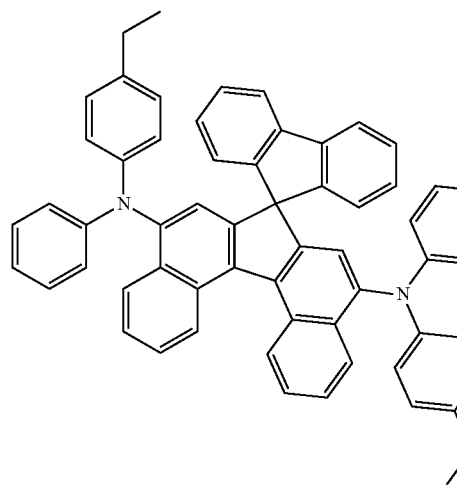
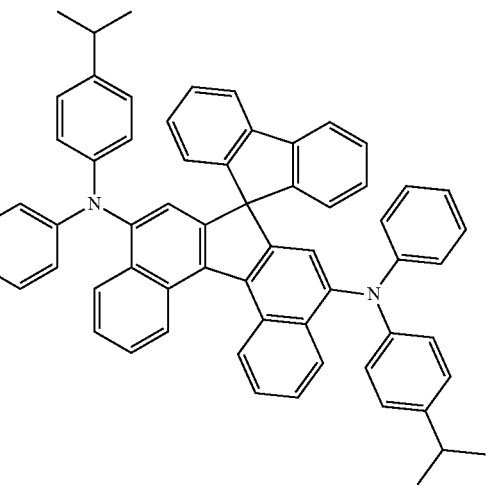
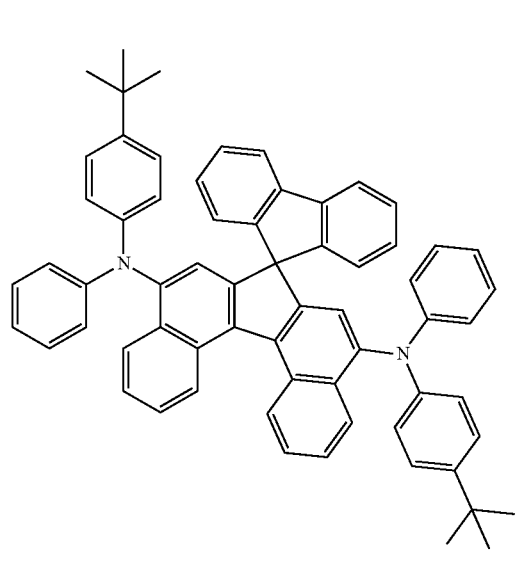
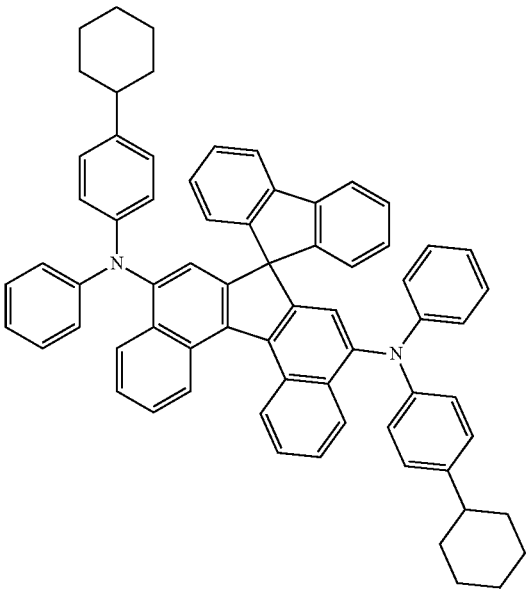

499
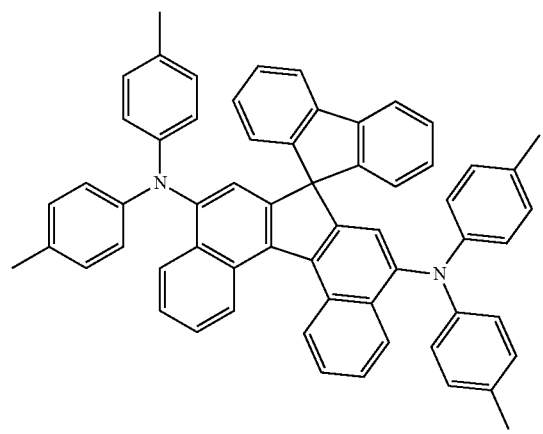
500
-continued
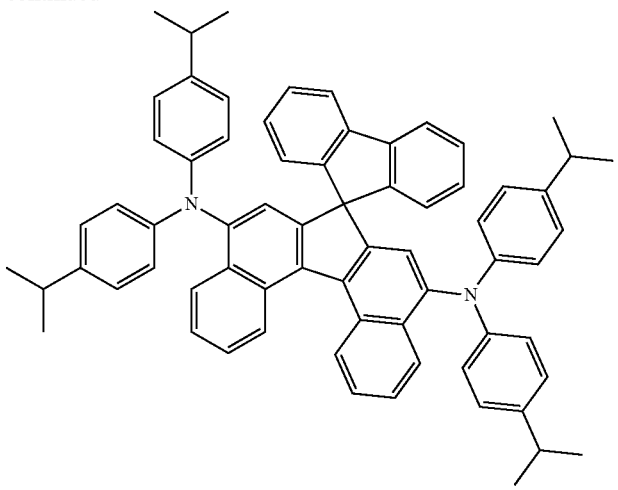
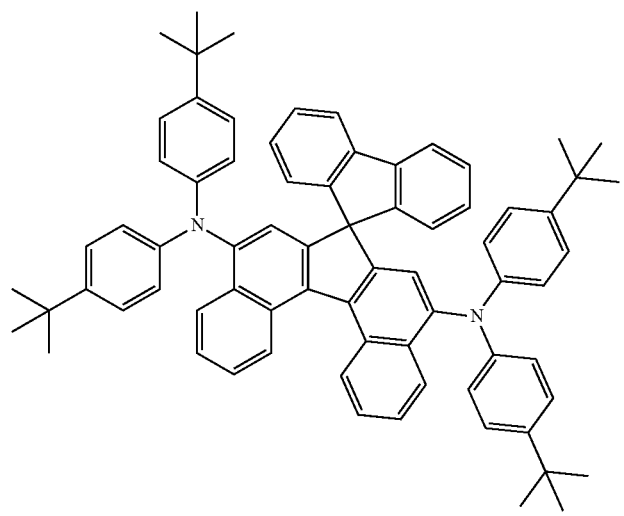
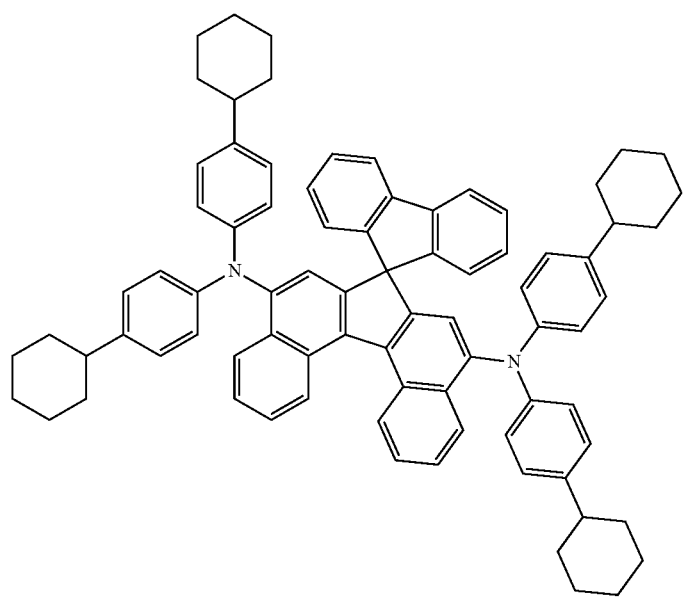

-continued
| 501 | 502 |
|---|---|
| 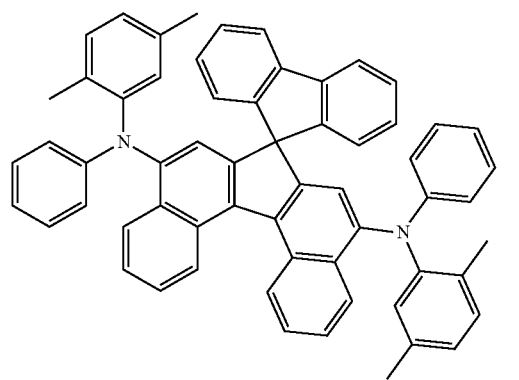 | 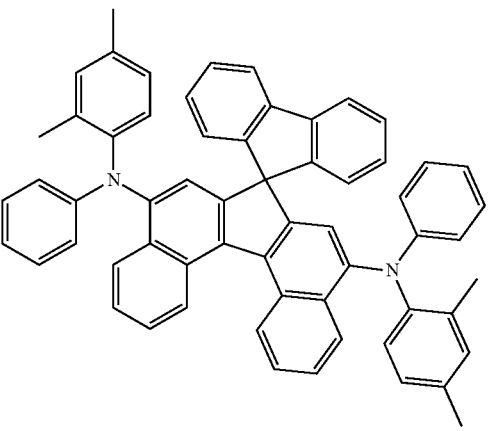 |
| 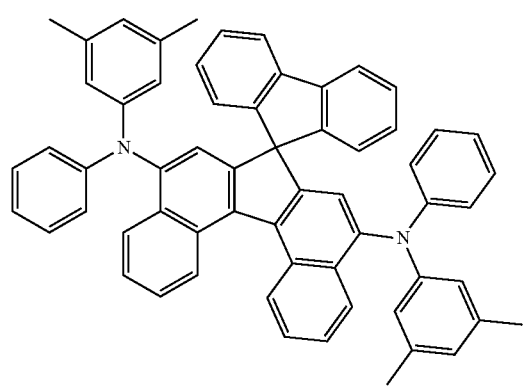 | 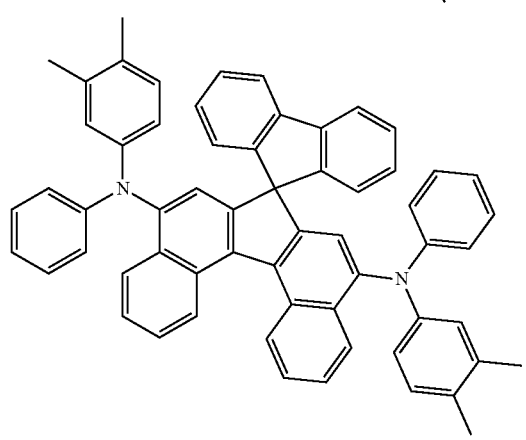 |
| 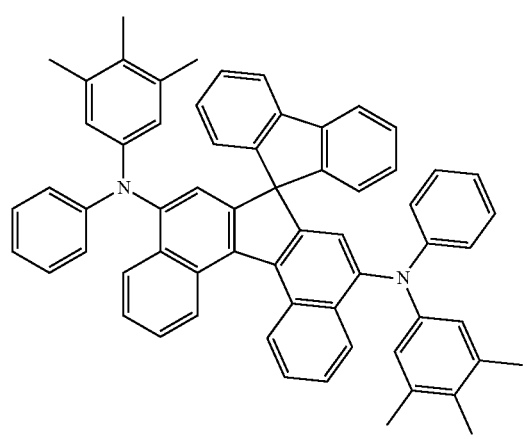 | 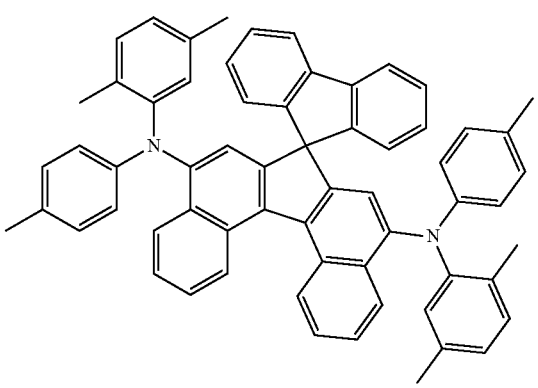 |
| 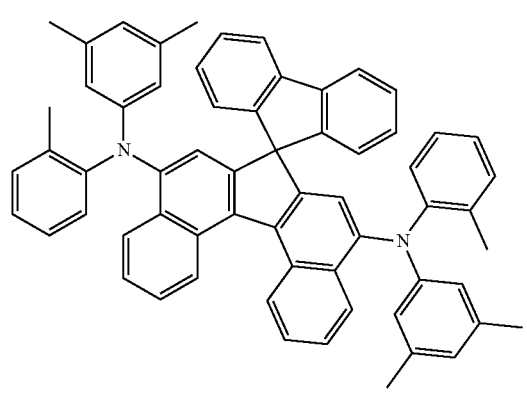 | 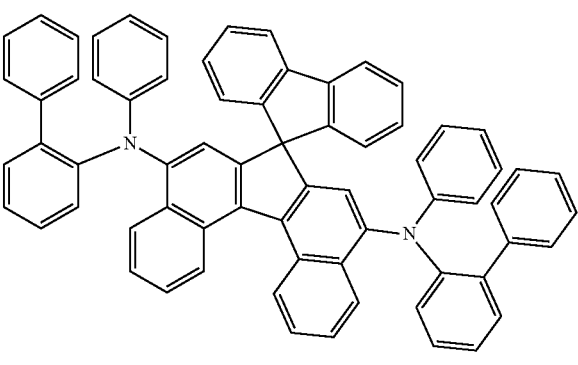 |

503
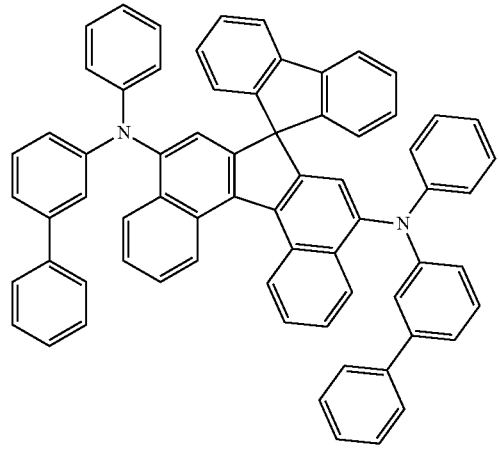
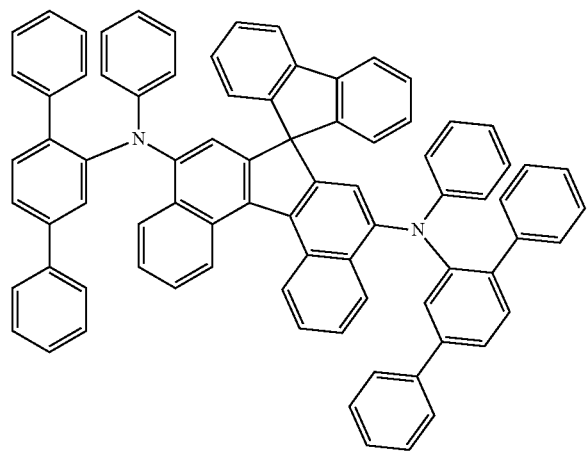
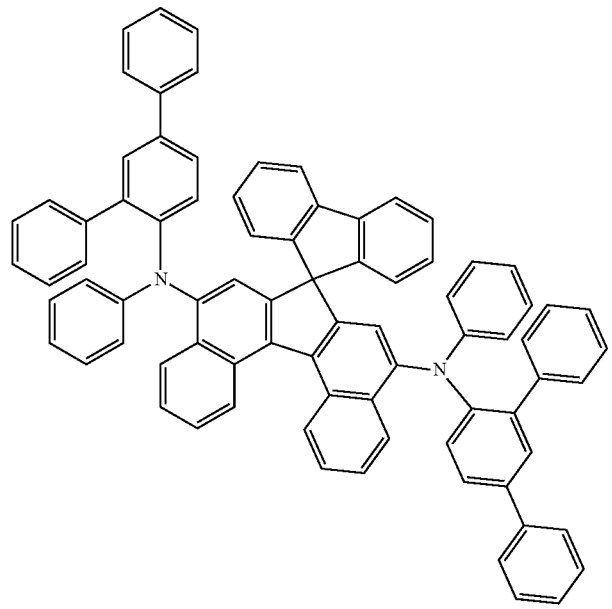
504
-continued
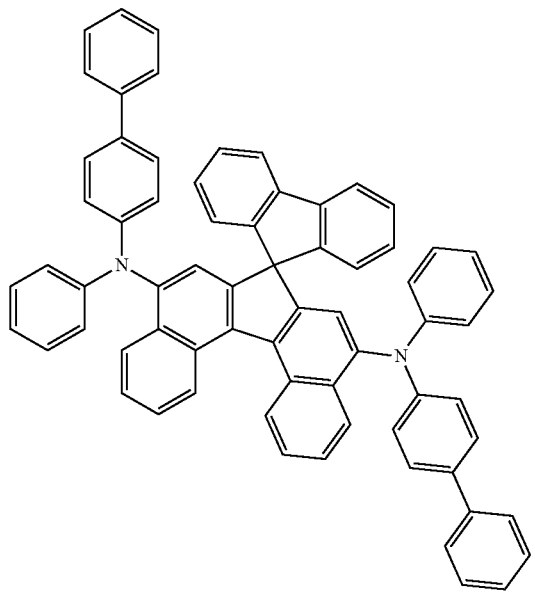
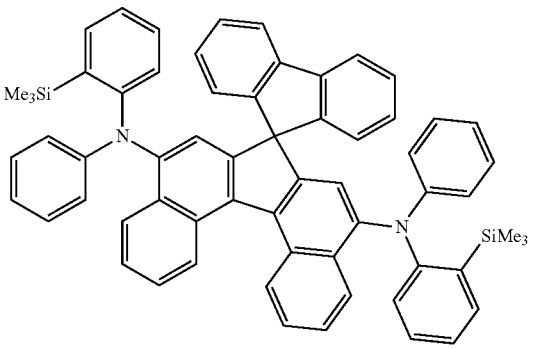

-continued
505
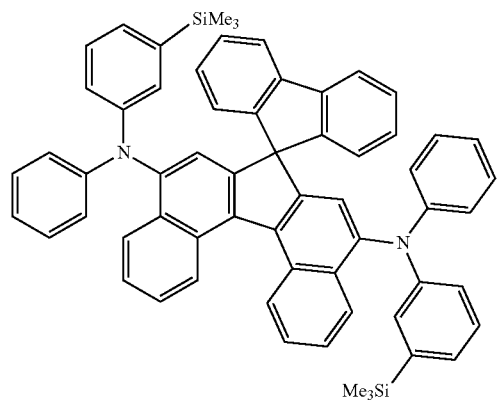
506
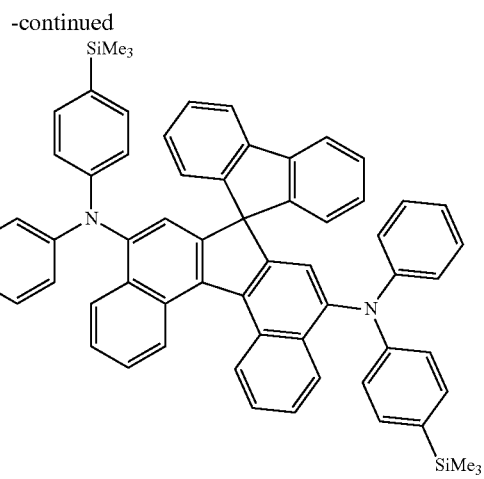
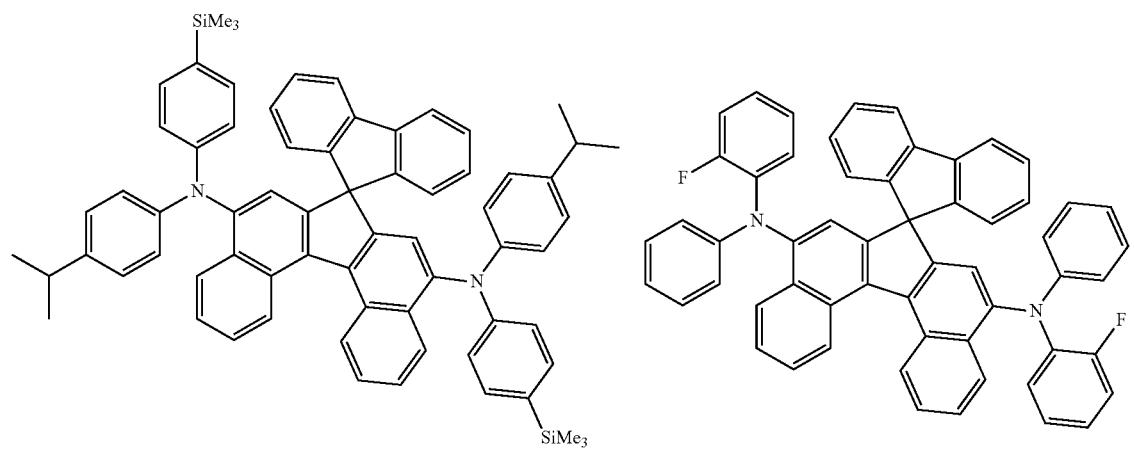
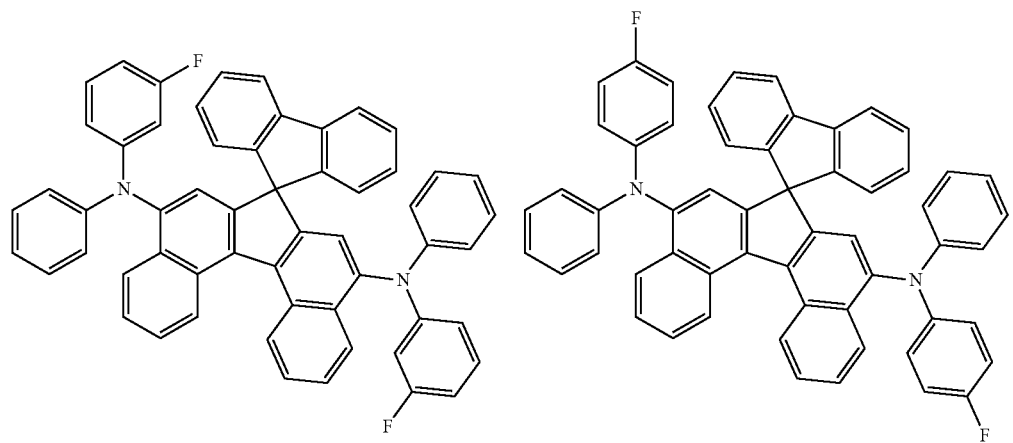

507 508
-continued
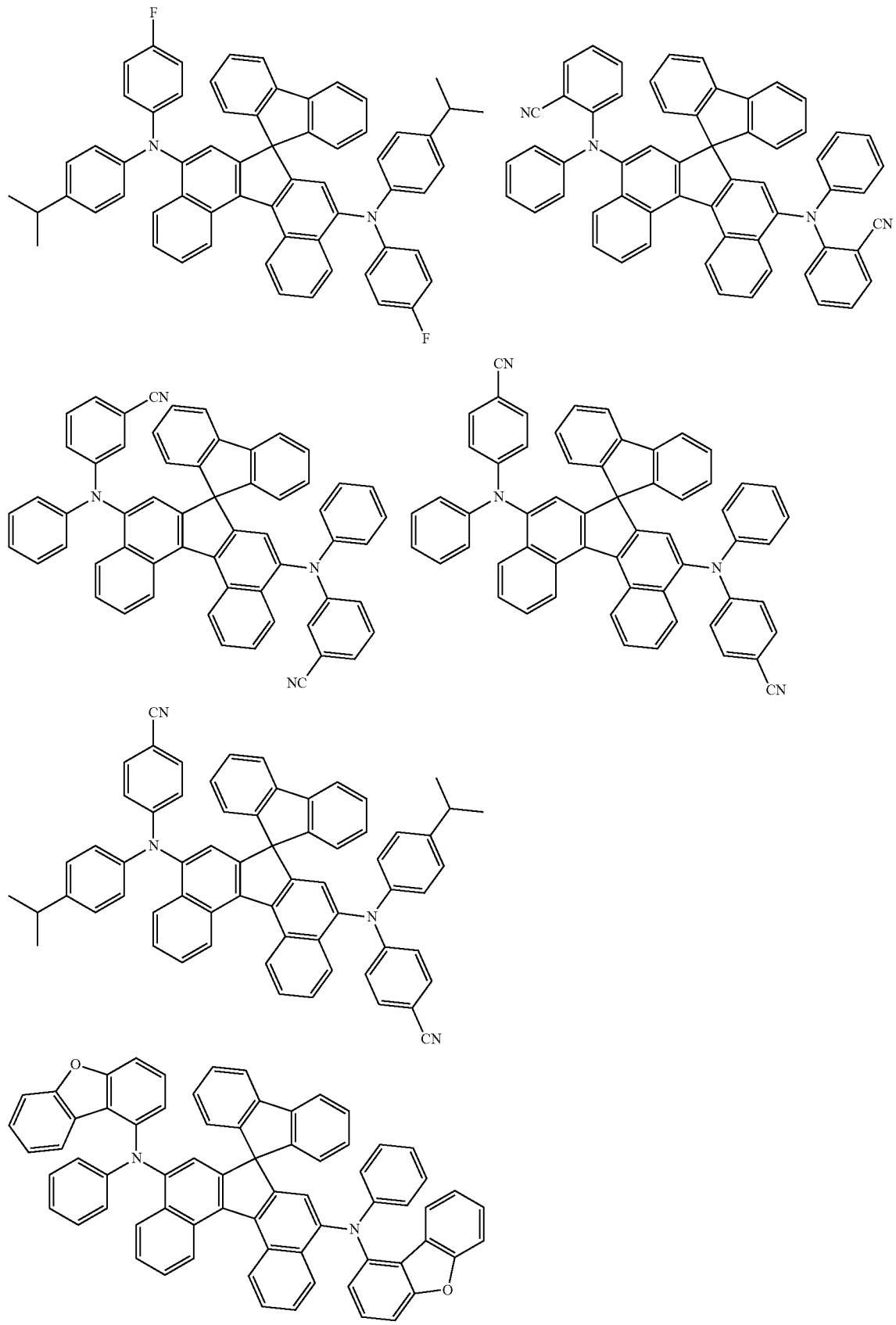

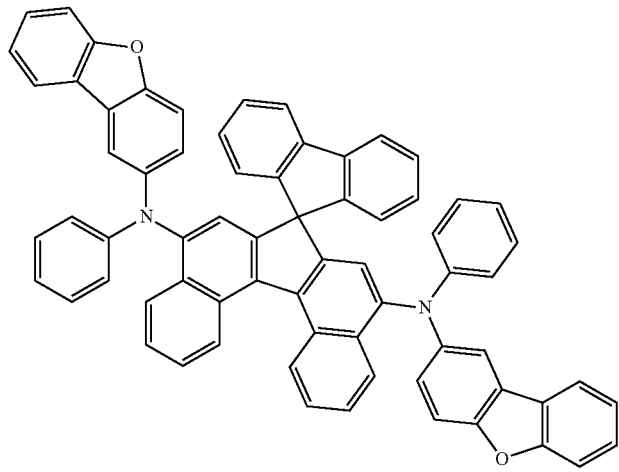
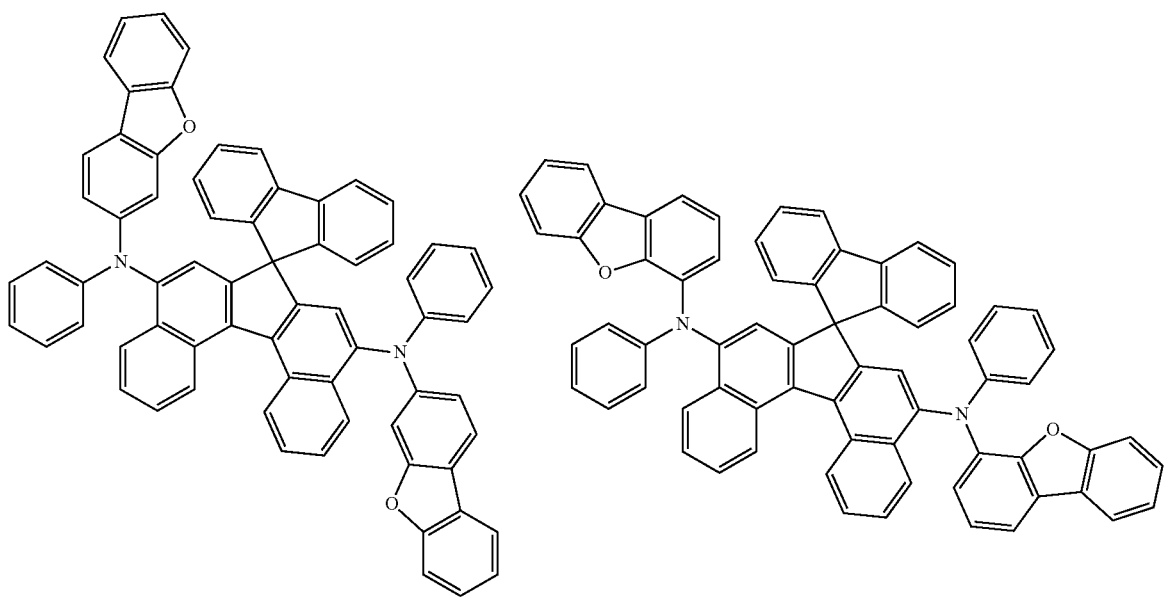
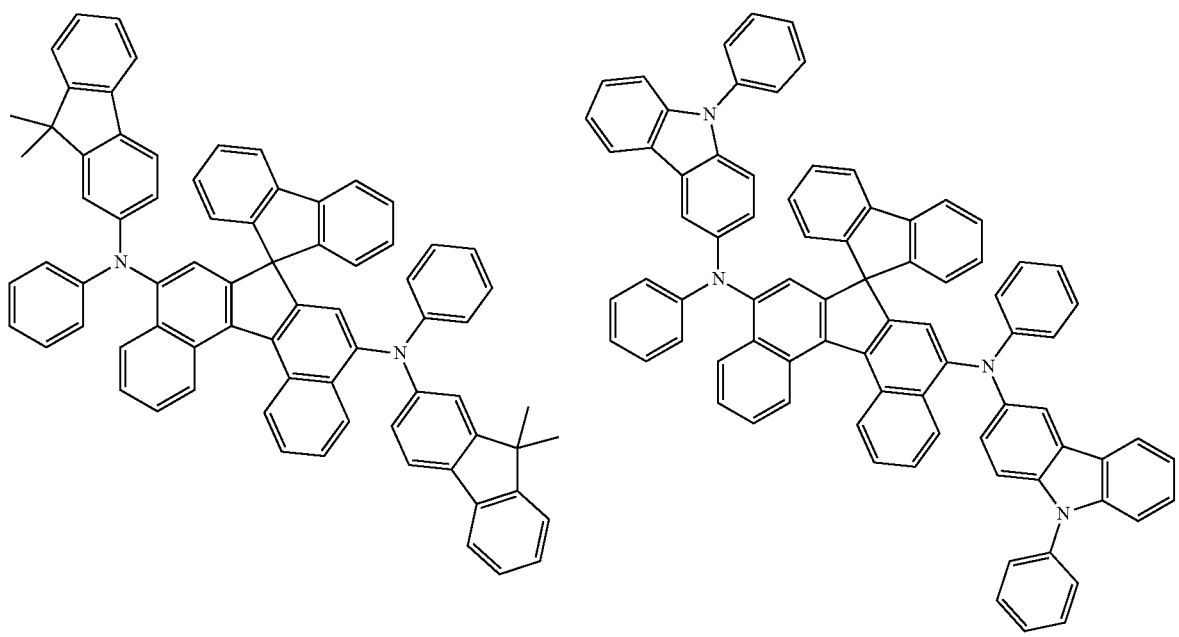

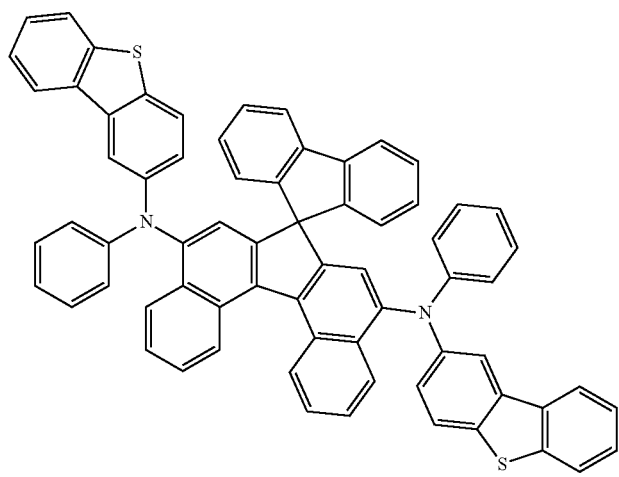
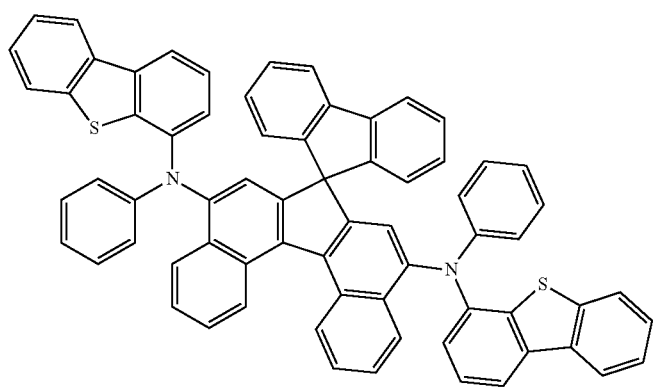
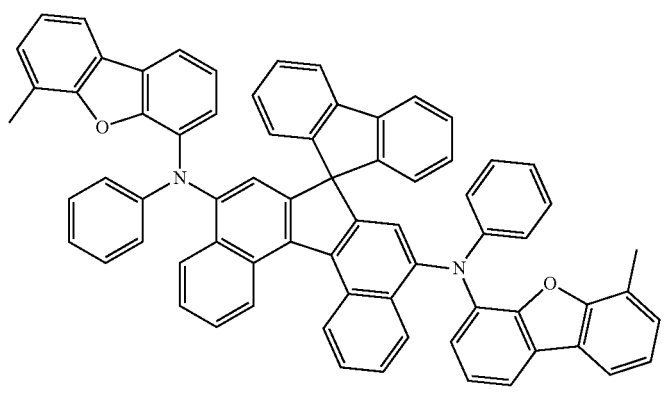
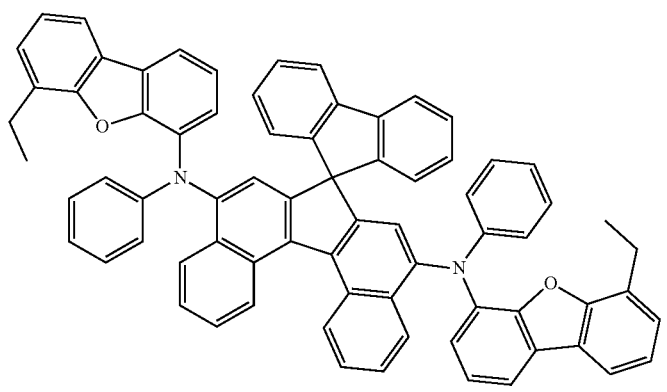

-continued
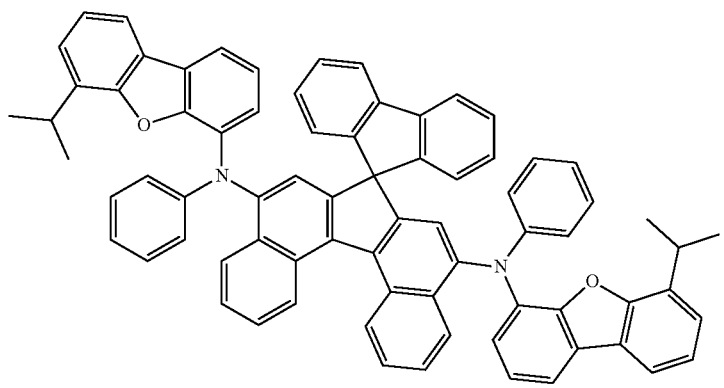
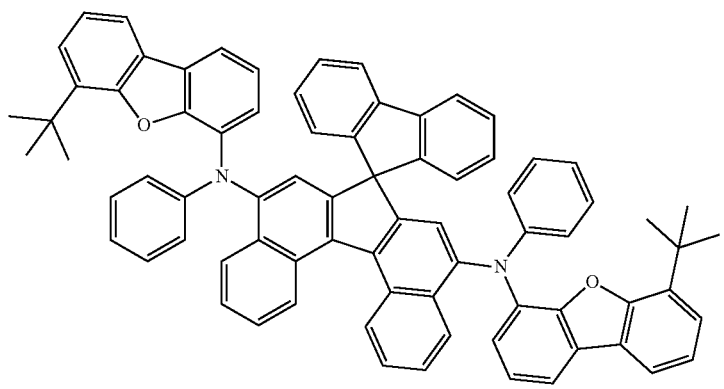
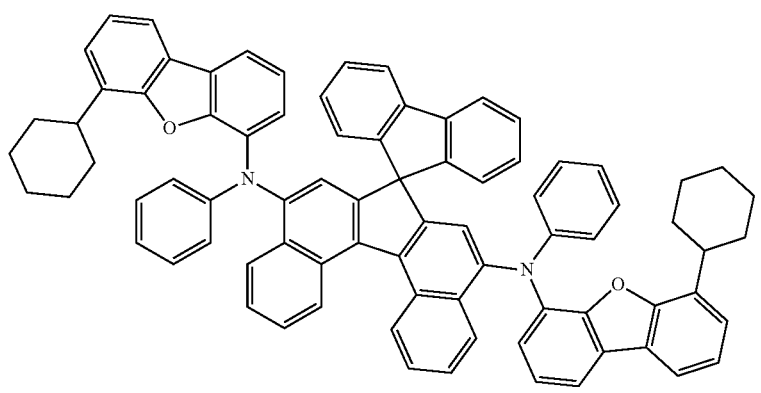
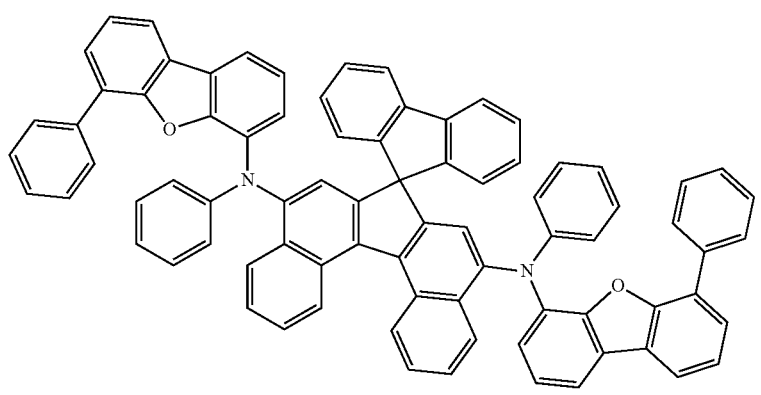

-continued
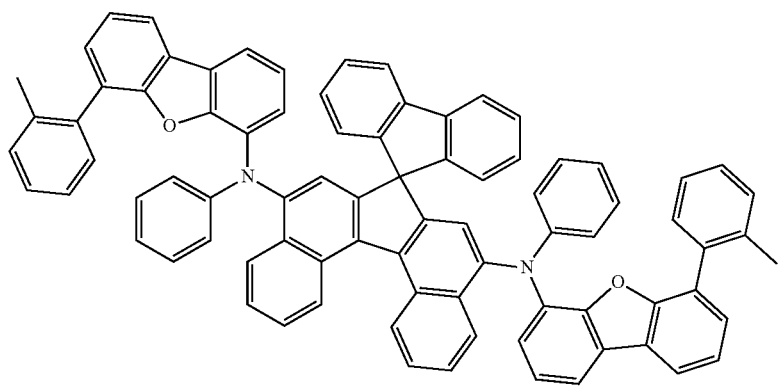
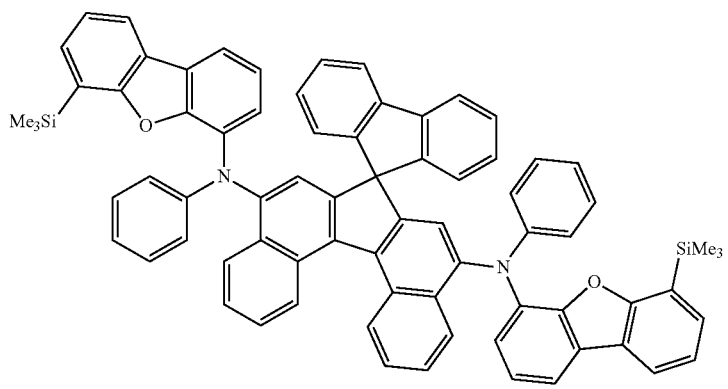
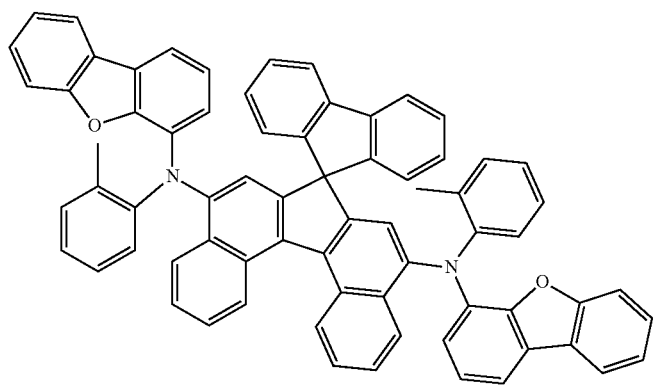
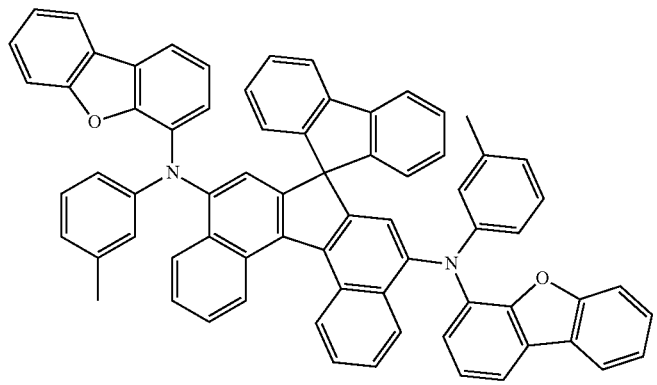

-continued
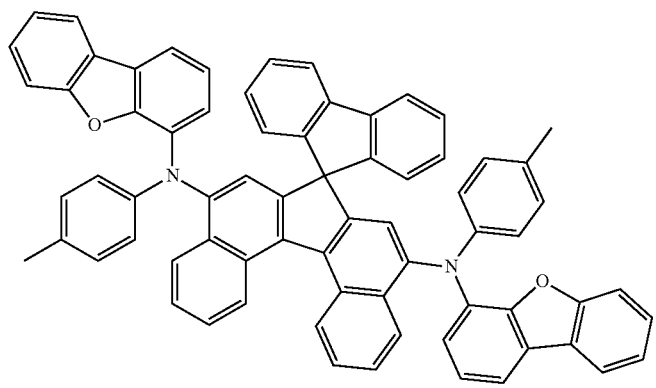
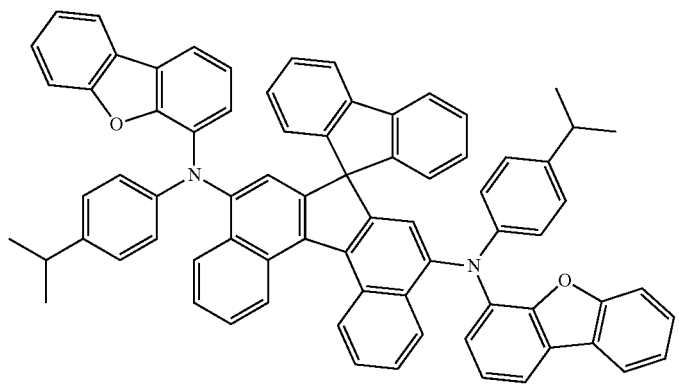
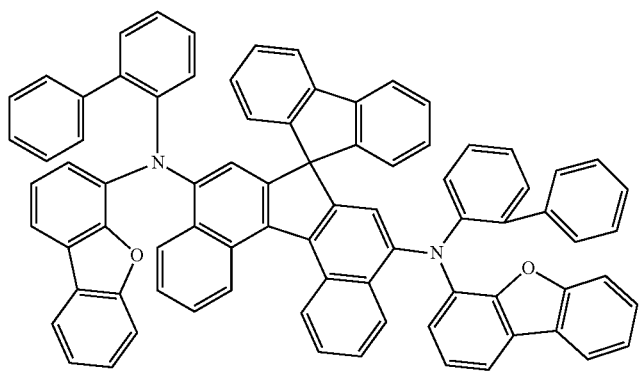
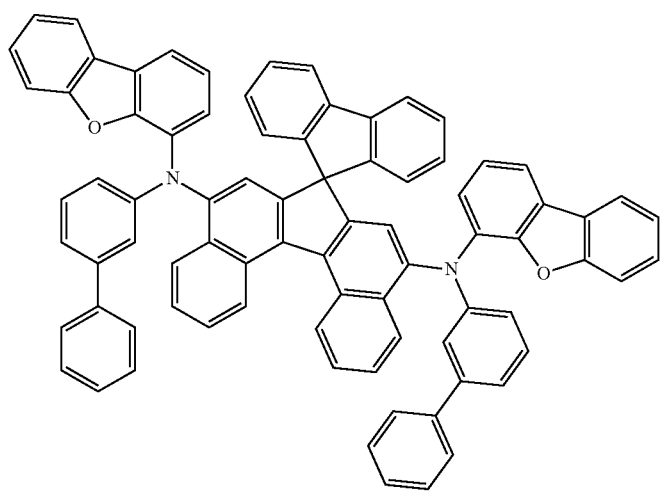

-continued
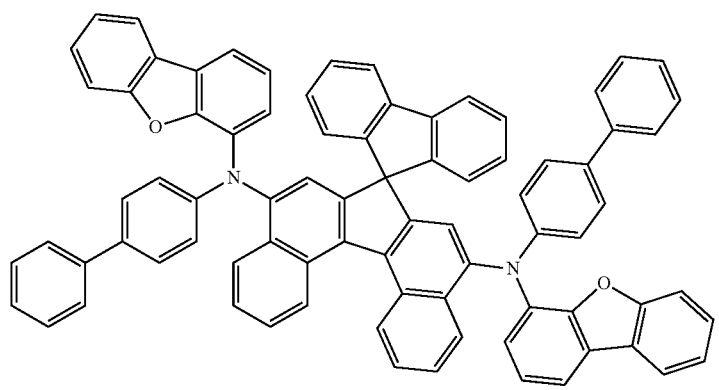
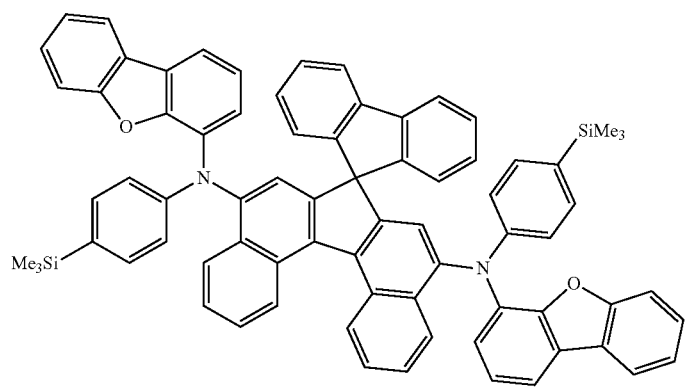
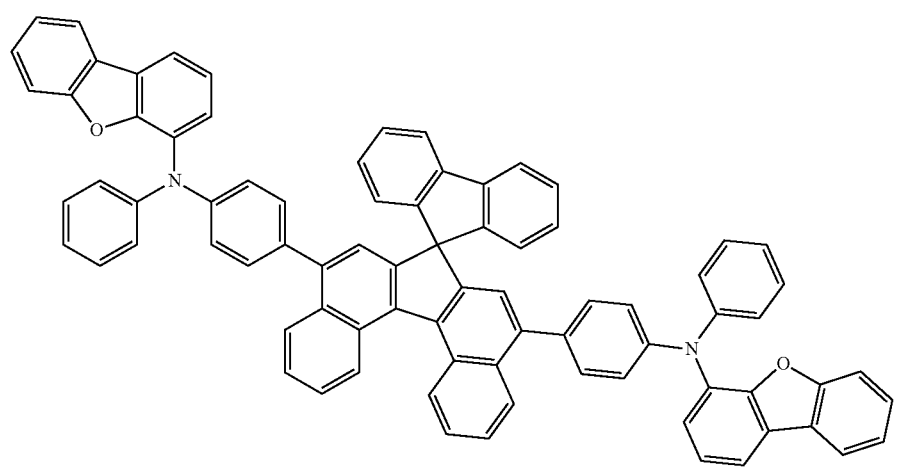
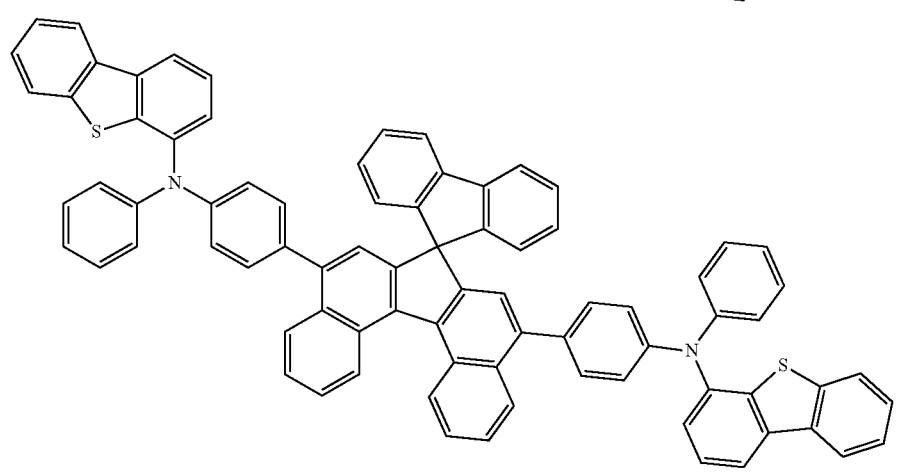

-continued
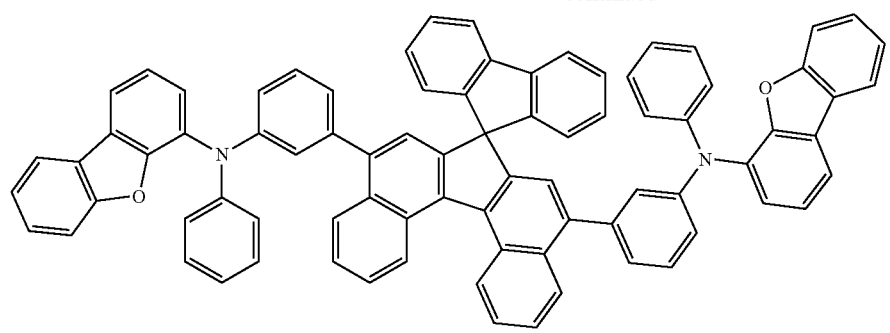 [SMILES: c1ccc(N(c2cccc(-c3cc4c(c5ccccc35)-c3c(cc(-c5cccc(N(c6ccccc6)c6cccc7c6sc6ccccc67)c5)c5ccccc35)C43c4ccccc4-c4ccccc43)c2)c2cccc3c2sc2ccccc23)cc1]
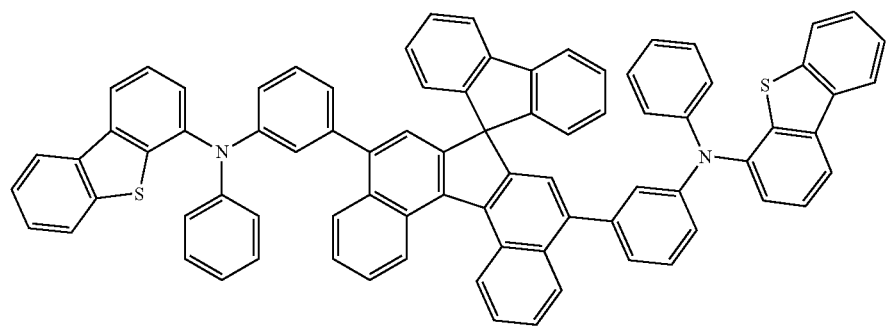
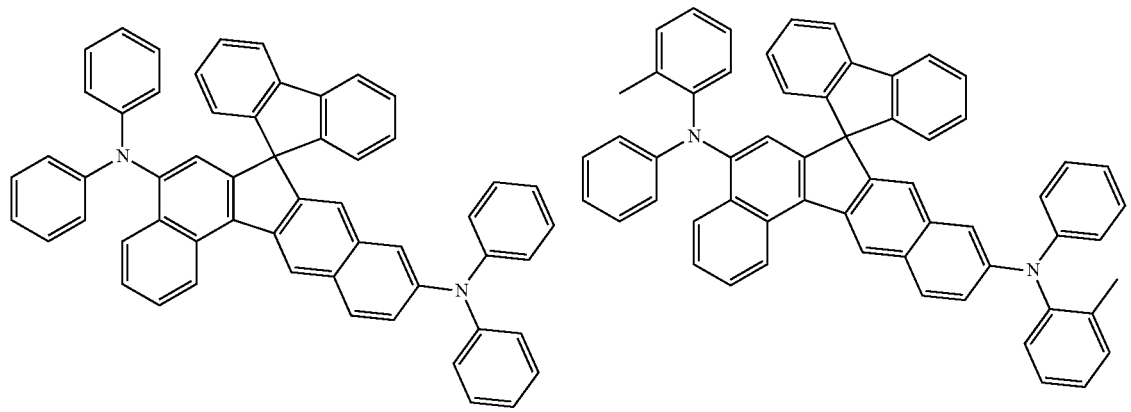
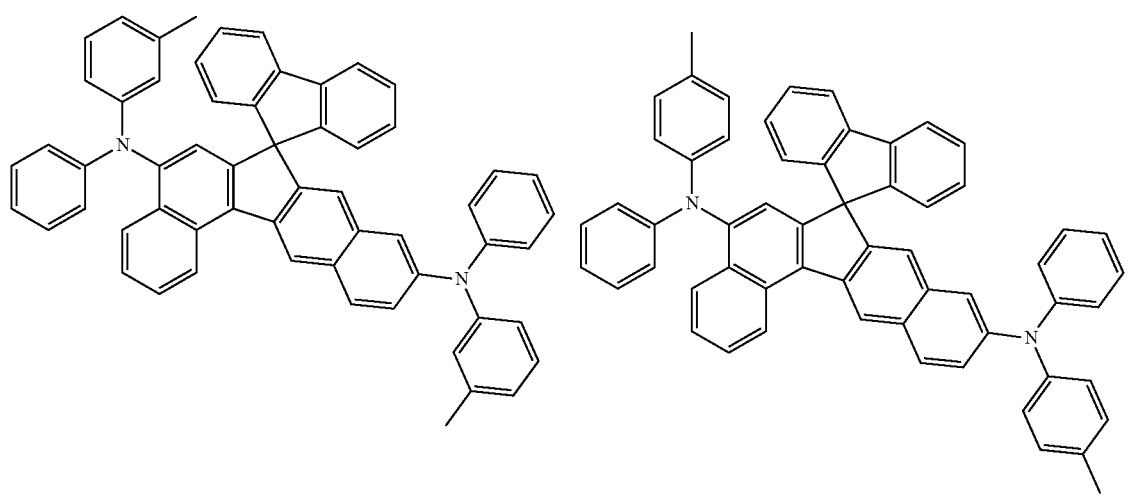

523 524
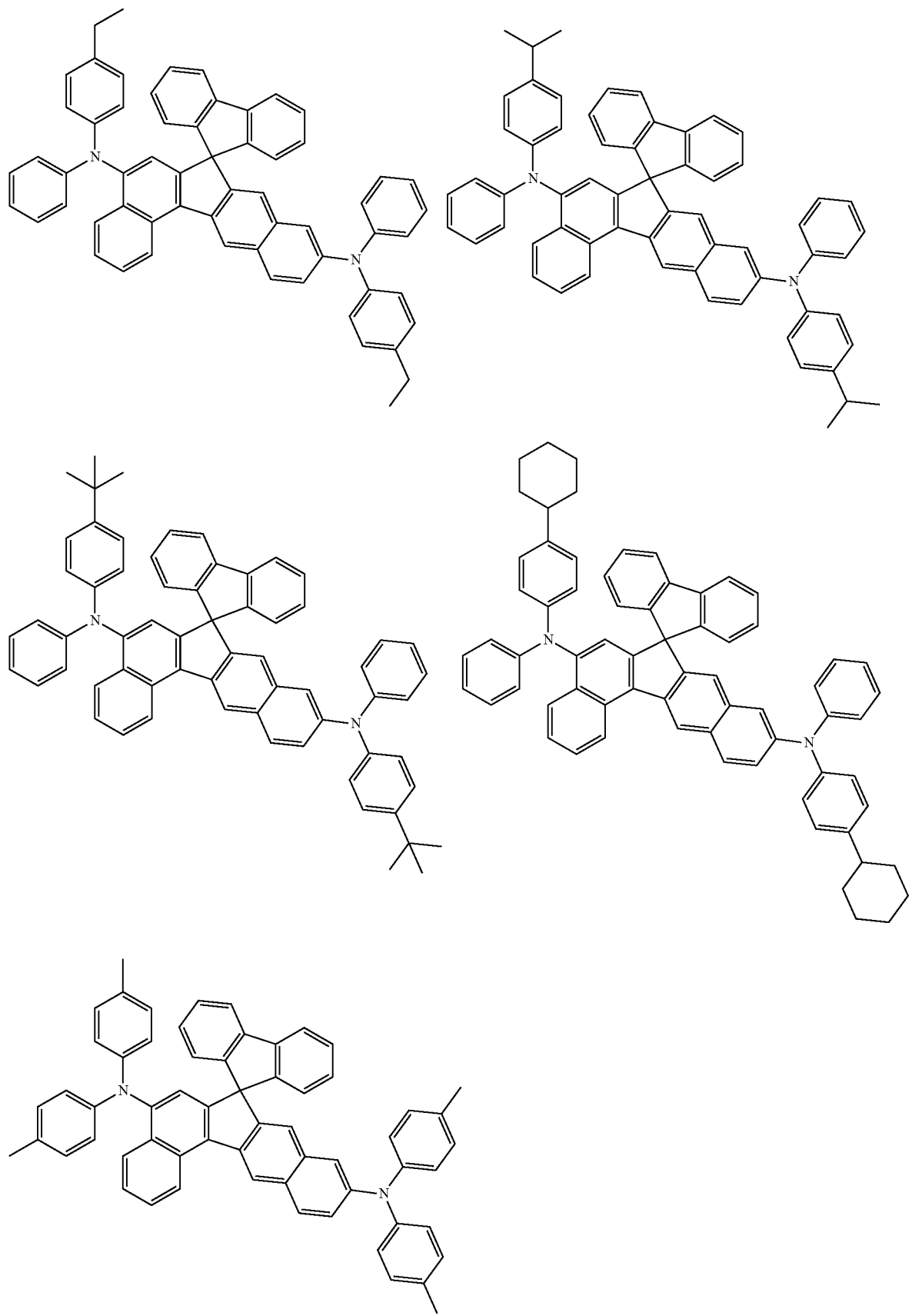
-continued

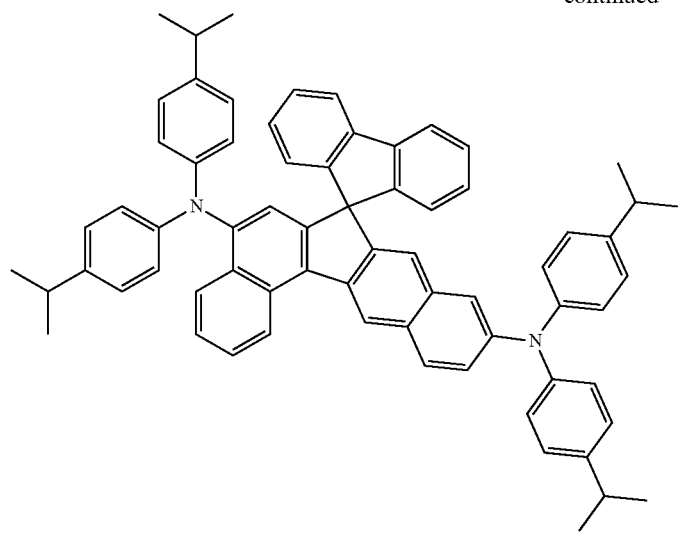
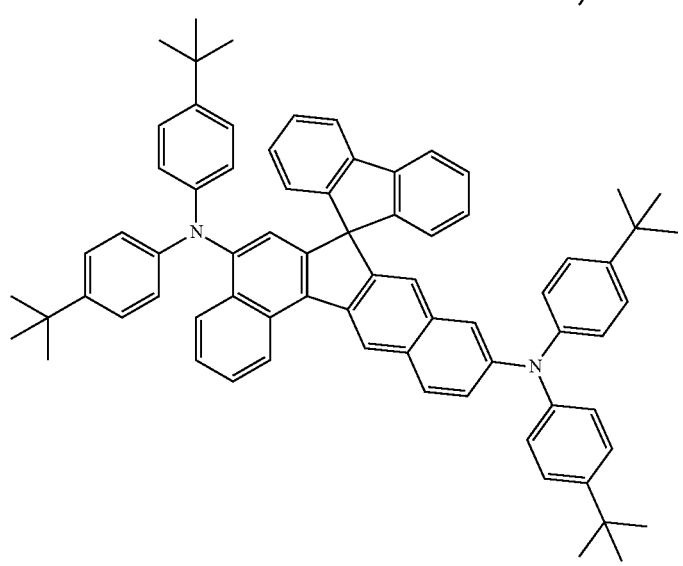
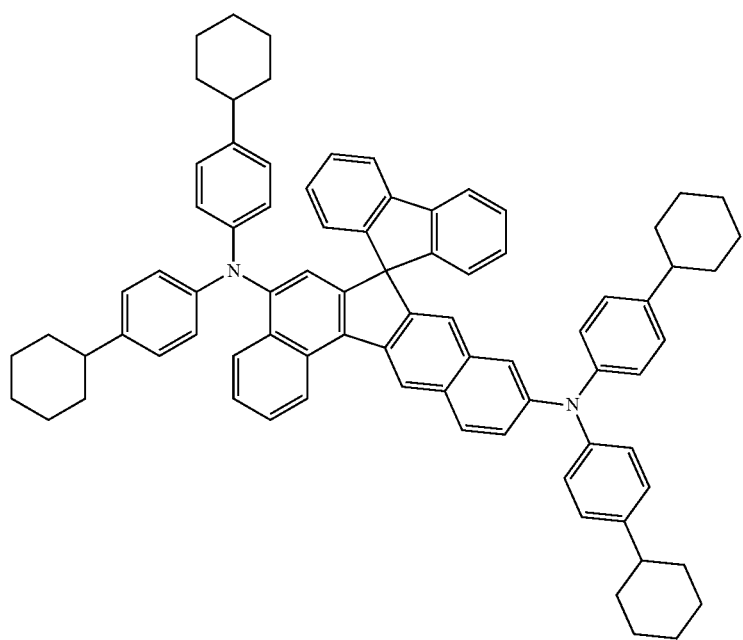

-continued
| 527 | 528 |
|---|---|
| 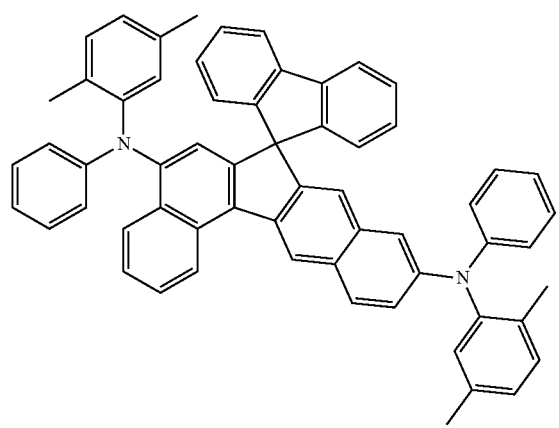 | 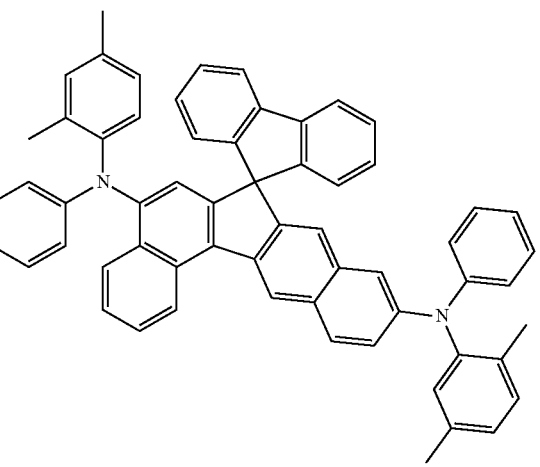 |
| 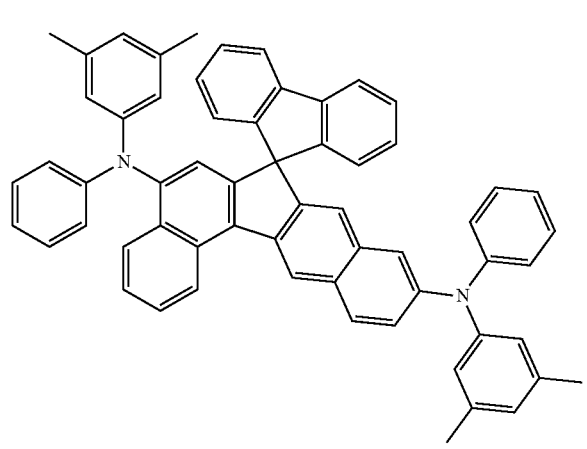 | 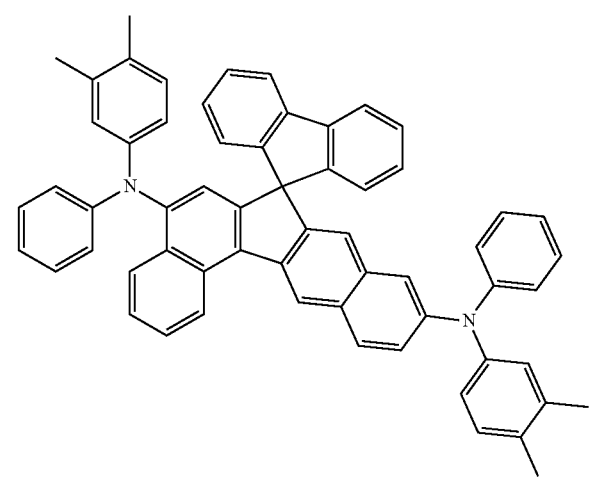 |
| 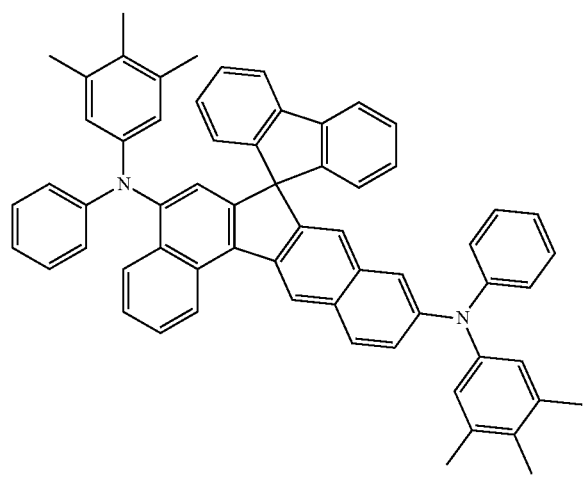 | 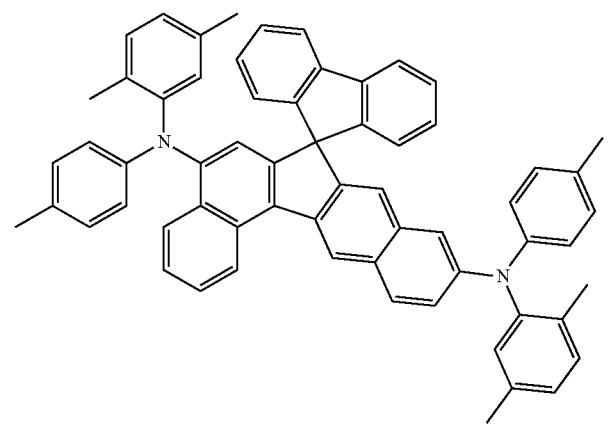 |

-continued
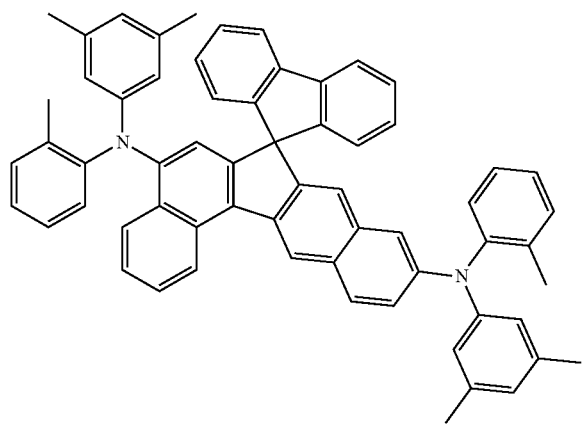
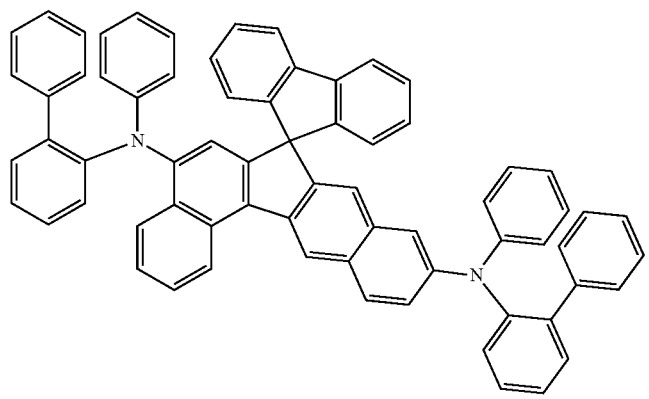
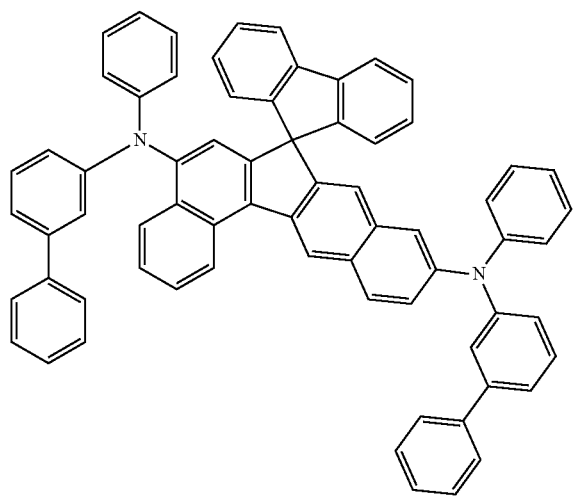

-continued
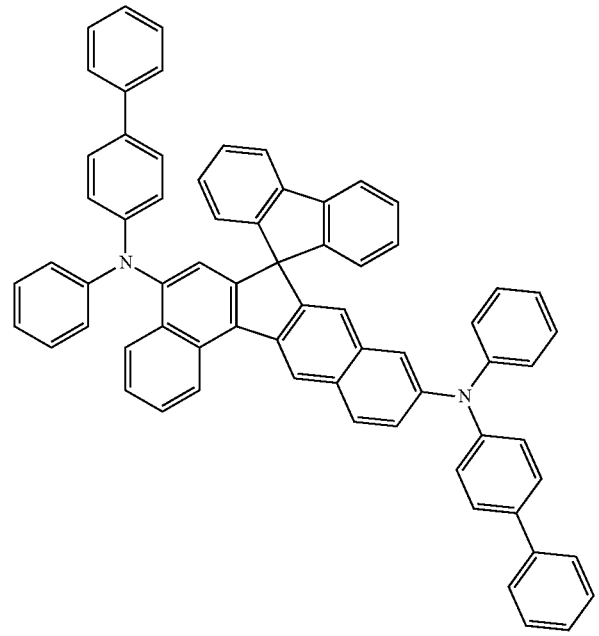
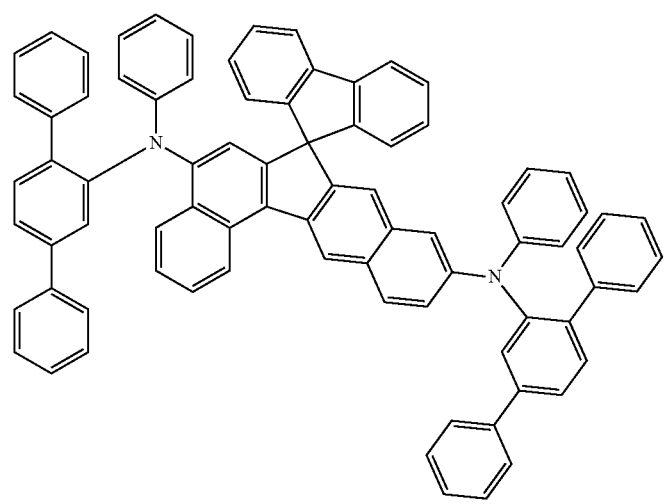

533
534
-continued
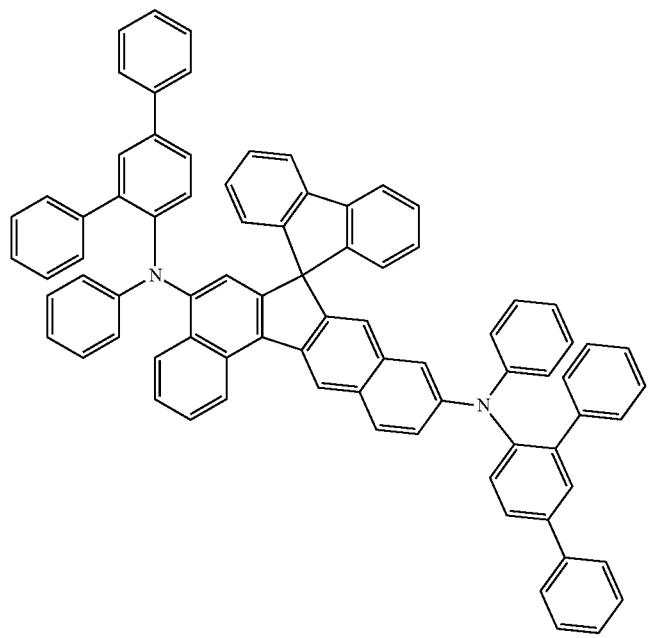
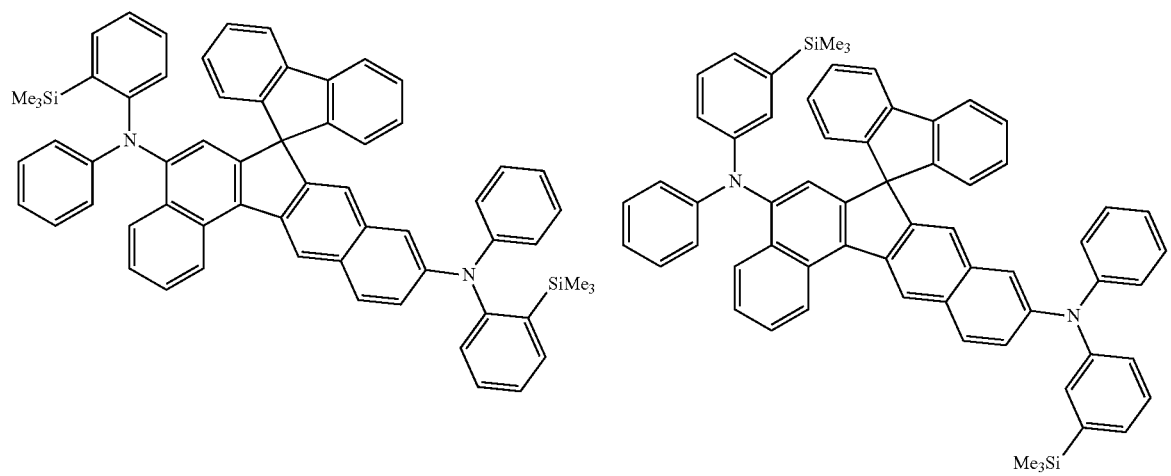 [SMILES: C[Si](C)(C)c1ccccc1N(c1ccccc1)c1ccc2cc3c(cc2c1)C1(c2ccccc2-c2ccccc21)c1cc(N(c2ccccc2)c2ccccc2[Si](C)(C)C)c2ccccc2c1-3 ; C[Si](C)(C)c1cccc(N(c2ccccc2)c2ccc3cc4c(cc3c2)C2(c3ccccc3-c3ccccc32)c2cc(N(c3ccccc3)c3cccc([Si](C)(C)C)c3)c3ccccc3c2-4)c1]
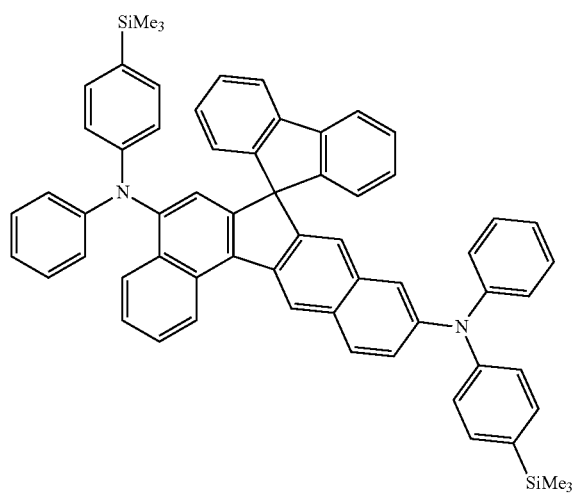

535
-continued
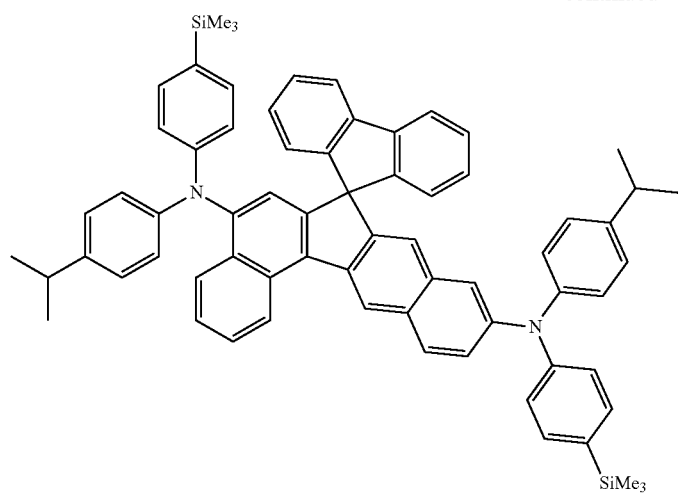
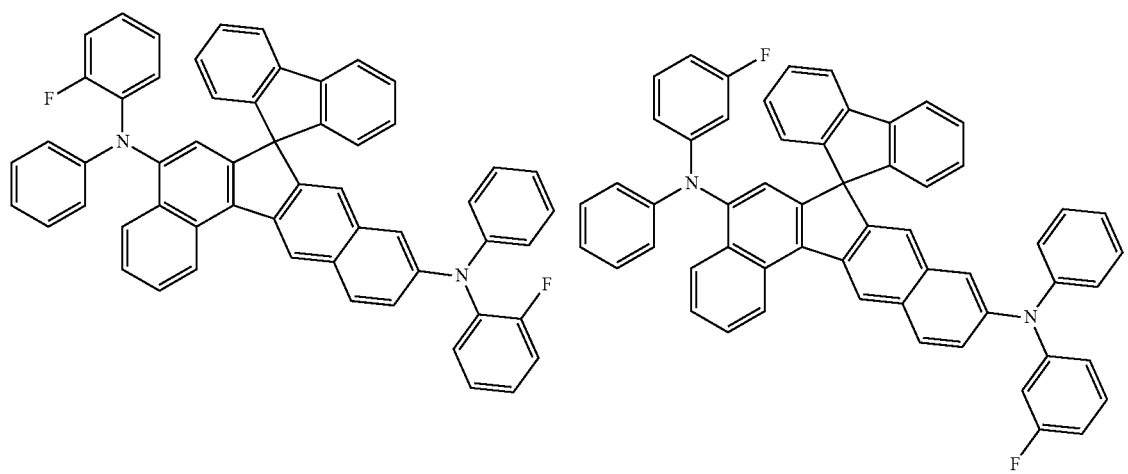
536
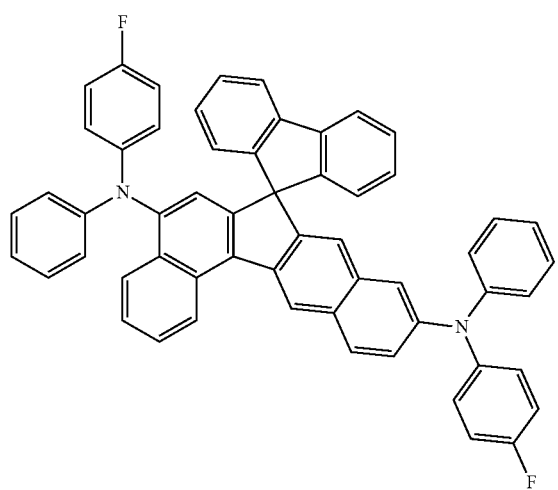

537 538
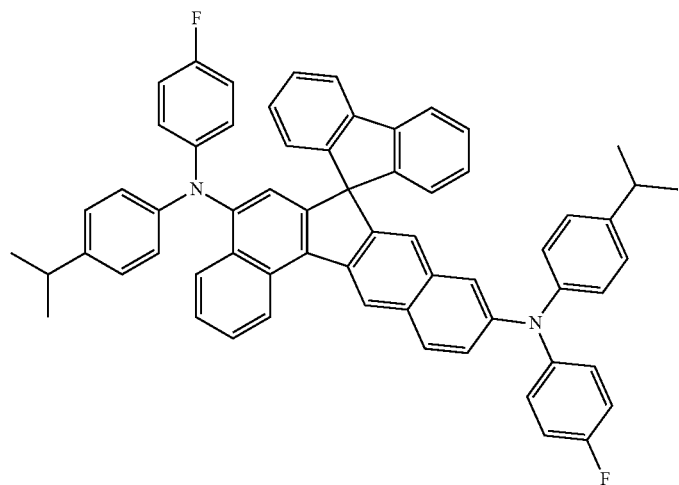
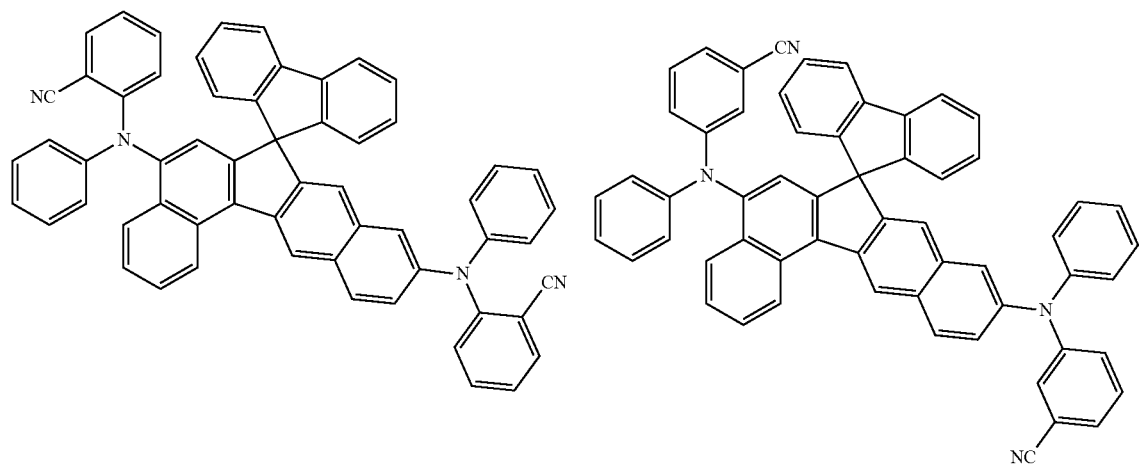
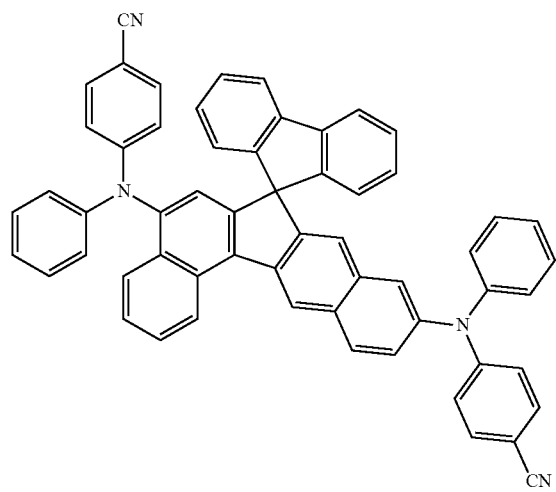

-continued
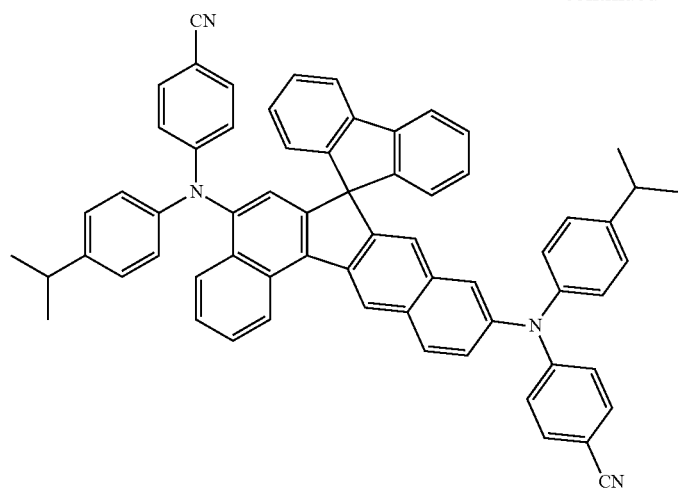
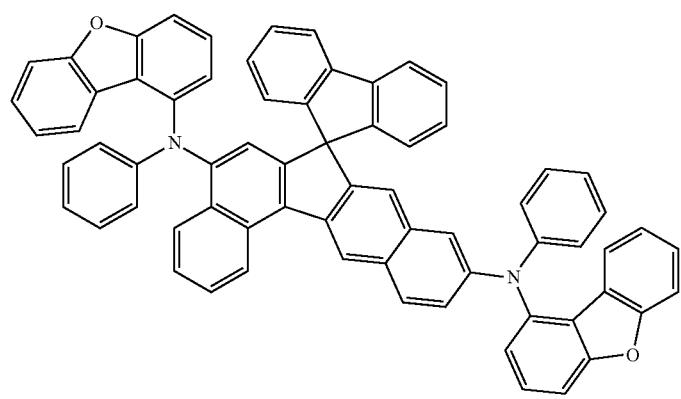
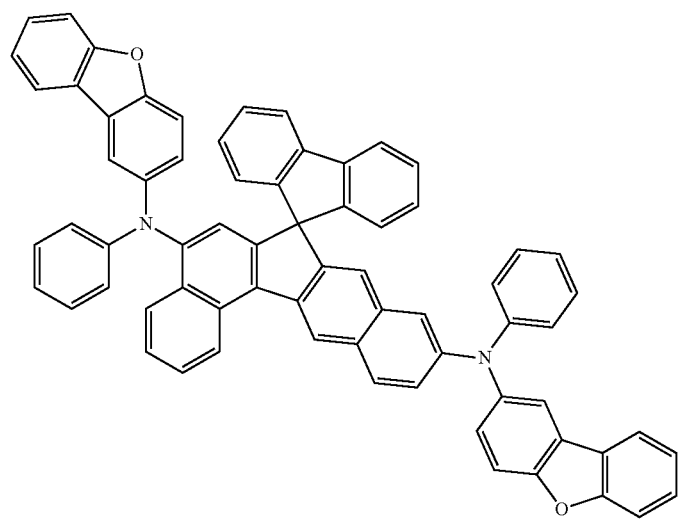

-continued
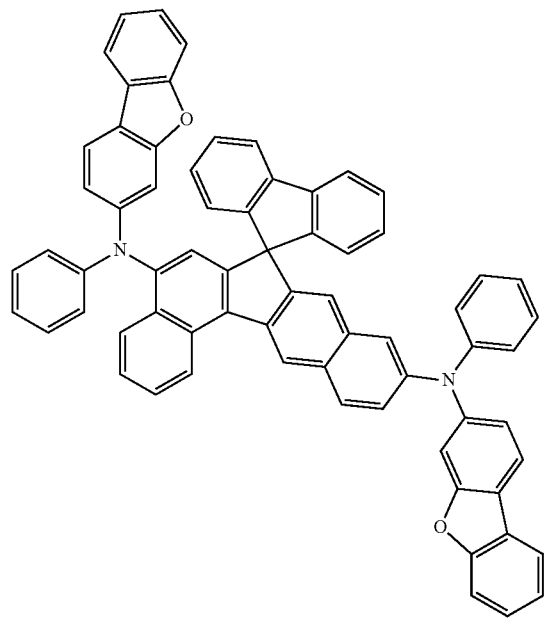
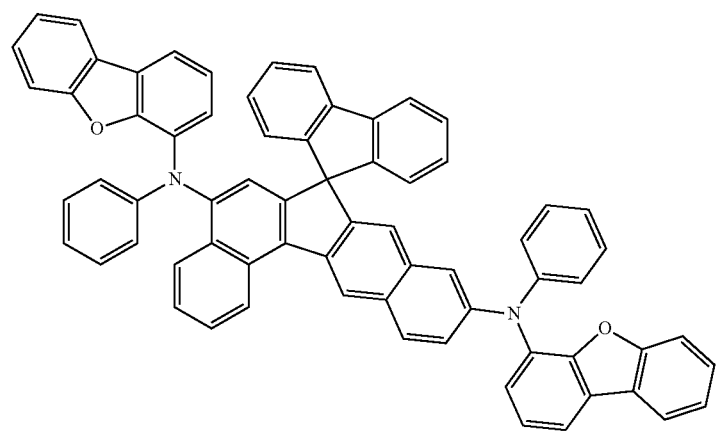
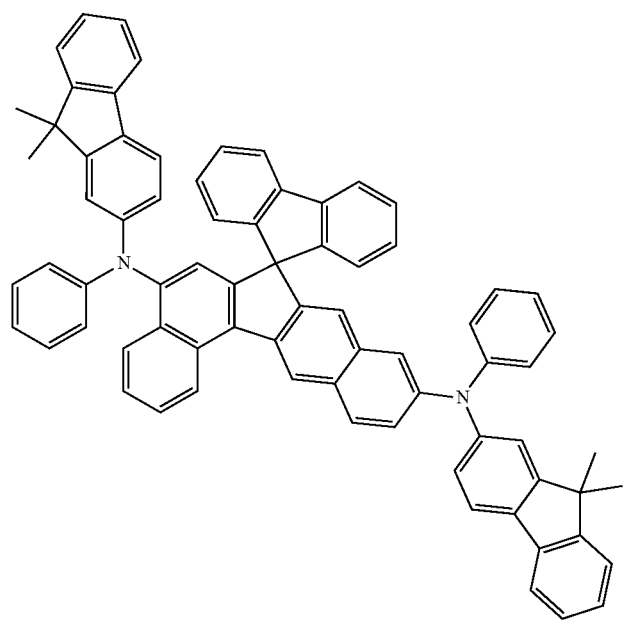

-continued
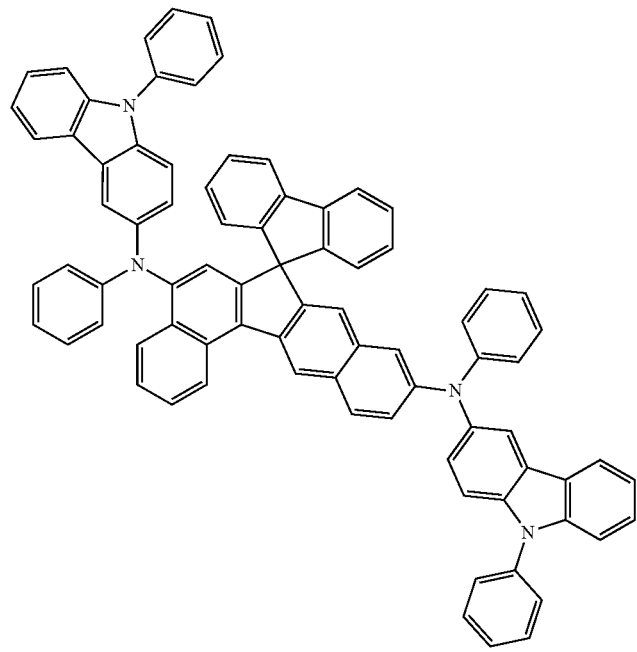
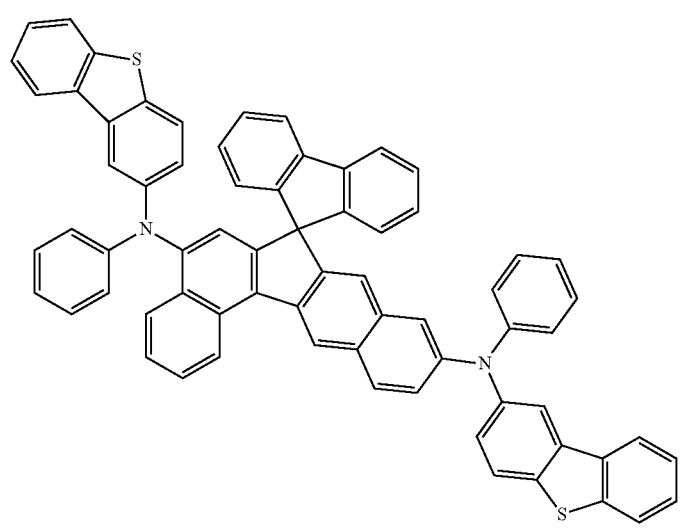
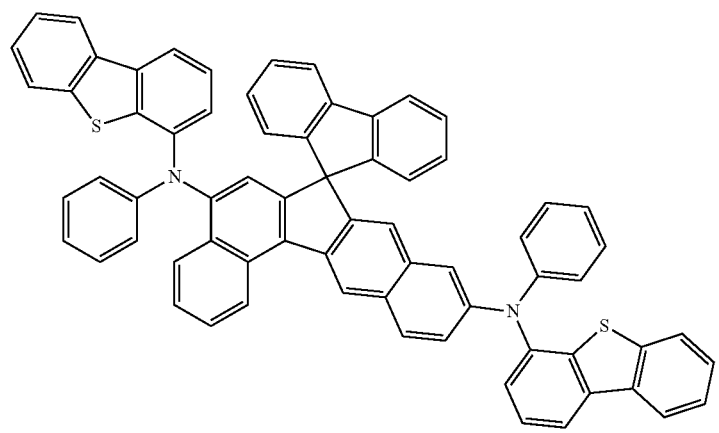

-continued
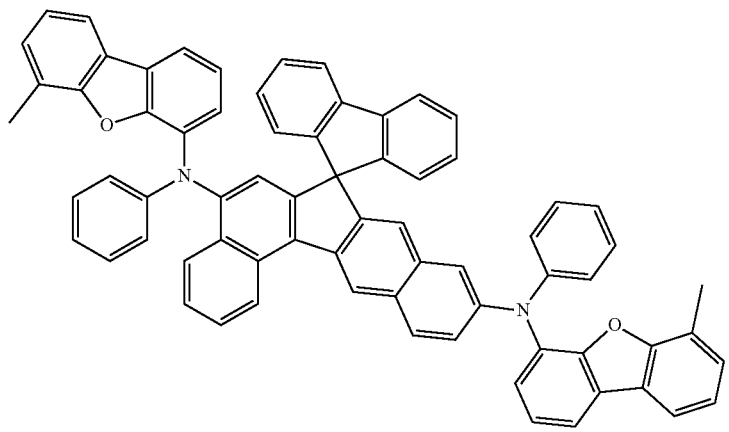
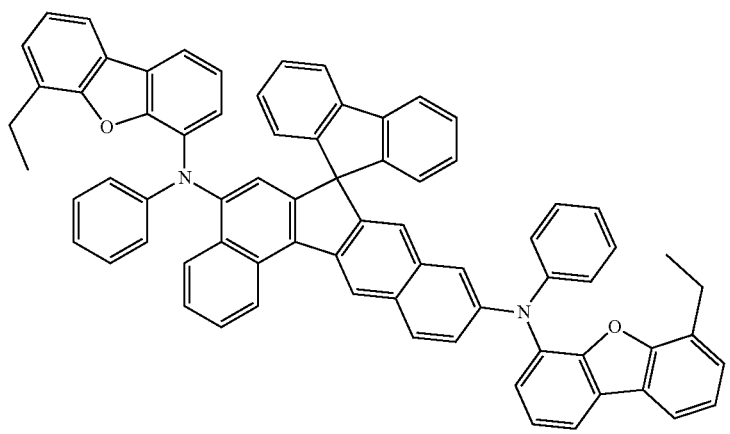
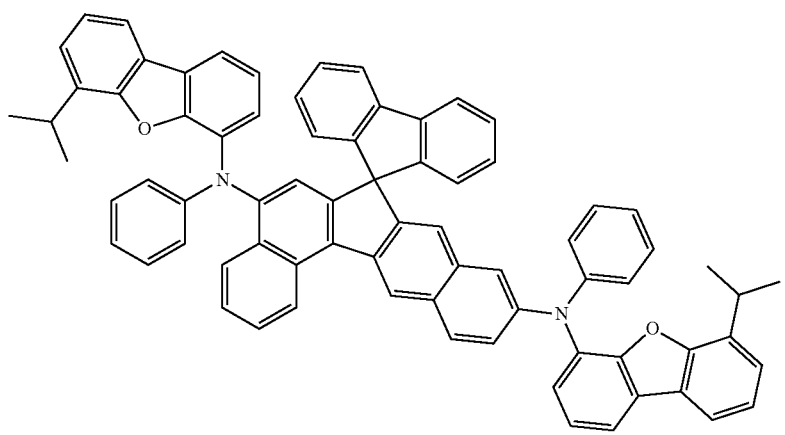
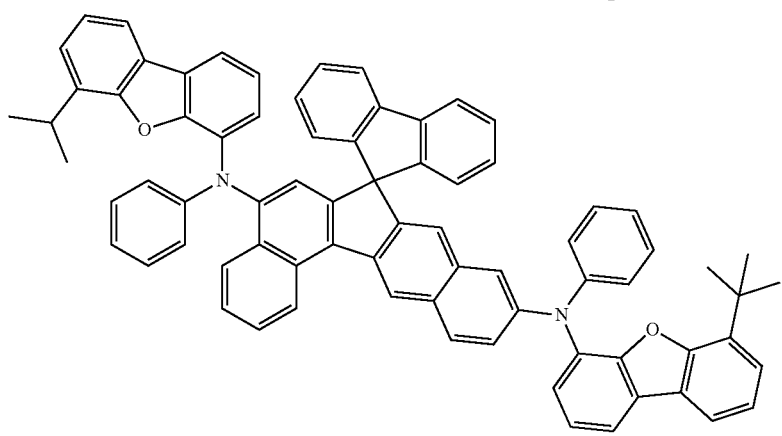

-continued
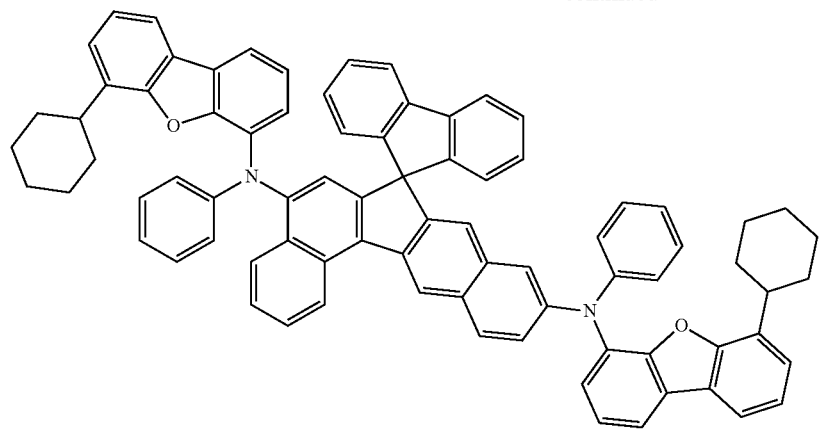
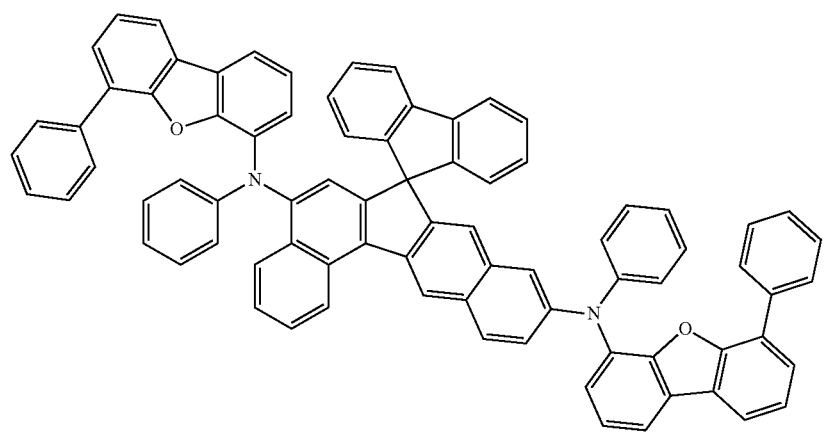
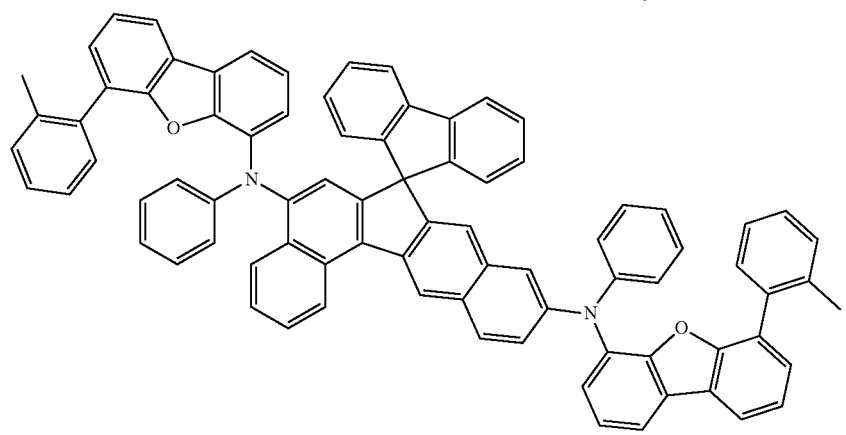
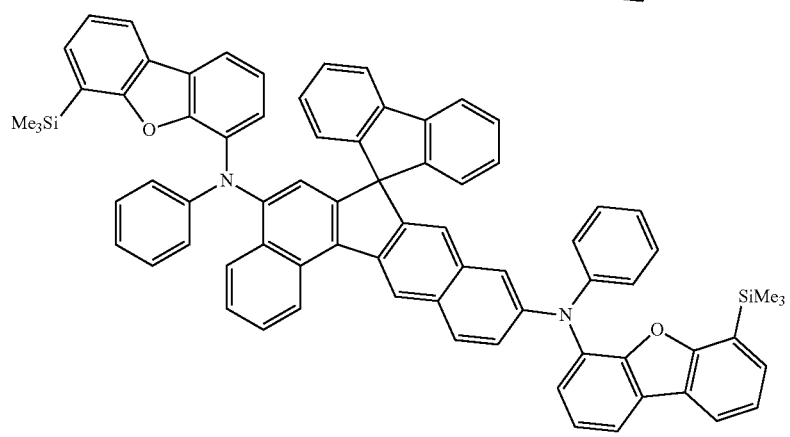

-continued
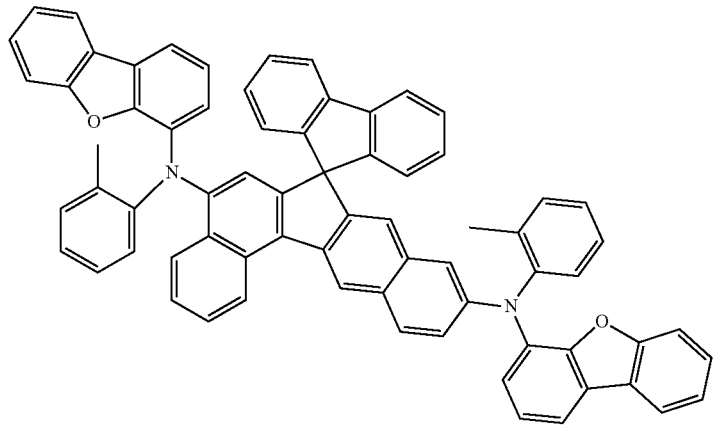
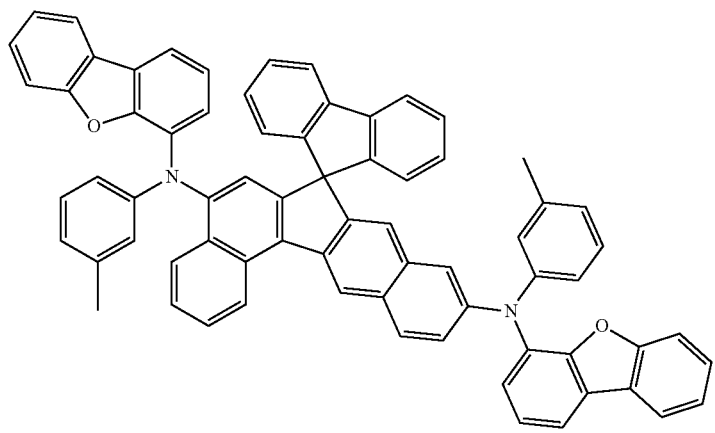
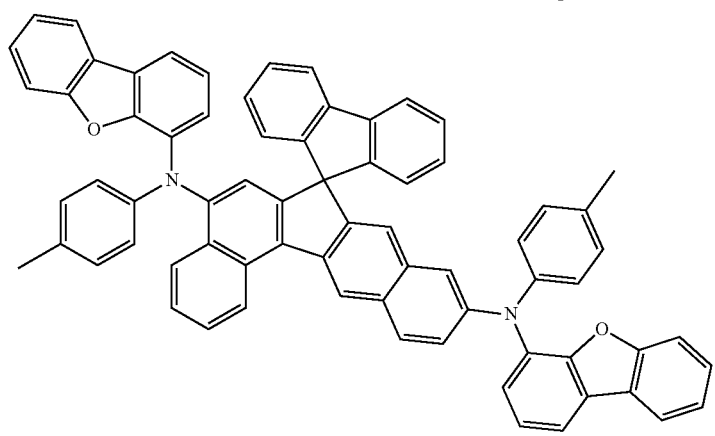
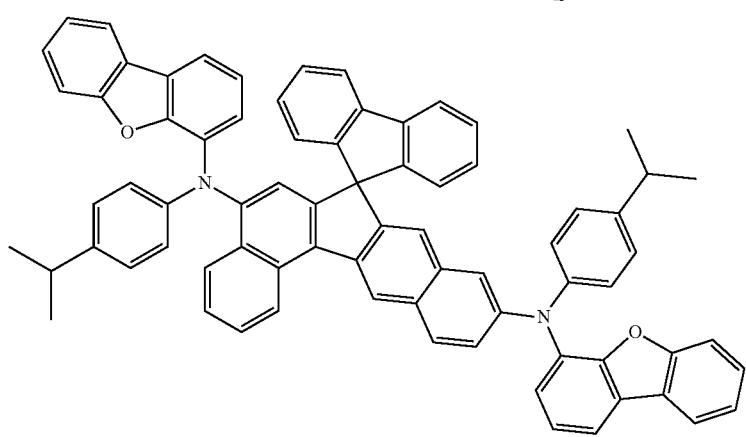

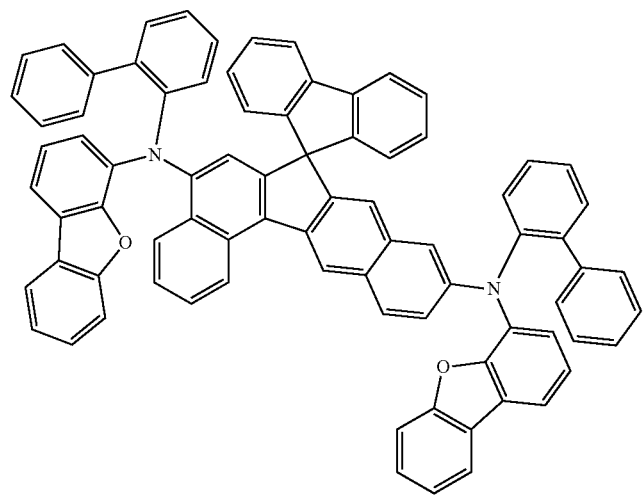
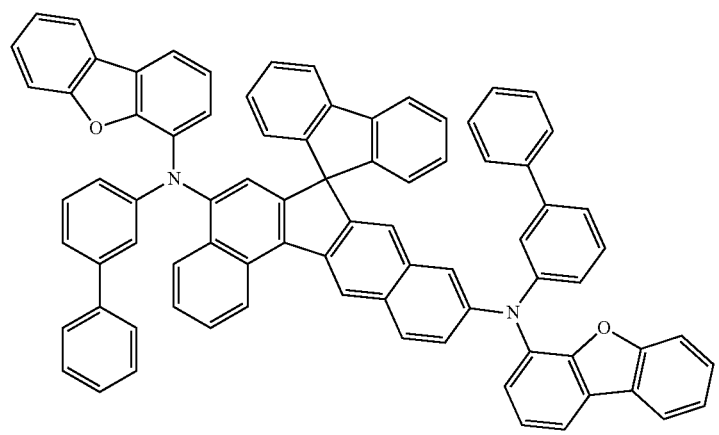
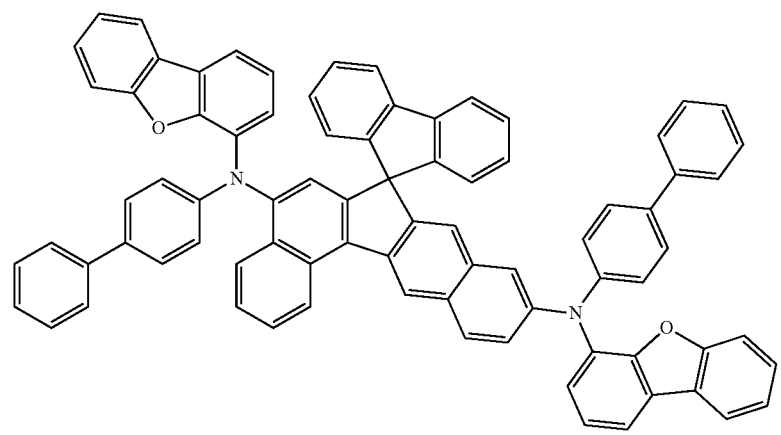

-continued
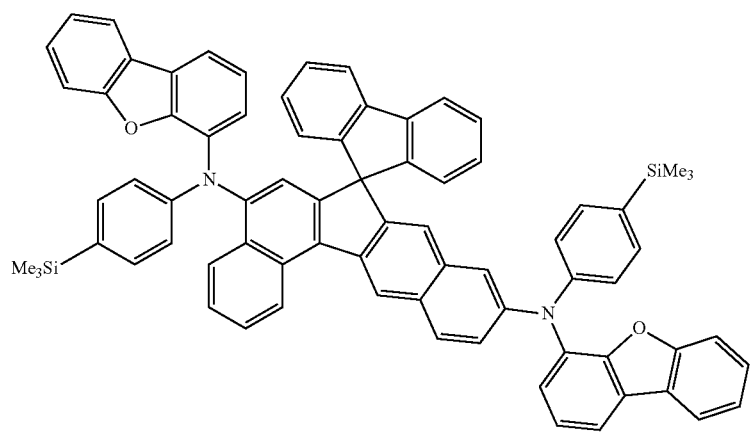
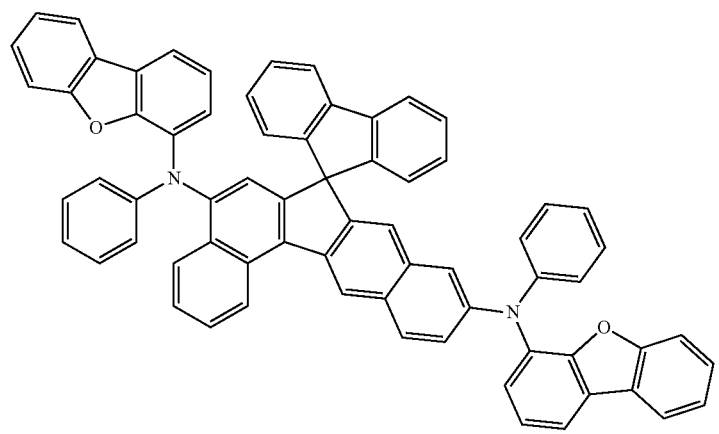
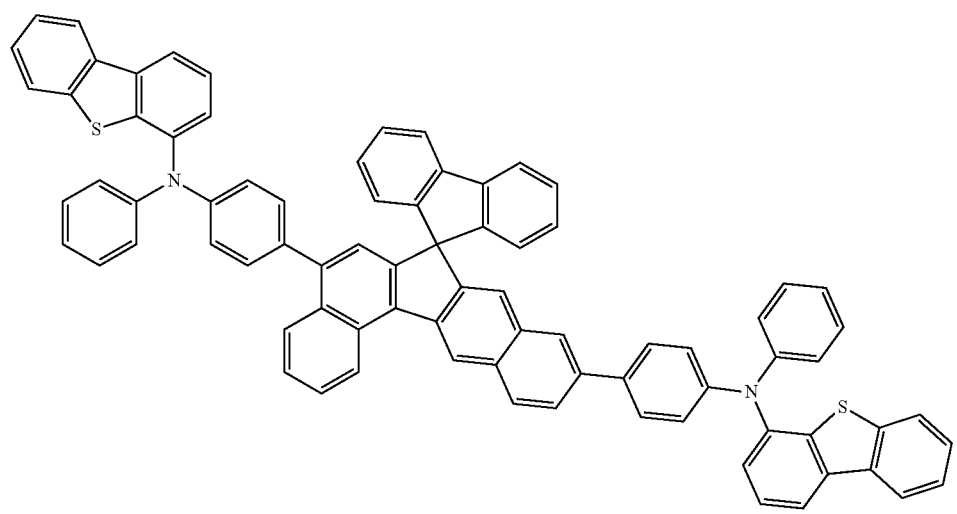
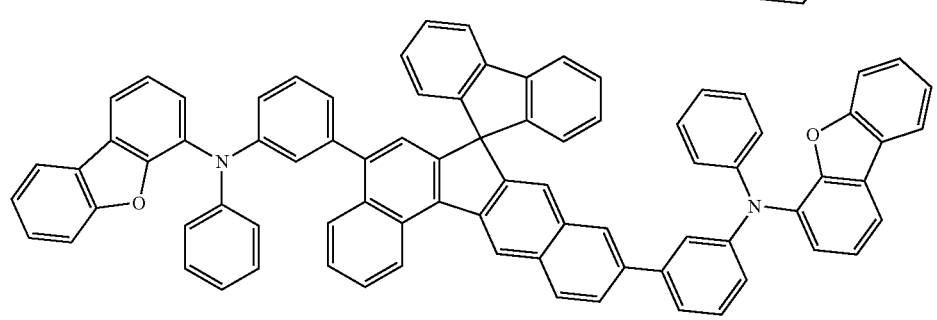

555 556
-continued
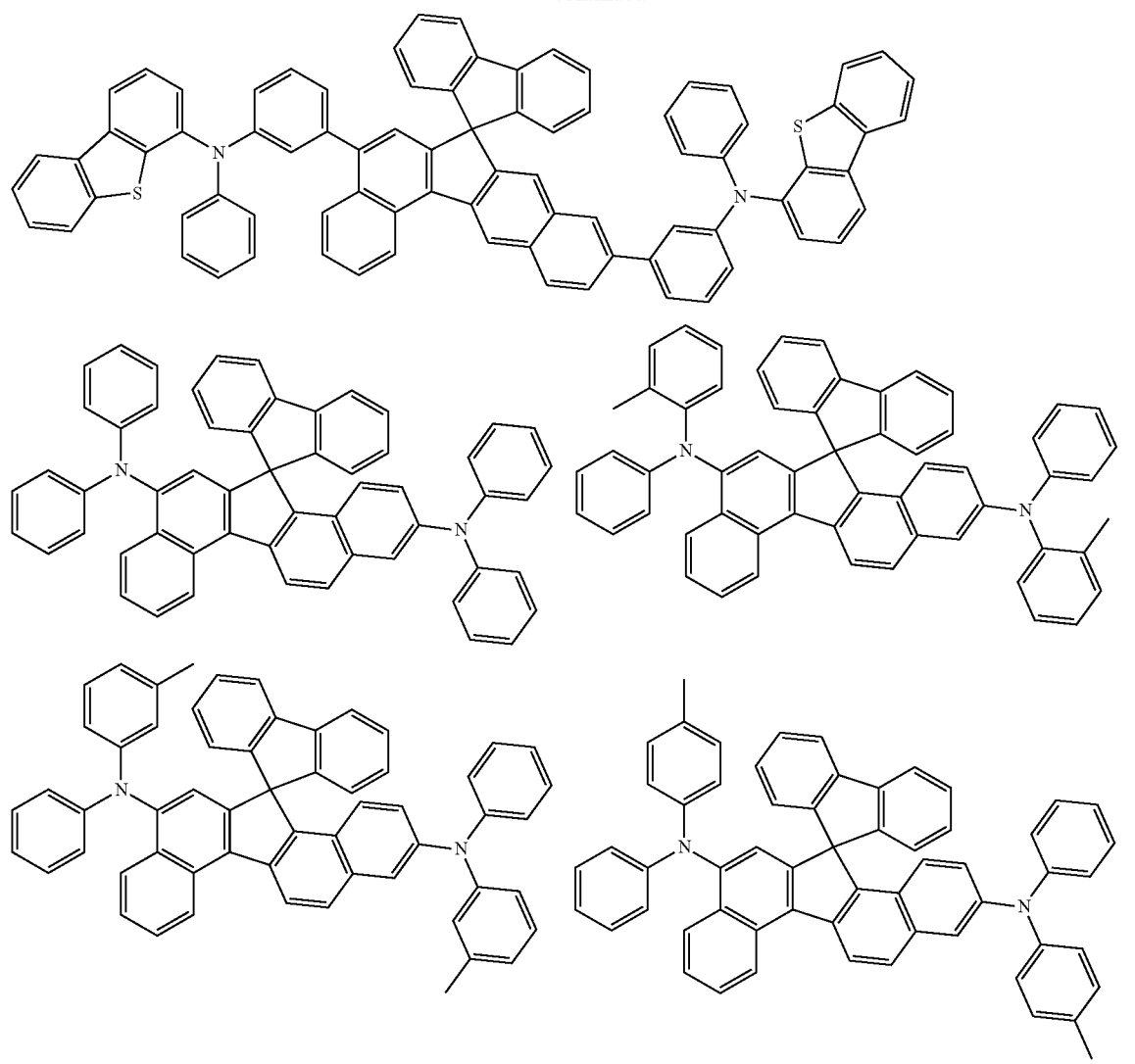
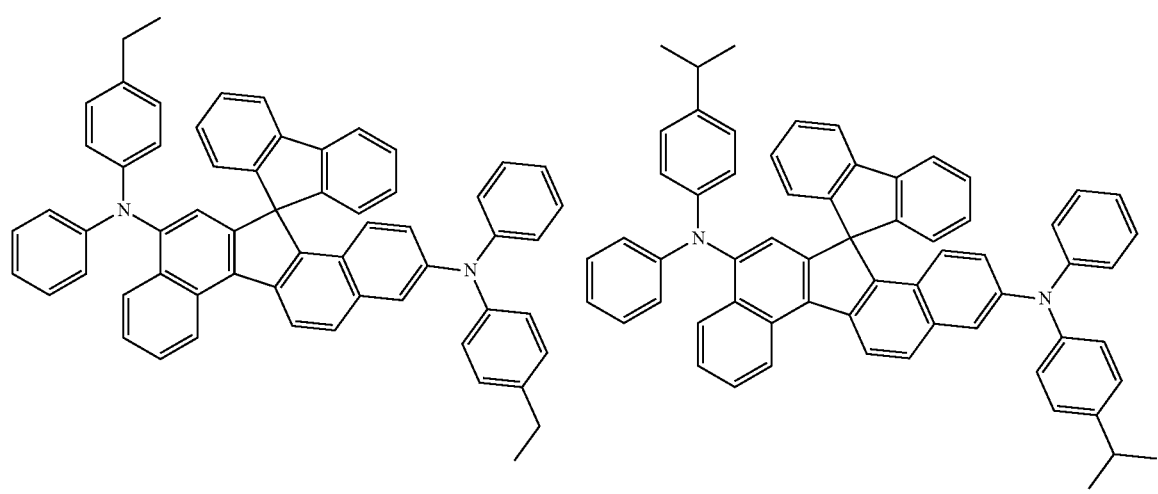

557 558
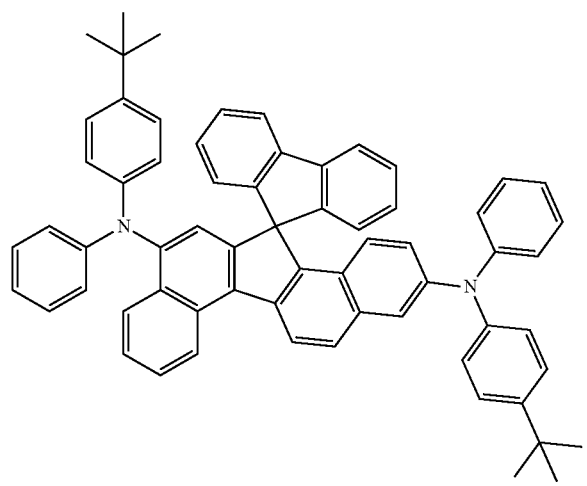
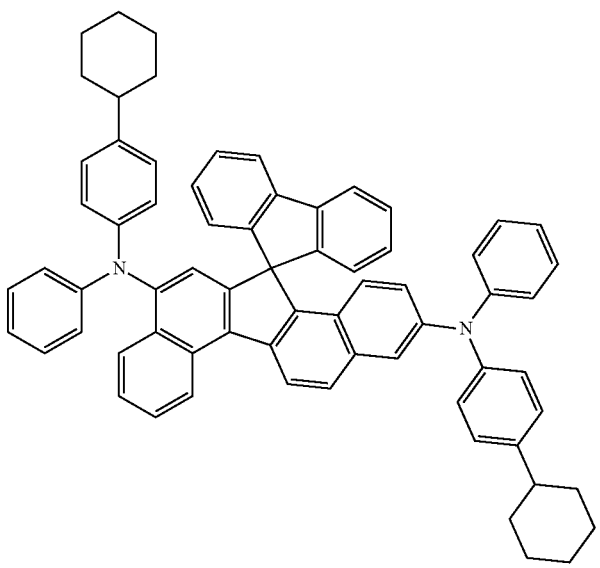
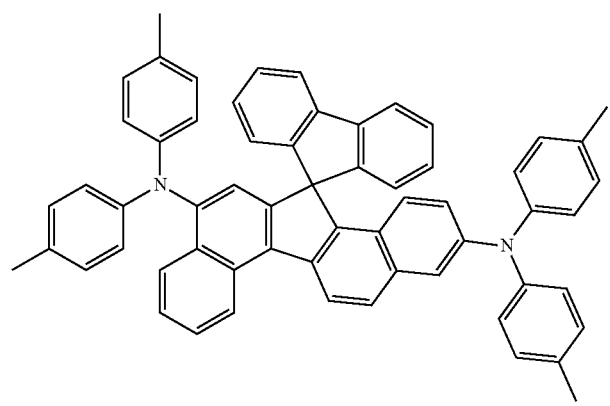
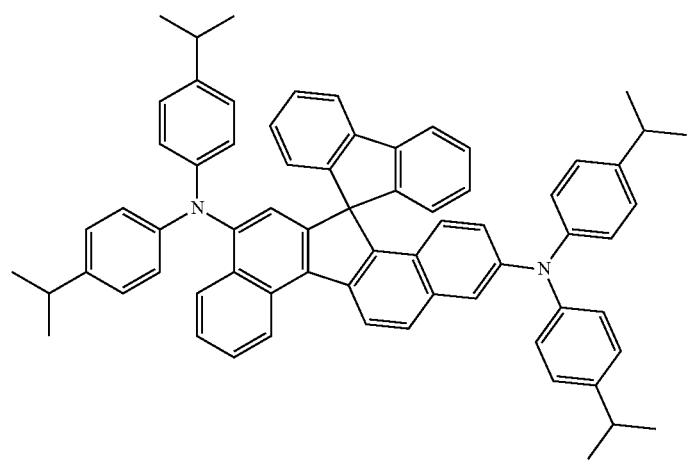

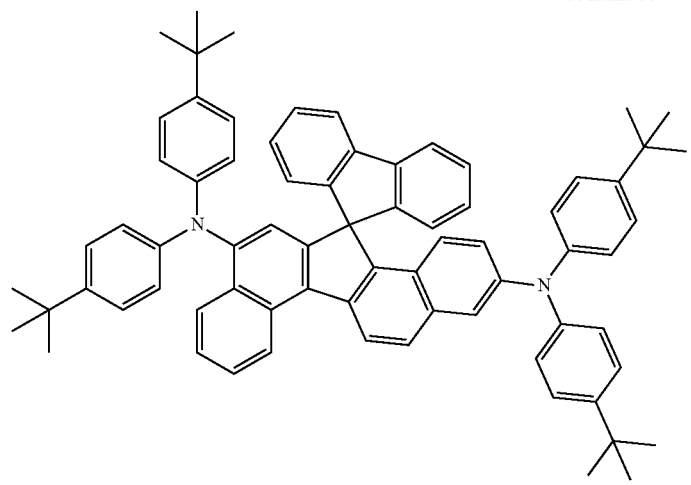
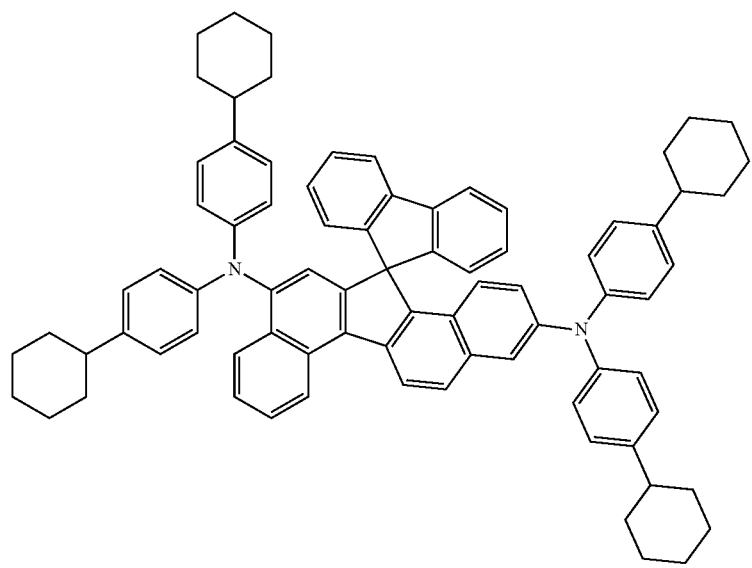
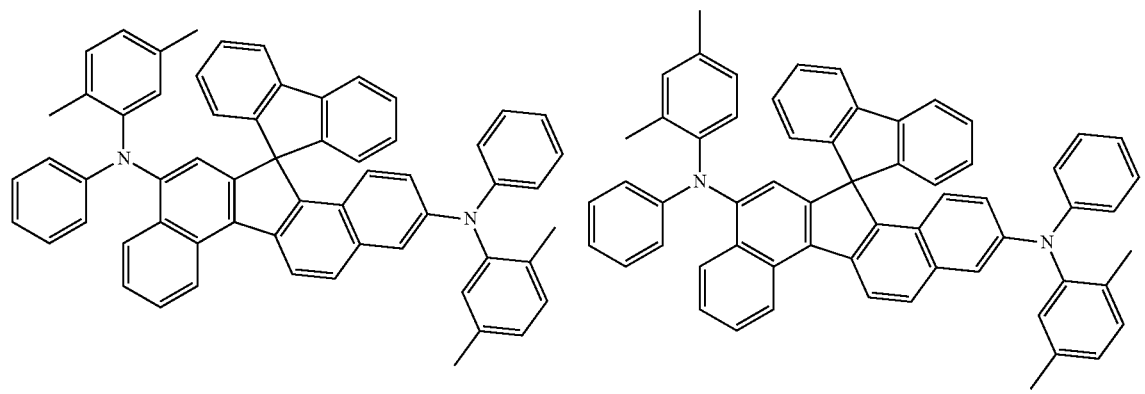

561 562
-continued
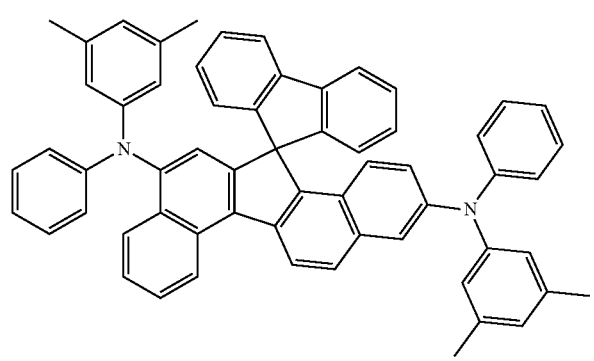
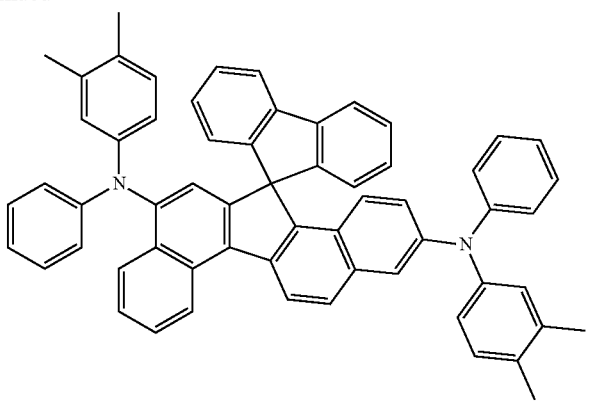
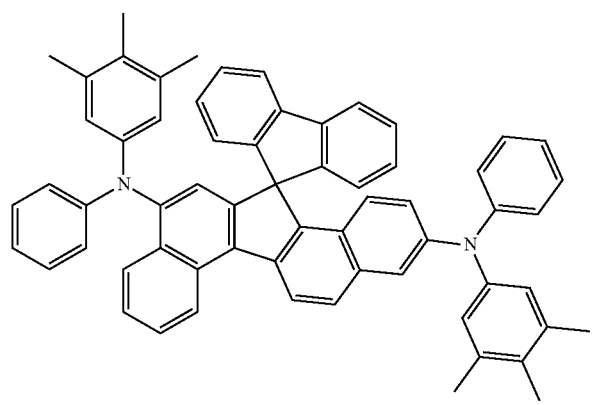
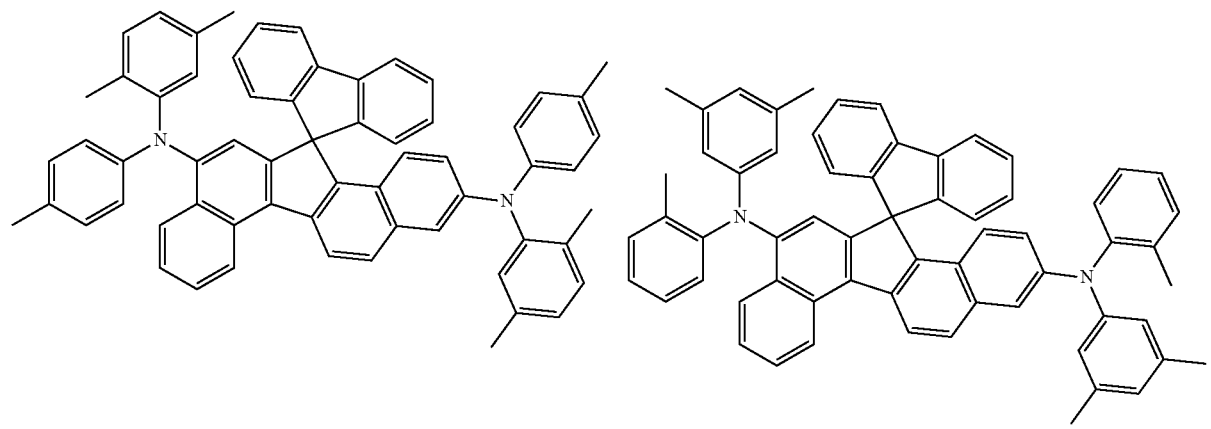
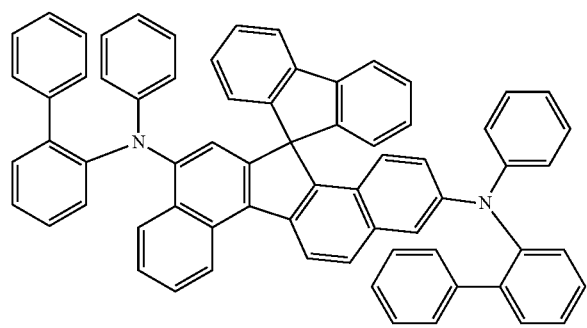

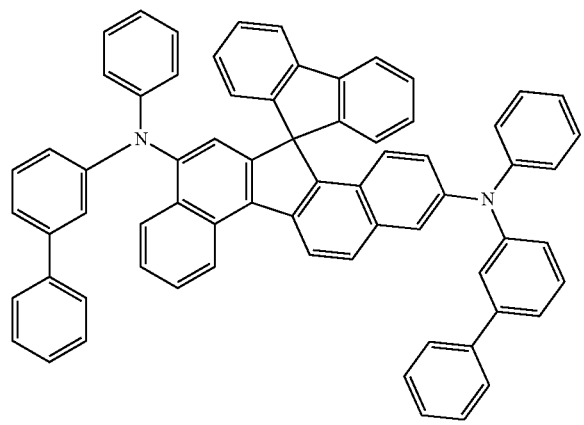
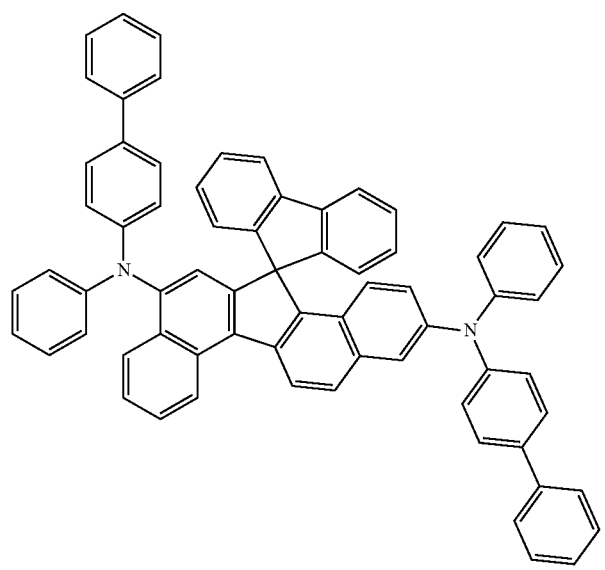
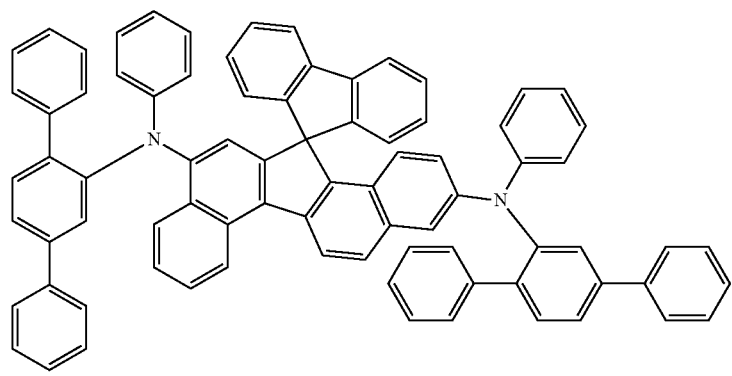

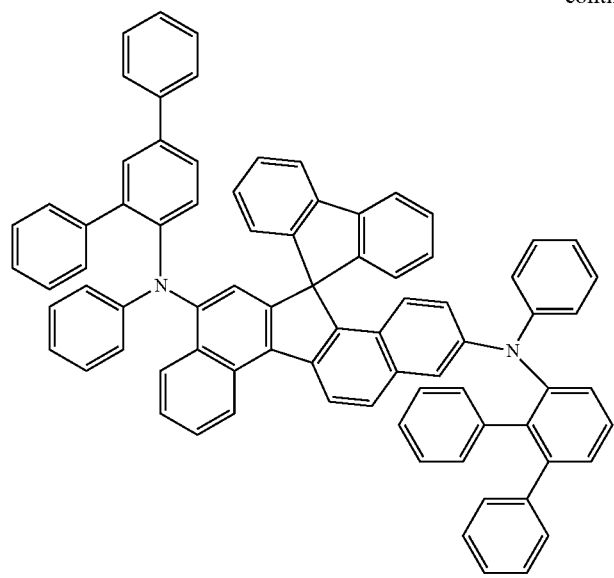
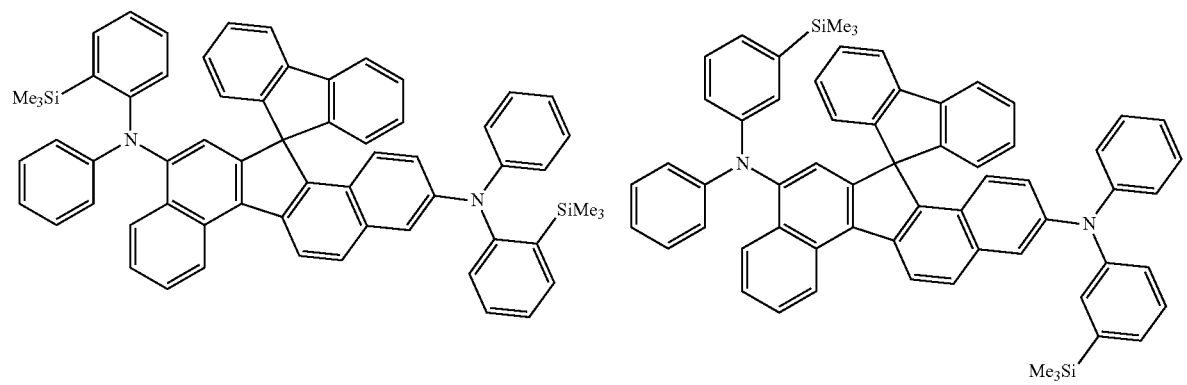 [SMILES: C[Si](C)(C)c1ccccc1N(c1ccccc1)c1ccc2c3c(ccc2c1)-c1c(cc(N(c2ccccc2)c2ccccc2[Si](C)(C)C)c2ccccc12)C31c2ccccc2-c2ccccc21 ; C[Si](C)(C)c1cccc(N(c2ccccc2)c2ccc3c4c(ccc3c2)-c2c(cc(N(c3ccccc3)c3cccc([Si](C)(C)C)c3)c3ccccc23)C42c3ccccc3-c3ccccc32)c1]
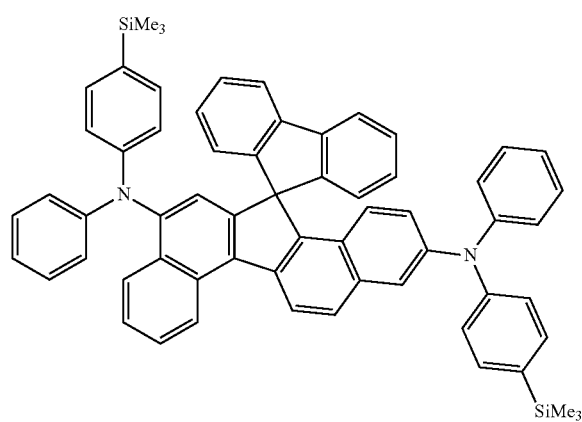

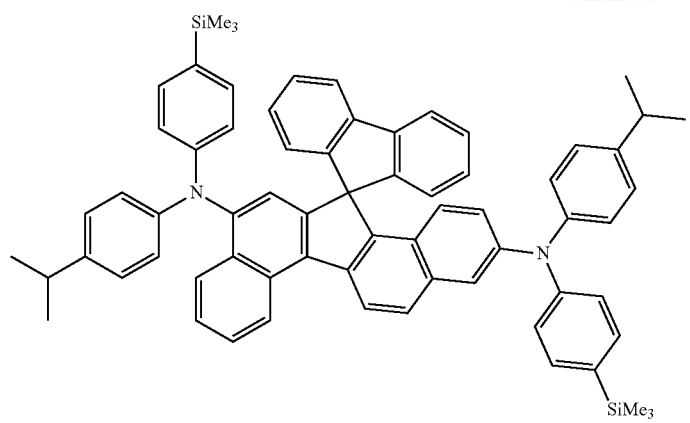
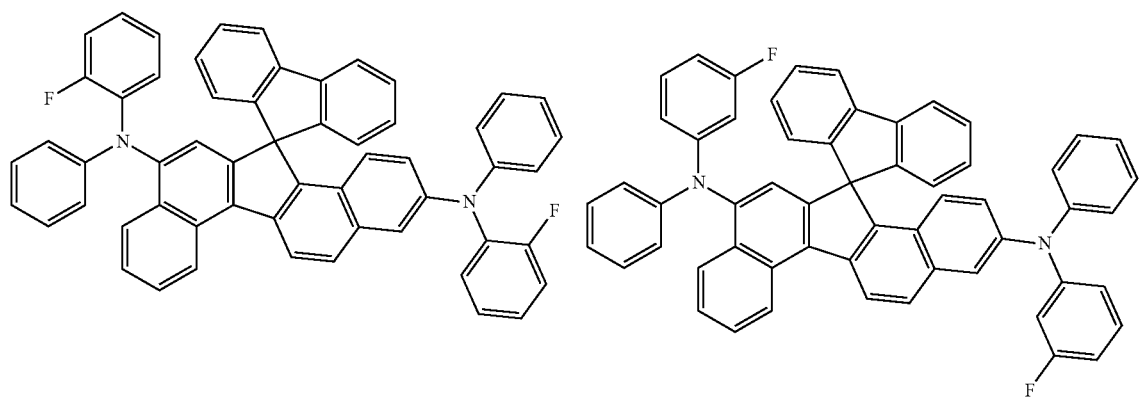
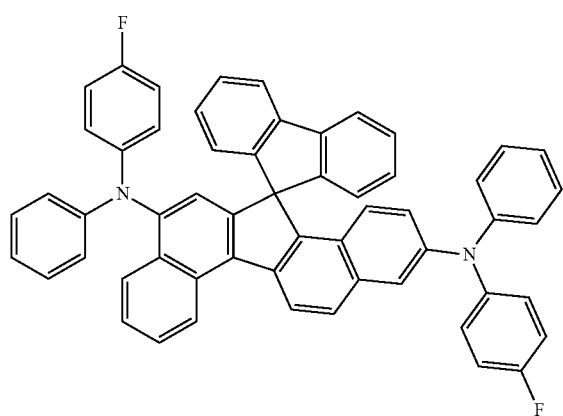
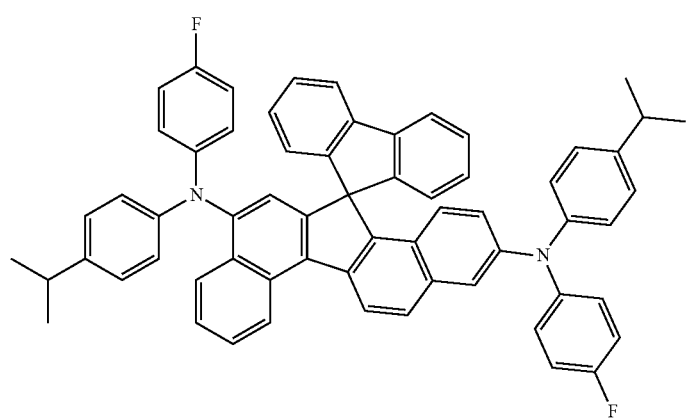

-continued
569    570
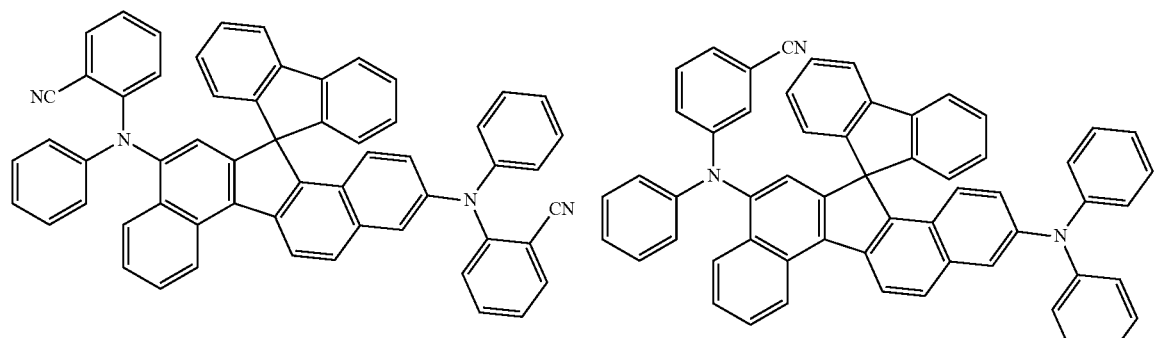
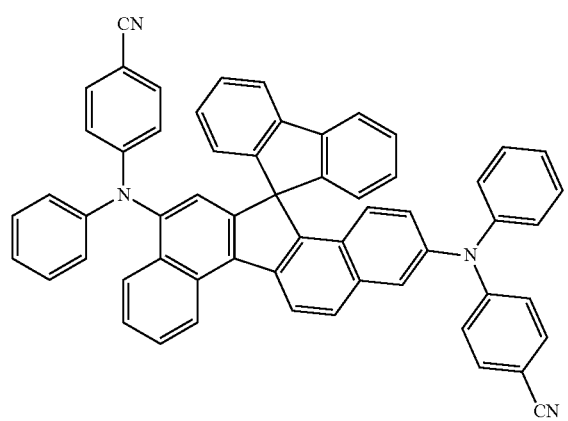
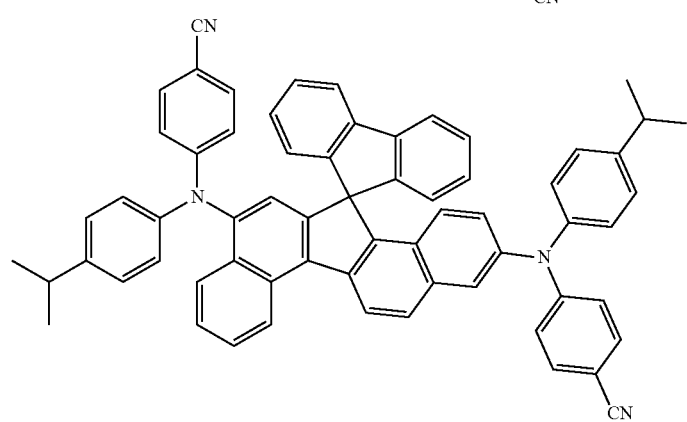
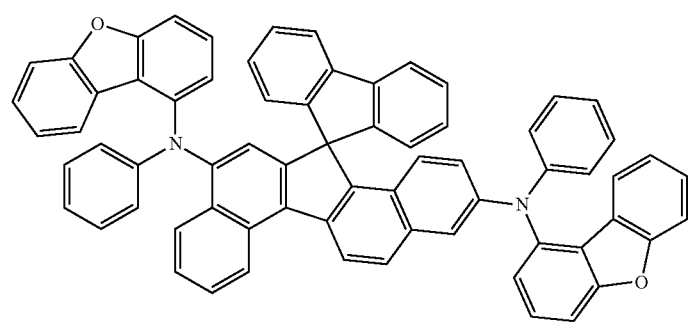

-continued
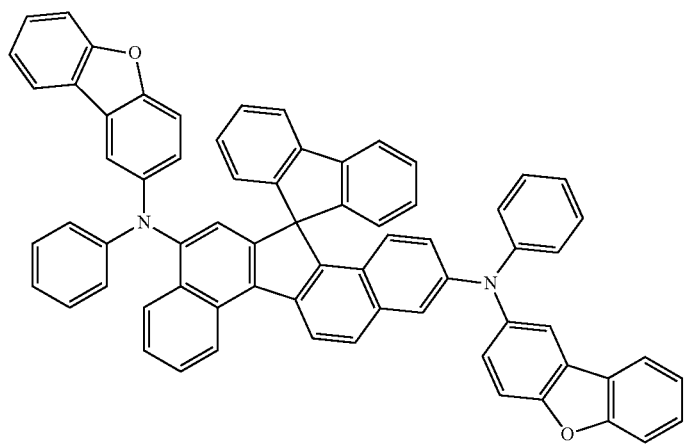
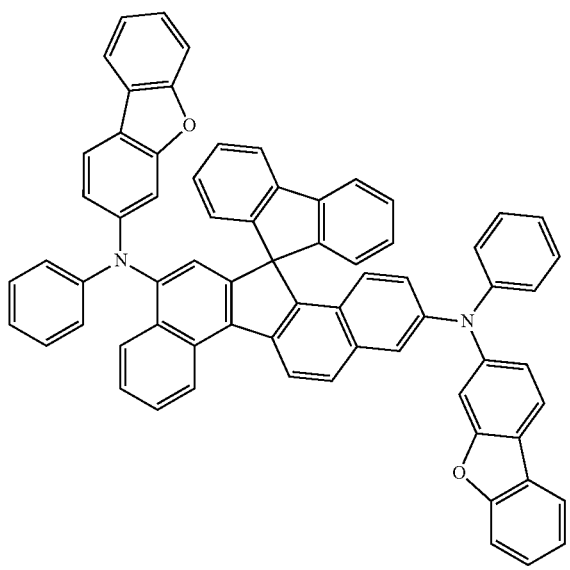
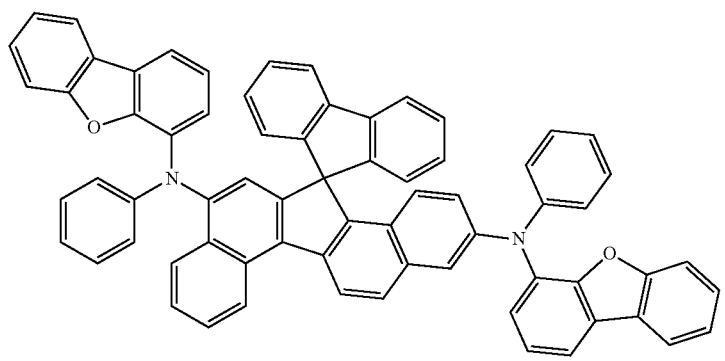

-continued
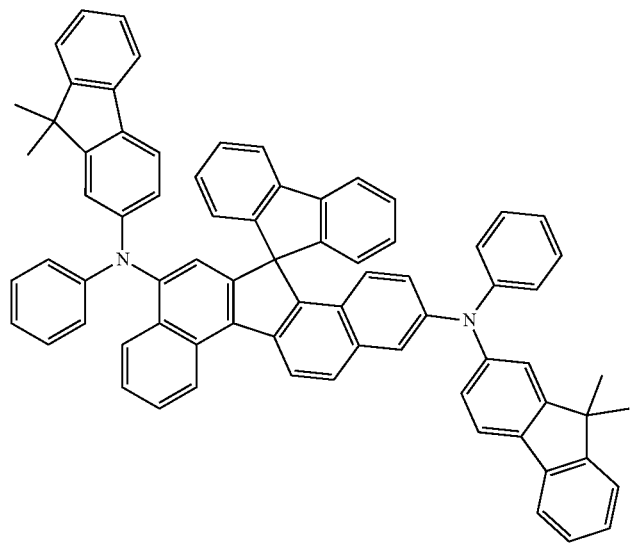
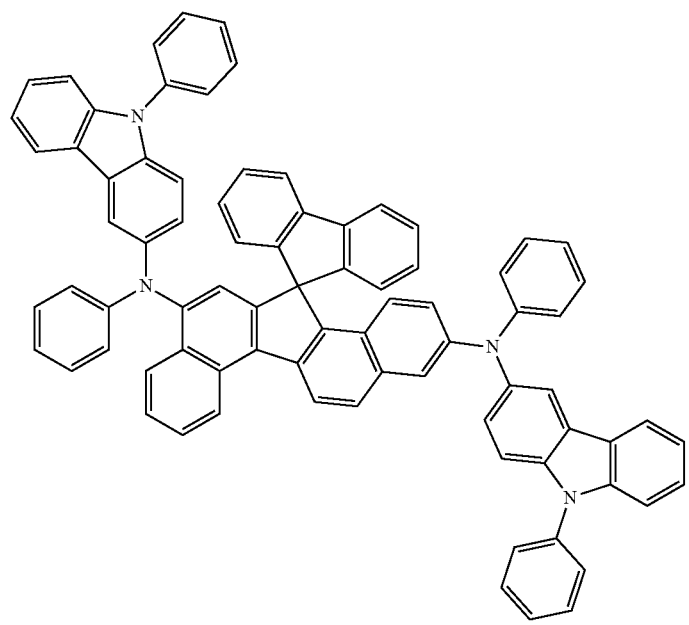
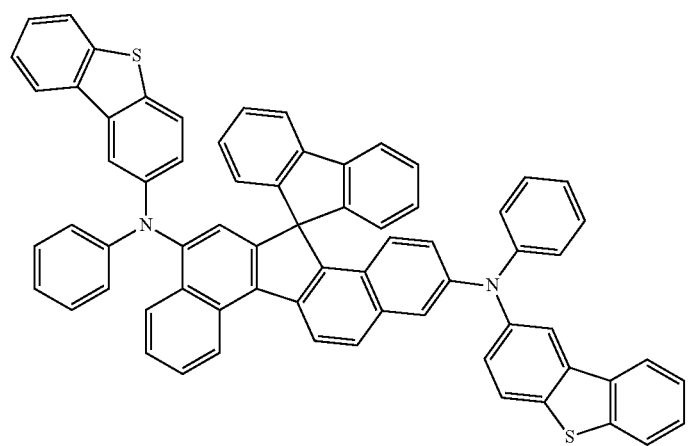

-continued
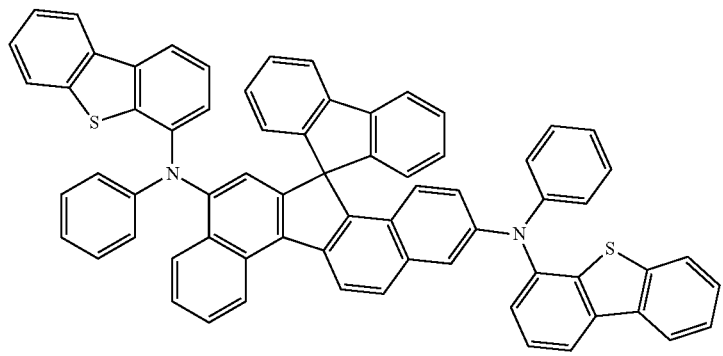
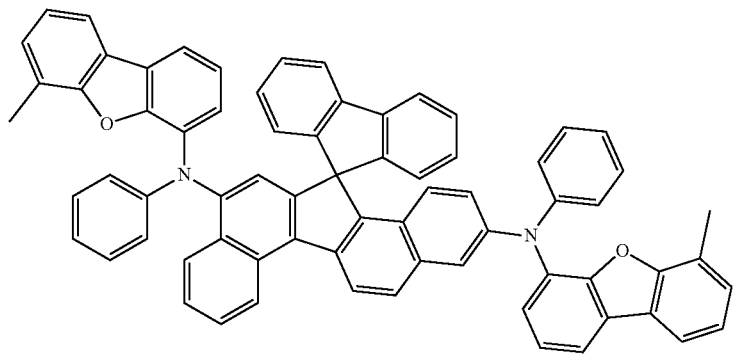
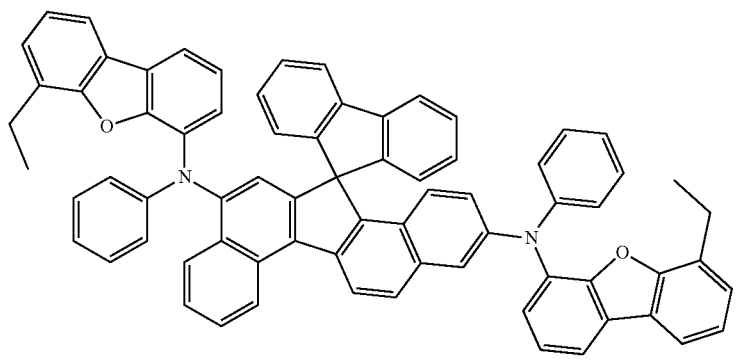
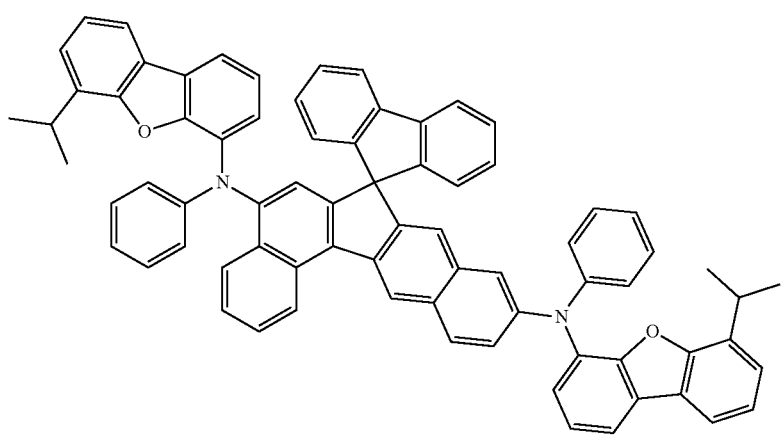

-continued
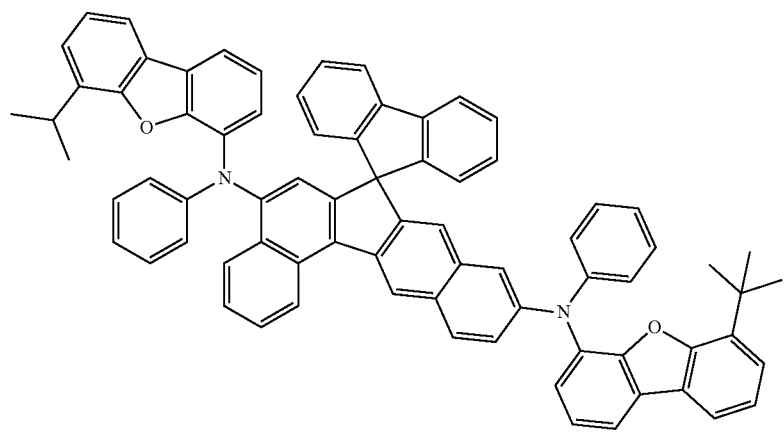
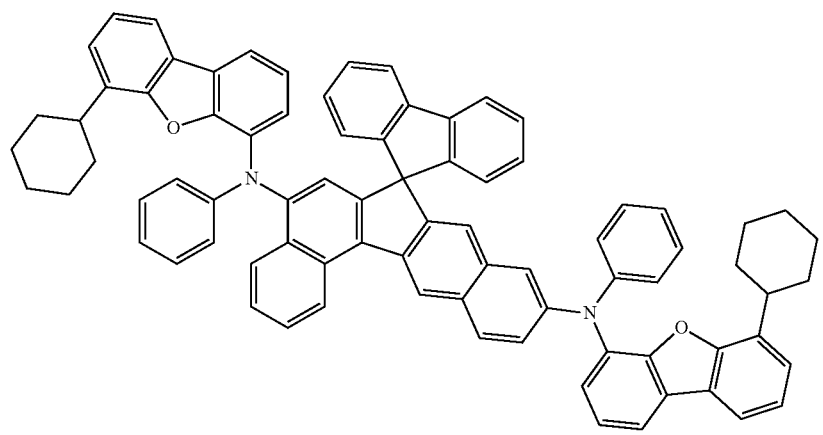
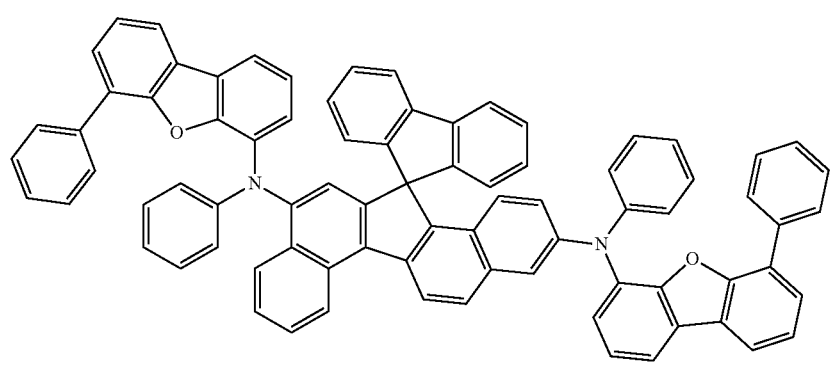
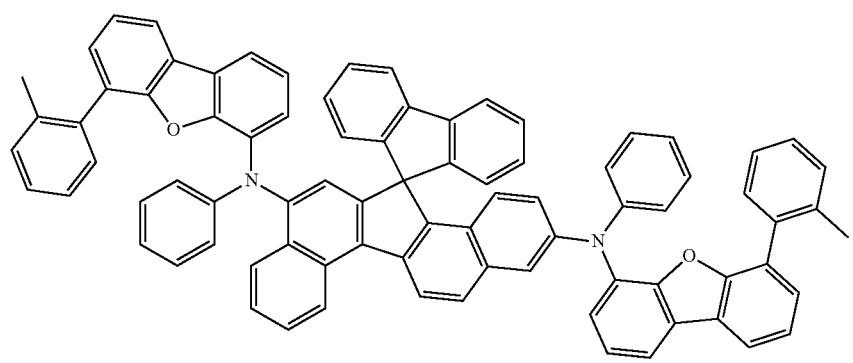

-continued
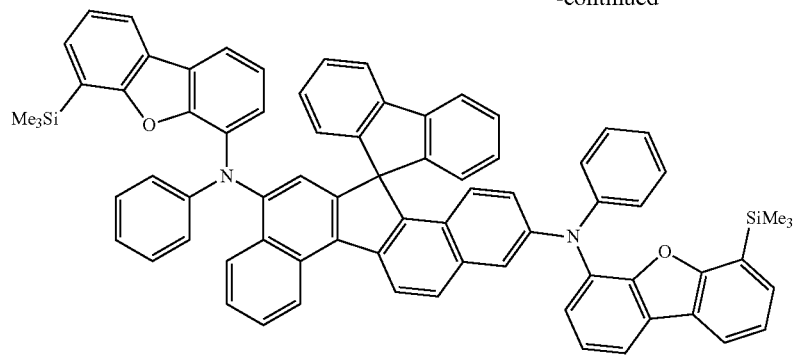
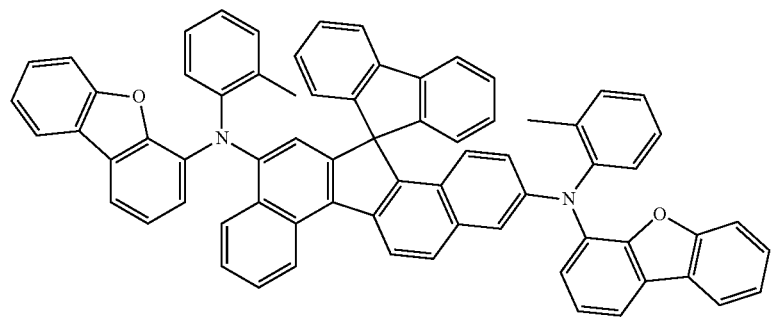
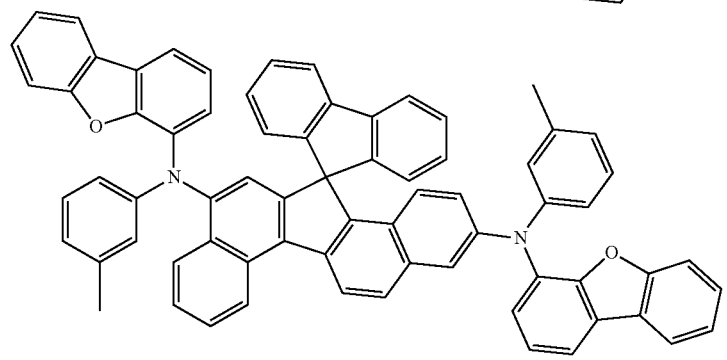
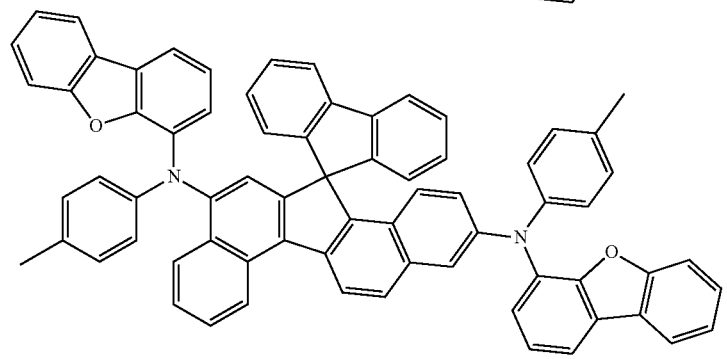
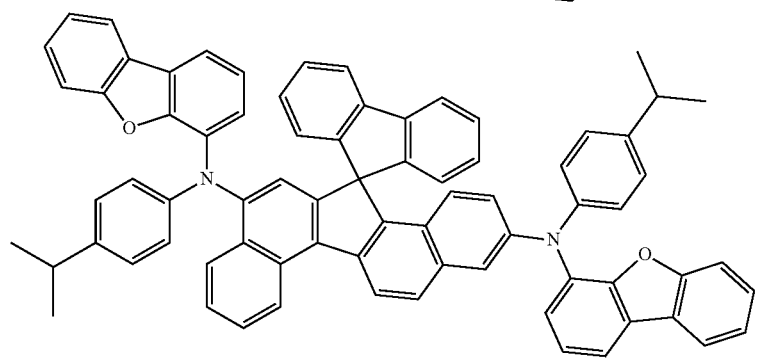

-continued
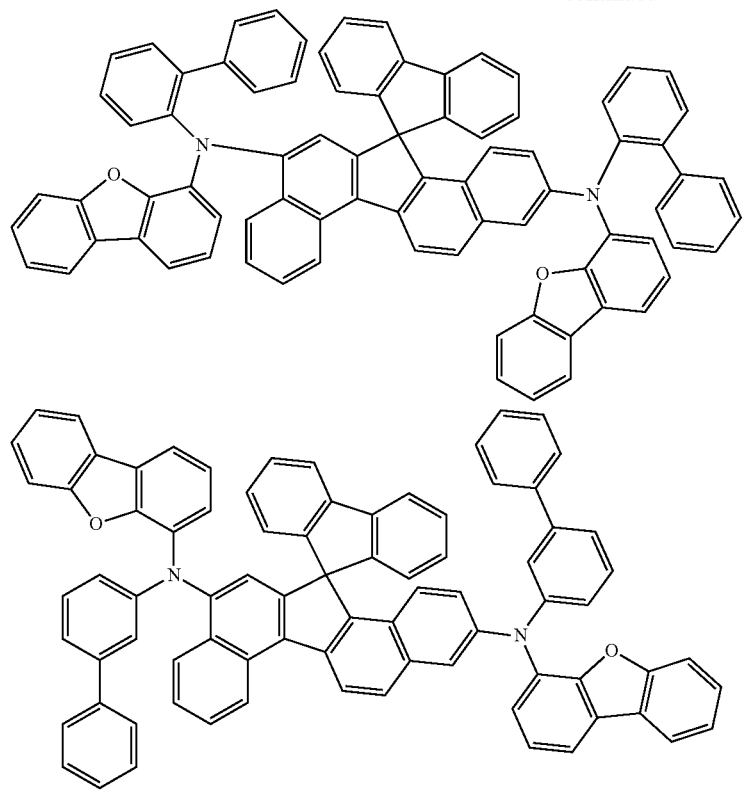
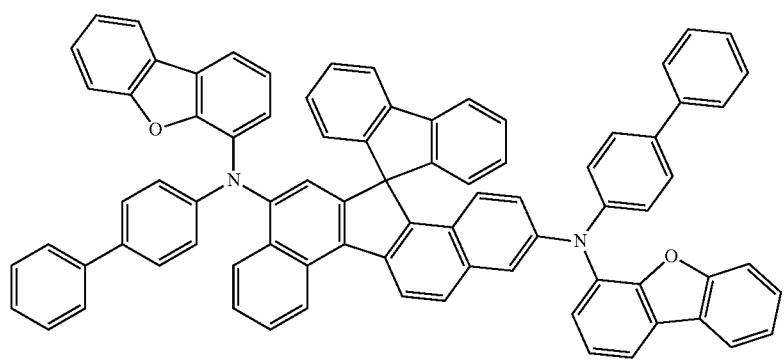
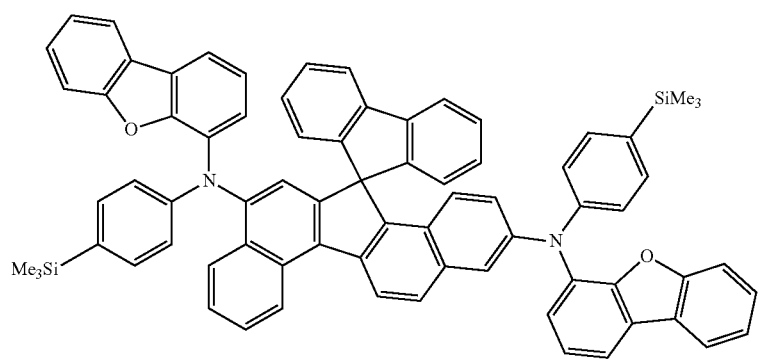

-continued
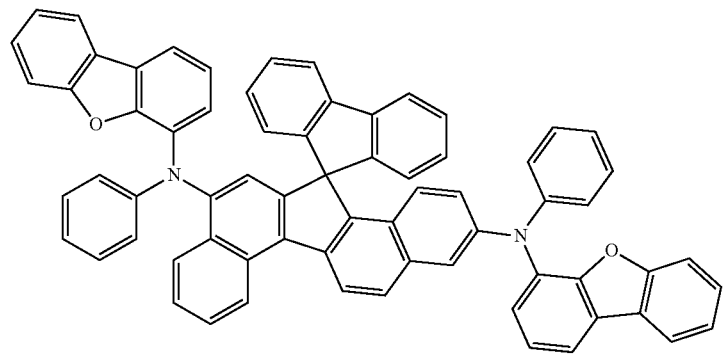
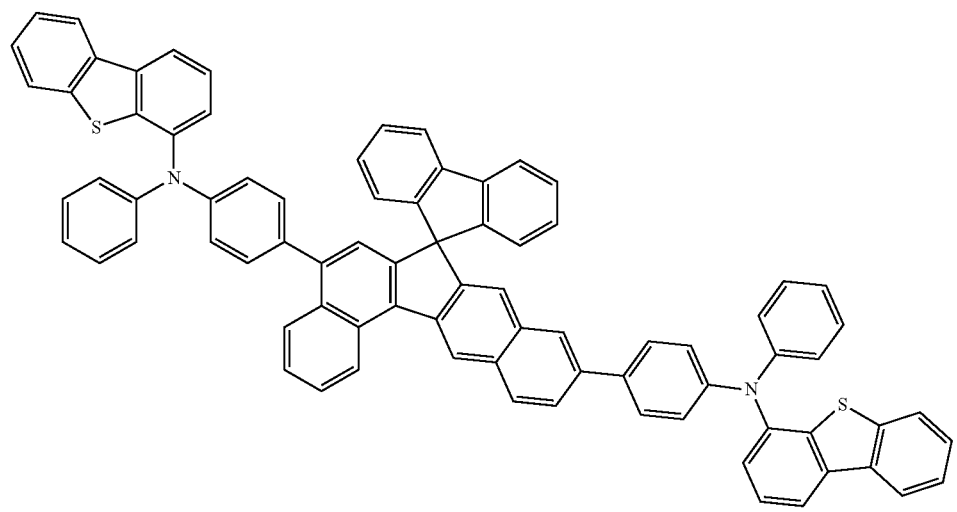
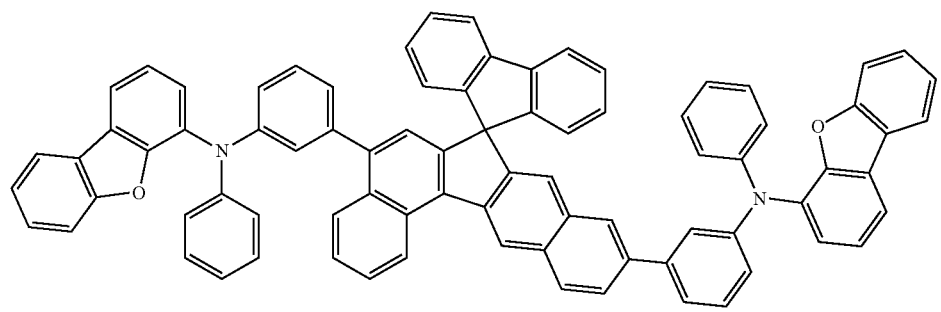
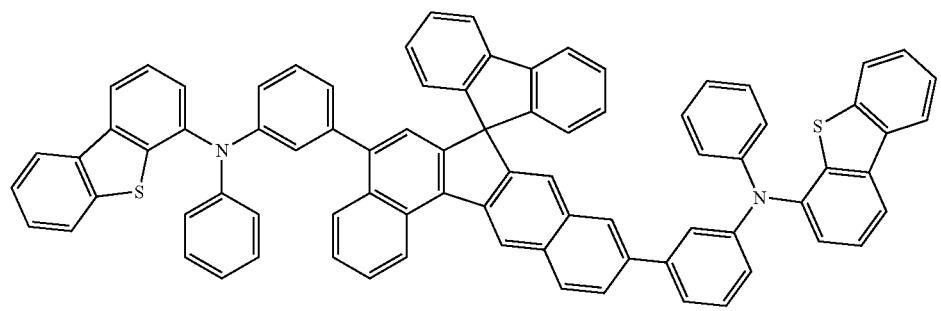

-continued
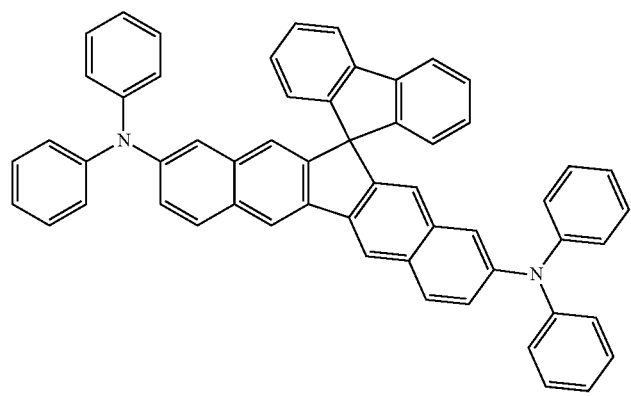
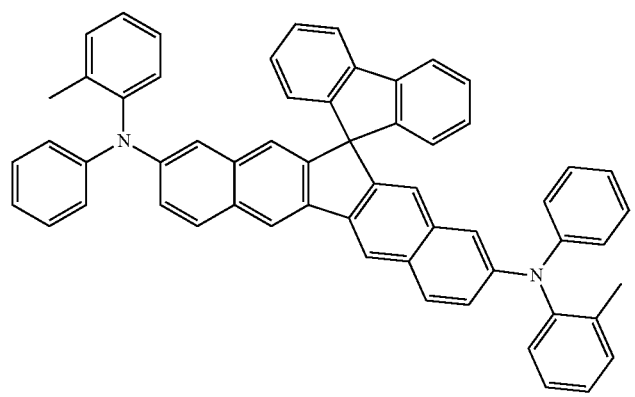
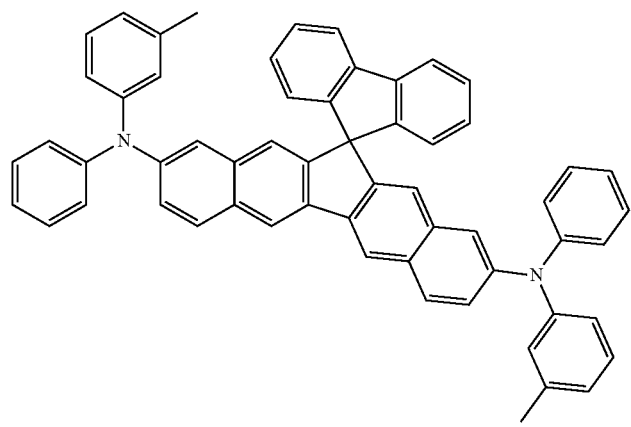
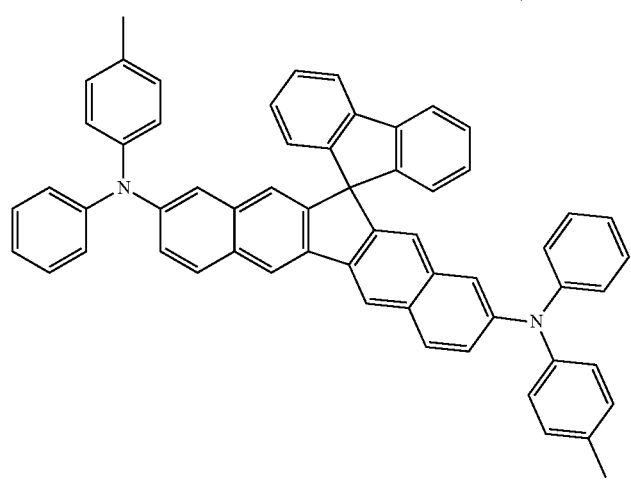

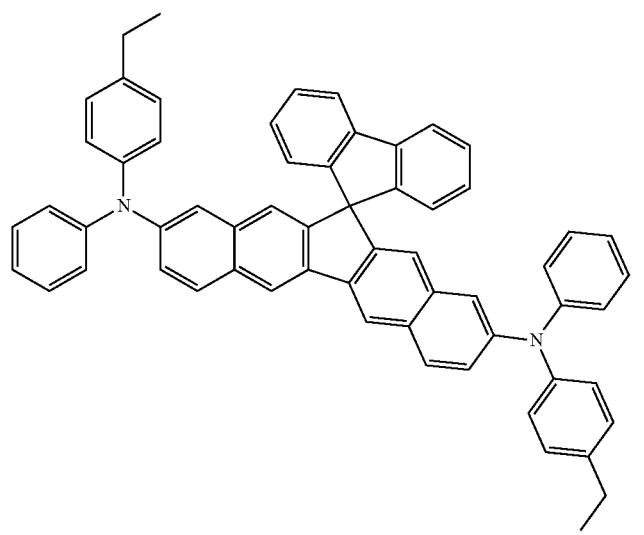
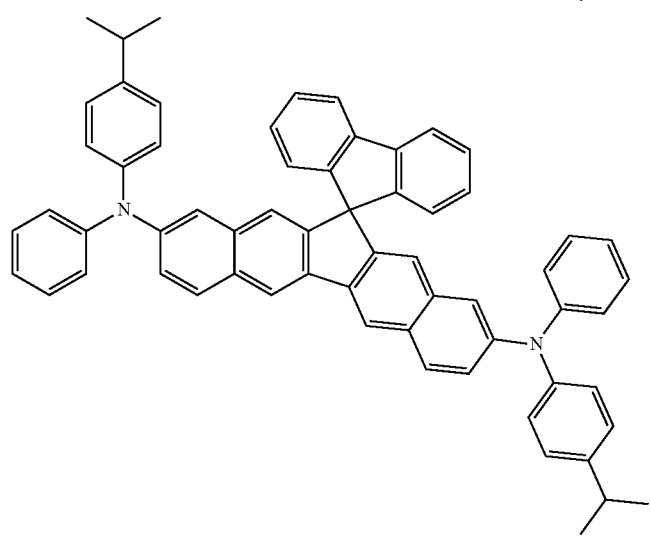
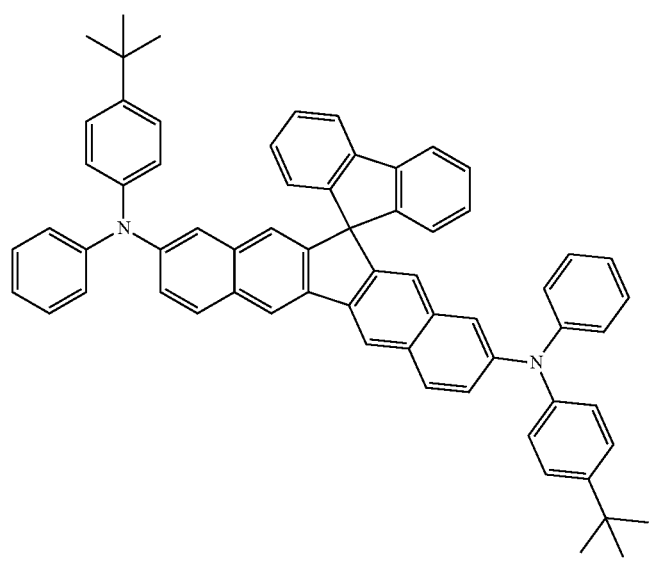 [SMILES: CC(C)(C)c1ccc(N(c2ccccc2)c2ccc3cc4c(cc3c2)C2(c3ccccc3-c3ccccc32)c2cc3cc(N(c5ccccc5)c5ccc(C(C)(C)C)cc5)ccc3cc2-4)cc1]

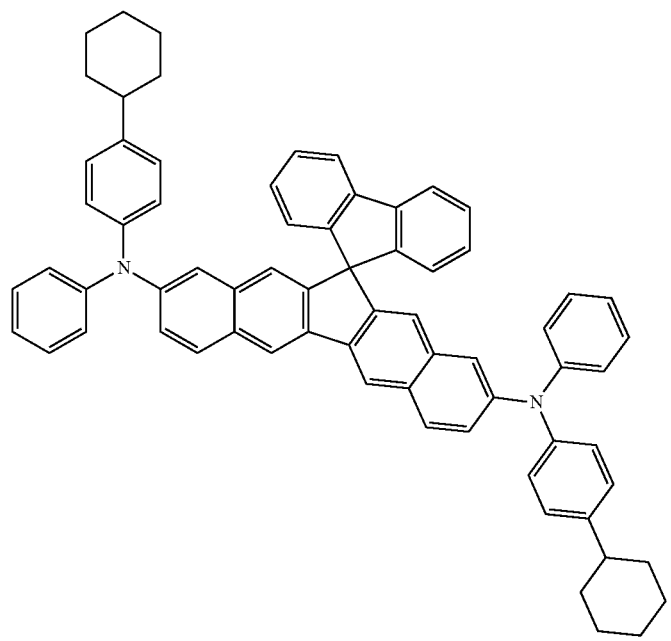
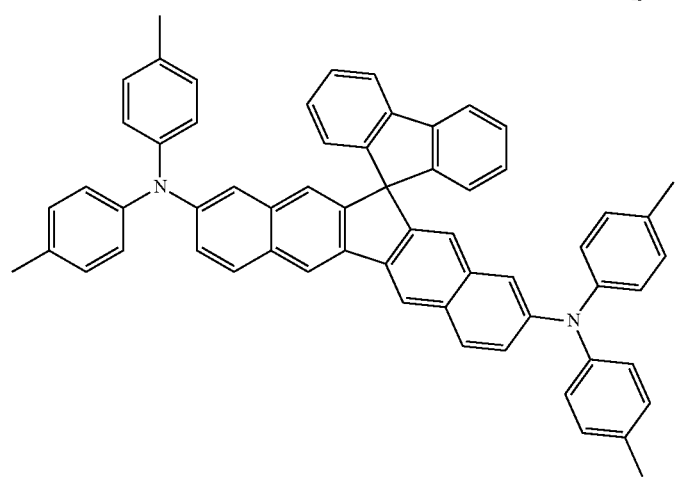
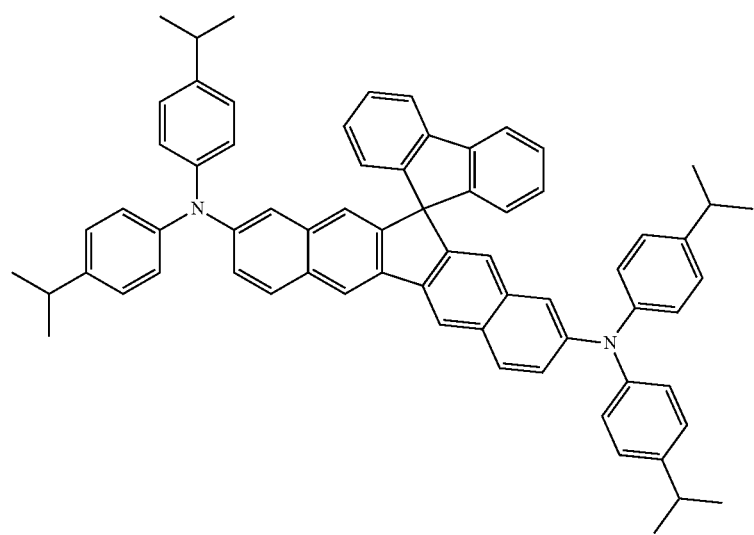

-continued
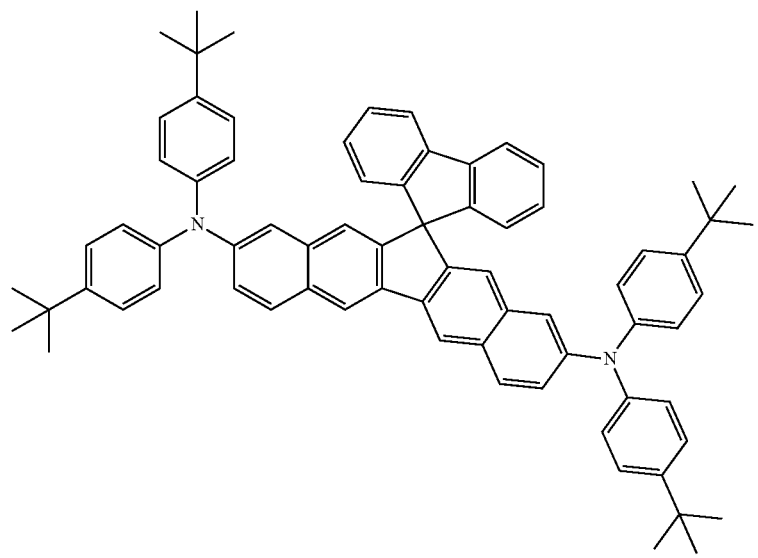
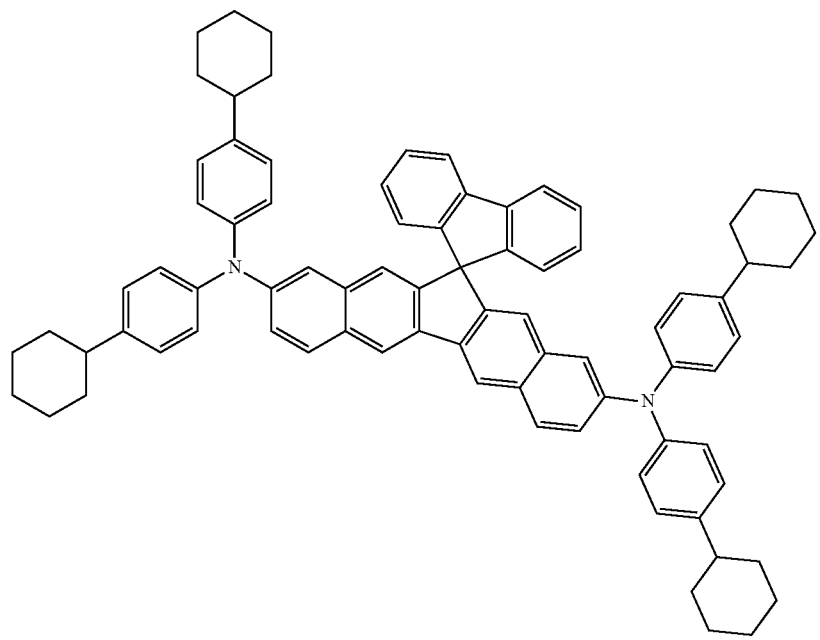
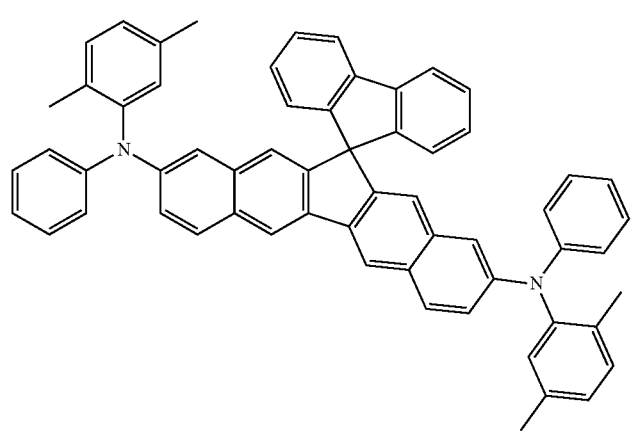

-continued
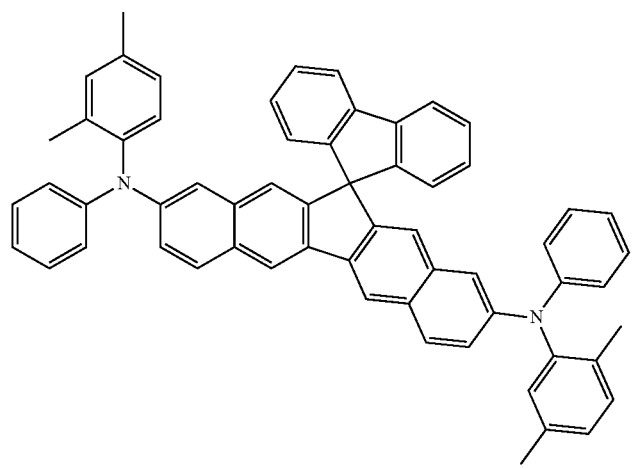
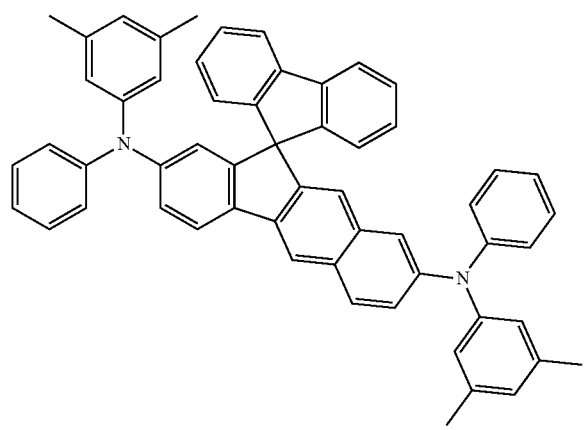
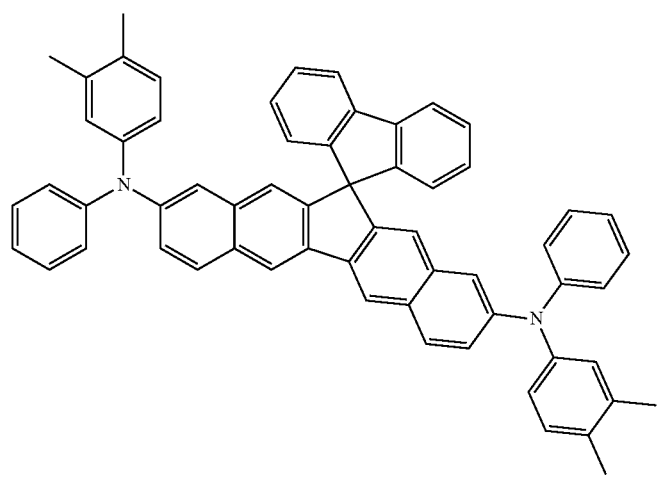

-continued
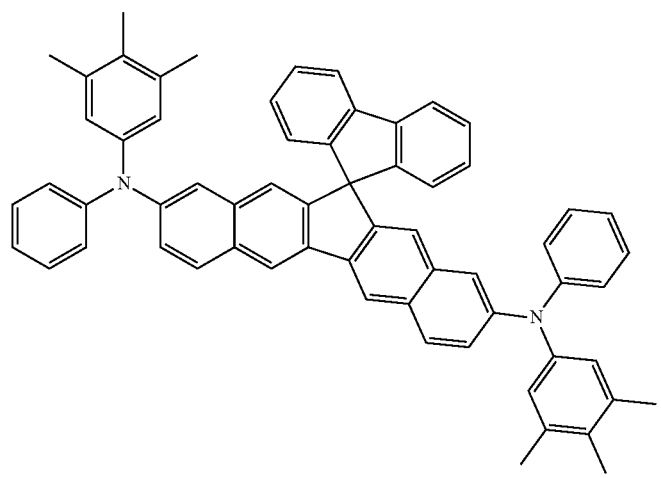
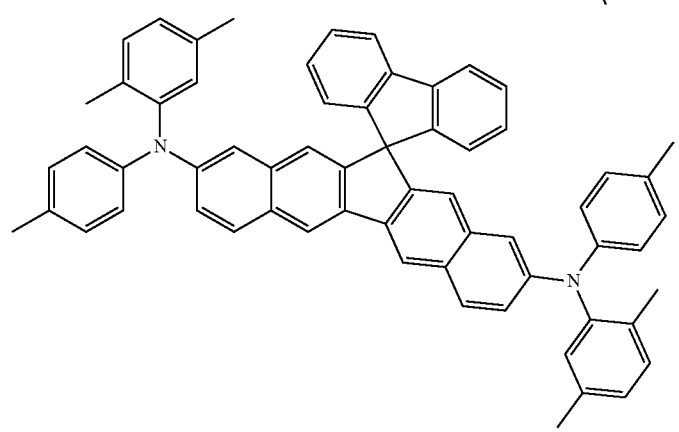
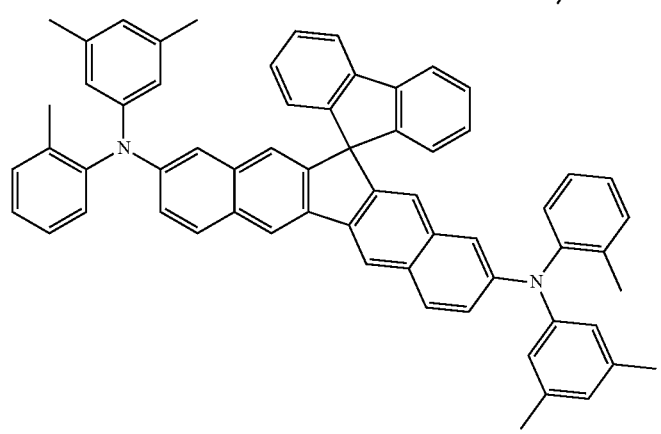
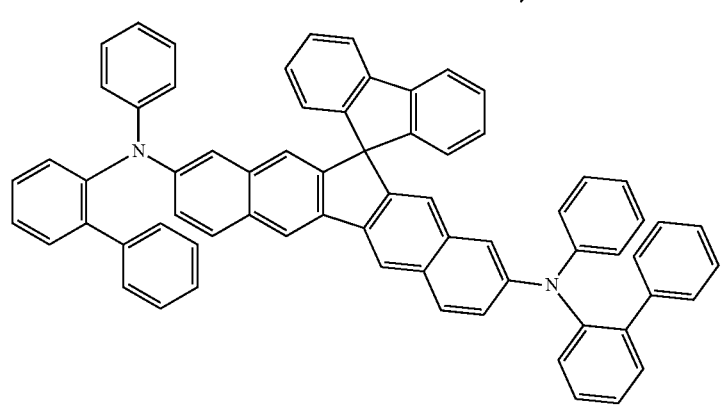

-continued
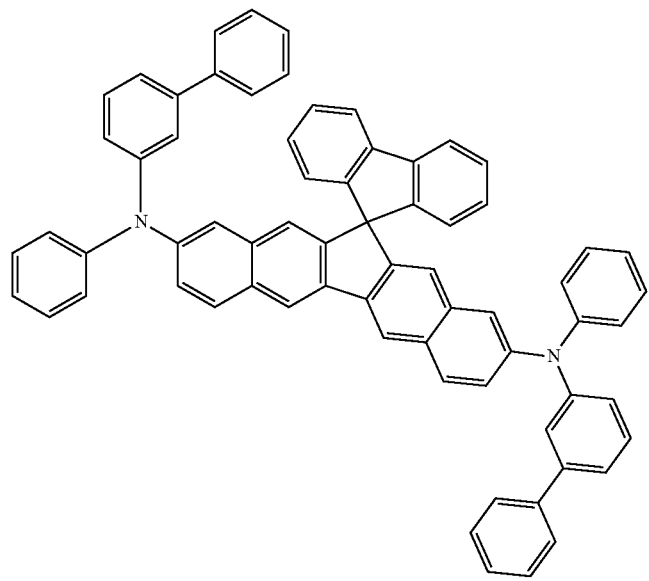
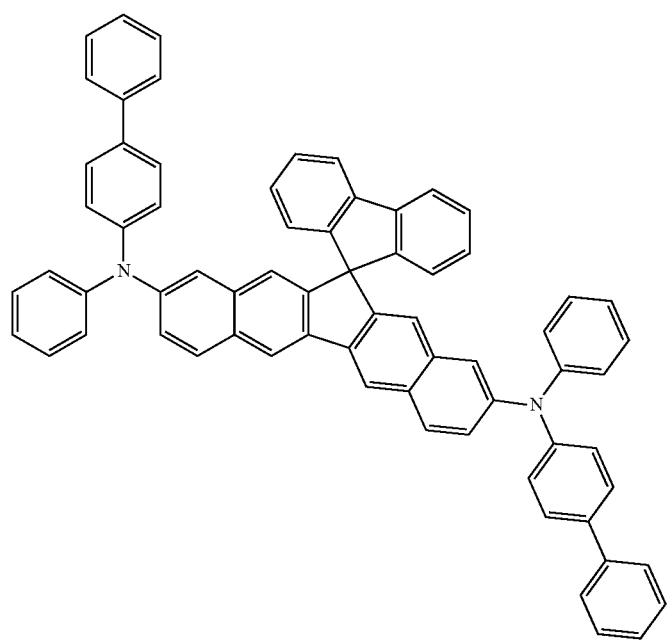

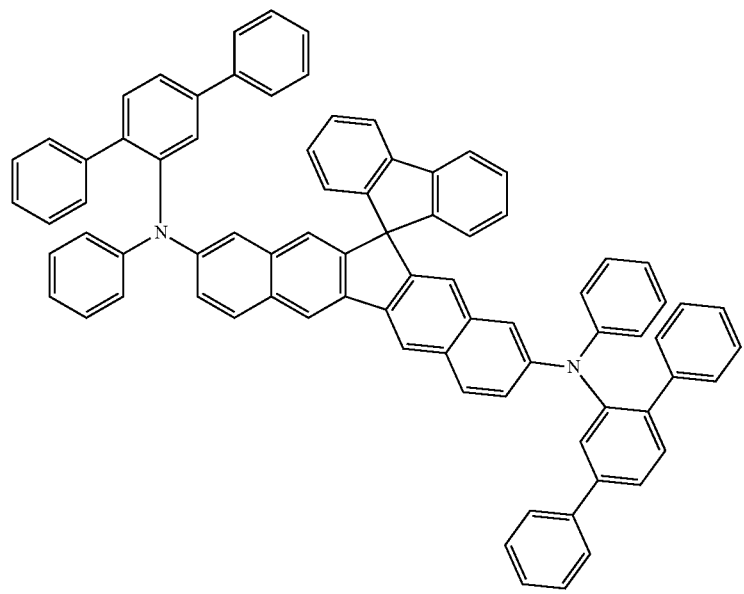
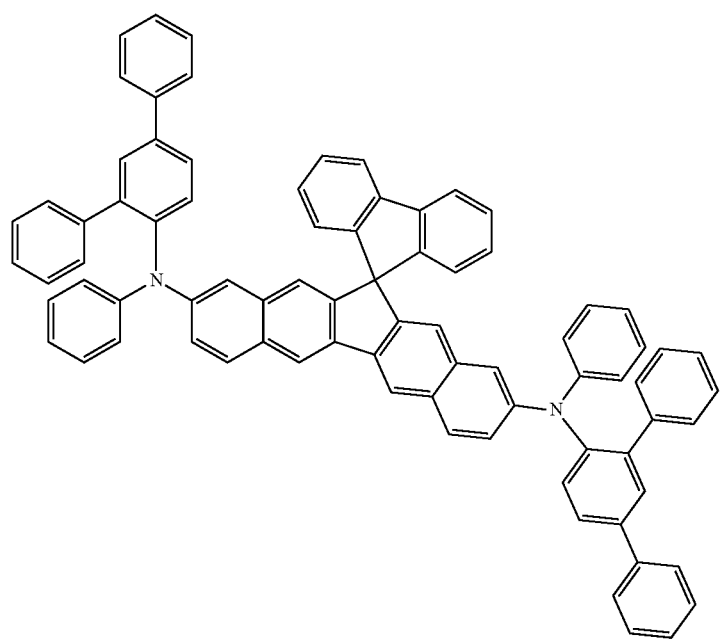
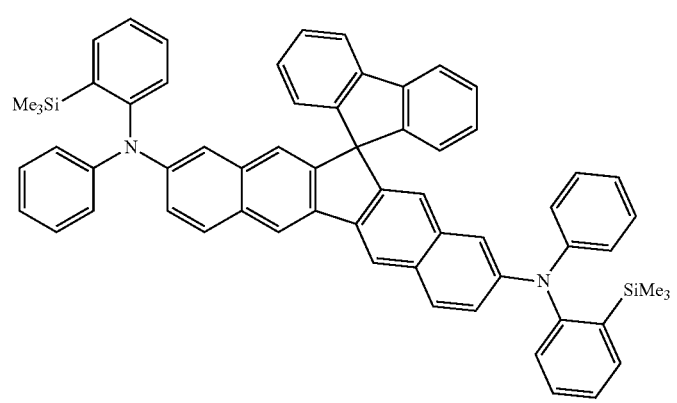

601
-continued
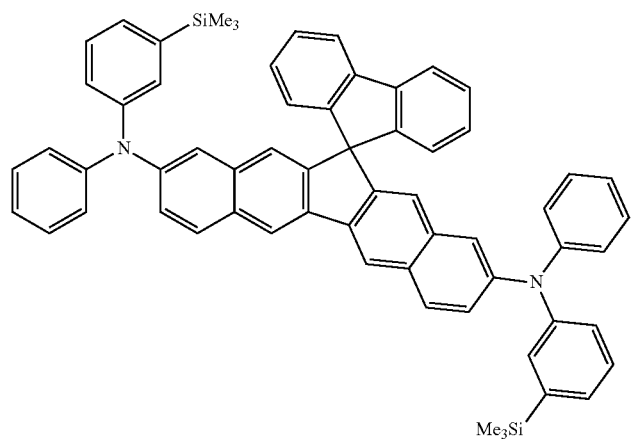
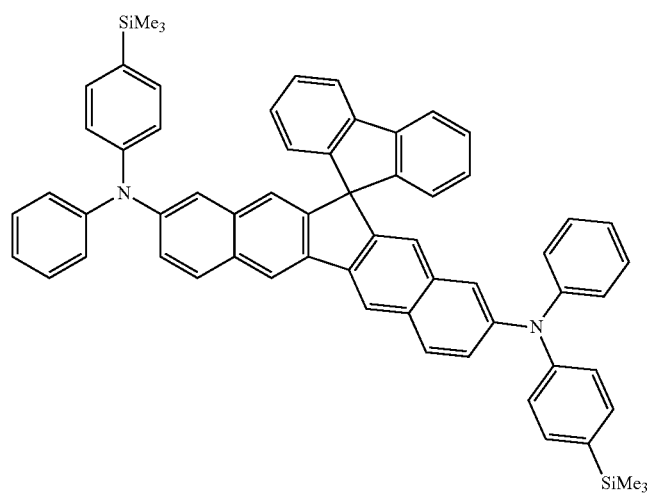
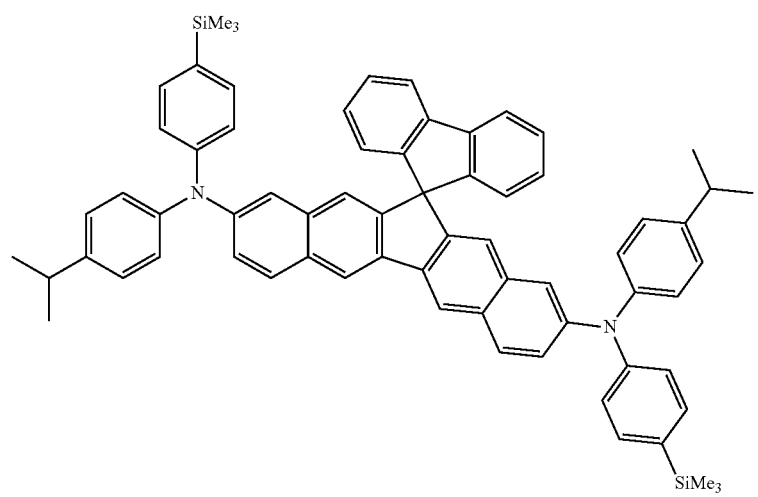
602

-continued
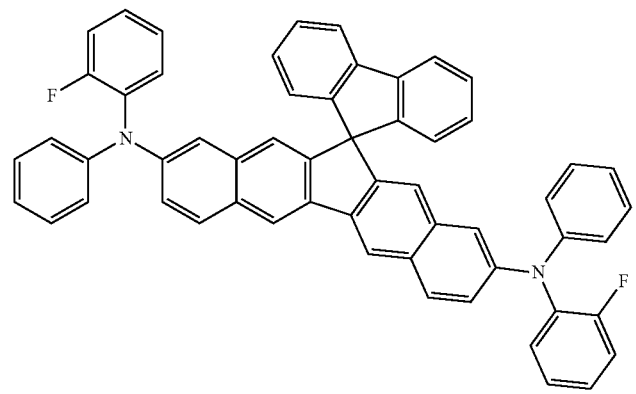
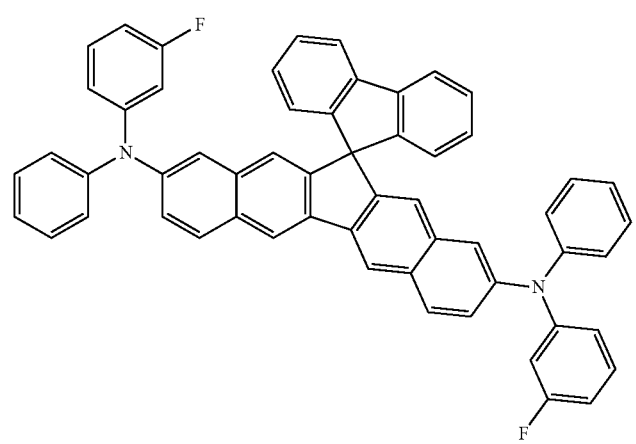 [SMILES: Fc1cccc(N(c2ccccc2)c2ccc3cc4c(cc3c2)C2(c3ccccc3-c3ccccc32)c2cc3cc(N(c5ccccc5)c5cccc(F)c5)ccc3cc2-4)c1]
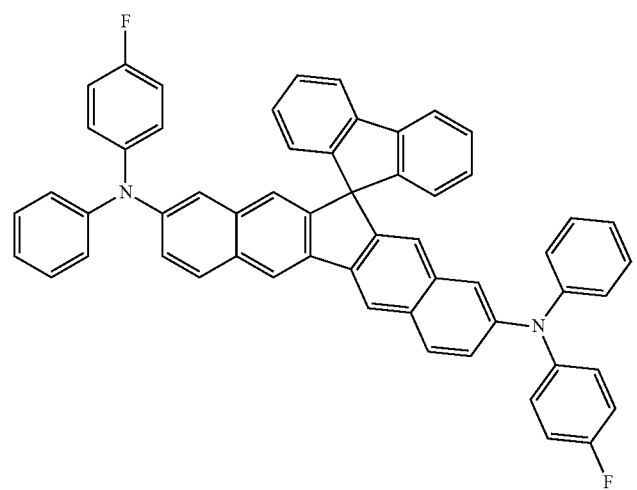

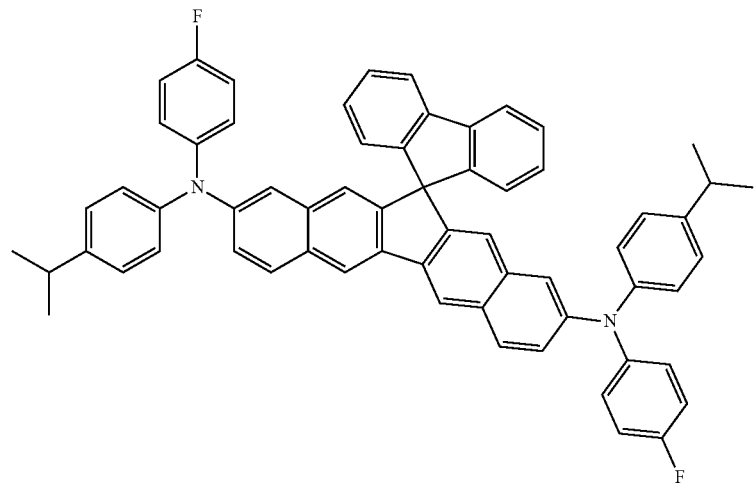
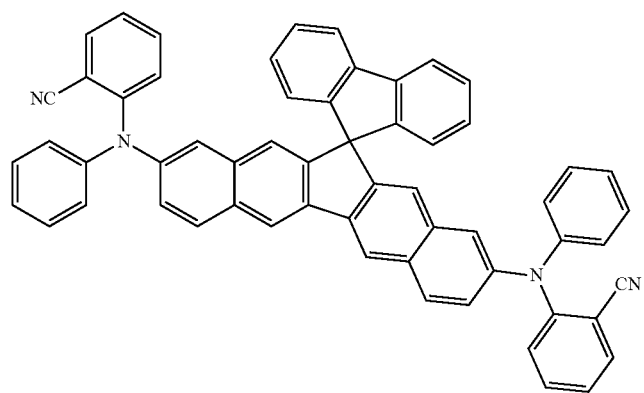
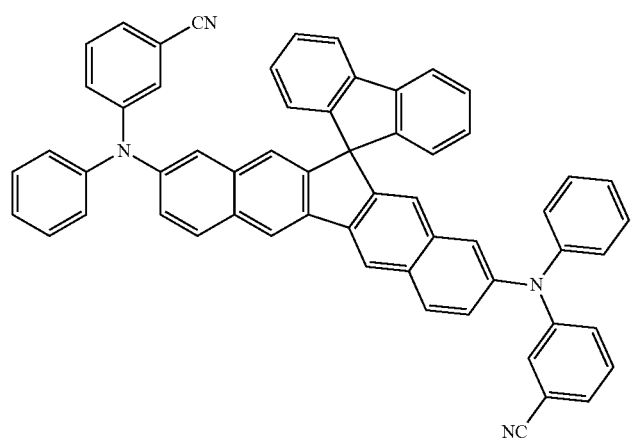

-continued
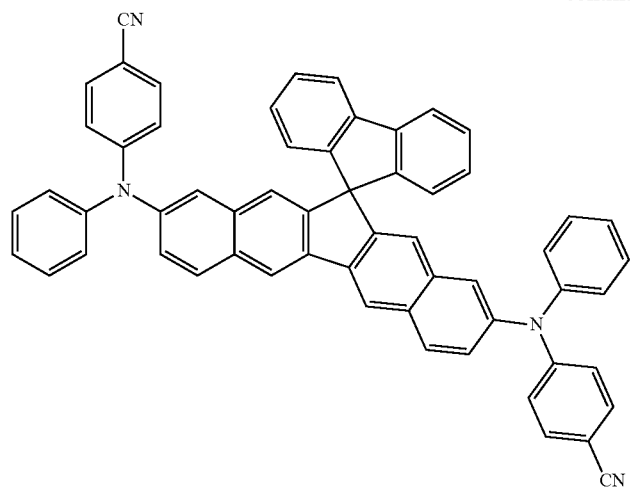
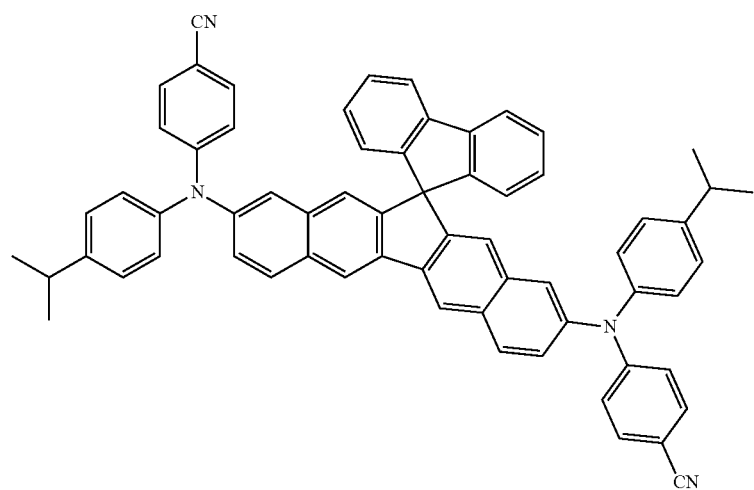
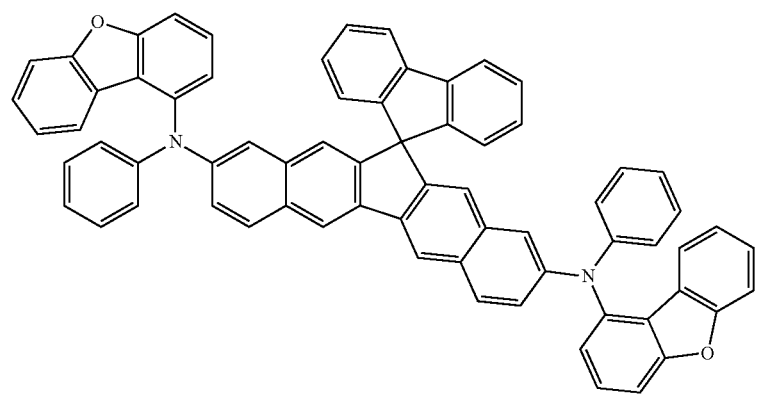

-continued
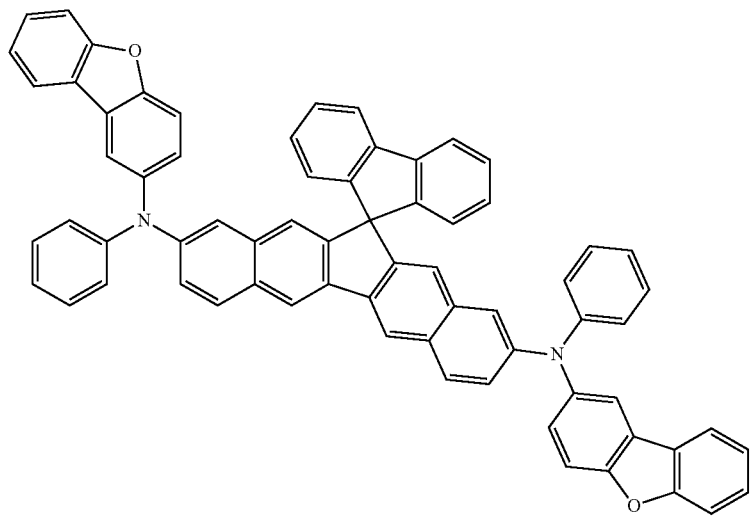
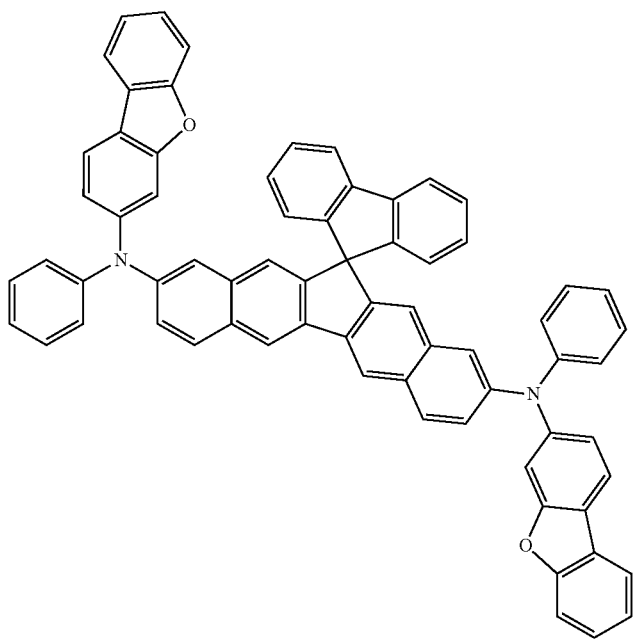
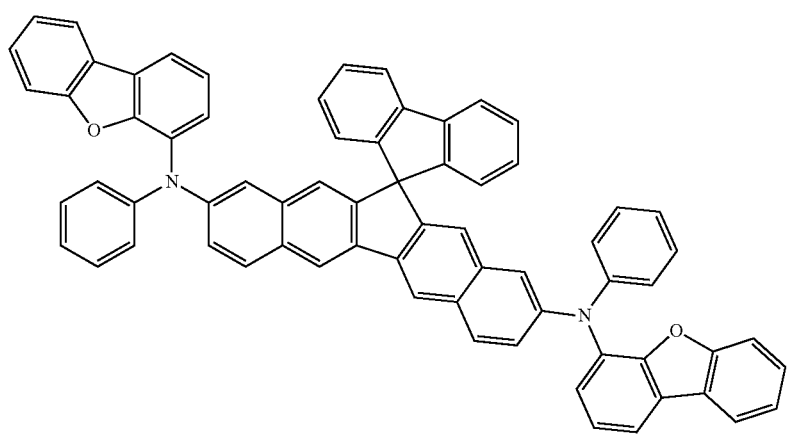

611
612
-continued
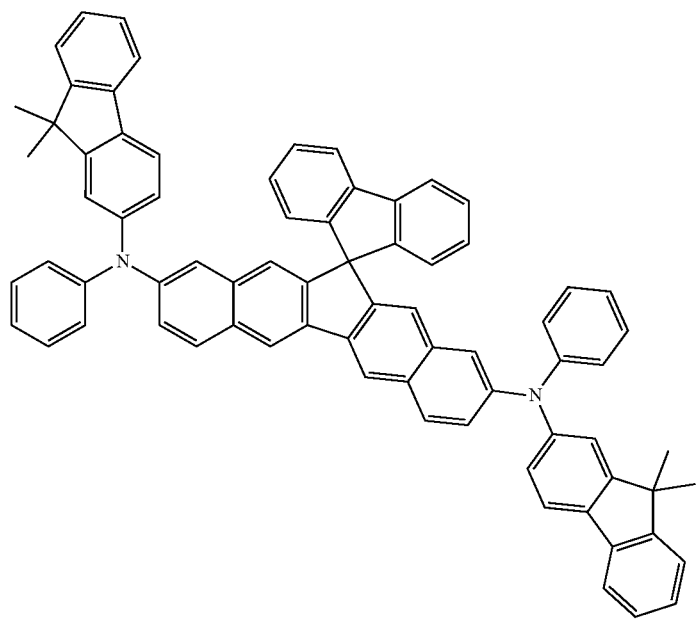
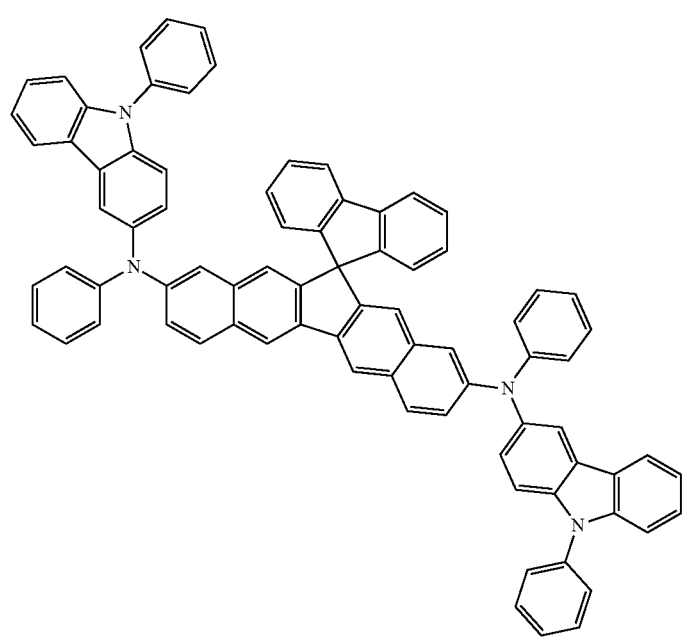

-continued
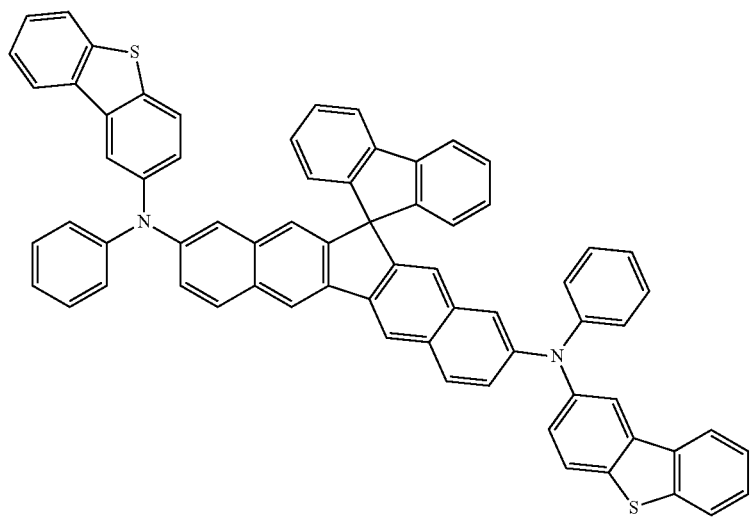
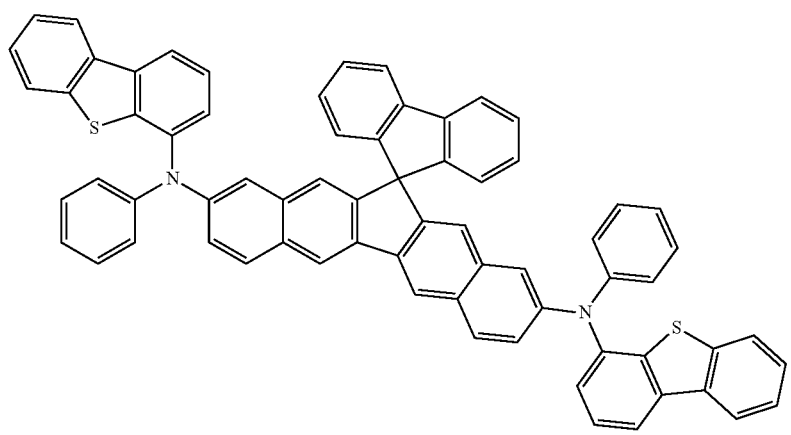
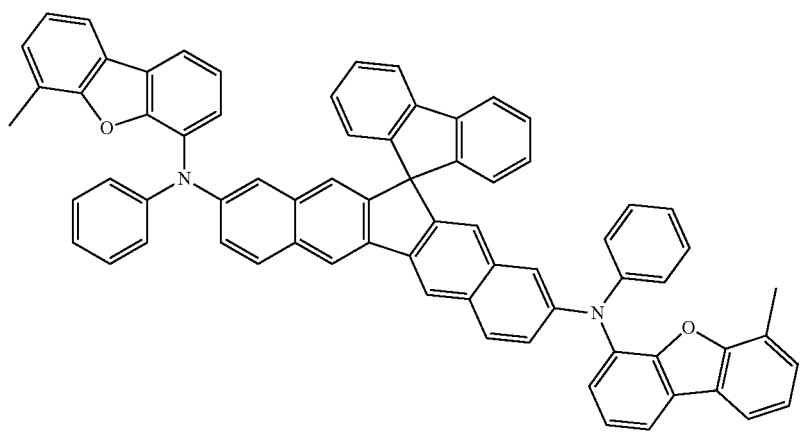

-continued
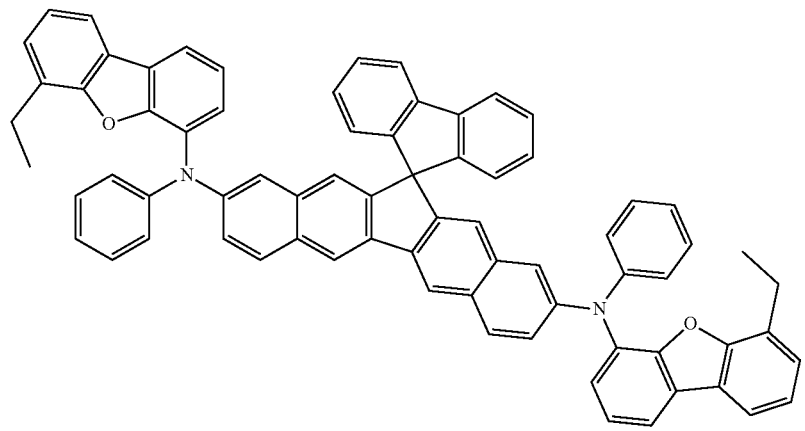
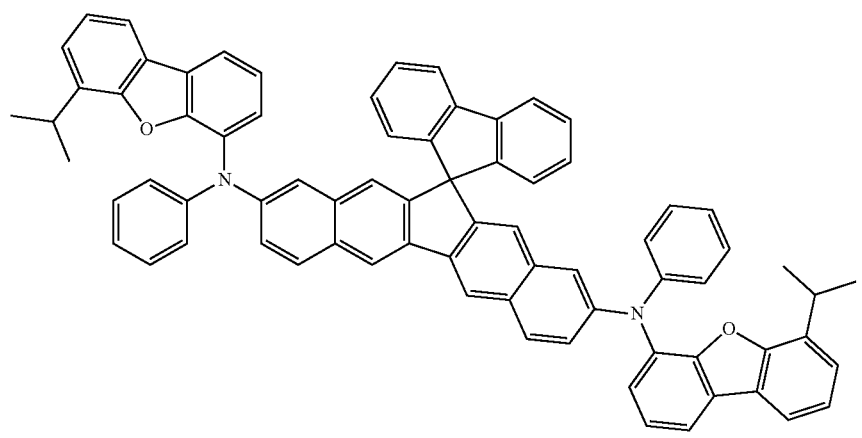
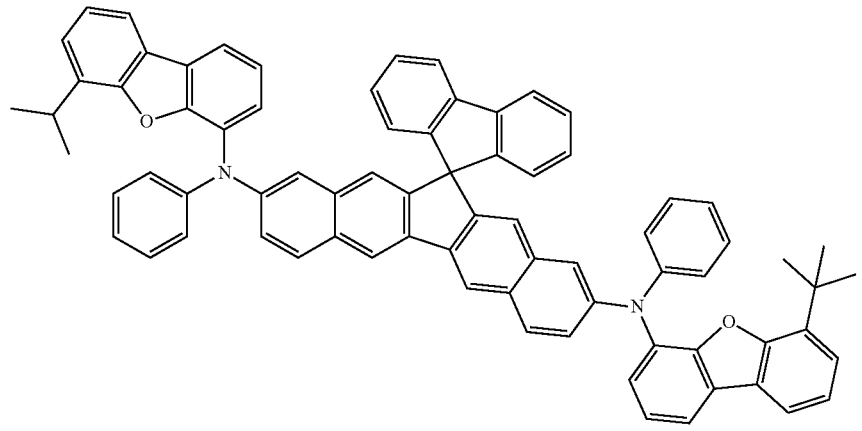
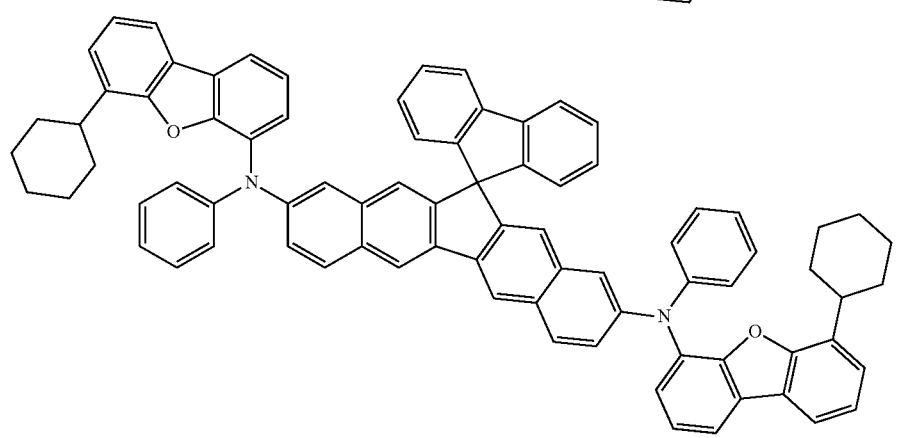

-continued
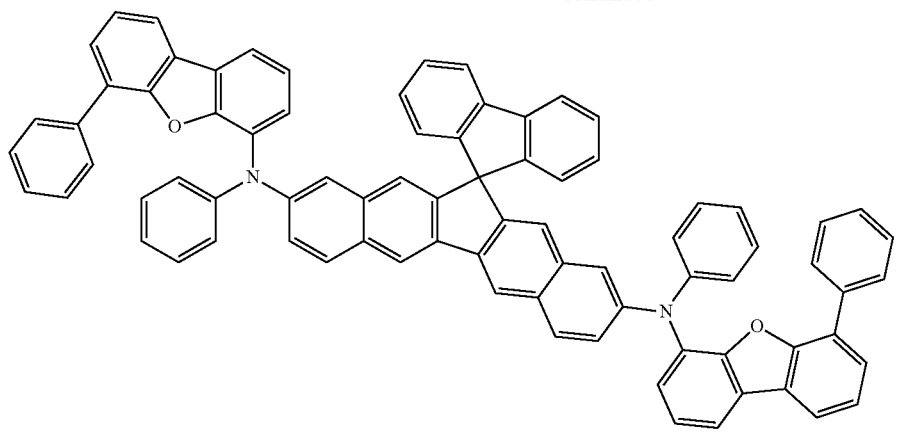
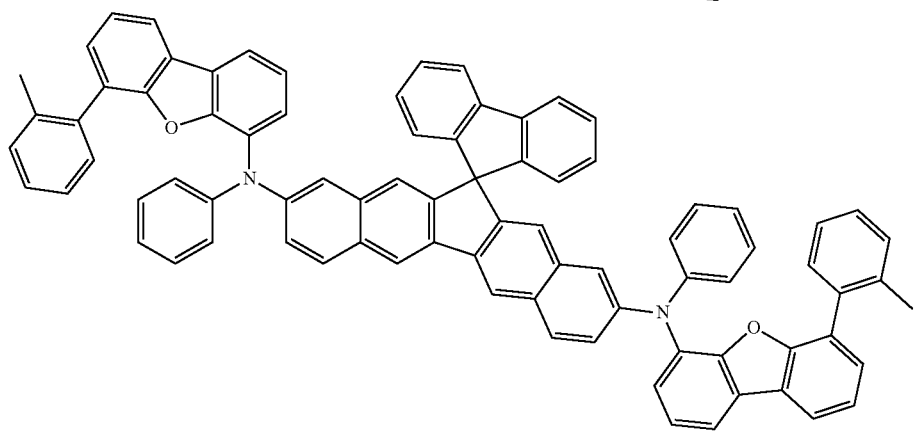
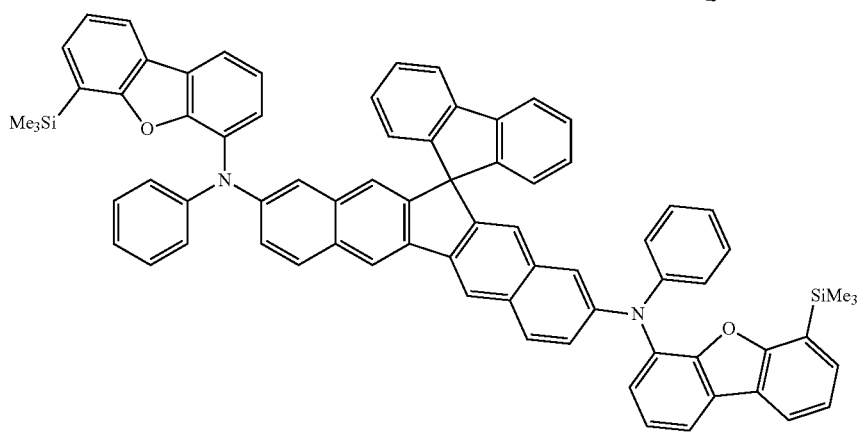
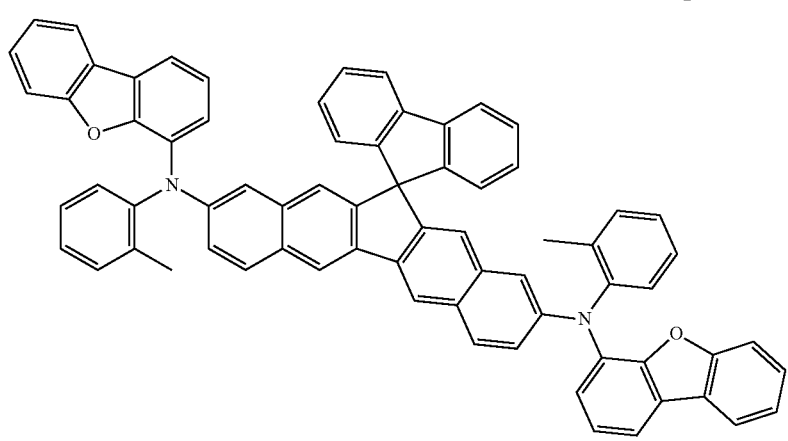

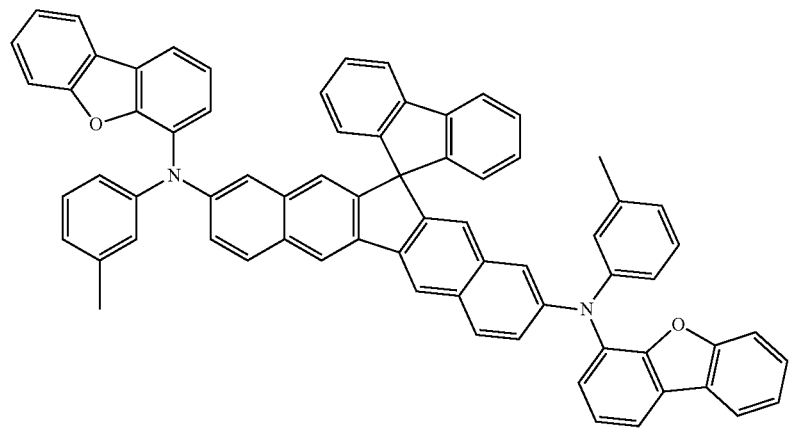
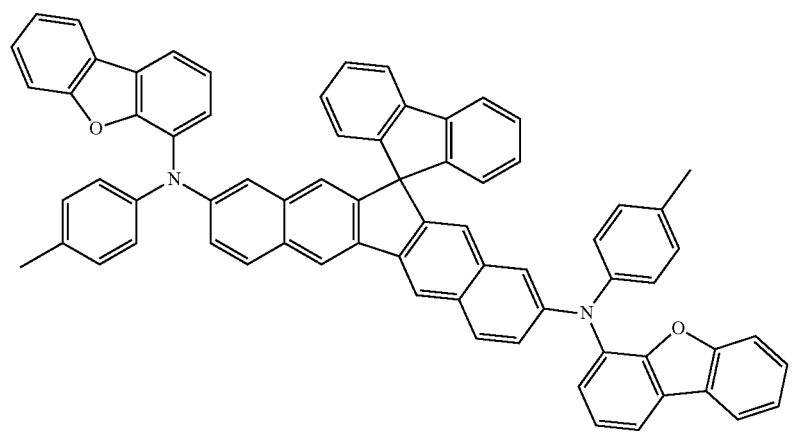
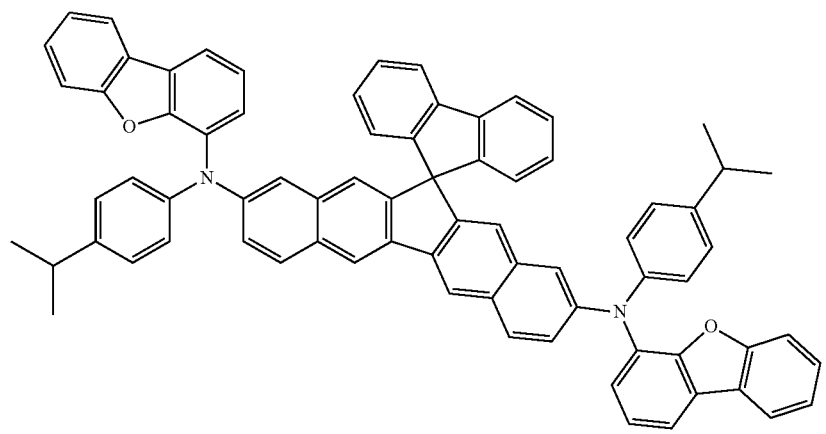

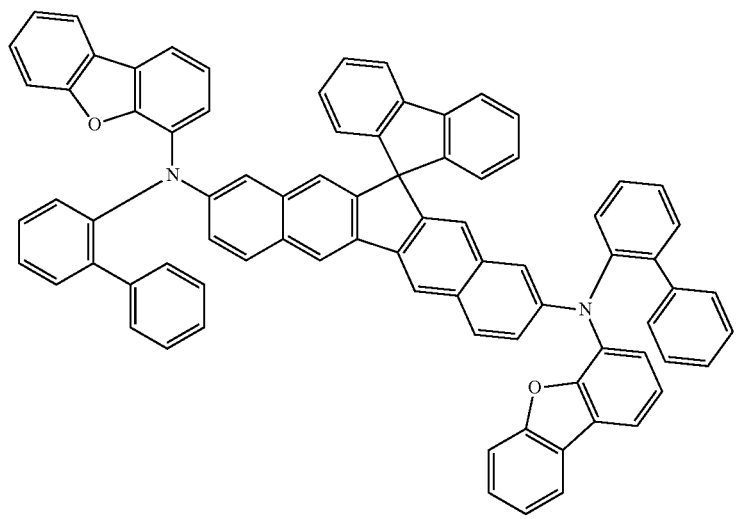
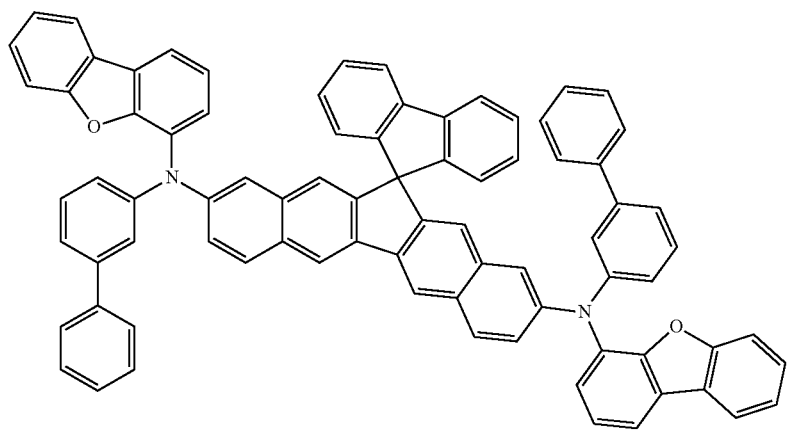
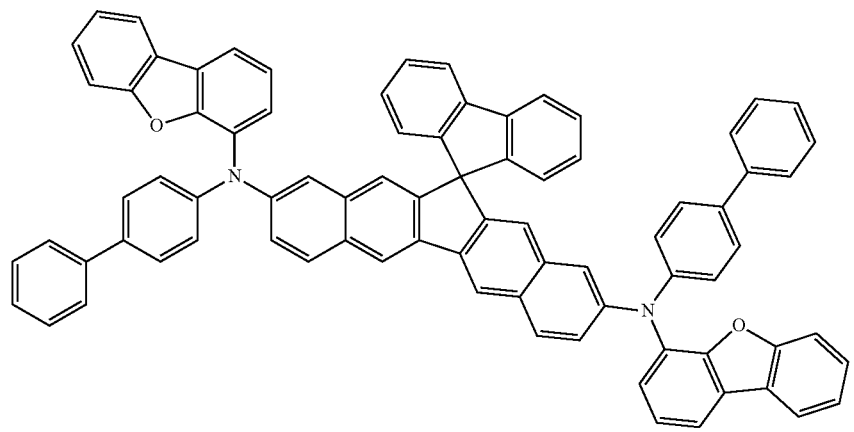

-continued
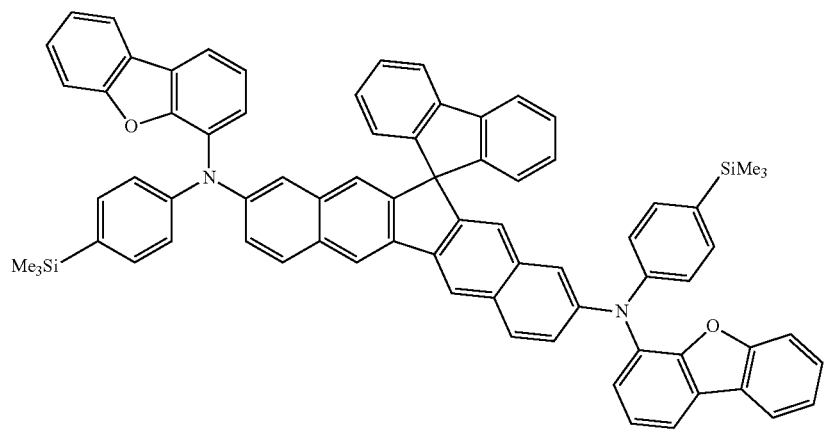
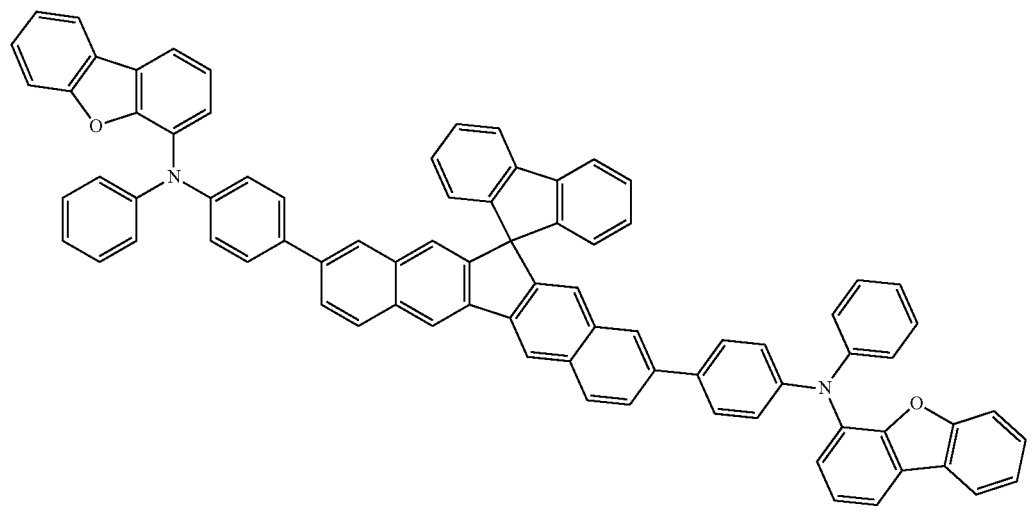
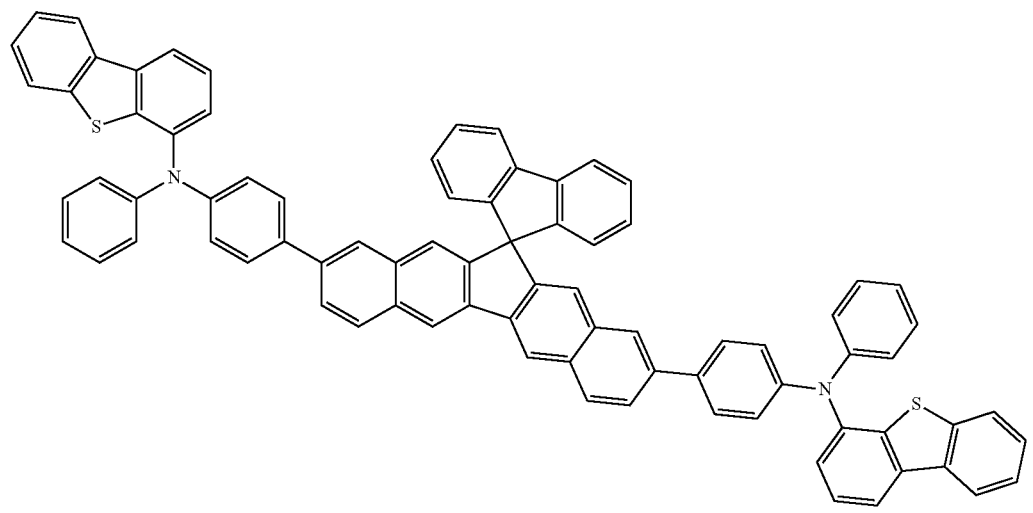

-continued
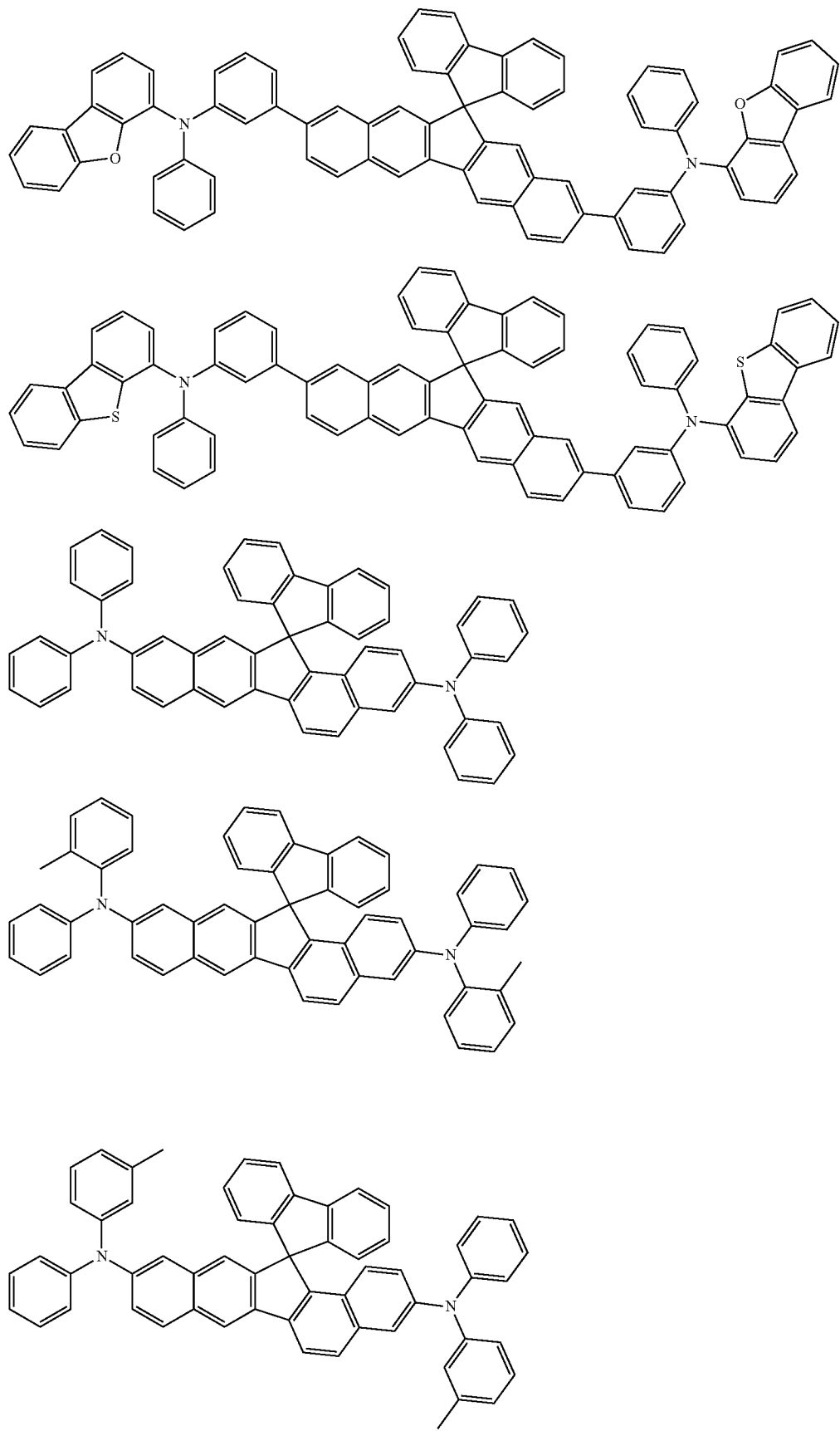

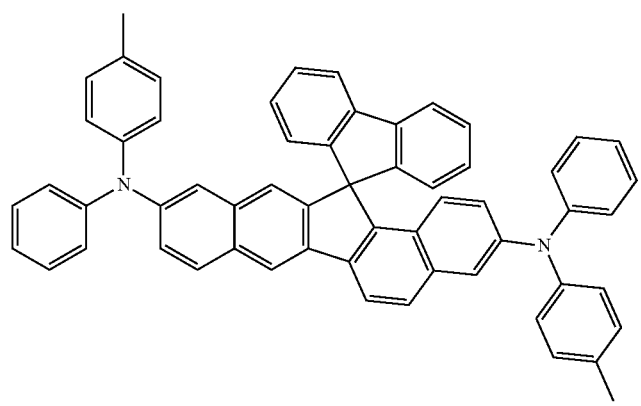
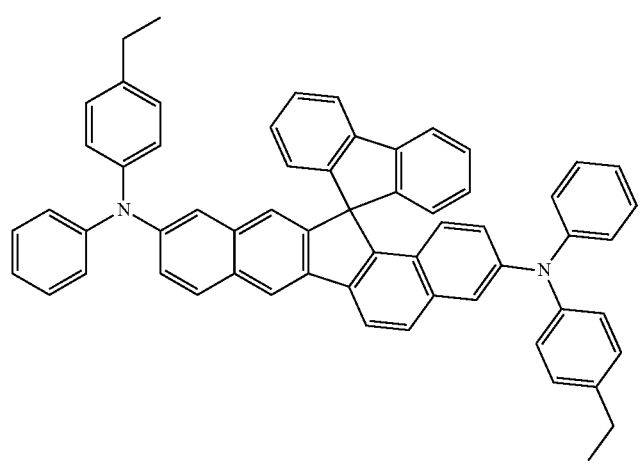
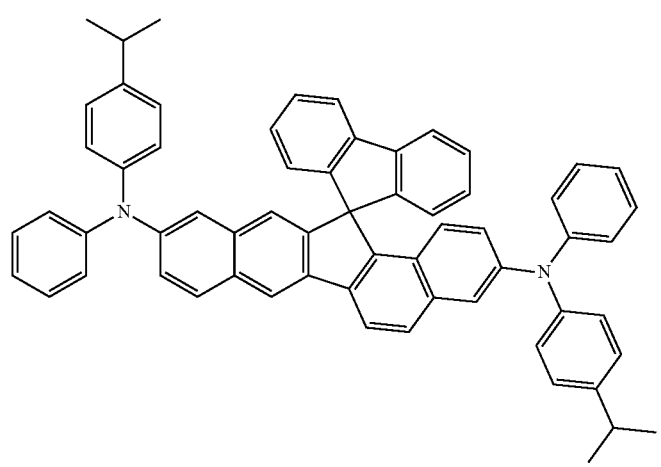

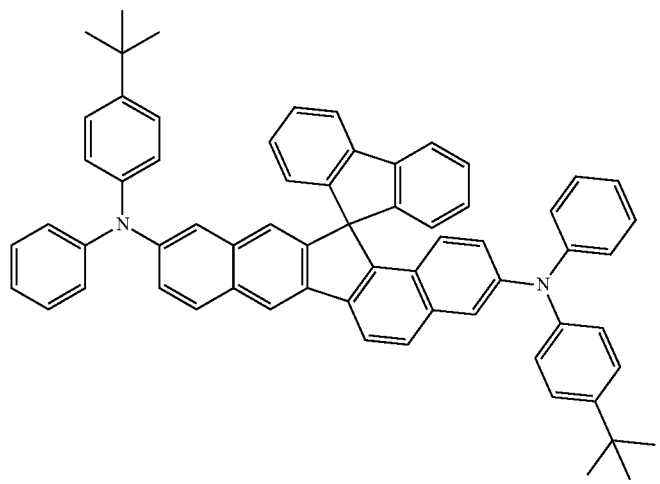 [SMILES: CC(C)(C)c1ccc(N(c2ccccc2)c2ccc3cc4c(cc3c2)C2(c3ccccc3-c3ccccc32)c2c-4ccc3cc(N(c4ccccc4)c4ccc(C(C)(C)C)cc4)ccc23)cc1]
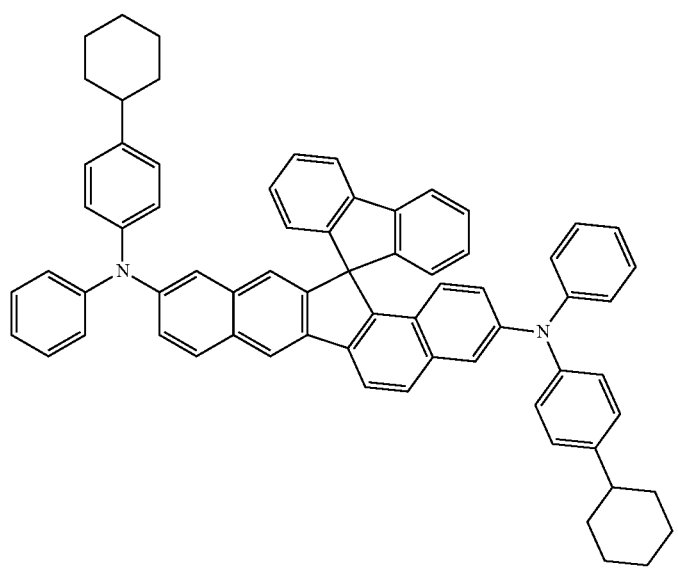
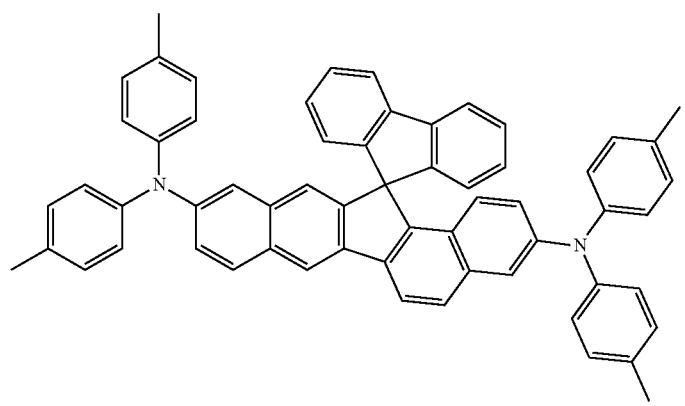

-continued
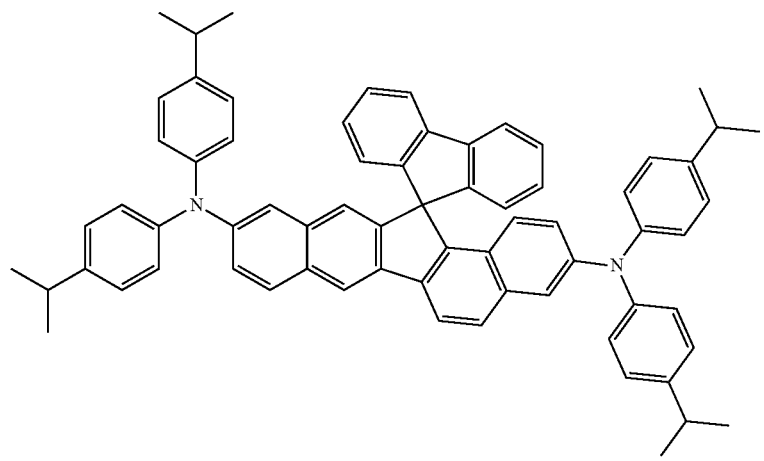
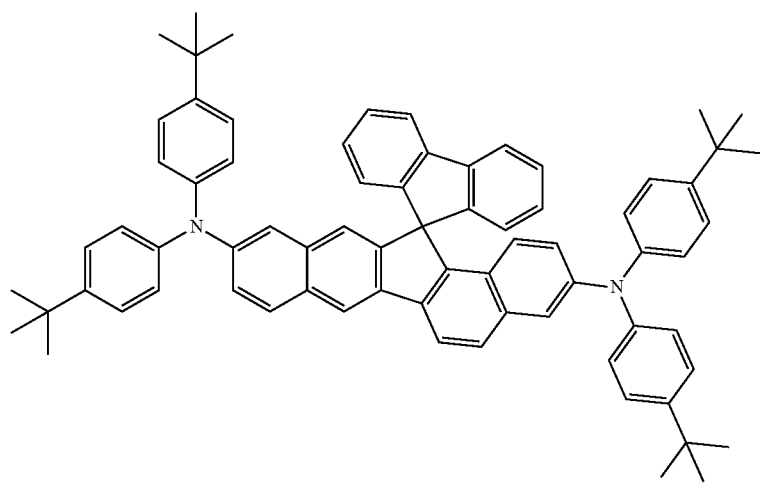
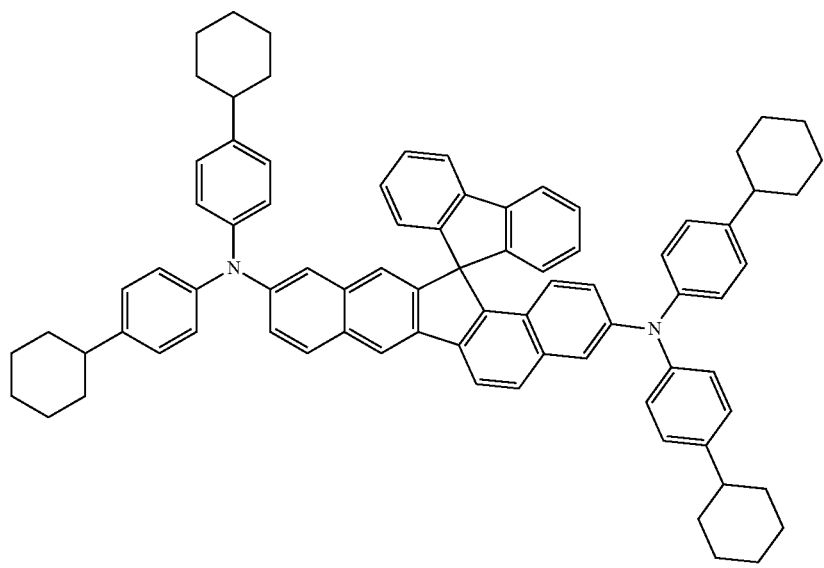

-continued
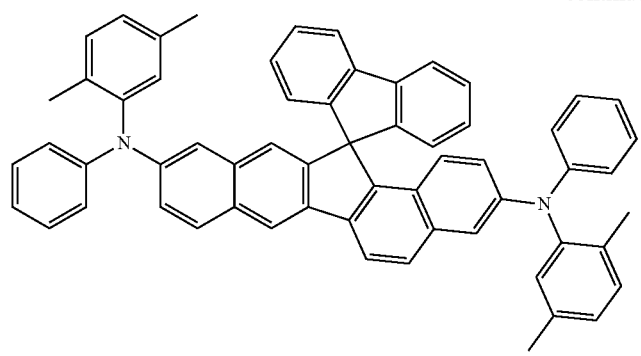
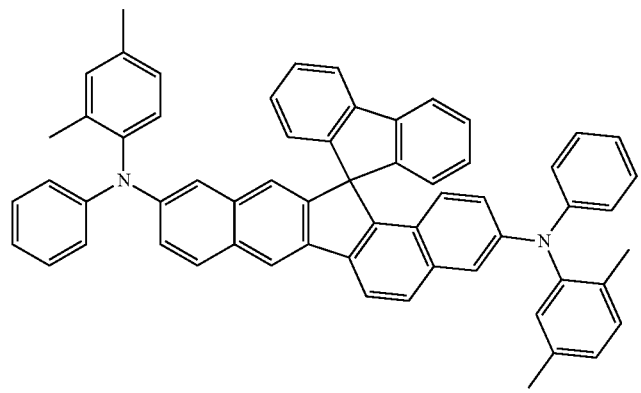
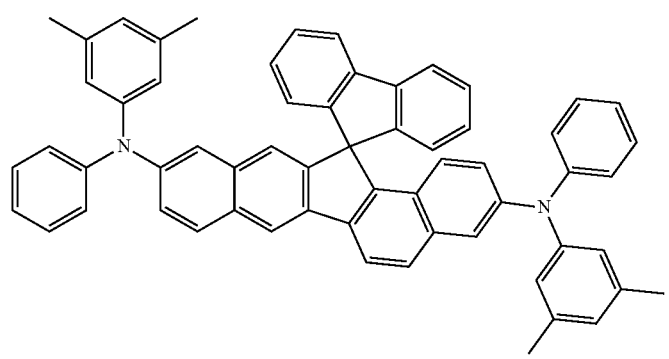
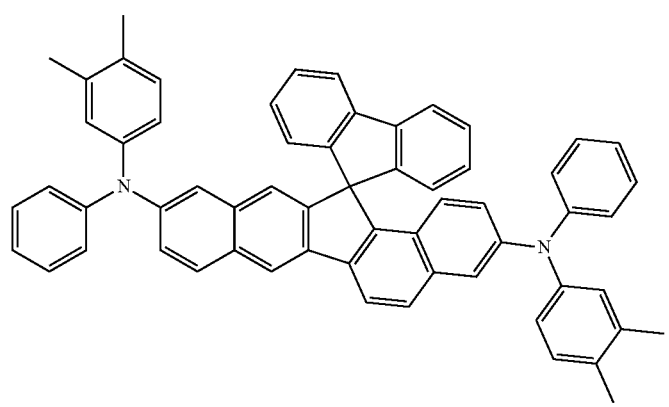

-continued
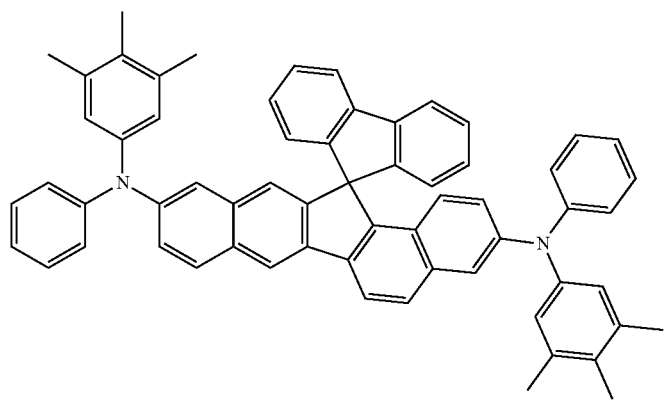
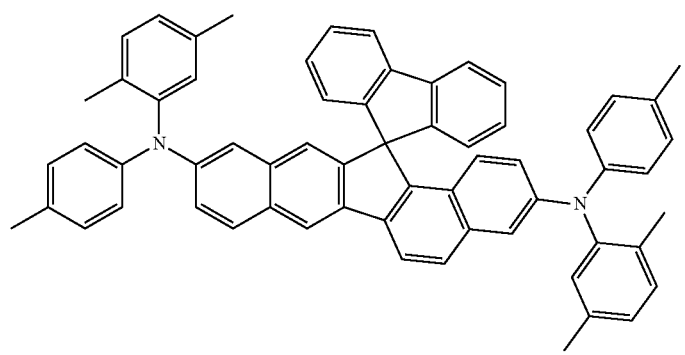
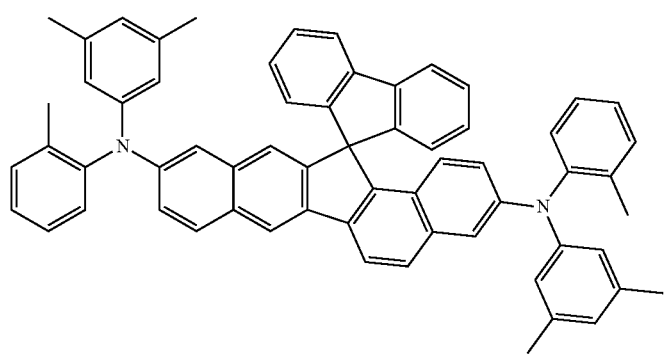
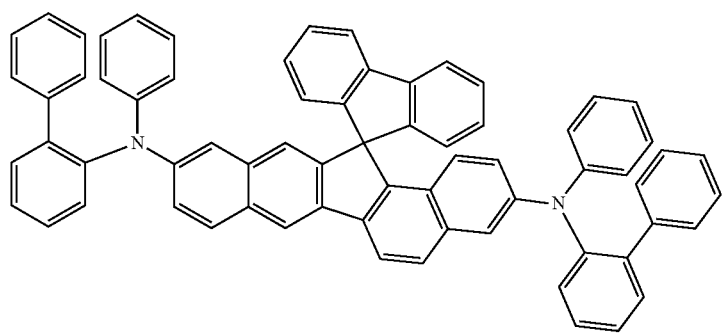

-continued
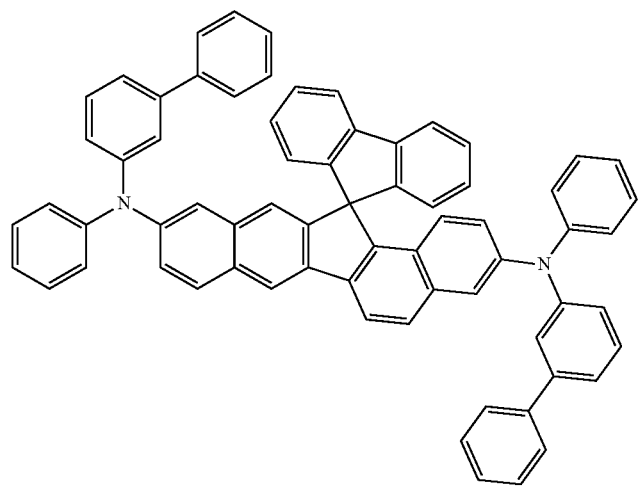
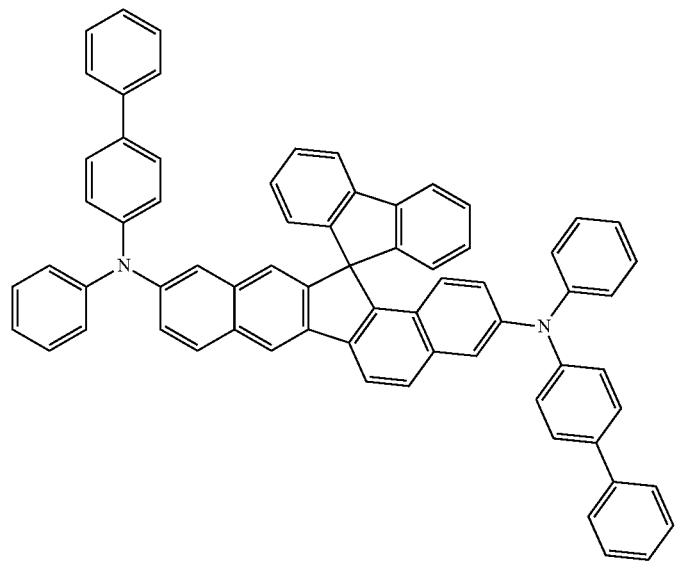
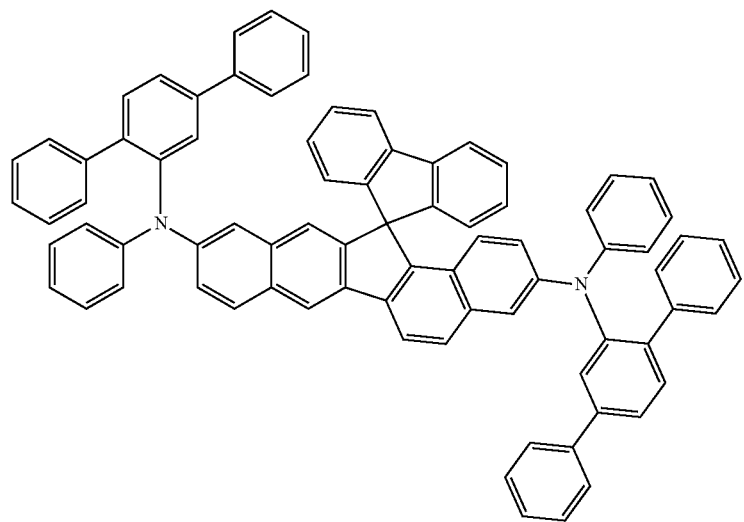

-continued
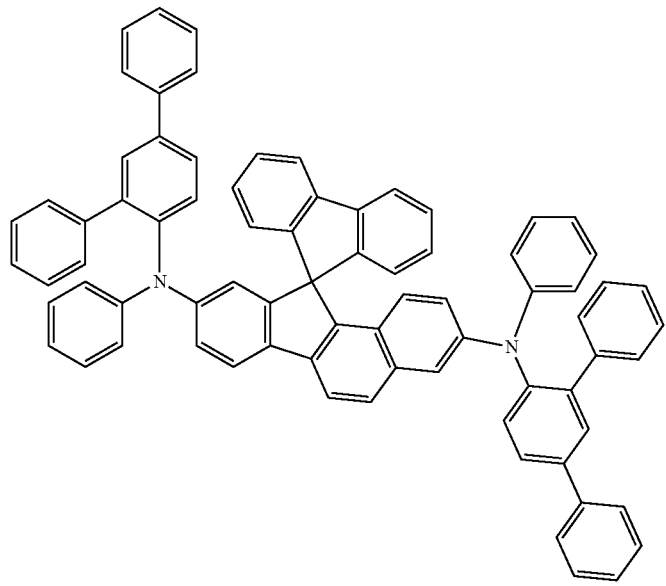
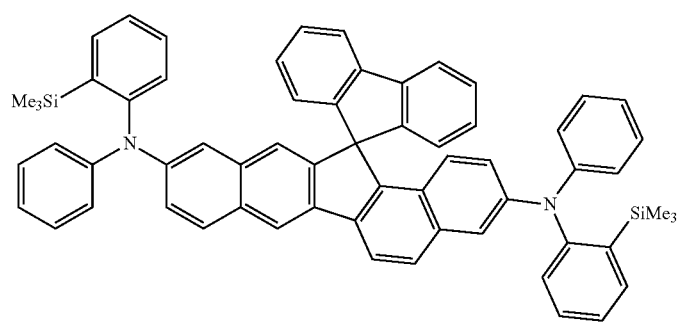
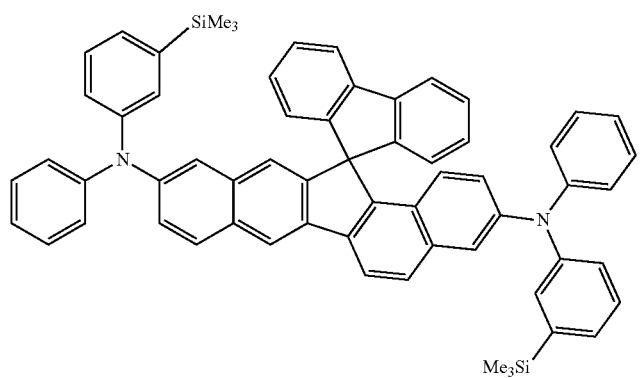
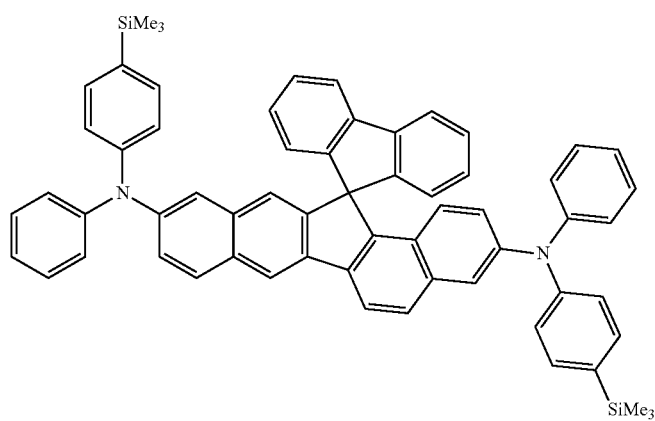

-continued
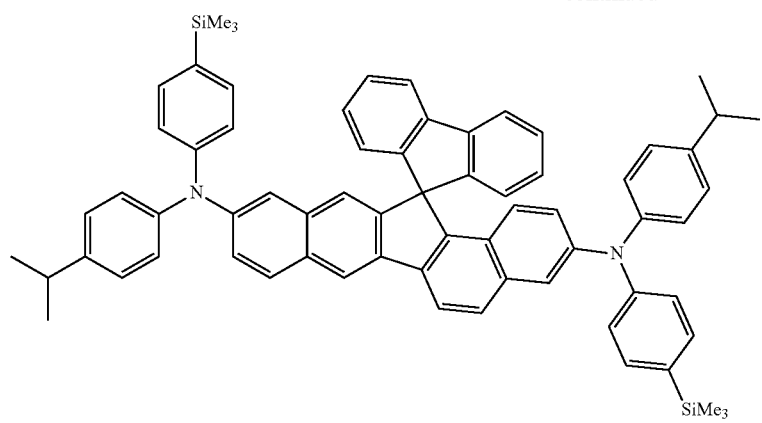
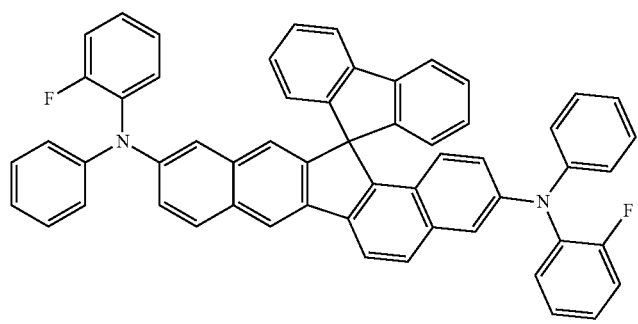
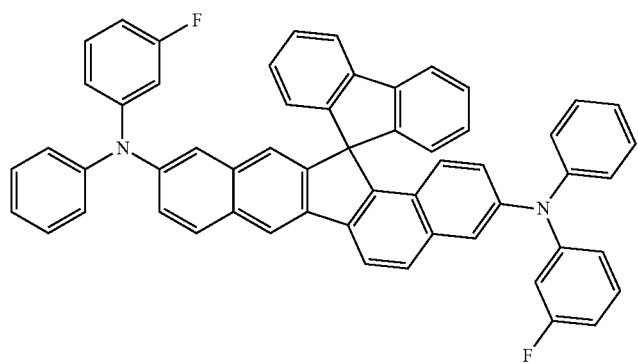
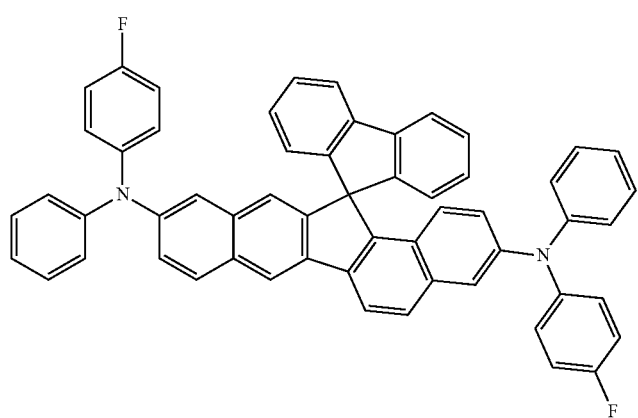

-continued
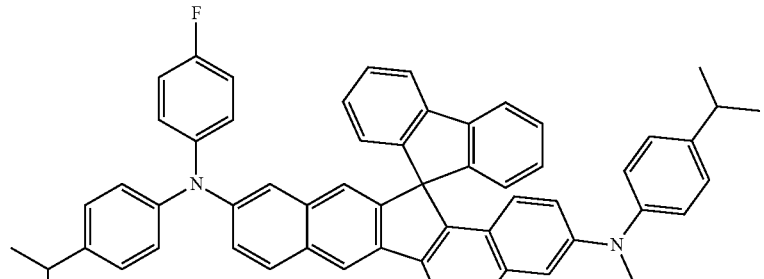
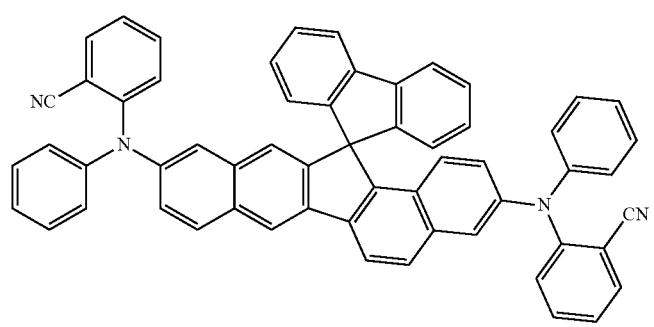
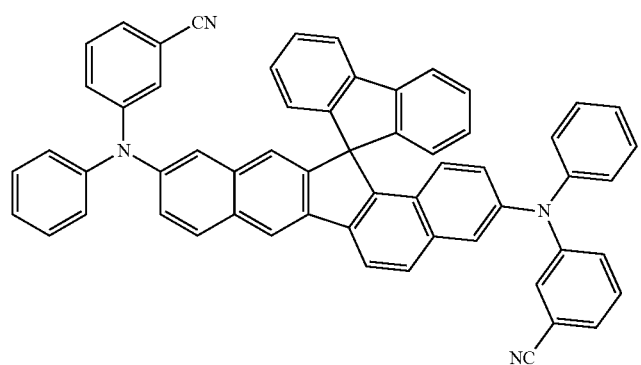
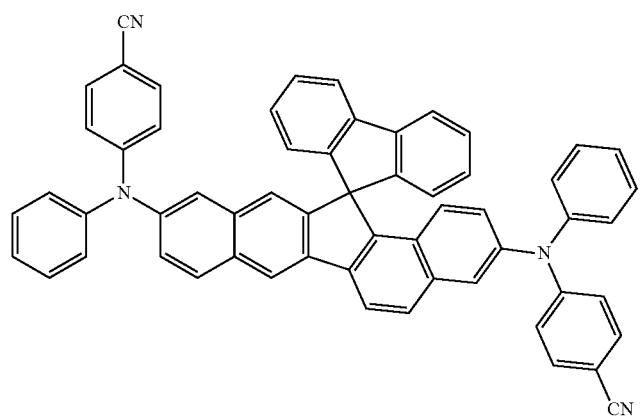

-continued
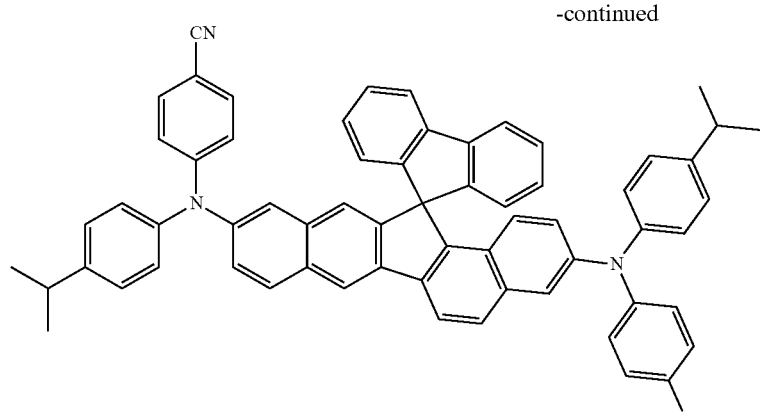
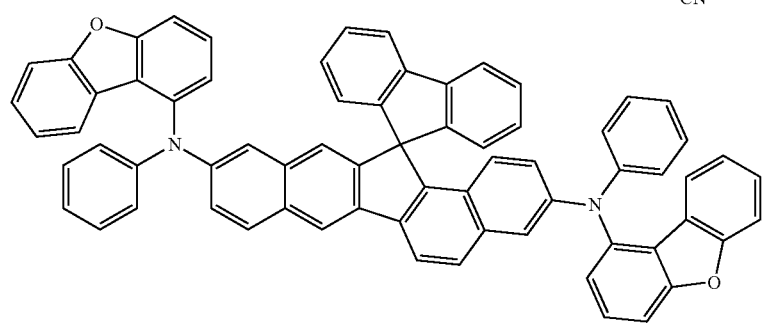
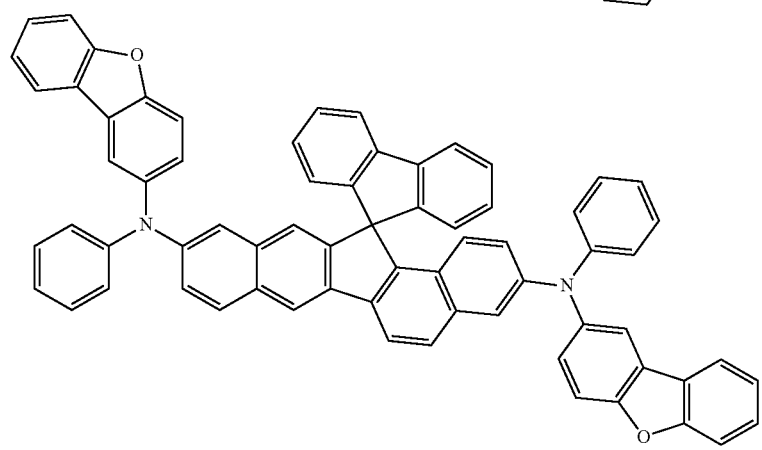
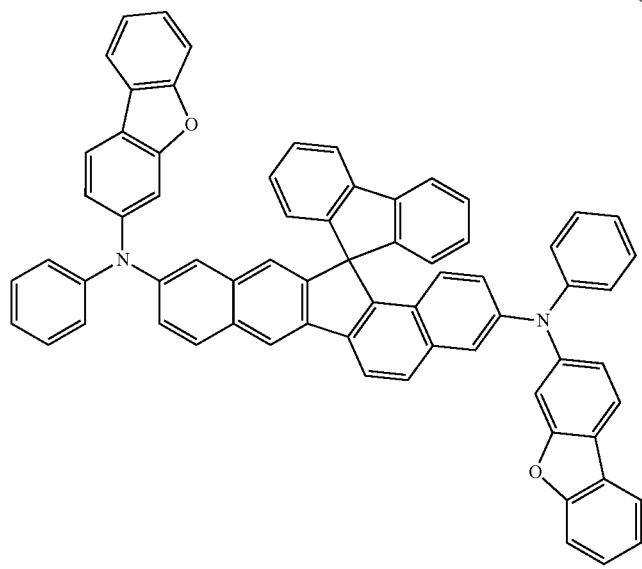

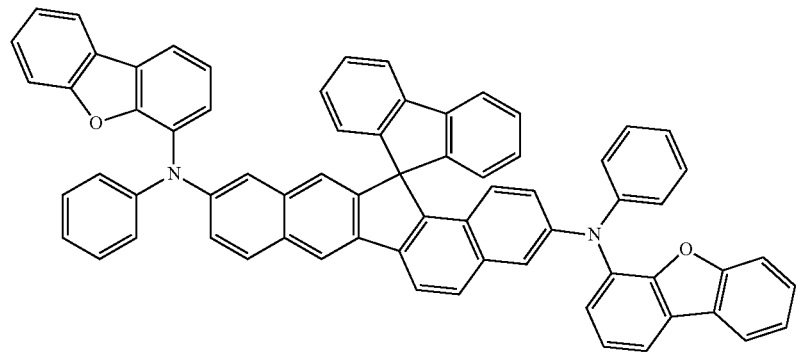
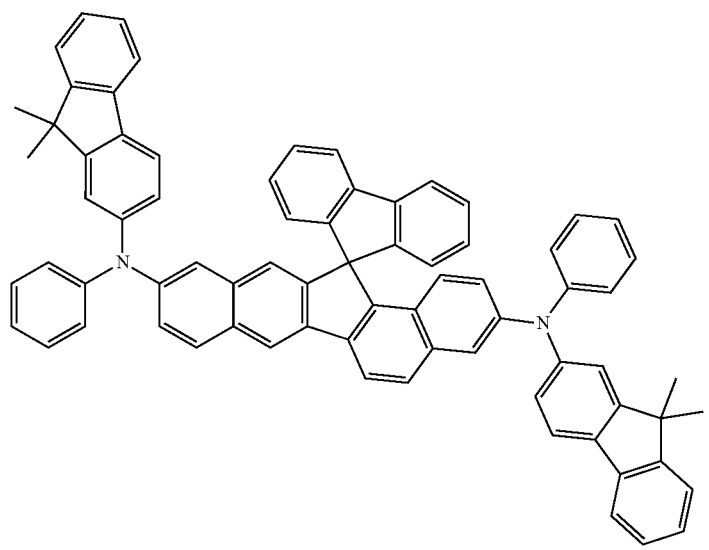
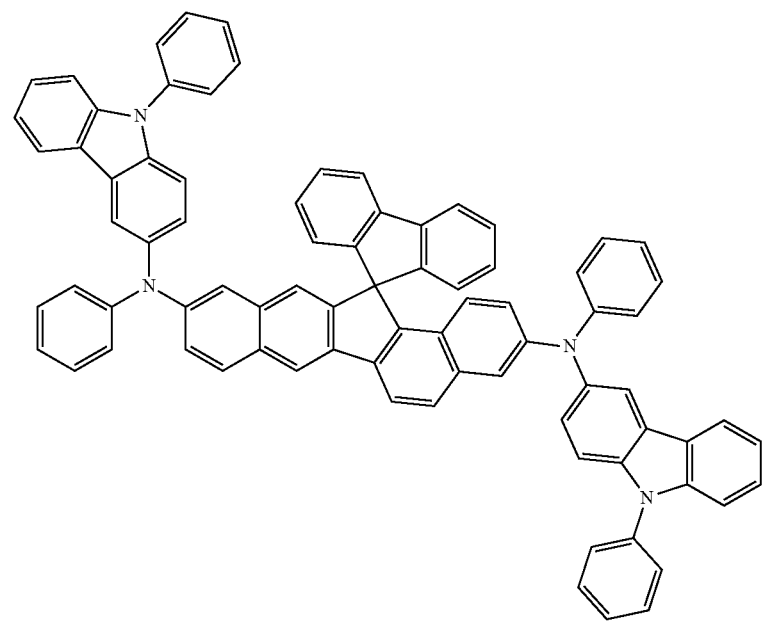

-continued
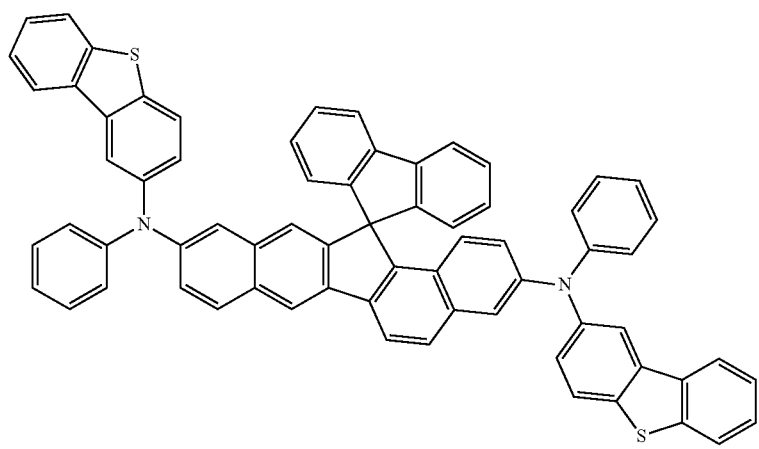
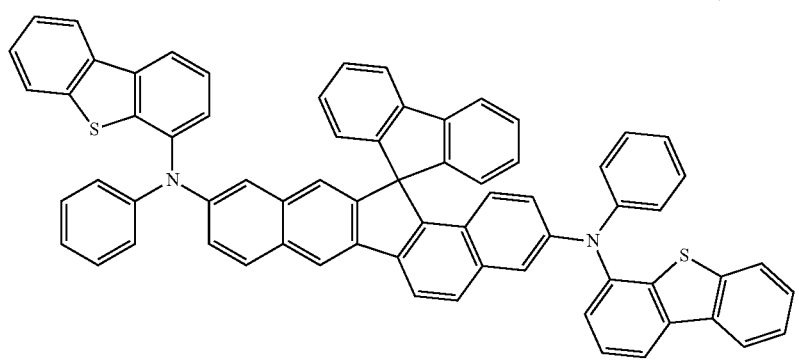
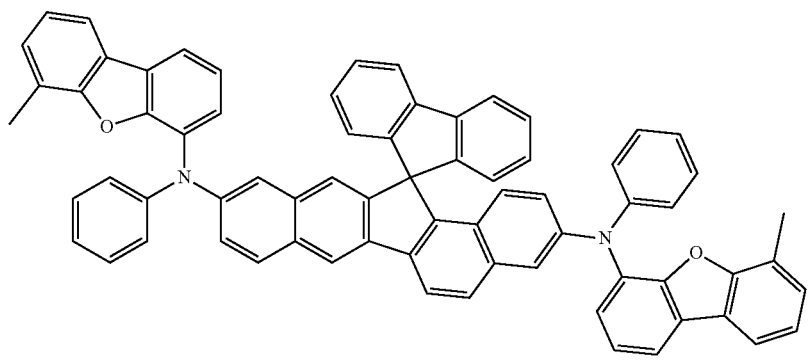
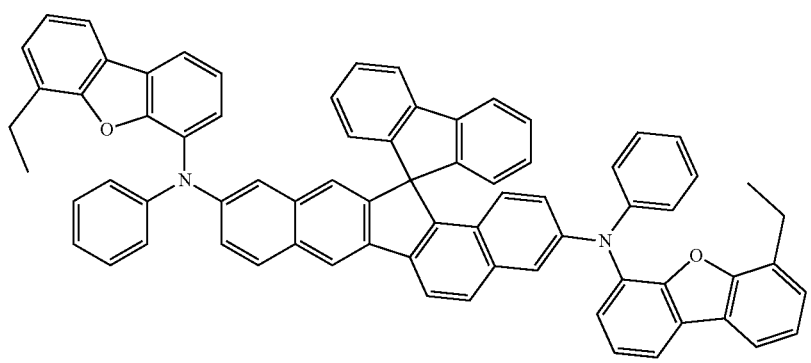

-continued
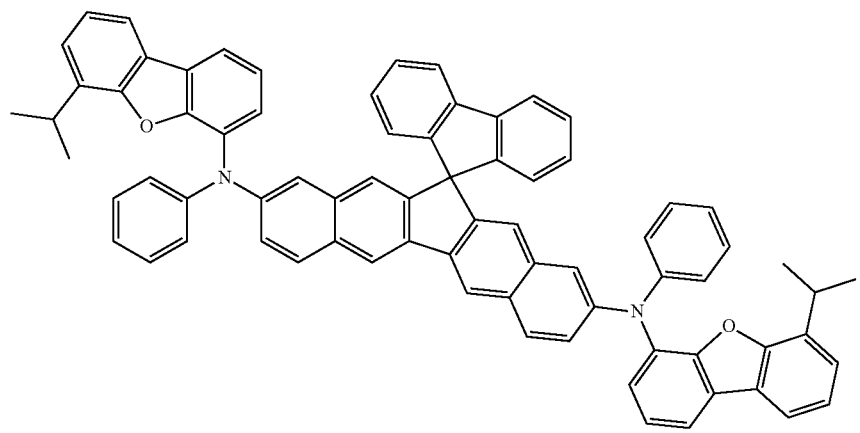
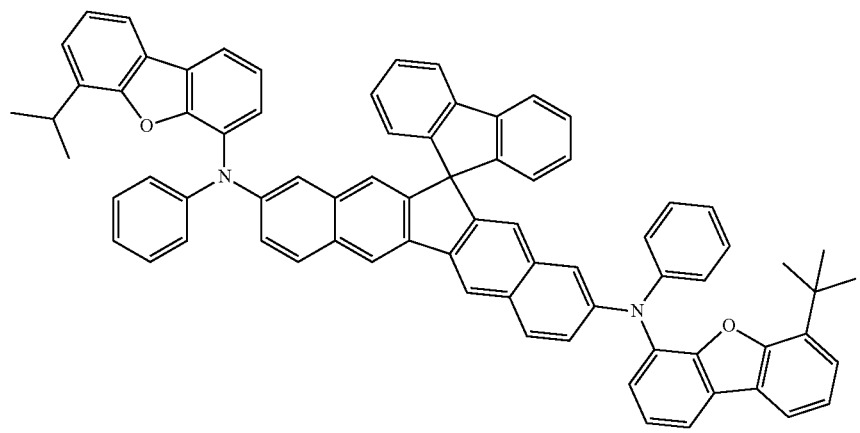
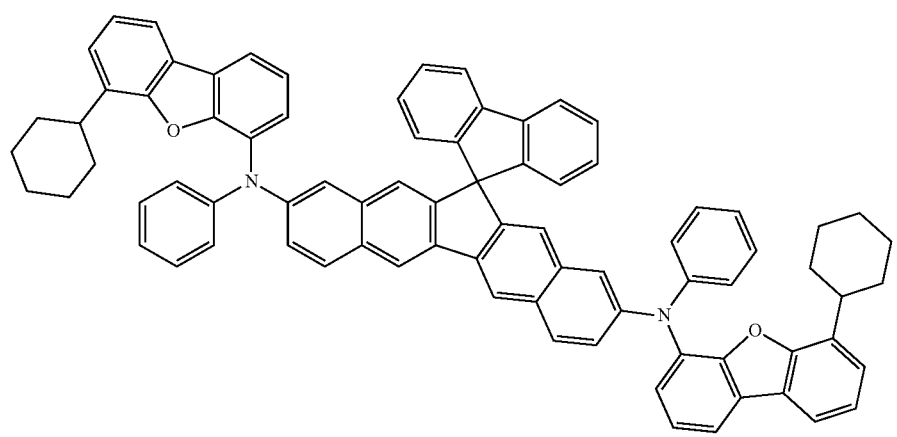
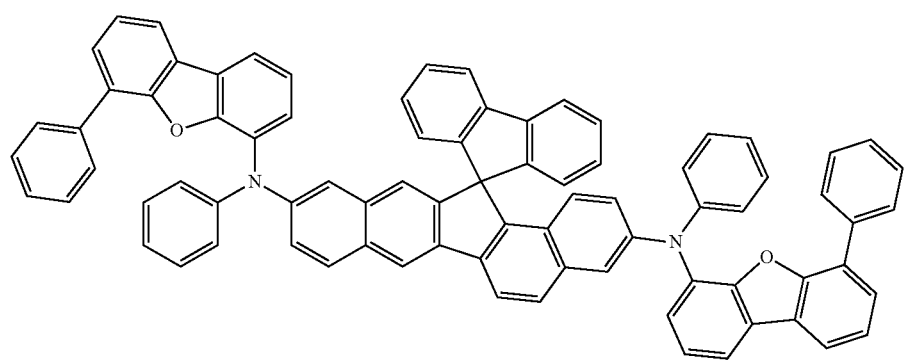

-continued
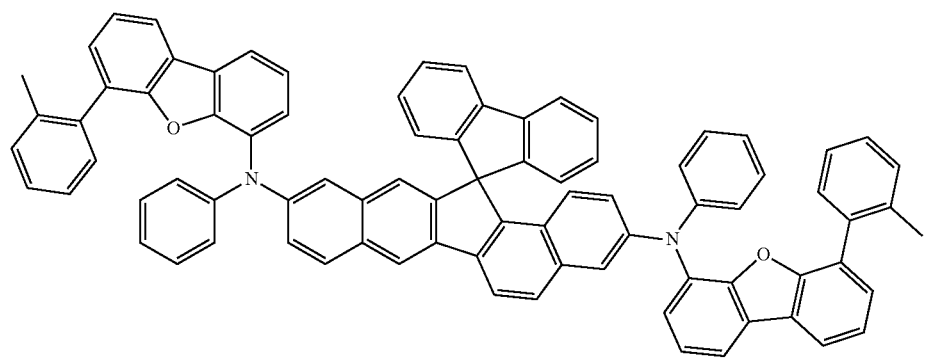
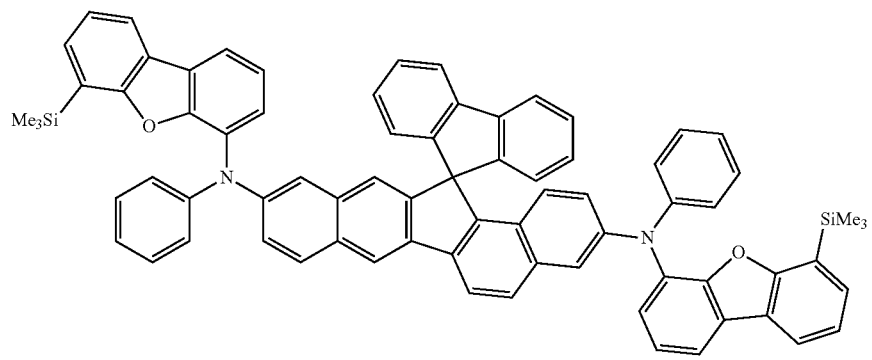
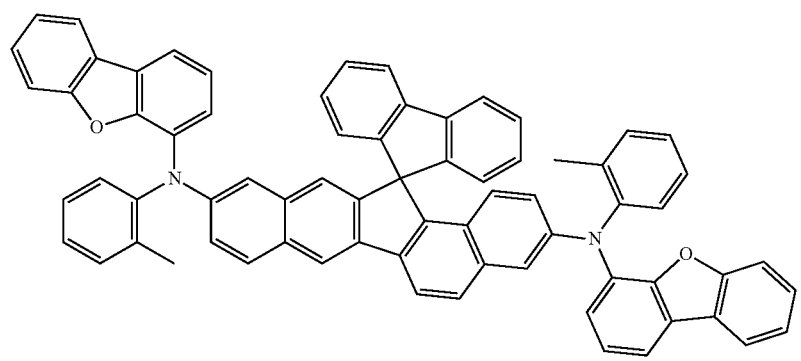
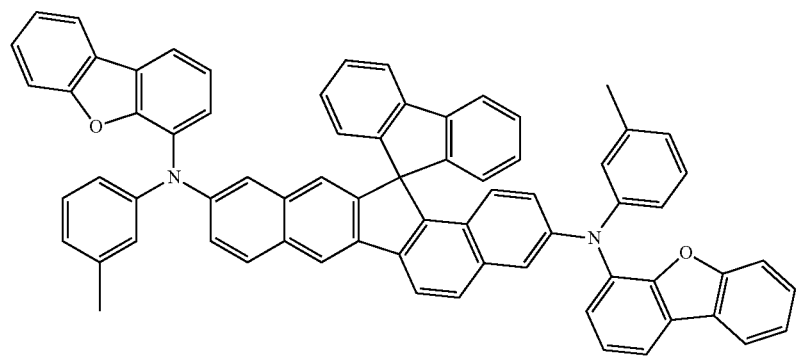

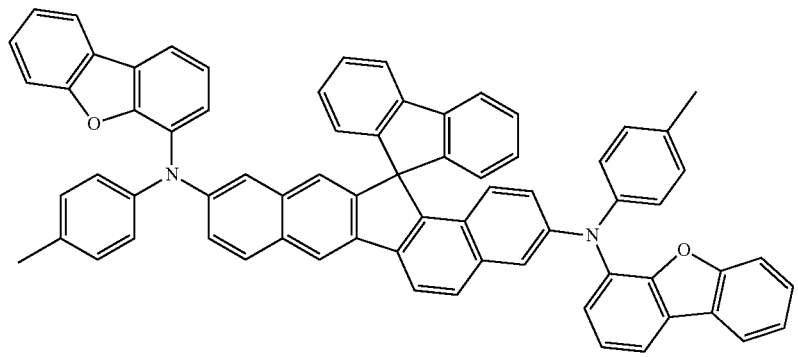
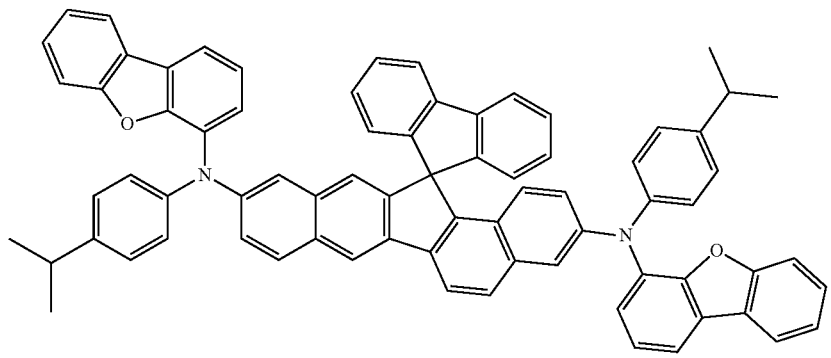
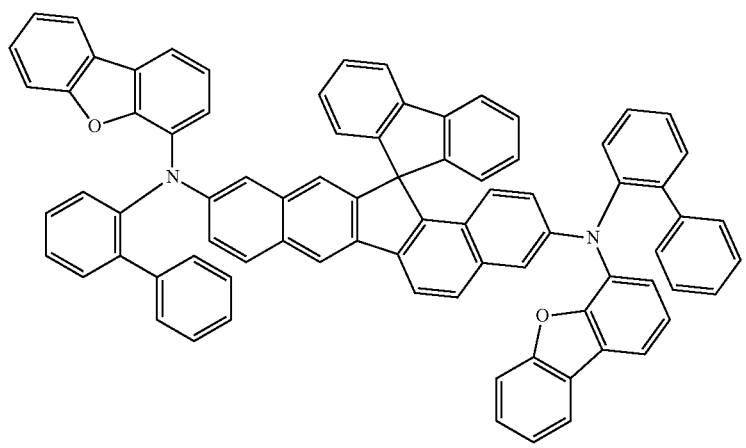
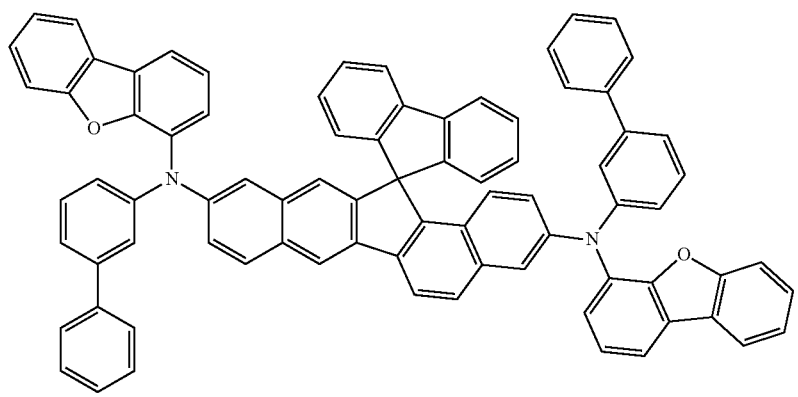

-continued
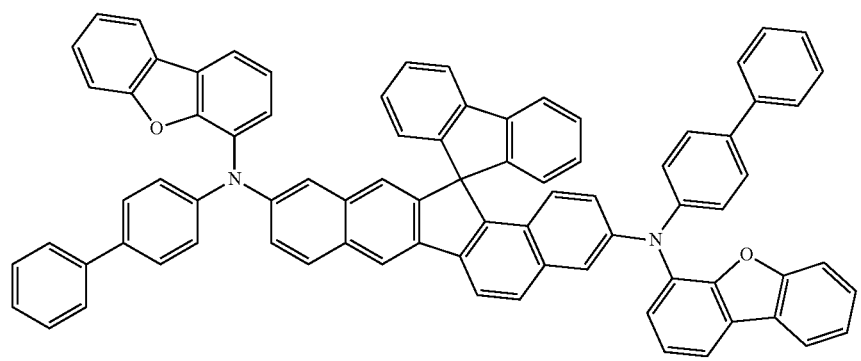
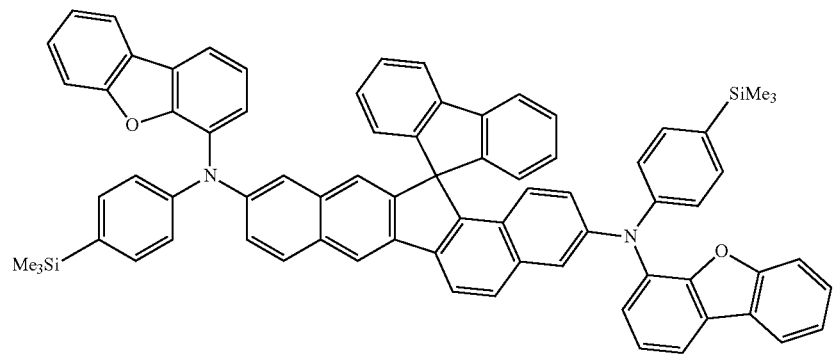
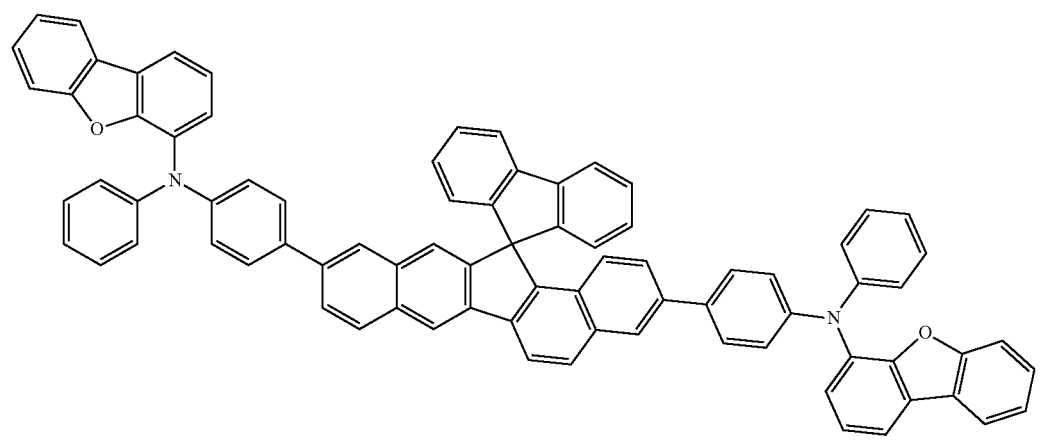
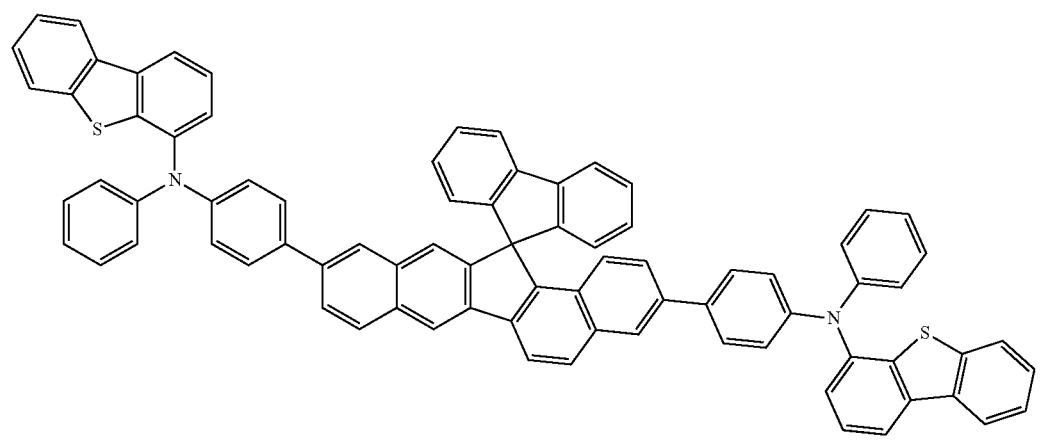

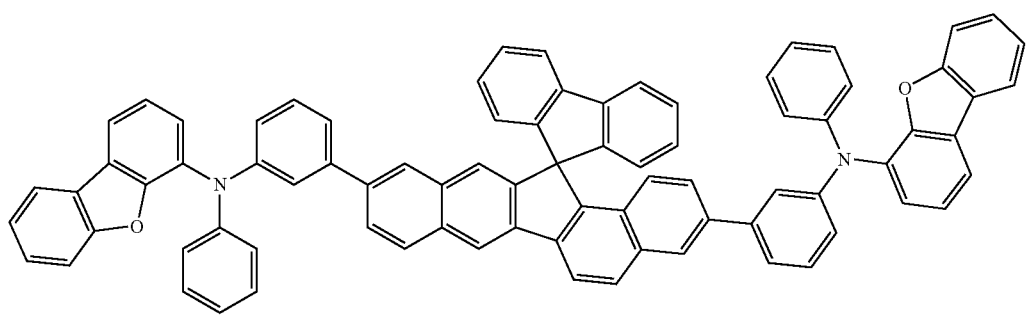
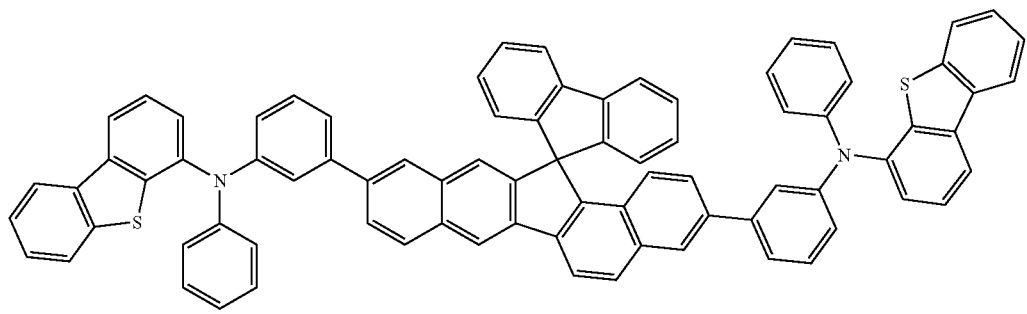
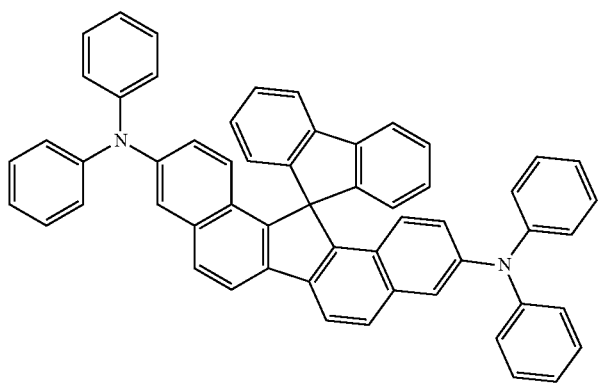
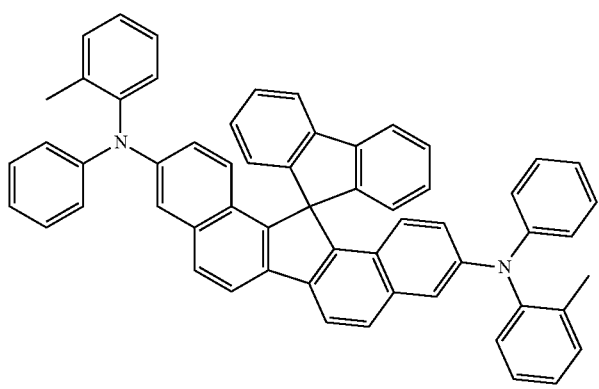

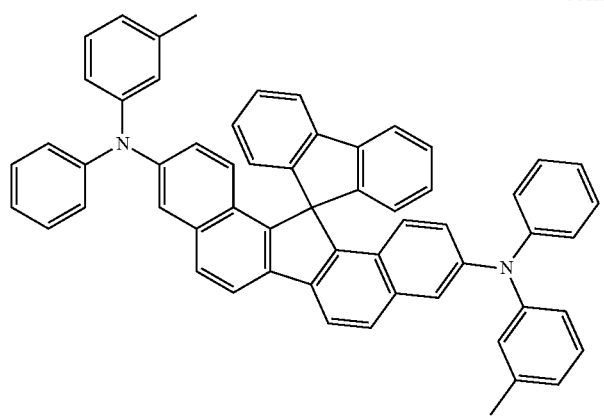
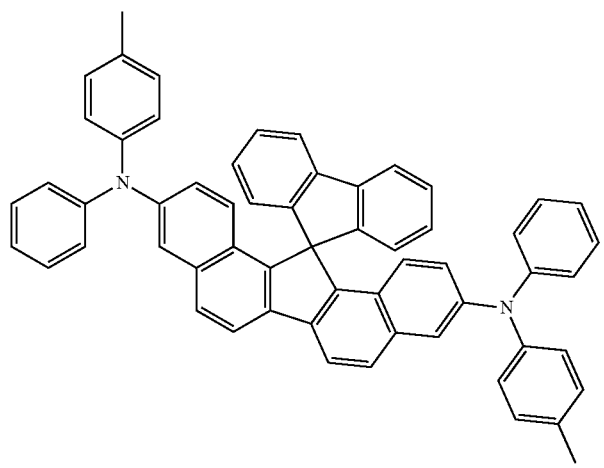
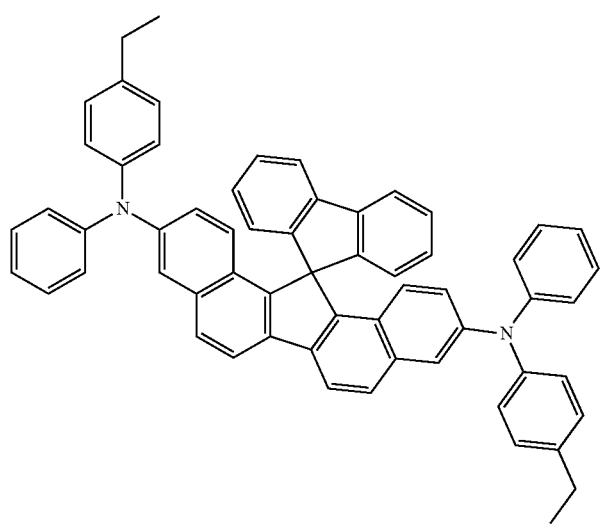

-continued
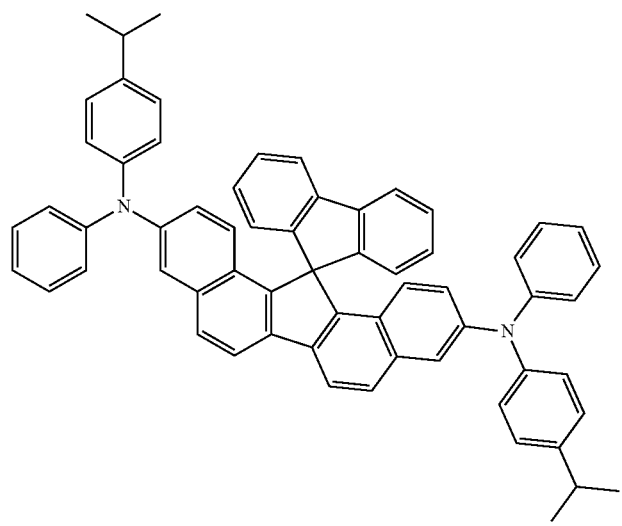
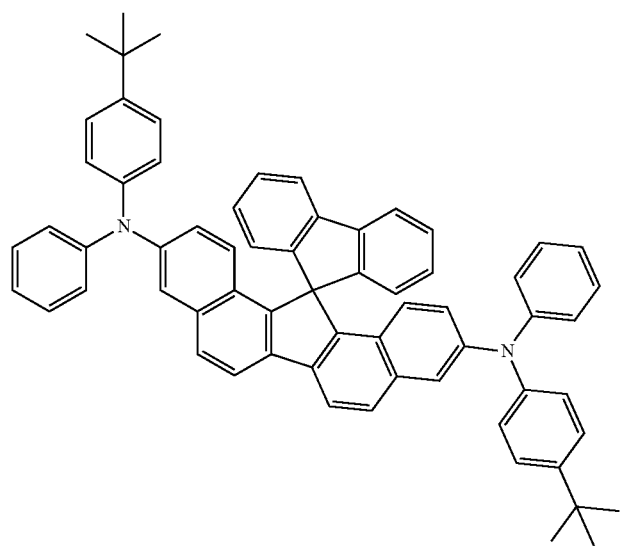 [SMILES: CC(C)(C)c1ccc(N(c2ccccc2)c2ccc3c4c(ccc3c2)-c2ccc3cc(N(c5ccccc5)c5ccc(C(C)(C)C)cc5)ccc3c2C42c3ccccc3-c3ccccc32)cc1]
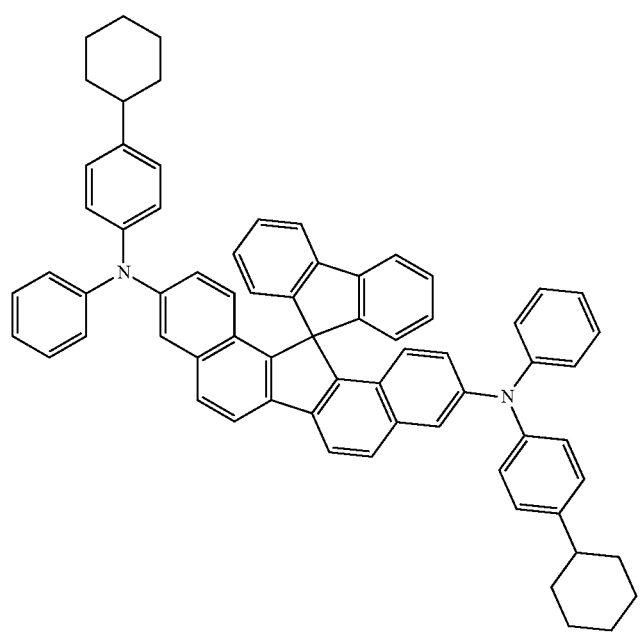

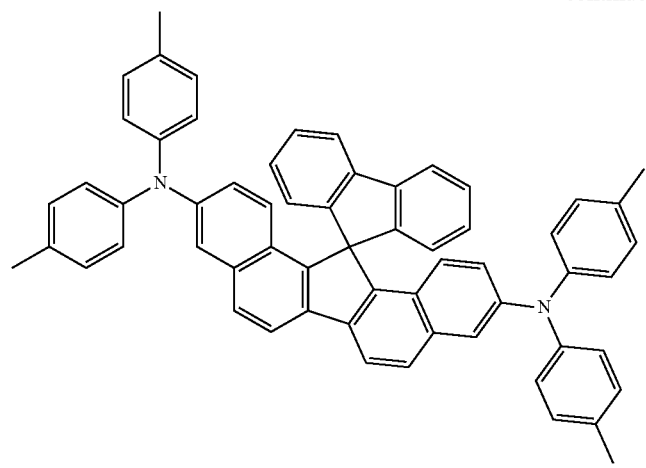
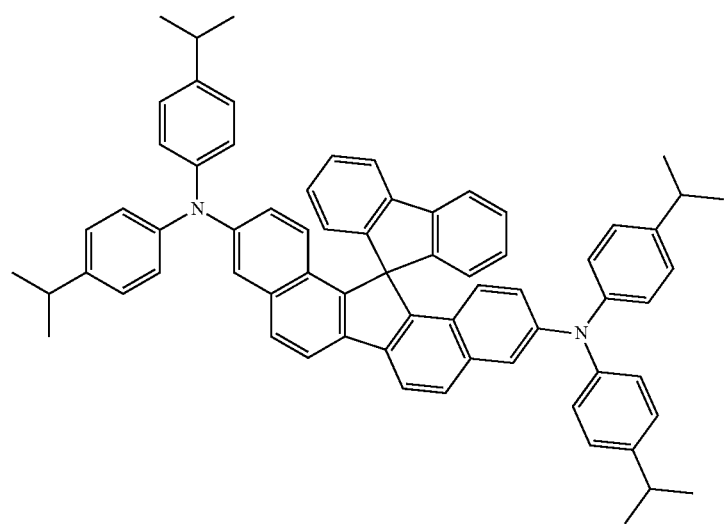
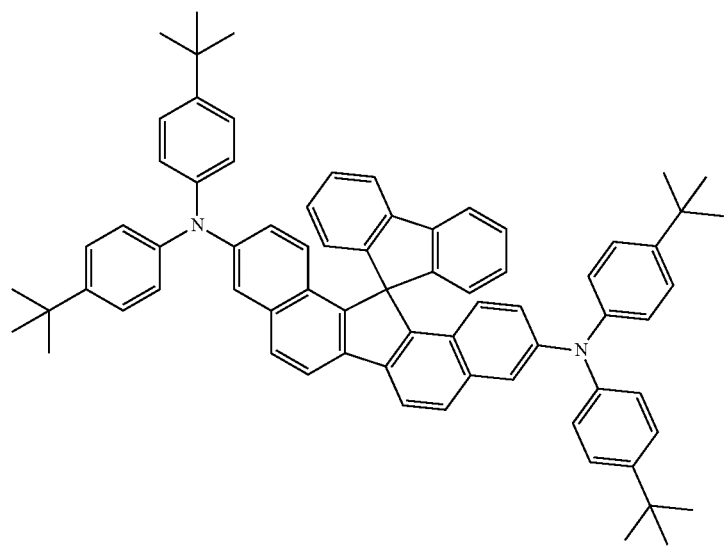

-continued
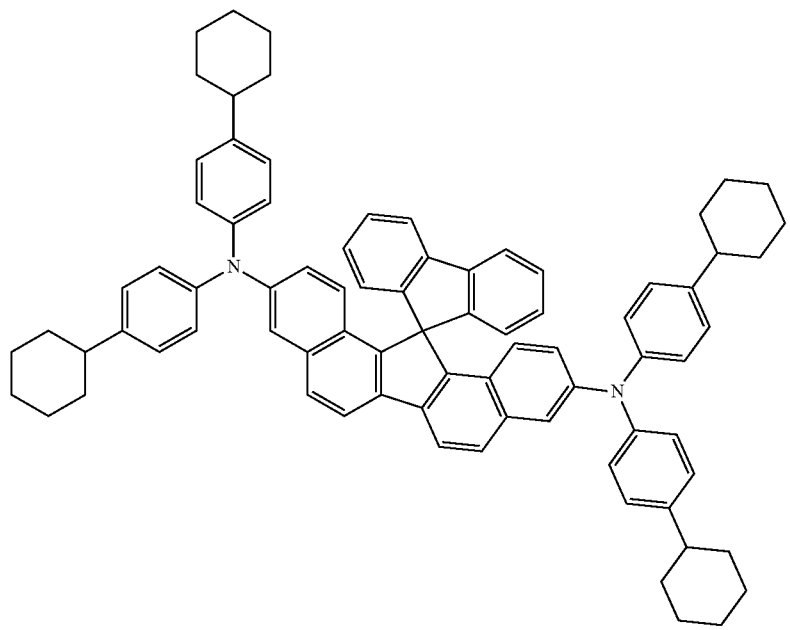
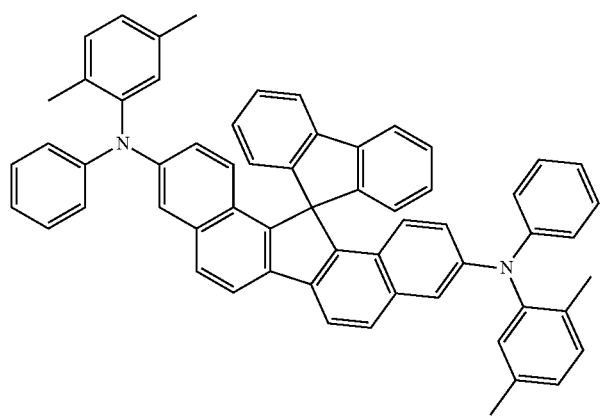
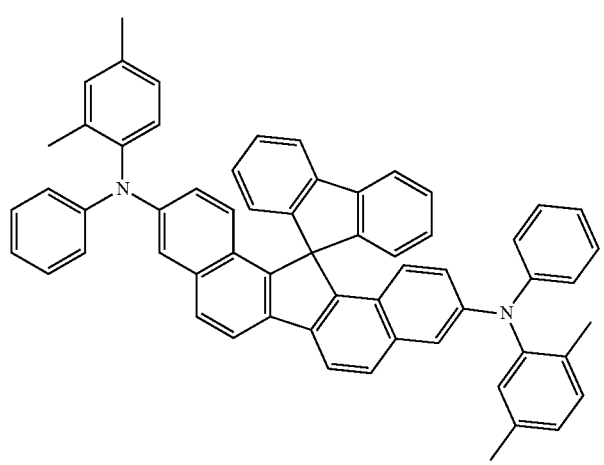

-continued
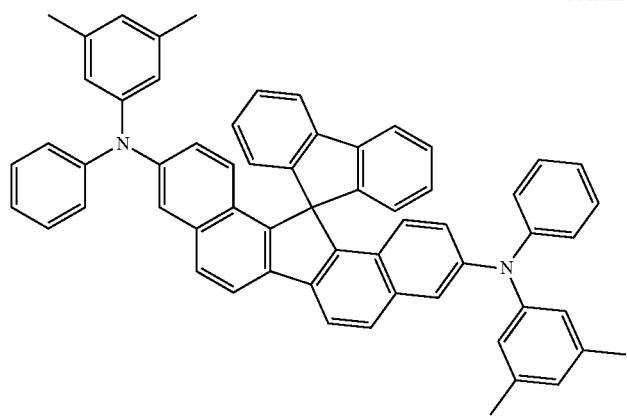
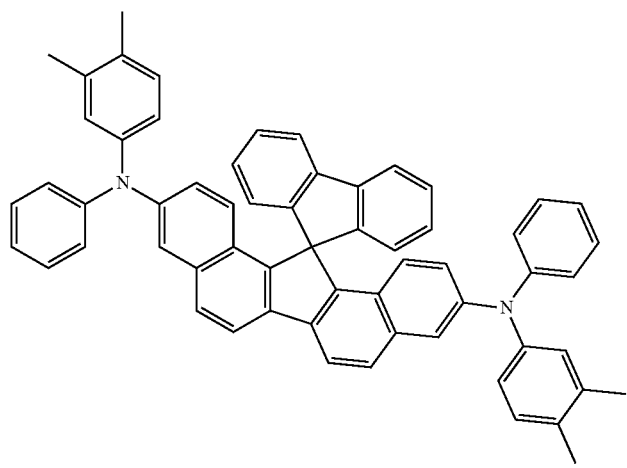
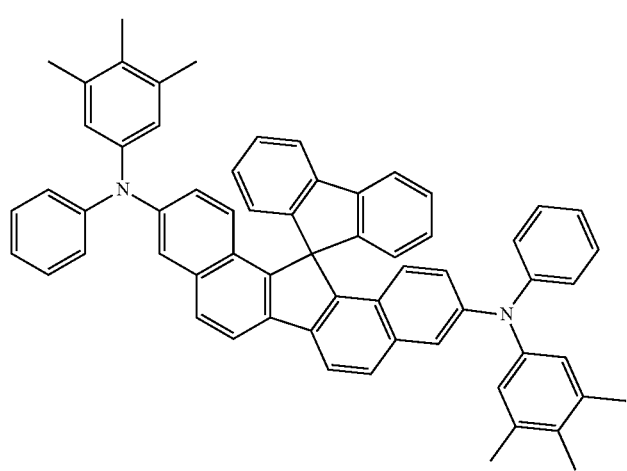

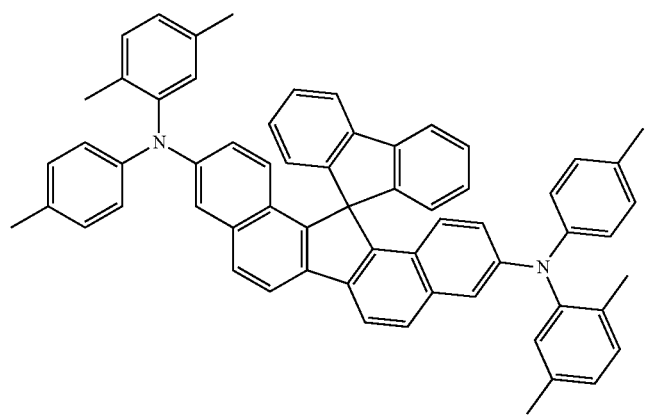
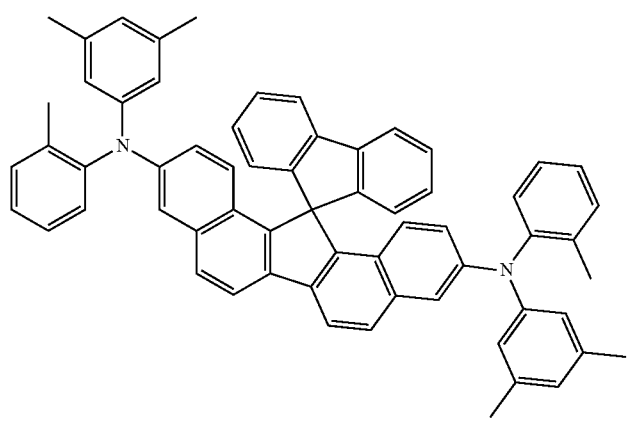
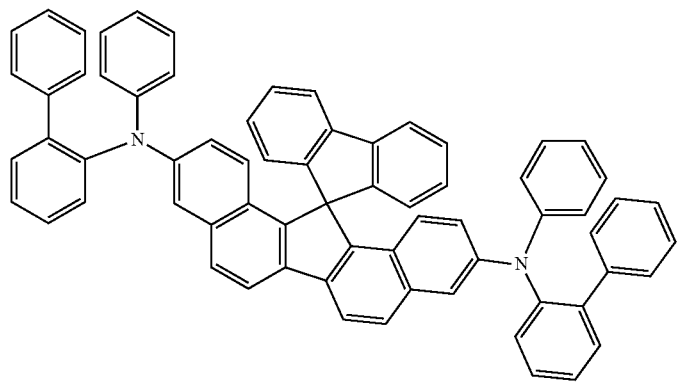

-continued
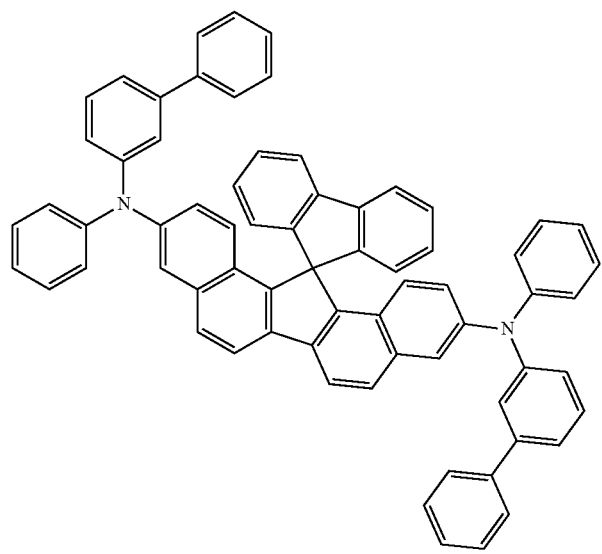
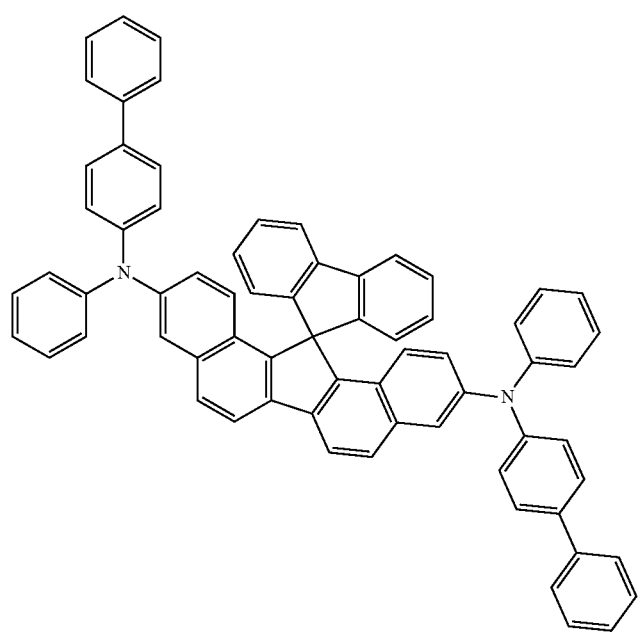

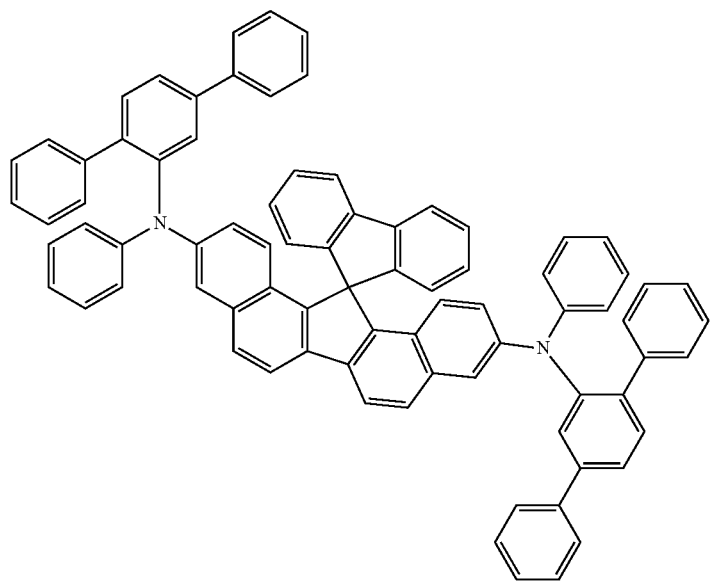
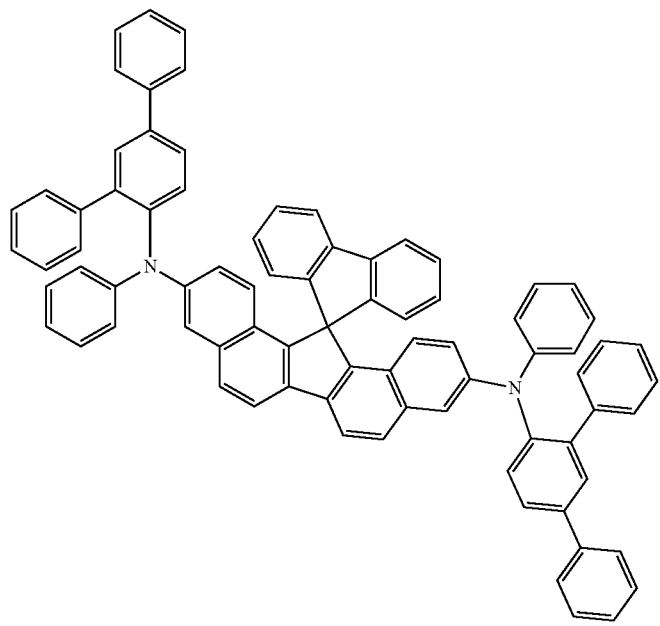
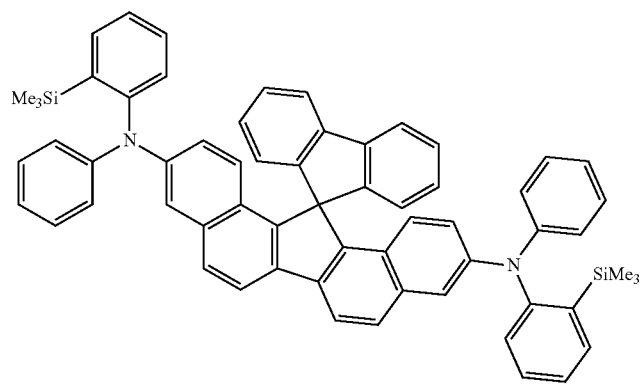

-continued
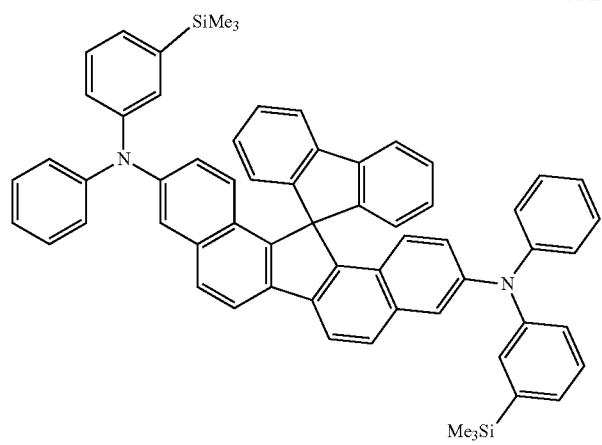
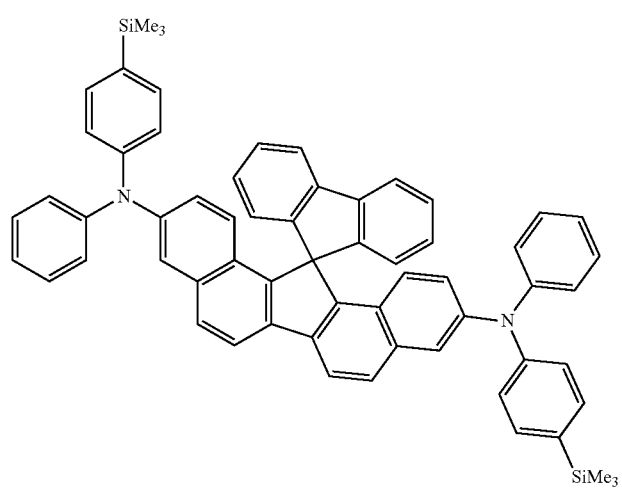
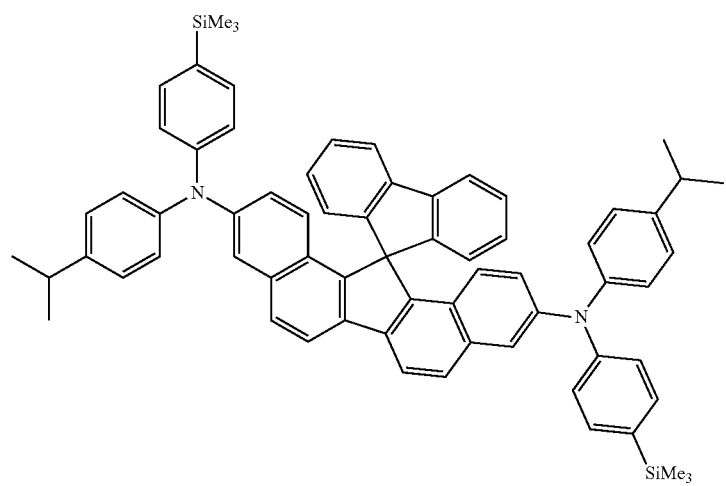

-continued
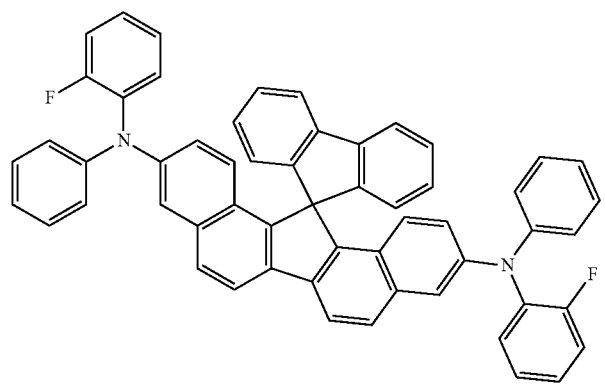
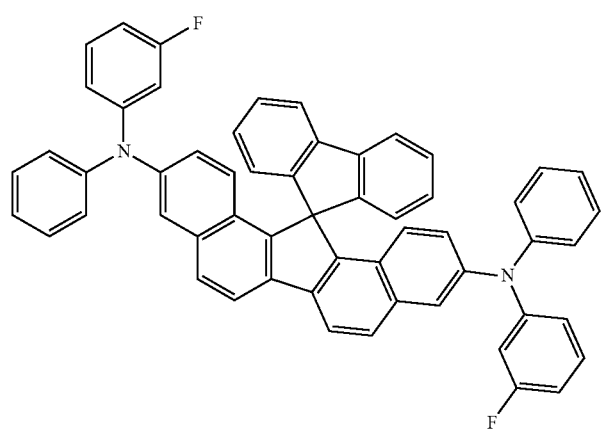
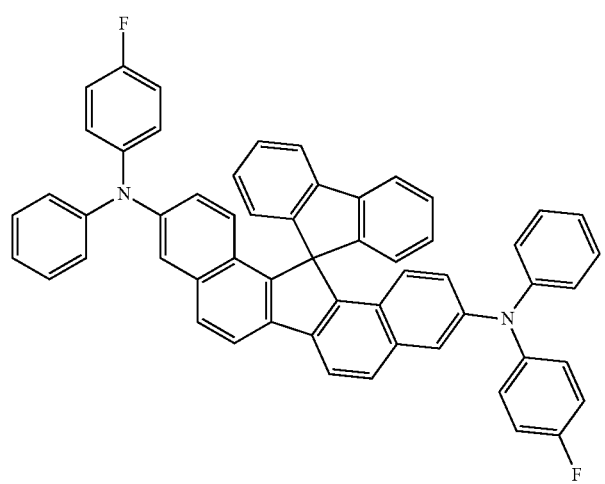

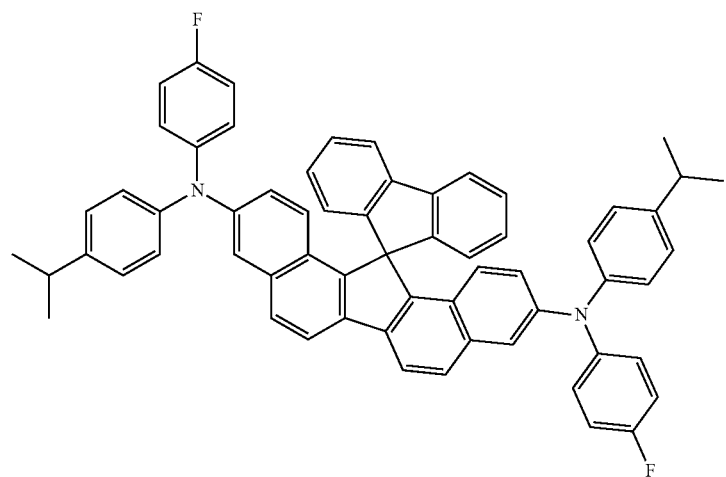
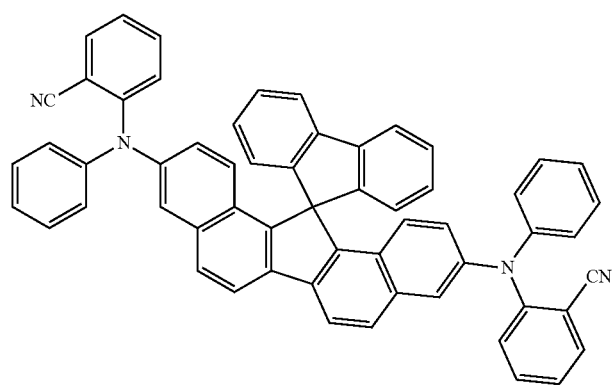
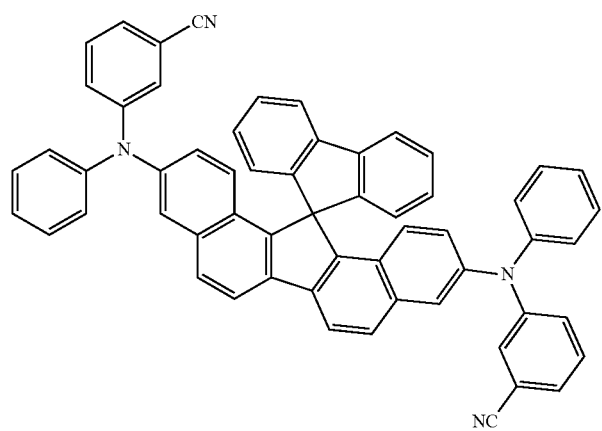

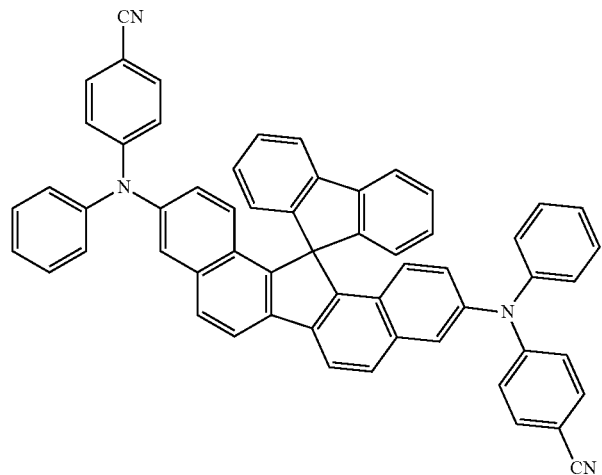
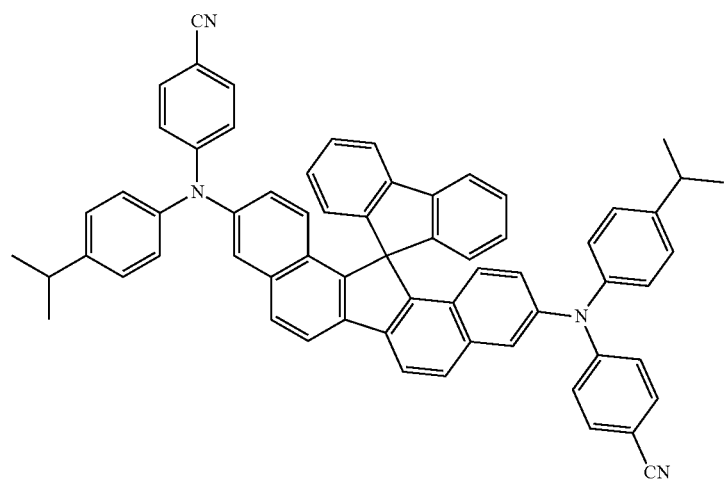
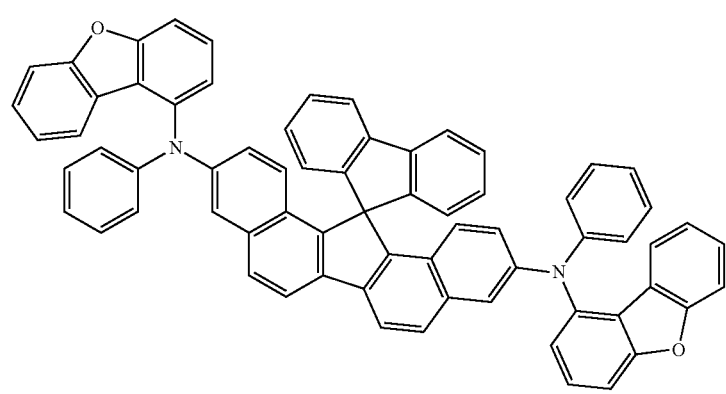

-continued
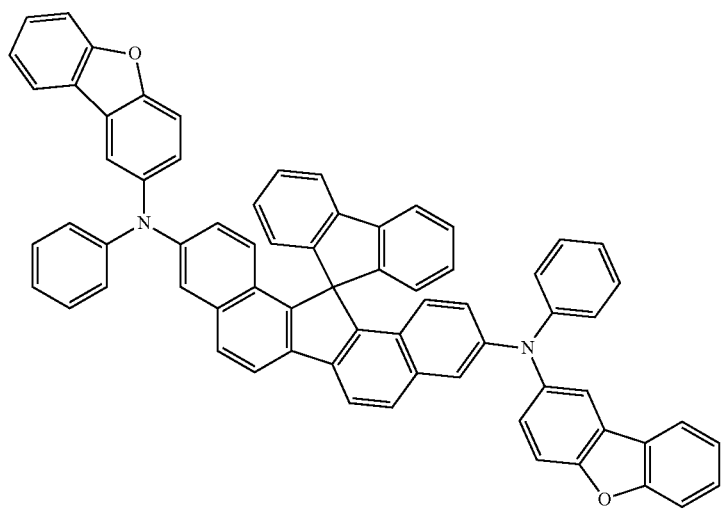
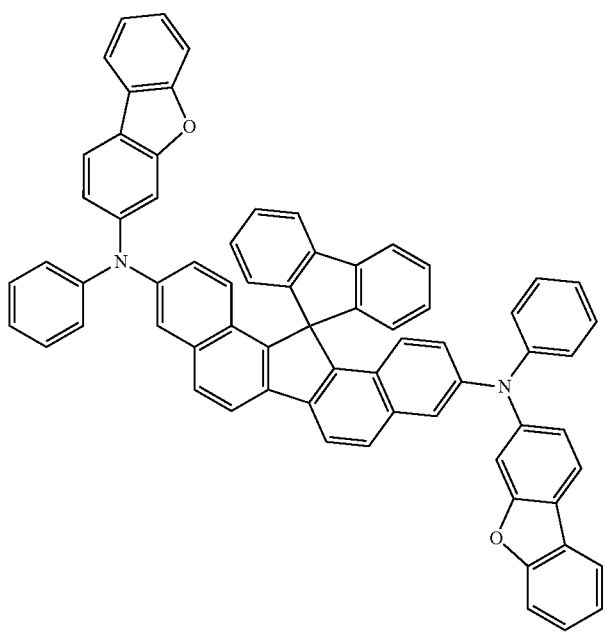
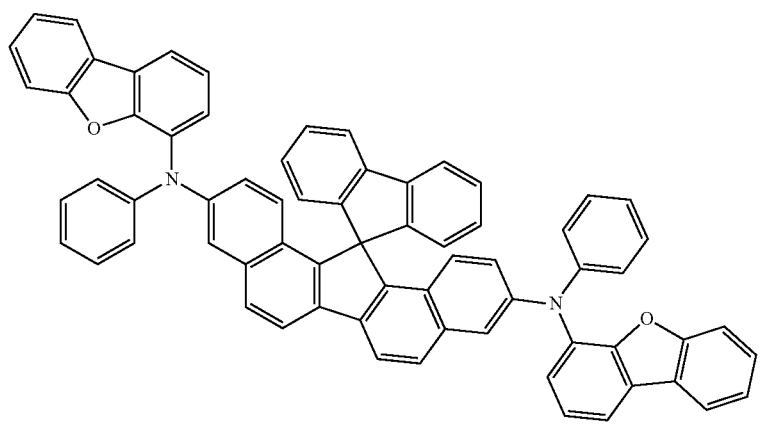

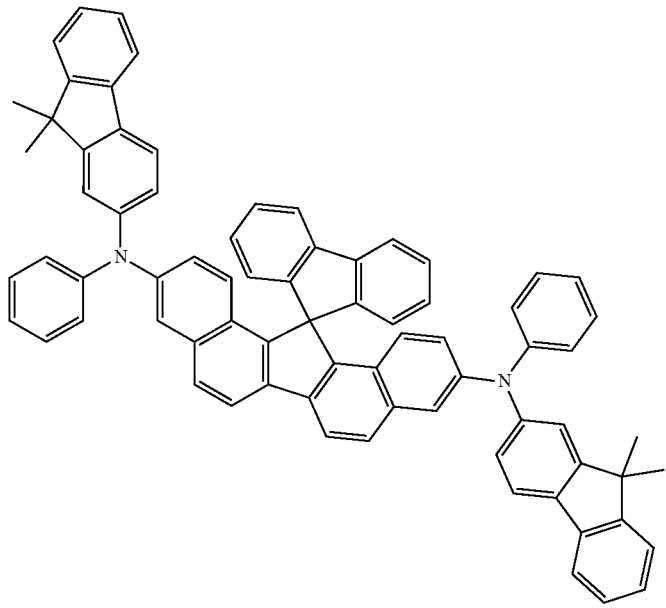
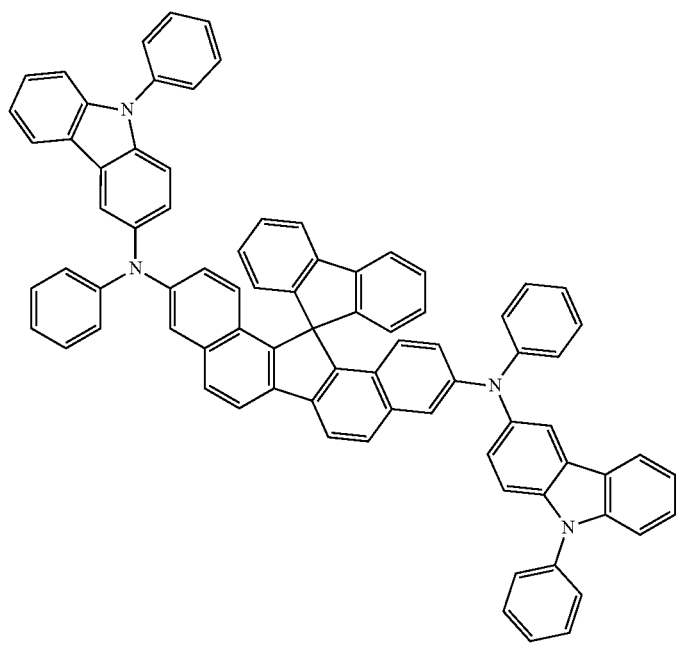

-continued
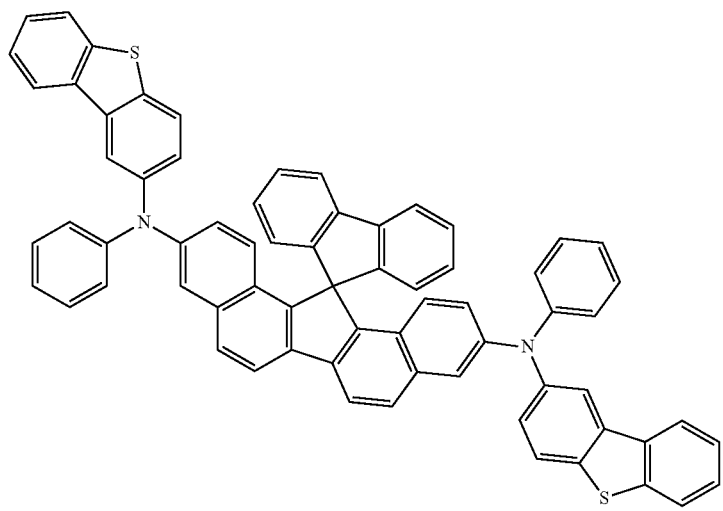
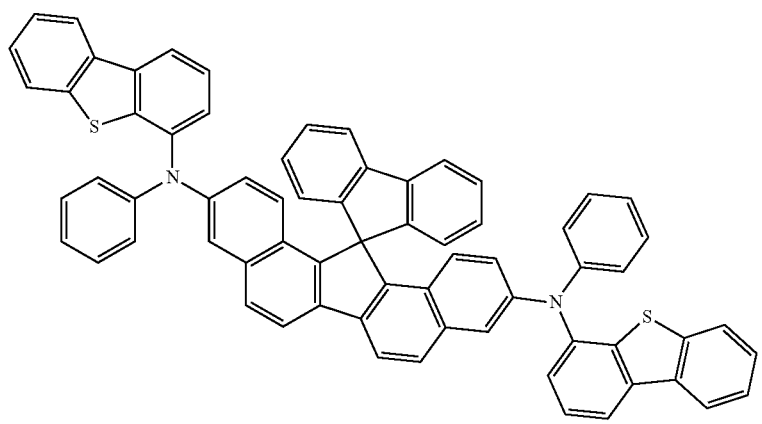
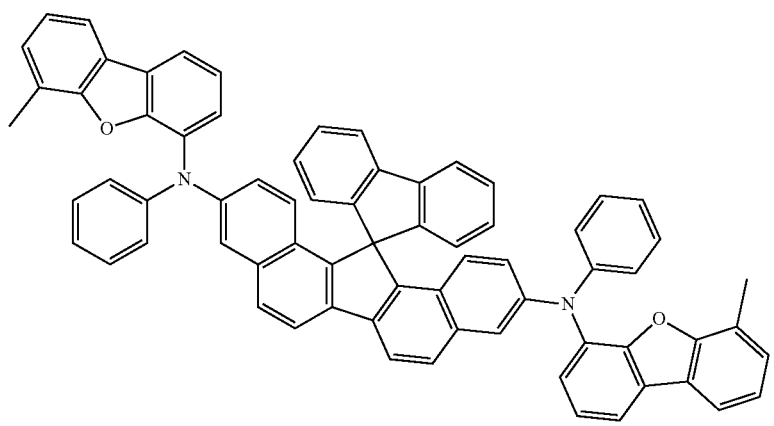

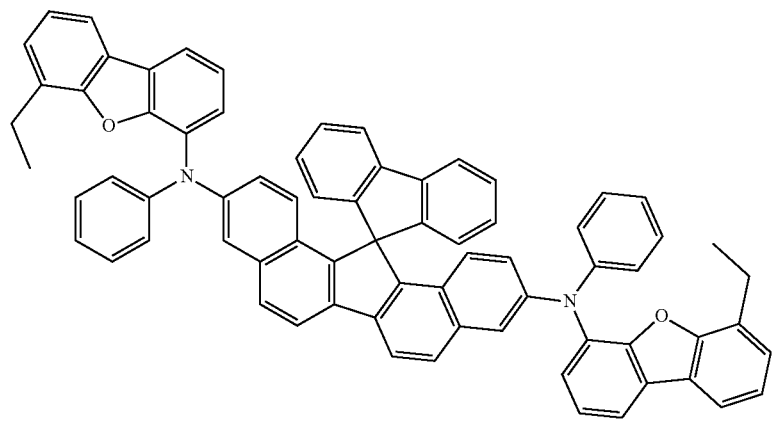
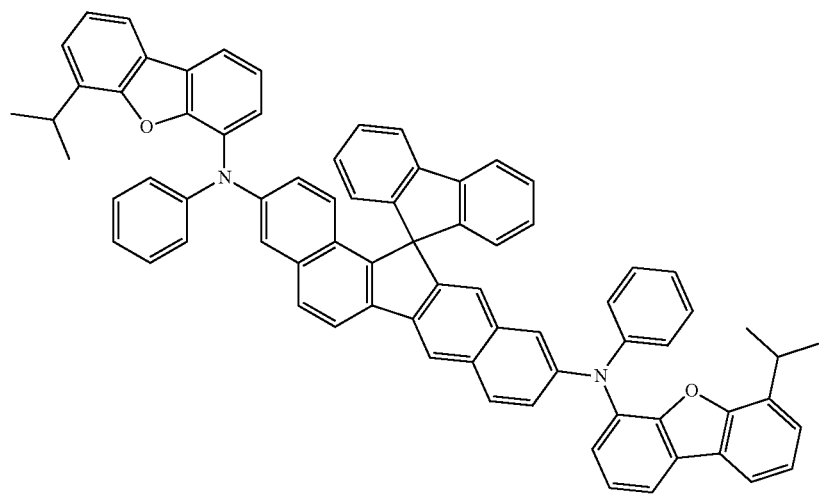
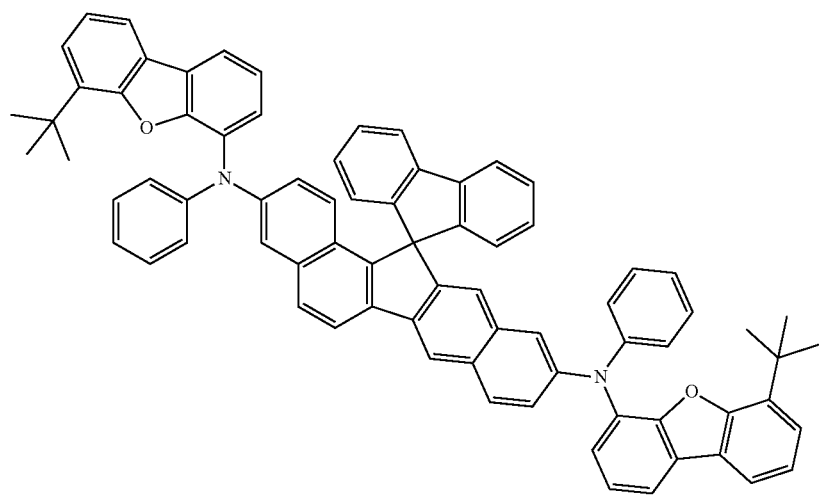

-continued
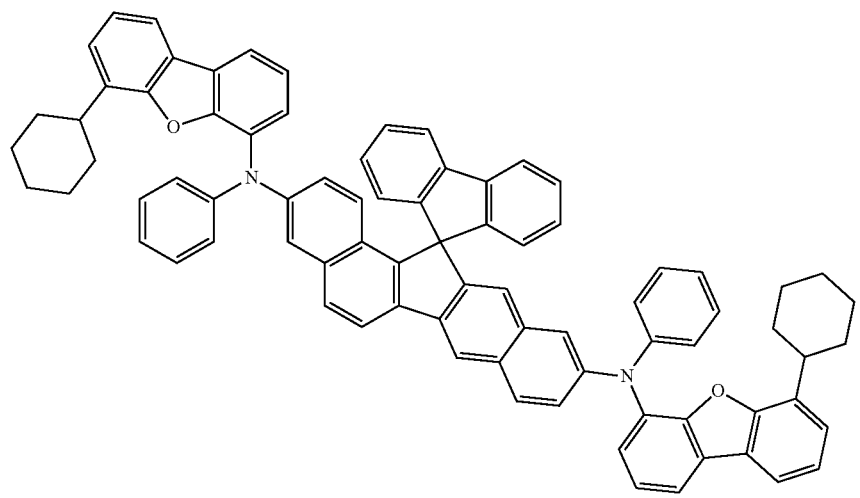
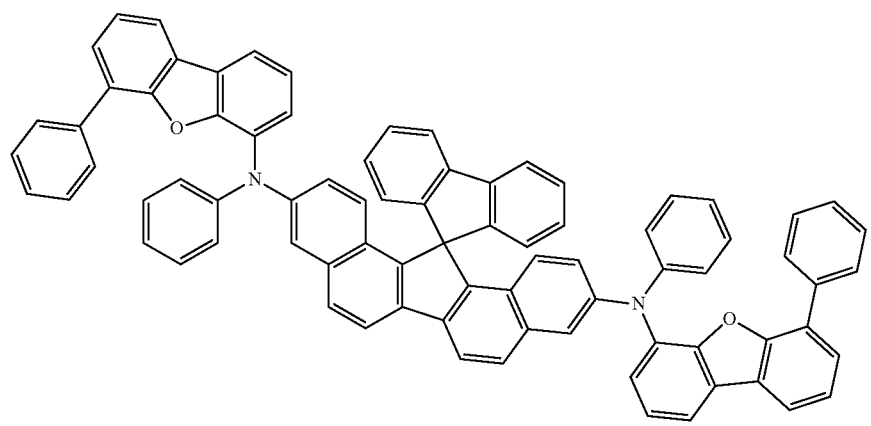
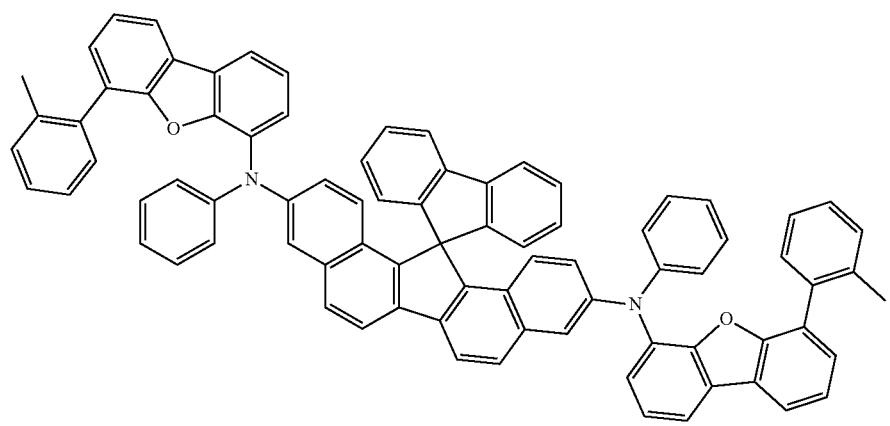

-continued
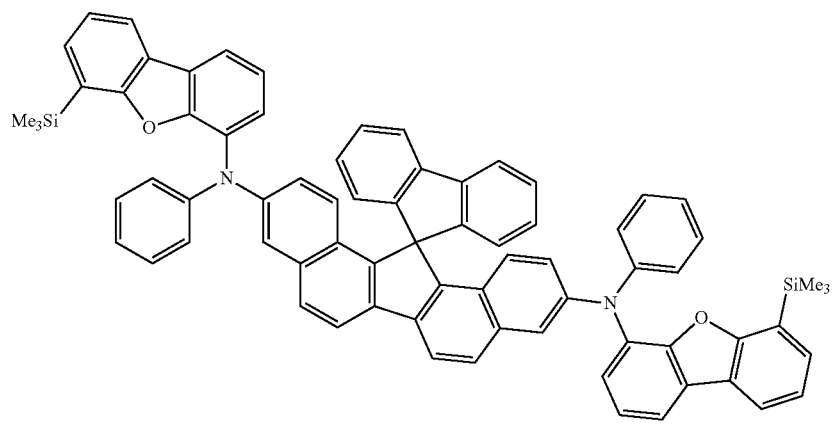
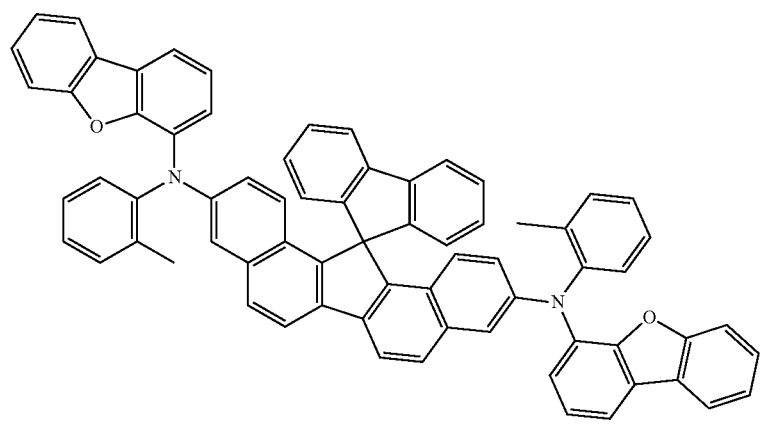
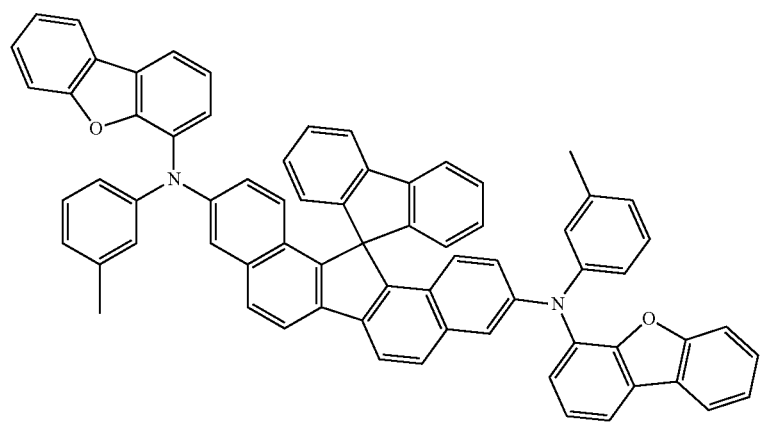
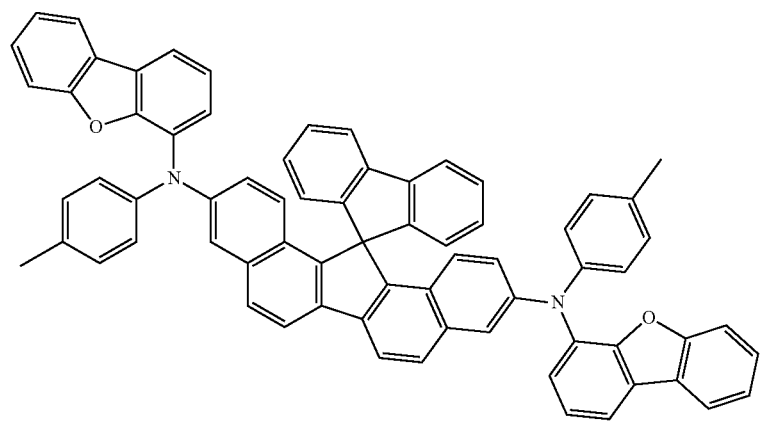

-continued
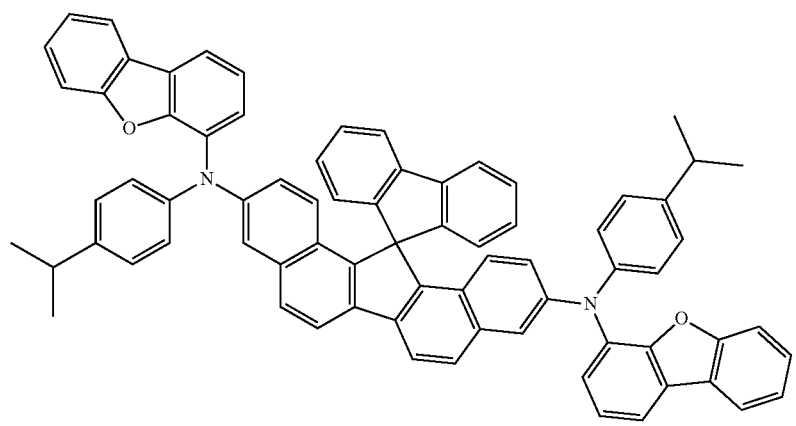
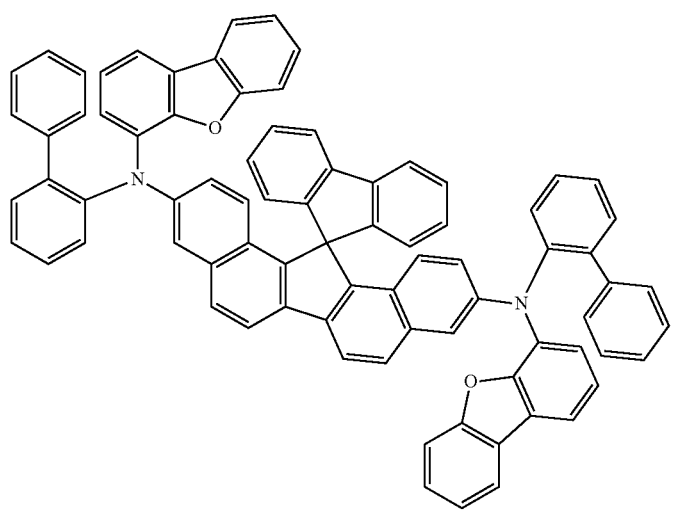
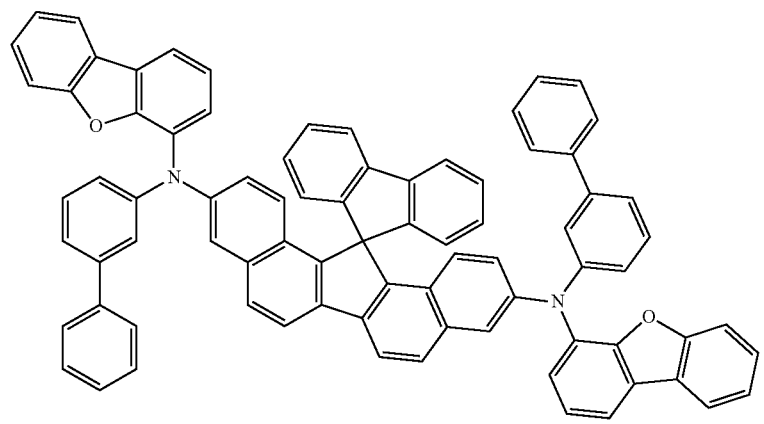

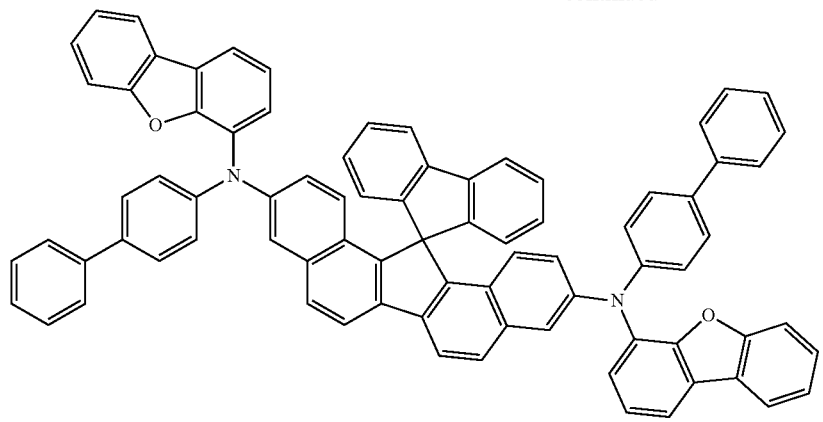
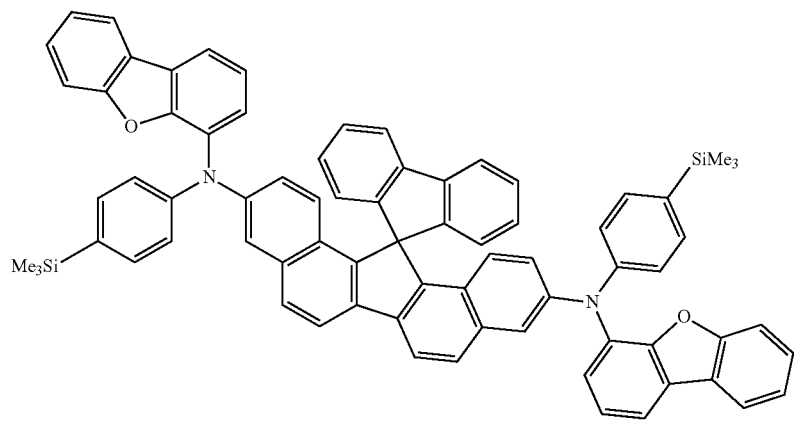
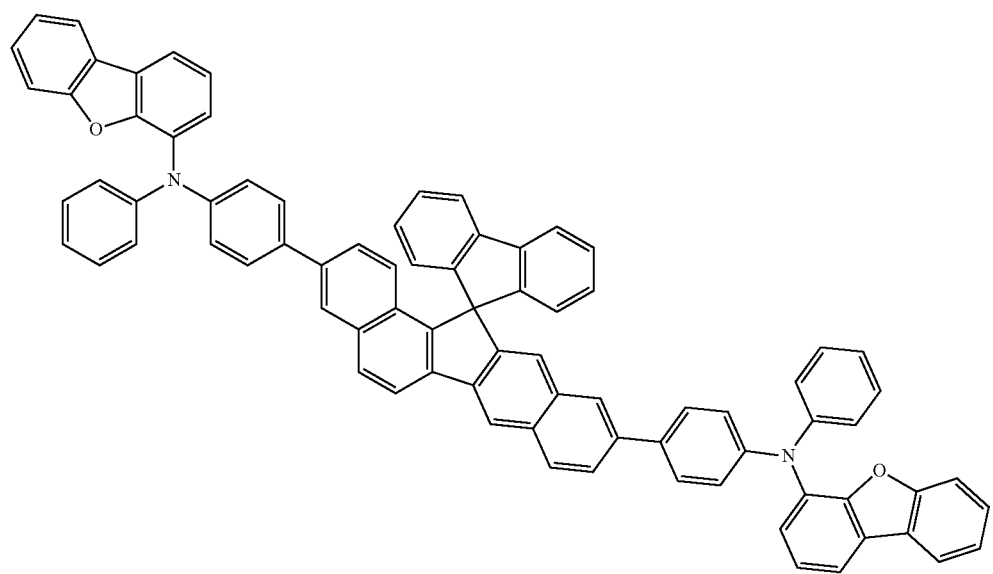

701
702
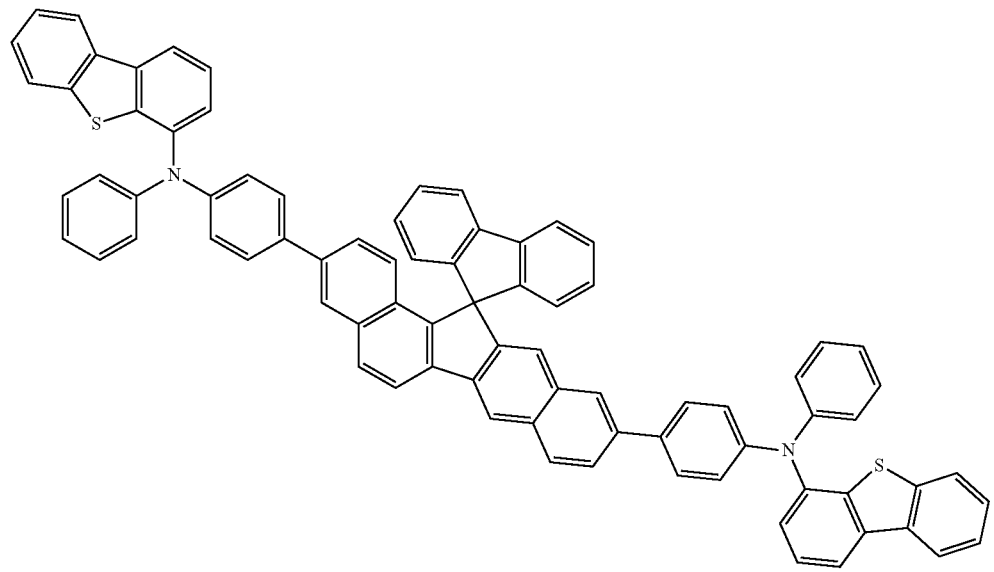
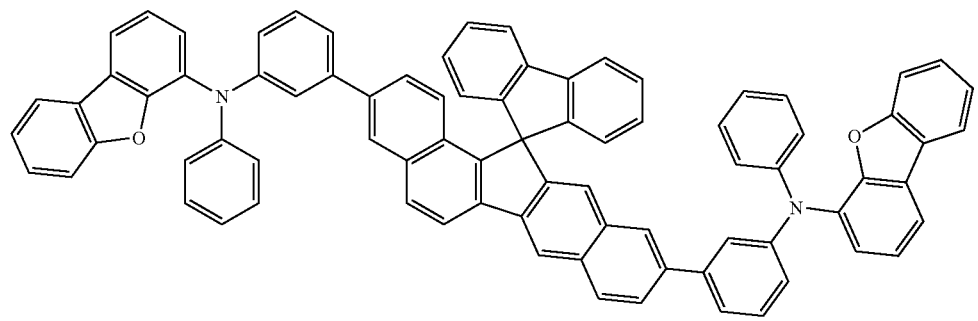
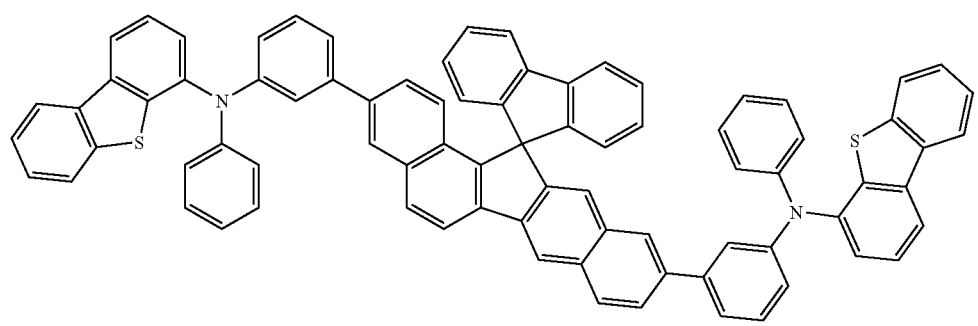
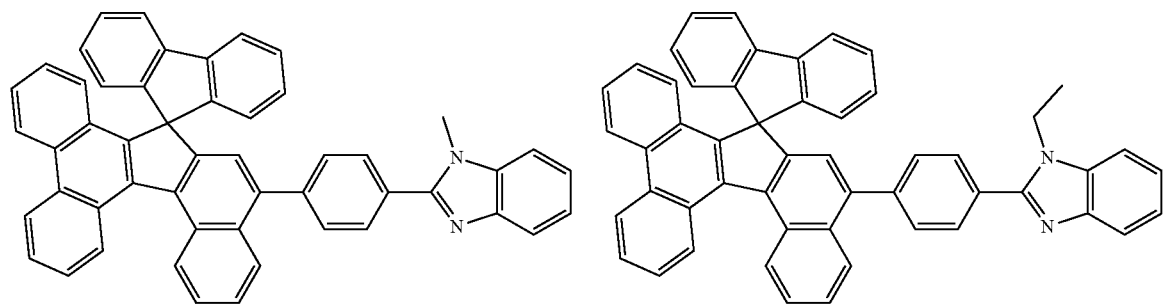

703 704
-continued
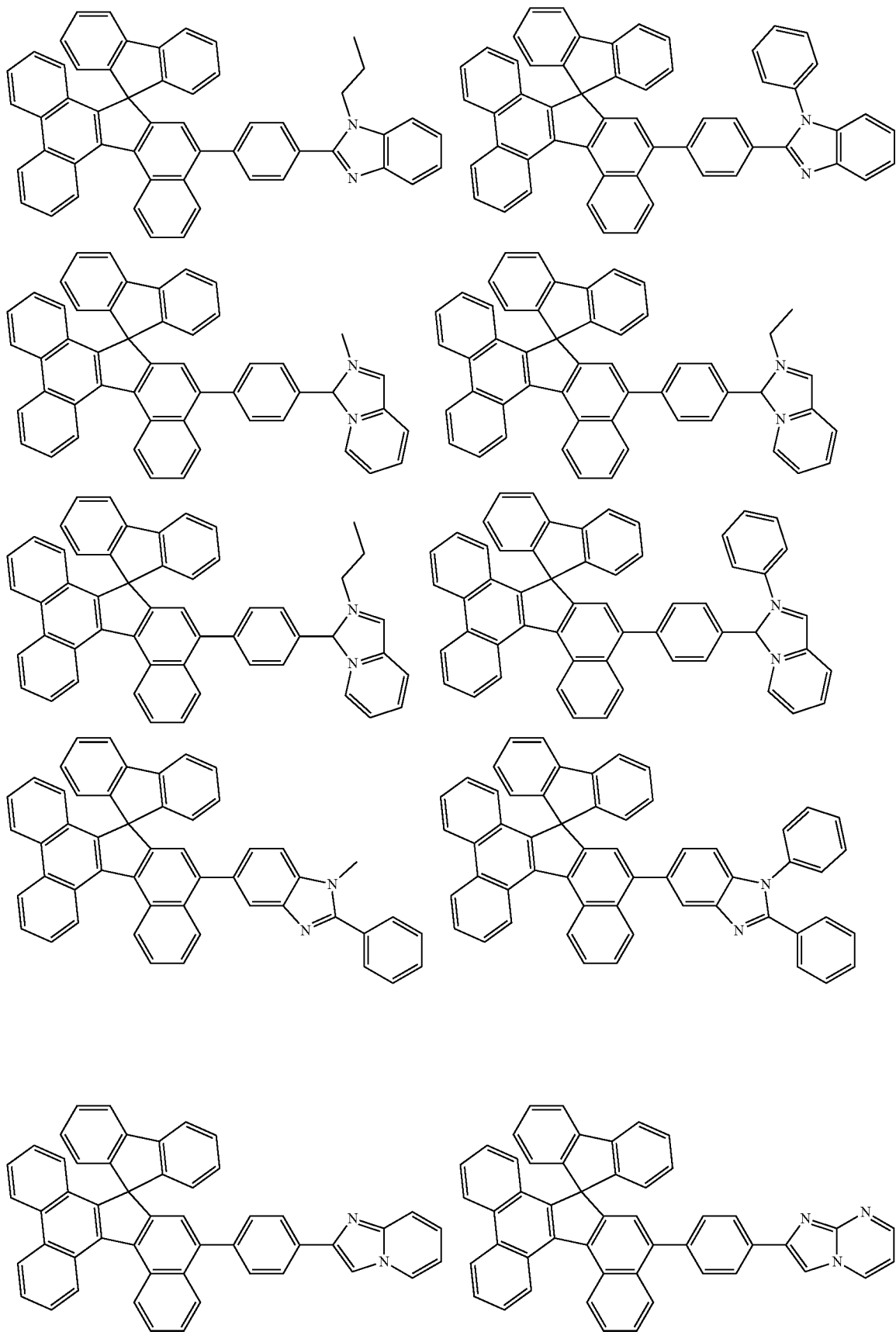

705 706
-continued
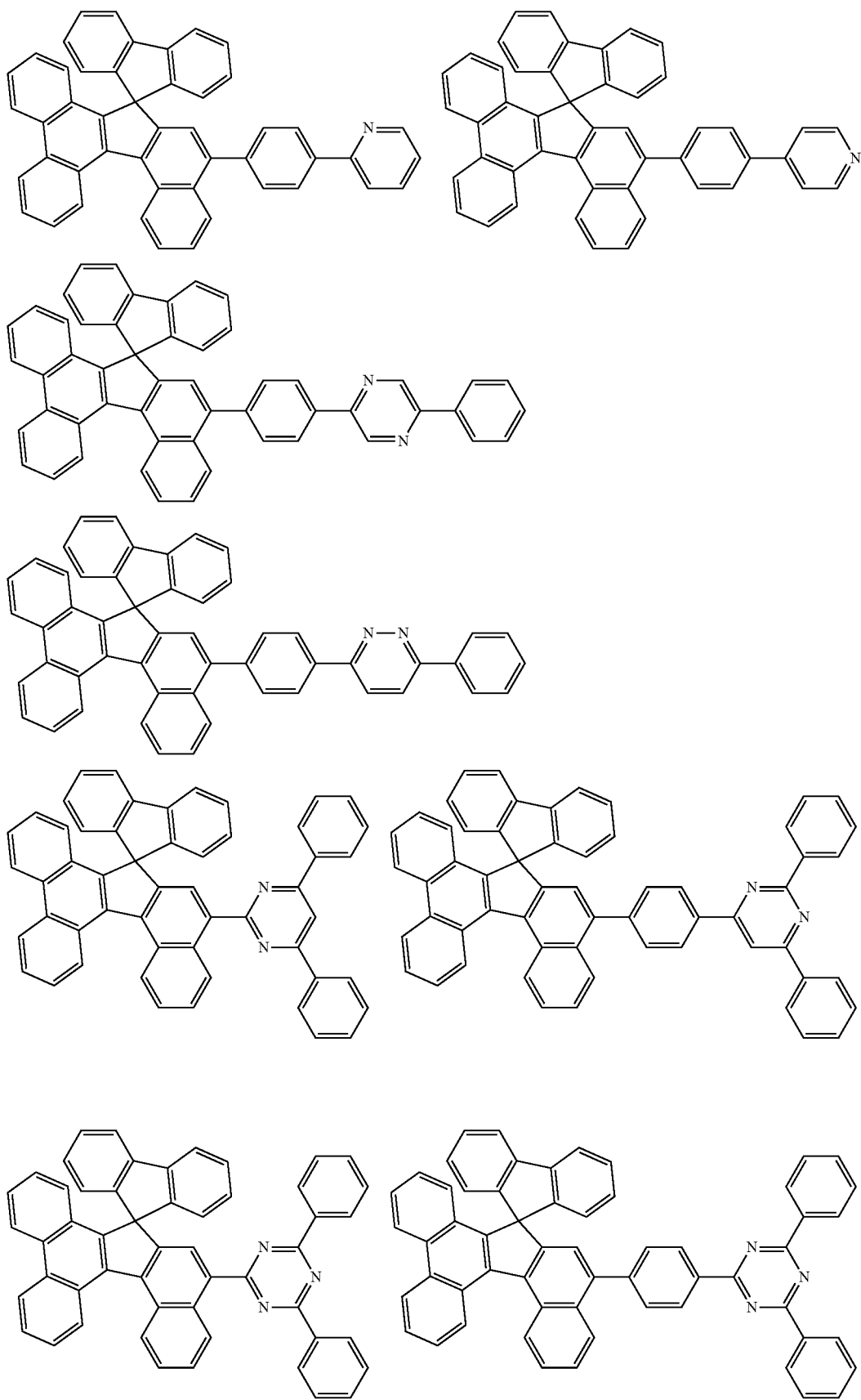

-continued
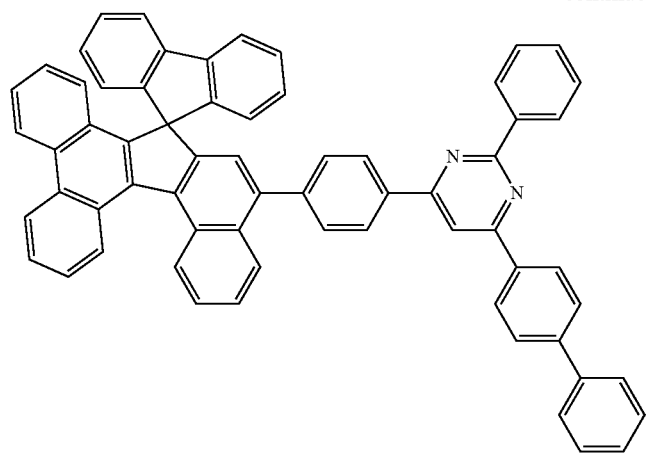
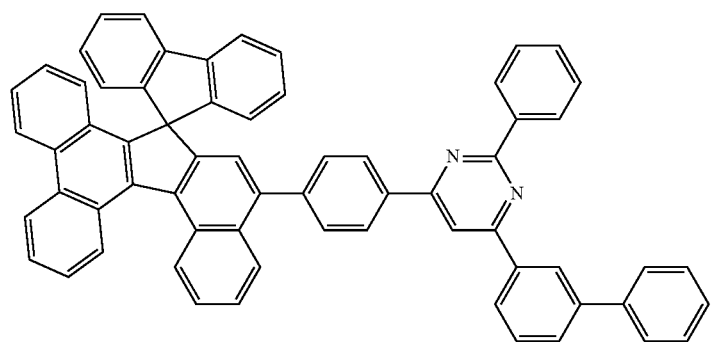
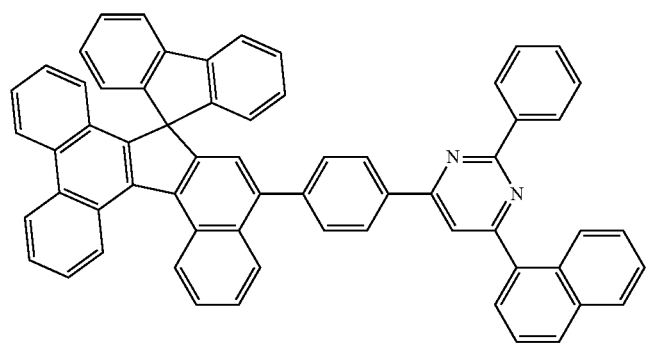
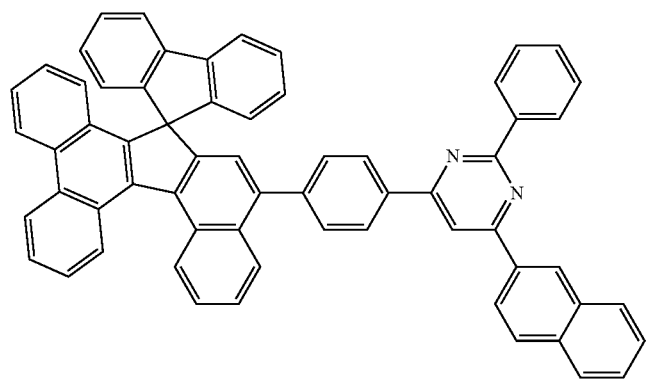

709                                                                 710
-continued
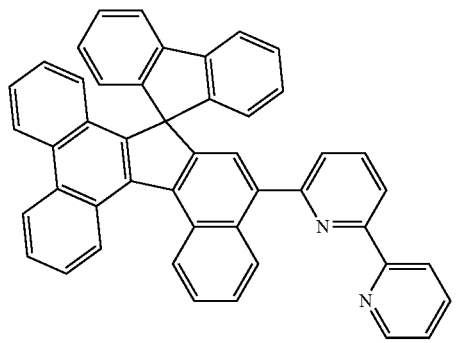 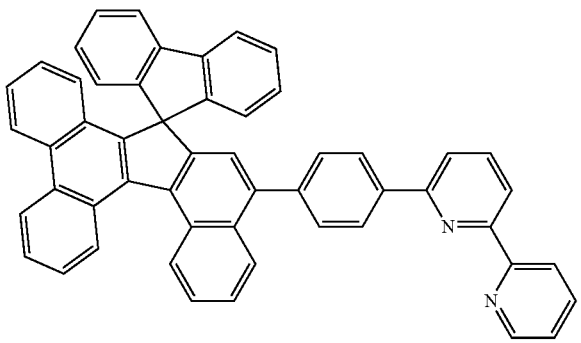
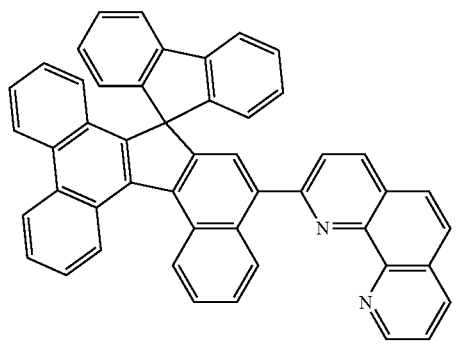 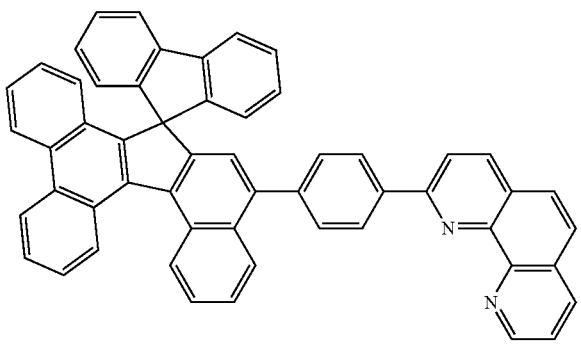
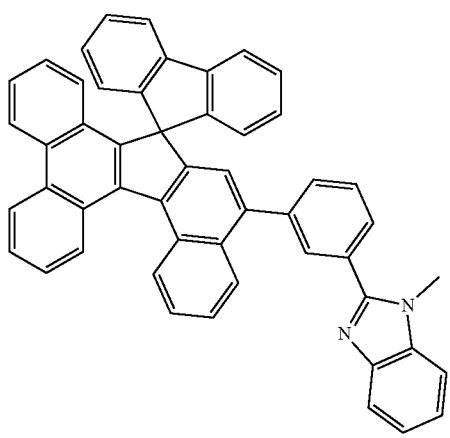 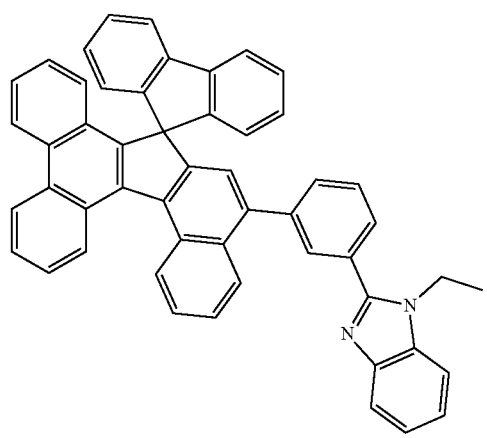
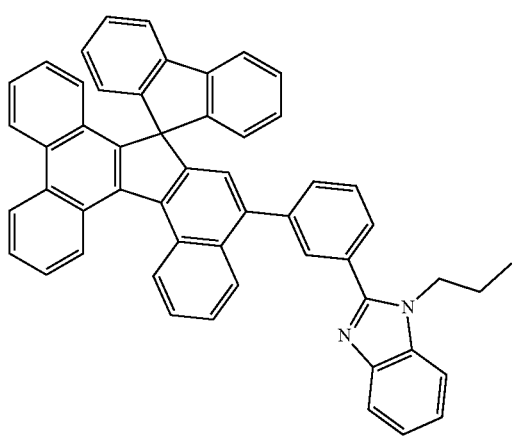 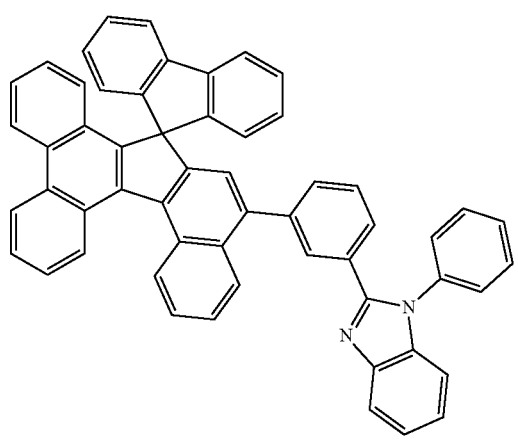

-continued
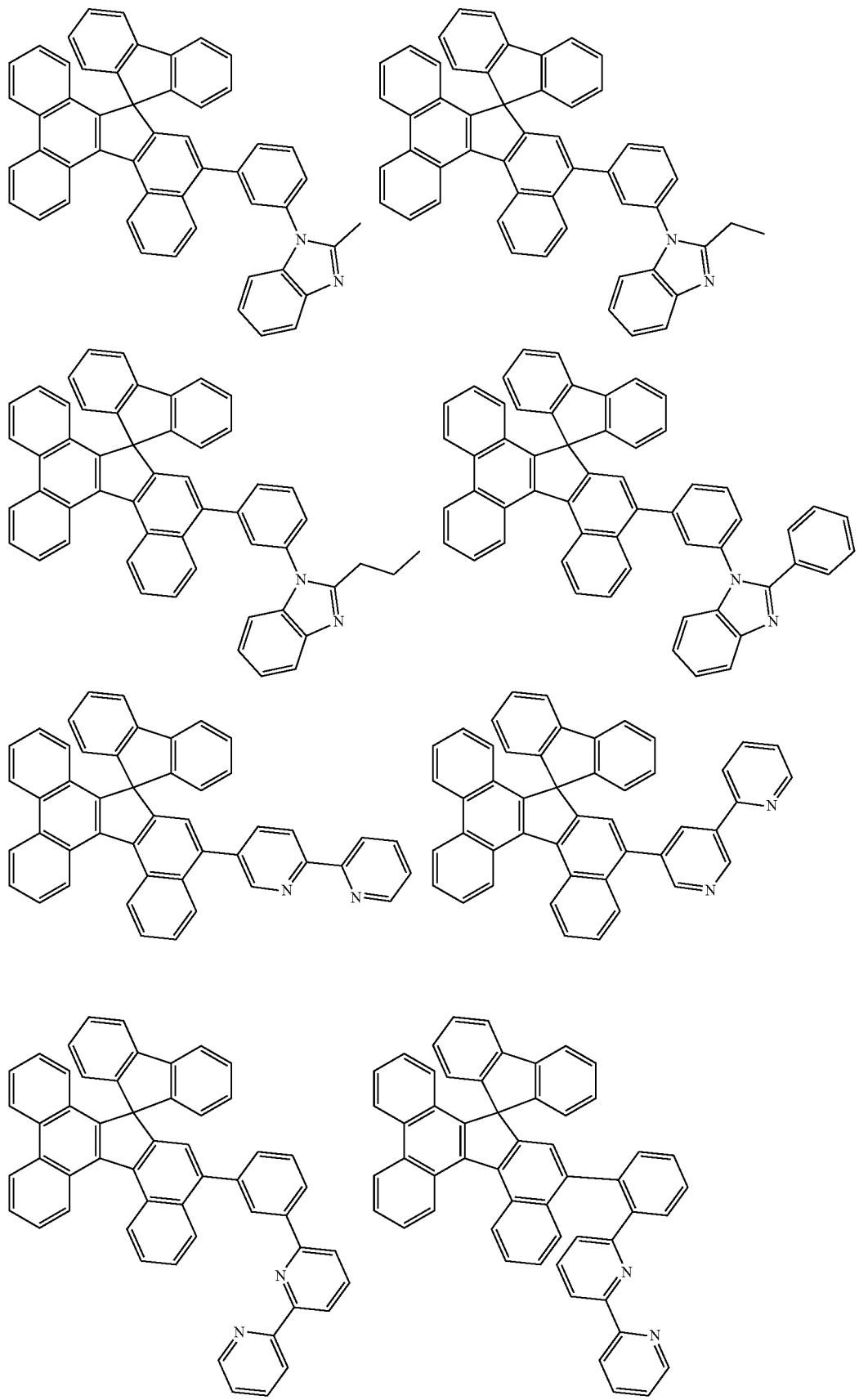

-continued
713
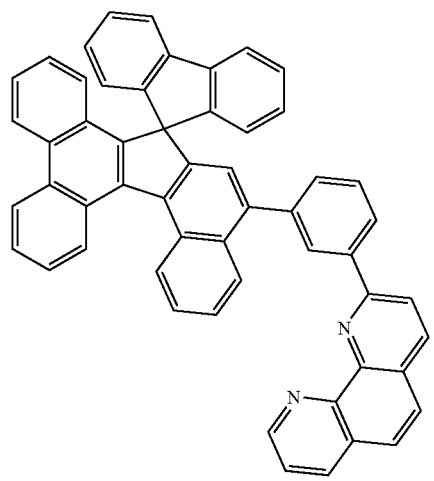
714
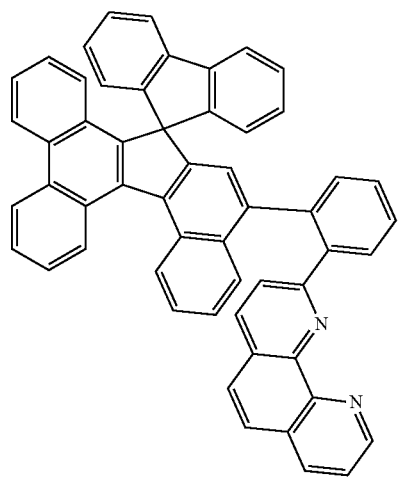
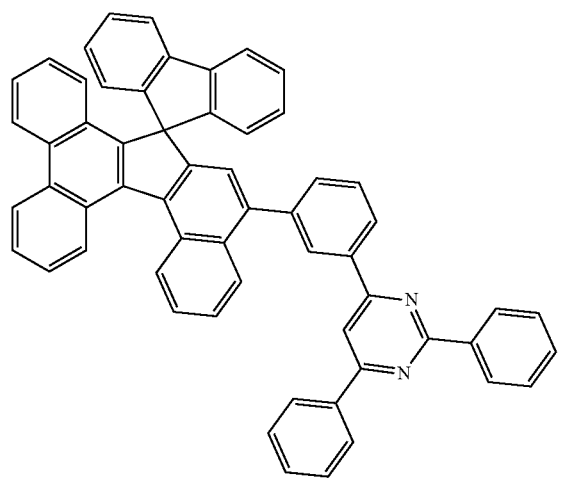
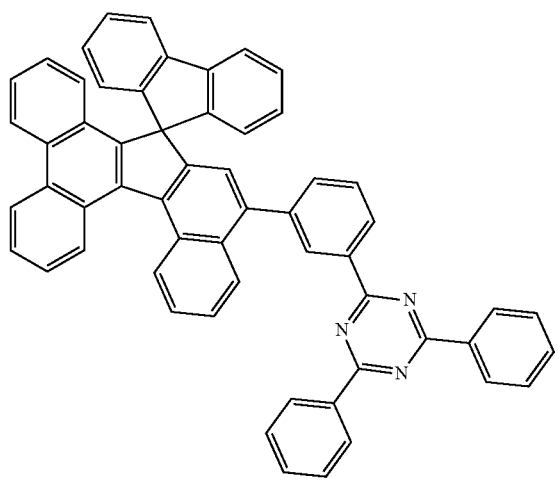
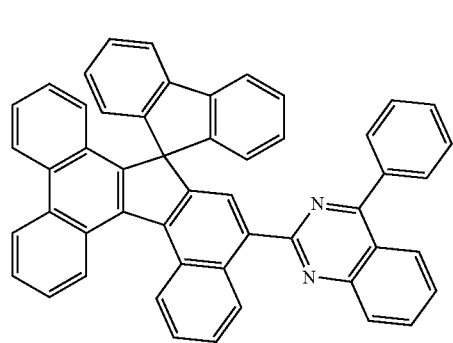
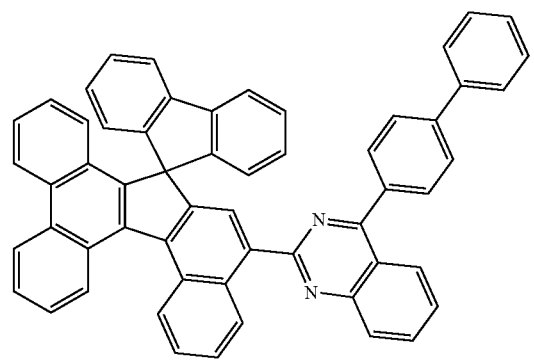

-continued
| 715 | 716 |
|---|---|
| 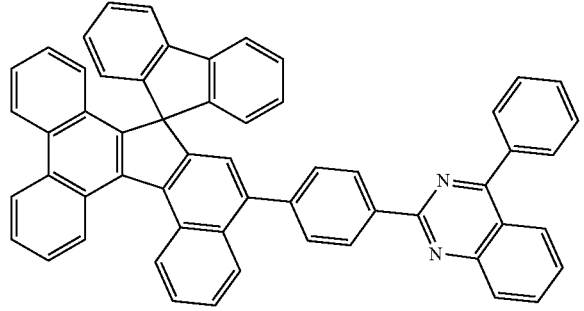 | 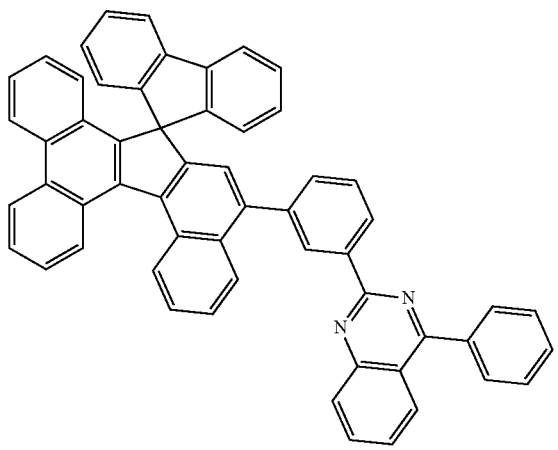 |азва
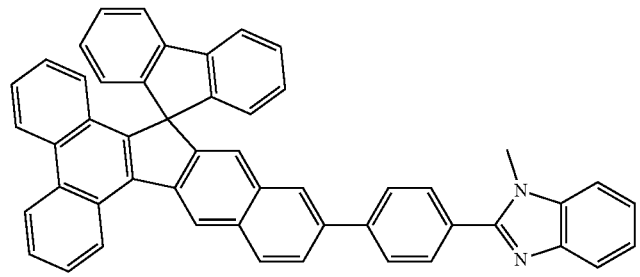
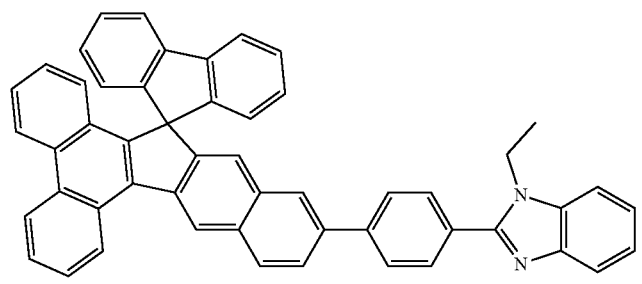
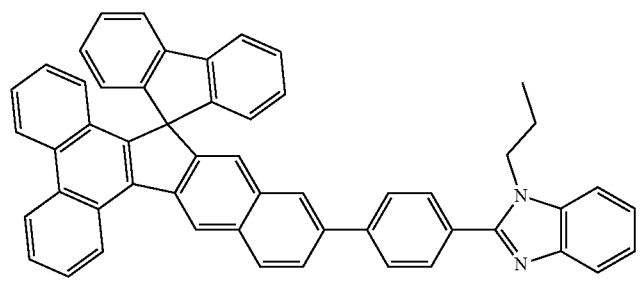
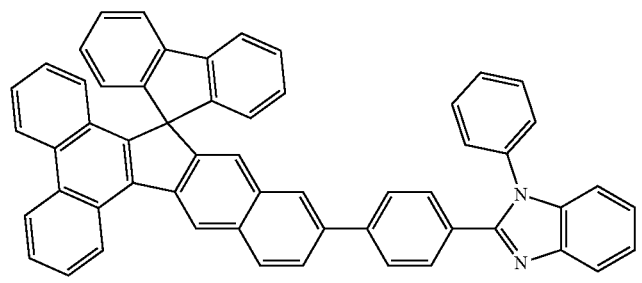

717 718
-continued
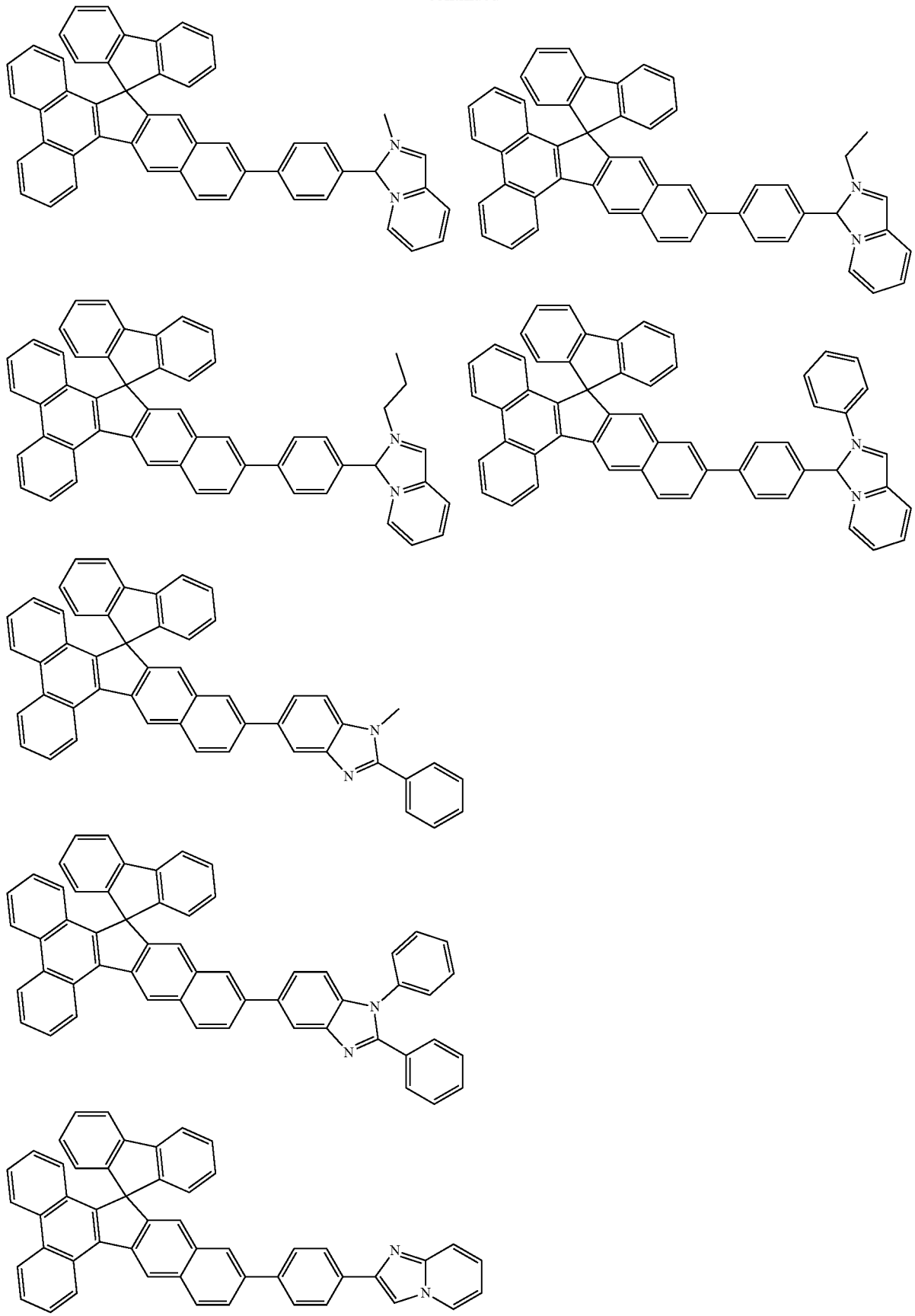

719
720
-continued
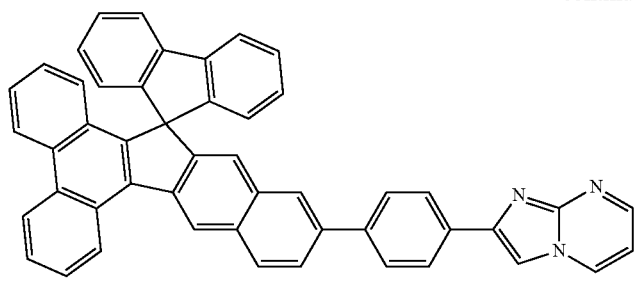
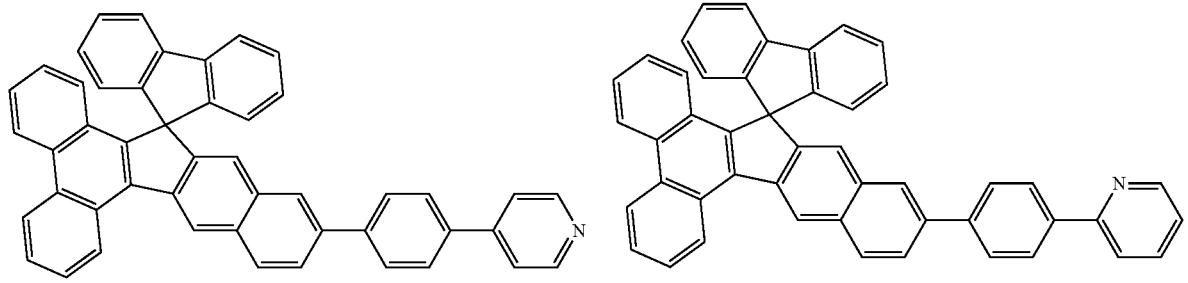
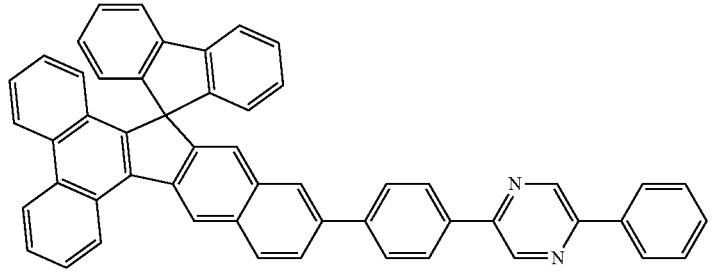
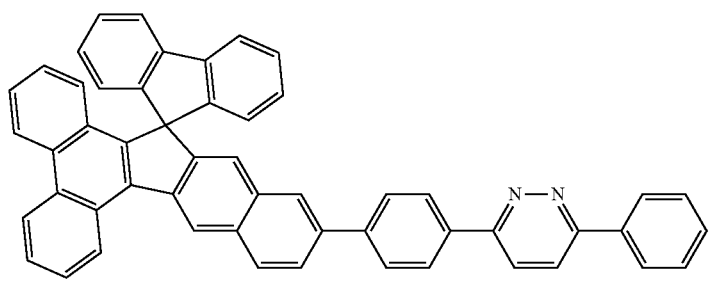
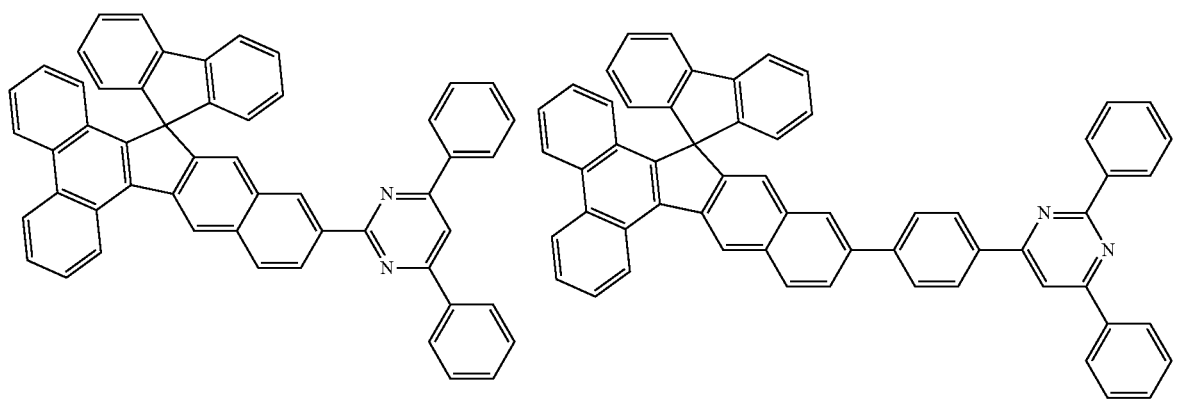

-continued
721
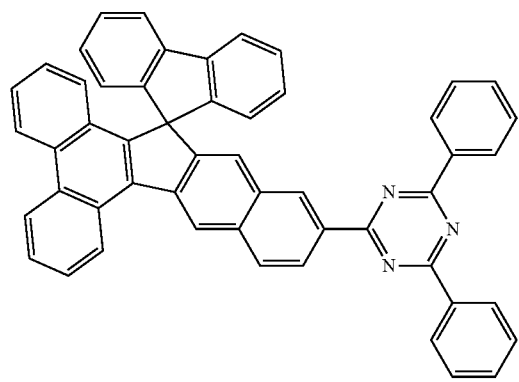
722
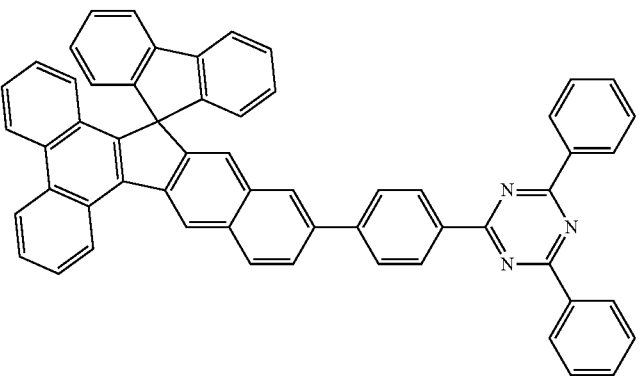
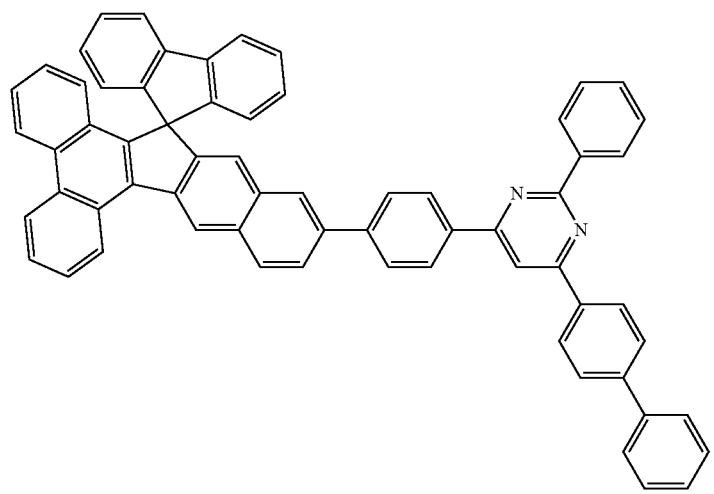
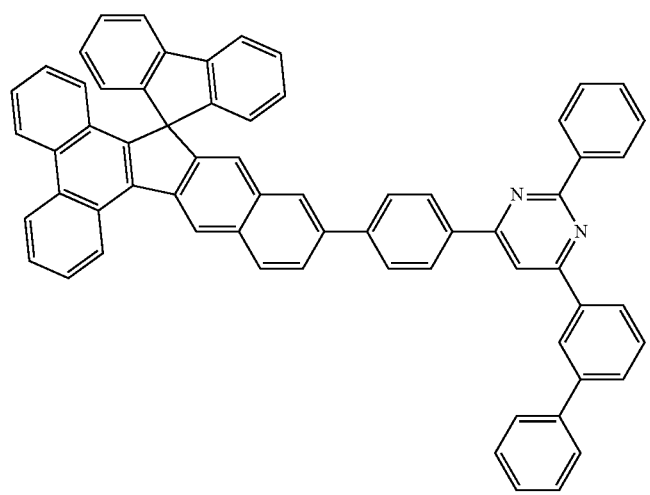

723  724
-continued
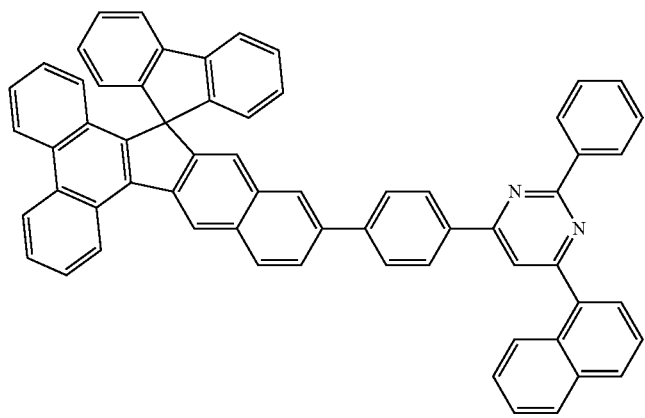
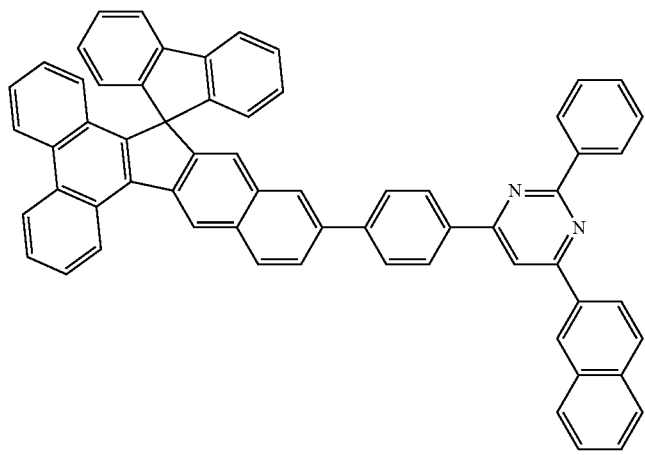
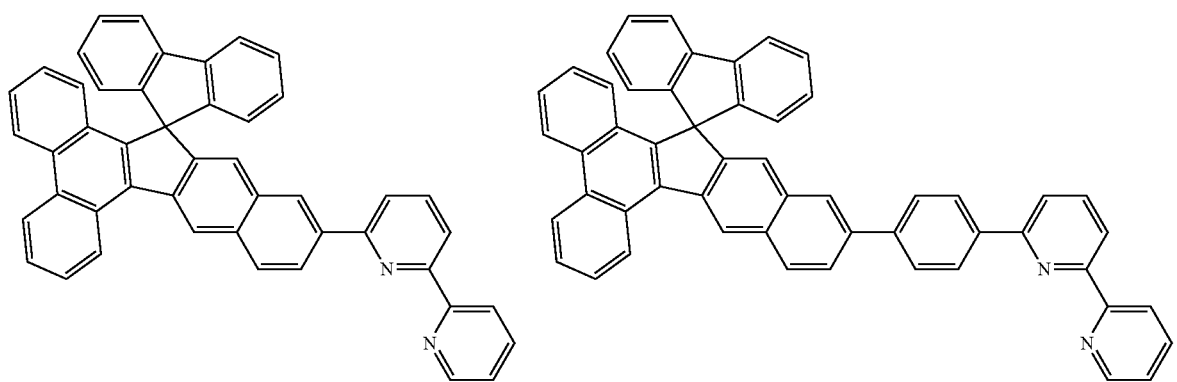
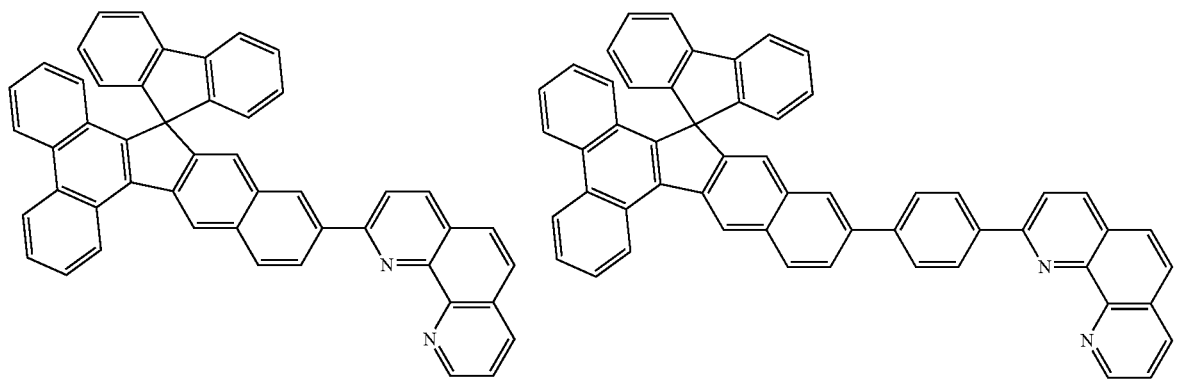

725 726
-continued
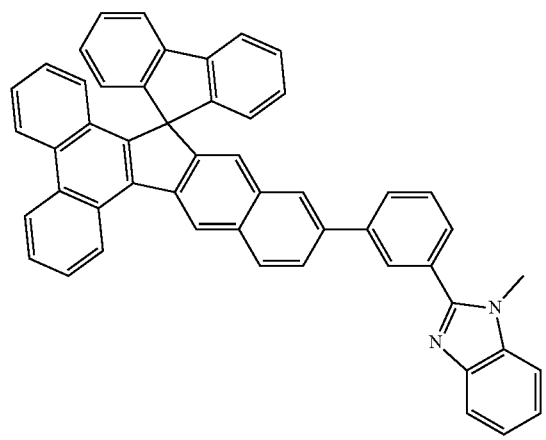
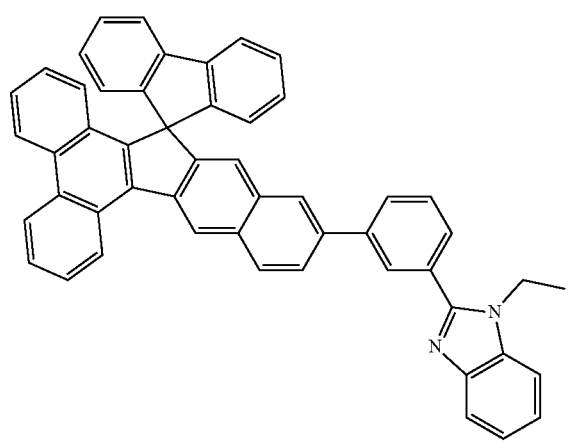
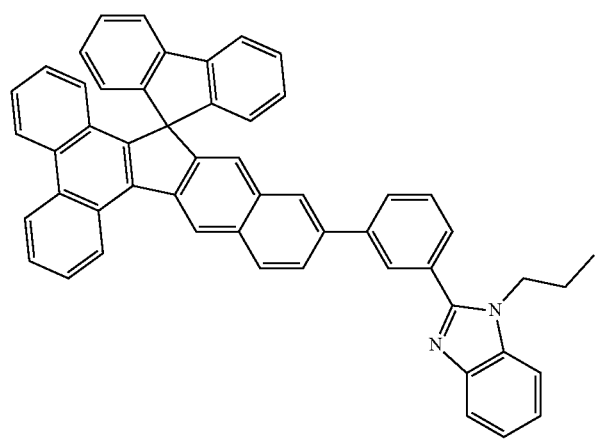
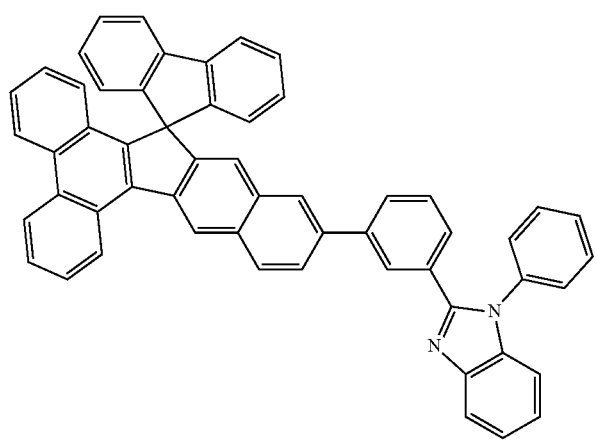
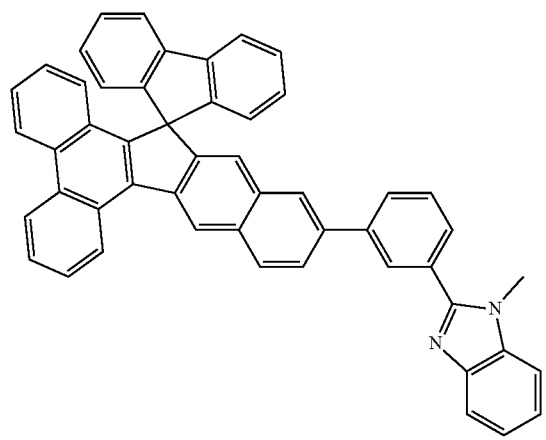
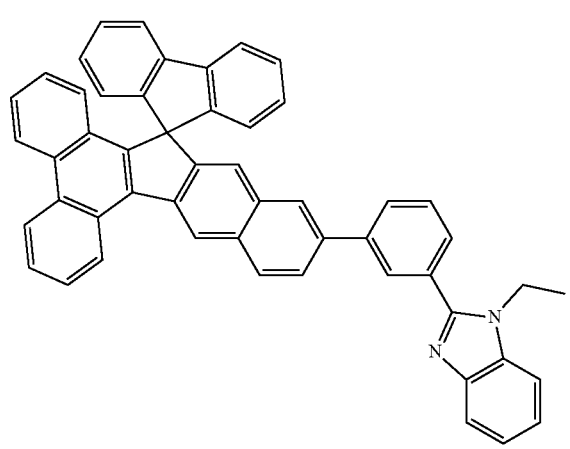

727 728
-continued
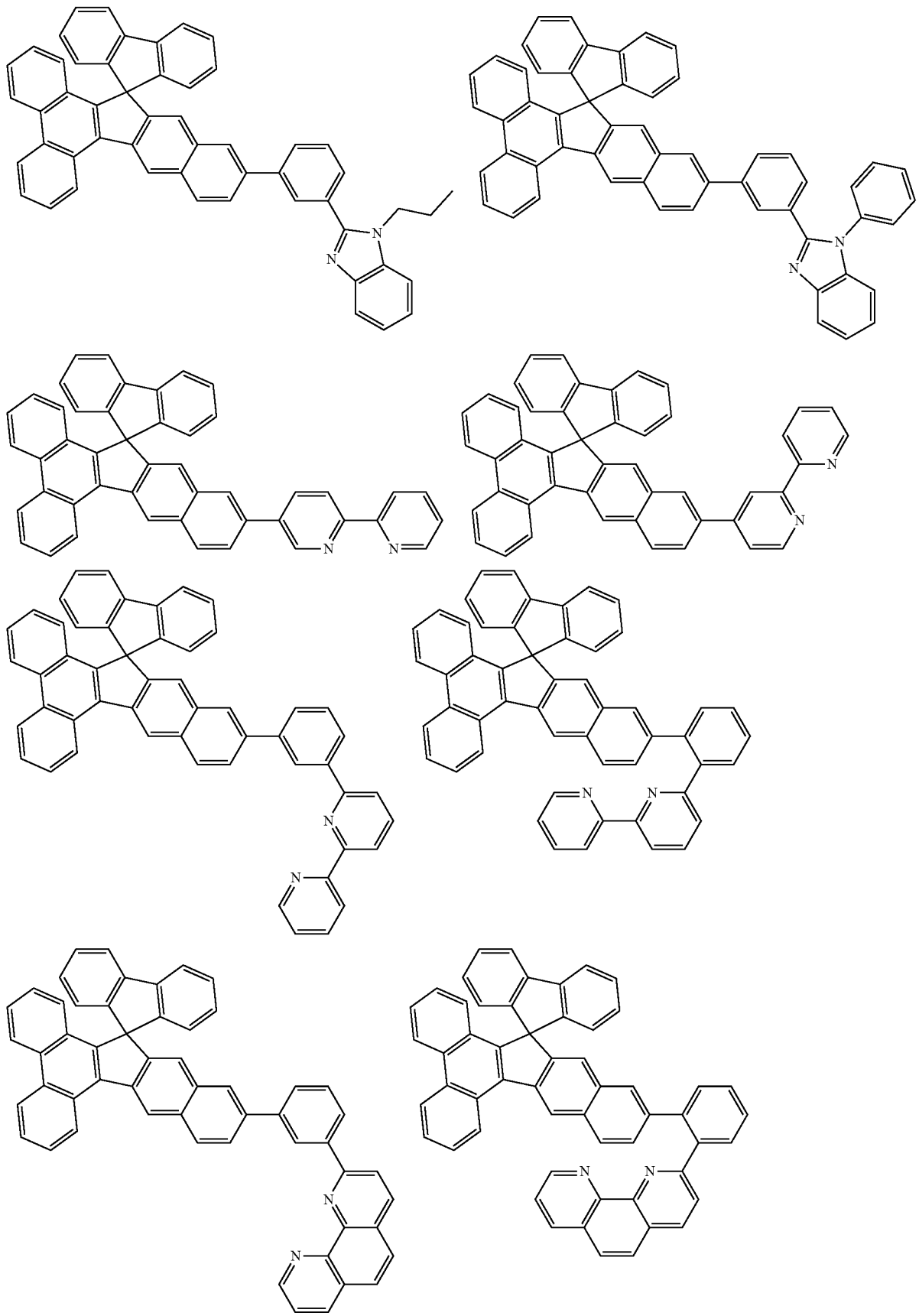

729
730
-continued
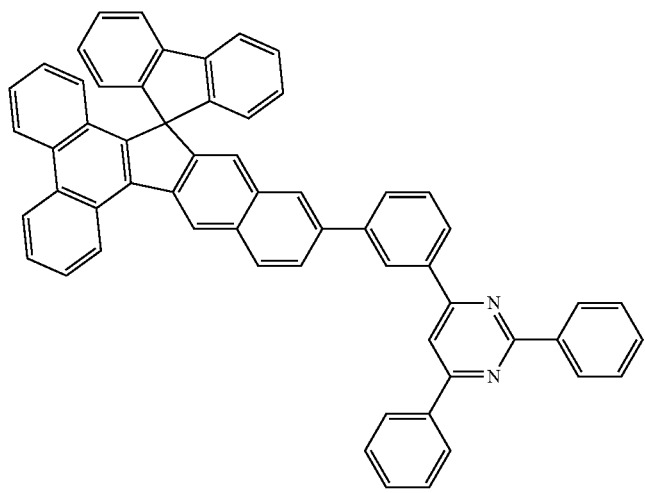
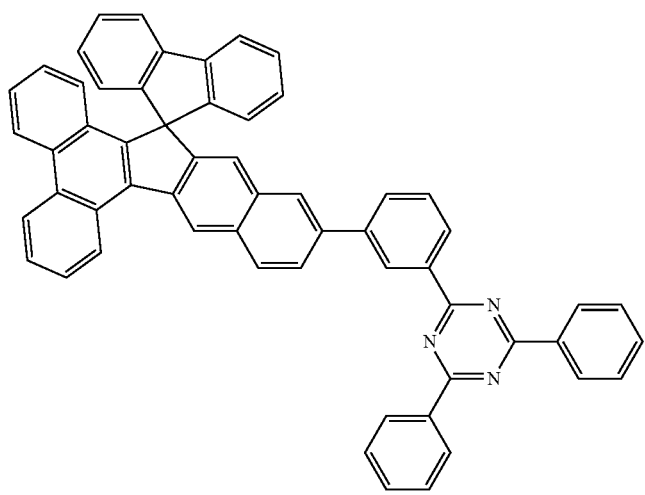
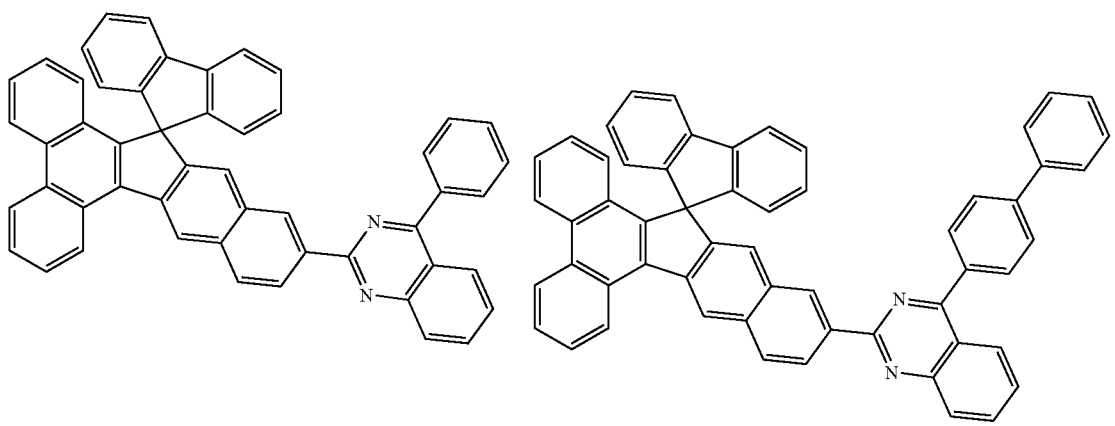

-continued
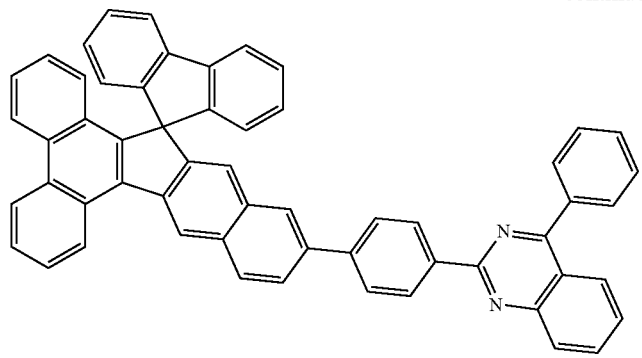
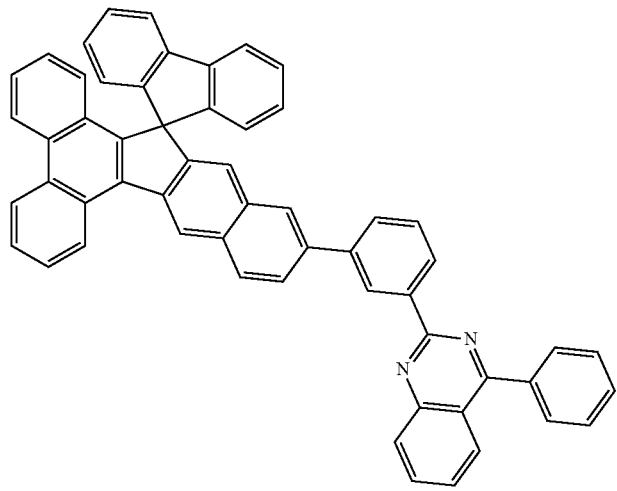
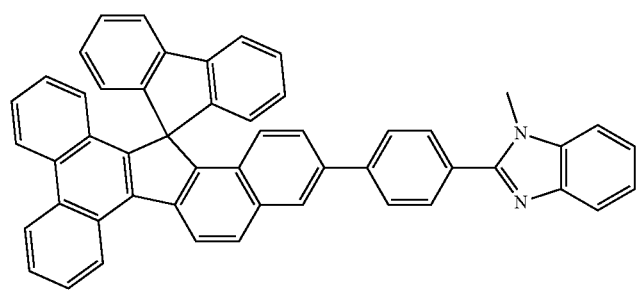
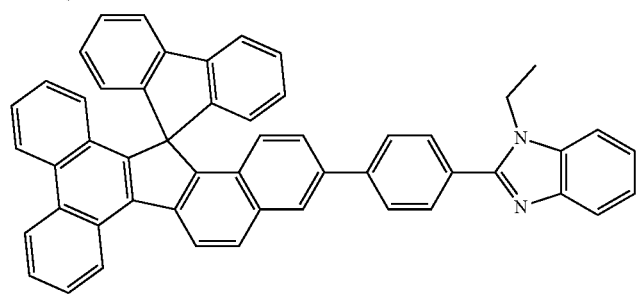
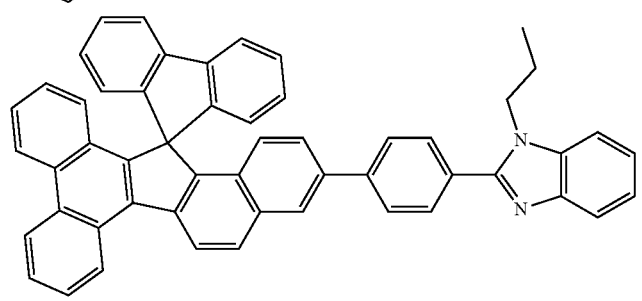

-continued
733
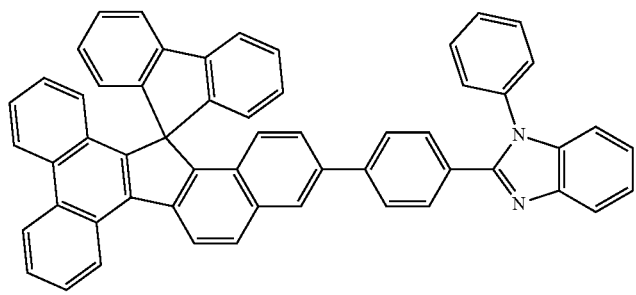
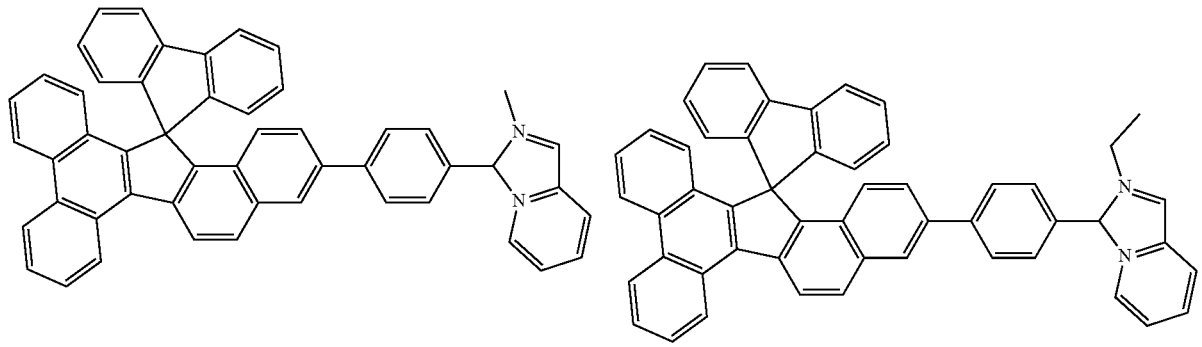
734
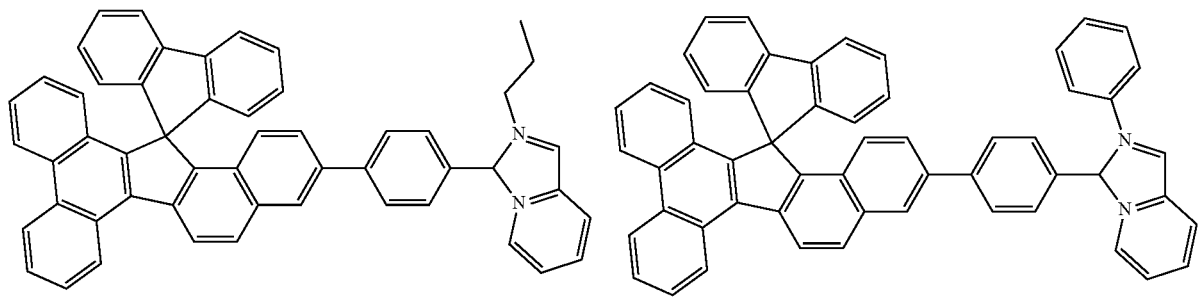
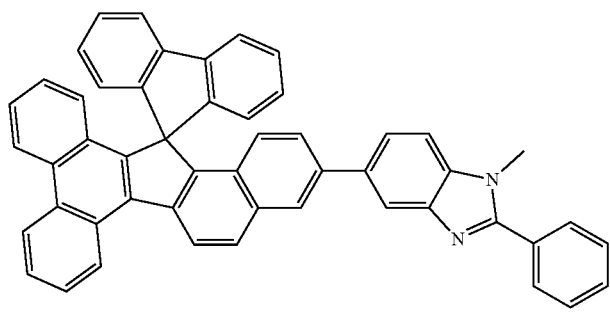
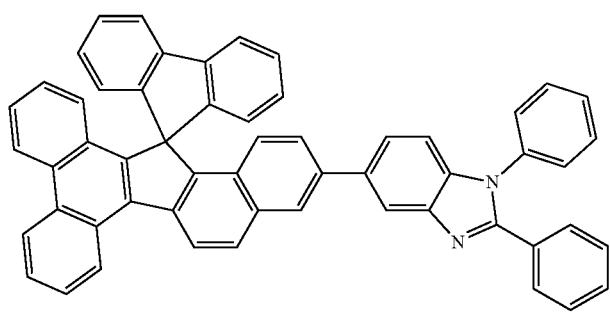

-continued
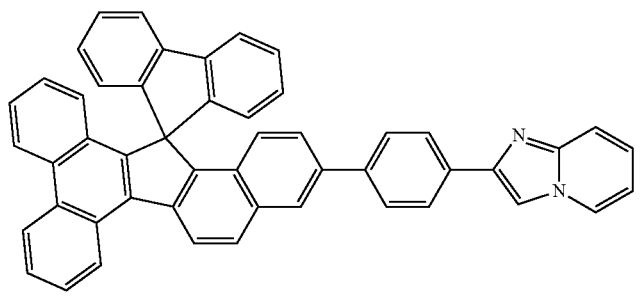
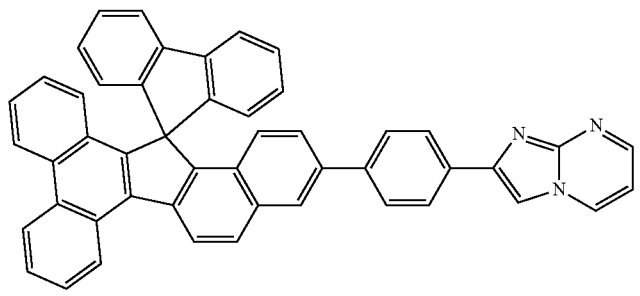
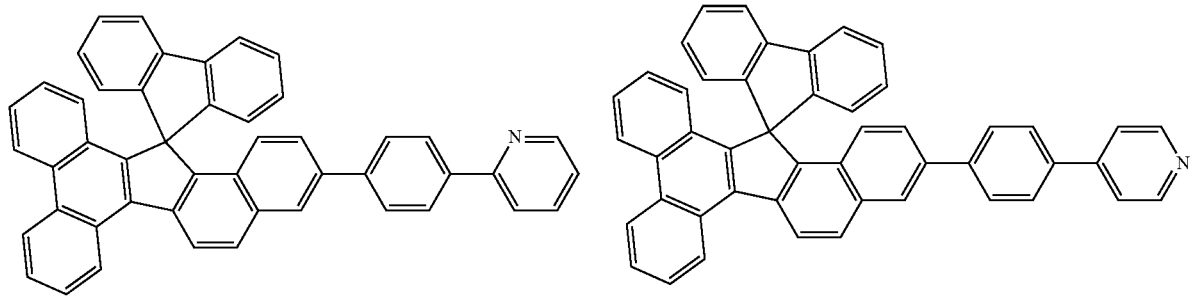
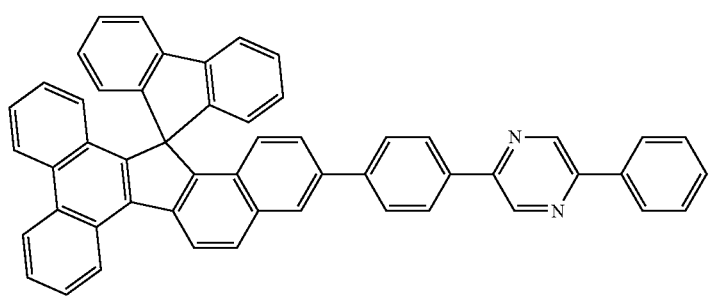
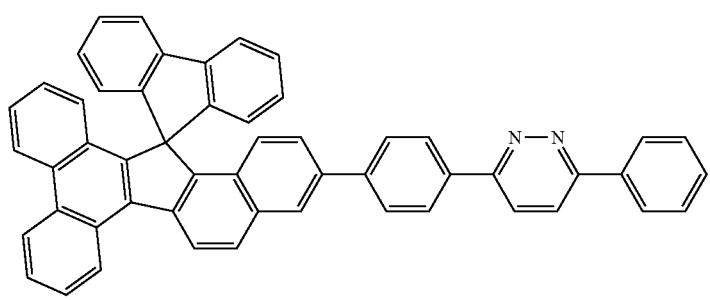

737 738
-continued
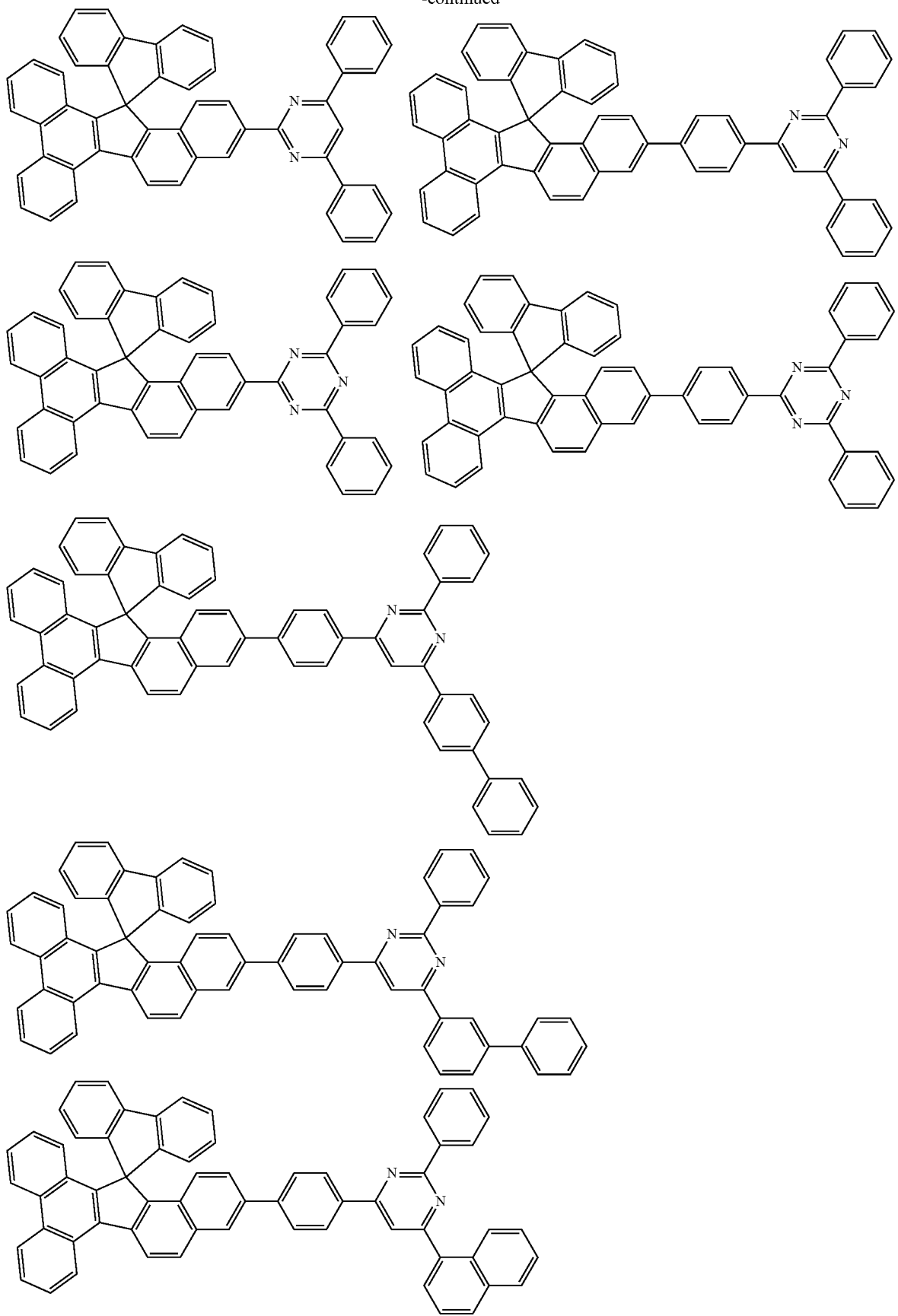

-continued
739   740
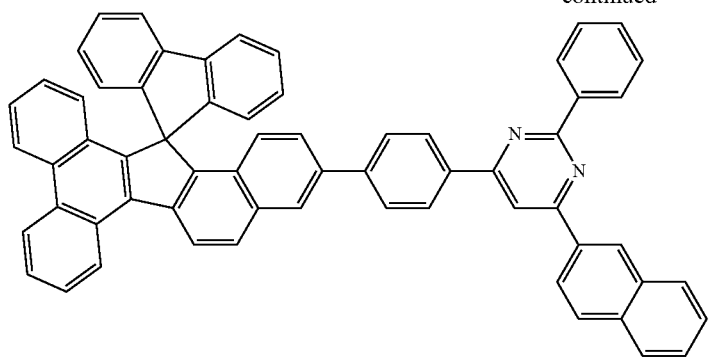
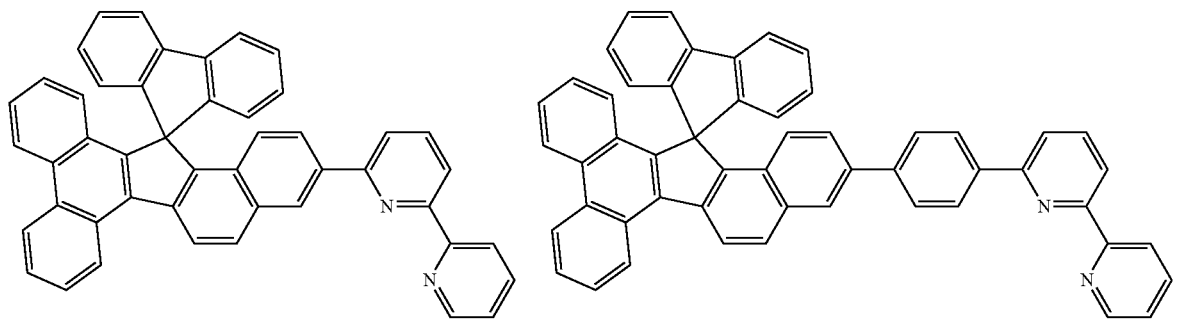
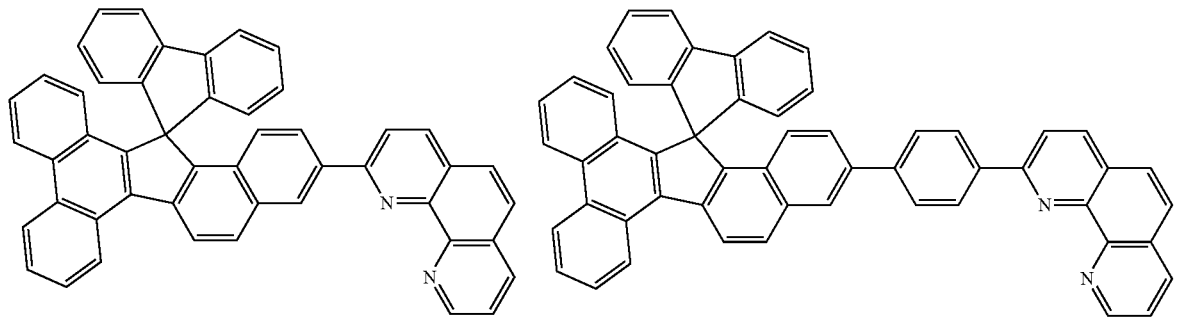
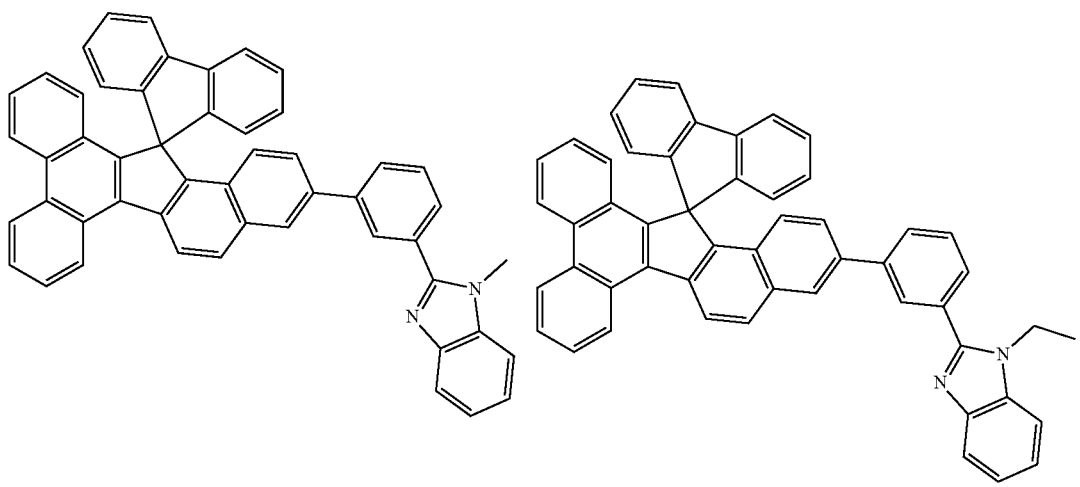

741 742
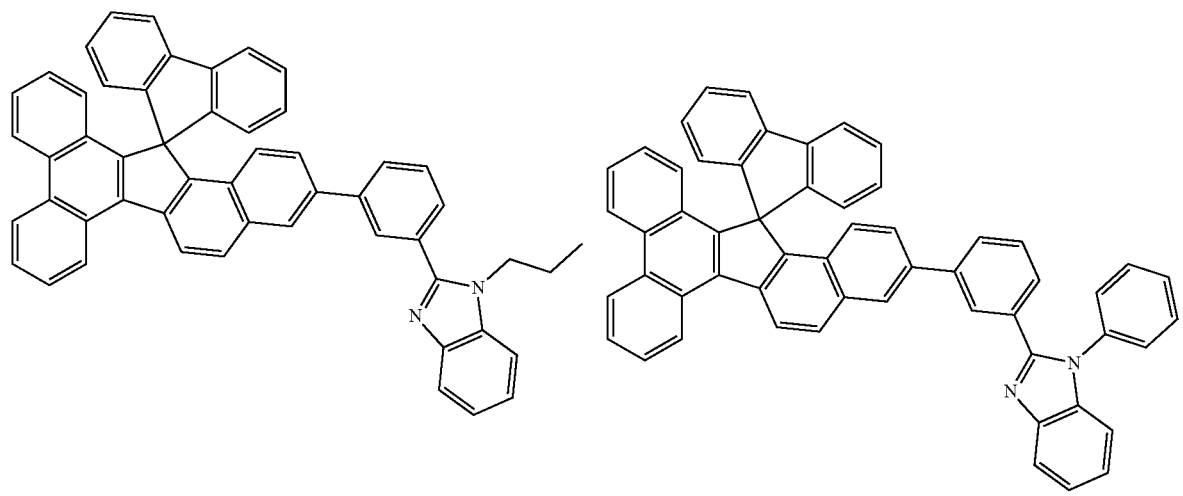
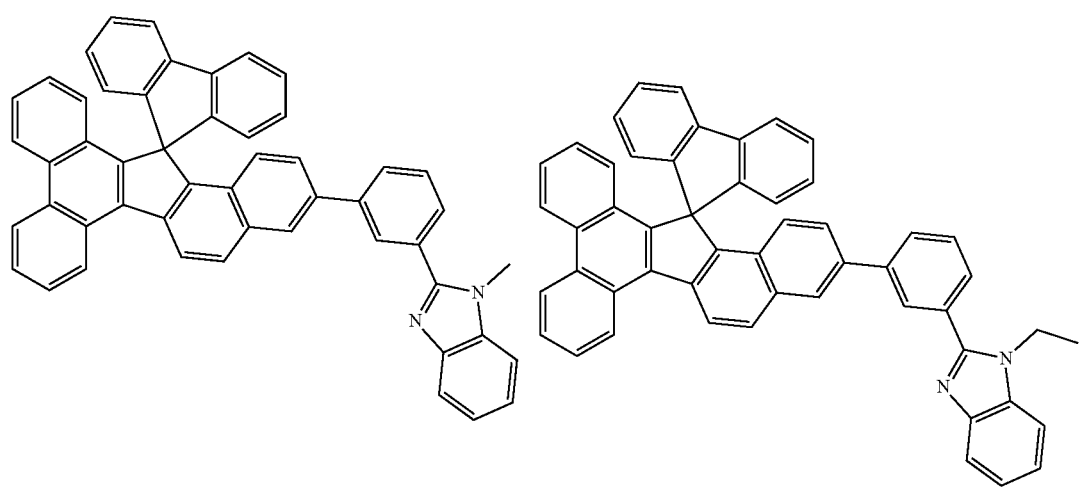
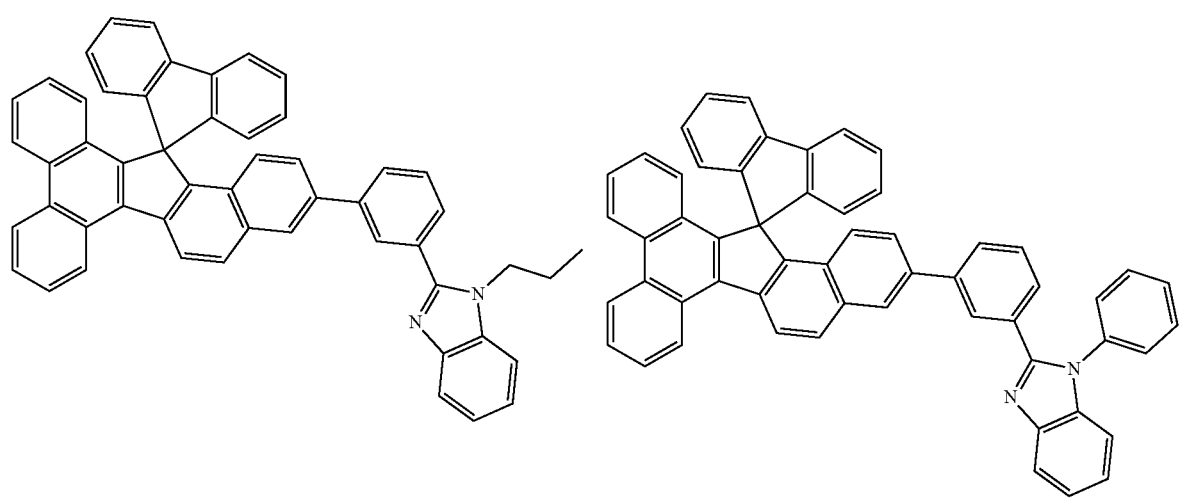

743 744
-continued
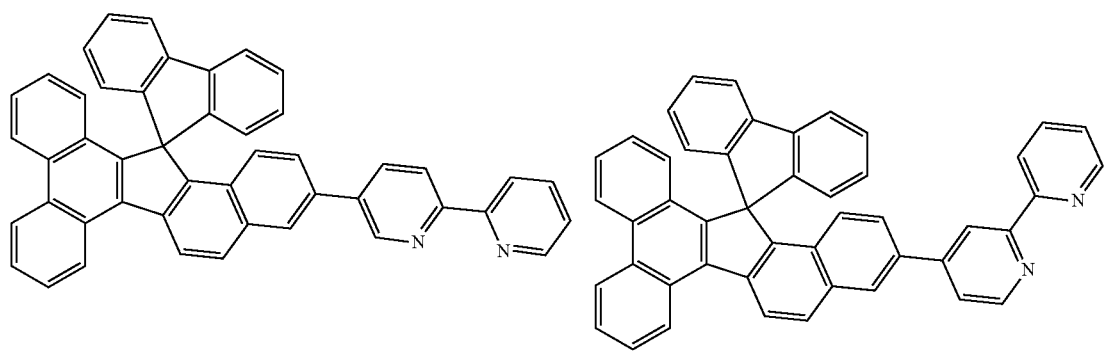
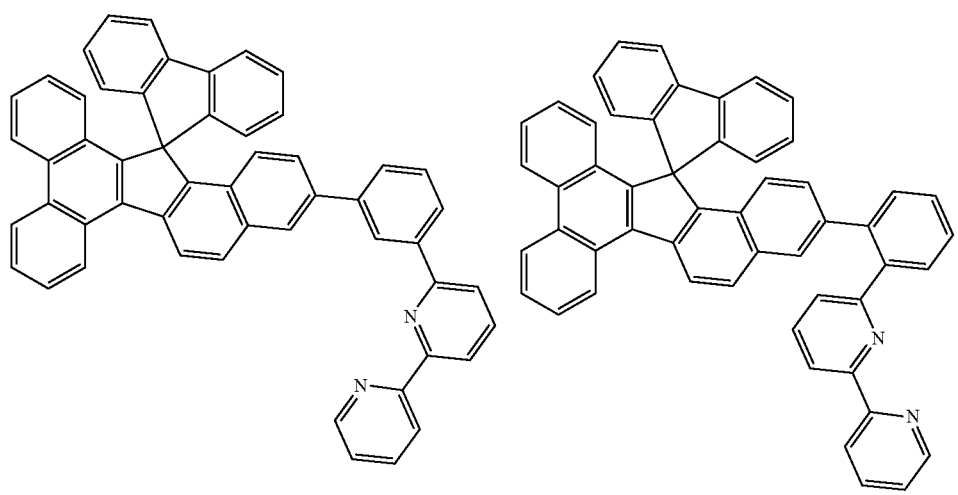
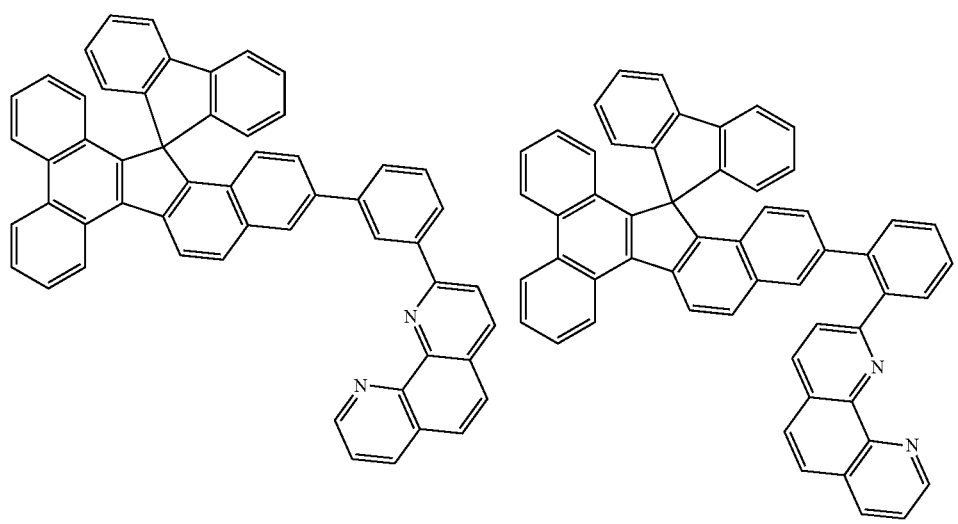

-continued
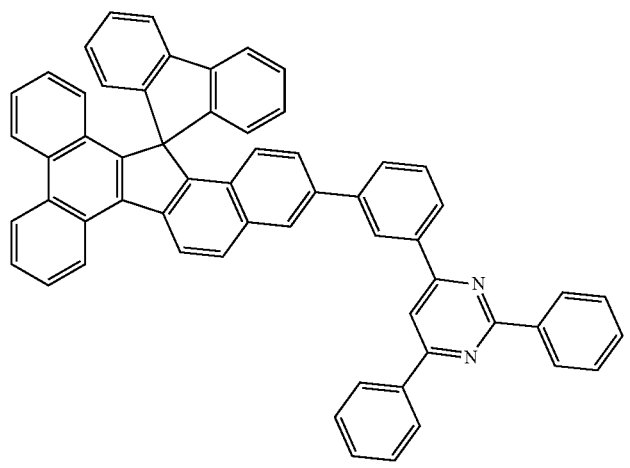
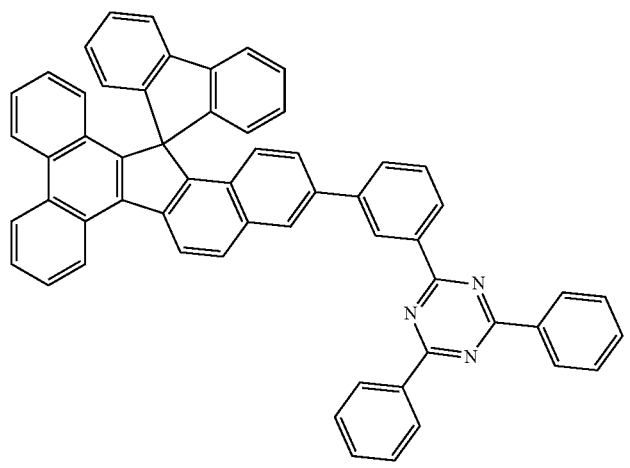
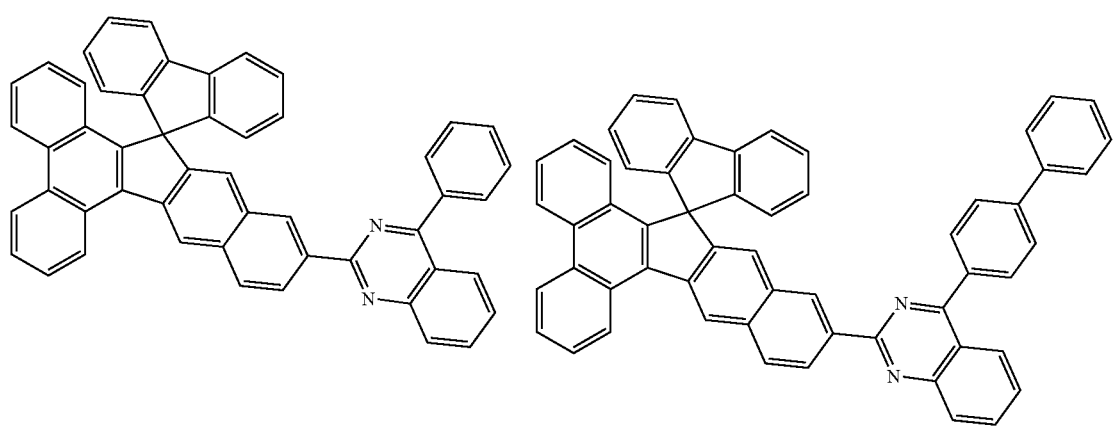
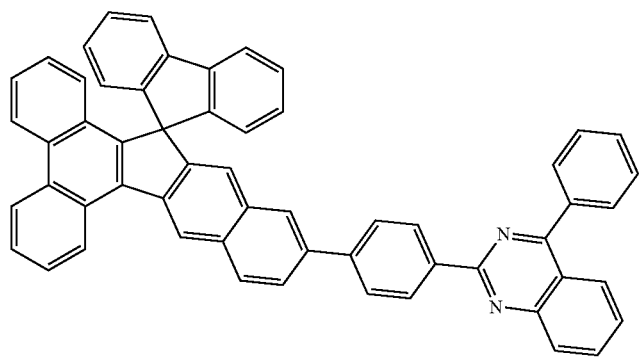

-continued
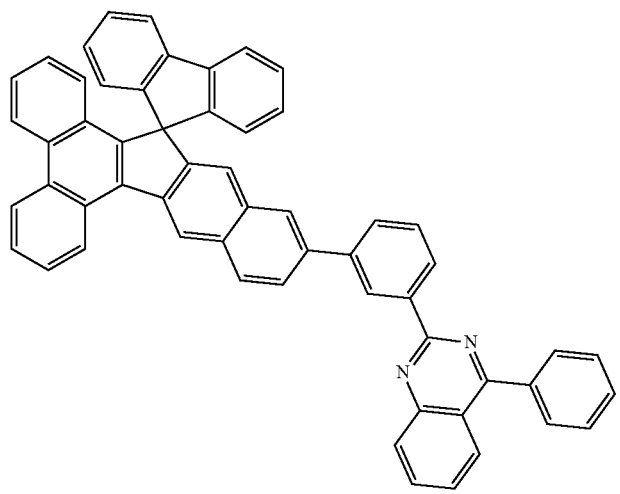
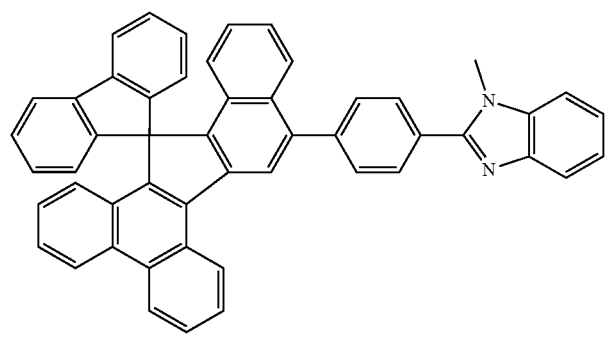
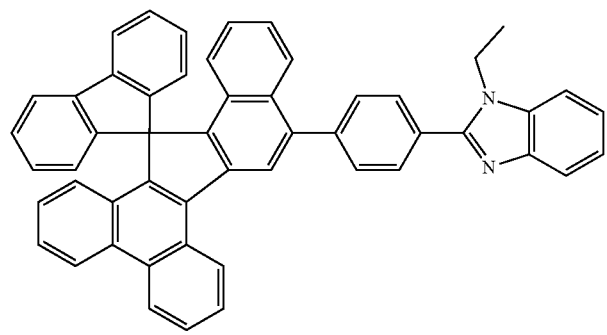
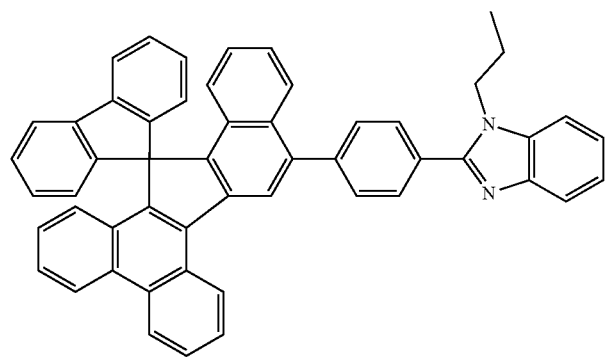

-continued
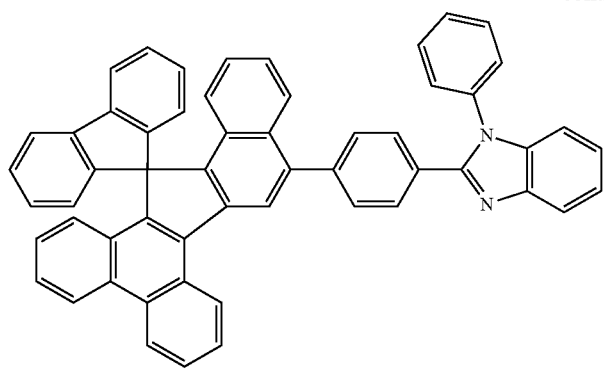
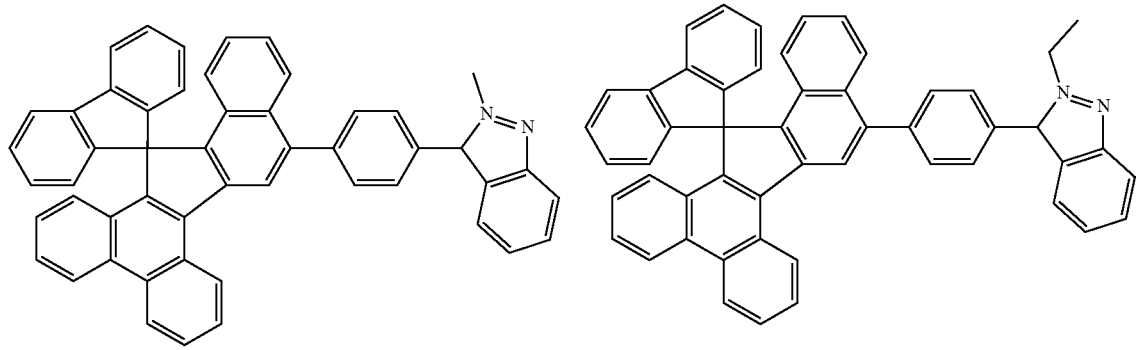
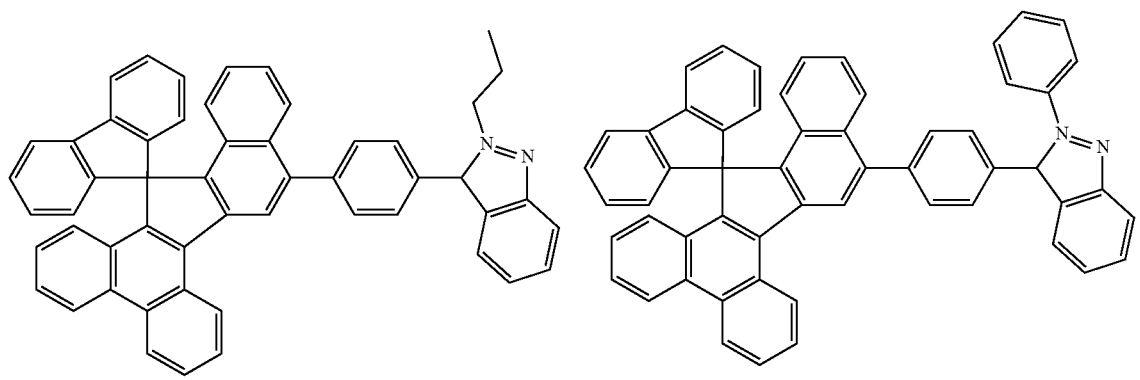
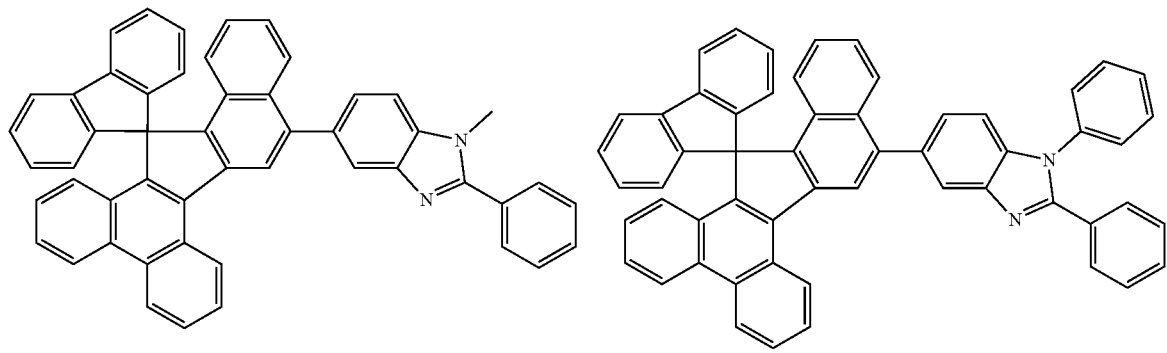

-continued
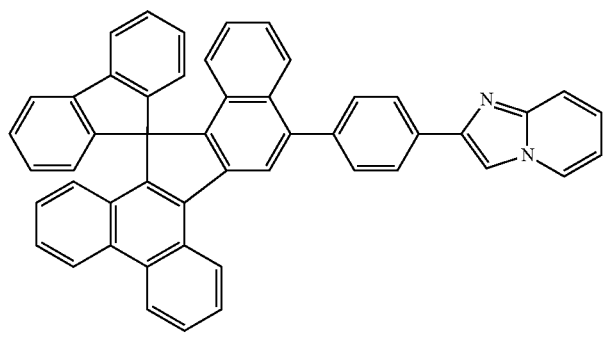
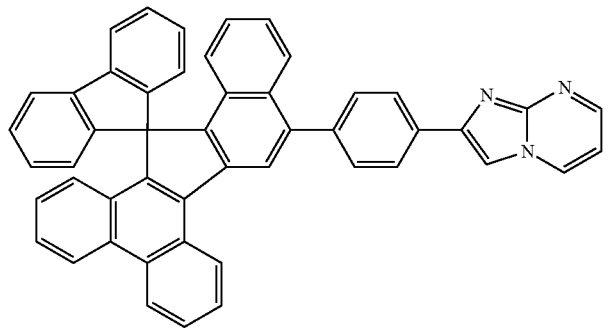
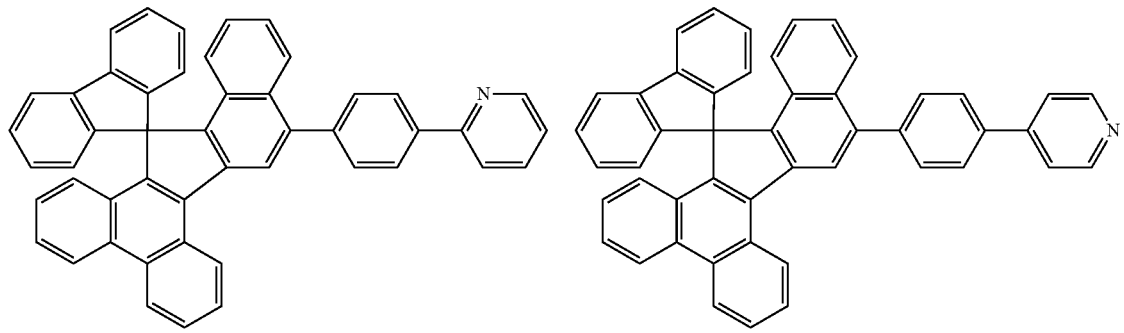
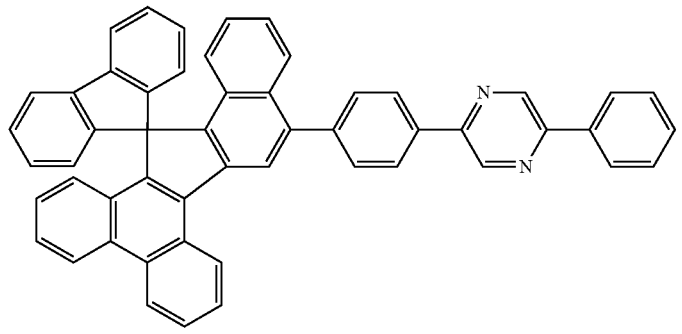
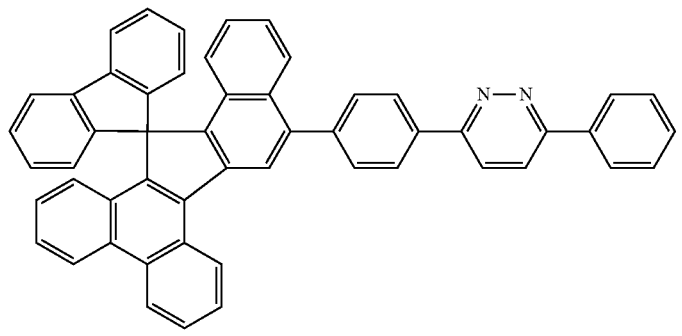

753 754
-continued
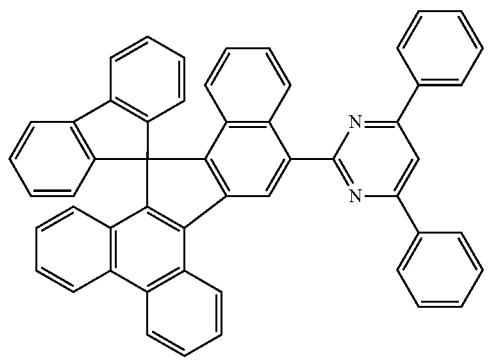
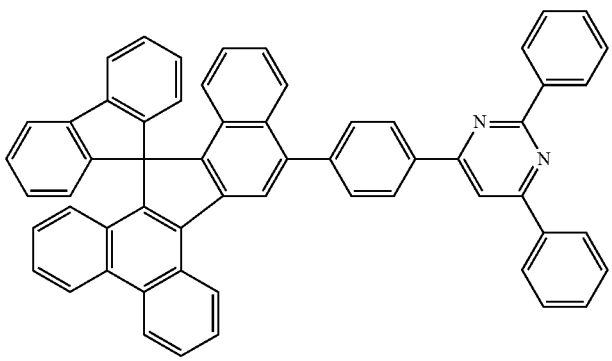
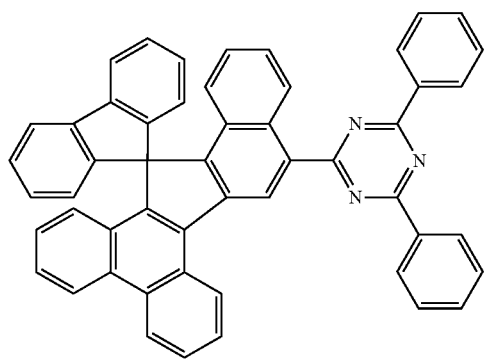
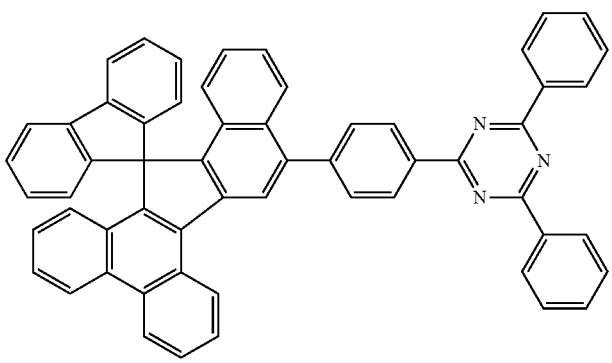
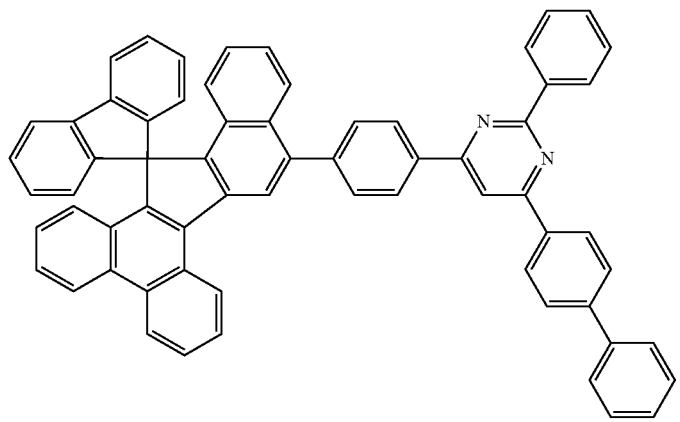
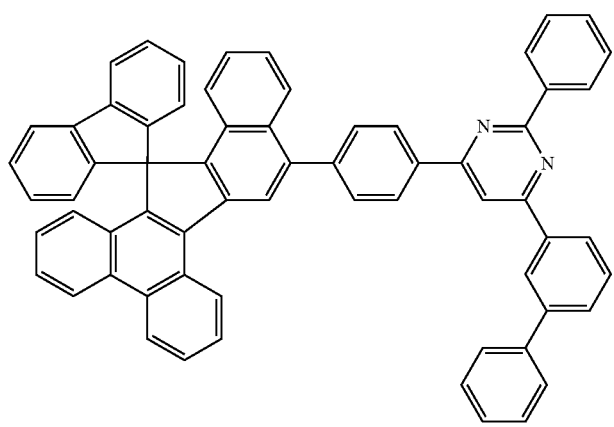

-continued
755
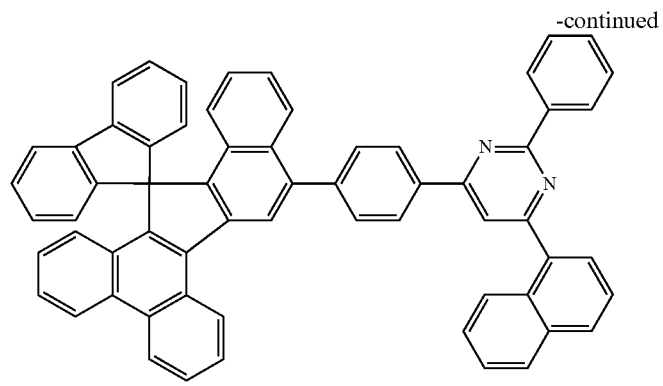
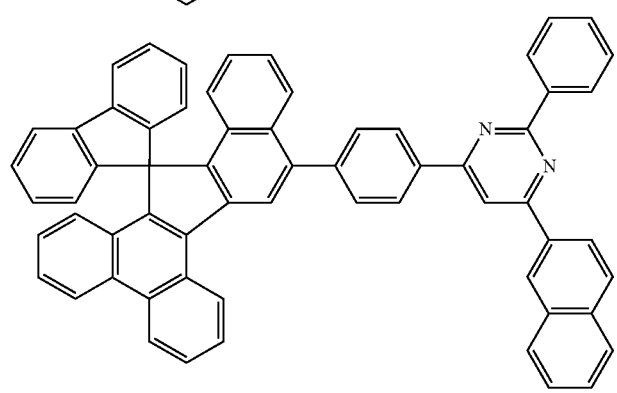
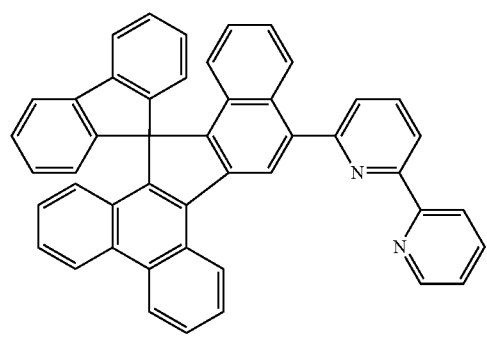
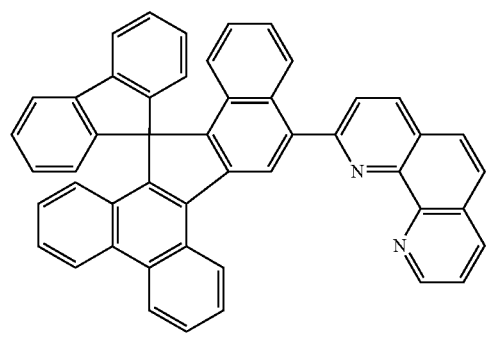
756
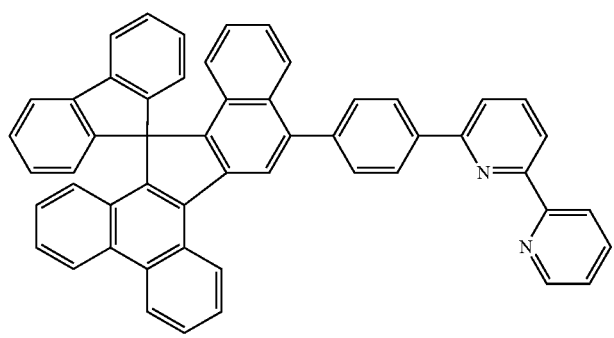
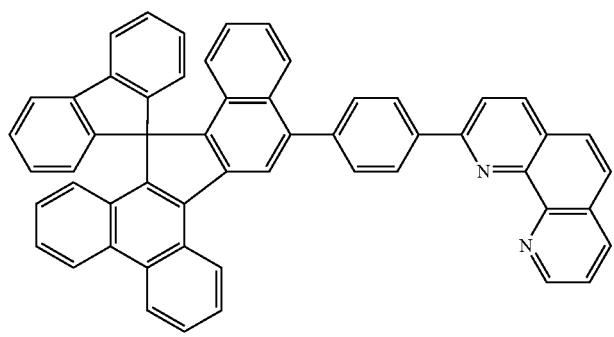

-continued
757
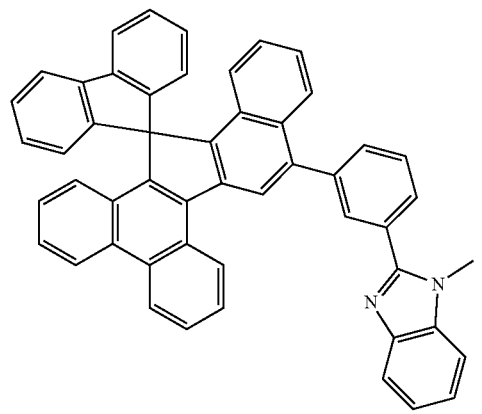
758
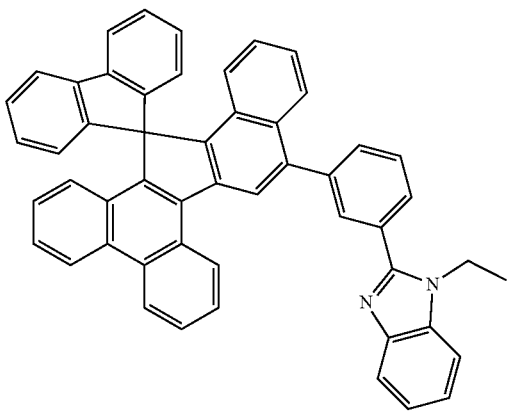
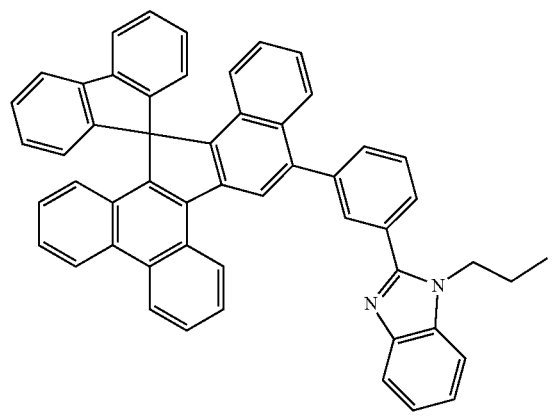
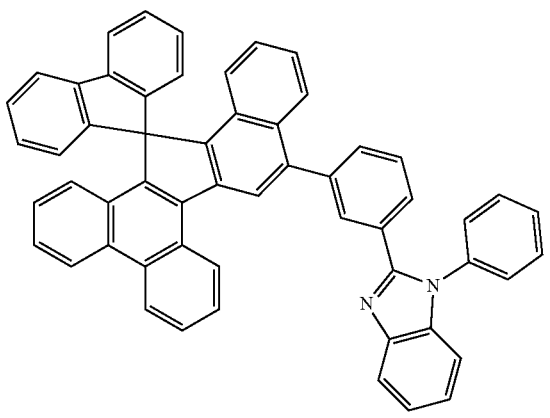
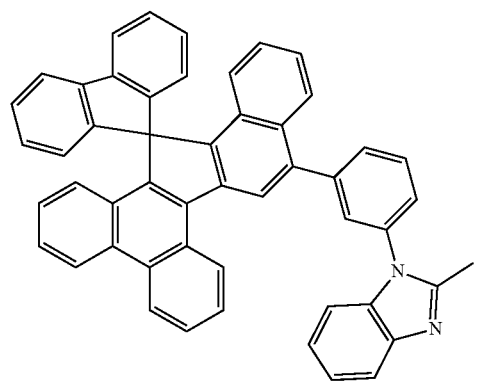
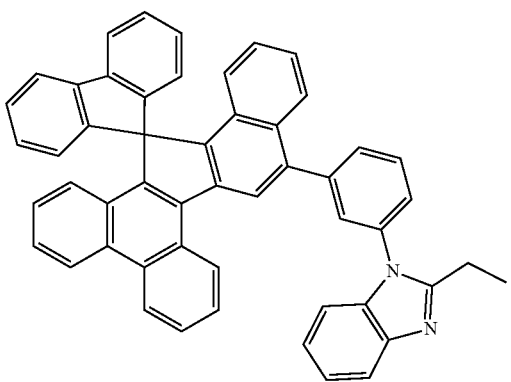
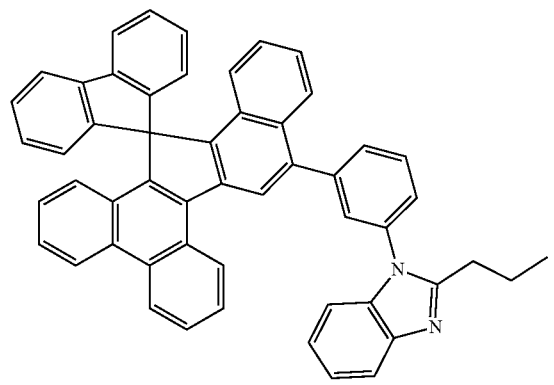
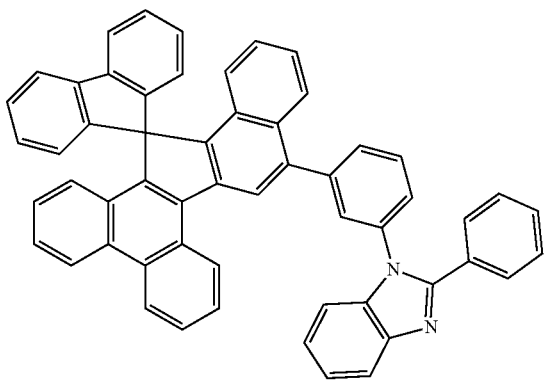

759 760
-continued
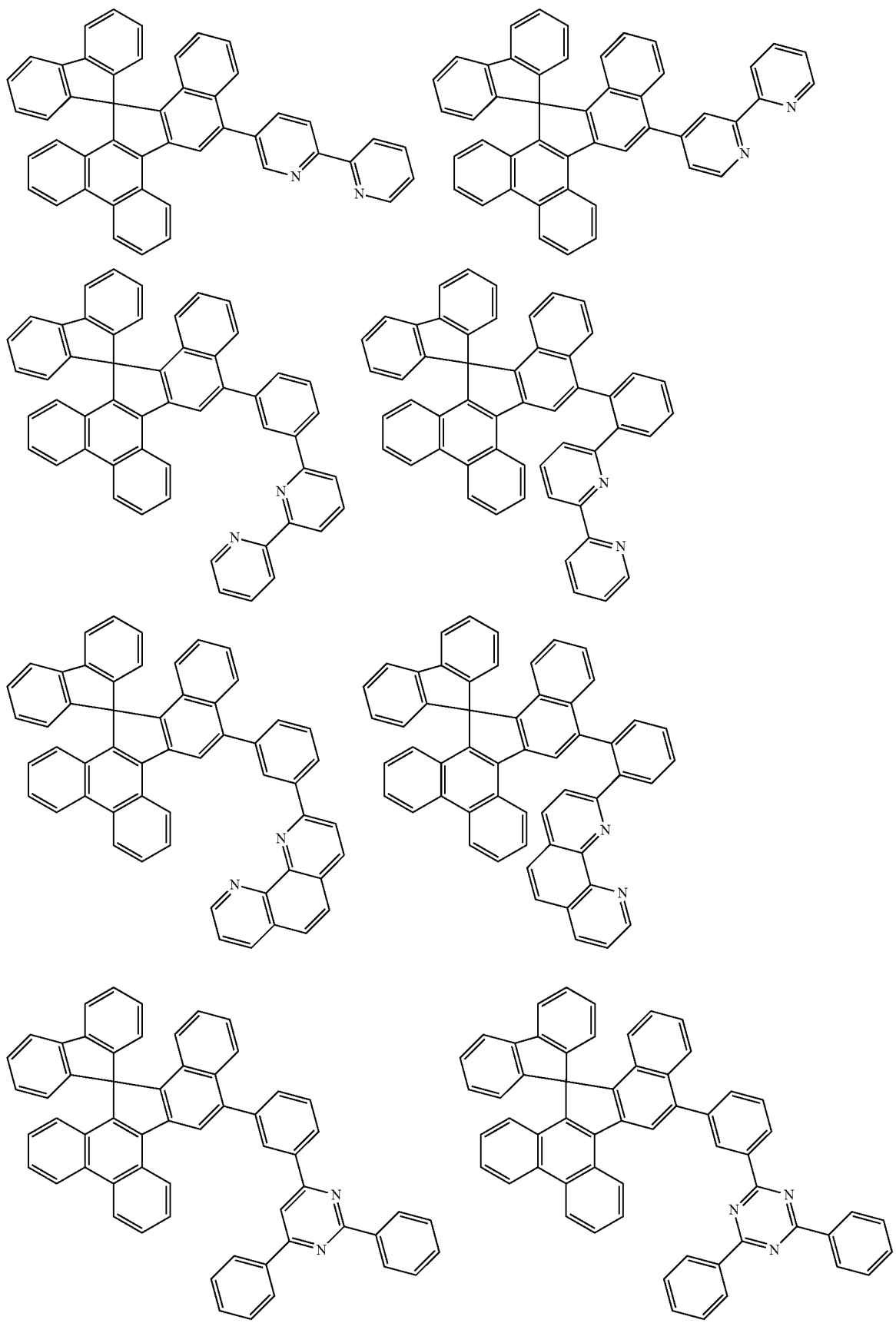

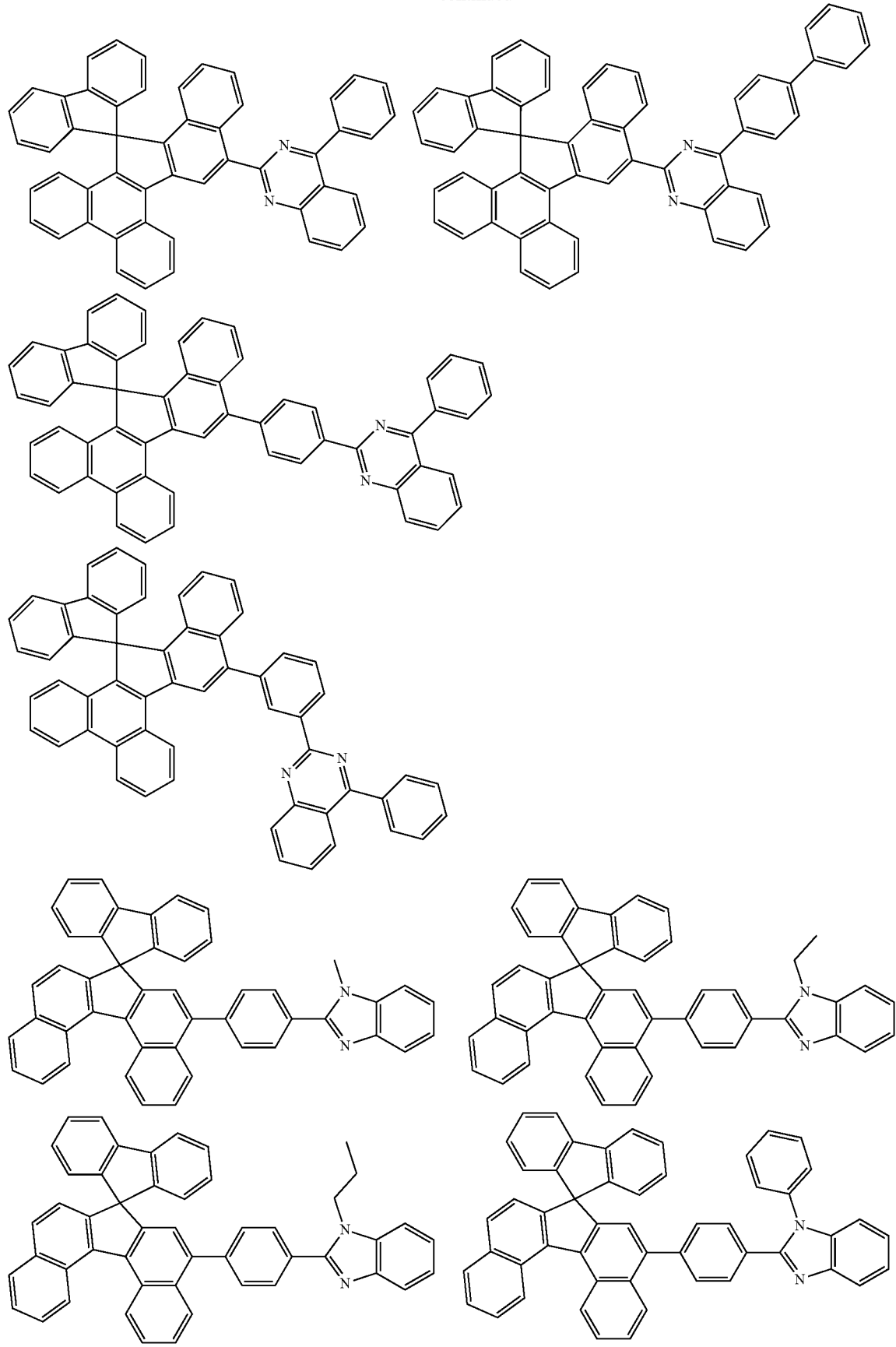

-continued
| 763 | 764 |
|---|---|
| 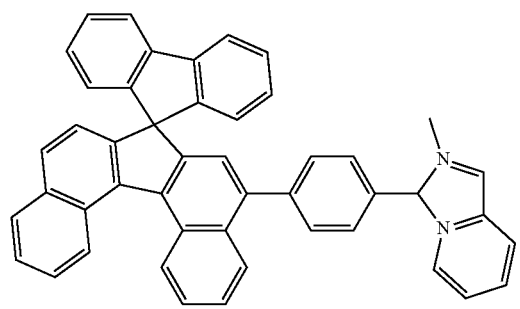 | 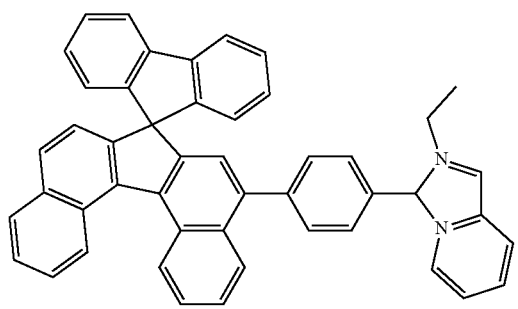 |
| 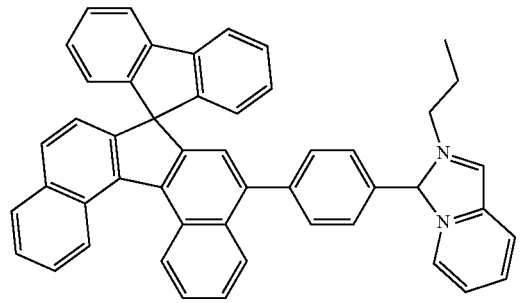 | 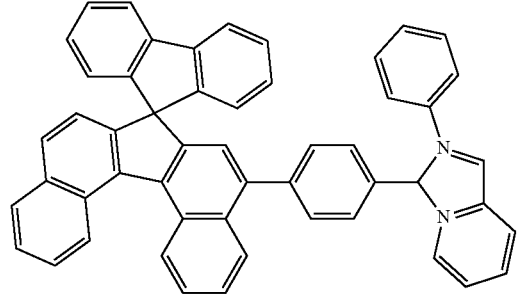 |
| 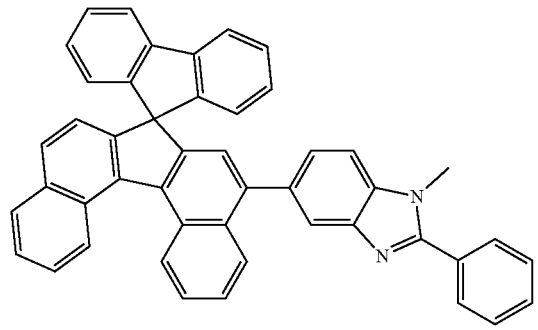 | 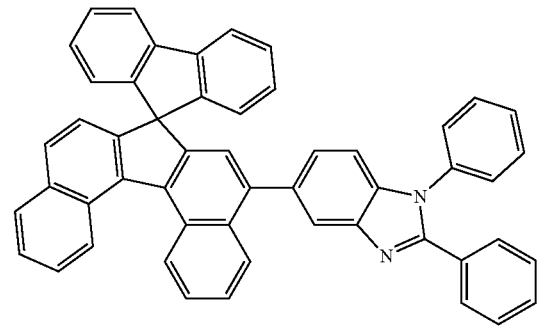 |
| 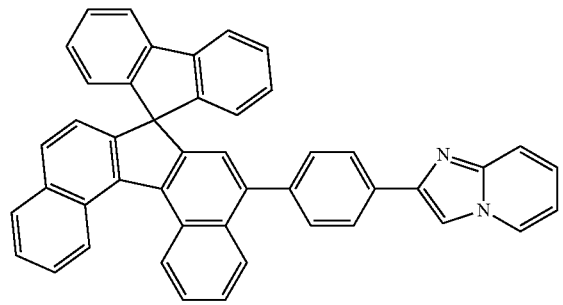 | 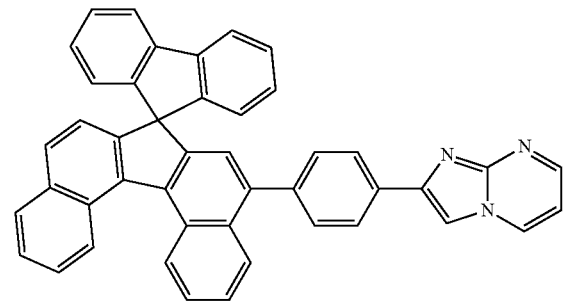 |
| 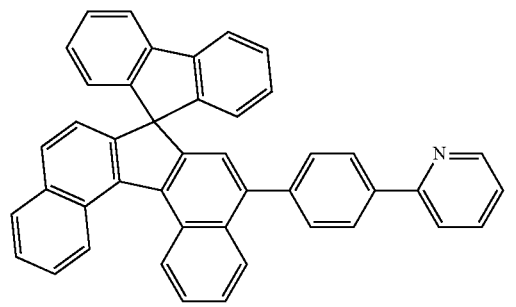 | 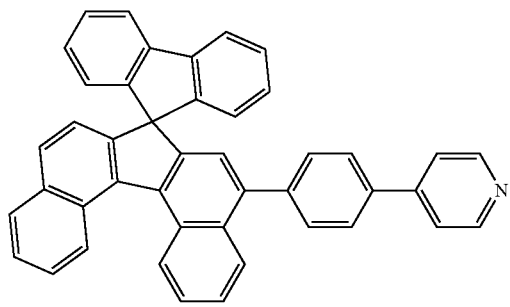 |

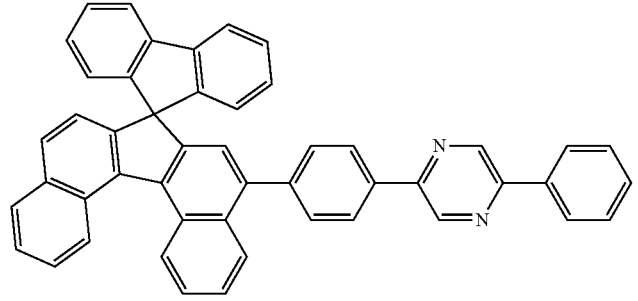
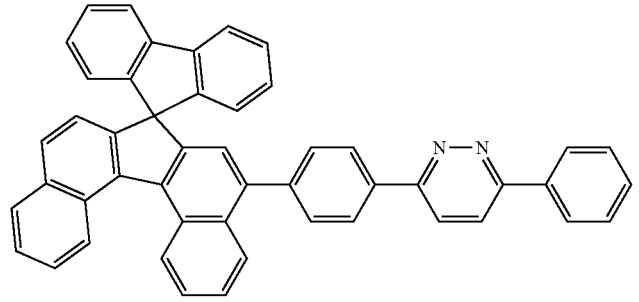
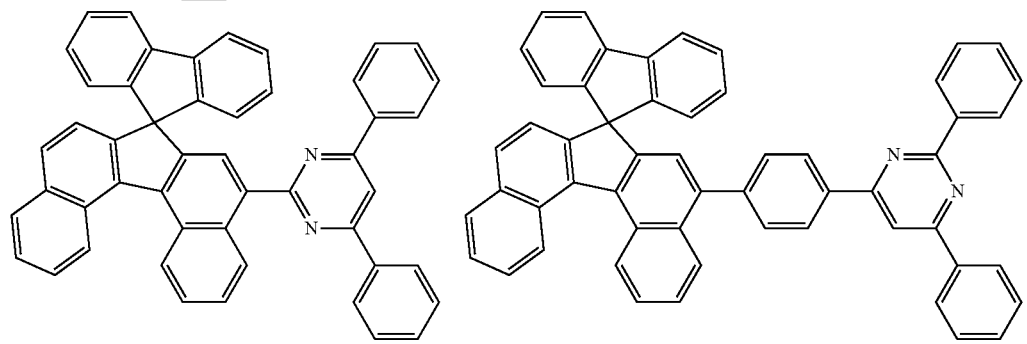
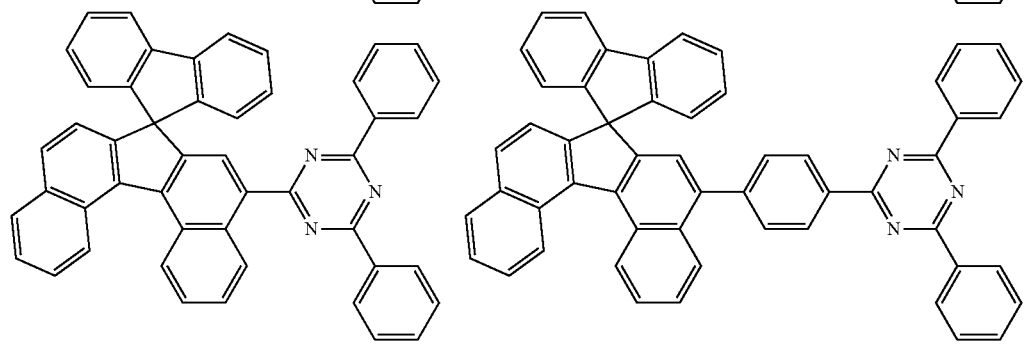
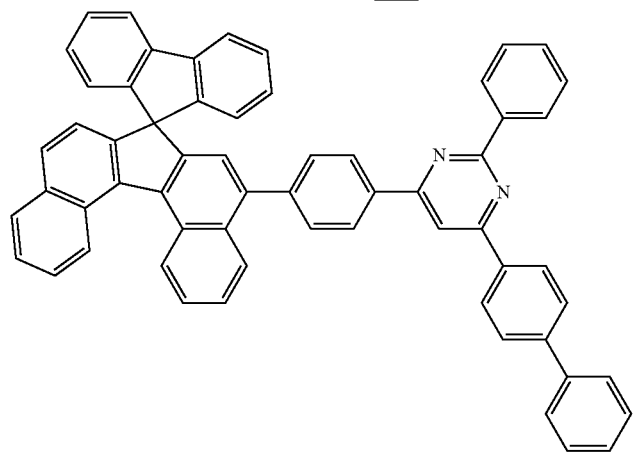

-continued
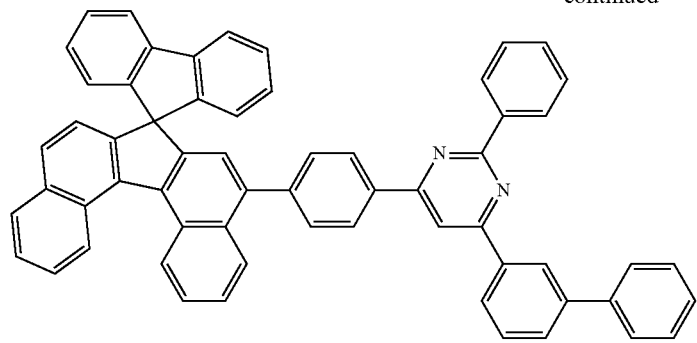
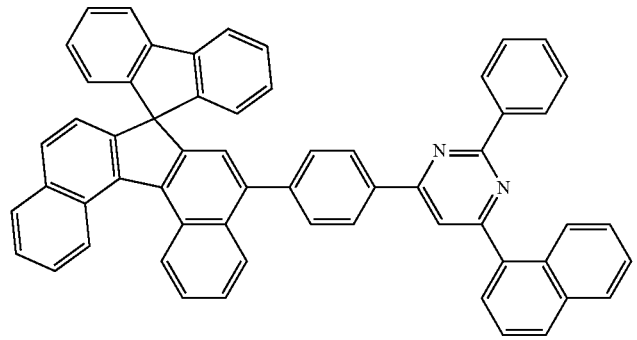
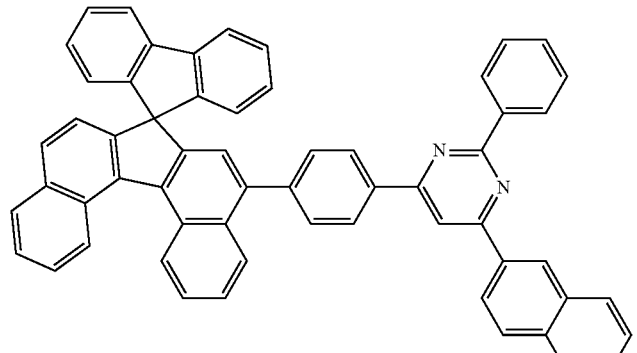
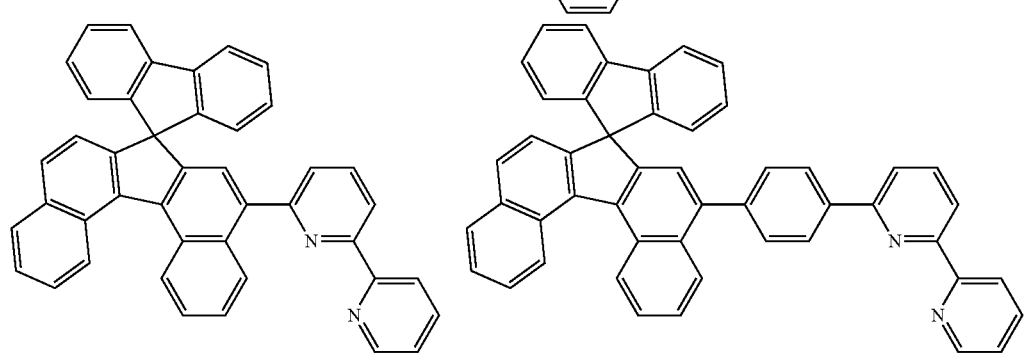
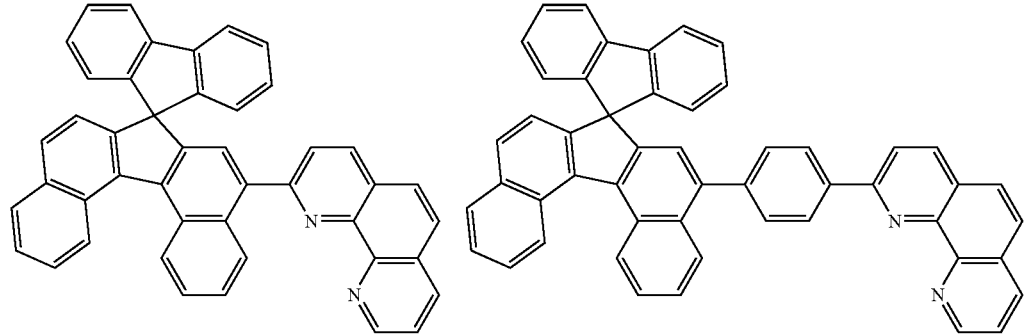

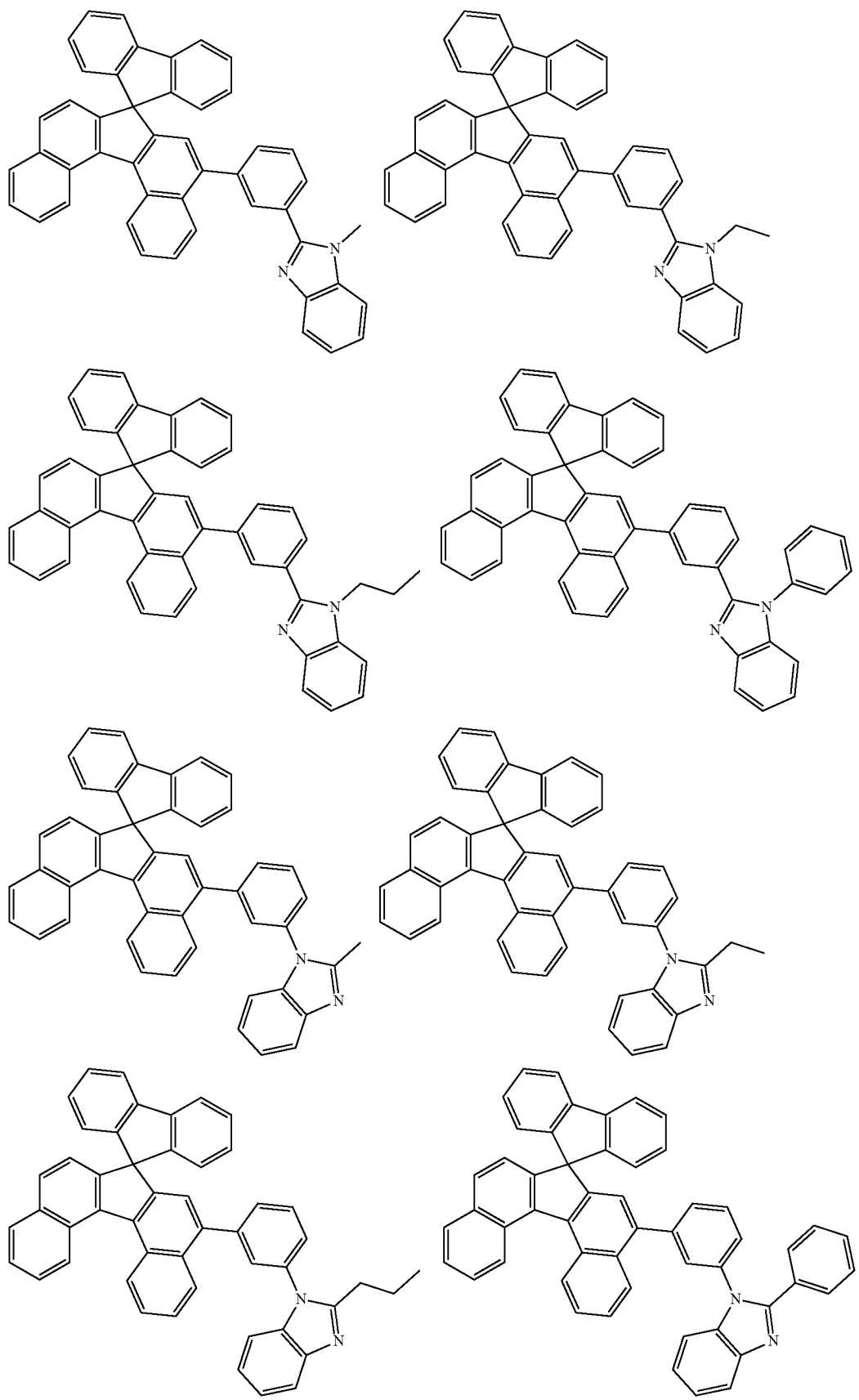

771
772
-continued
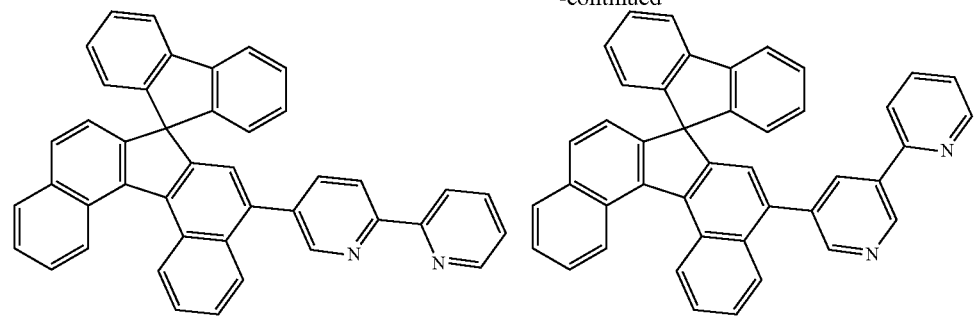
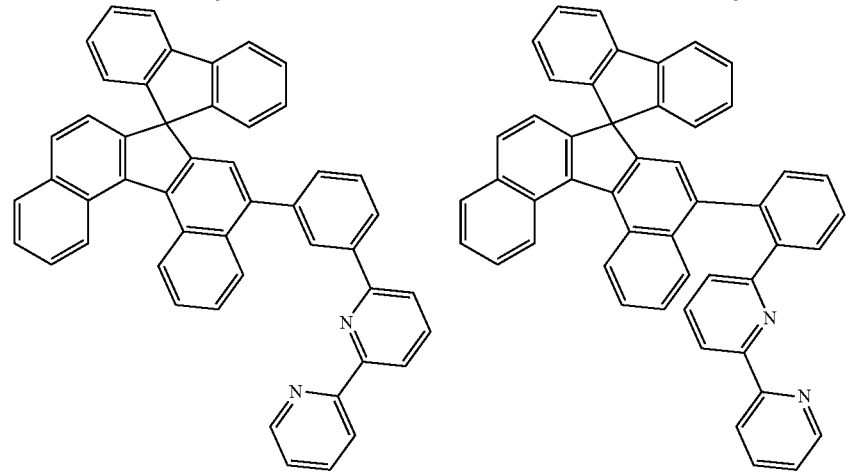
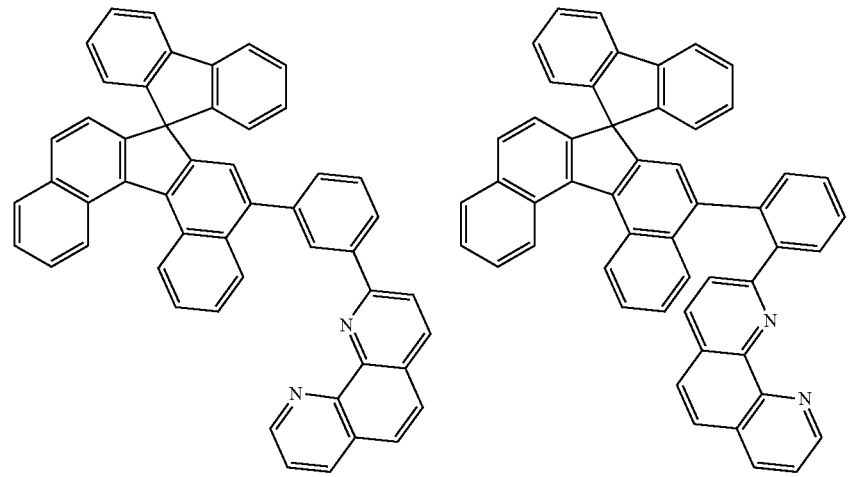
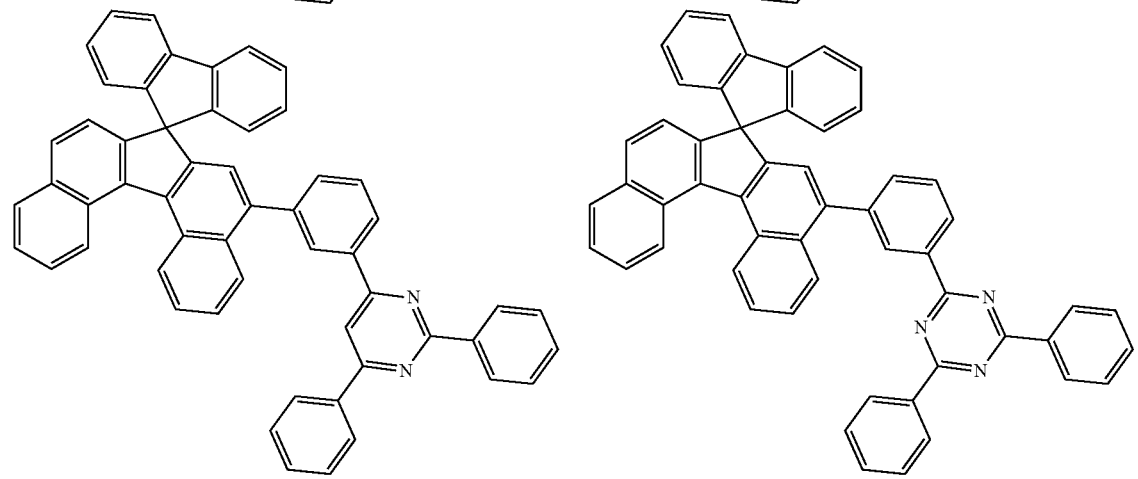

773 774
-continued
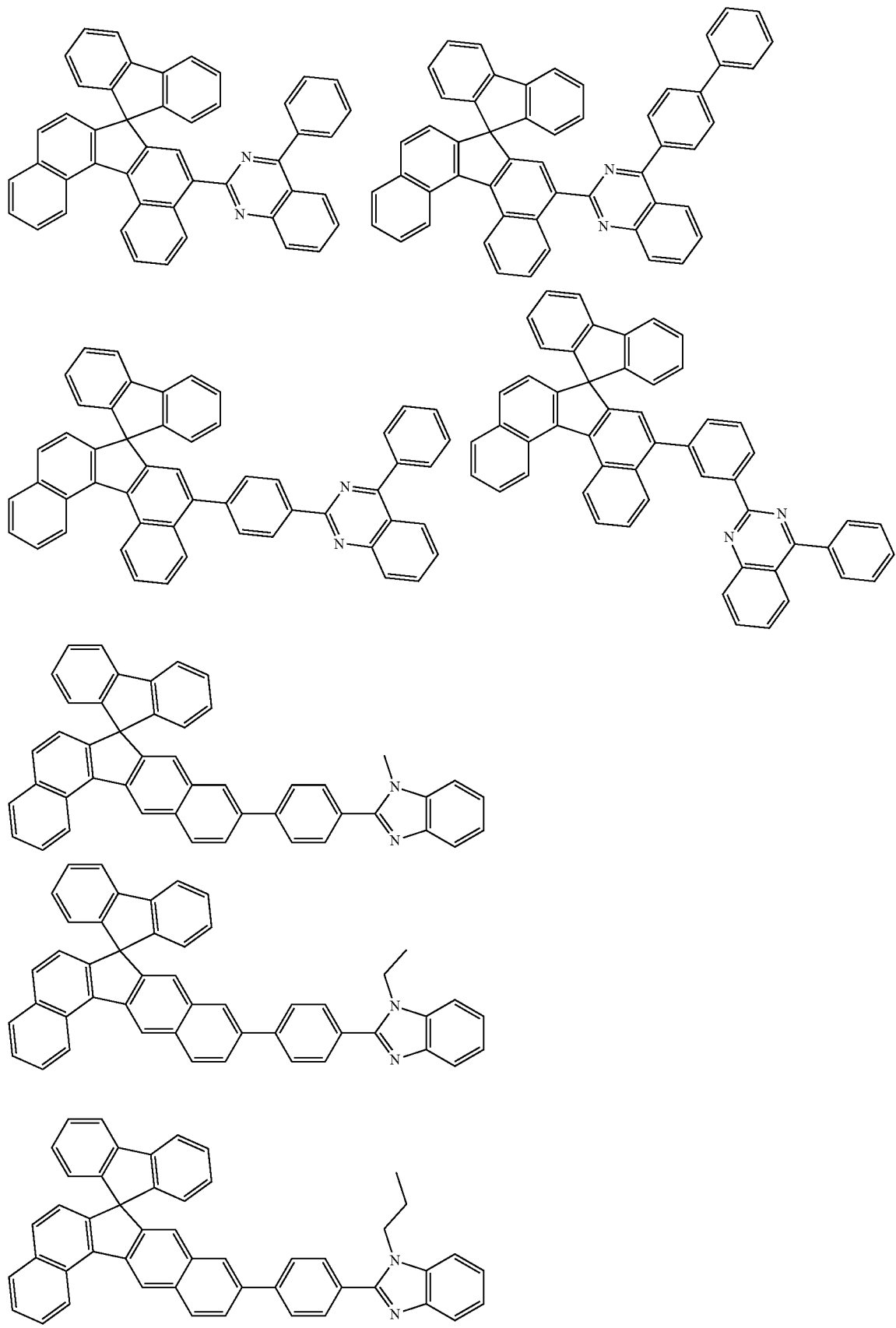

-continued
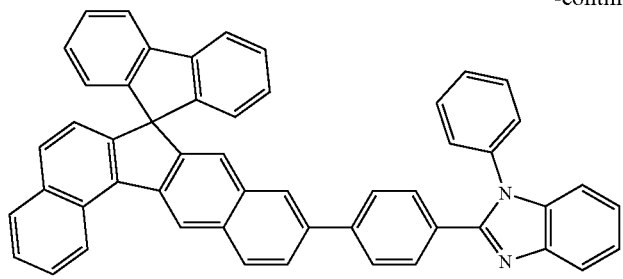
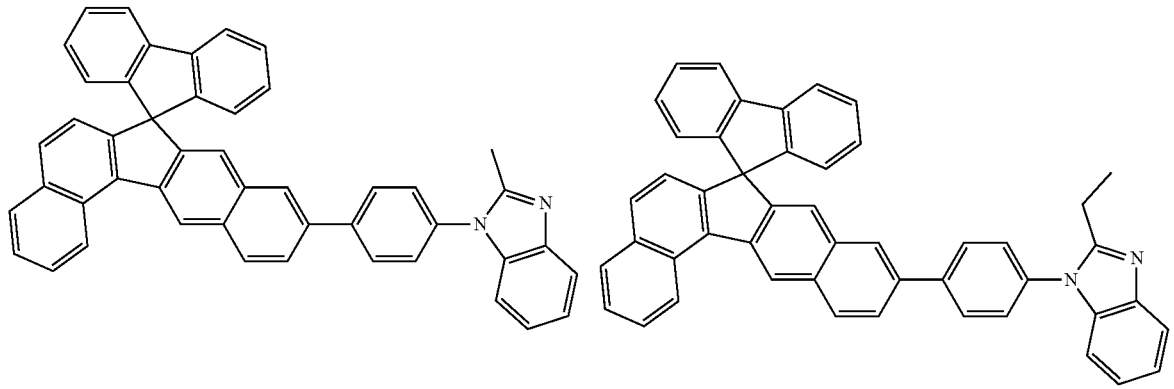
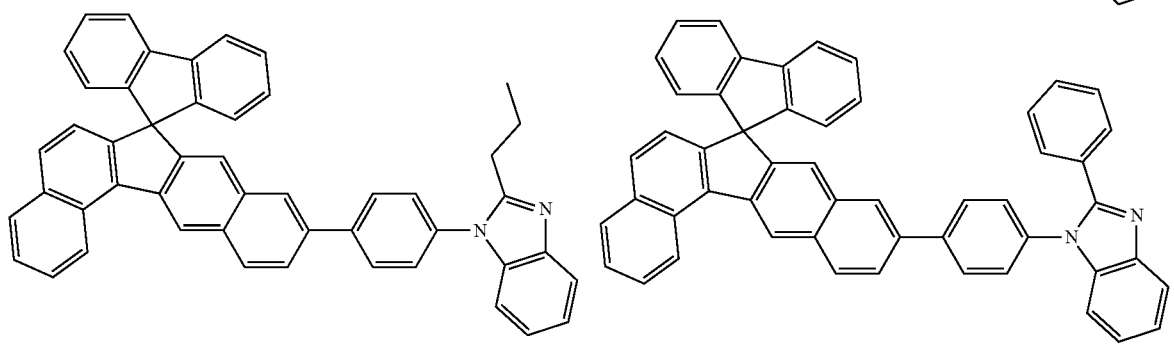
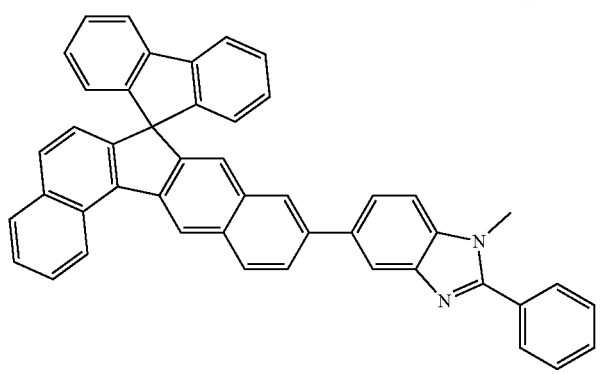
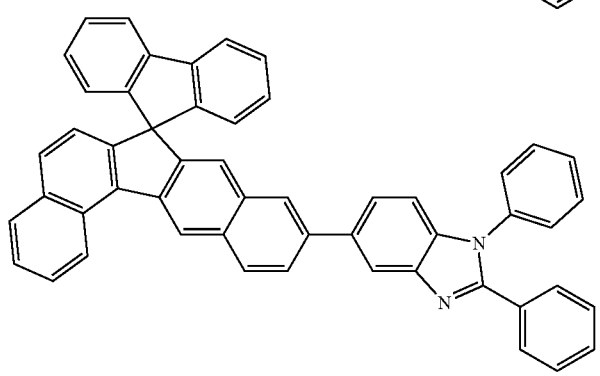

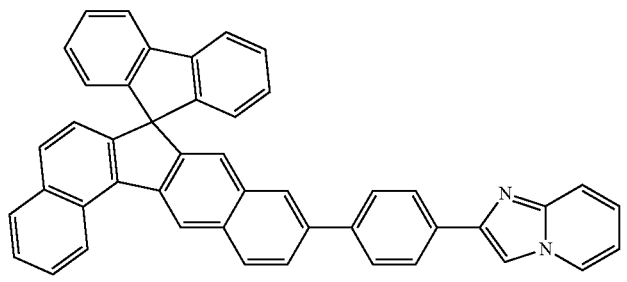
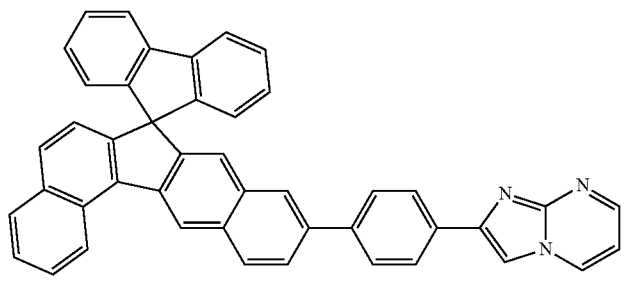
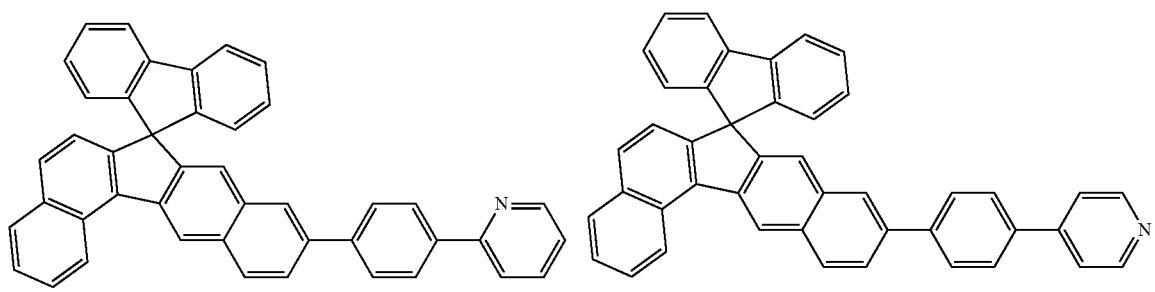
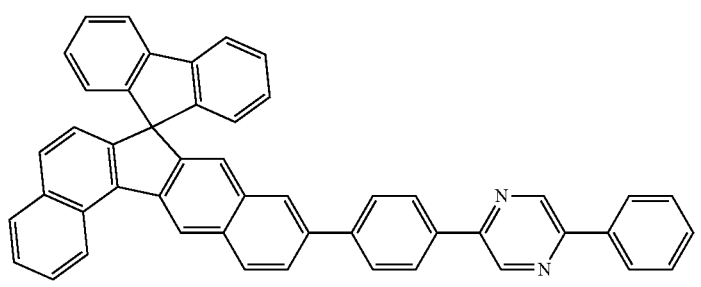
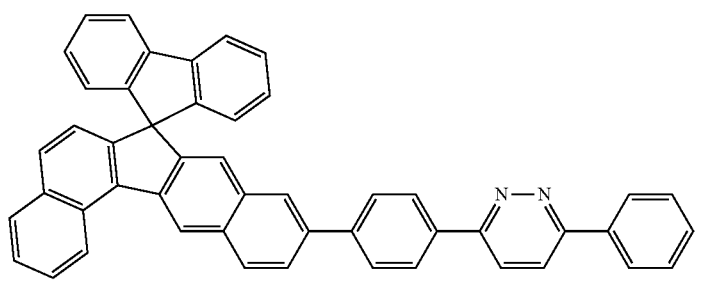

-continued
779
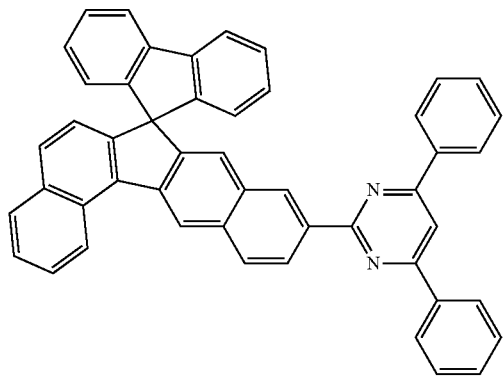
780
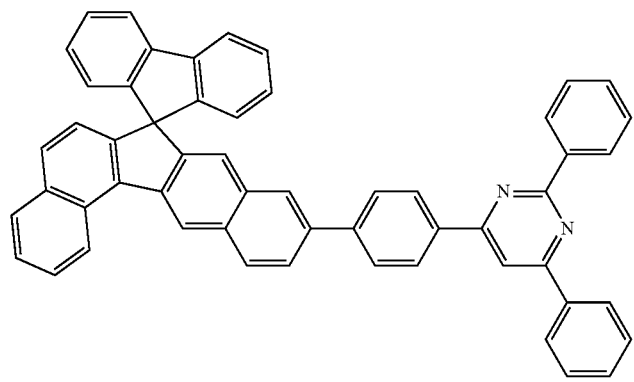
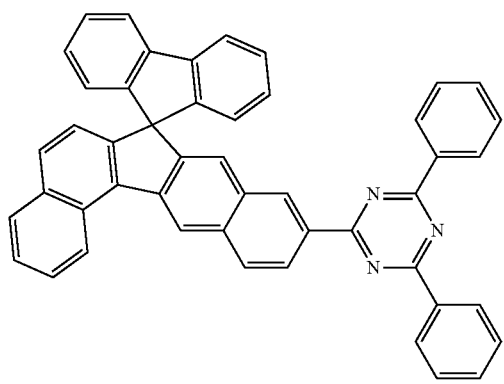
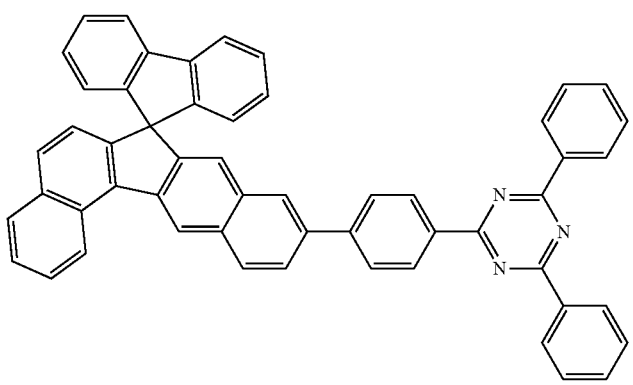
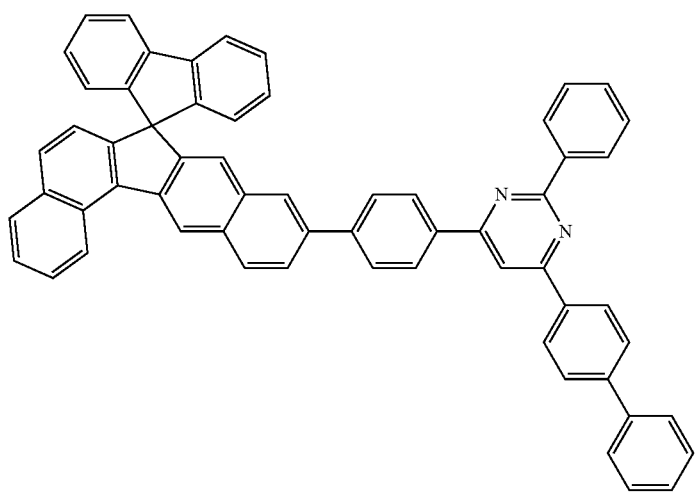

781
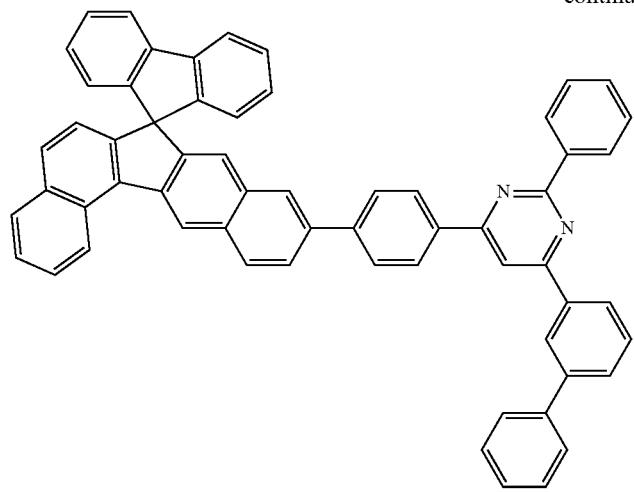
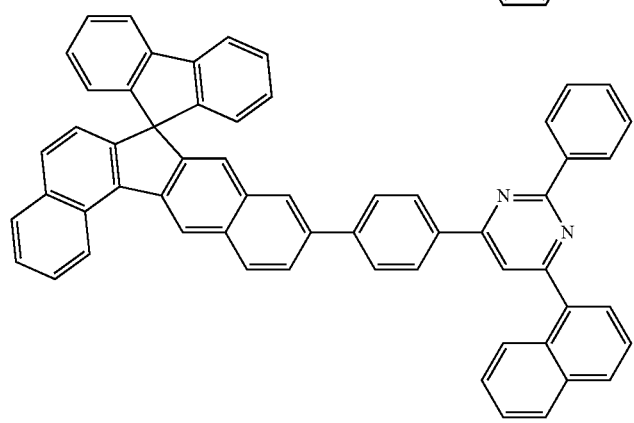
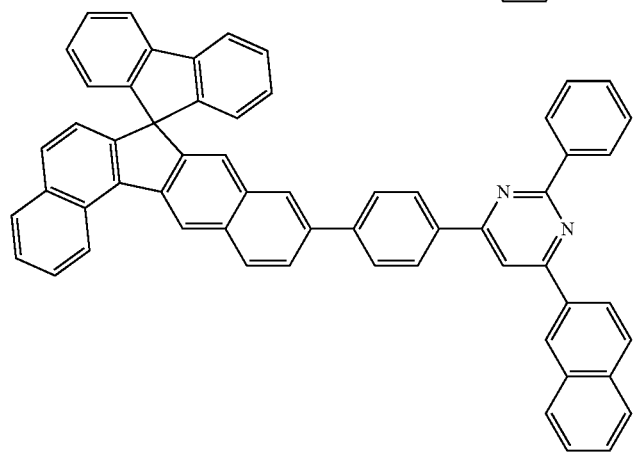
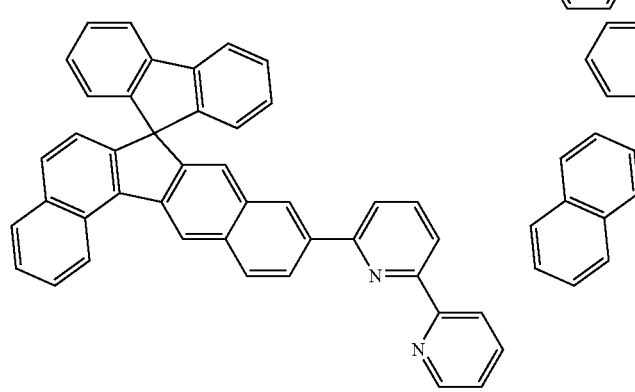
782
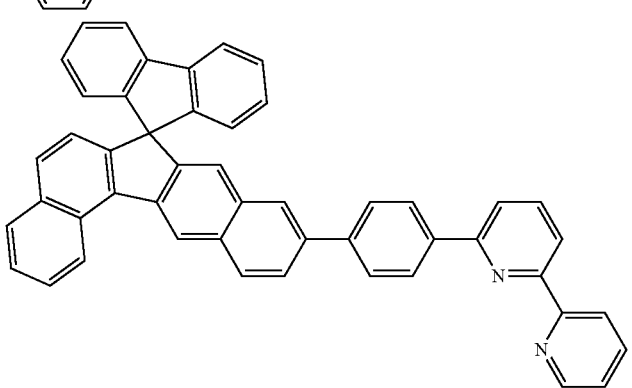

783
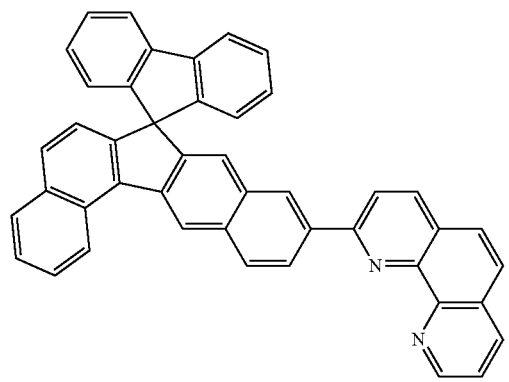
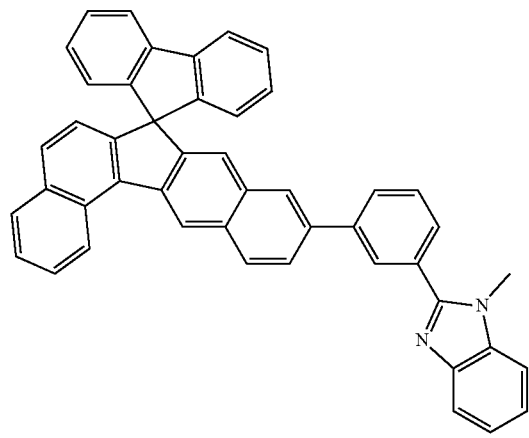
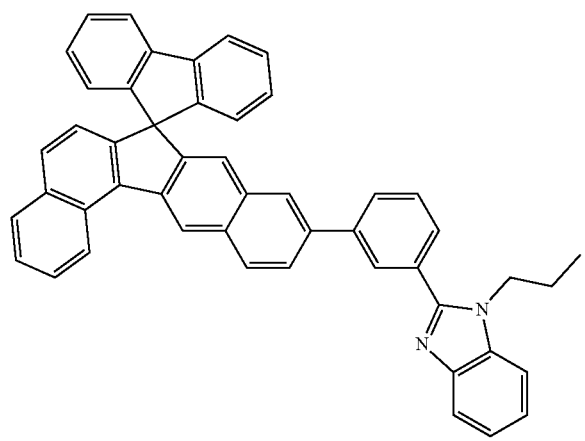
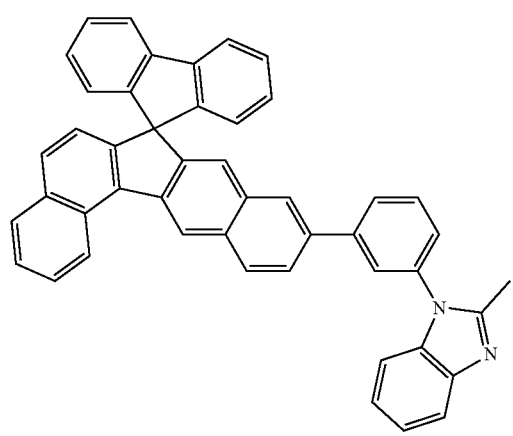
784
-continued
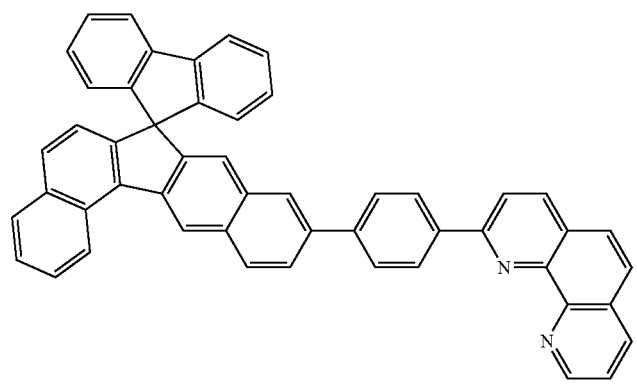
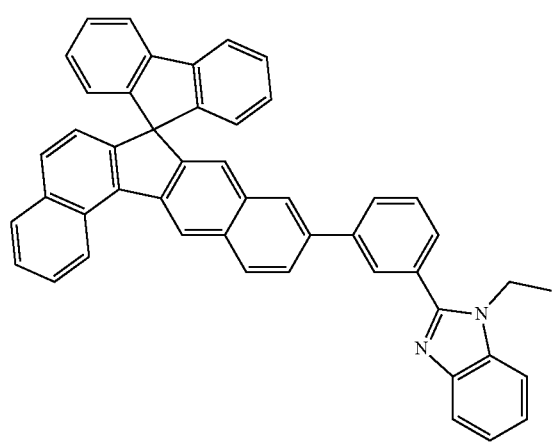
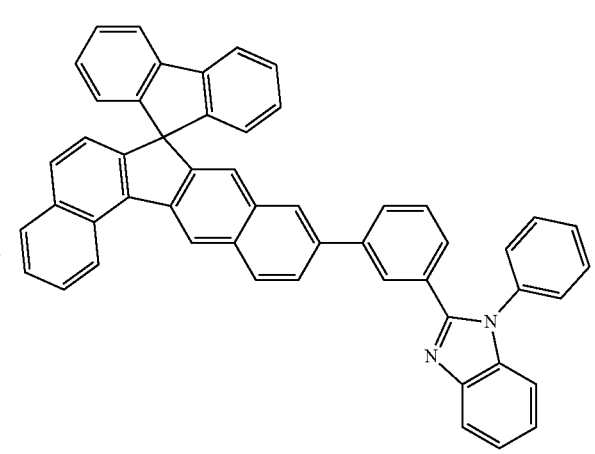
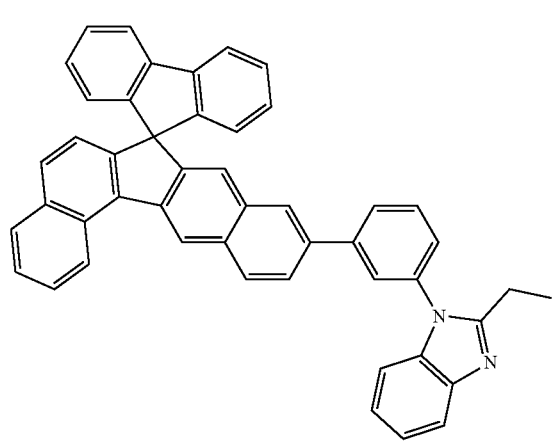

785 786
-continued
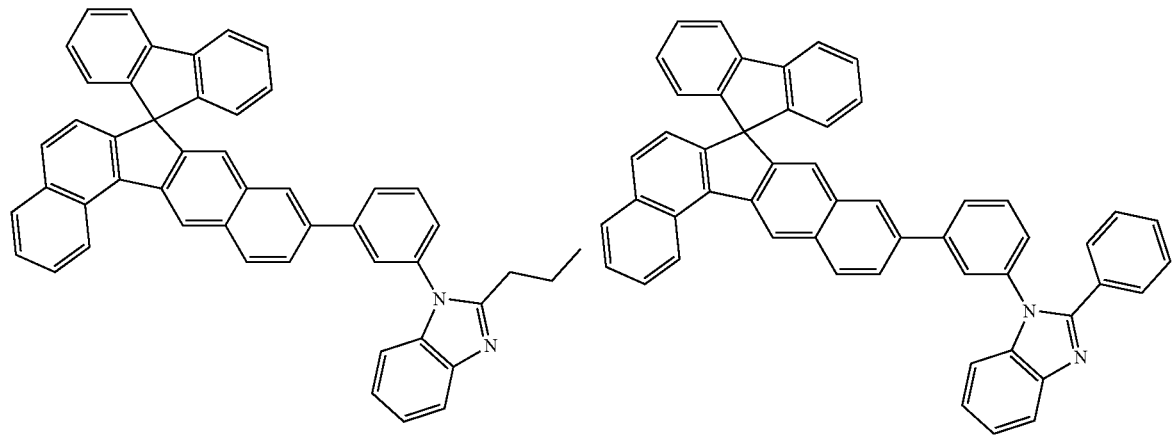
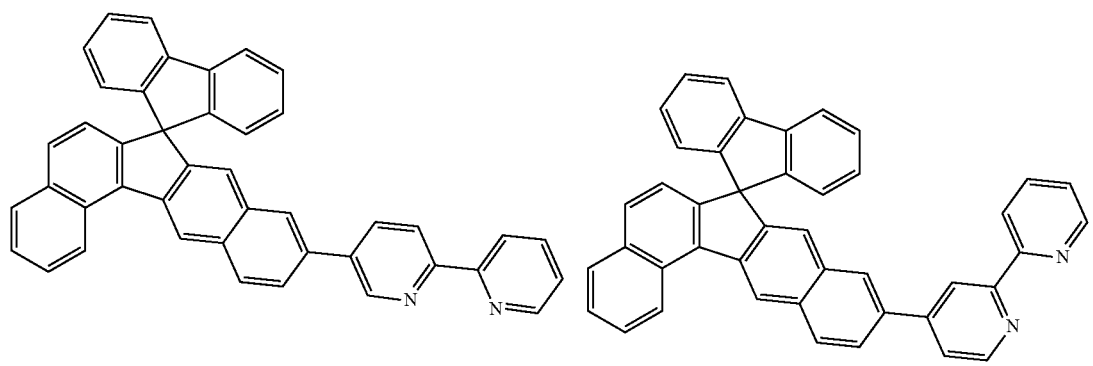
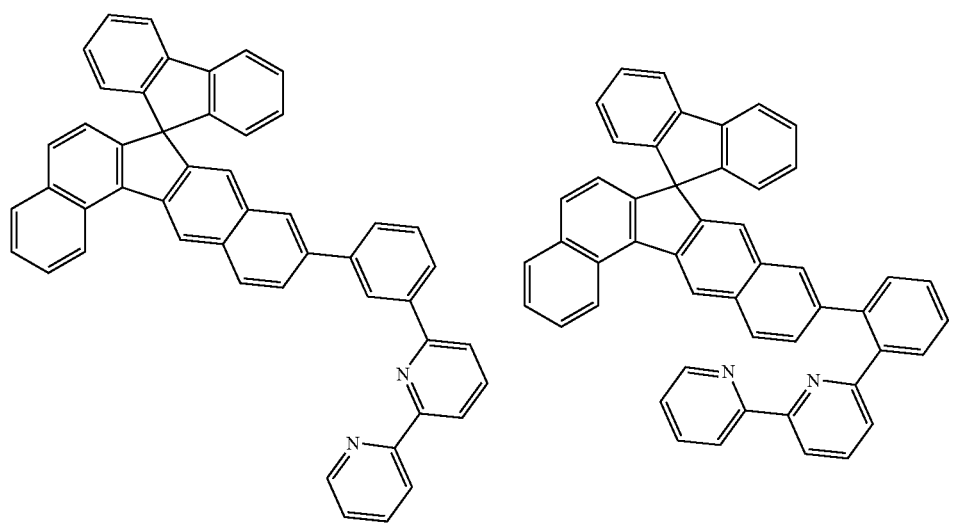

787
788
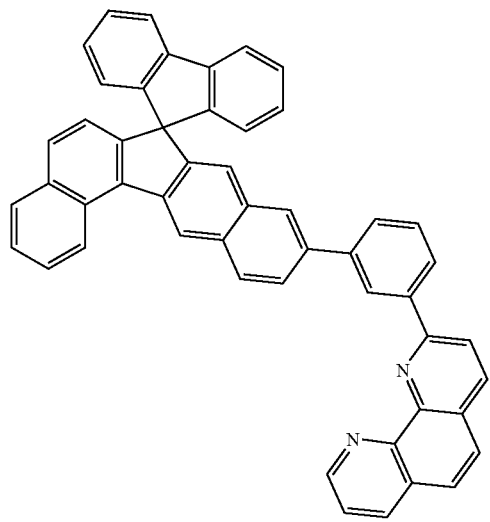
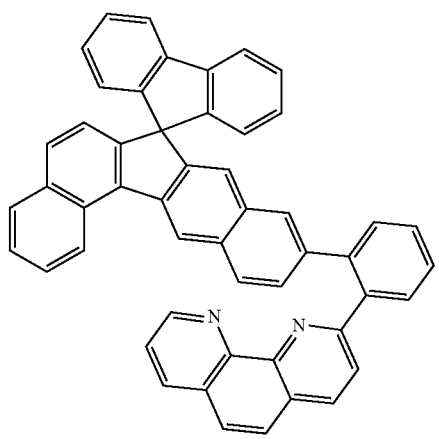
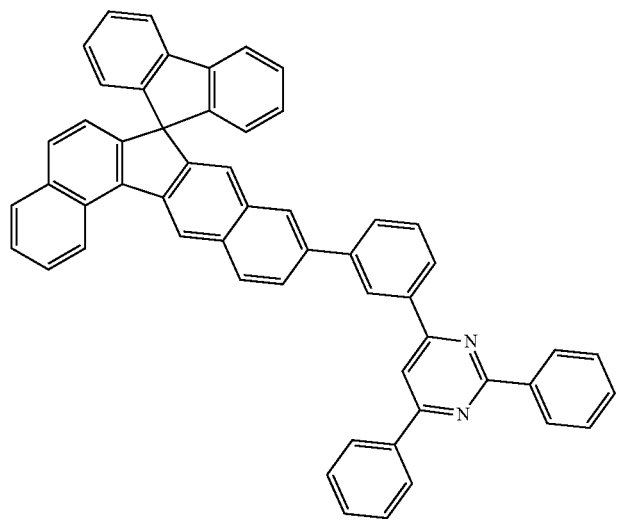
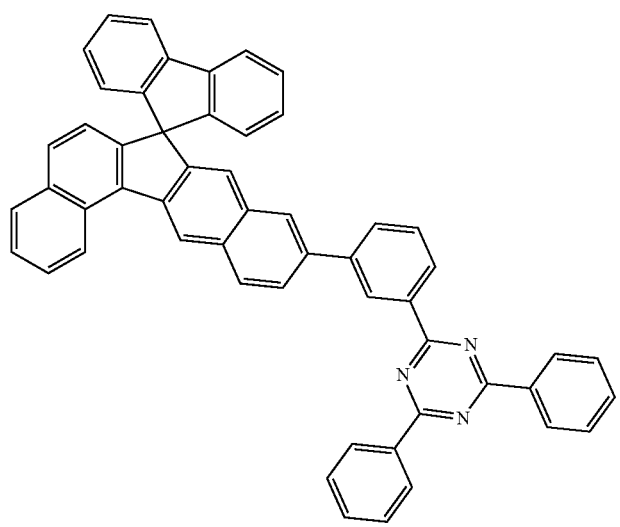

| 789 | 790 |
|---|---|
| 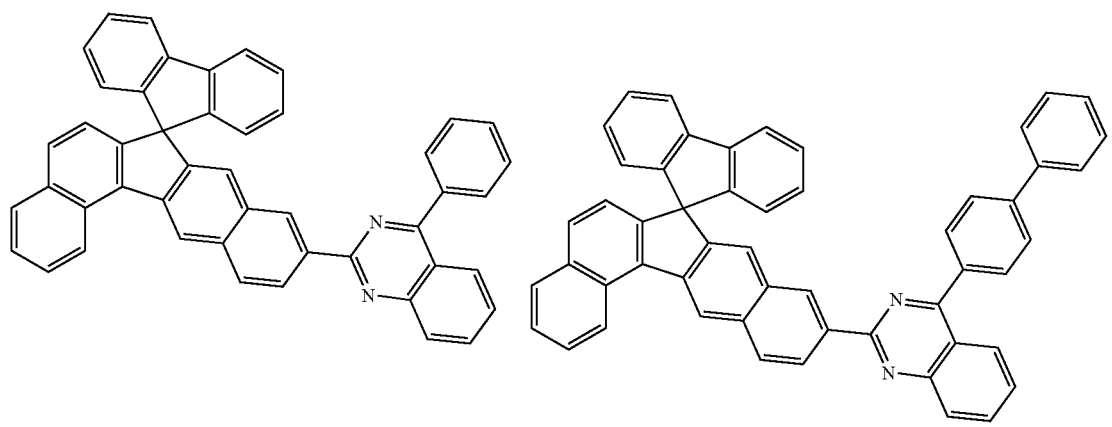 | |
| 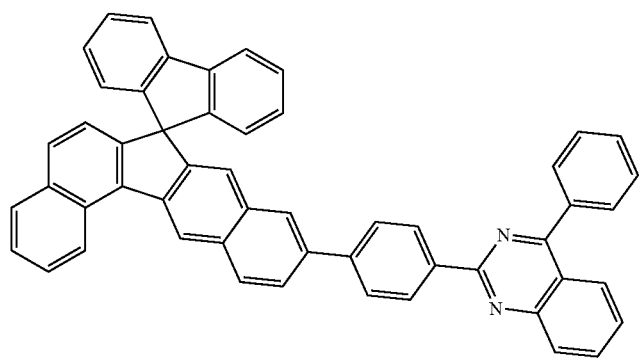 | |
| 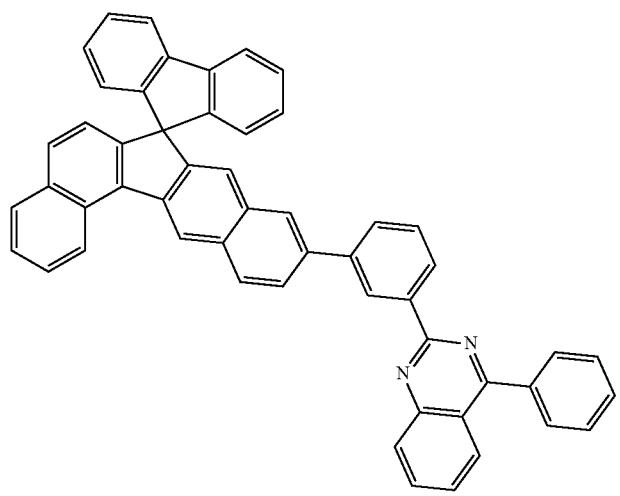 | |
| 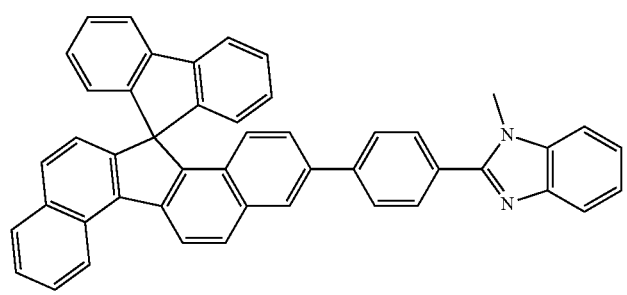 | |

791                                          792
-continued
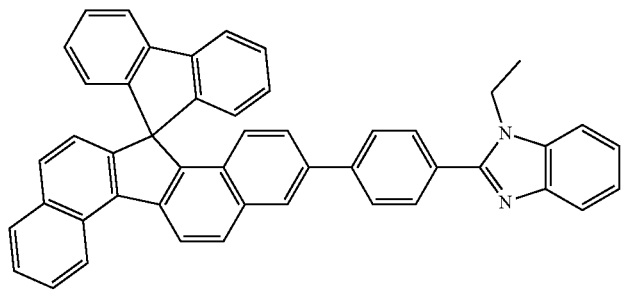
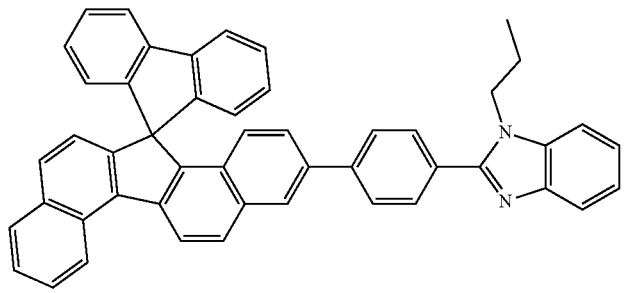
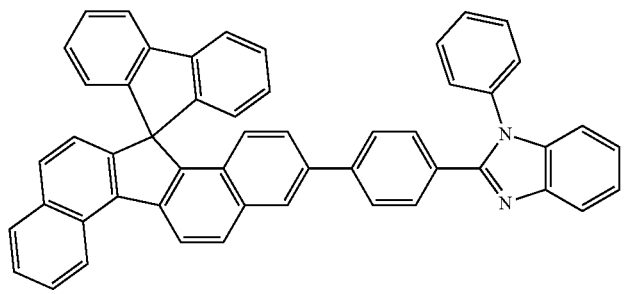
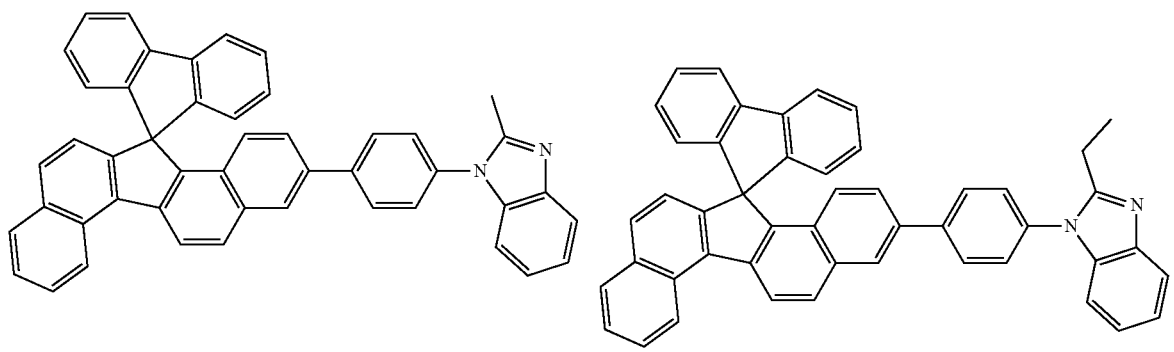
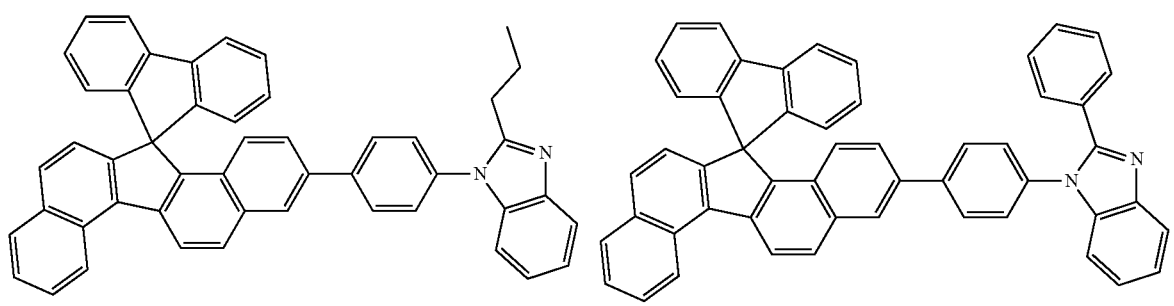

793
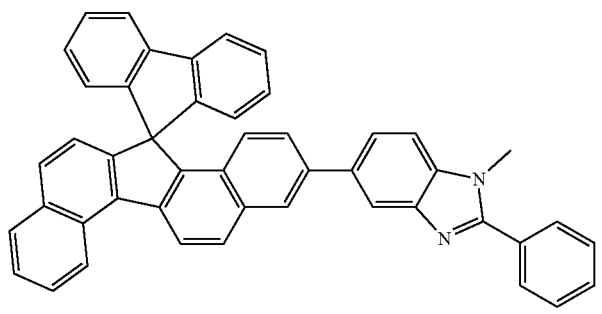
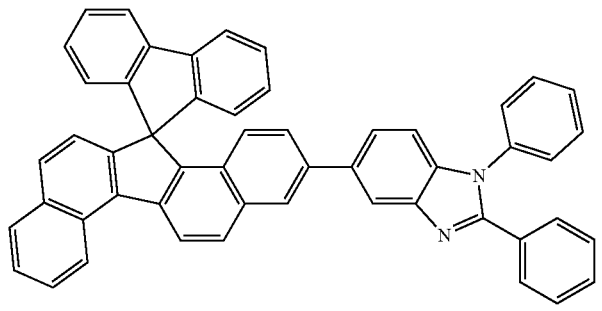
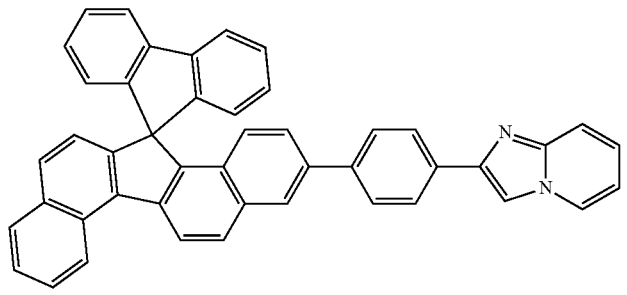
-continued
794
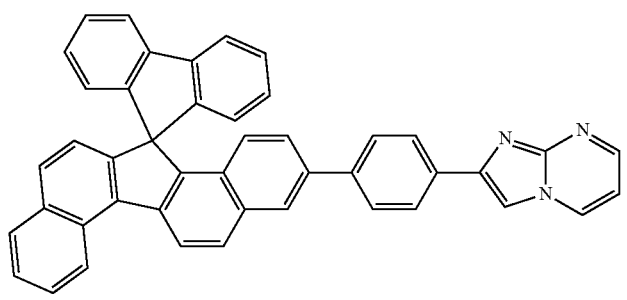
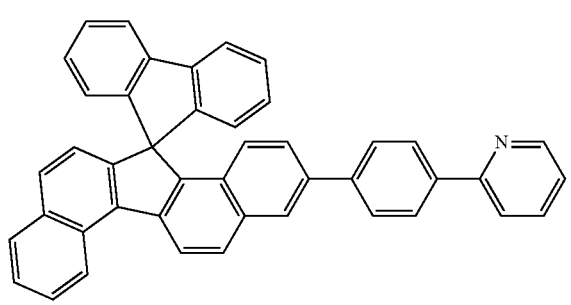
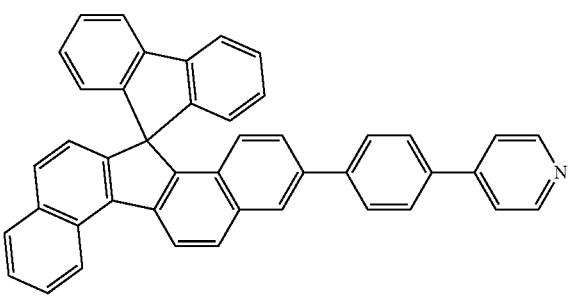

-continued
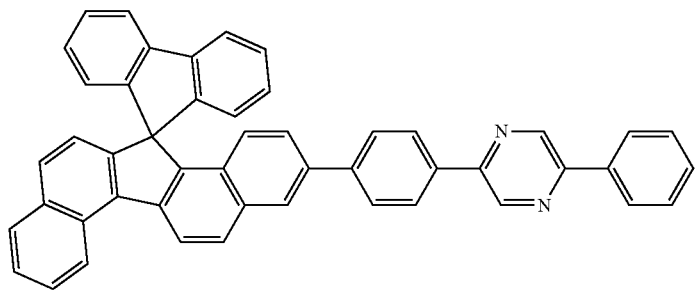
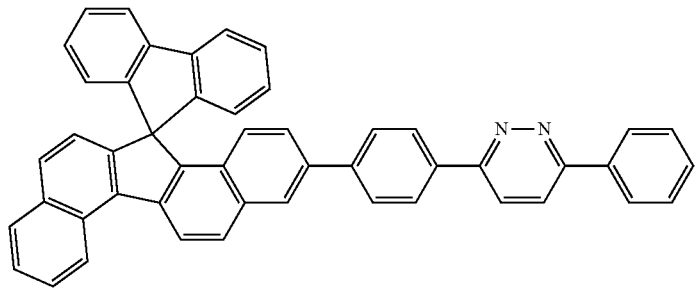
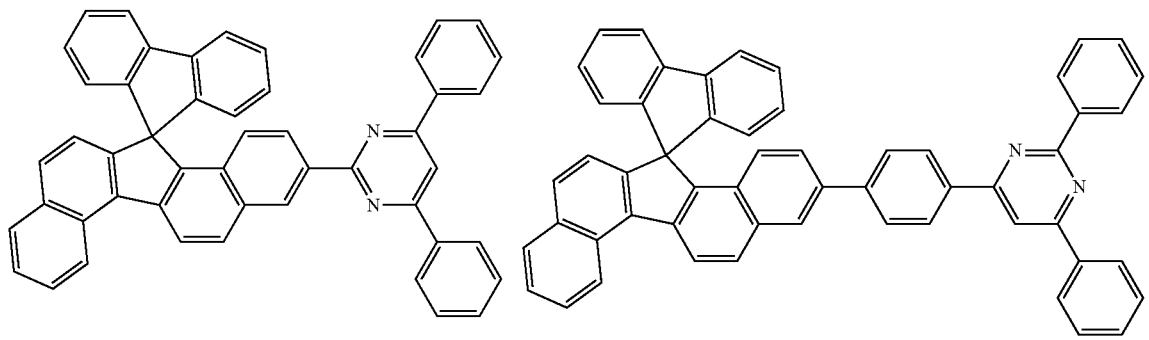
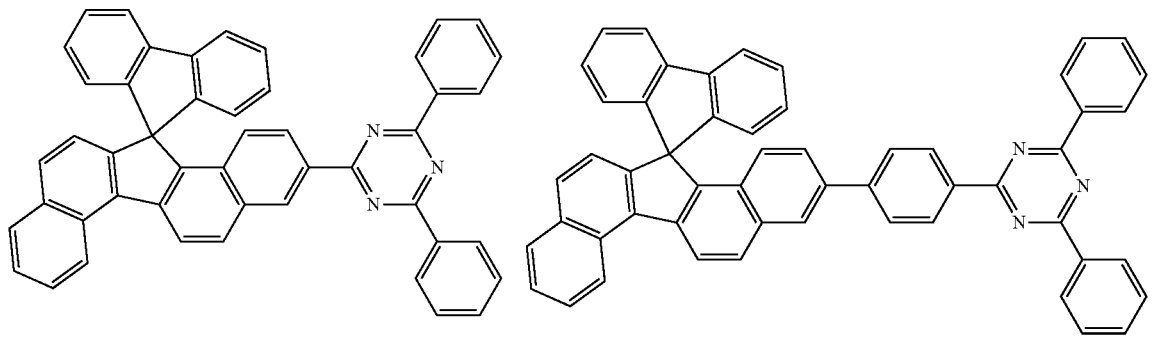
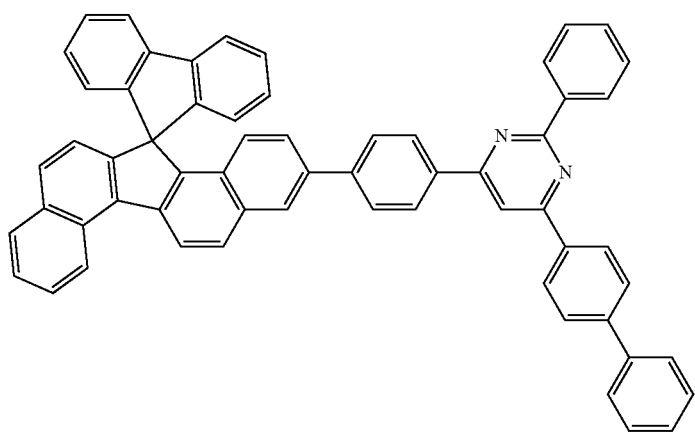

797
798
-continued
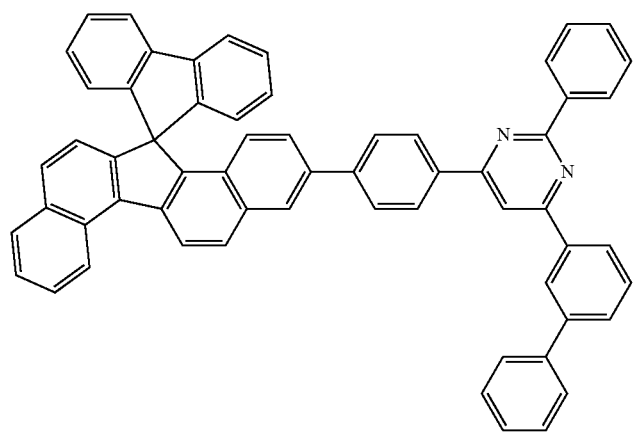
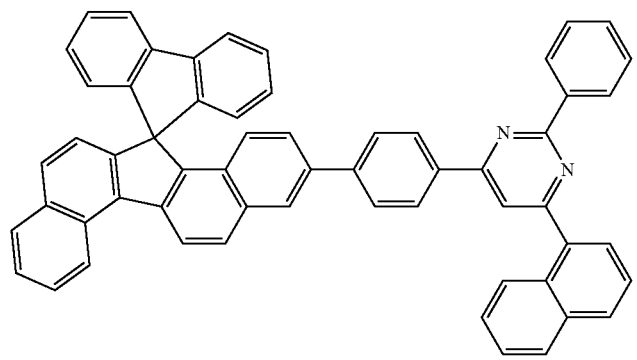
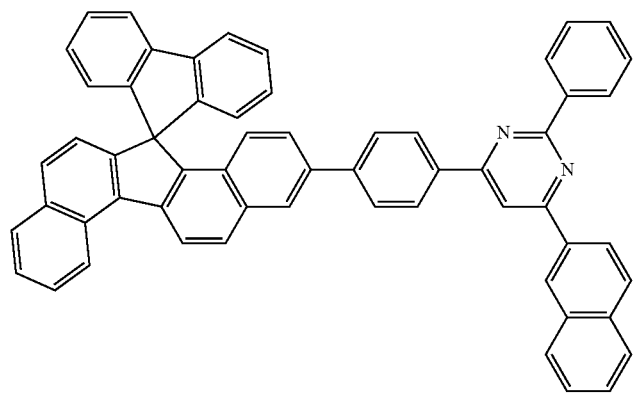
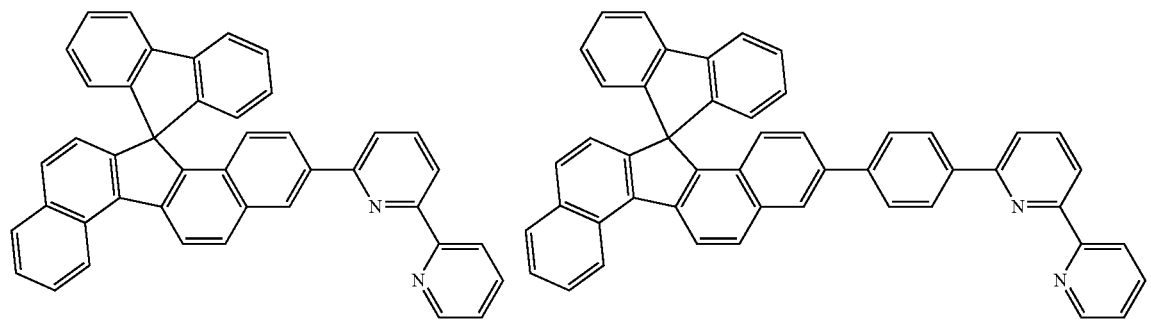

799
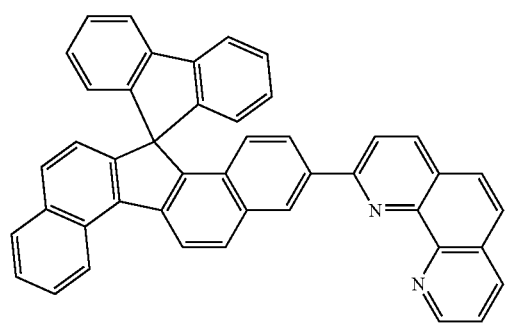
800
-continued
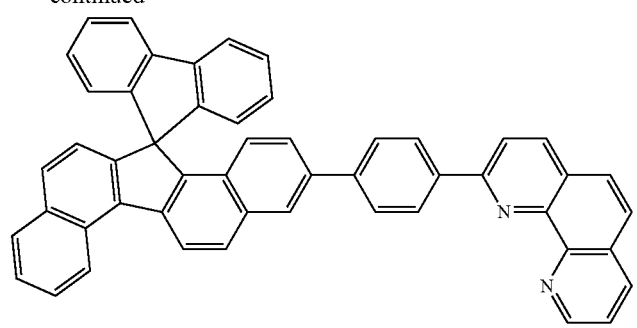
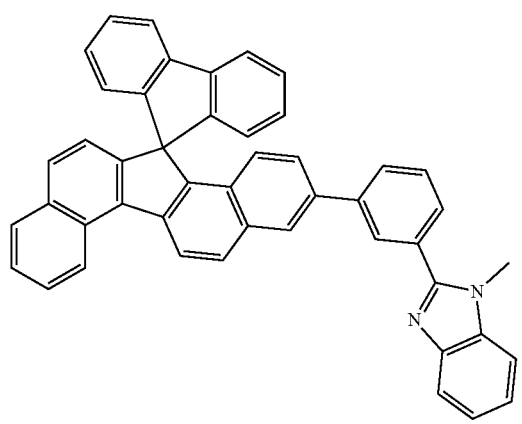
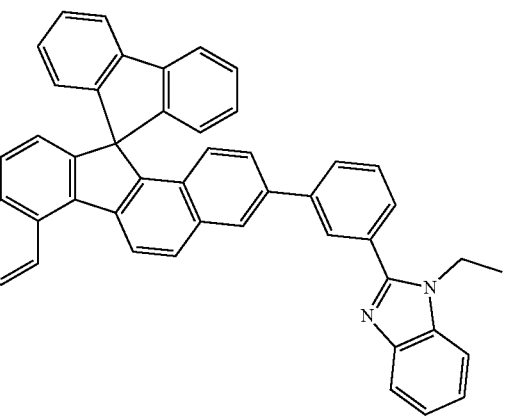
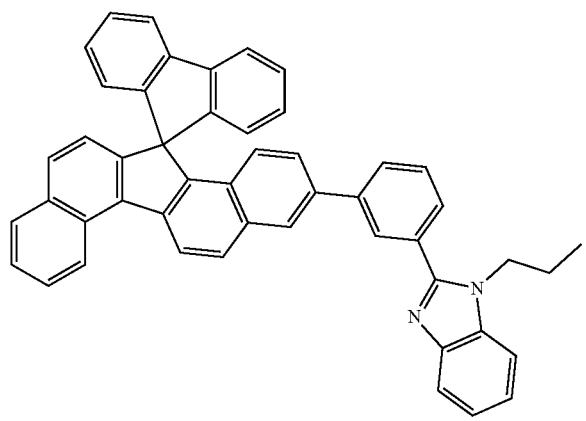
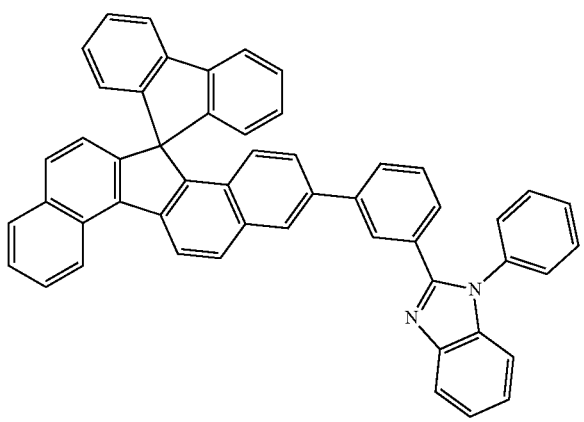

-continued
| 801 | 802 |
|---|---|
| 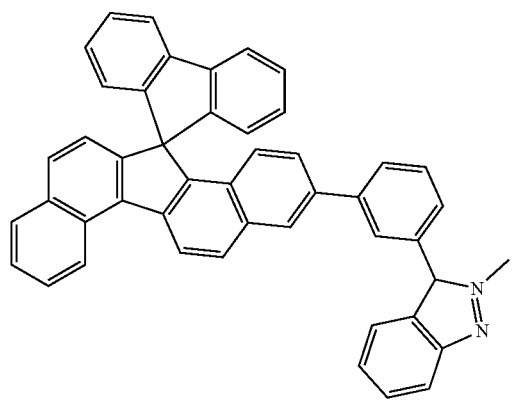 | 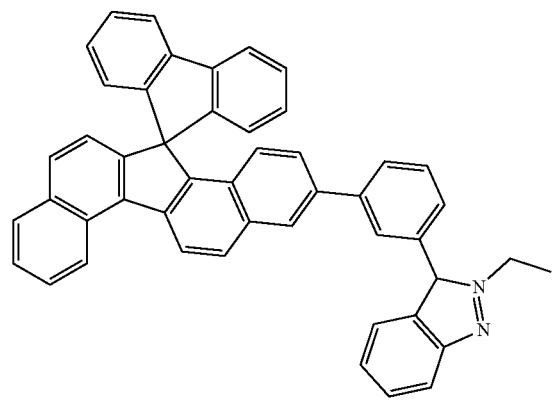 |
| 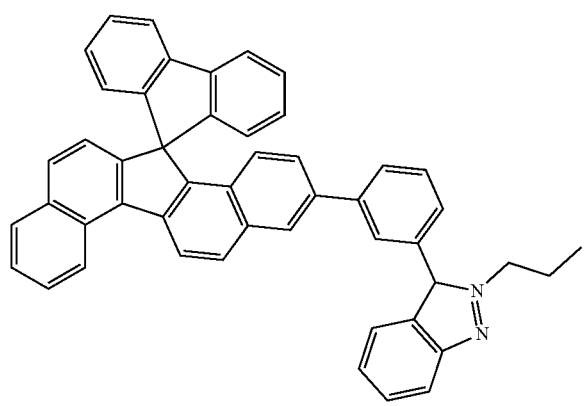 | 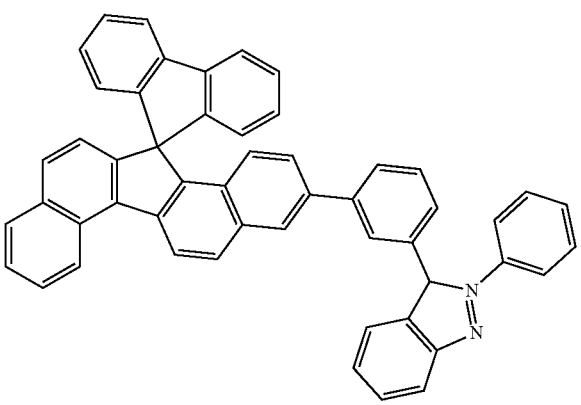 |
| 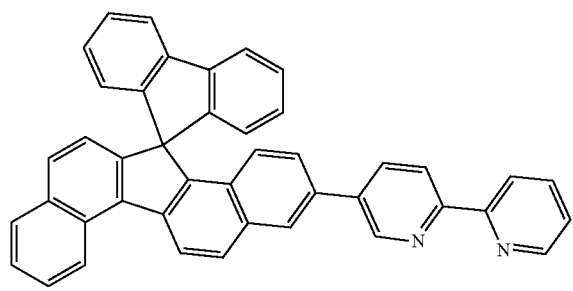 | 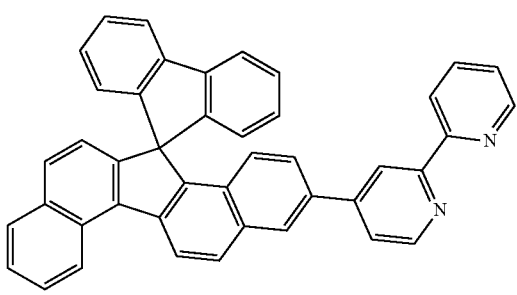 |

803
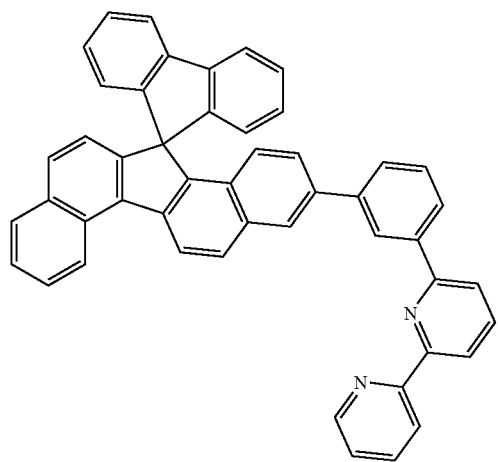
804
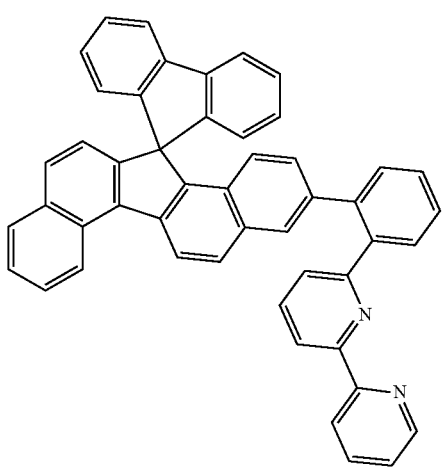
-continued
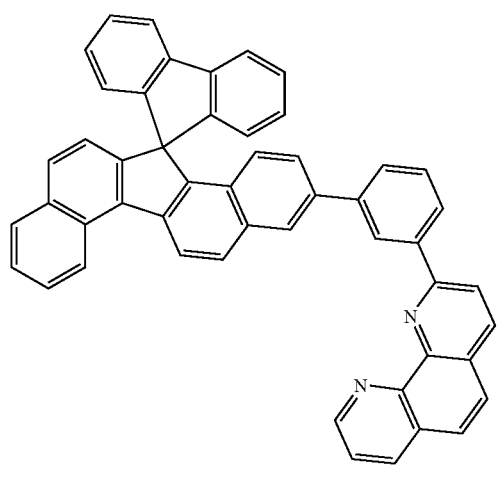
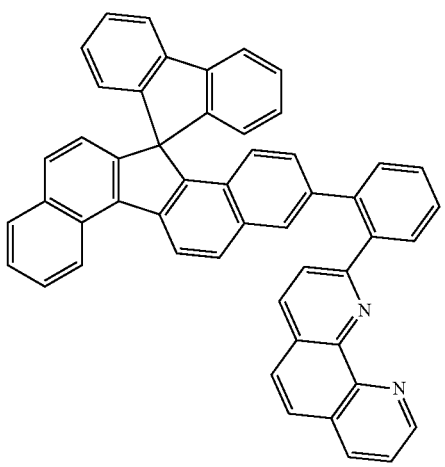
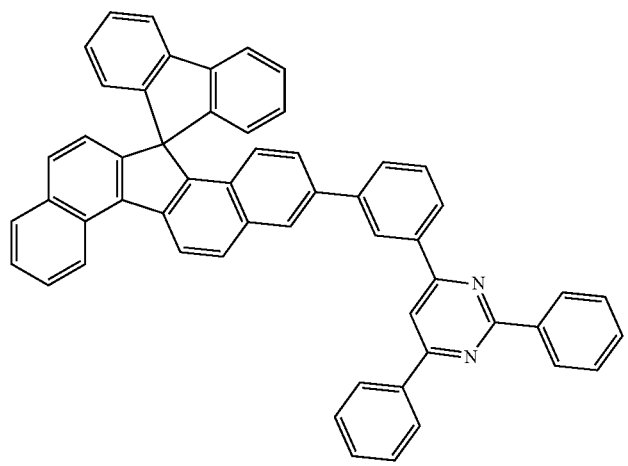

805
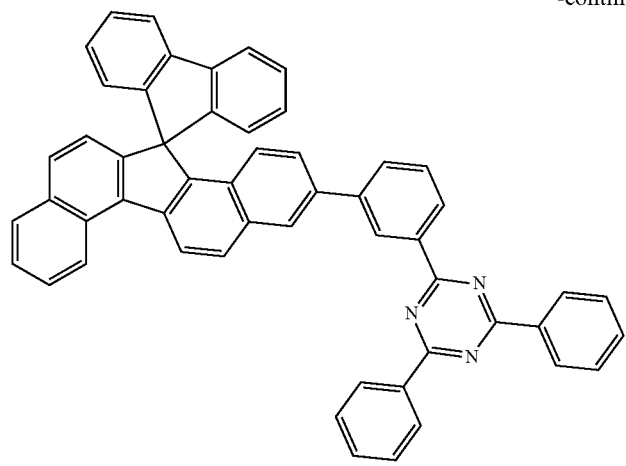
-continued
806
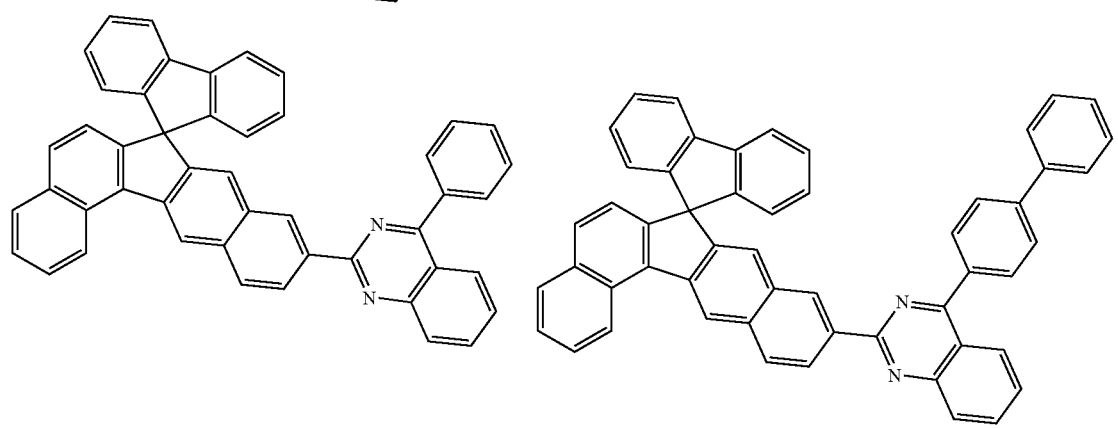
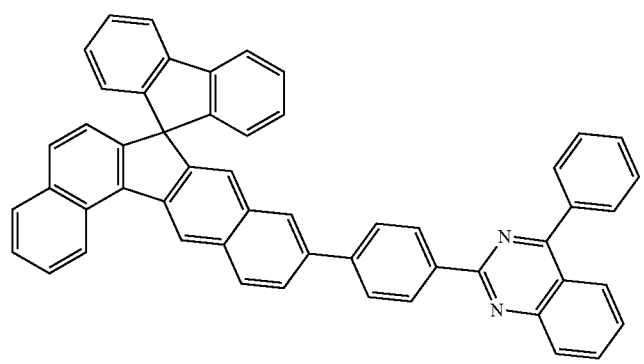
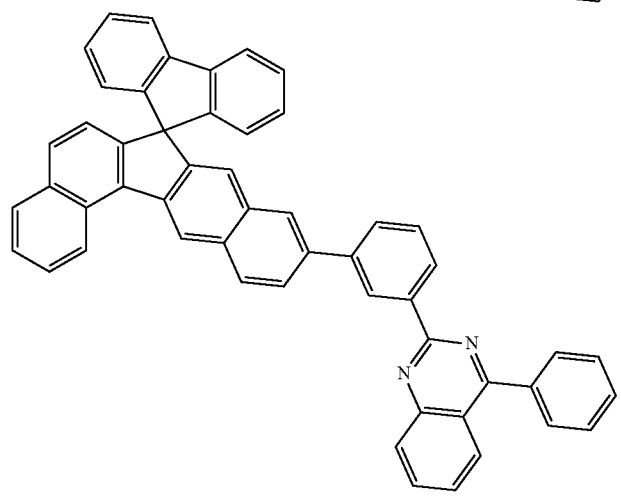

807
-continued
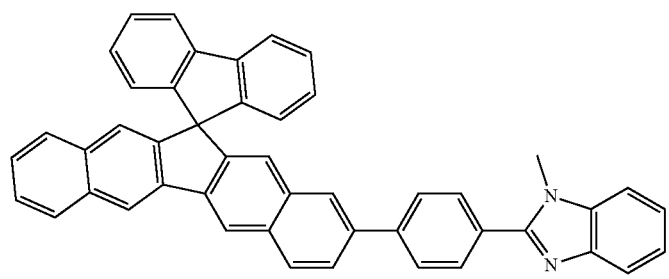
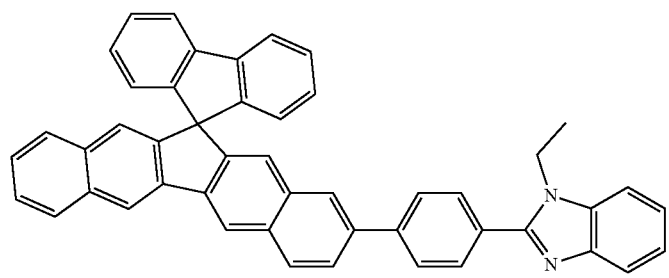
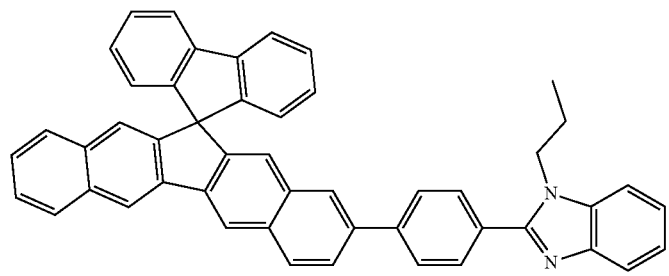
808
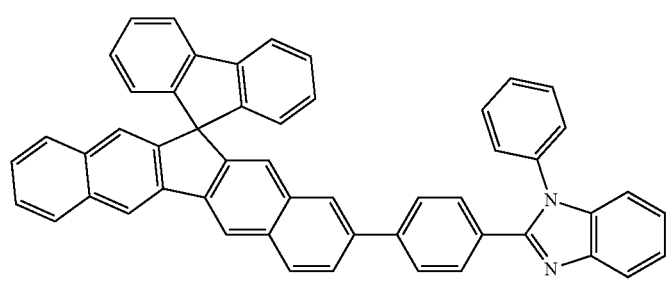
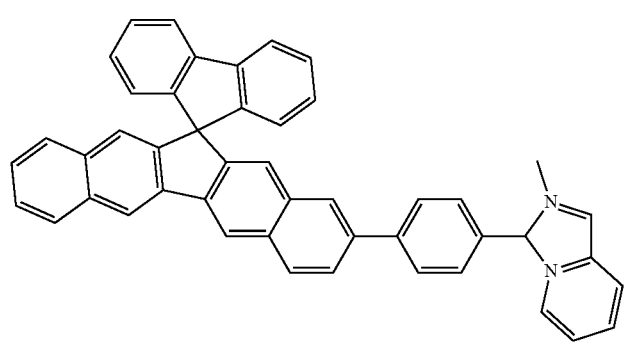

-continued
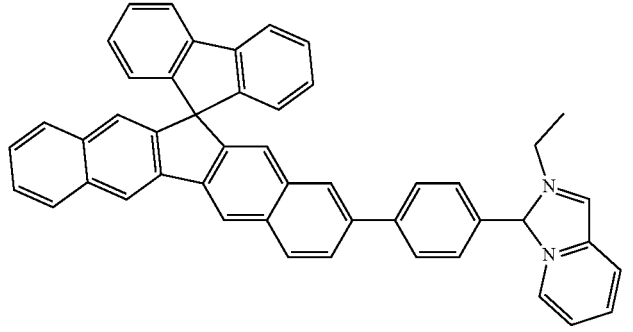
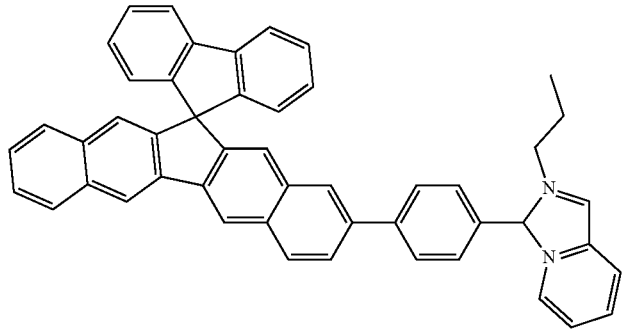
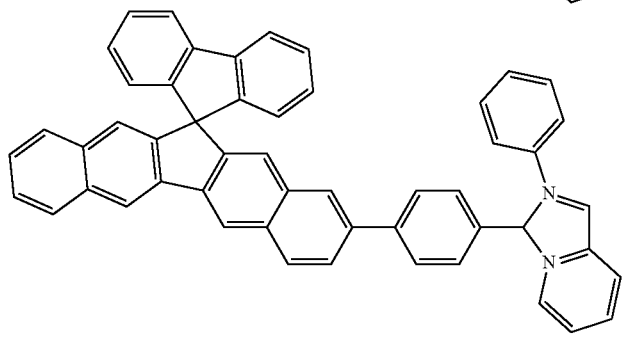
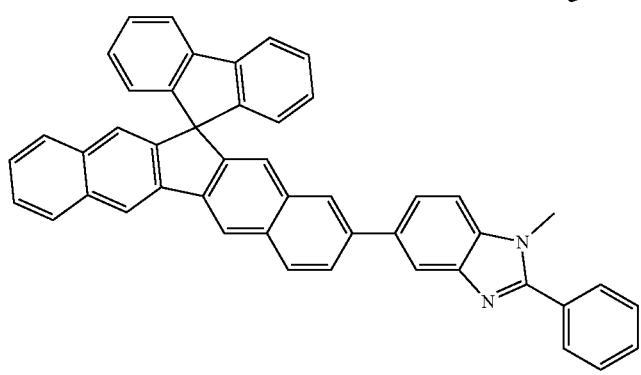
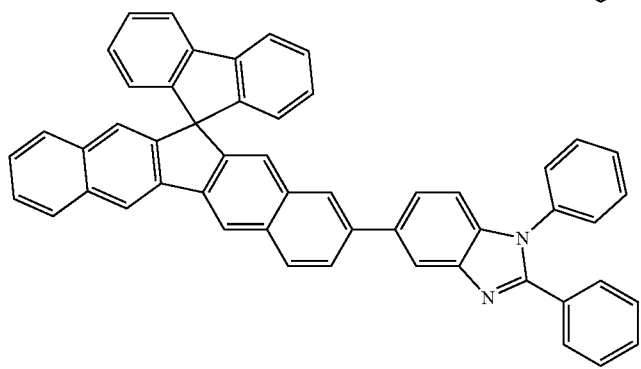

-continued
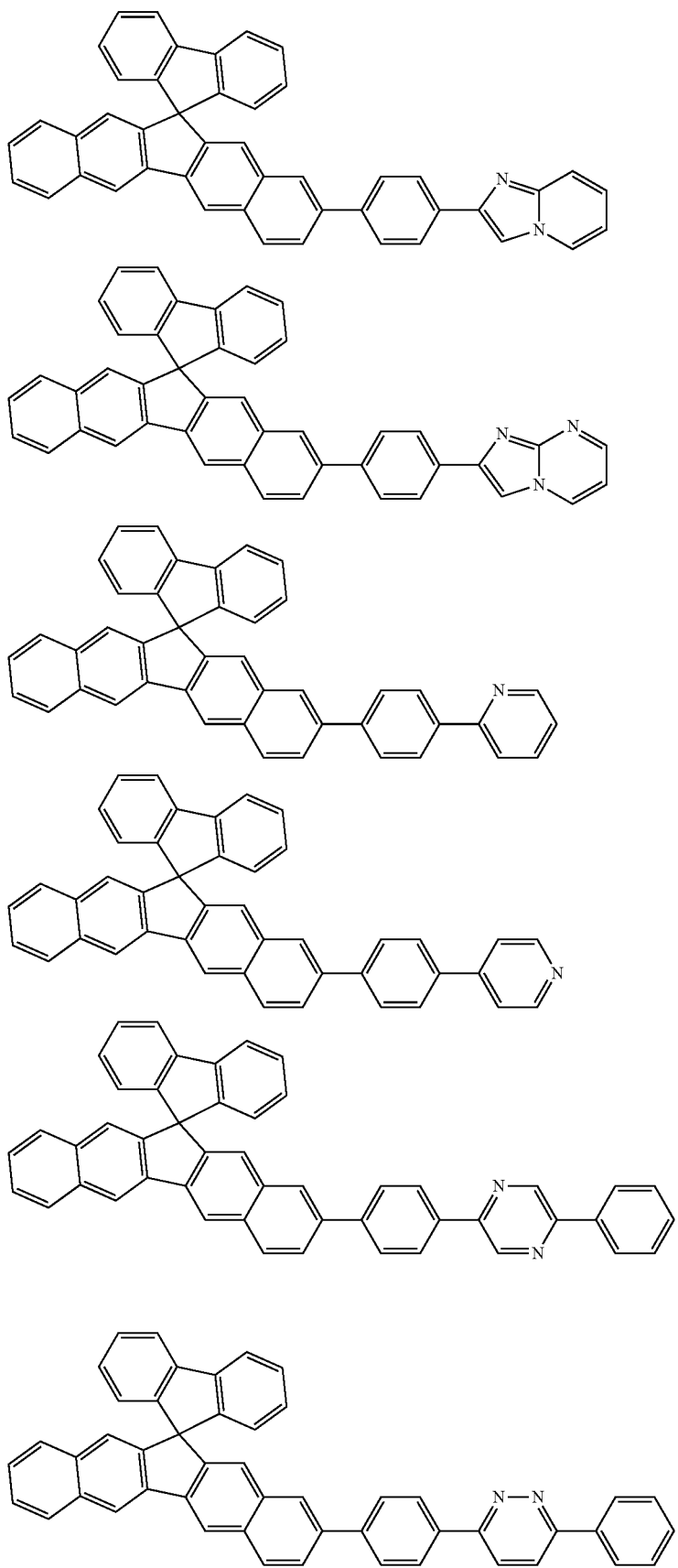

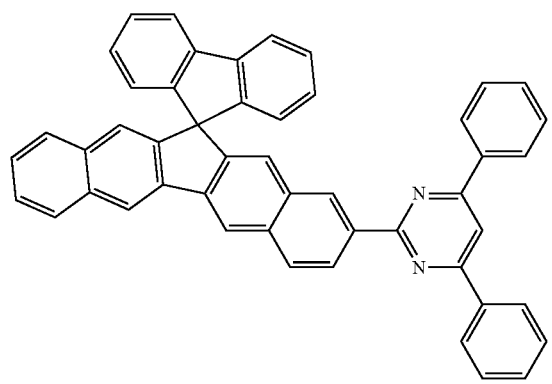
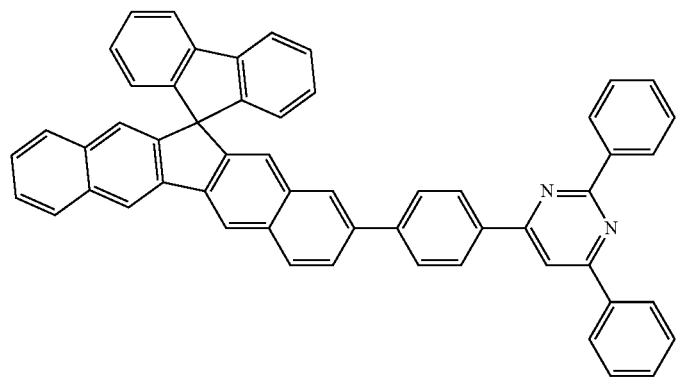
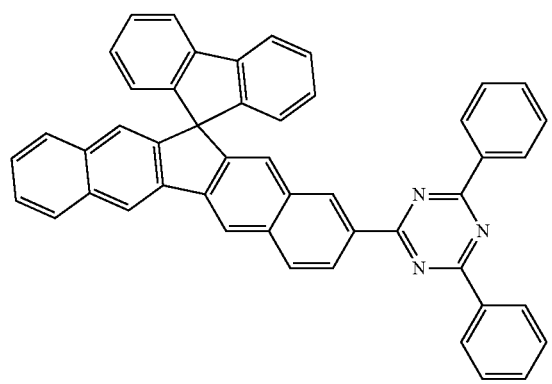
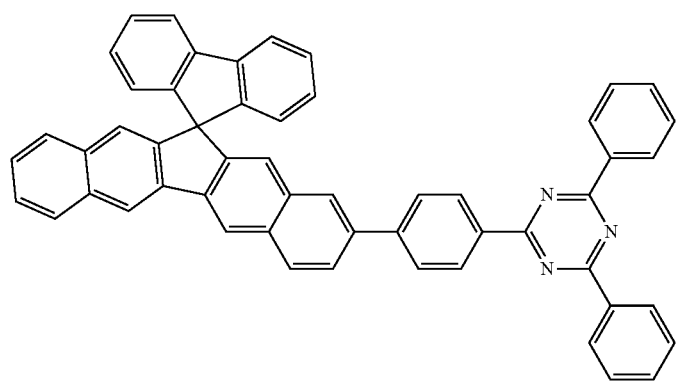

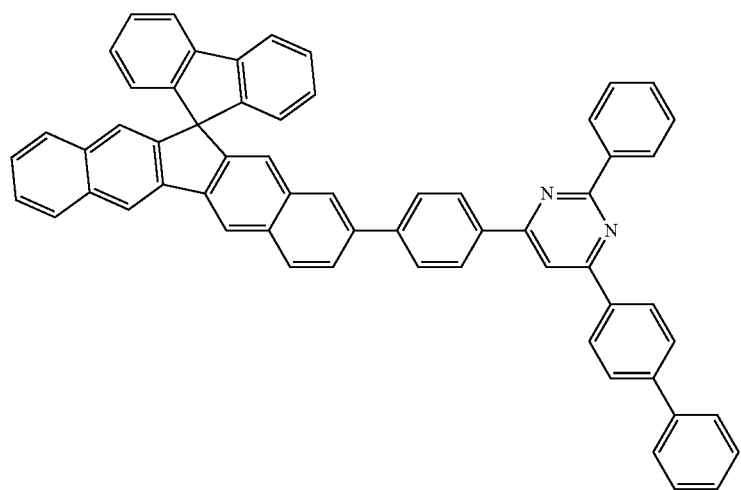
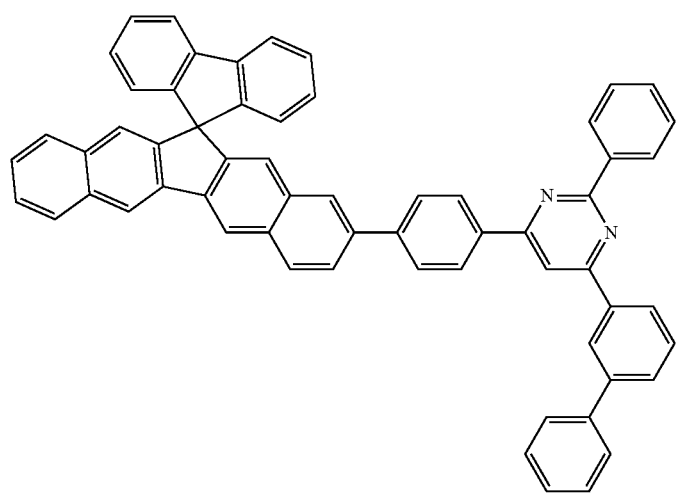
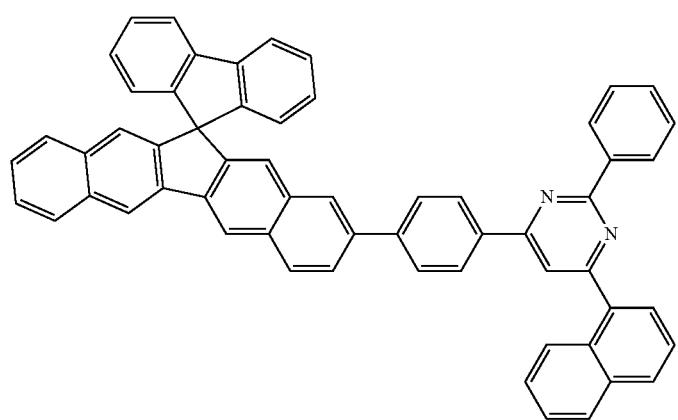

817
818
-continued
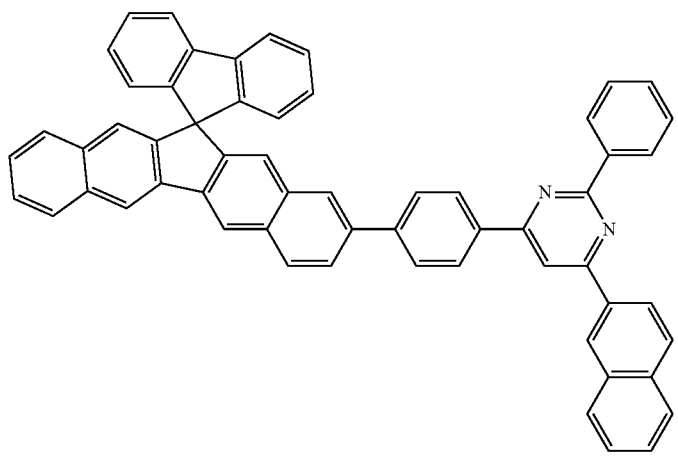
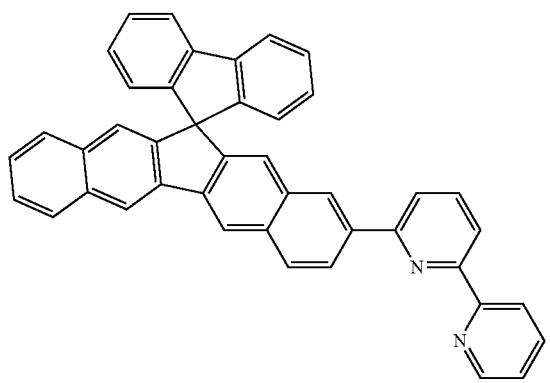
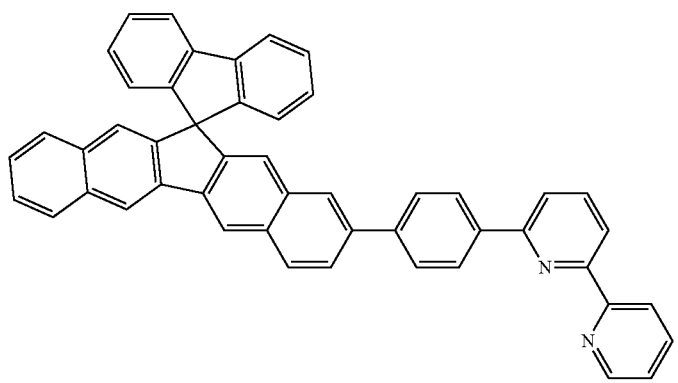
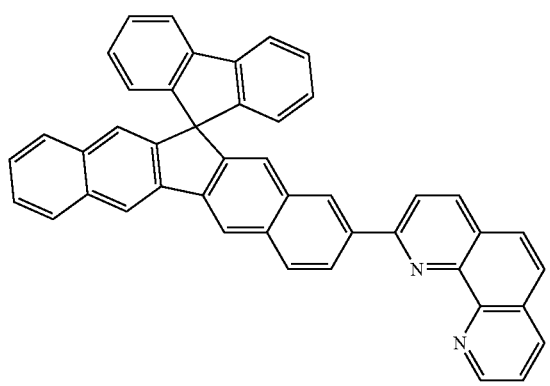

-continued
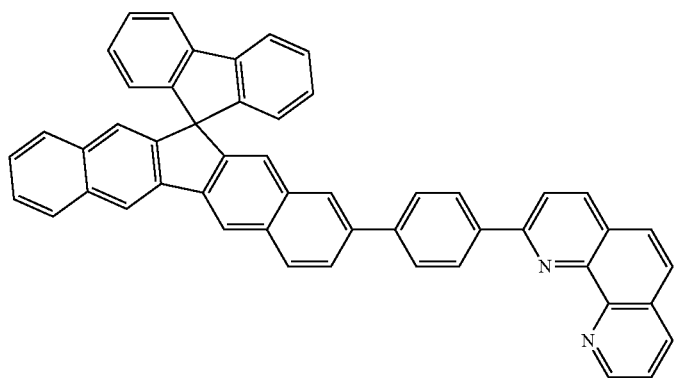
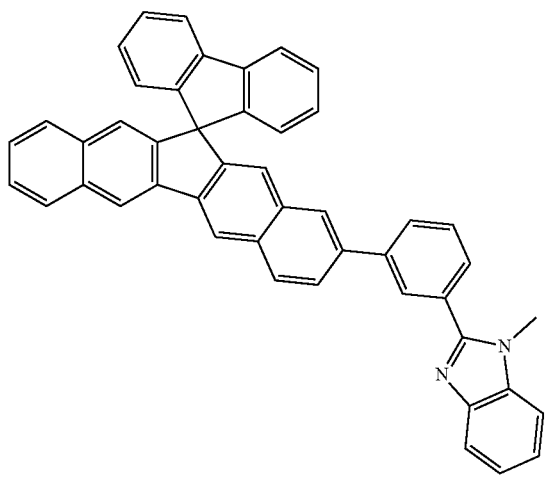
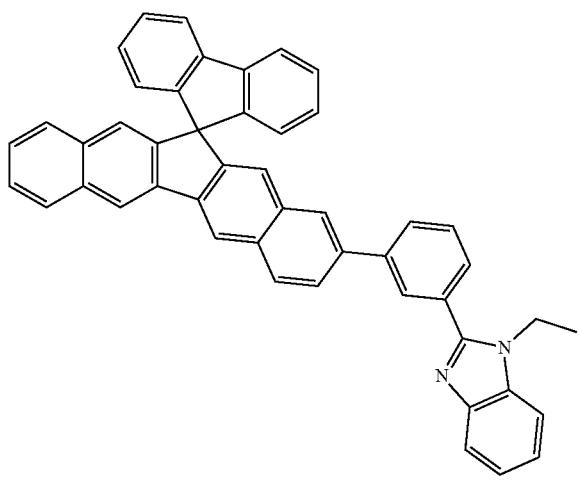

821
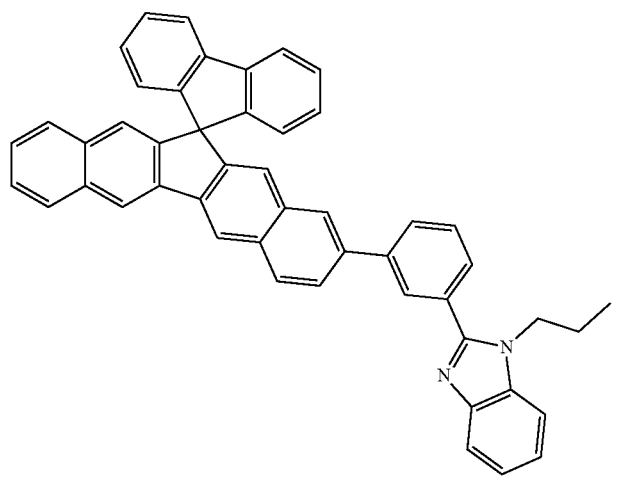
822
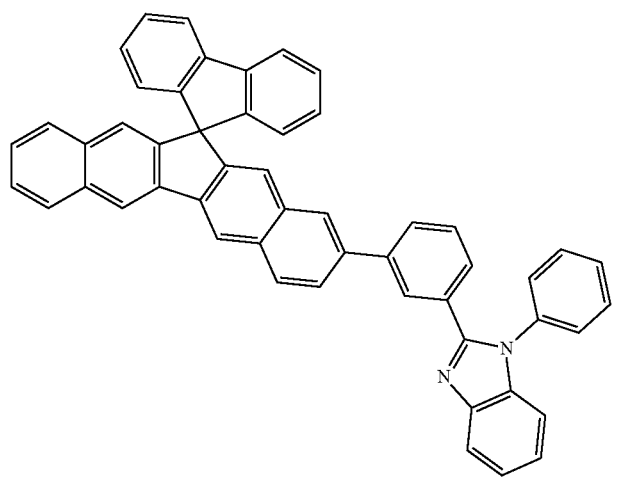
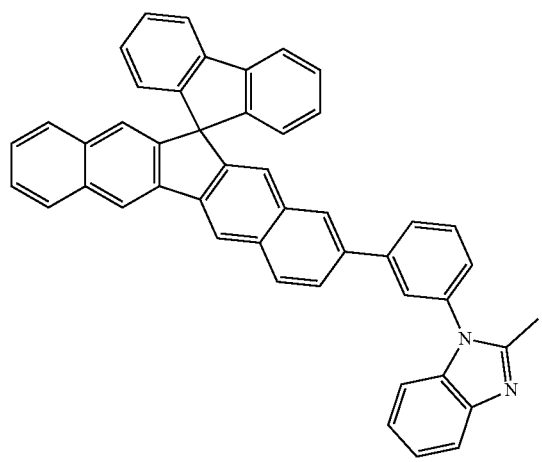

-continued
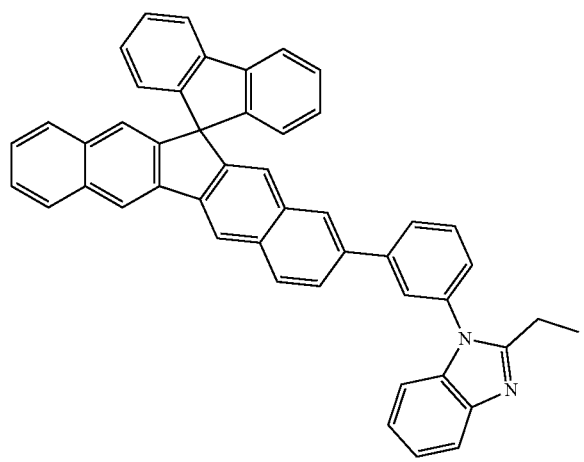
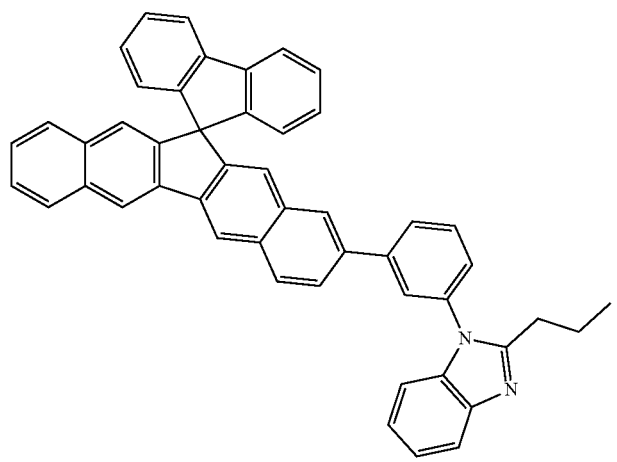
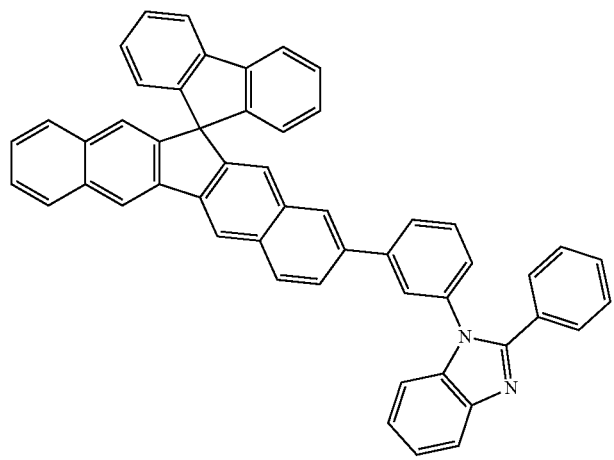
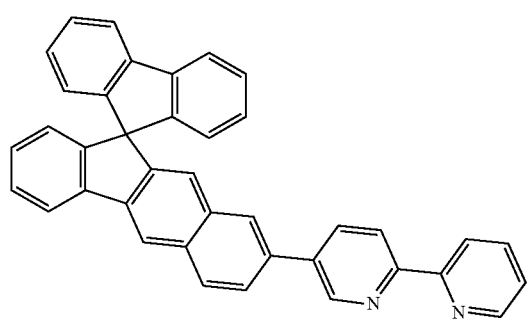

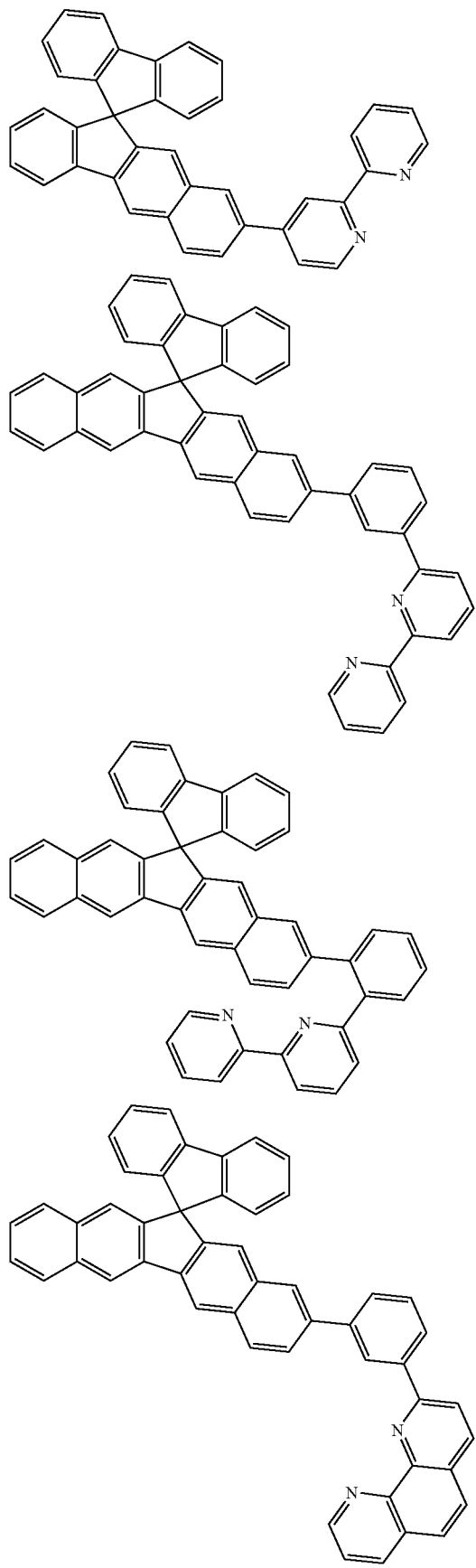

-continued
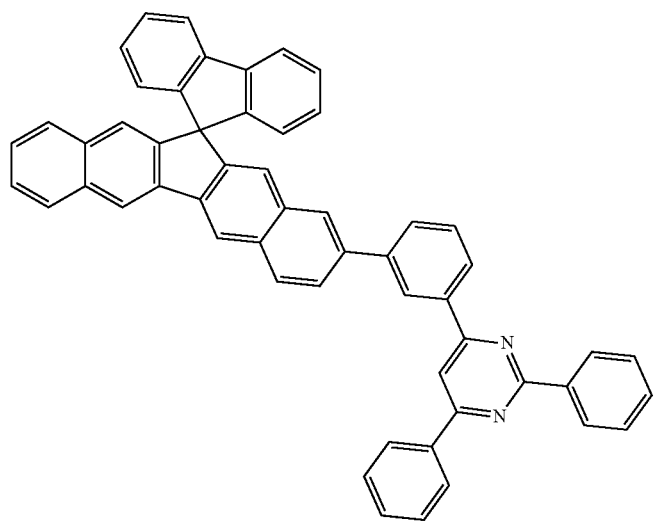
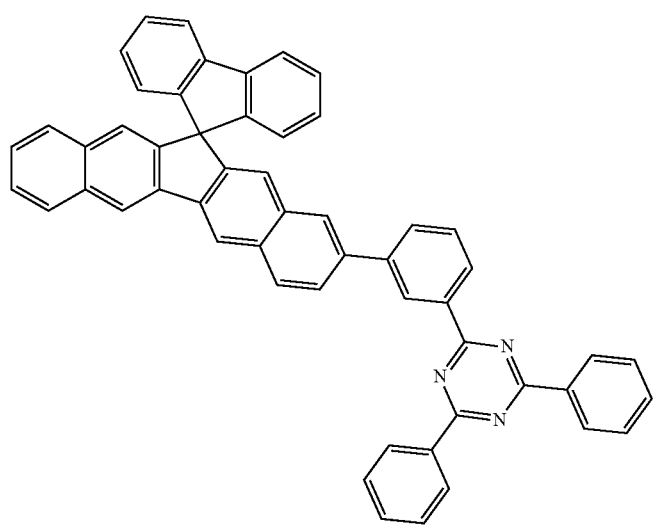
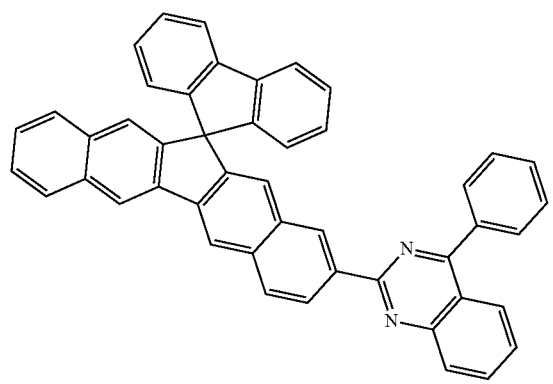

-continued
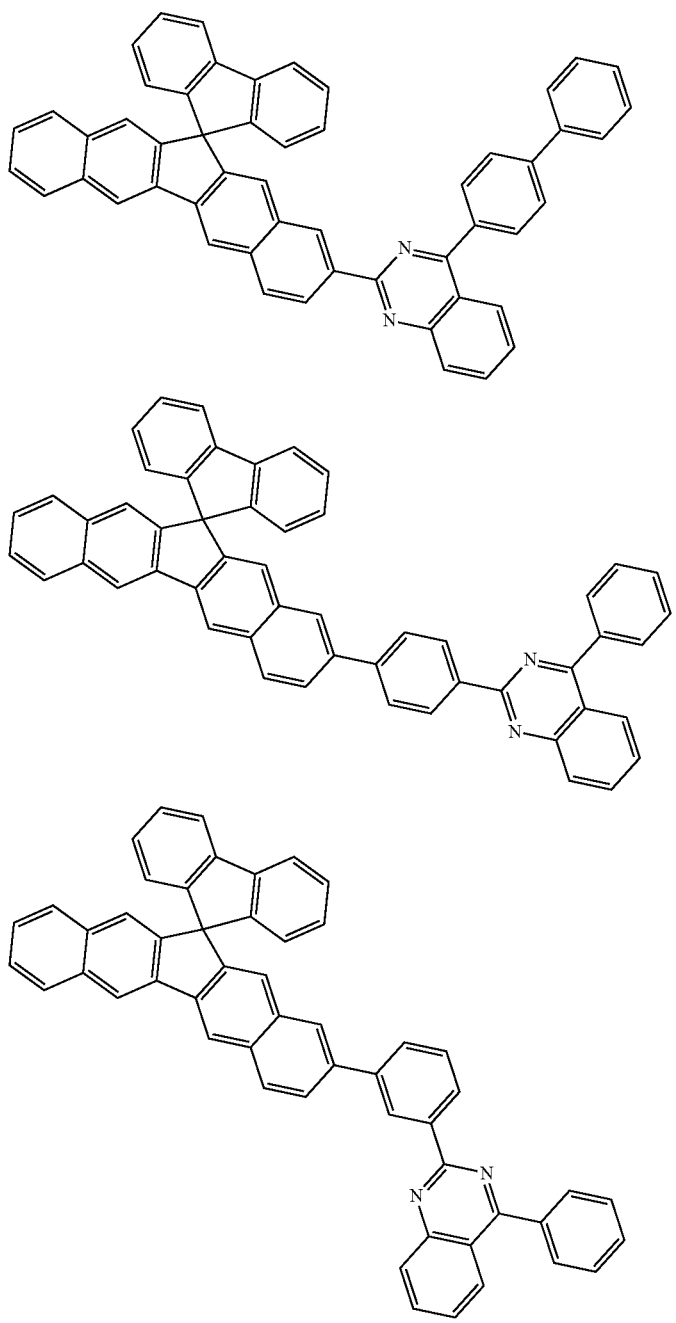
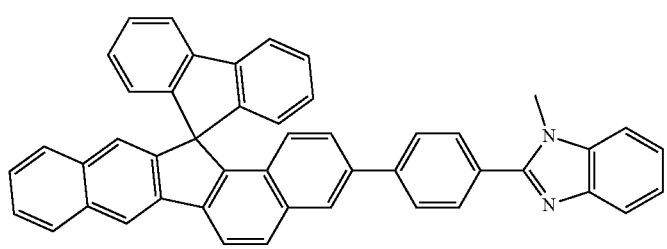

-continued
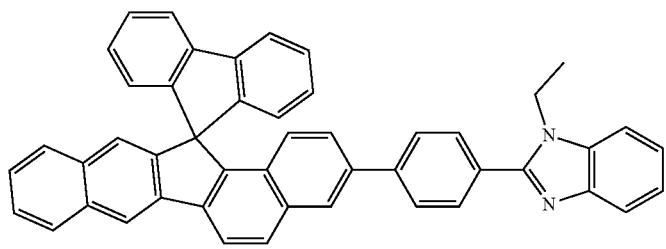
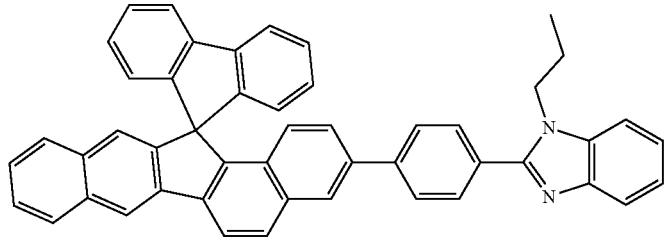
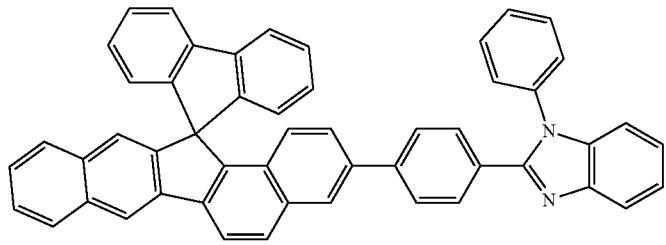
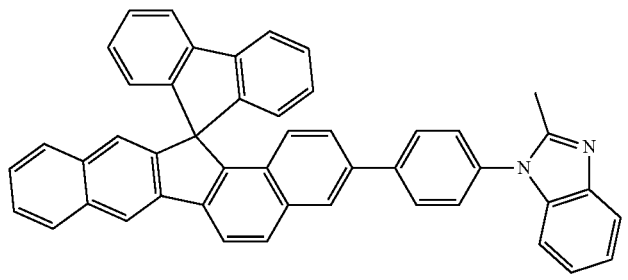
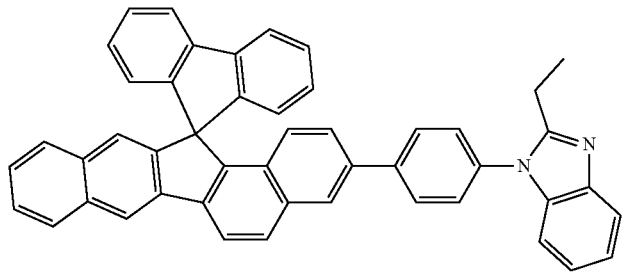
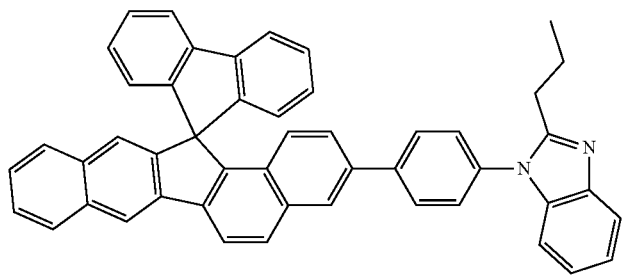

833
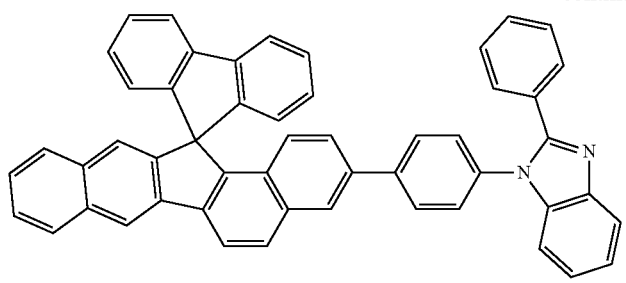
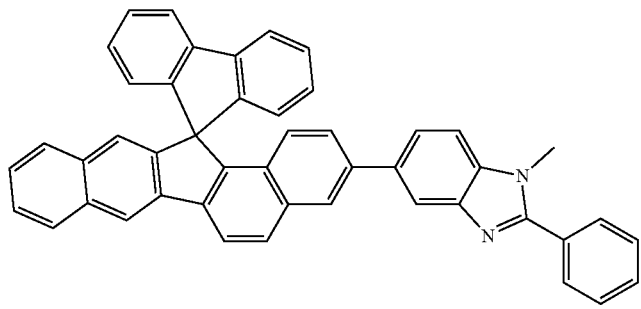
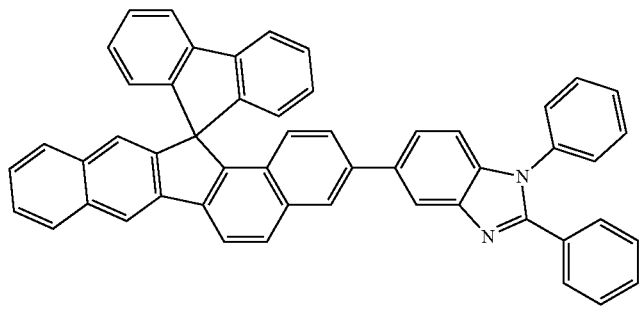
834
-continued
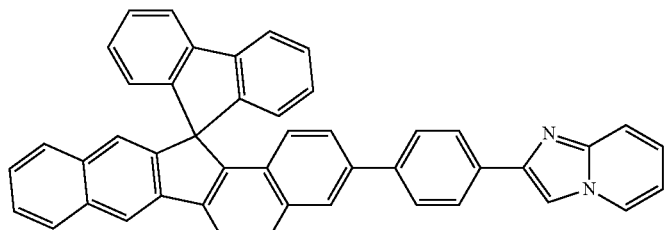
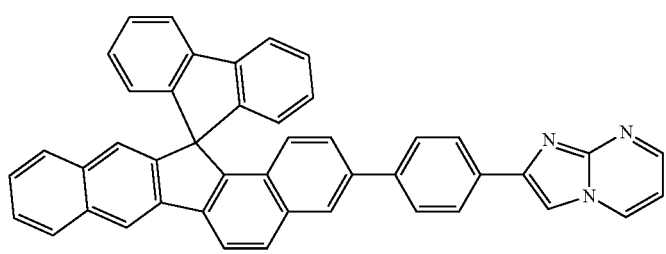
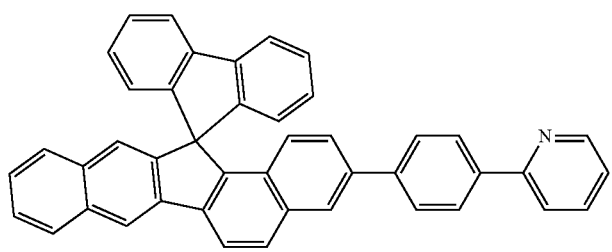

-continued
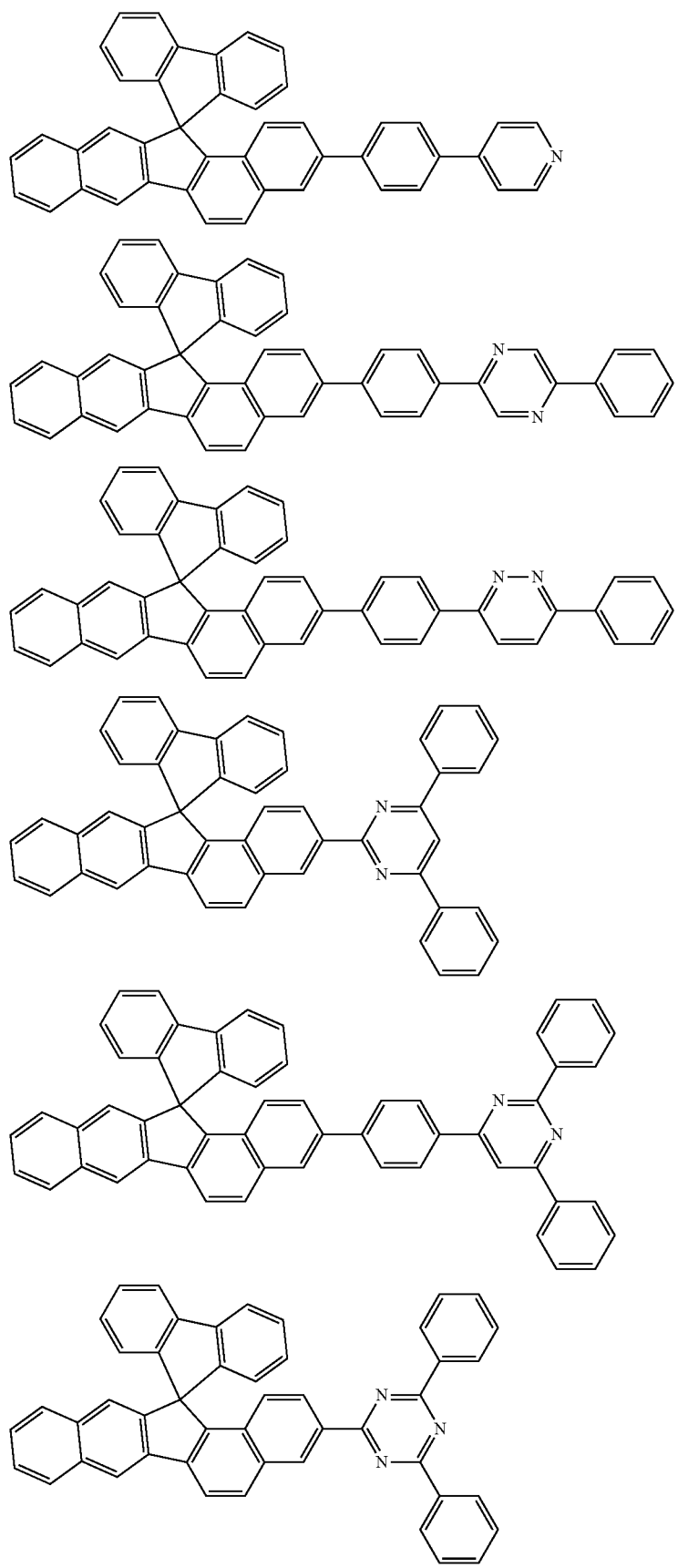

-continued
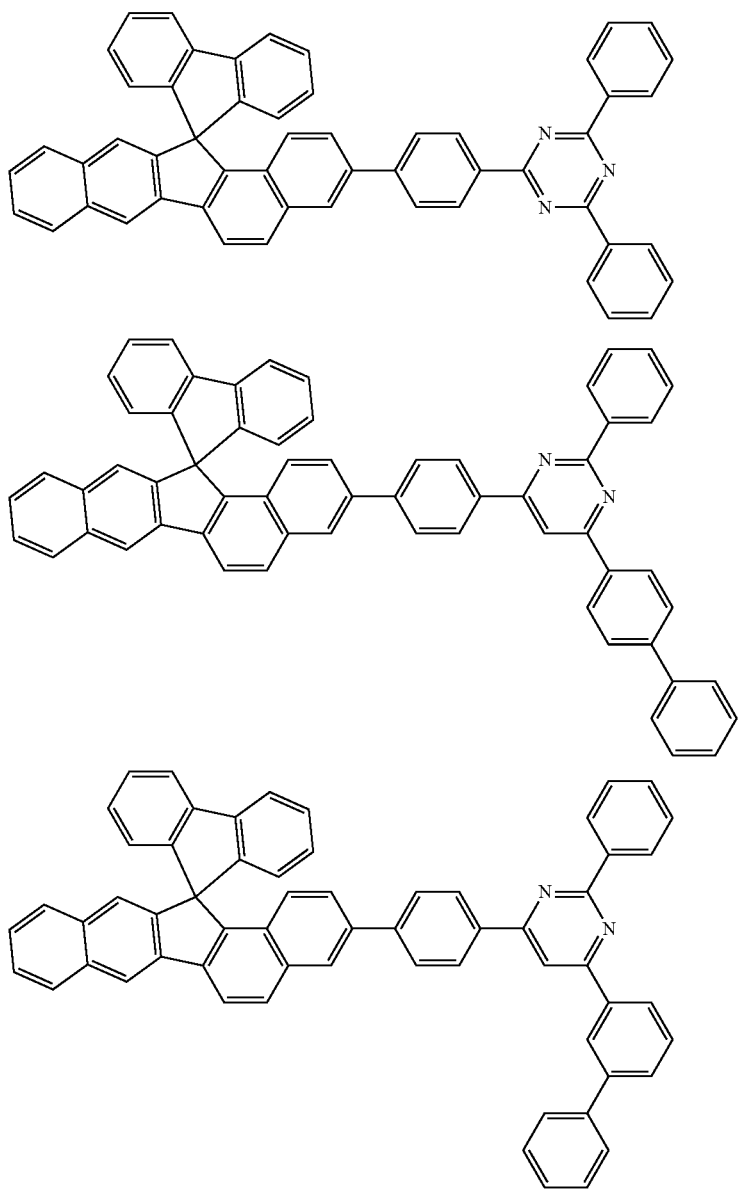
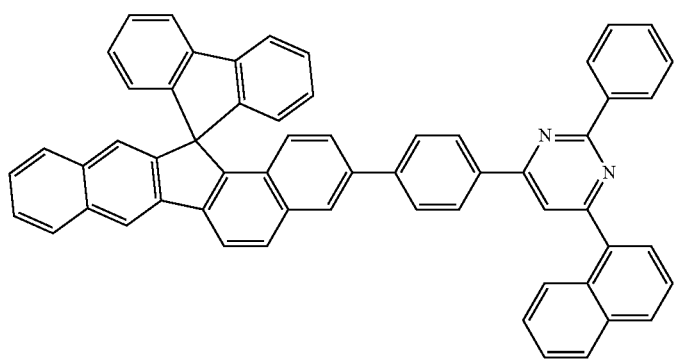

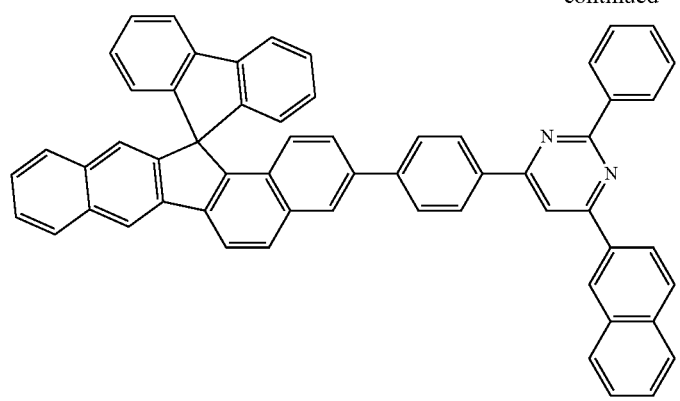
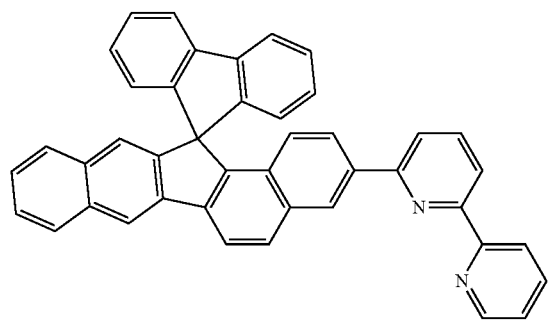
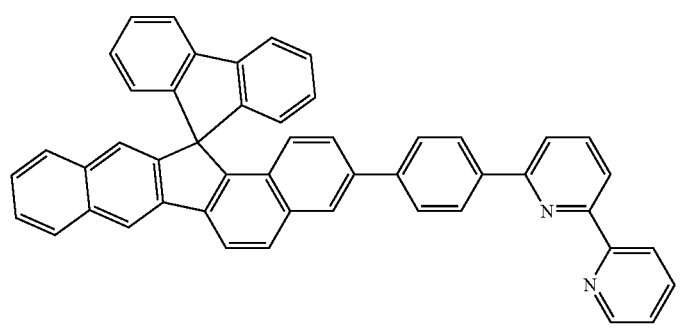
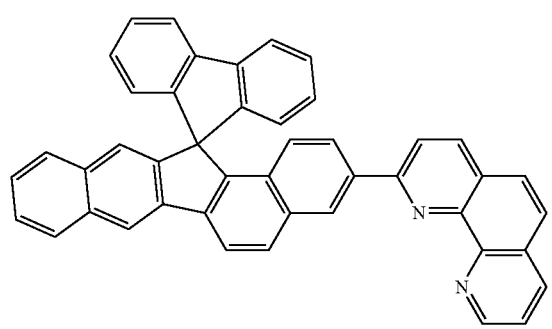
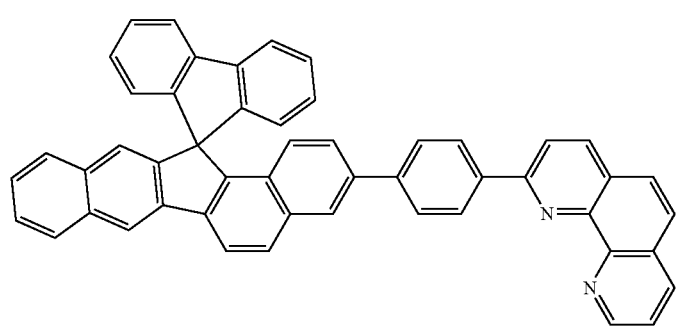

841 842
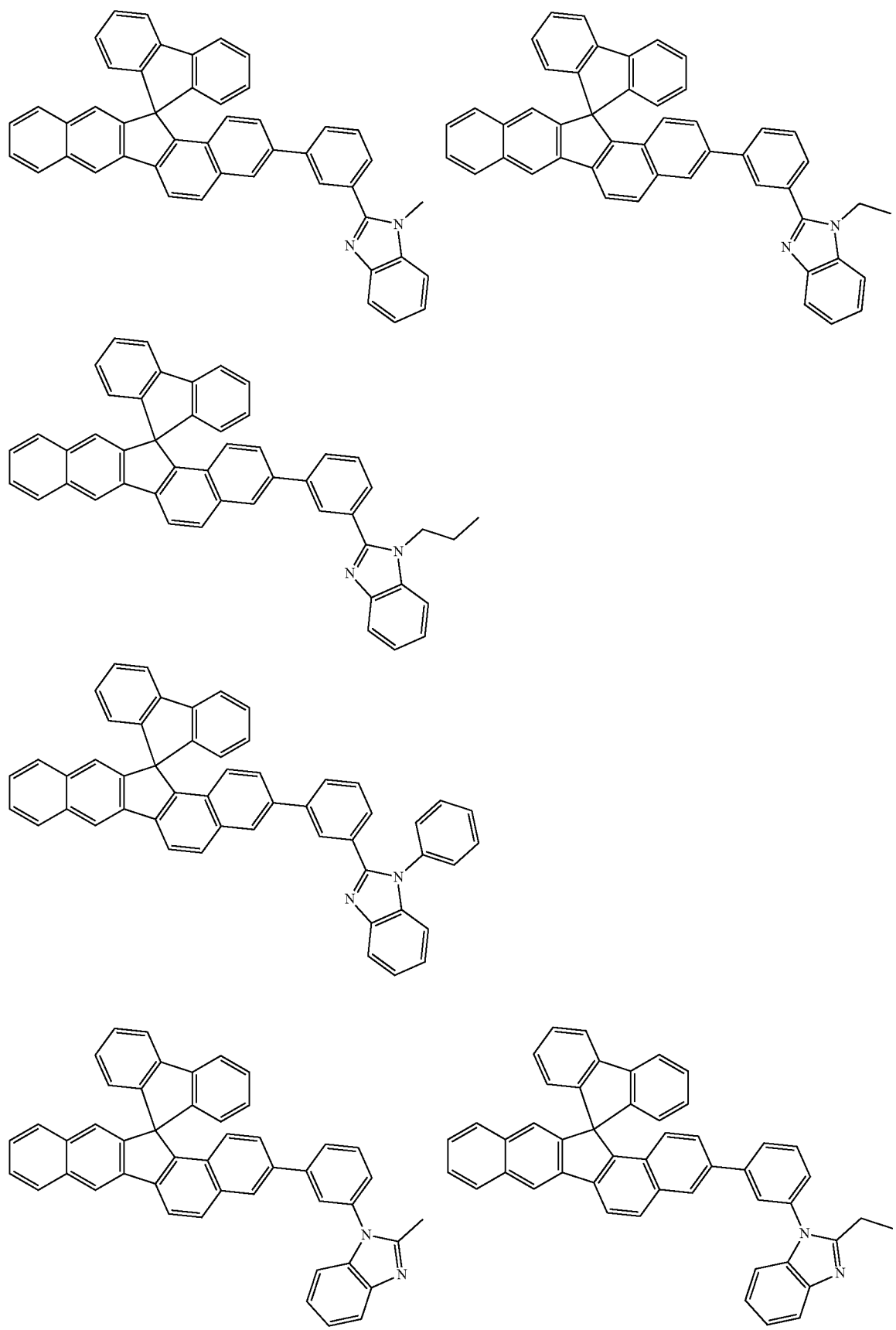

843 844
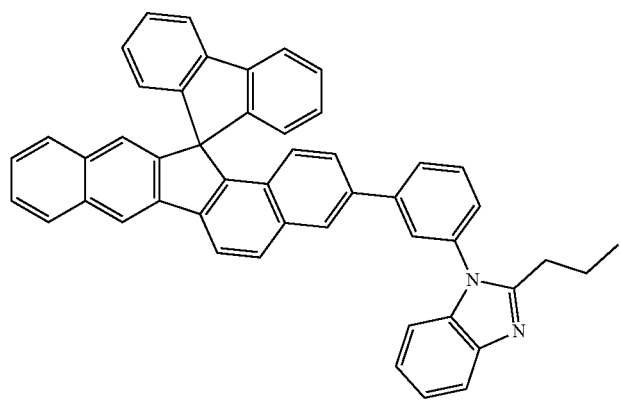
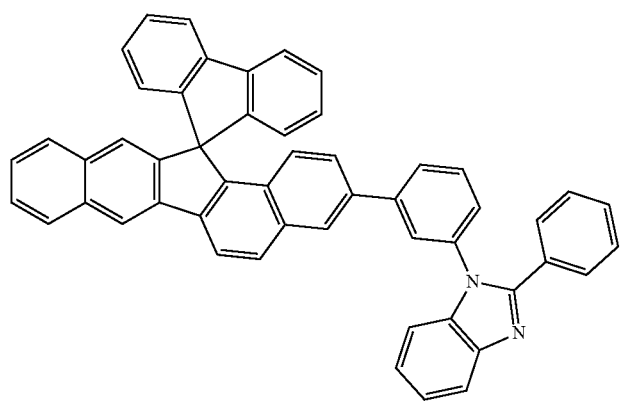
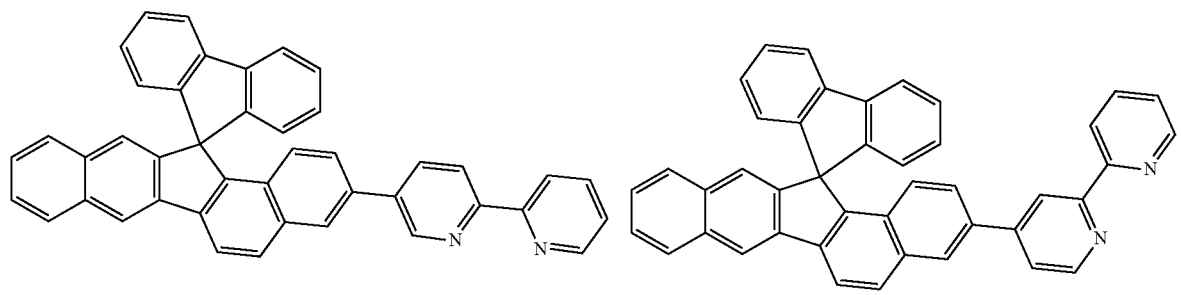
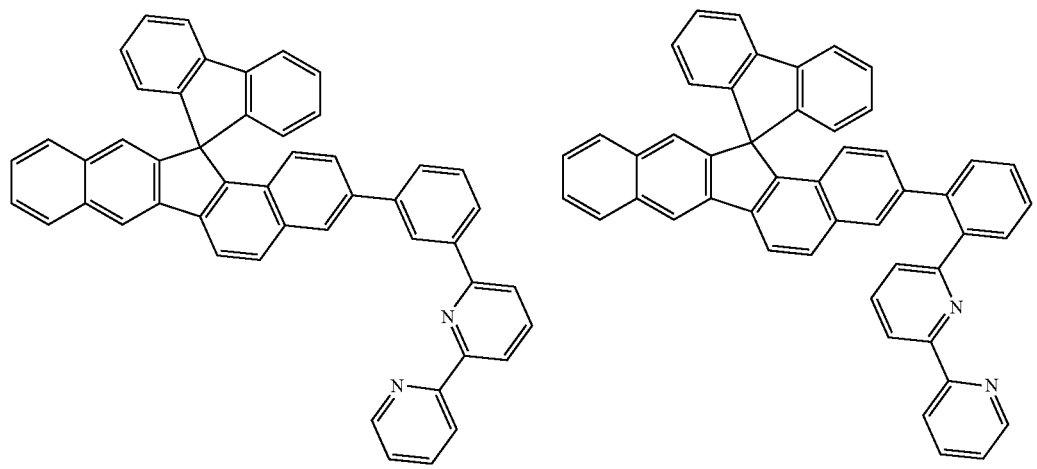

845 846
-continued
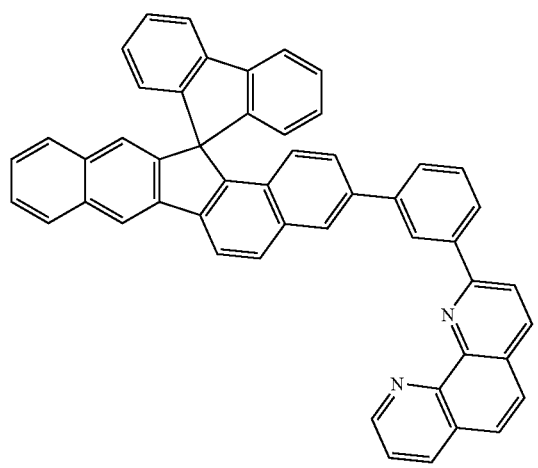
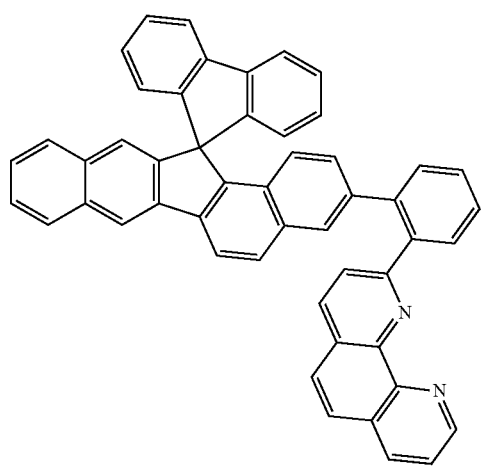
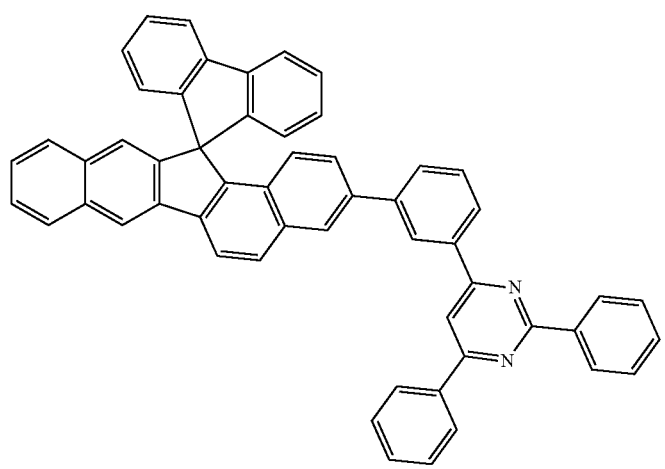
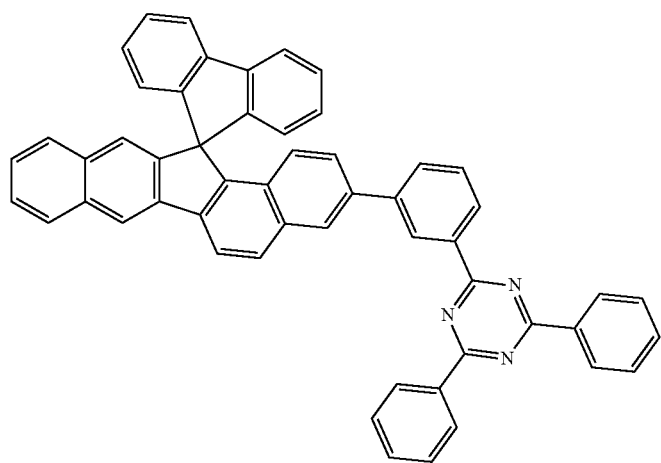

847 848
-continued
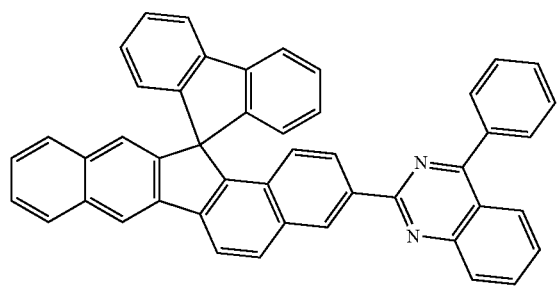
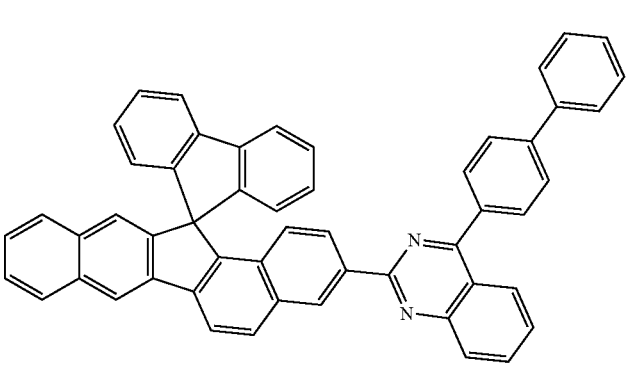
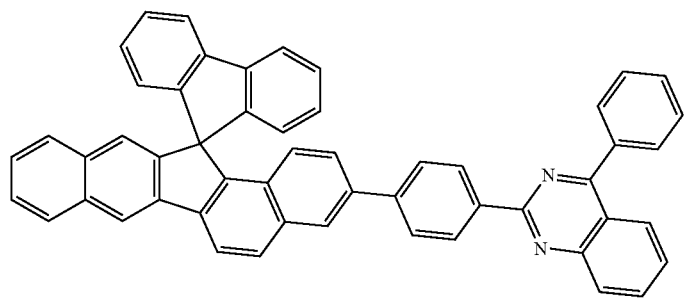
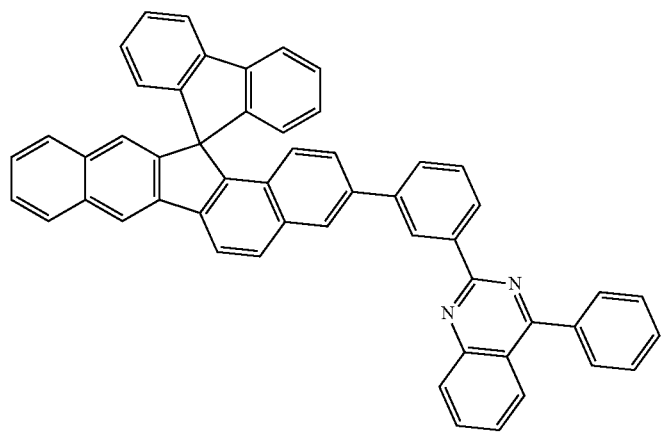
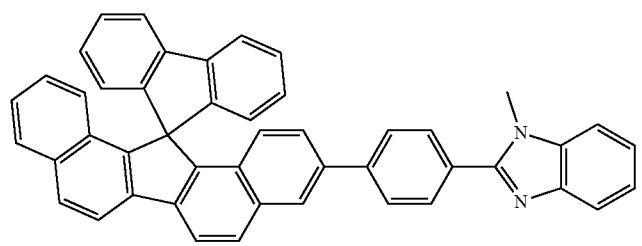
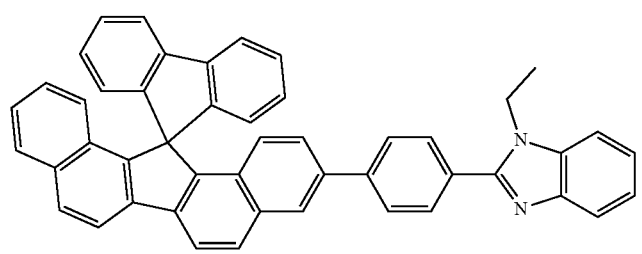

-continued
| 849 | 850 |
|---|---|
| 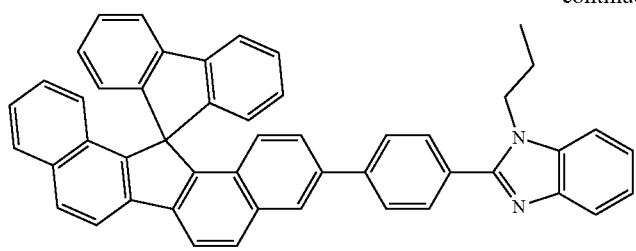 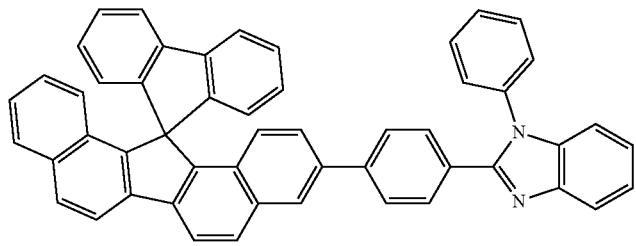 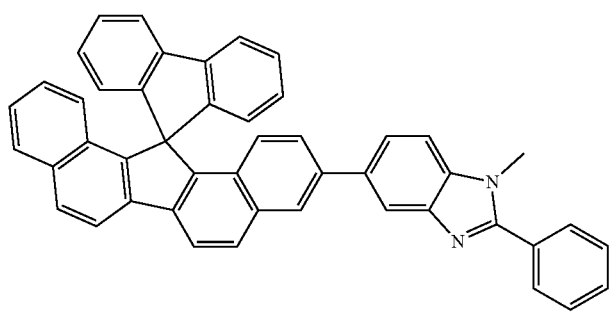 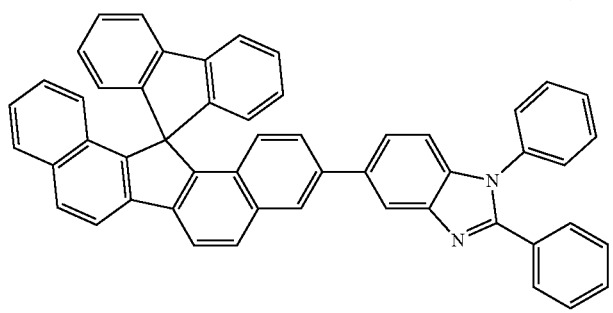 | 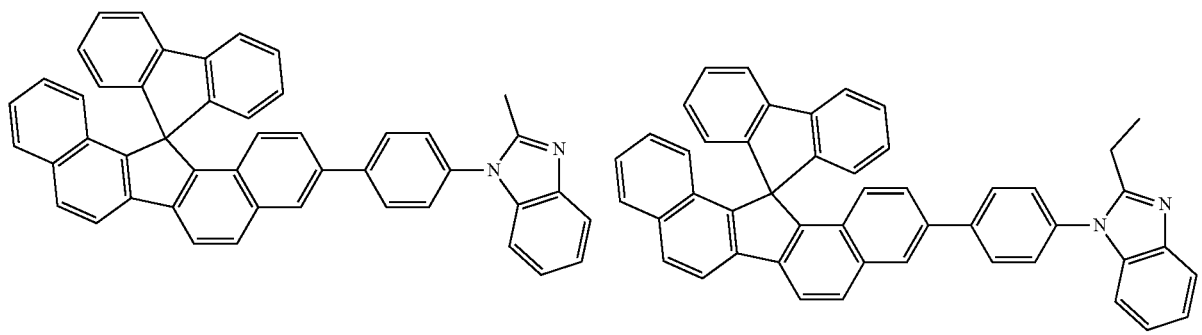 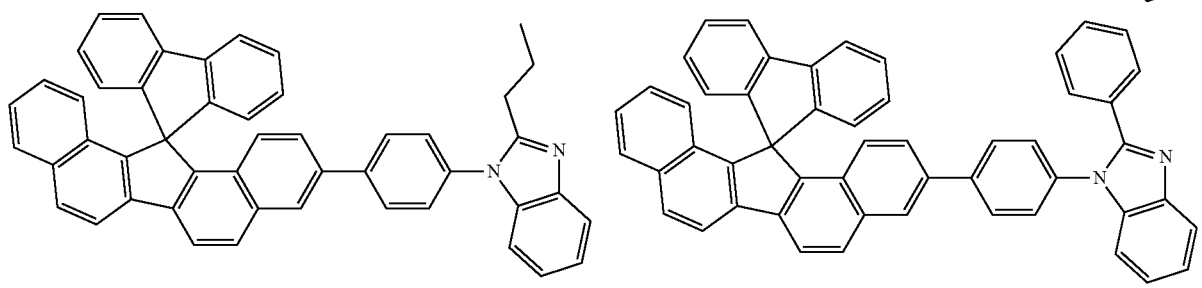 |

851
852
-continued
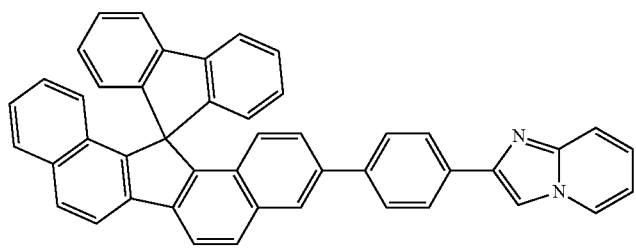
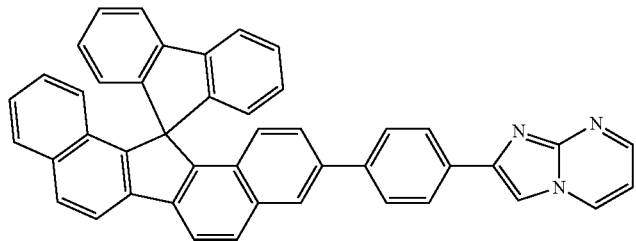
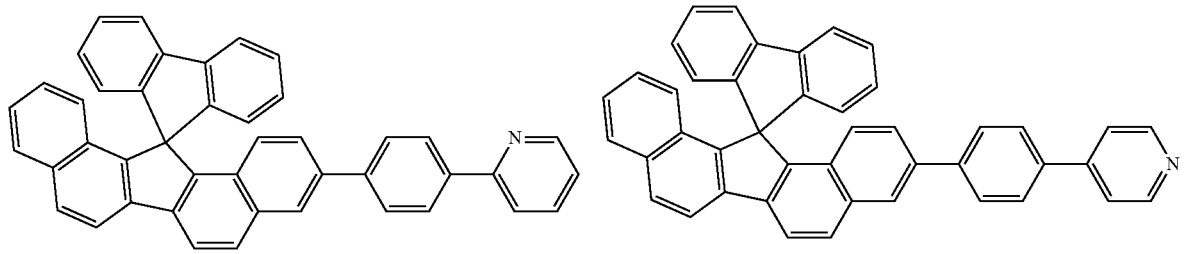
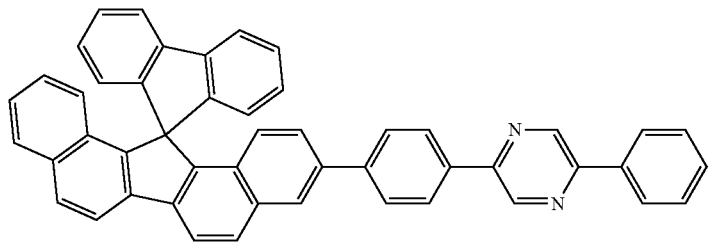
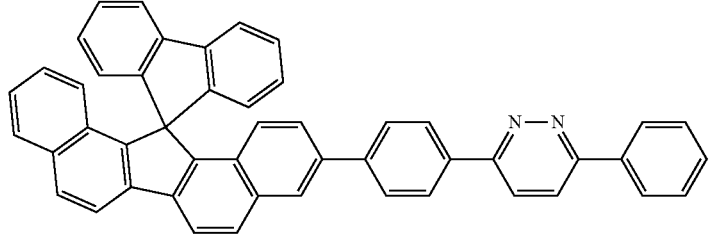
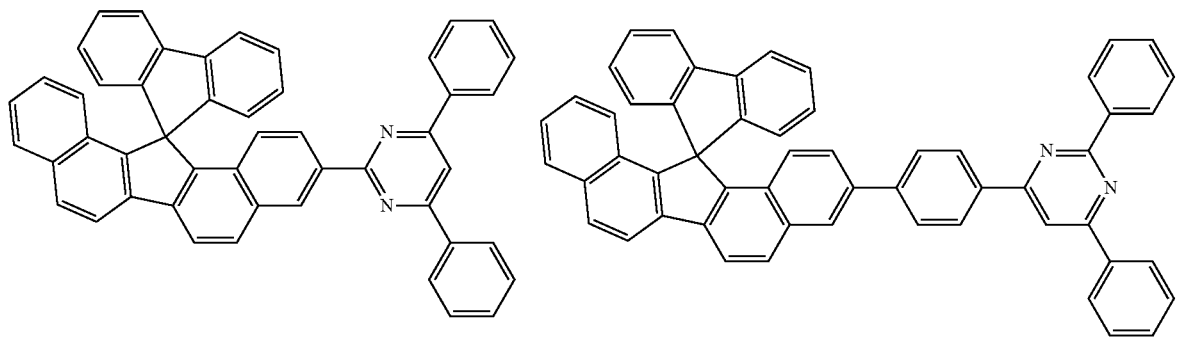

-continued
| 853 | 854 |
|---|---|
| 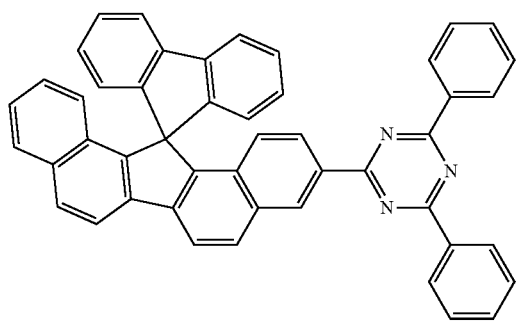 | 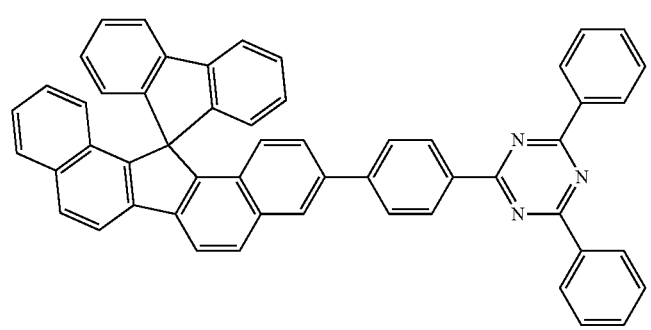 |
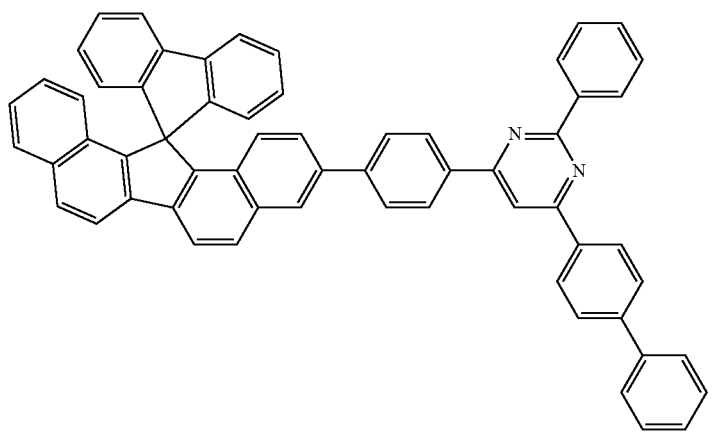
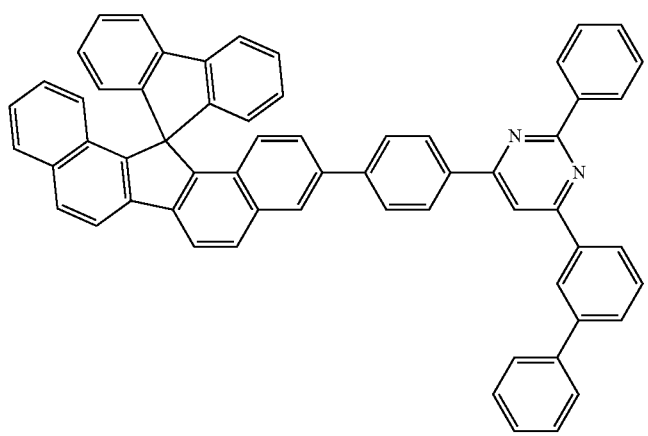
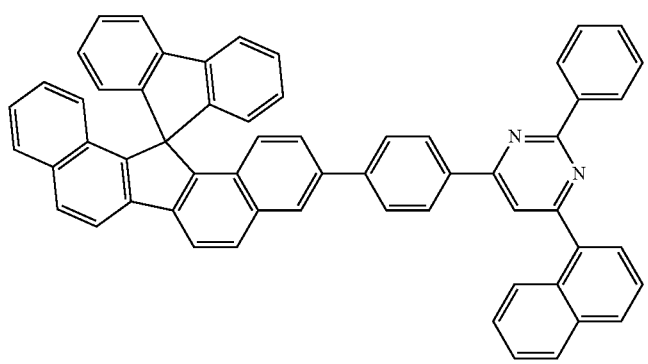

855
-continued
856
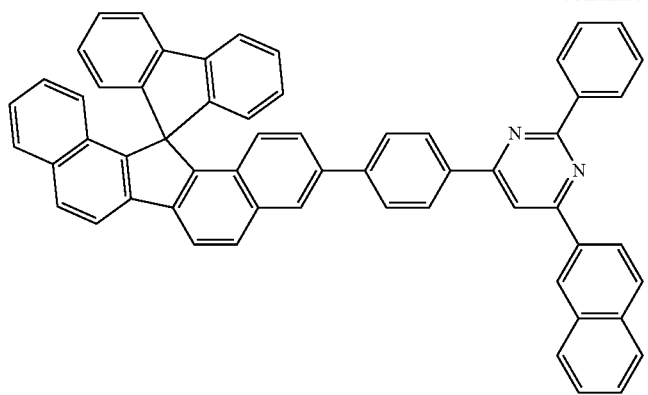
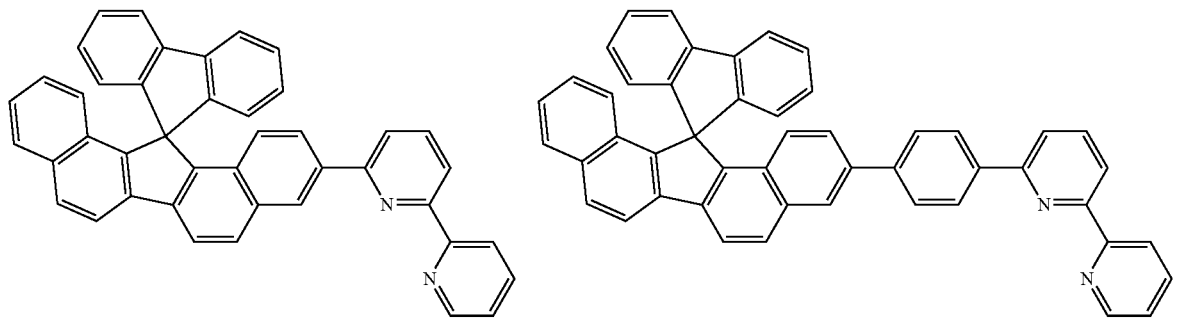
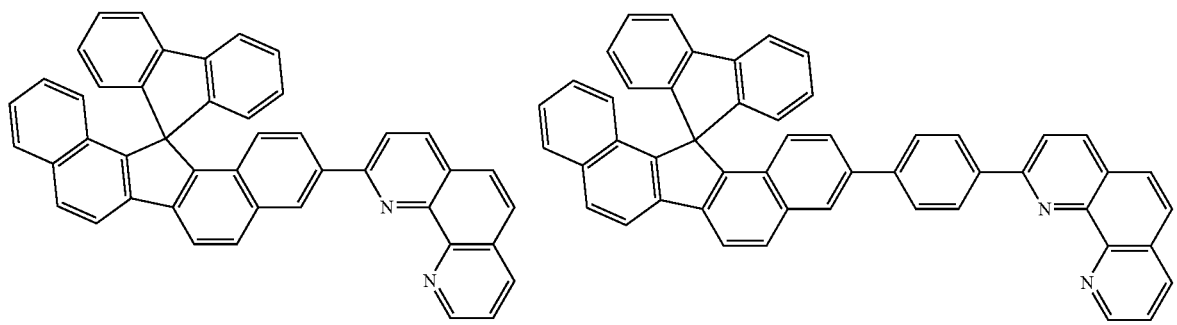
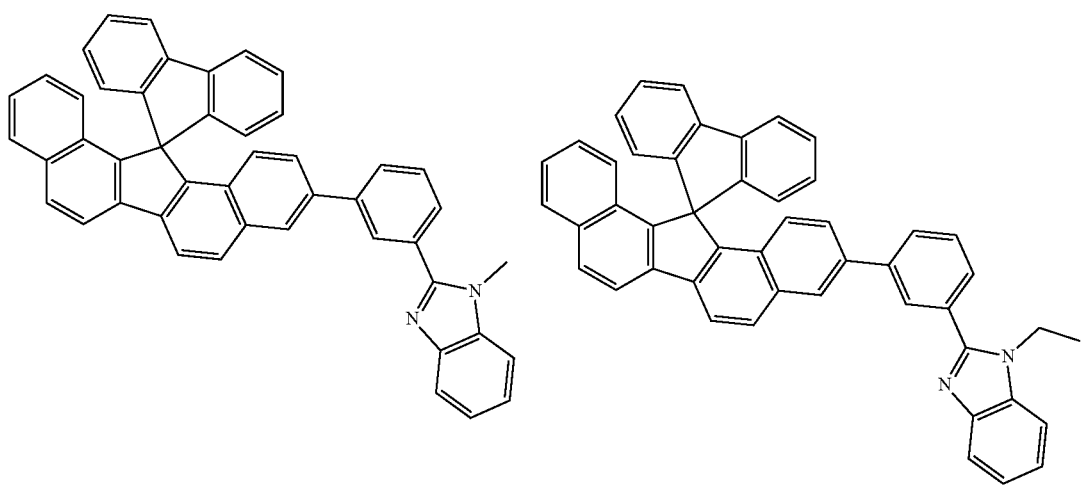

857 858
-continued
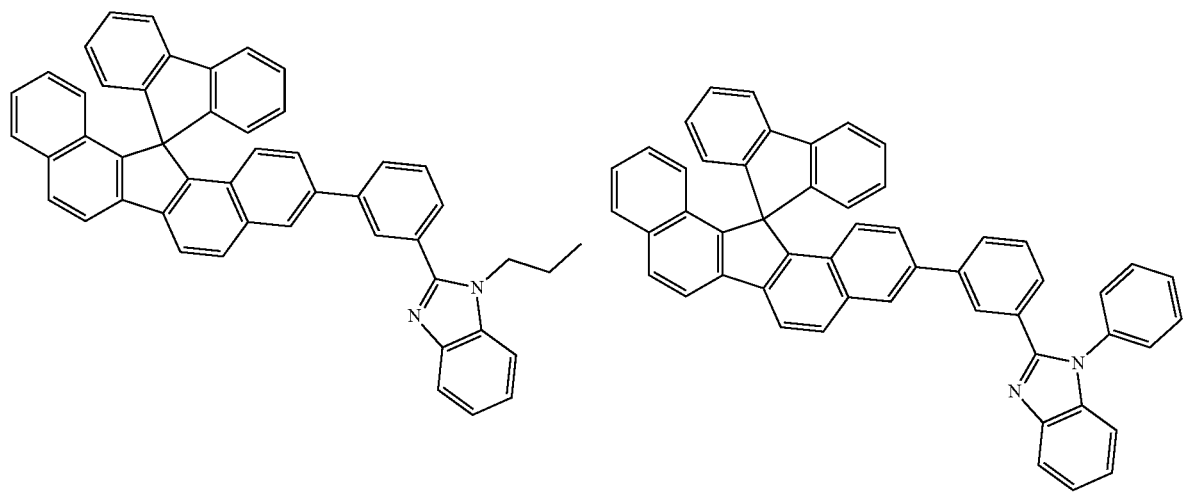
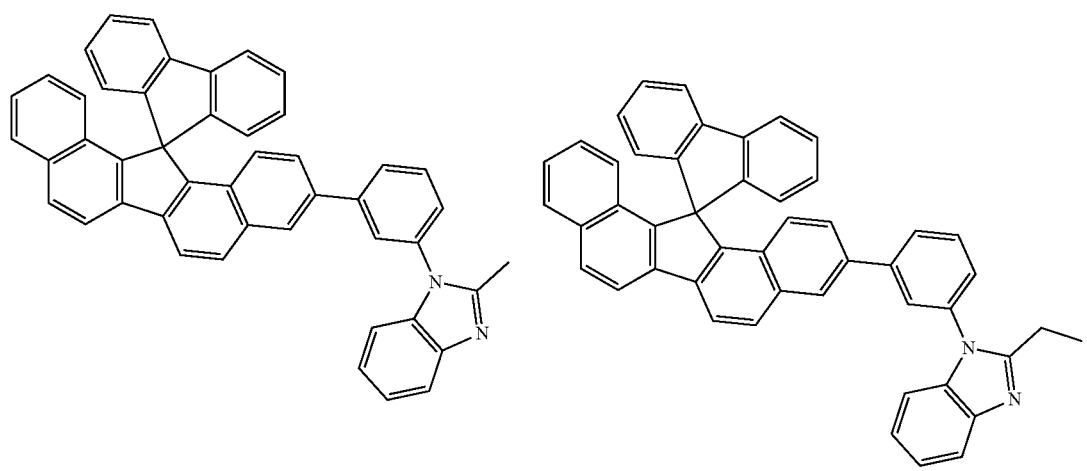
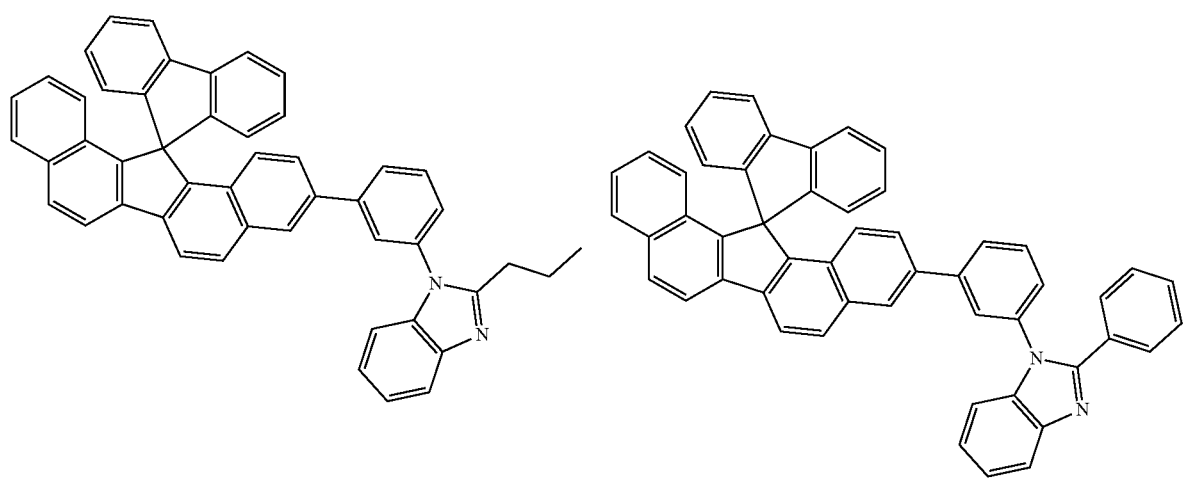

859 860
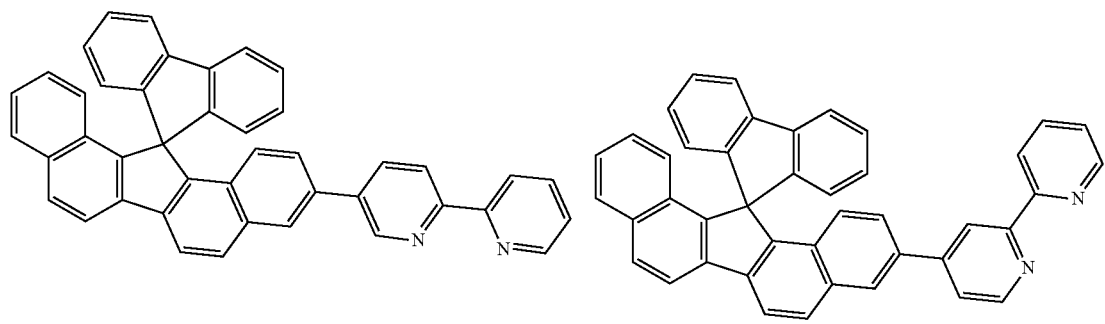
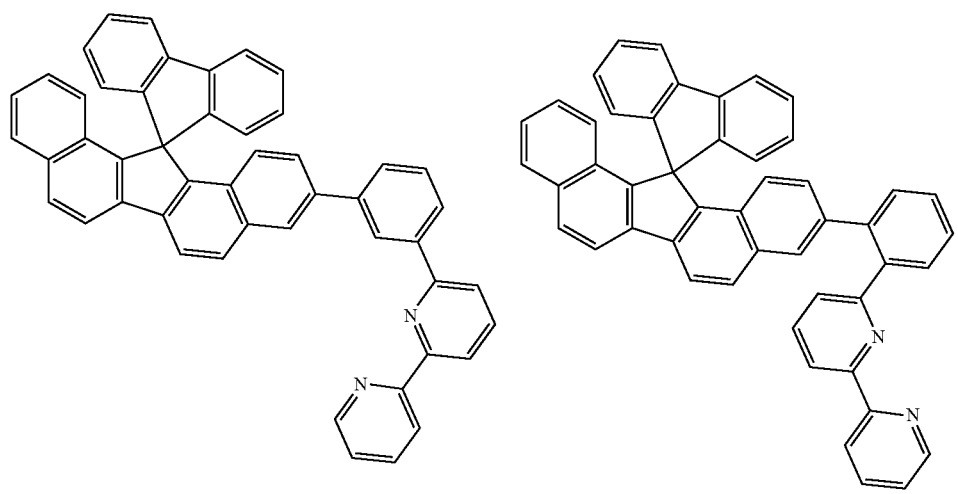
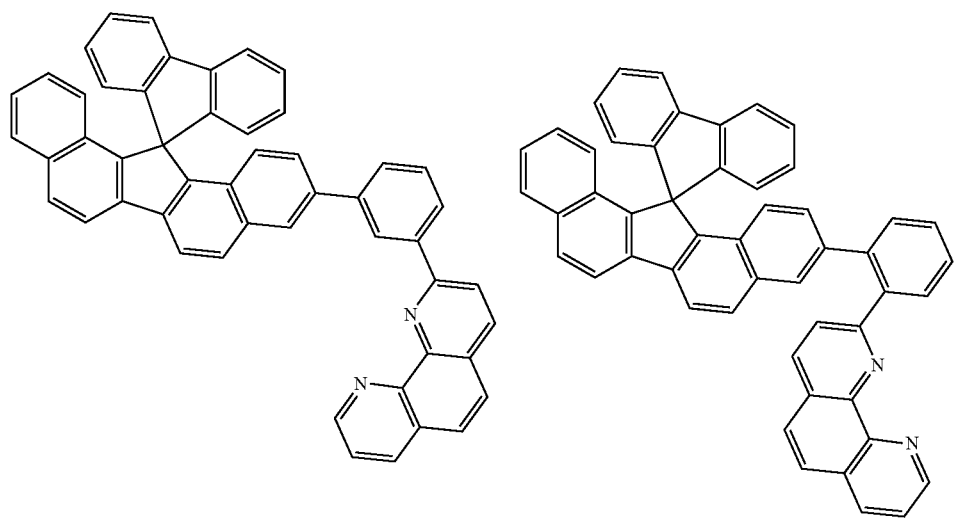

861
862
-continued
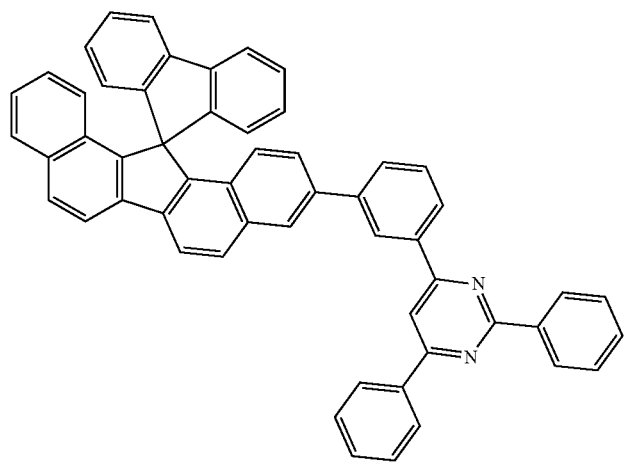
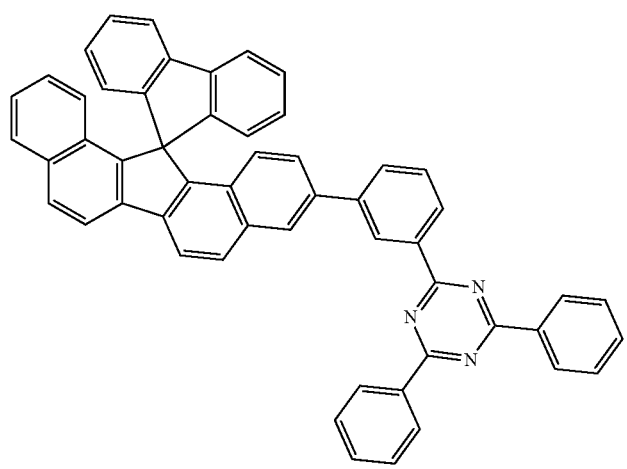
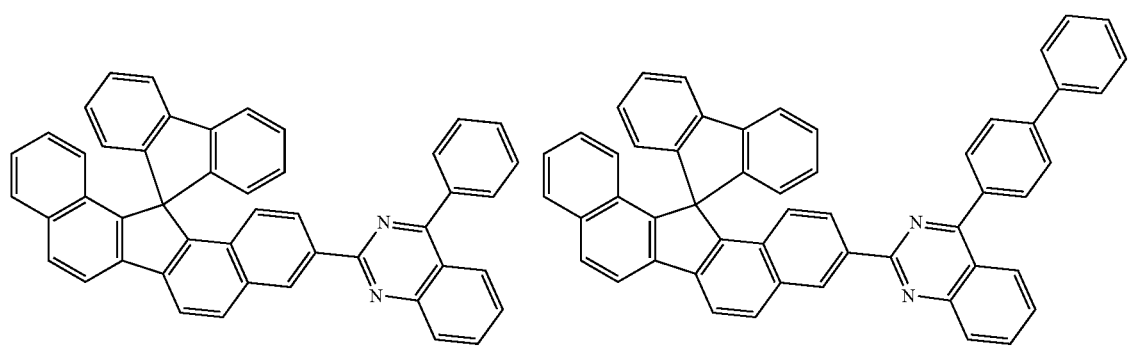
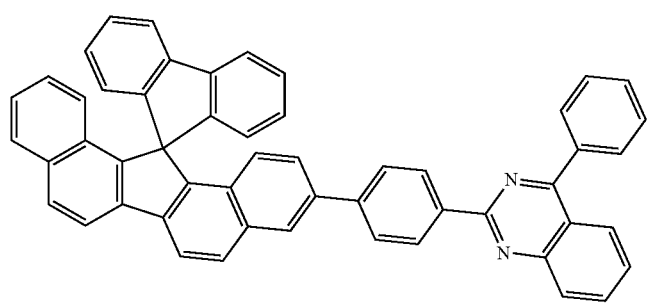

-continued
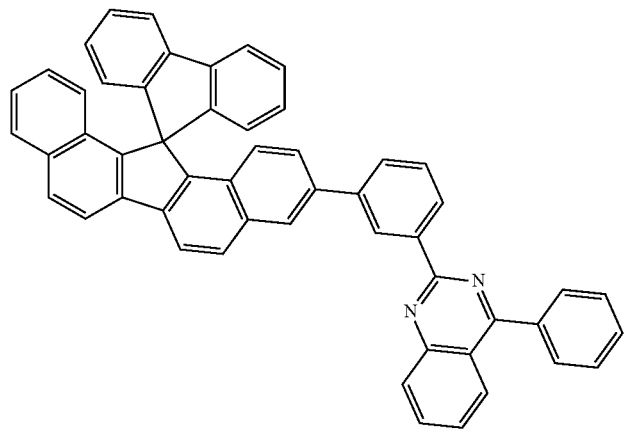
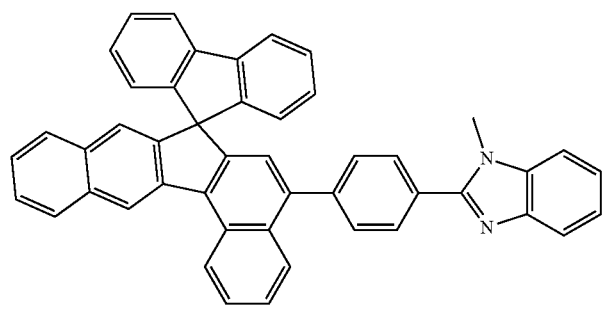
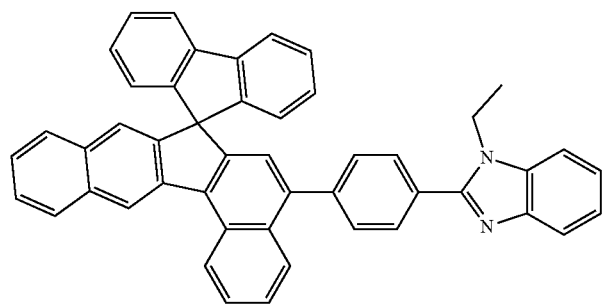
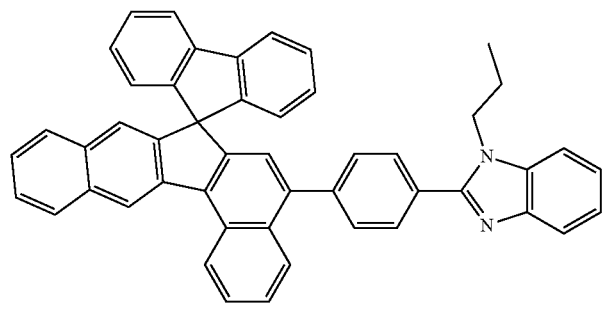
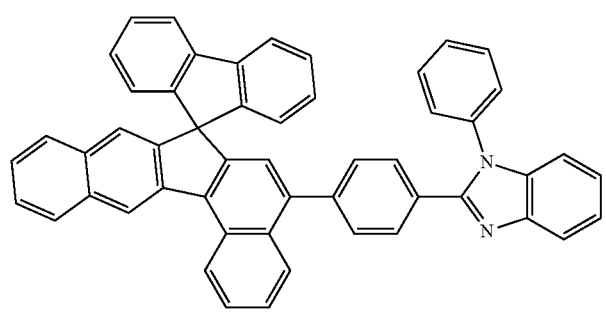

-continued
865
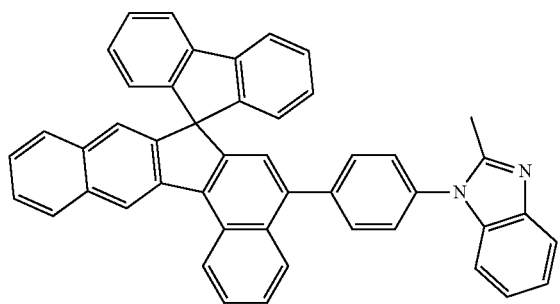
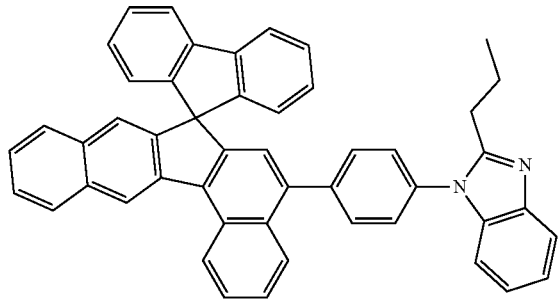
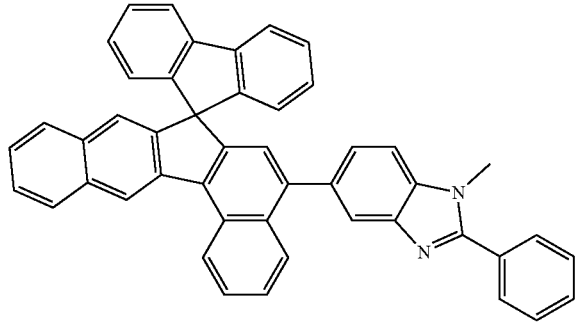
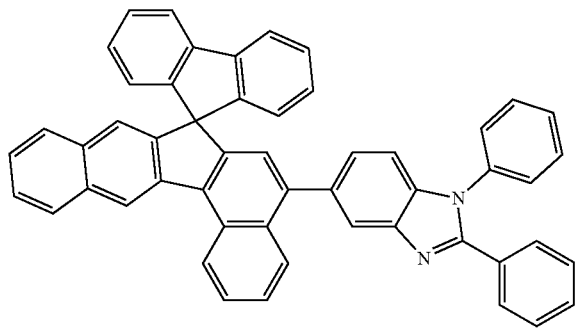
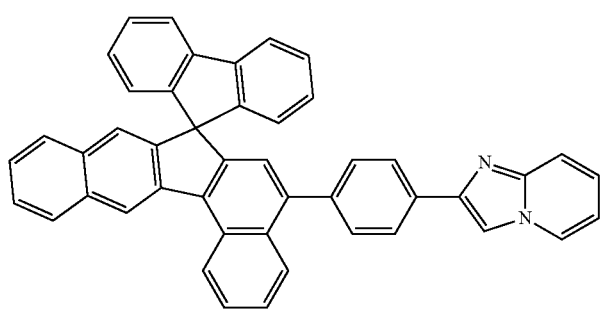
866
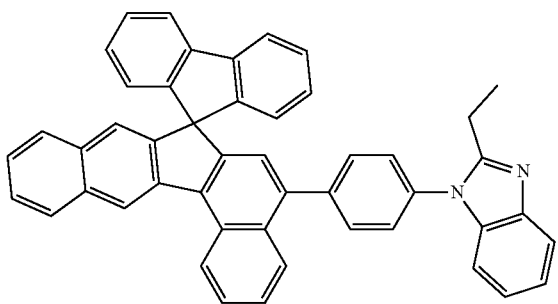
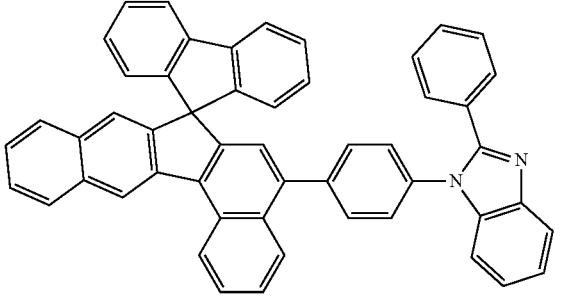

867
-continued
868
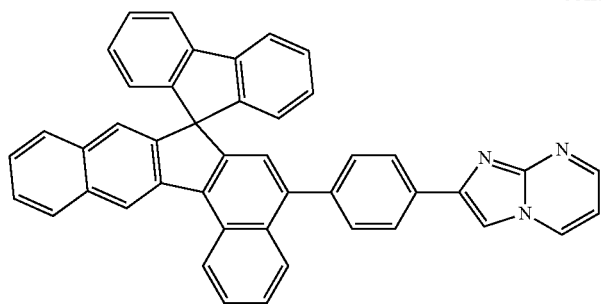
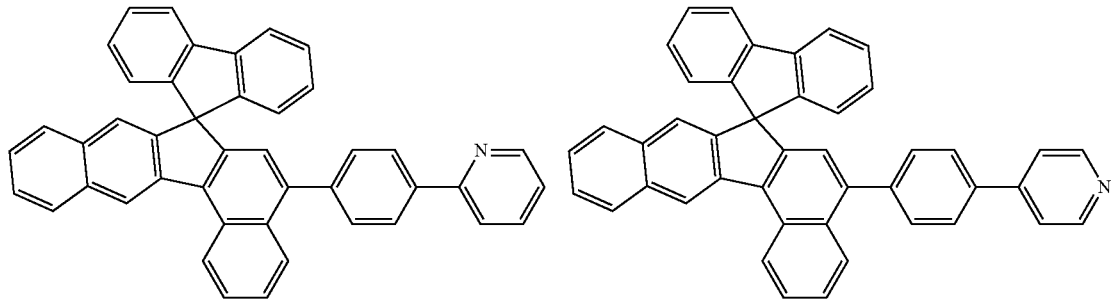
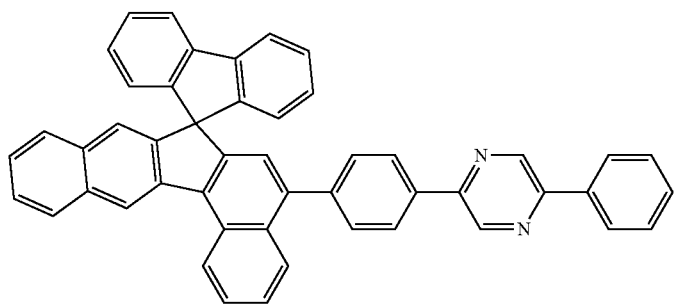
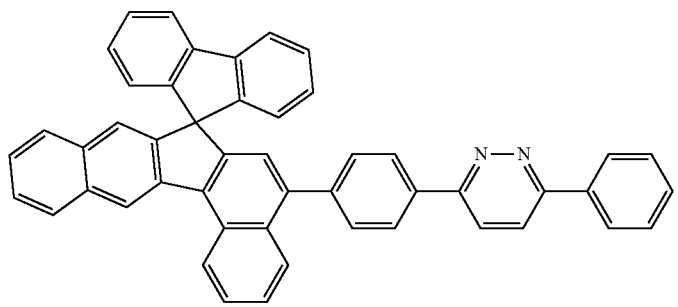
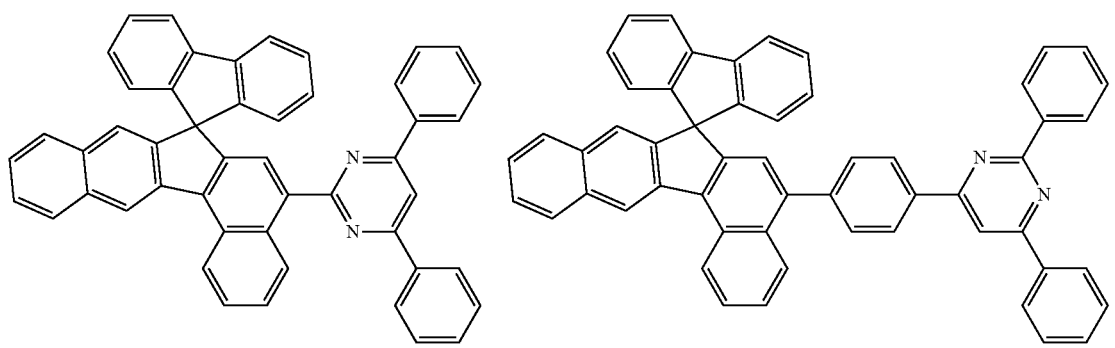

-continued
| 869 | 870 |
|---|---|
| 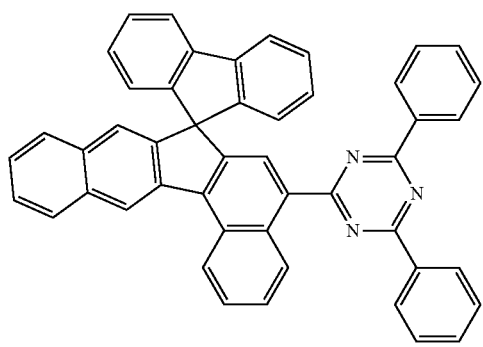 | 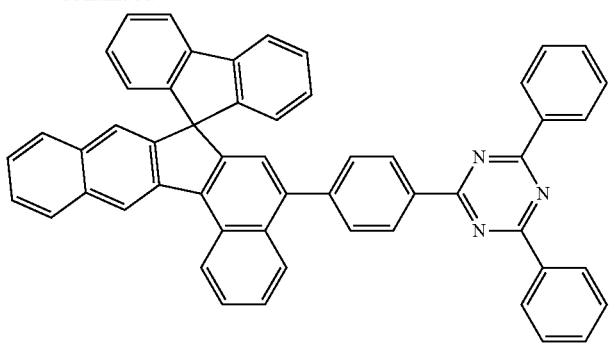 |
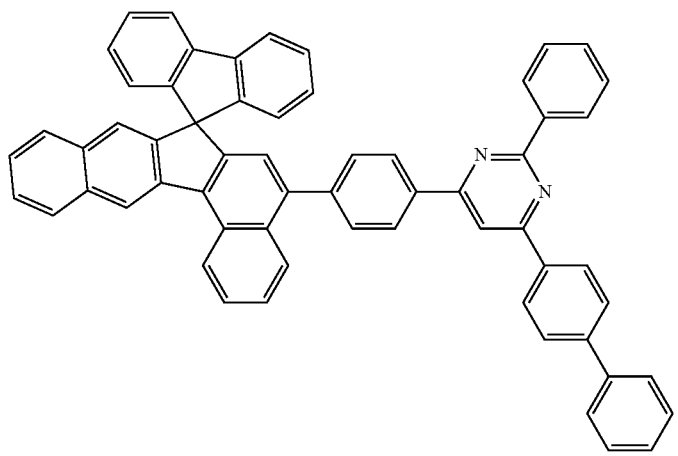
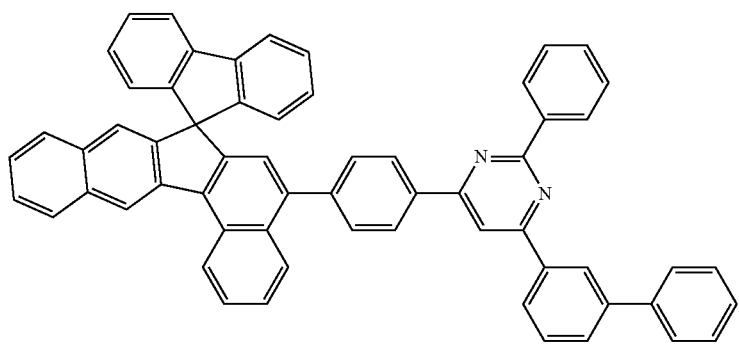
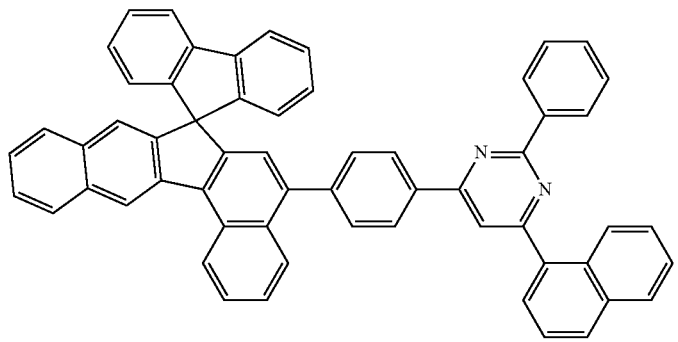

871 872
-continued
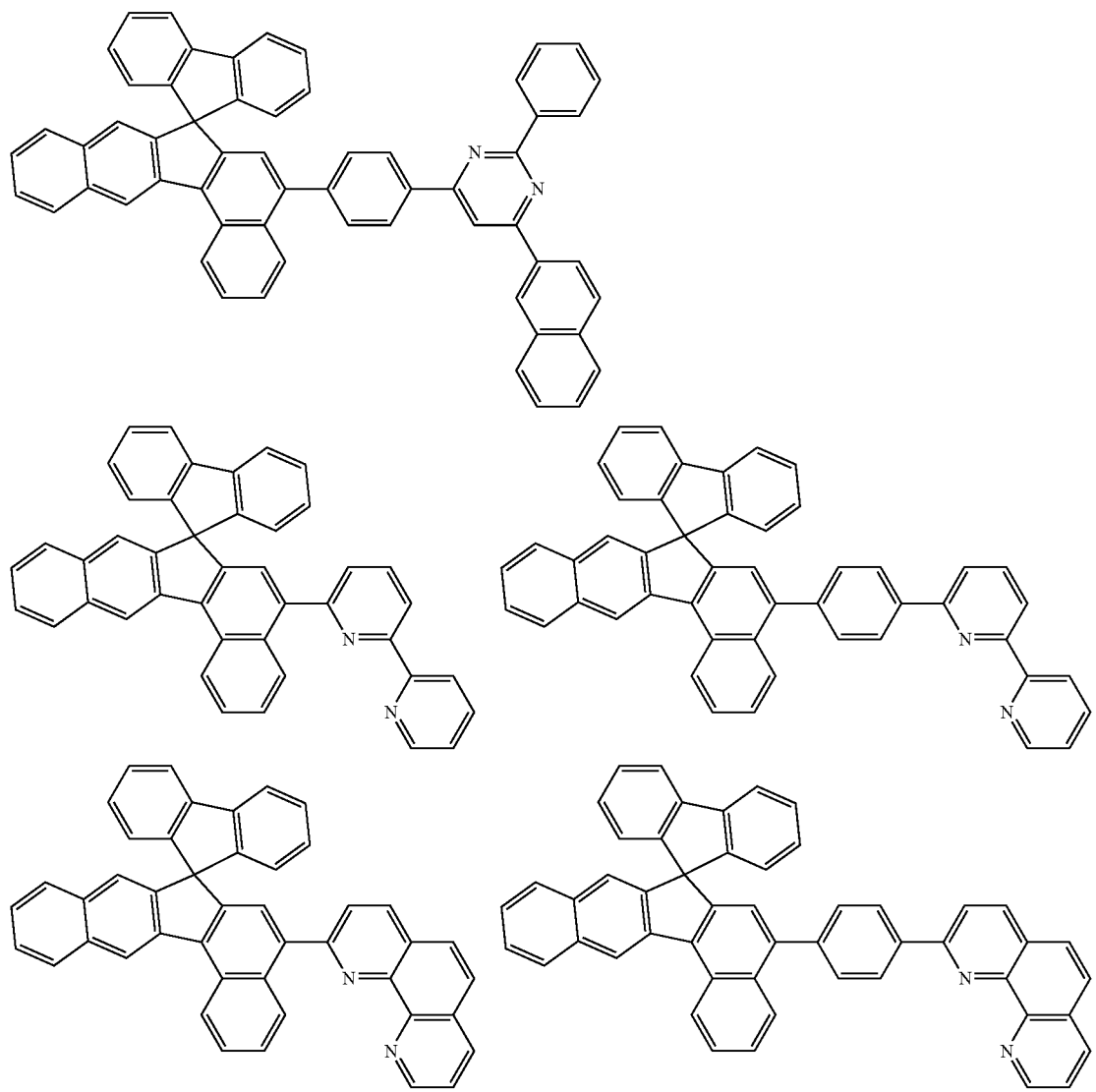
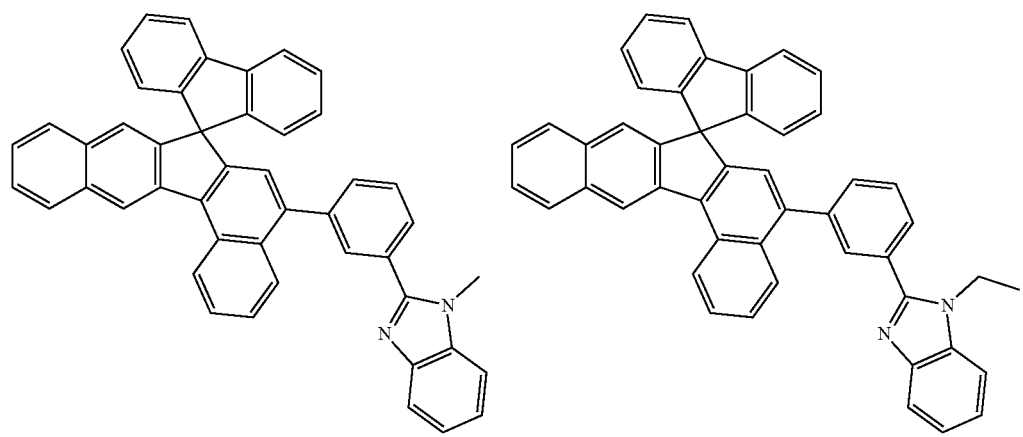

-continued
873 874
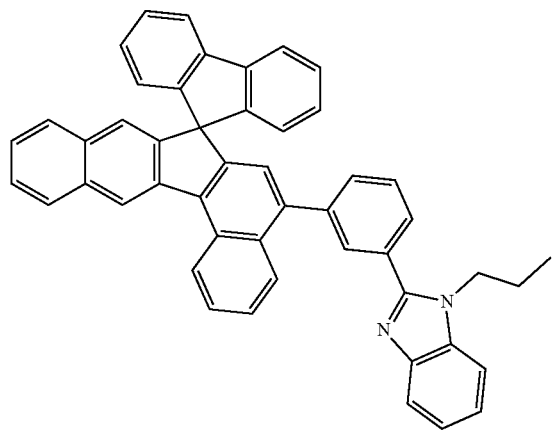 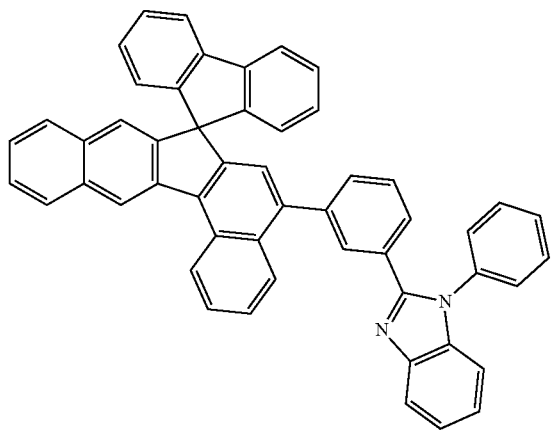
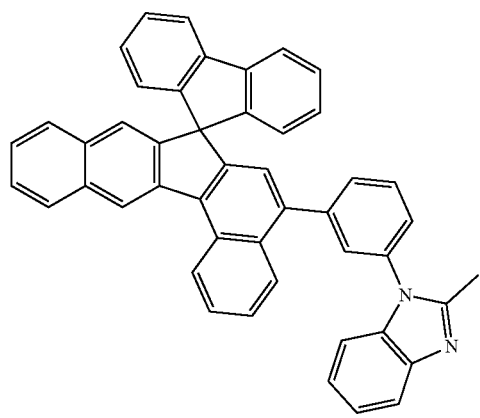 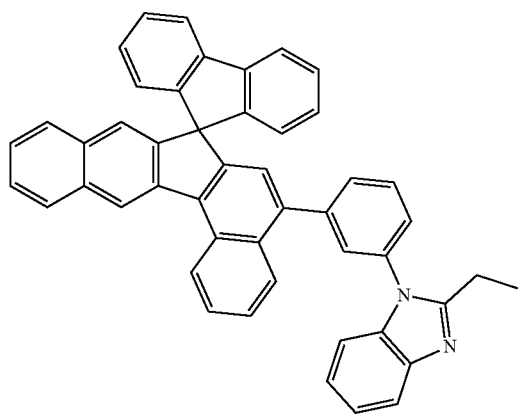
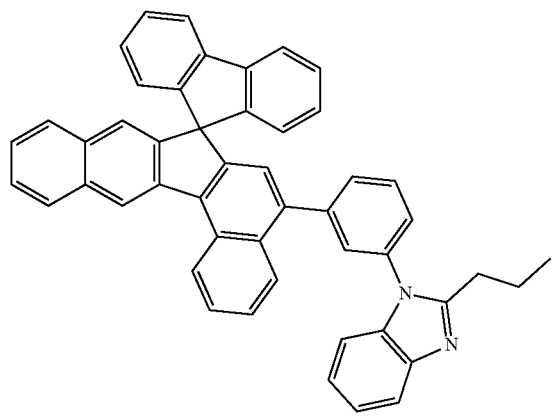 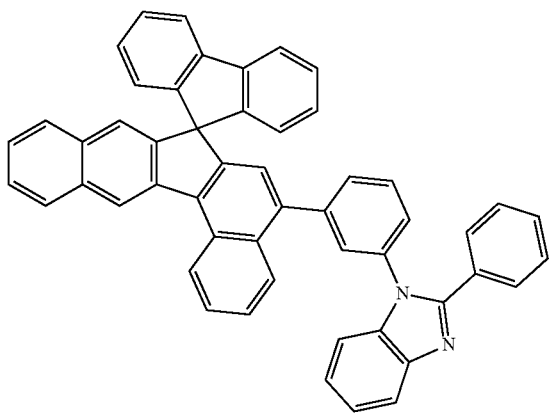
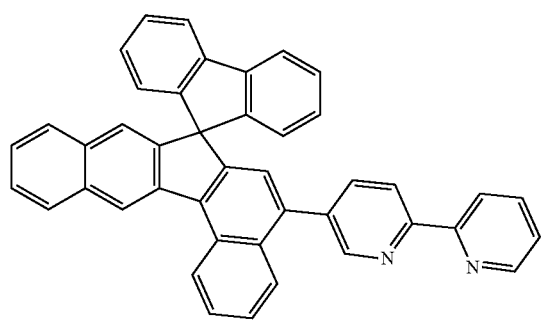 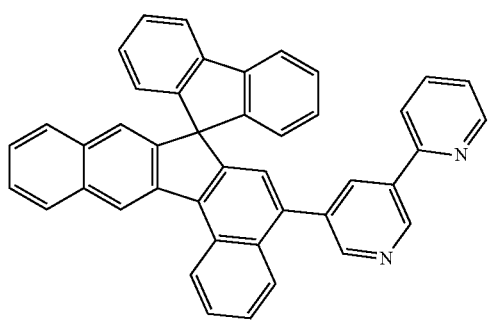

875
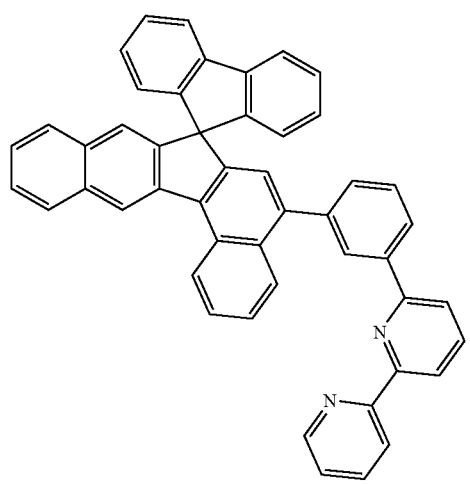
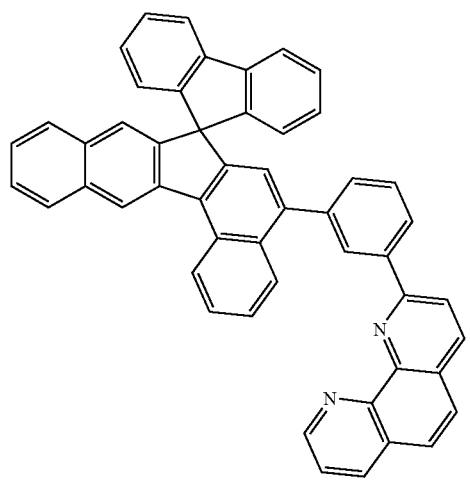
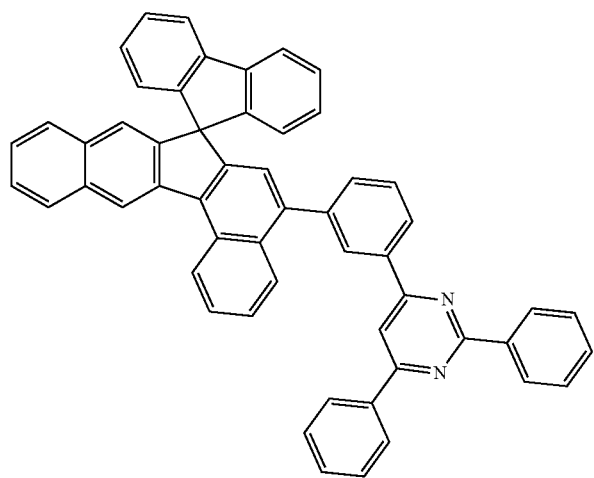
-continued
876
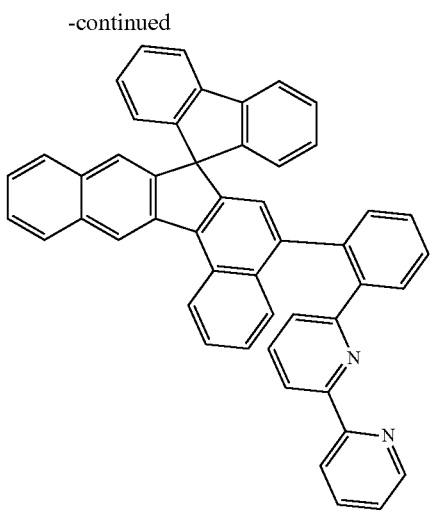
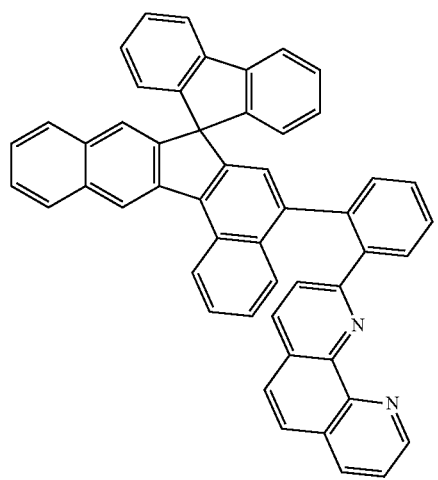
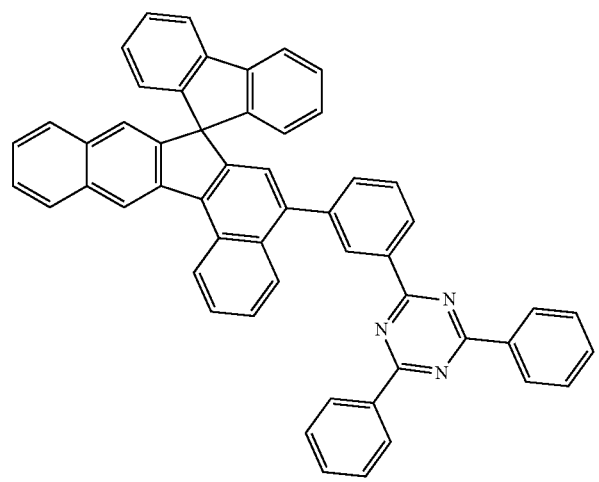

-continued
877
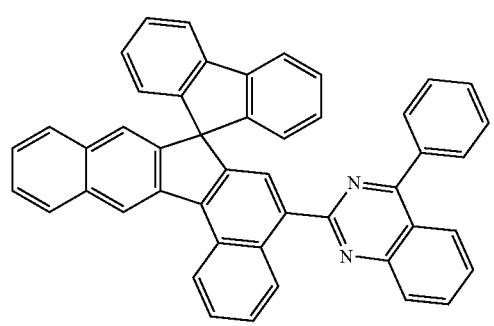
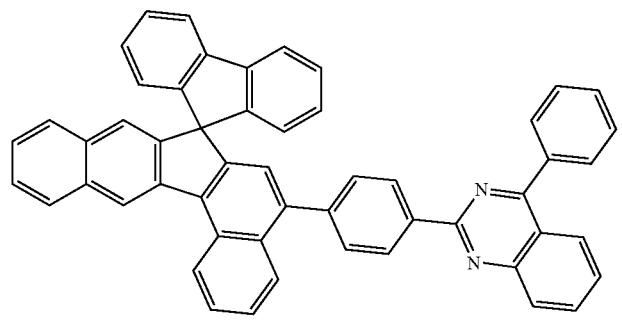
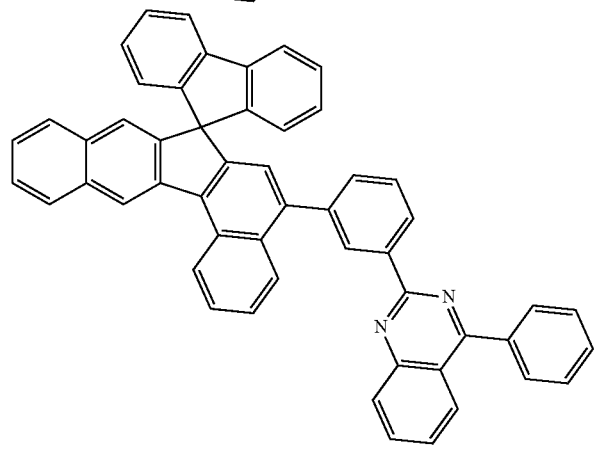
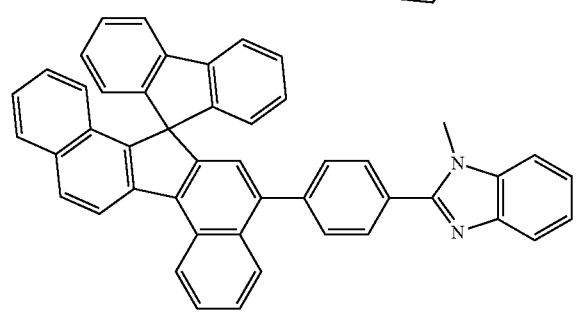
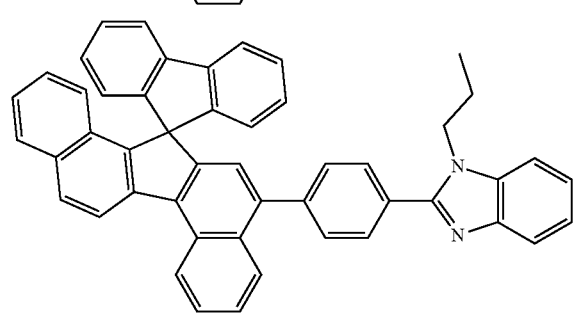
878
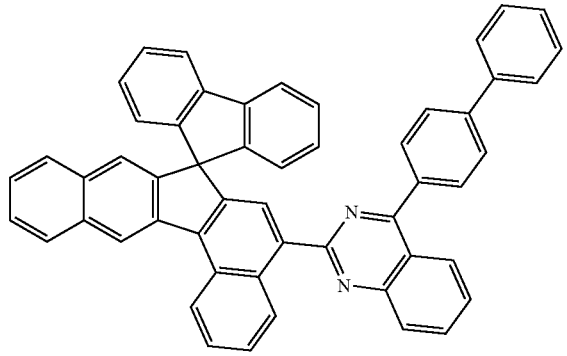
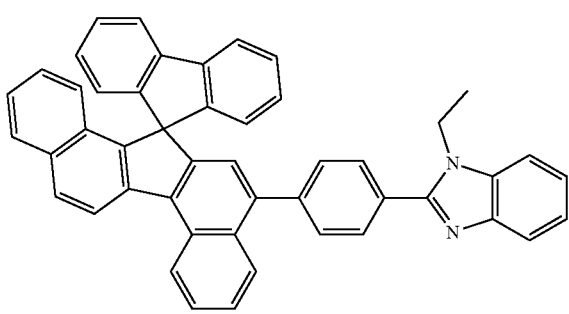
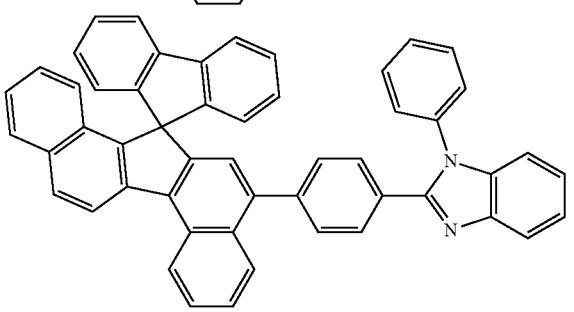

879     880
-continued
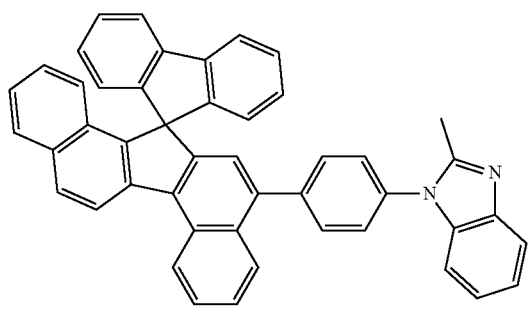 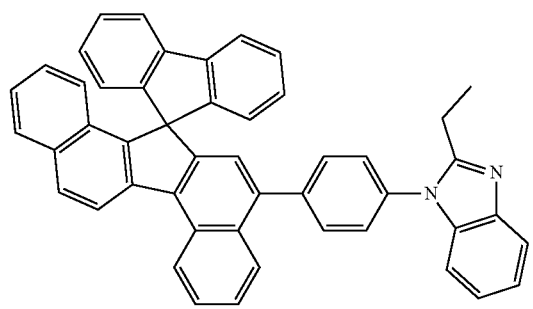
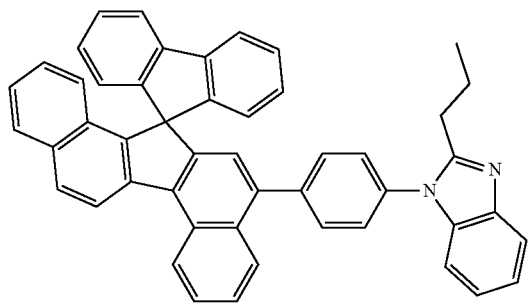 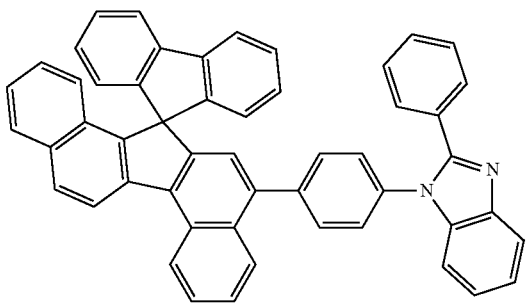
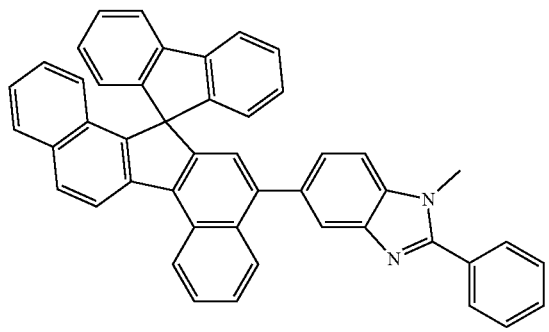 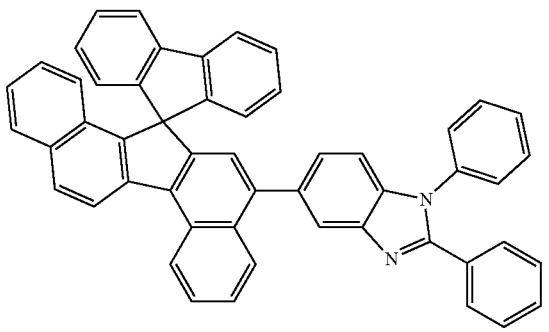
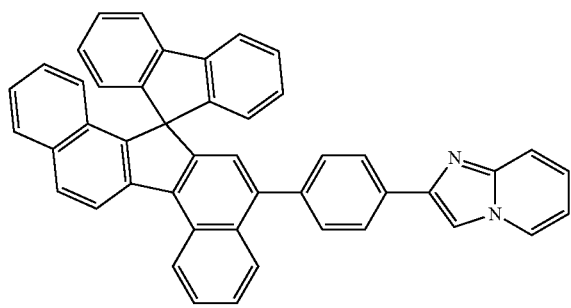 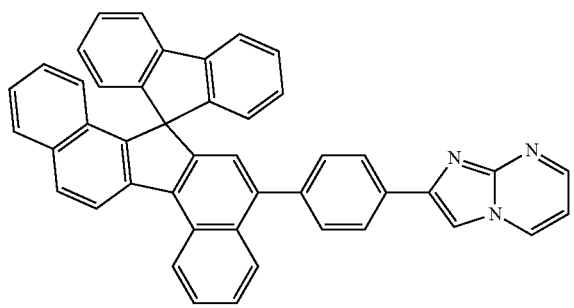
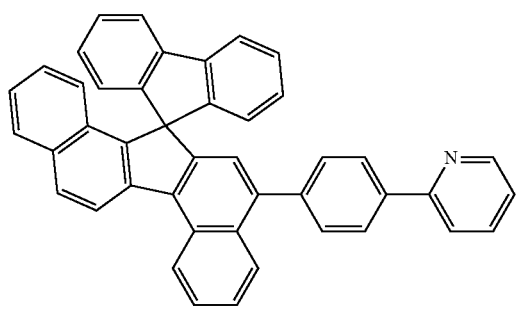 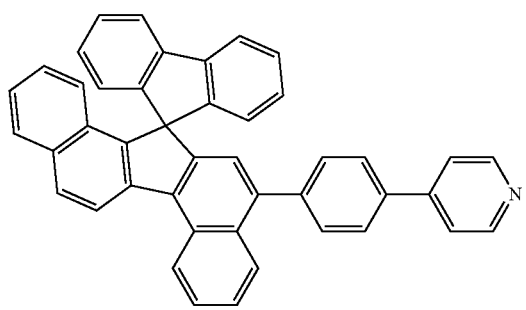

-continued
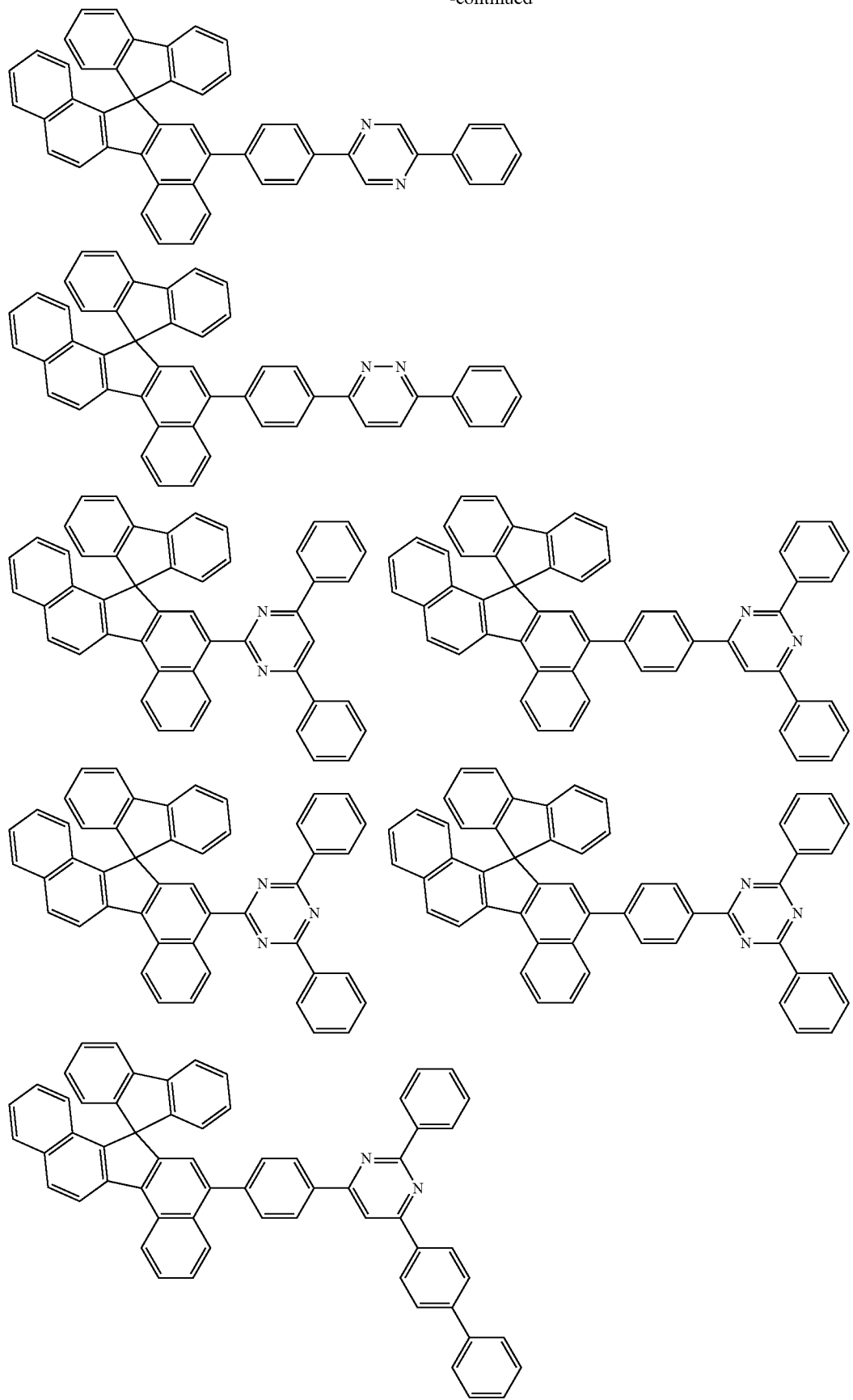

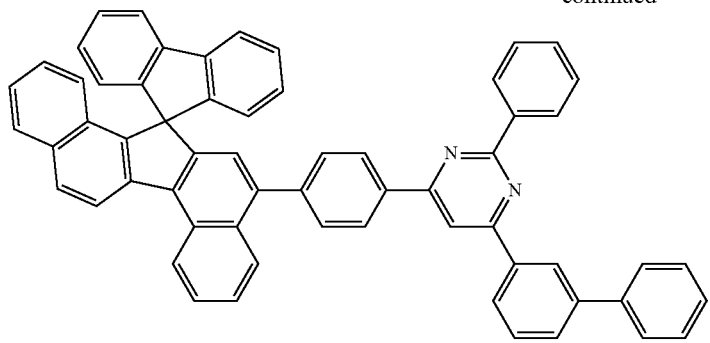
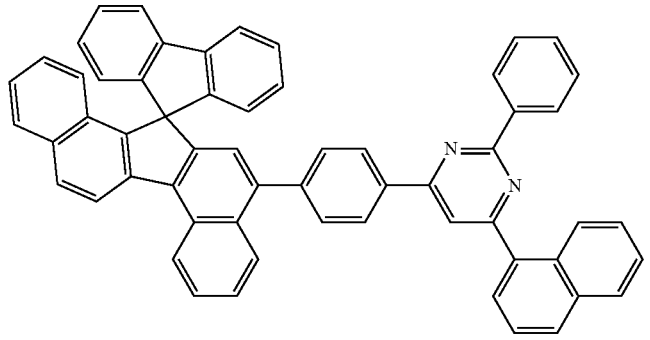
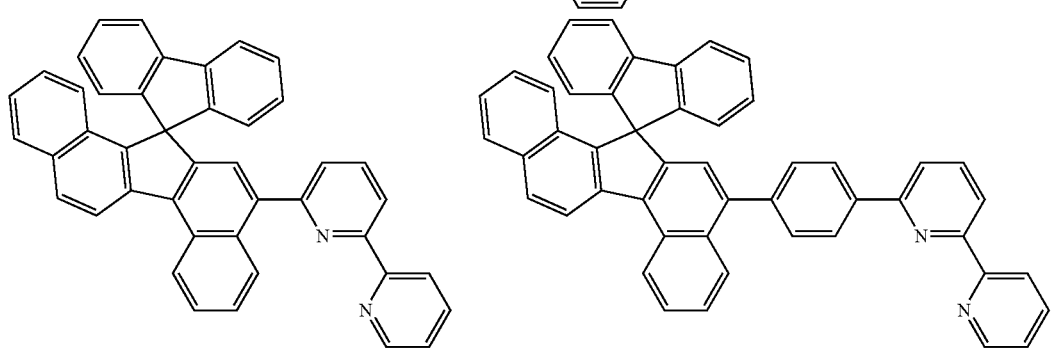
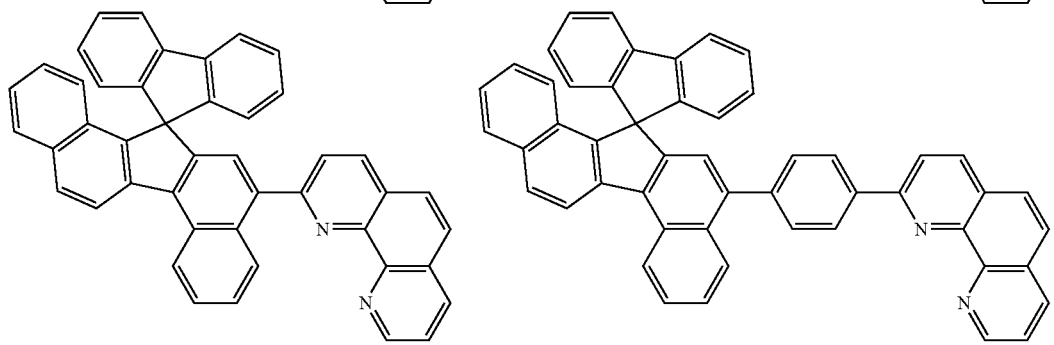

885 886
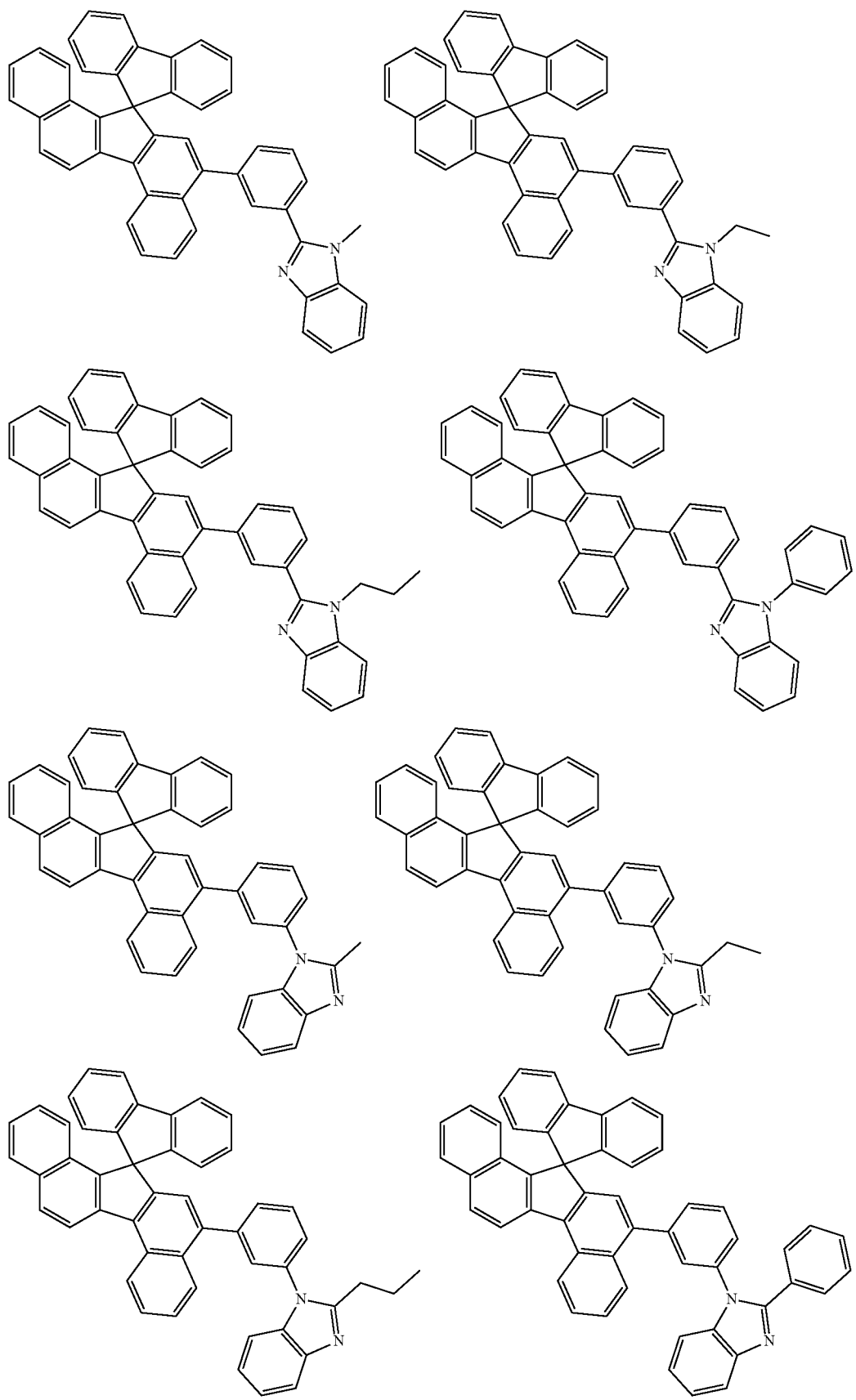

887
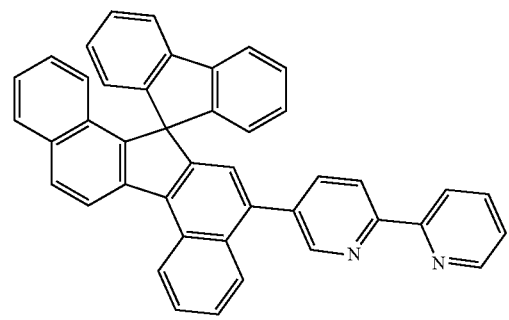
888
-continued
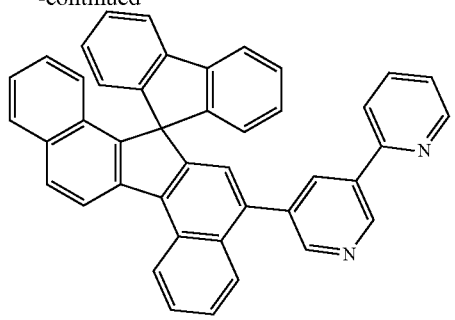
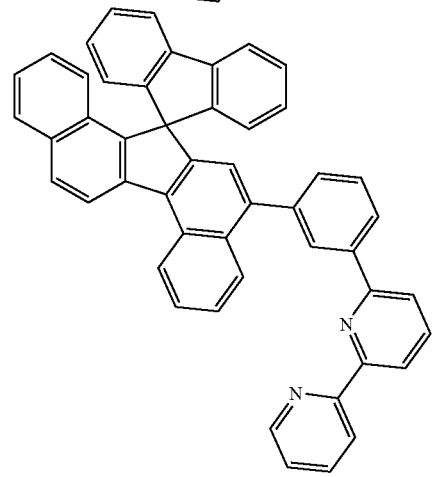
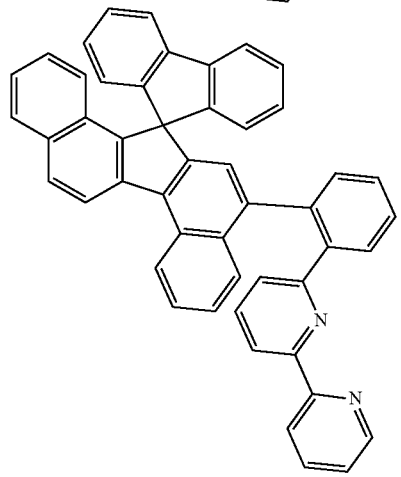
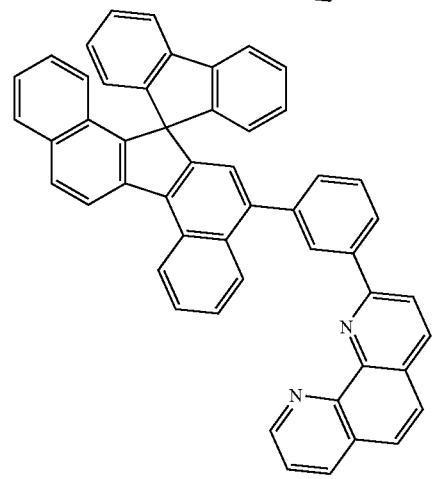
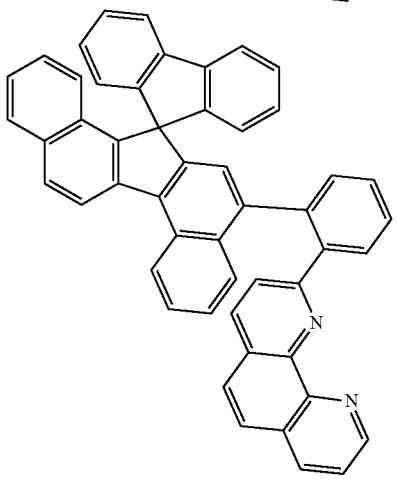
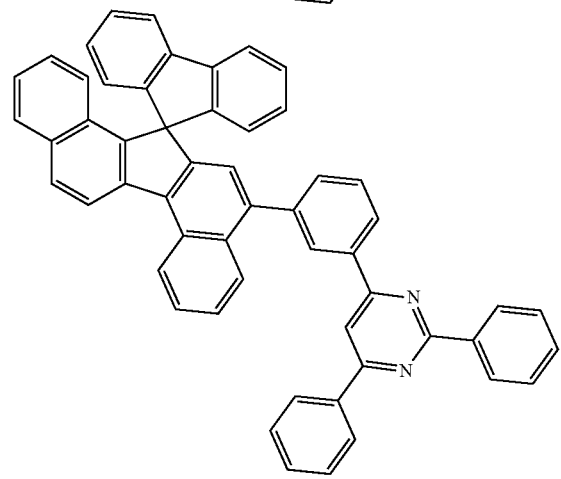
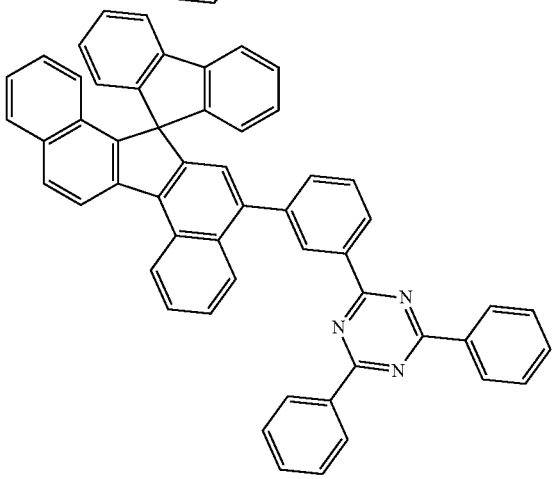

889 890
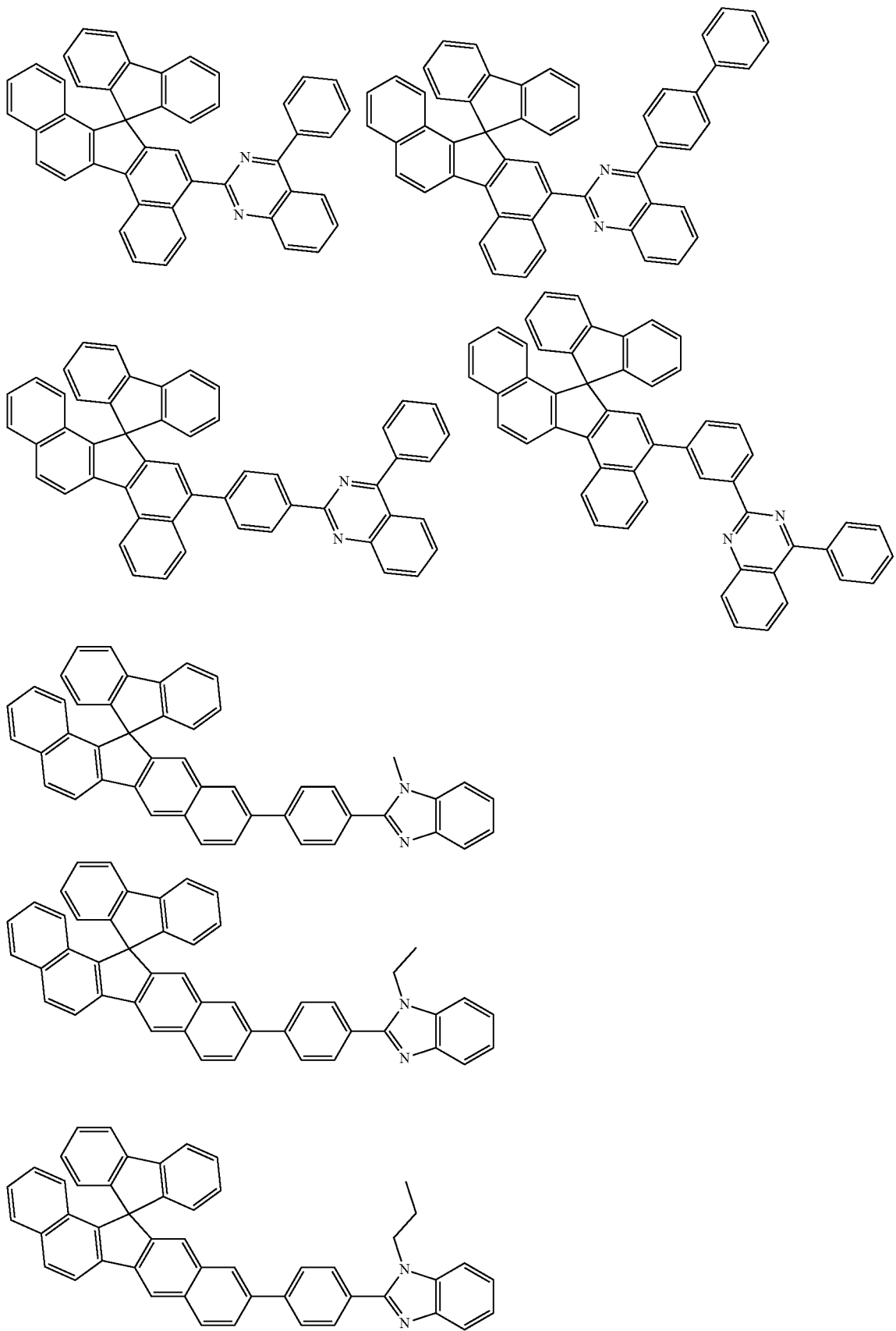
-continued 891 892
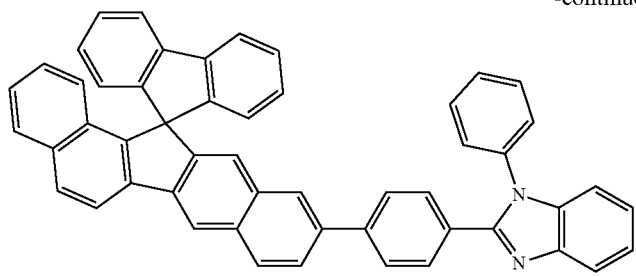
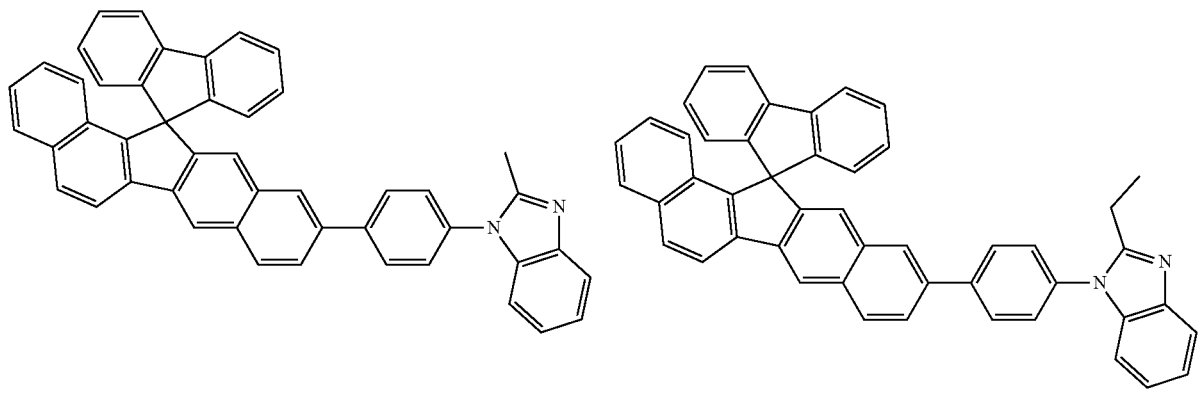
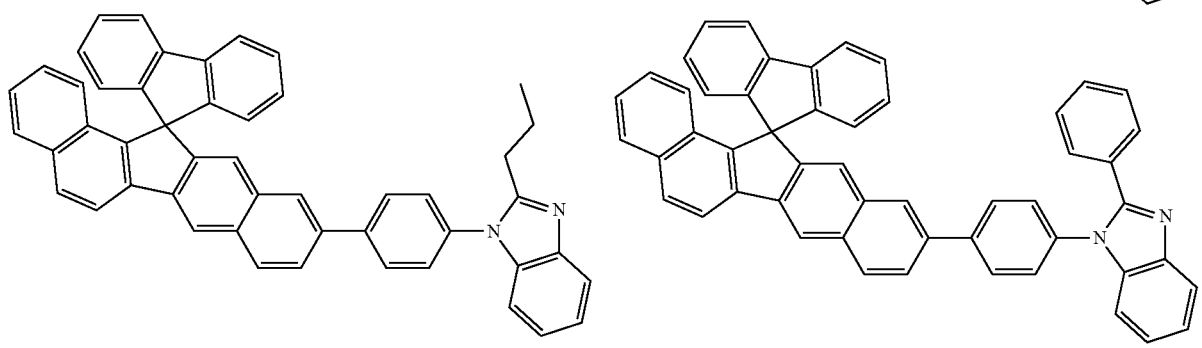
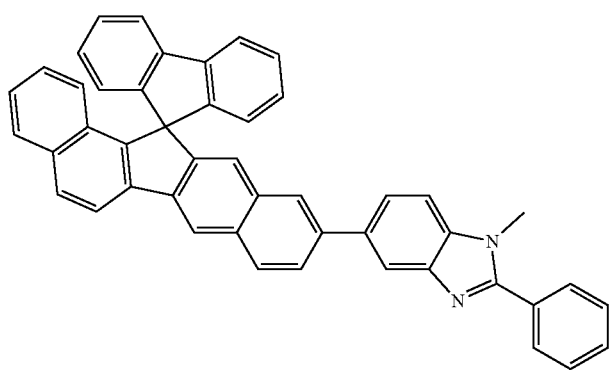
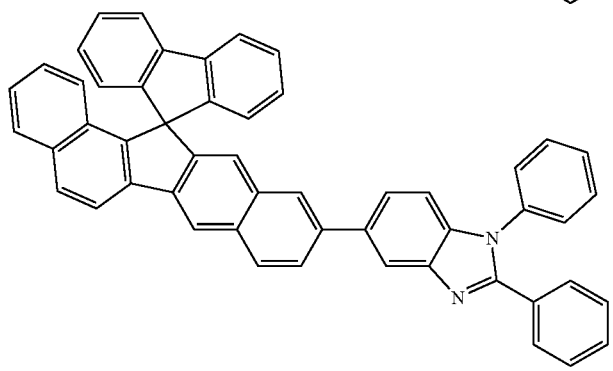

893
894
-continued
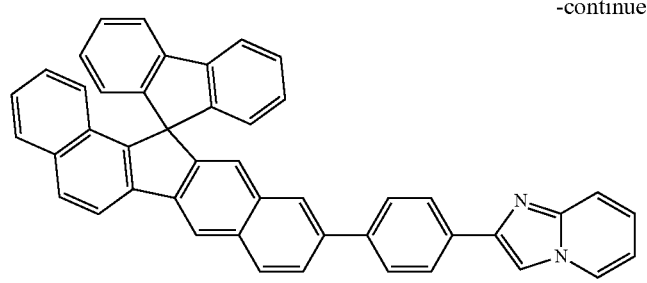
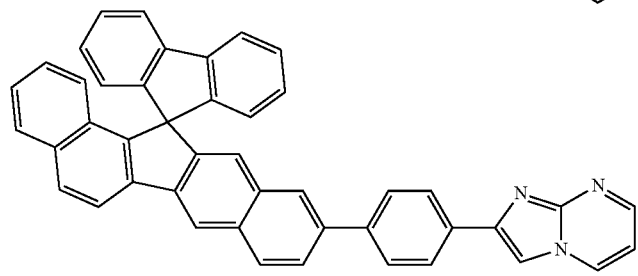
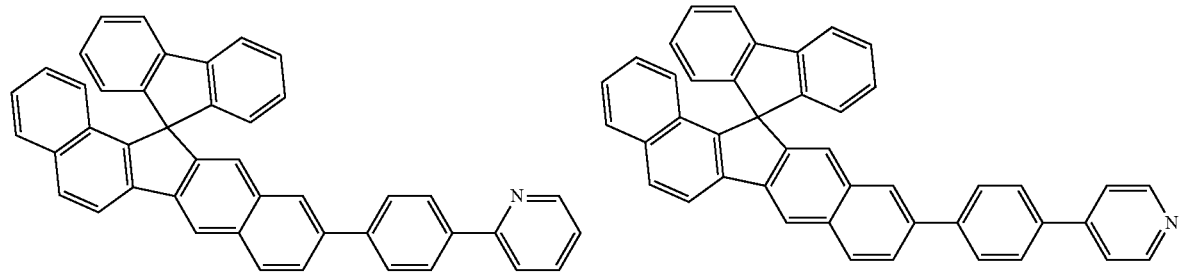
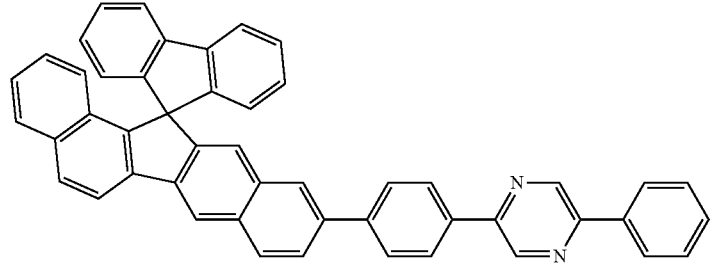
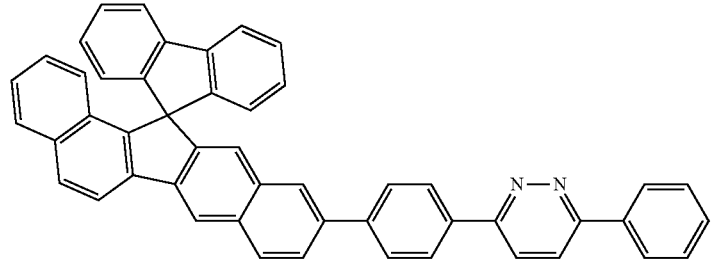
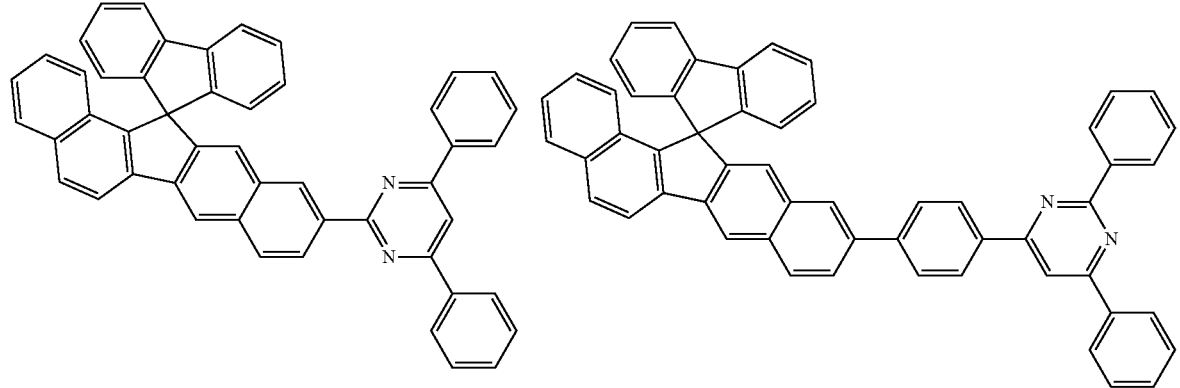

-continued
895 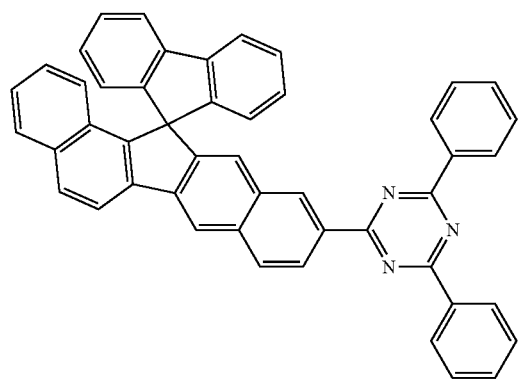
896 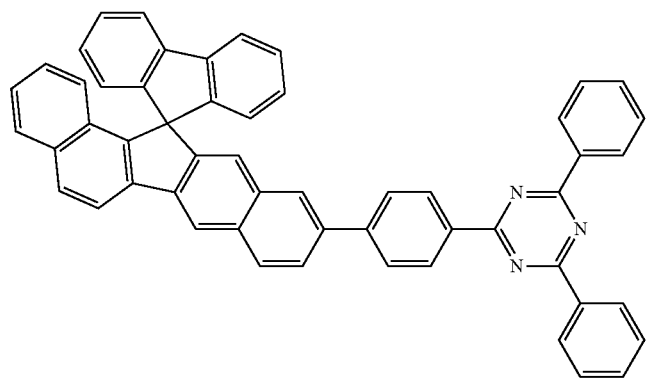
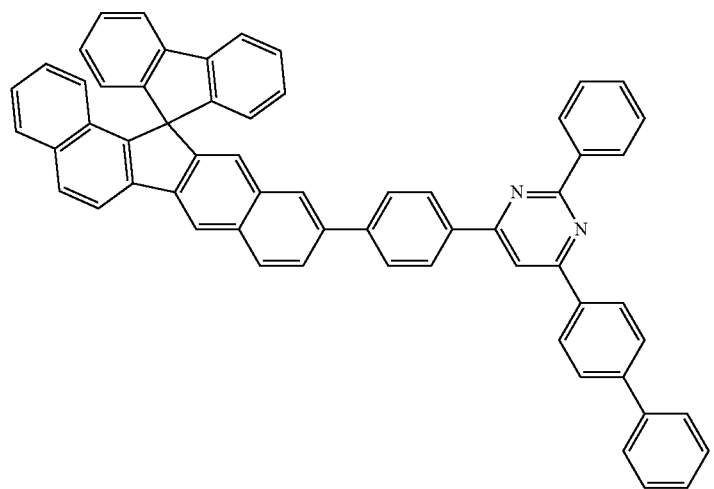
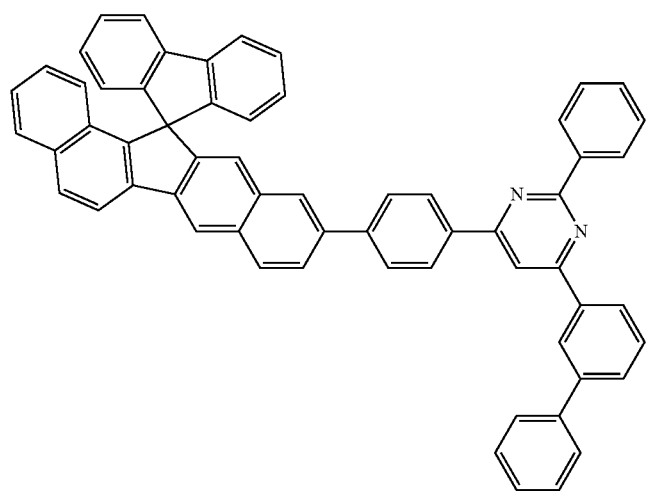

897 898
-continued
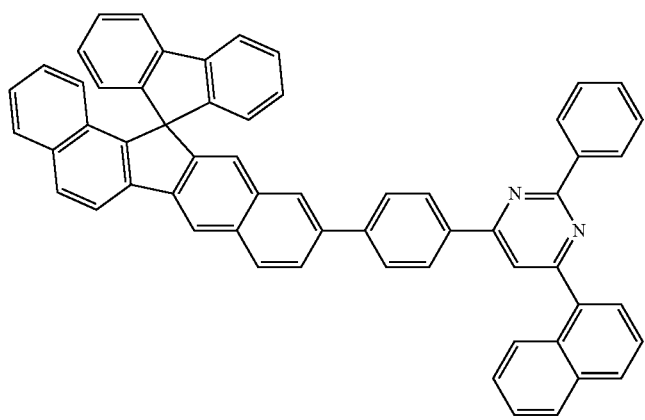
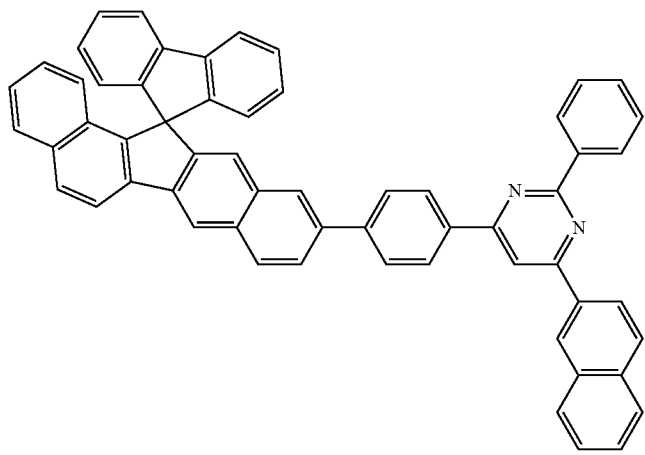
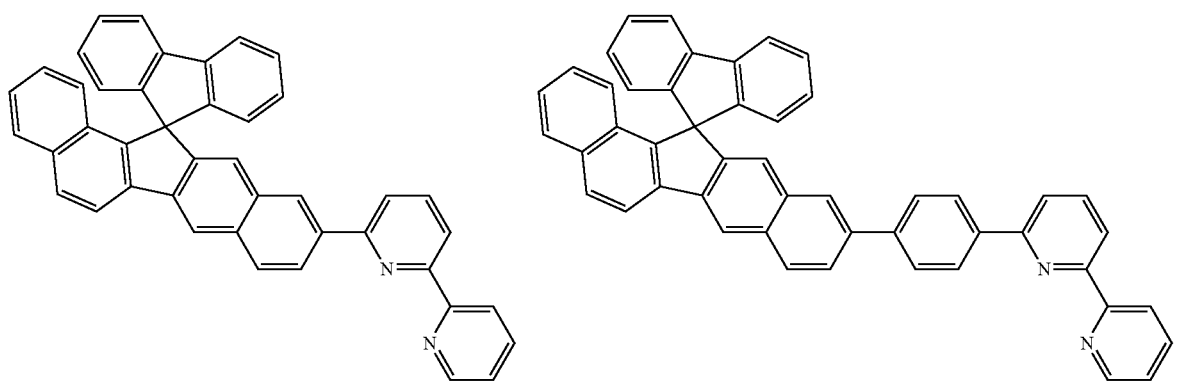
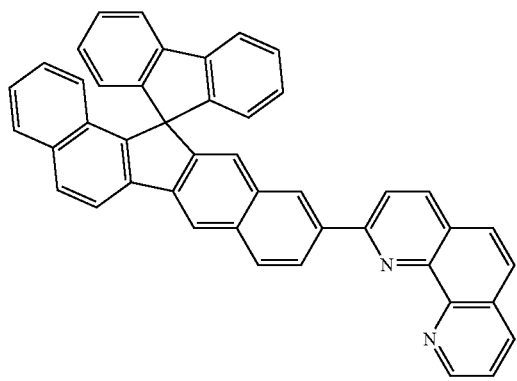
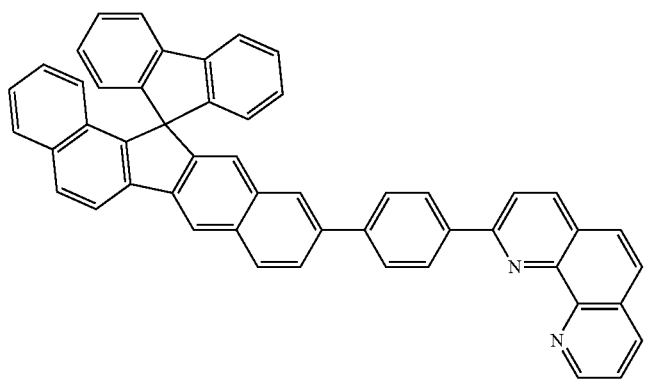

-continued
| 899 | 900 |
|---|---|
| 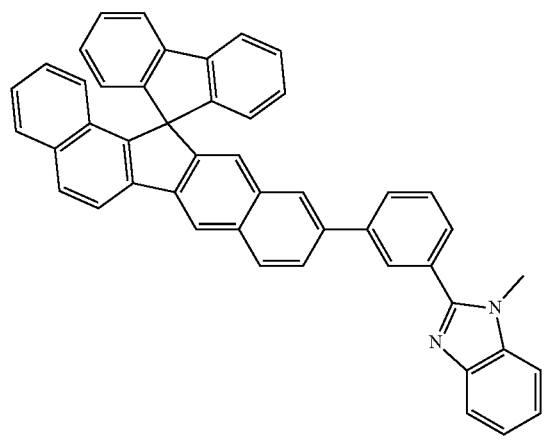 | 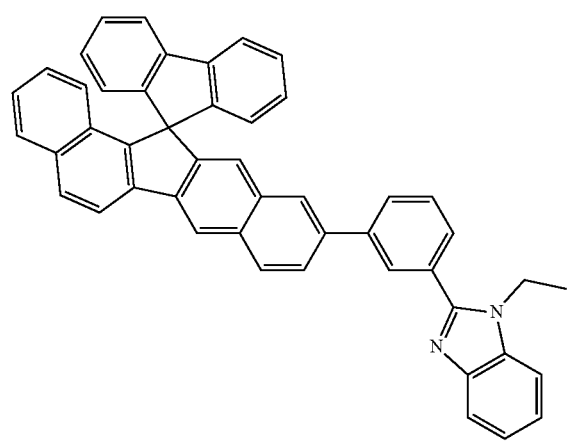 |
| 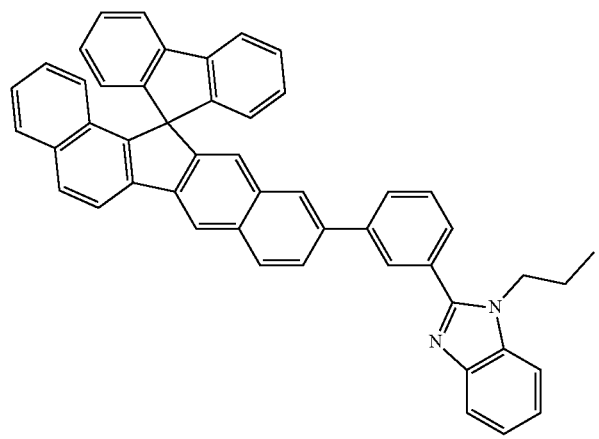 | 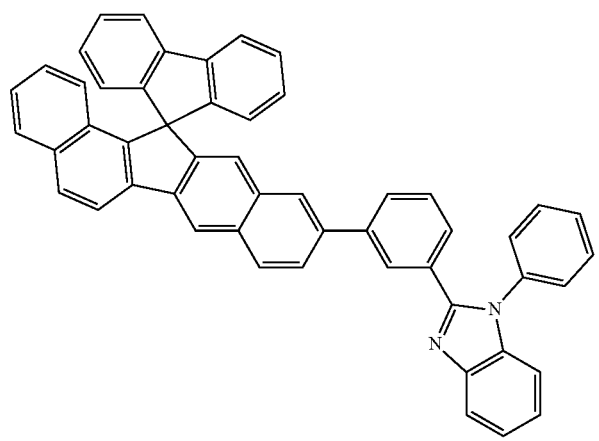 |
| 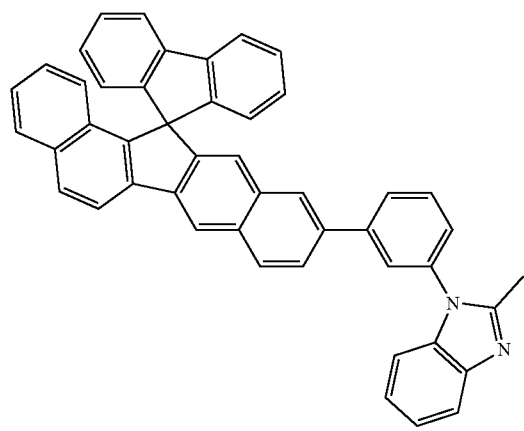 | 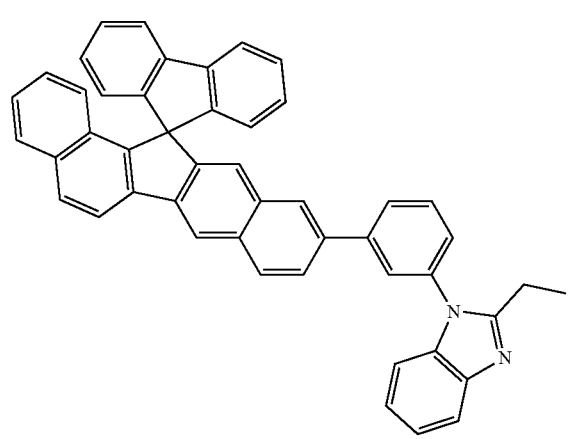 |

-continued
| 901 | 902 |
|---|---|
| 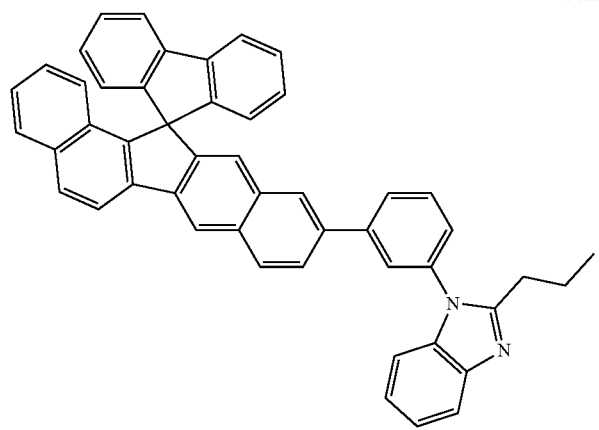 | 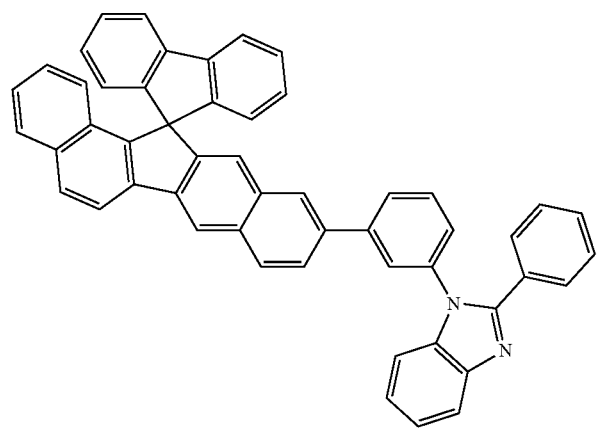 |
| 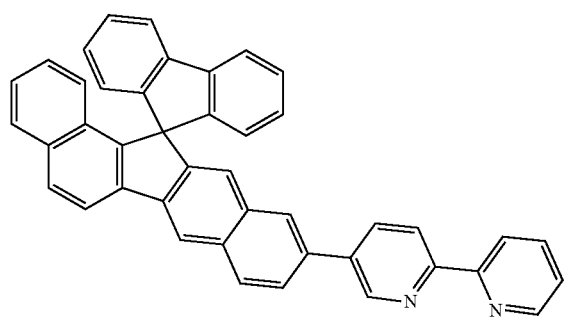 | 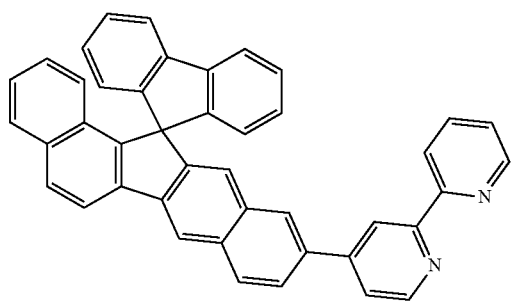 |
| 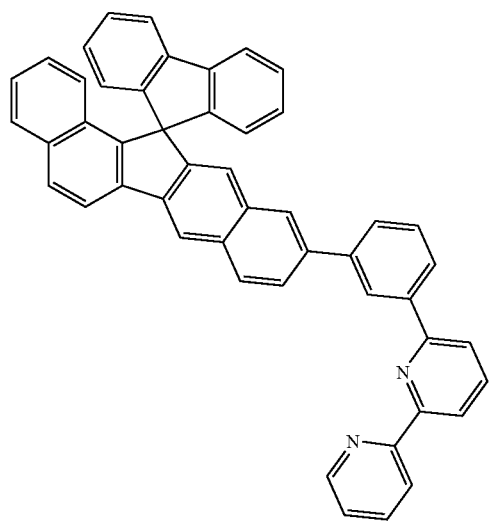 | 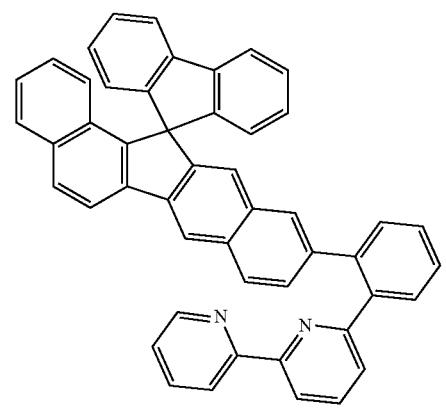 |

903
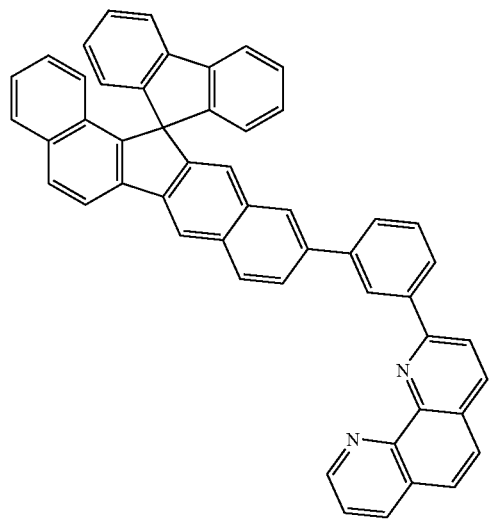
904
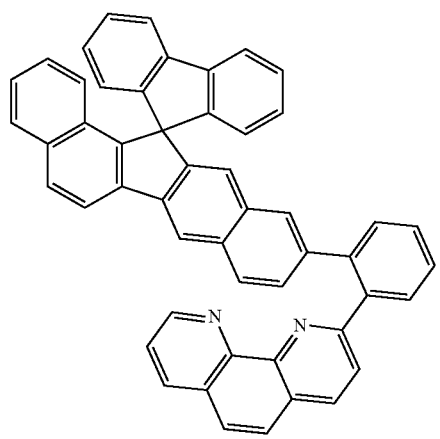
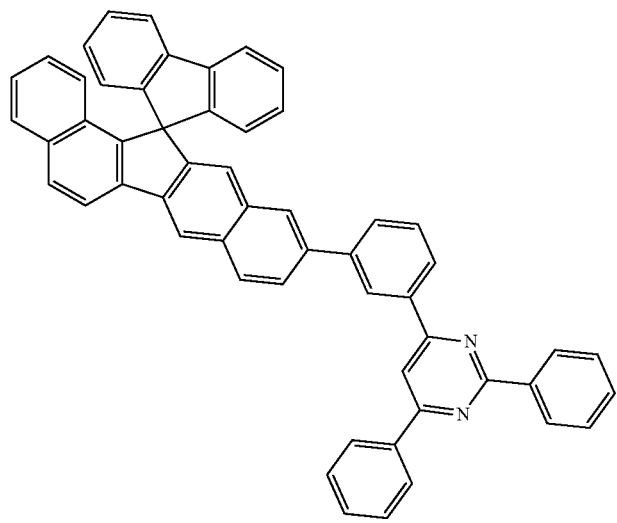
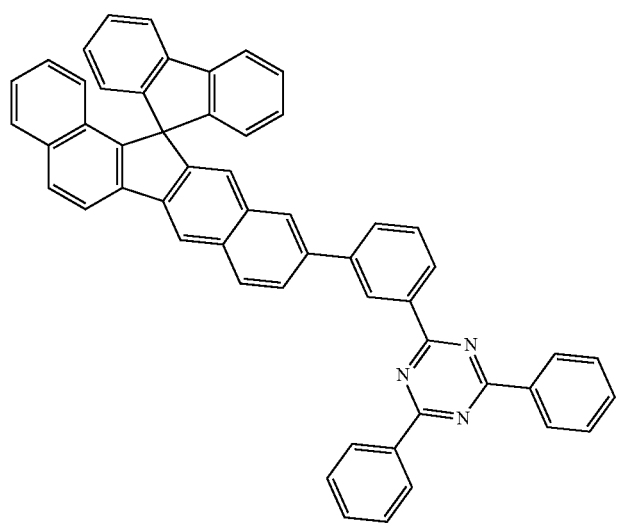

905
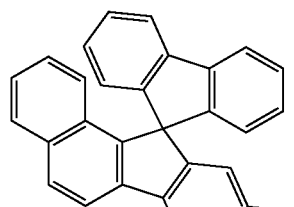
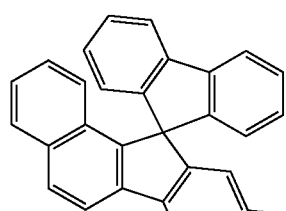
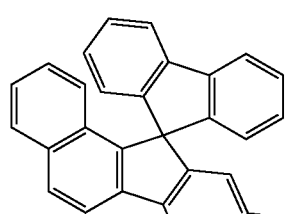
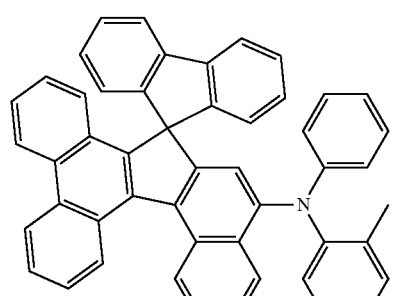
906
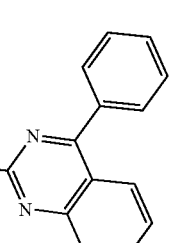
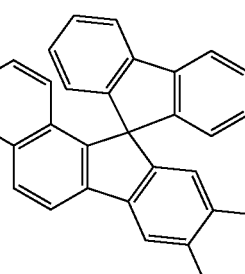
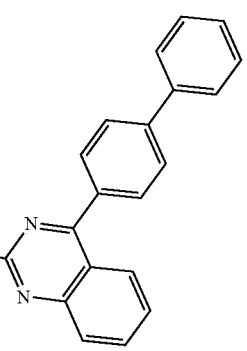
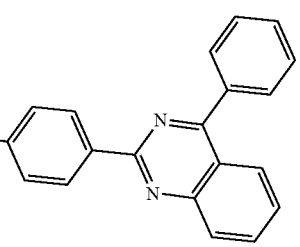
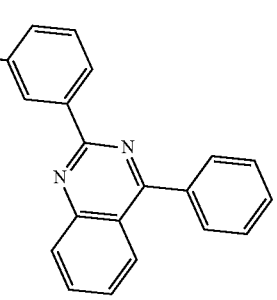
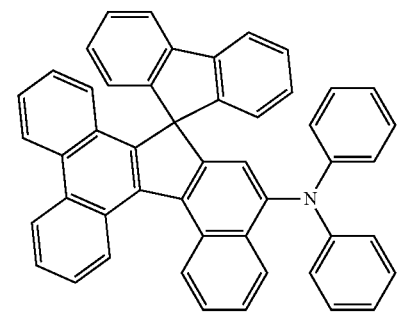
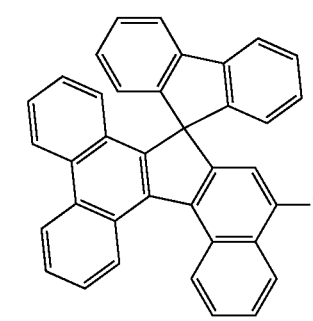
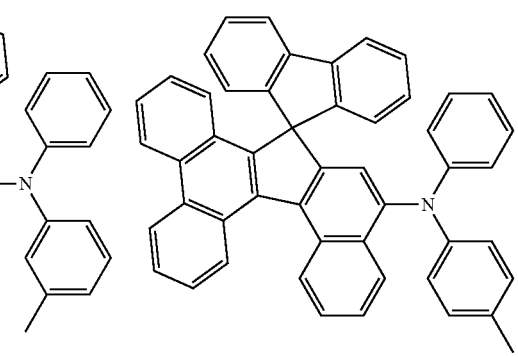

907
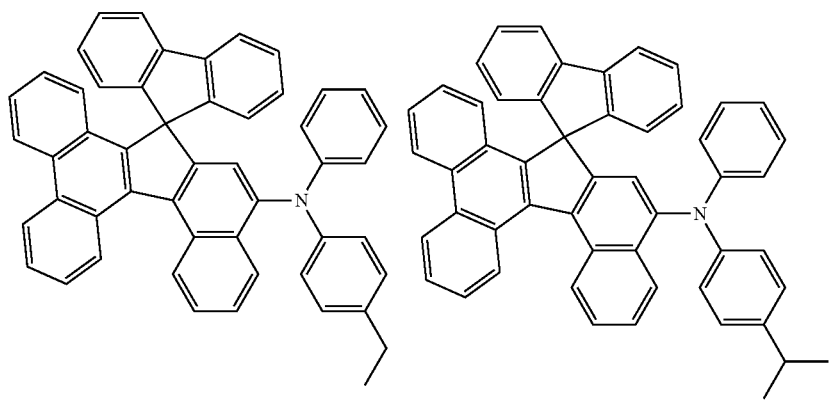
908
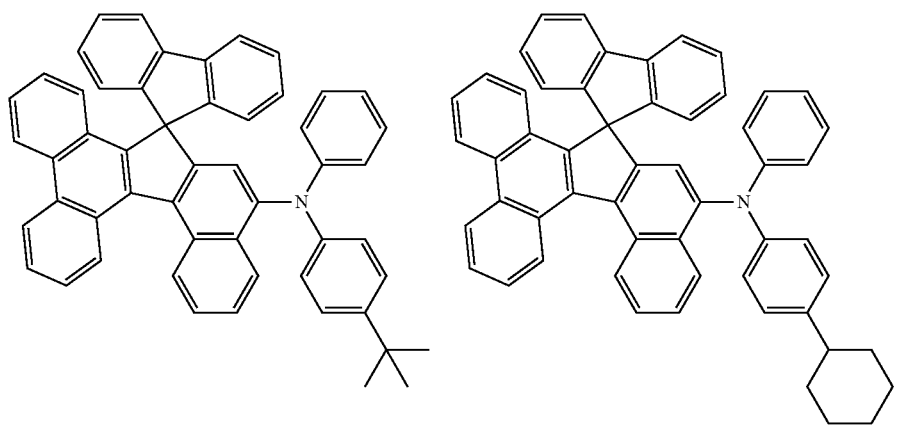
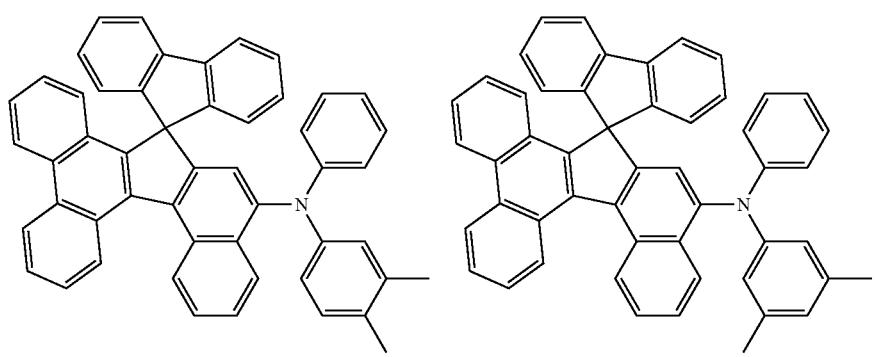
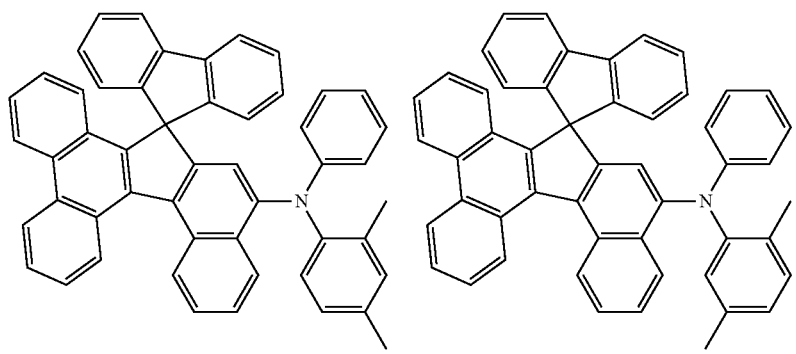

909
910
-continued
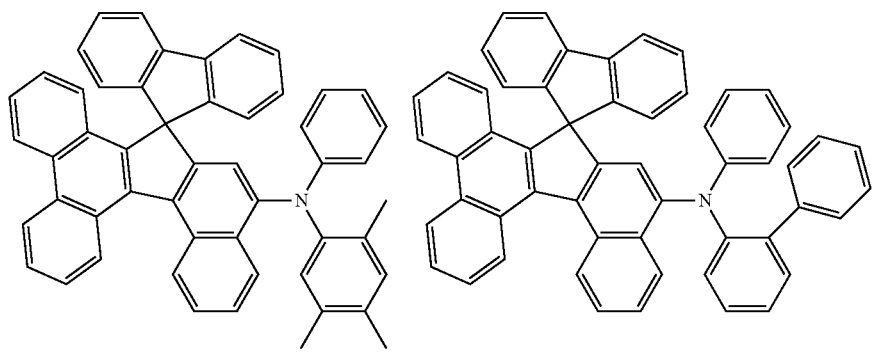
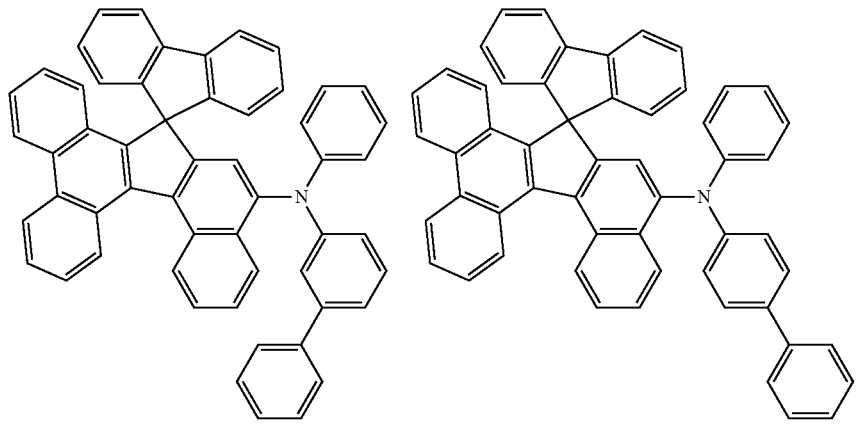
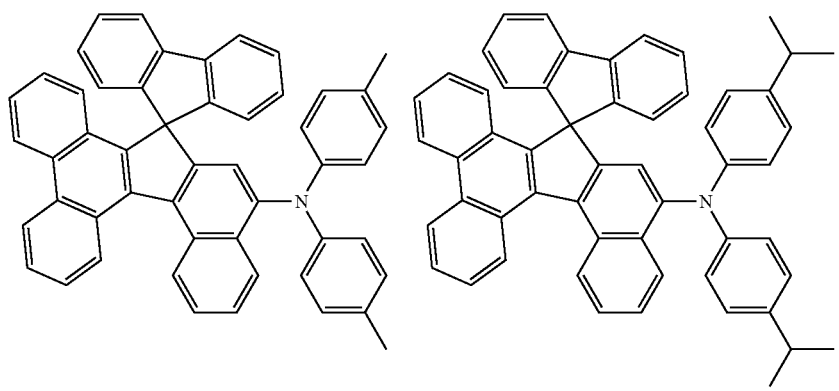
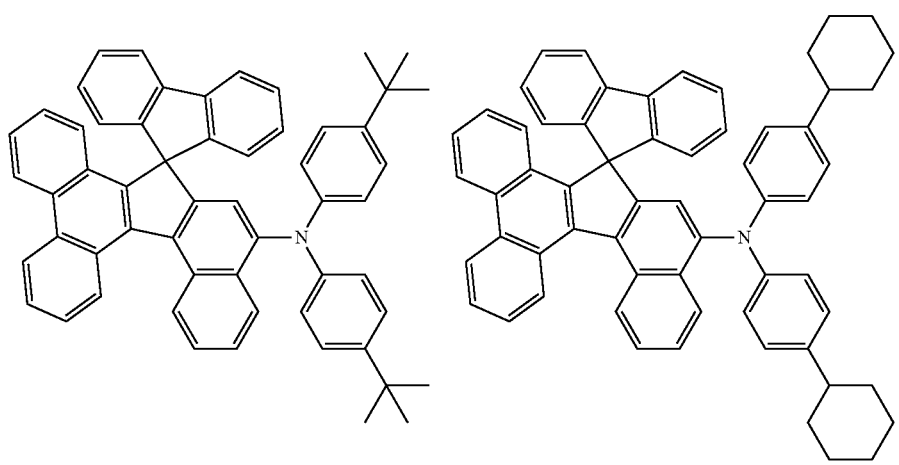

-continued
| 911 | 912 |
|---|---|
| 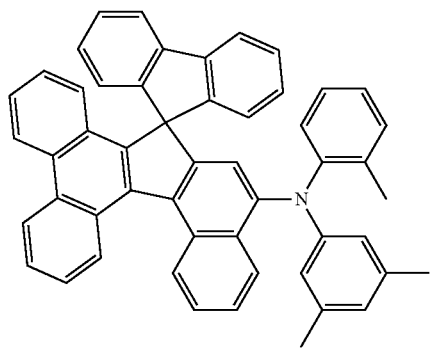 | 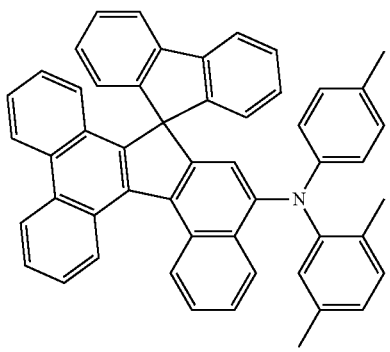 |
| 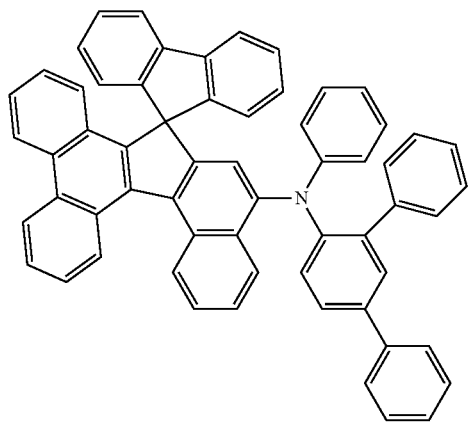 | 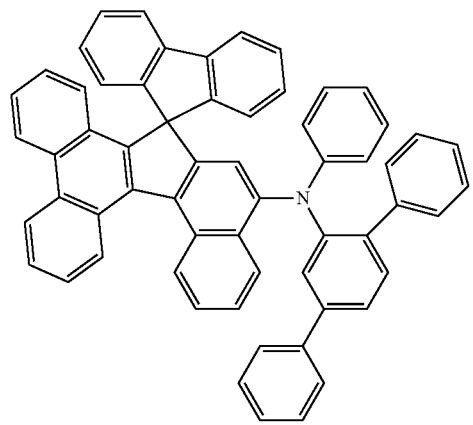 |
| 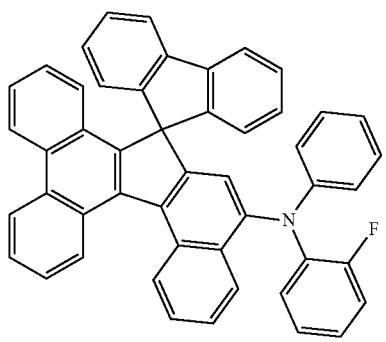 | 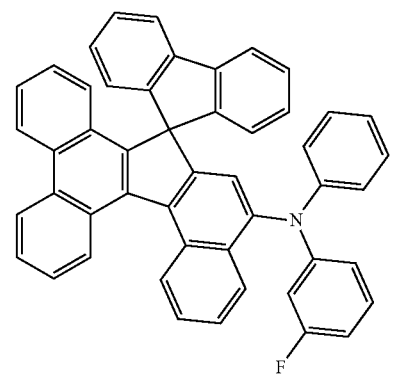 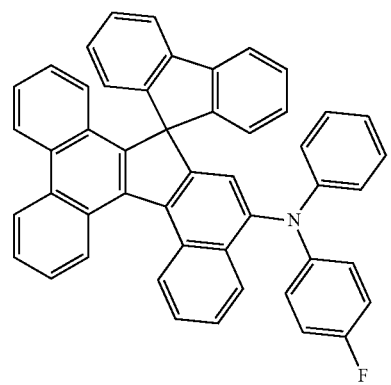 |
| 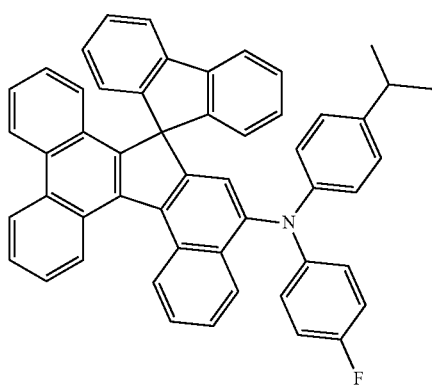 | 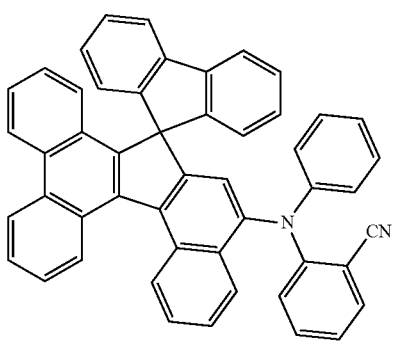 |

913
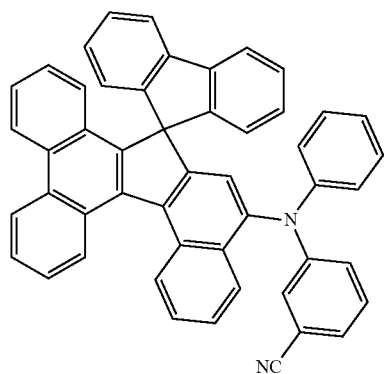
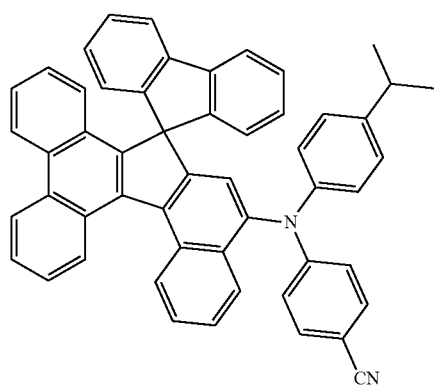
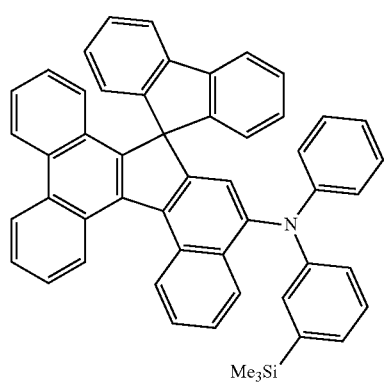
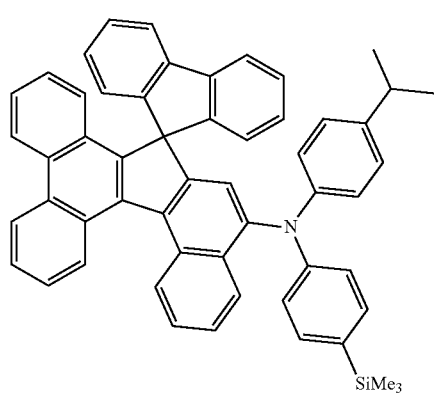
914
-continued
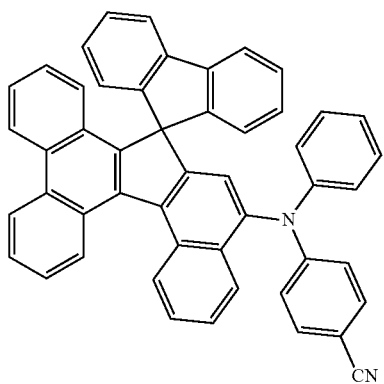
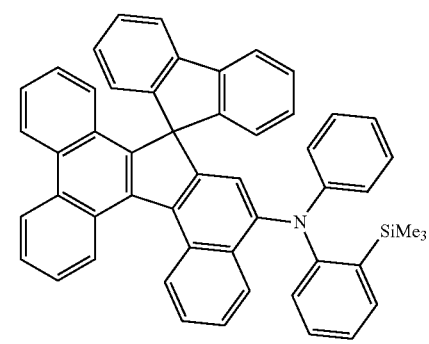
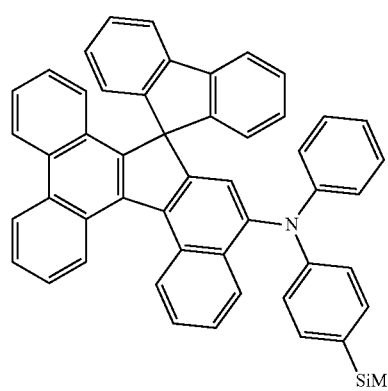
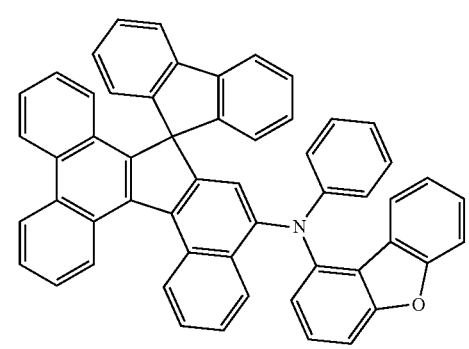

915
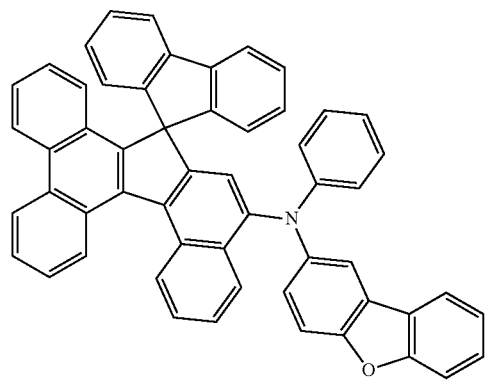
-continued
916
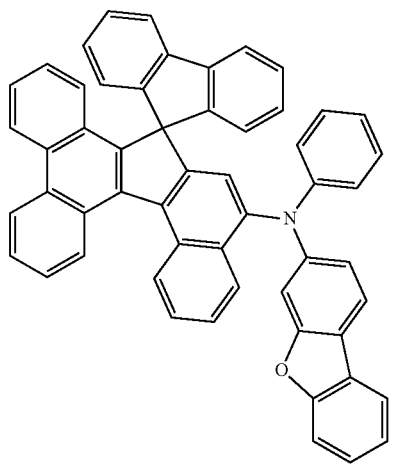
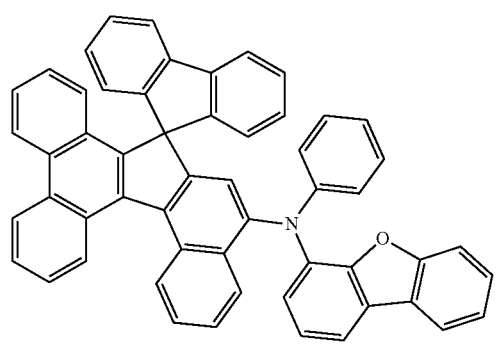
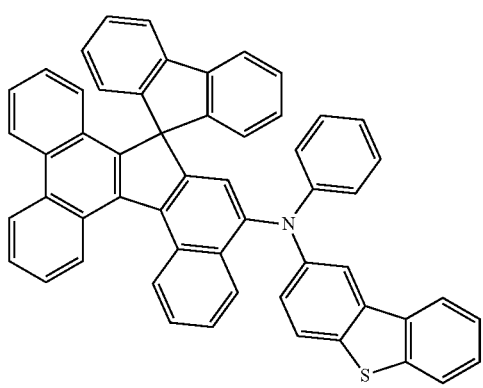
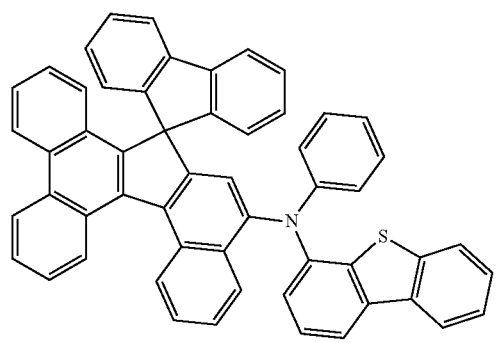
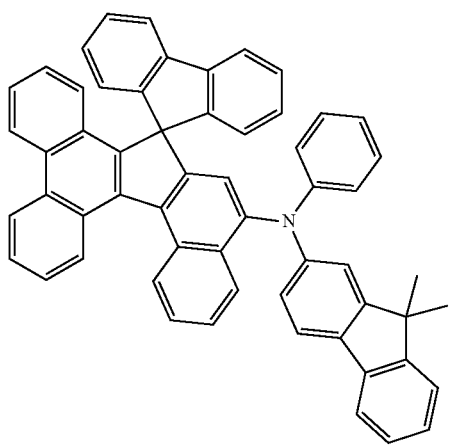

-continued
917
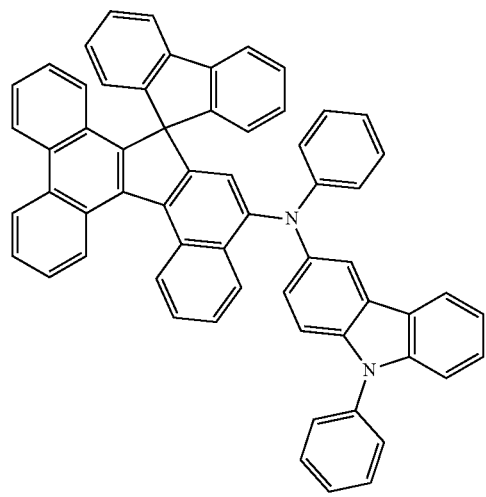
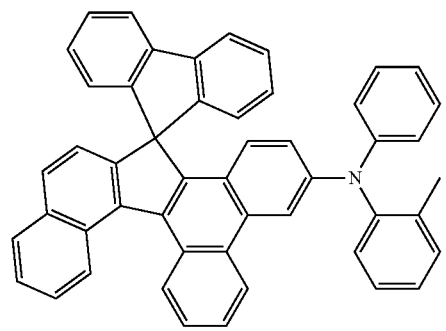
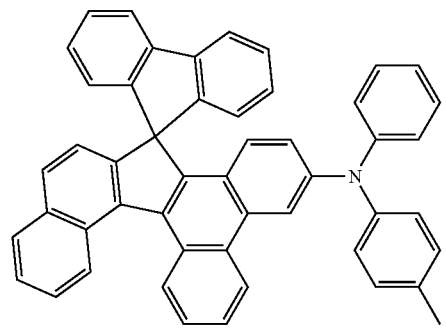
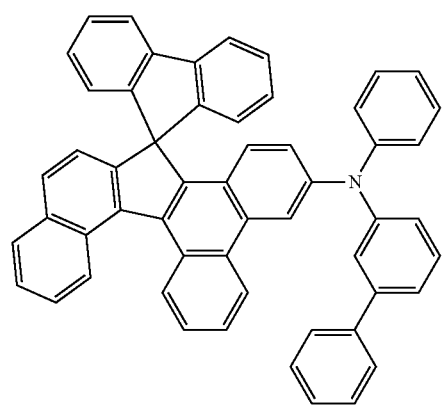
918
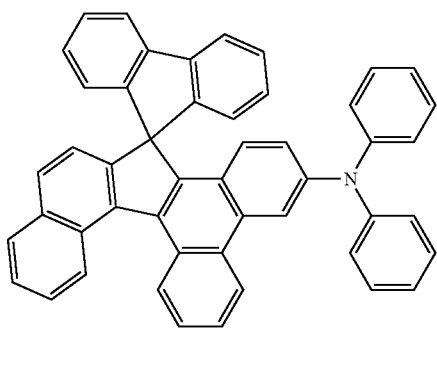
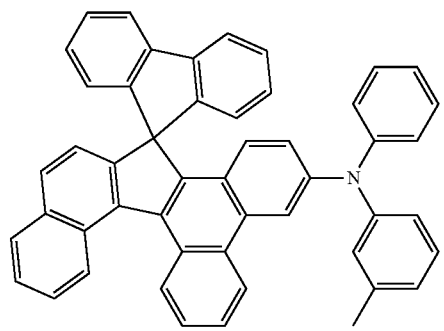
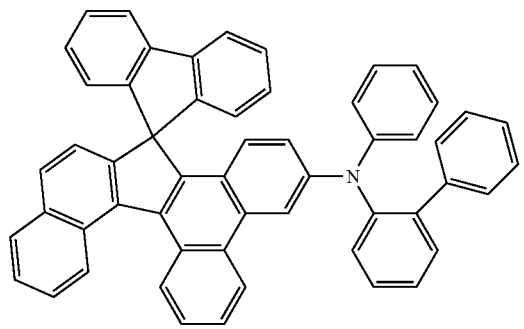
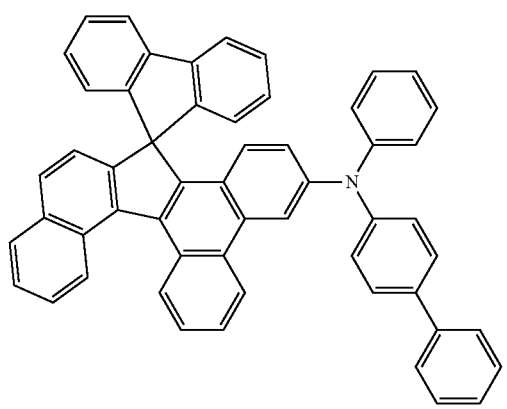

-continued
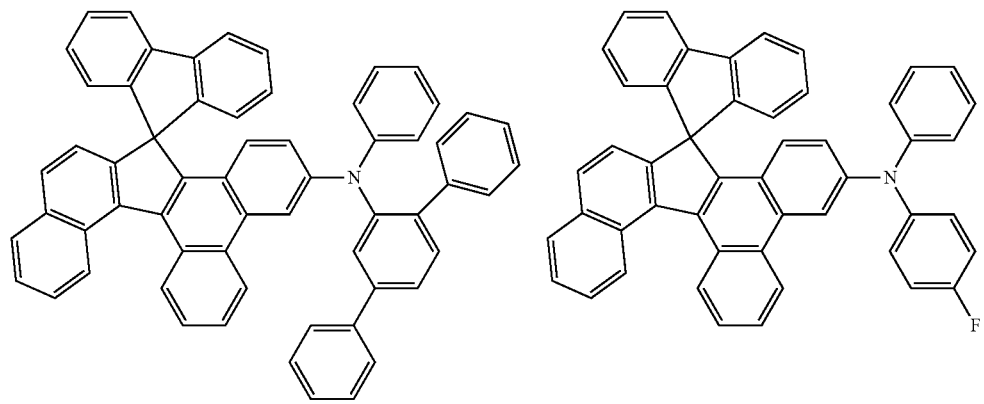
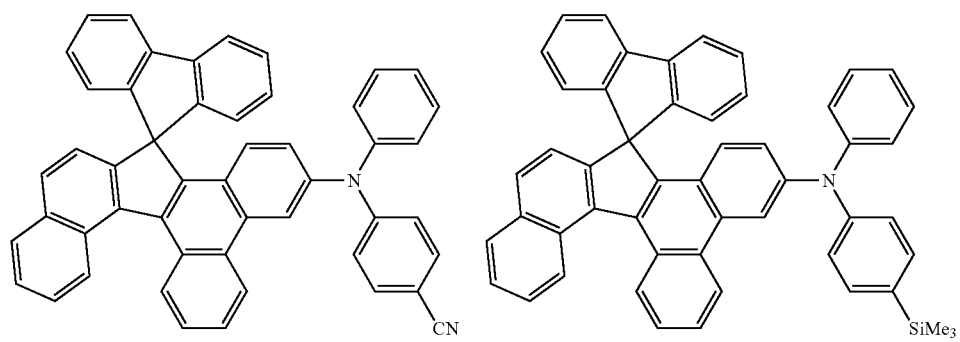
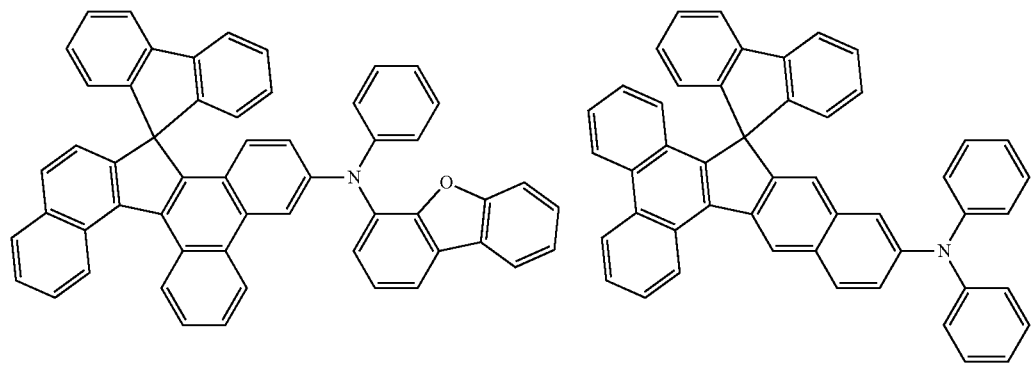
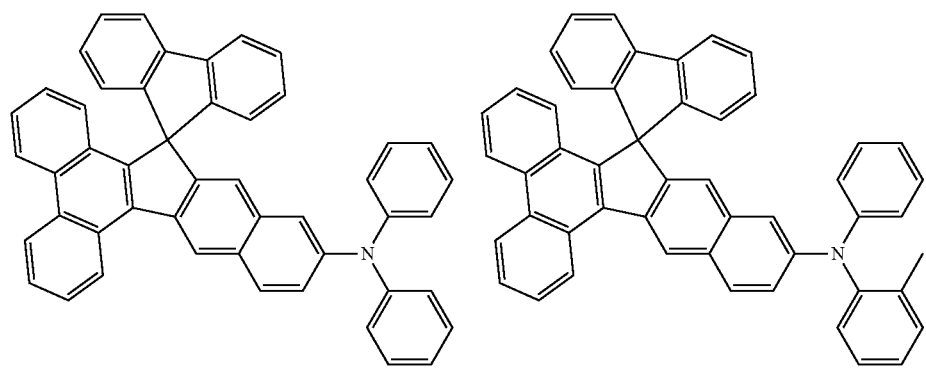

921 922
-continued
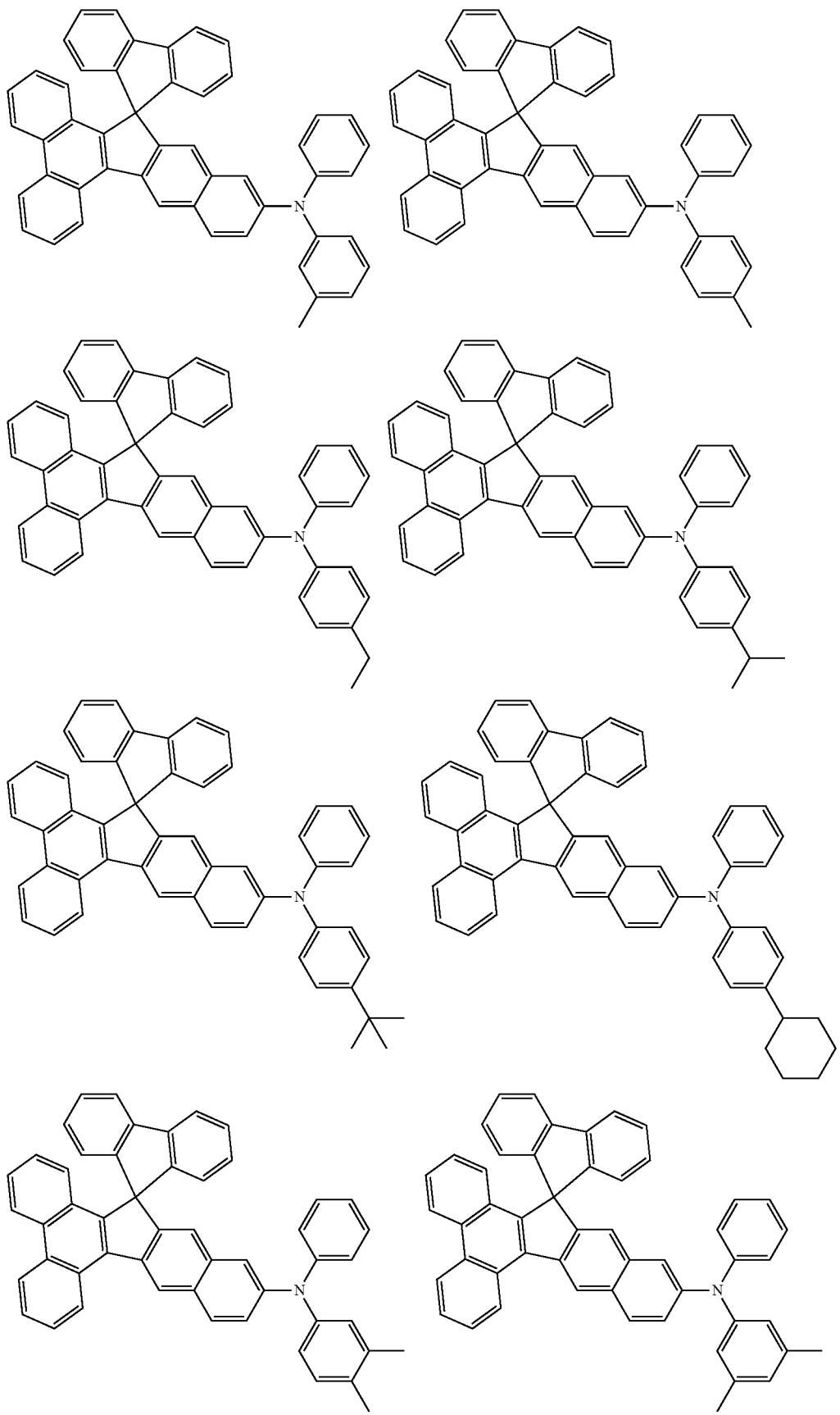

923
924
-continued
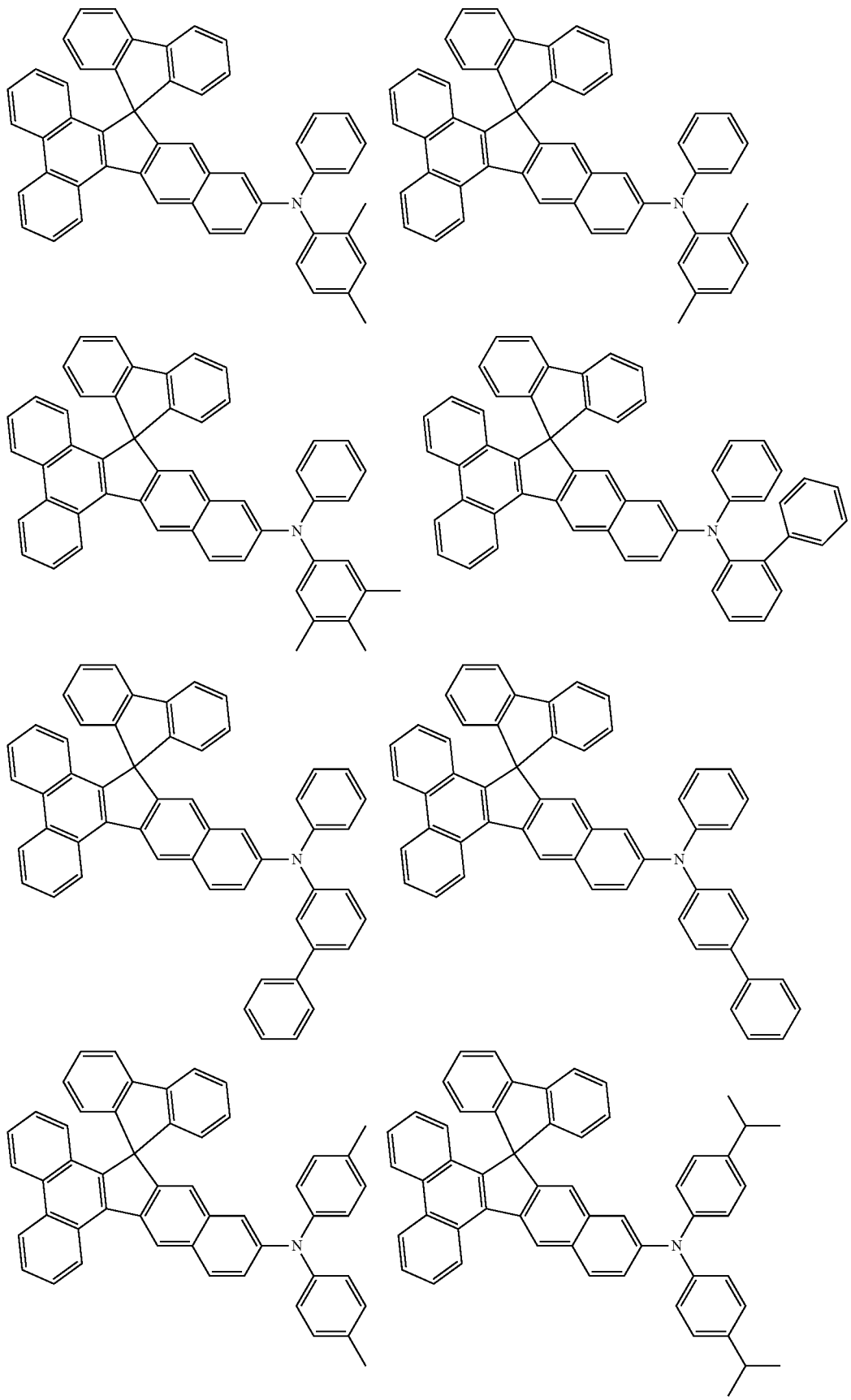

925
-continued
926
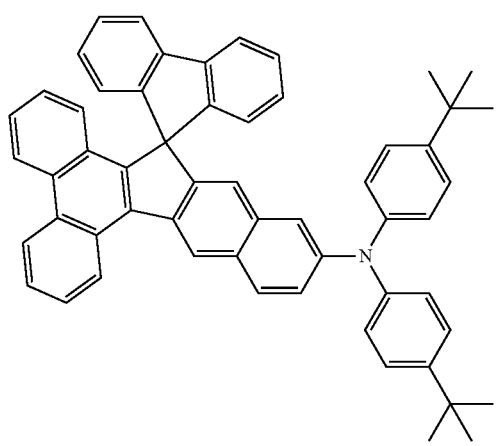
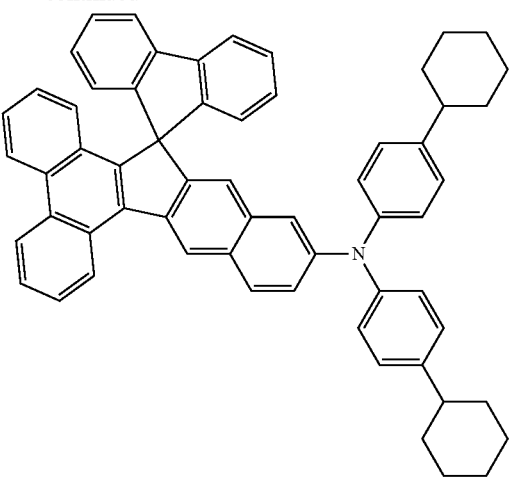
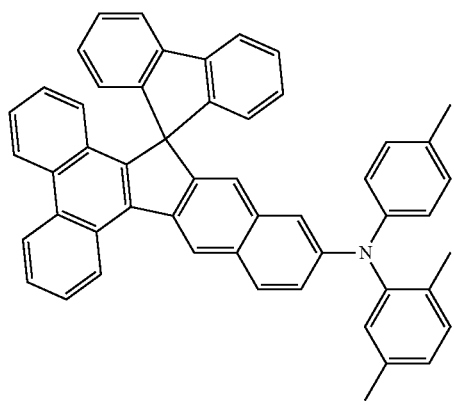
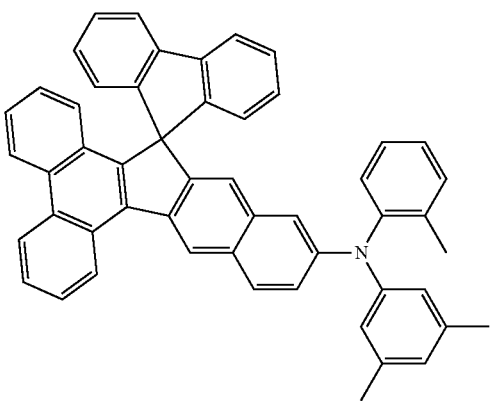
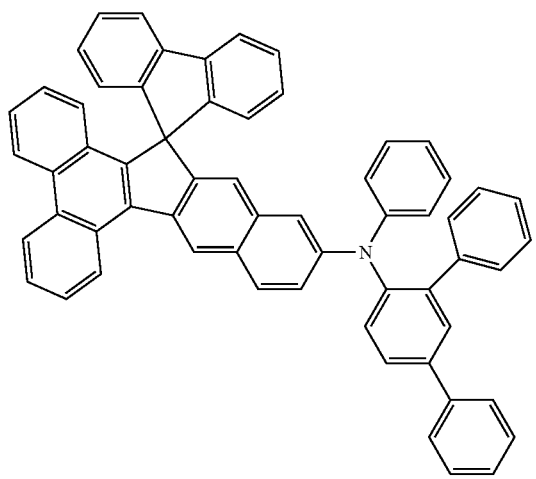
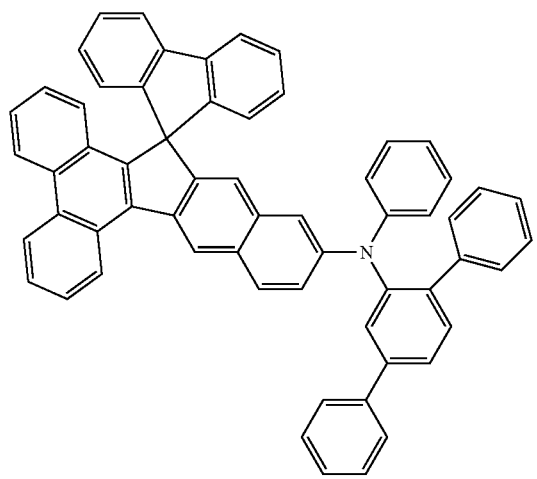

-continued
| 927 | 928 |
|---|---|
| 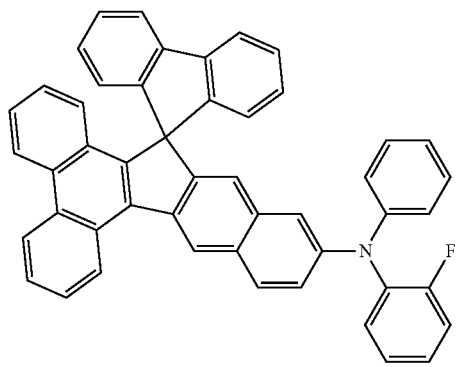 | 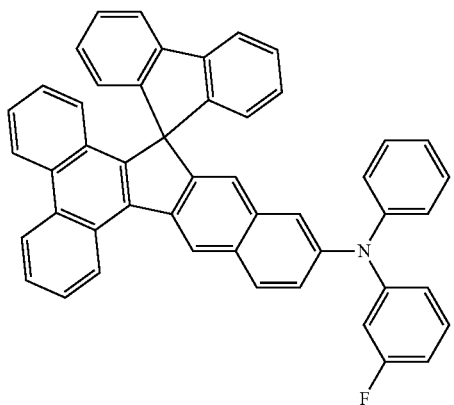 |
| 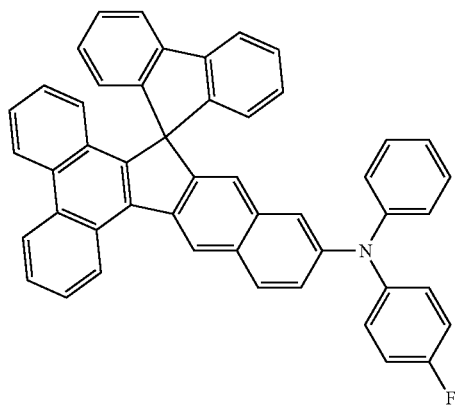 | 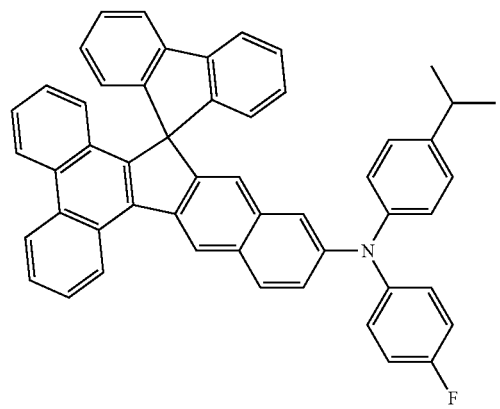 |
| 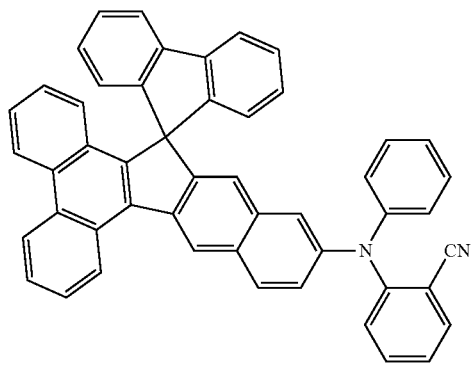 | 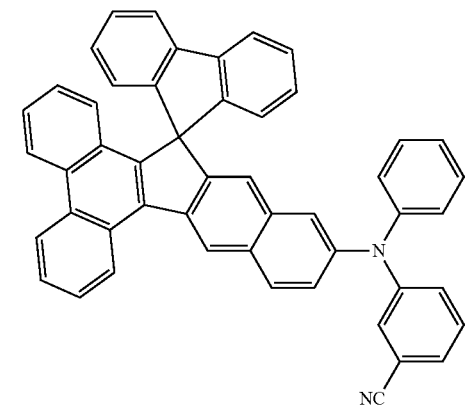 |
| 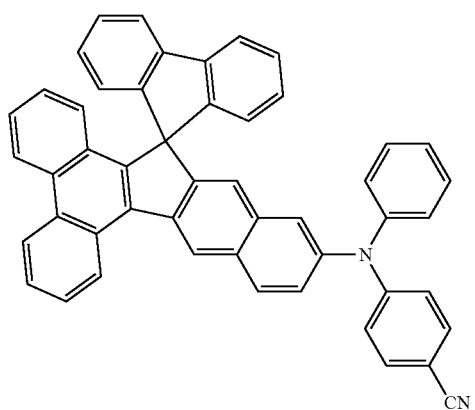 | 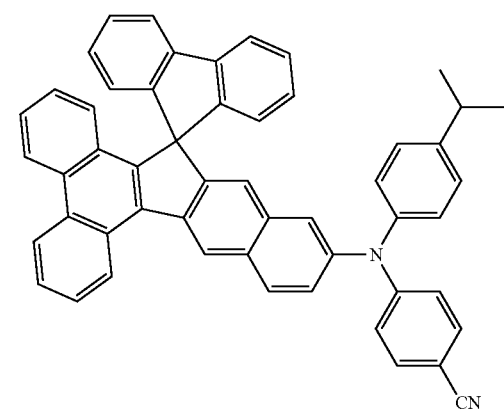 |

-continued
929
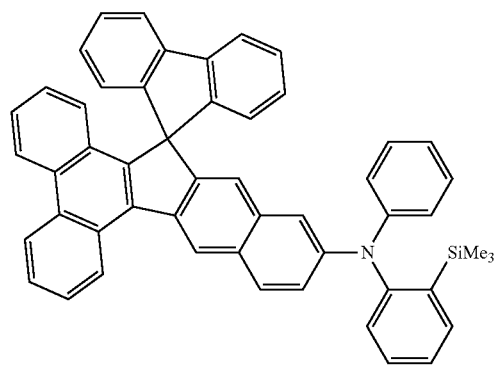
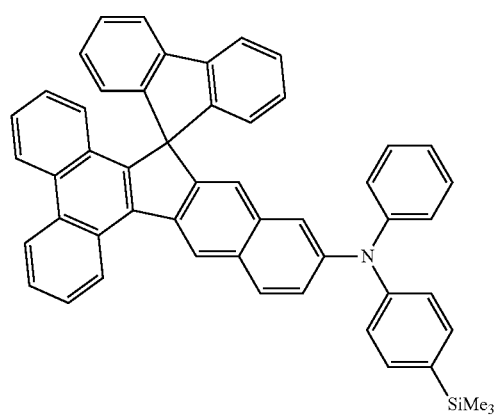
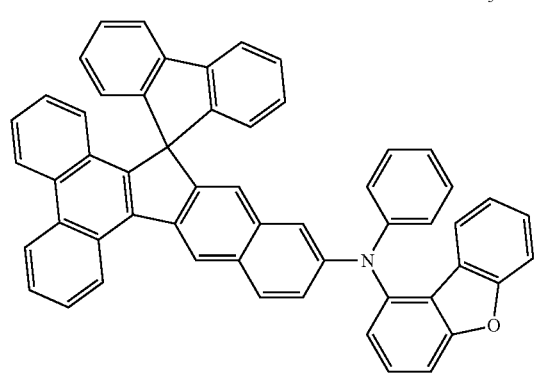
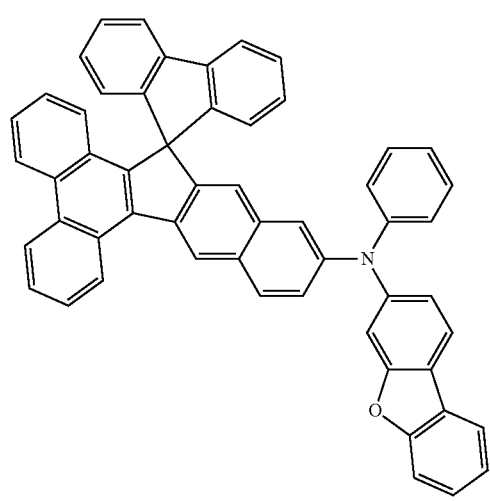
930
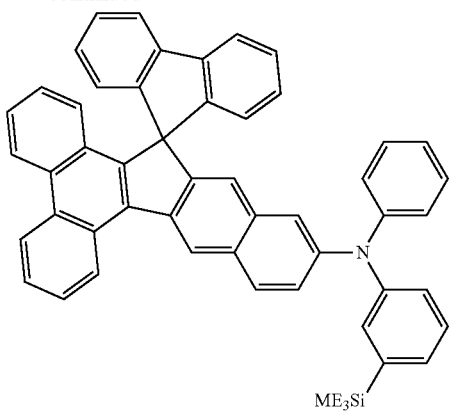
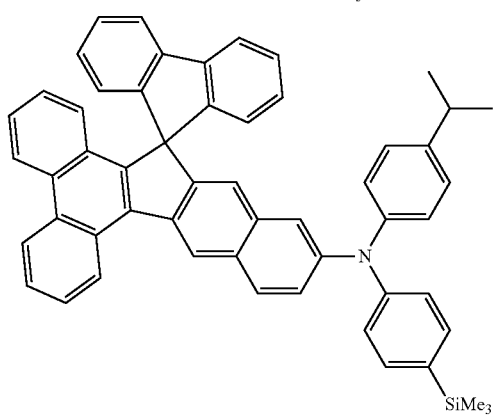
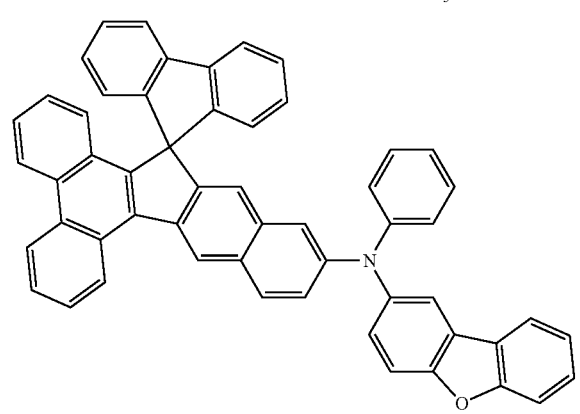
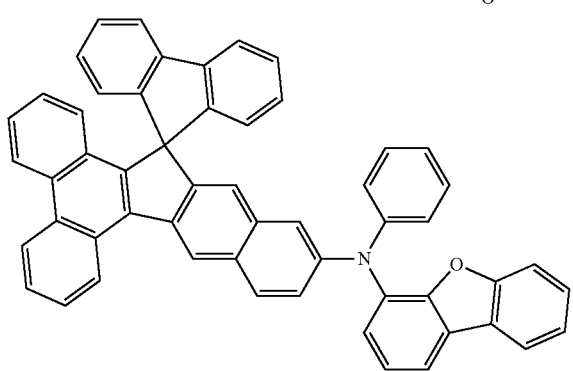

-continued
| 931 | 932 |
|---|---|
| 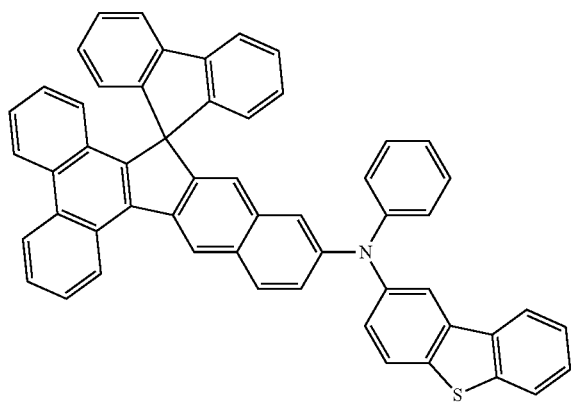 | 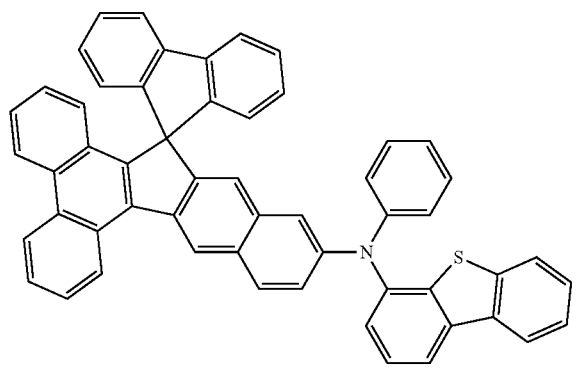 |
| 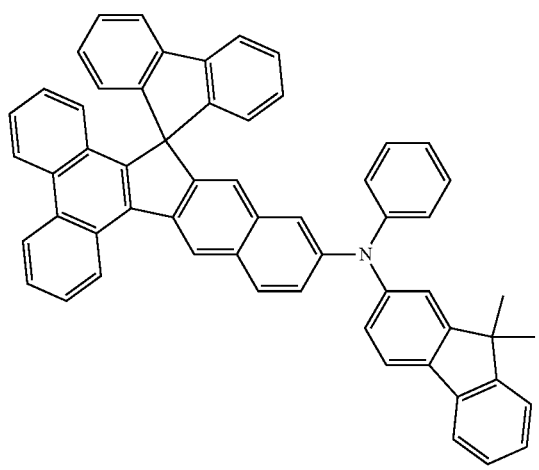 | 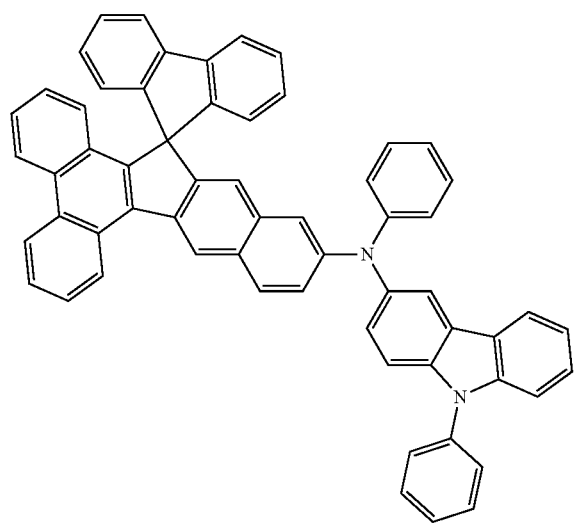 |
| 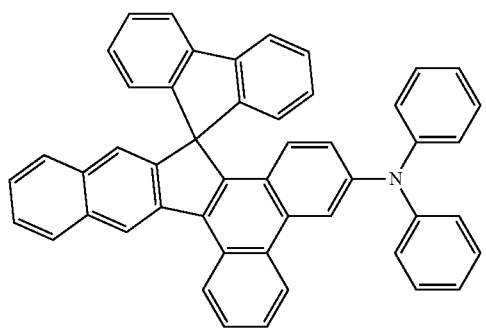 | 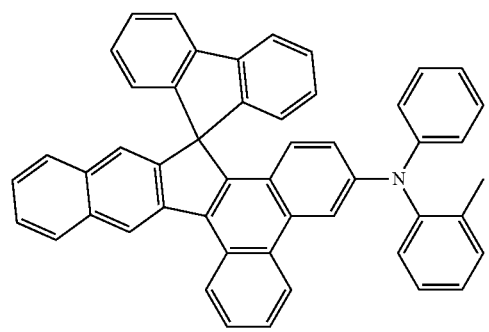 |
| 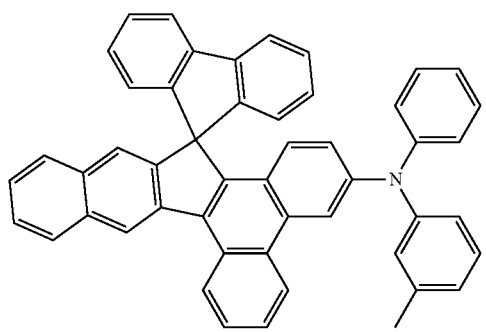 | 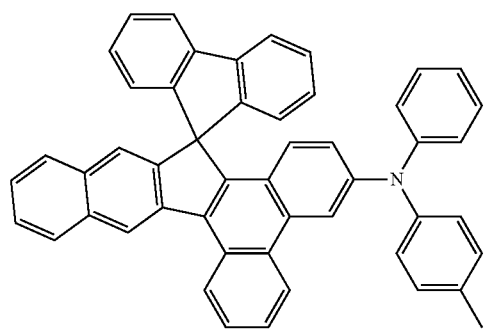 |

-continued
| 933 | 934 |
|---|---|
| 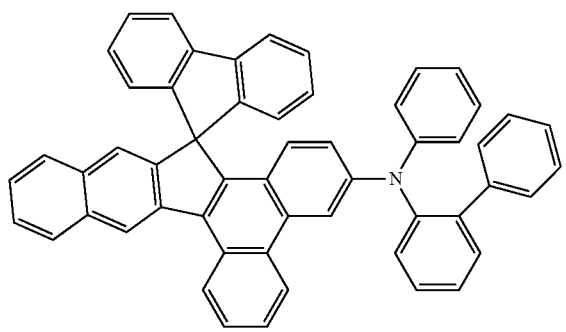 | 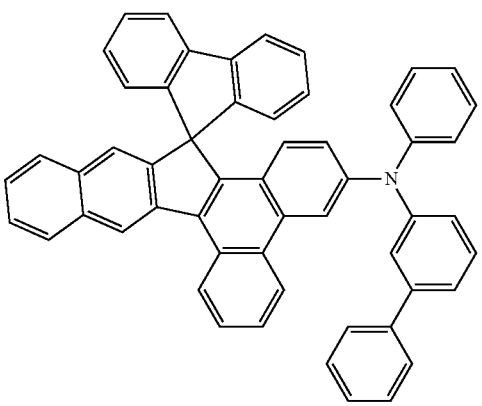 |
| 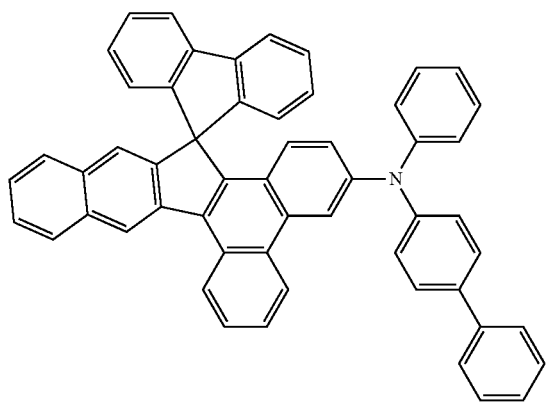 | 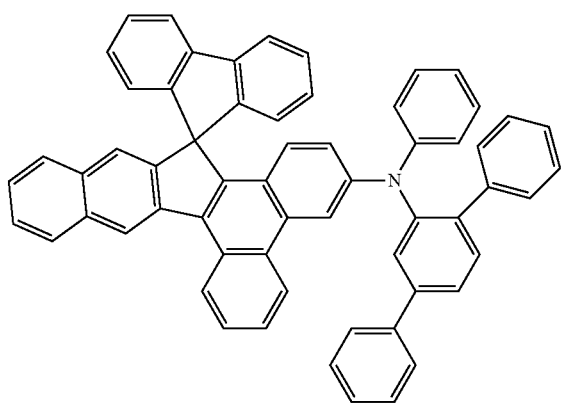 |
| 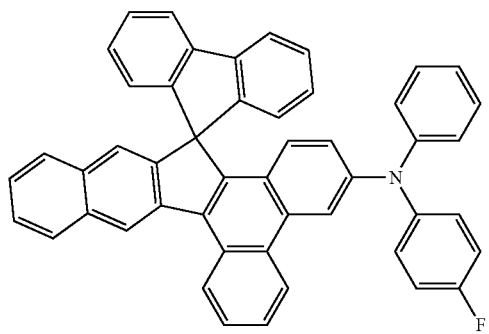 | 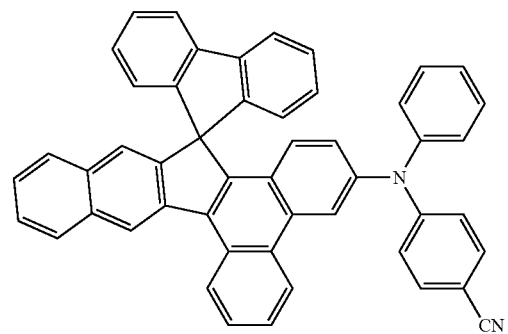 |
| 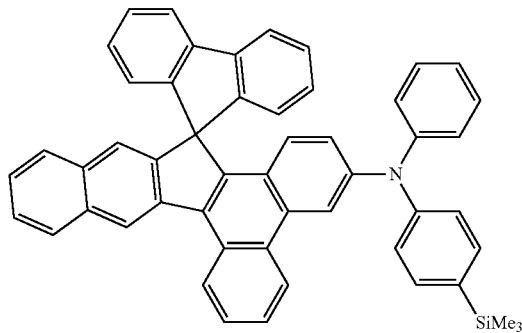 | 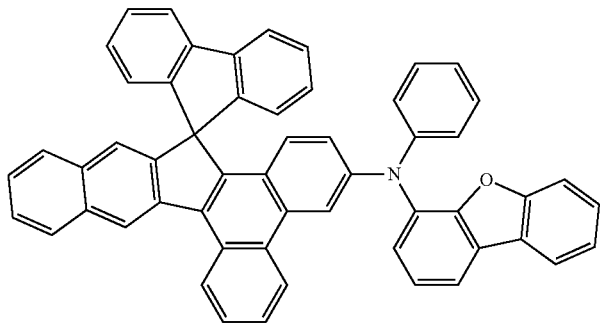 |

935 936
-continued
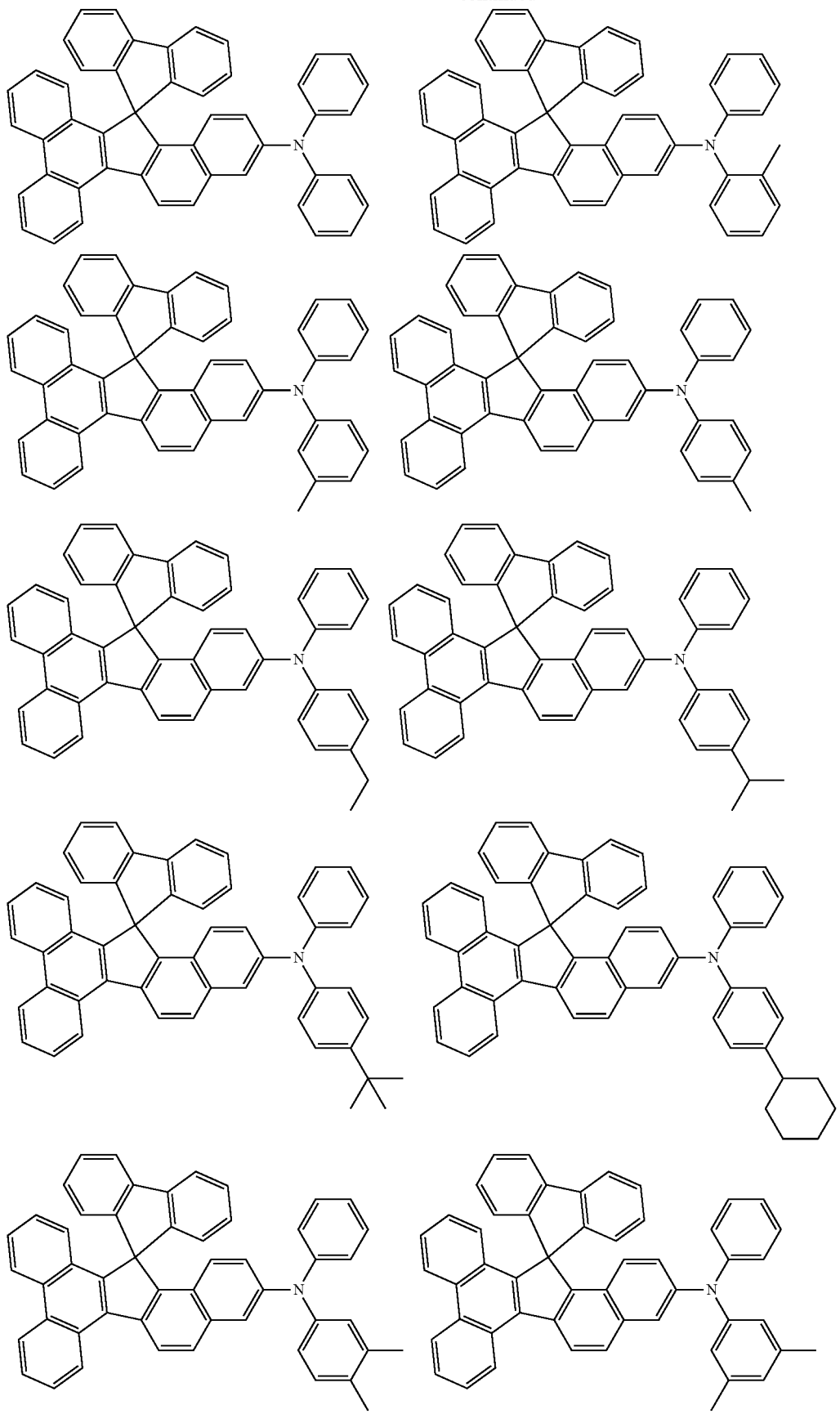

-continued
937
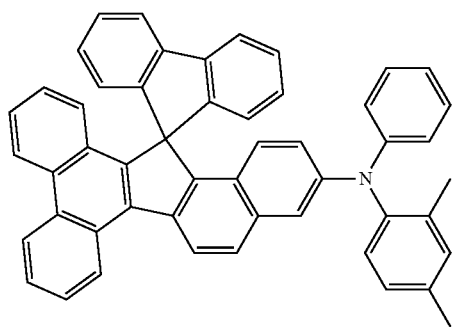
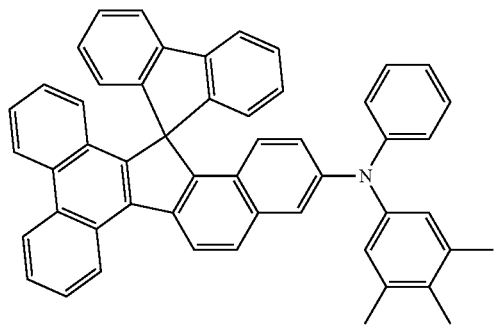
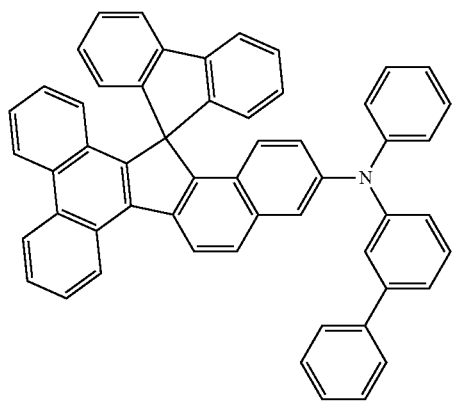
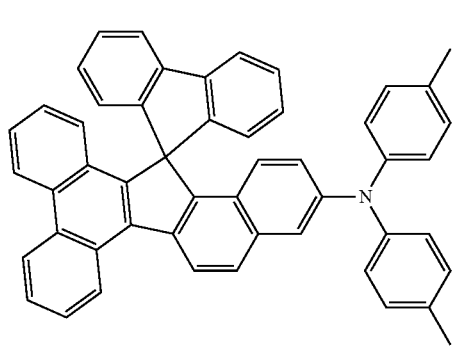
938
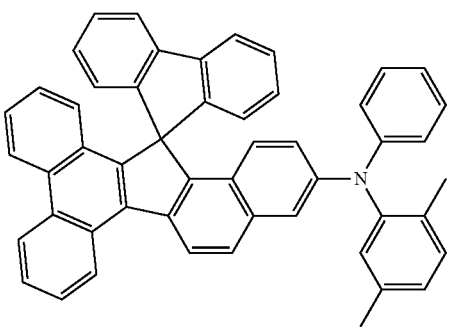
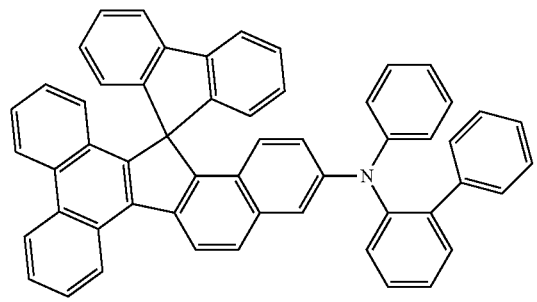
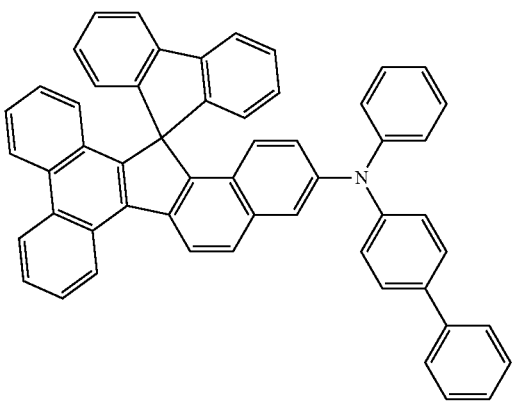
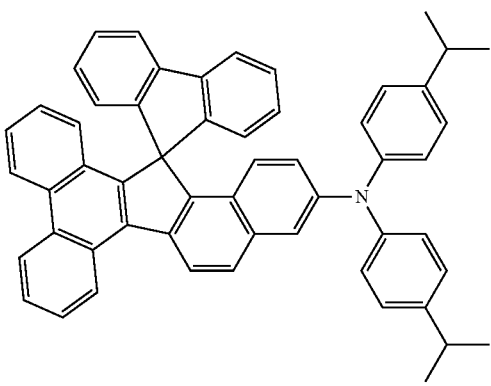

-continued
939
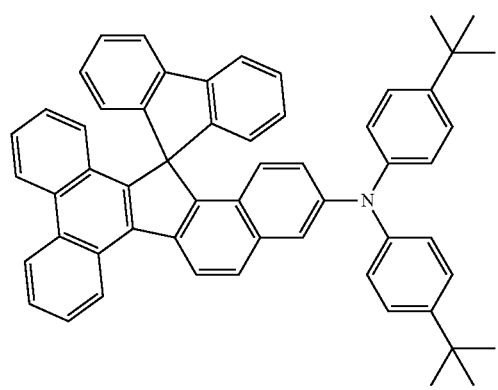
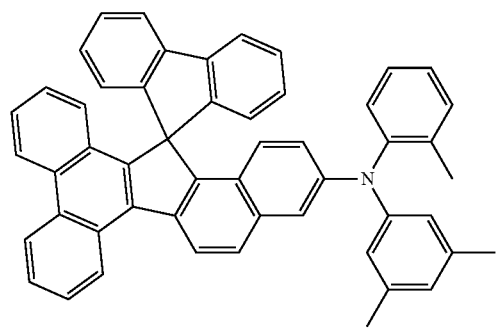
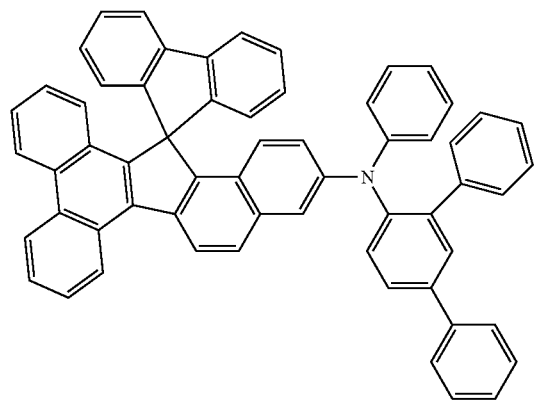
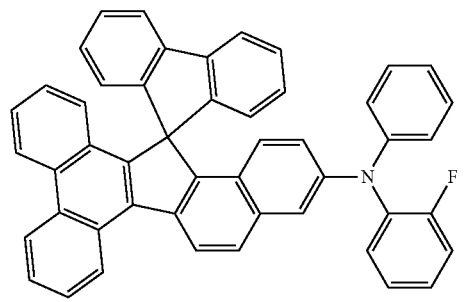
940
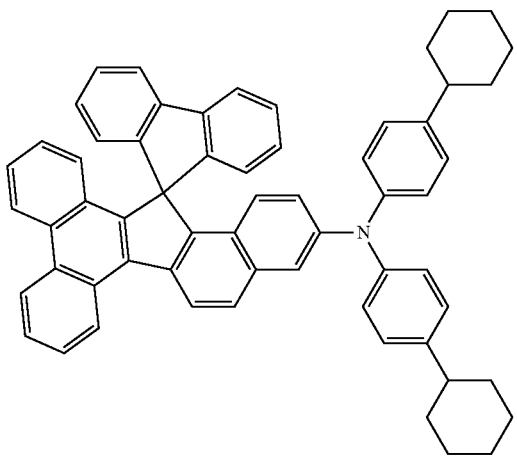
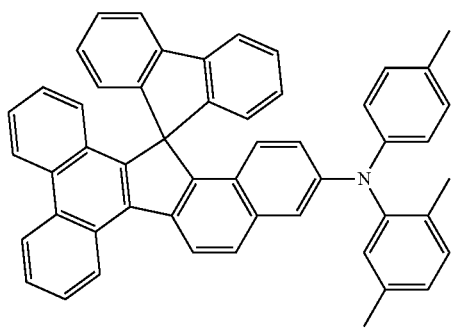
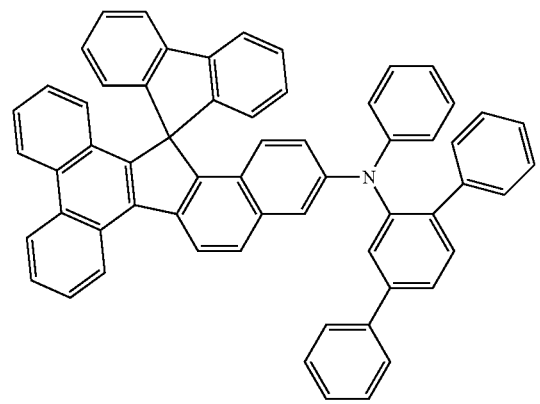
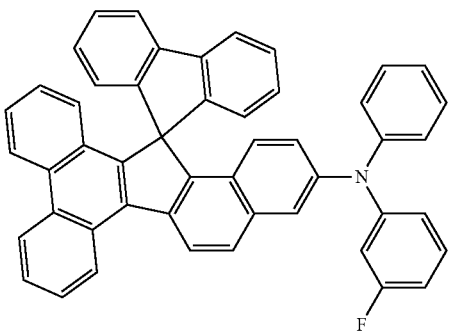

-continued
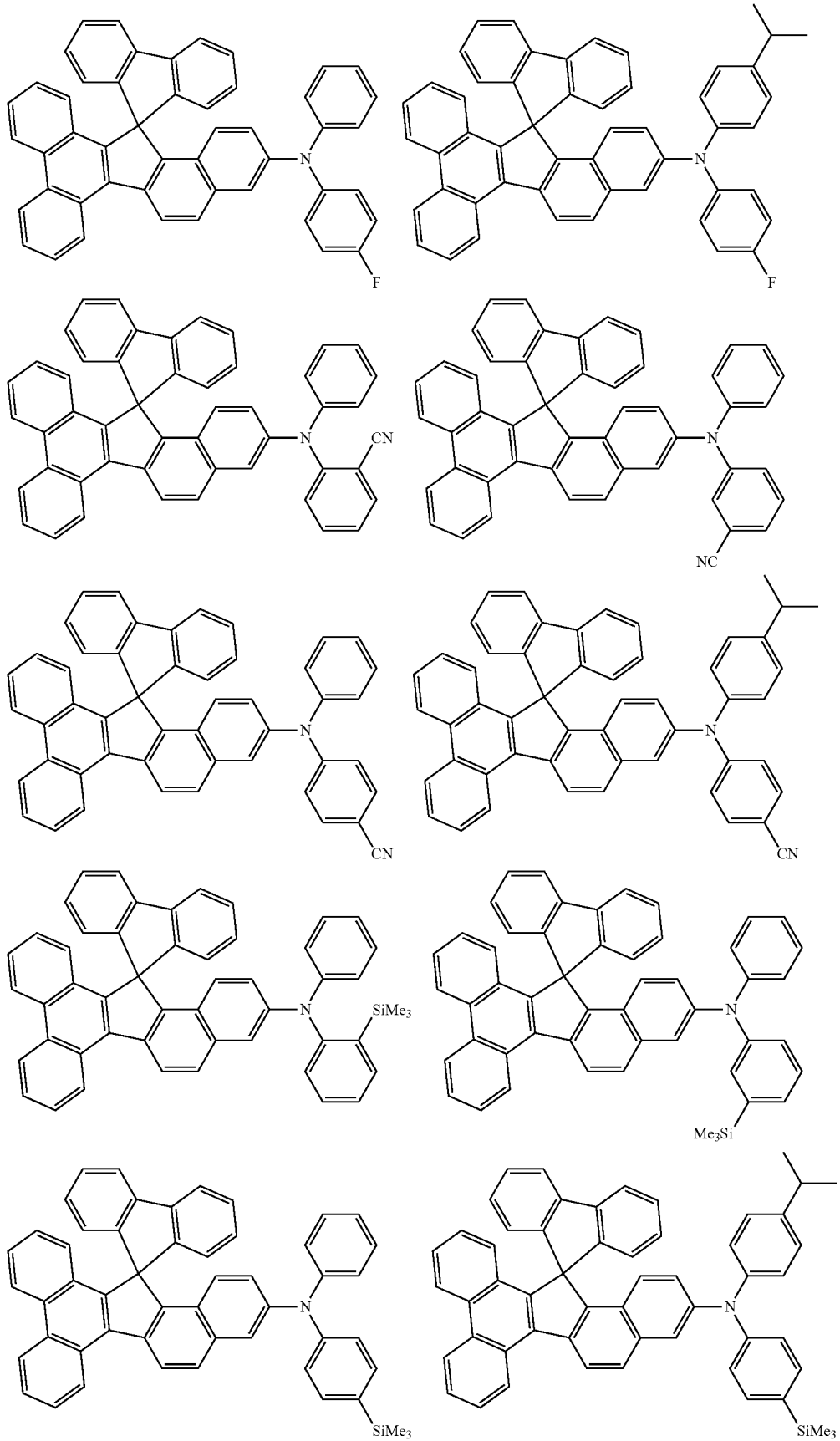

-continued
| 943 | 944 |
|---|---|
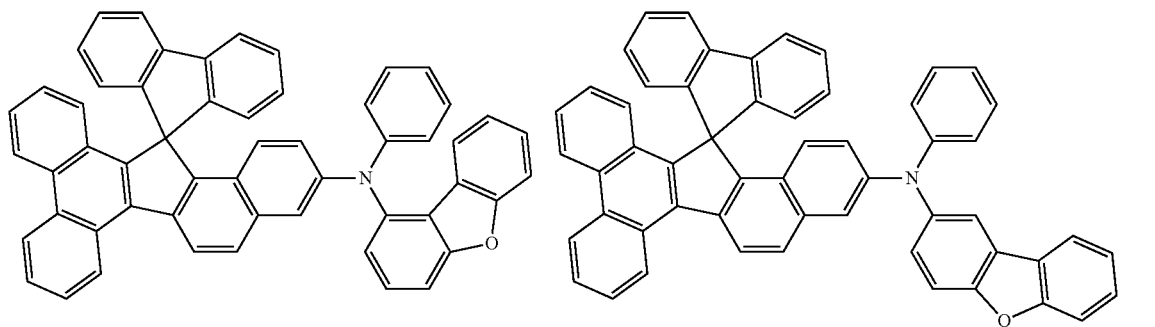
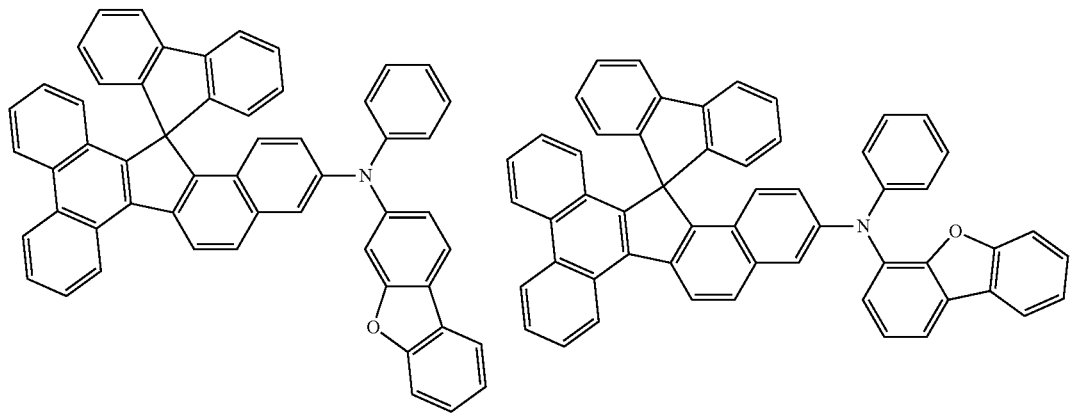
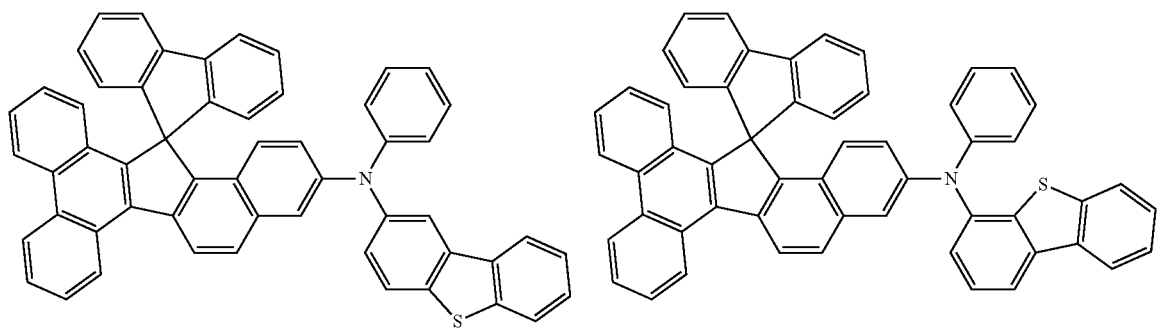
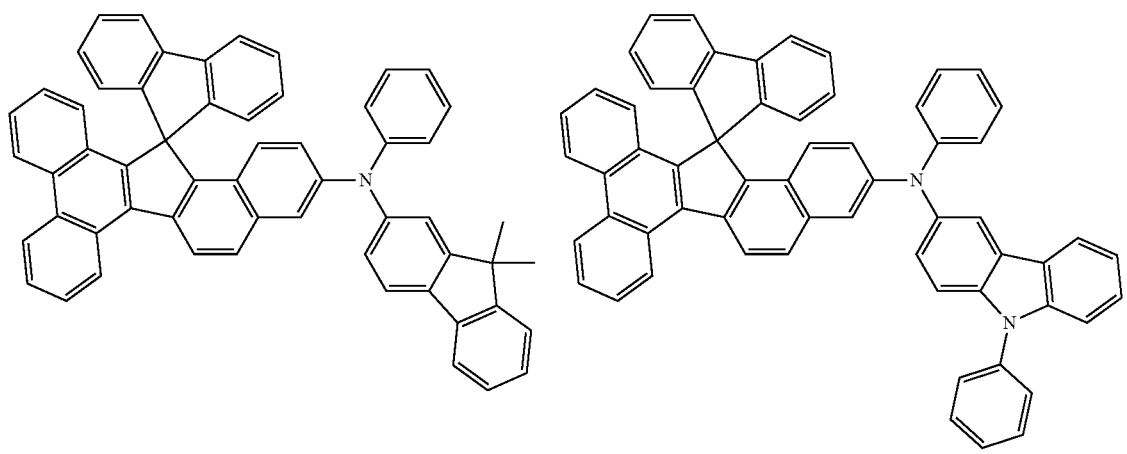

945
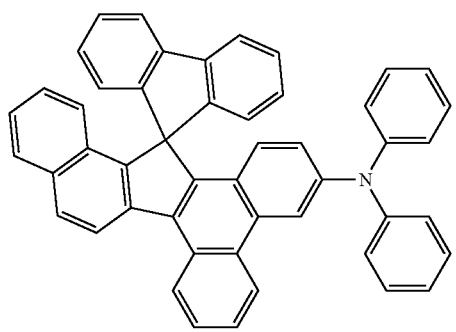
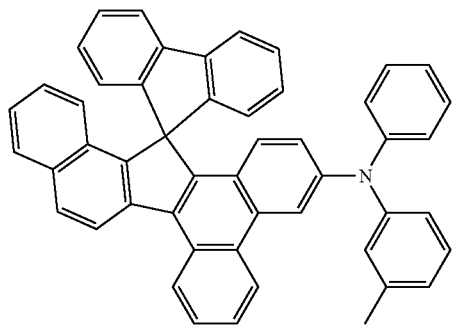
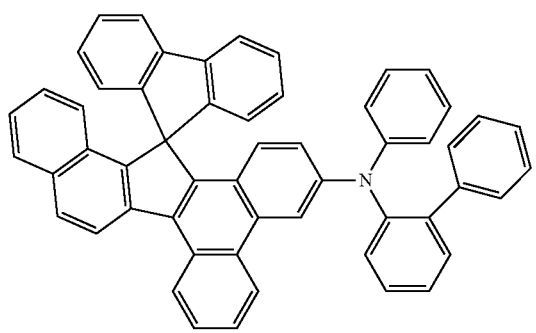
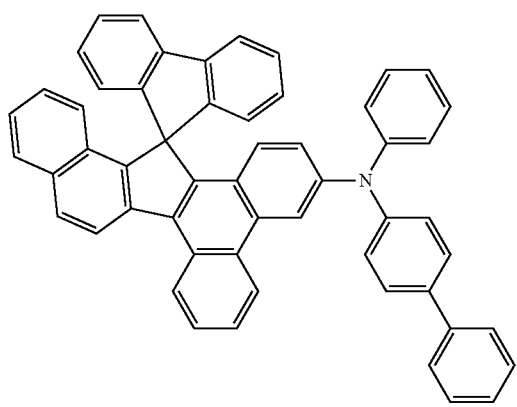
946
-continued
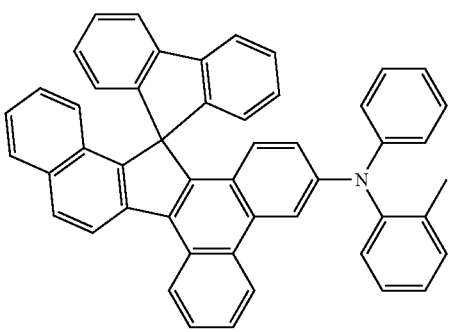
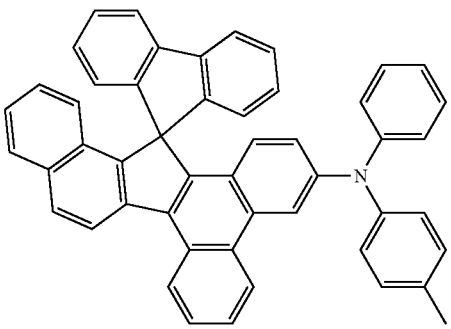
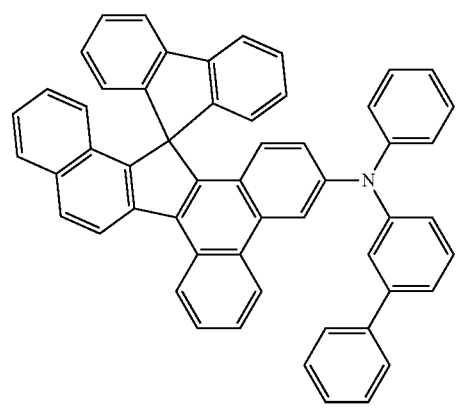
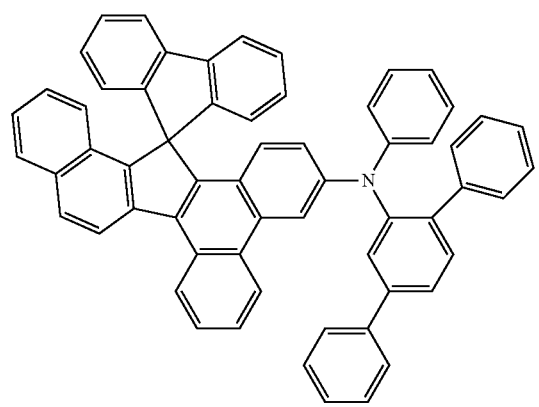

-continued
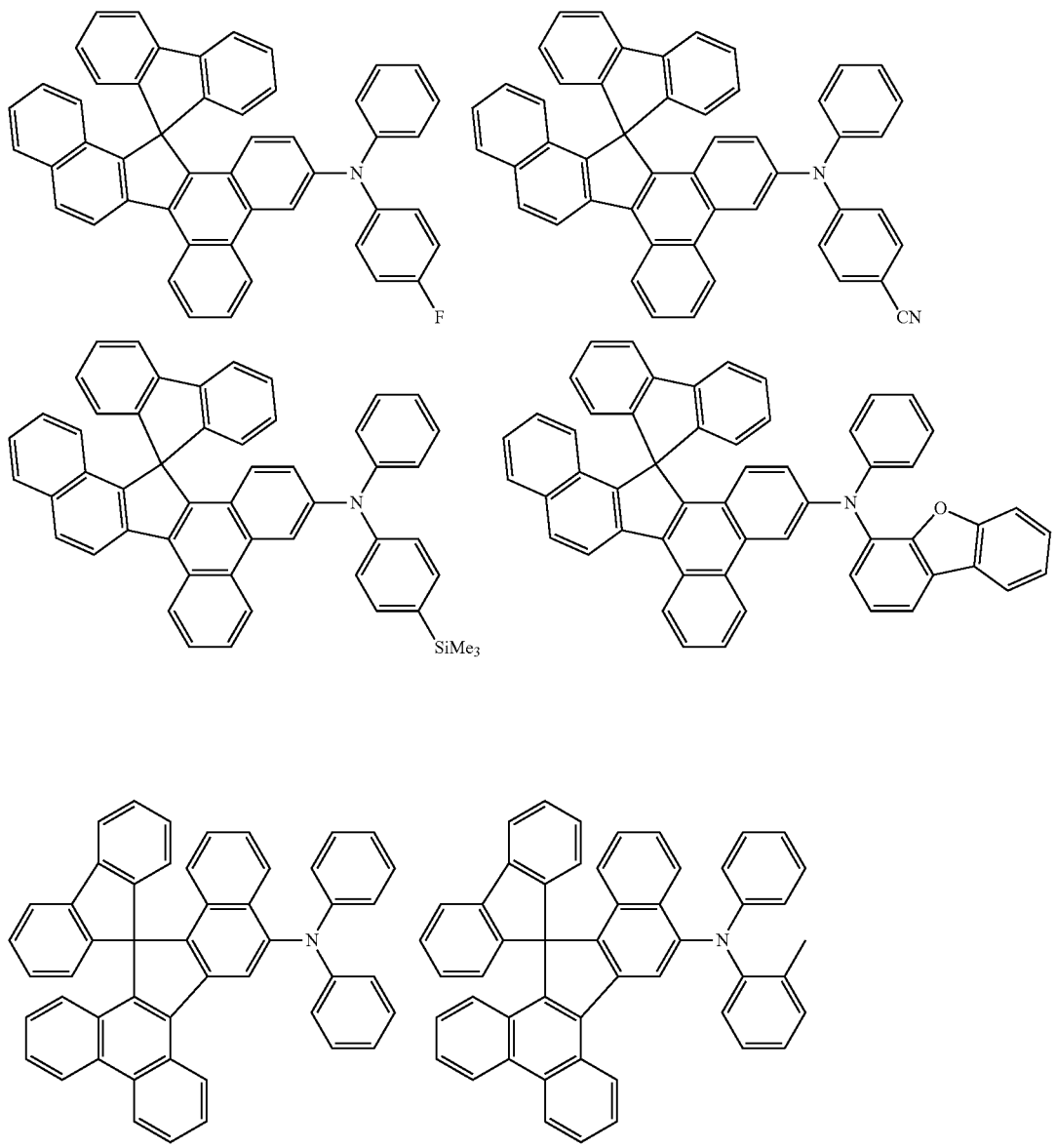
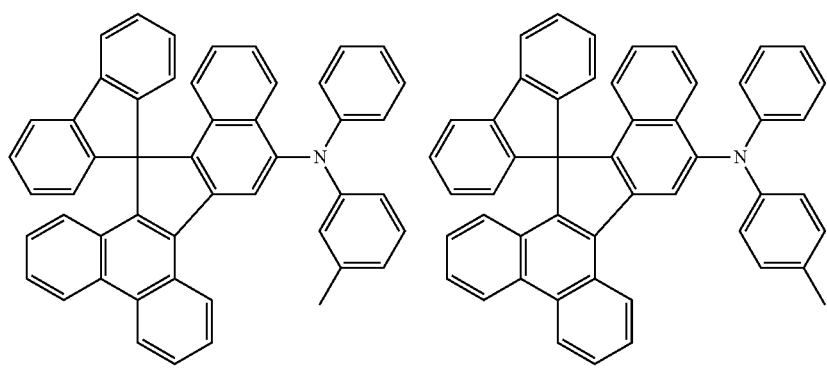

-continued
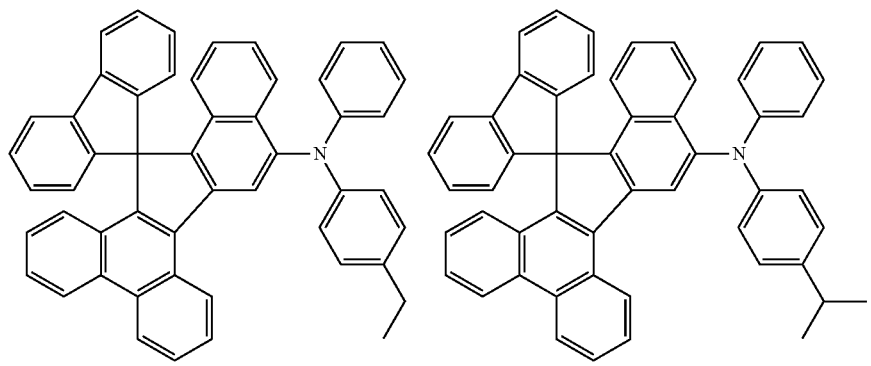
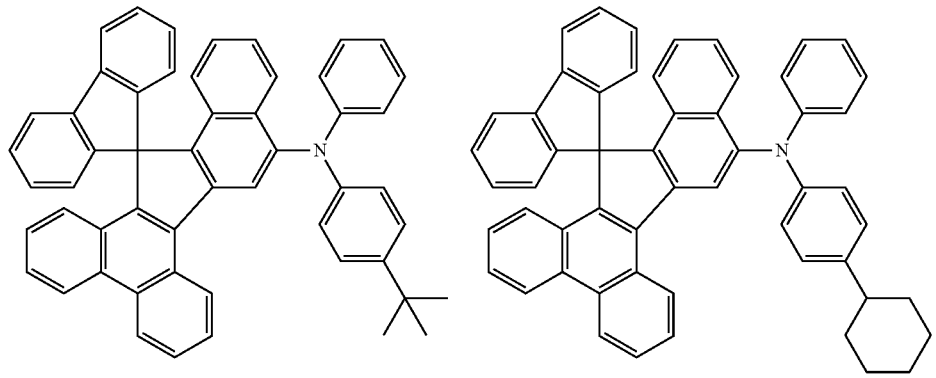
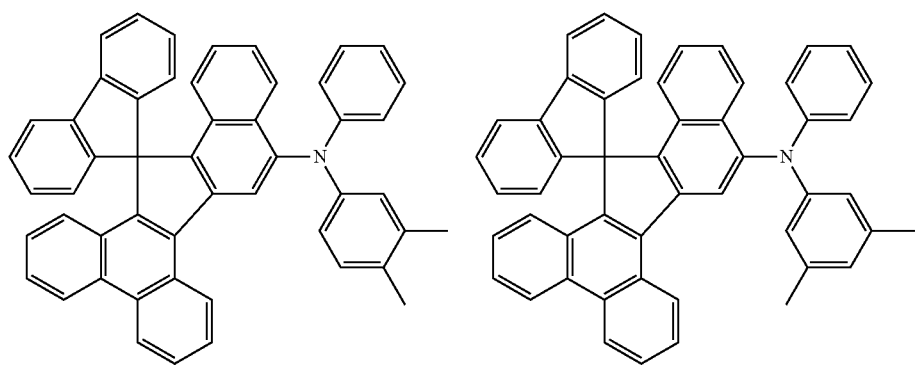
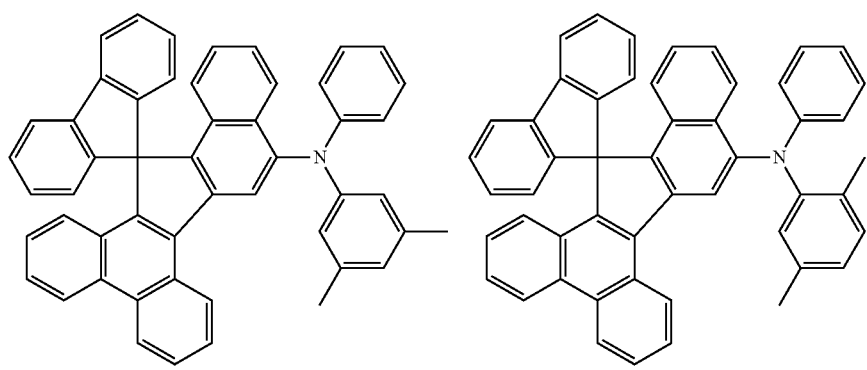

-continued
| 951 | 952 |
|---|---|
| 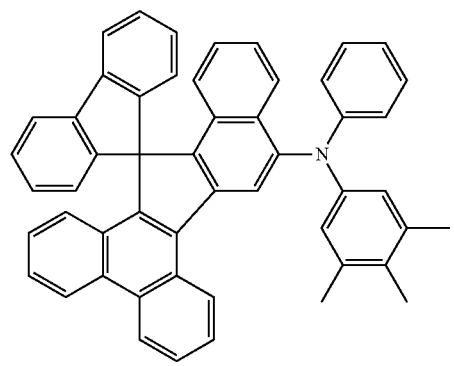 | 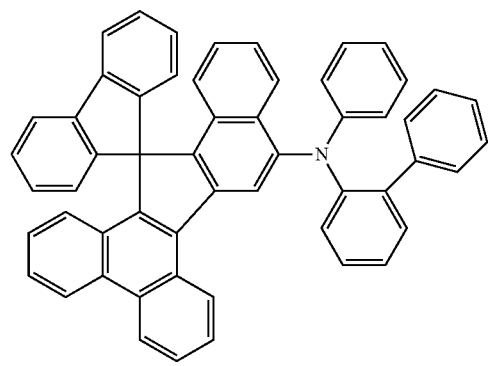 |
| 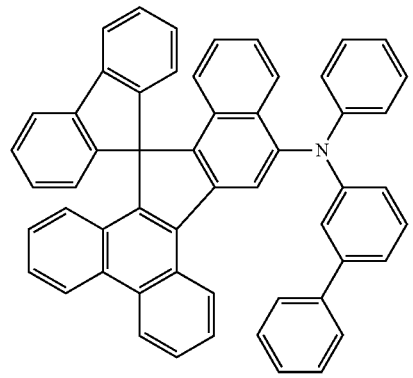 | 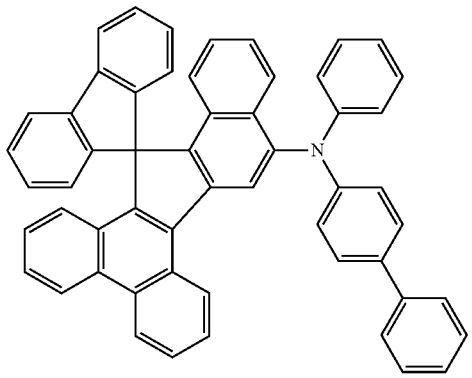 |
| 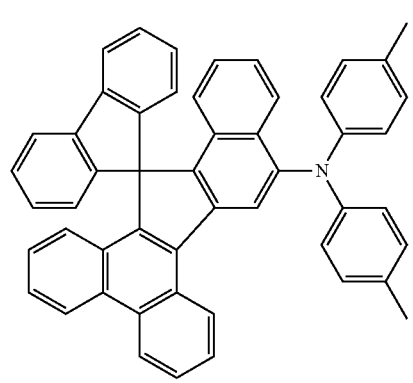 | 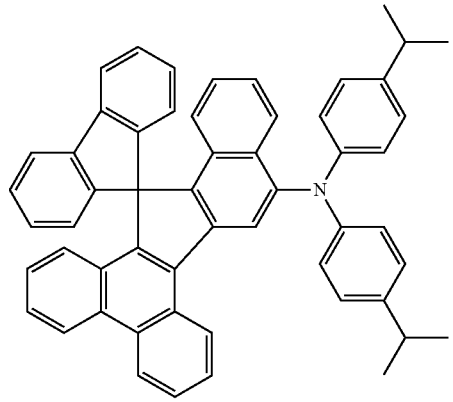 |
| 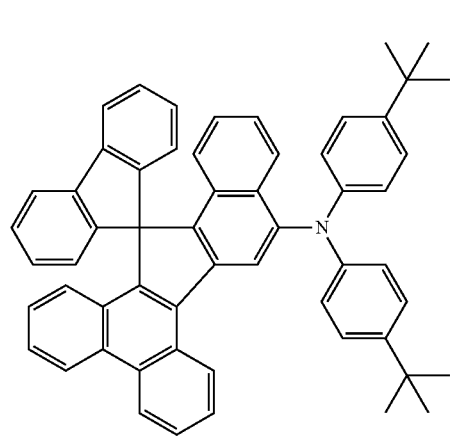 | 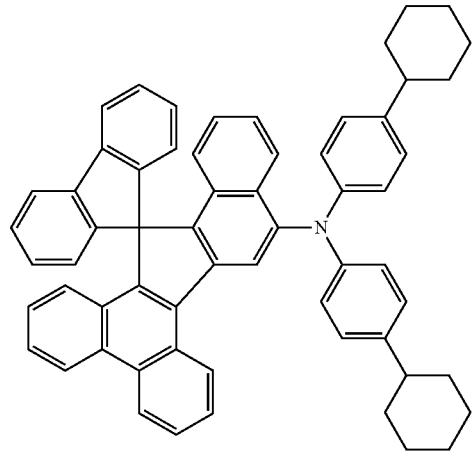 |

953    954
-continued
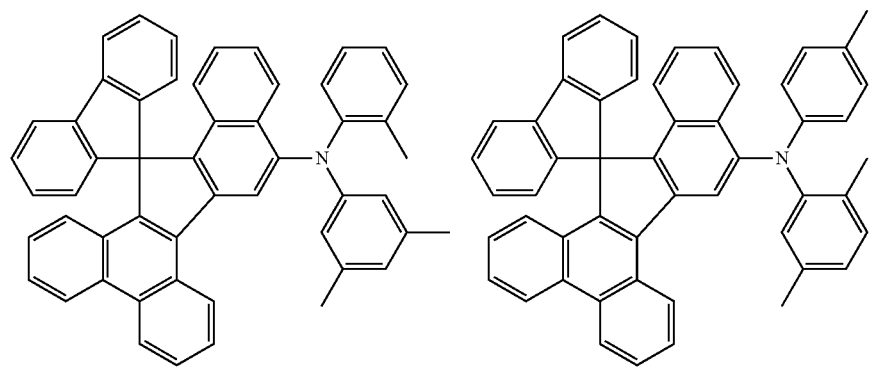
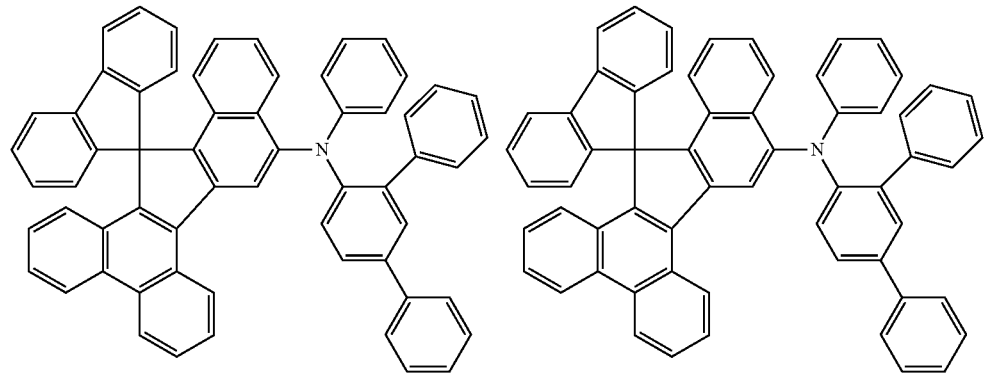
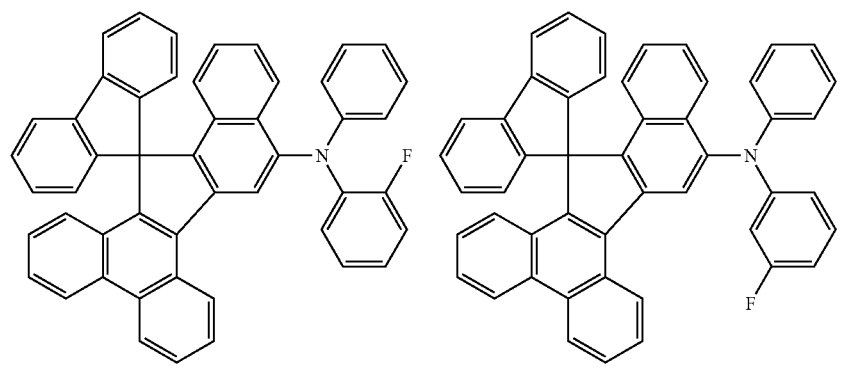
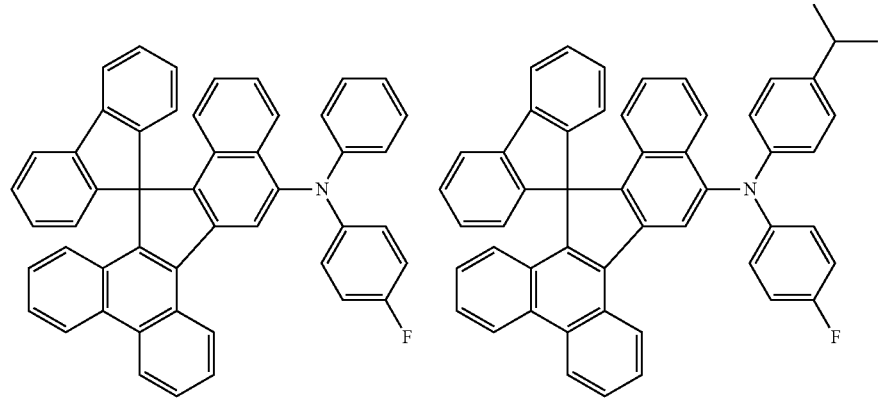

-continued
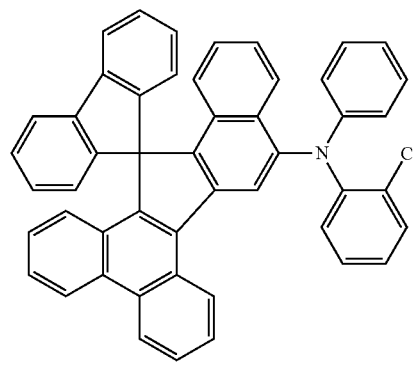
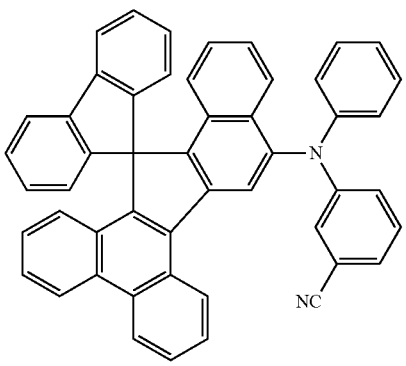
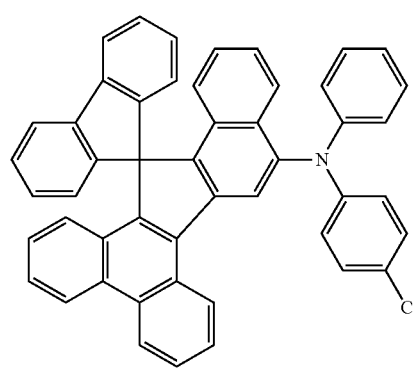
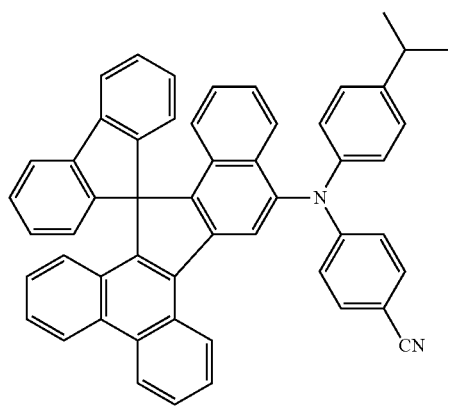
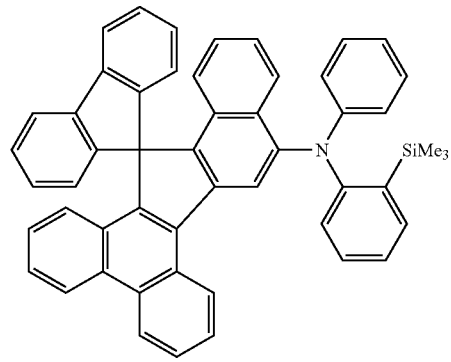
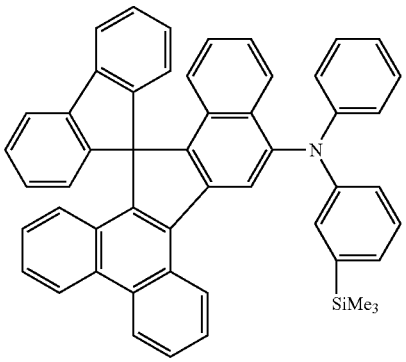
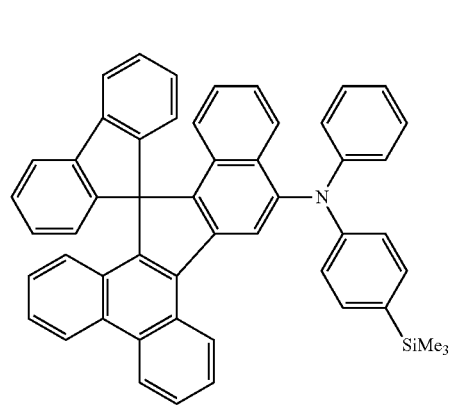
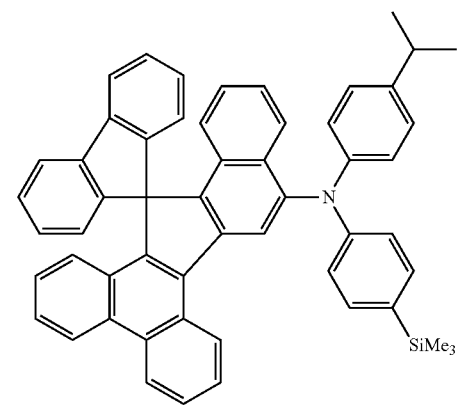

-continued
| 957 | 958 |
|---|---|
| 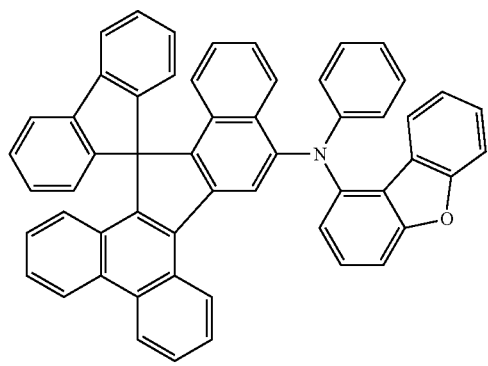 | 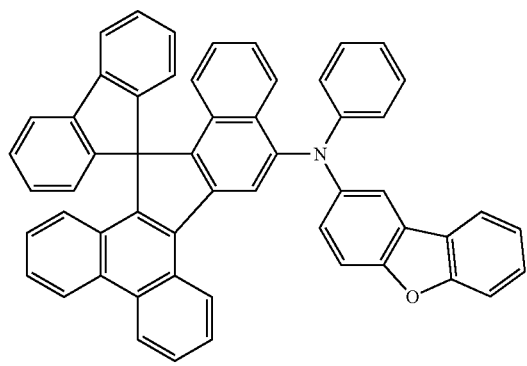 |
| 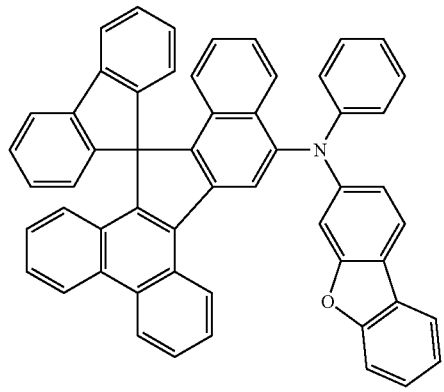 | 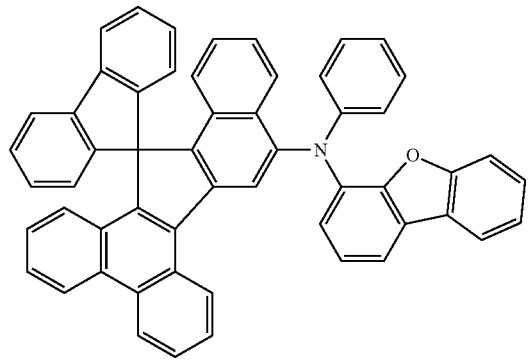 |
| 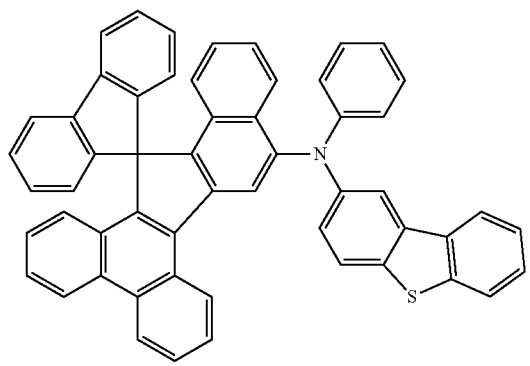 | 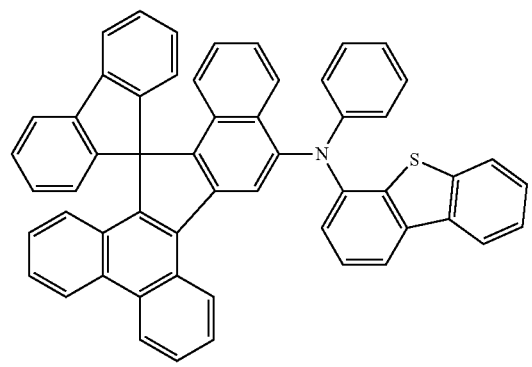 |
| 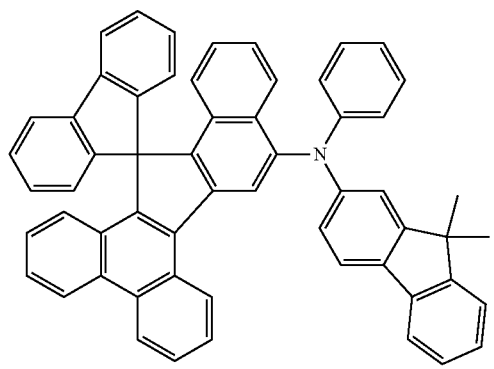 | 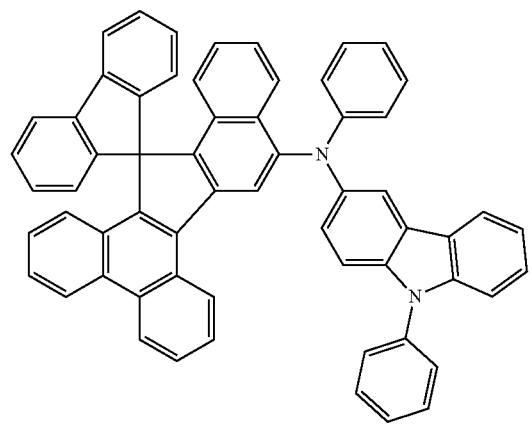 |

959                                                                 960
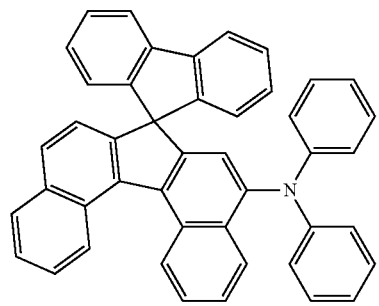 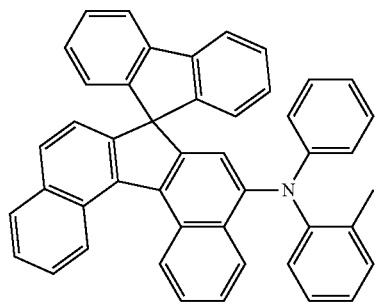 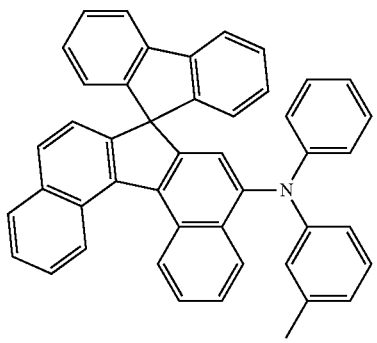
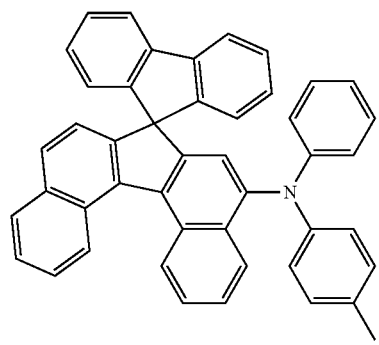 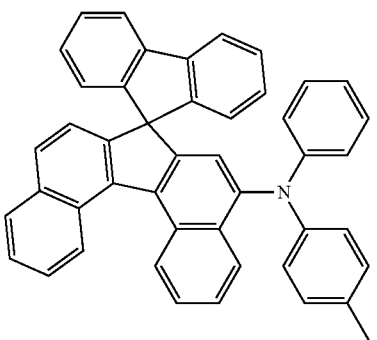 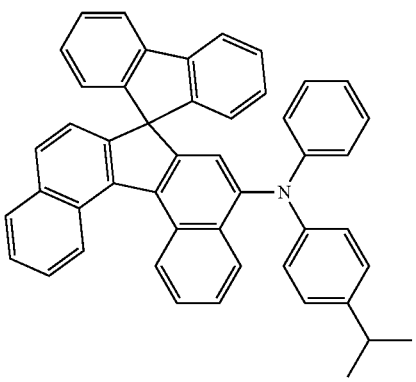
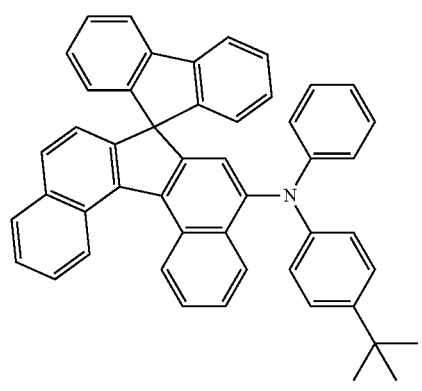 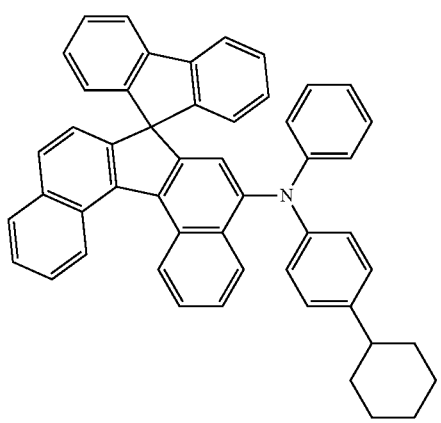
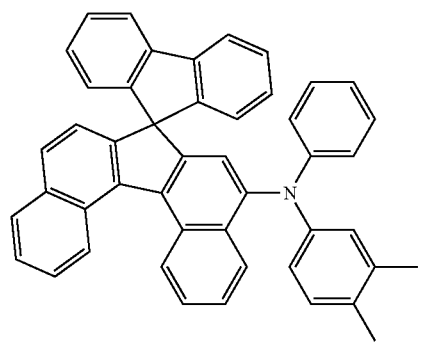 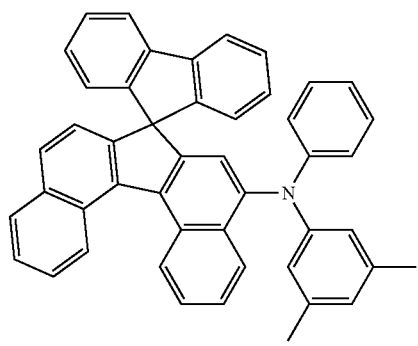

961
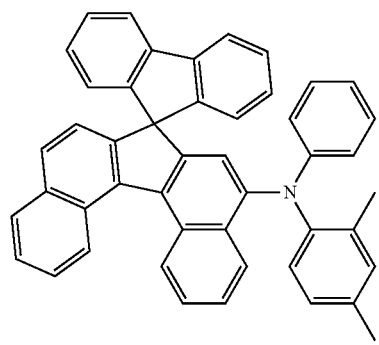
-continued
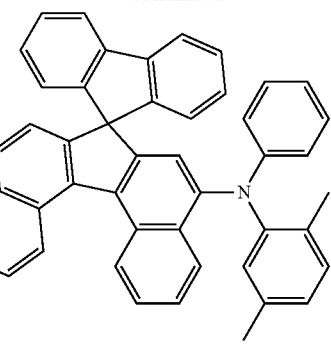
962
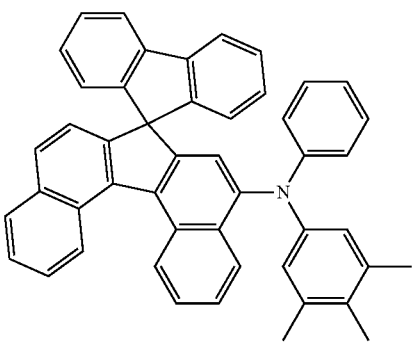
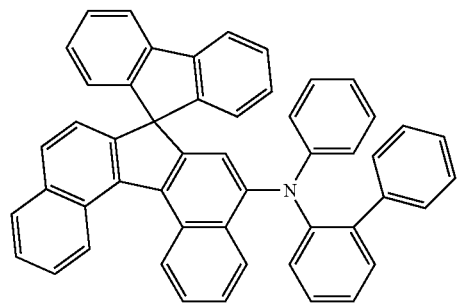
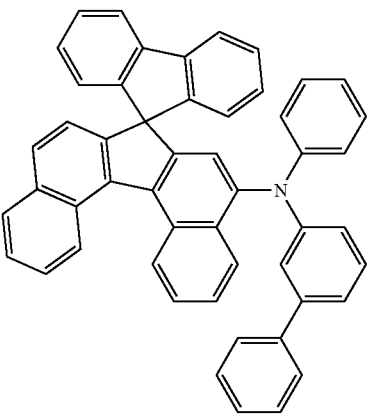
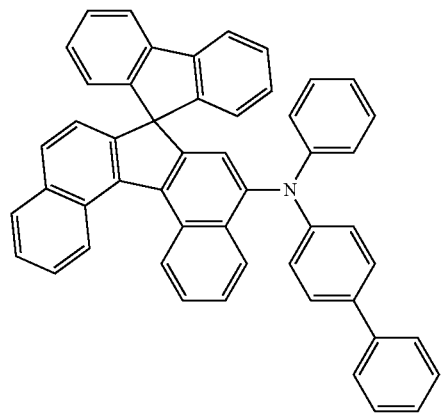
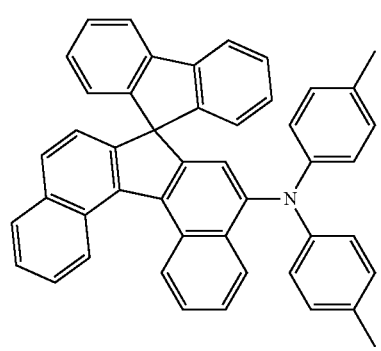
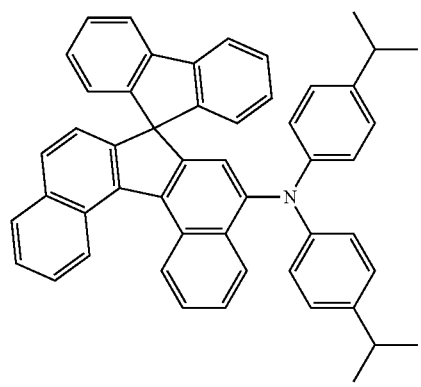
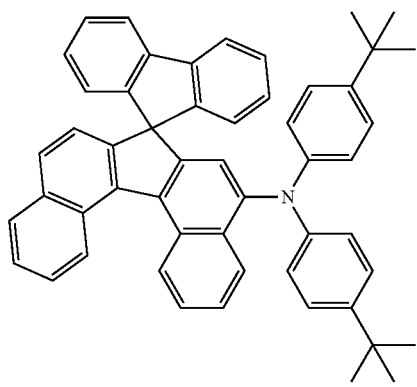

-continued
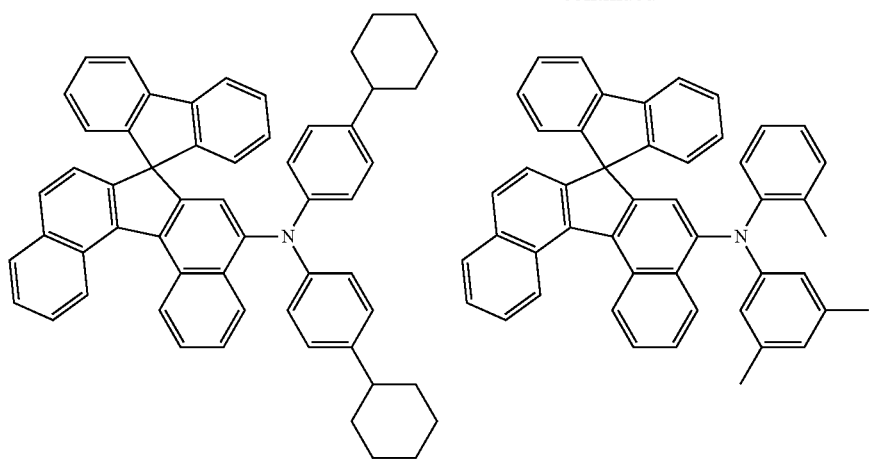
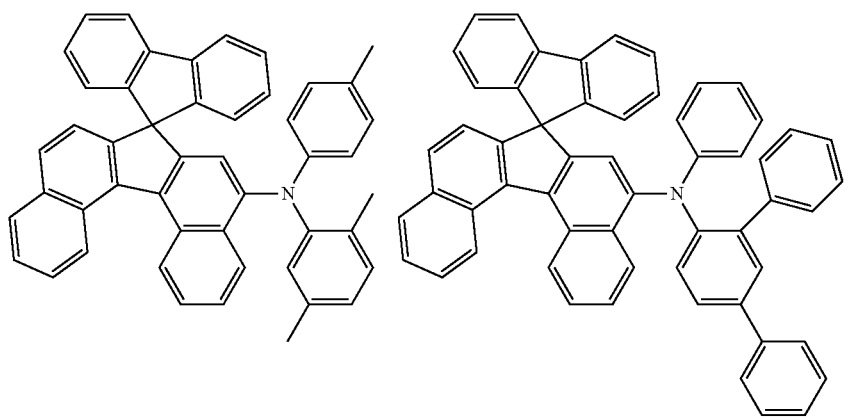
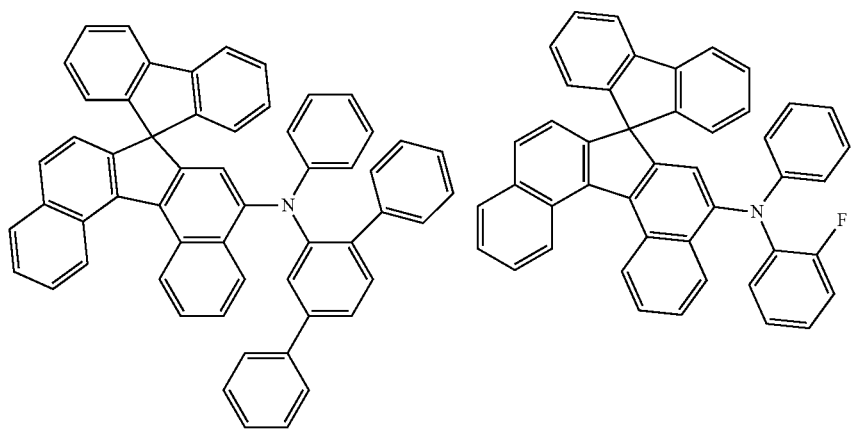
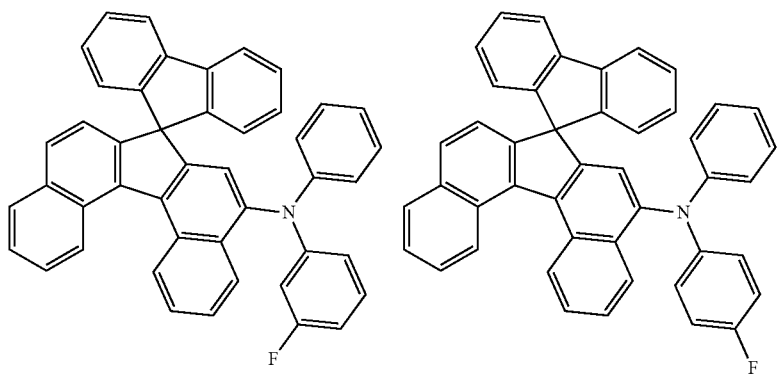

-continued
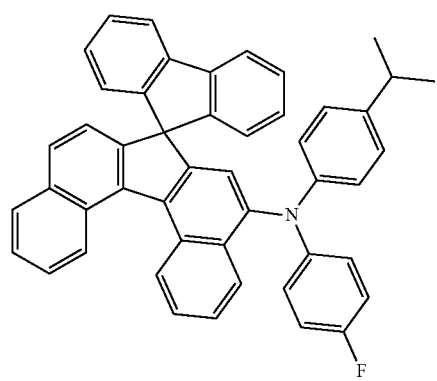
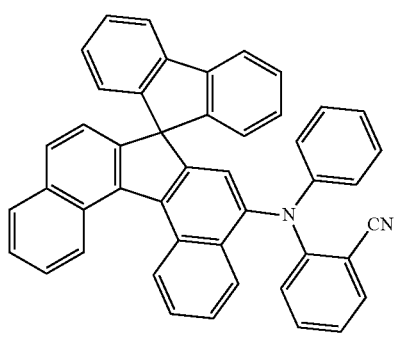
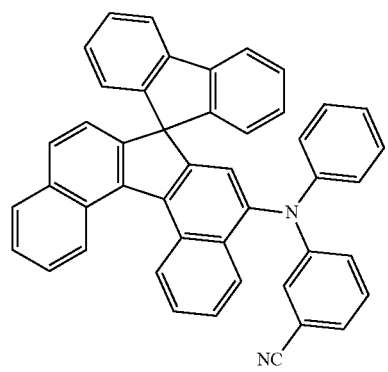
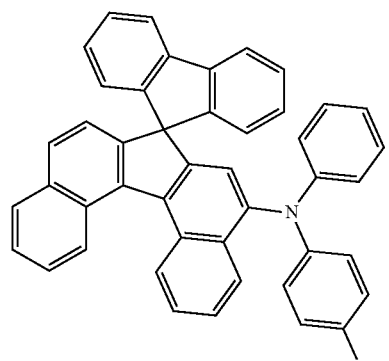
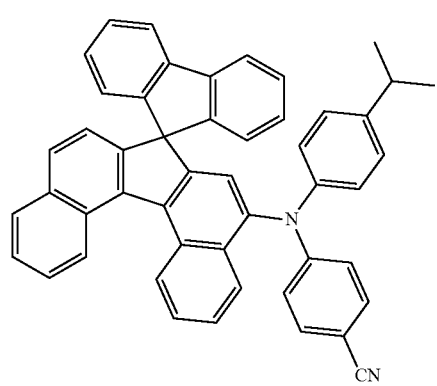
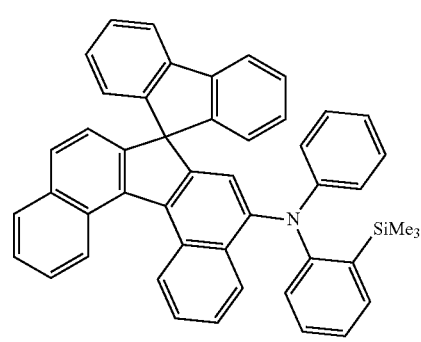
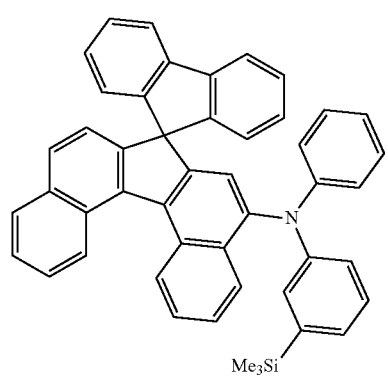
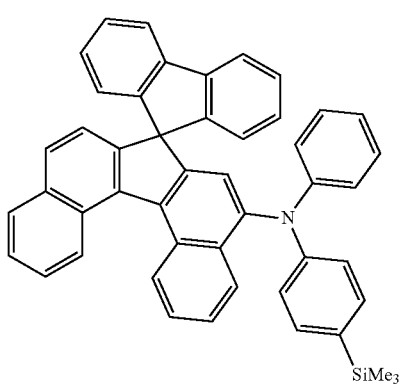

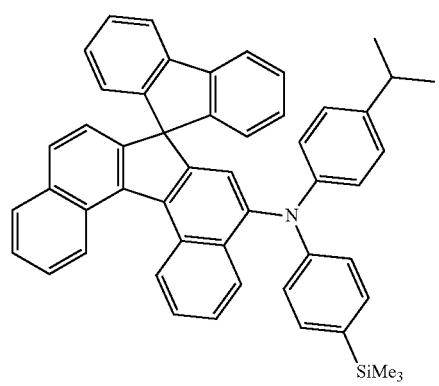
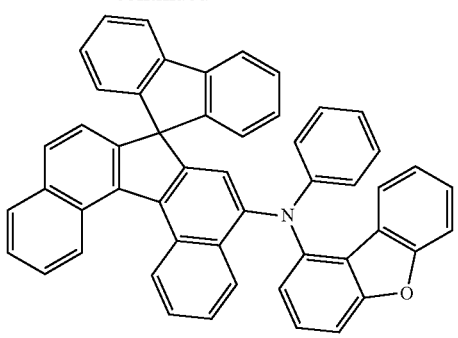
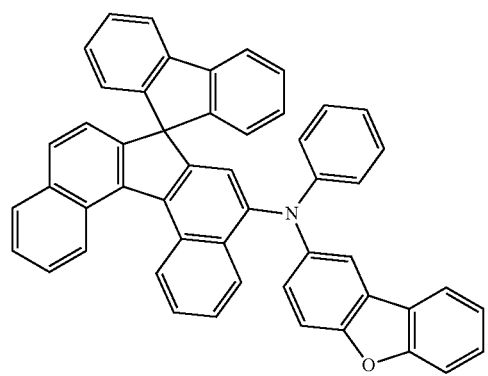
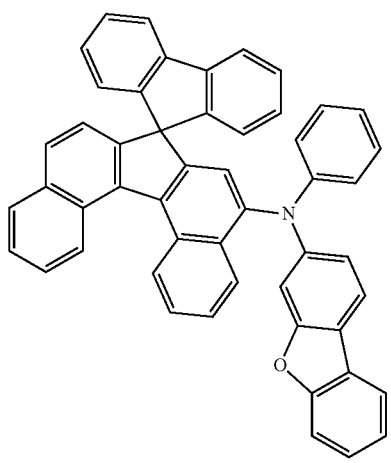
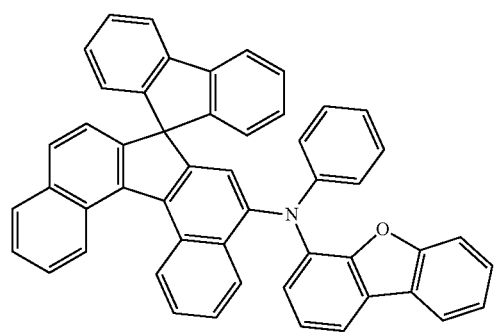
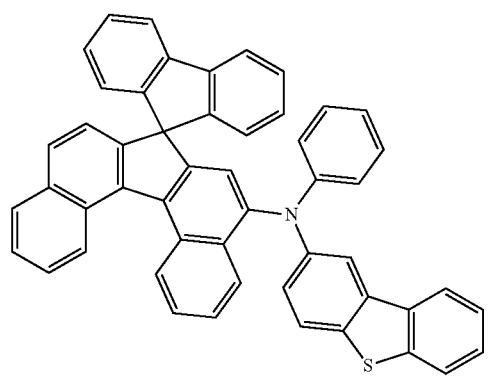
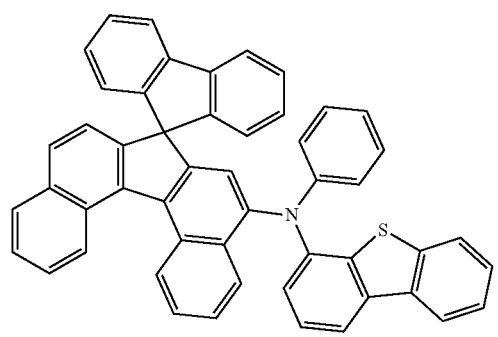
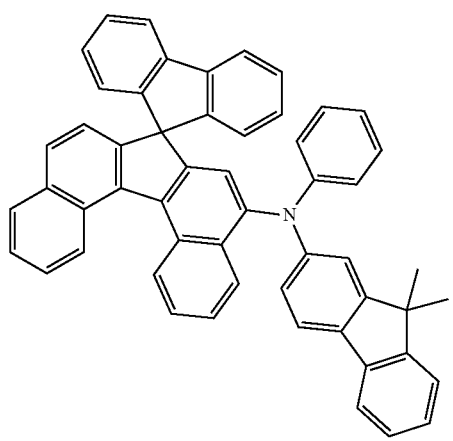

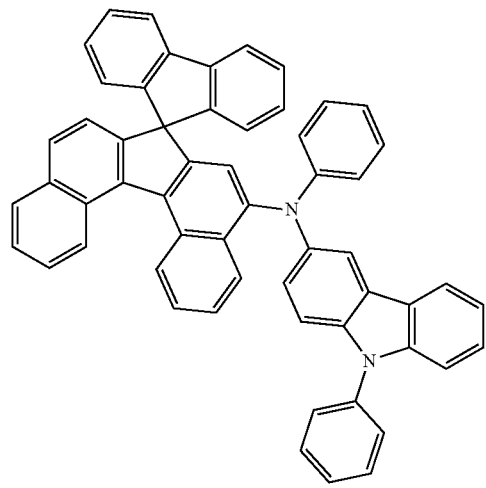
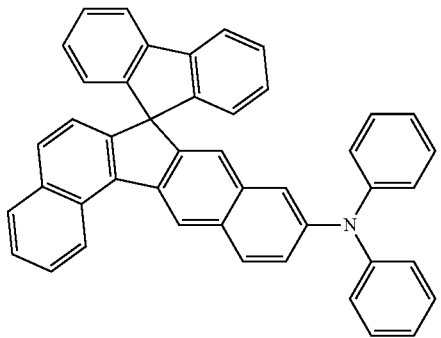
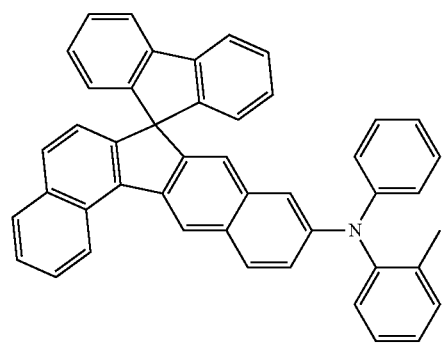
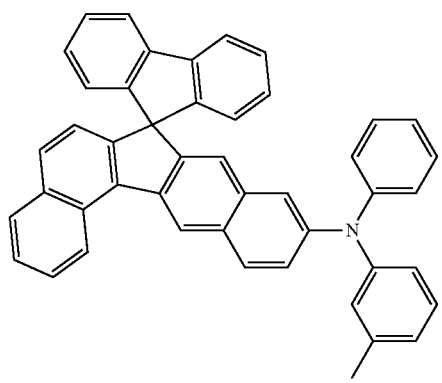
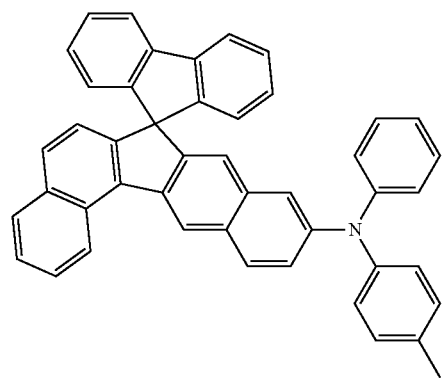
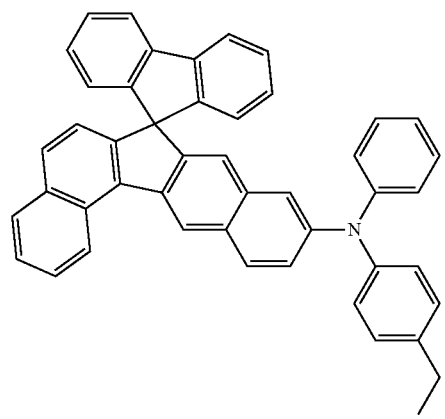
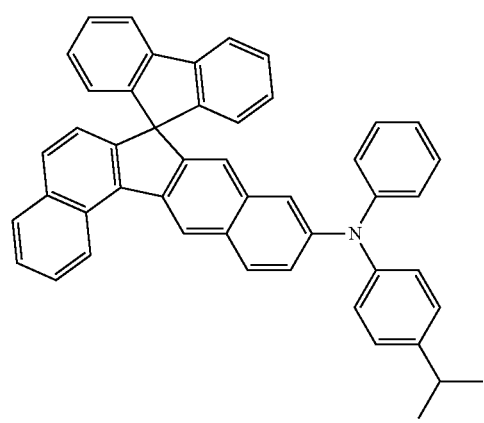
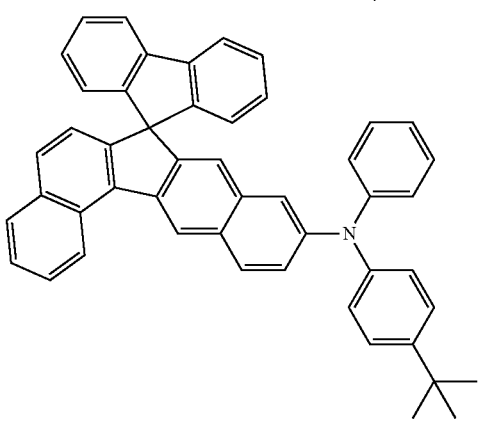

971
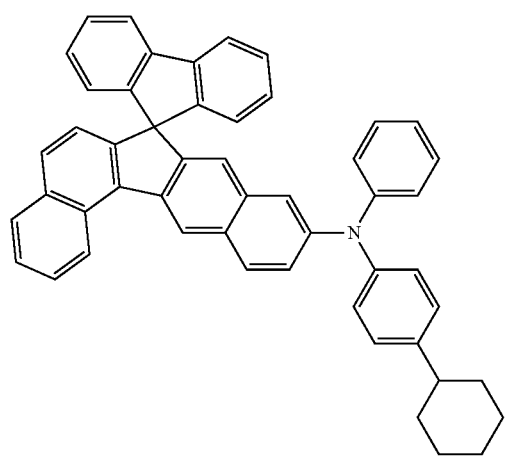
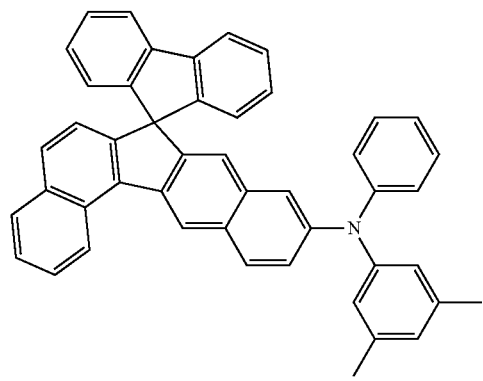
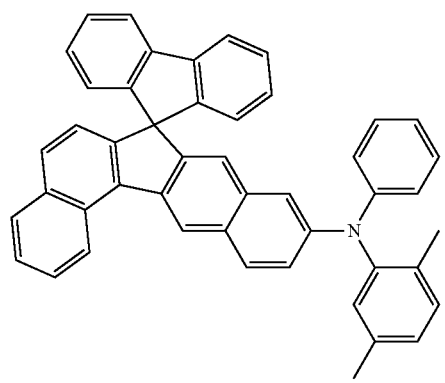
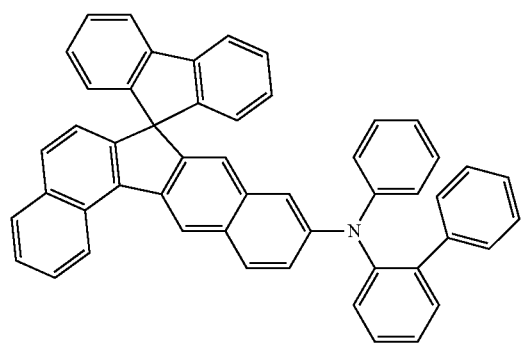
972
-continued
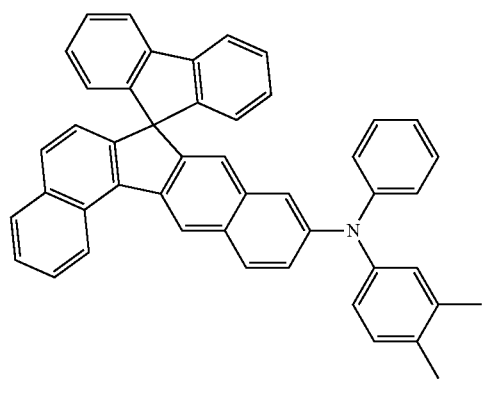
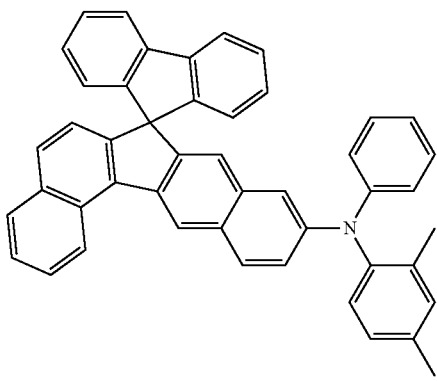
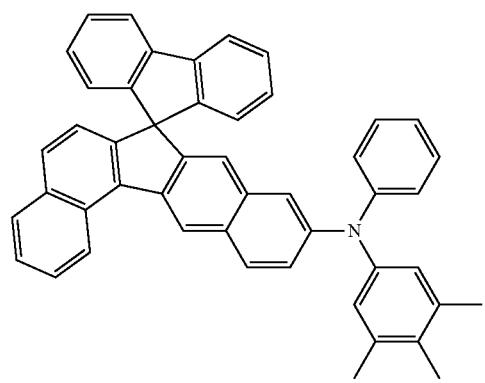
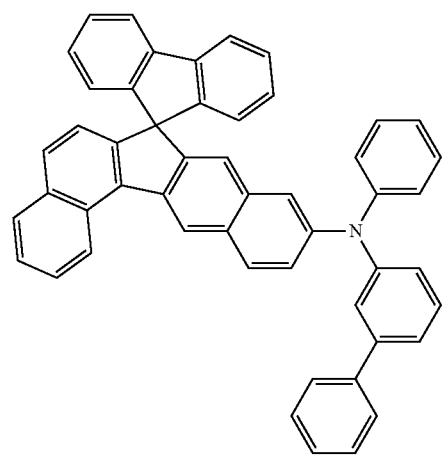

973
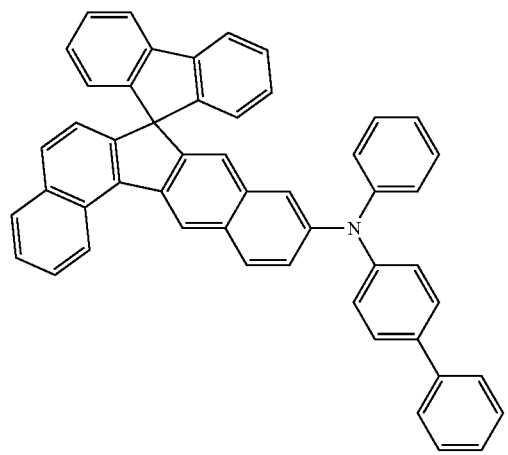
-continued
974
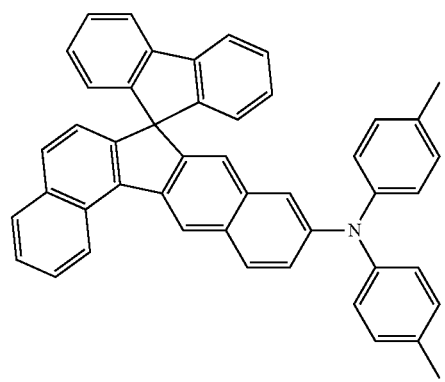
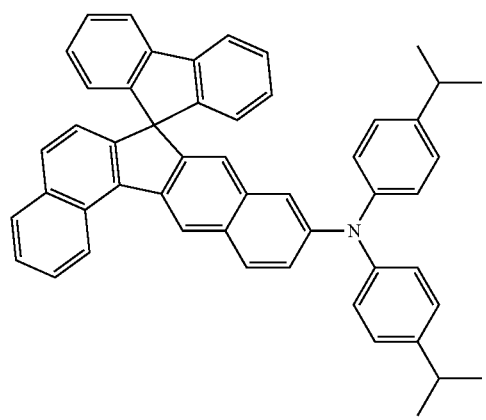
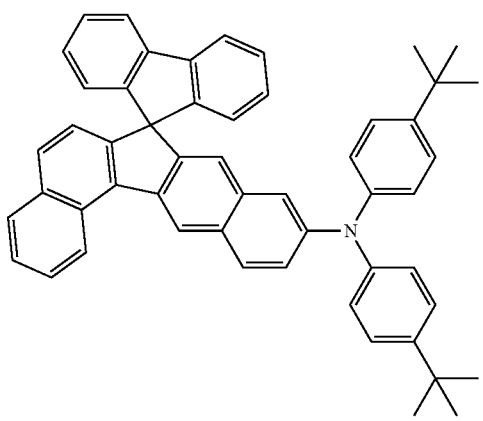
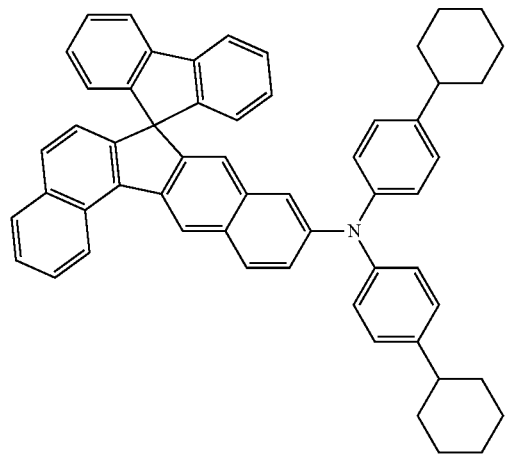
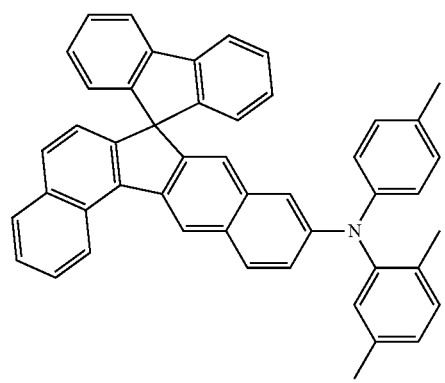

975
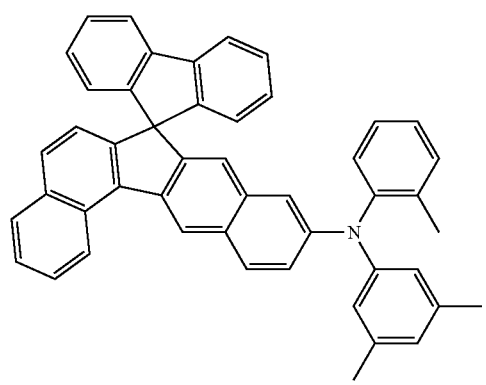
976
-continued
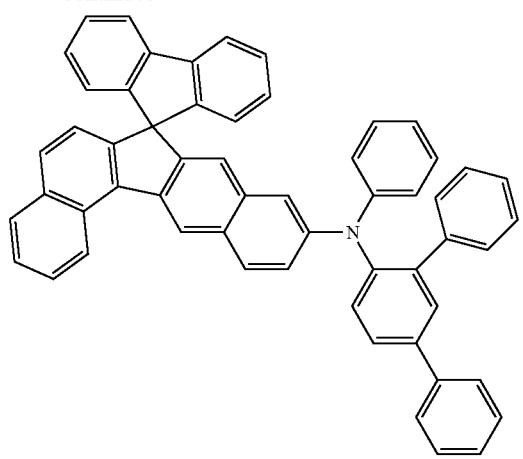
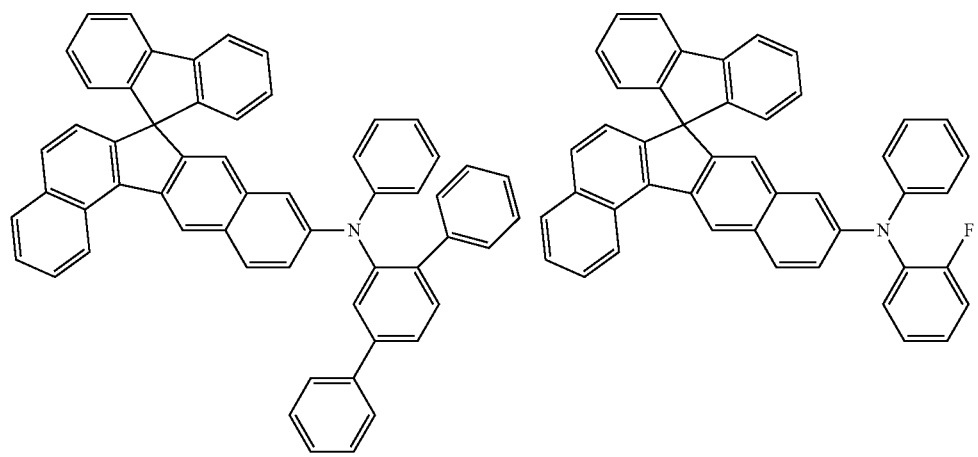
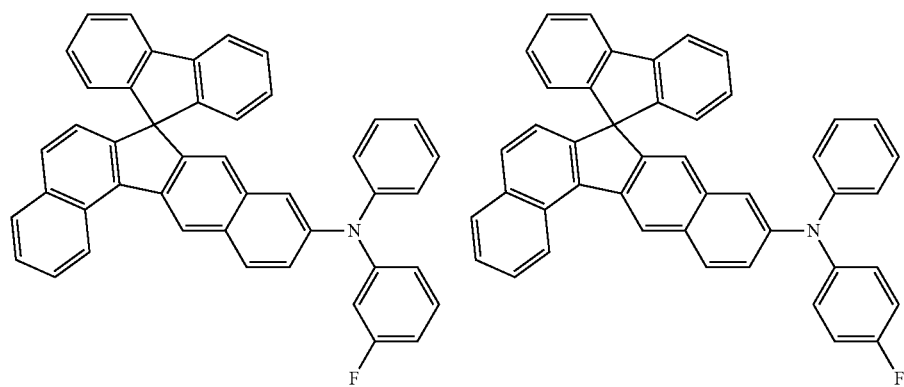
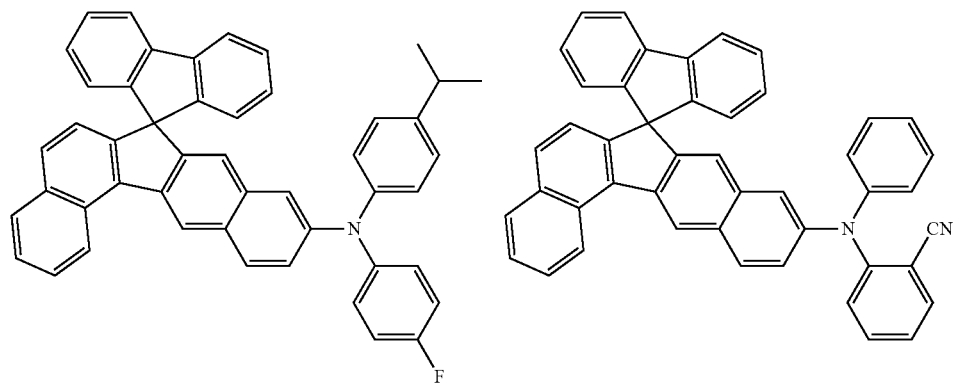

-continued
977
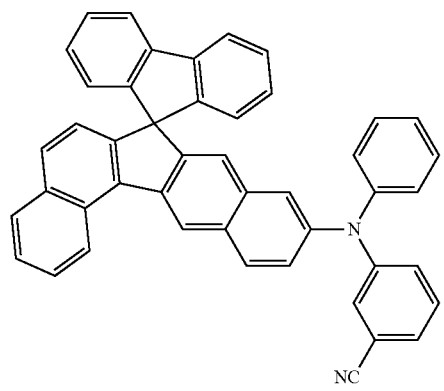 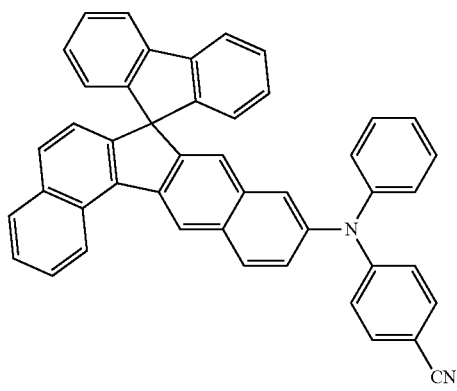
978
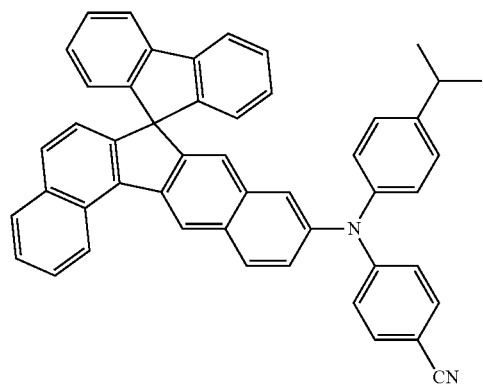 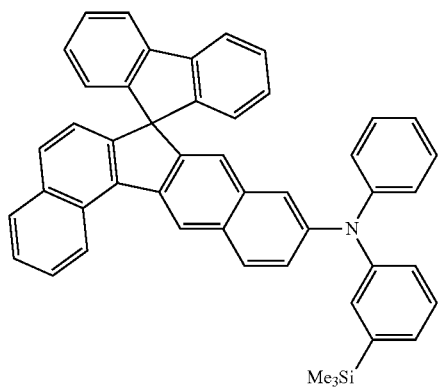
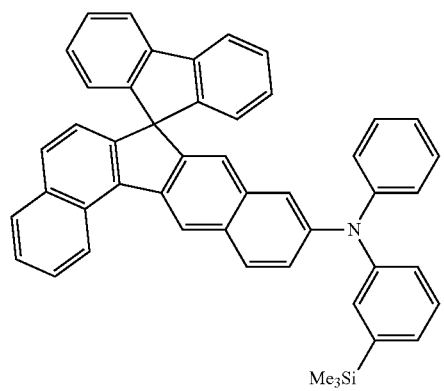 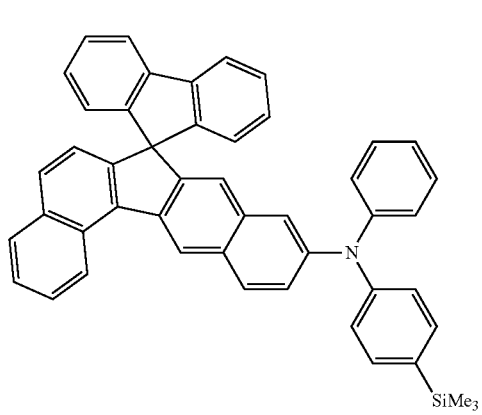
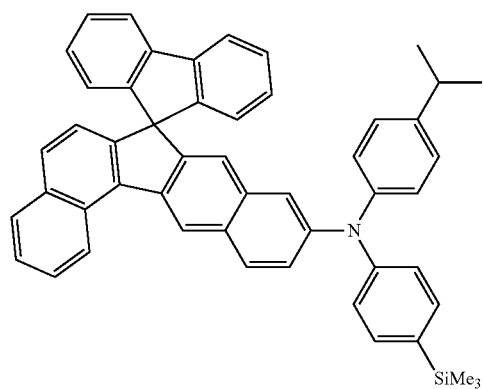 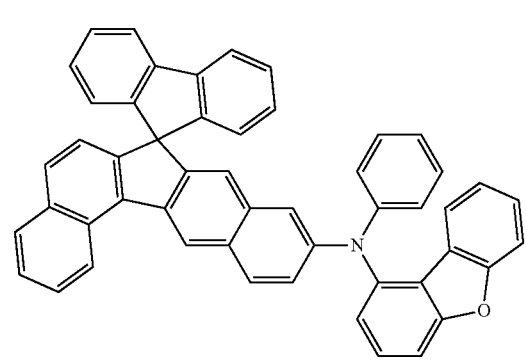

-continued
| 979 | 980 |
|---|---|
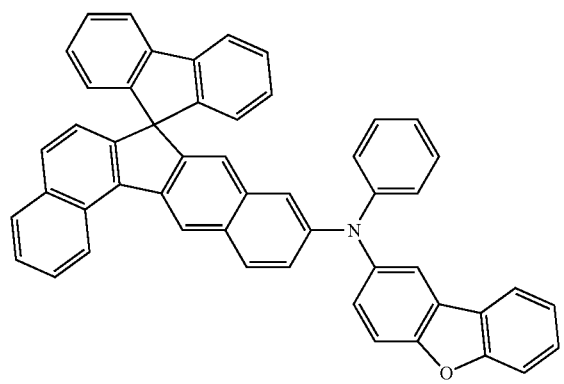

981 982
-continued
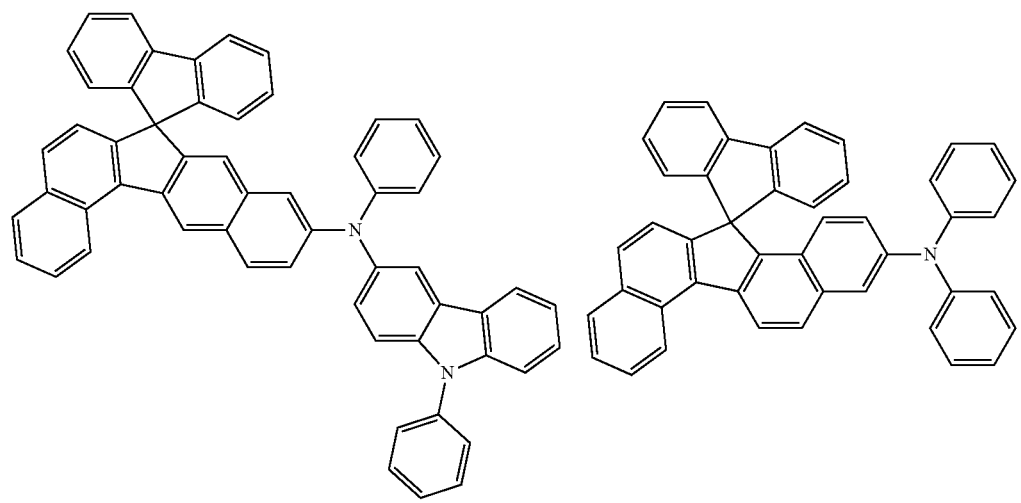
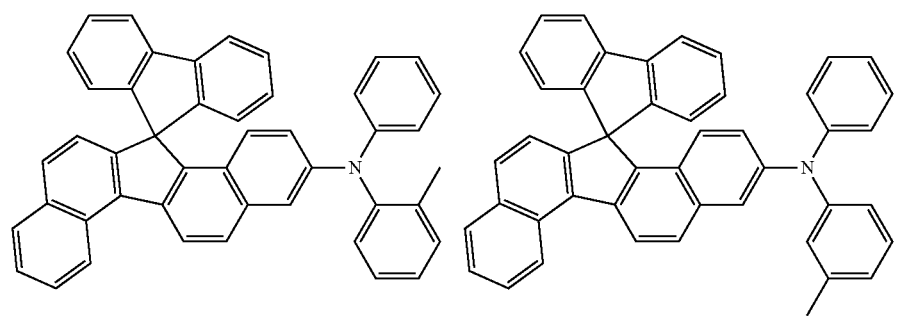
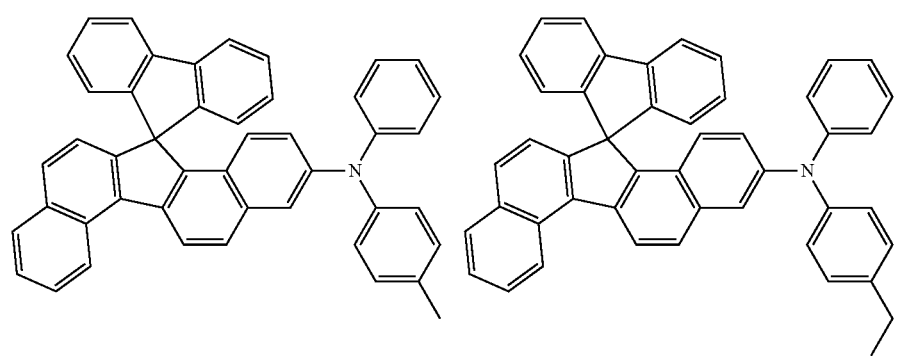
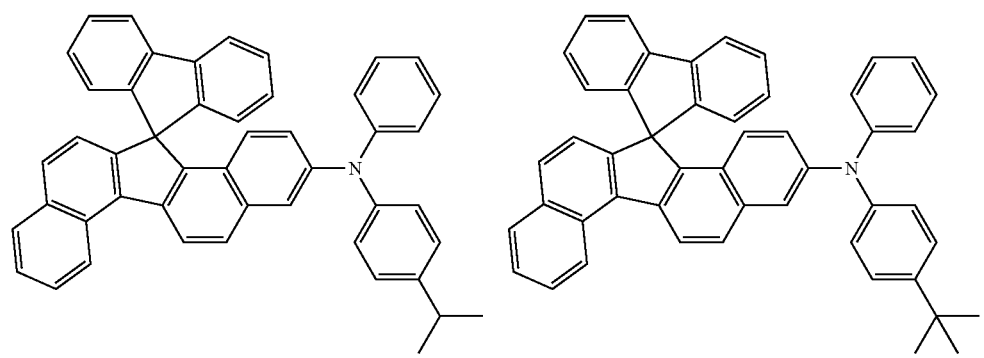

983  984
-continued
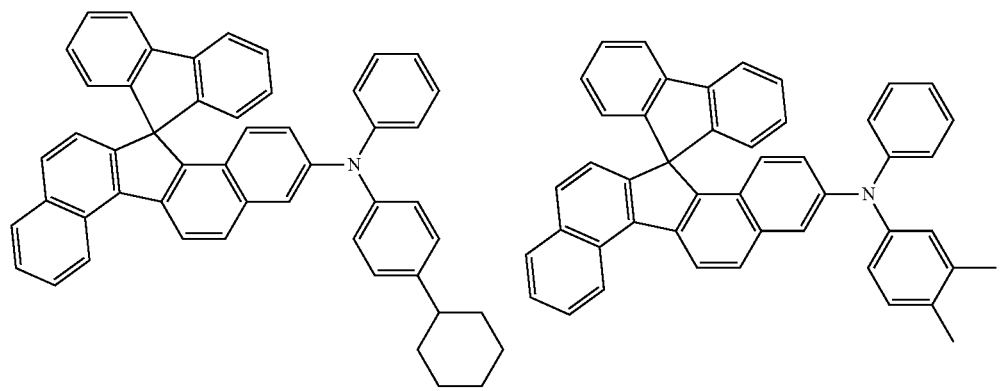
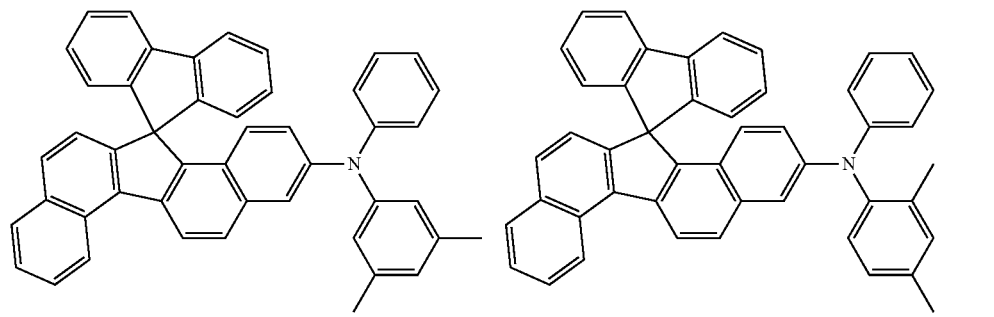
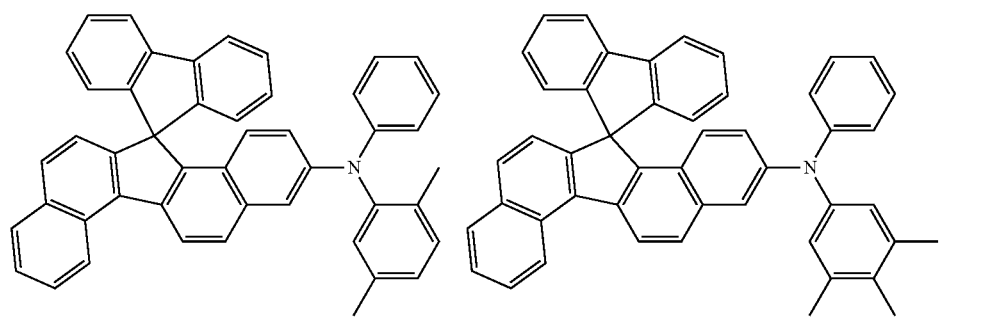
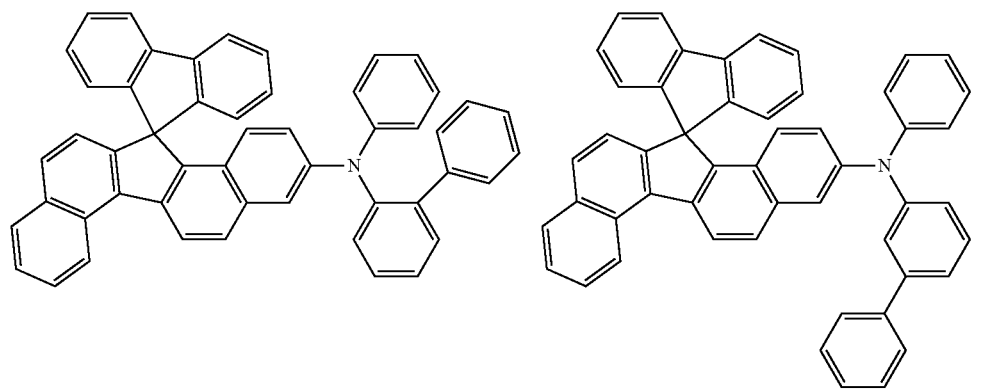

985  986
-continued
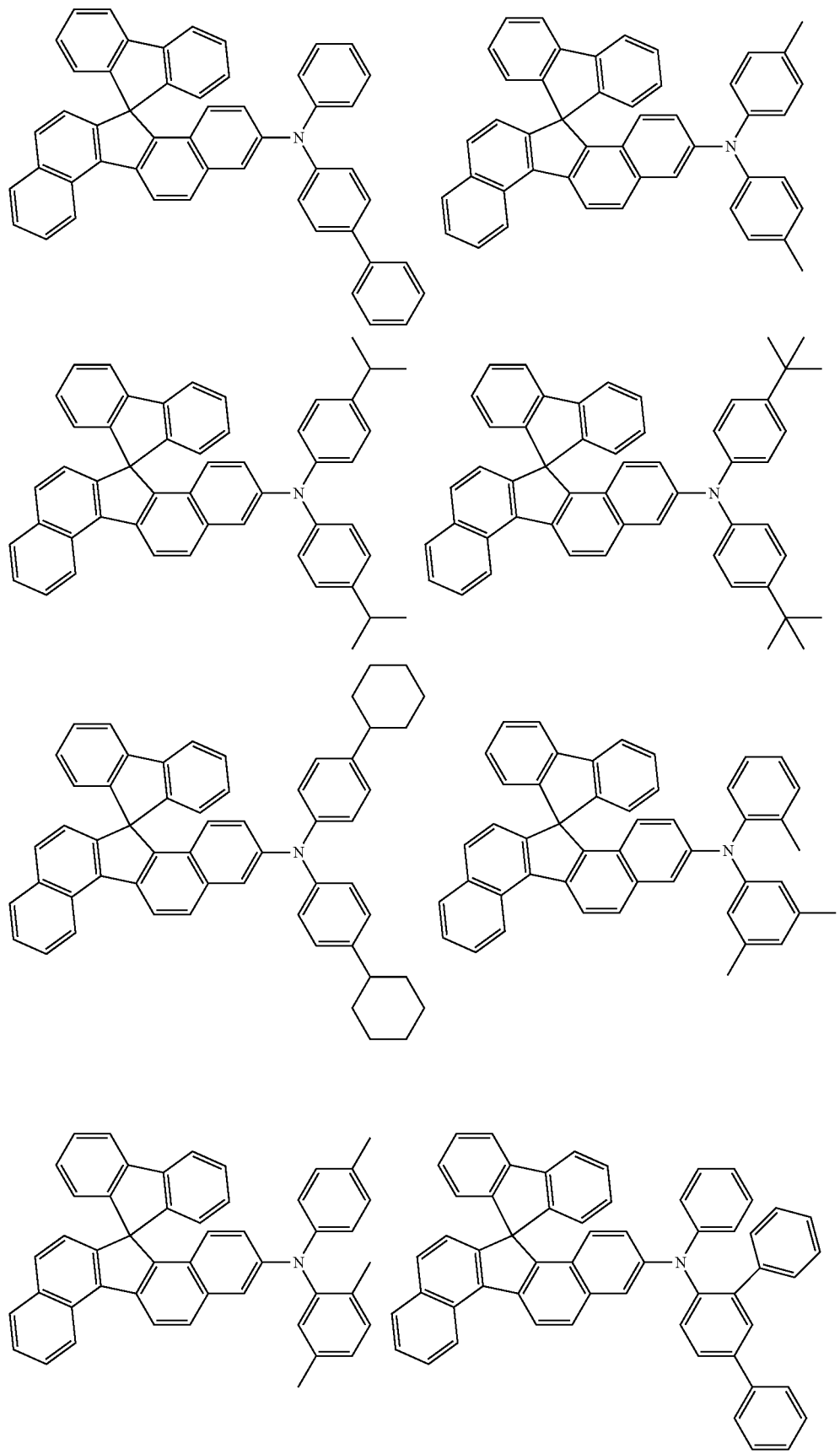

-continued
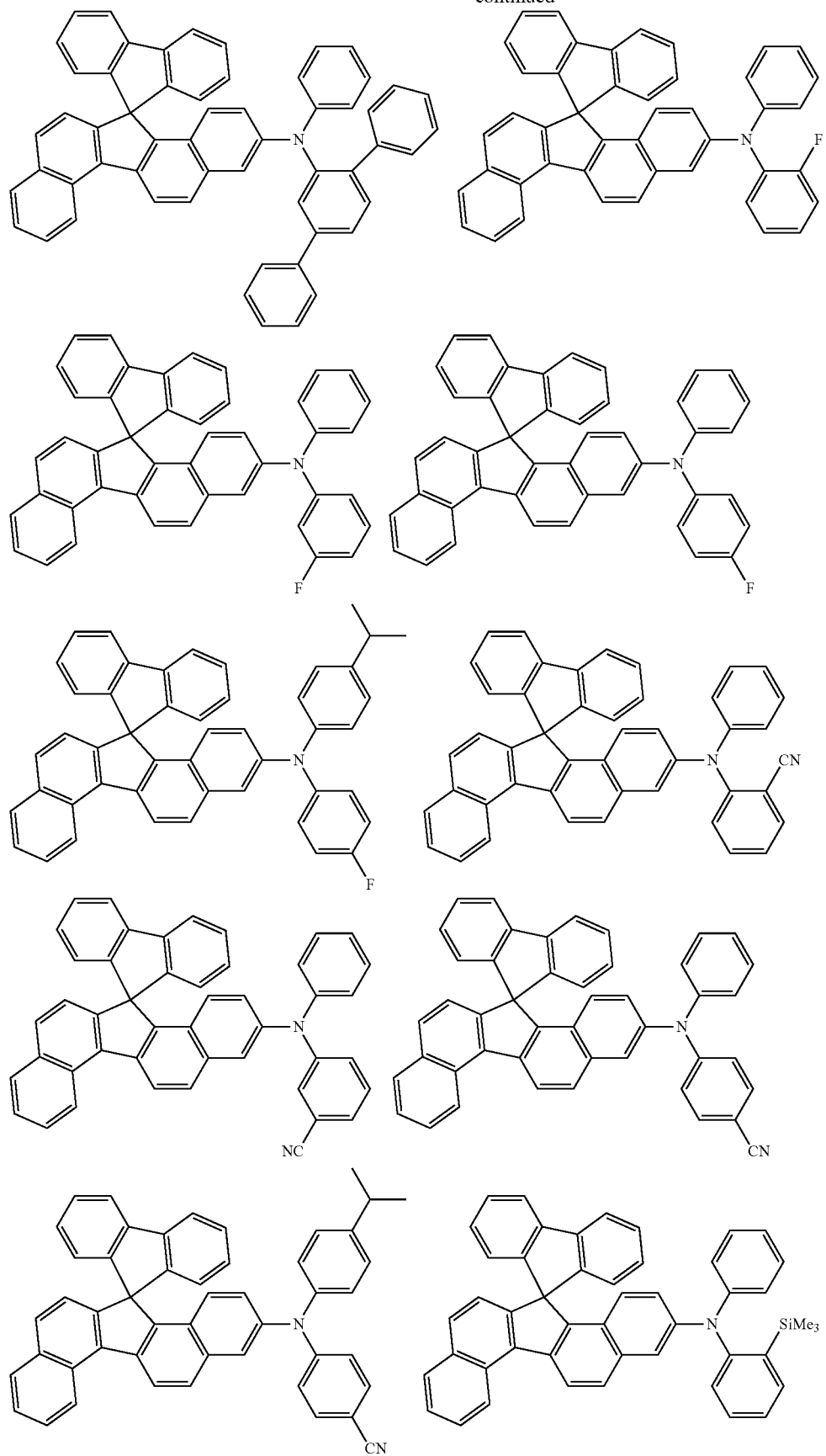

-continued
989
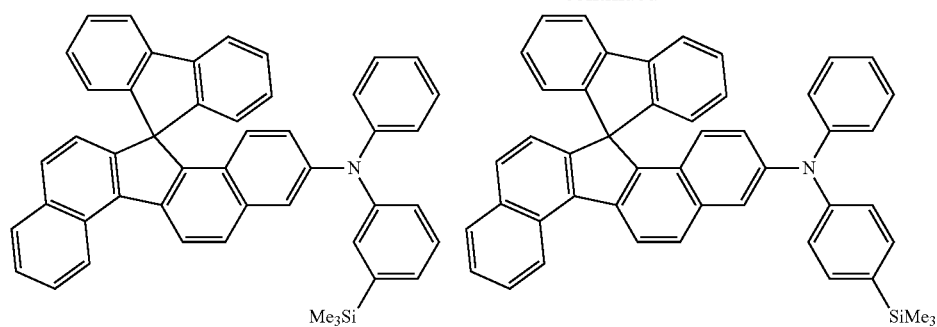
990
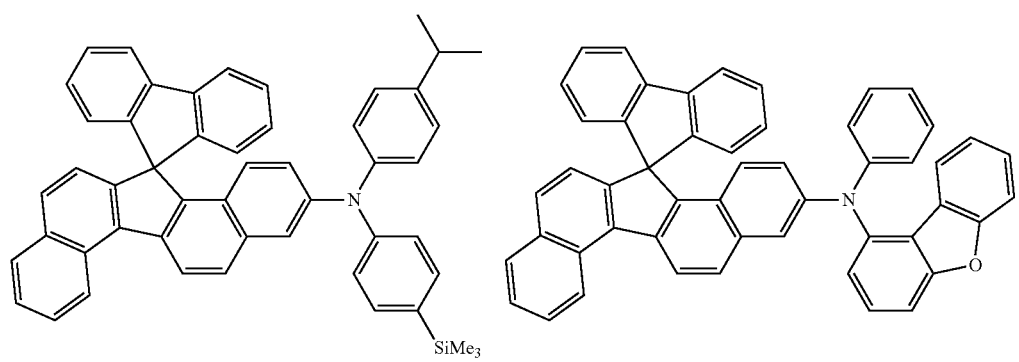
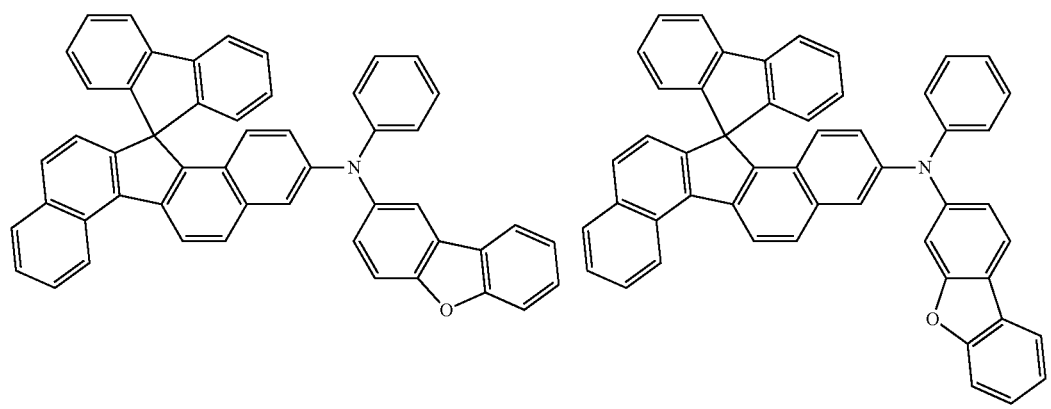
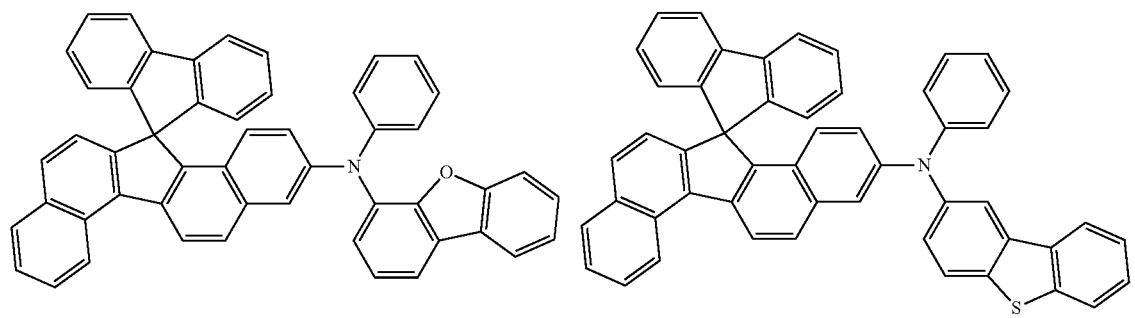

991 992
-continued
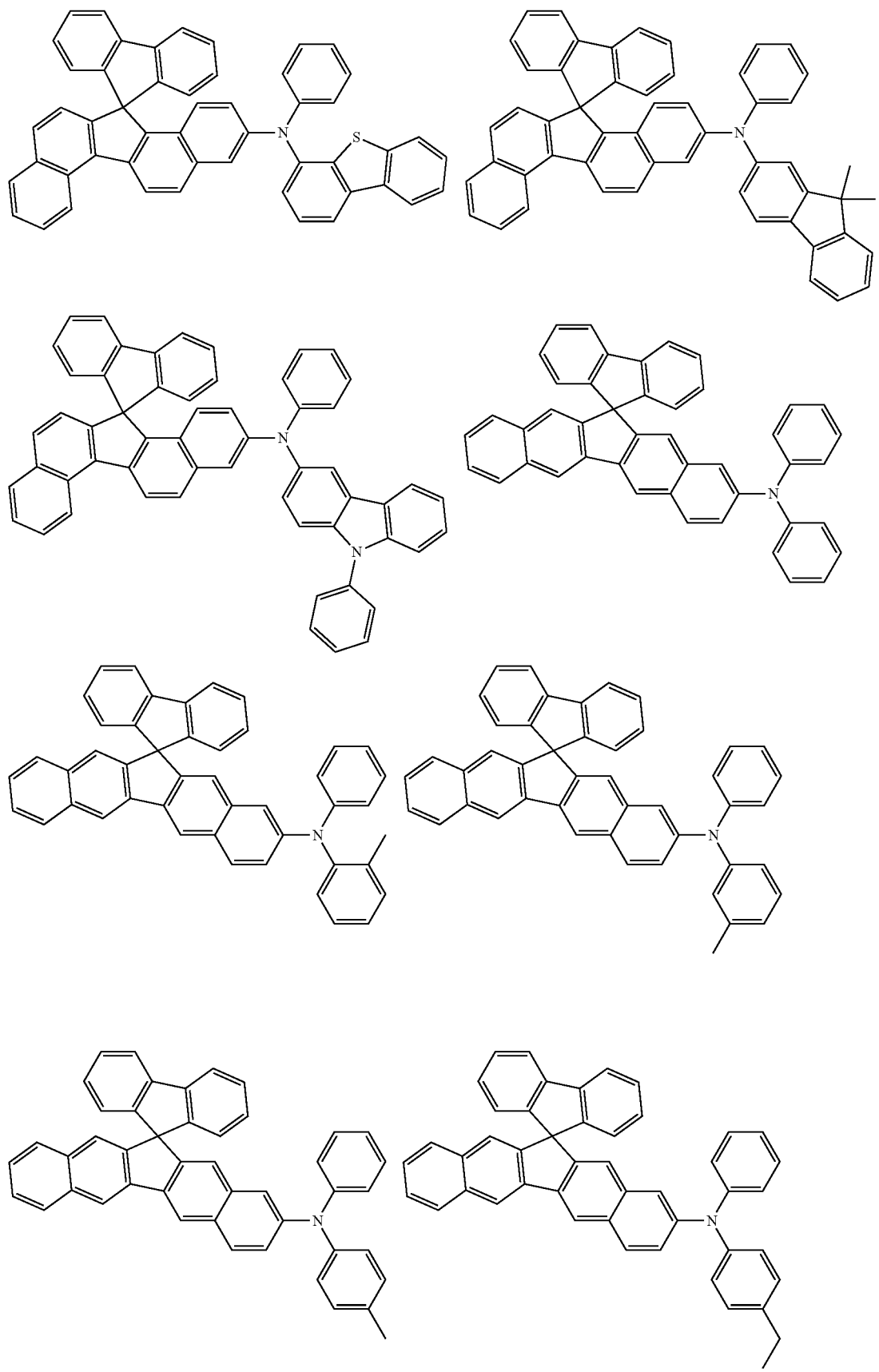

993
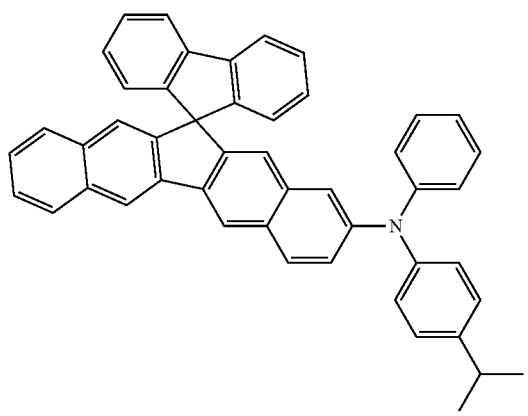
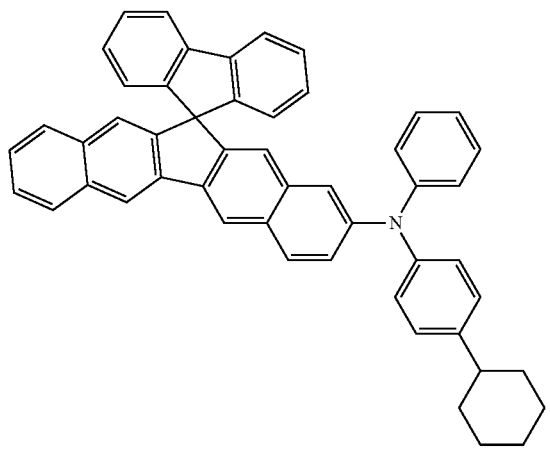
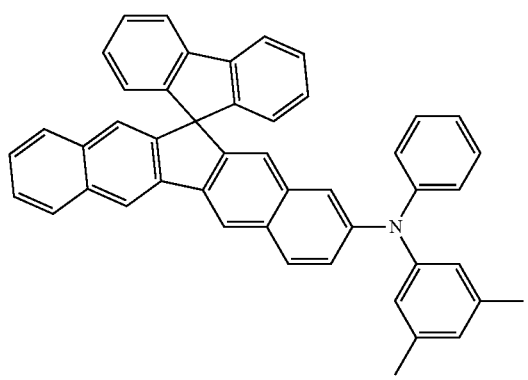
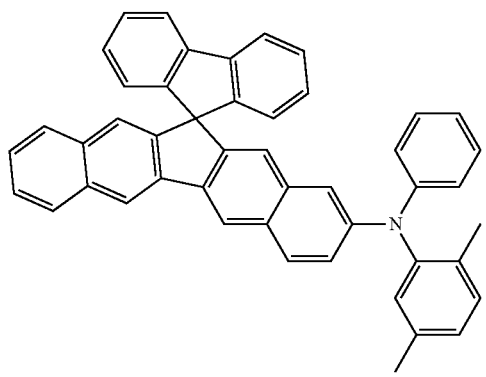
994
-continued
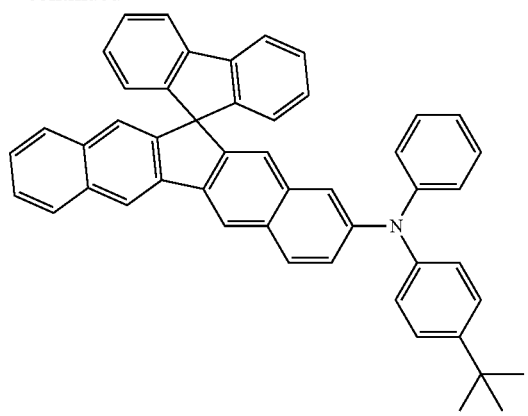
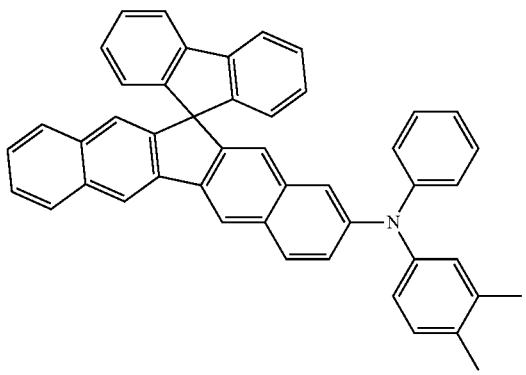
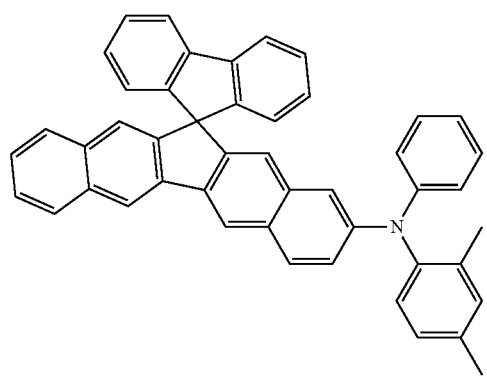
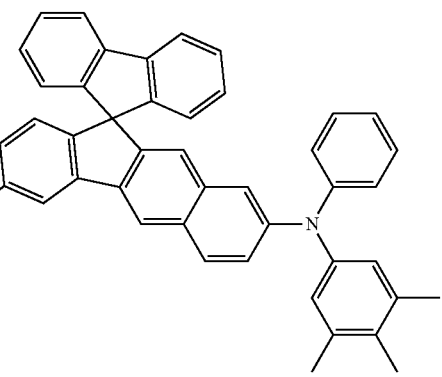

995 996
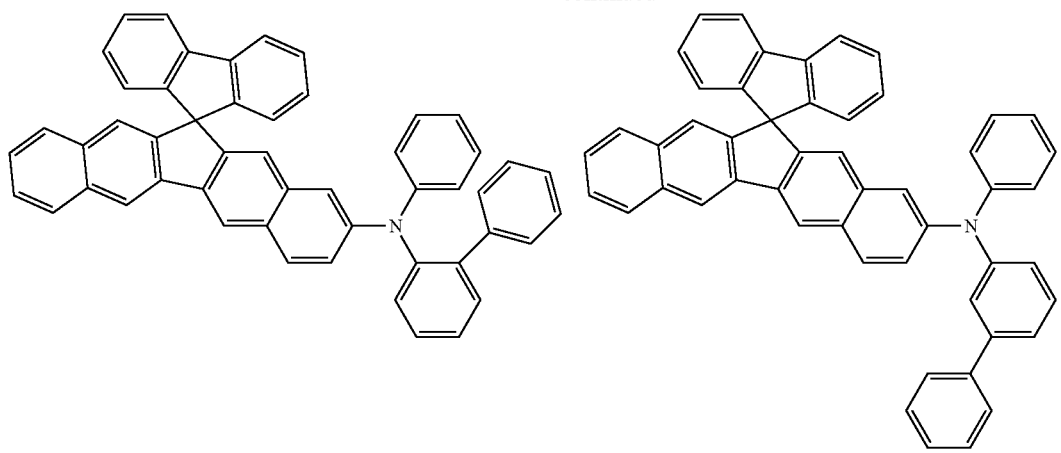
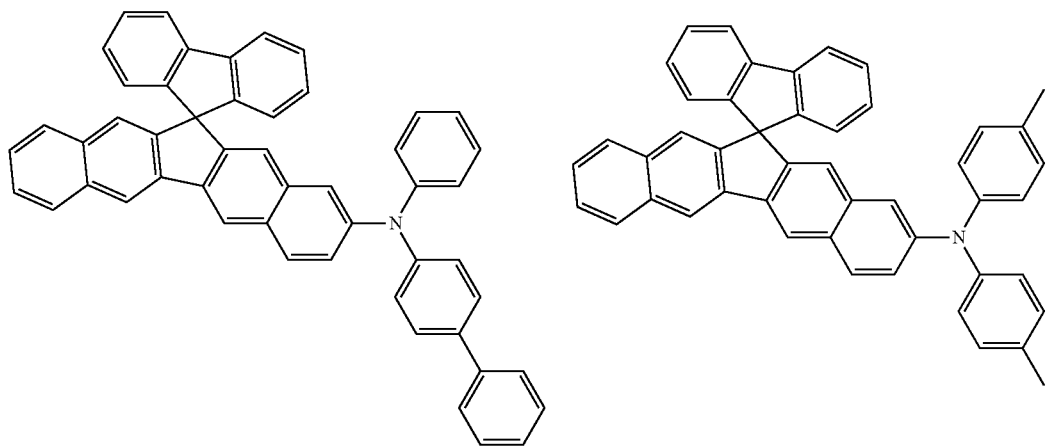
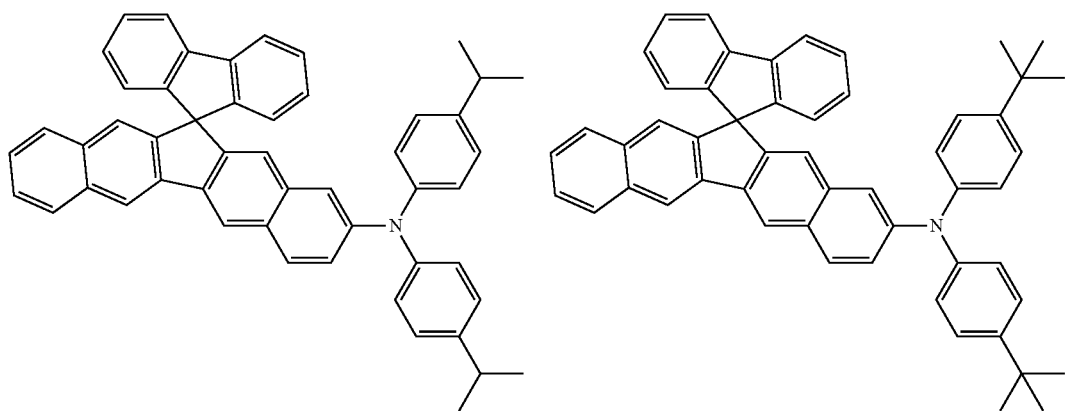

-continued
| 997 | 998 |
|---|---|
| 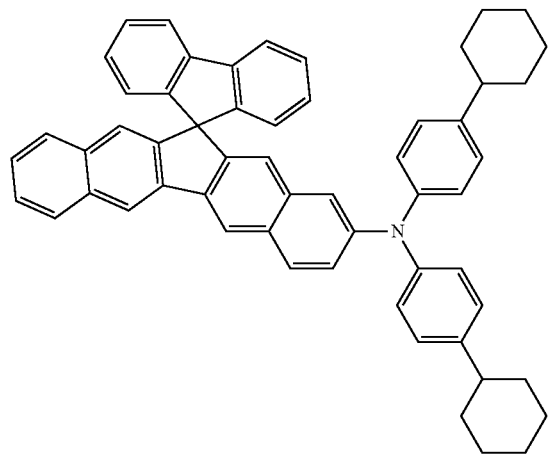 | 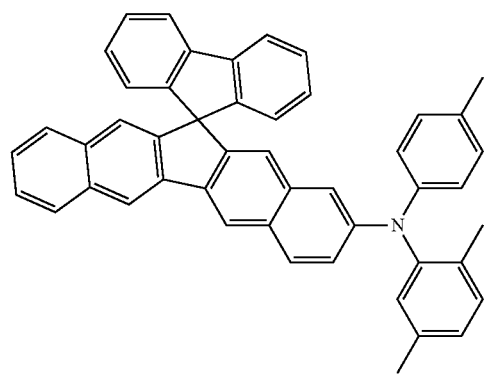 |
| 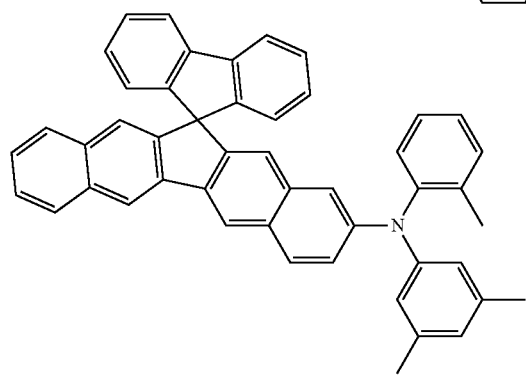 | 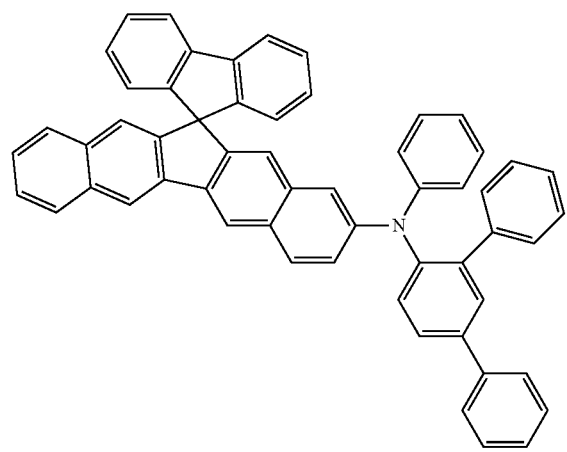 |
| 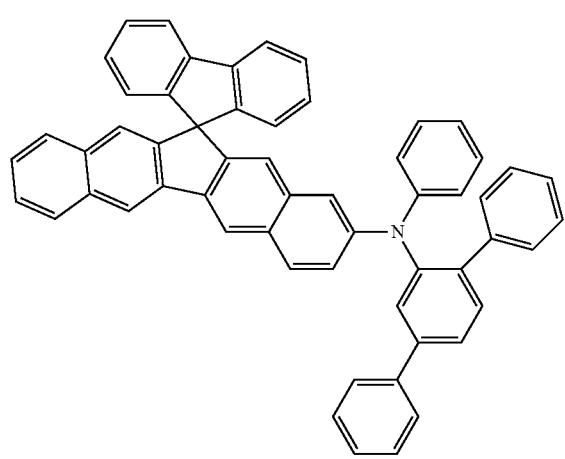 | 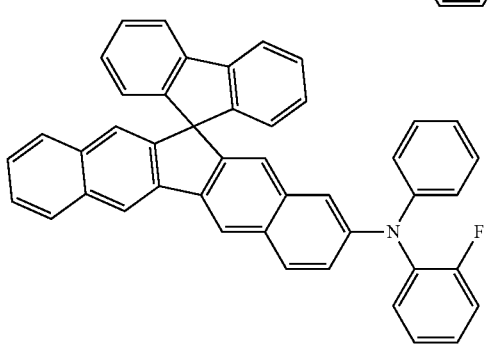 |
| 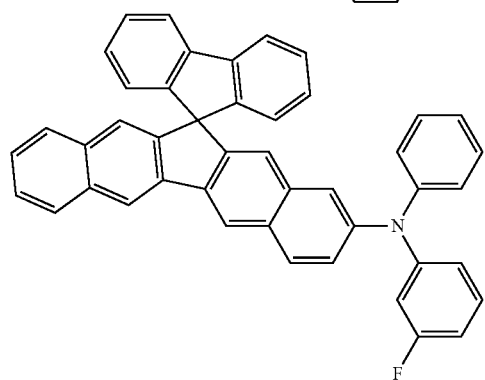 | 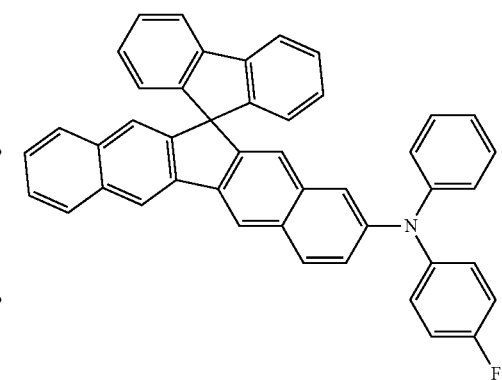 |

-continued
| 999 | 1000 |
|---|---|
| 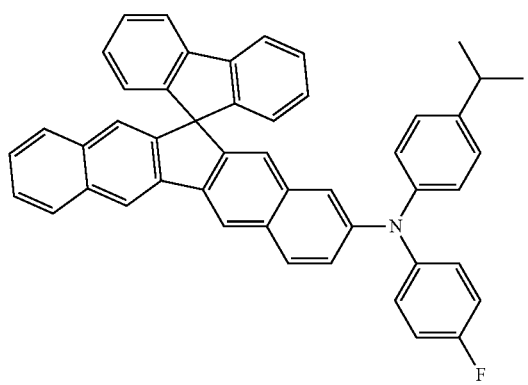 | 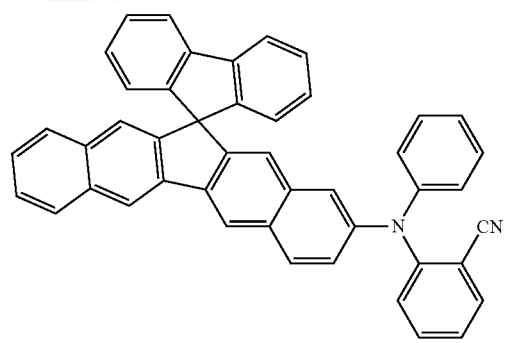 |
| 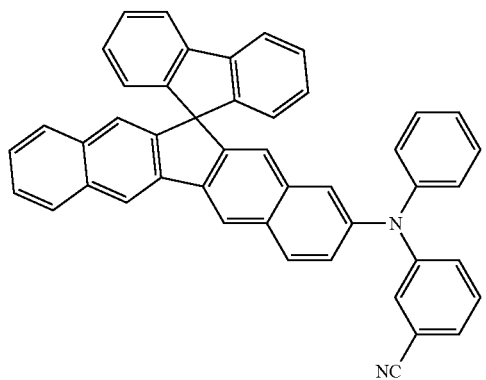 | 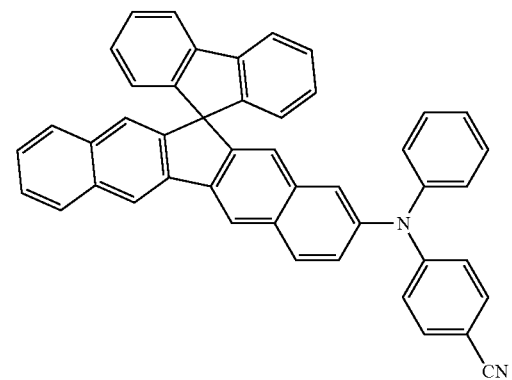 |
| 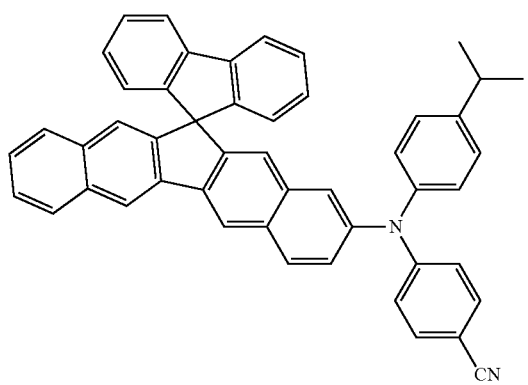 | 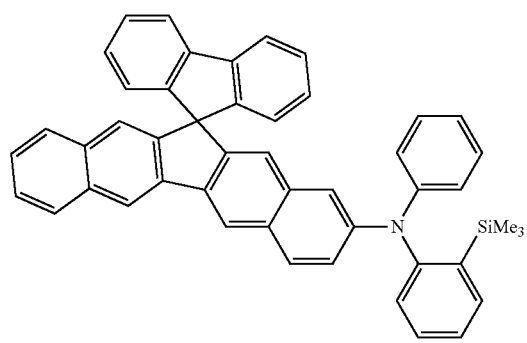 |
| 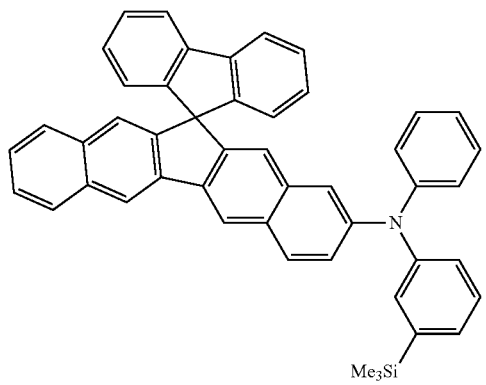 | 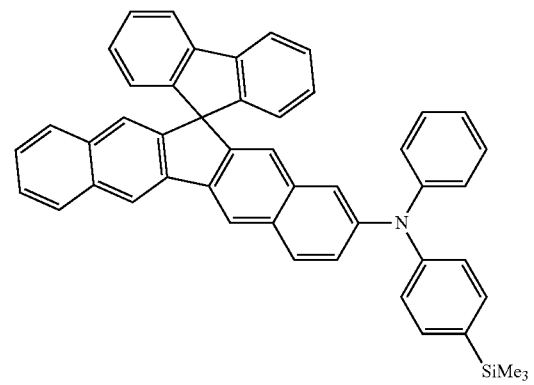 |

-continued
1001
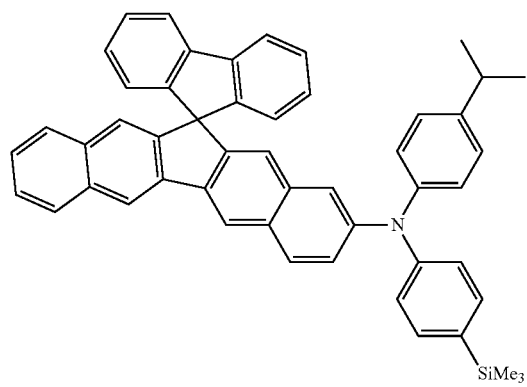
1002
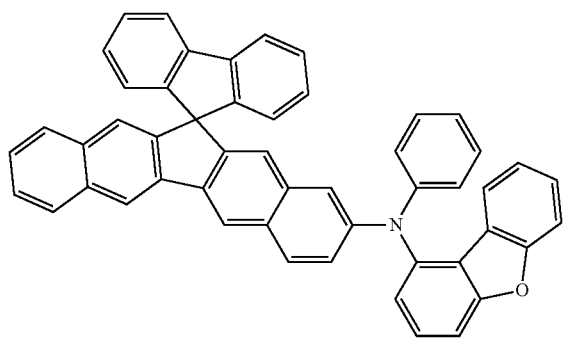
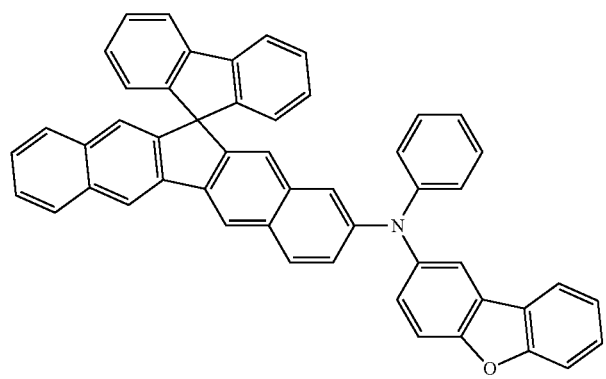
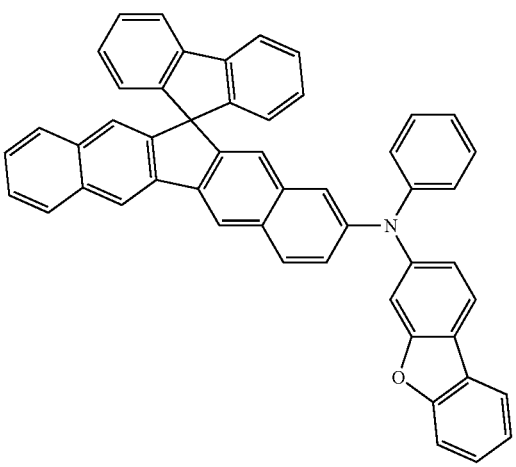
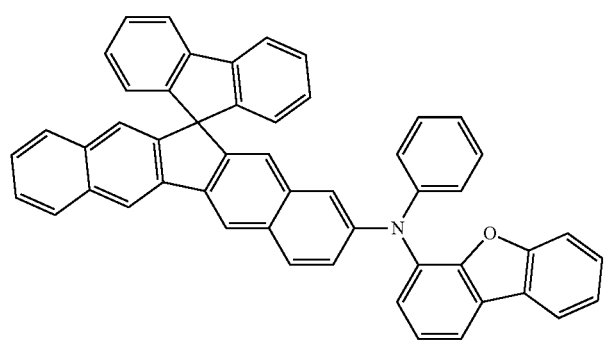
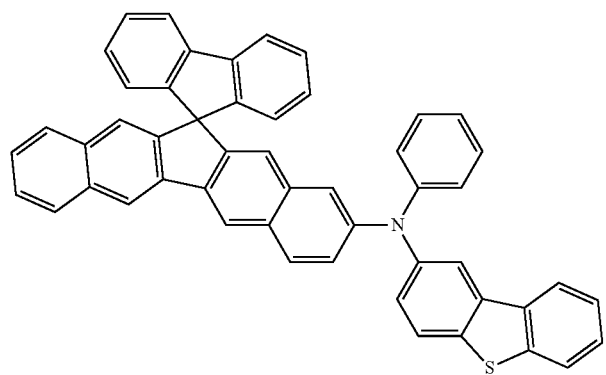

-continued
| 1003 | 1004 |
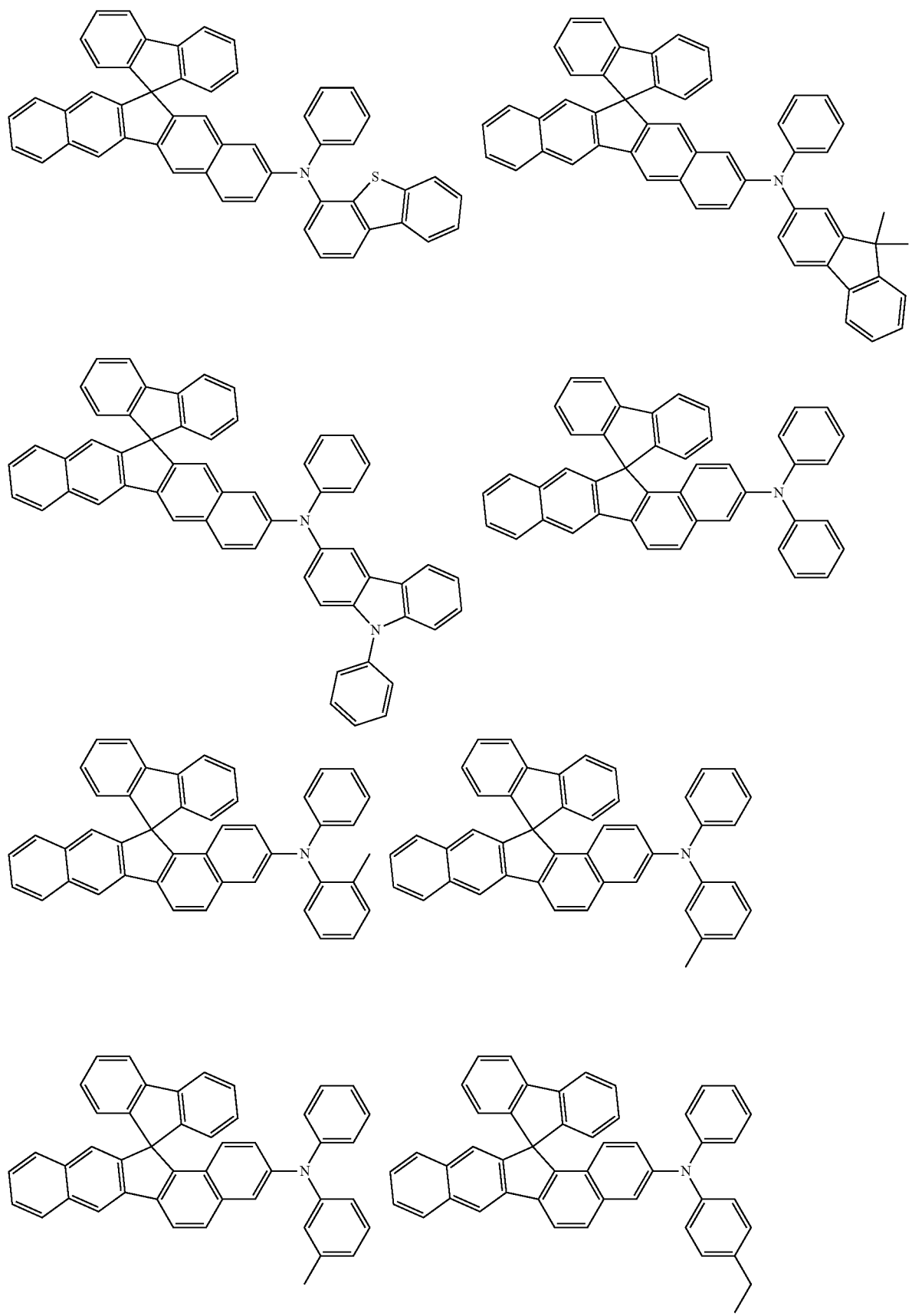

1005
1006
-continued
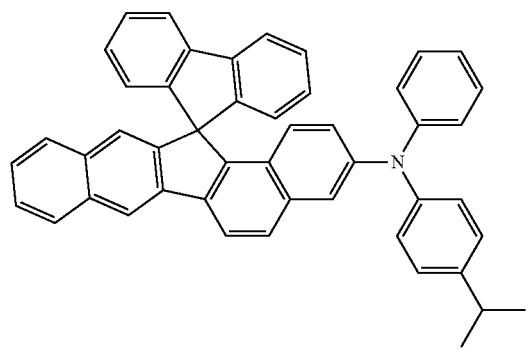
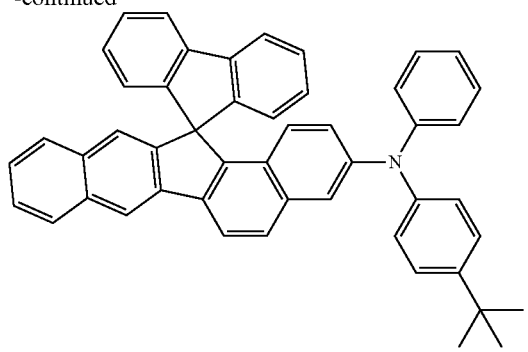
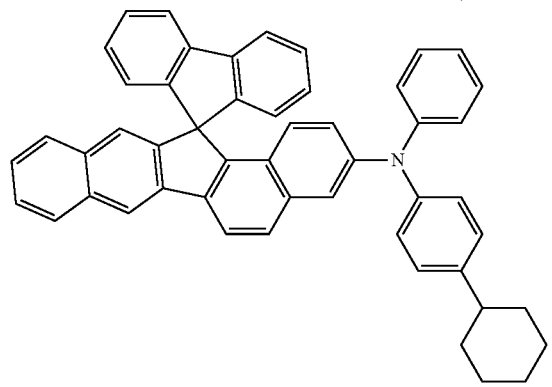
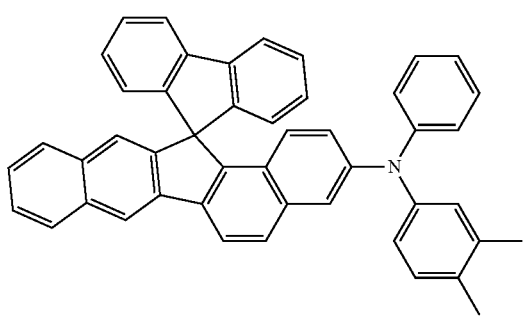
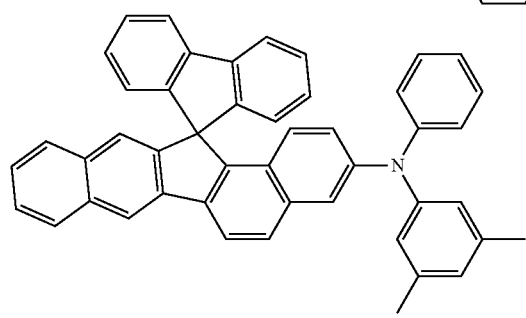
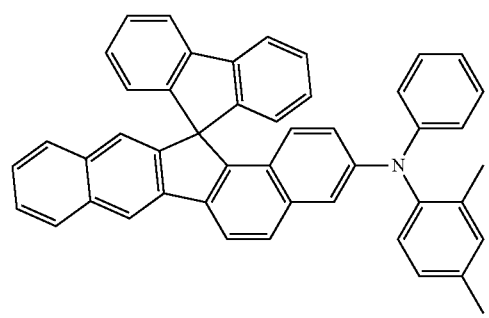
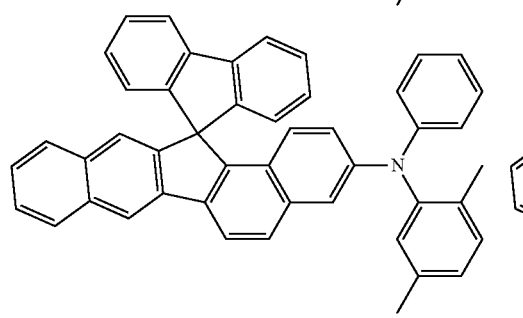
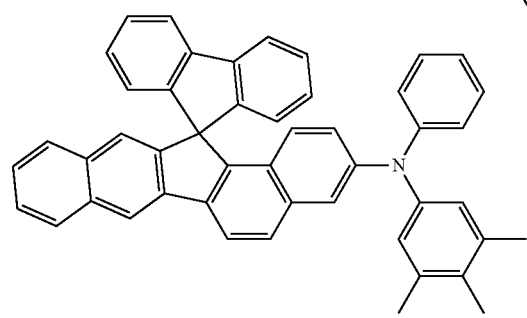
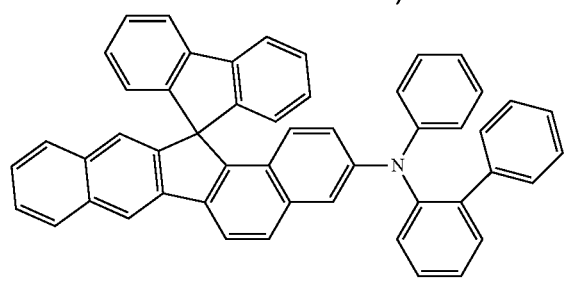
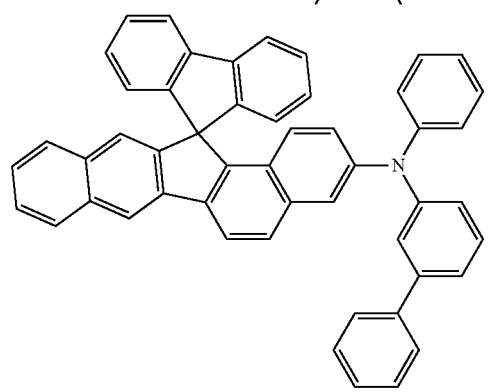

1007 1008
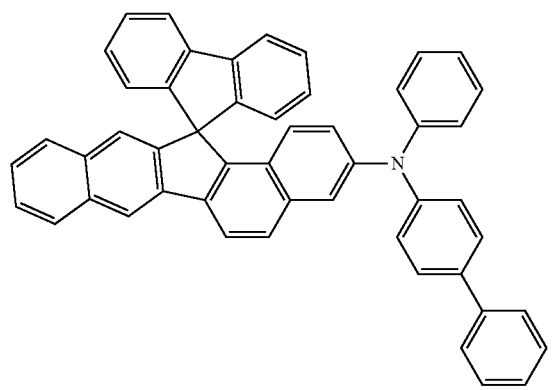
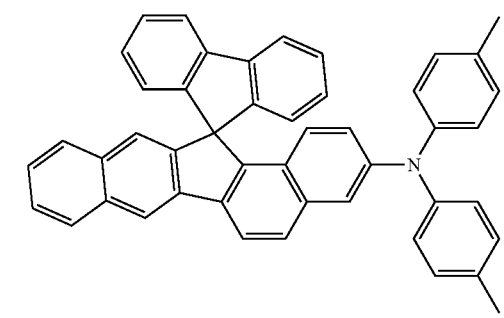
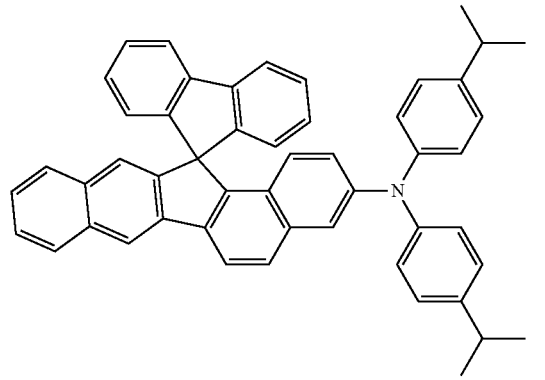
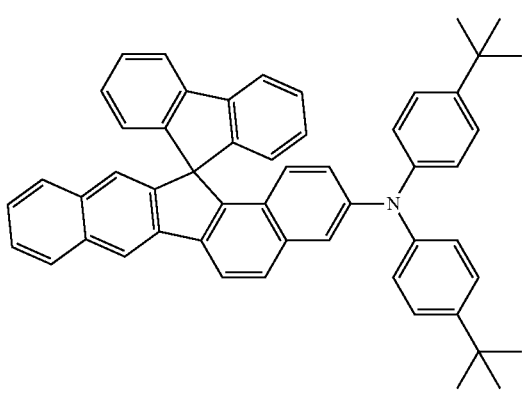
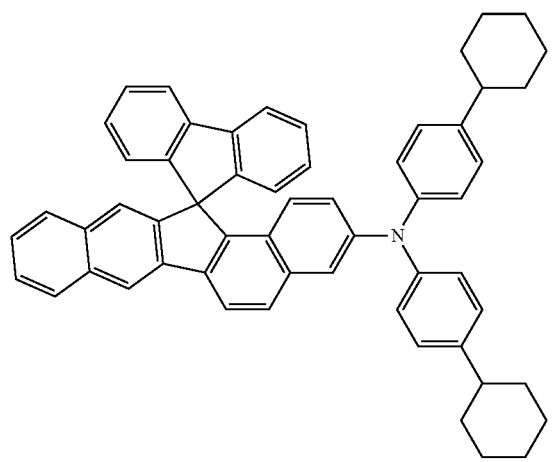
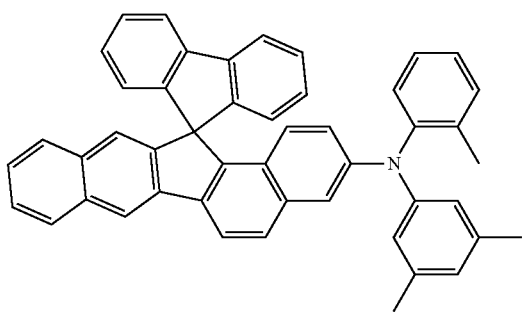
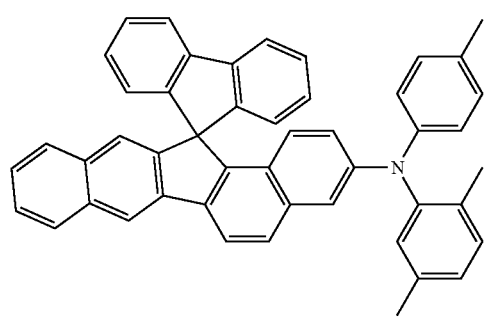
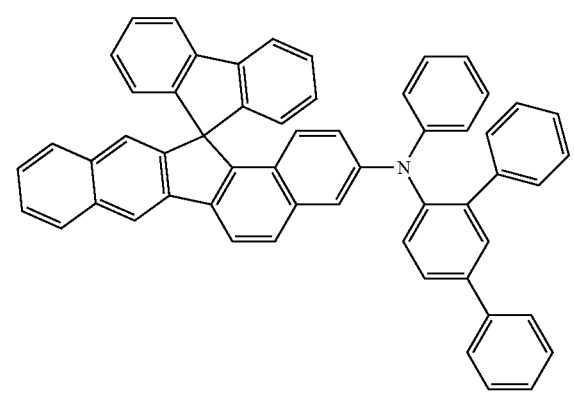

1009 1010
-continued
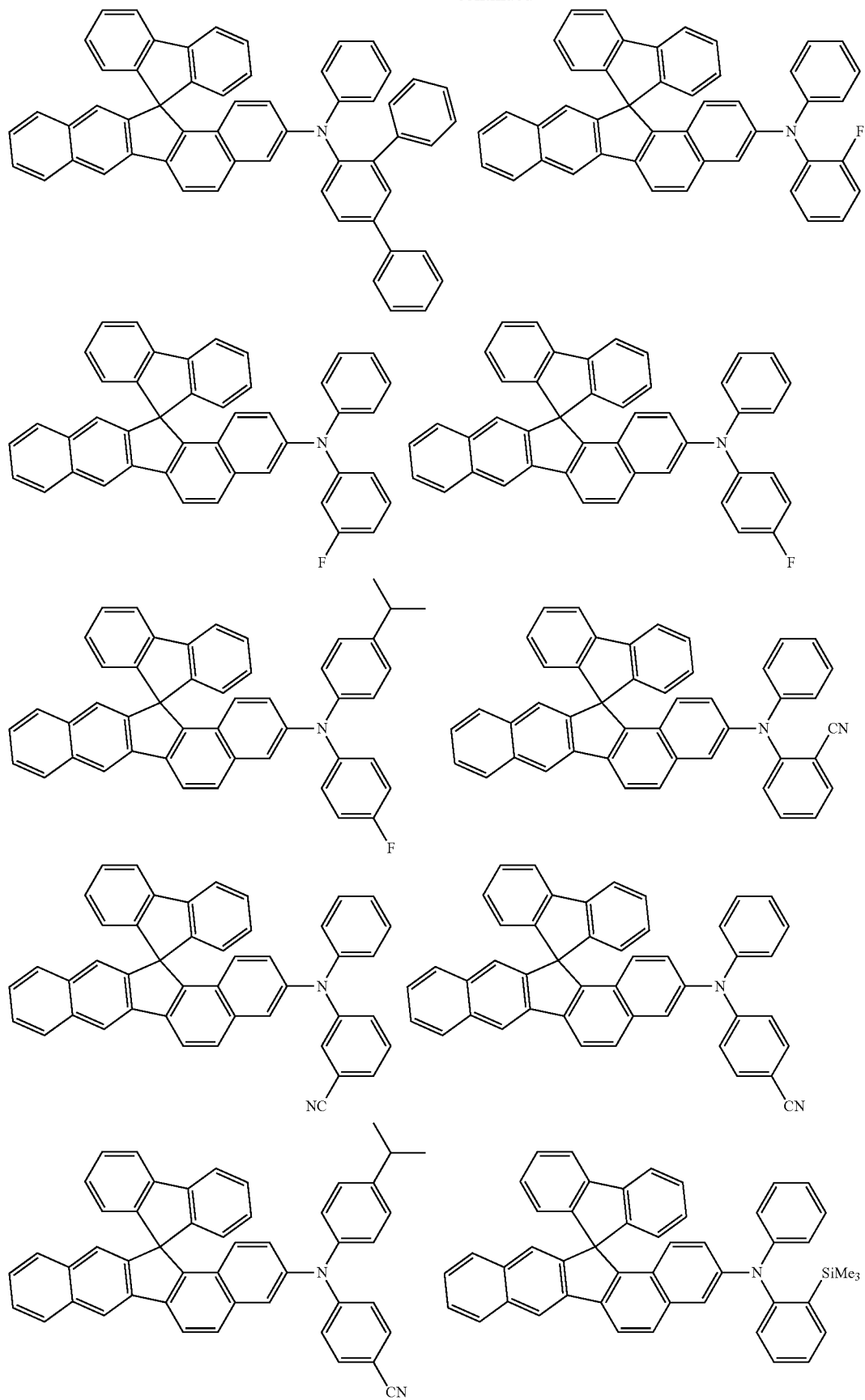

-continued
| 1011 | 1012 |
|---|---|
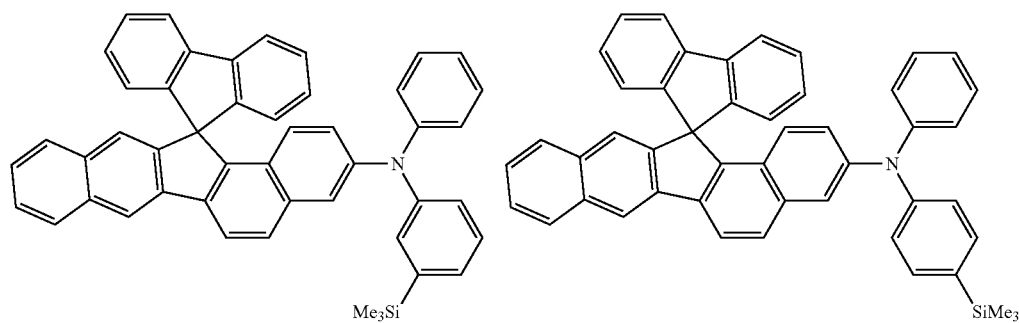
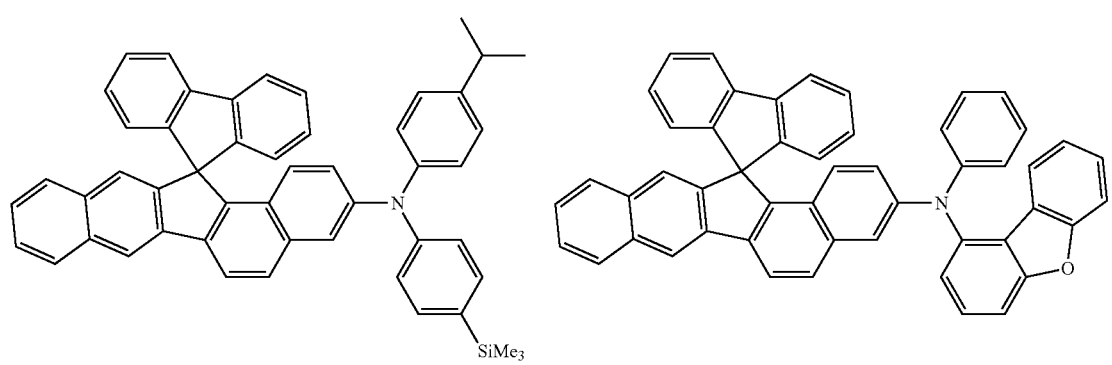
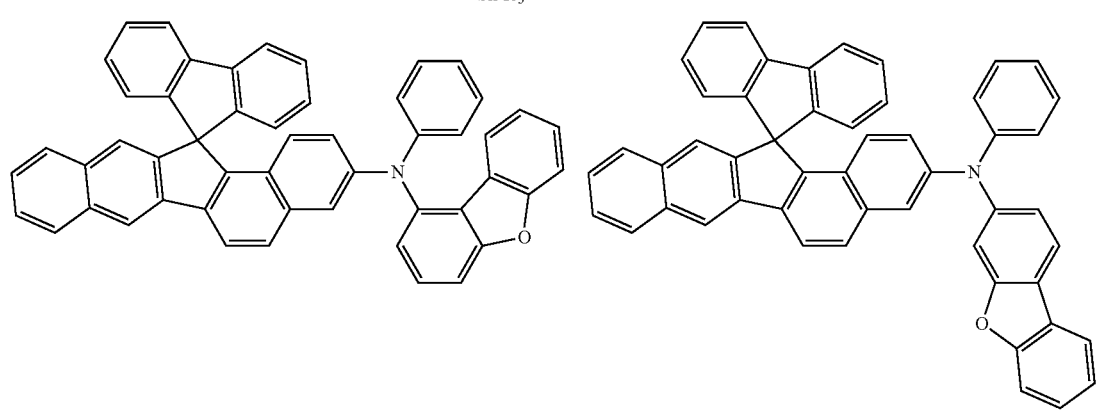
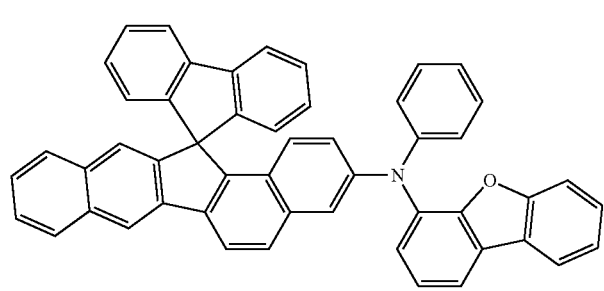
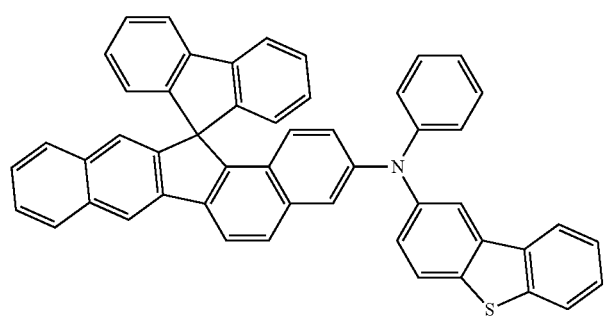

-continued
1013
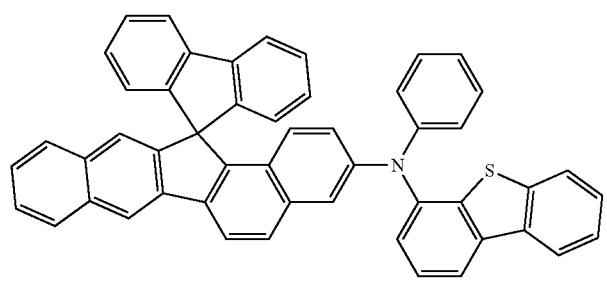
1014
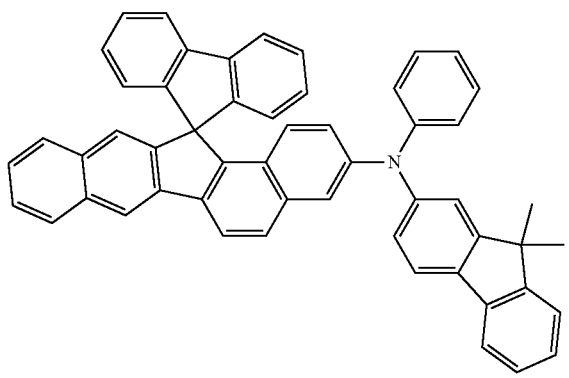
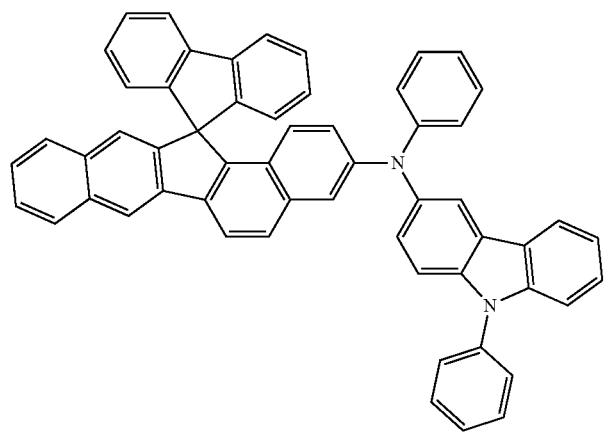
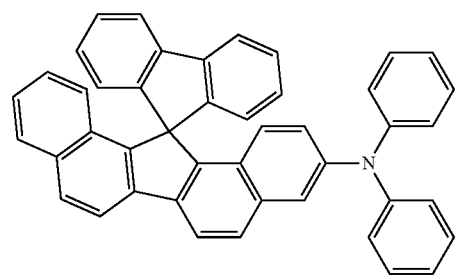
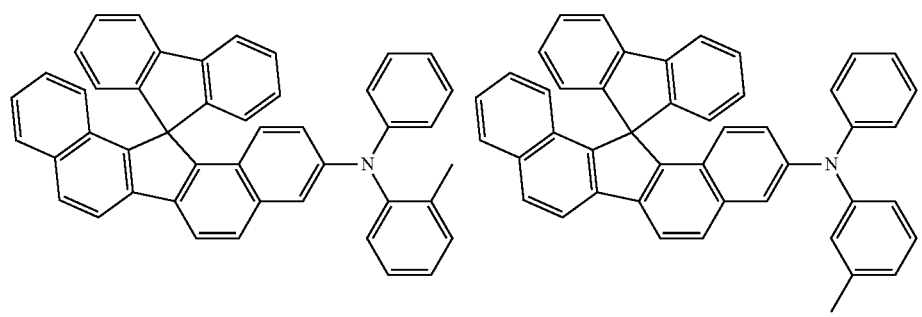
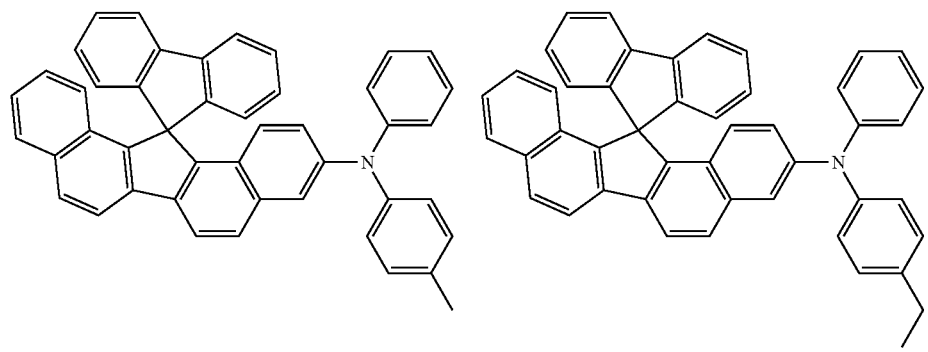

-continued
|1015|1016|
|---|---|
|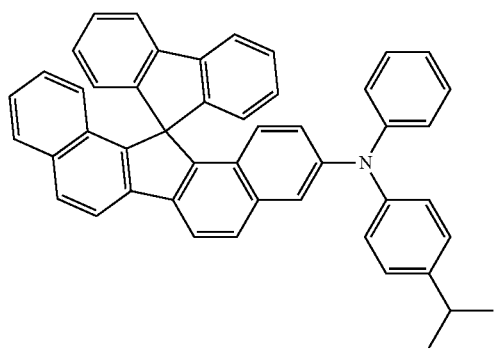|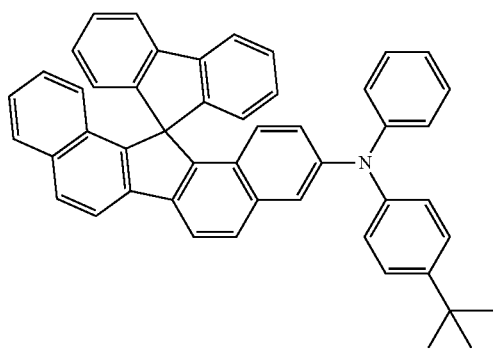|
|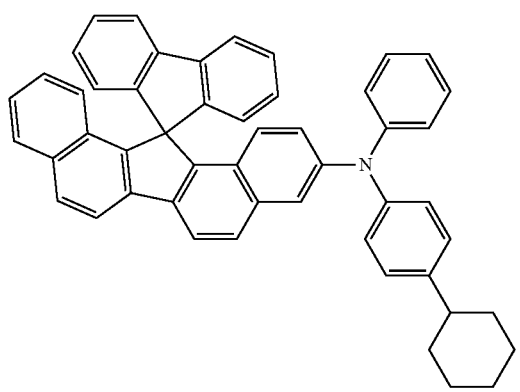|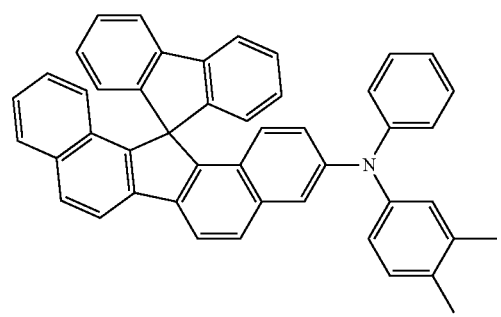|
|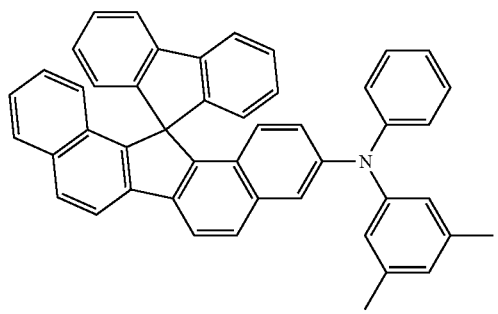|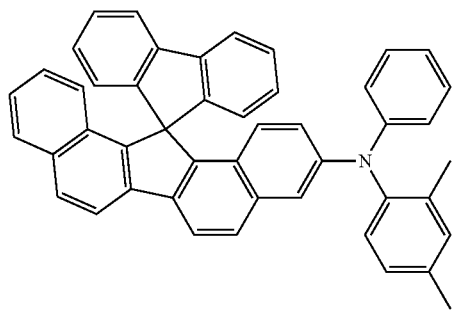|
|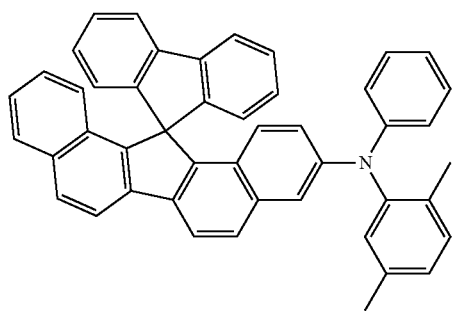|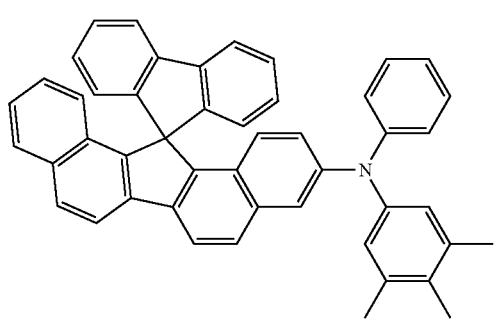|

1017            -continued            1018
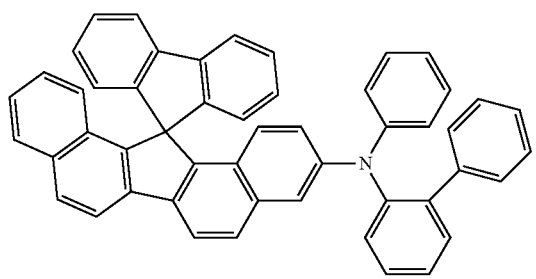
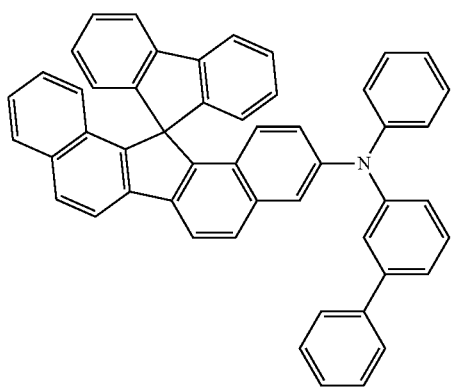
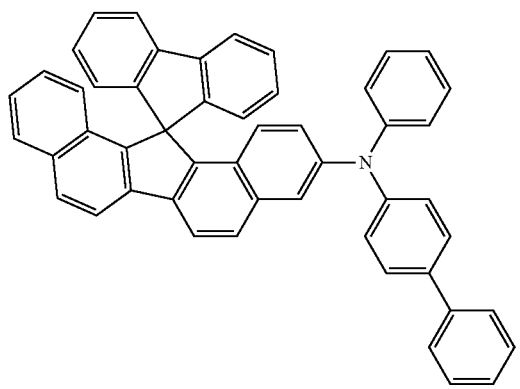
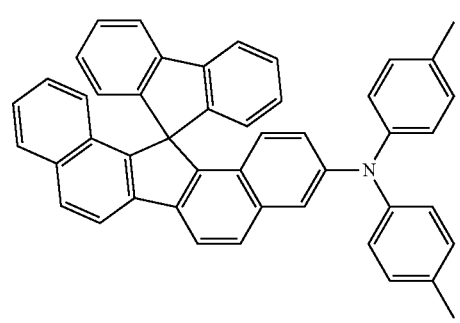
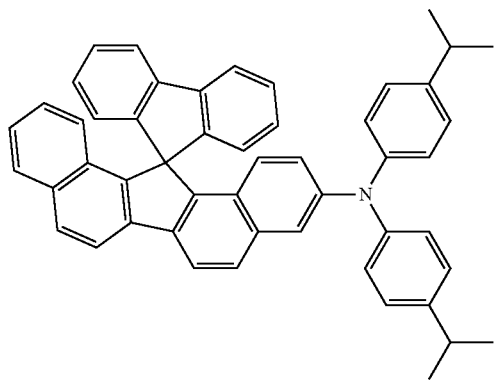
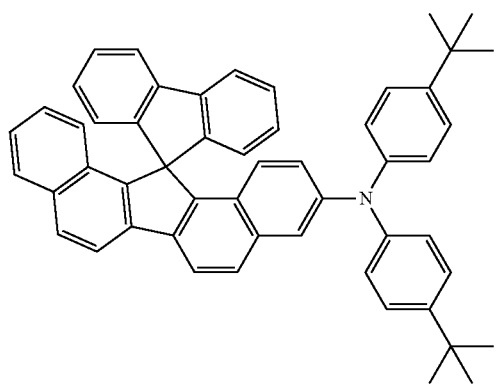
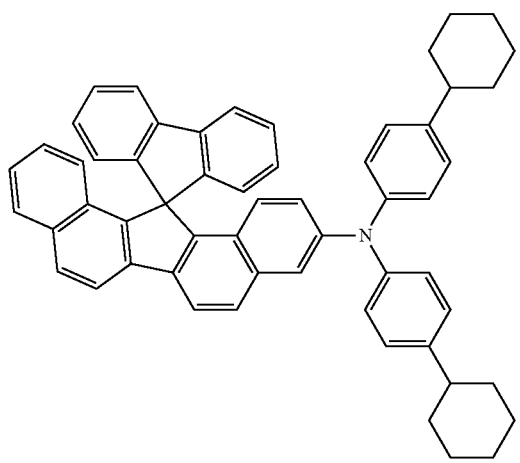
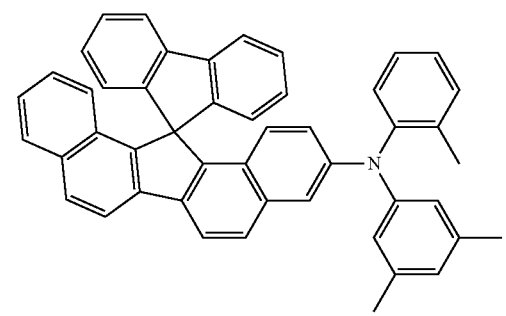

1019
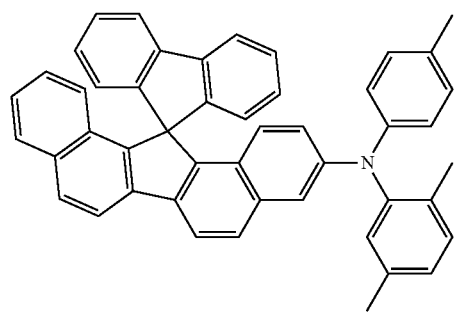
-continued
1020
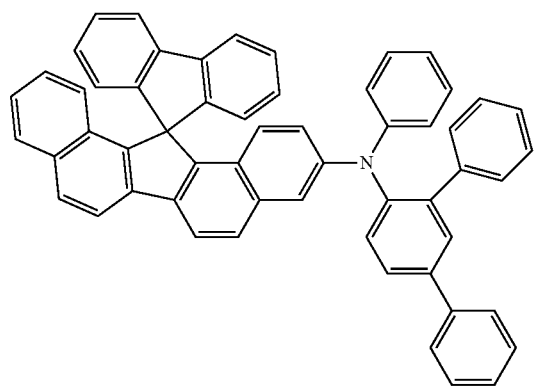
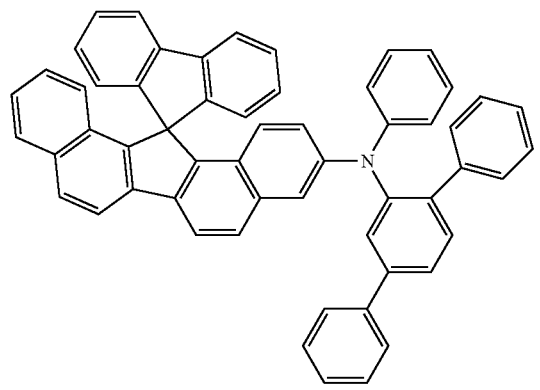
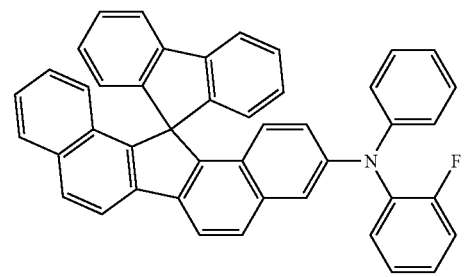
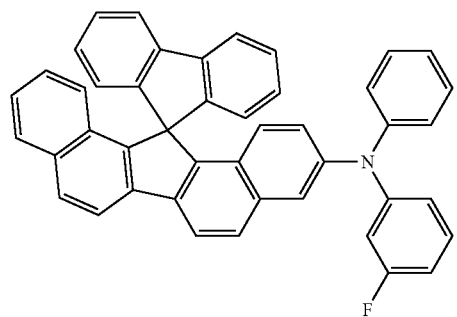
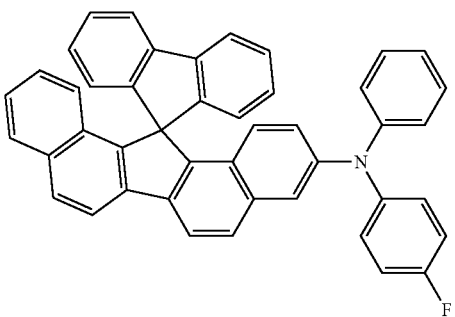
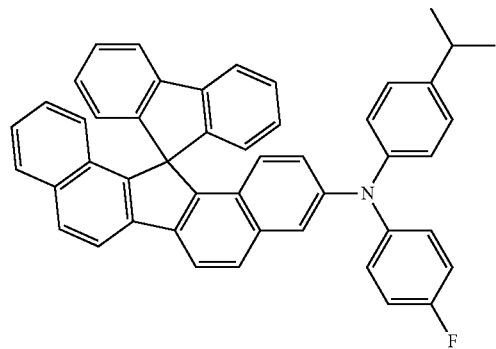
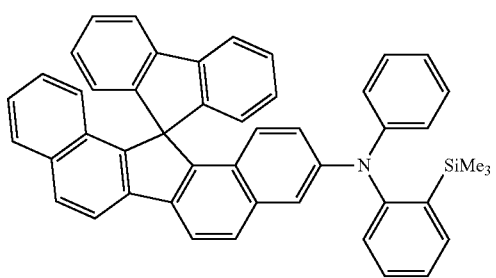

-continued
| 1021 | 1022 |
|---|---|
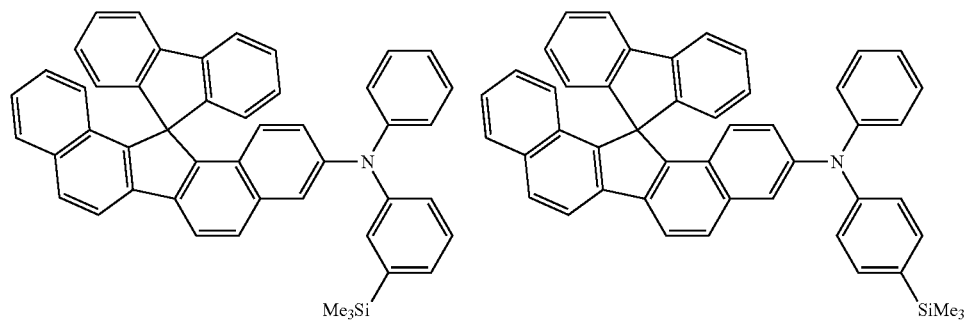
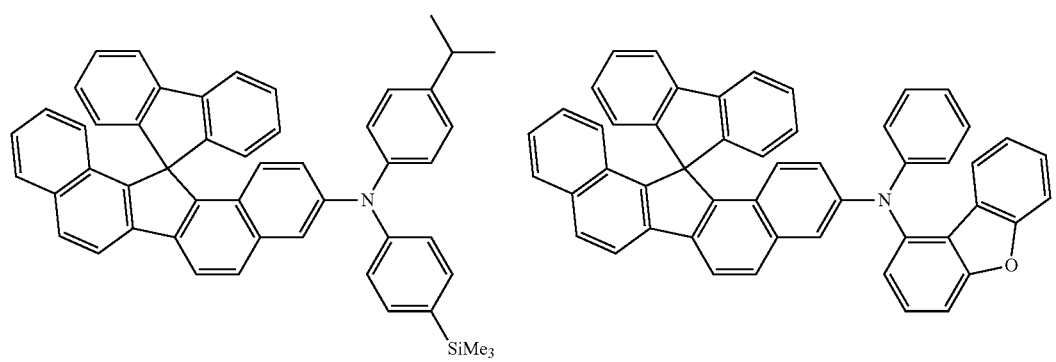
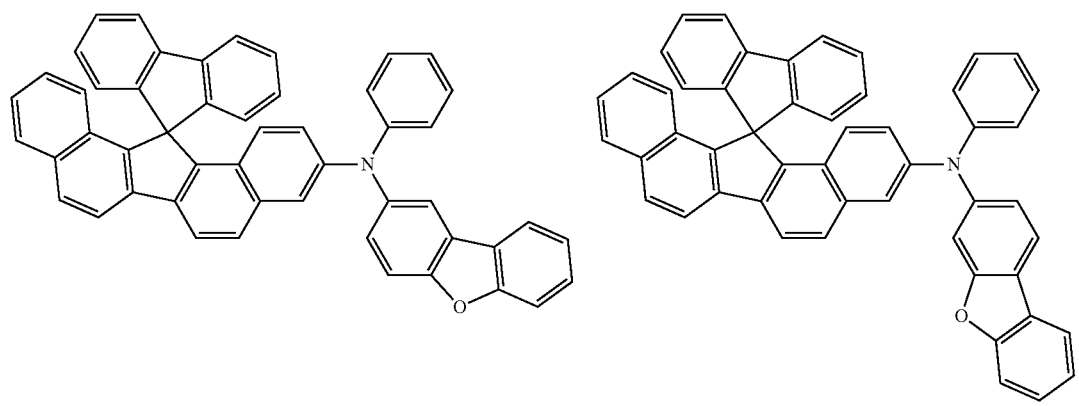
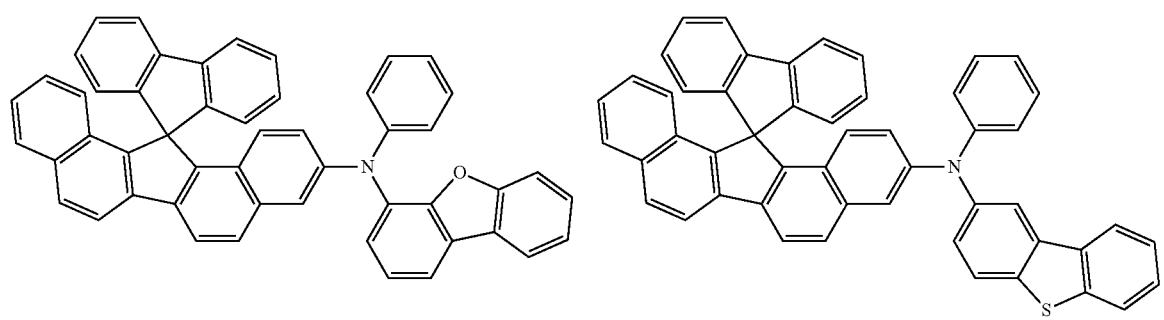

-continued
| 1023 | 1024 |
|---|---|
| 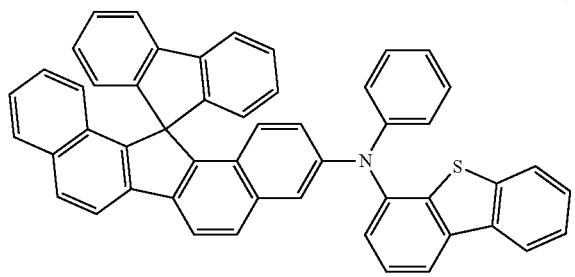 | 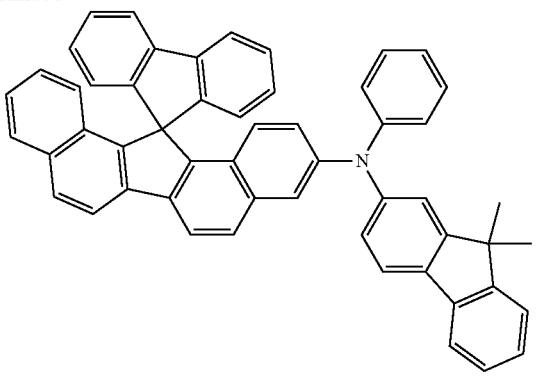 |
| 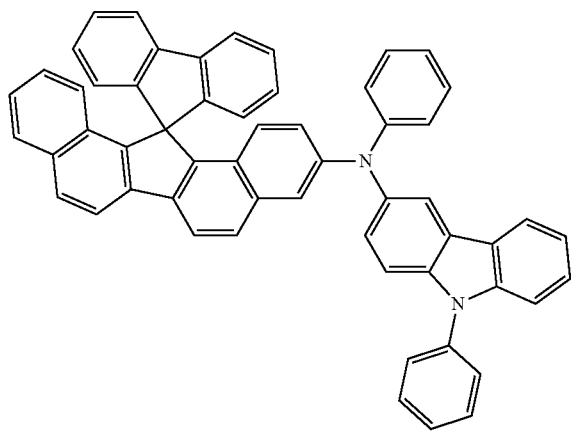 | 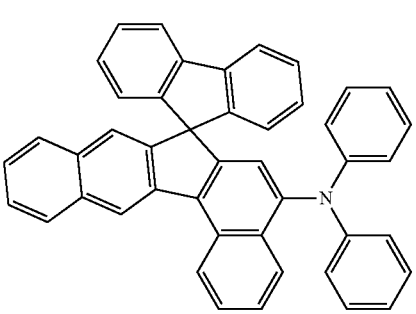 |
| 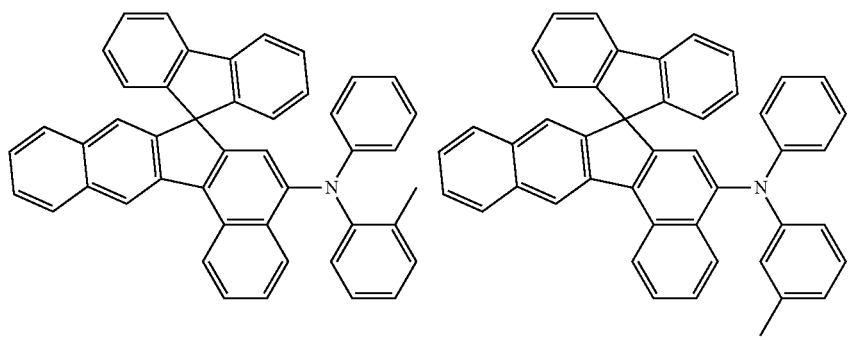 | 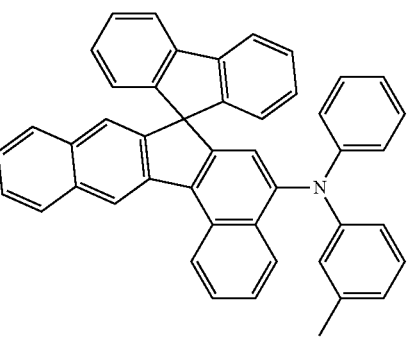 |
| 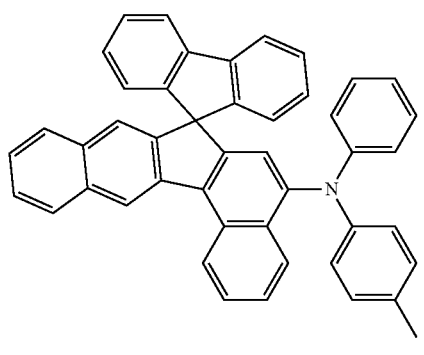 | 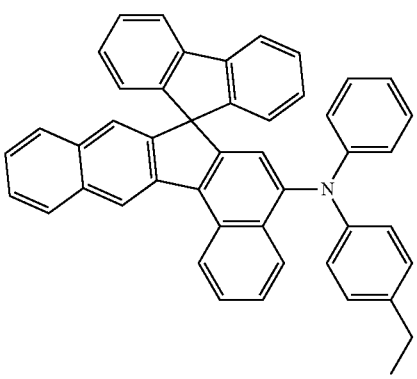 |

1025
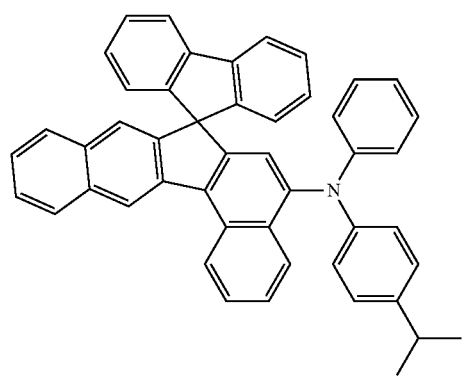
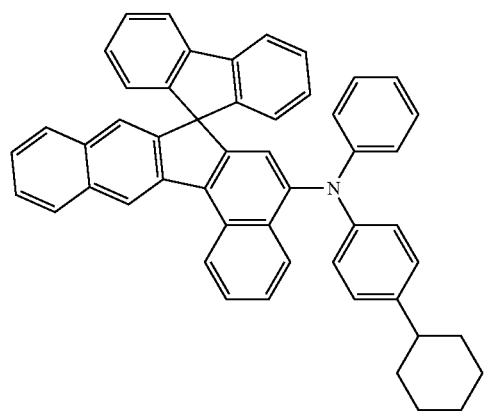
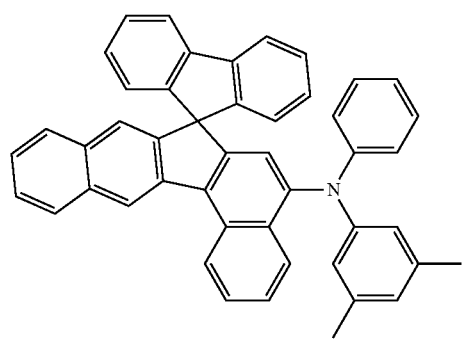
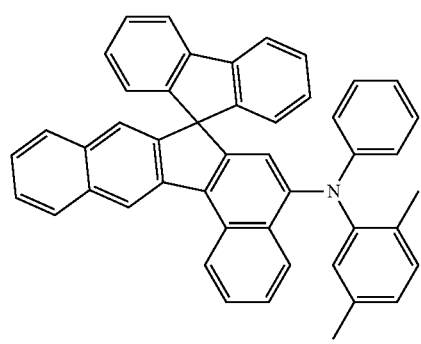
1026
-continued
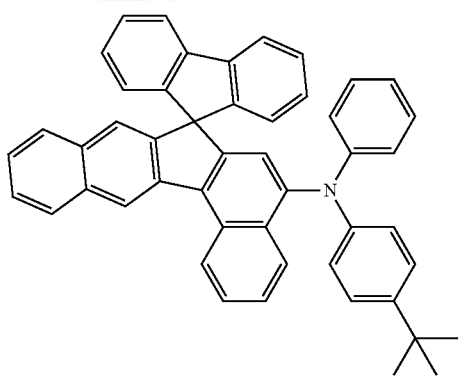
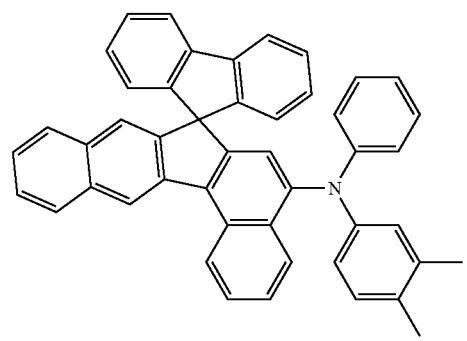
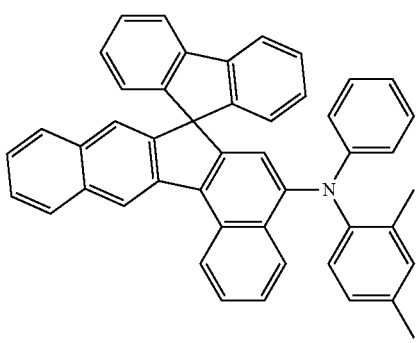
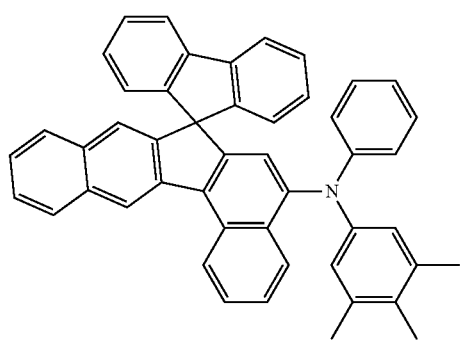

1027    1028
-continued
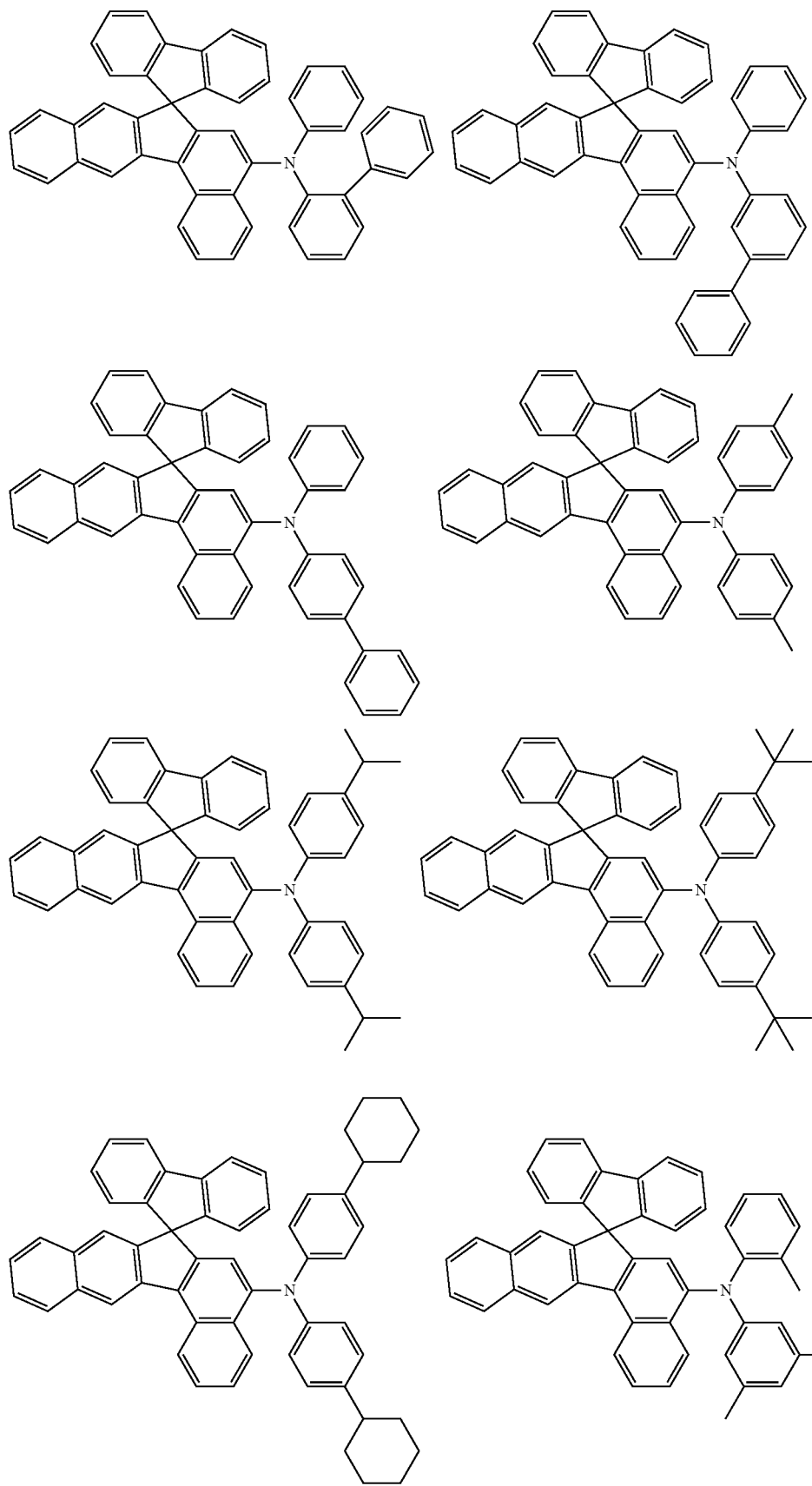

1029
-continued
1030
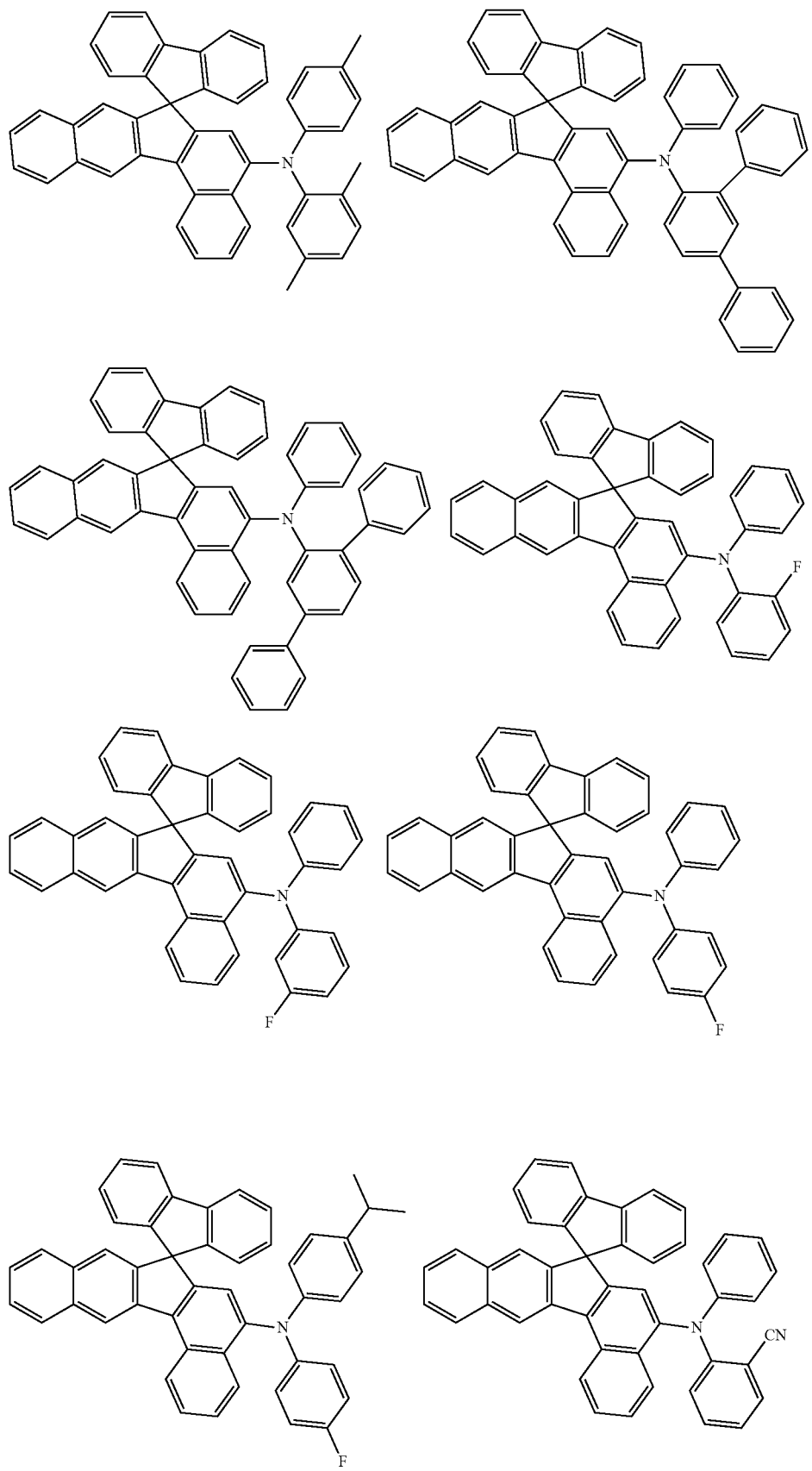

1031
-continued
1032
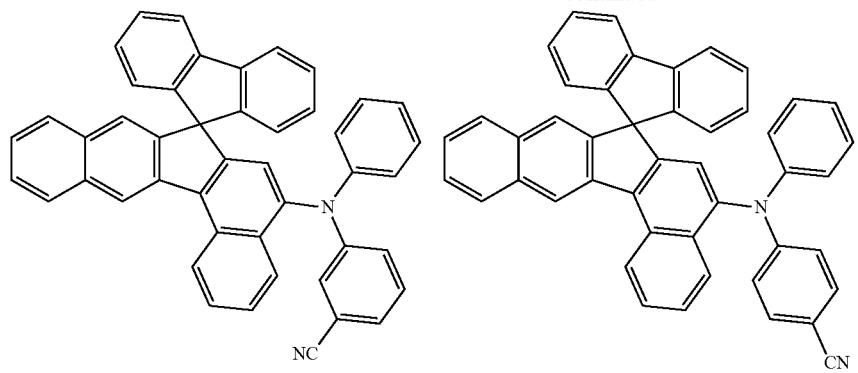
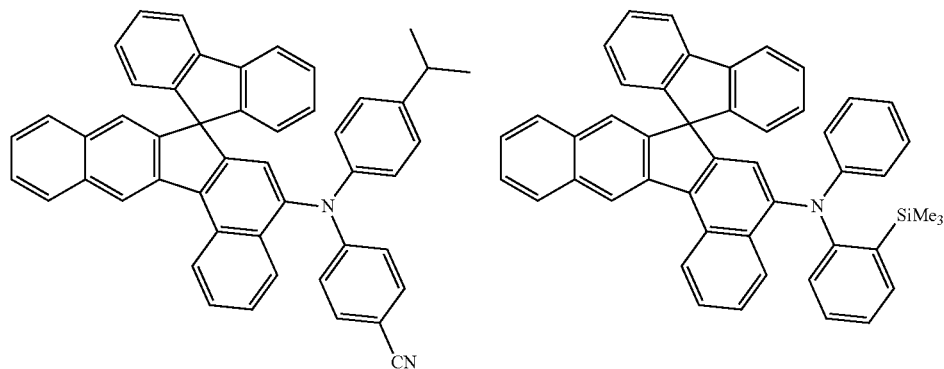
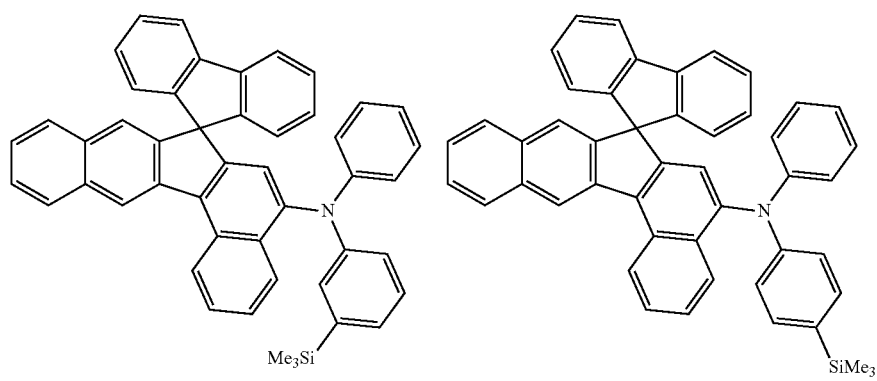
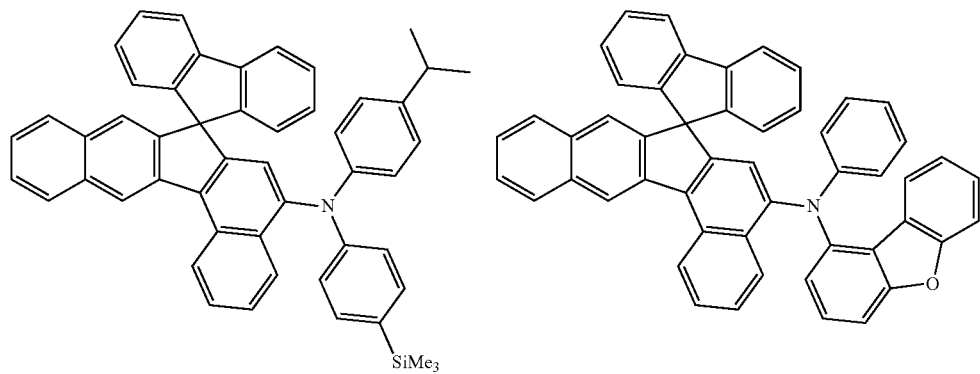

-continued
| 1033 | 1034 |
|---|---|
| 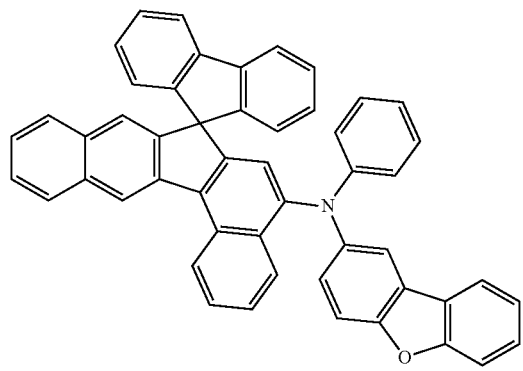 | 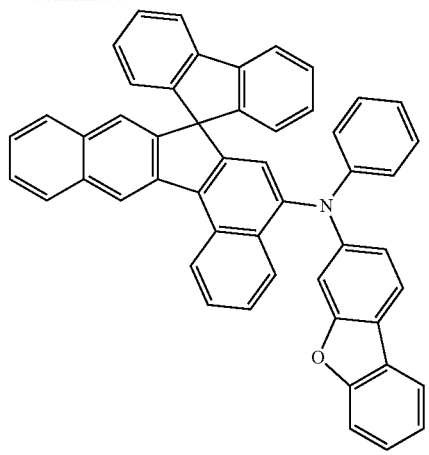 |
| 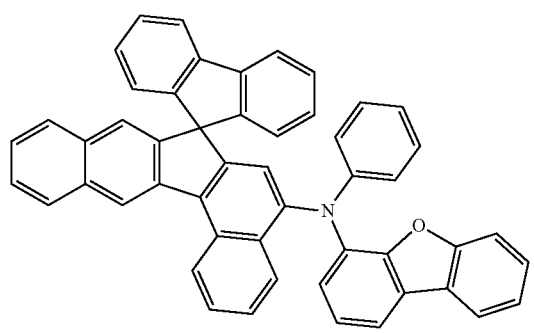 | 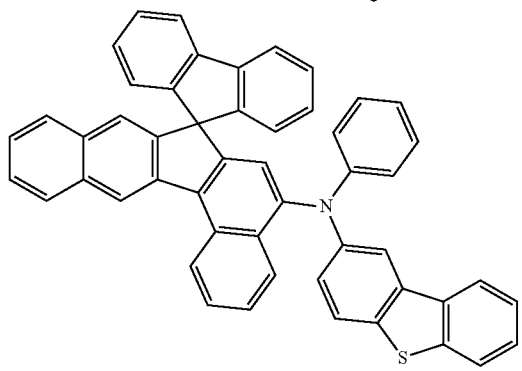 |
| 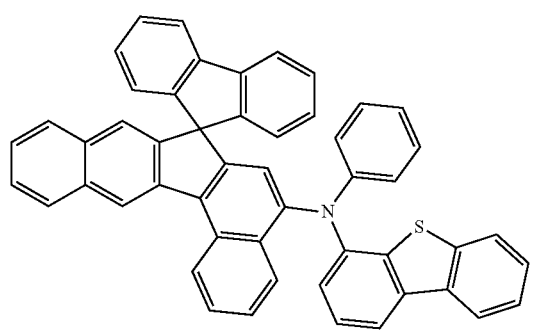 | 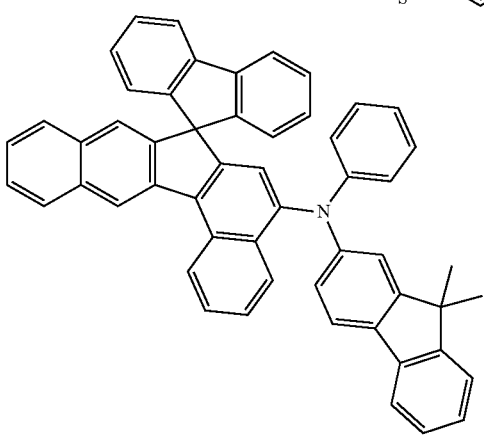 |
| 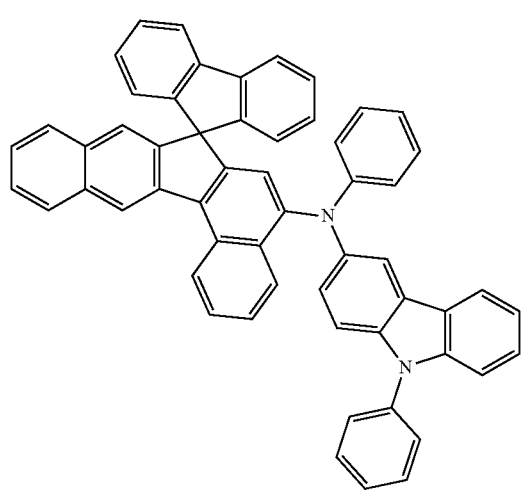 | 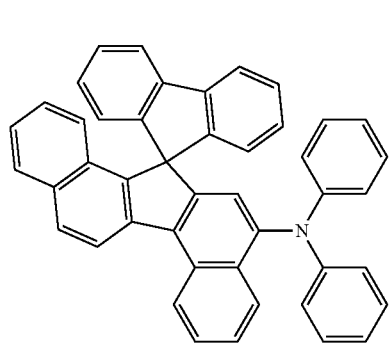 |

1035
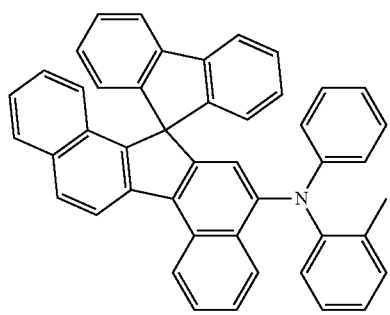
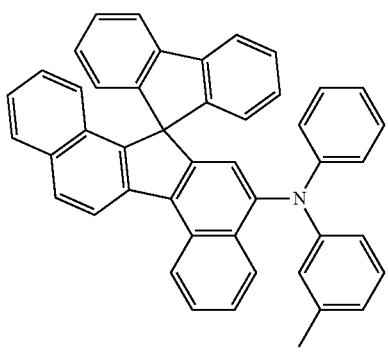
-continued
1036
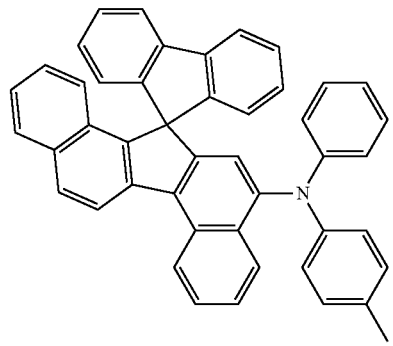
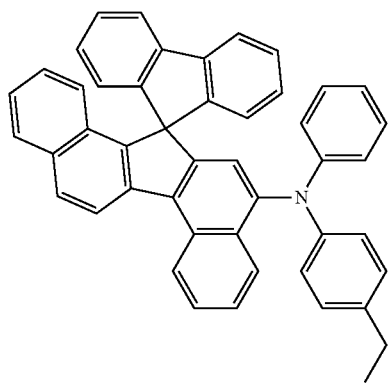
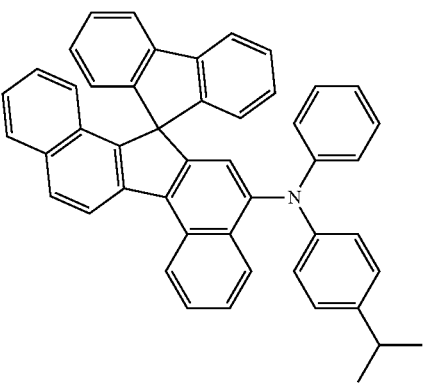
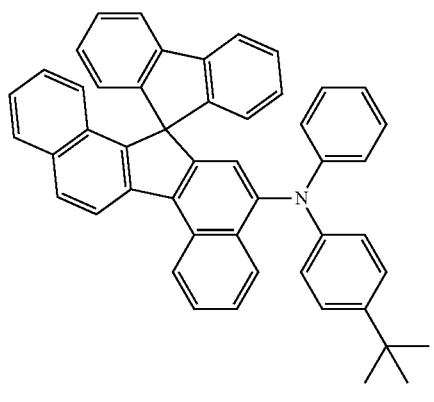
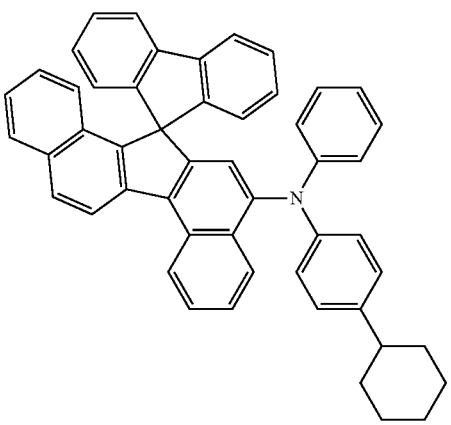
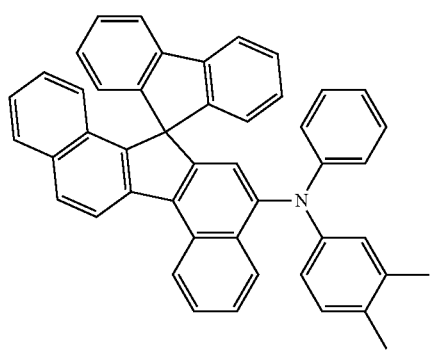
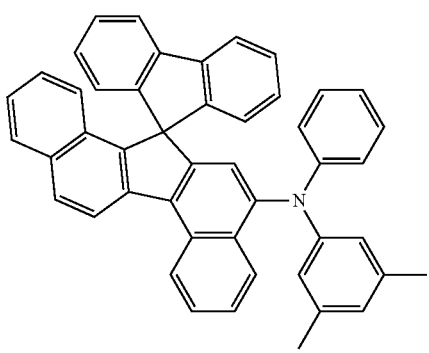

1037
1038
-continued
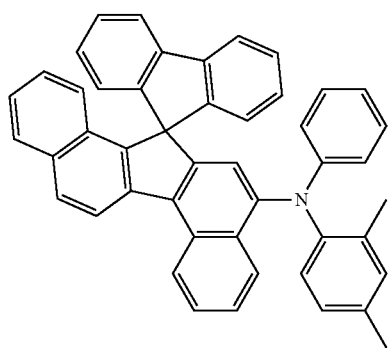

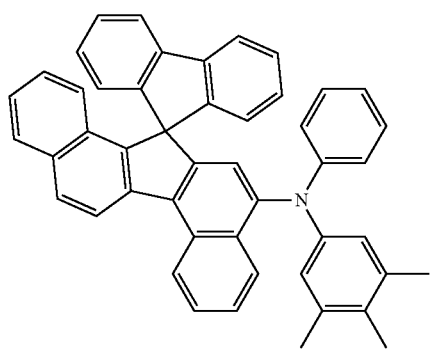
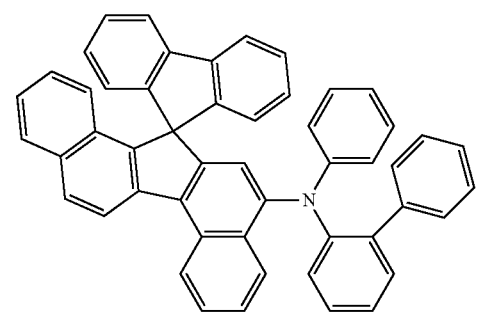
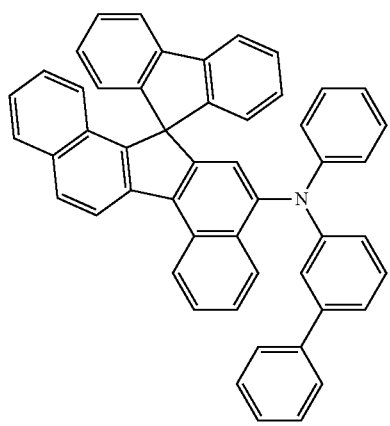
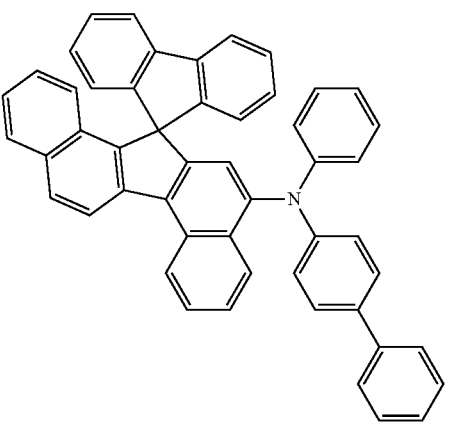
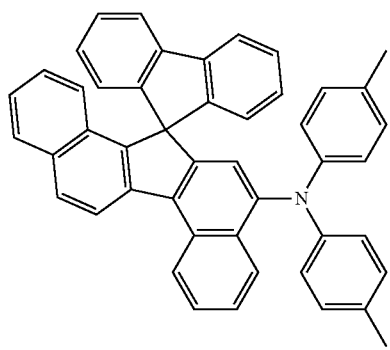
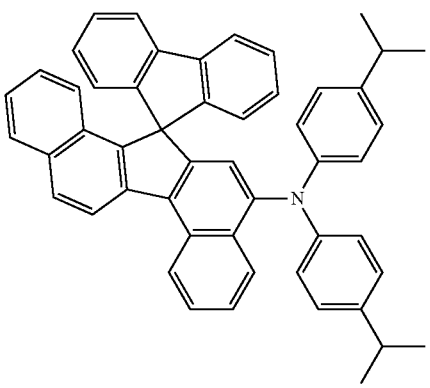

| 1039 | 1040 |
|---|---|
| 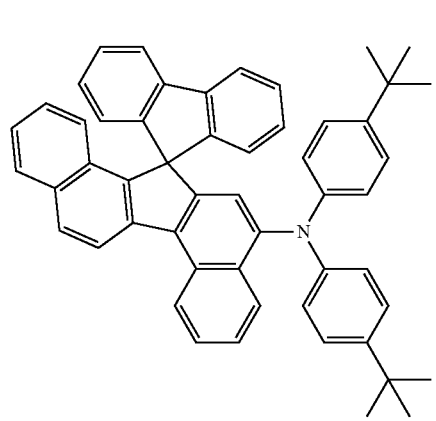 | 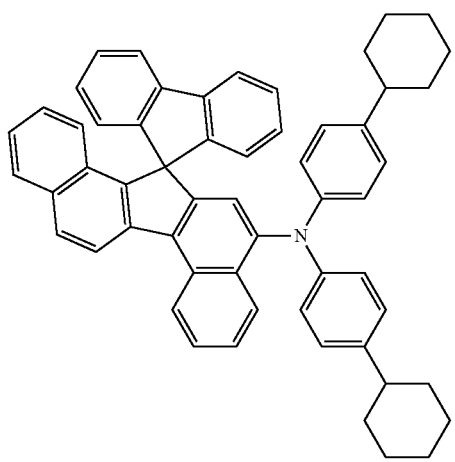 |
| 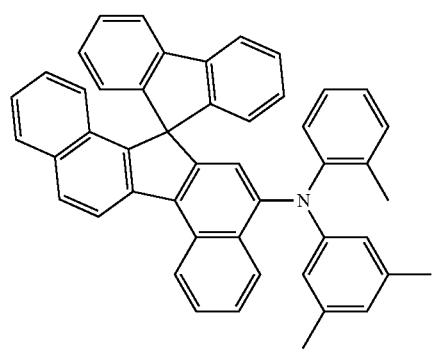 | 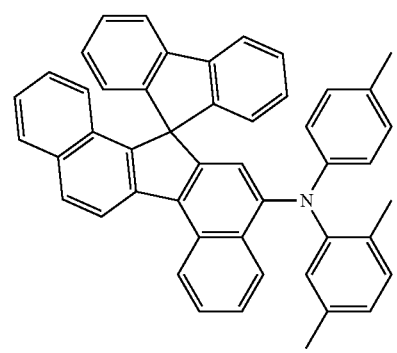 |
| 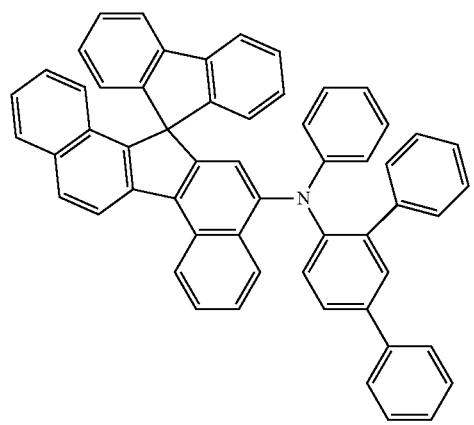 | 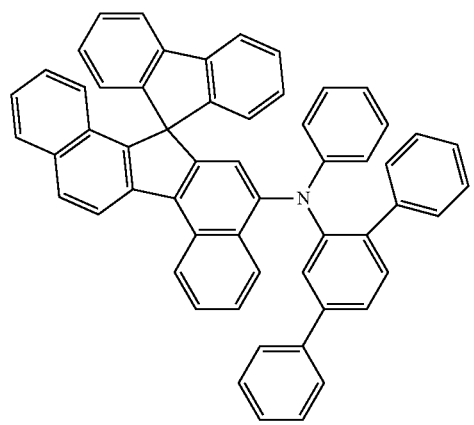 |
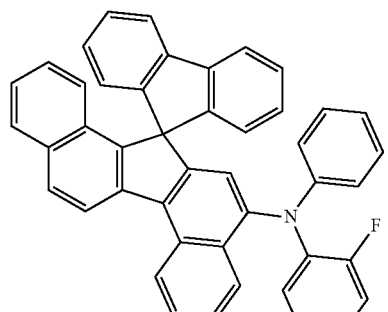 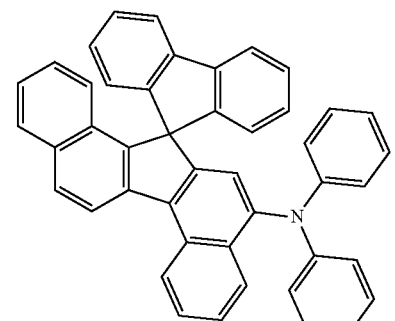 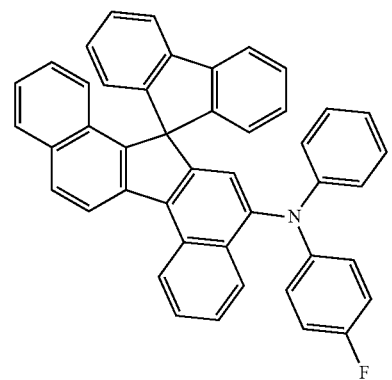

1041
-continued
1042
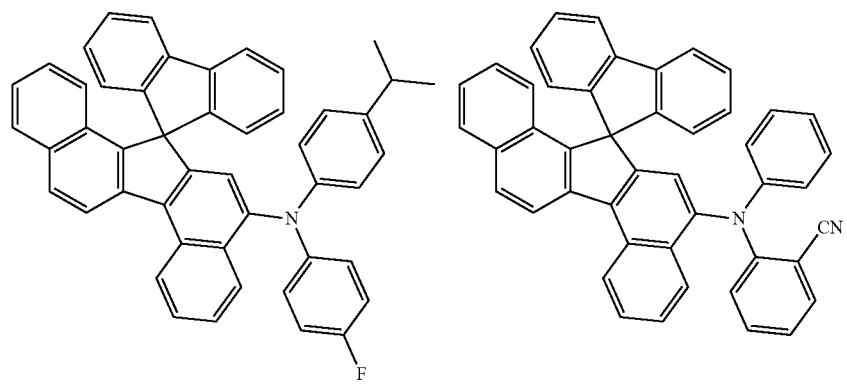
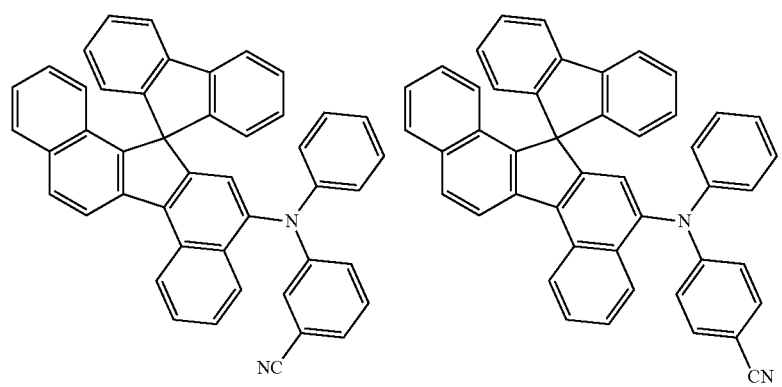
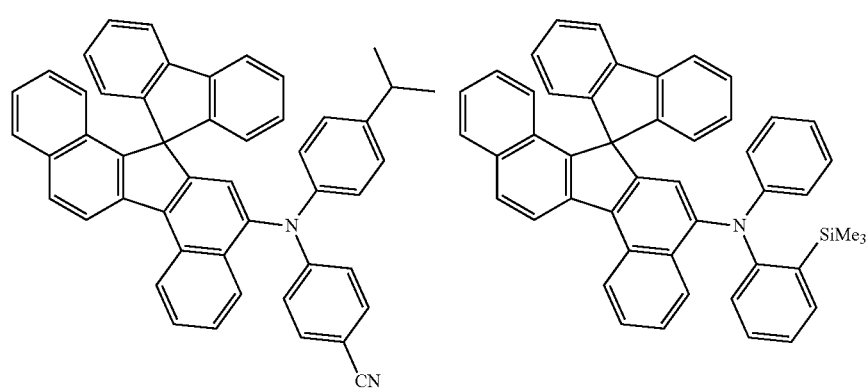
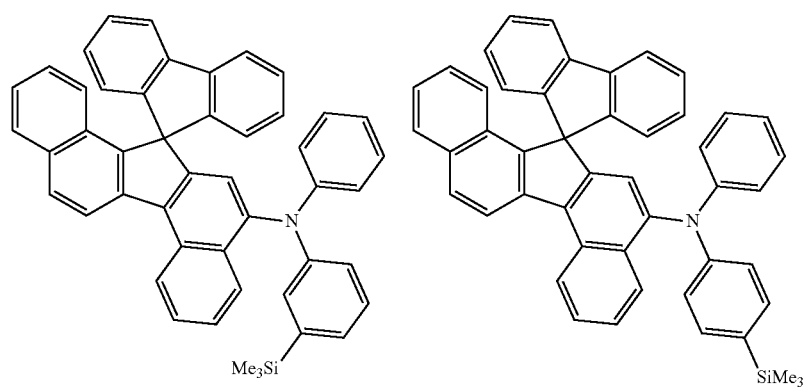

1043
-continued
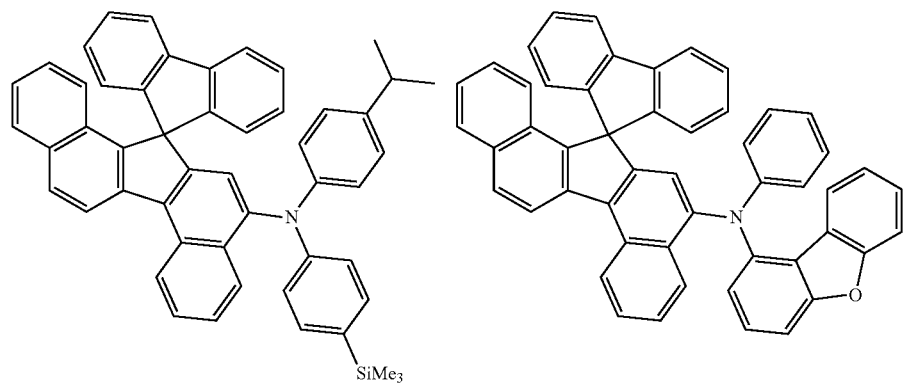
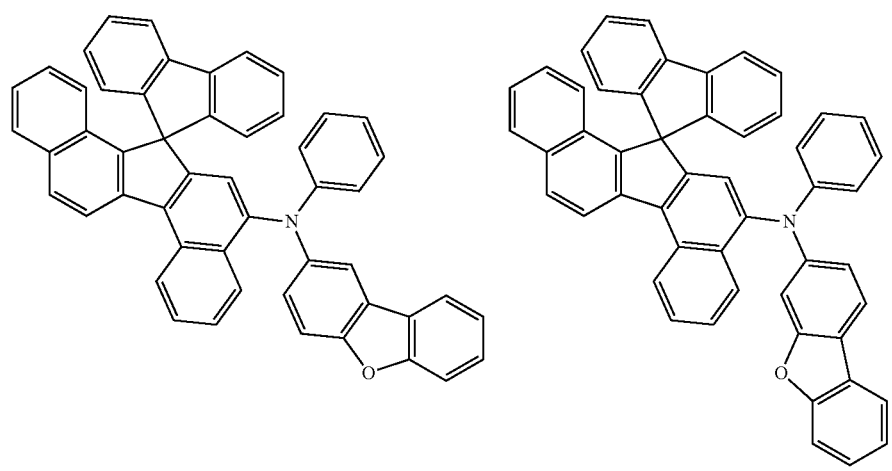
1044
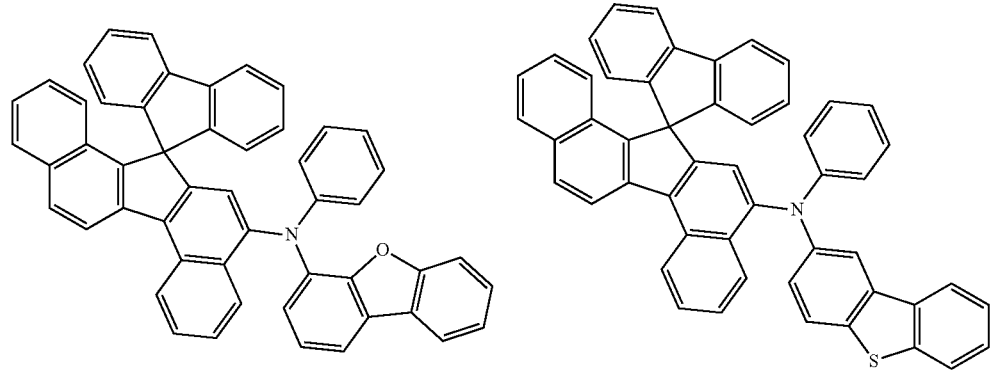
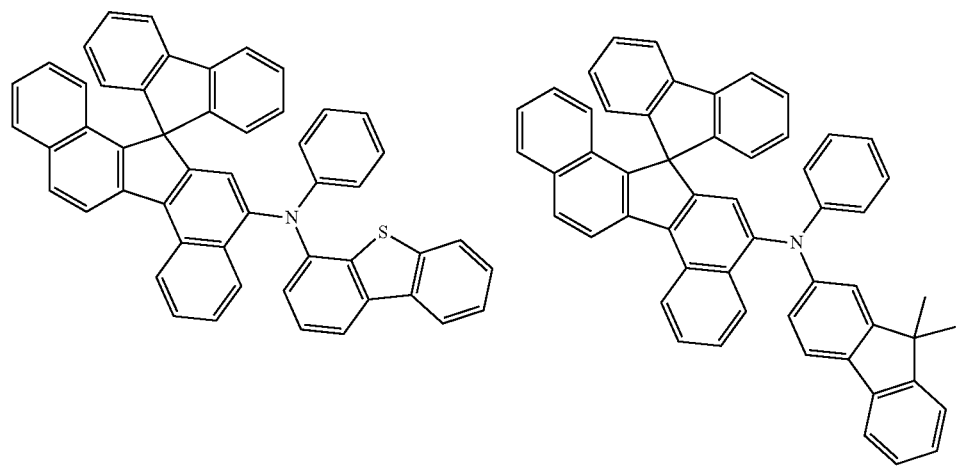

1045
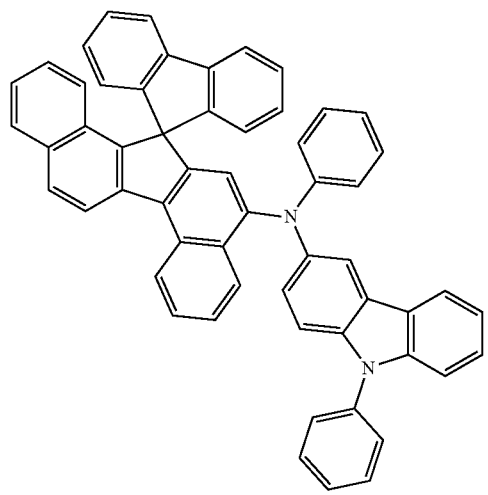
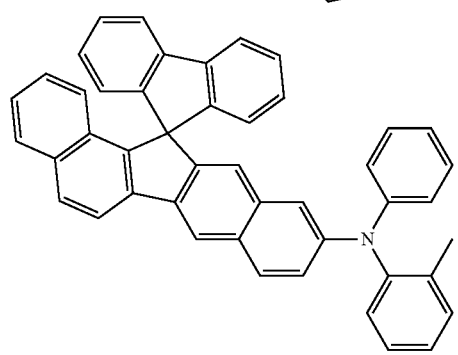
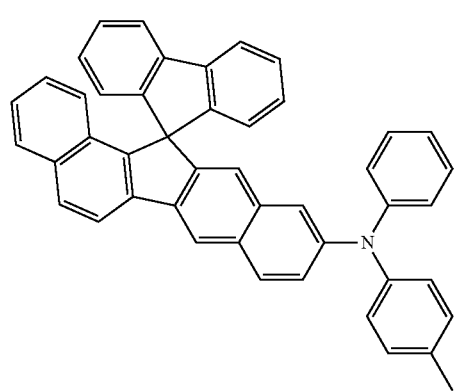
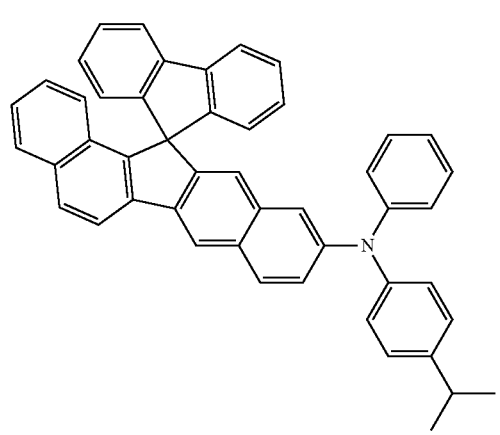
1046
-continued
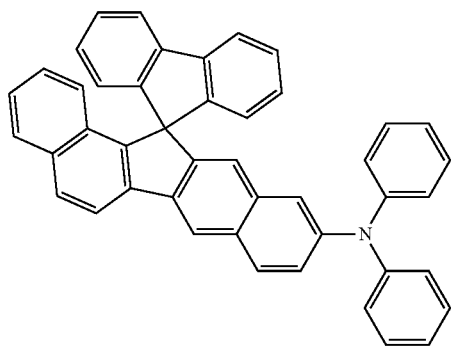
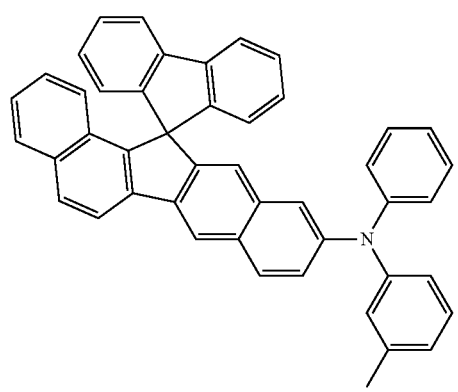
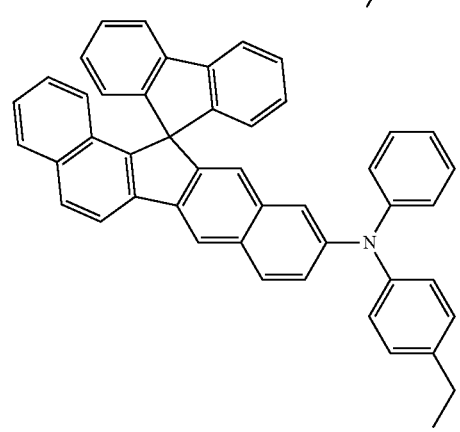
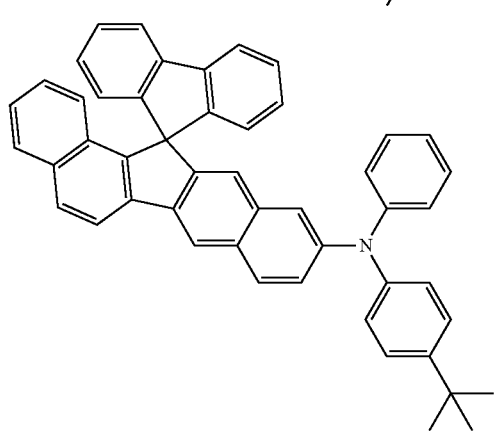

1047 1048
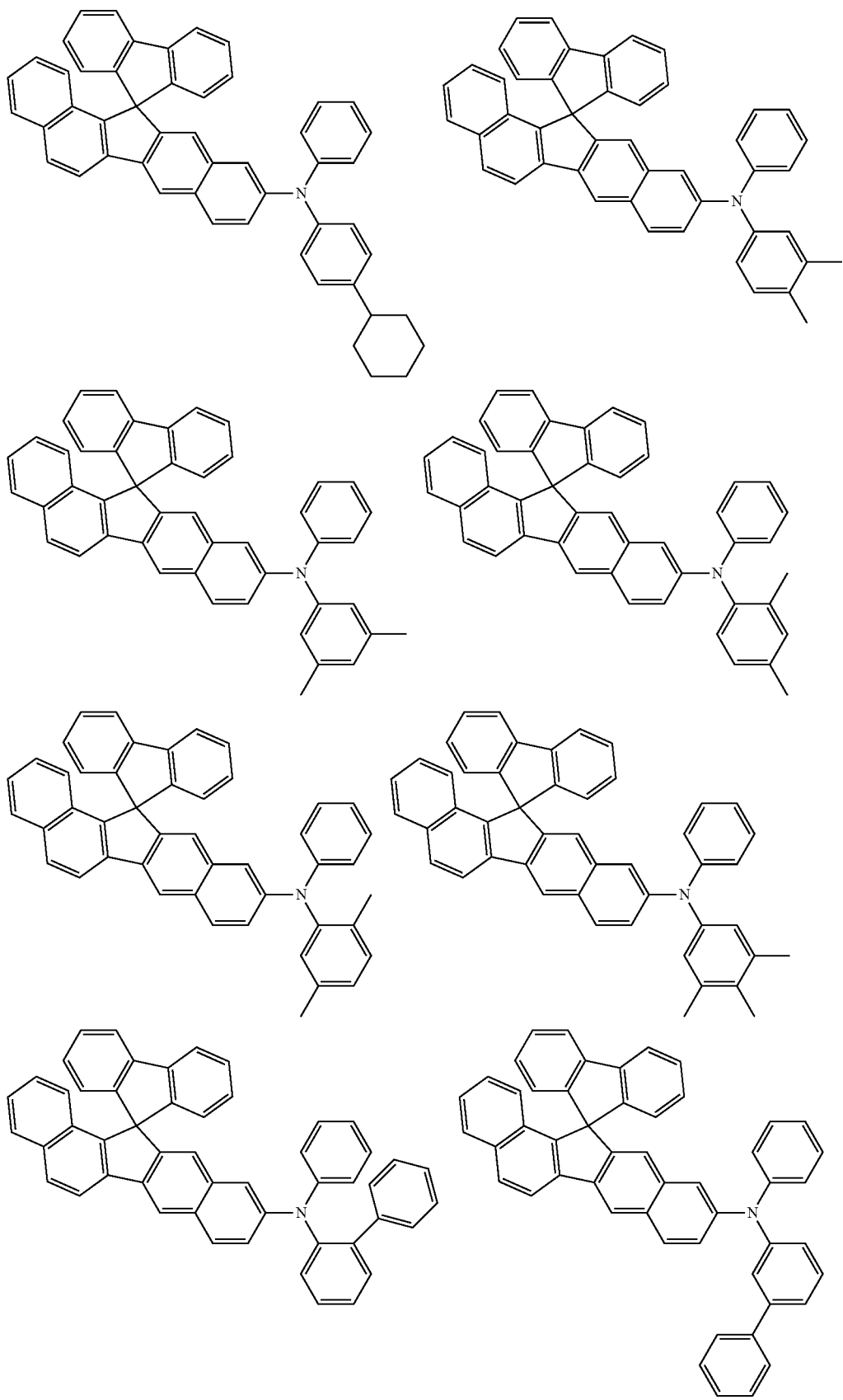
-continued

-continued
| 1049 | 1050 |
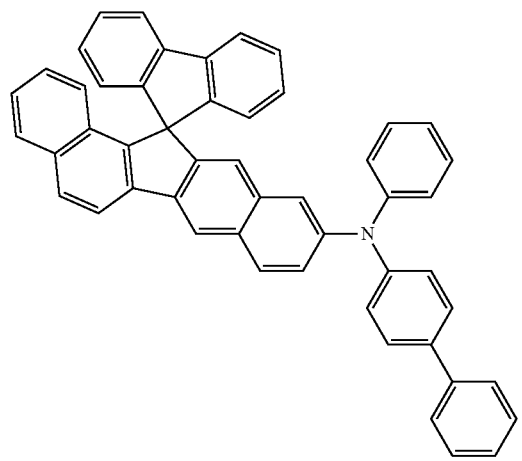

-continued
1051
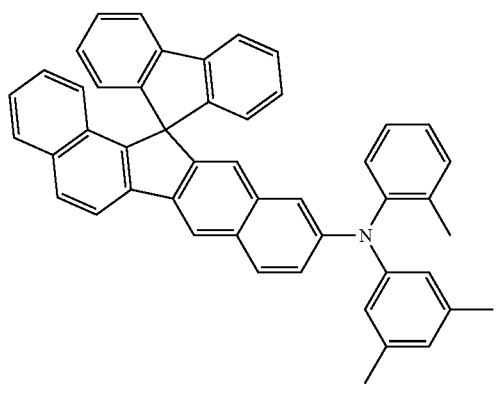
1052
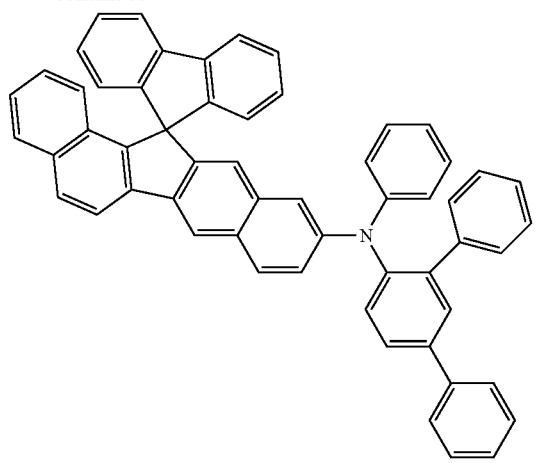
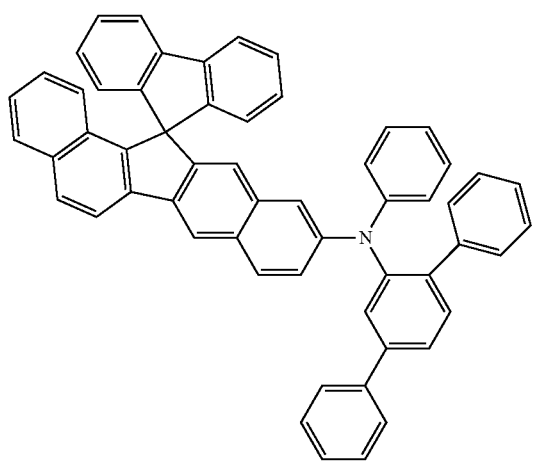
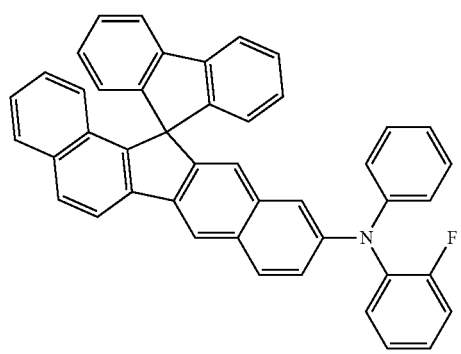
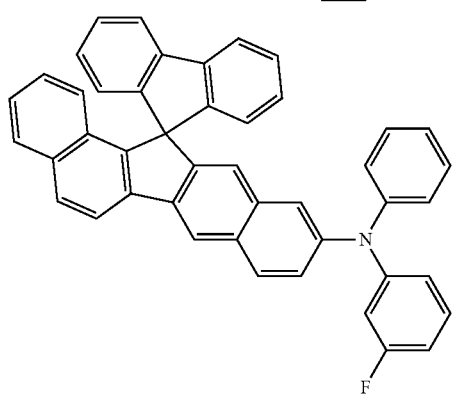
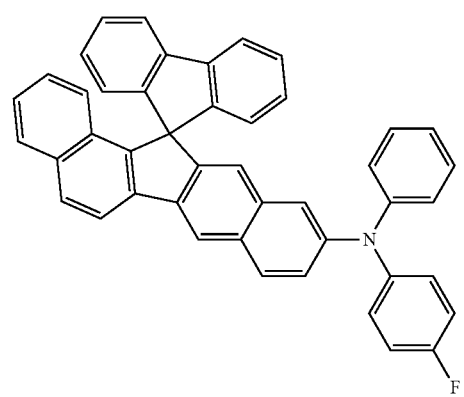
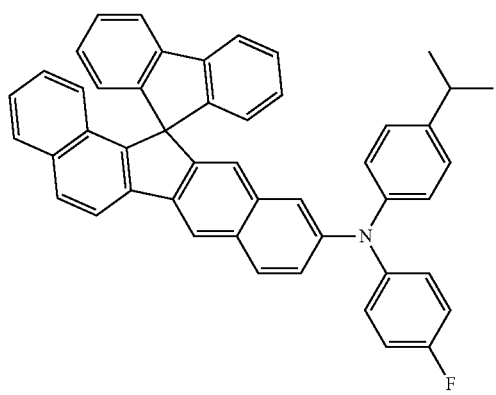
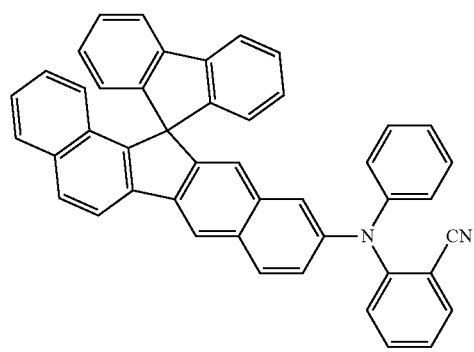

1053 1054
-continued
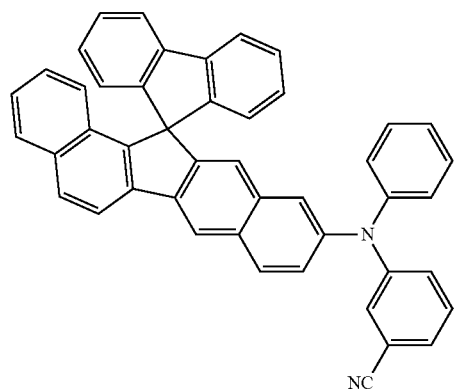
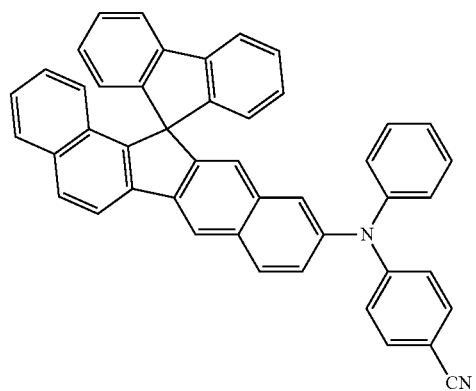
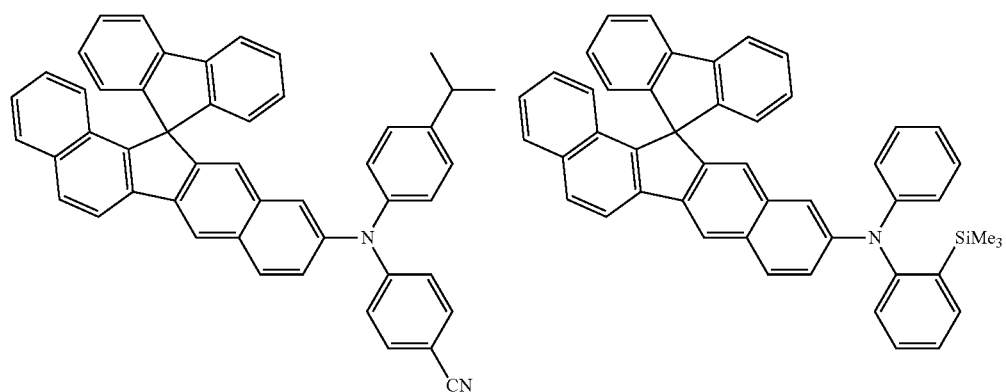
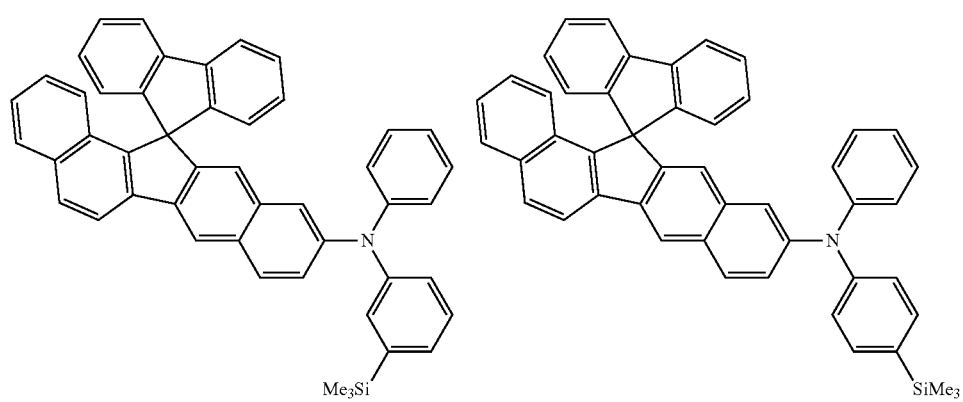
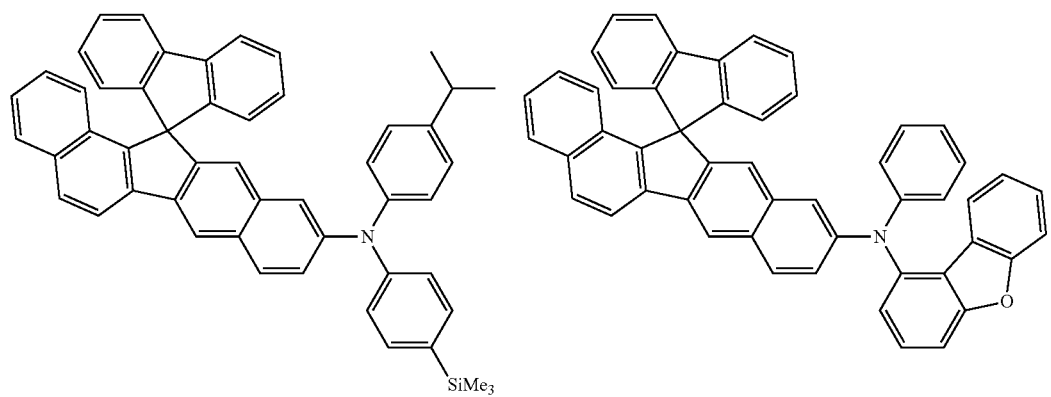

1055 | 1056
-continued
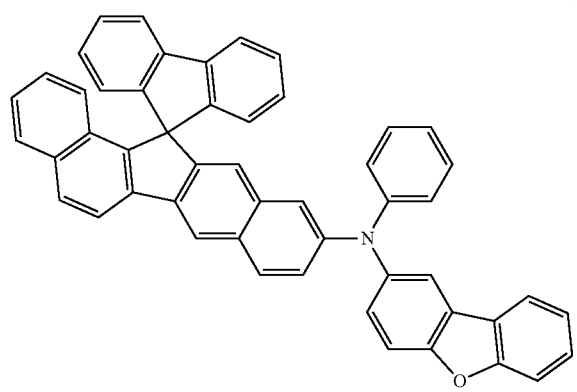
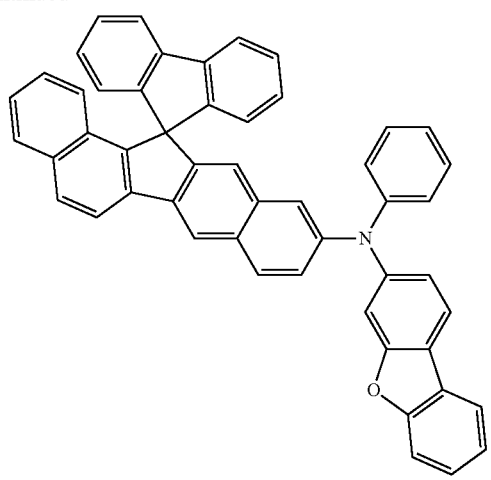
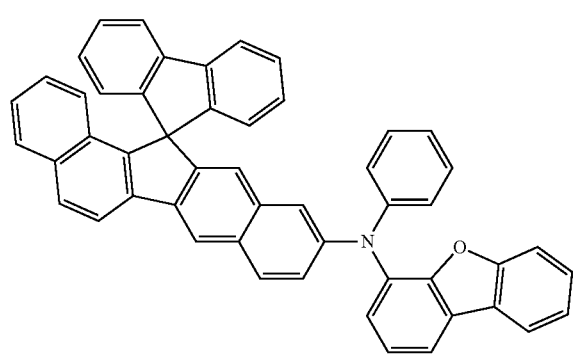
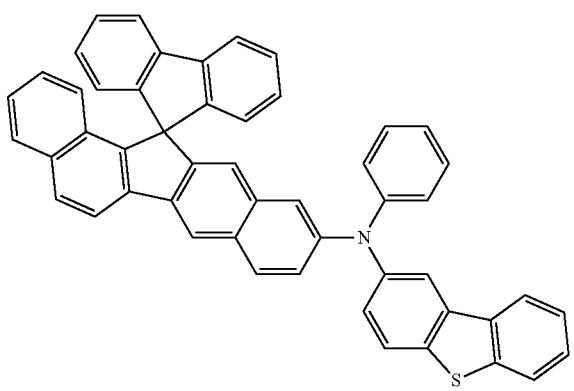
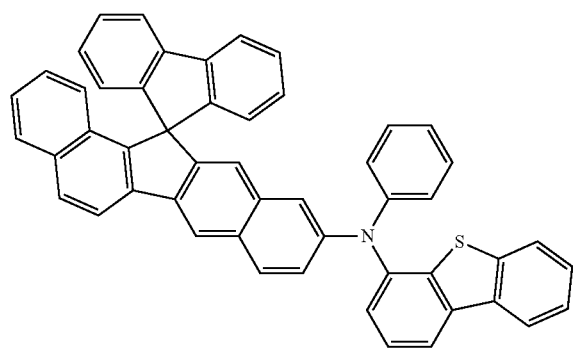
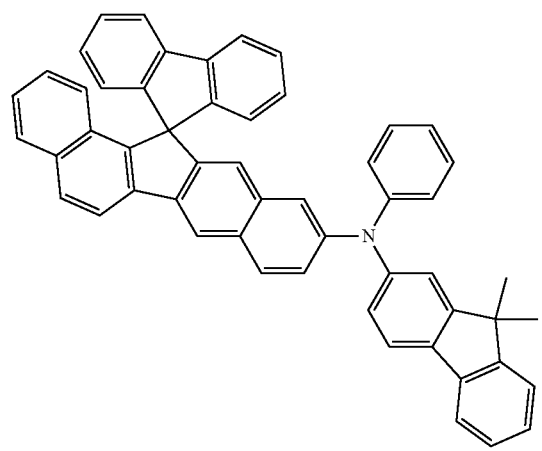

1057
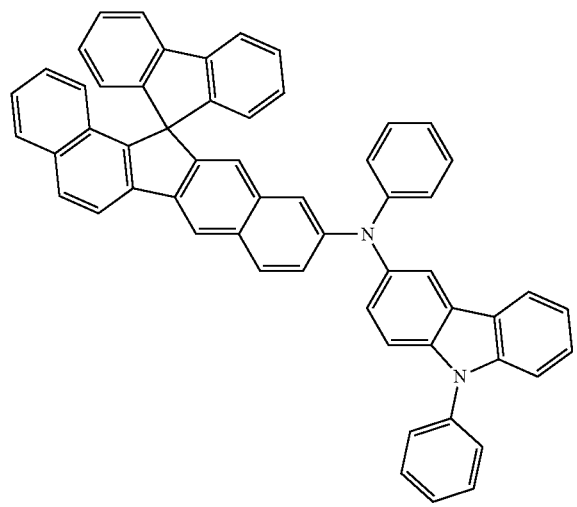
1058
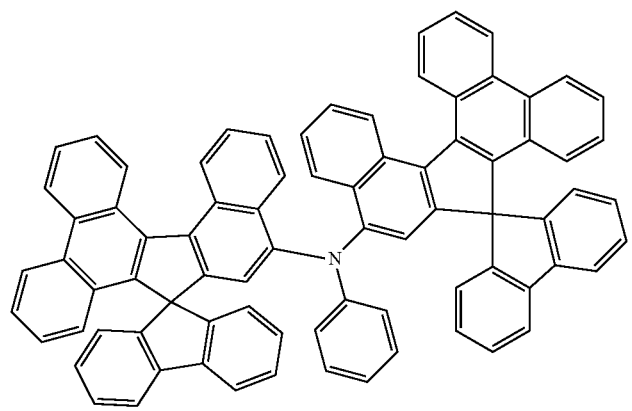
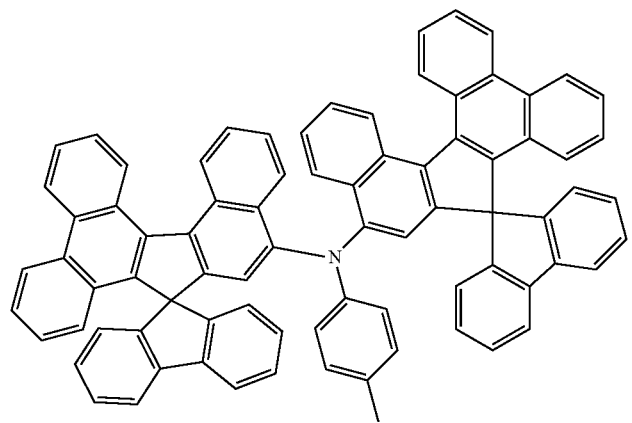

-continued
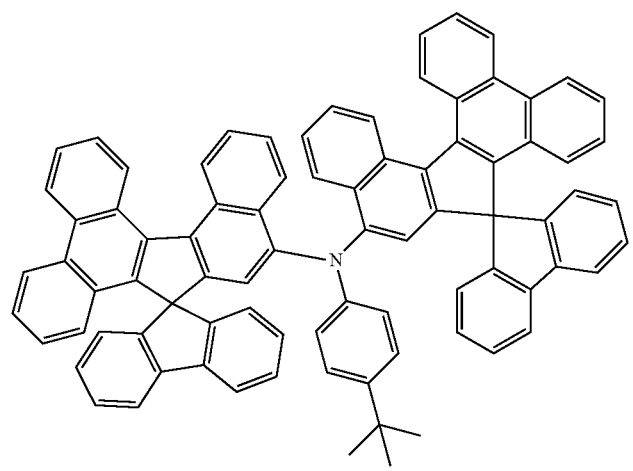

-continued
1061
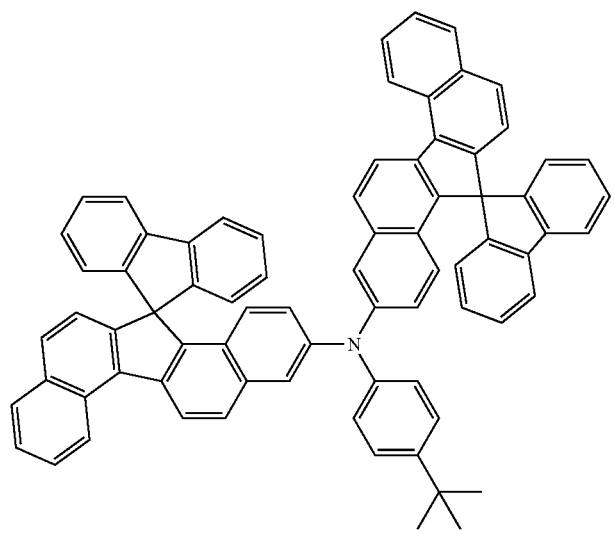
1062
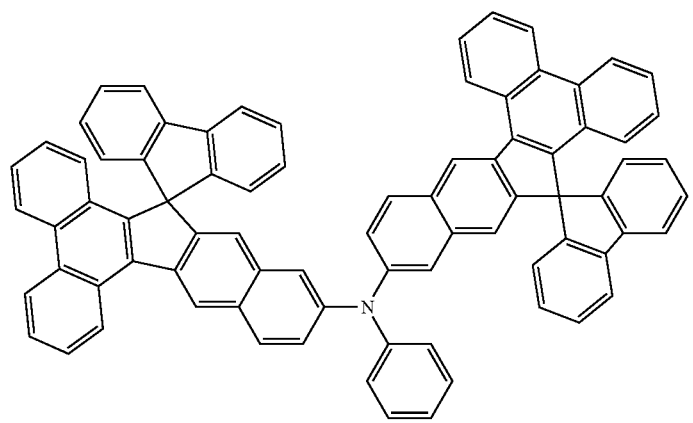
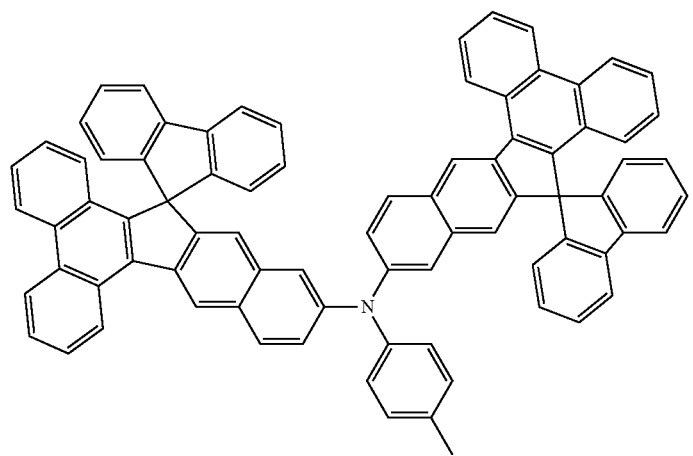

1063
-continued
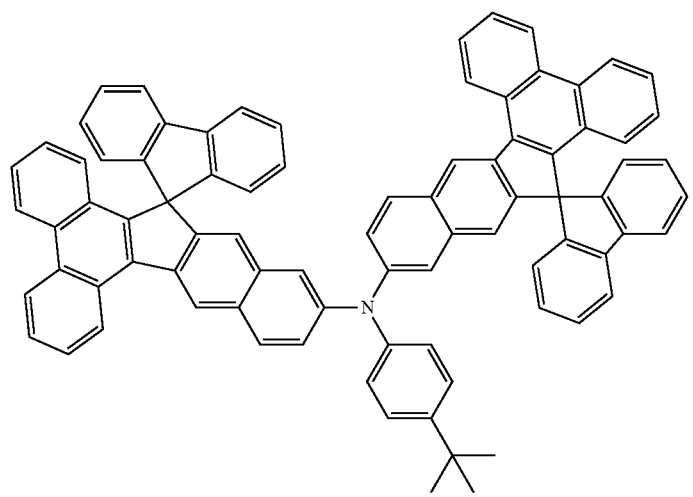
1064
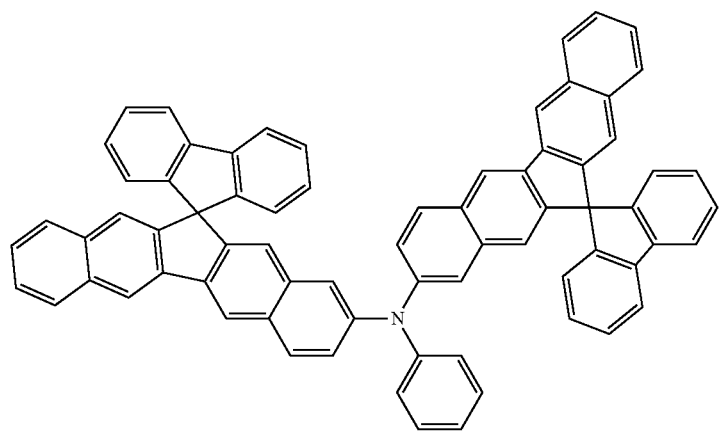
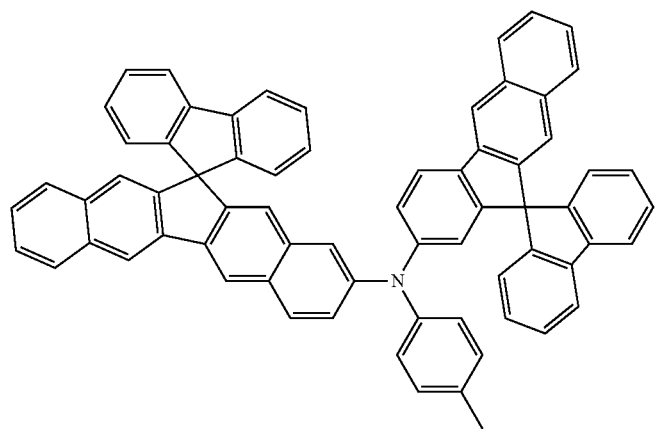

-continued
| 1065 | 1066 |
|---|---|
| 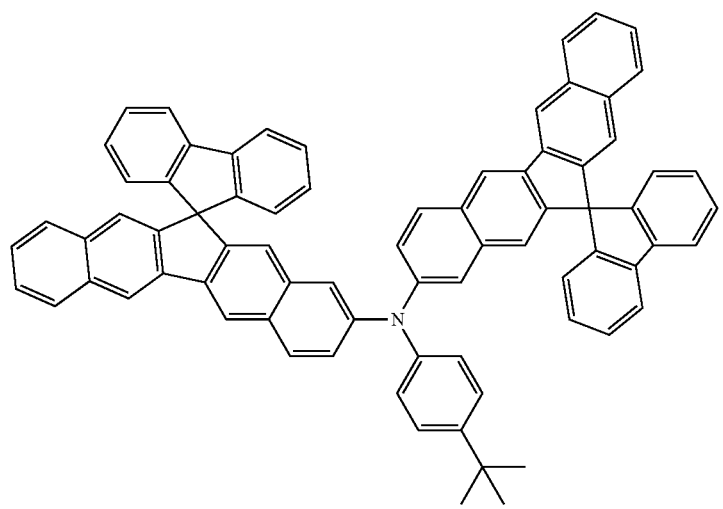 | |
| 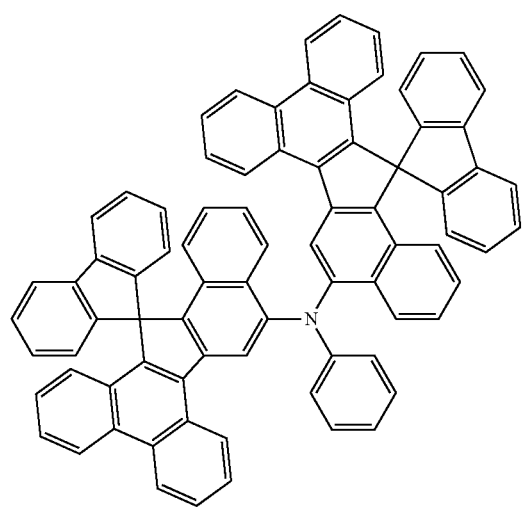 | 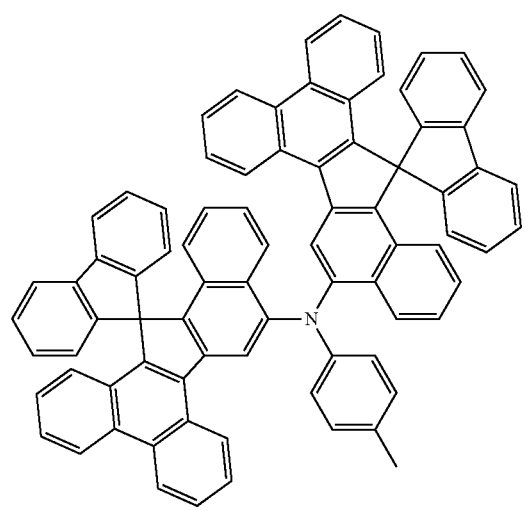 |
| 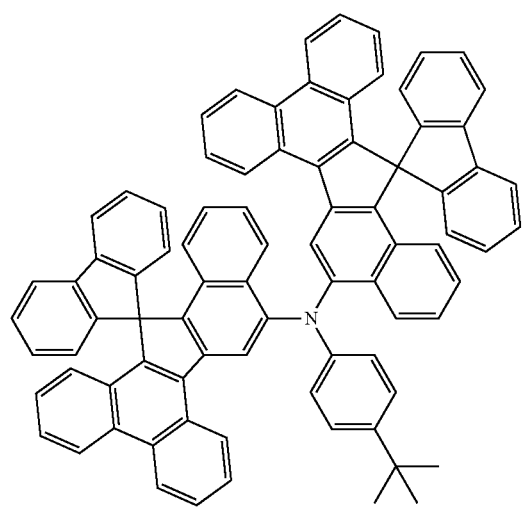 | 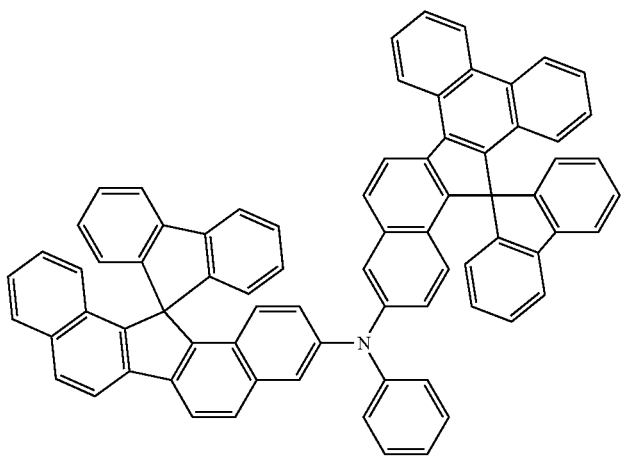 |

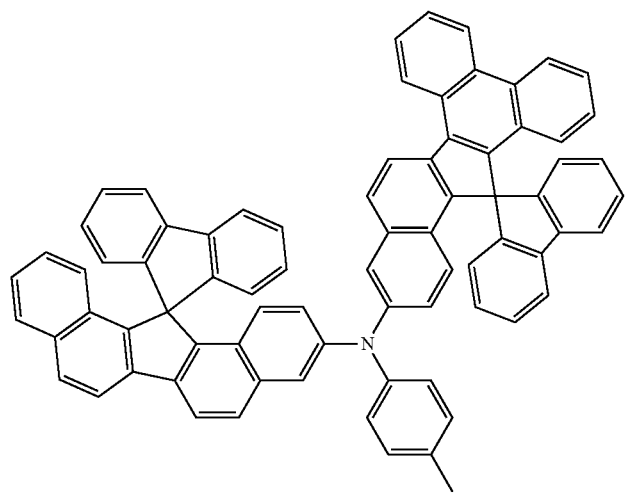
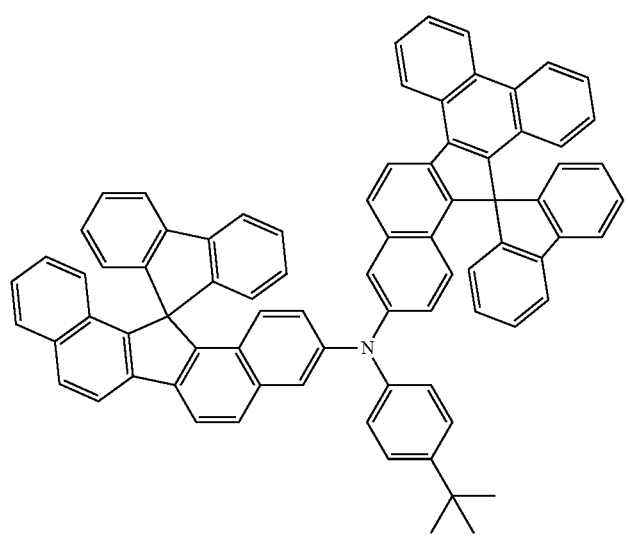
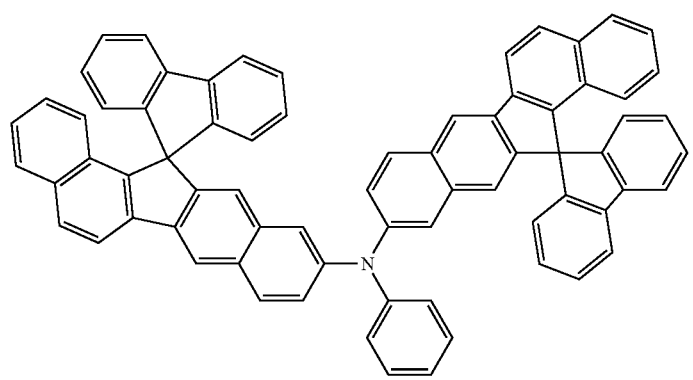

1069
-continued
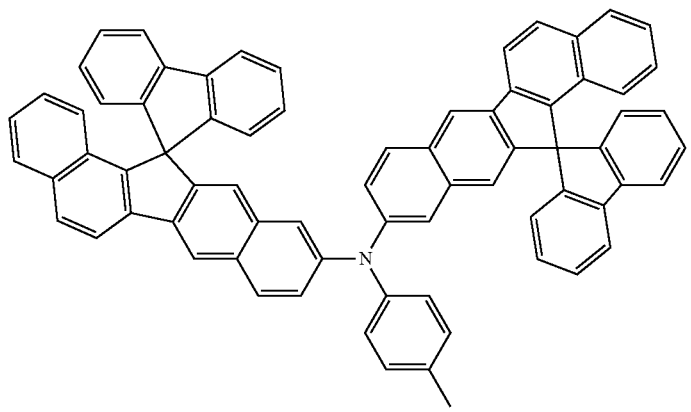
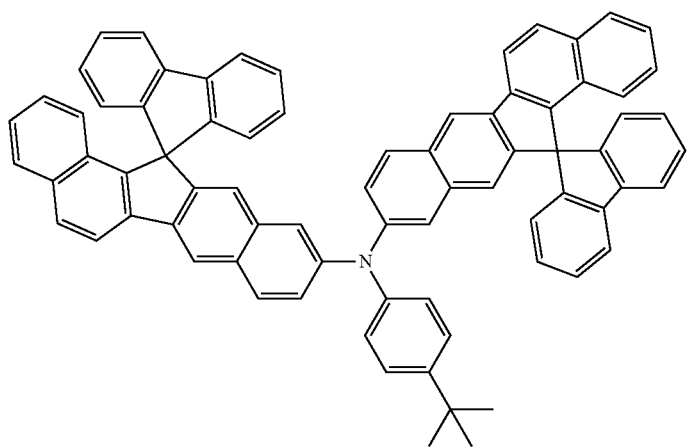
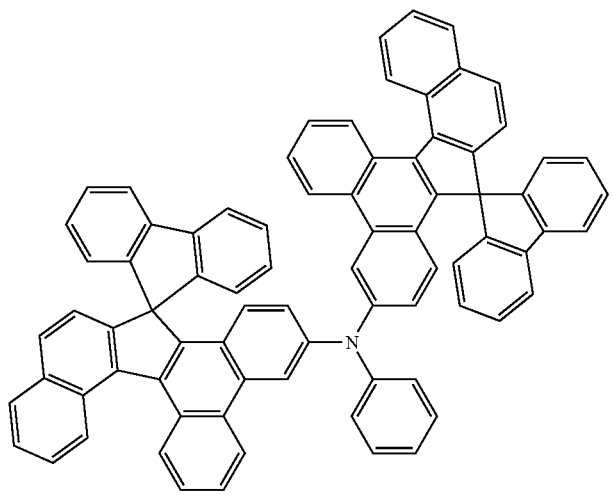
1070

1071 1072
-continued
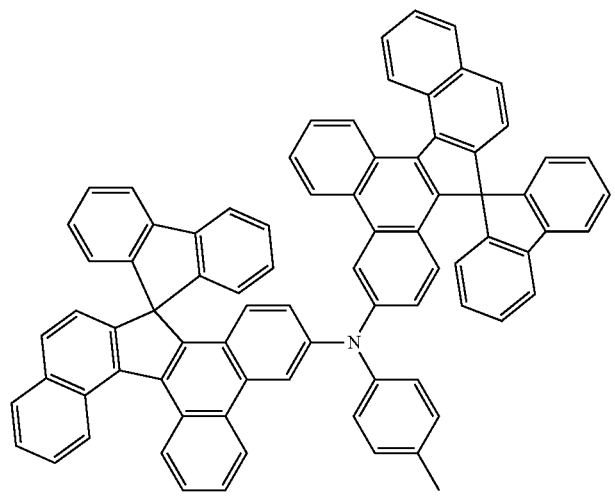

1073     1074
-continued
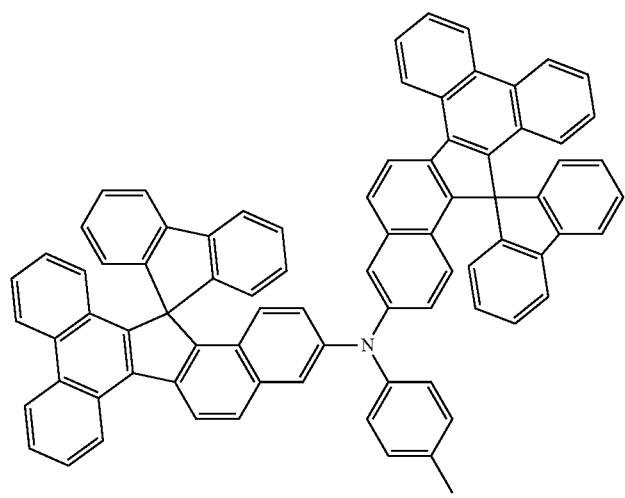
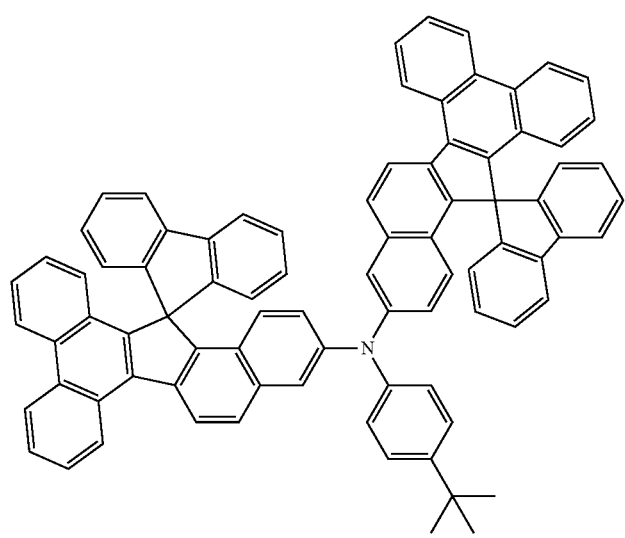
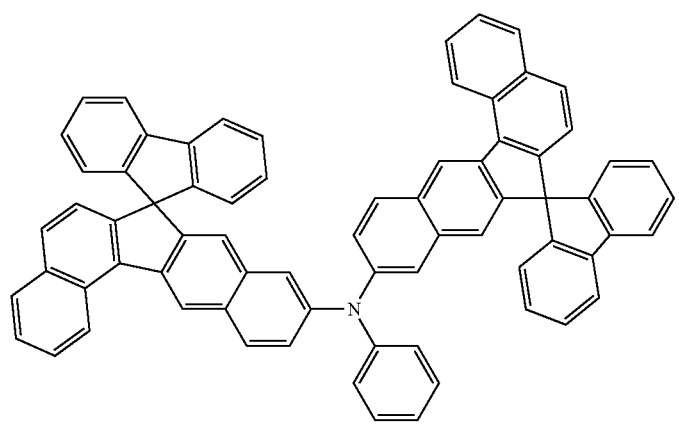

-continued
| 1075 | 1076 |
|---|---|
| 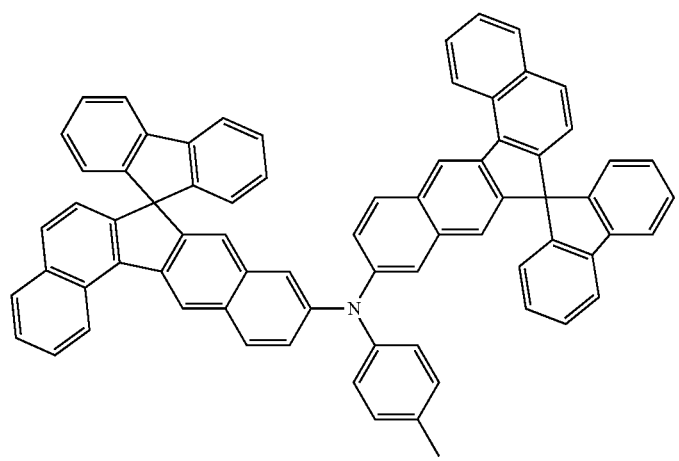 | |
| 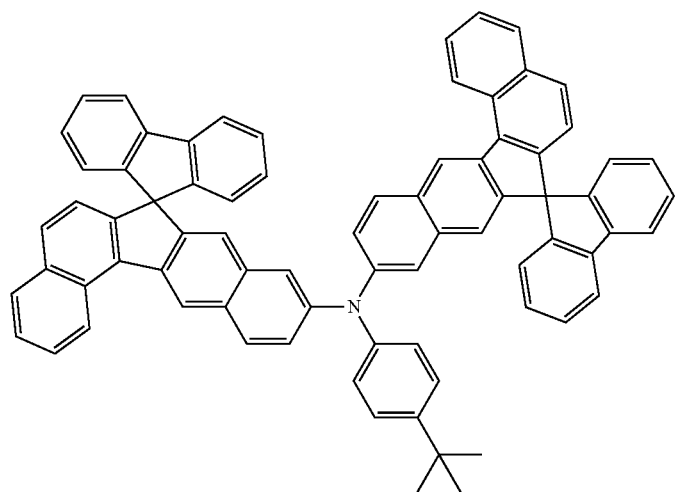 | |
| 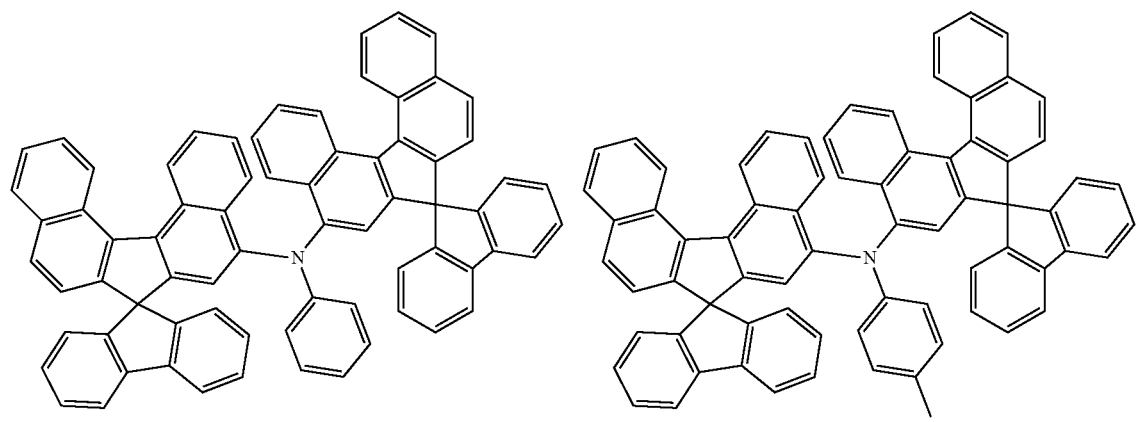 | |

-continued
1077
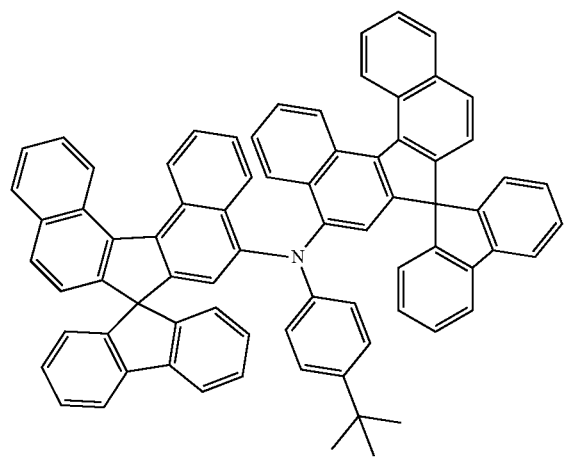
1078
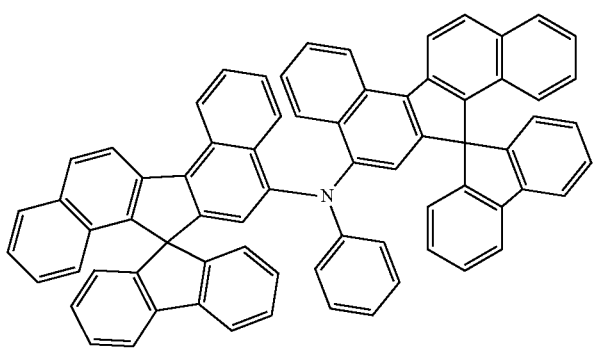
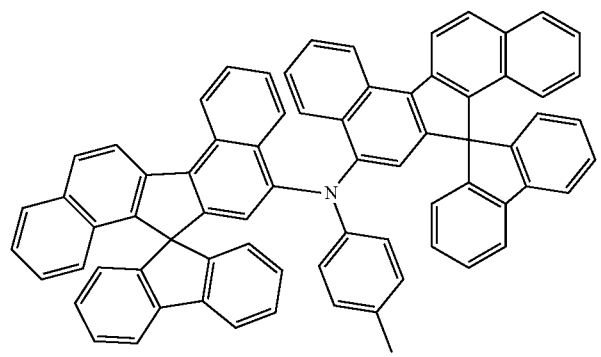
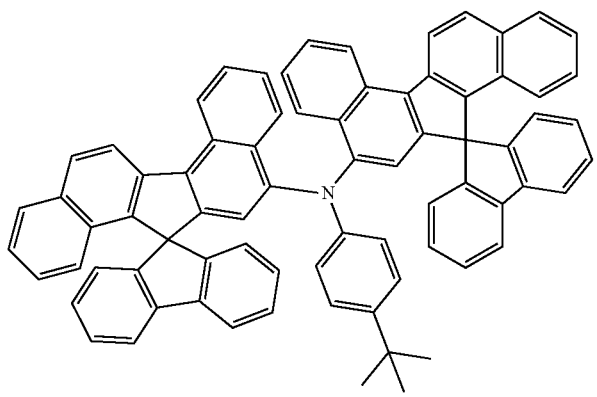
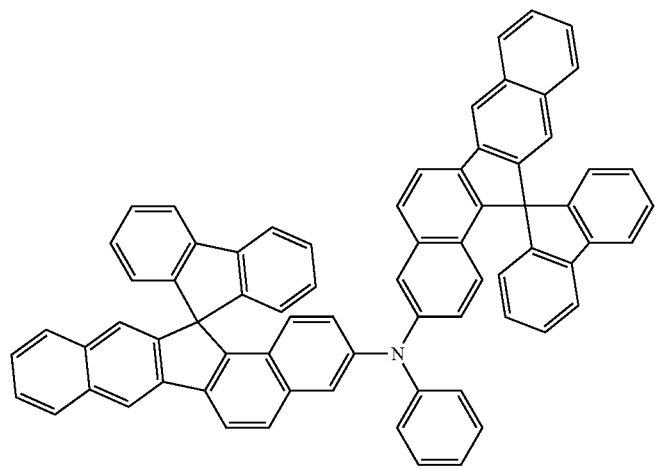

-continued
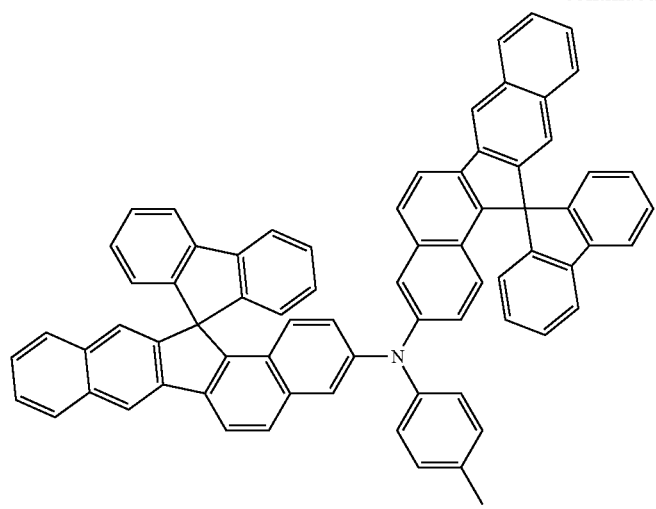
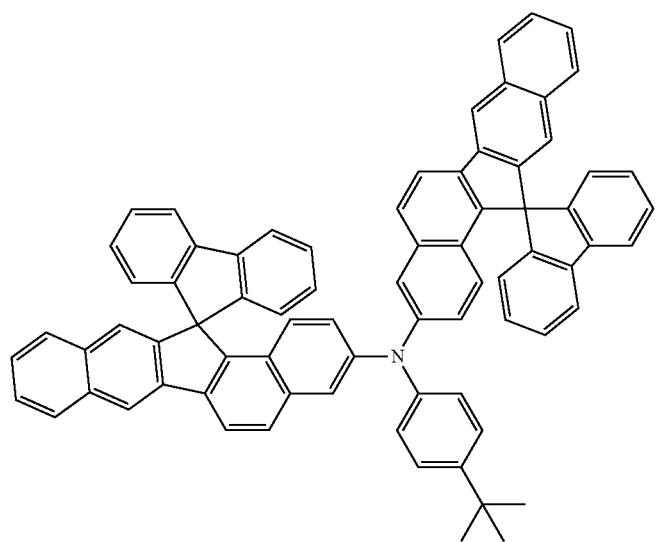
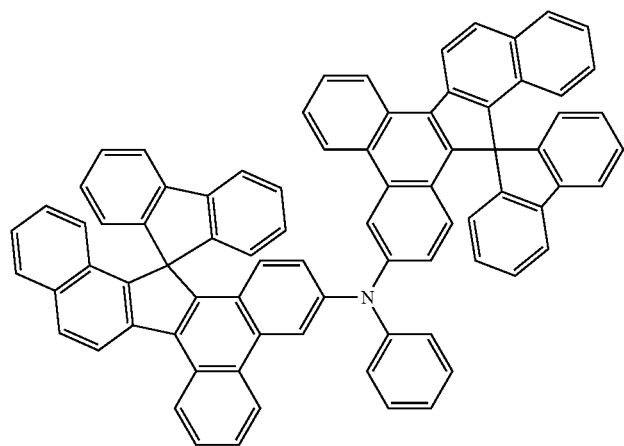

1081
-continued
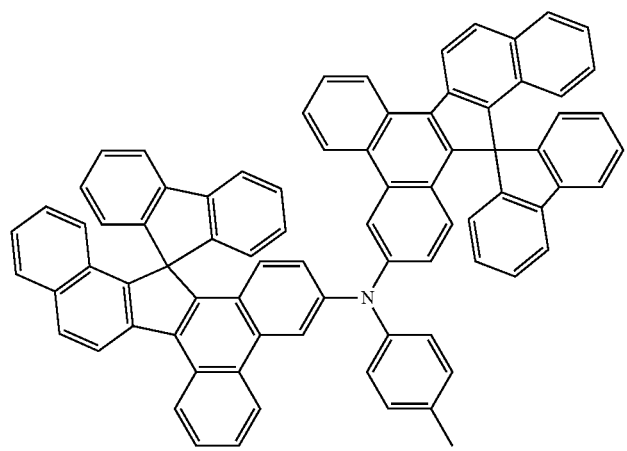
1082
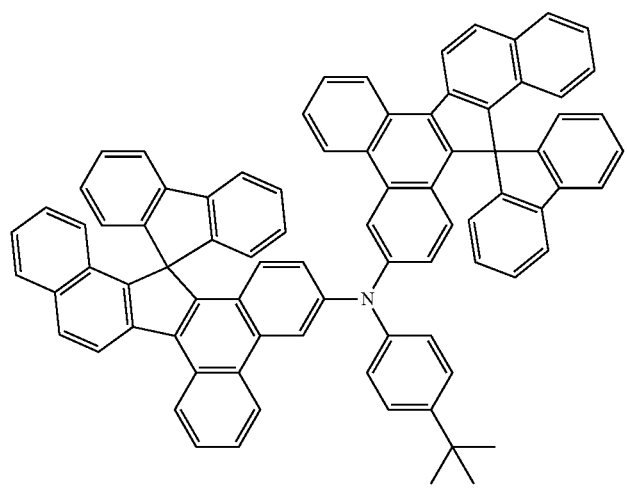
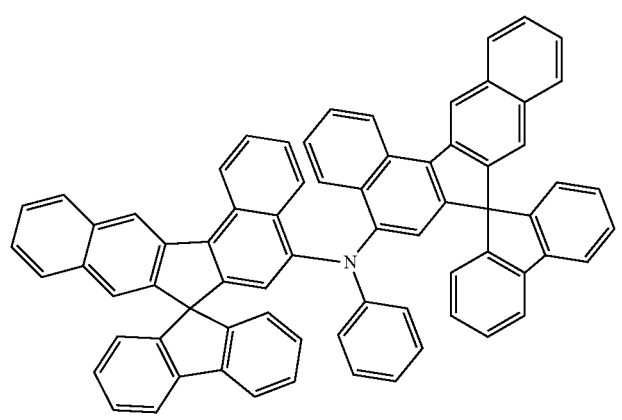

1083 1084
-continued
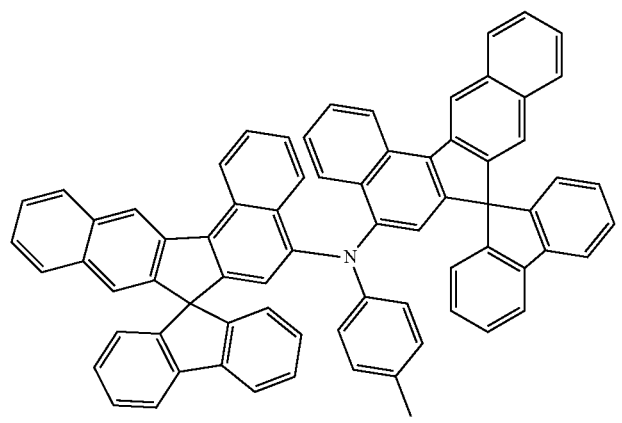
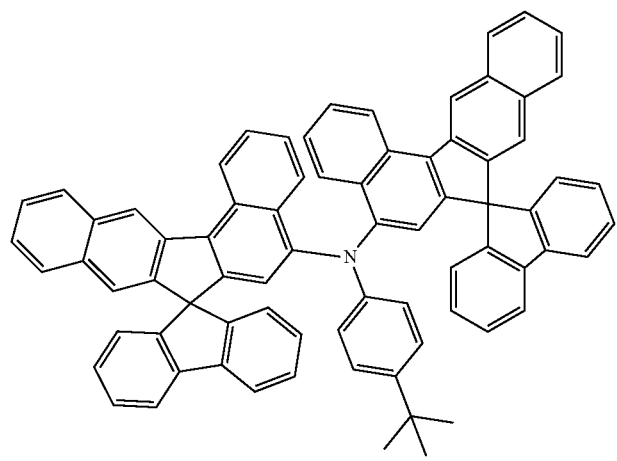
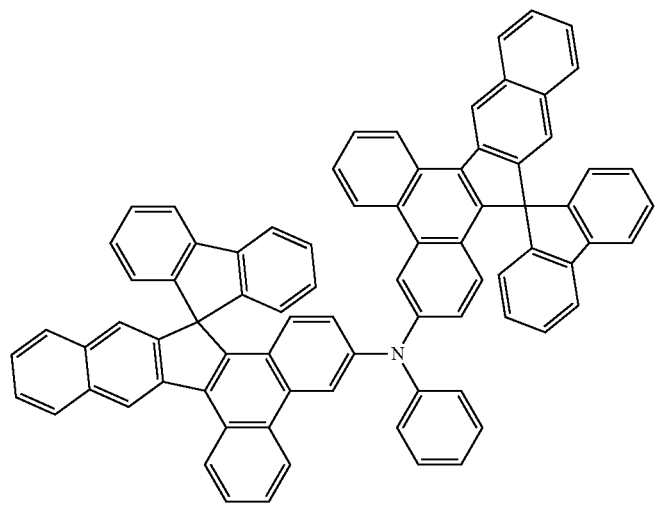

-continued
| 1085 | 1086 |
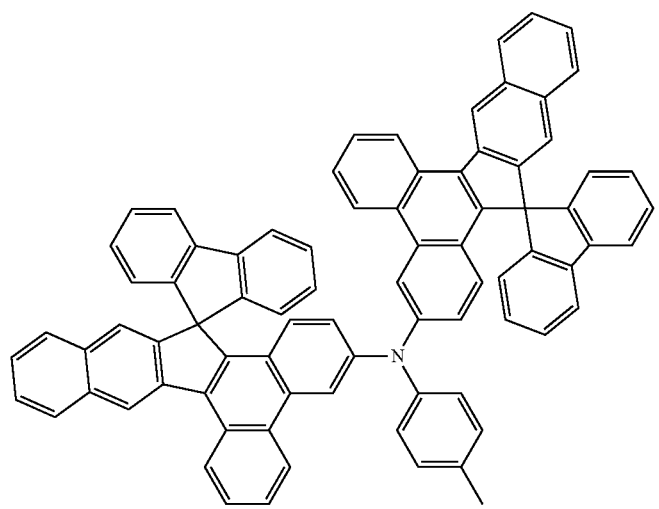
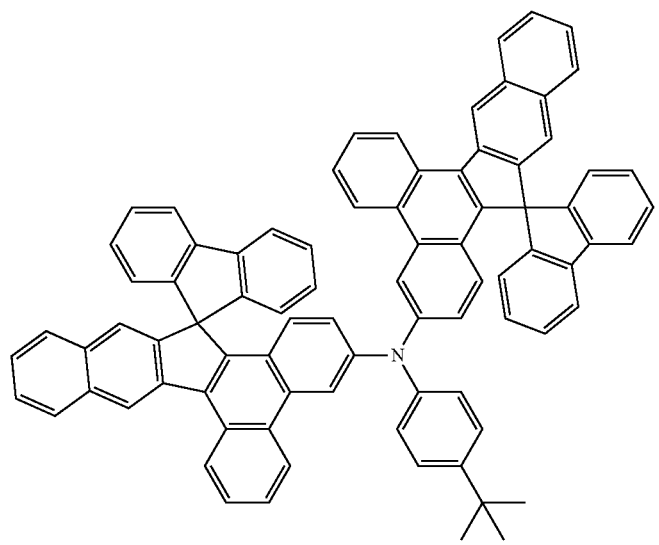
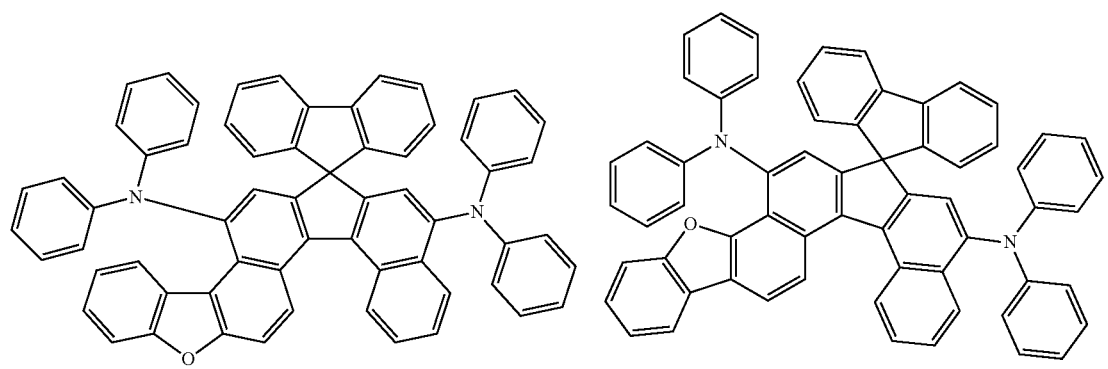

-continued
| 1087 | 1088 |
|---|---|
| 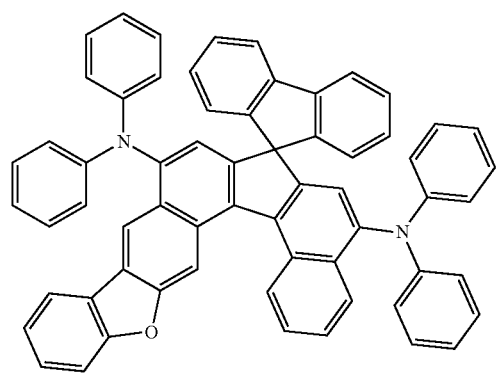 | 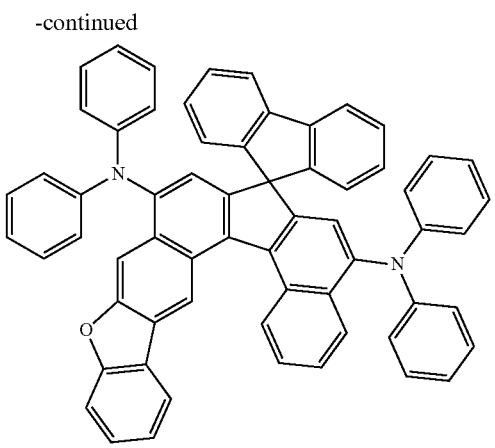 |
| 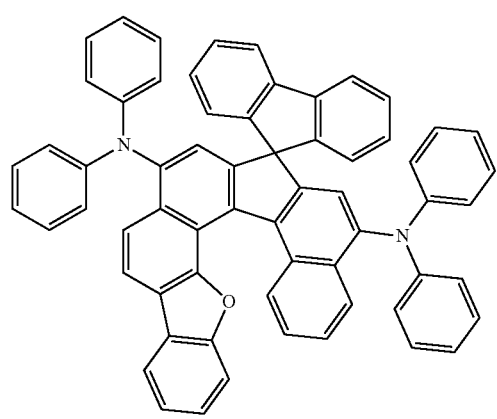 | 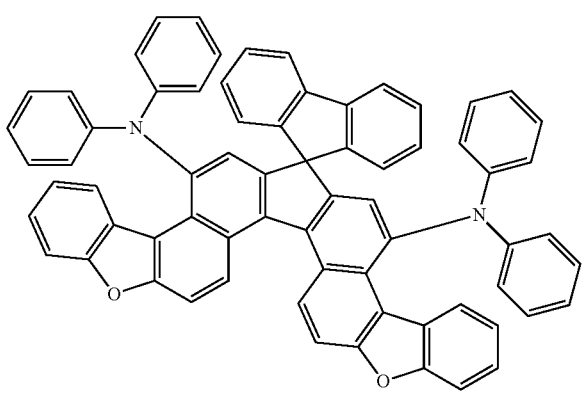 |
| 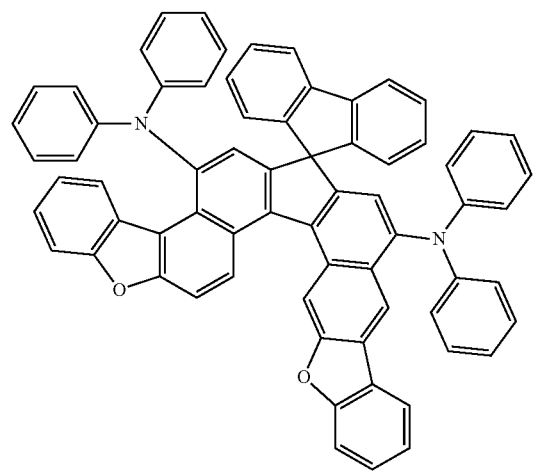 | 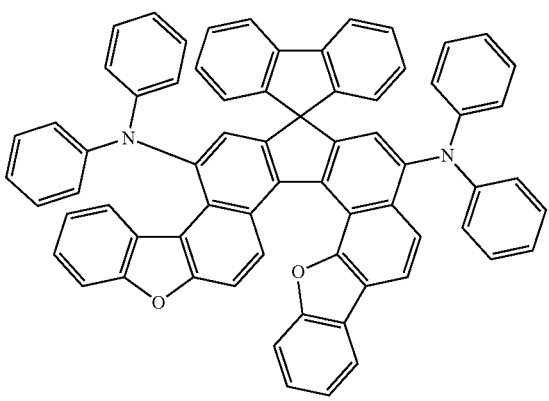 |

-continued
| 1089 | 1090 |
|---|---|
| 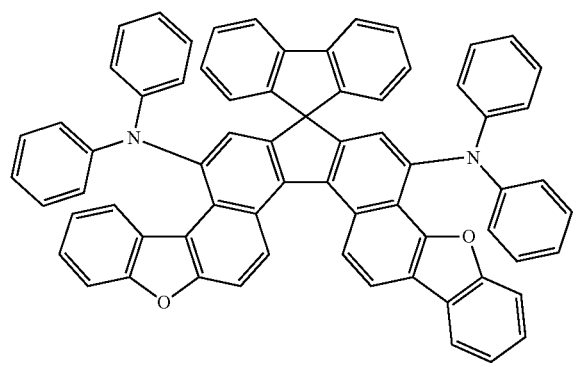 | 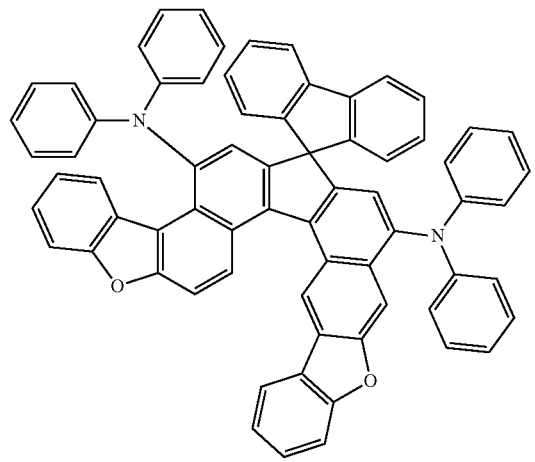 |
| 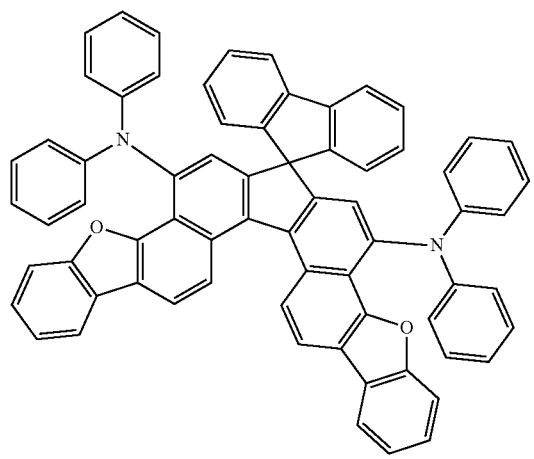 | 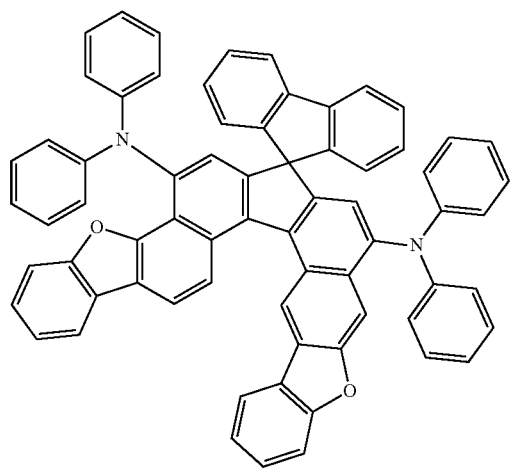 |
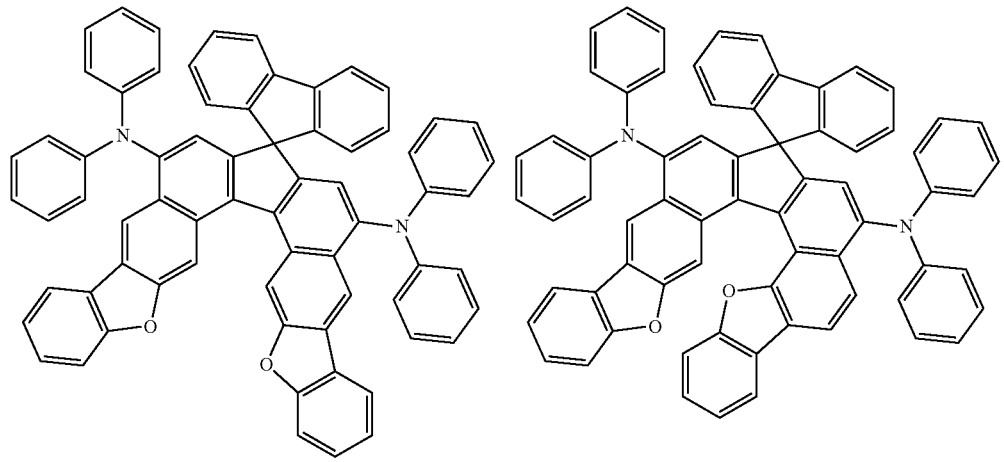

-continued
1091
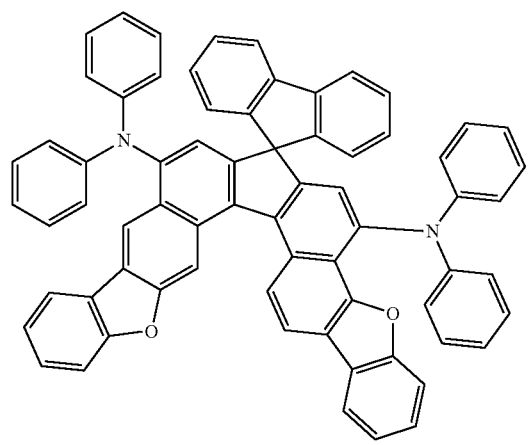
1092
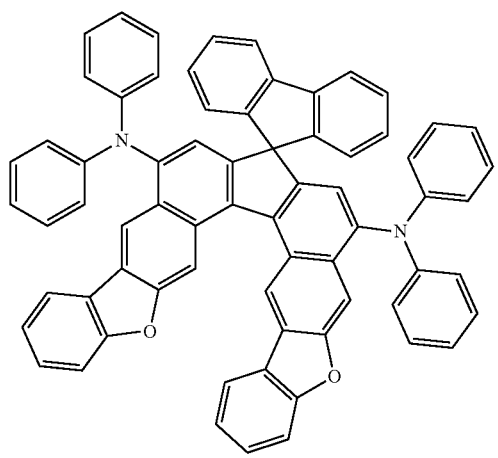
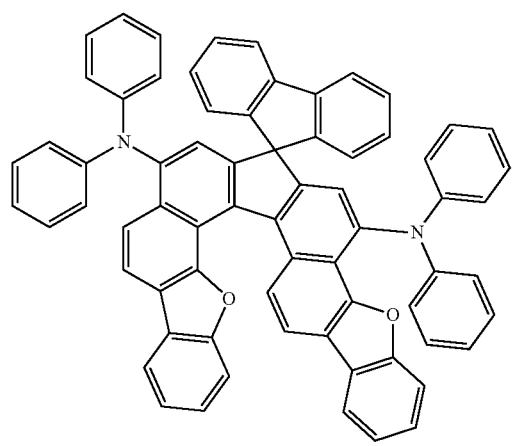
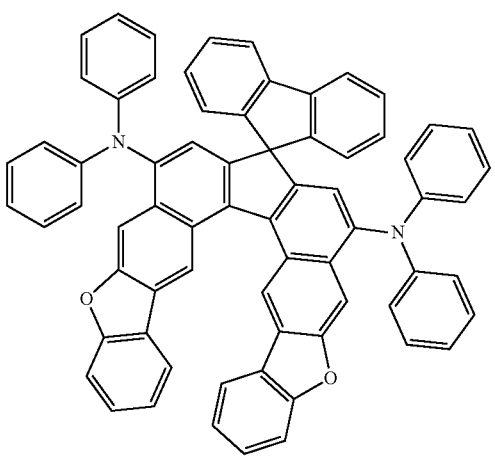
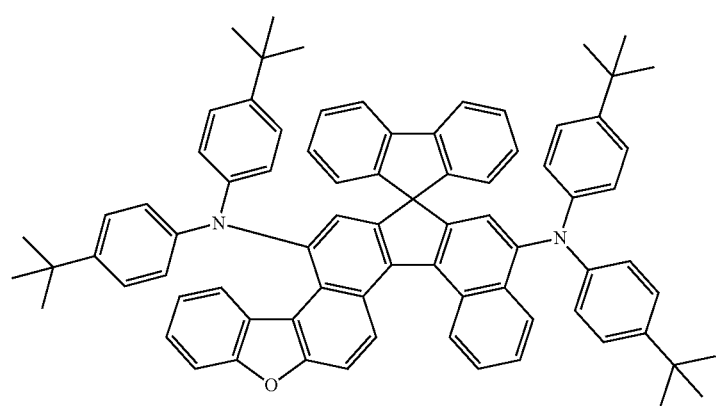

1093 1094
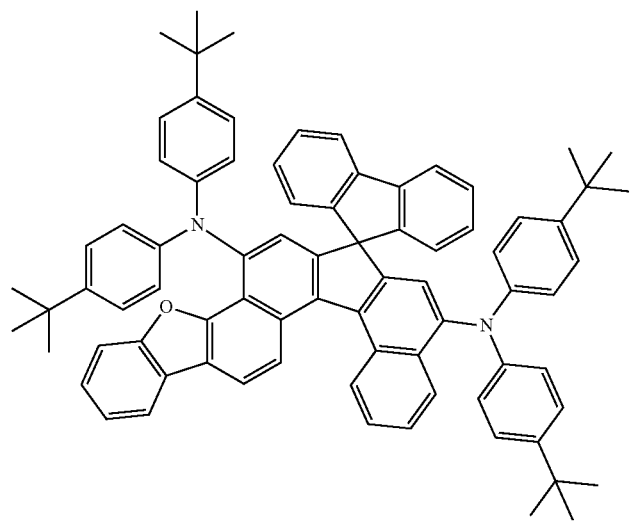
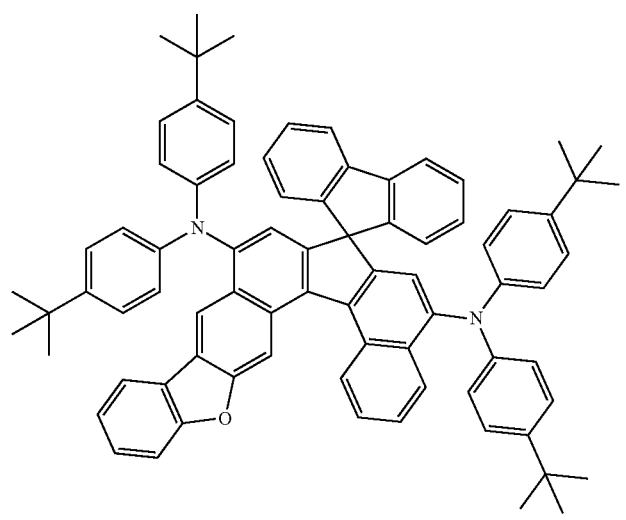
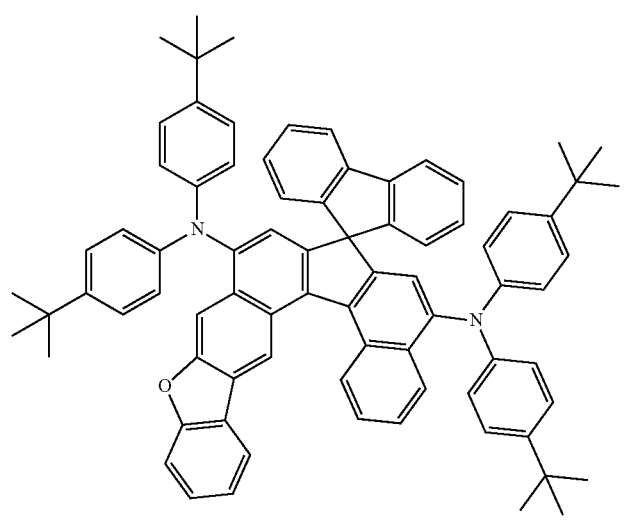

-continued
| 1095 | 1096 |
|---|---|
| 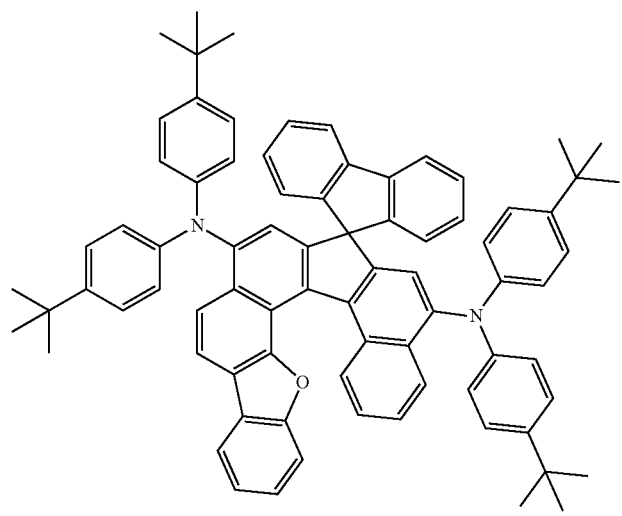 | |
| 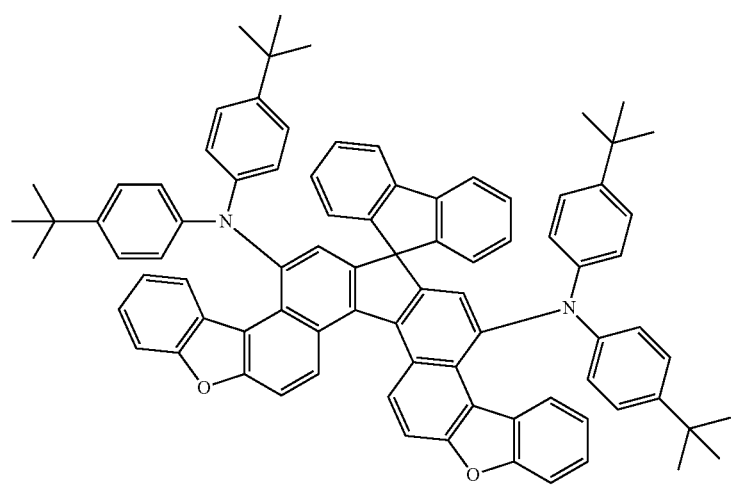 | |
| 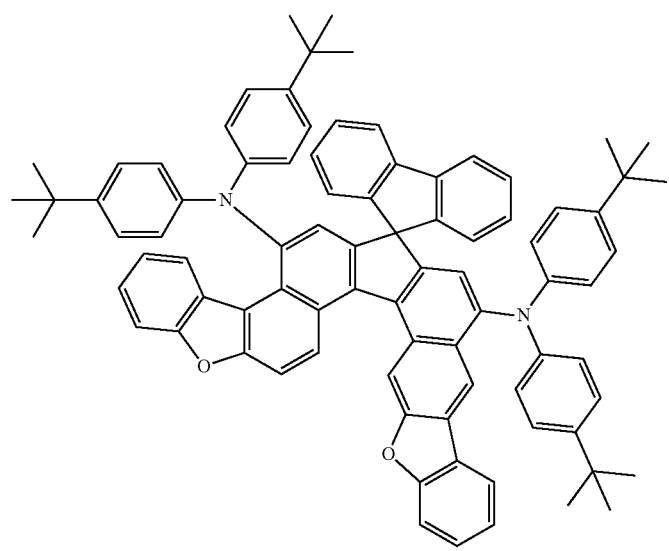 | |

1097 1098
-continued
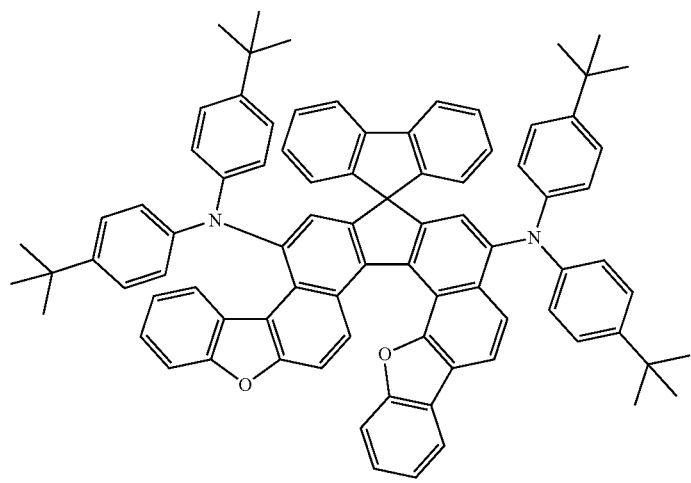
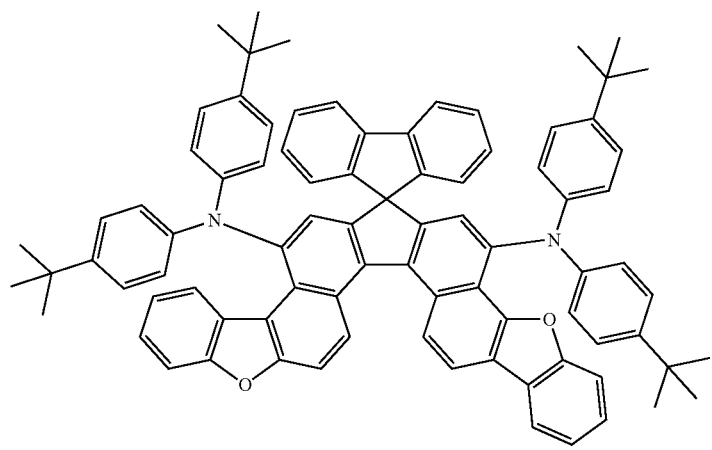
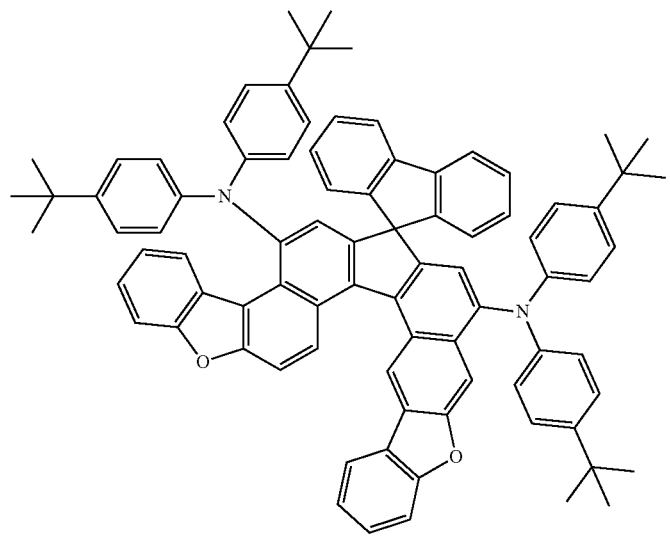

-continued
1099
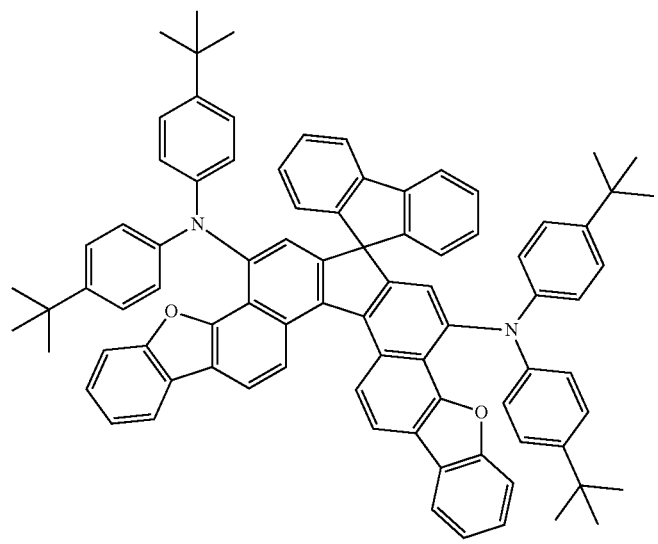
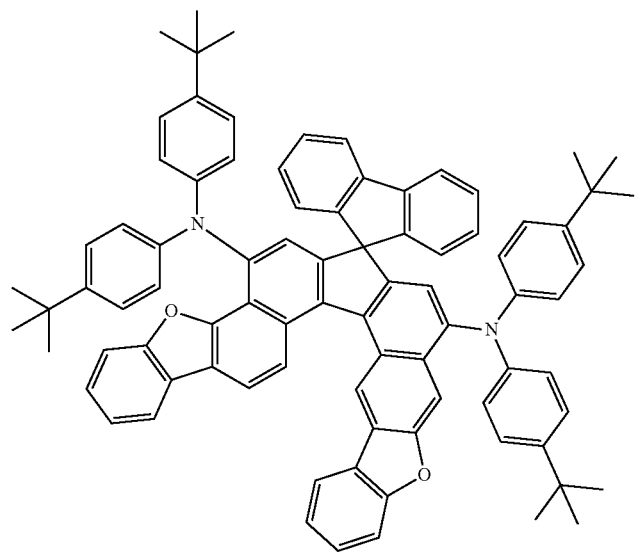
1100
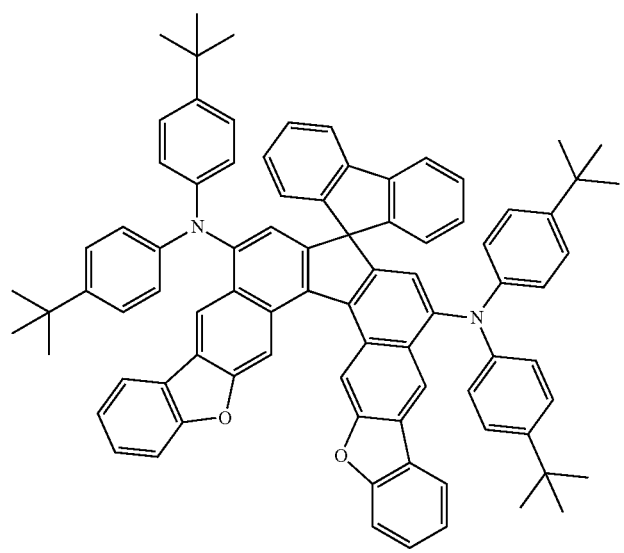

-continued
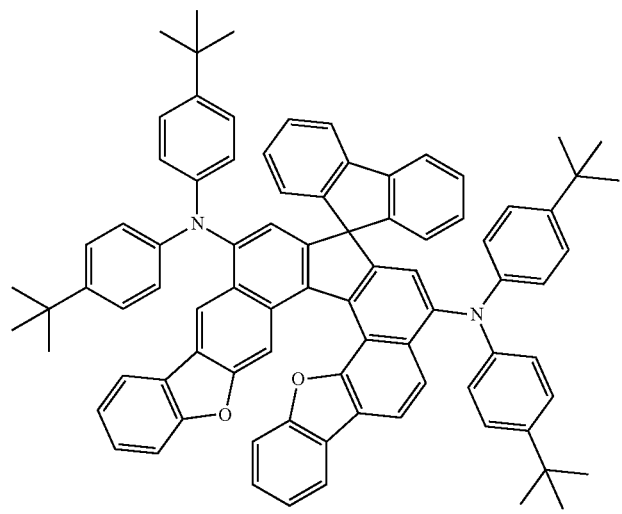
1101
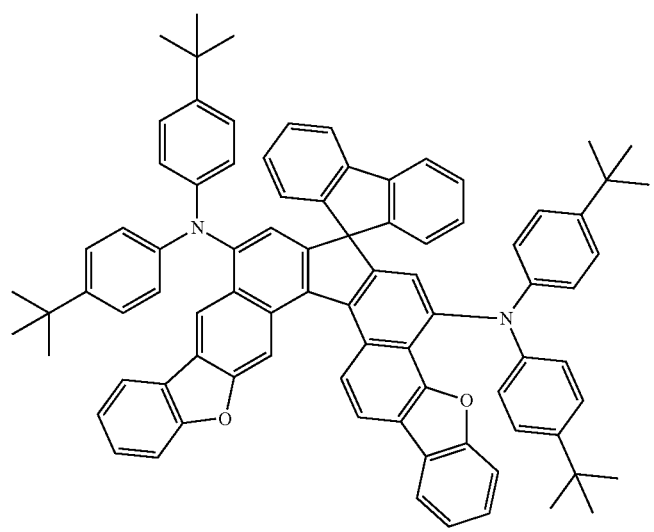
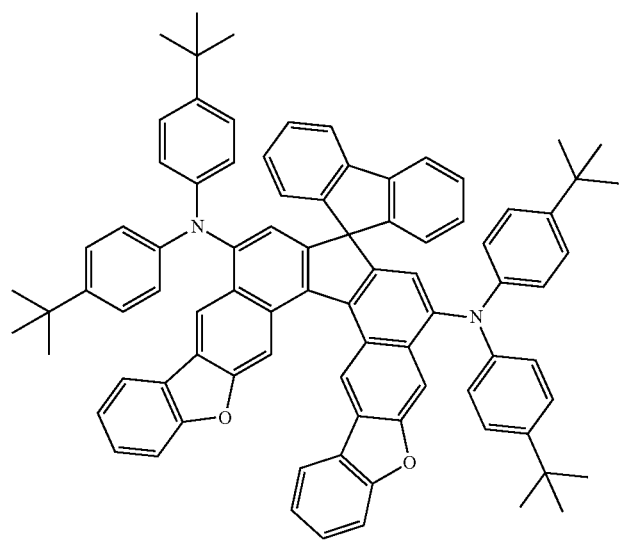
1102

1103 1104
-continued
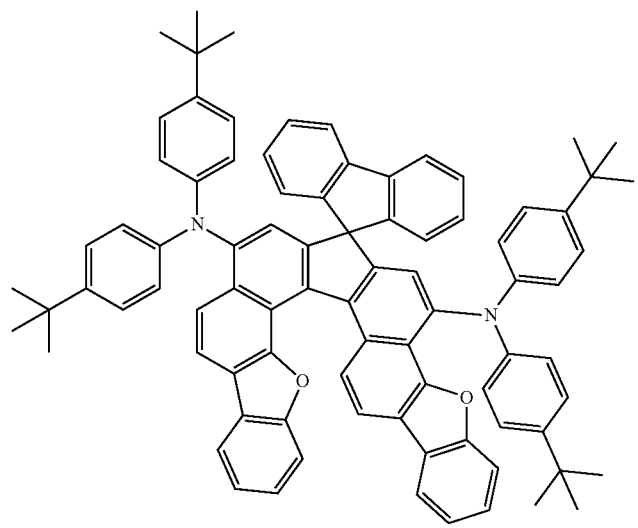
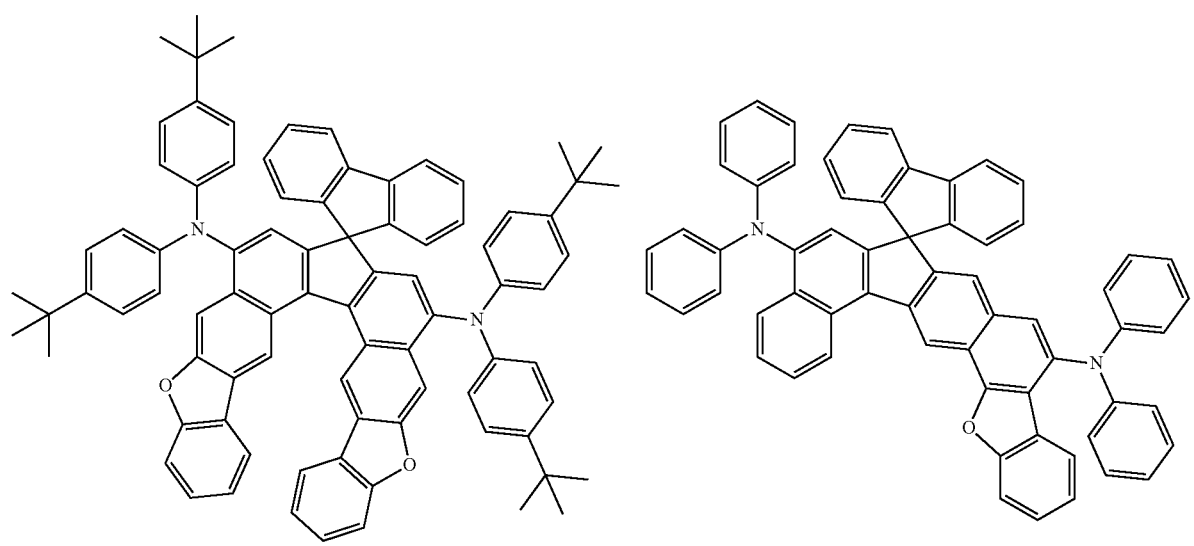
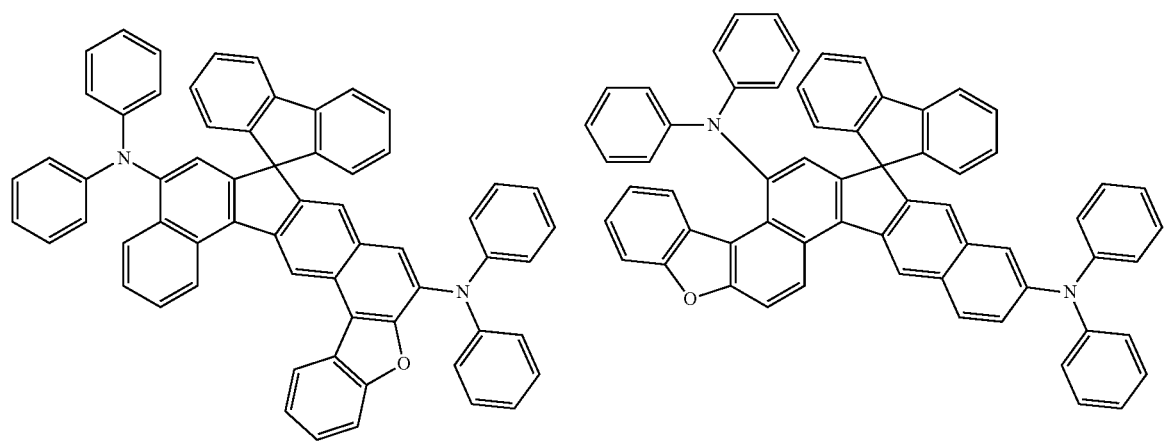

1105 1106
-continued
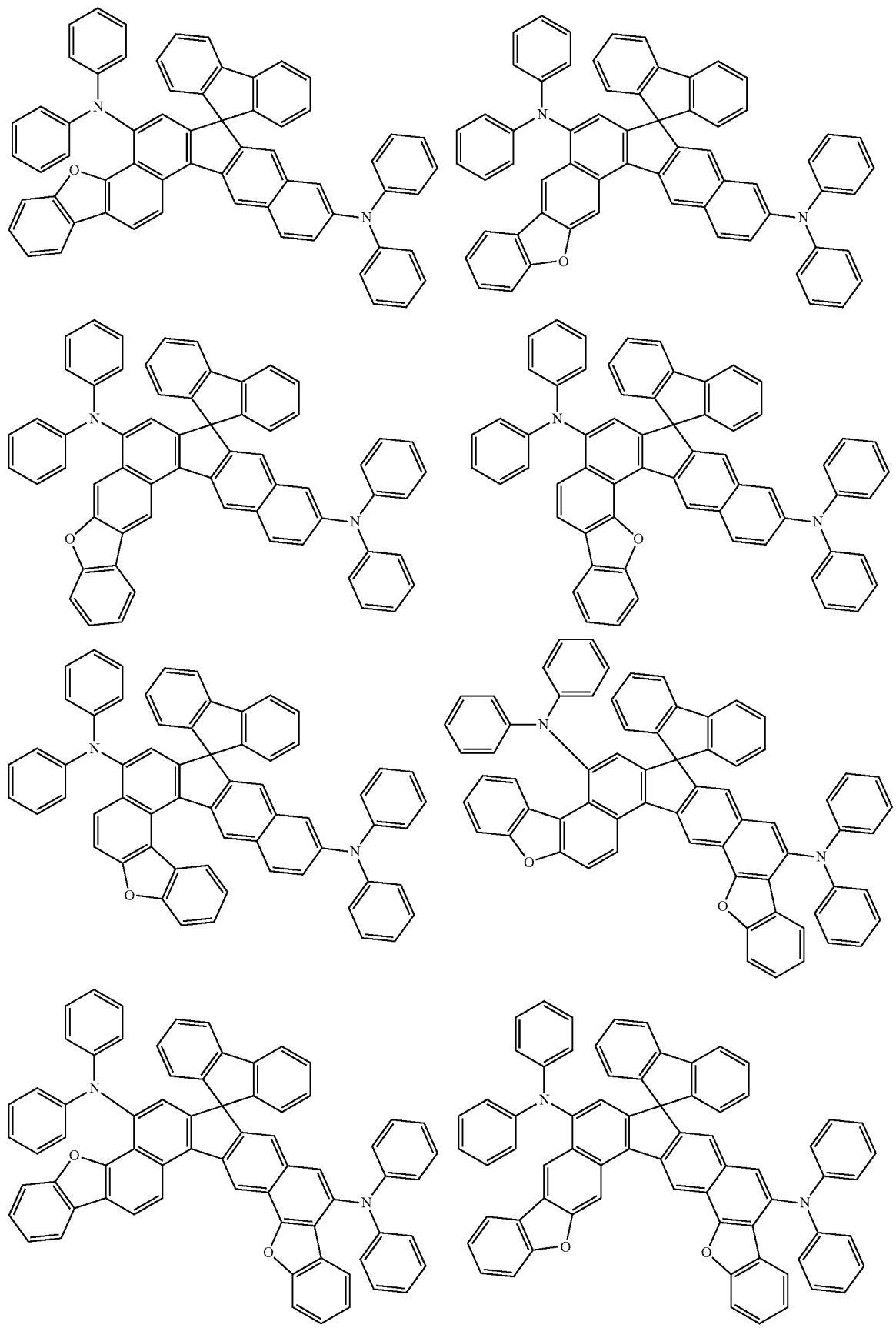

-continued
1107
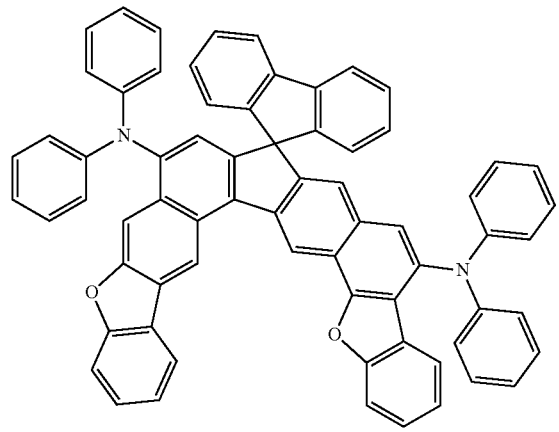
1108
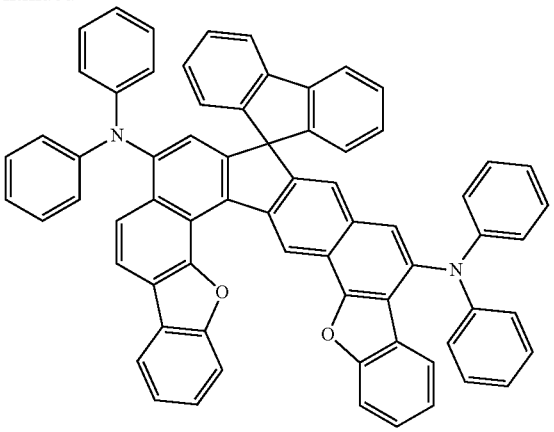
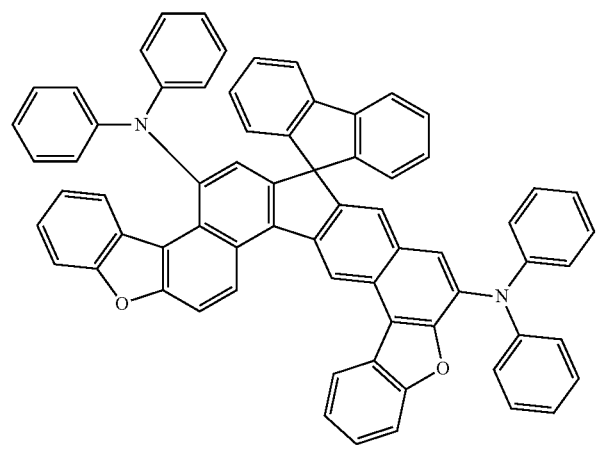
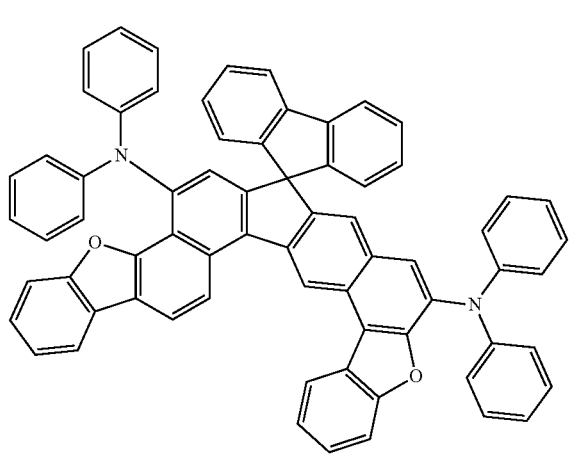
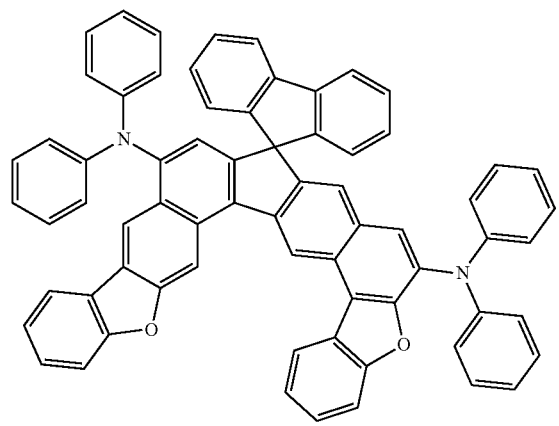
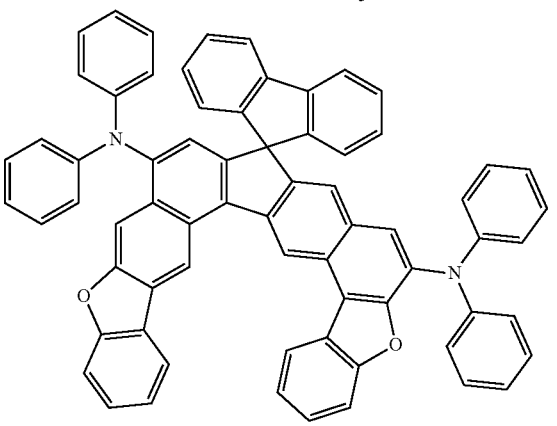
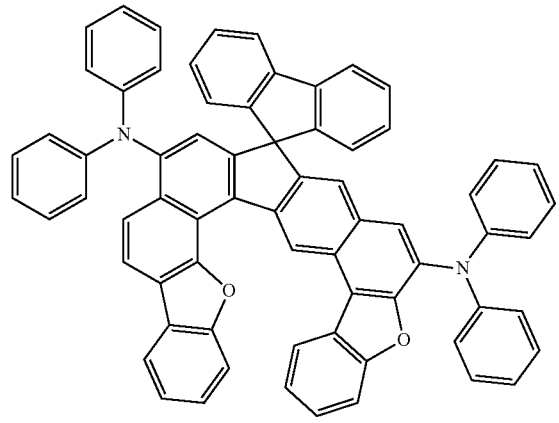

1109  1110
-continued
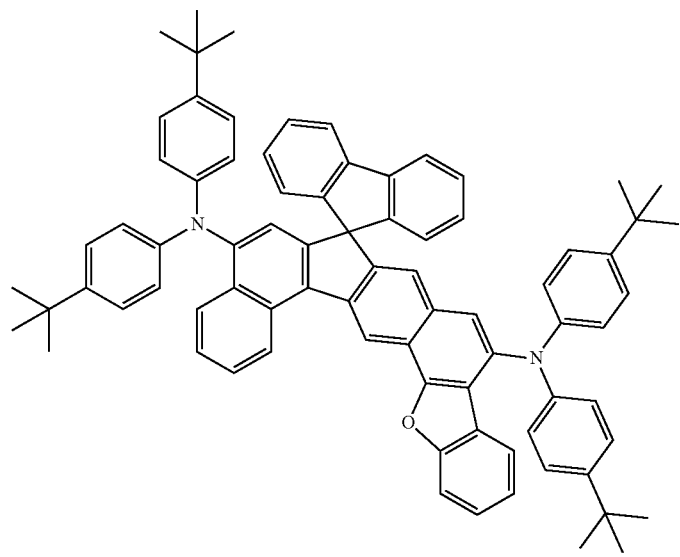 [SMILES: CC(C)(C)c1ccc(N(c2ccc(C(C)(C)C)cc2)c2cc3c(c4ccccc24)-c2cc4c(cc2C32c3ccccc3-c3ccccc32)cc(N(c2ccc(C(C)(C)C)cc2)c2ccc(C(C)(C)C)cc2)c2c3ccccc3oc42)cc1]
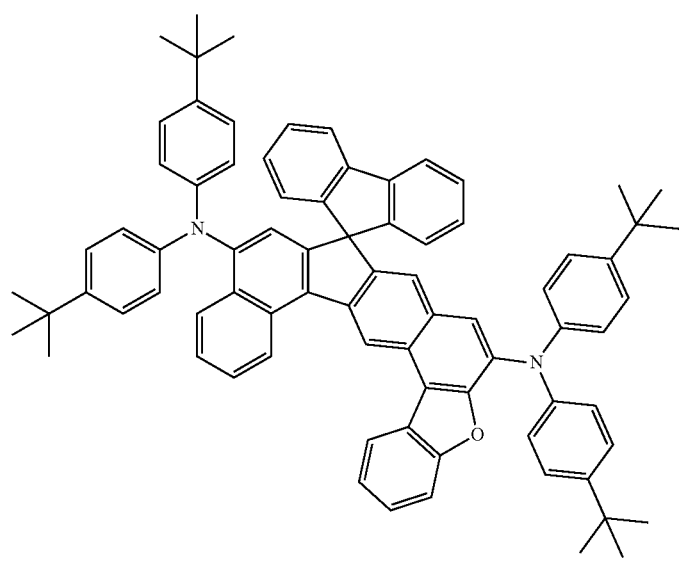
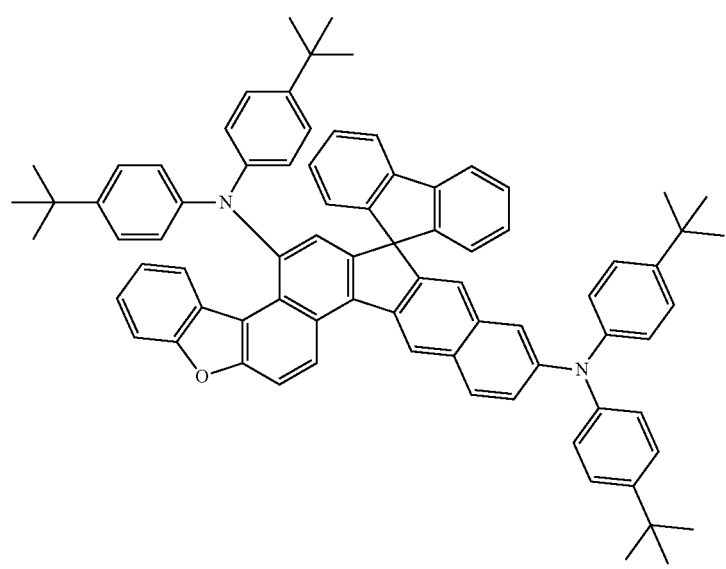

1111
-continued
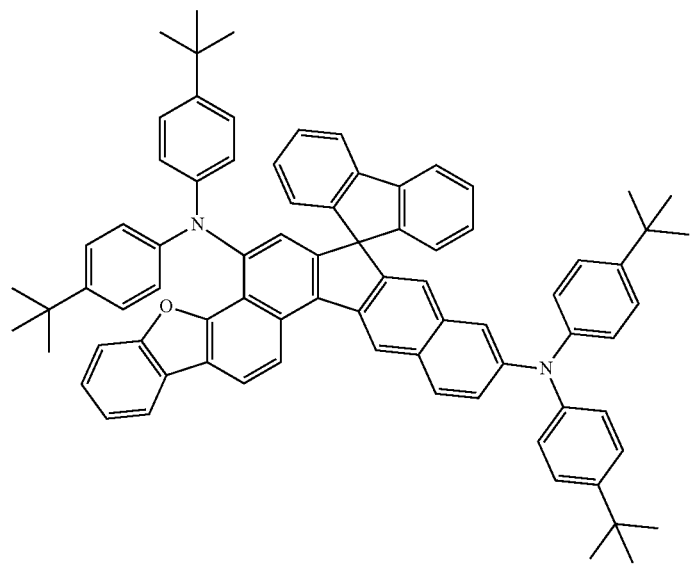
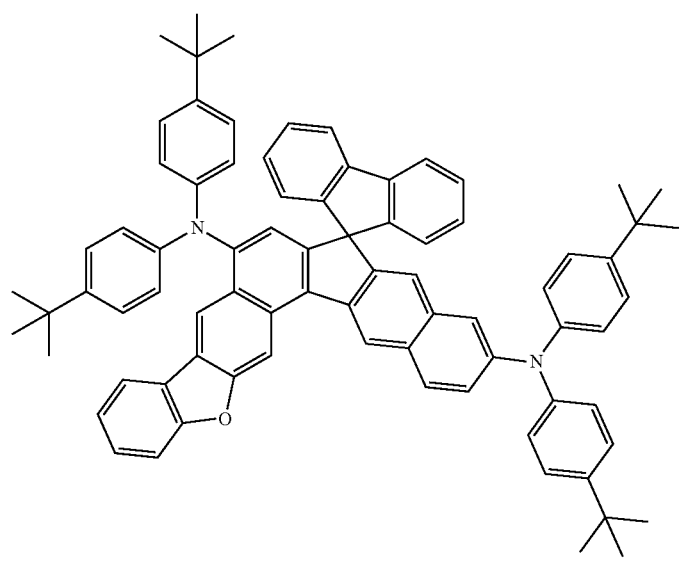
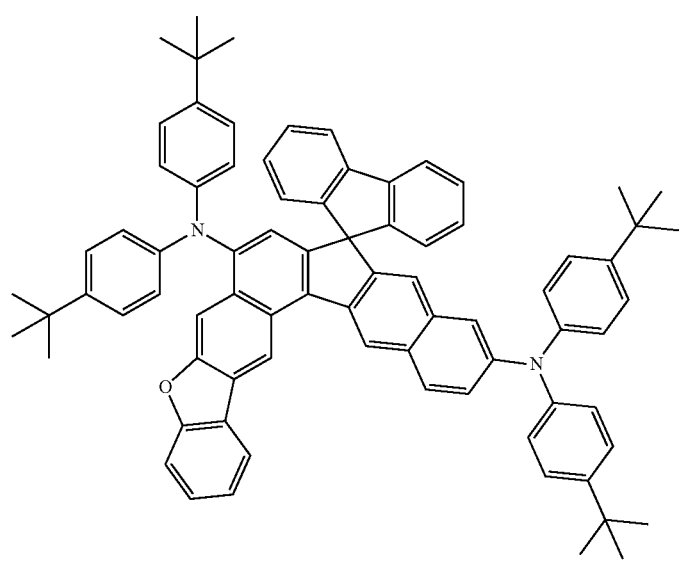
1112

1113
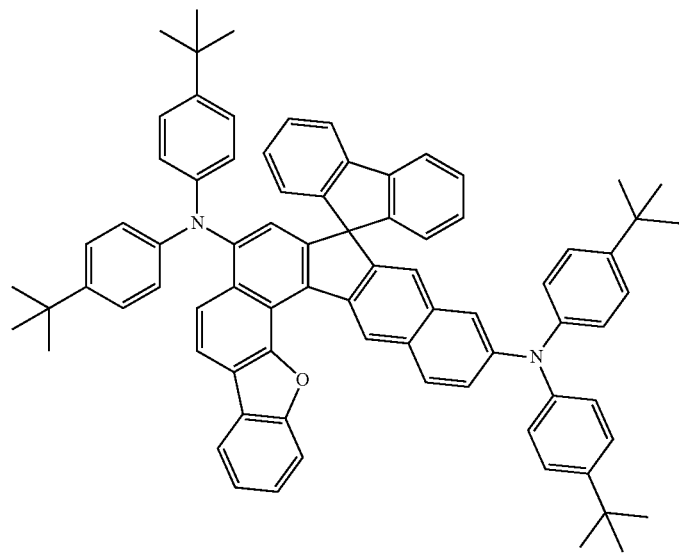
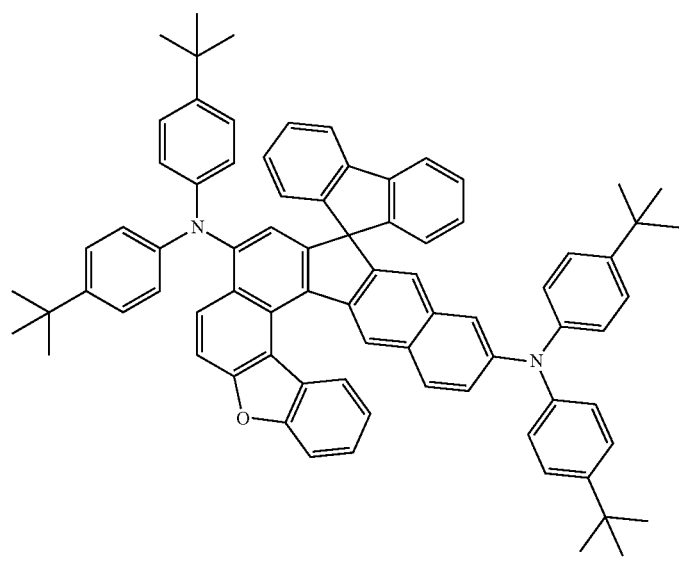
1114
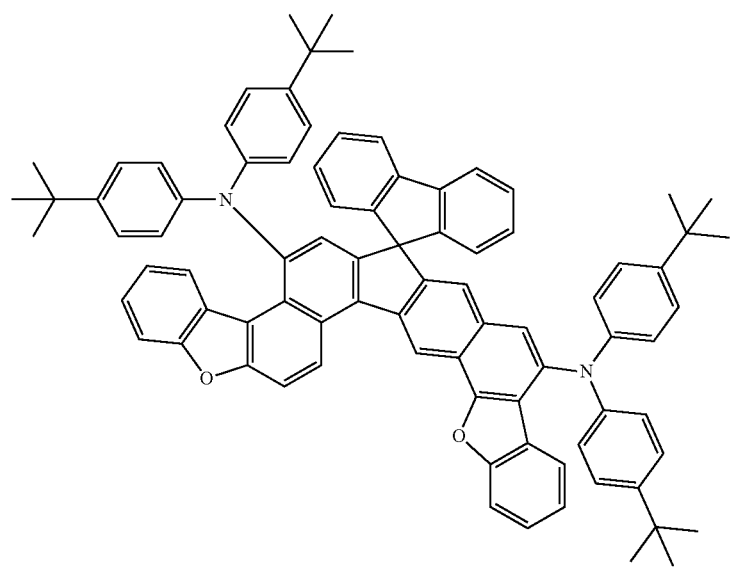

1115
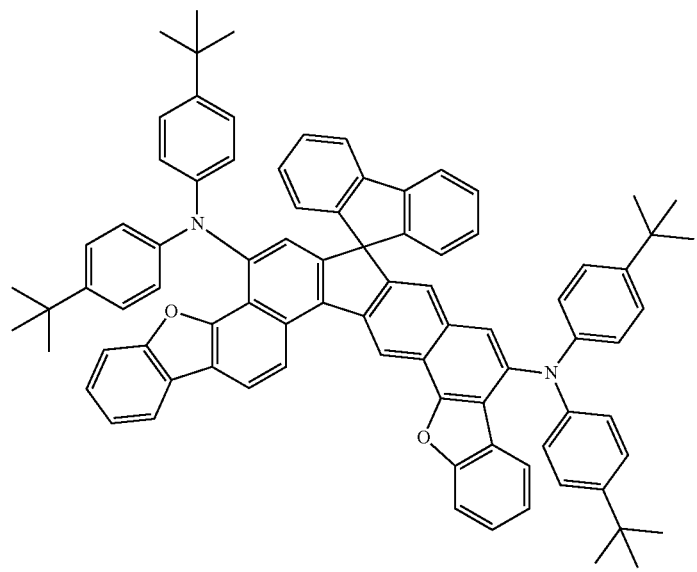
1116
-continued
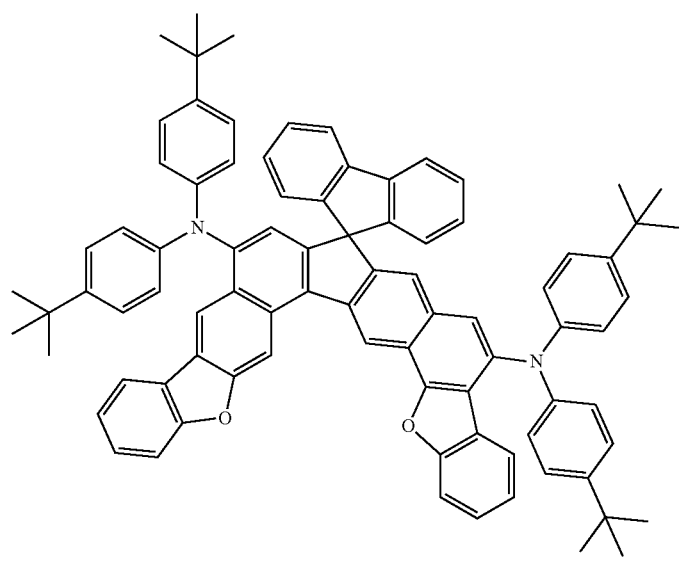
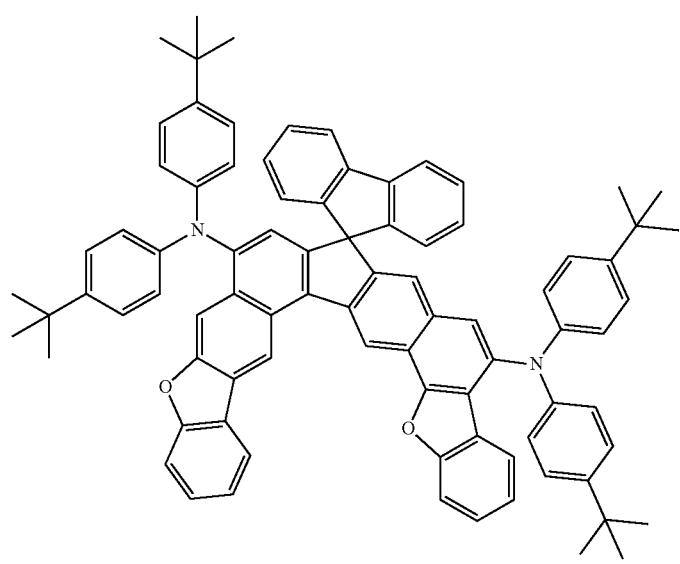

1117 1118
-continued
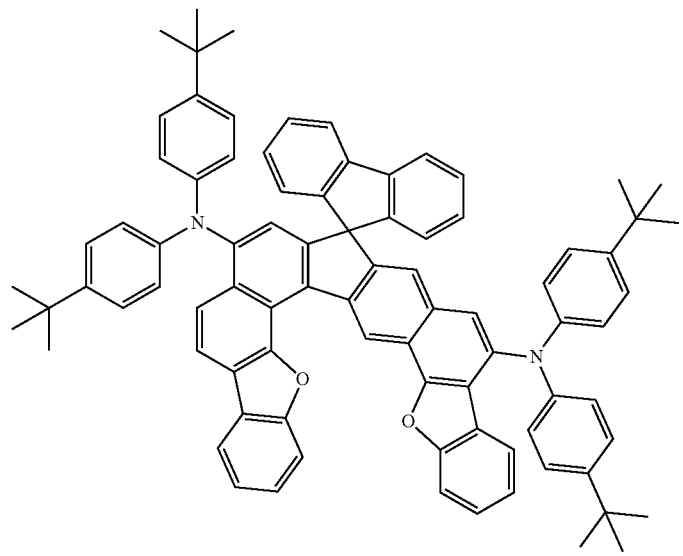
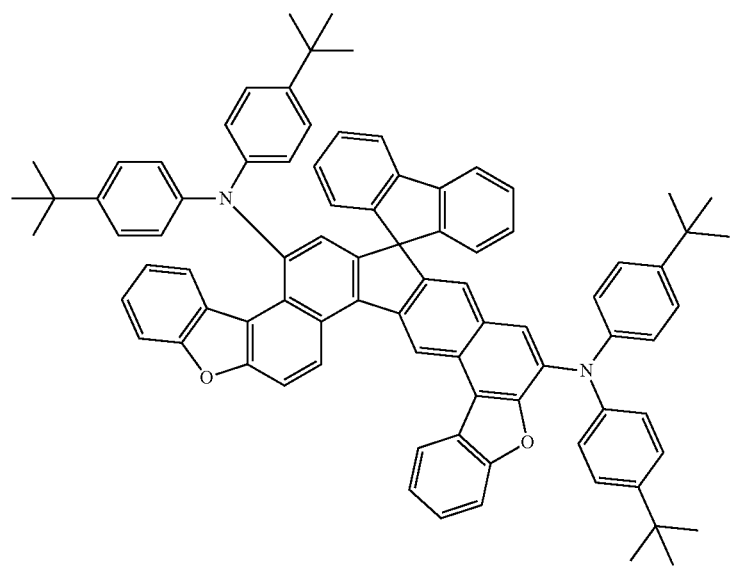
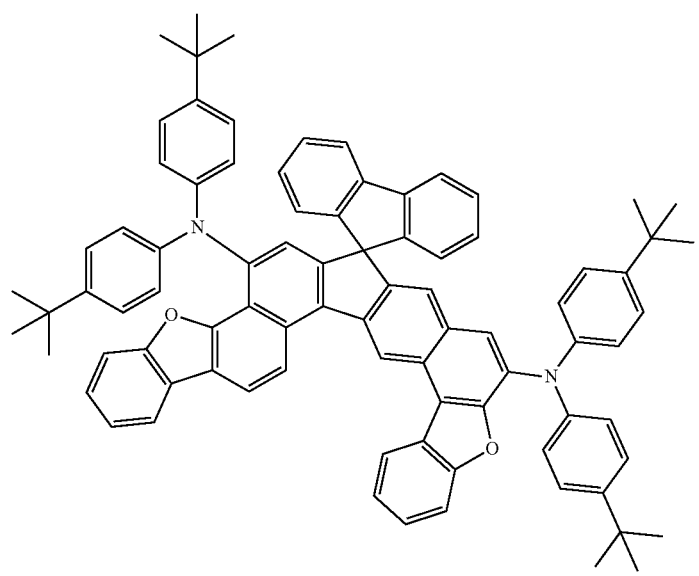

1119 1120
-continued
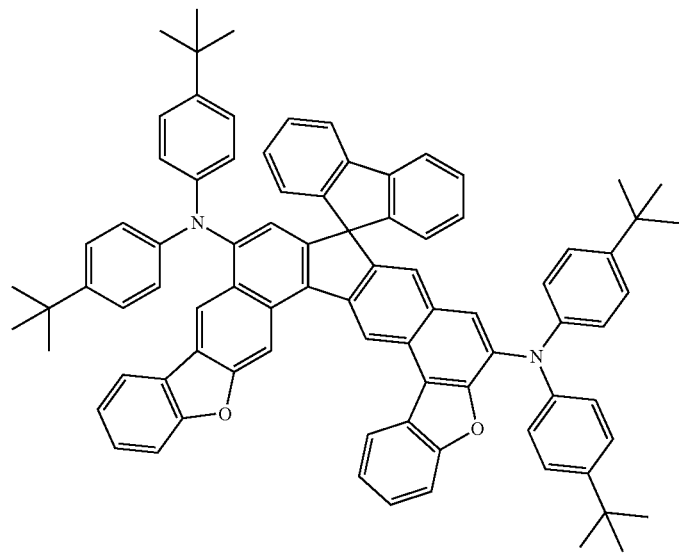
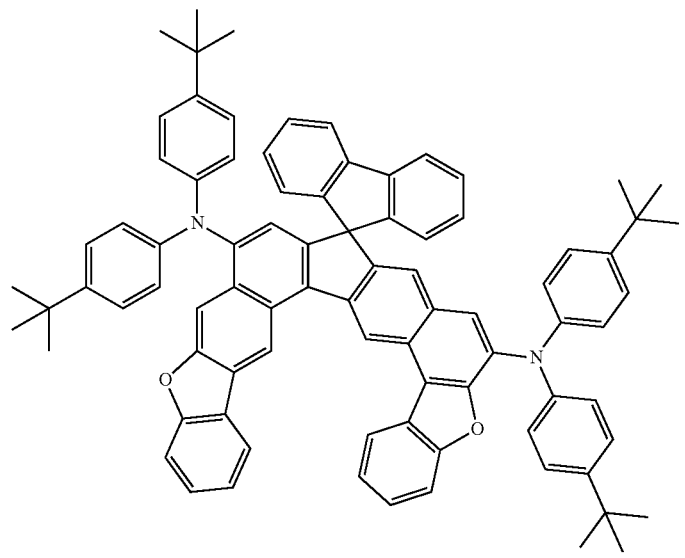
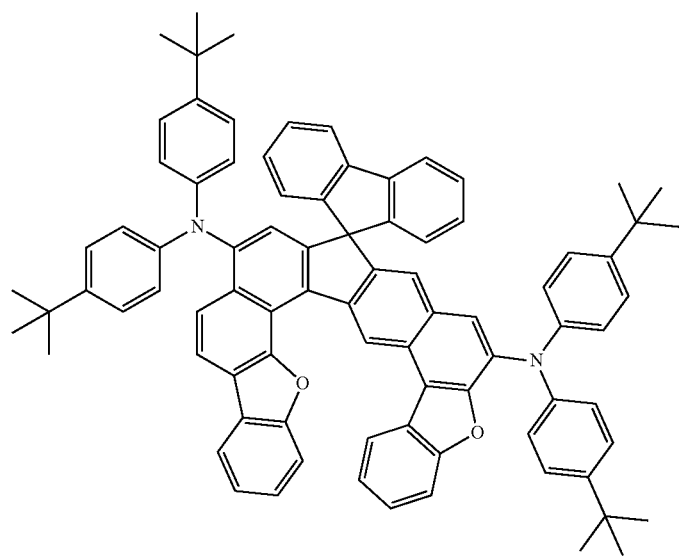

1121  1122
-continued
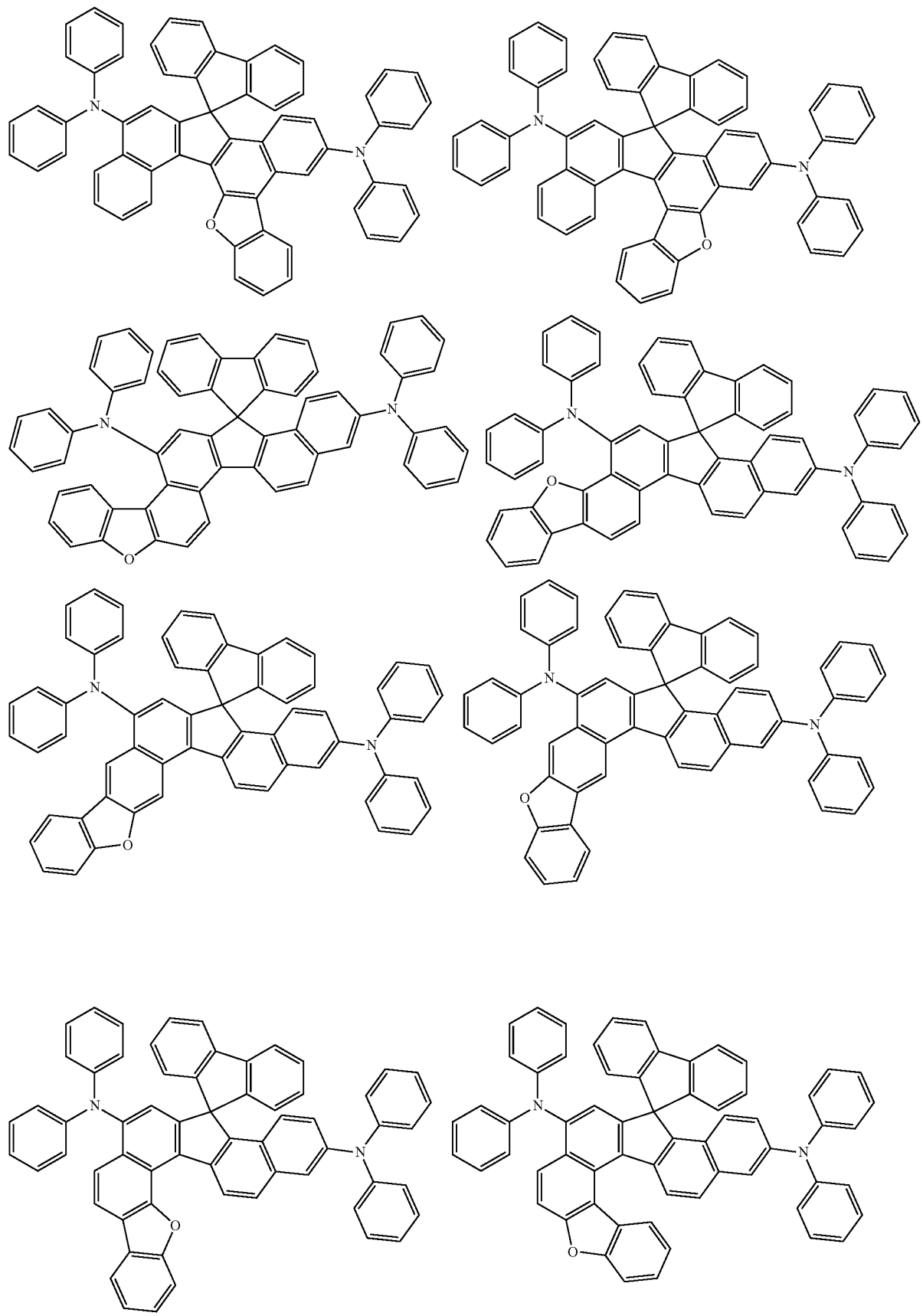

-continued
1123 1124
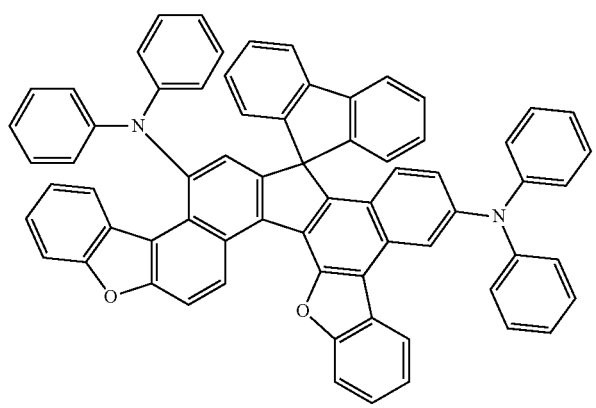 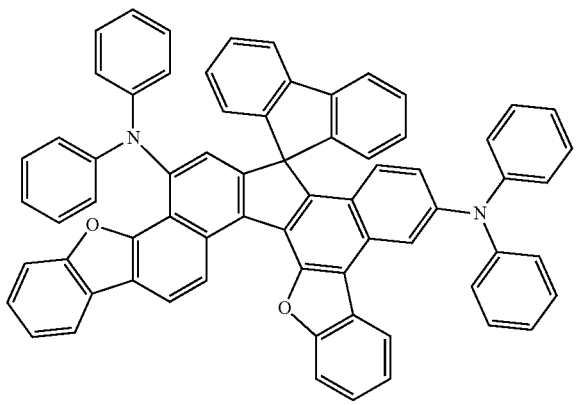
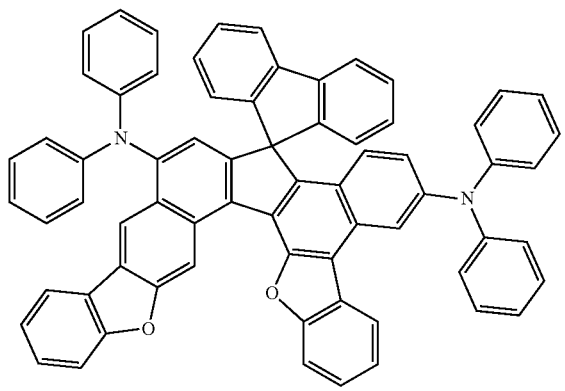 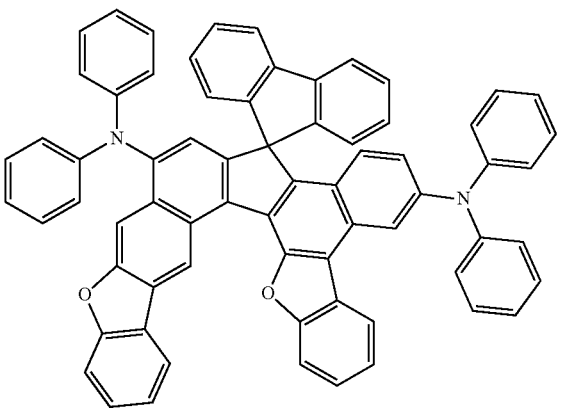
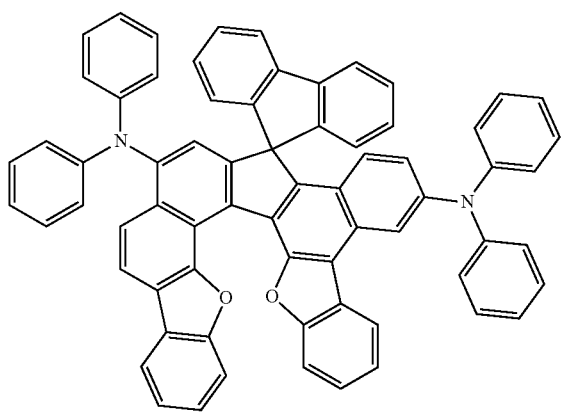 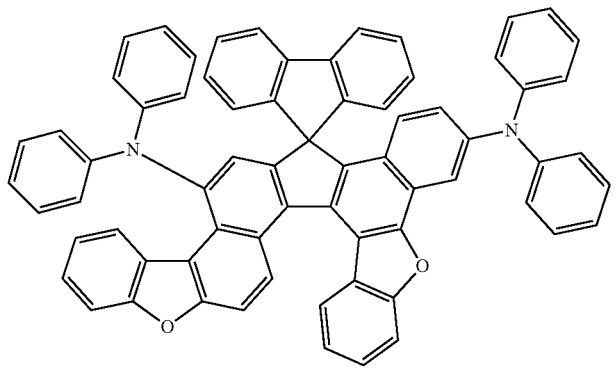
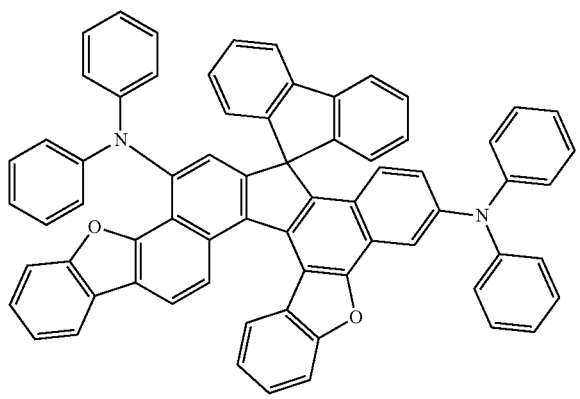 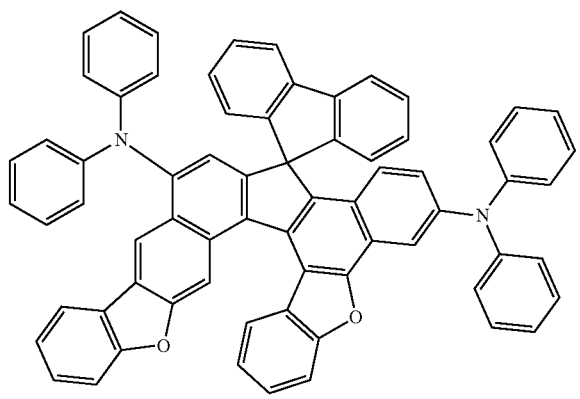

1125
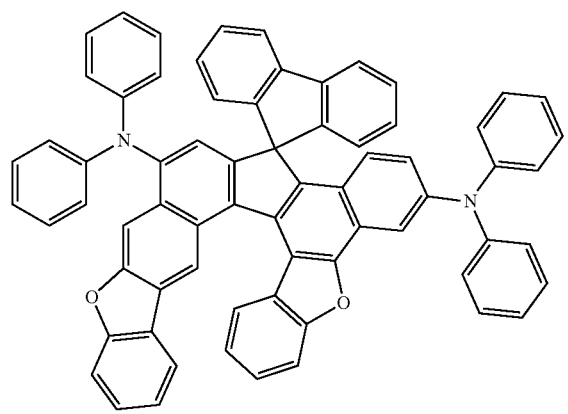
-continued
1126
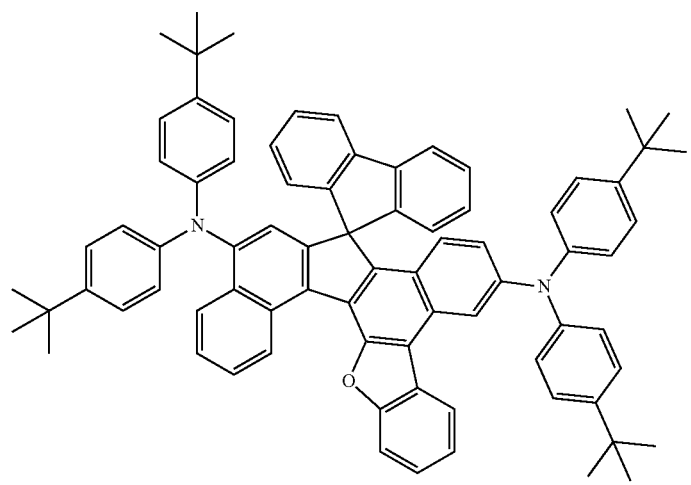
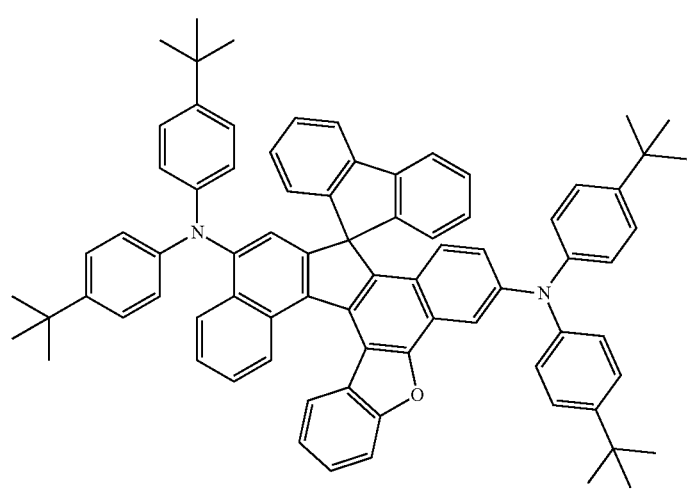

1127
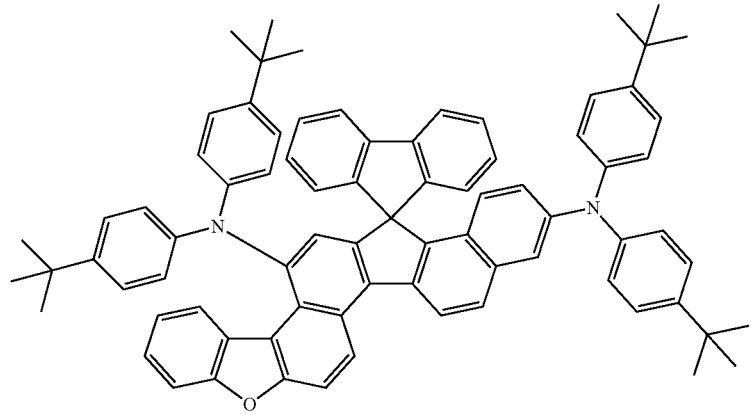
1128
-continued
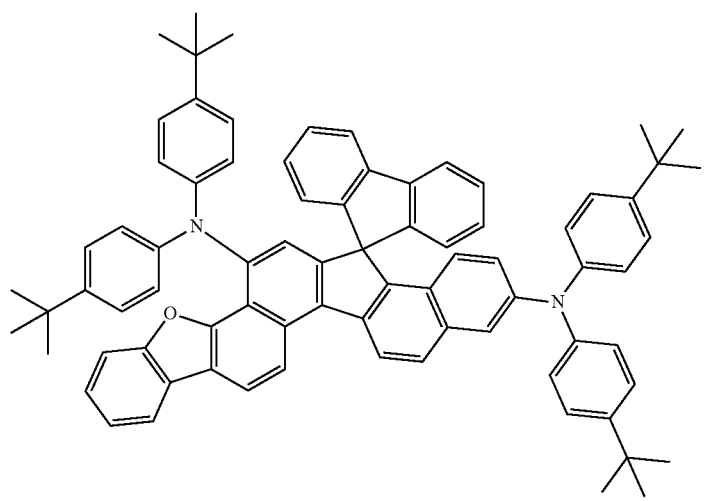
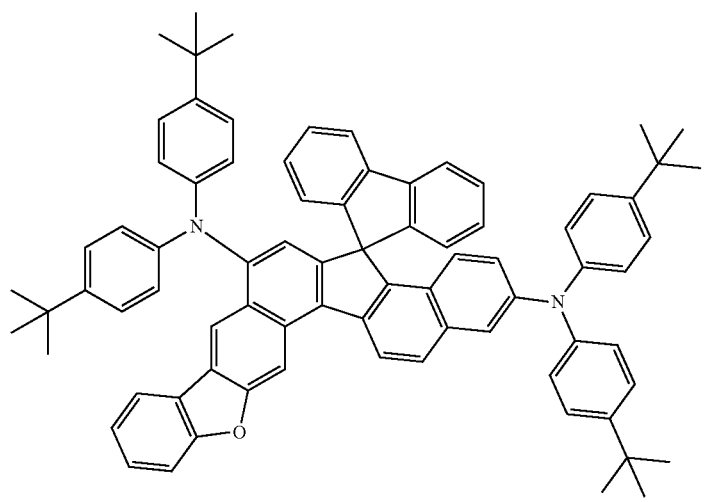

1129 1130
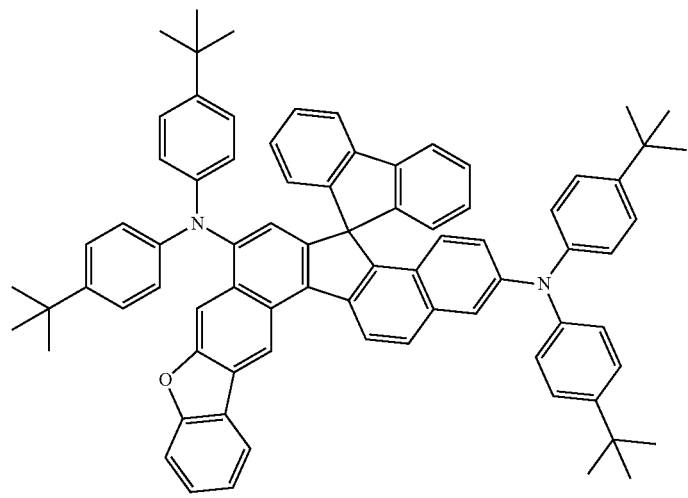
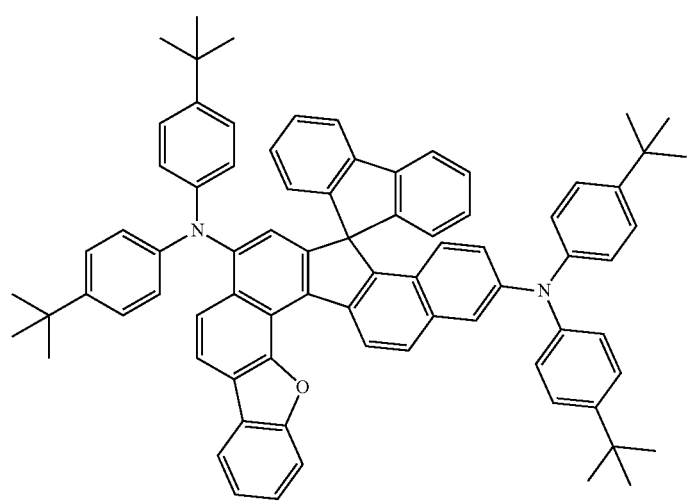
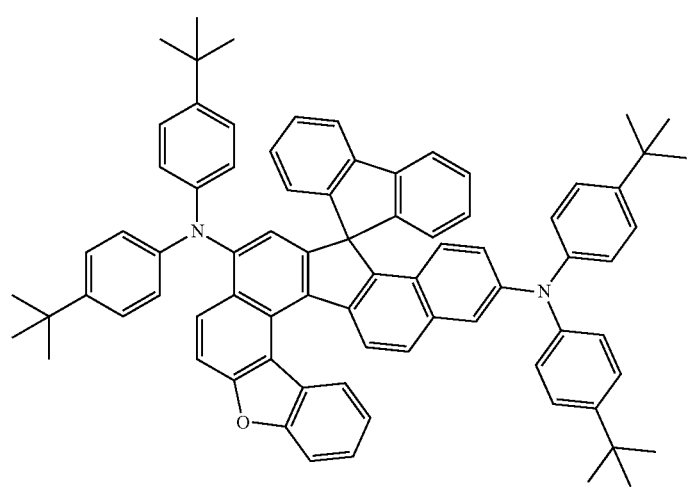

| 1131 | 1132 |
|---|---|
| 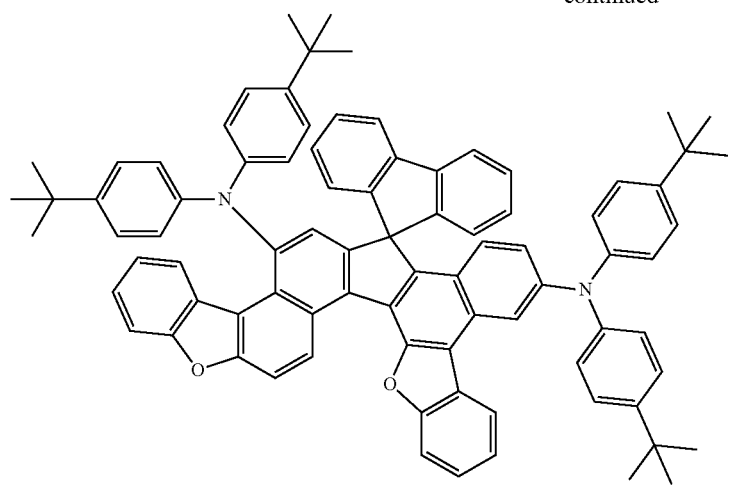 | |
| 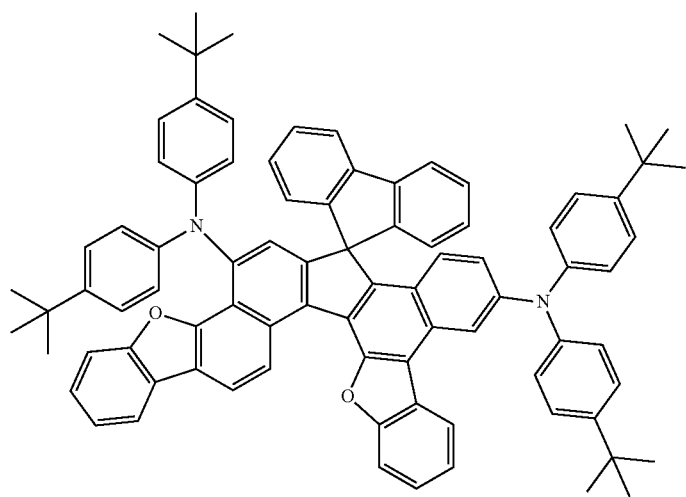 | |
| 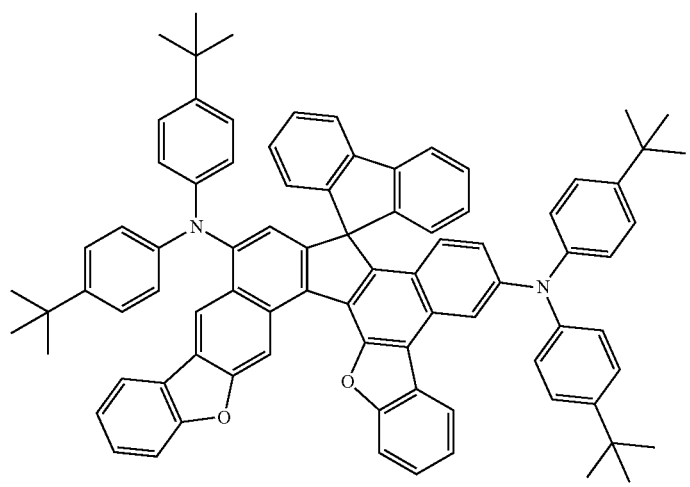 | |

1133
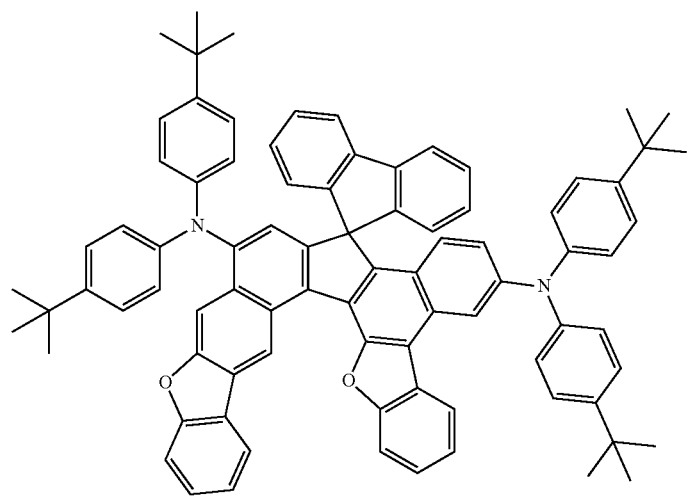
1134
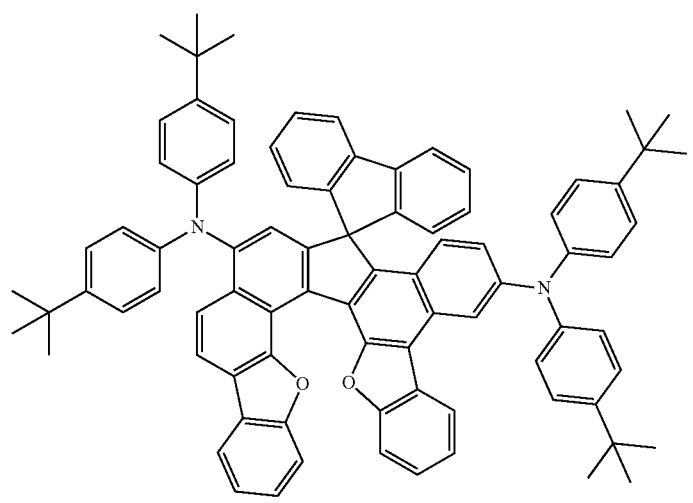
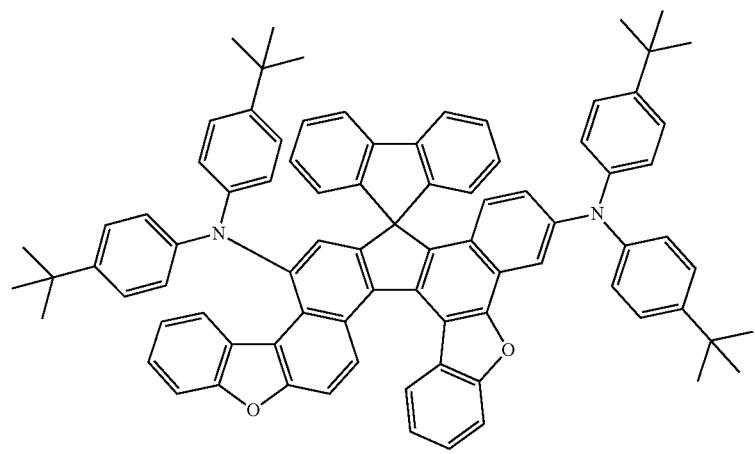

1135
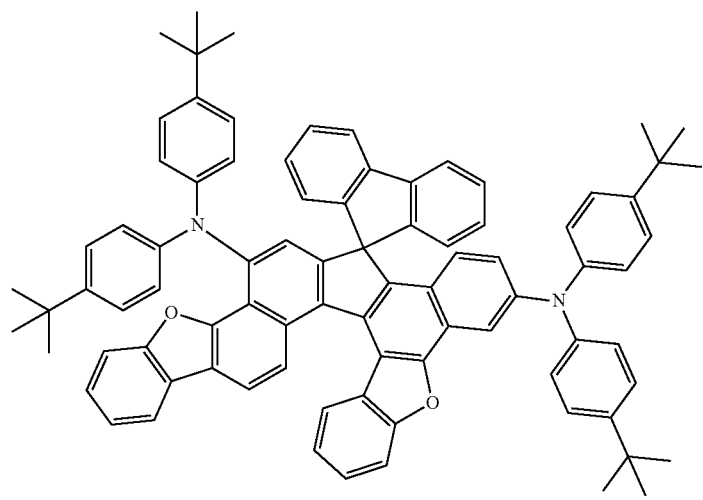
1136
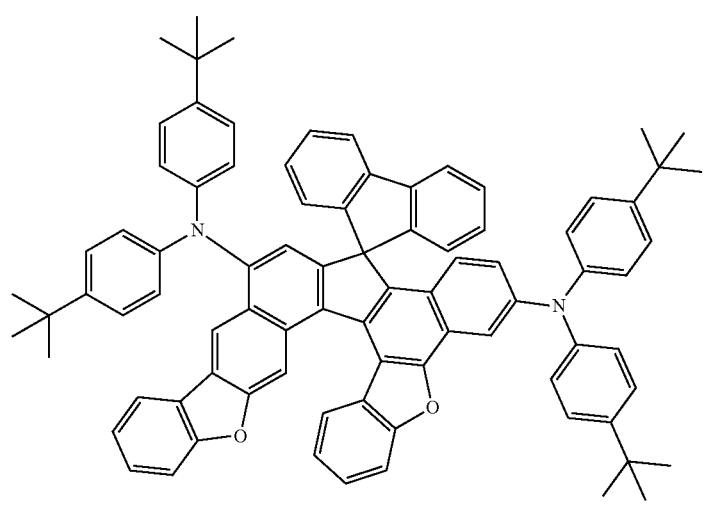
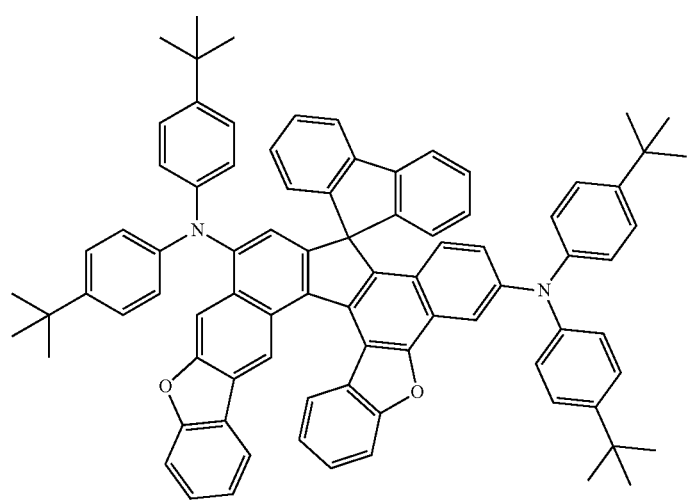

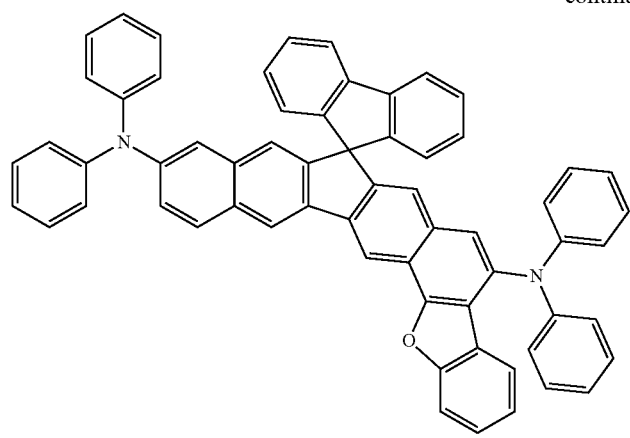
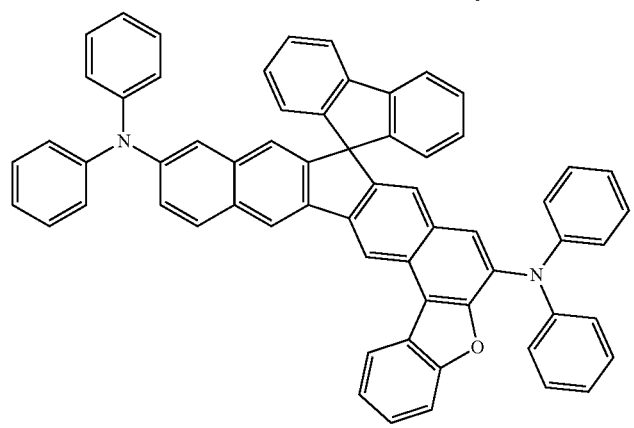
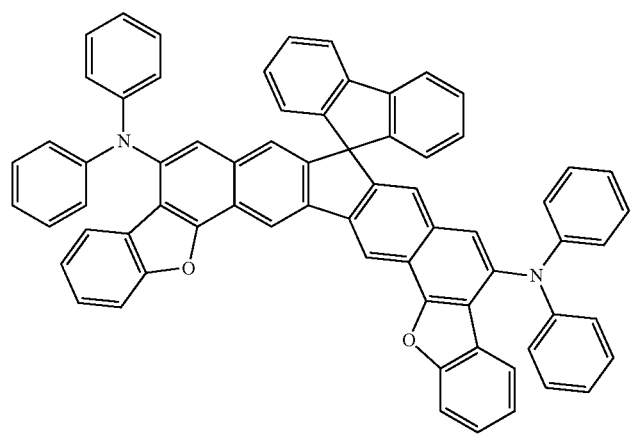
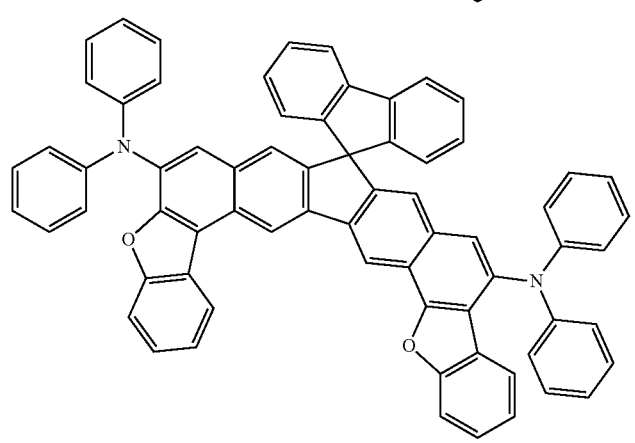

1139
-continued
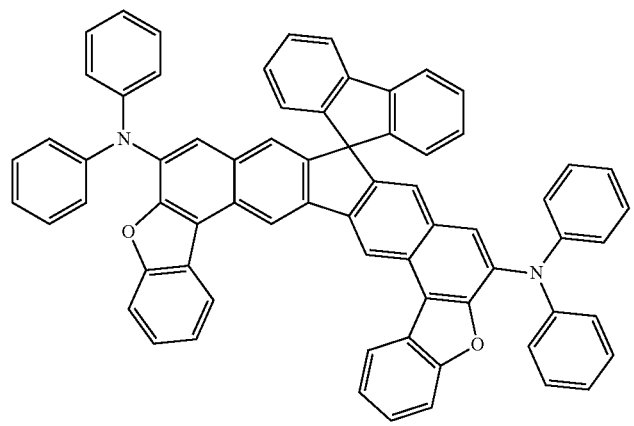
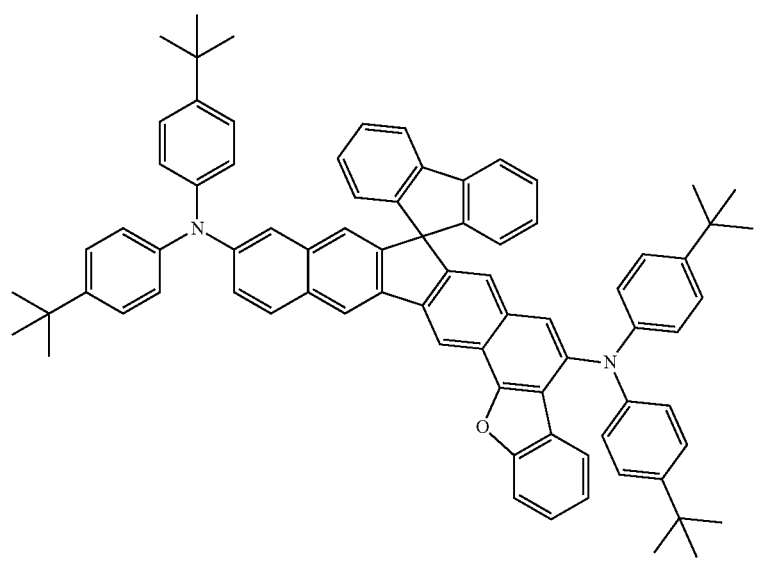
1140
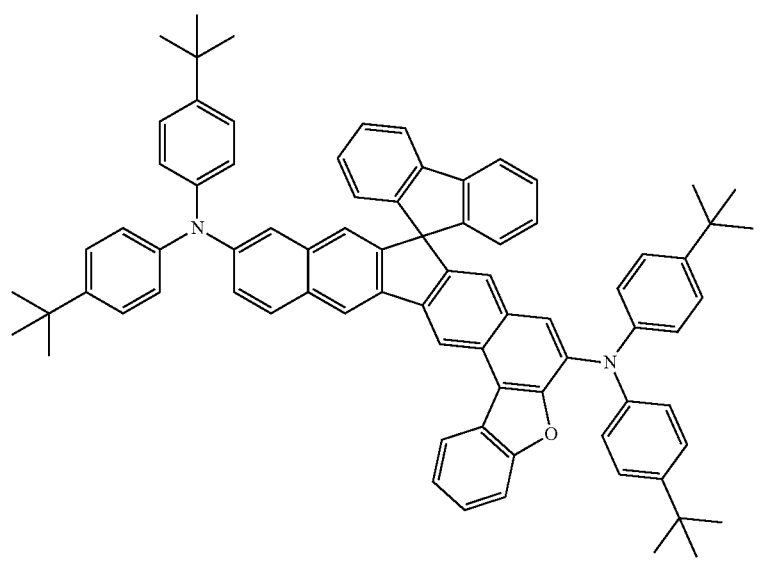

1141
-continued
1142
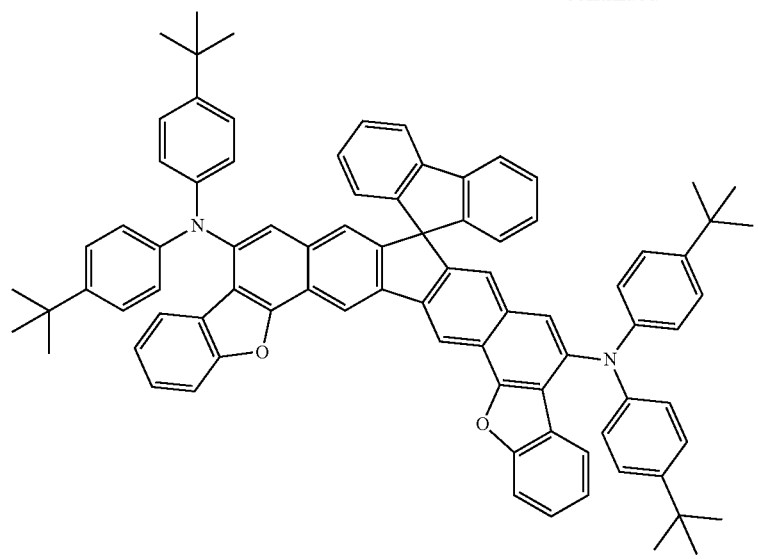
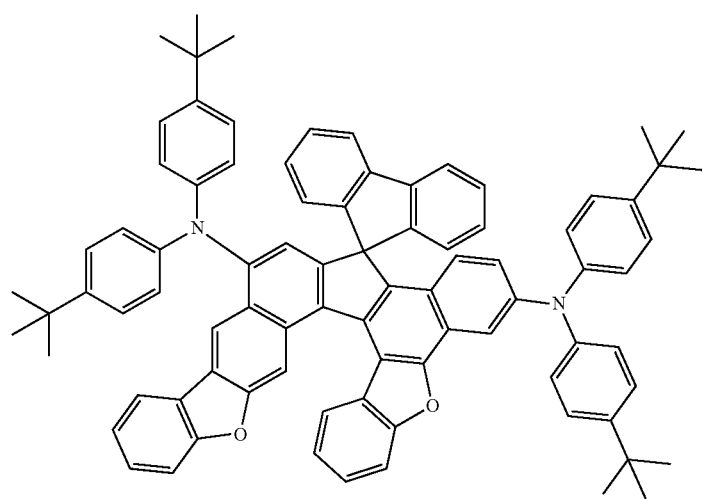
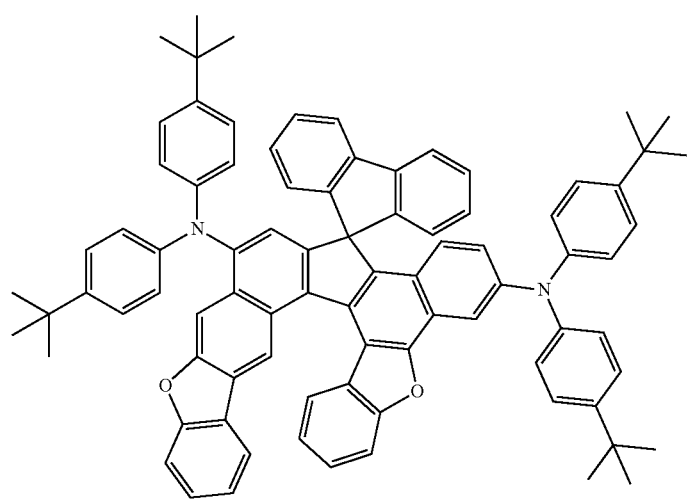

1143 1144
-continued
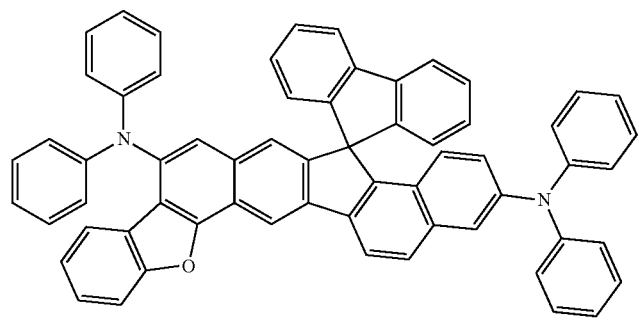
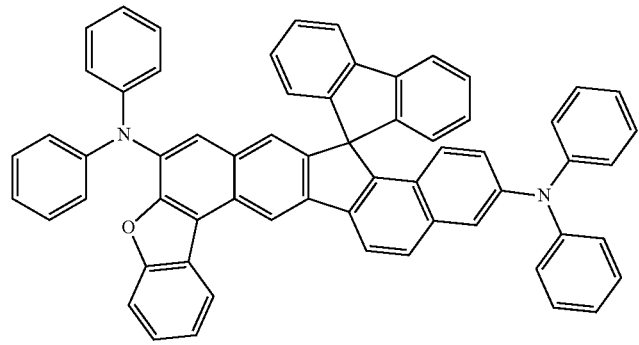
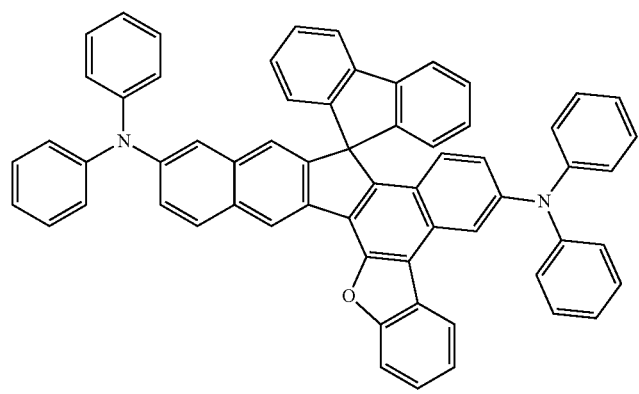
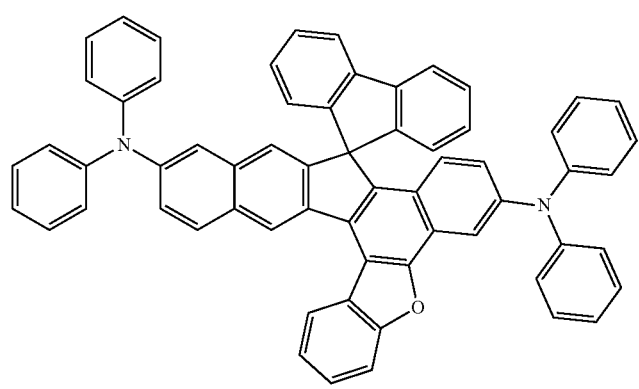

1145
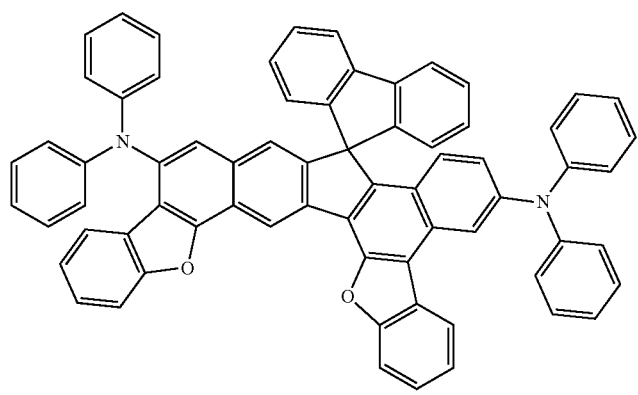
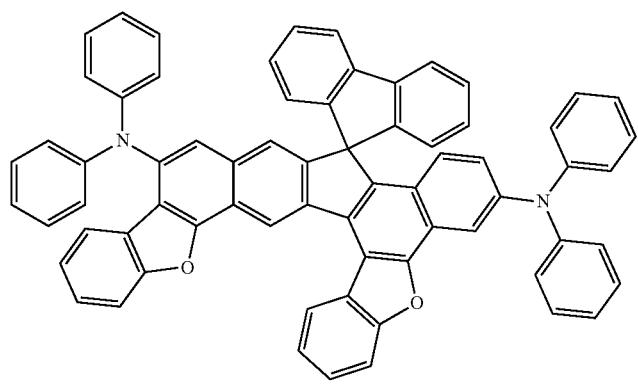
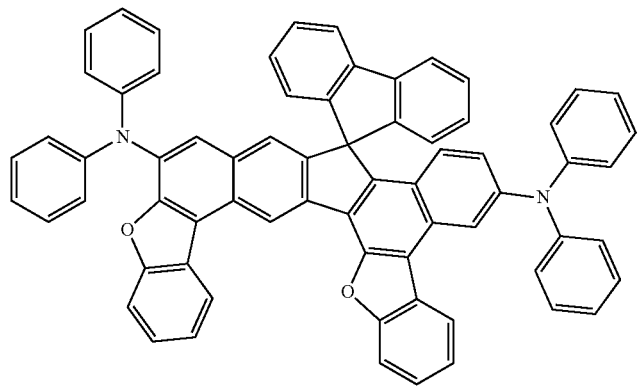
1146
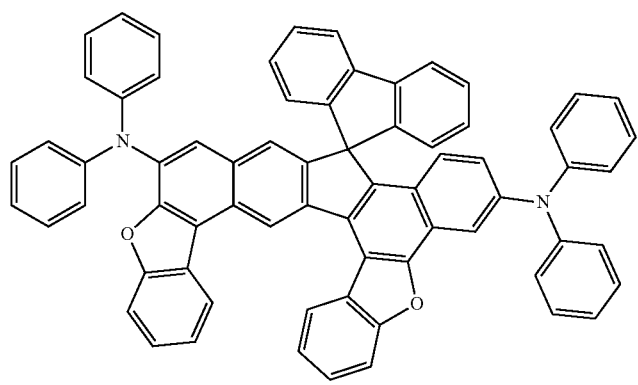

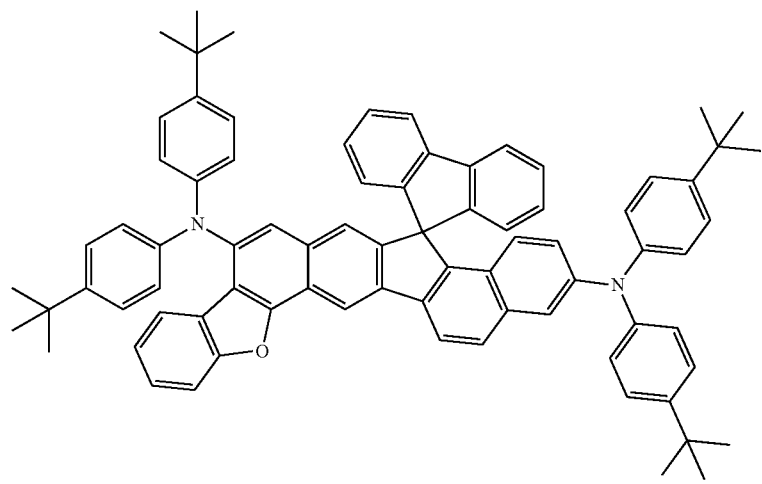
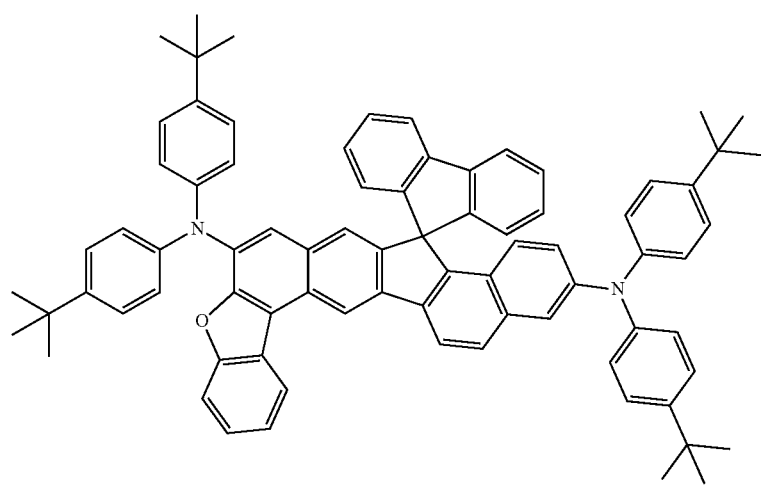
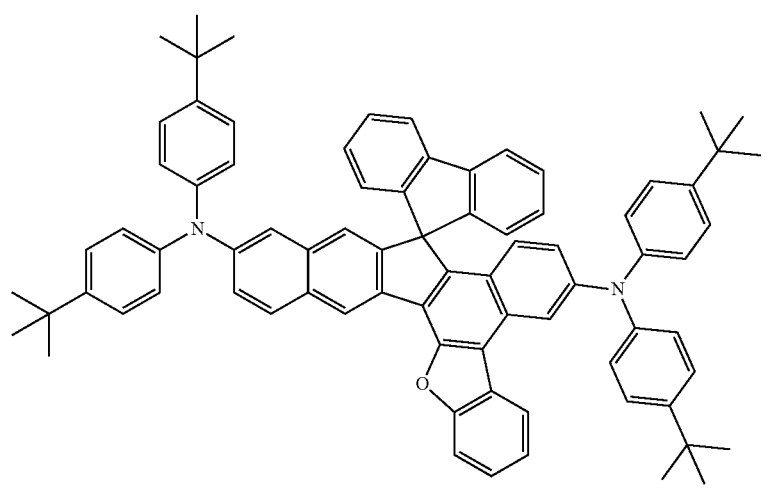

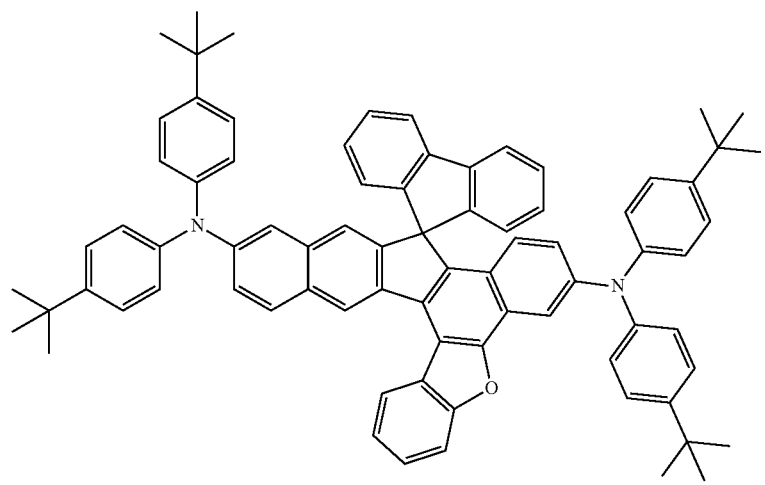
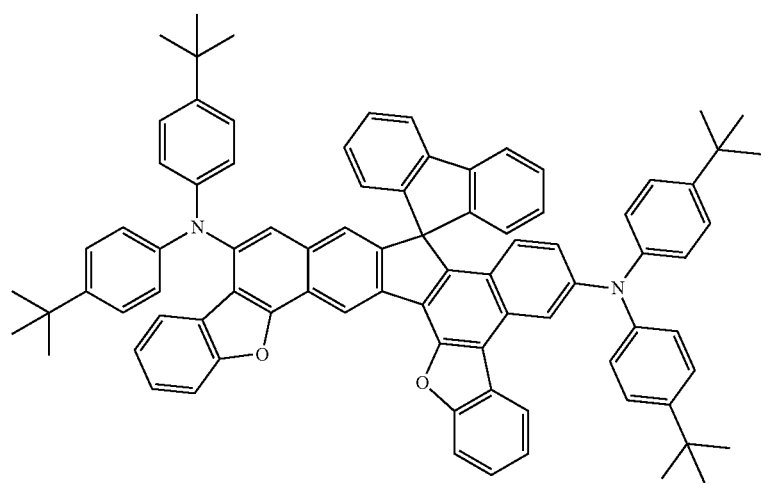
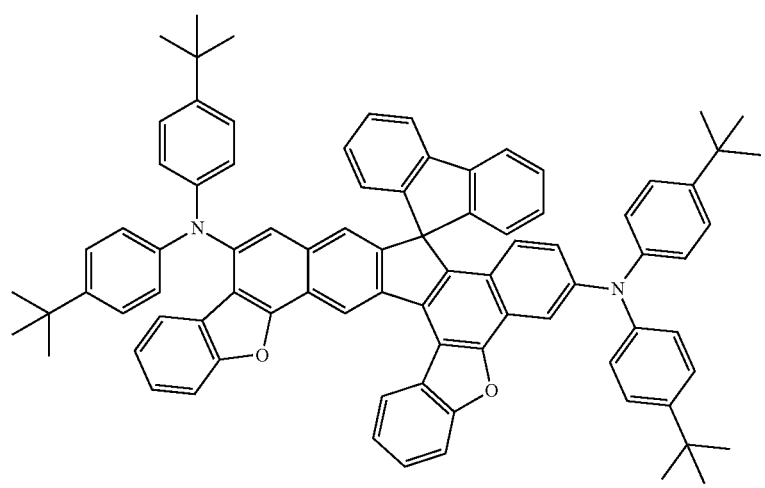

1151                    1152
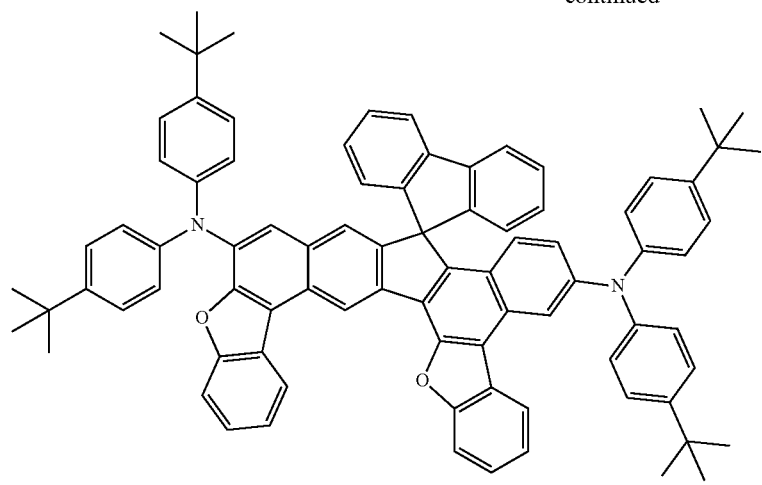
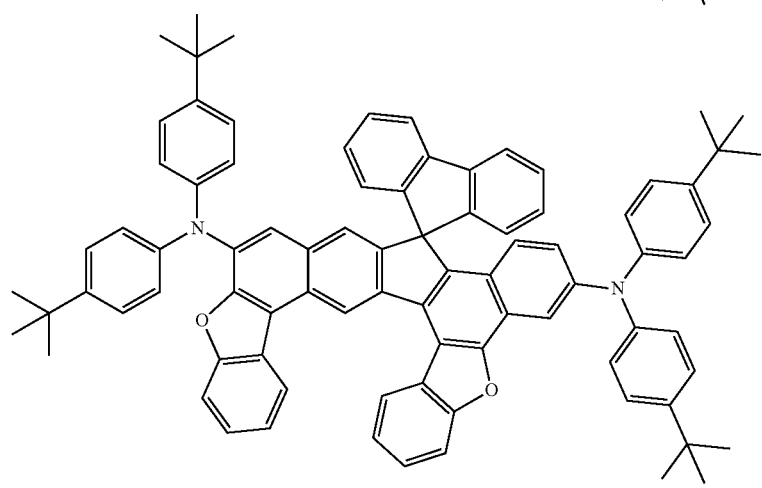
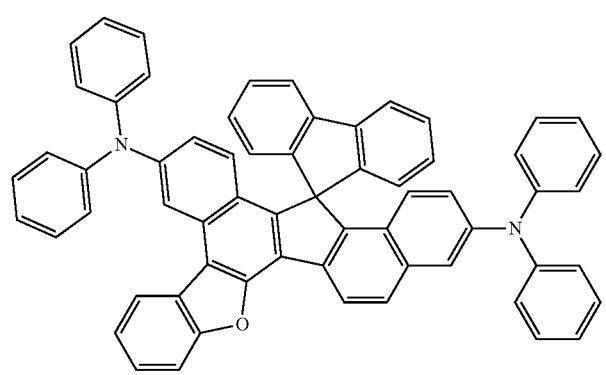
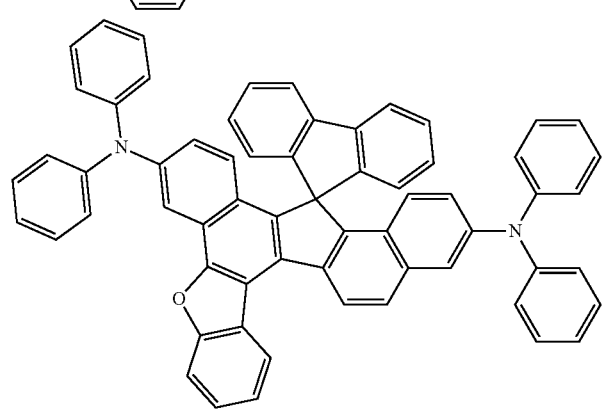

1153
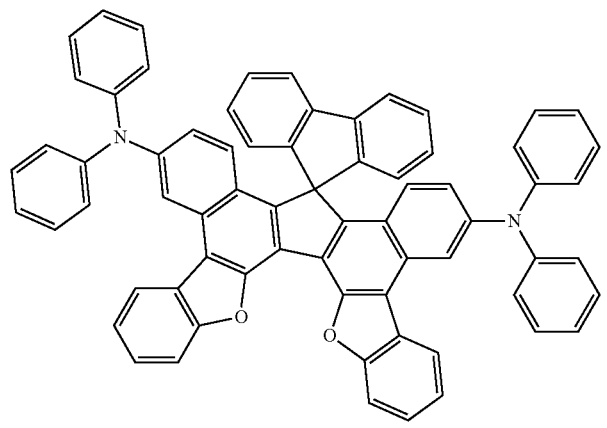
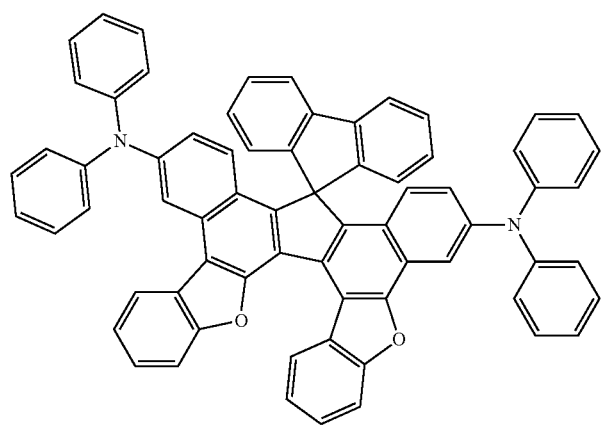
1154
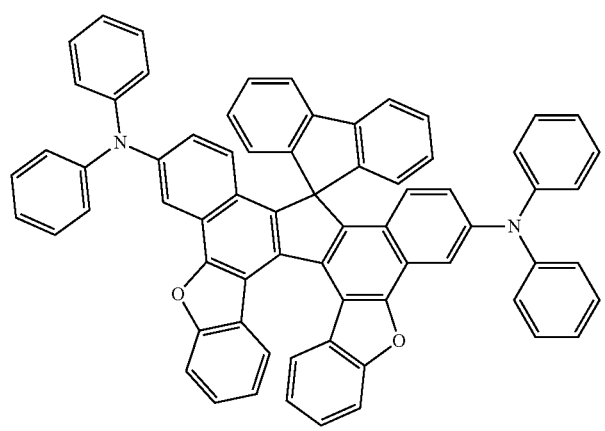

1155
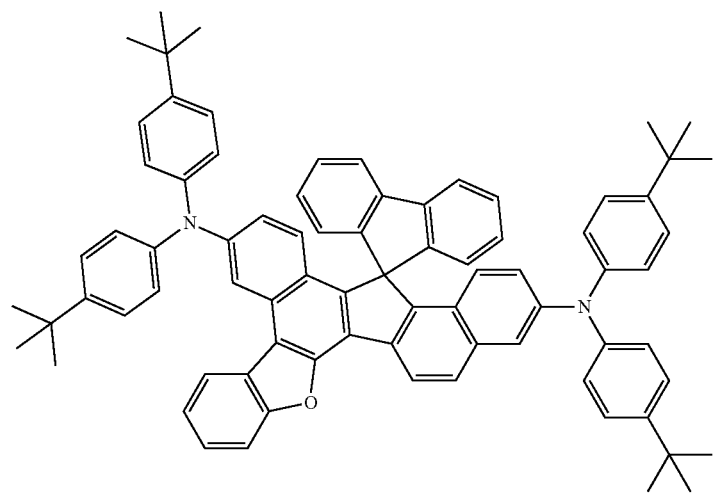
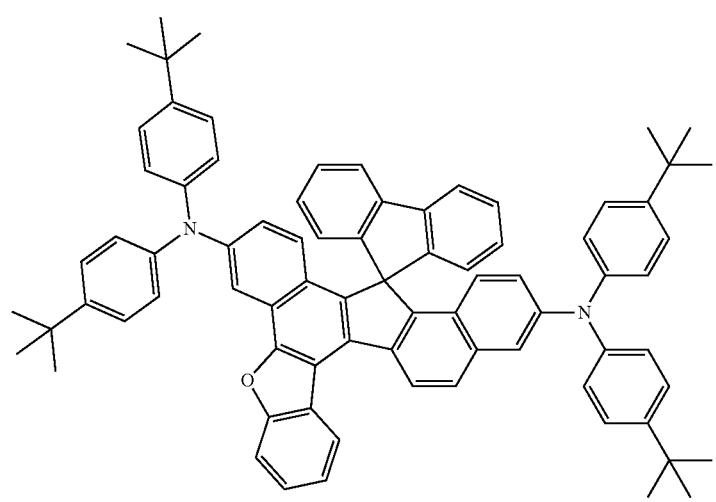
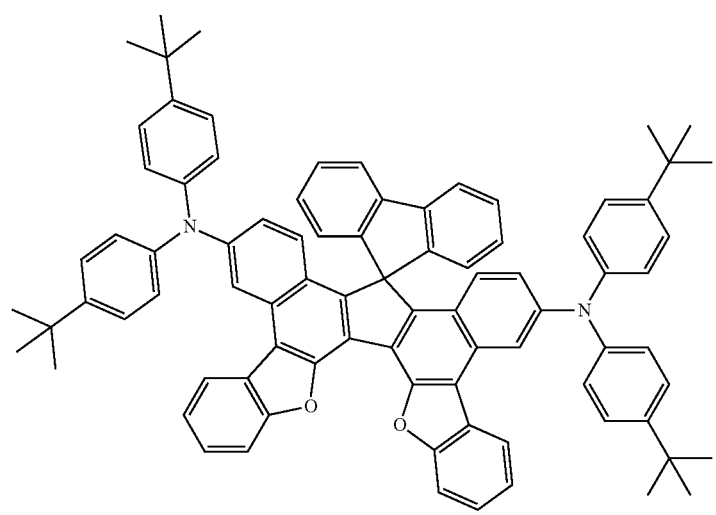
1156

1157 1158
-continued
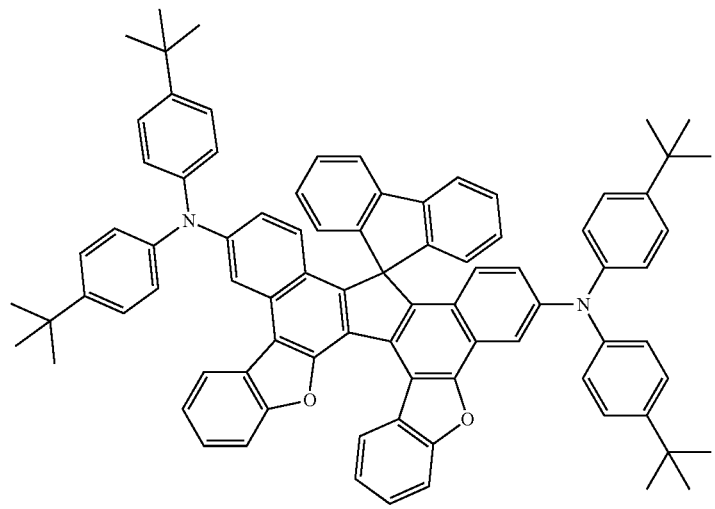
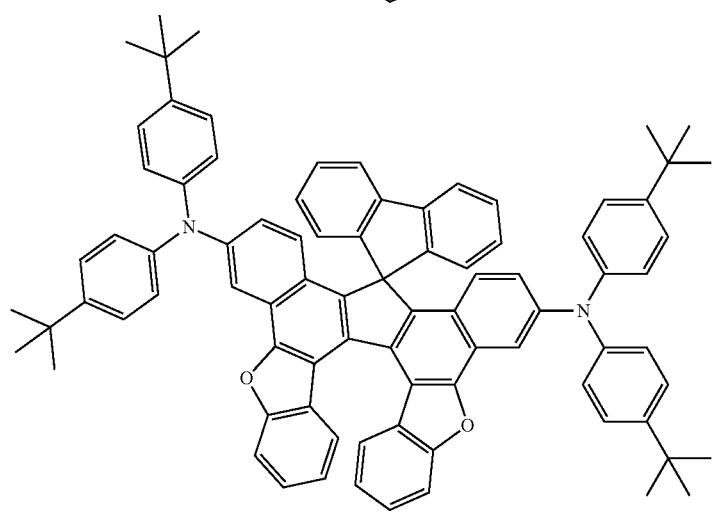
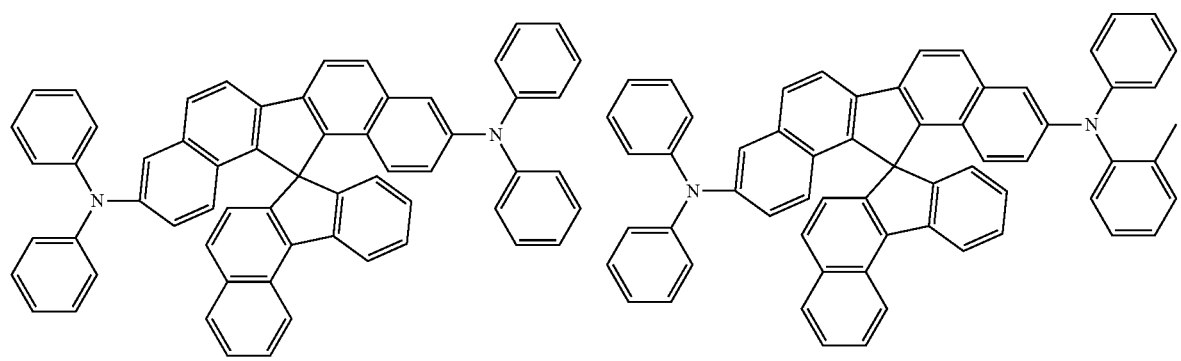
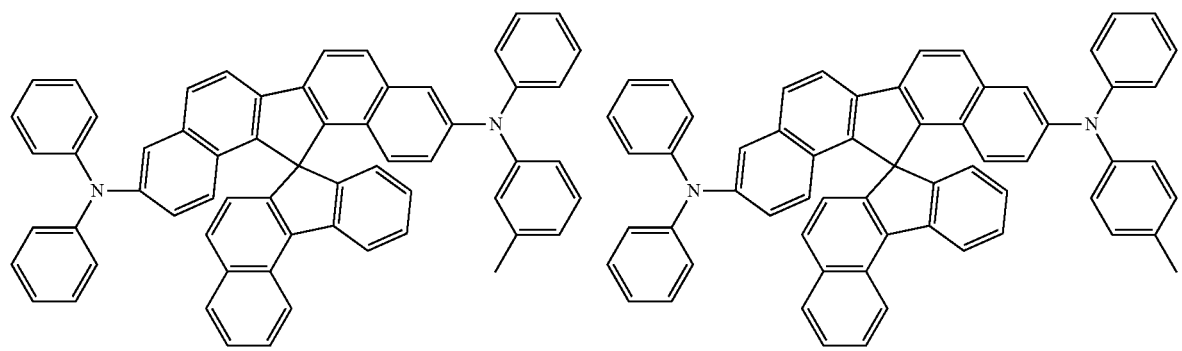

-continued
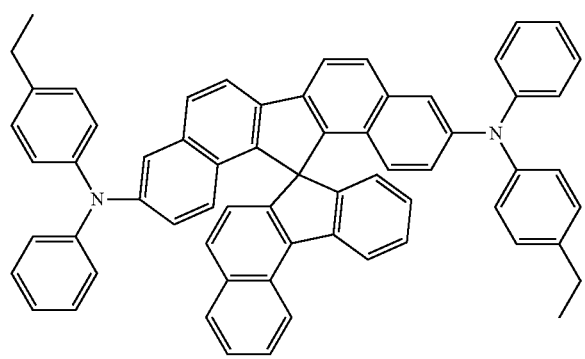
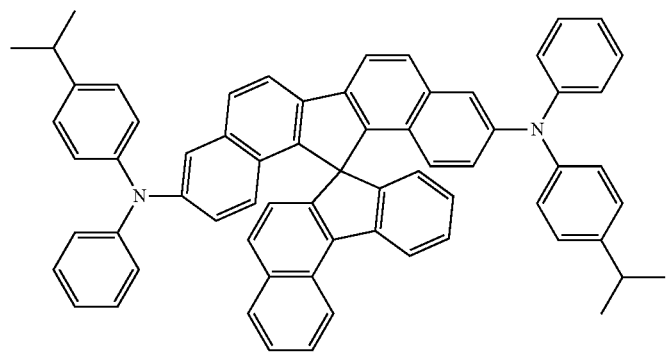
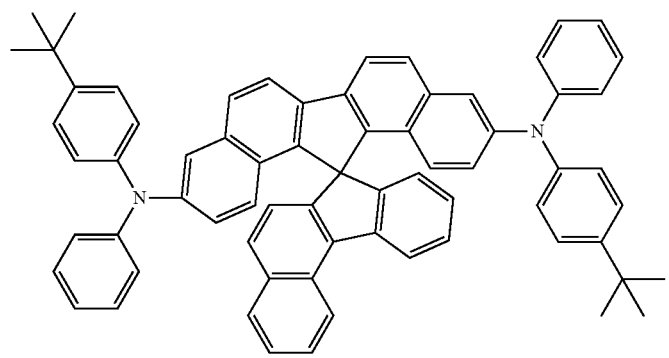
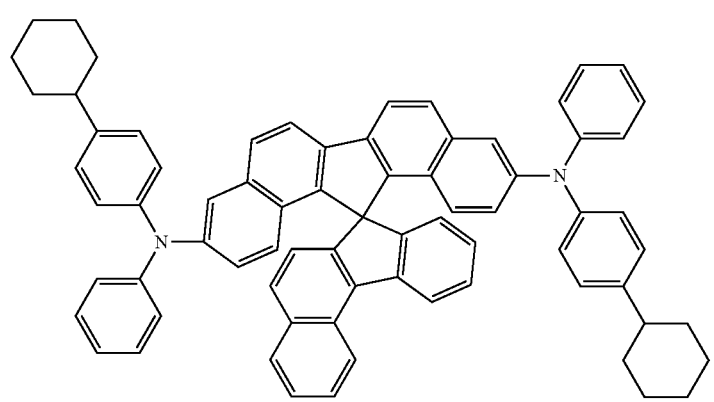

1161
-continued
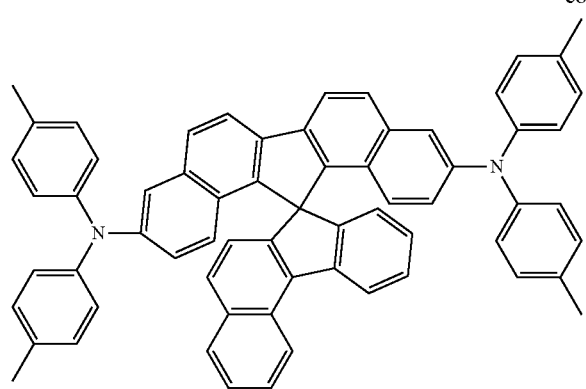
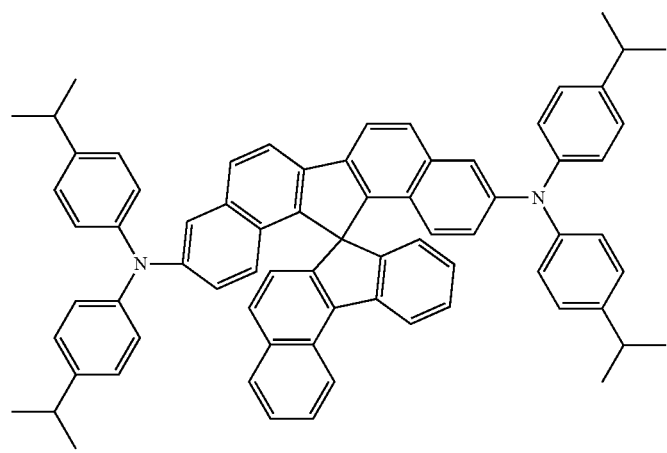
1162
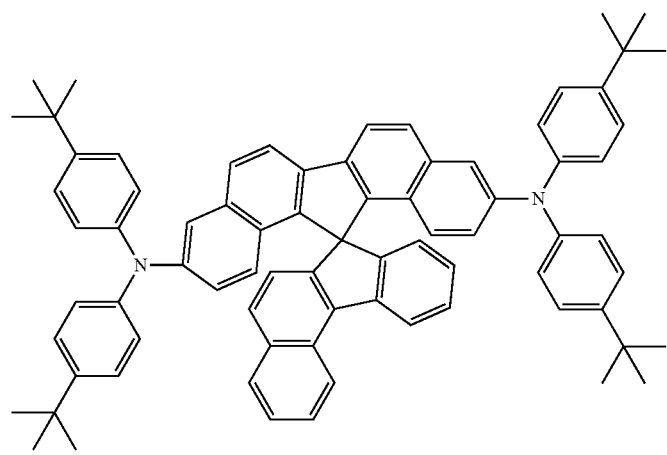

-continued
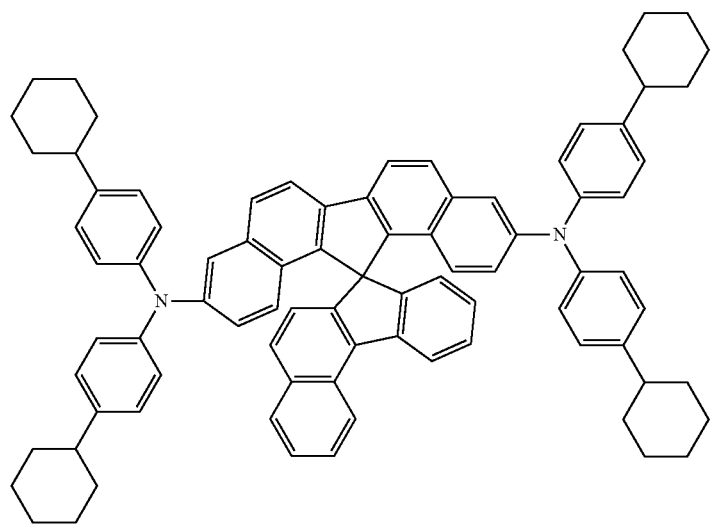
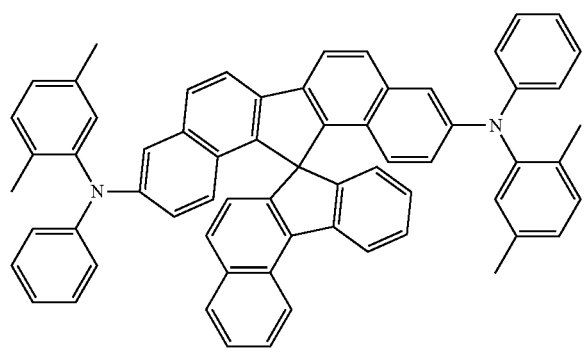
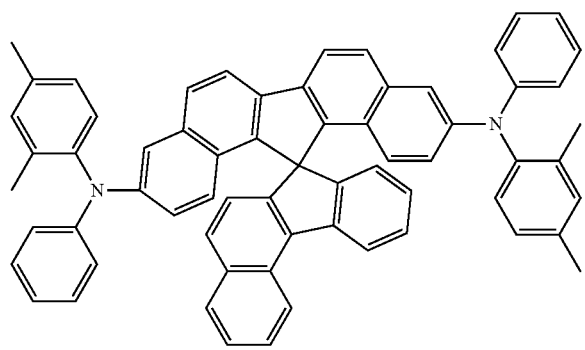
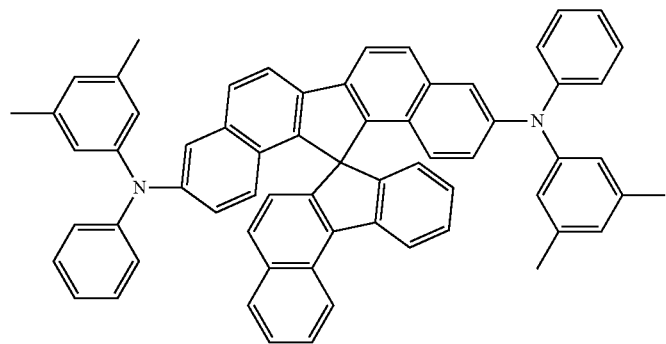

1165
-continued
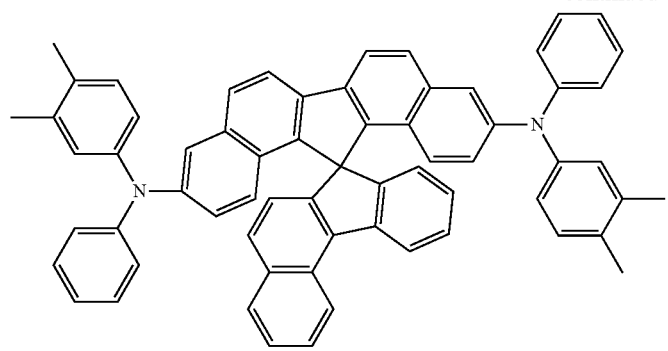
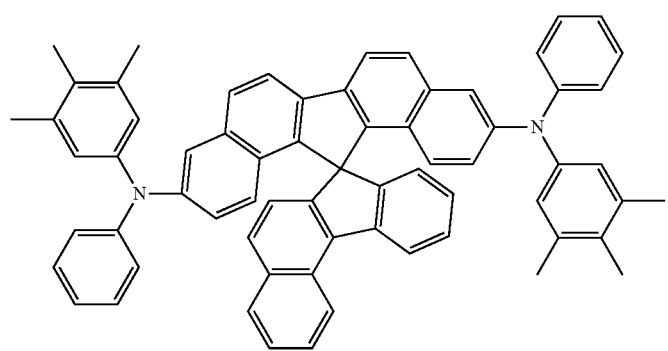
1166
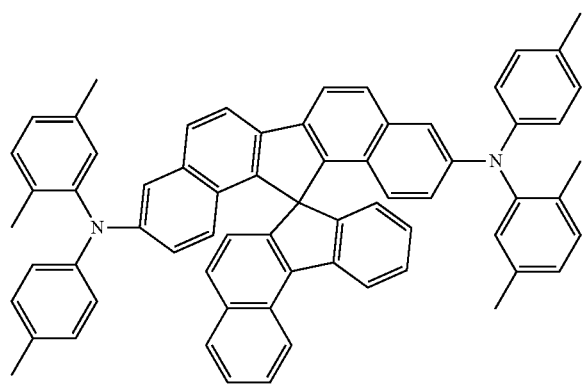
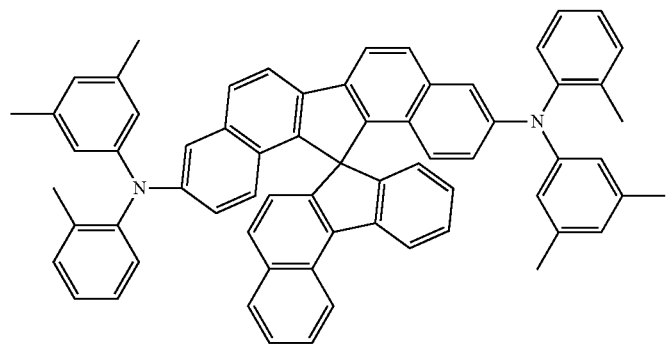

-continued
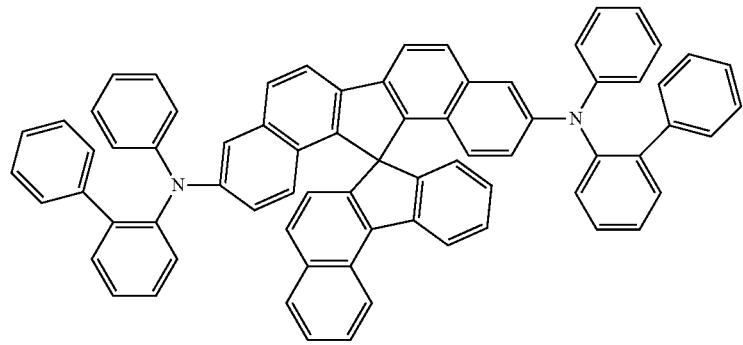
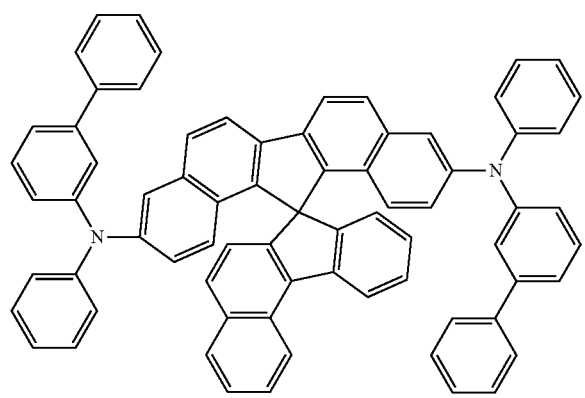
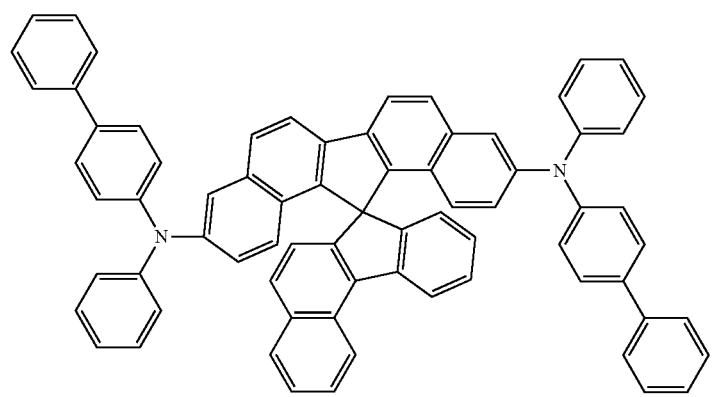
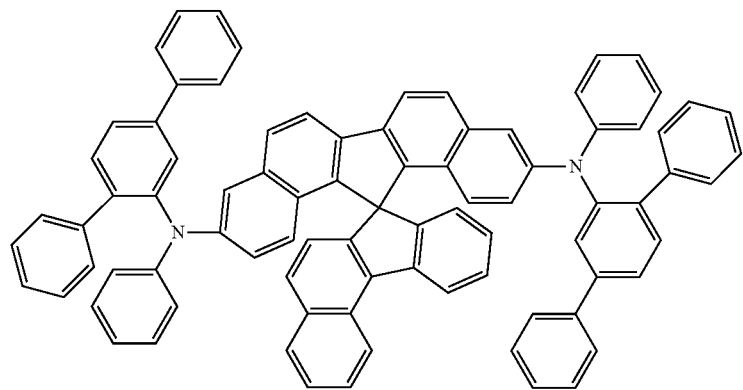

-continued
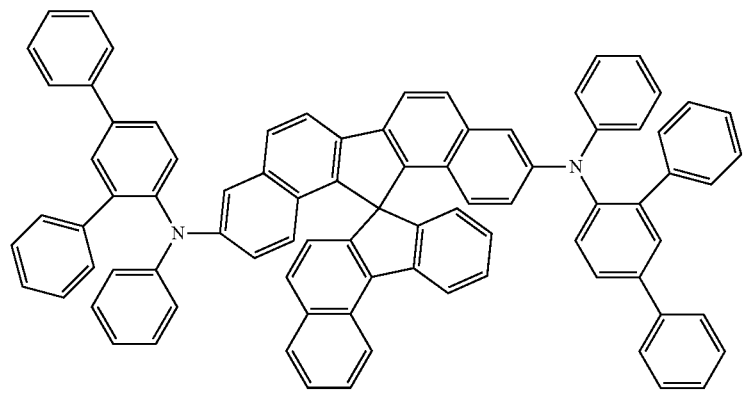
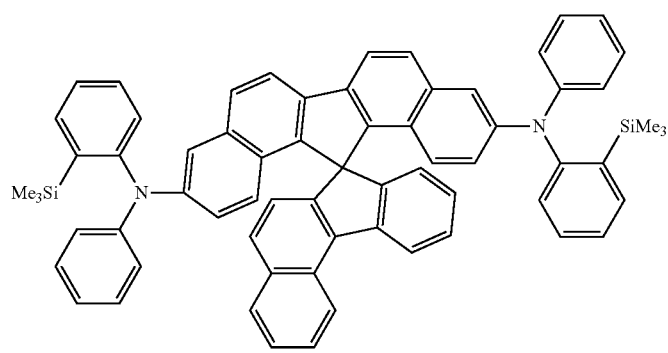
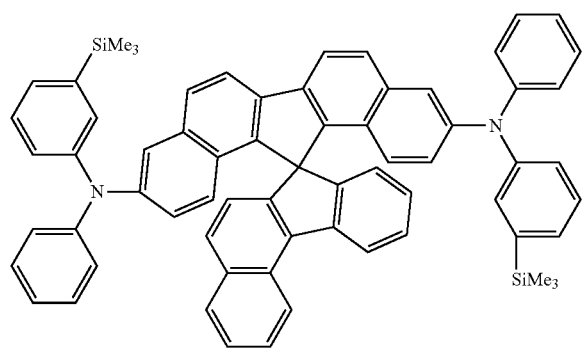
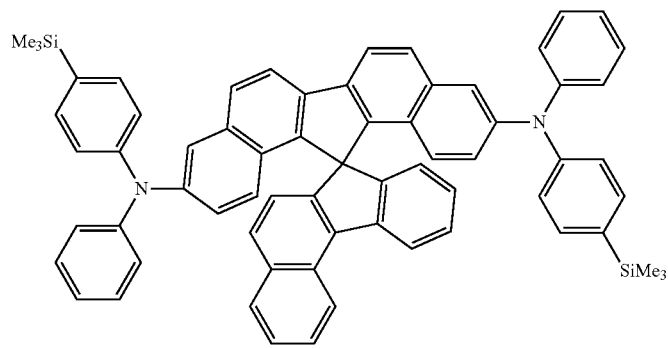

1171  -continued  1172
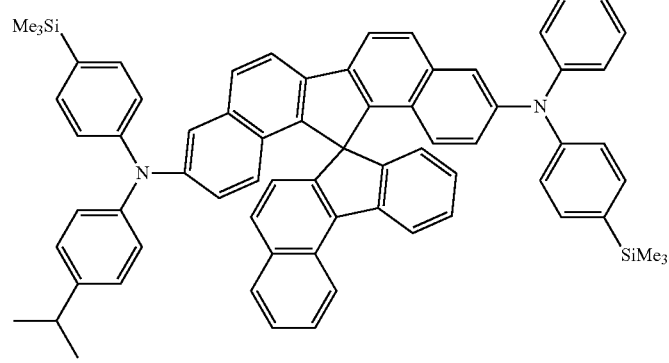
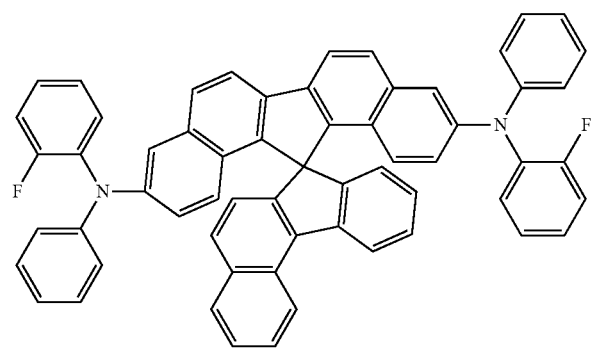
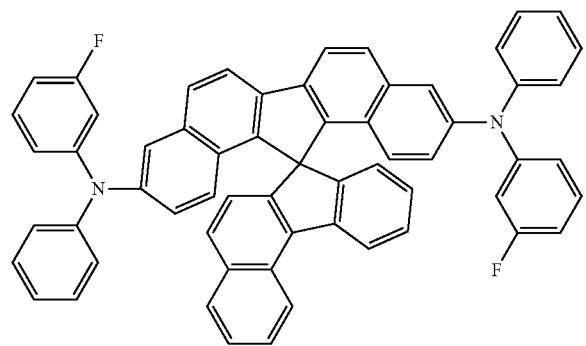
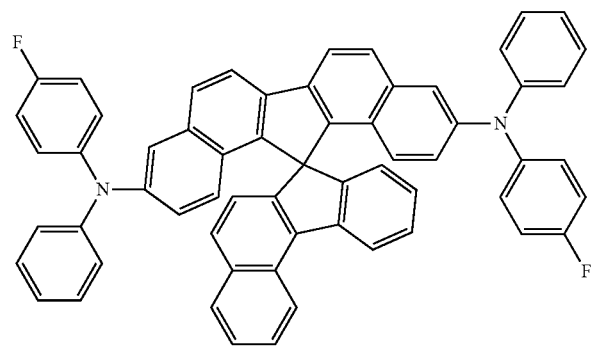

-continued
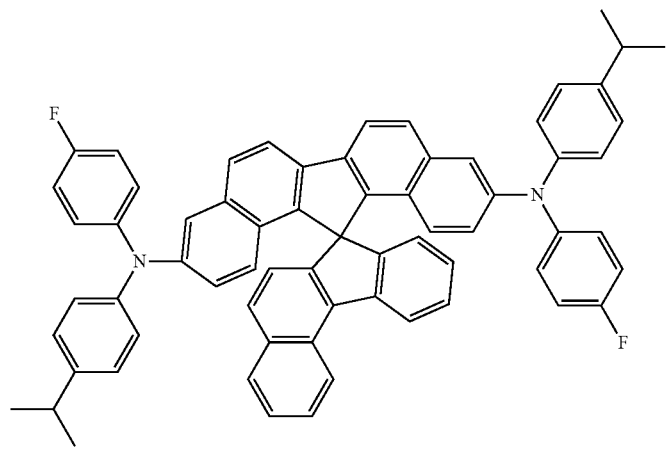
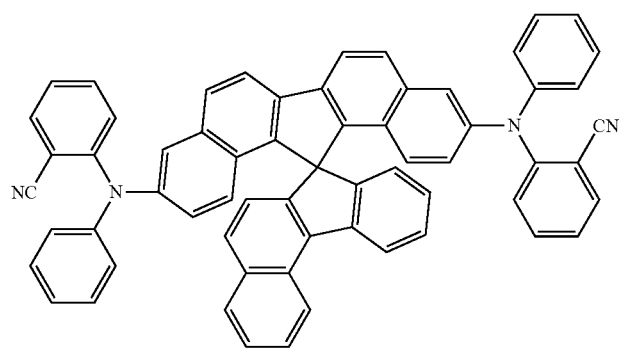
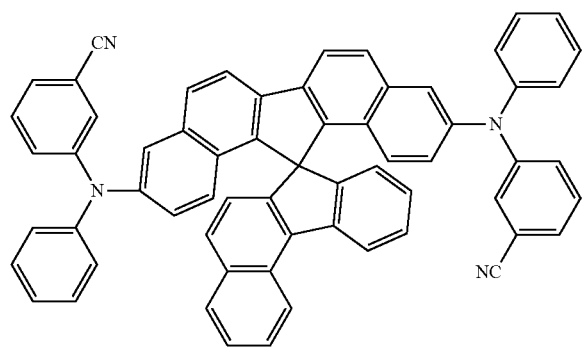
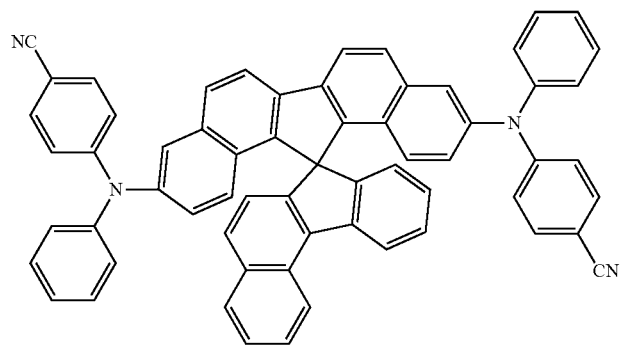

1175 1176
-continued
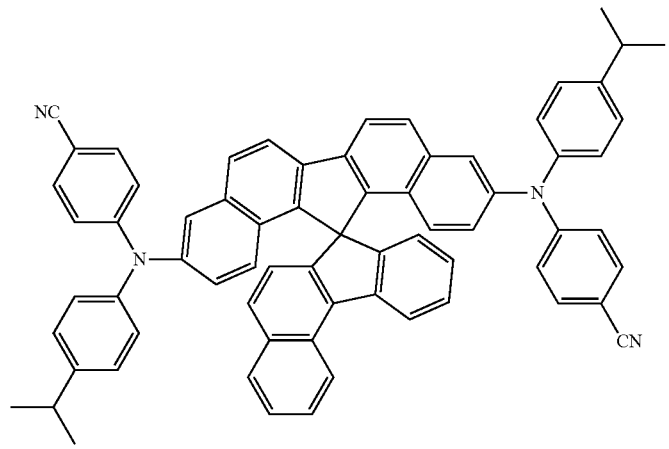
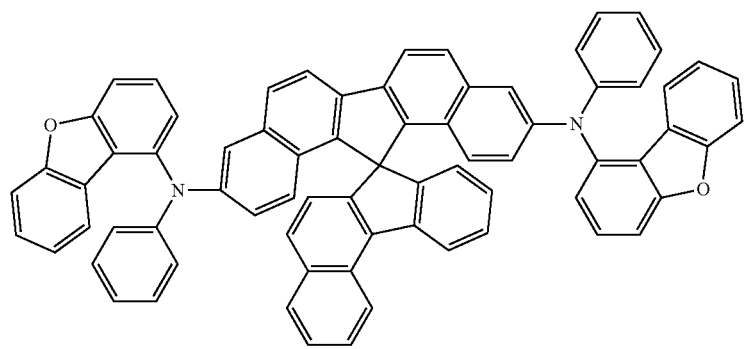
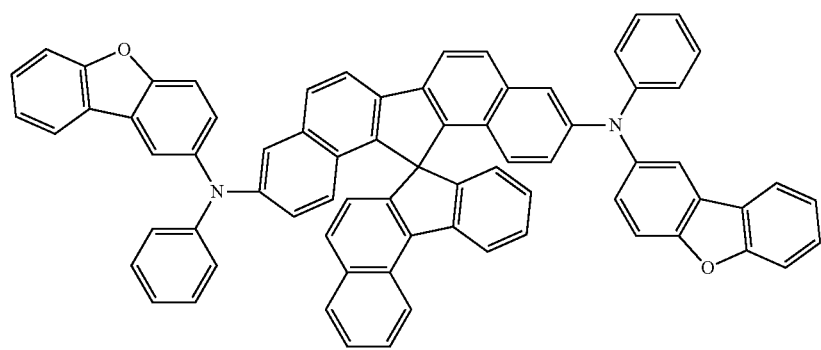
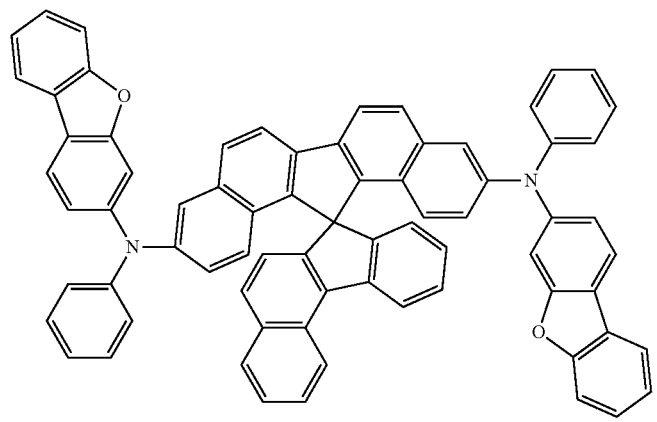

-continued
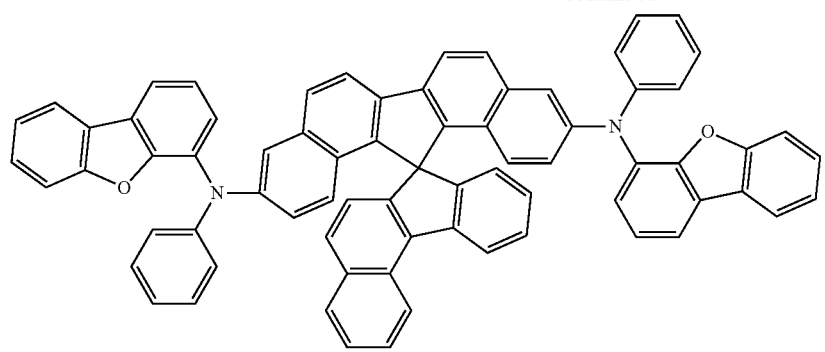
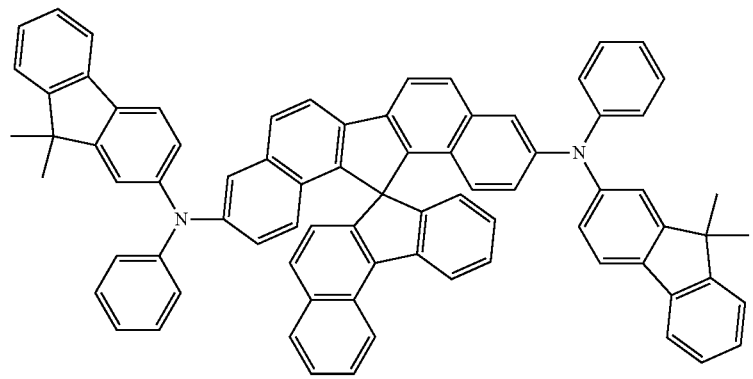
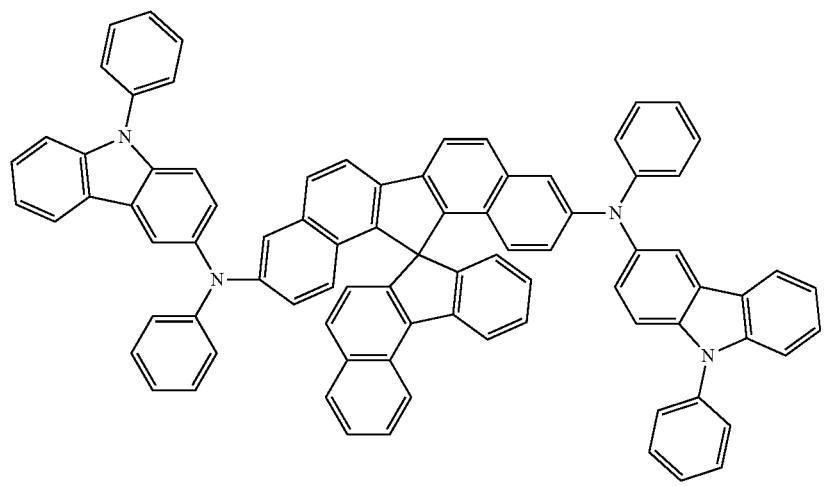
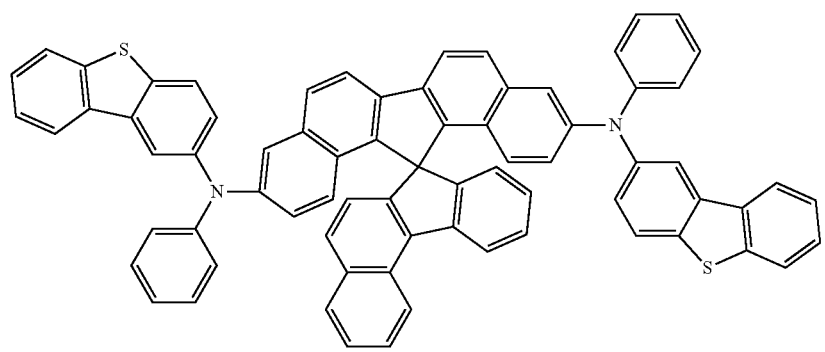

-continued
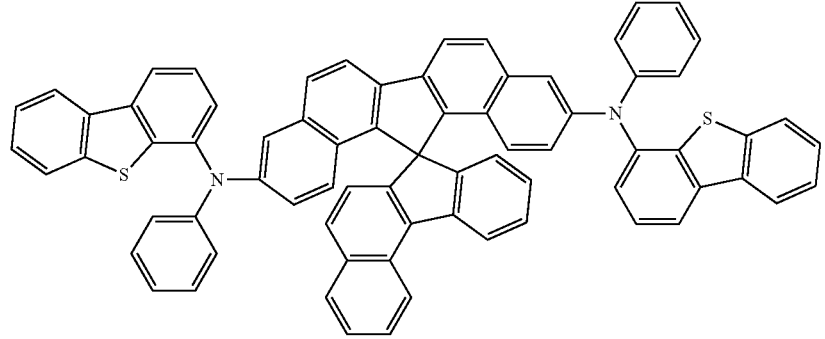
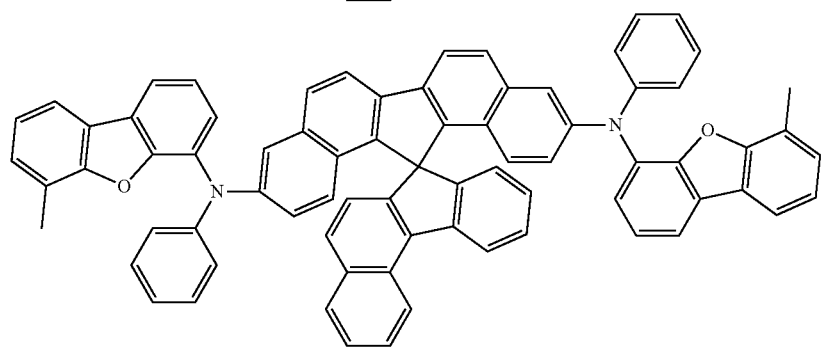
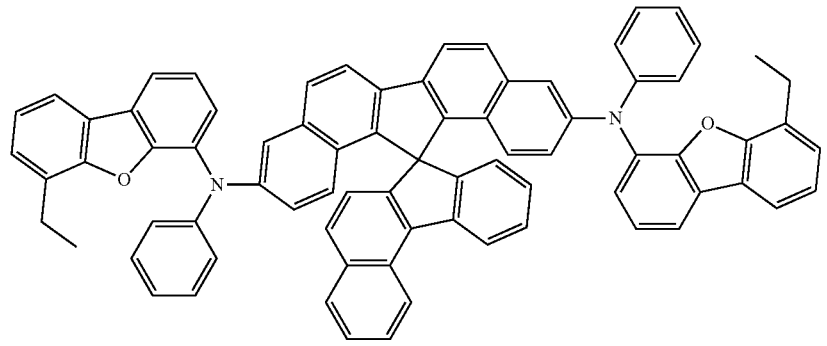
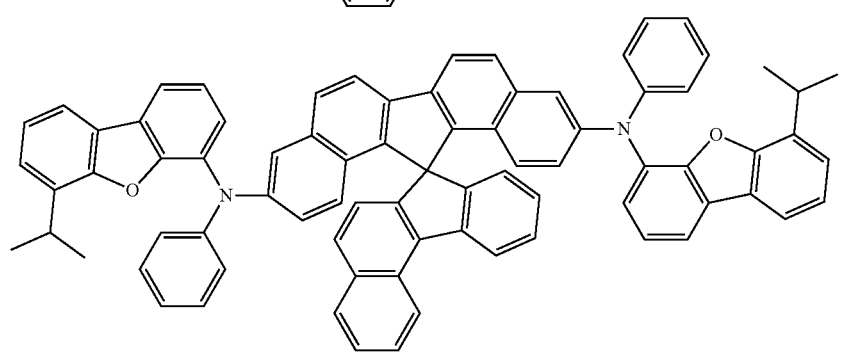
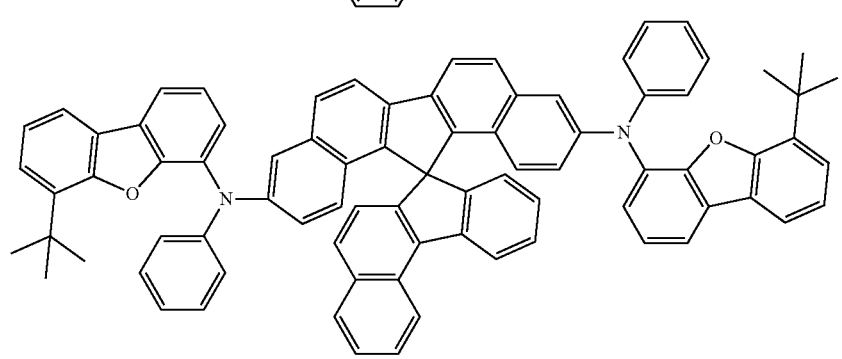

-continued
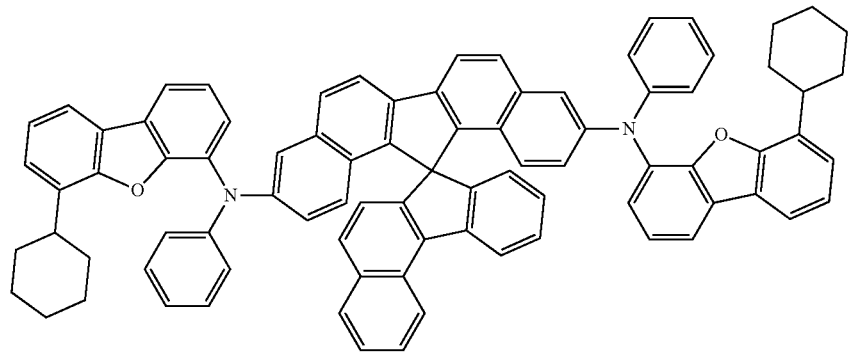
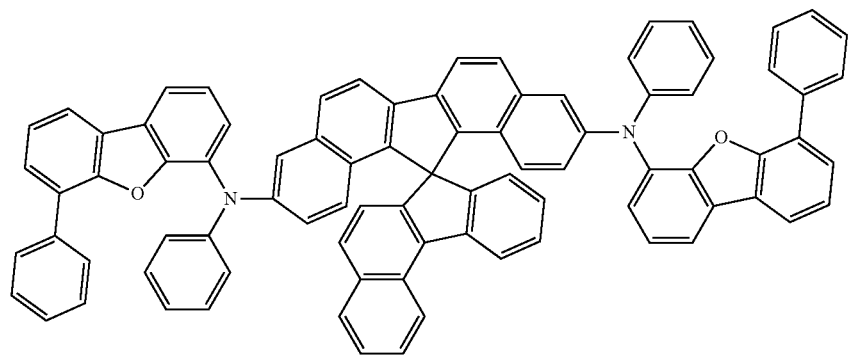
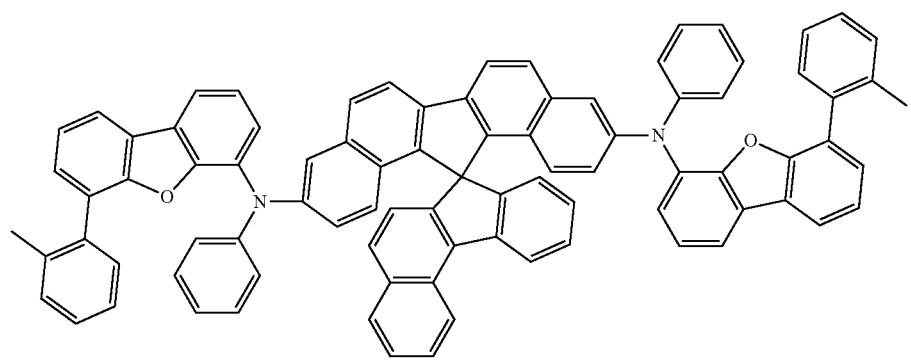
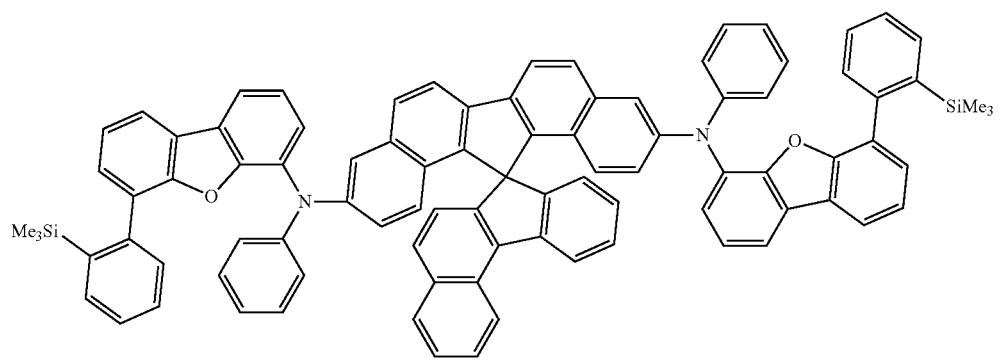

-continued
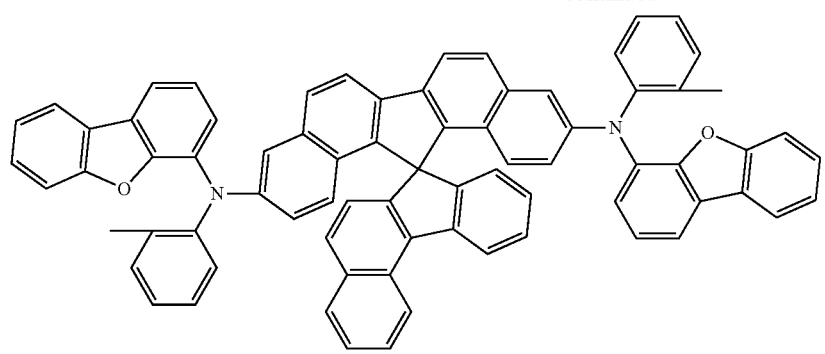
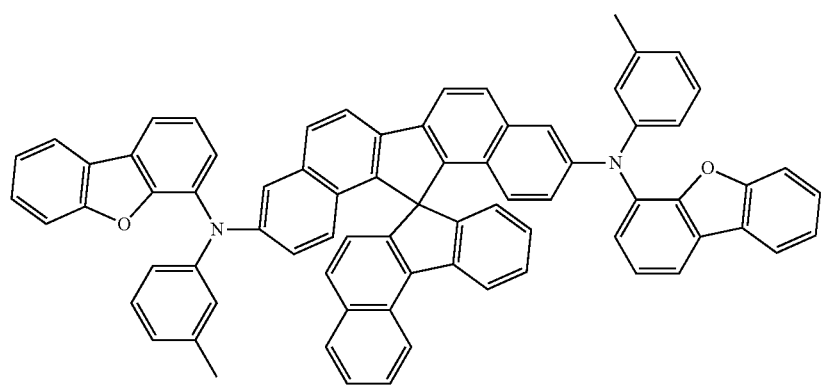
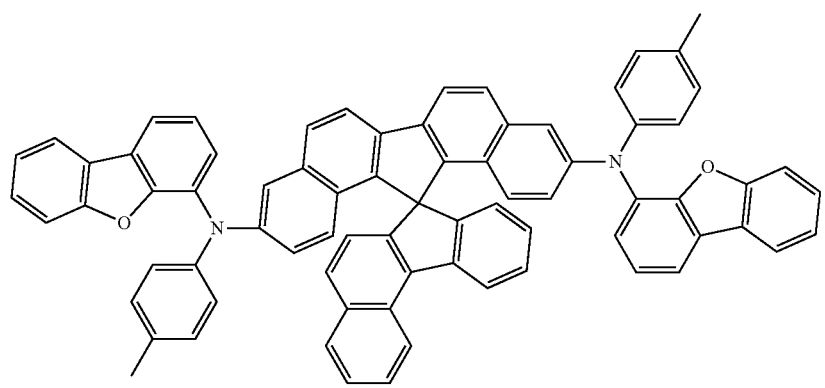
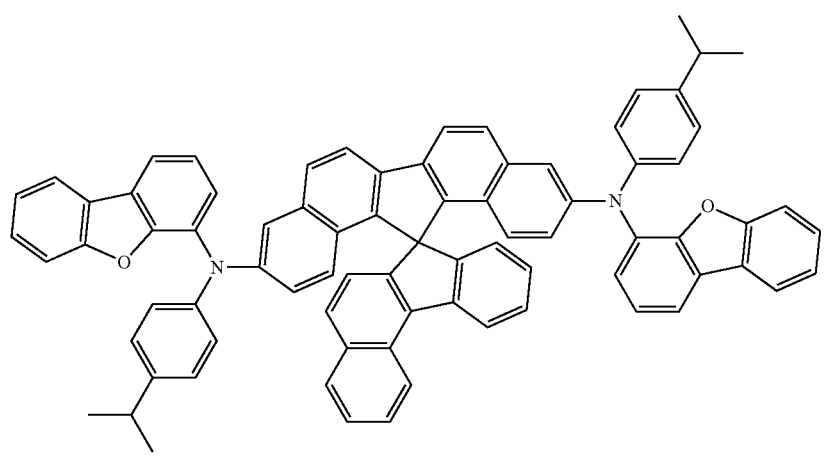

-continued
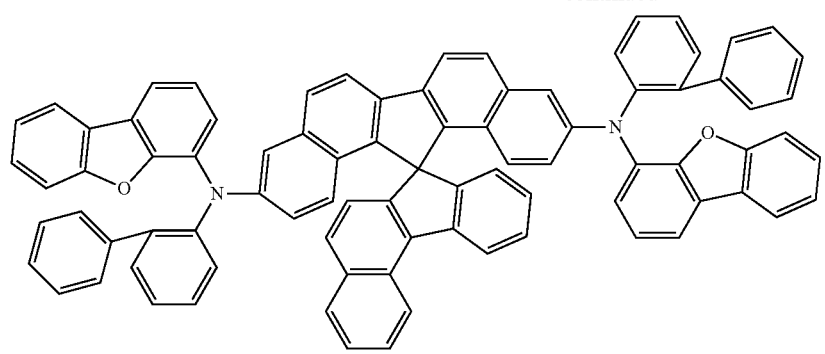
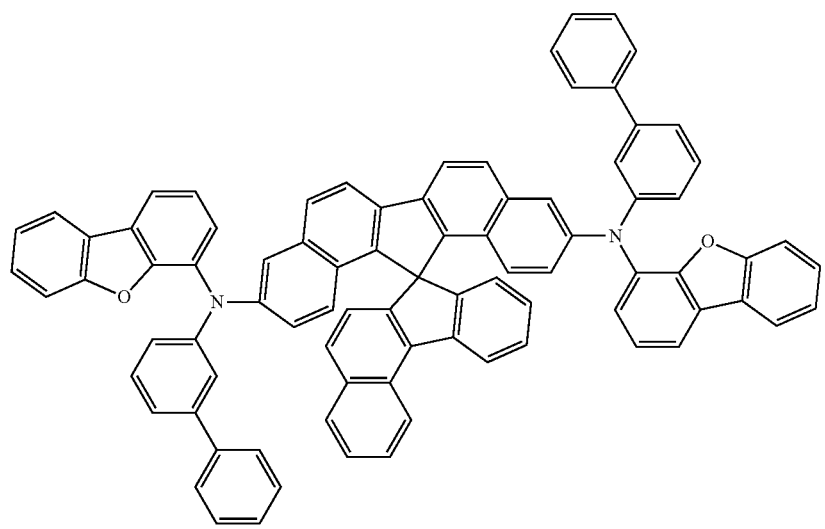
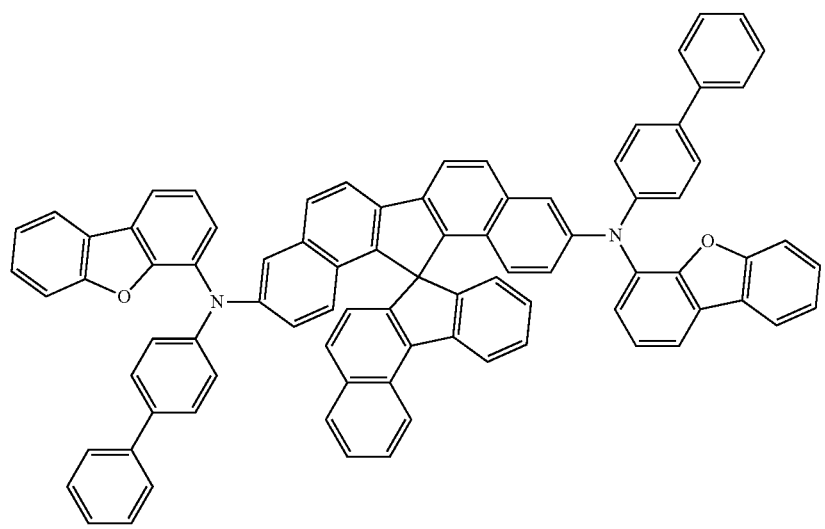

-continued
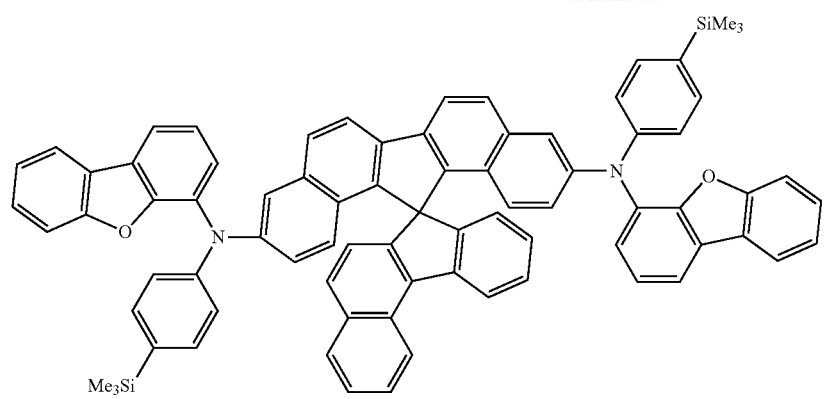
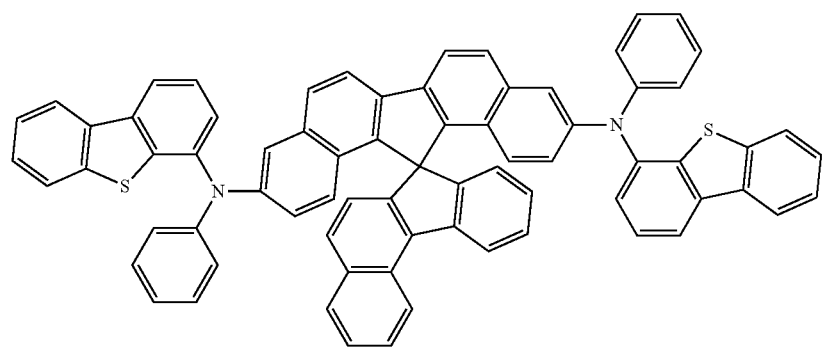
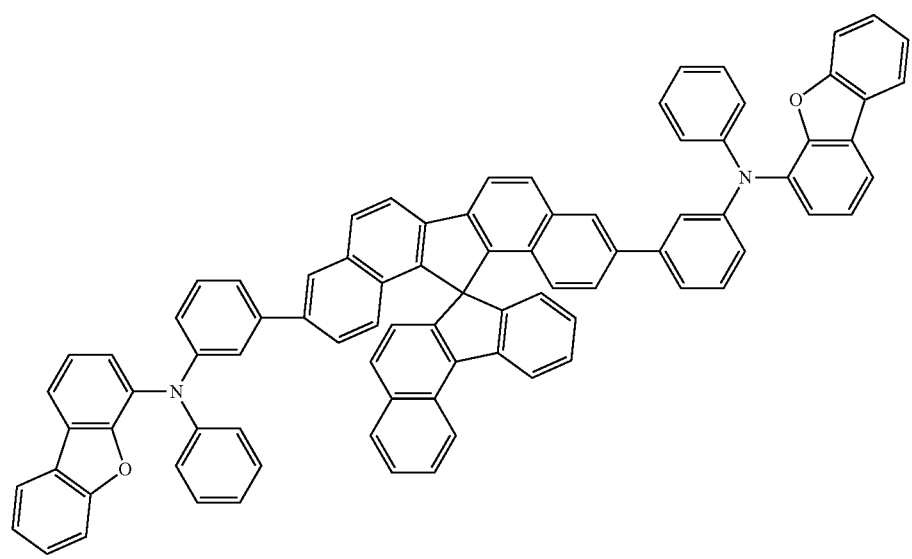
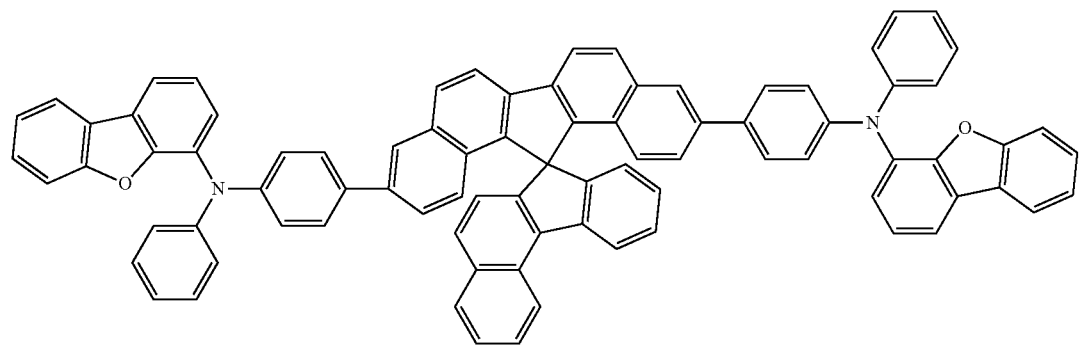

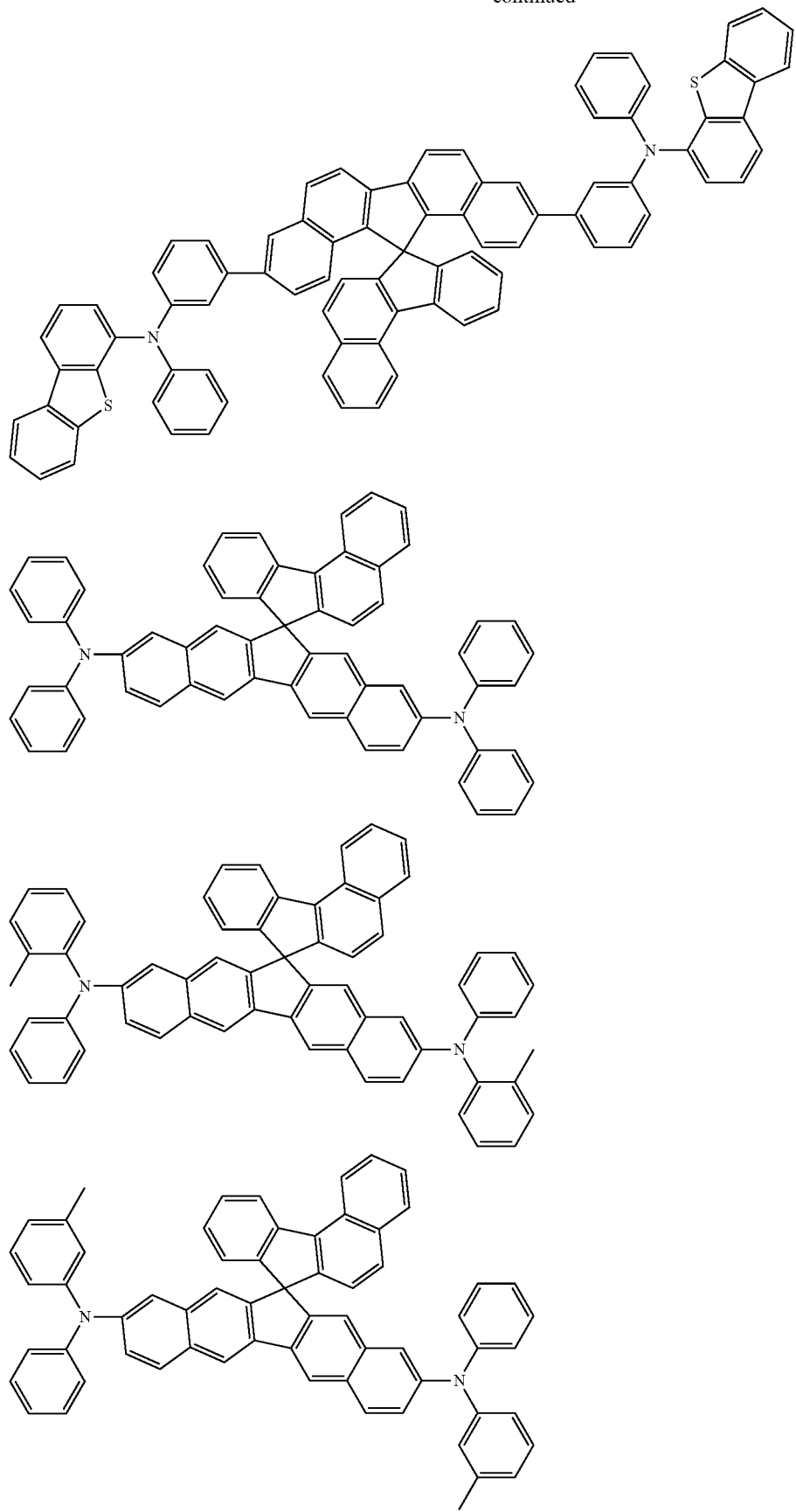

1191
-continued
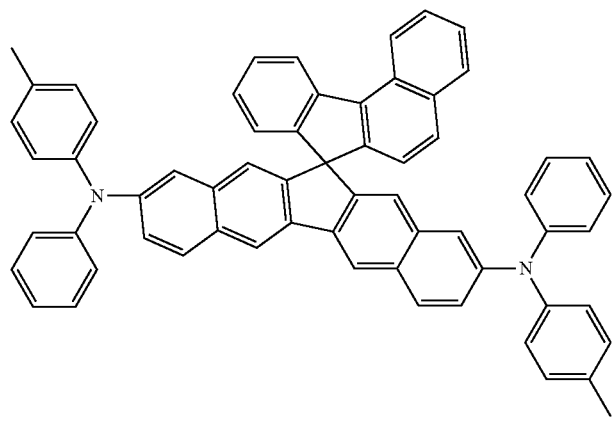
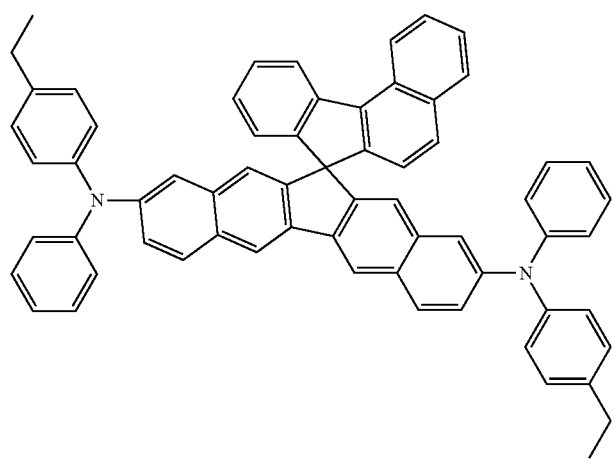
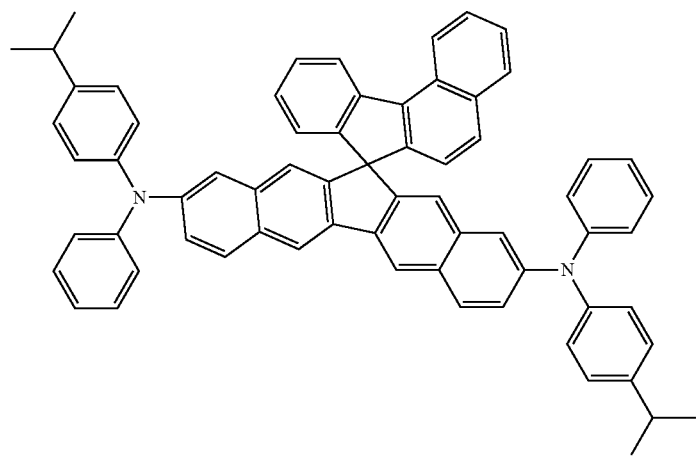
1192

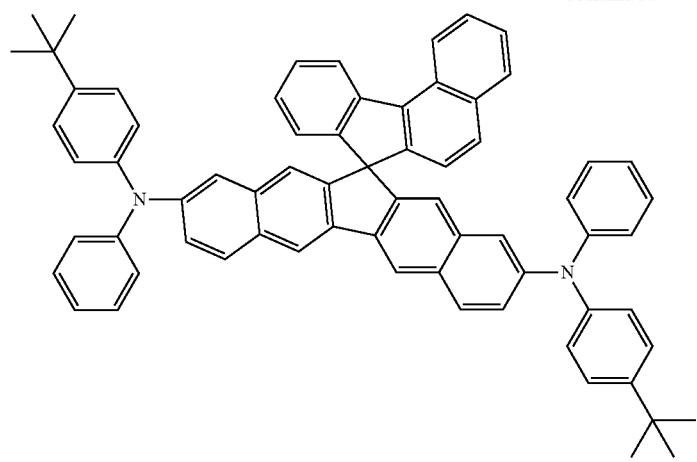
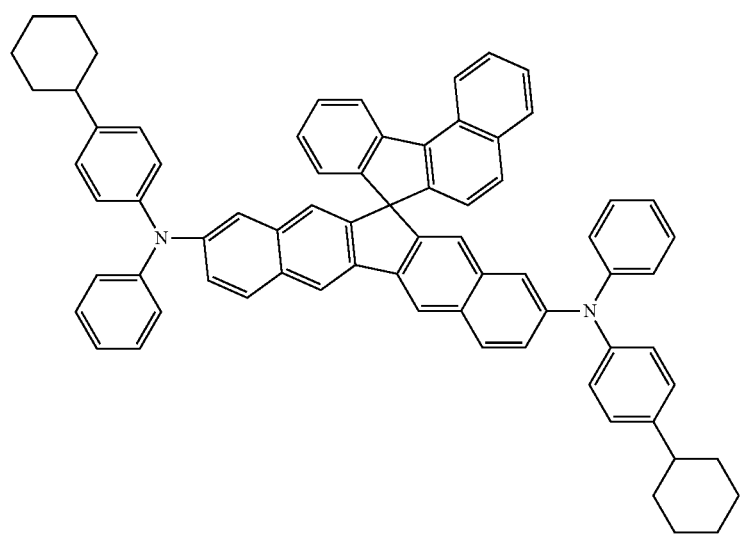
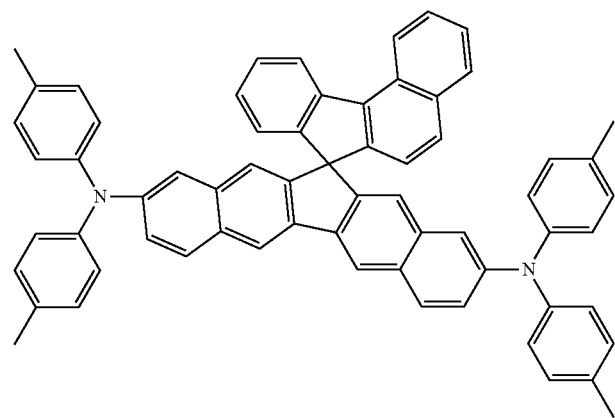

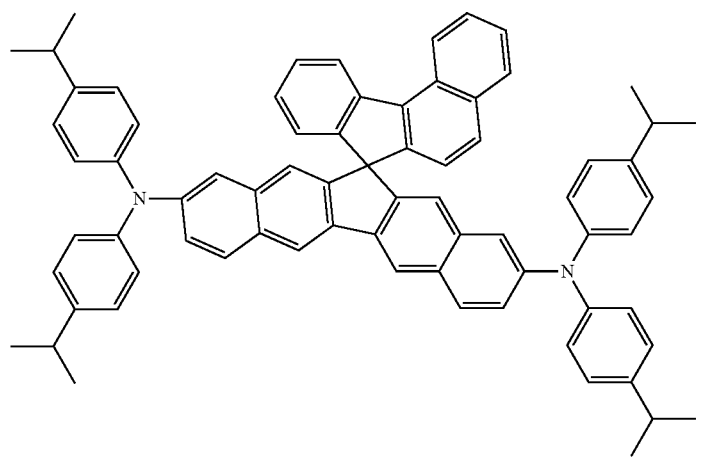
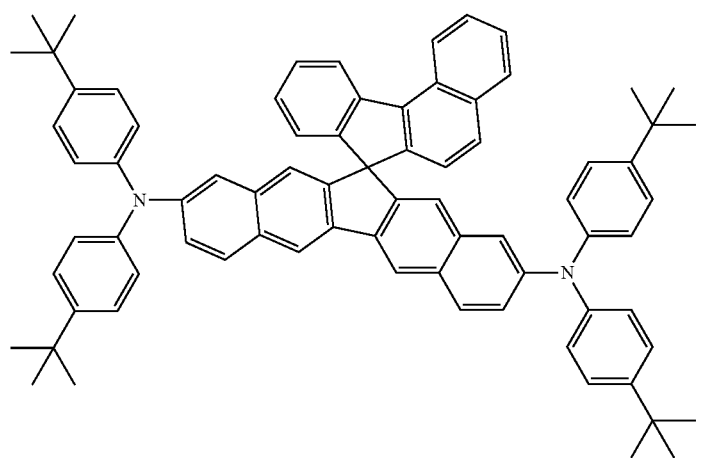
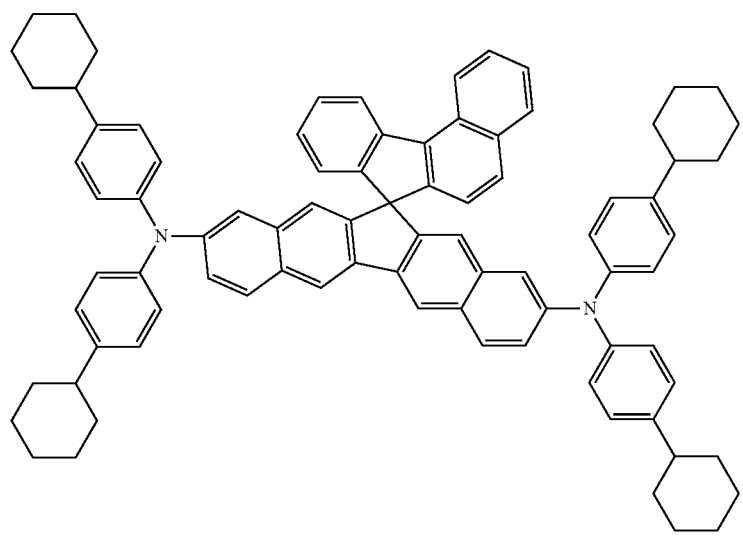

-continued
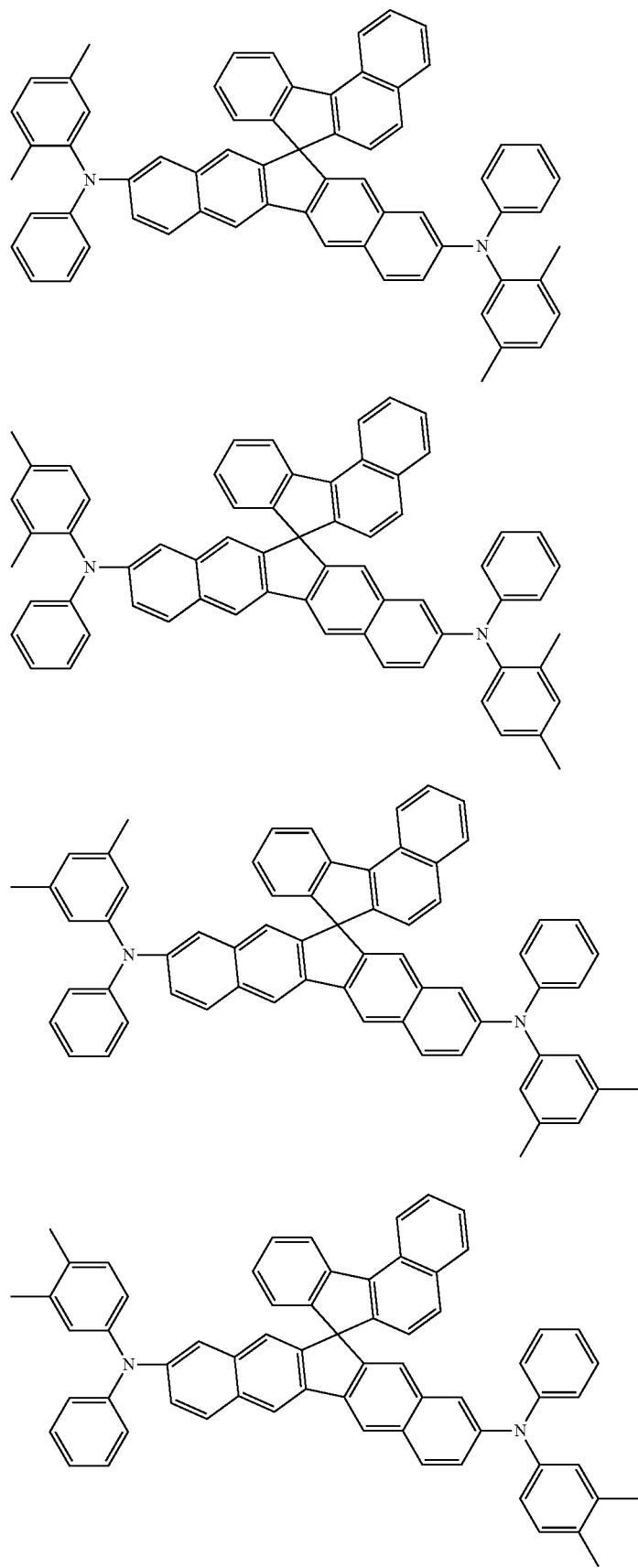

-continued
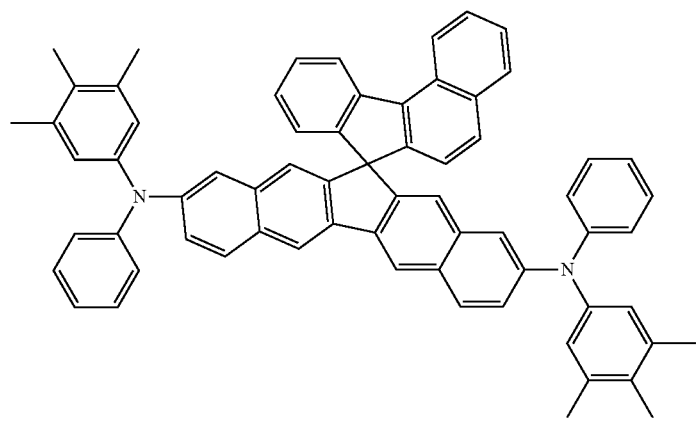
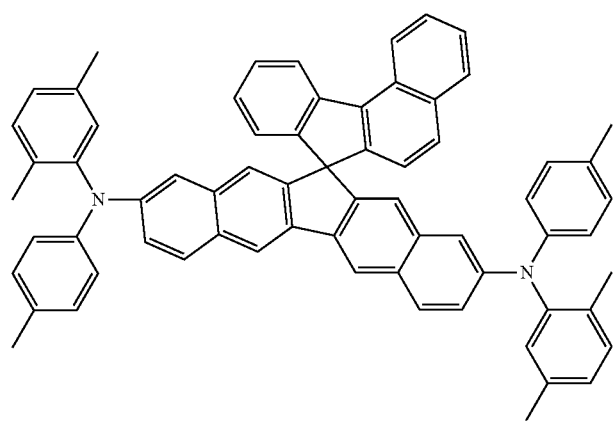
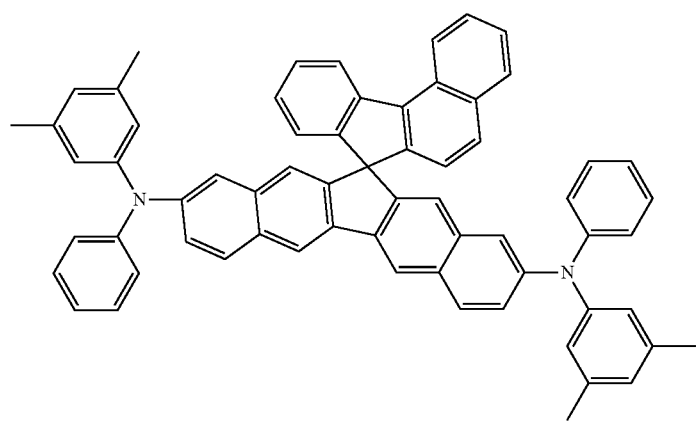
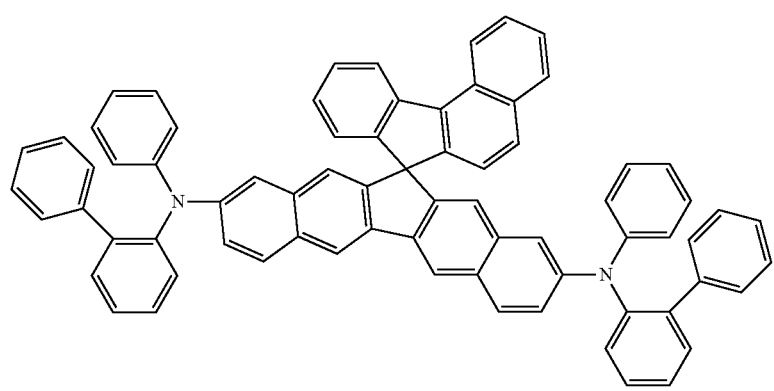

-continued
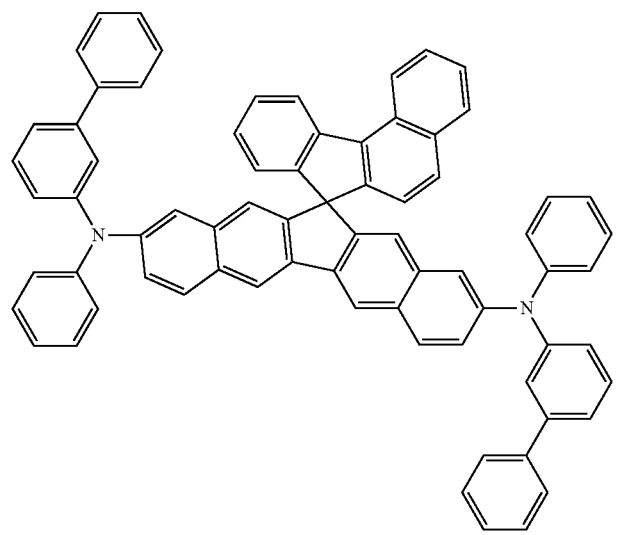
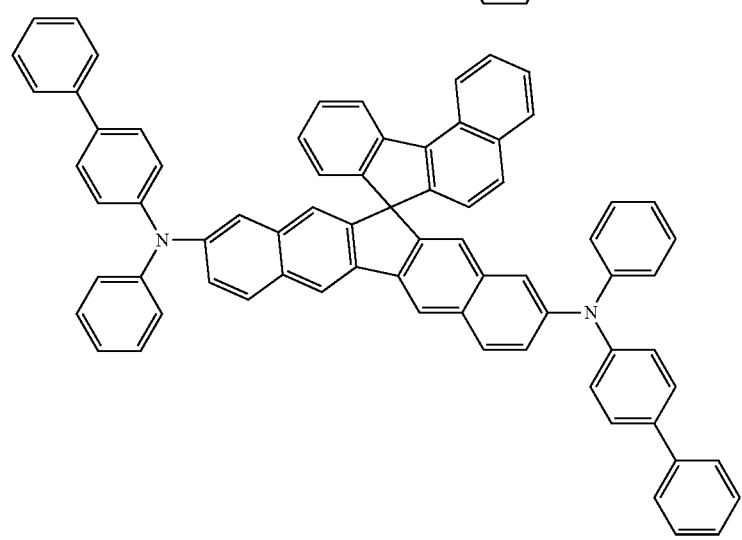
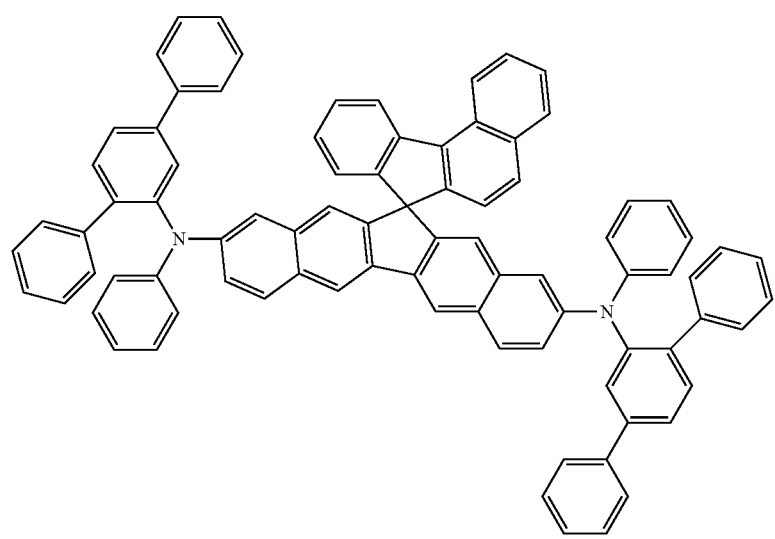

1203 1204
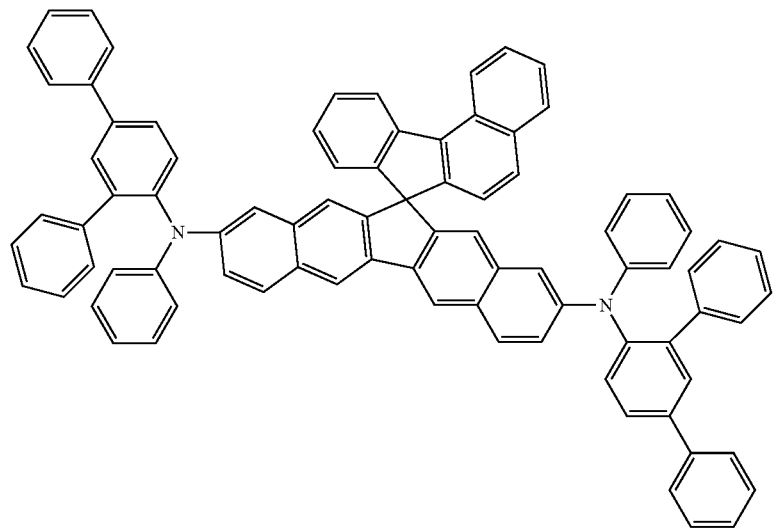
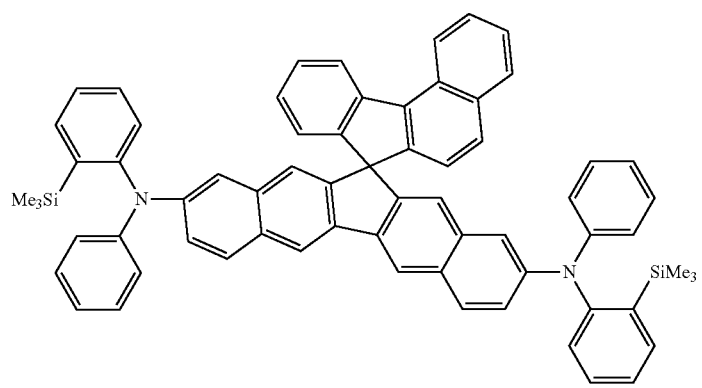
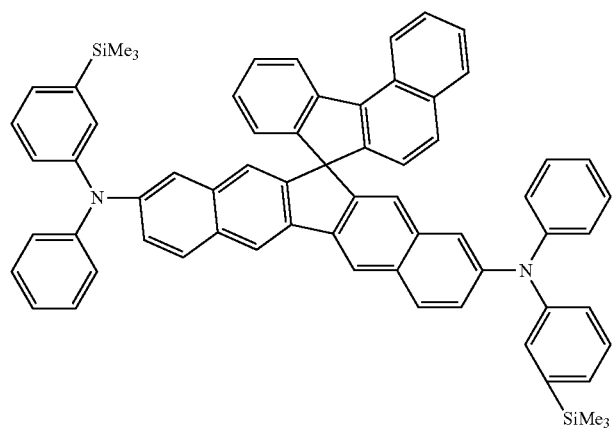

1205    1206
-continued
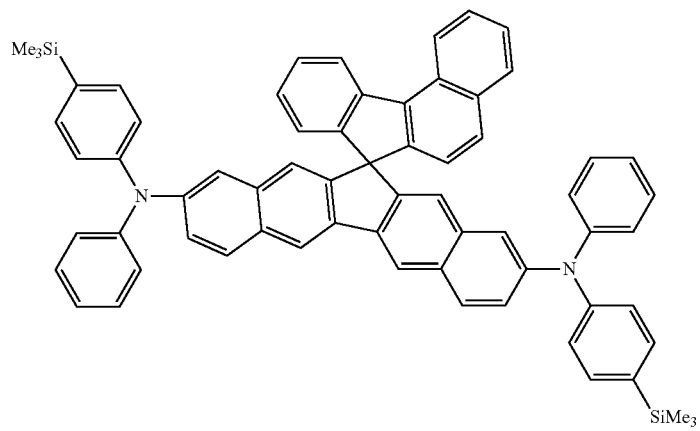
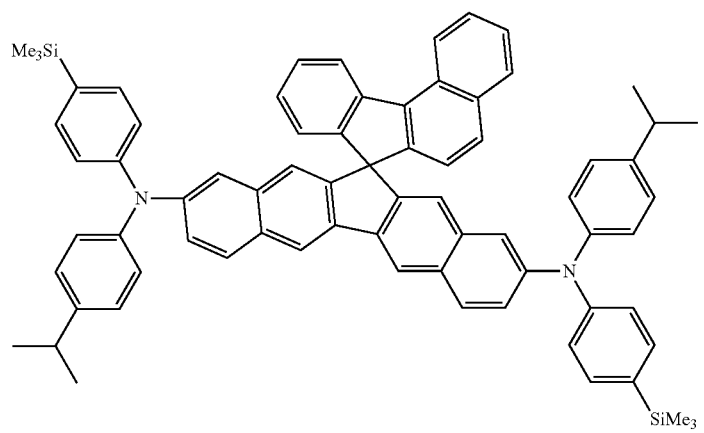
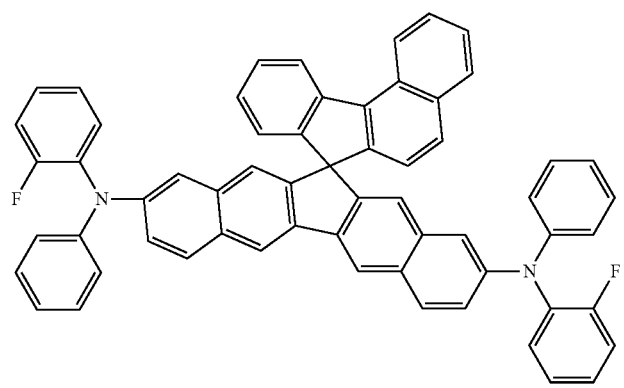
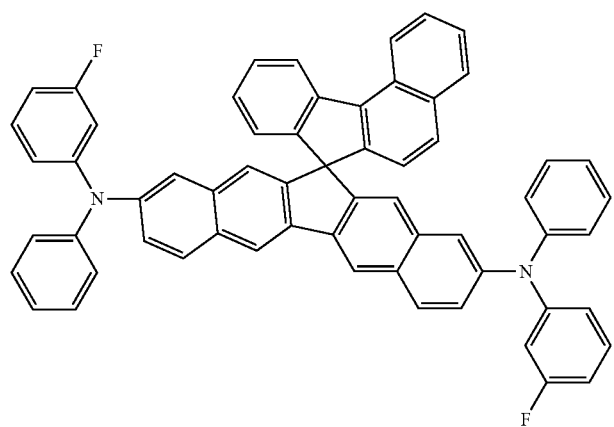

-continued
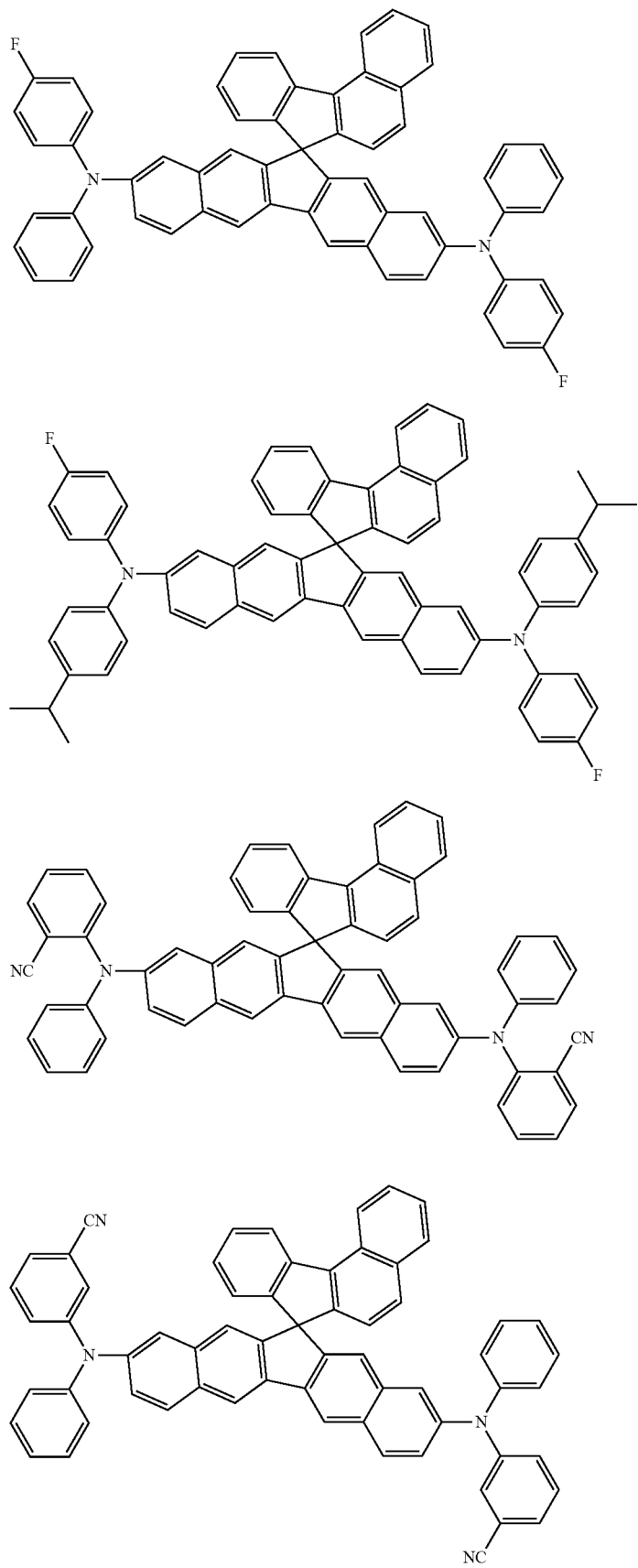

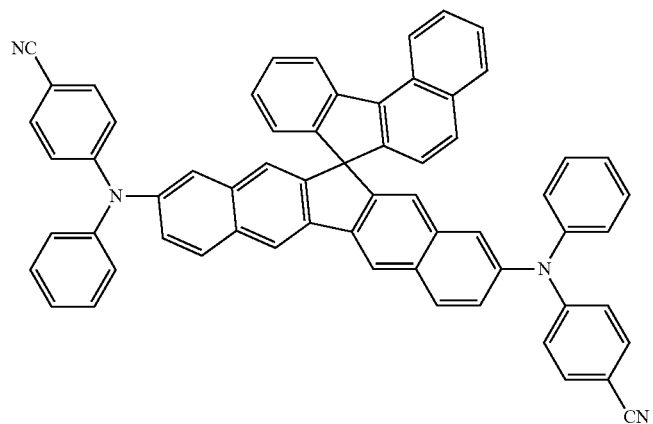
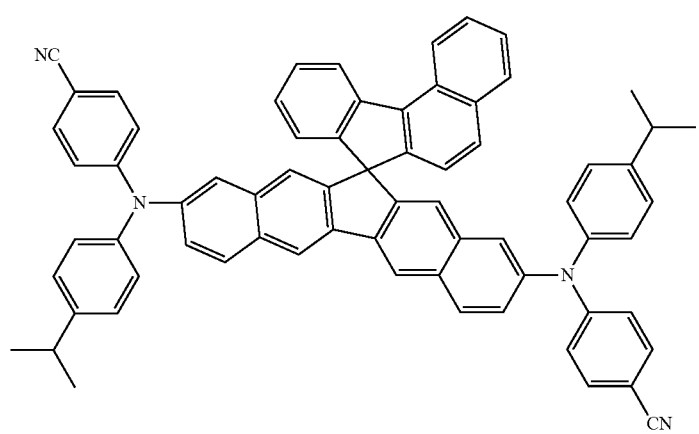
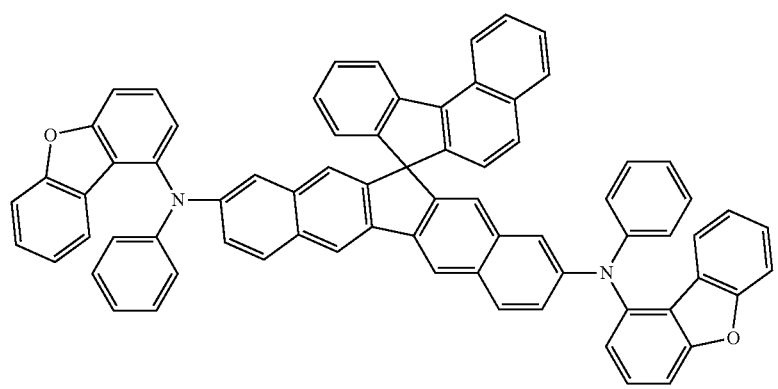
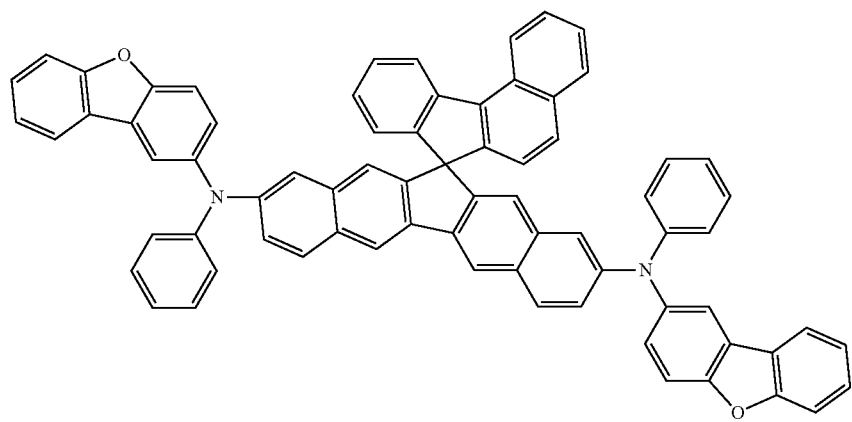

1211
1212
-continued
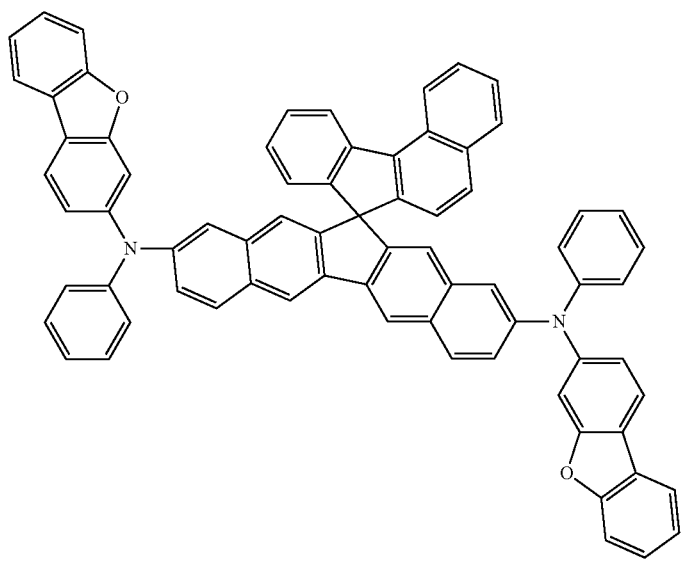
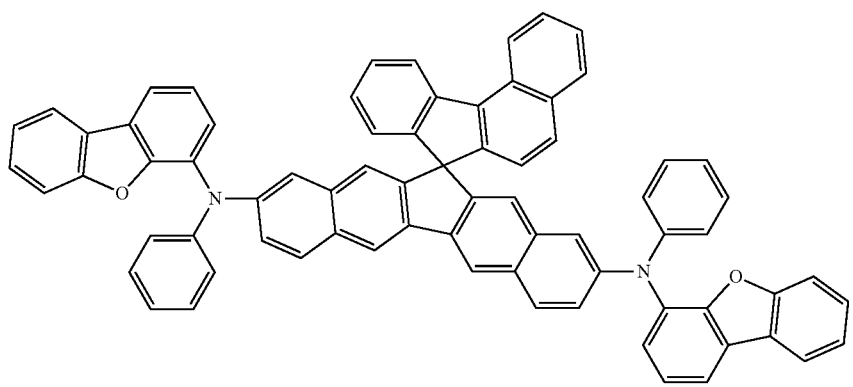
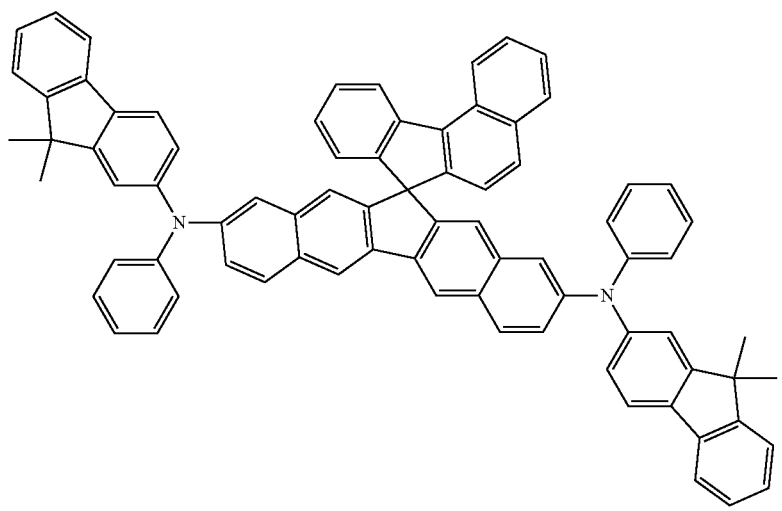

1213 1214
-continued
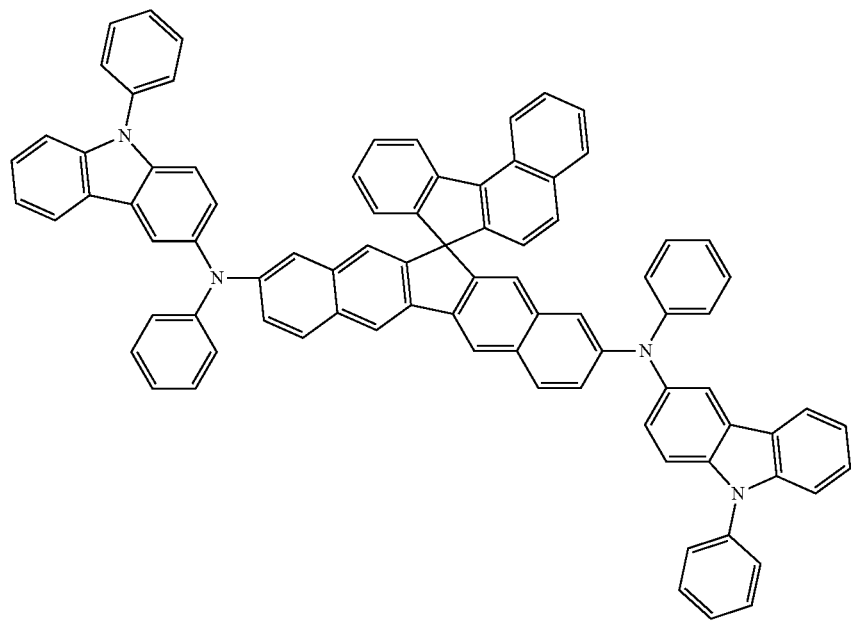
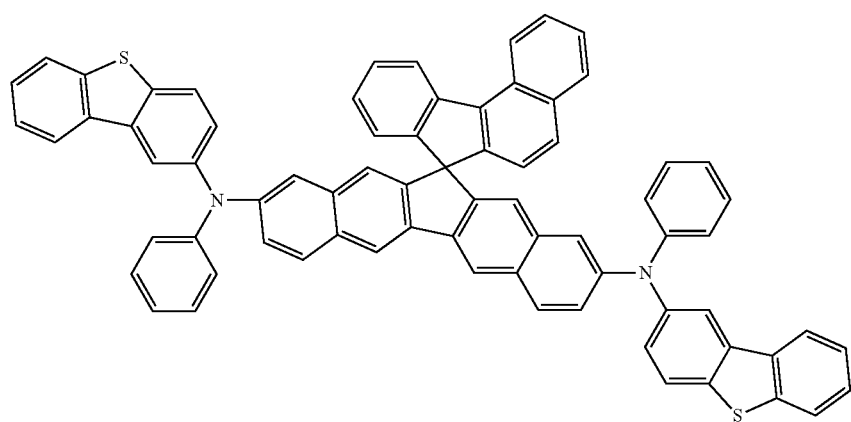
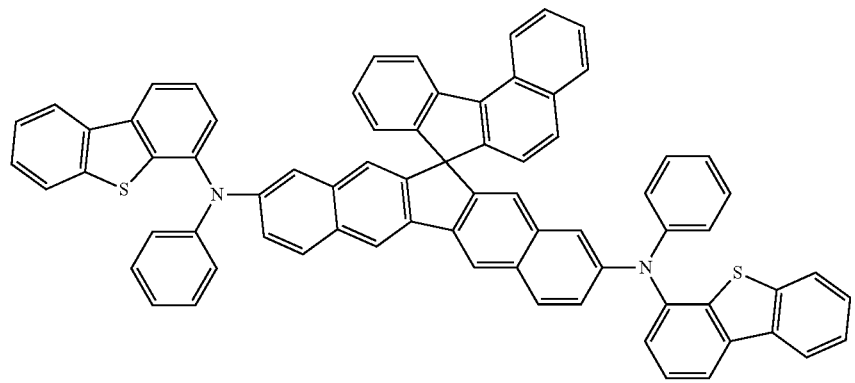

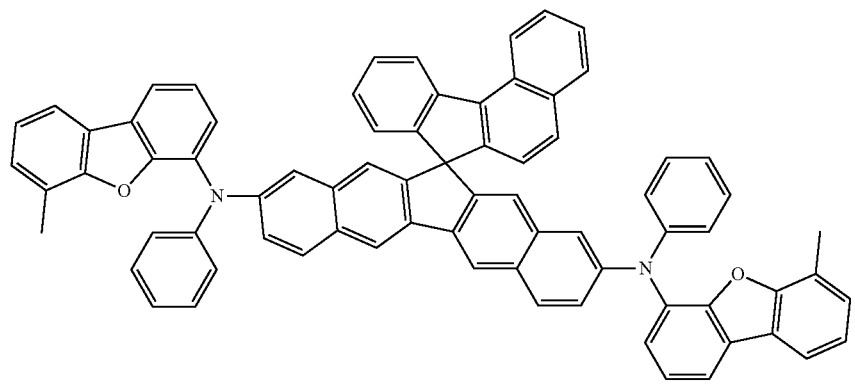
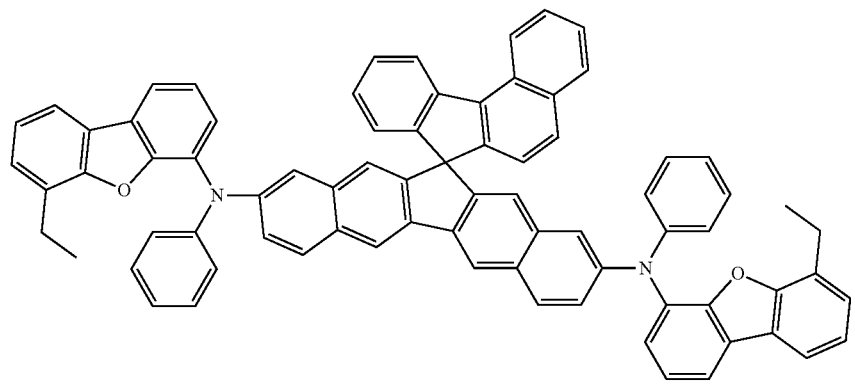
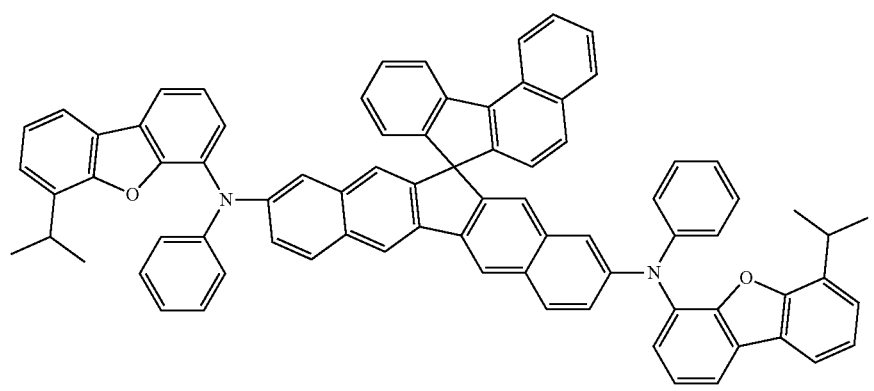
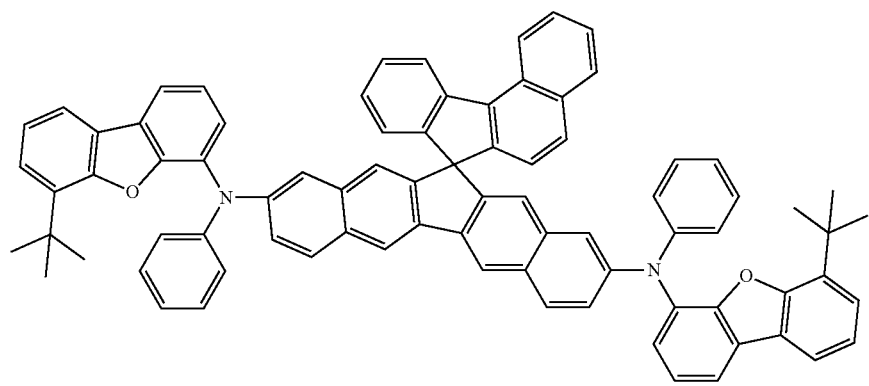

-continued
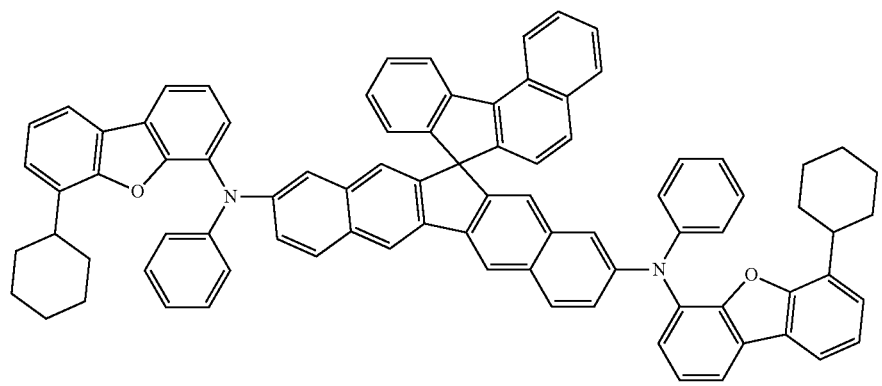
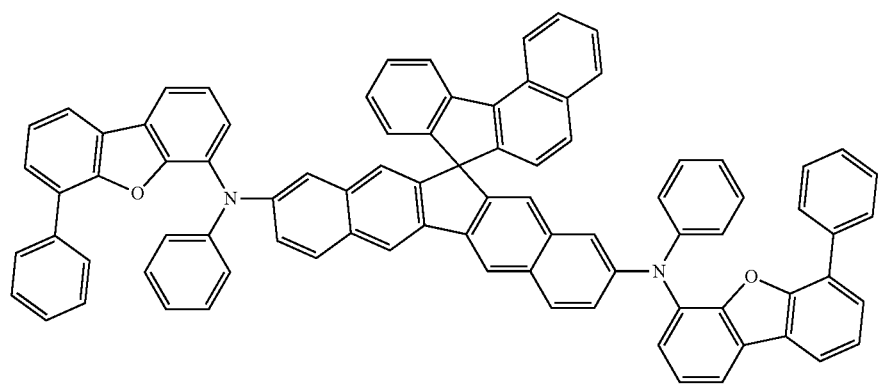
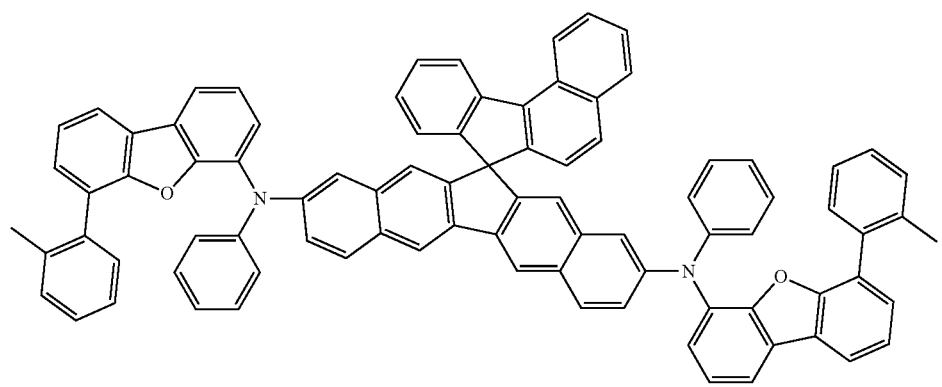
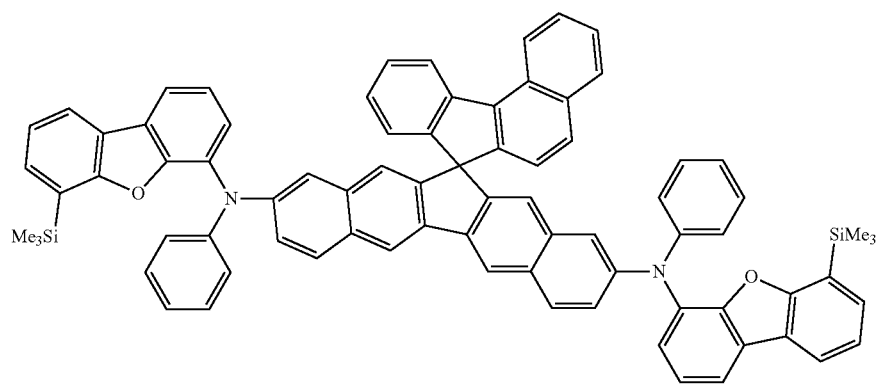

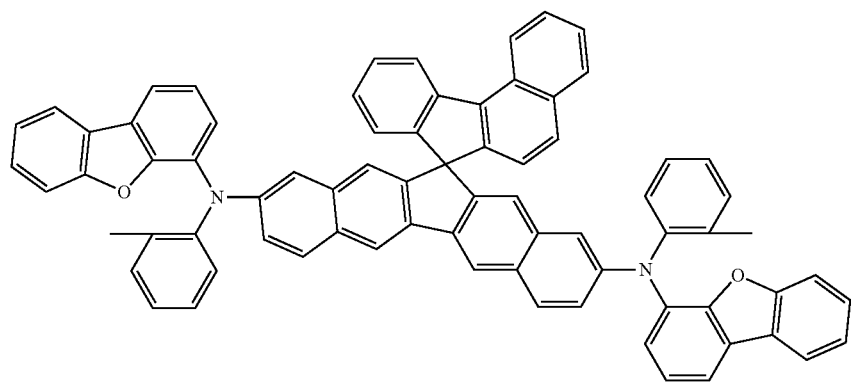
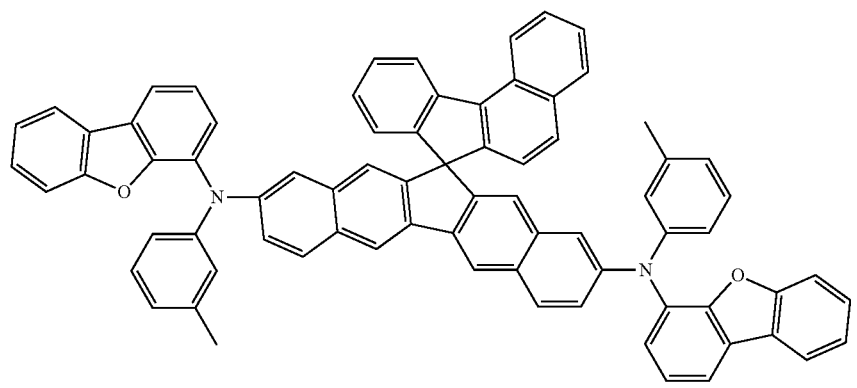
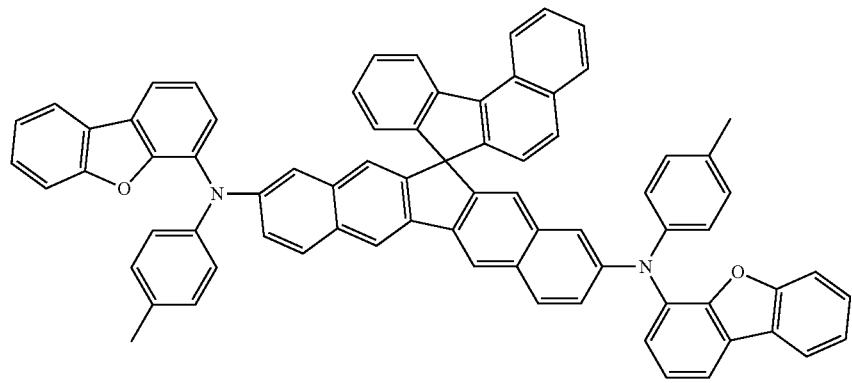
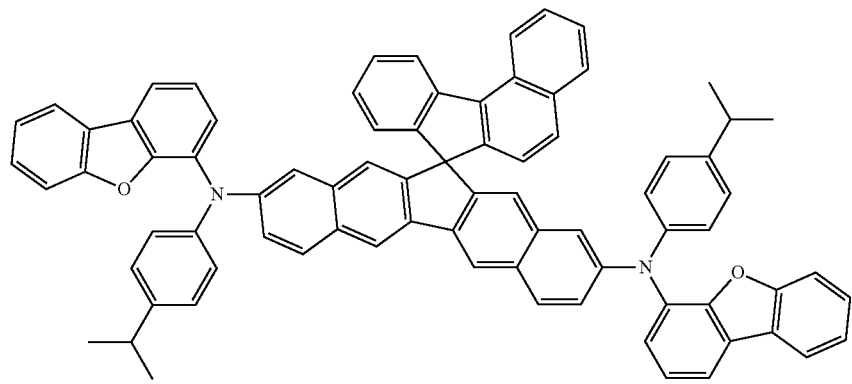

1221
-continued
1222
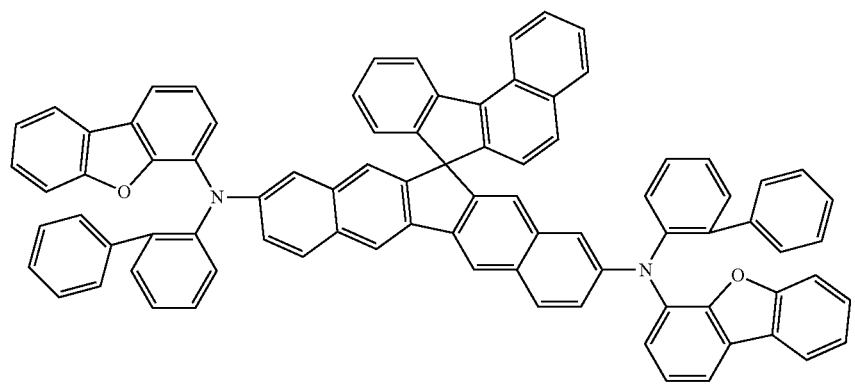
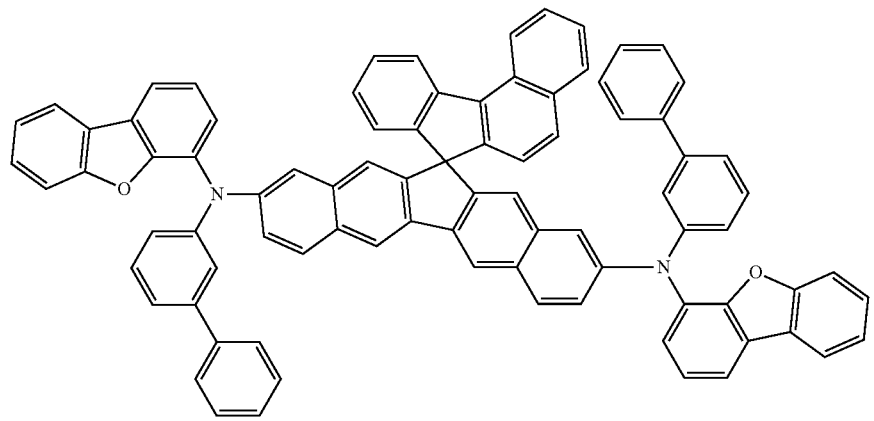
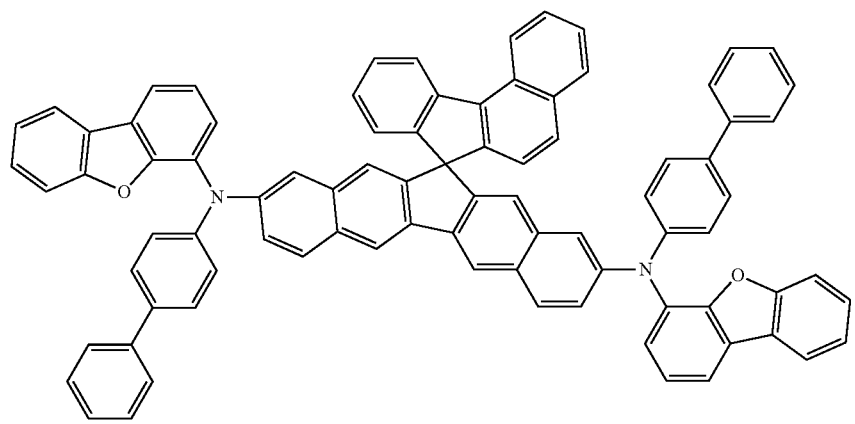
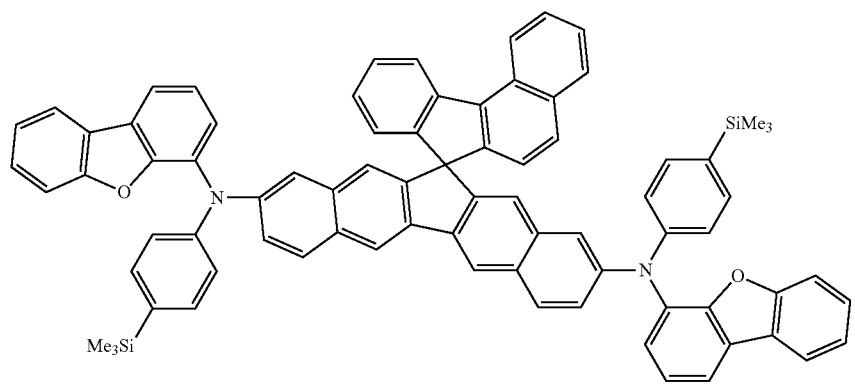

1223 1224
-continued
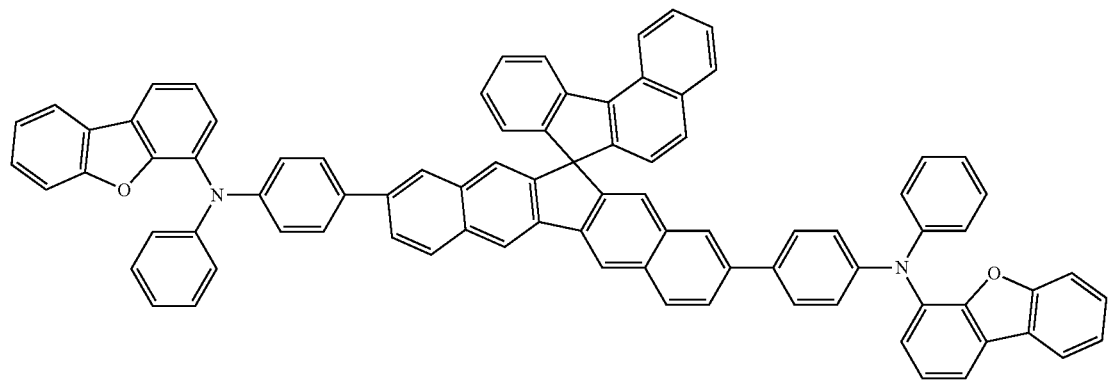
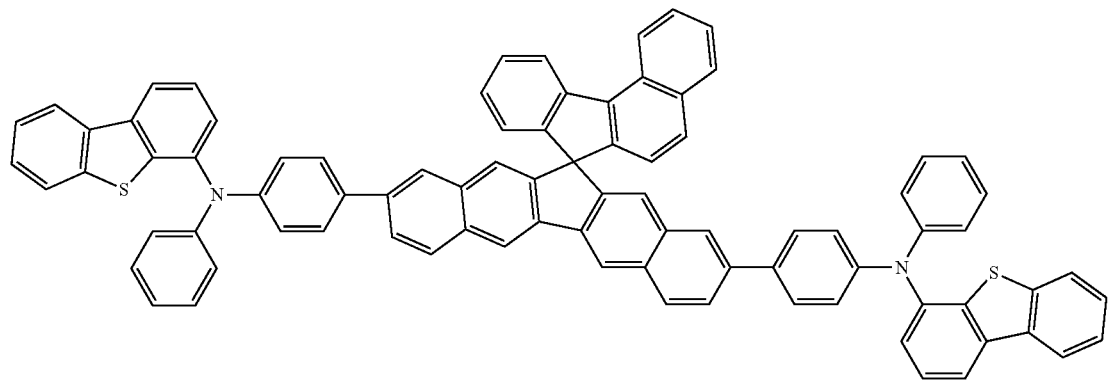
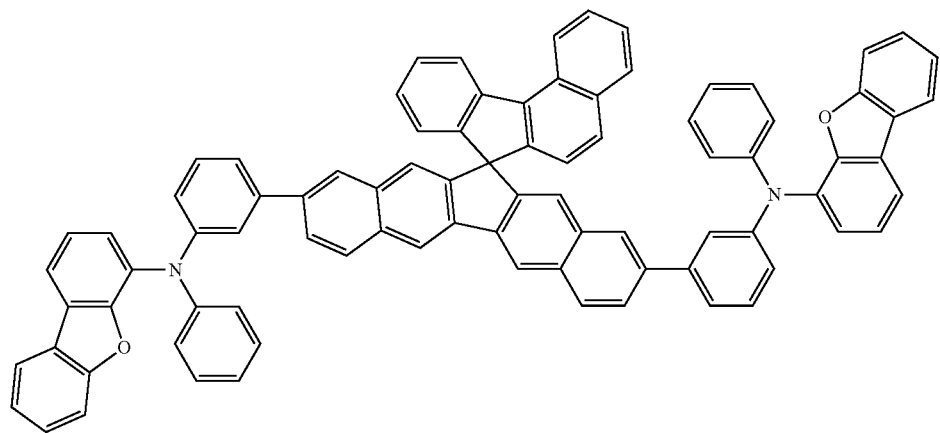
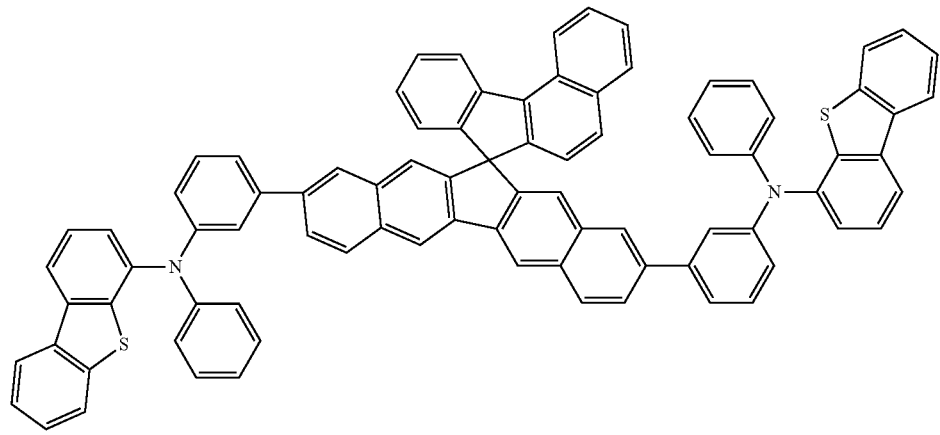

1225
-continued
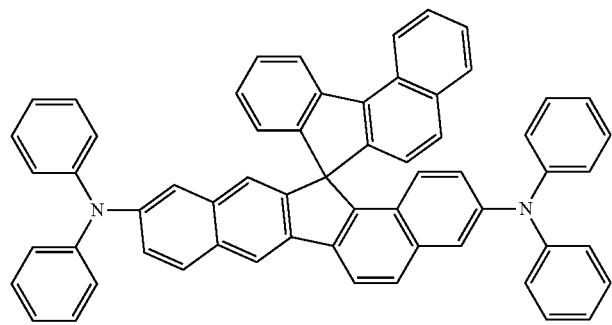
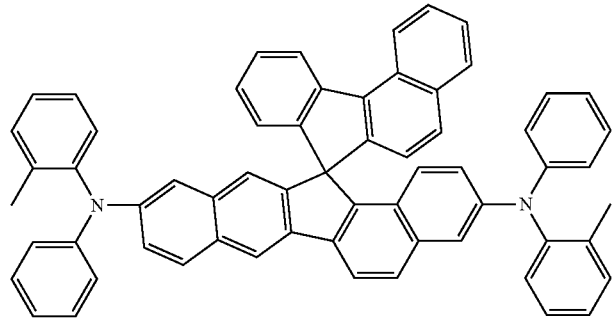
1226
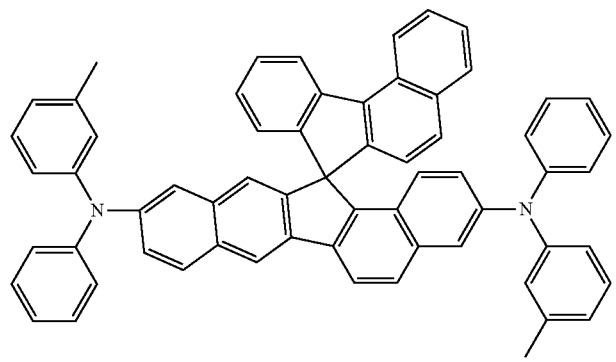
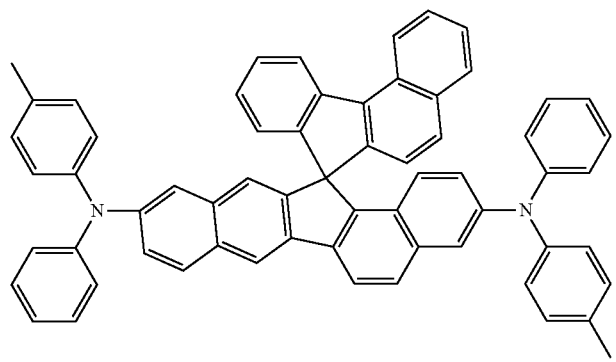

1227
1228
-continued
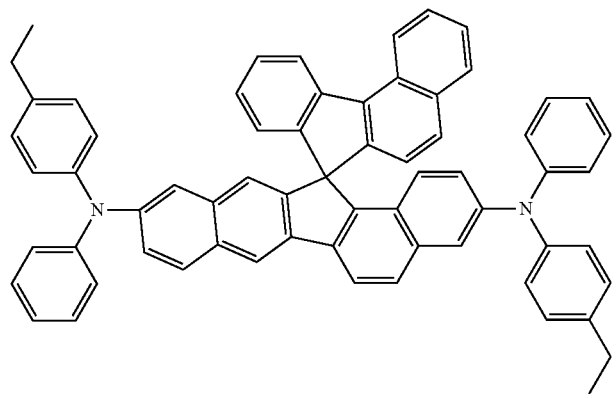
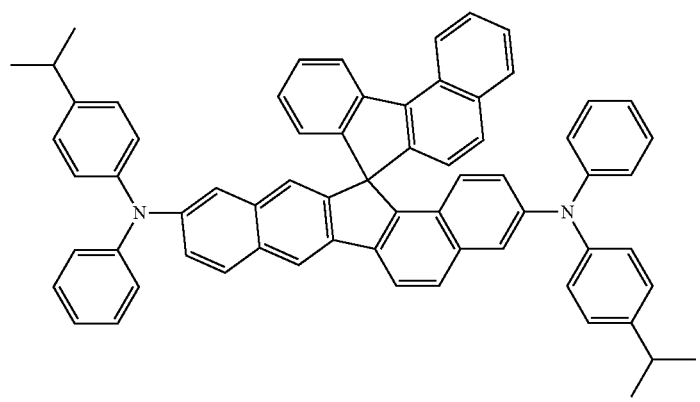
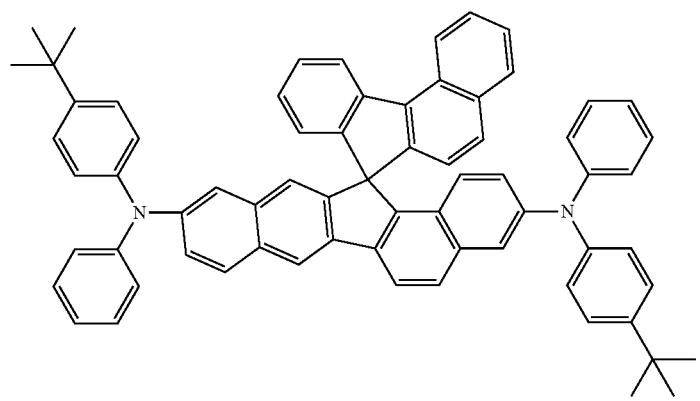
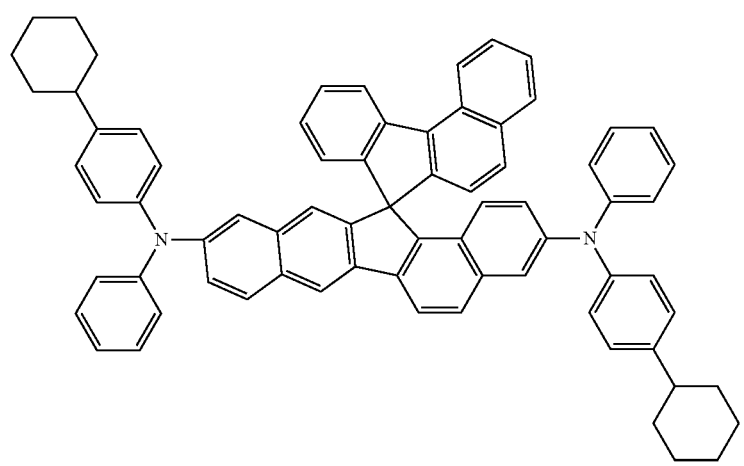

-continued
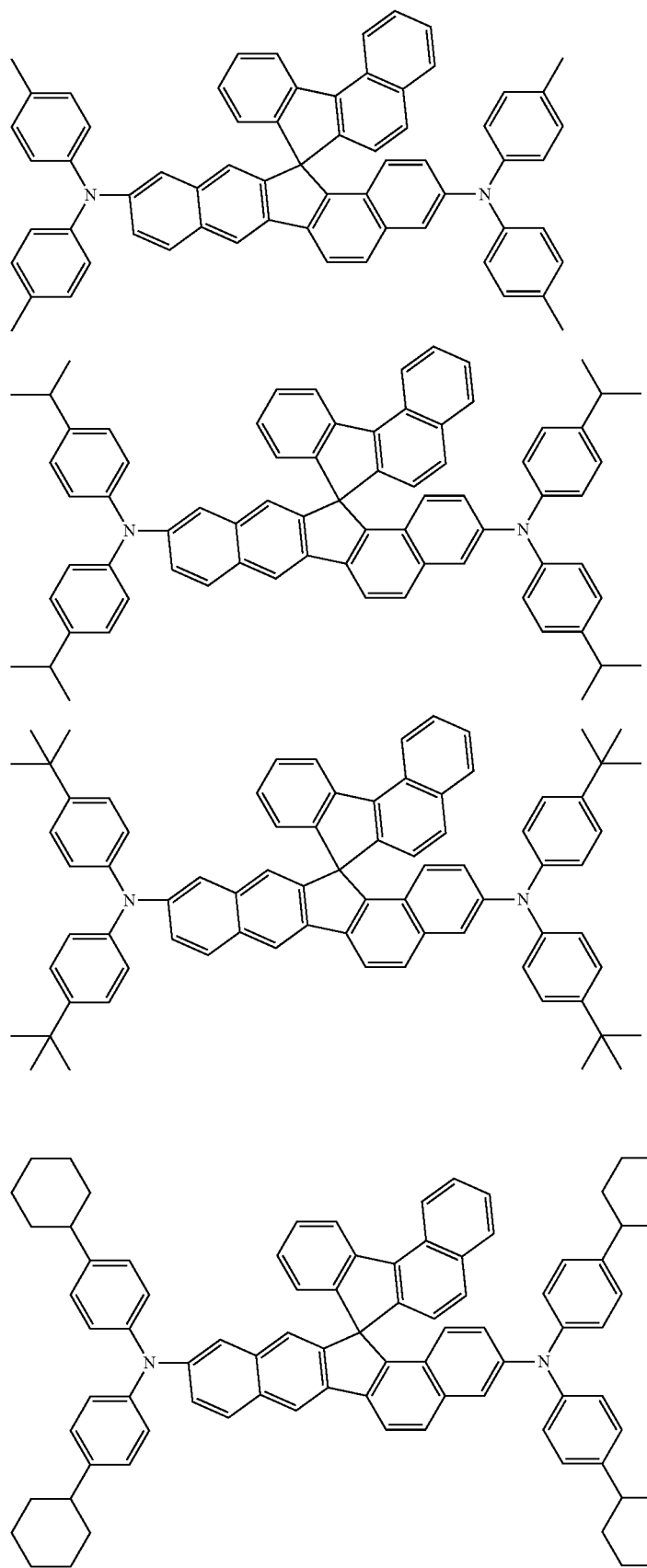

1231
-continued
1232
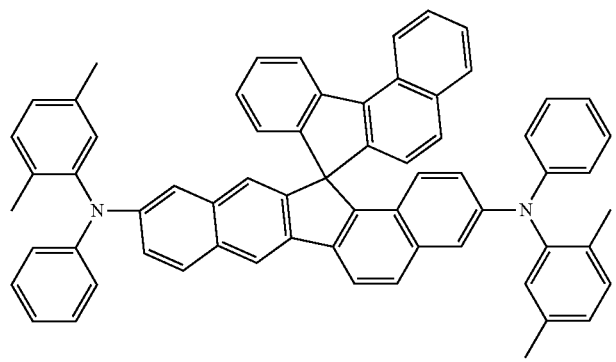
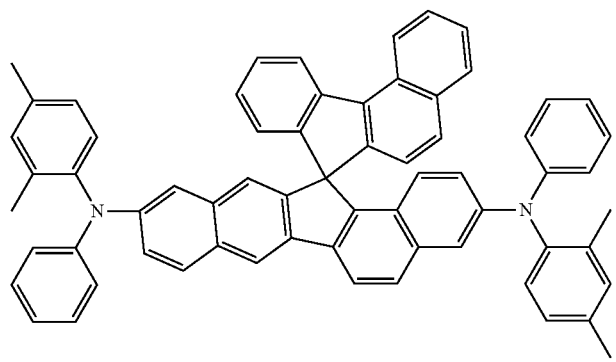
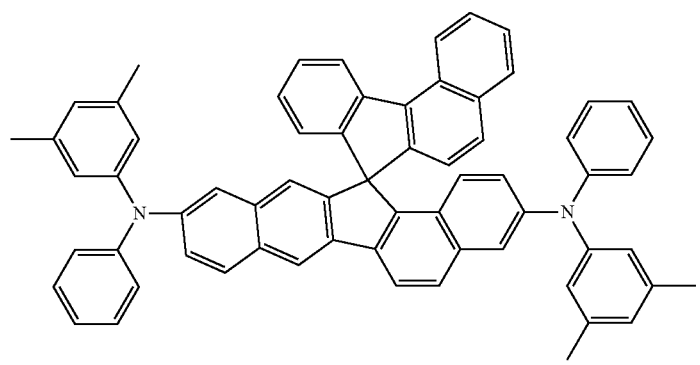
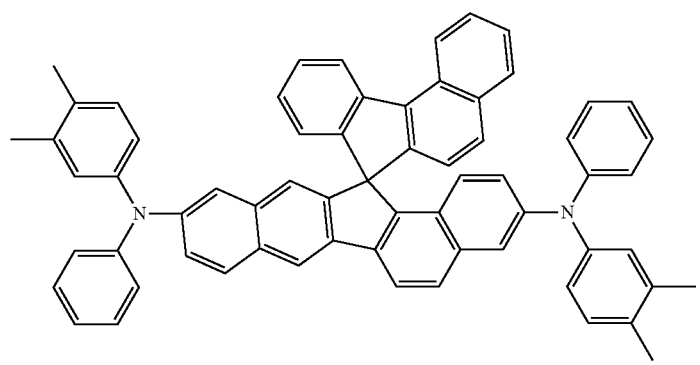

1233 1234
-continued
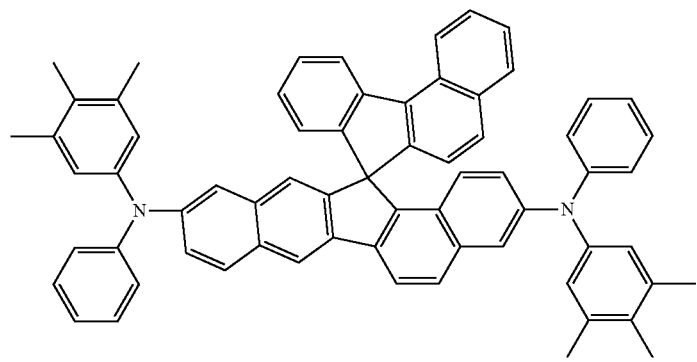
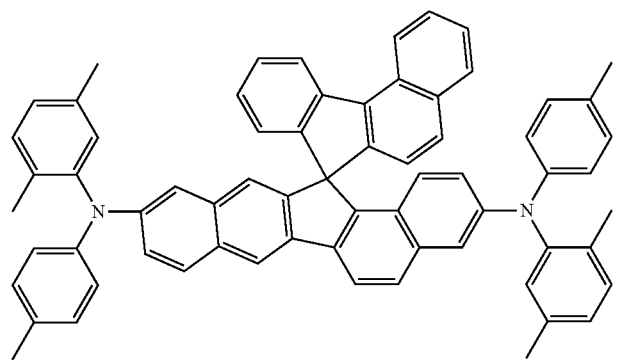
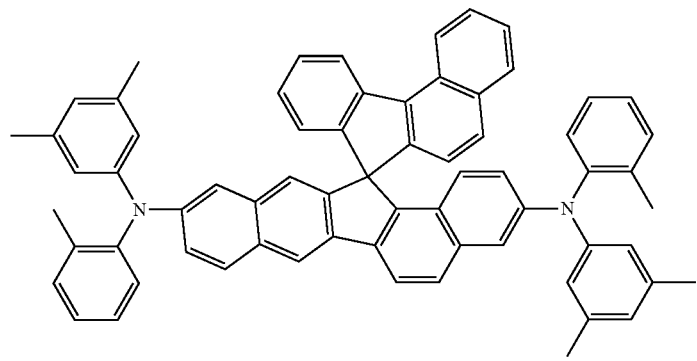
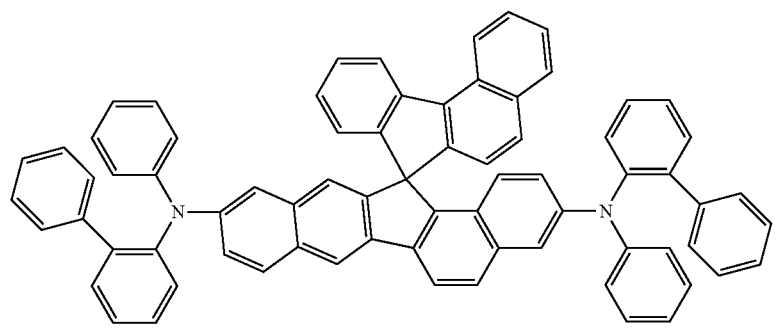

1235
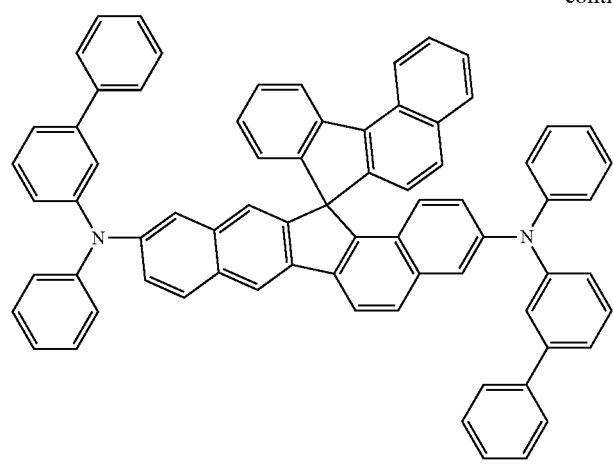
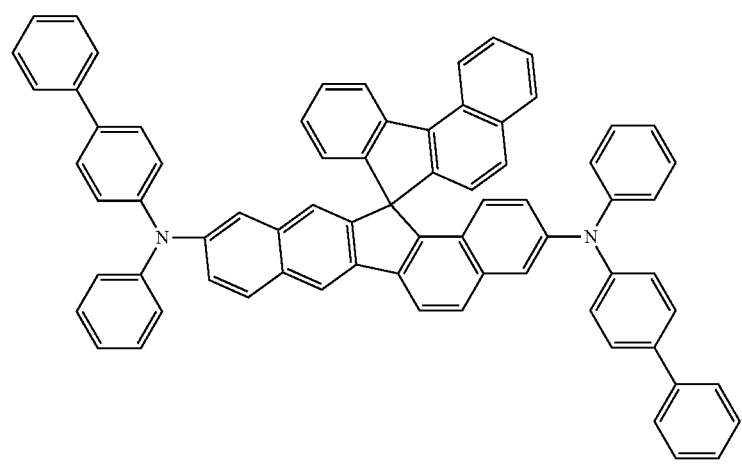
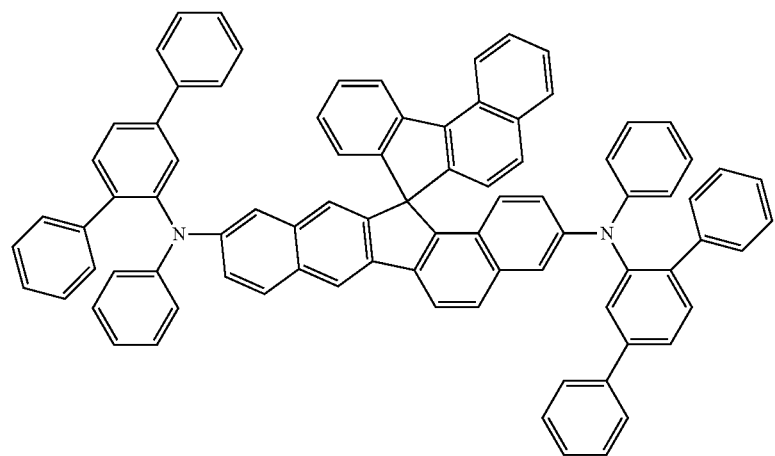
1236

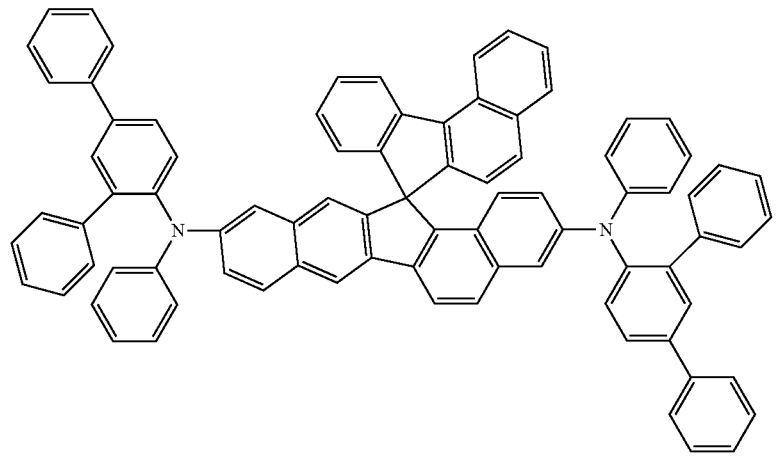
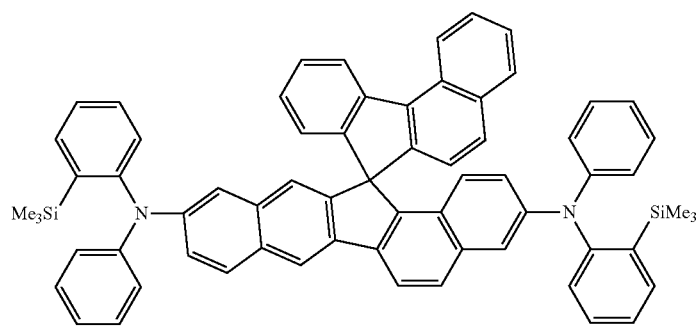
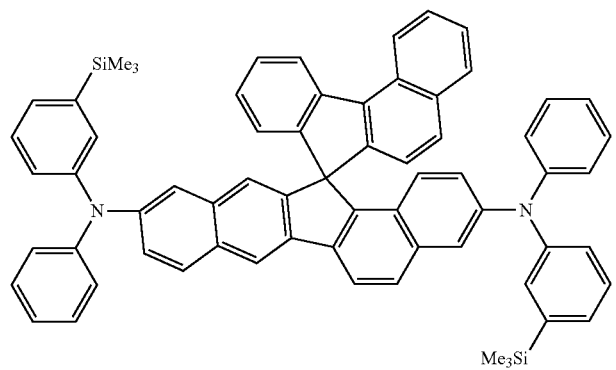
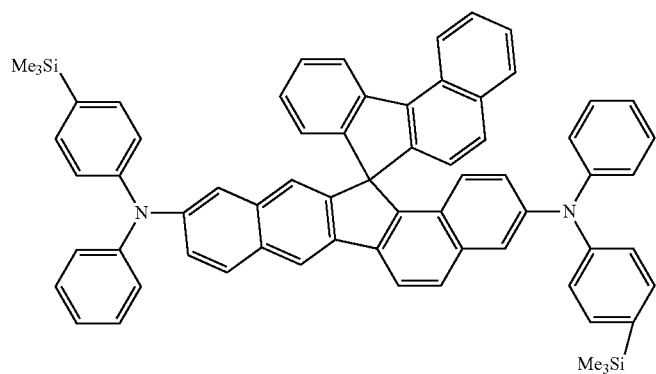

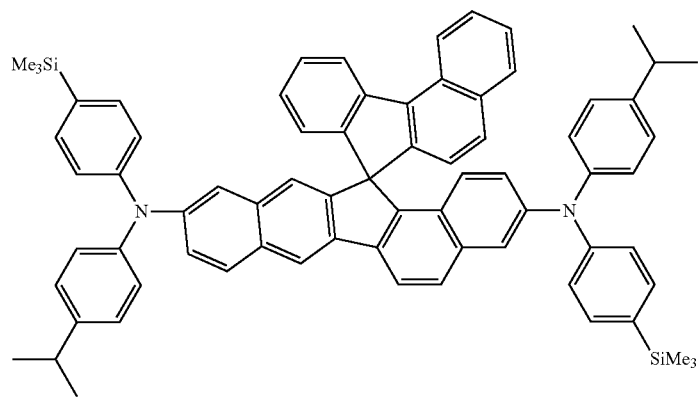
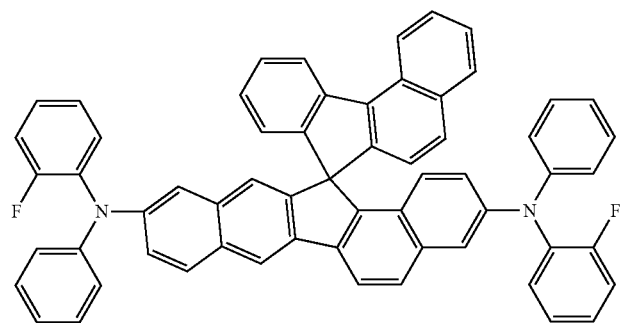
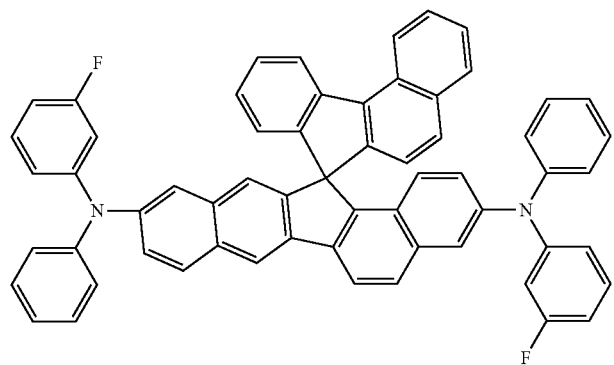
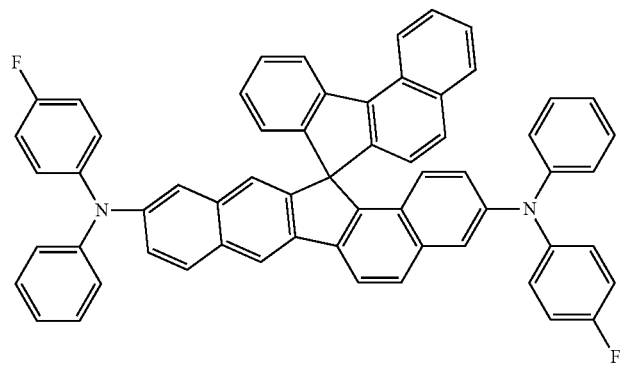

1241                                    1242
-continued
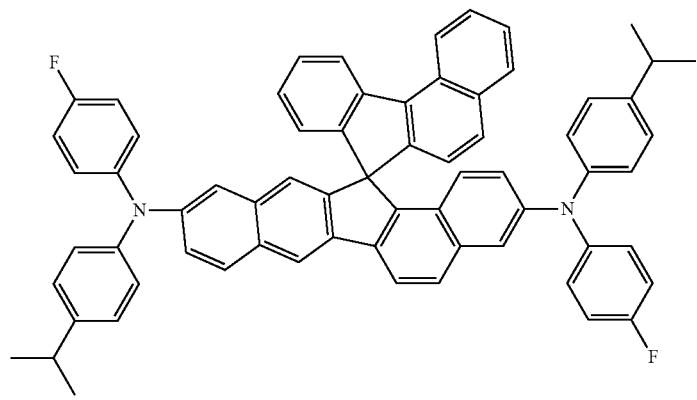
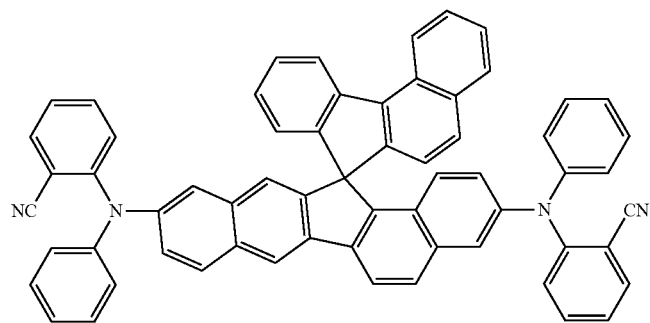
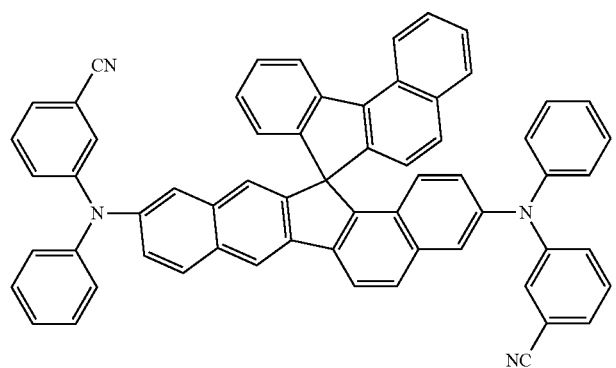
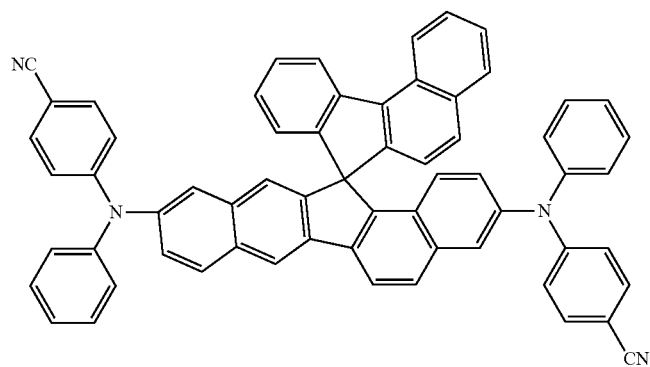

-continued
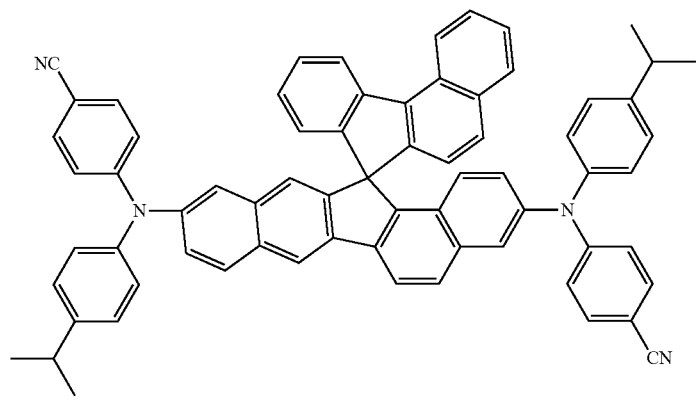
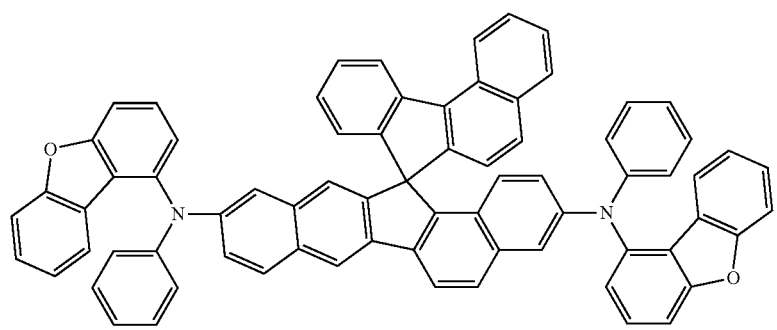
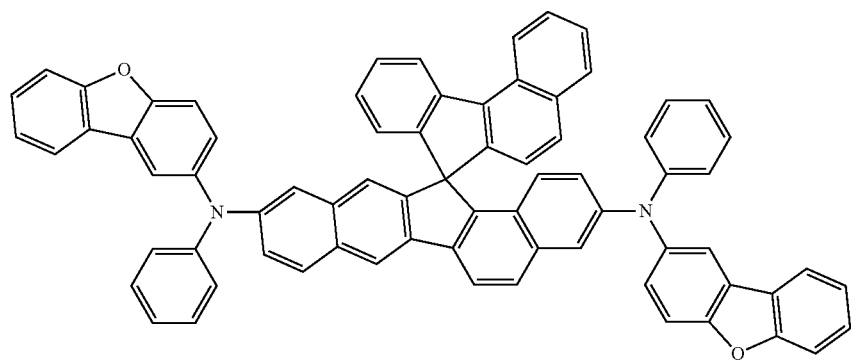
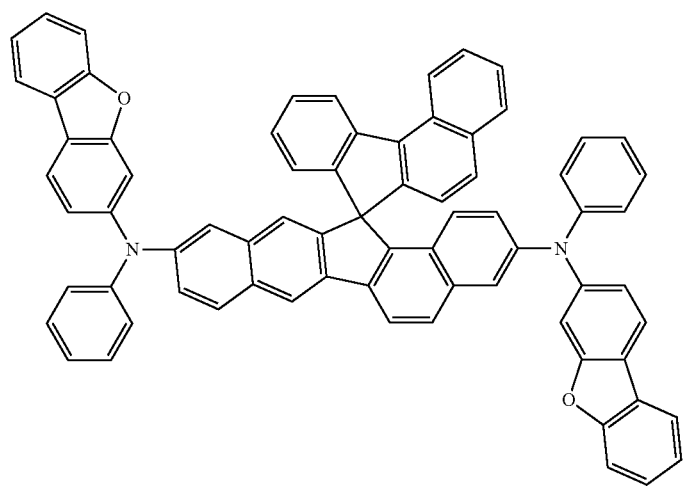

-continued
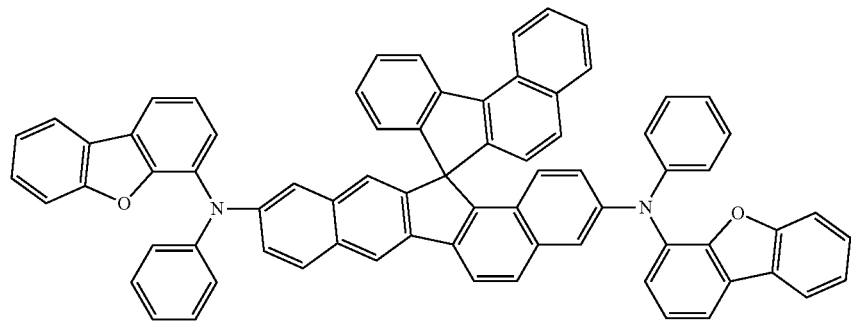
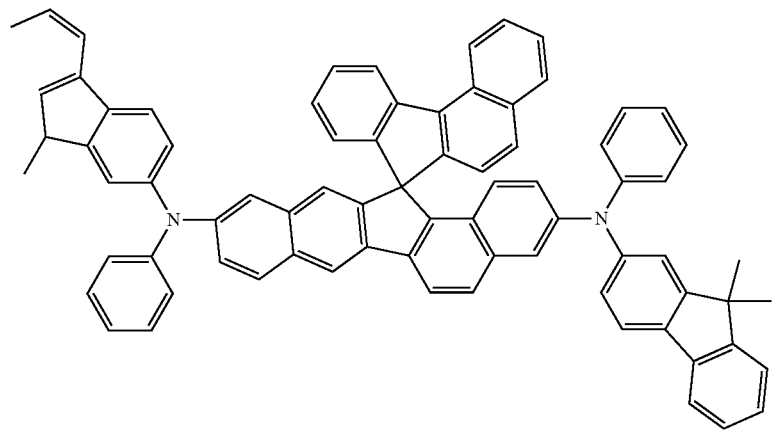
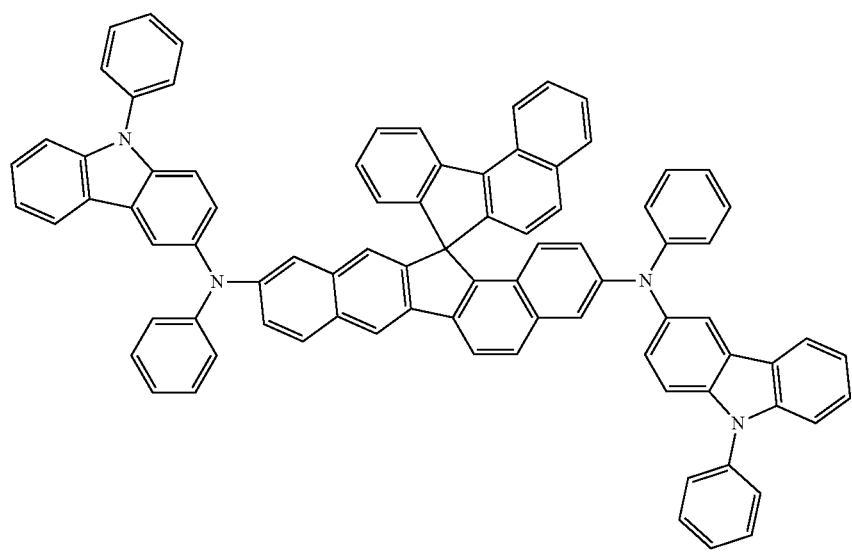
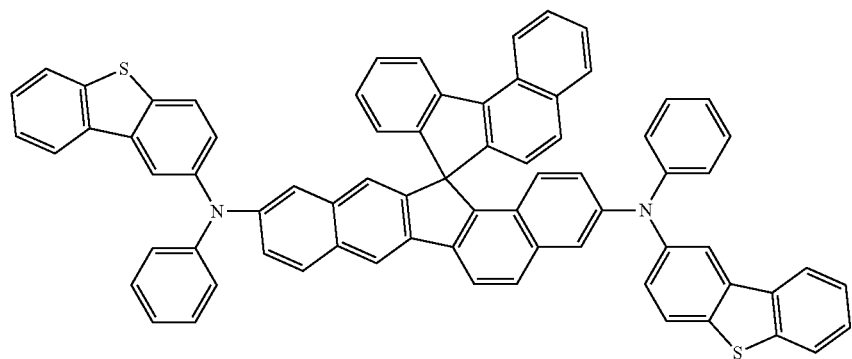

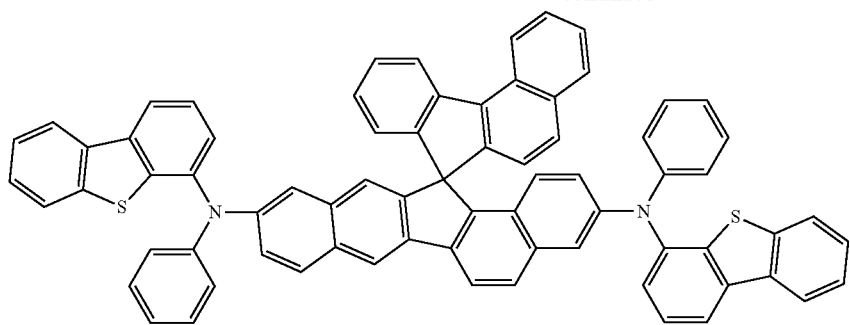
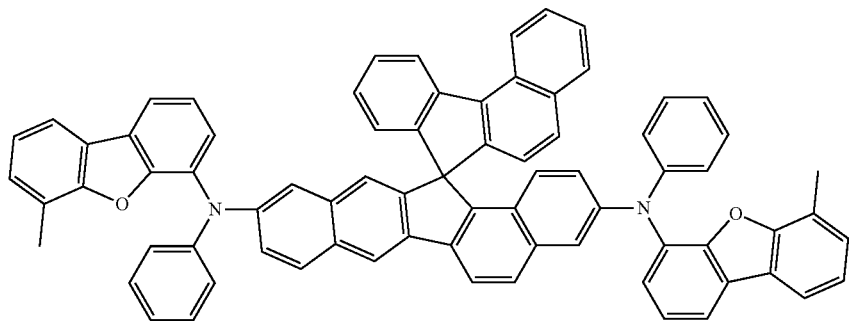
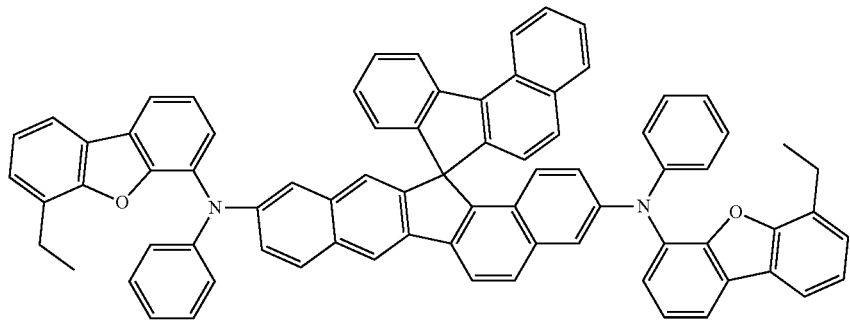
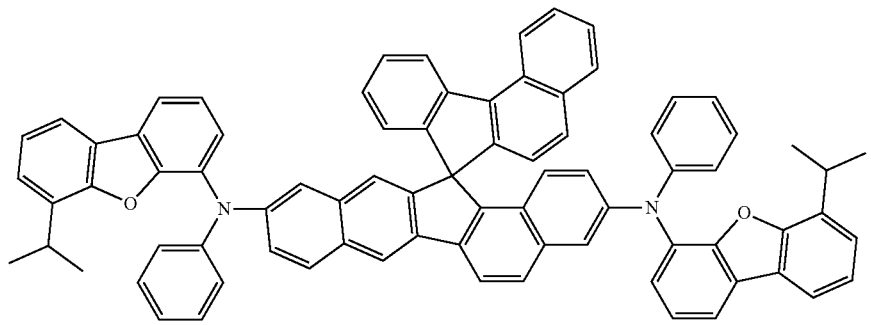
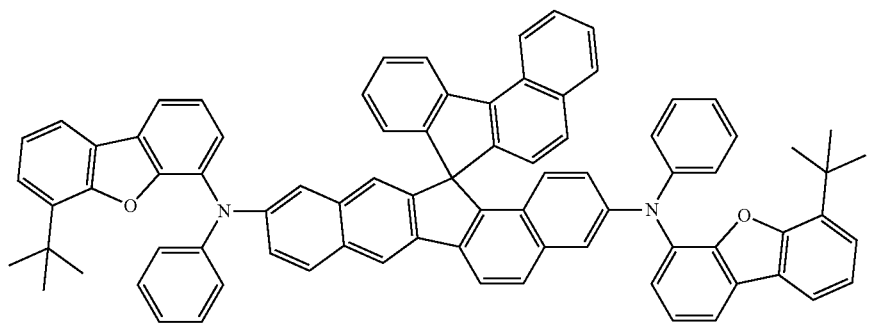

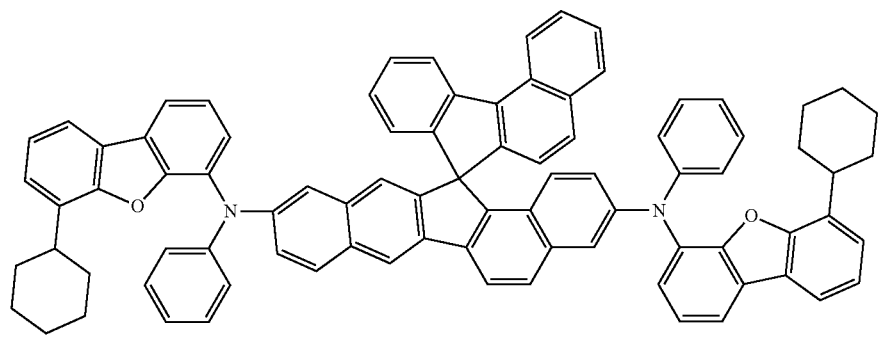
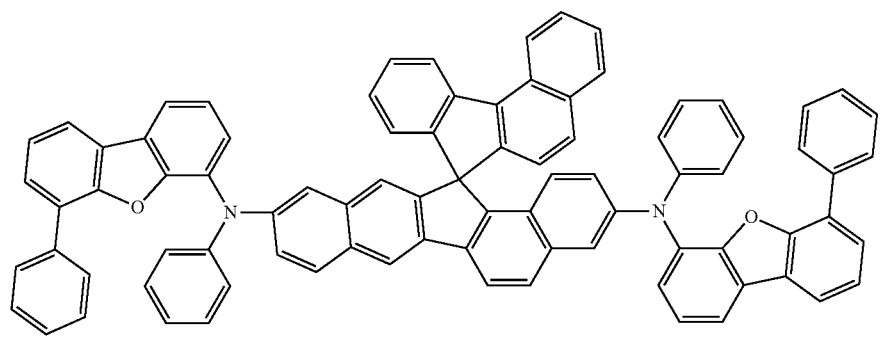
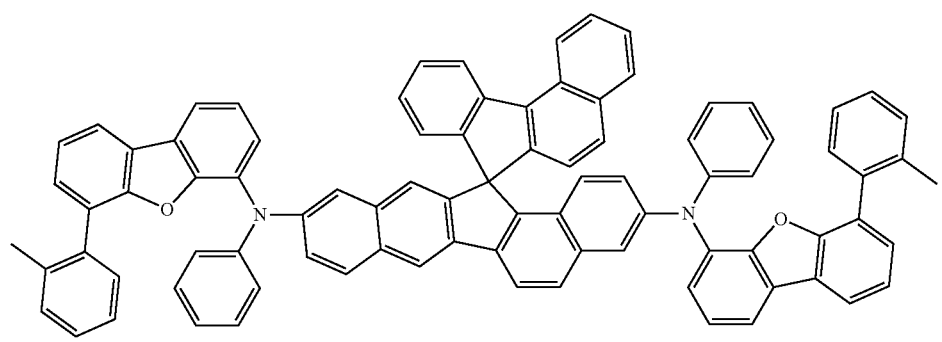
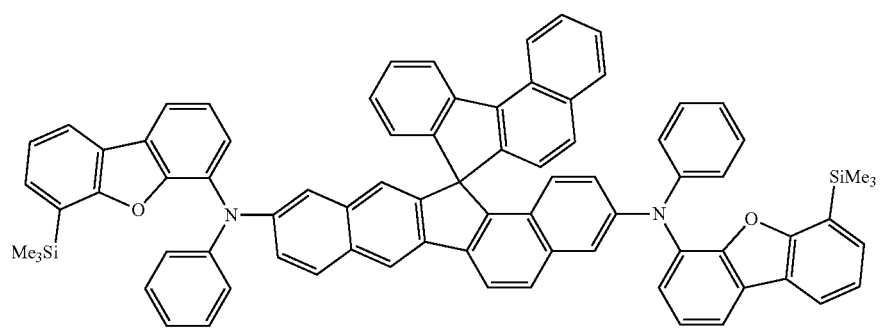
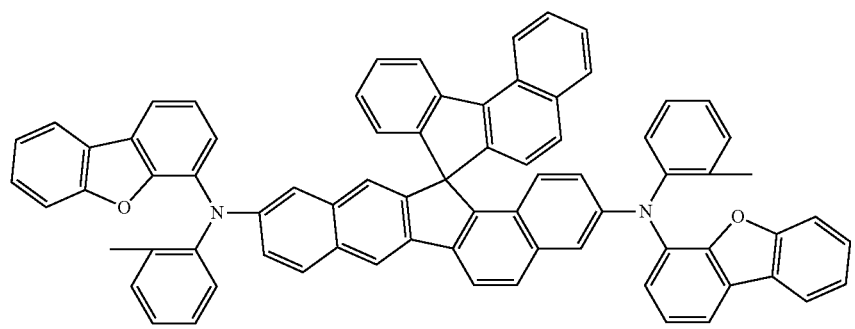

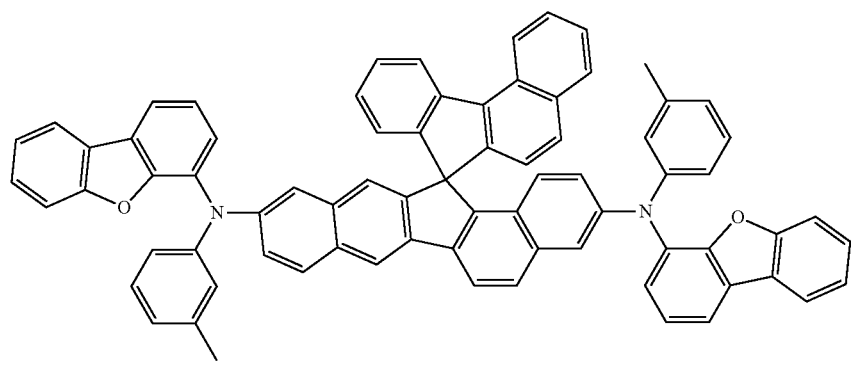
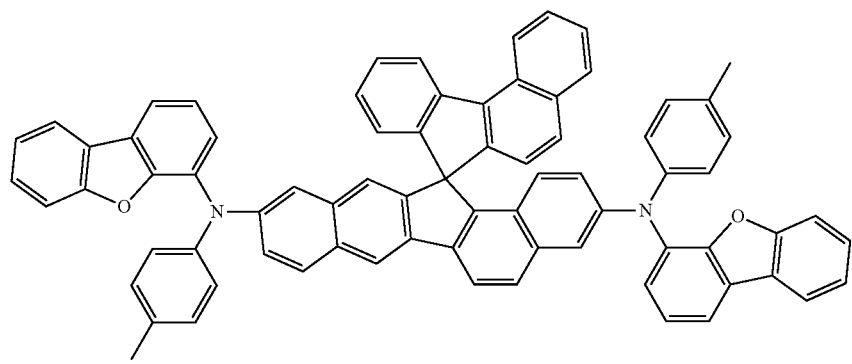
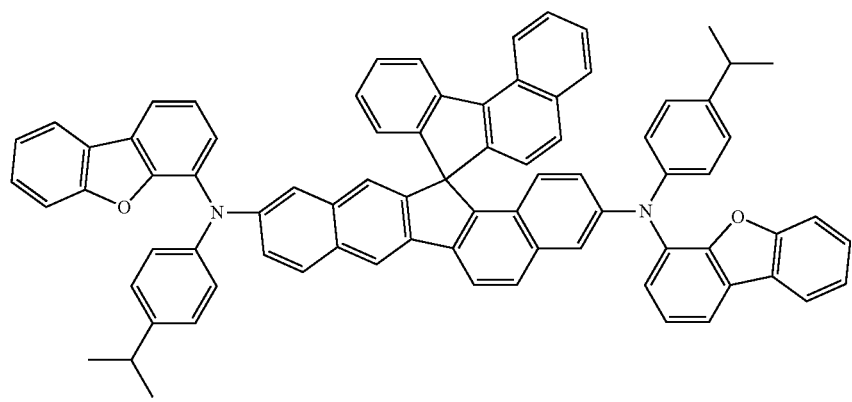
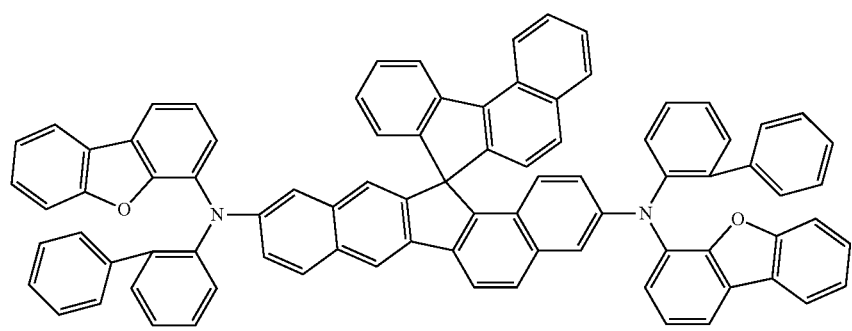

1253                                                              1254
-continued
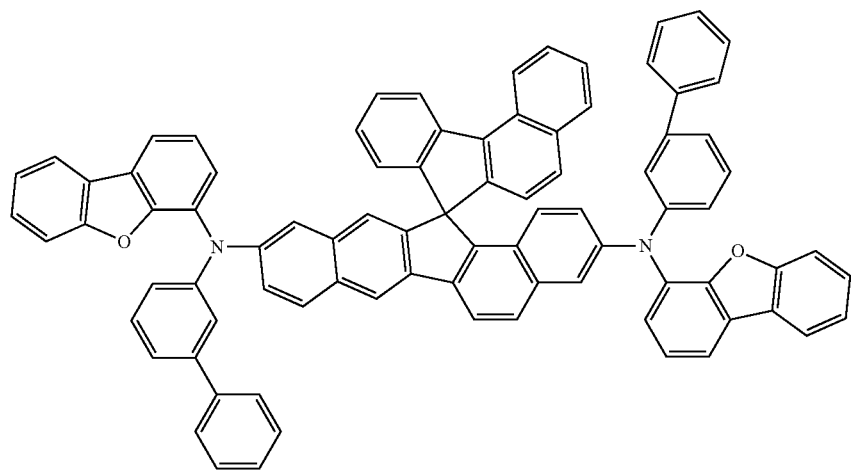
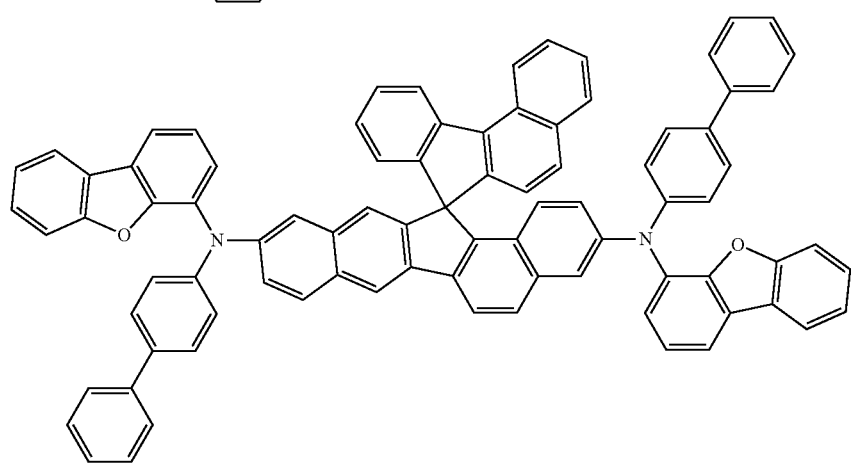
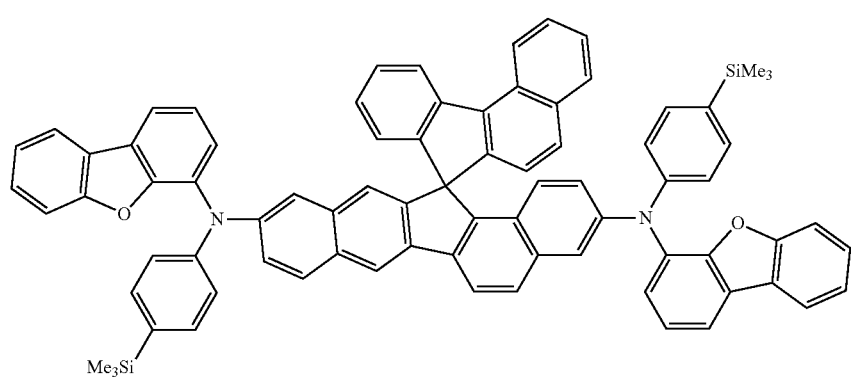
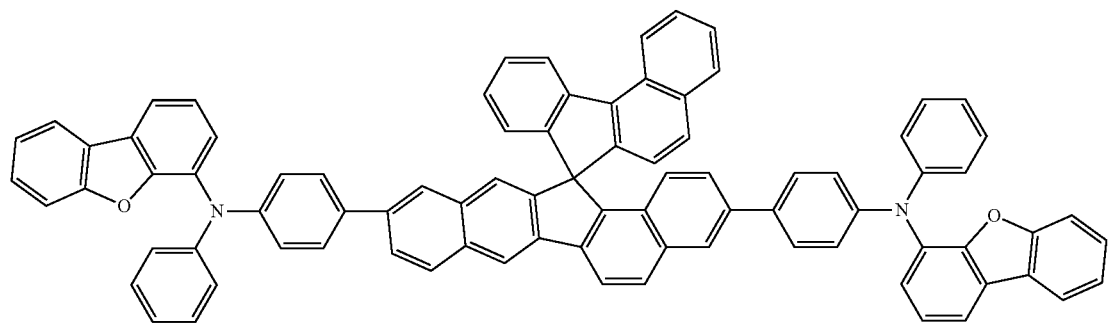

1255 1256
-continued
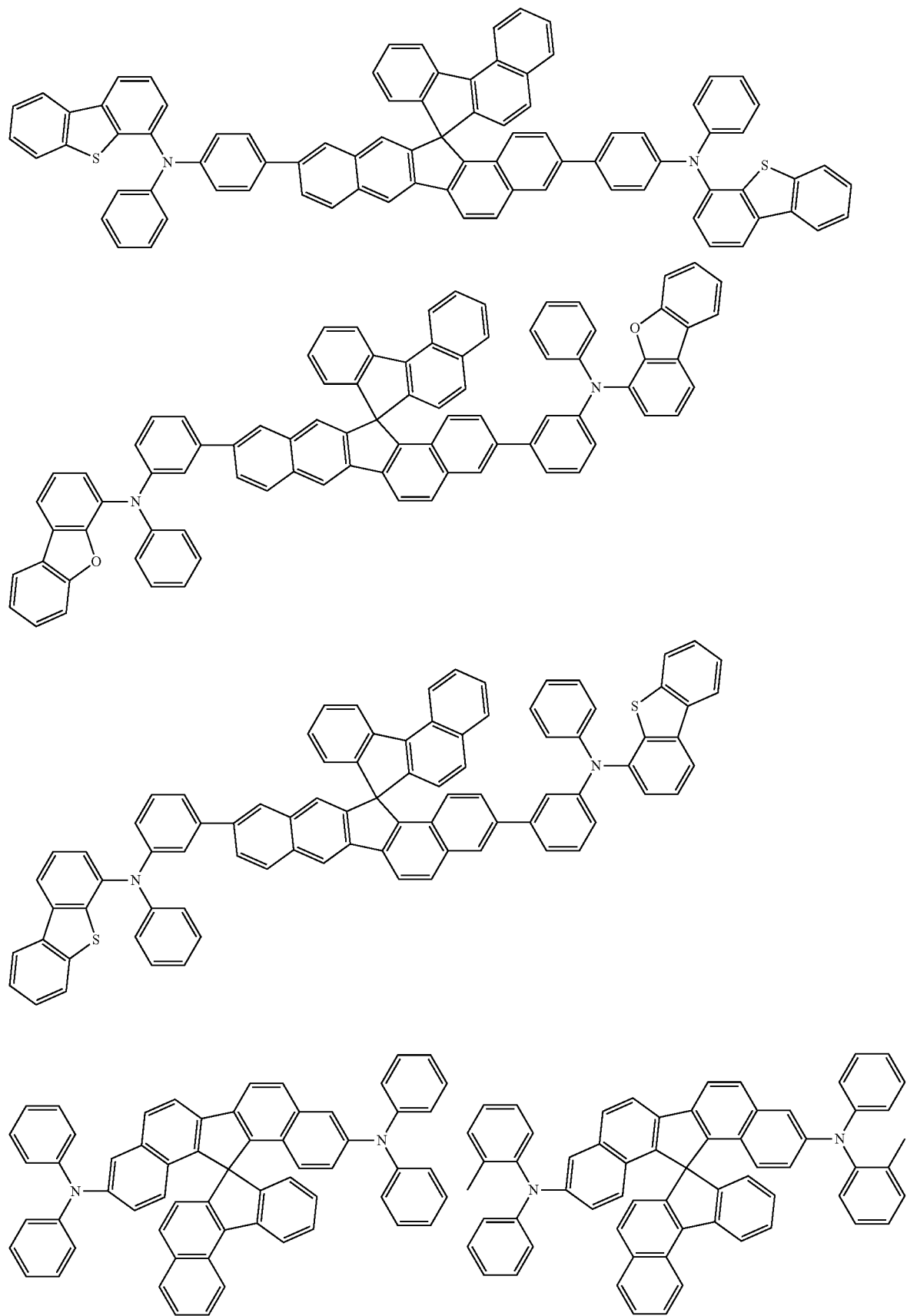

-continued
| 1257 | 1258 |
|---|---|
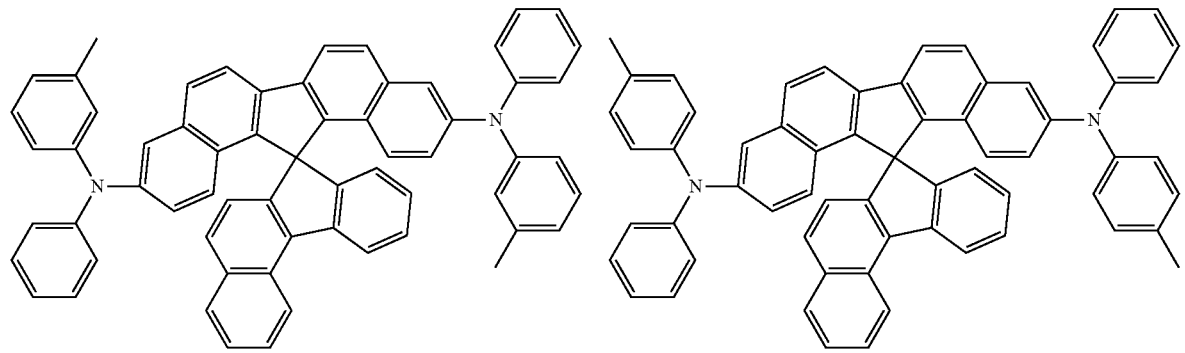
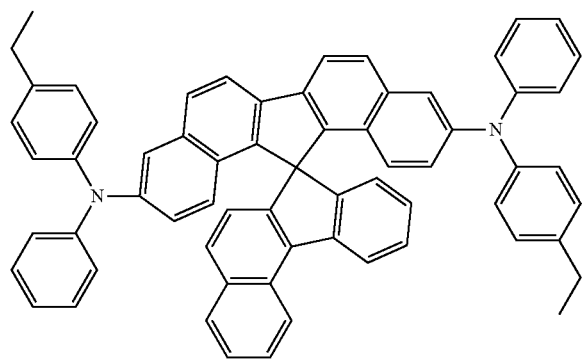
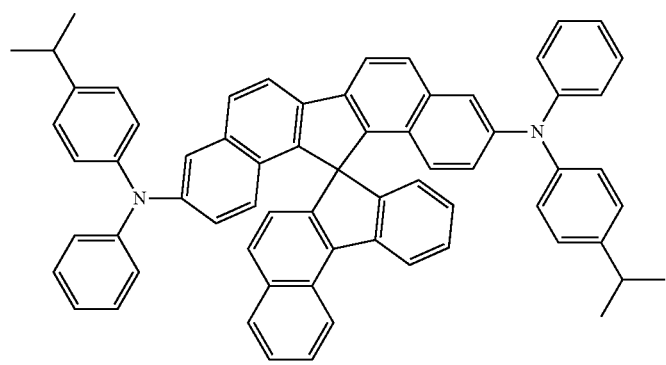
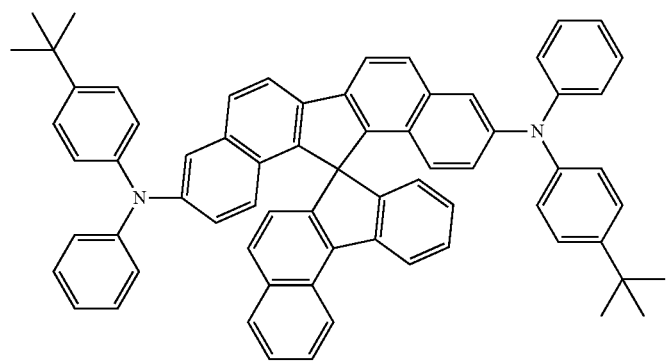

1259 1260
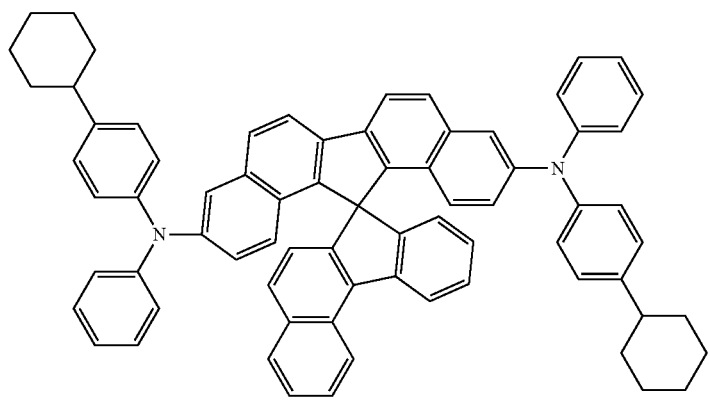
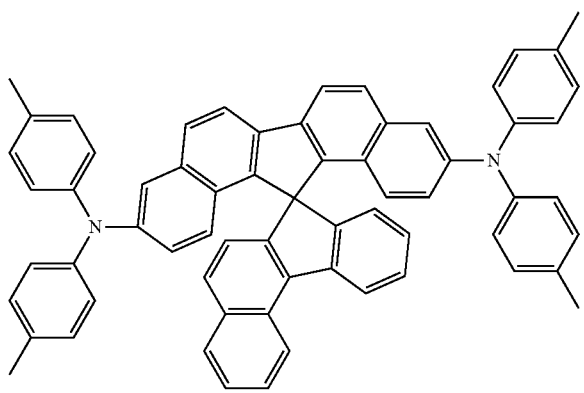
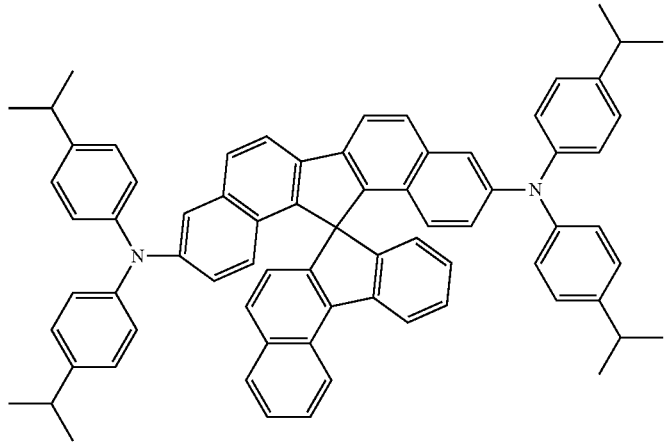
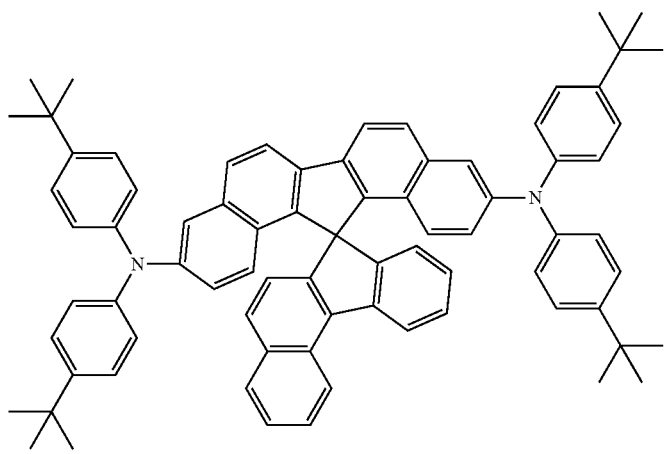

1261
1262
-continued
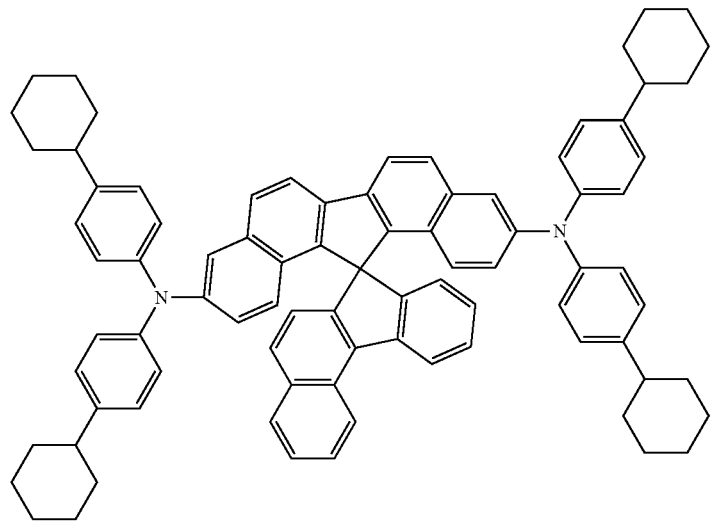
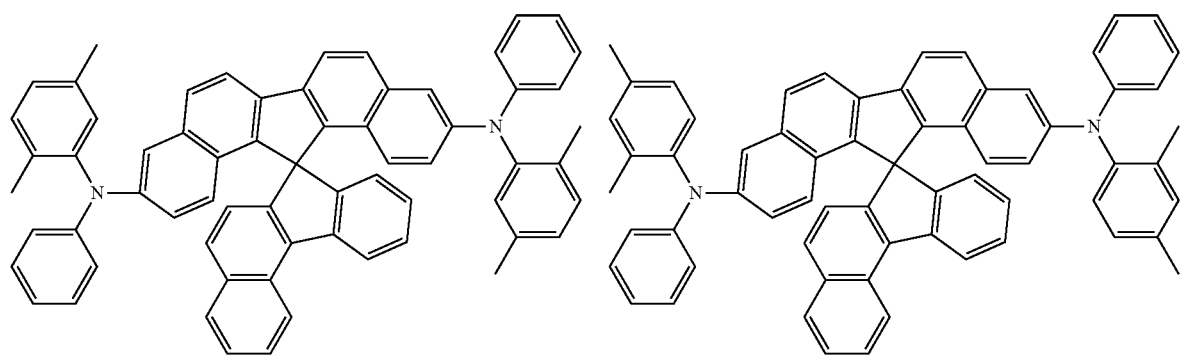
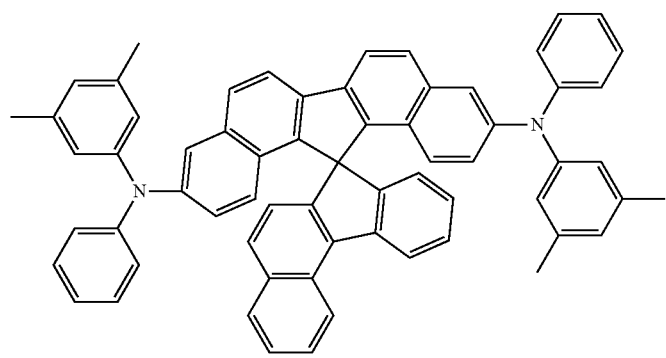
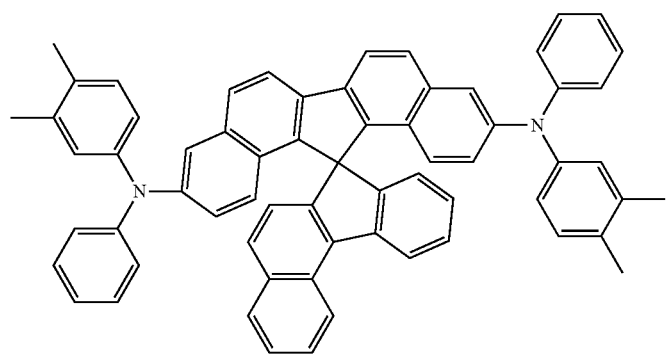

1263
1264
-continued
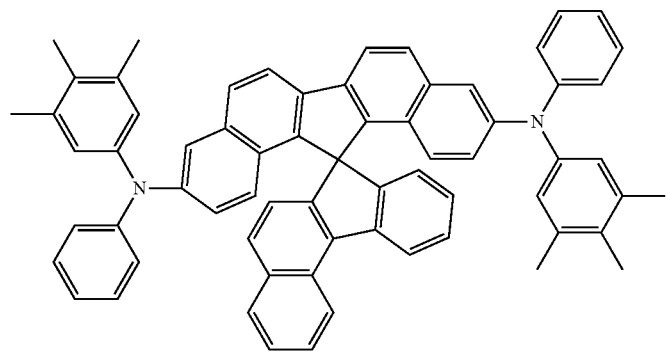
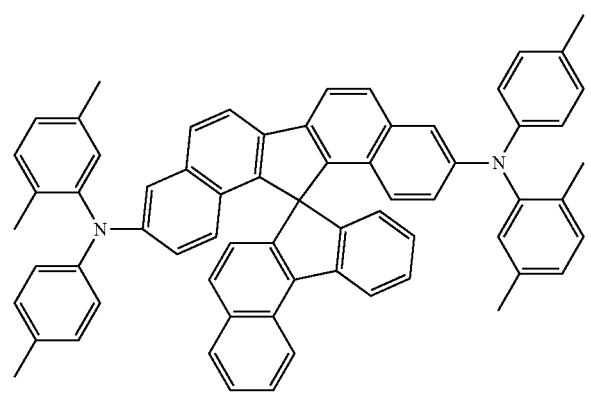
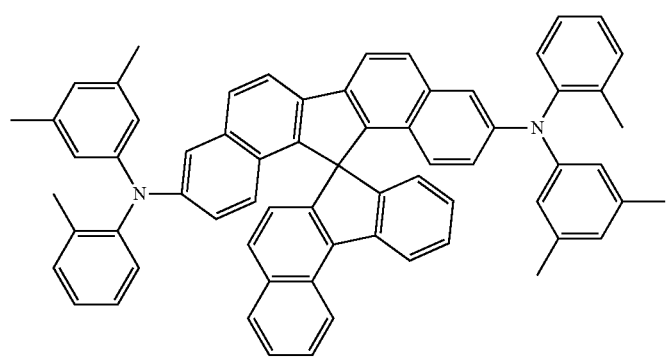
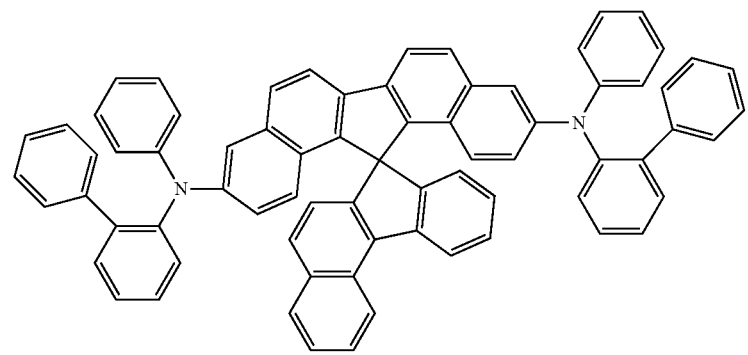

-continued
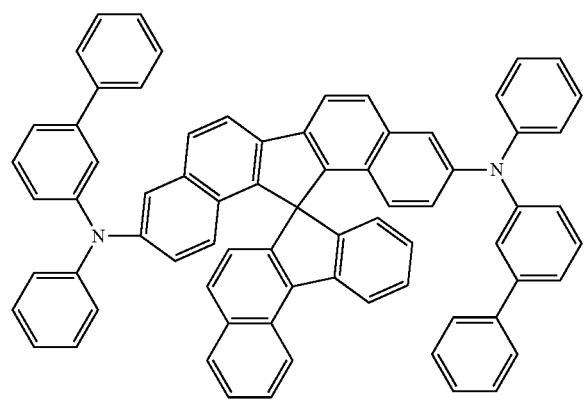
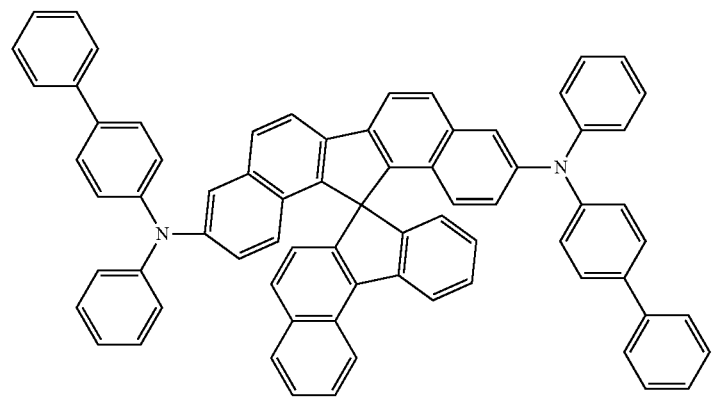
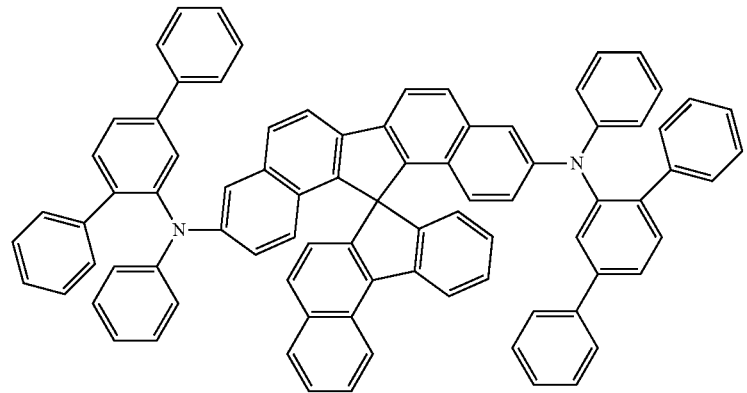
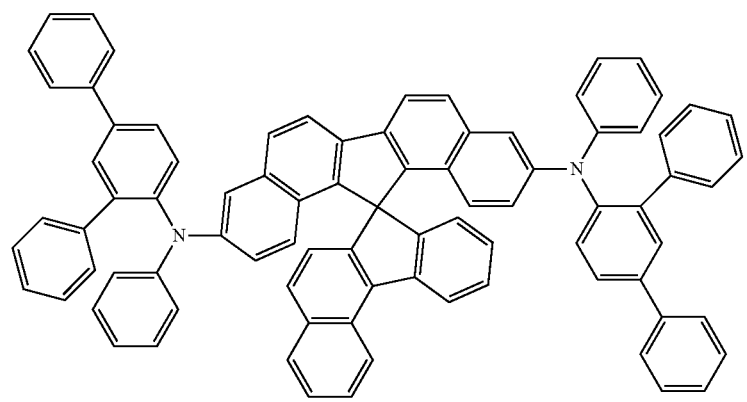

1267
-continued
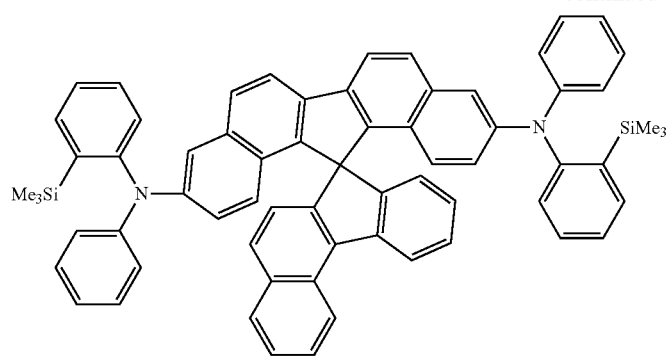
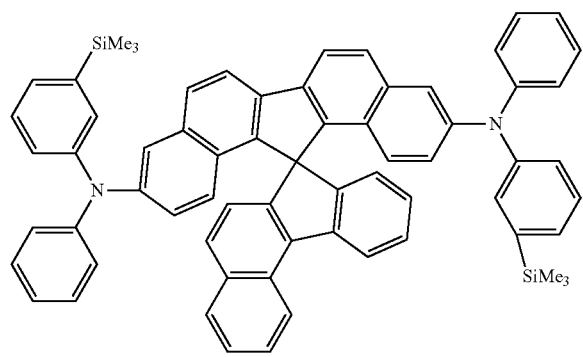
1268
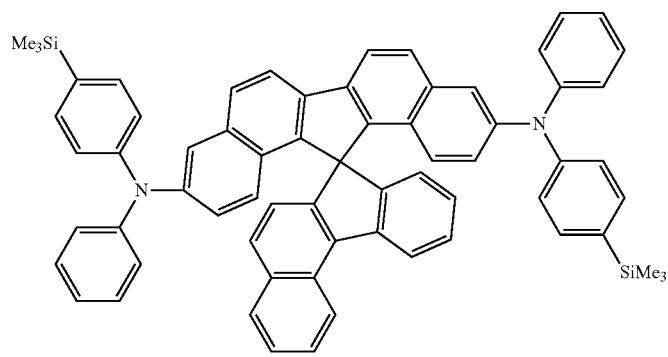
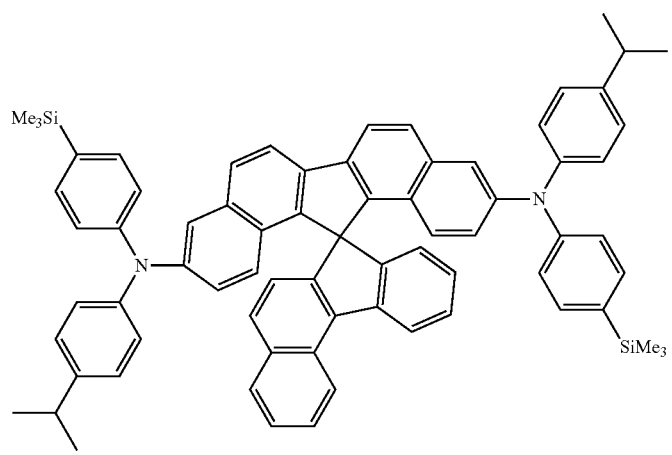

-continued
| 1269 | 1270 |
|---|---|
| 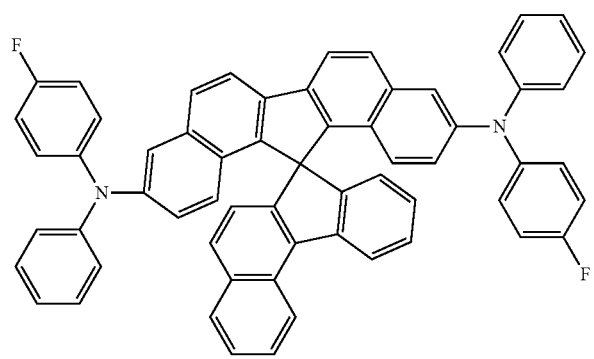 | 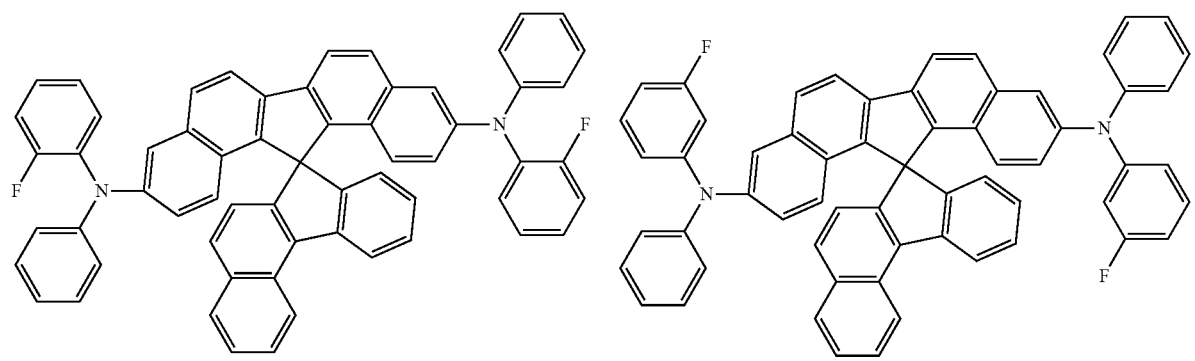 |
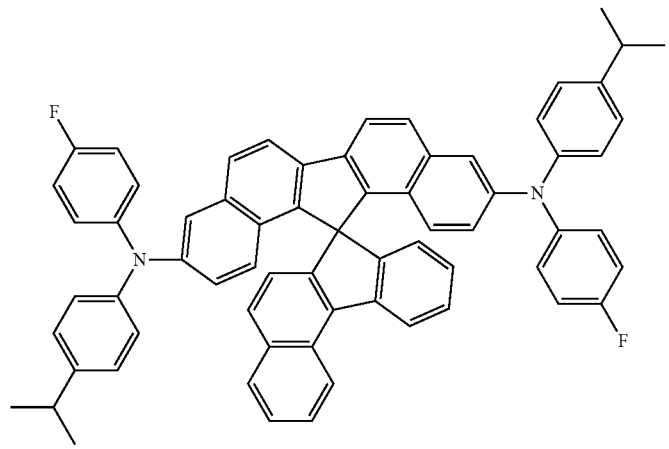
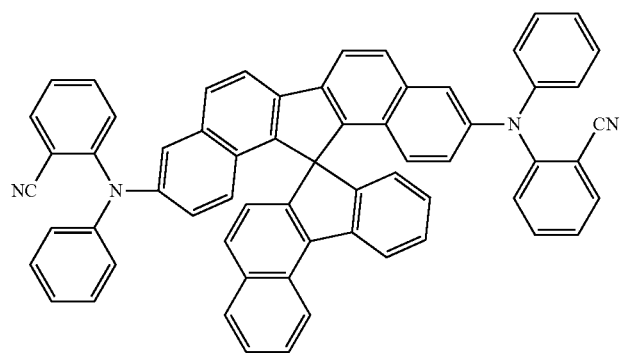

1271
-continued
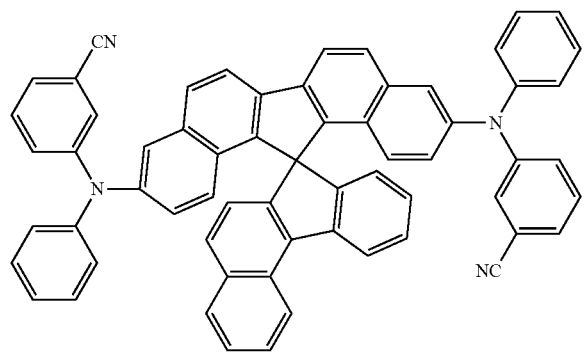
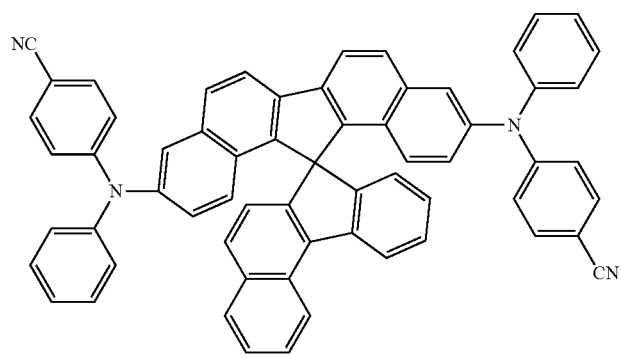
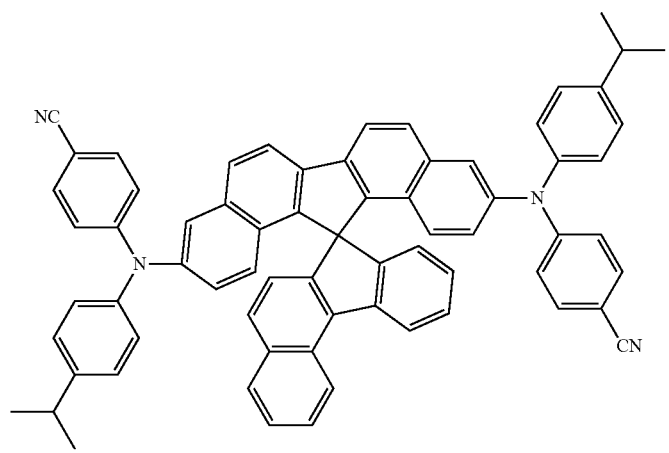
1272
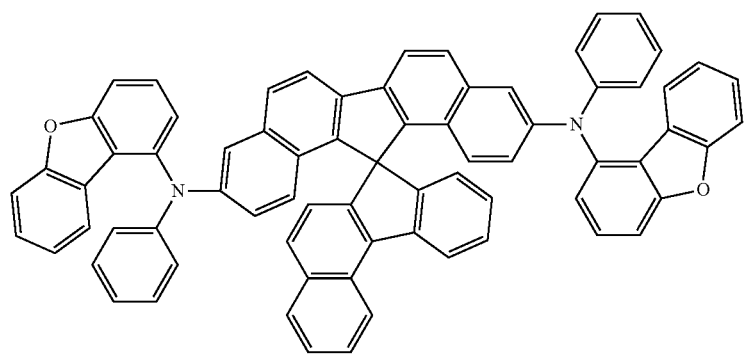

-continued
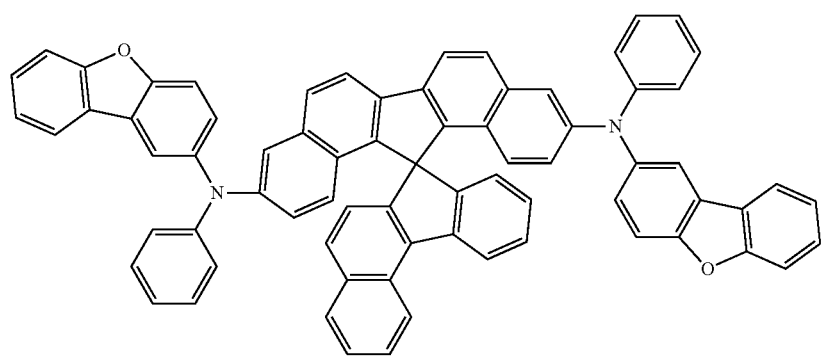
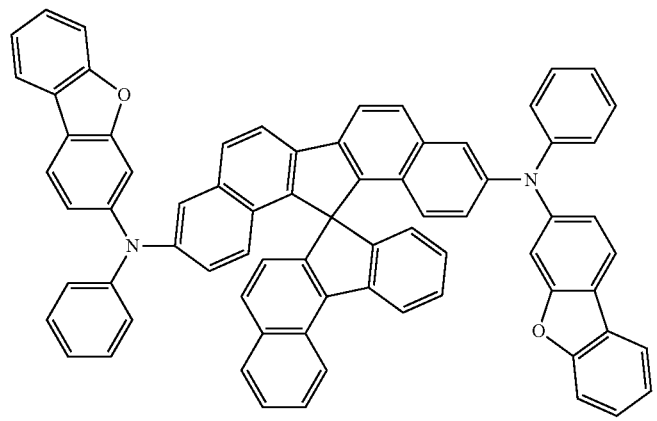
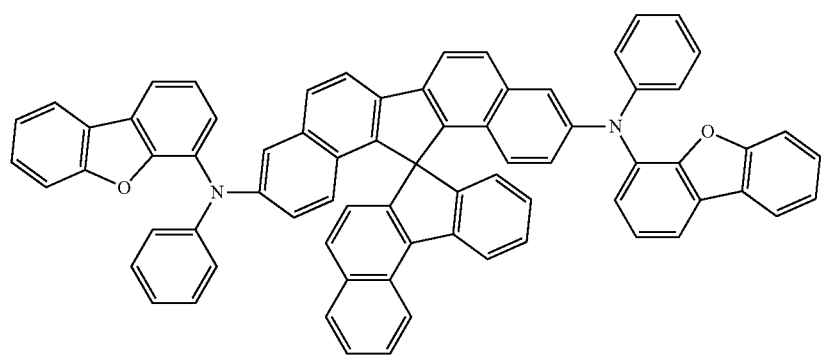
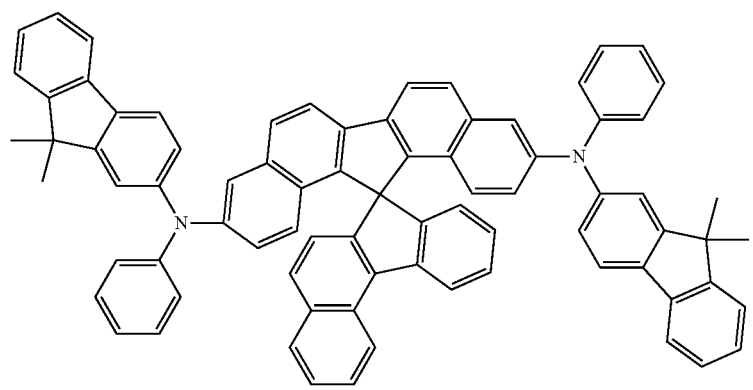

1275
1276
-continued
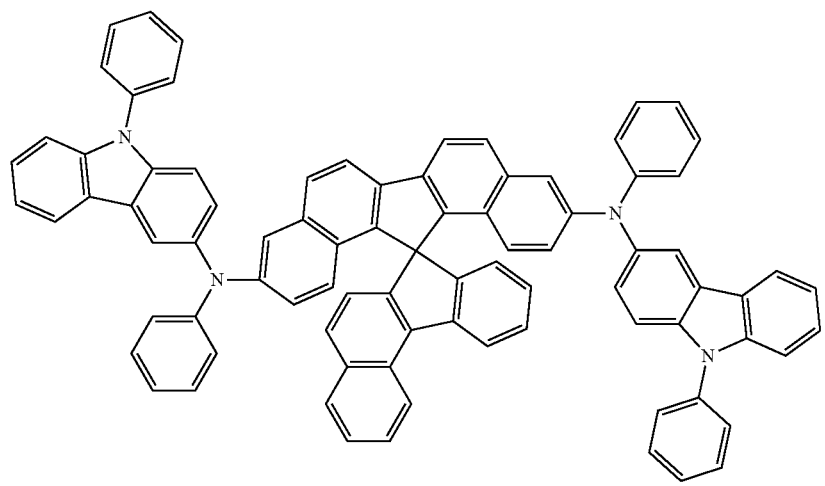
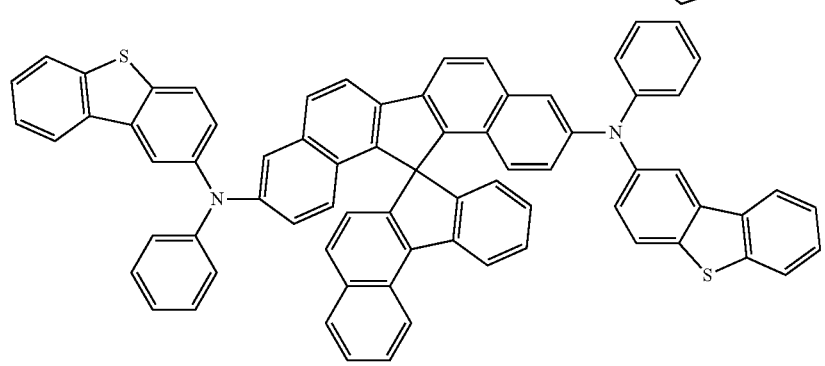
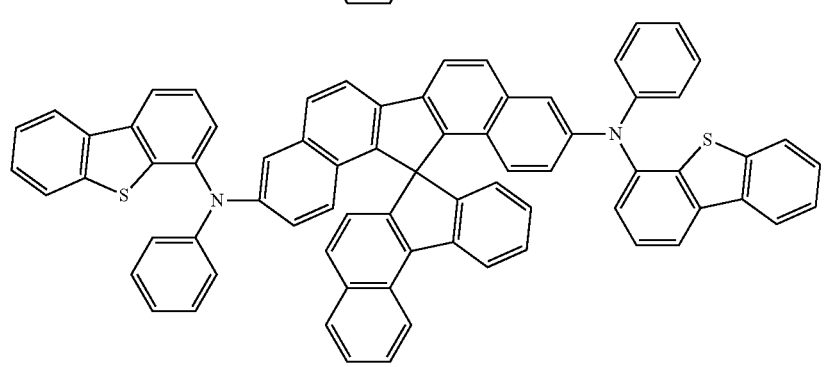
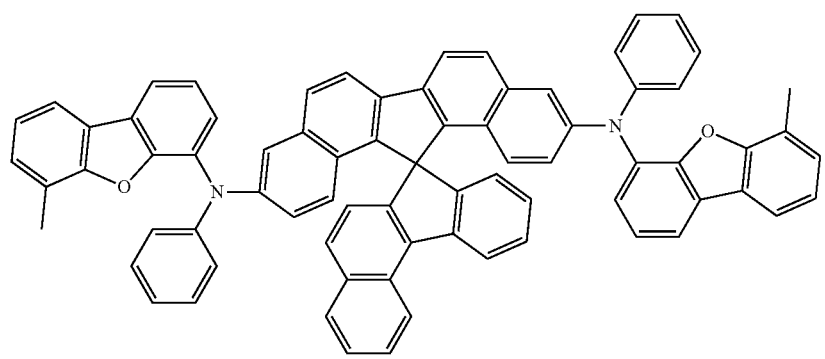

-continued
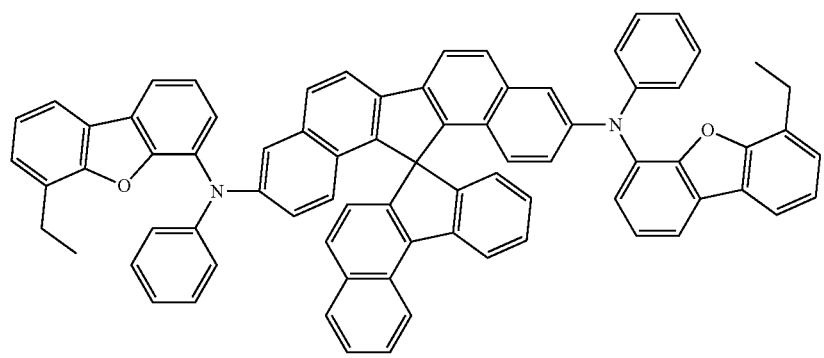
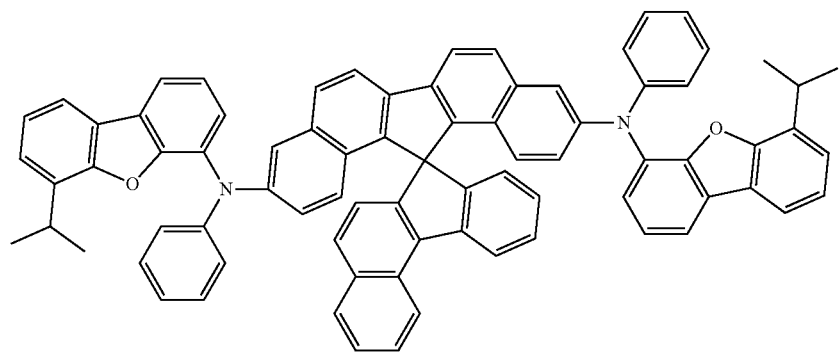
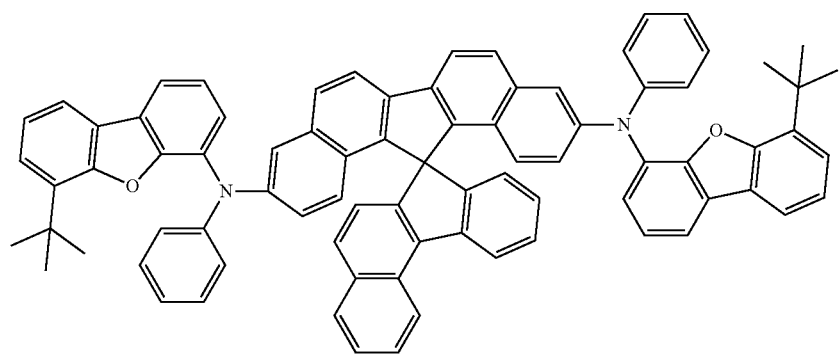
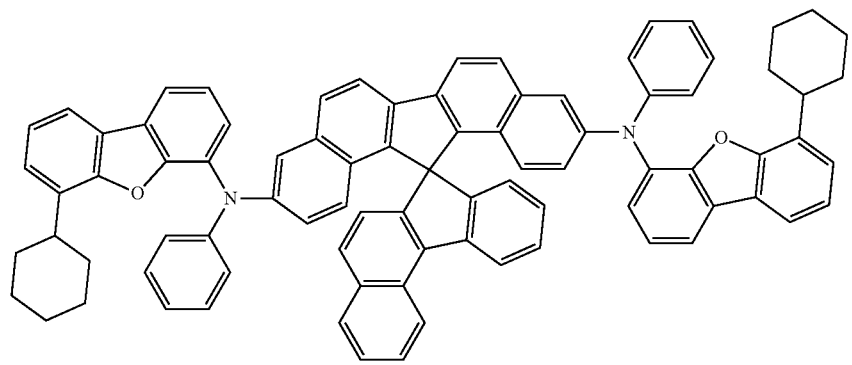

-continued
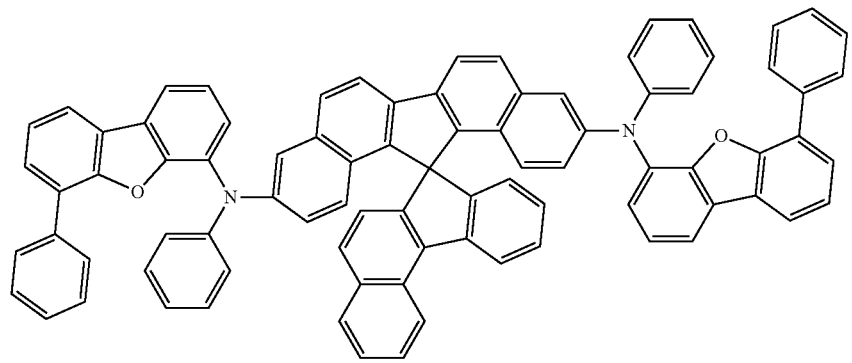
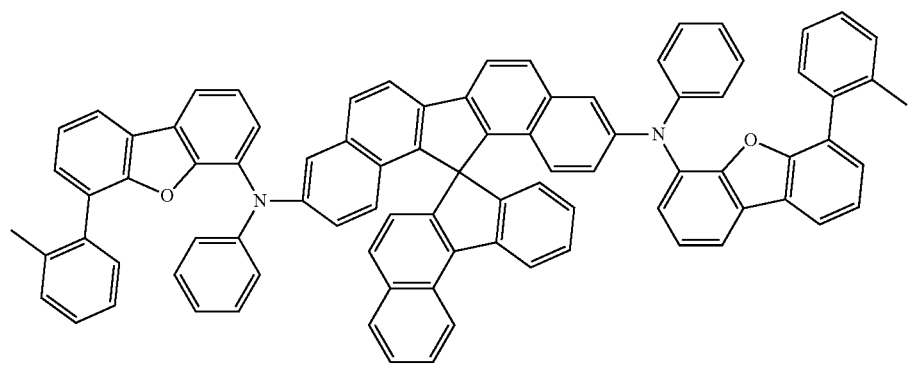
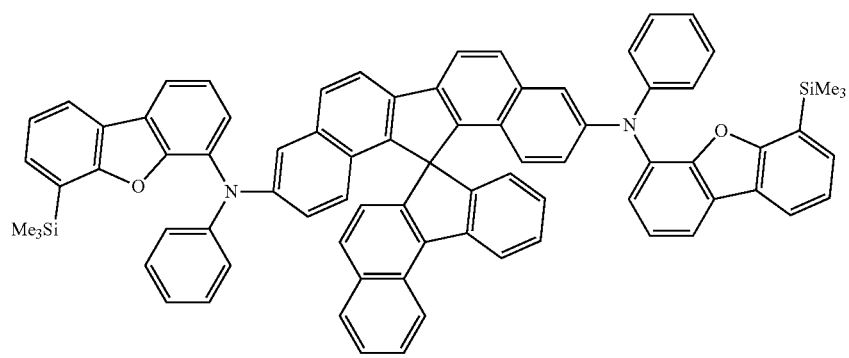
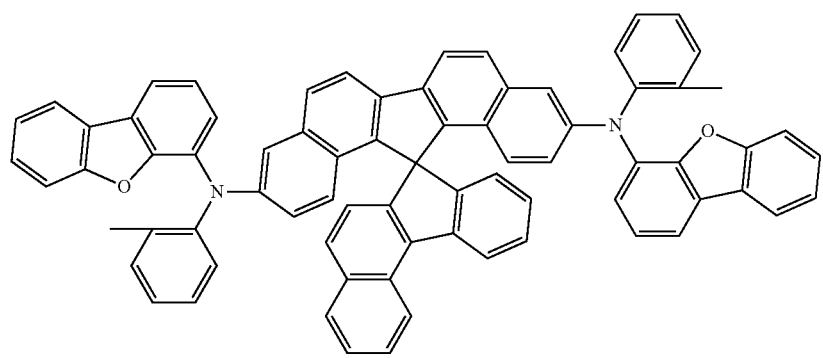

-continued
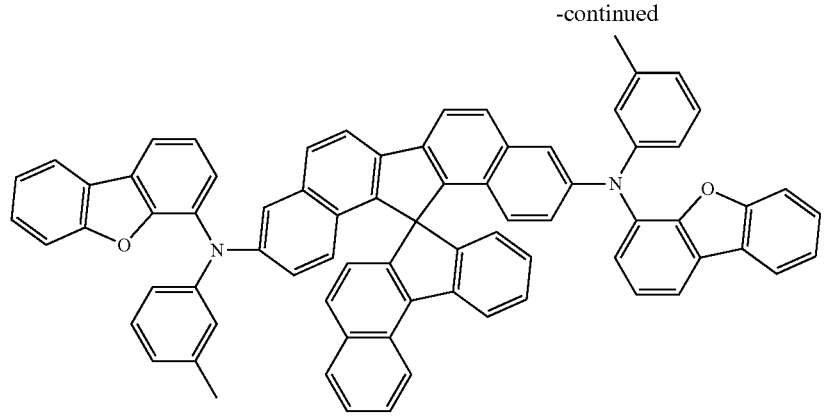
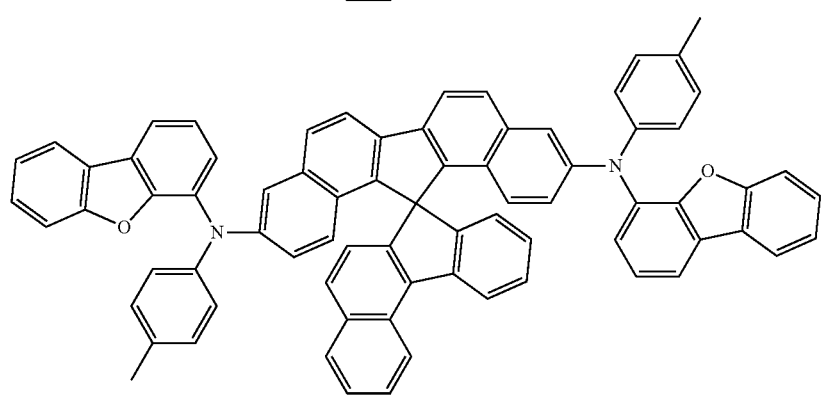
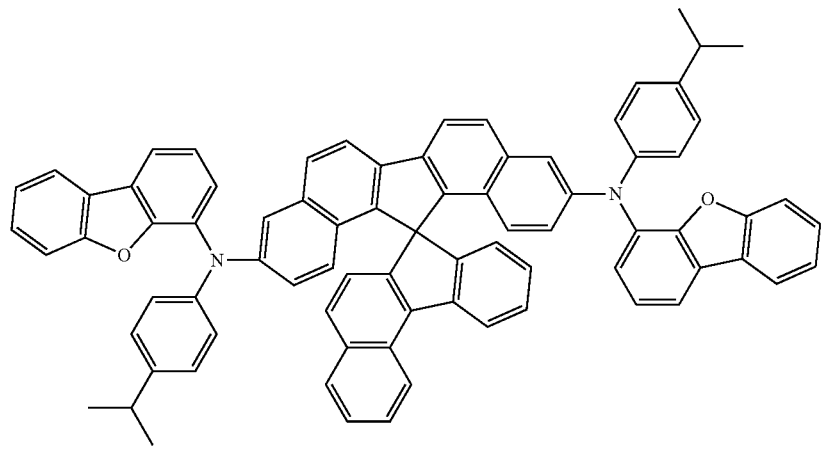
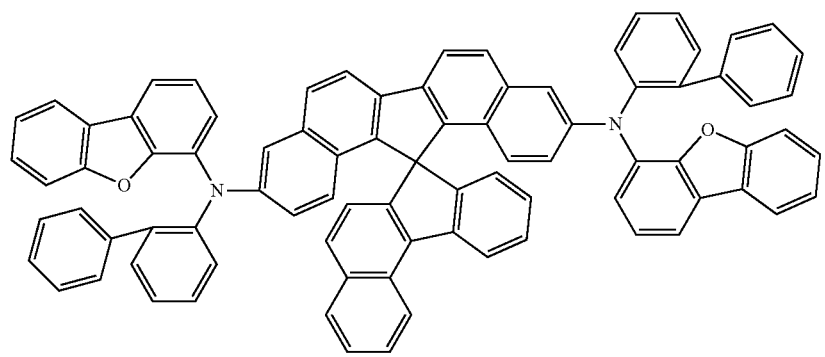

-continued
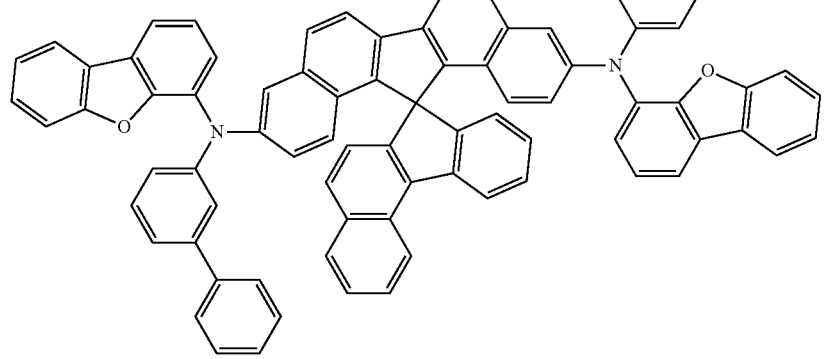
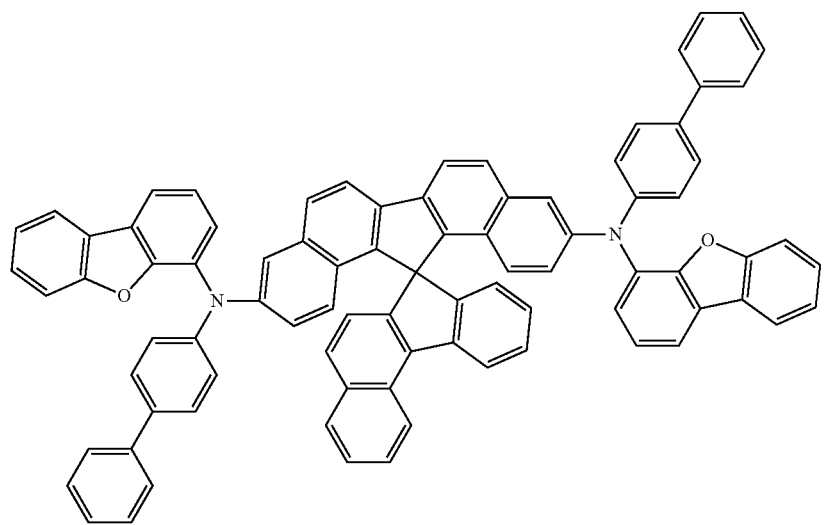
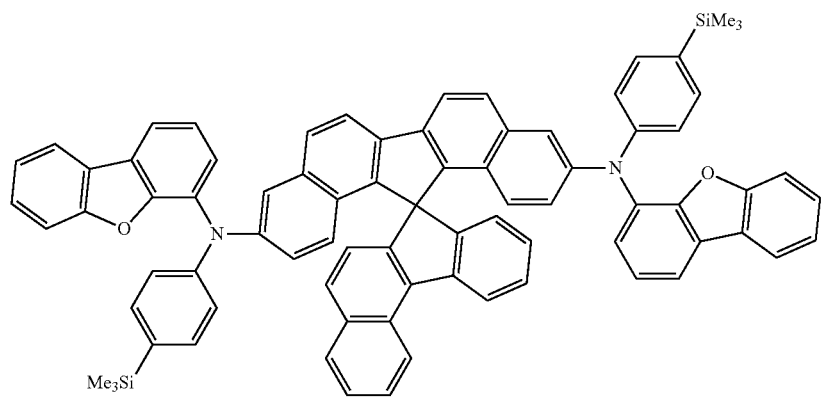

1285
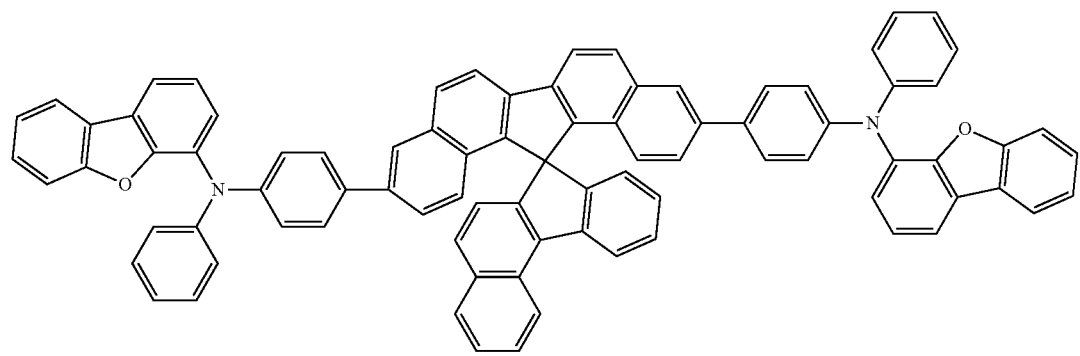
1286
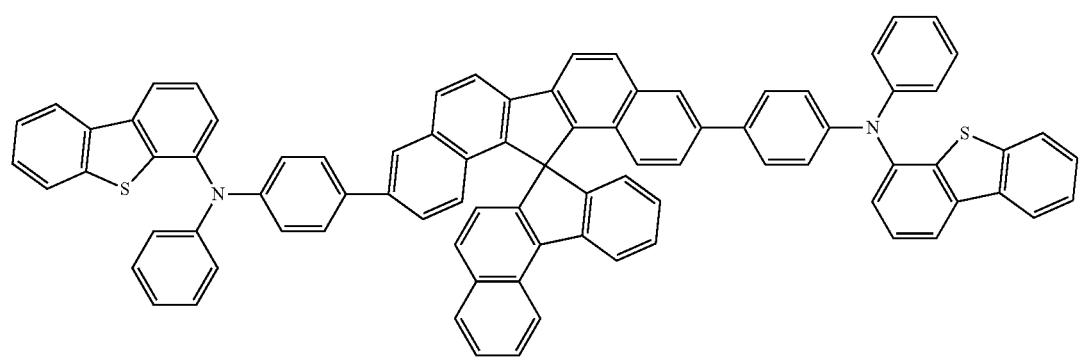
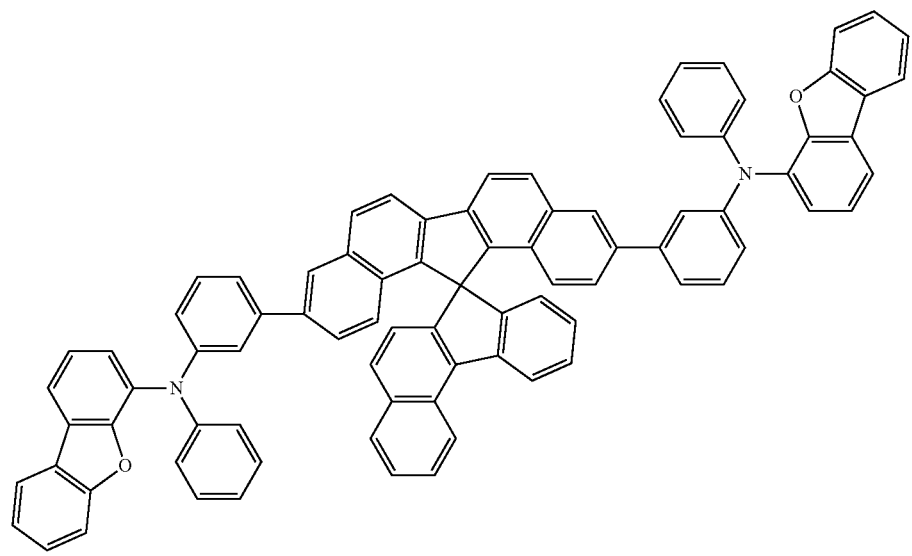

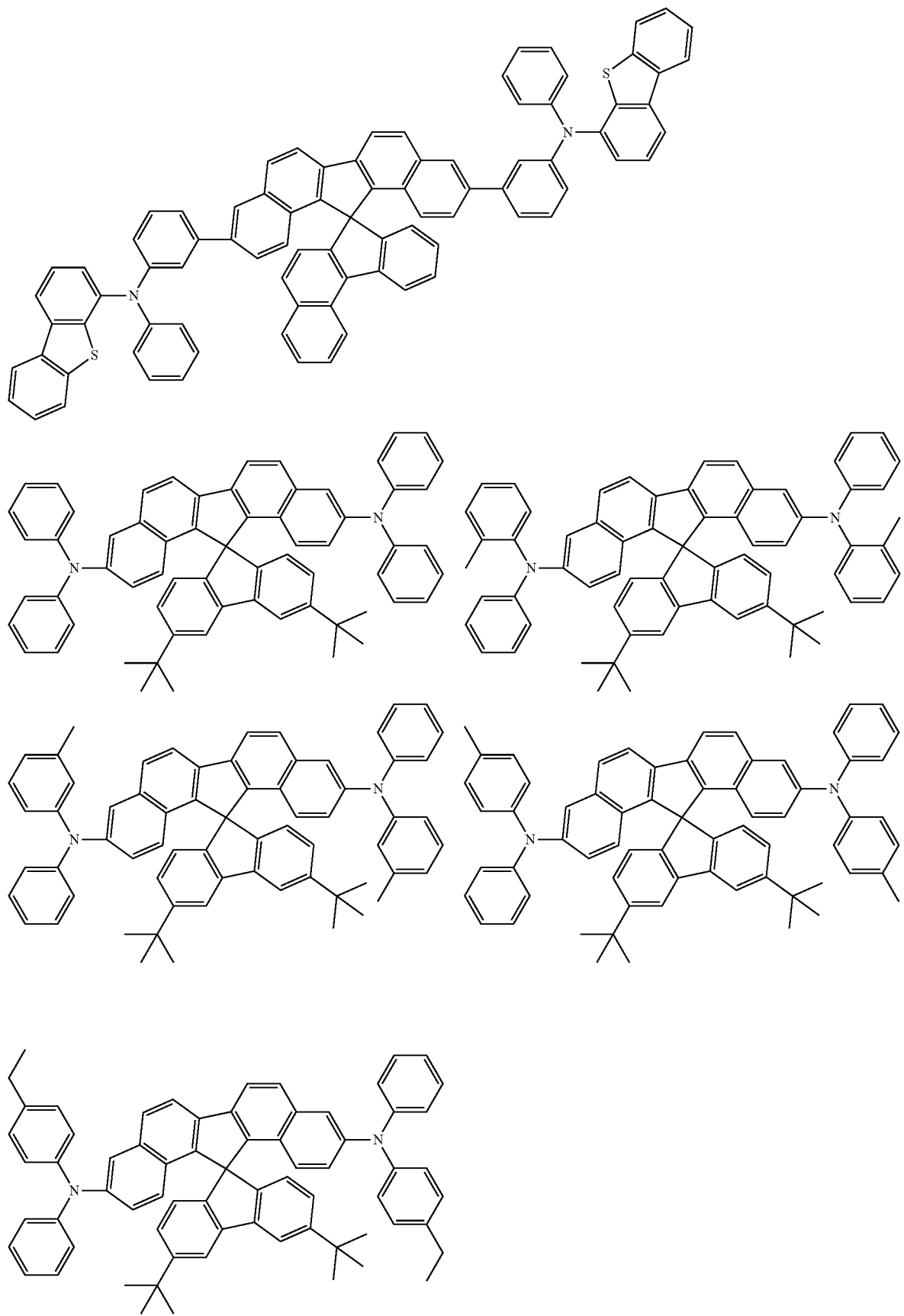

1289
-continued
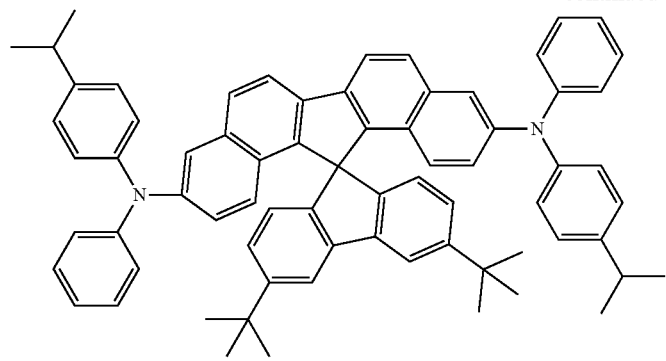
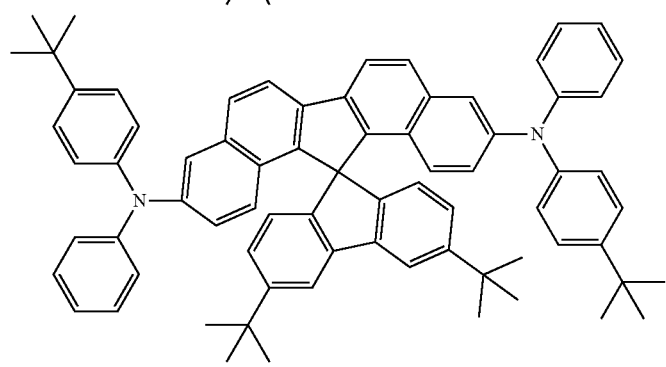
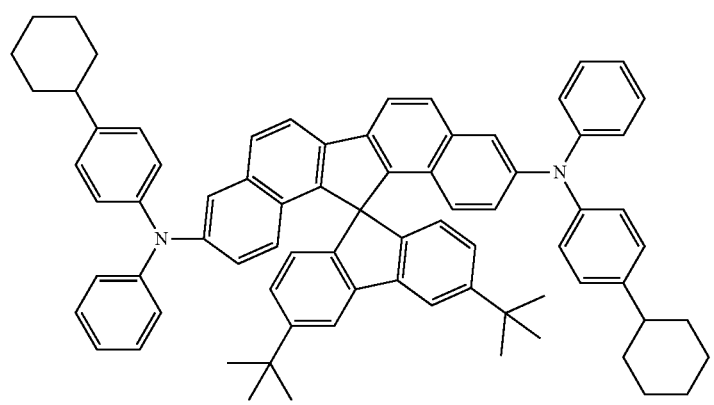
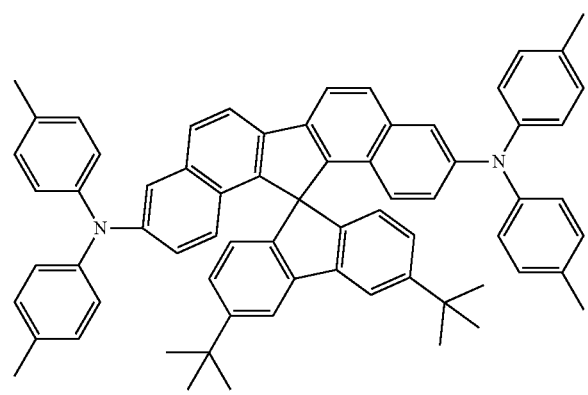
1290

1291
-continued
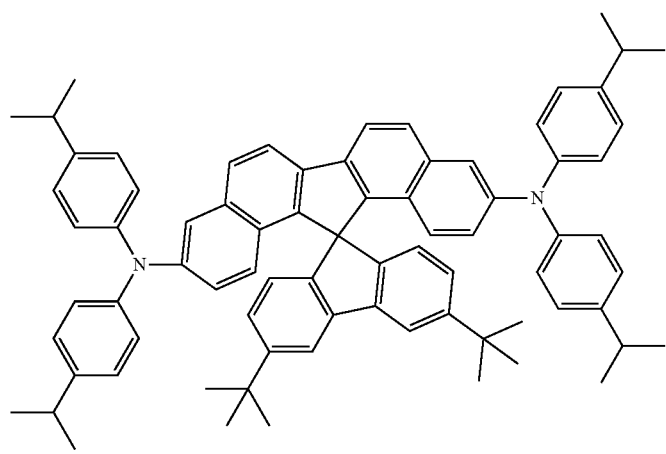
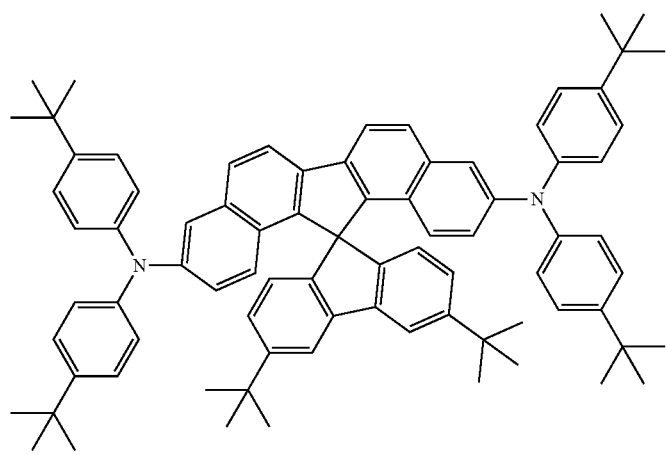
1292
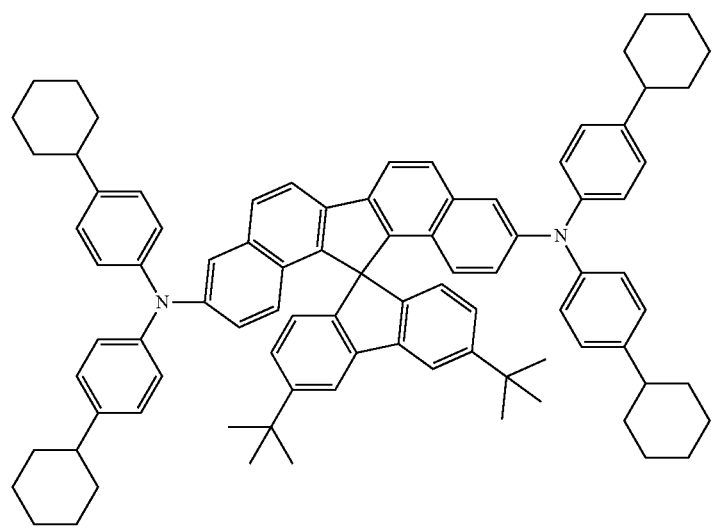

-continued
| 1293 | 1294 |
|---|---|
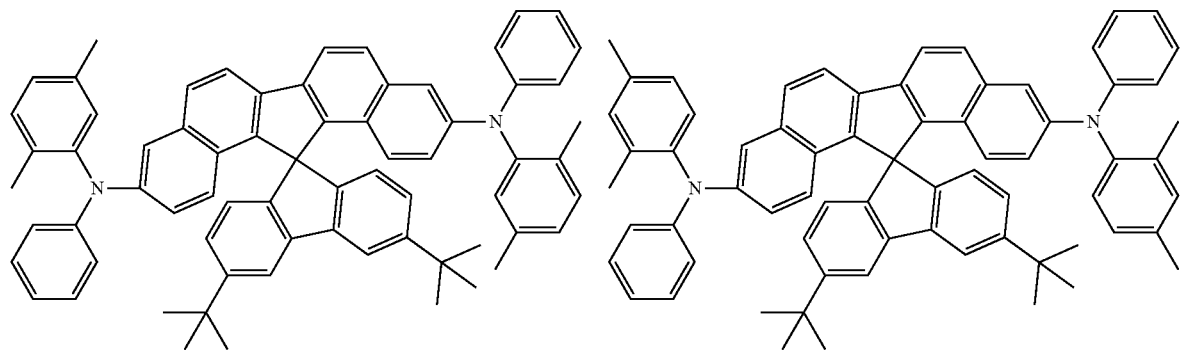
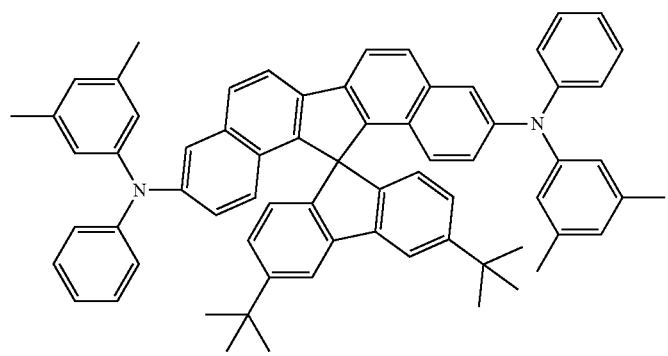
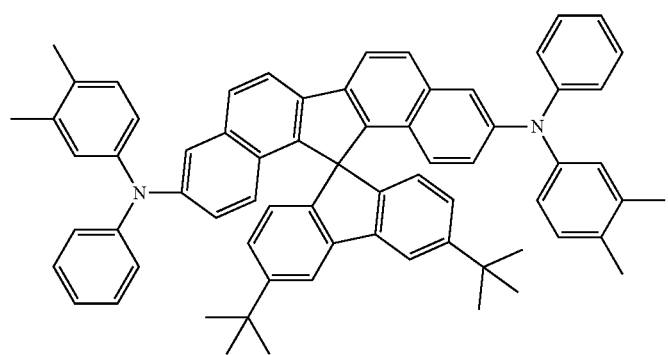
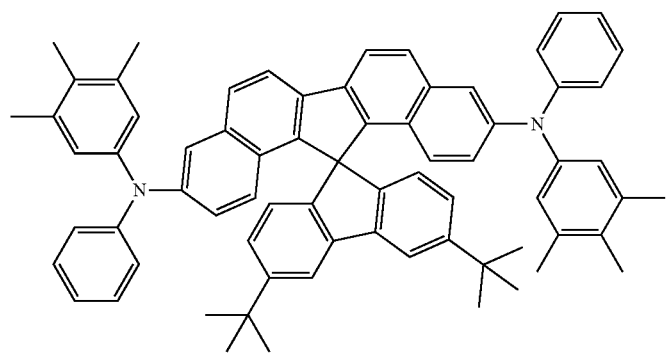

1295                                    1296
-continued
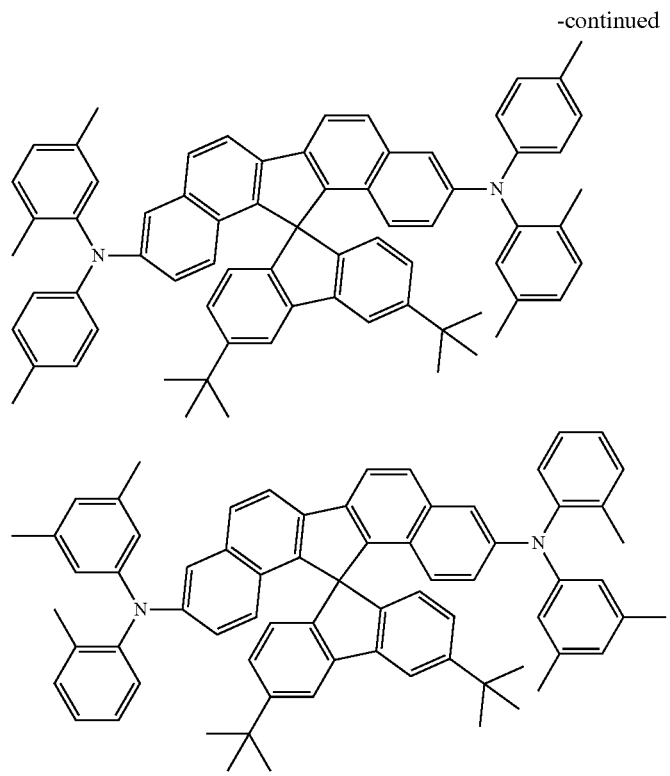
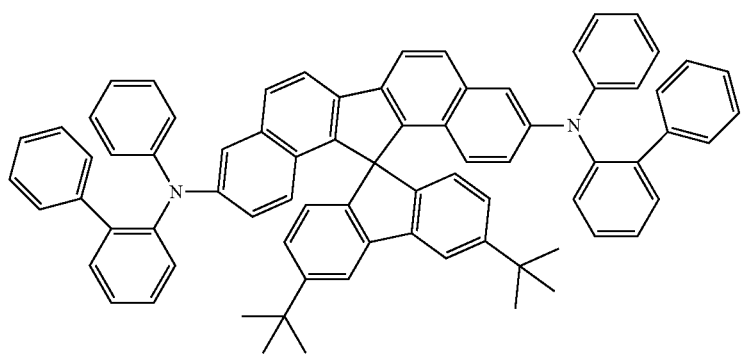
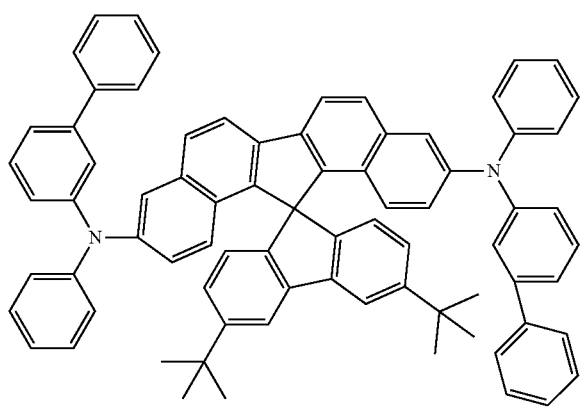

1297
-continued
1298
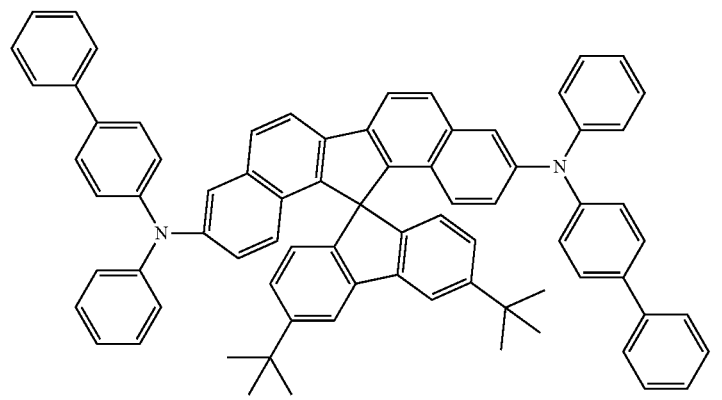
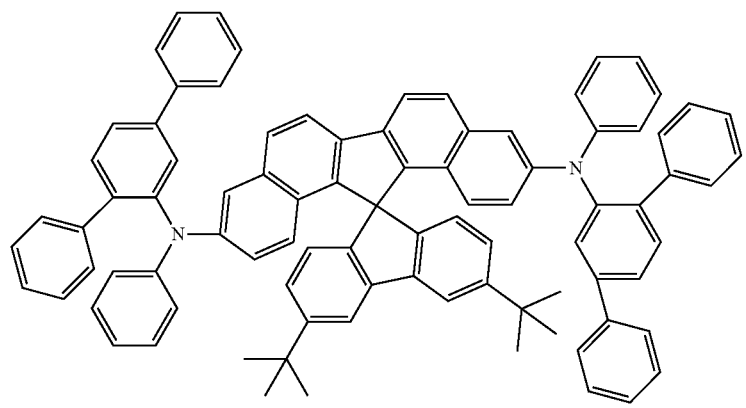
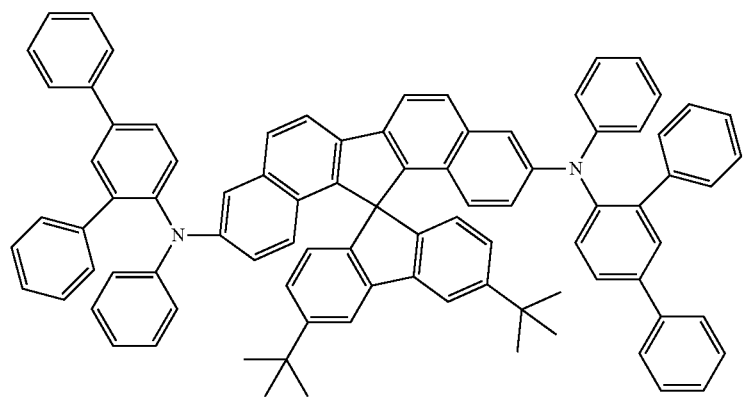
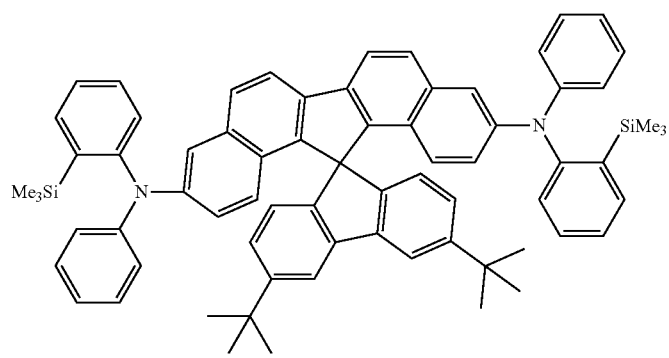

1299 1300
-continued
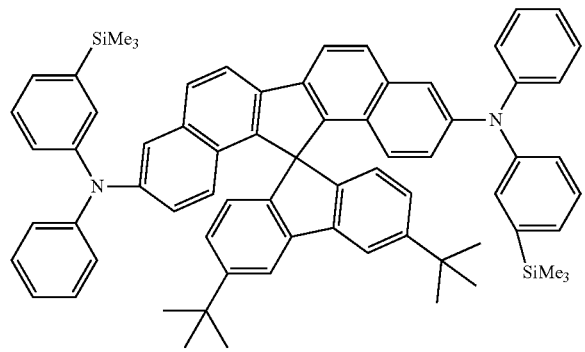
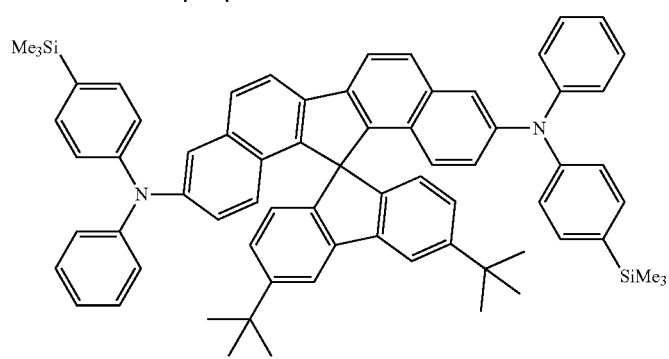
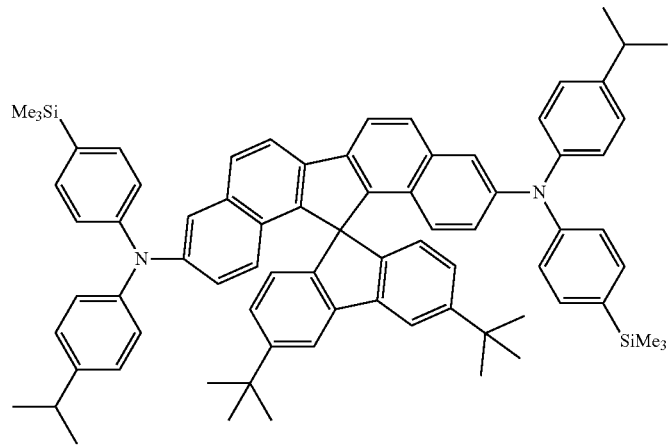
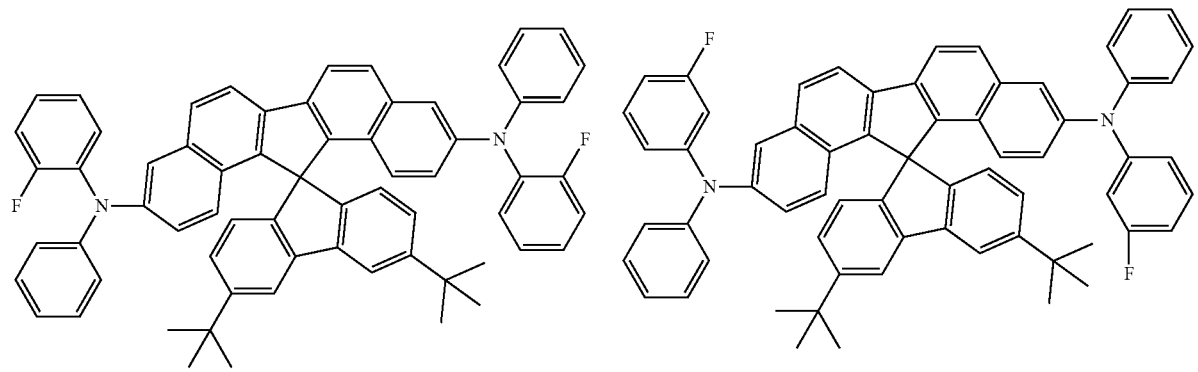

-continued
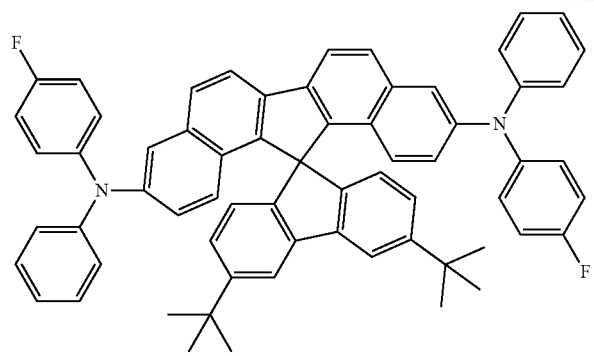
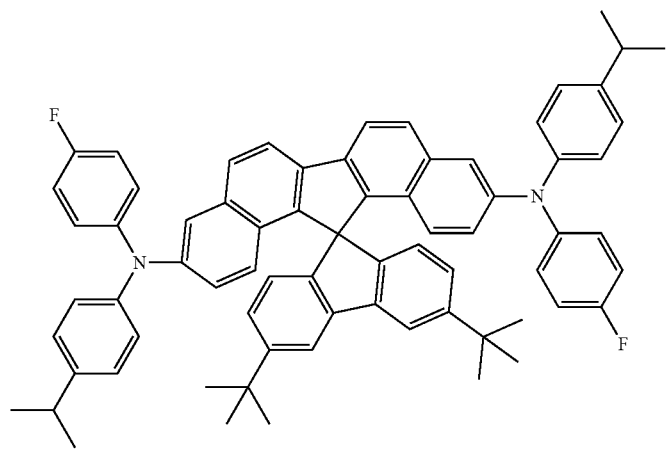
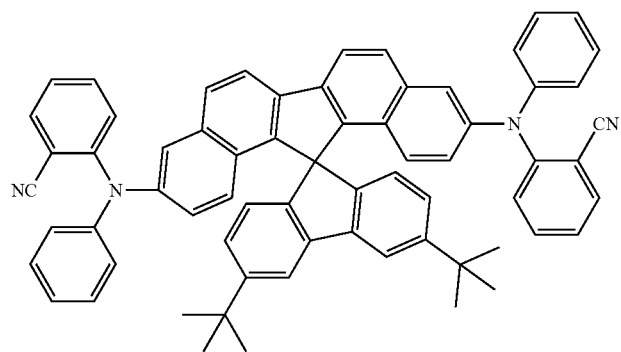
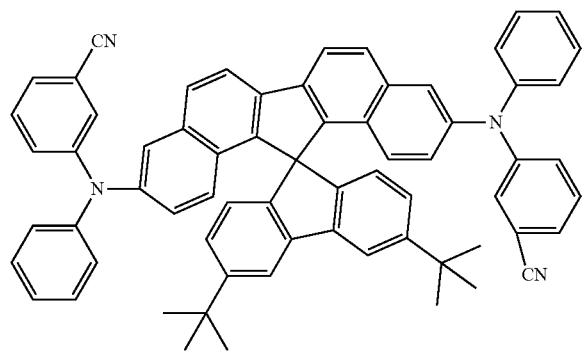

1303
-continued
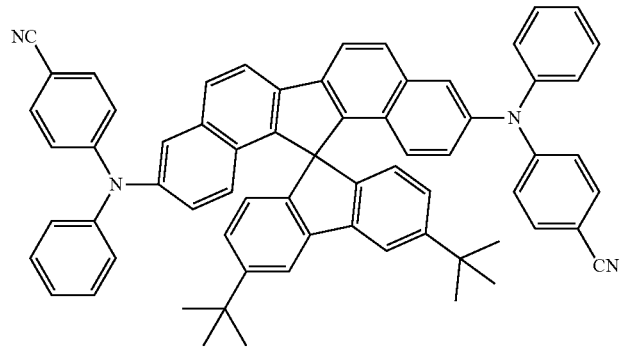
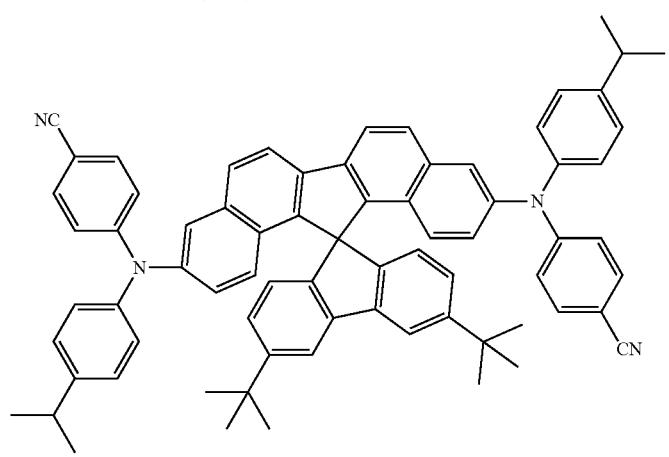
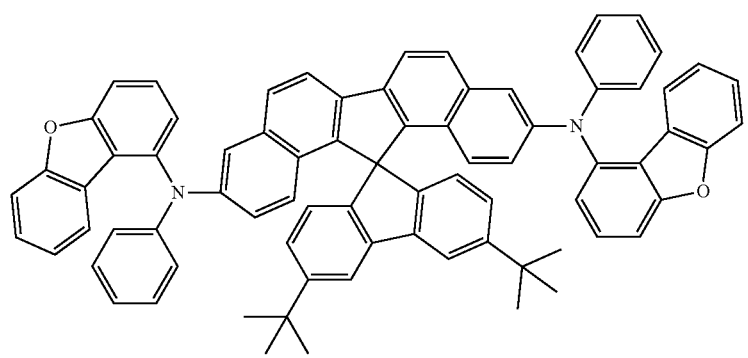
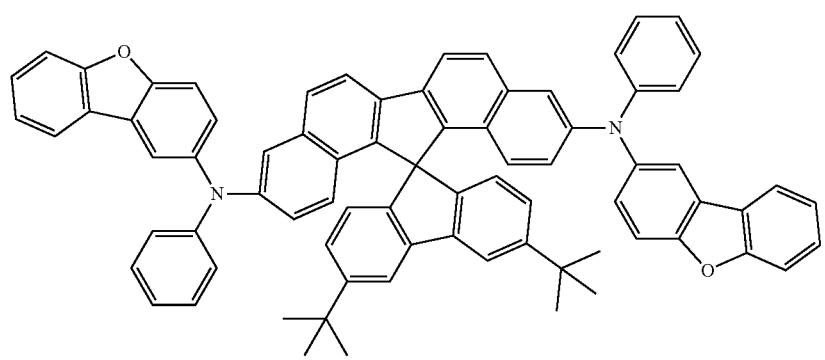
1304

1305
1306
-continued
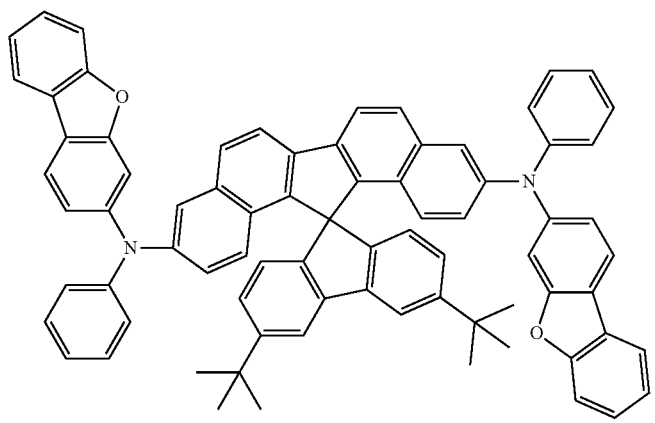
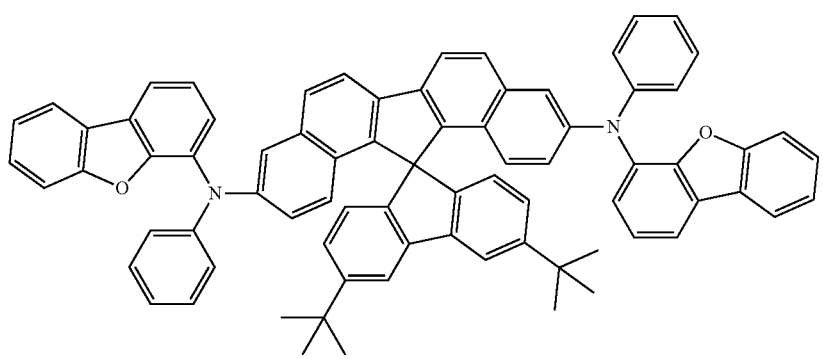
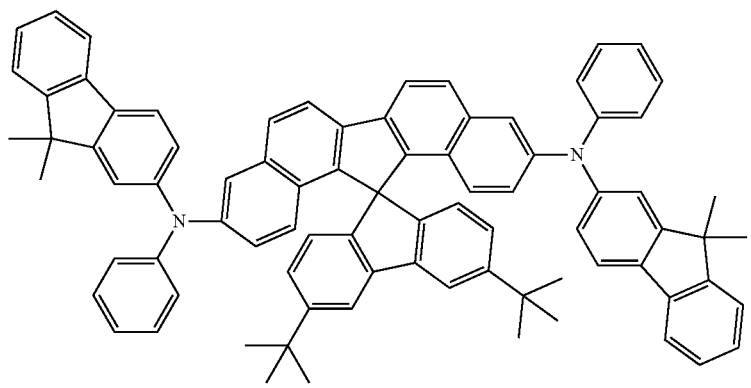
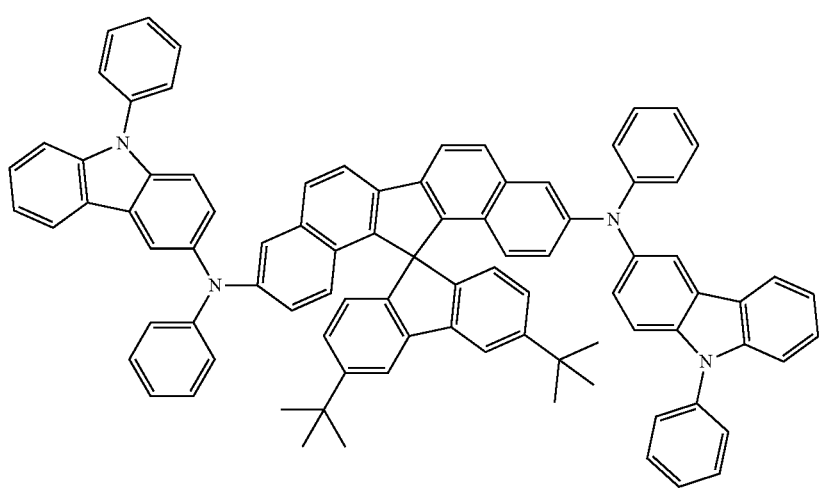

1307
1308
-continued
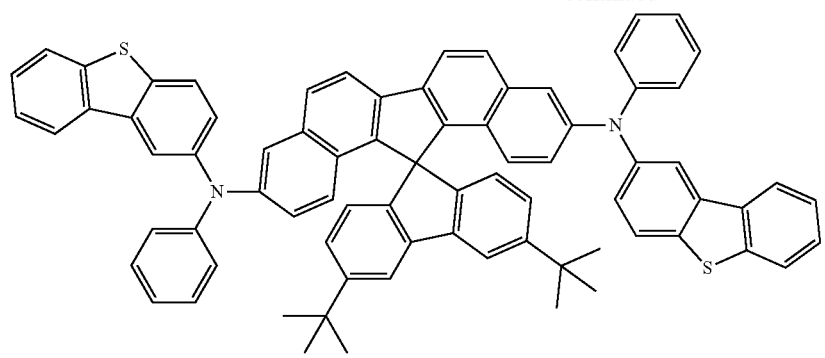
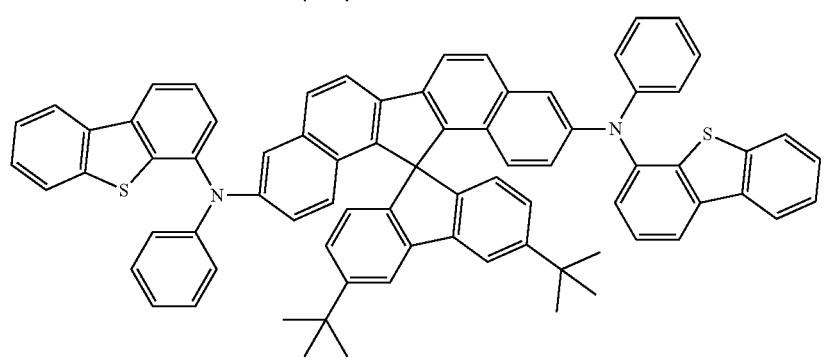
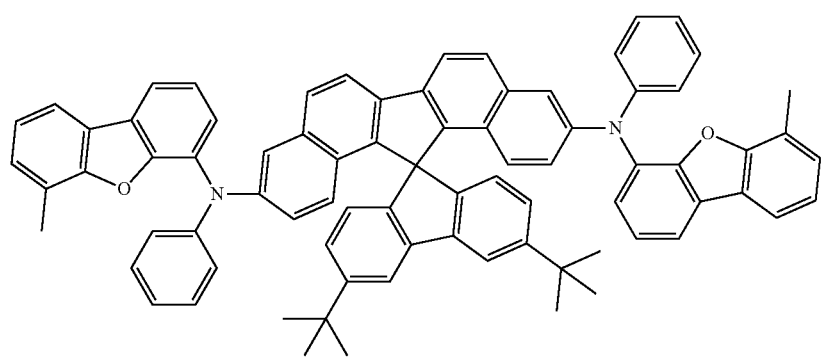
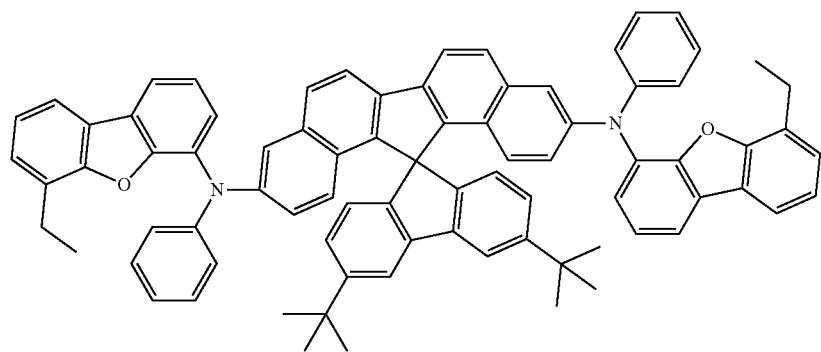

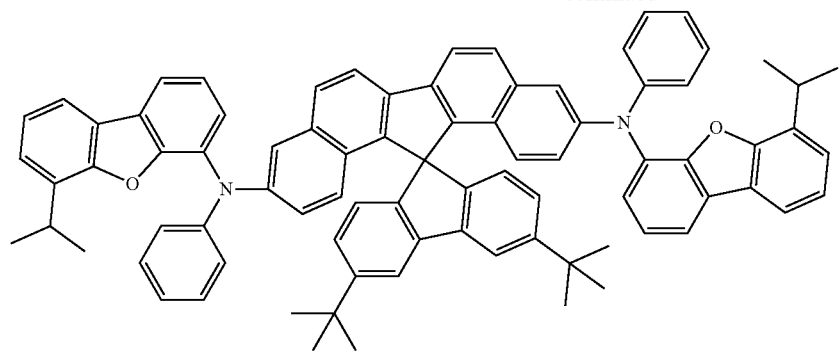
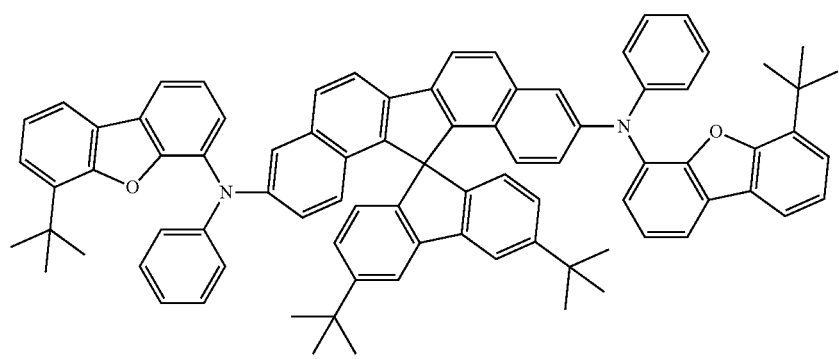
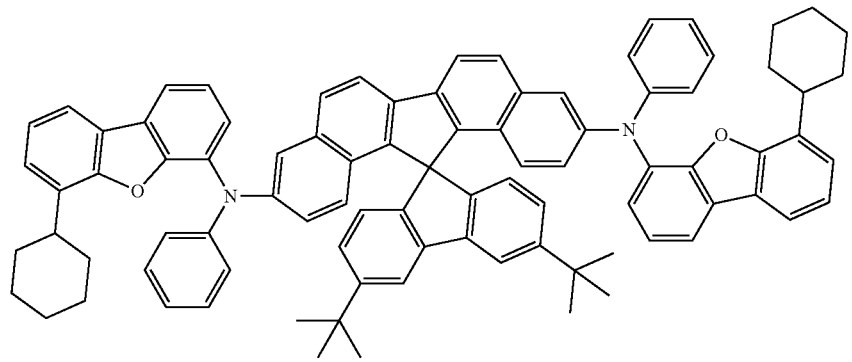
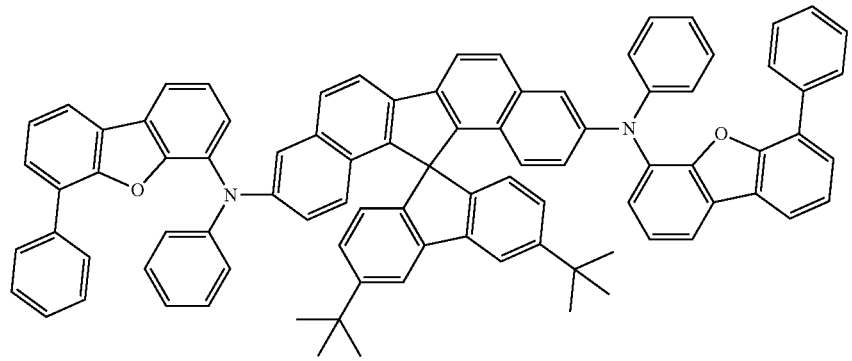

-continued
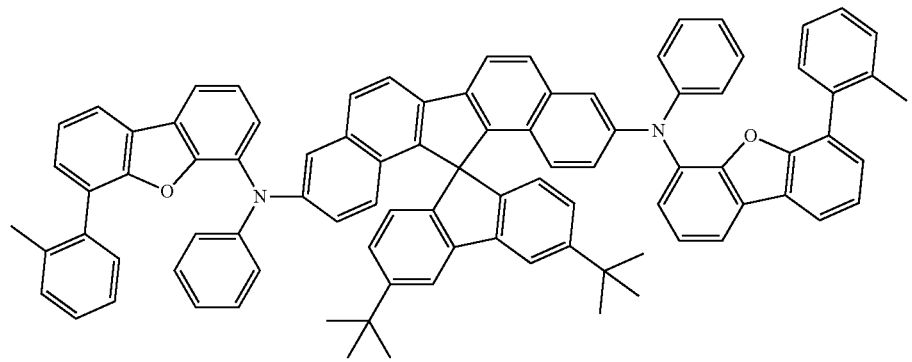
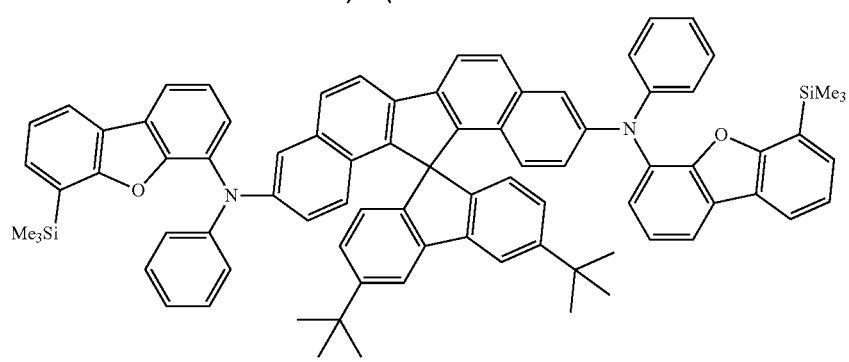
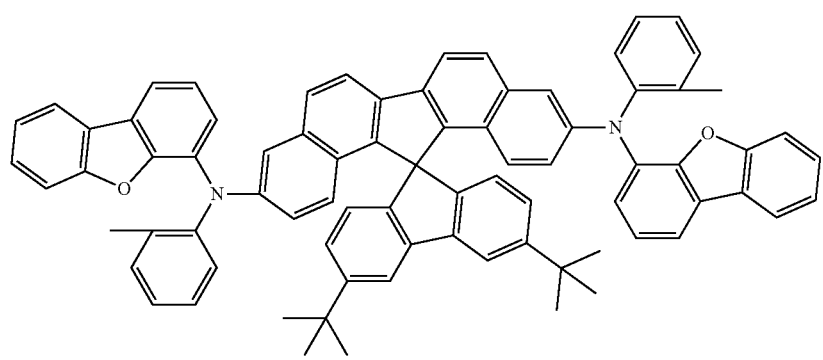
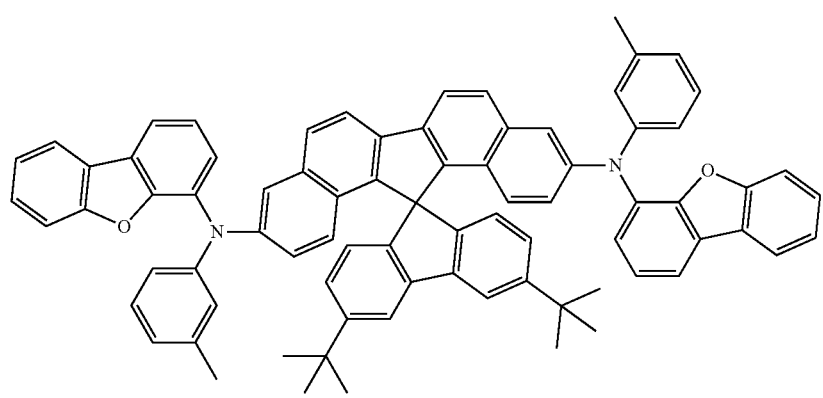

1313
1314
-continued
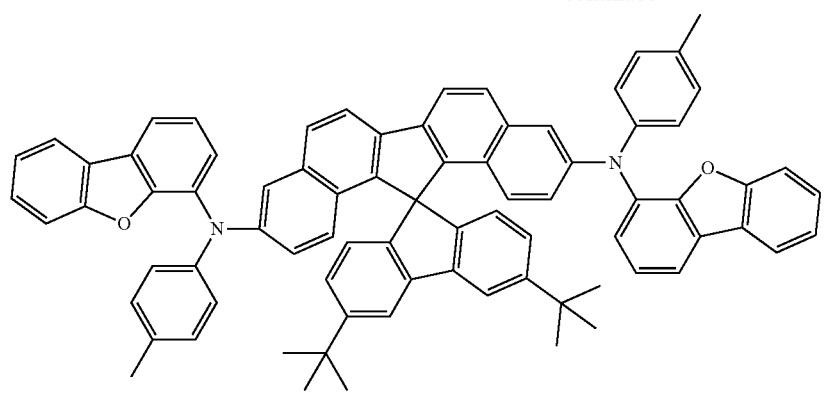
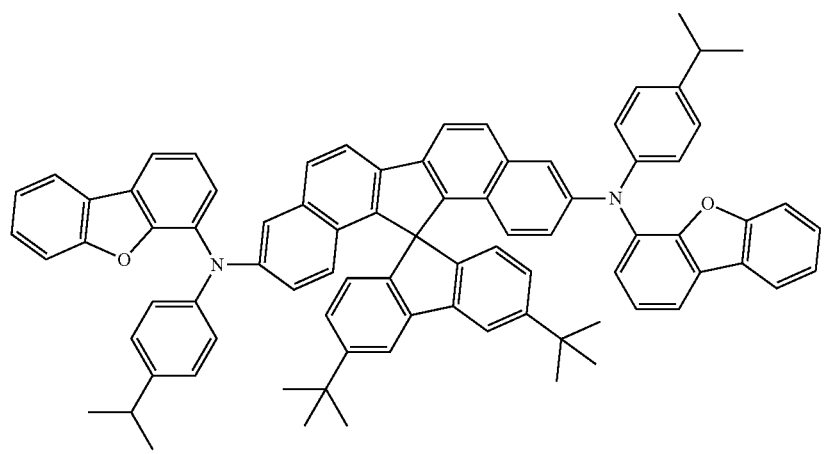
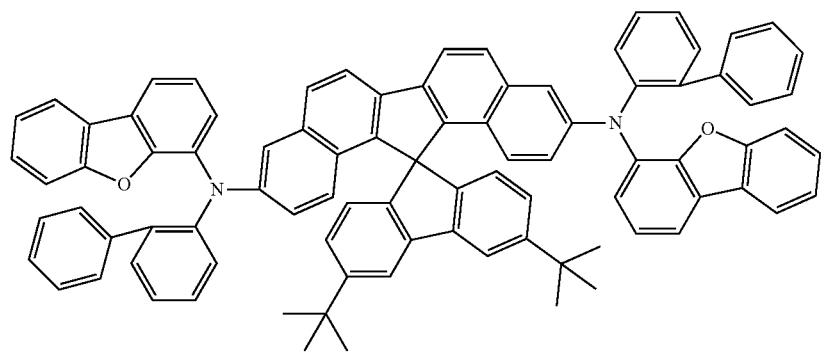
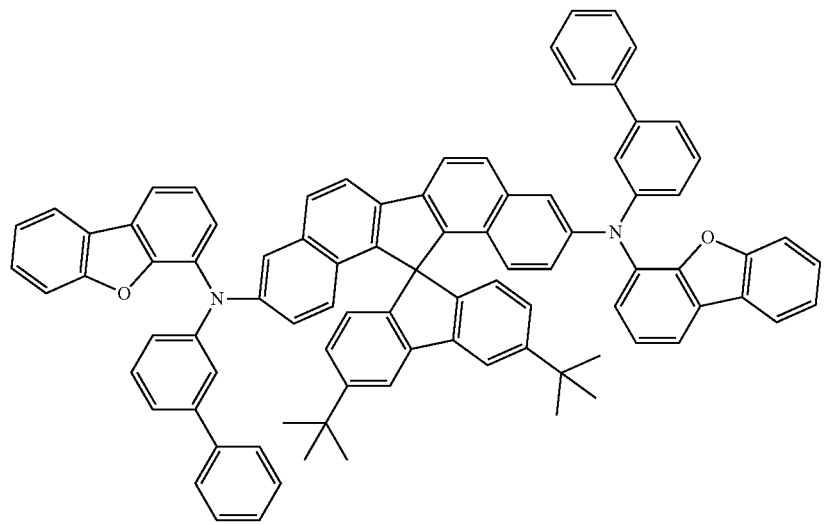

1315
1316
-continued
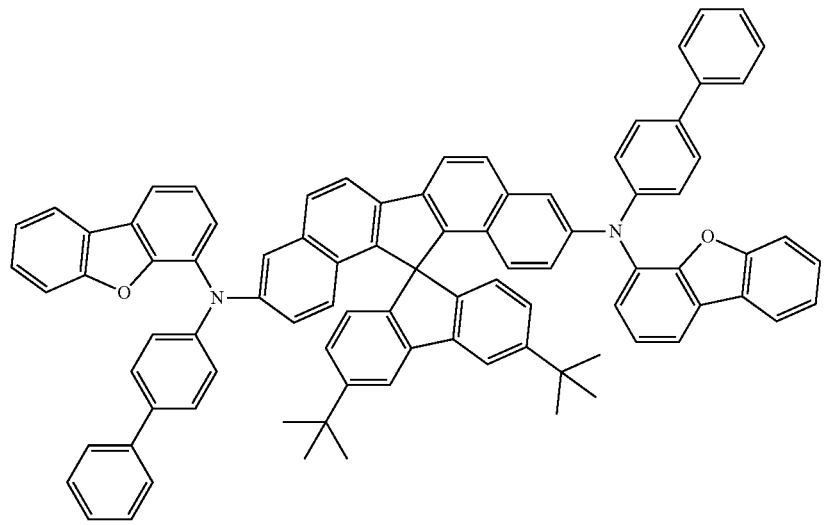
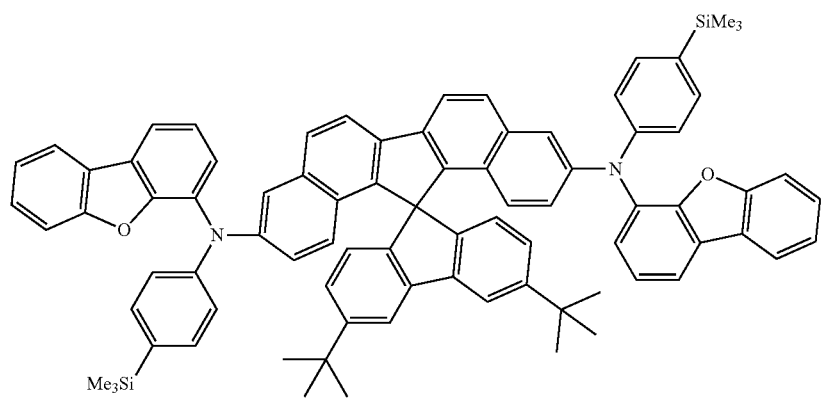
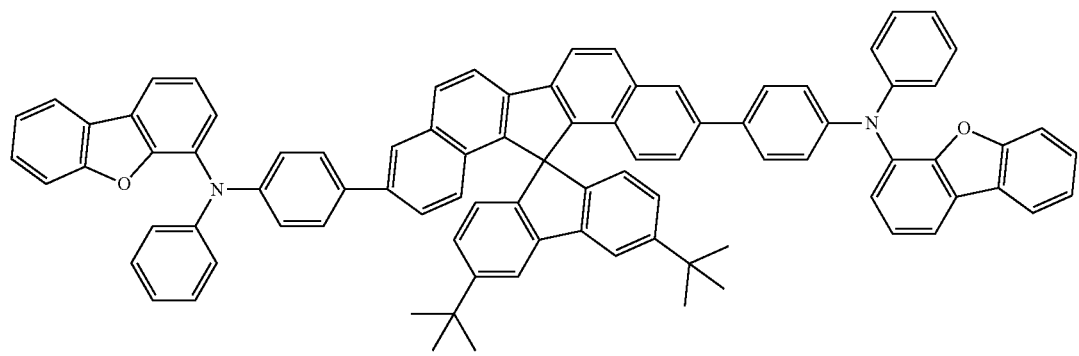
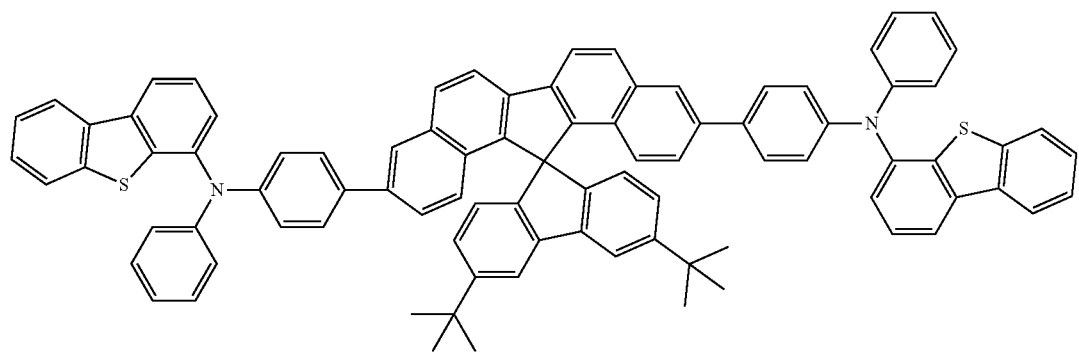

1317 1318
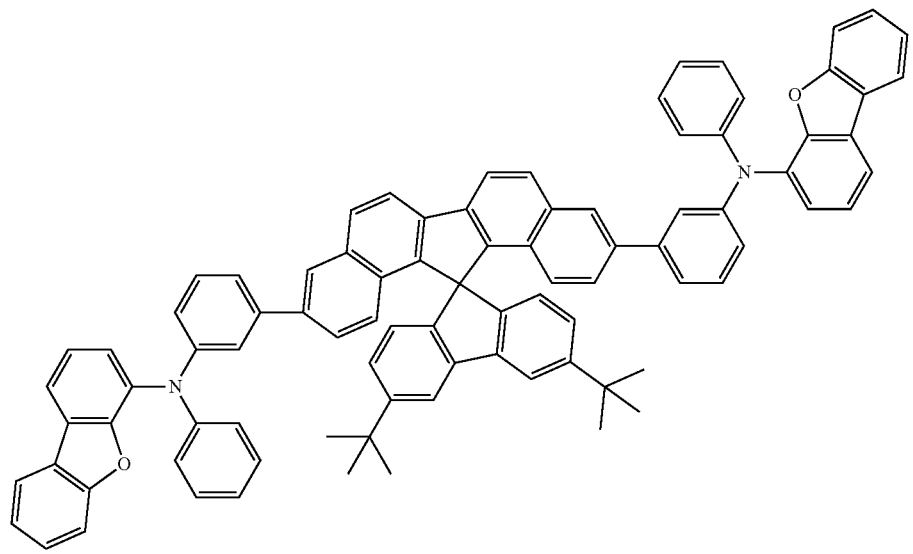
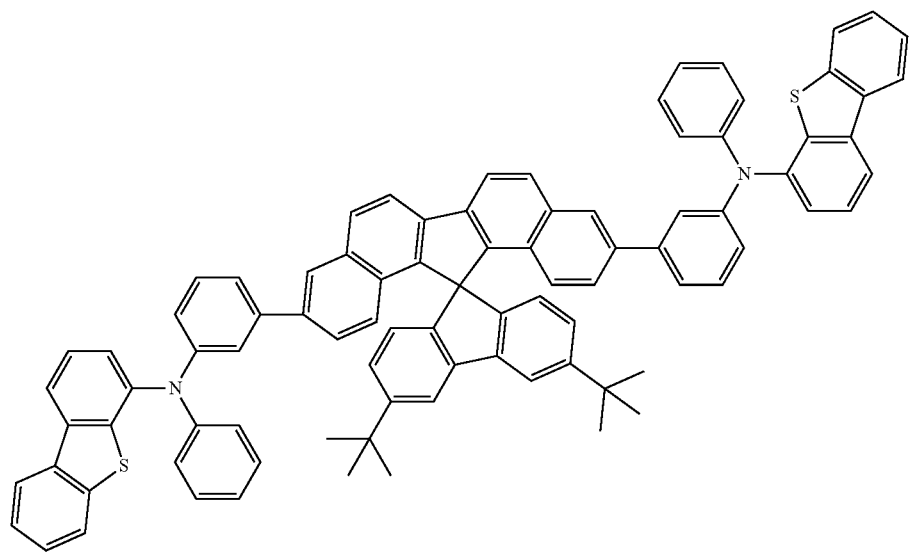
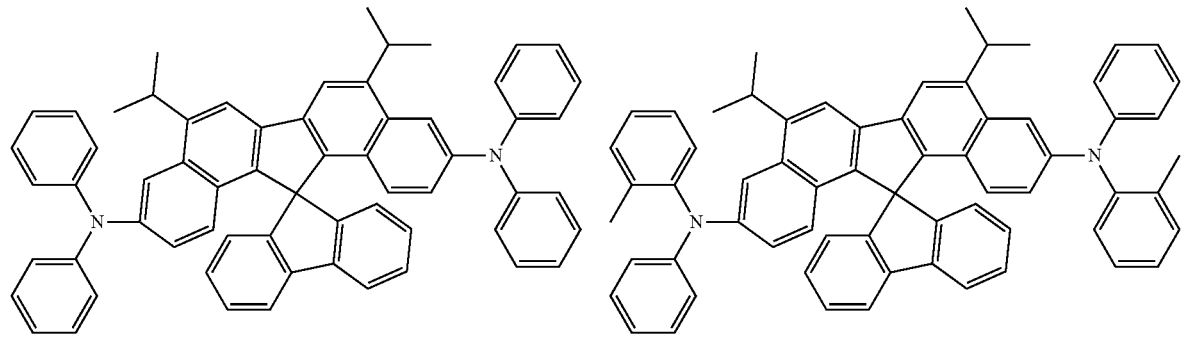

1319 1320
-continued
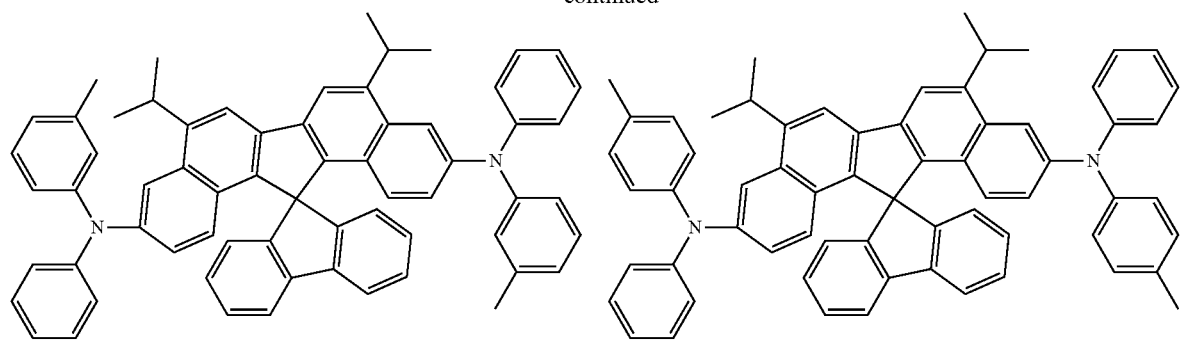
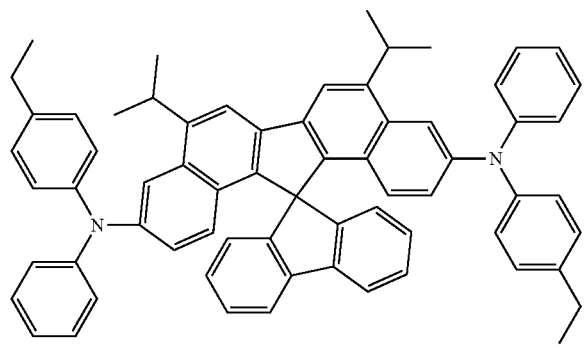
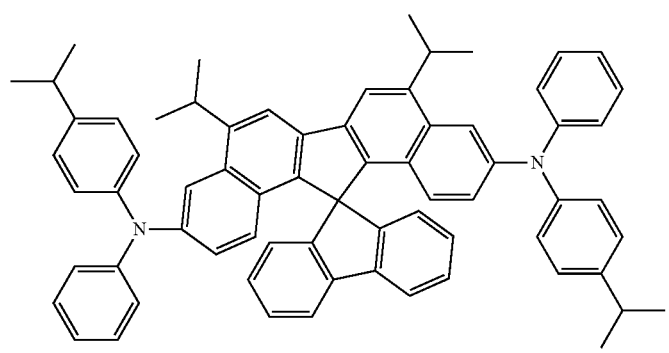
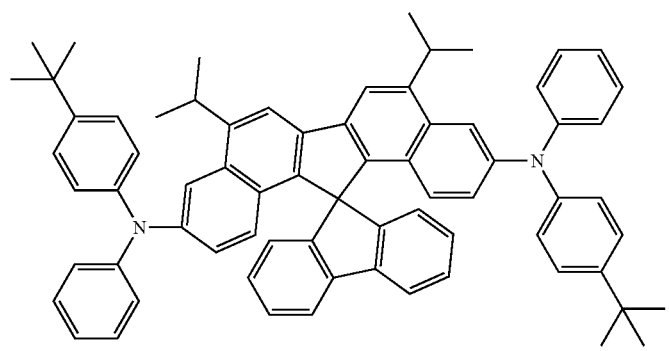

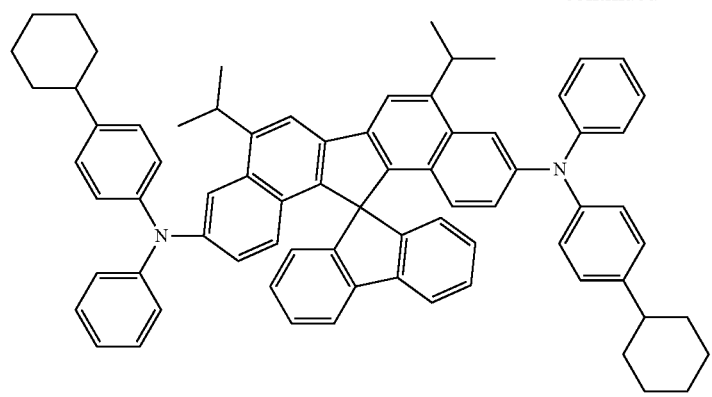
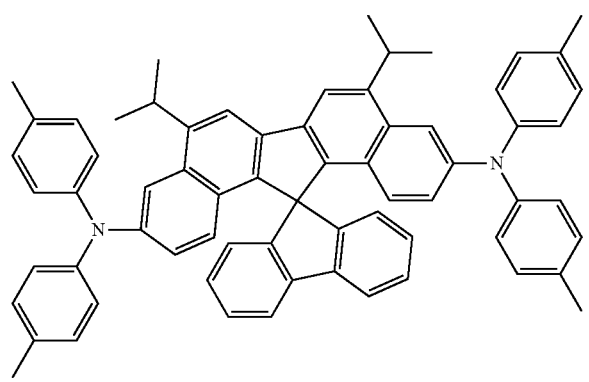
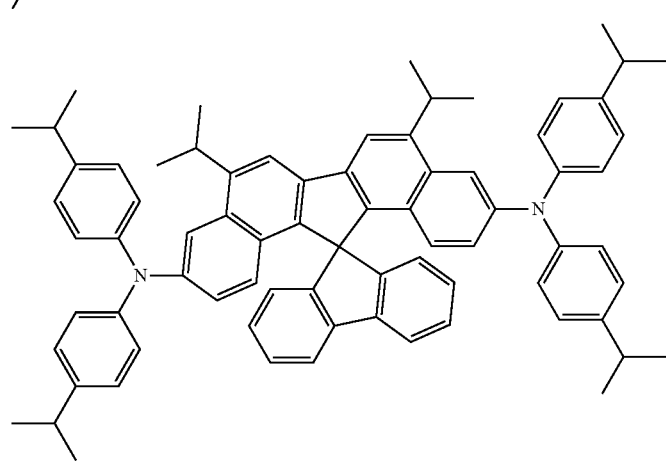
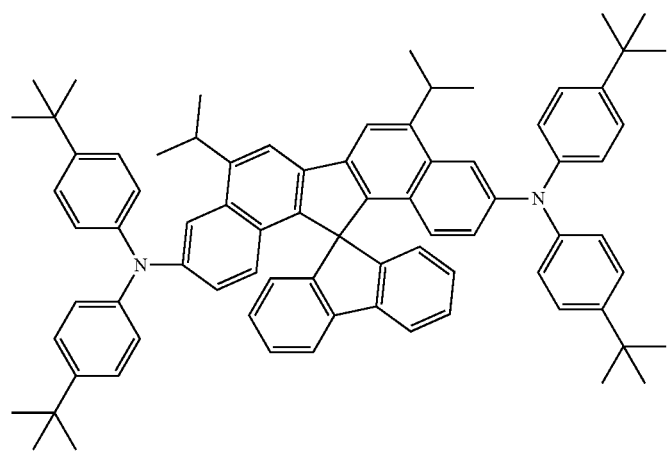

-continued
1323
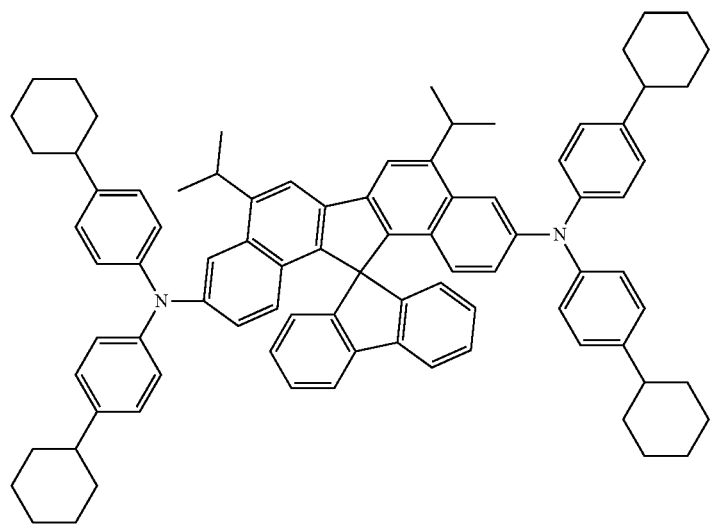
1324
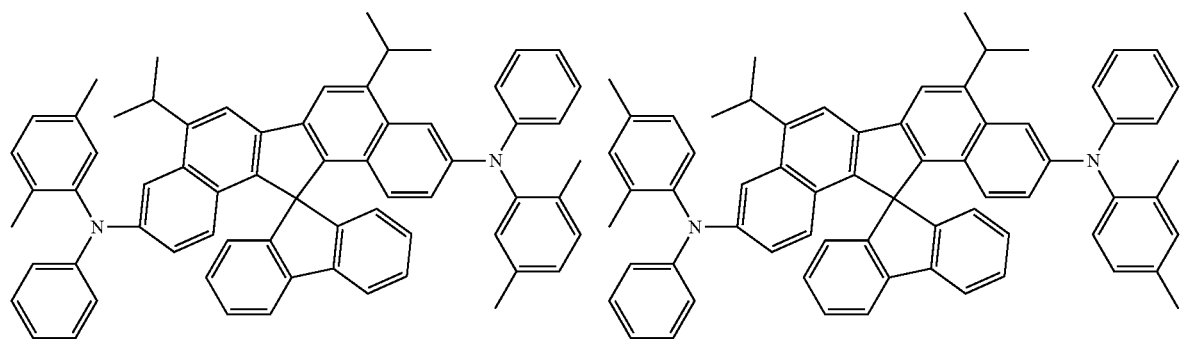
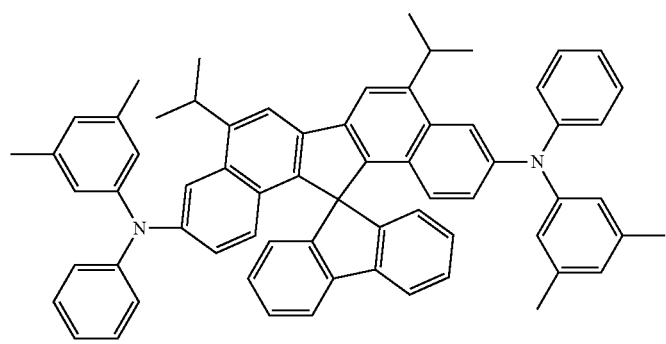
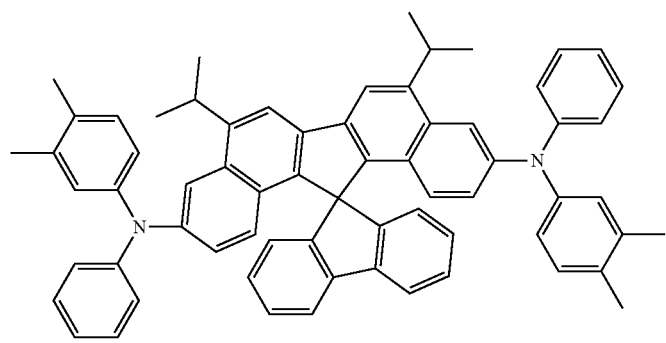

1325  1326
-continued
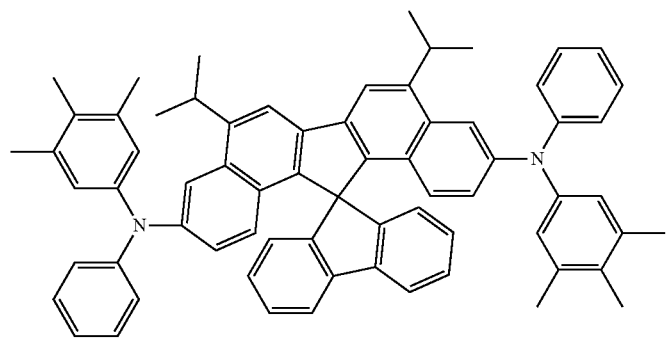
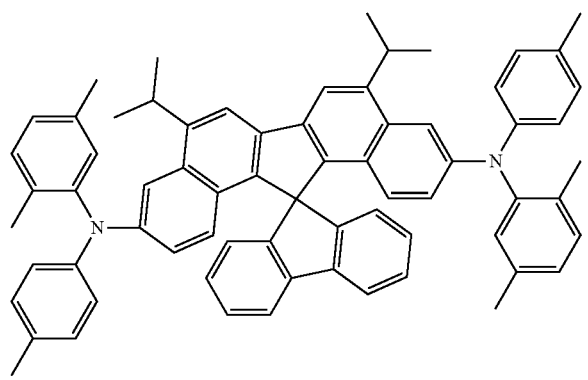
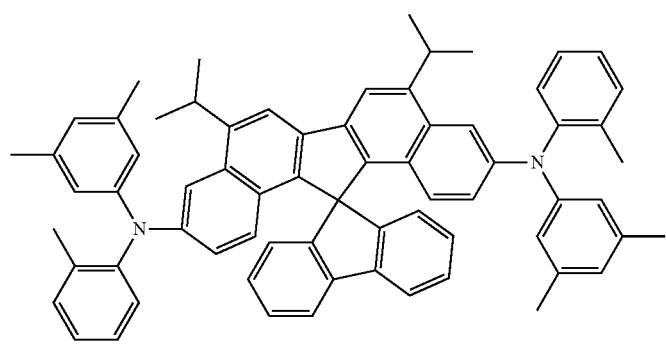
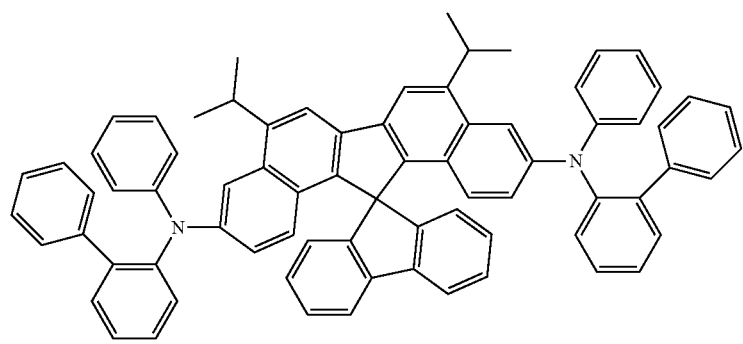

-continued
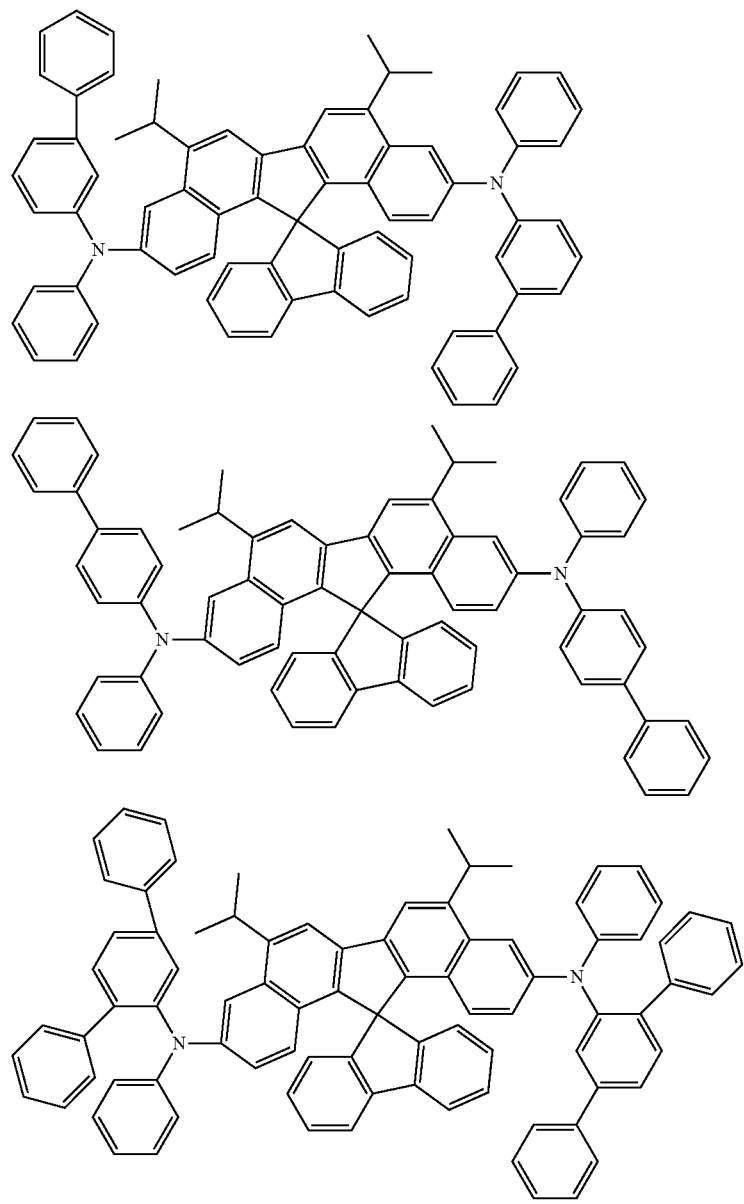
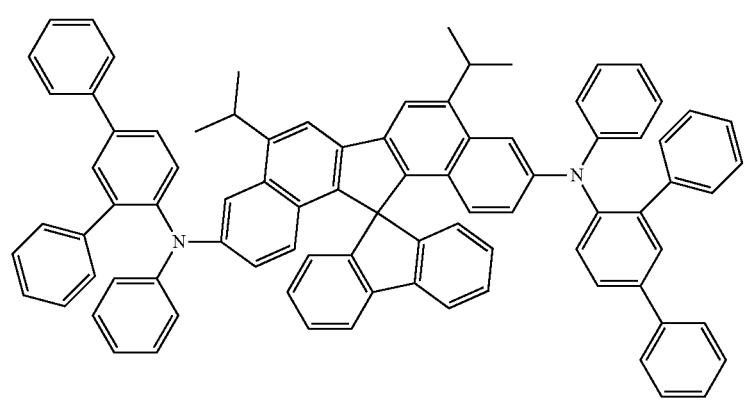

-continued
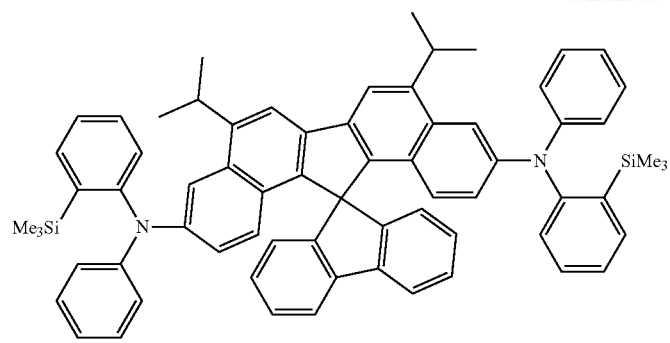
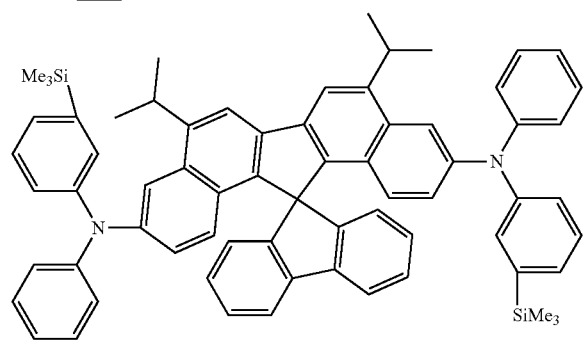
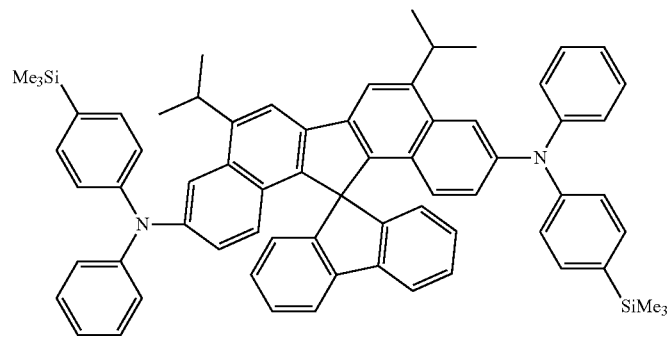
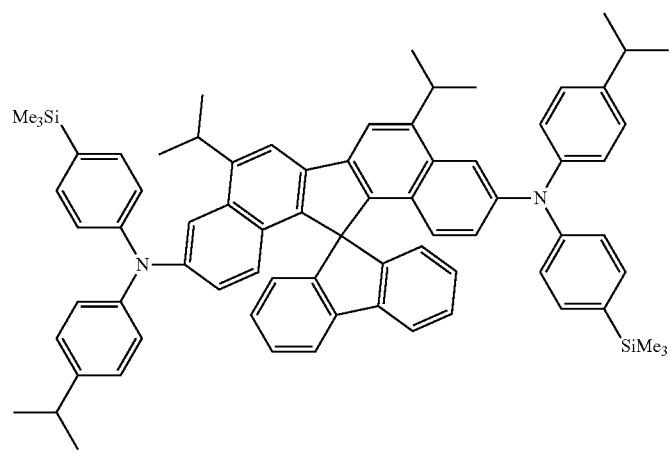

1331 1332
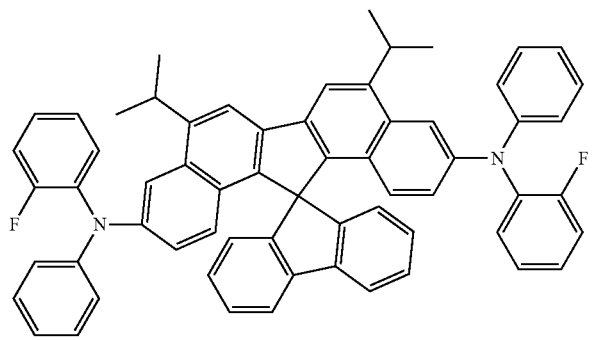
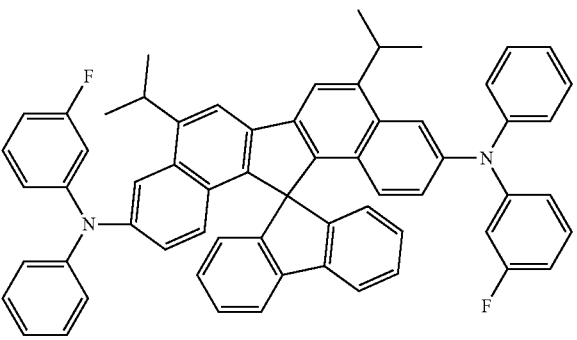
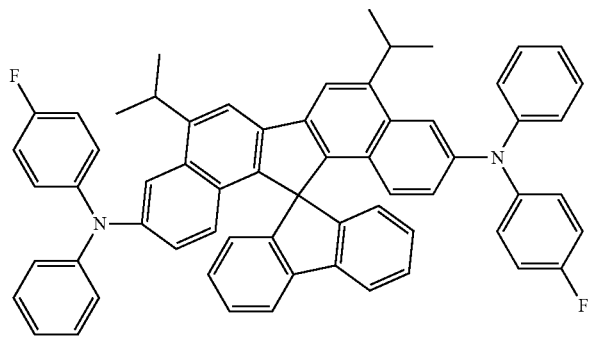
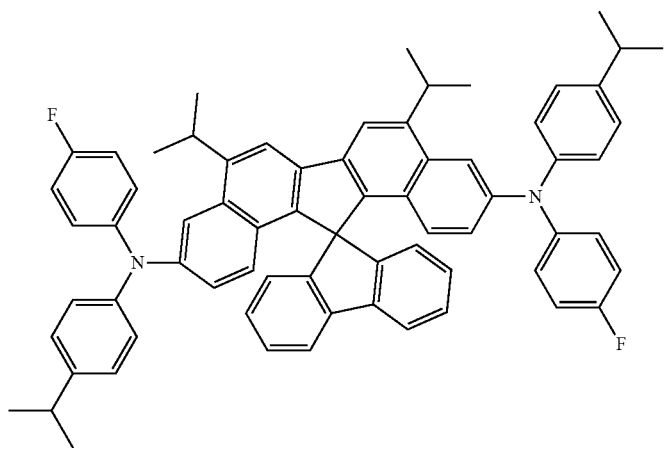
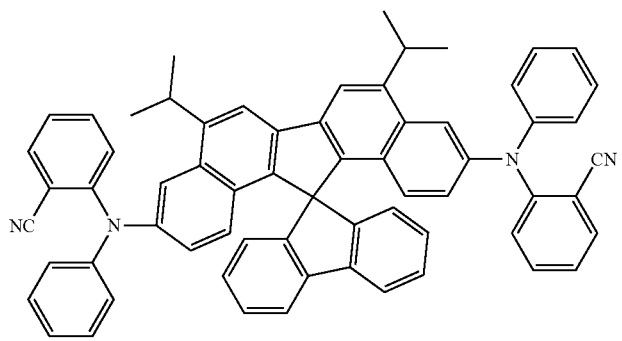

1333 1334
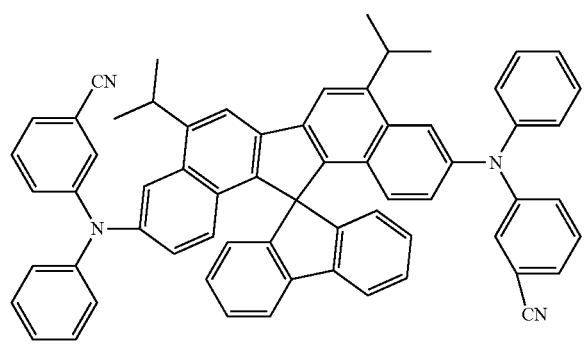
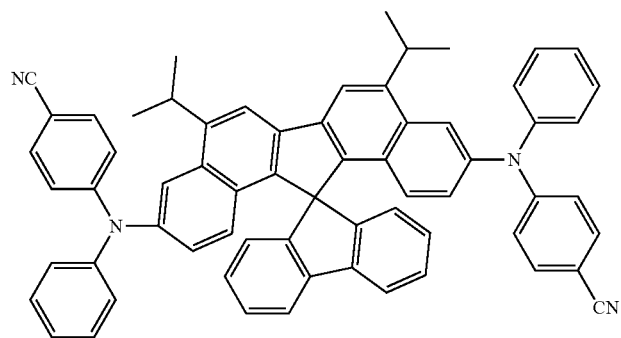
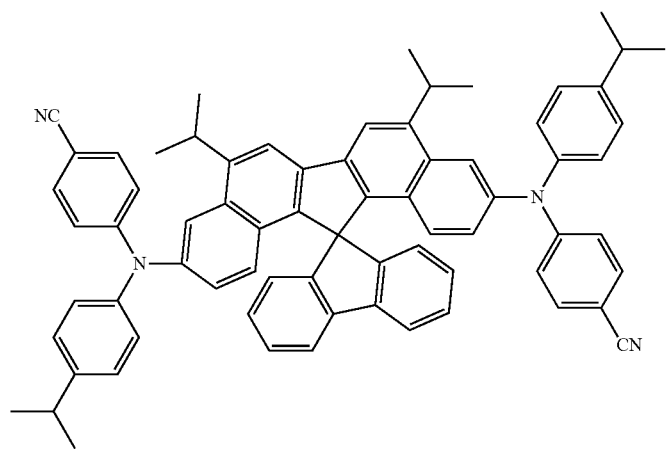
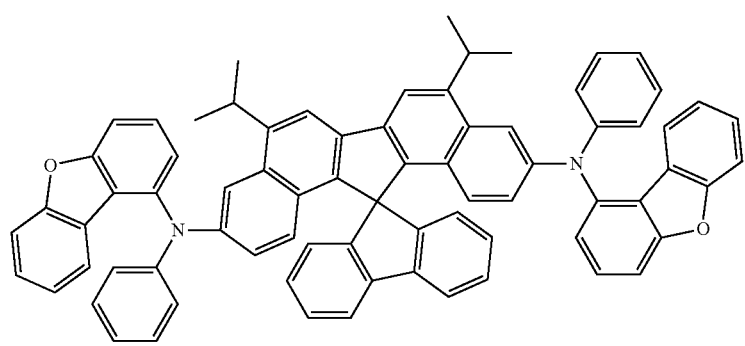

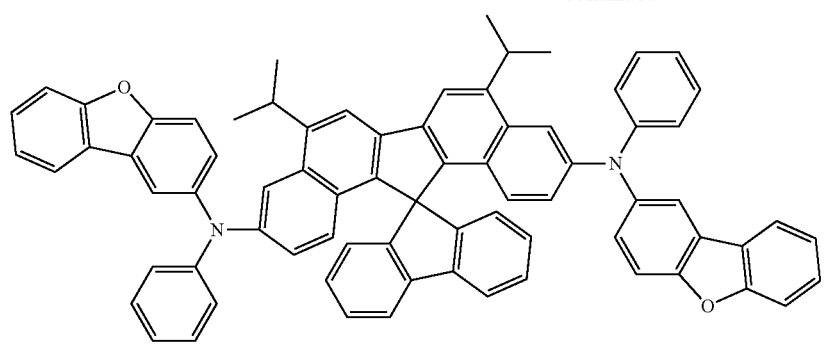
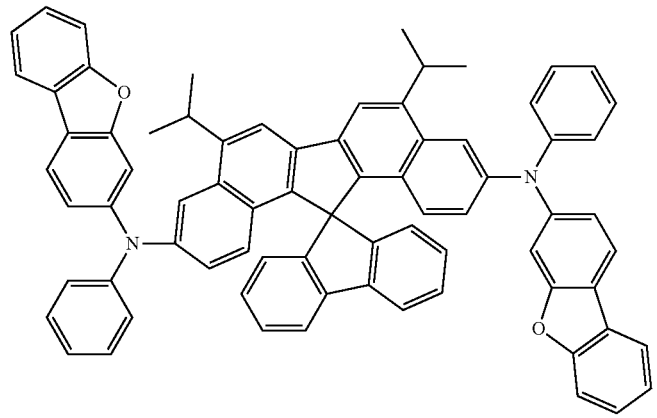
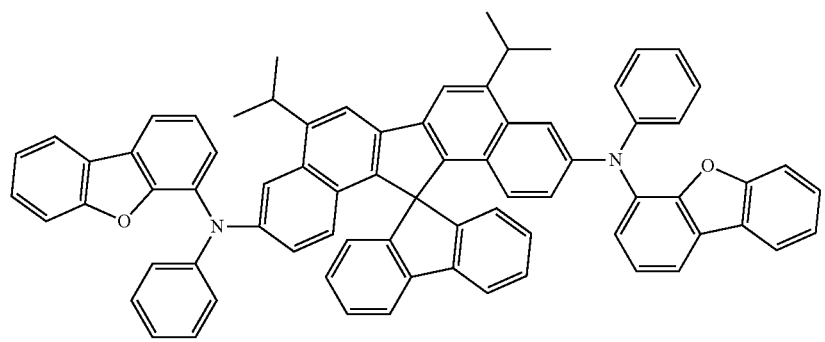
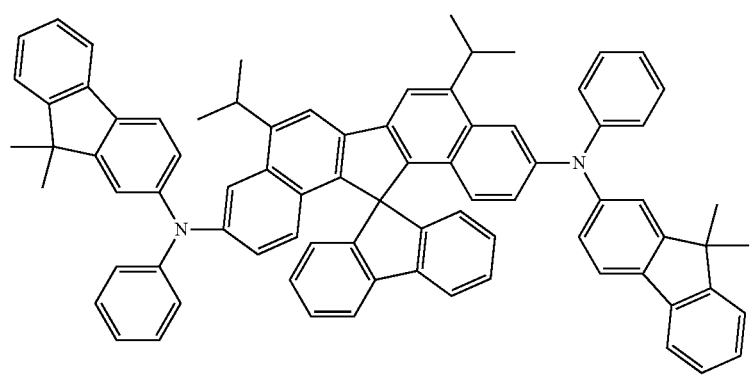

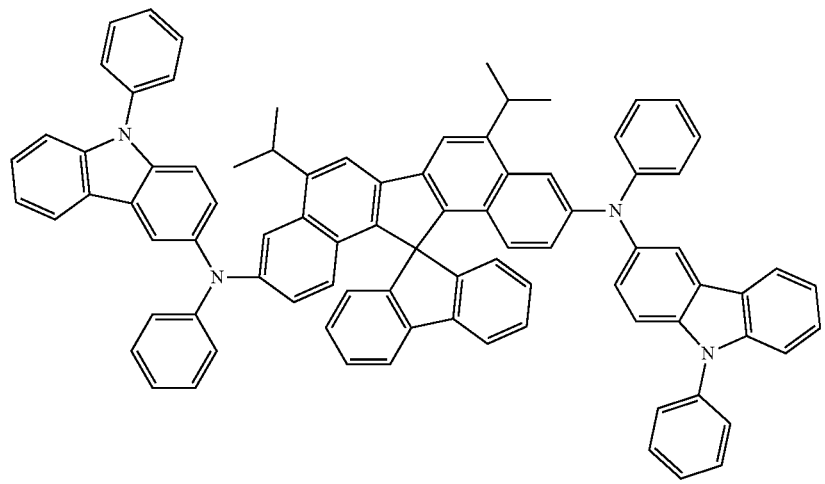
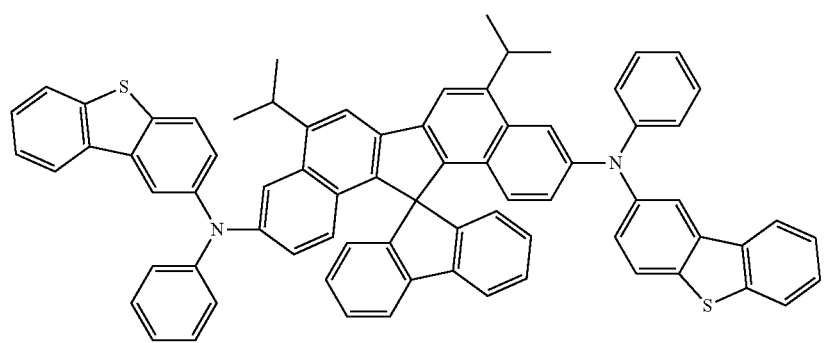
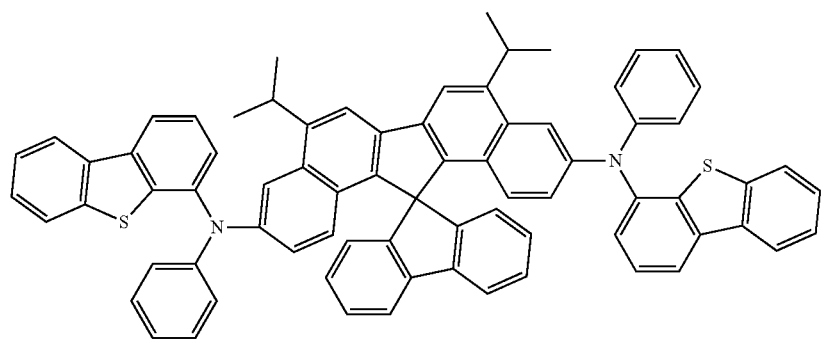
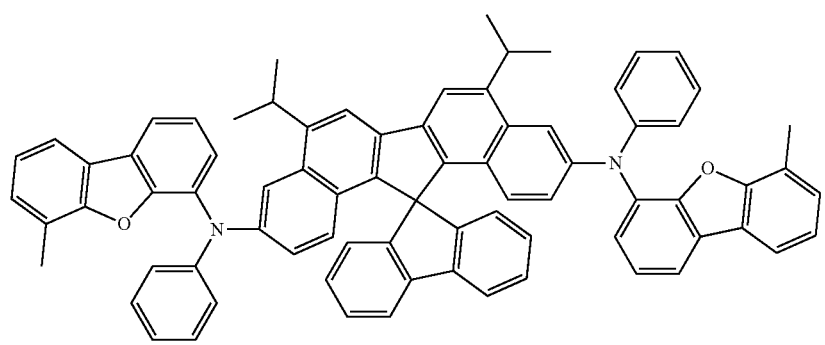

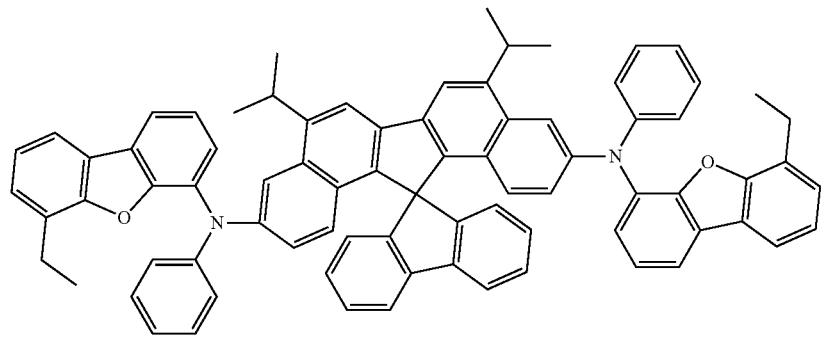
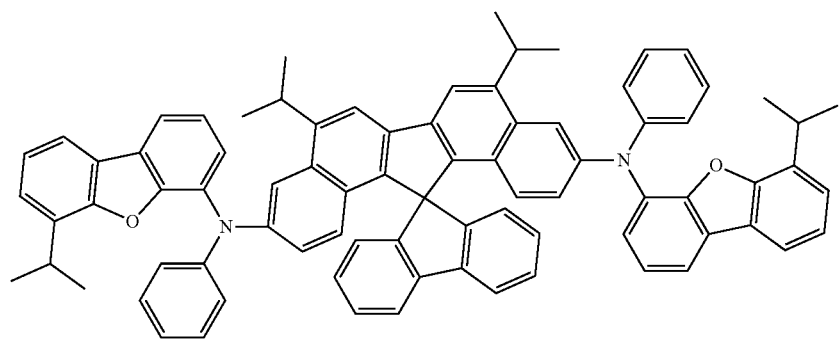
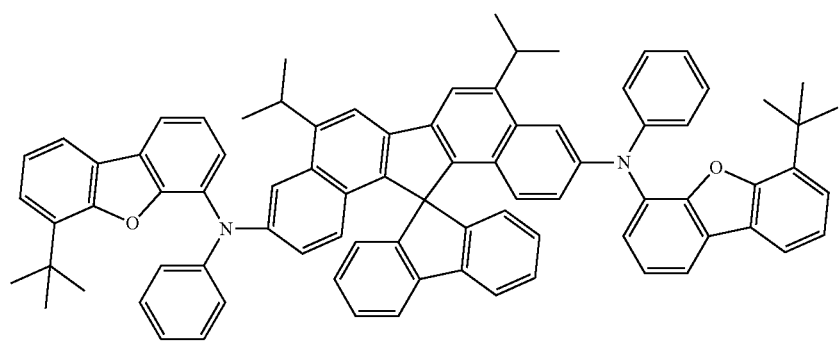
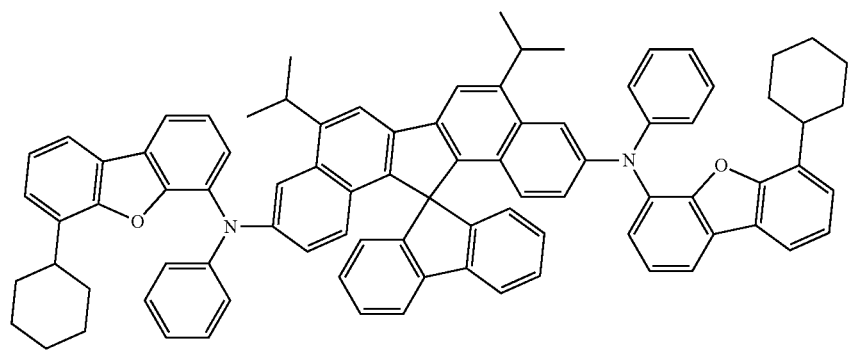
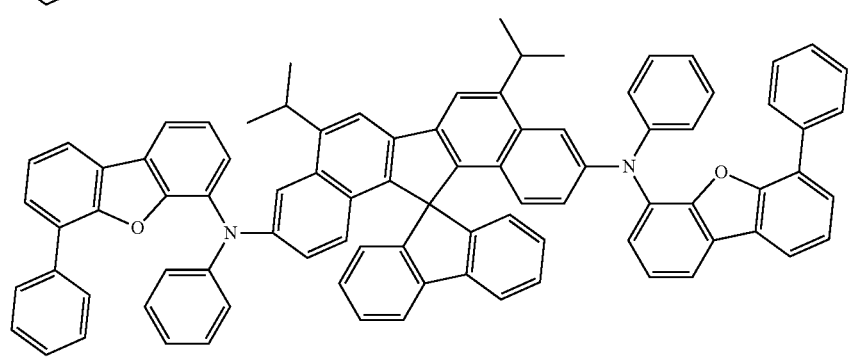

-continued
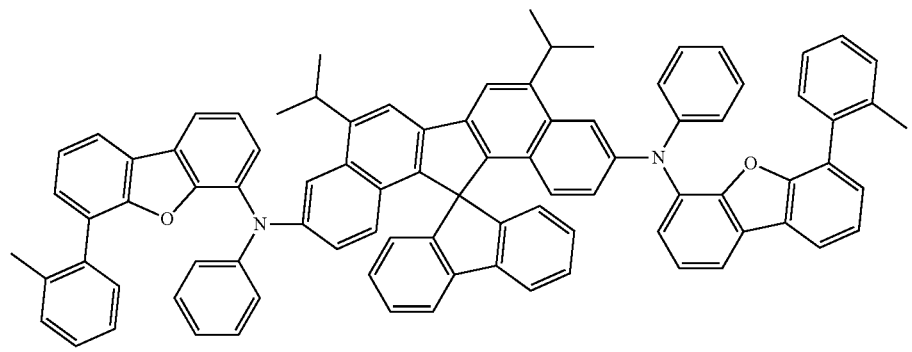
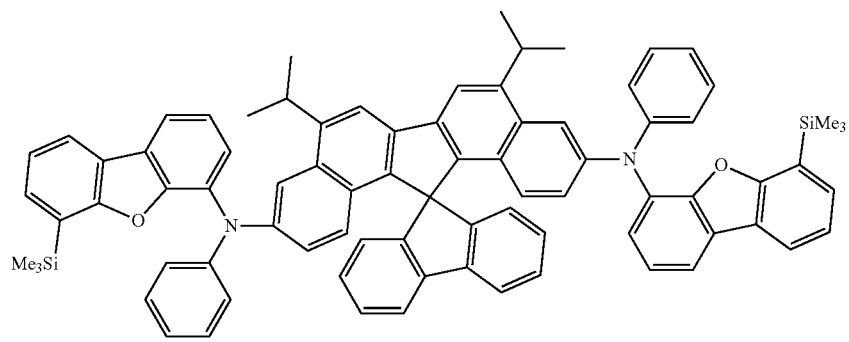
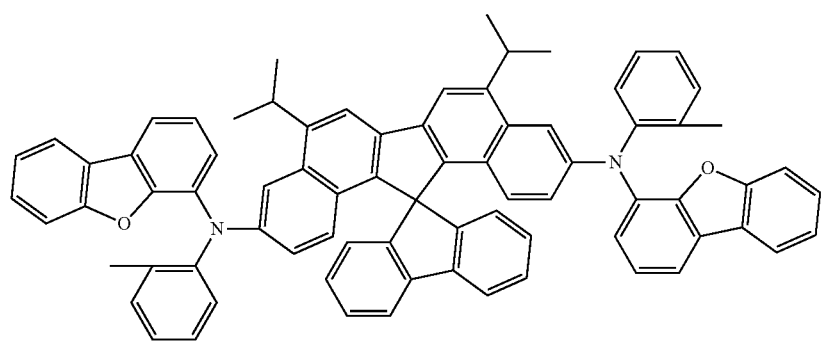
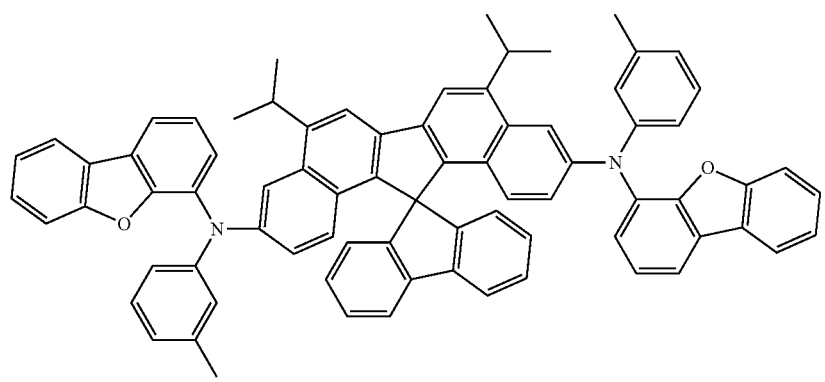

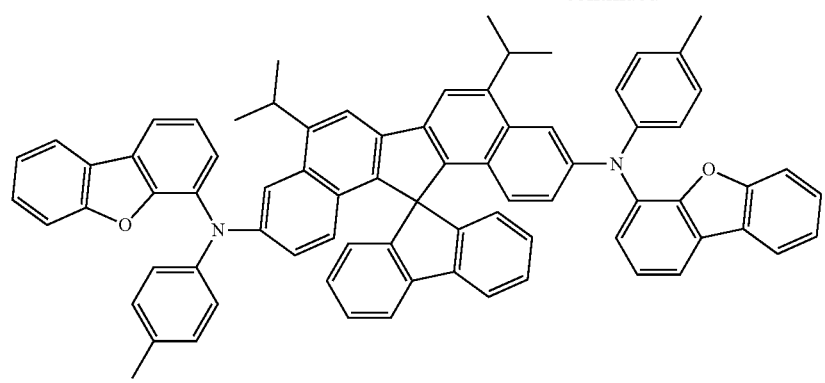
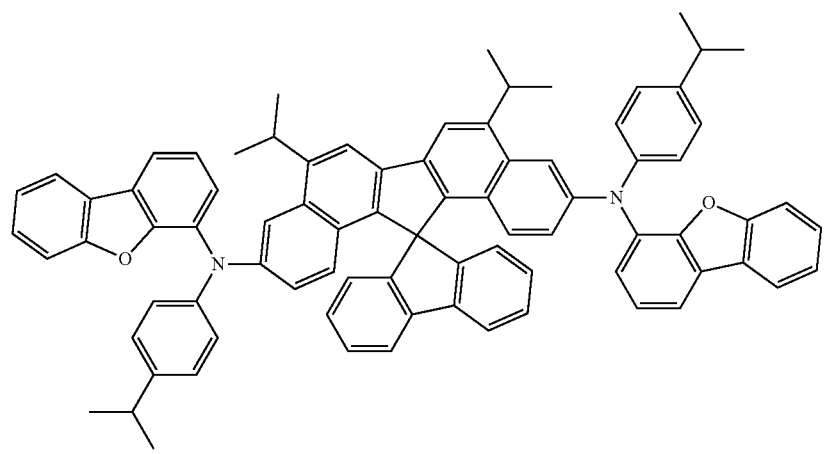
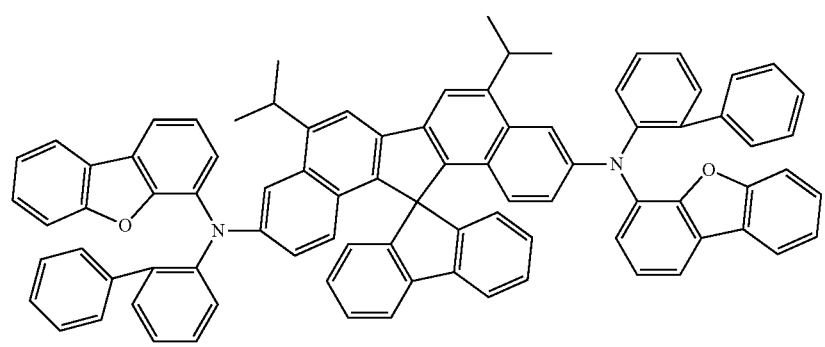
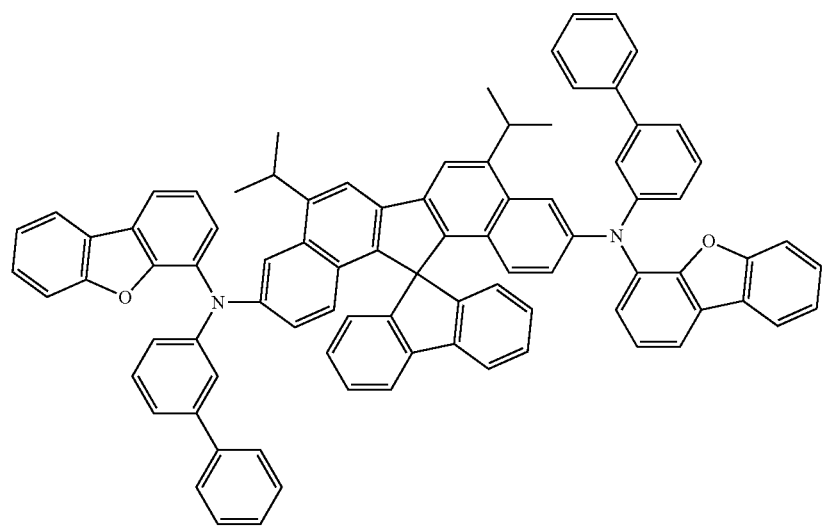

1345
-continued
1346
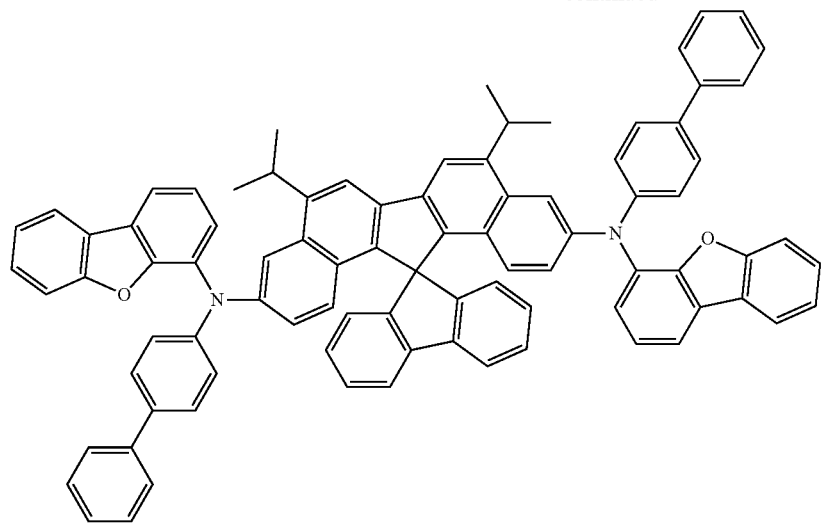
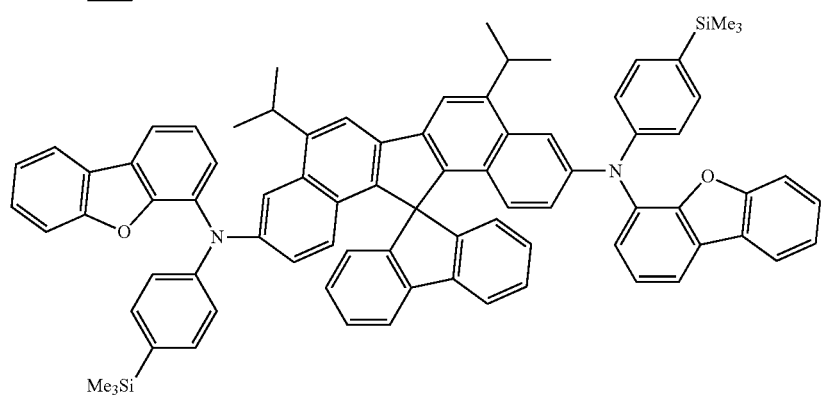
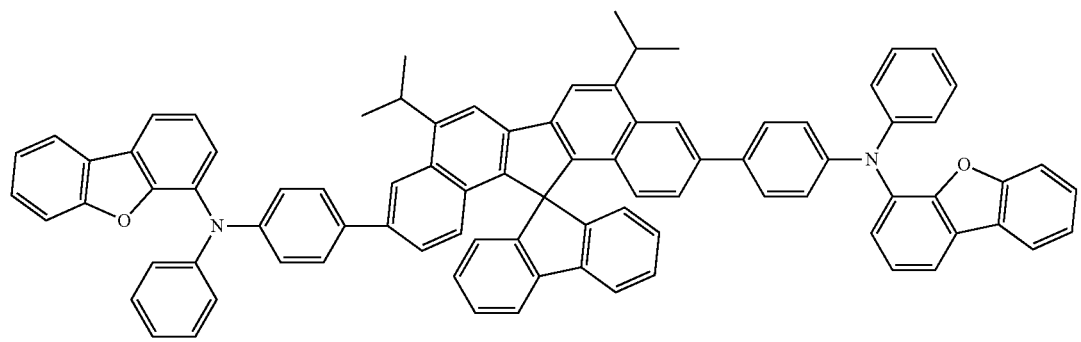
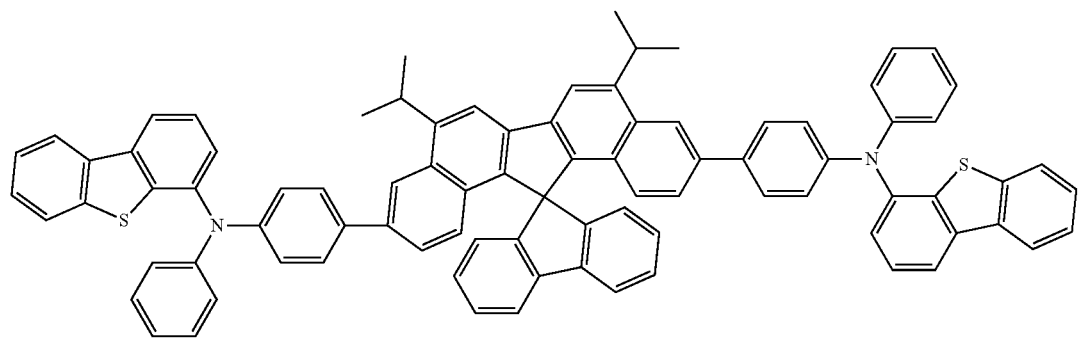

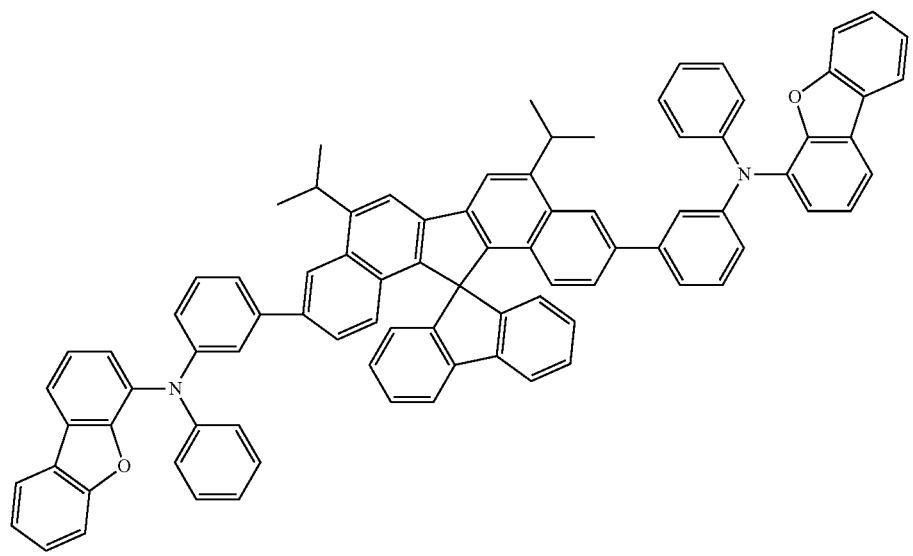
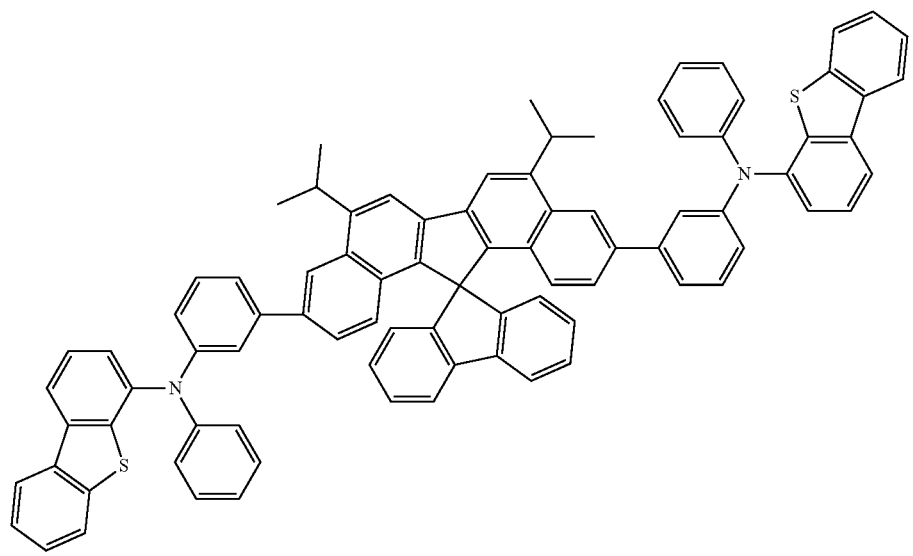
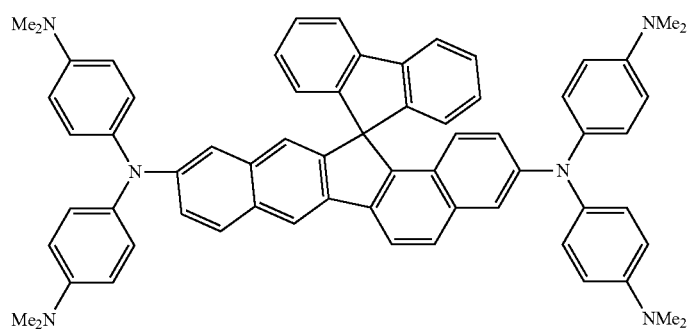

-continued
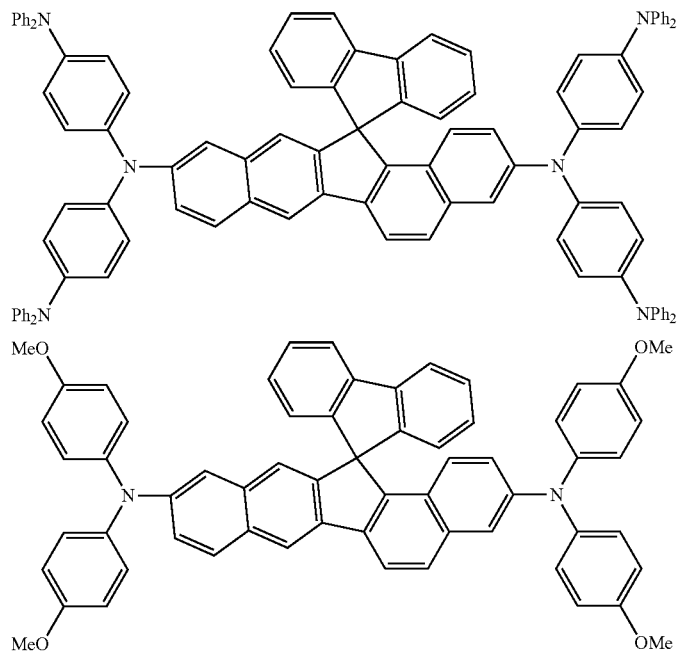
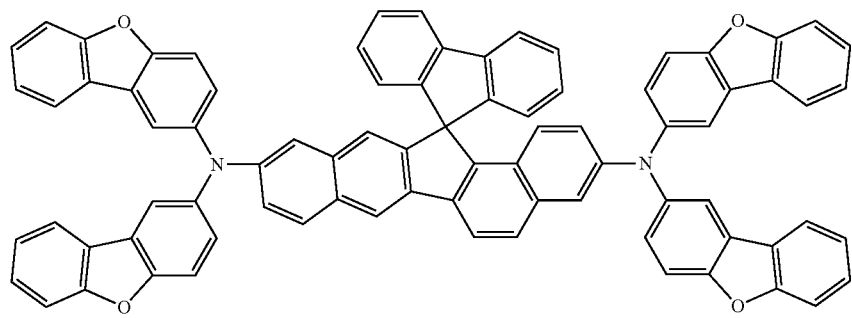
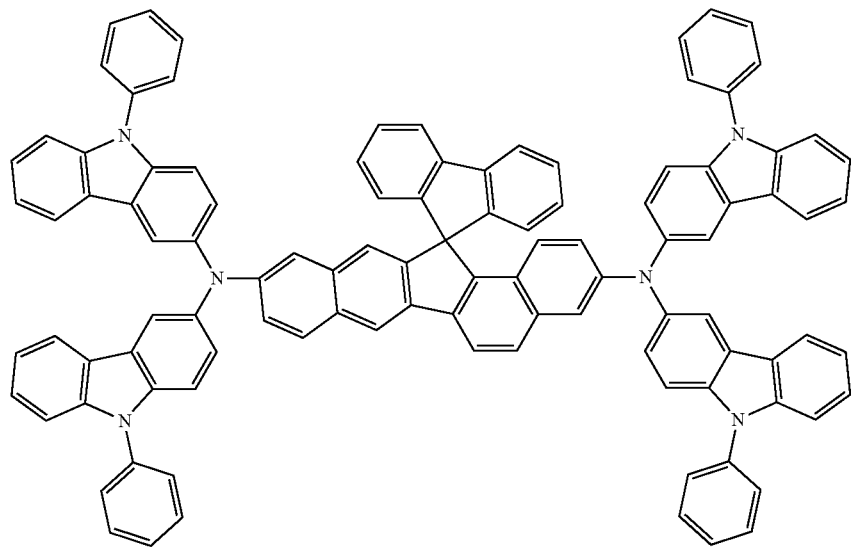

-continued
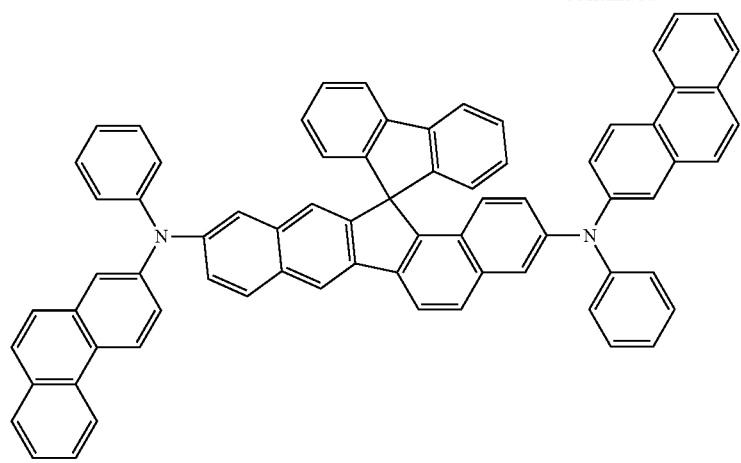
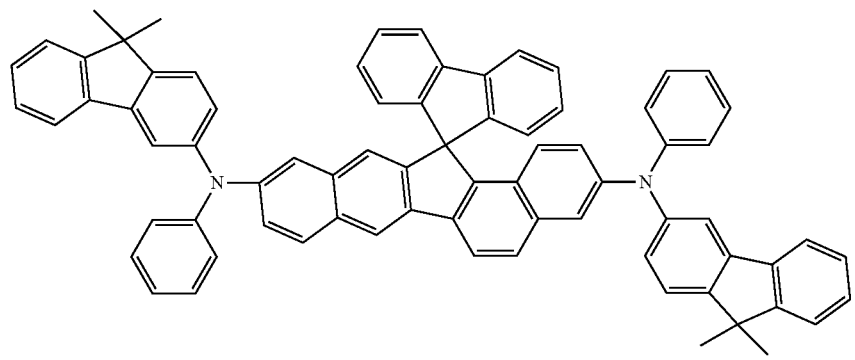
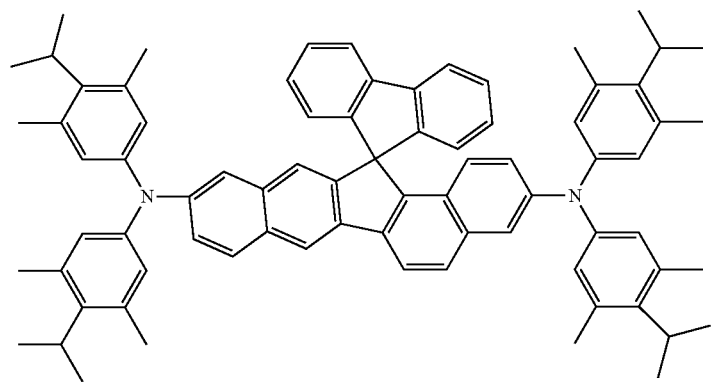
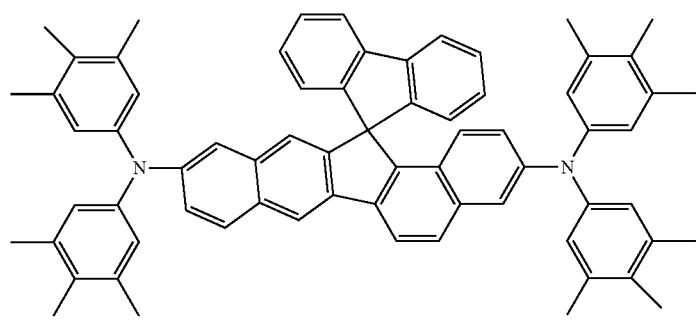

-continued
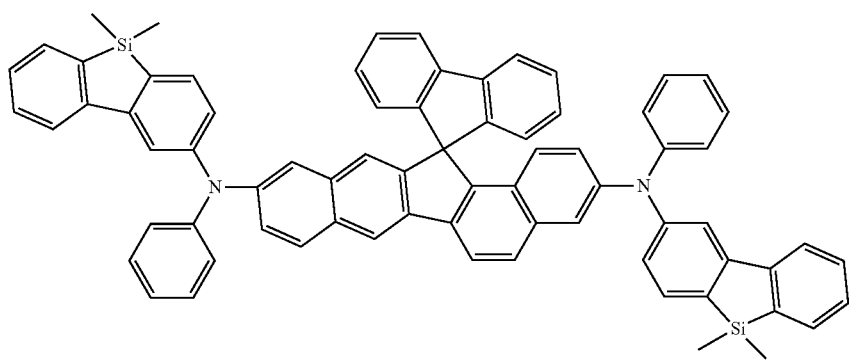
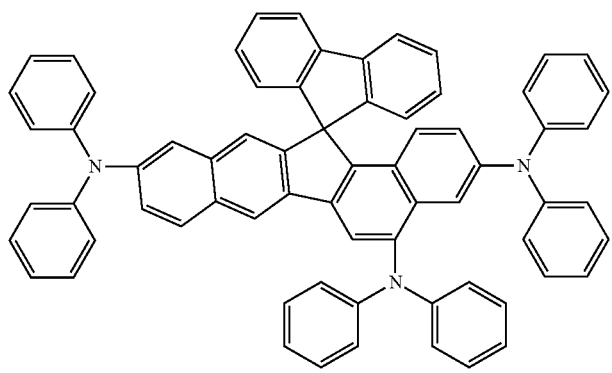
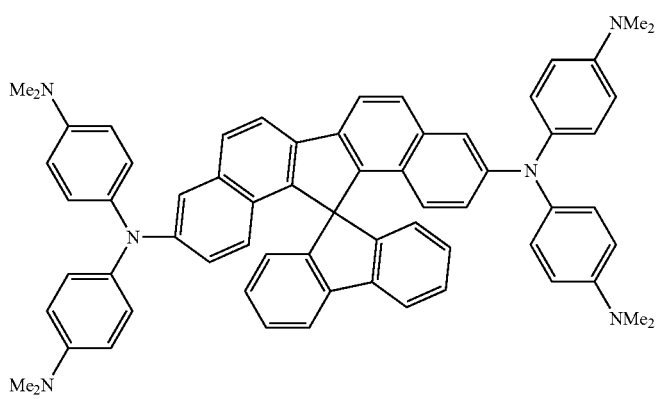
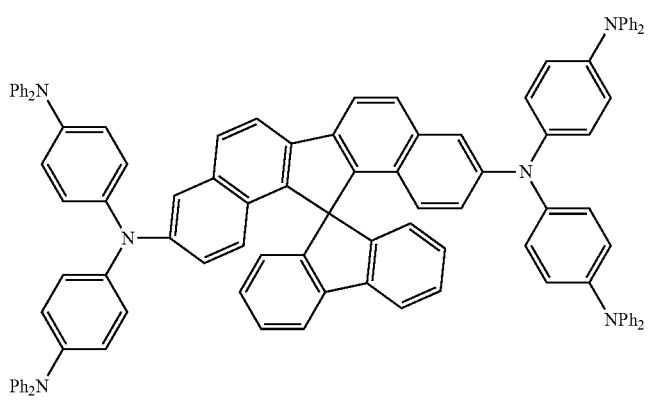

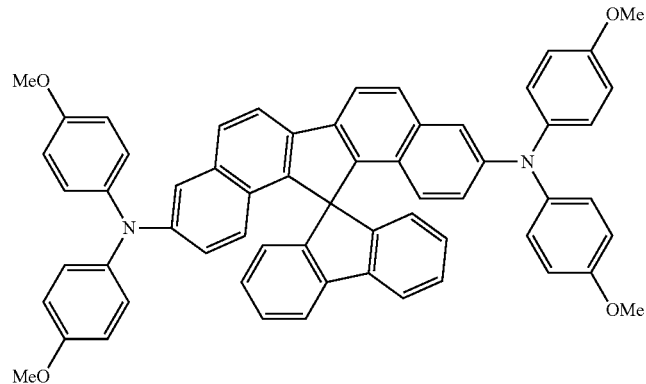
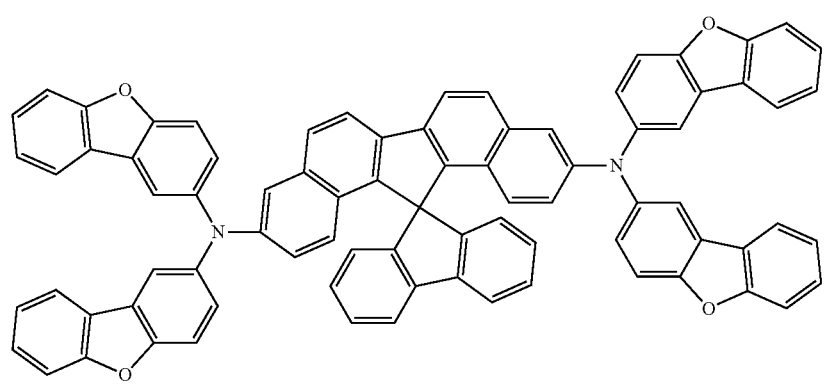
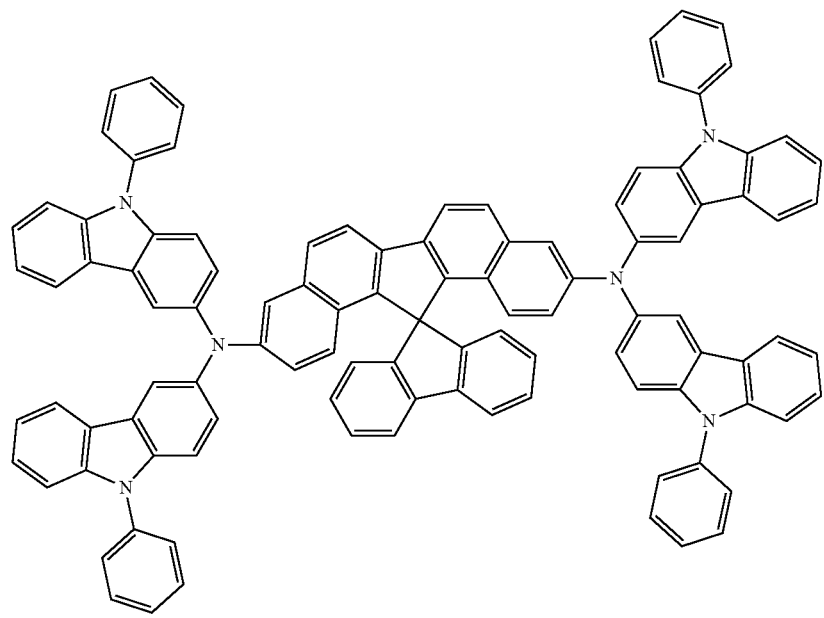

-continued
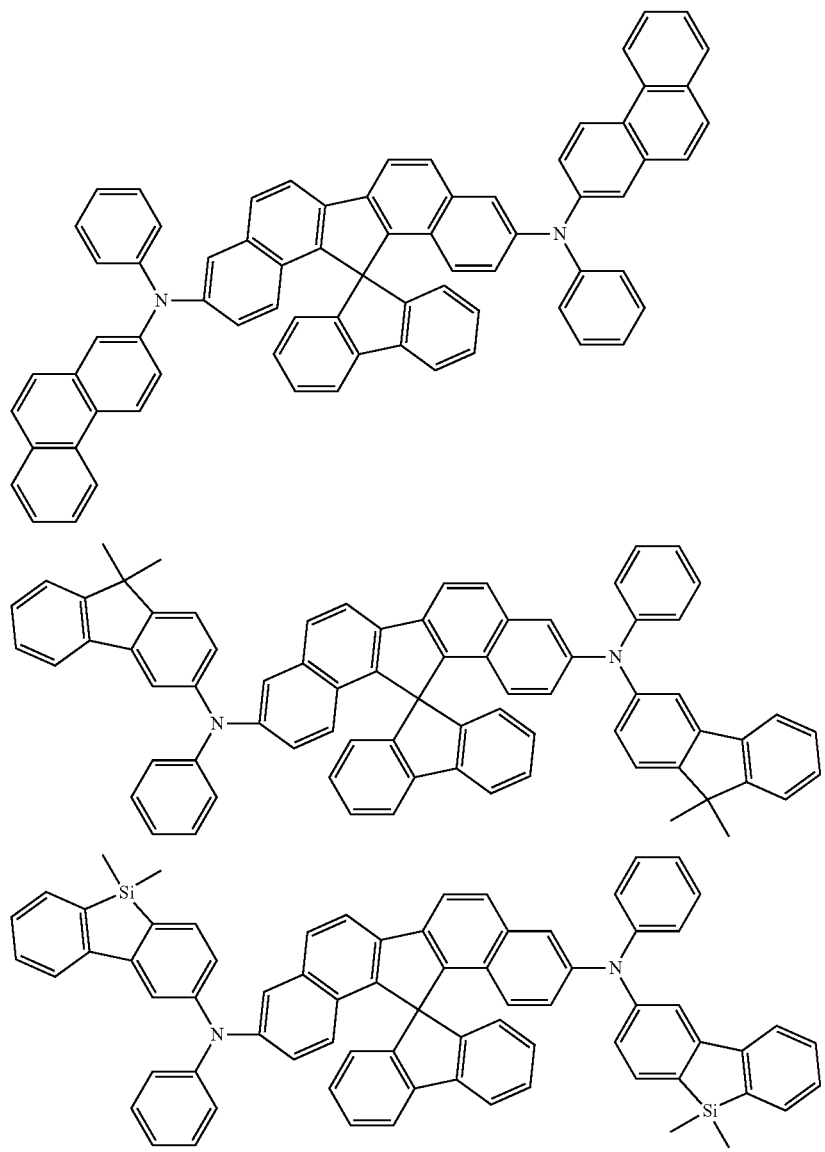
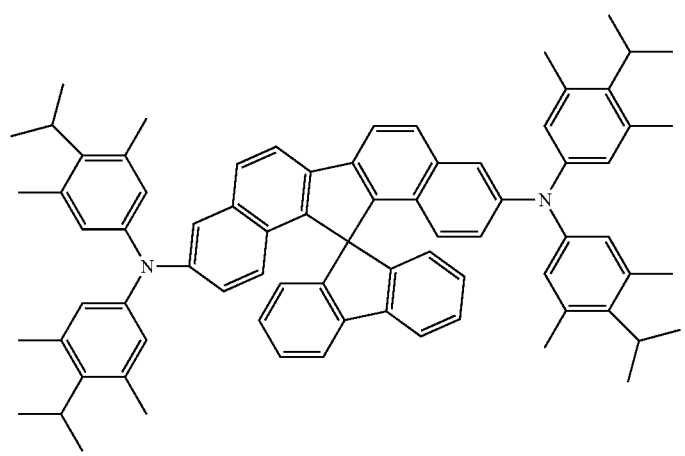

-continued

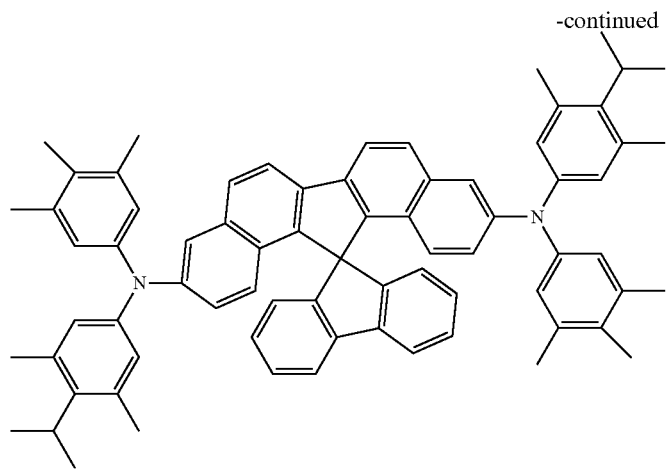

The compounds of the invention are useful as a material for organic EL devices.

The production method of the compound of the invention is not particularly limited, and the compound can be easily produced by using or modifying a known synthetic reaction while referring to the examples described below.

Organic EL Device

The organic EL device of the invention will be described below.

The organic EL device comprises an organic thin film layer between a cathode and an anode. The organic thin film layer comprises a light emitting layer and at least one layer of the organic thin film layer comprises the compound of the invention. The organic EL device of the invention includes one operating at low driving voltage and having a long lifetime, and also includes one emitting blue light with a high color purity.

Examples of the organic thin film layer which comprises the compound of the invention include a hole transporting layer, a light emitting layer, an electron transporting layer, a space layer, and a blocking layer, although not particularly limited thereto.

In view of the emission efficiency and the device lifetime, the compound of the invention comprising an amino group is preferably used in a light emitting layer preferably as a dopant material. The compound of the invention comprising a heteroaryl group, particularly a nitrogen-containing heteroaryl group is preferably used in an electron transporting layer or a blocking layer between a light emitting layer and an electron transporting layer. In view of the driving voltage and the emission efficiency, the compound of the invention comprising an anthracene skeleton is preferably used in a light emitting layer preferably as a host material, particularly a fluorescent host material.

The organic EL device of the invention may be any of a fluorescent or phosphorescent single color emitting device, a white-emitting device of fluorescent-phosphorescent hybrid type, a simple-type emitting device having a single emission unit, and a tandem emitting device having two or more emission units. The "emission unit" referred to herein is the smallest unit for emitting light by the recombination of injected holes and injected electrons, which comprises one or more organic layers, wherein at least one layer is a light emitting layer.

Representative device structures of the simple-type organic EL device are shown below:

(1) Anode/Emission Unit/Cathode

The emission unit may be a laminated unit comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the emission unit are shown below:

(a) Hole transporting layer/Light emitting layer (/Electron transporting layer);

(b) Hole transporting layer/First fluorescent emitting layer/Second fluorescent emitting layer (/Electron transporting layer);

(c) Hole transporting layer/Phosphorescent emitting layer/Space layer/Fluorescent emitting layer (/Electron transporting layer);

(d) Hole transporting layer/First phosphorescent emitting layer/Second phosphorescent emitting layer/Space layer/Fluorescent emitting layer (/Electron transporting layer);

(e) Hole transporting layer/First phosphorescent emitting layer/Space layer/Second phosphorescent emitting layer/Space layer/Fluorescent emitting layer (/Electron transporting layer); and (f) Hole transporting layer/Phosphorescent emitting layer/Space layer/First fluorescent emitting layer/Second fluorescent emitting layer (/Electron transporting layer).

The emission color of the fluorescent emitting layer and that of the phosphorescent emitting layer may be different. For example, the layered structure of the laminated emission layer (d) may be Hole transporting layer/First phosphorescent emitting layer (red emission)/Second phosphorescent emitting layer (green emission)/Sp ace layer/Fluorescent emitting layer (blue emission) (/Electron transporting layer).

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such an electron blocking layer or a hole blocking layer, electrons and holes are confined in the light emitting layer to increase the charge recombination in the light emitting layer, thereby improving the emission efficiency.

Representative device structure of the tandem-type organic EL device is shown below:
(2) Anode/First Emission Unit/Intermediate Layer/Second Emission Unit/Cathode.

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials which can supply electrons to the first emission unit and holes to the second emission unit.

A schematic structure of an example of the organic EL device is shown in FIG. 1, wherein the organic EL device 1 comprises a substrate 2, an anode 3, a cathode 4, and an emission unit (organic thin film layer) 10 disposed between the anode 3 and the cathode 4. The emission unit 10 comprises a light emitting layer 5 which includes at least one fluorescent emitting layer comprising a fluorescent host material and a fluorescent dopant material. A hole injecting layer/hole transporting layer 6 may be disposed between the light emitting layer 5 and the anode 3, and an electron injecting layer/electron transporting layer 7 may be disposed between the light emitting layer 5 and the cathode 4. An electron blocking layer may be disposed on the side of anode 3 of the light emitting layer 5, and a hole blocking layer may be disposed on the side of cathode 4 of the light emitting layer 5. With these blocking layers, electrons and holes are confined in the light emitting layer 5 to increase the exciton generation in the light emitting layer 5.

In the present specification, a host material is referred to as a fluorescent host material when combinedly used with a fluorescent dopant material and as a phosphorescent host material when combinedly used with a phosphorescent dopant material. Therefore, the fluorescent host material and the phosphorescent host material are not distinguished from each other merely by the difference in their molecular structures. Namely, in the present invention, the fluorescent host material means a material for constituting a fluorescent emitting layer containing a fluorescent dopant material and does not mean a material that cannot be utilized as a material for a phosphorescent emitting layer. The same applies to the phosphorescent host material.

Substrate

The organic EL device of the invention is formed on a light-transmissive substrate. The light-transmissive substrate serves as a support for the organic EL device and preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of the organic EL device injects holes to the hole transporting layer or the light emitting layer, and an anode having a work function of 4.5 eV or more is effective. Examples of the material for anode include indium tin oxide alloy (ITO), tin oxide (NESA), indium zinc oxide, gold, silver, platinum, and cupper. The anode is formed by making the electrode material into a thin film by a method, such as a vapor deposition method and a sputtering method. When getting the light emitted from the light emitting layer through the anode, the transmittance of anode to visible light is preferably 10% or more. The sheet resistance of anode is preferably several hundreds Ω/or less. The film thickness of anode depends upon the kind of material and generally 10 nm to 1 μm, preferably 10 to 200 nm.

Cathode

The cathode injects electrons to an electron injecting layer, an electron transporting layer or a light emitting layer, and formed preferably by a material having a small work function. Examples of the material for cathode include, but not limited to, indium, aluminum, magnesium, a magnesium-indium alloy, a magnesium-aluminum alloy, an aluminum-lithium alloy, an aluminum-scandium-lithium alloy, and a magnesium-silver alloy. Like the anode, the cathode is formed by making the material into a thin film by a method, such as a vapor deposition method and a sputtering method. The emitted light may be taken through the cathode, if necessary.

The materials other than the compound of the invention, which are usable in each layer, will be described below.

Light Emitting Layer

The light emitting layer is an organic layer having a light emitting function and comprises a host material and a dopant material when a doping system is employed. The major function of the host material is to promote the recombination of electrons and holes and confine excitons in the light emitting layer. The dopant material causes the excitons generated by recombination to emit light efficiently.

In case of a phosphorescent device, the major function of the host material is to confine the excitons generated on the dopant in the light emitting layer.

To control the carrier balance in the light emitting layer, the light emitting layer may be a double host (host/co-host) layer, for example, a layer in which an electron transporting host material and a hole transporting host material are combinedly used.

The light emitting layer may be a double dopant layer in which two or more kinds of dopant materials having a high quantum yield are combinedly used and each dopant emits light with its own color. For example, a common light emitting layer formed by co-depositing a host, a red-emitting dopant and a green-emitting dopant emits yellow light.

The light emitting layer may be a double dopant layer in which two or more kinds of dopant materials having a high quantum yield are combinedly used and each dopant emits light with its own color. For example, a light emitting layer formed by co-depositing a host, a red-emitting dopant and a green-emitting dopant emits yellow light.

The quantum efficiency of the light emitting layer can be improved by a laminate of two or more light emitting layers, because electrons and holes are accumulated in the interface between the light emitting layers, and therefore, the recombination region is concentrated in the interface between the light emitting layers.

The easiness of hole injection to the light emitting layer and the easiness of electron injection to the light emitting layer may be different from each other. Also, the hole transporting ability and the electron transporting ability each being expressed by mobility of holes and electrons in the light emitting layer may be different from each other.

The light emitting layer is formed, for example, by a known method, such as a vapor deposition method, a spin coating method, and LB method. The light emitting layer can be formed also by making a solution of a binder, such as resin, and the material for the light emitting layer in a solvent into a thin film by a method, such as a spin coating method.

The light emitting layer is preferably a molecular deposit film. The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The thickness of the light emitting layer is preferably 5 to 50 nm, more preferably 7 to 50 nm, and still more preferably 10 to 50 nm. If 5 nm or more, the light emitting layer is formed easily. If 50 nm or less, the increase in the driving voltage is prevented.

Dopant Material

The fluorescent dopant material (fluorescent emitting material) used in the light emitting layer is a compound which emits light by releasing the energy of excited singlet state and is not particularly limited as long as capable of emitting light by releasing the energy of excited singlet state. Examples thereof include a fluoranthene derivative, a styrylarylene derivative, a pyrene derivative, an arylacetylene derivative, a fluorene derivative, a boron complex, a perylene derivative, an oxadiazole derivative, an anthracene derivative, a styrylamine derivative, and an arylamine derivative, with an anthracene derivative, a fluoranthene derivative, a styrylamine derivative, an arylamine derivative, a styrylarylene derivative, a pyrene derivative, and a boron complex being preferred, and an anthracene derivative, a fluoranthene derivative, a styrylamine derivative, an arylamine derivative, and a boron complex being more preferred.

The content of the fluorescent dopant in the light emitting layer is not particularly limited and selected according to the use of the device, and preferably 0.1 to 70% by mass, more preferably 1 to 30% by mass, and still more preferably 1 to 20% by mass, and still further preferably 1 to 10% by mass. If being 0.1% by mass or more, the amount of light emission is sufficient. If being 70% by mass or less, the concentration quenching is avoided.

Host Material

An anthracene derivative or a polycyclic aromatic compound, preferably an anthracene derivative is preferably used as the host material for the light emitting layer.

For example, the following anthracene derivative represented by formula (5) is used as the host material for a blue emitting layer:

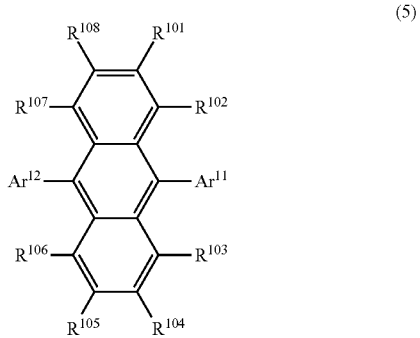

(5)

wherein:

each of $Ar^{11}$ and $Ar^{12}$ is independently a substituted or unsubstituted monocyclic group having 5 to 50 ring atoms or a substituted or unsubstituted fused ring group having 8 to 50 ring atoms; and each of $R^{101}$ to $R^{108}$ is independently a group selected from a hydrogen atom; a substituted or unsubstituted monocyclic group having 5 to 50, preferably 5 to 30, more preferably 5 to 20, and still more preferably 5 to 12 ring atoms; a substituted or unsubstituted fused ring group having 8 to 50, preferably 8 to 30, more preferably 8 to 20, and still more preferably 8 to 14 ring atoms; a group comprising a combination of the monocyclic group and the fused ring group; a substituted or unsubstituted alkyl group having 1 to 50, preferably 1 to 20, more preferably 1 to 10, and still more preferably 1 to 6 carbon atoms; a substituted or unsubstituted cycloalkyl group having 3 to 50, preferably 3 to 20, more preferably 3 to 10, and still more preferably 5 to 8 ring carbon atoms; a substituted or unsubstituted alkoxy group having 1 to 50, preferably 1 to 20, more preferably 1 to 10, and still more preferably 1 to 6 carbon atoms; a substituted or unsubstituted aralkyl group having 7 to 50, preferably 7 to 20, more preferably 7 to 14 carbon atoms; a substituted or unsubstituted aryloxy group having 6 to 50, preferably 6 to 20, more preferably 6 to 12 ring carbon atoms; a substituted or unsubstituted silyl group; a halogen atom; and a cyano group.

In a preferred anthracene derivative, $R^{101}$ to $R^{108}$ are all hydrogen atoms, or one of $R^{101}$ and $R^{108}$, one of $R^{104}$ and $R^{105}$, both of $R^{101}$ and $R^{105}$, or both of $R^{108}$ and $R^{104}$ are selected from a monocyclic group having 5 to 50 ring atoms, preferably a phenyl group, a biphenylyl group, and a terphenylyl group; a substituted or unsubstituted alkyl group having 1 to 50 carbon atoms, preferably a methyl group, an ethyl group, a n-propyl group, an isopropyl group, a n-butyl group, an isobutyl group, a s-butyl group, and a t-butyl group; and a substituted silyl group, preferably a trimethylsilyl group. An anthracene derivative wherein $R^{101}$ to $R^{108}$ are all hydrogen atoms is more preferred.

The monocyclic group of formula (5) is a group composed of only a non-fused ring structure.

Examples of the monocyclic group having 5 to 50 ring atoms include an aromatic group, such as a phenyl group, a biphenylyl group, a terphenylyl group, and a quaterphenylyl group; and a heterocyclic group, such as a pyridyl group, a pyrazyl group, a pyrimidyl group, a triazinyl group, a furyl group, and a thienyl group, with a phenyl group, a biphenylyl group, and a terphenylyl group being preferred.

The fused ring group of formula (5) is a group wherein two or more ring structures are fused to each other.

Examples of the fused ring group having 8 to 50 ring atoms include a fused aromatic ring group, such as a naphthyl group, a phenanthryl group, an anthryl group, a chrysenyl group, a benzanthryl group, a benzophenanthryl group, a triphenylenyl group, a benzochrysenyl group, an indenyl group, a fluorenyl group, a 9, 9-dimethylfluorenyl group, a benzofluorenyl group, a dibenzofluorenyl group, a fluoranthenyl group, and a benzofluoranthenyl group; and a fused heterocyclic group, such as a benzofuranyl group, a benzothiophenyl group, an indolyl group, a dibenzofuranyl group, a dibenzothiophenyl group, a carbazolyl group, a quinolyl group, and a phenanthrolinyl group; with a naphthyl group, a phenanthryl group, an anthryl group, a 9, 9-dimethylfluorenyl group, a fluoranthenyl group, a benzanthryl group, a dibenzothiophenyl group, a dibenzofuranyl group, and a carbazolyl group being preferred.

The substituent of $Ar^{11}$ and $Ar^{12}$ is preferably selected from the monocyclic groups and the fused ring groups mentioned above.

In formula (5), examples of the alkyl group, the cycloalkyl group, the alkoxy group, the alkyl portion and the aryl portion of the aralkyl group, the aryloxy group, and the substituted silyl group (an alkylsilyl group and an arylsilyl group) are the same as those mentioned above with respect to $R^1$ and $R^2$ of formula (1). The halogen atom includes a fluorine atom, a chlorine atom, a bromine atom, and an iodine atom.

In formula (5), preferably $R^{101}$ to $R^{108}$ are all hydrogen atoms, or one of $R^{101}$ and $R^{108}$, one of $R^{104}$ and $R^{105}$, both of $R^{101}$ and $R^{105}$, or both of $R^{108}$ and $R^{104}$ are selected from a monocyclic group having 5 to 50 ring atoms, preferably a phenyl group, a biphenylyl group, and a terphenylyl group; a substituted or unsubstituted alkyl group having 1 to 50 carbon atoms, preferably a methyl group, an ethyl group, a n-propyl group, an isopropyl group, a n-butyl group, an isobutyl group, a s-butyl group, and a t-butyl group; and a substituted silyl group, preferably a trimethylsilyl group. More preferably, $R^{101}$ to $R^{108}$ are all hydrogen atoms.

The anthracene derivative represented by formula (5) is preferably any of the following anthracene derivatives (A), (B) and (C), which are selected according to the constitution and the required properties of the organic EL device in which the anthracene derivative is to be used.

Anthracene Derivative (A)

The anthracene derivative (A) is represented by formula (5) wherein $Ar^{11}$ and $Ar^{12}$ independently represent a substituted or unsubstituted fused ring group having 8 to 50 ring atoms and may be the same or different.

An anthracene derivative of formula (5) wherein $Ar^{11}$ and $Ar^{12}$ are different substituted or unsubstituted fused ring groups (inclusive of the difference in the positions connecting to the anthracene ring) is particularly preferable. Preferred examples of the fused ring are as described above, with a naphthyl group, a phenanthryl group, a benzanthryl group, a 9, 9-dimethylfluorenyl group, and a dibenzofuranyl group being more preferred.

Anthracene Derivative (B)

The anthracene derivative (B) is represented by formula (5) wherein one of $Ar^{11}$ and $Ar^{12}$ is a substituted or unsubstituted monocyclic group having 5 to 50 ring atoms and the other is a substituted or unsubstituted fused ring group having 8 to 50 ring atoms.

In a preferred anthracene derivative (B), $Ar^{12}$ is a naphthyl group, a phenanthryl group, a benzanthryl group, a 9, 9-dimethylfluorenyl group, or a dibenzofuranyl group; and $Ar^{11}$ is an unsubstituted phenyl group or a substituted phenyl group having a substituent selected from the monocyclic group and the fused ring group, for example, a phenyl group, a biphenyl group, a naphthyl group, a phenanthryl group, a 9, 9-dimethylfluorenyl group, and a dibenzofuranyl group In another preferred anthracene derivative (B), $Ar^{12}$ is a substituted or unsubstituted fused ring group having 8 to 50 ring atoms and $Ar^{11}$ is an unsubstituted phenyl group. The fused ring group is particularly preferably a phenanthryl group, a 9, 9-dimethylfluorenyl group, a dibenzofuranyl group, or a benzanthryl group.

Anthracene Derivative (C)

The anthracene derivative (C) is represented by formula (5) wherein $Ar^{11}$ and $Ar^{12}$ each independently represent a substituted or unsubstituted monocyclic group having 5 to 50 ring atoms.

In a preferred anthracene derivative (C), both of $Ar^{11}$ and $Ar^{12}$ are substituted or unsubstituted phenyl groups.

In a more preferred anthracene derivative (C), $Ar^{11}$ is an unsubstituted phenyl group and $Ar^{12}$ is a phenyl group having a substituent selected from the monocyclic group and the fused ring group; or $Ar^{11}$ and $Ar^{12}$ each independently represent a phenyl group having a substituent selected from the monocyclic group and the fused ring group.

Examples of the monocyclic substituent and the fused ring substituent are as described above. Preferably, the monocyclic substituent is a phenyl group or a biphenyl group, and the fused ring substituent is a naphthyl group, a phenanthryl group, a 9, 9-dimethylfluorenyl group, a dibenzofuranyl group, or a benzanthryl group.

Examples of the anthracene derivative represented by formula (5) are described below.

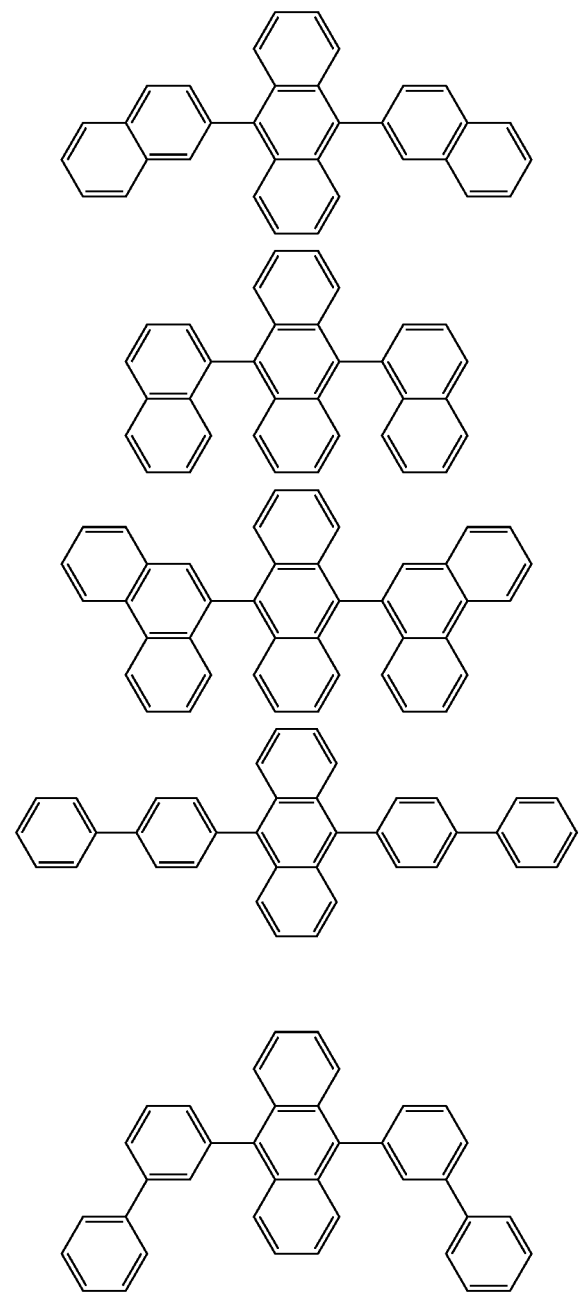

1367
-continued
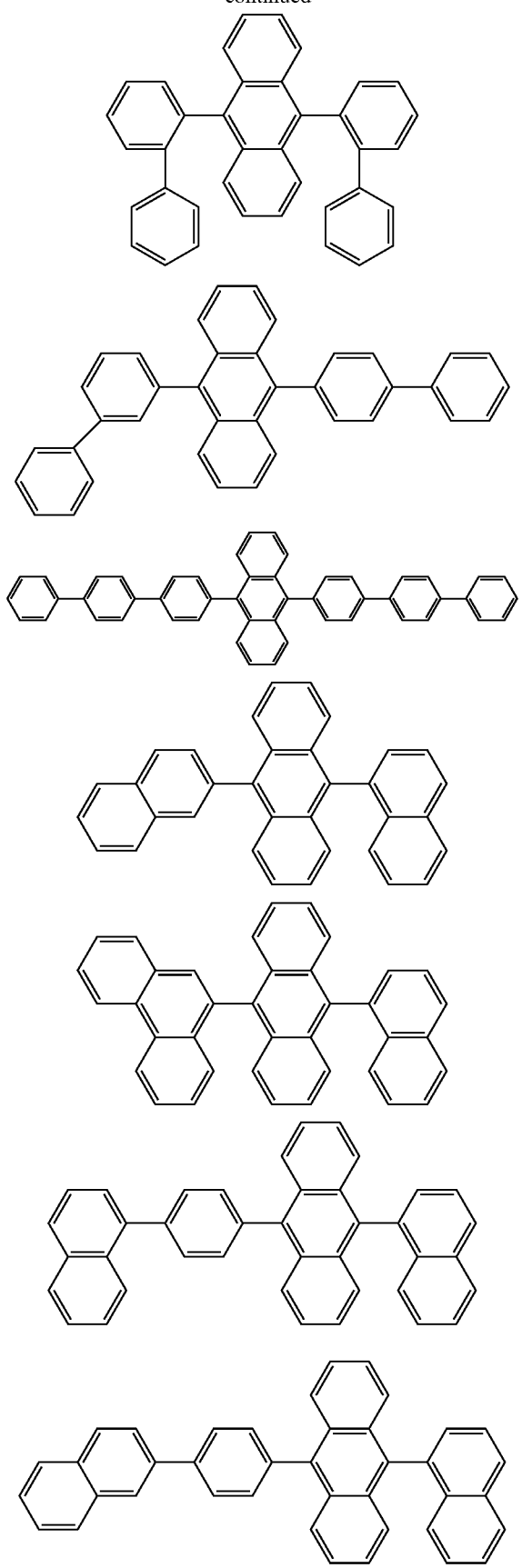
1368
-continued
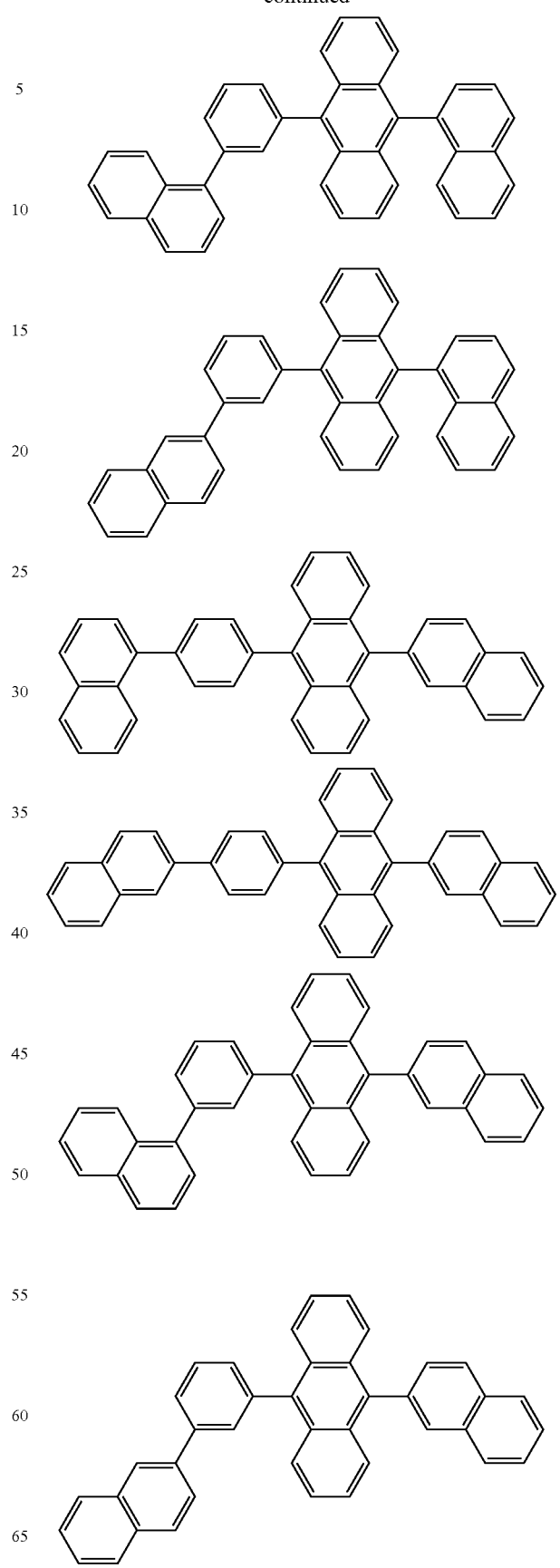

1369
-continued
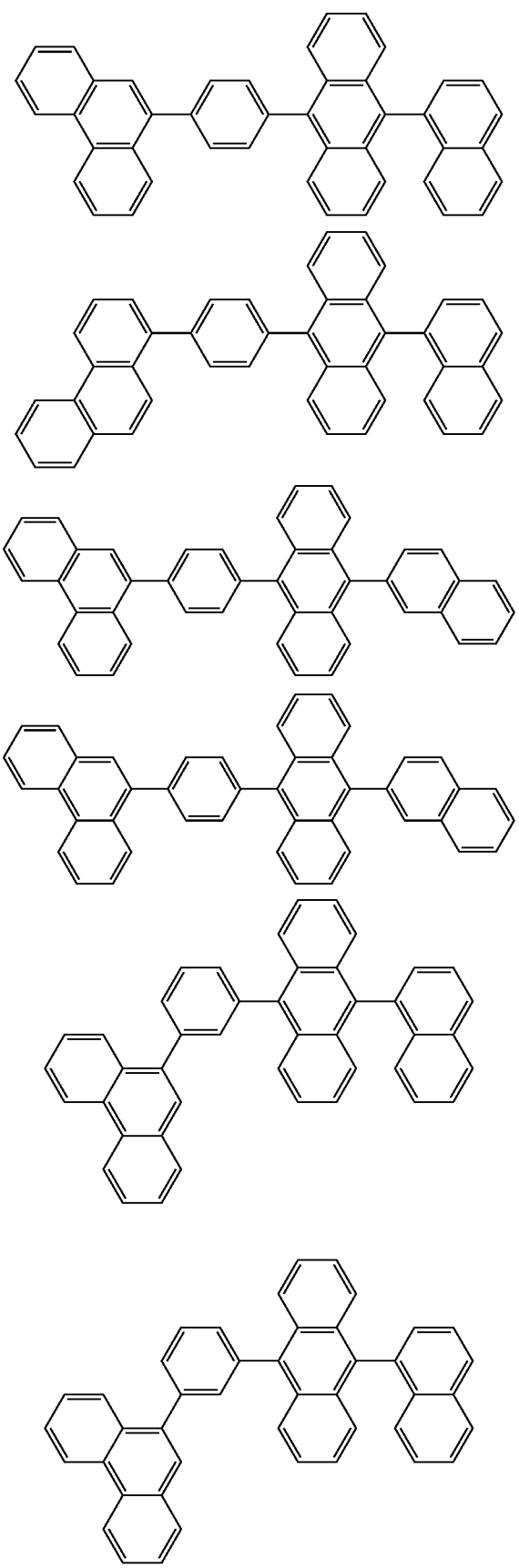
1370
-continued
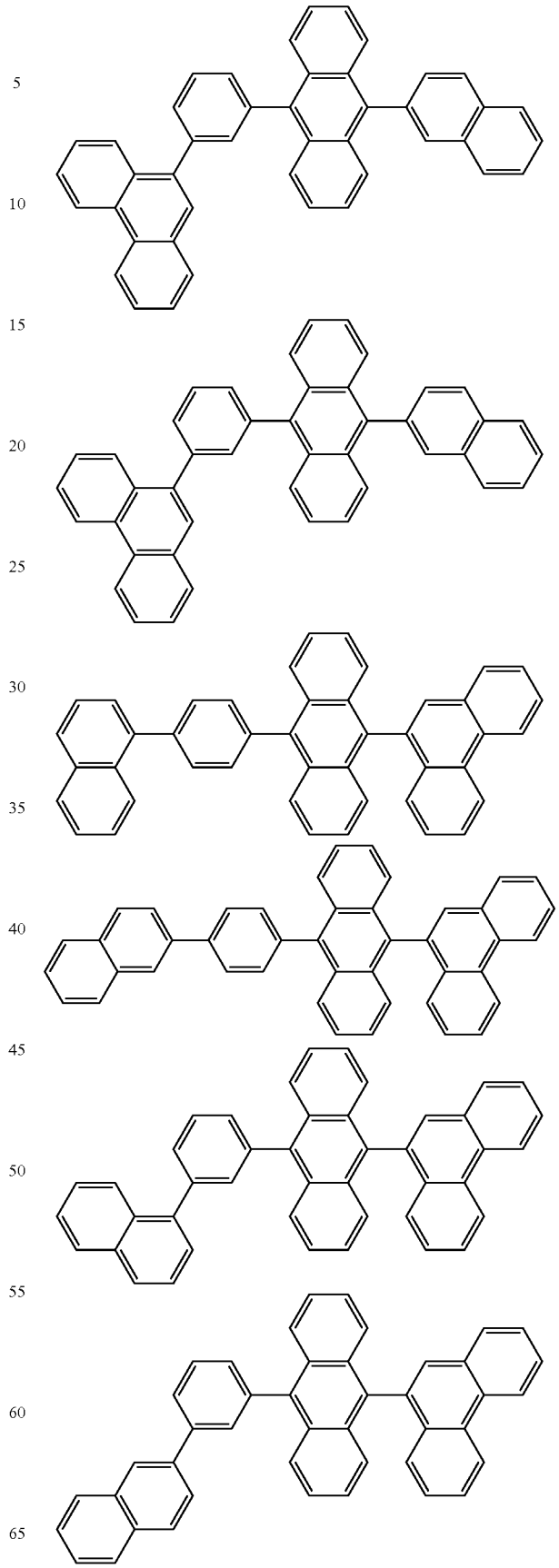

1371
-continued

1372
-continued

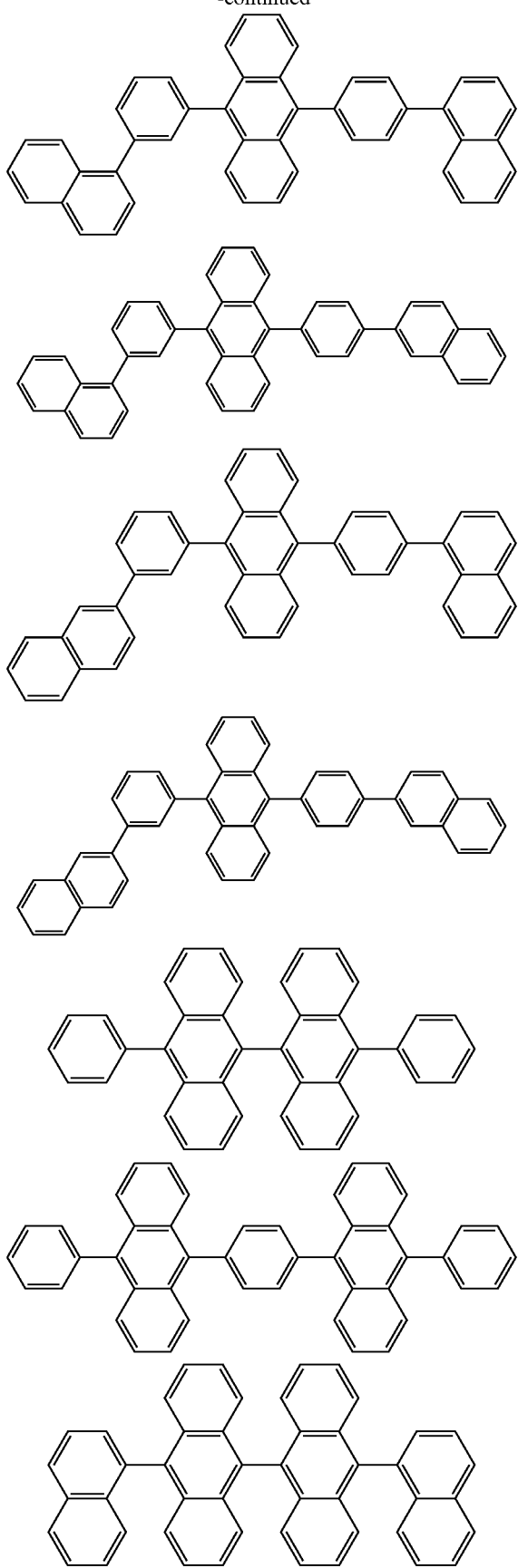

1375
-continued
1376
-continued
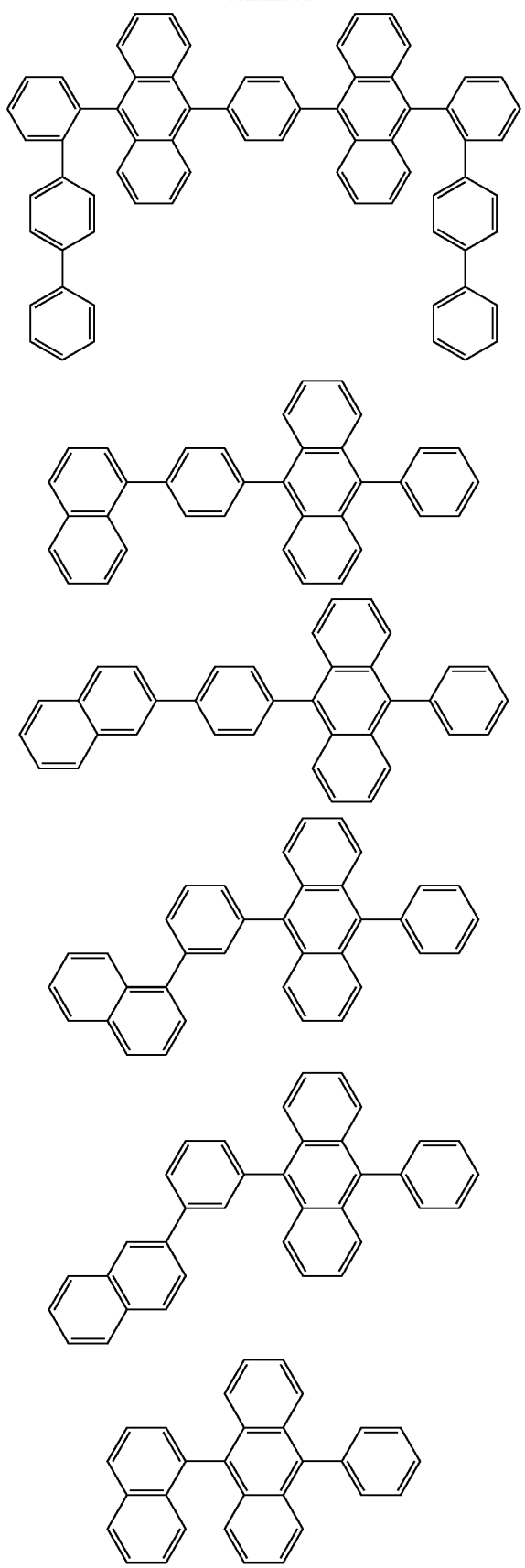
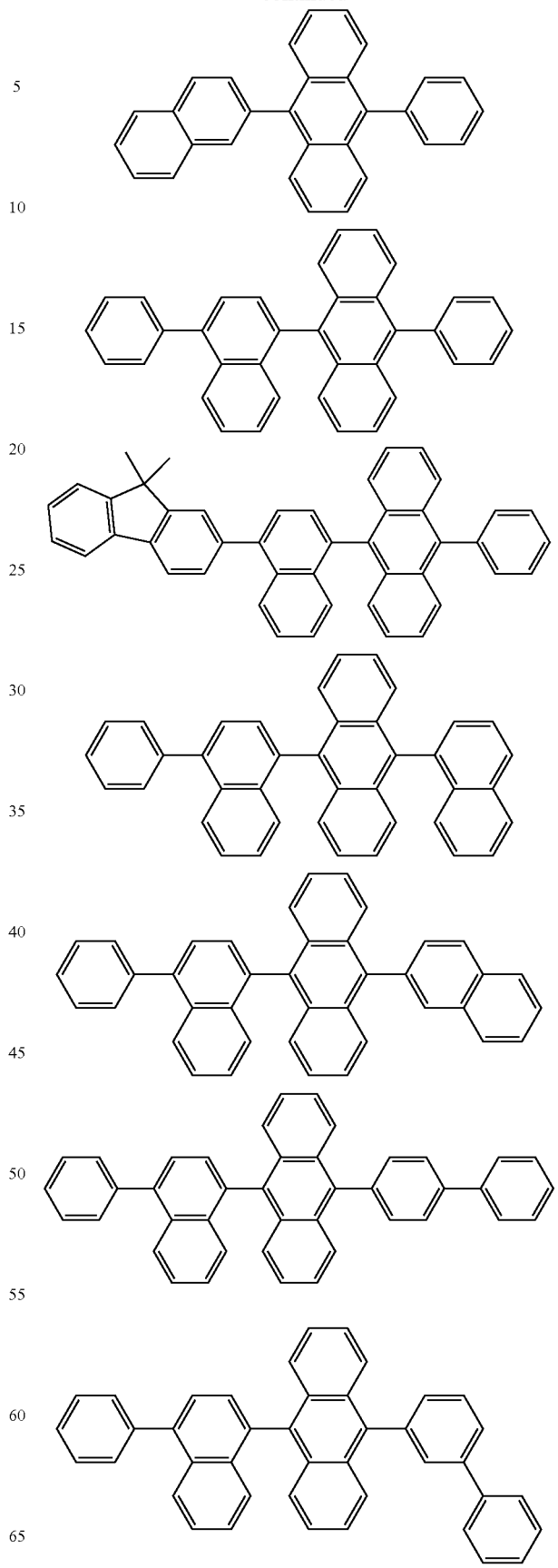

1377
-continued
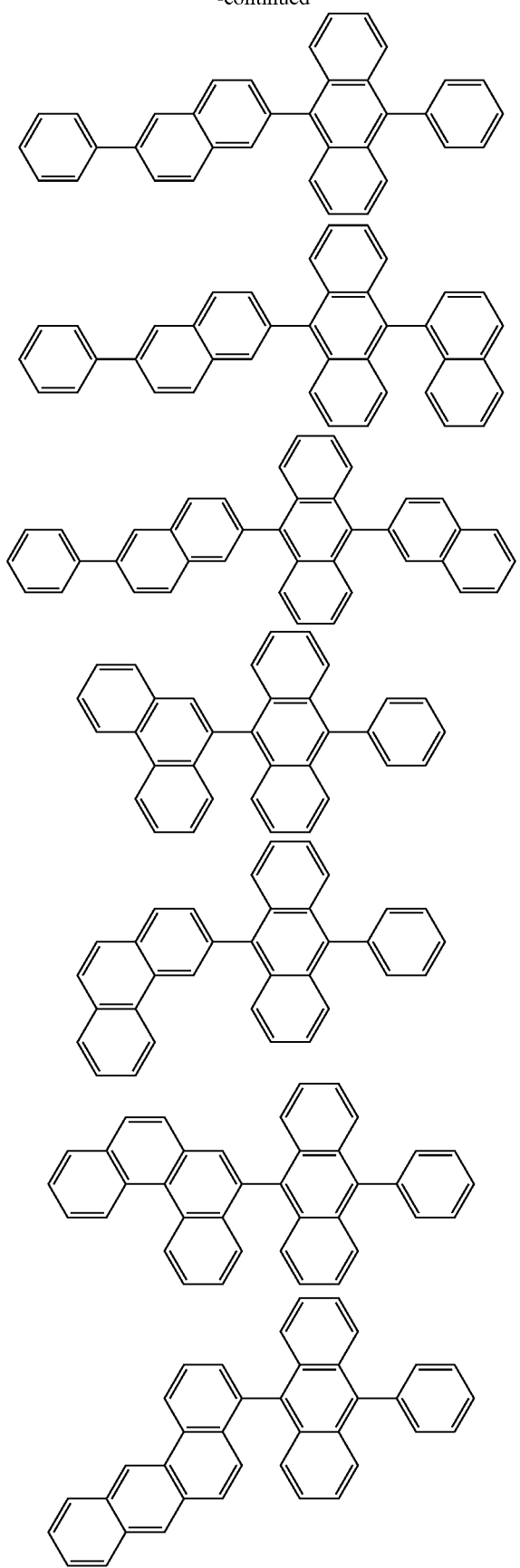
1378
-continued
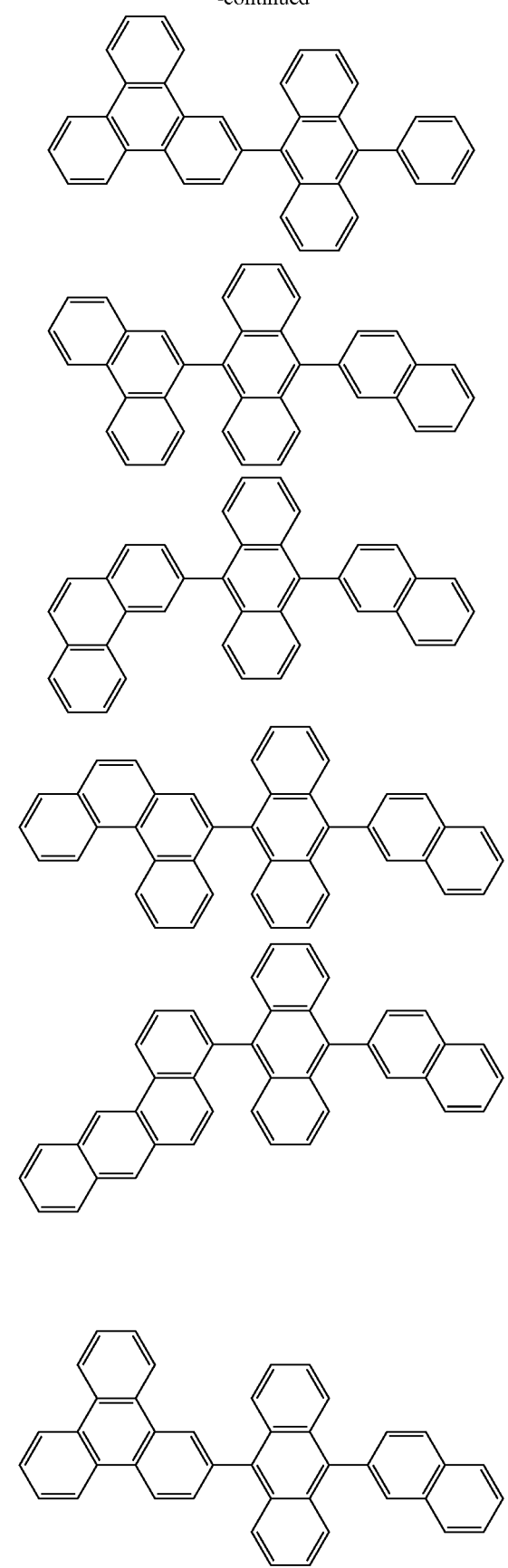

1379
-continued
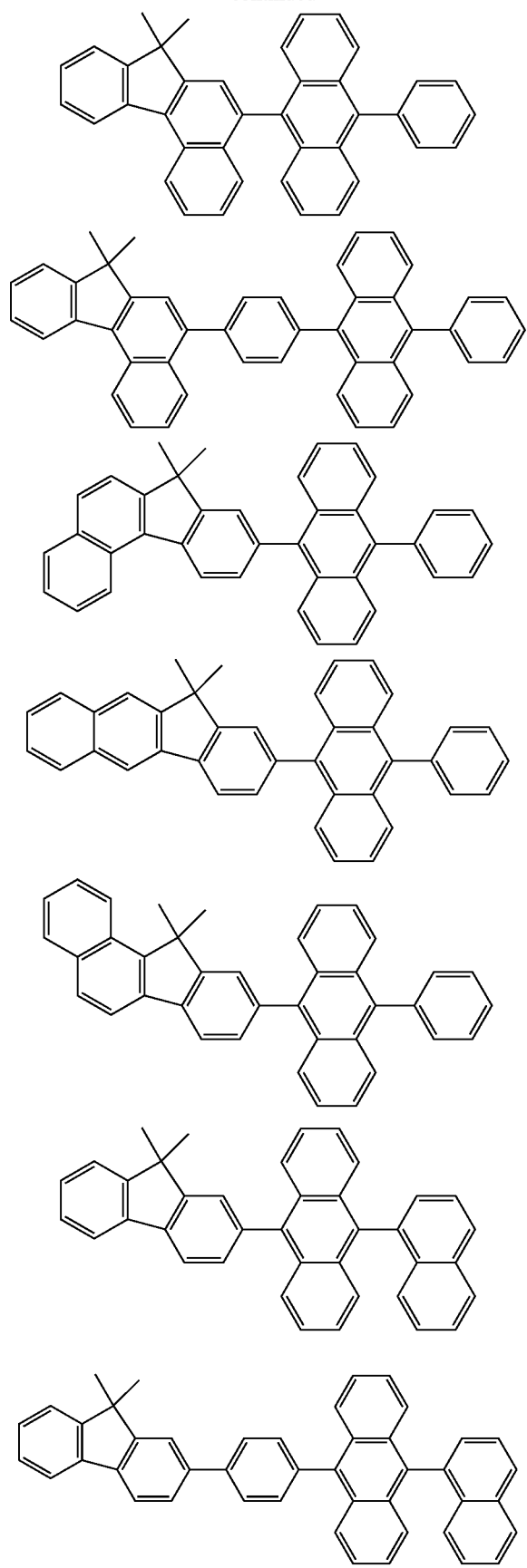
1380
-continued
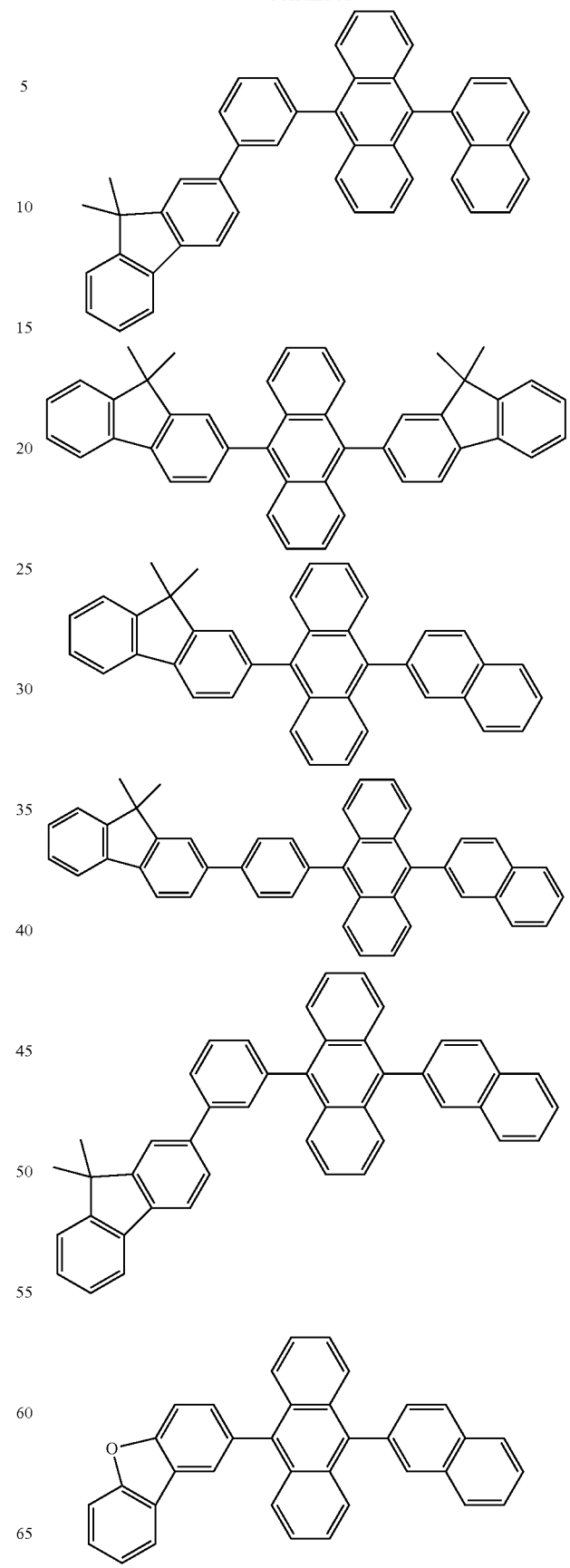

1381
-continued
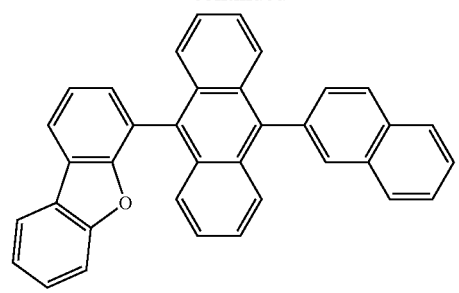
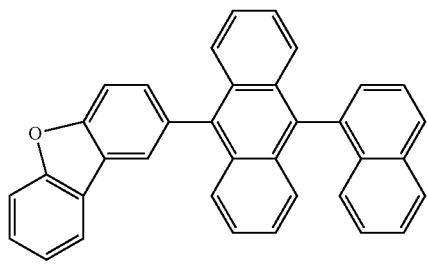
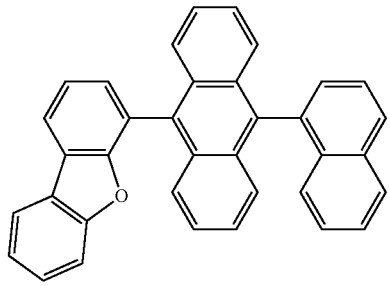
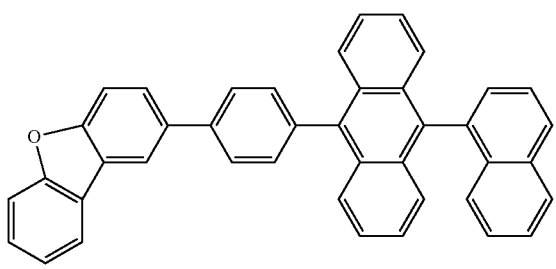
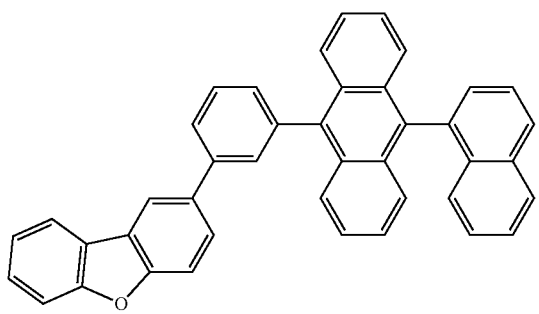
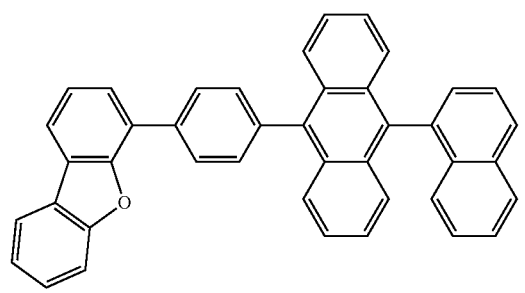
1382
-continued
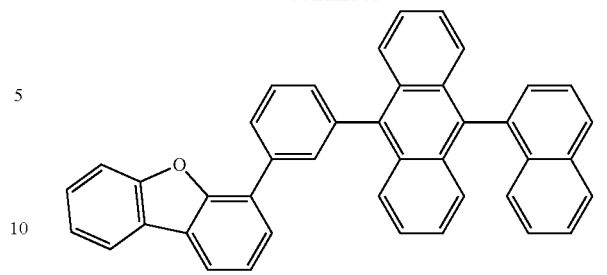
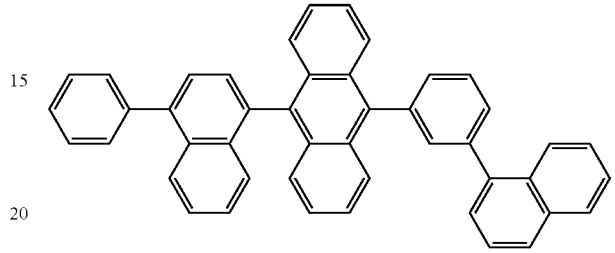
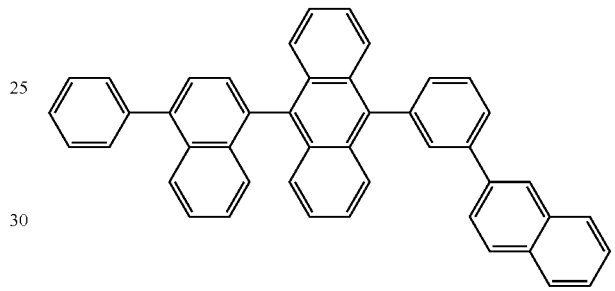
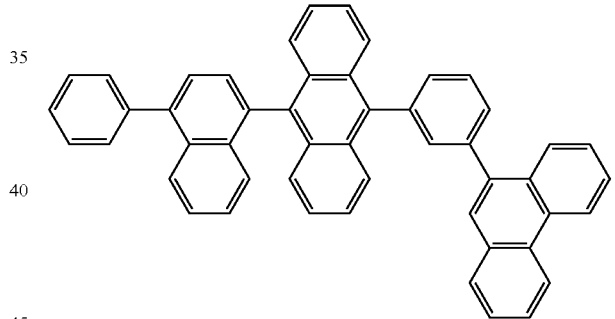
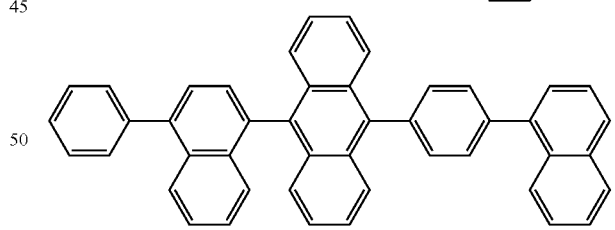
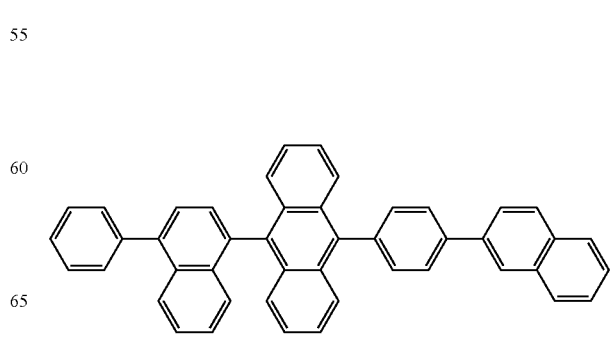

1383
-continued
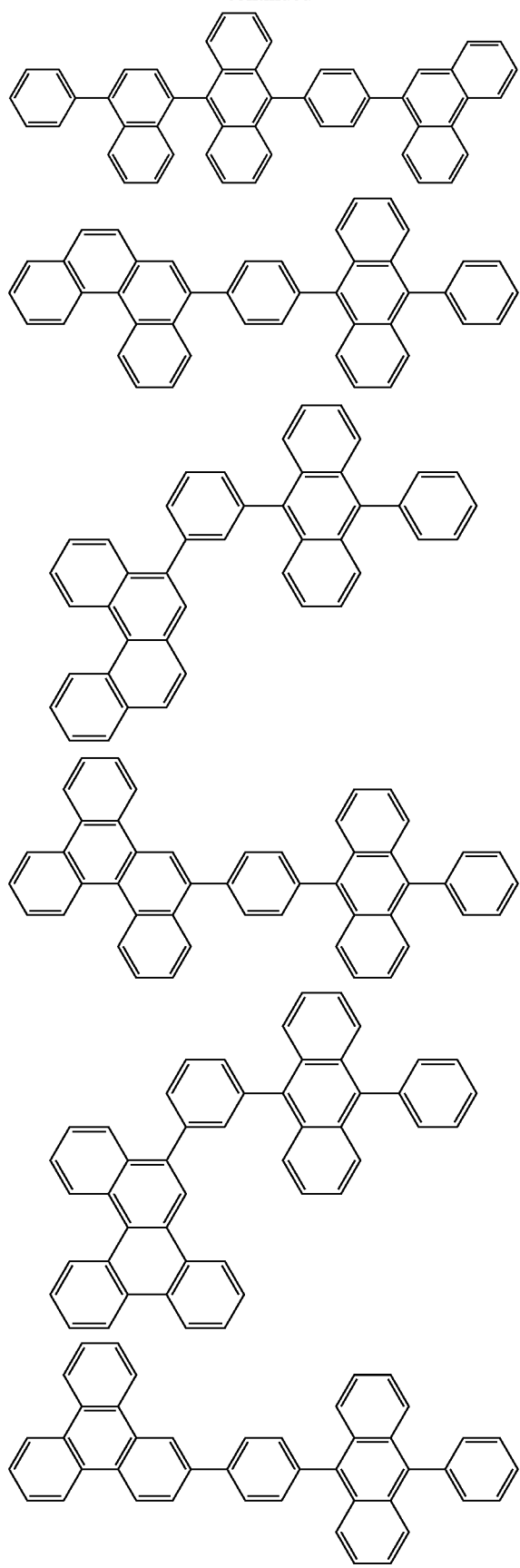
1384
-continued
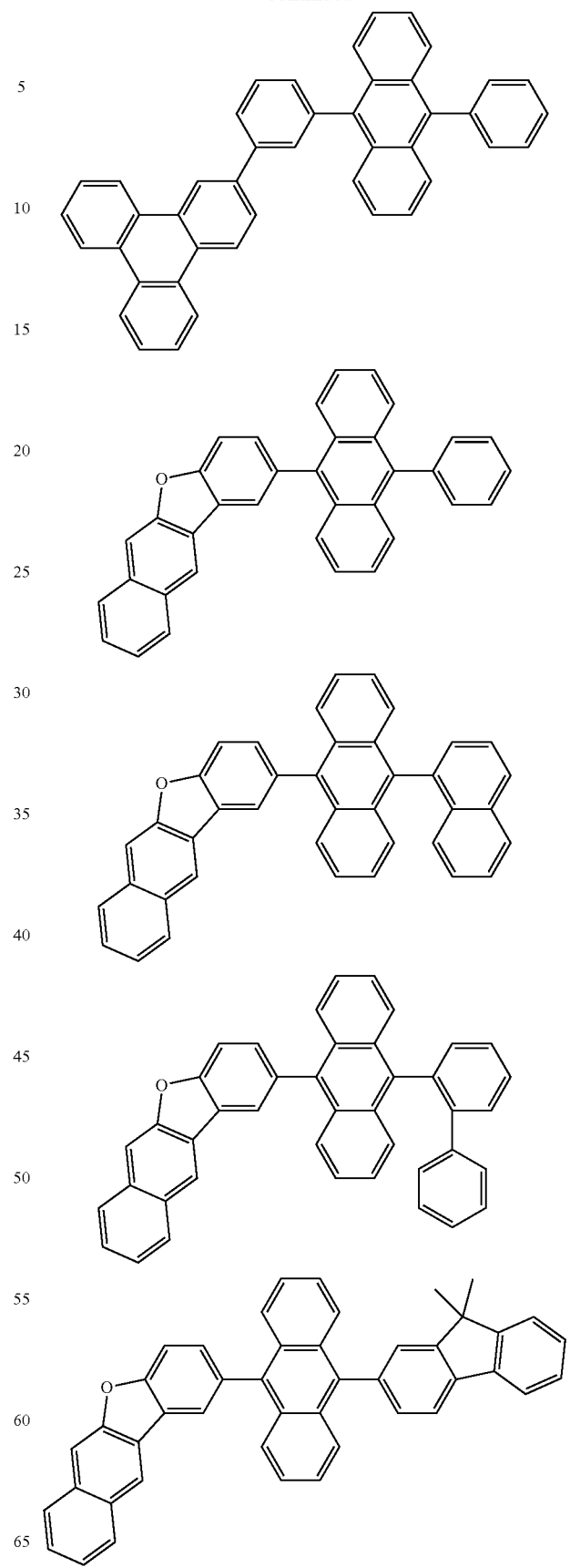

1385
-continued
1386
-continued
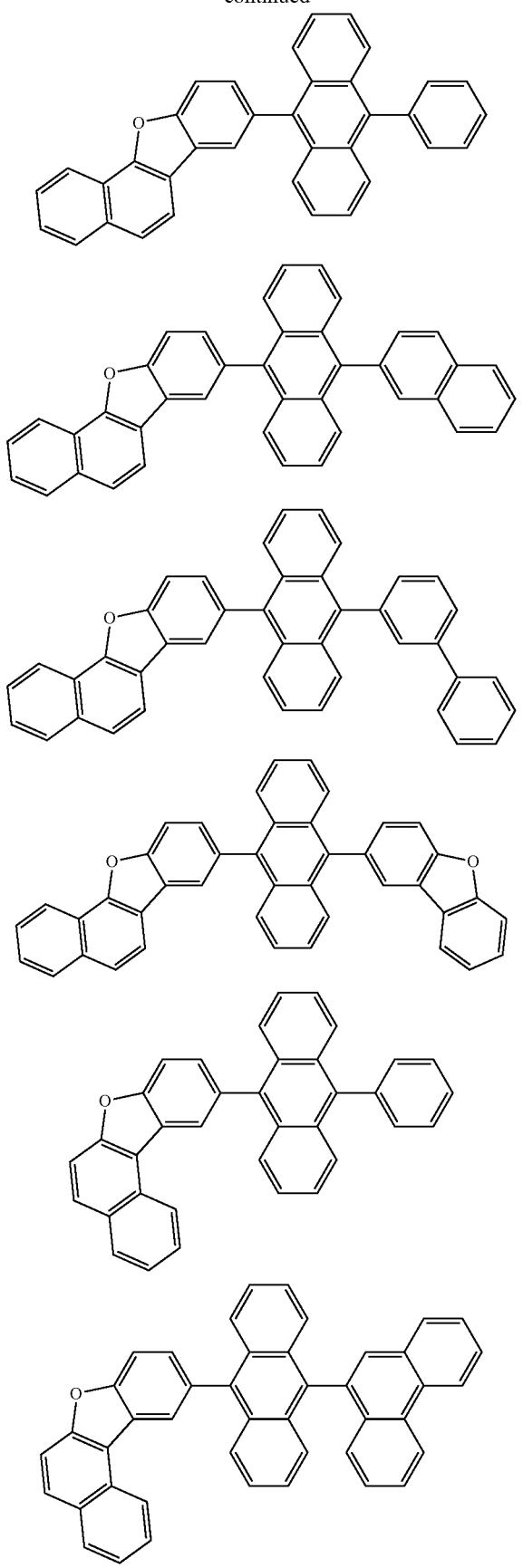
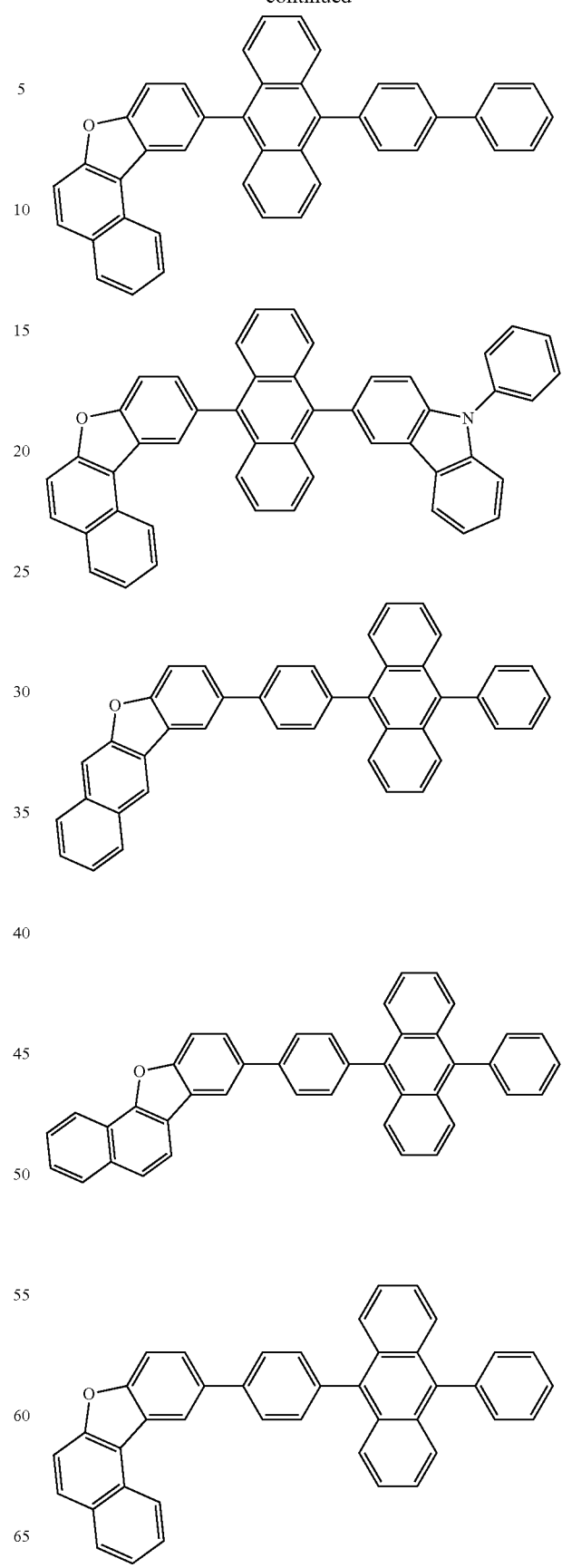

-continued

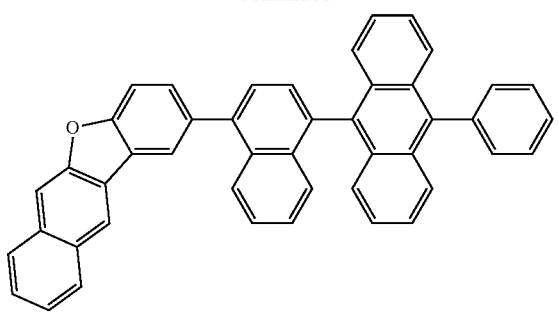

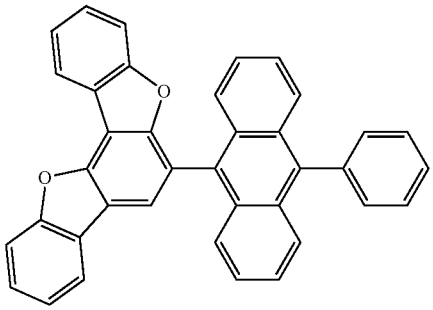

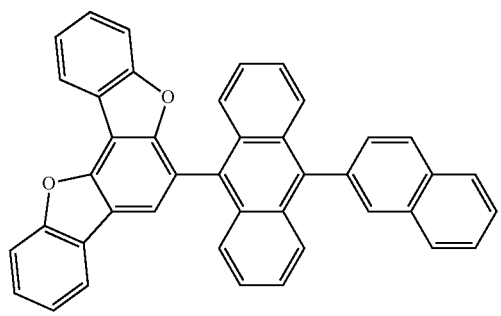

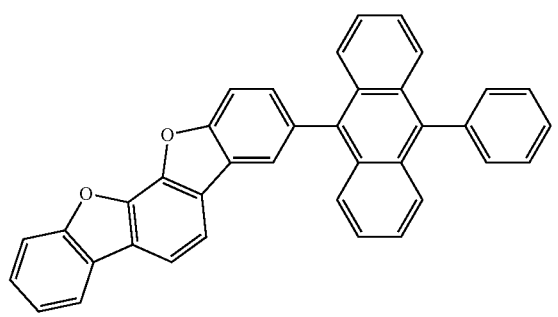

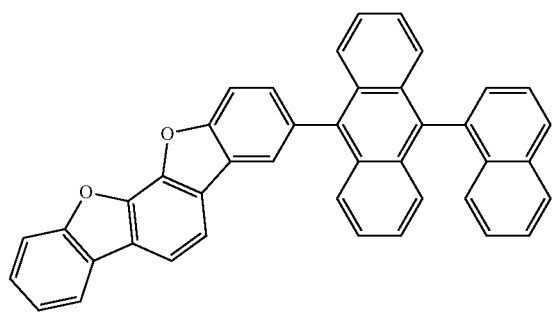

Electron-Donating Dopant Material

The organic EL device of the invention preferably comprises an electron-donating dopant material in the interfacial region between the cathode and the light emission unit. With such a construction, the organic EL device has an improved luminance and an elongated lifetime. The electron-donating dopant material is a metal having a work function of 3.8 eV or less or a compound containing such a metal. Examples thereof include at least one selected from an alkali metal, an alkali metal complex, an alkali metal compound, an alkaline earth metal, an alkaline earth metal complex, an alkaline earth metal compound, a rare earth metal, a rare earth metal complex, and a rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred. Examples of the alkaline earth metal compound include BaO, SrO, CaO, and a mixture thereof, such as $Ba_xSr_{1-x}O$ (0<x<1) and $Ba_xCA^1_{-x}O$ (0<x<1), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal are not particularly limited as long as containing at least one metal ion selected from alkali metal ions, alkaline earth metal ions, and rare earth metal ions, respectively. Examples of the ligand include quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and a derivative thereof.

The electron-donating dopant material is added to the interfacial region preferably into a form of layer or island. The electron-donating dopant material is added preferably by co-depositing the electron-donating dopant material with the organic compound (light emitting material, electron injecting material, etc.) for forming the interfacial region by a resistance heating deposition method, thereby dispersing the electron-donating dopant material into the organic material. The disperse concentration expressed by the molar ratio of the organic material and the electron-donating dopant material is 100:1 to 1:100.

When the electron-donating dopant material is formed into a form of layer, a light emitting material or an electron injecting material is made into a layer to form an interfacial organic layer, and then, the electron-donating dopant material alone is deposited by a resistance heating deposition method into a layer having a thickness preferably 0.1 to 15 nm. When the electron-donating dopant material is formed into a form of island, a light emitting material or an electron injecting material is made into a form of island to form an interfacial organic layer, and then, the electron-donating dopant material alone is deposited by a resistance heating deposition method into a form of island having a thickness preferably 0.05 to 1 nm.

The molar ratio of the main component and the electron-donating dopant material in the organic EL device is preferably 5:1 to 1:5.

Electron Transporting Layer

The electron transporting layer is an organic layer disposed between the light emitting layer and the cathode and transports electrons from the cathode to the light emitting layer. If two or more electron transporting layers are provided, the organic layer closer to the cathode may be called an electron injecting layer in some cases. The electron injecting layer injects electrons from the cathode to the organic layer unit efficiently.

An aromatic heterocyclic compound having one or more heteroatoms in its molecule is preferably used as the electron transporting material for the electron transporting layer, with a nitrogen-containing ring derivative being particularly preferred. The nitrogen-containing ring derivative is preferably an aromatic ring compound having a nitrogen-containing 6- or 5-membered ring or a fused aromatic ring compound having a nitrogen-containing 6- or 5-membered ring.

The nitrogen-containing ring derivative is preferably, for example, a chelate metal complex having a nitrogen-containing ring represented by formula (A):

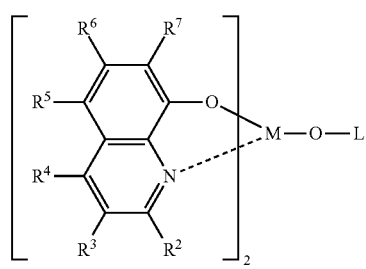

(A)

In formula (A), each of $R^2$ to $R^7$ is independently a hydrogen atom, a halogen atom, a hydroxyl group, an amino group, a hydrocarbon group having 1 to 40, preferably 1 to 20, more preferably 1 to 10, and still more preferably 1 to 6 carbon atoms, an alkoxy group having 1 to 40, preferably 1 to 20, more preferably 1 to 10, and still more preferably 1 to 6 carbon atoms, an aryloxy group having 6 to 40, preferably 6 to 20, more preferably 6 to 12 ring carbon atoms, an alkoxycarbonyl group having 2 to 40, preferably 2 to 20, more preferably 2 to 10, and still more preferably 2 to 5 carbon atoms, or an aromatic heterocyclic group having 9 to 40, preferably 9 to 30, more preferably 9 to 20 ring atoms, each optionally having a substituent.

M is aluminum (Al), gallium (Ga), or indium (In), with In being preferred.

L is a group represented by formula (A') or (A"):

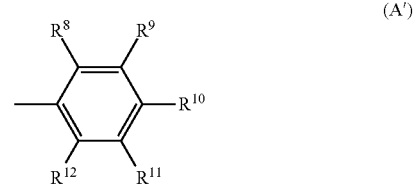

(A')

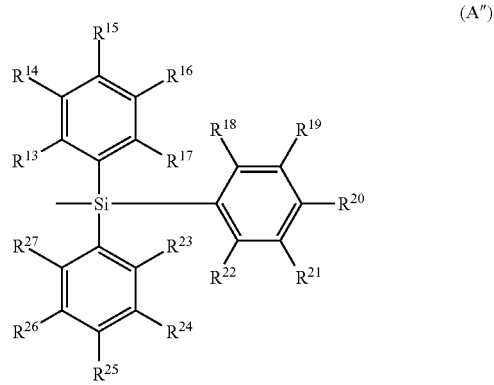

(A")

each of $R^8$ to $R^{12}$ in formula (A') is independently a hydrogen atom or a substituted or unsubstituted hydrocarbon group having 1 to 40, preferably 1 to 20, more preferably 1 to 10, and still more preferably 1 to 6 carbon atoms, and adjacent groups may form a ring structure; and $R^{13}$ to $R^{27}$ in formula (A") each independently represent a hydrogen atom or a substituted or unsubstituted hydrocarbon group having 1 to 40, preferably 1 to 20, more preferably 1 to 10, and still more preferably 1 to 6 carbon atoms, and adjacent groups may form a ring structure.

Examples of the hydrocarbon group having 1 to 40 carbon atoms represented by $R^8$ to $R^{12}$ of formula (A') and $R^{13}$ to $R^{27}$ of formula (A") are the same as mentioned above with respect to $R^2$ to $R^7$ of formula (A).

Examples of the divalent group to be formed when adjacent groups selected from $R^8$ to $R^{12}$ and $R^{13}$ to $R^{27}$ form a ring structure include a tetramethylene group, a pentamethylene group, a hexamethylene group, a diphenylmethane-2,2'-diyl group, a diphenylethane-3,3'-diyl group, and a diphenylpropane-4,4'diyl group.

The electron transporting compound for the electron transporting layer is preferably a metal complex, such as 8-hydroxyquinoline or its derivative, an oxadiazole derivative, and a nitrogen-containing heterocyclic derivative.

Electron transporting compounds which have a good thin film-forming property are preferably used. Examples of the electron transporting compound are shown below.

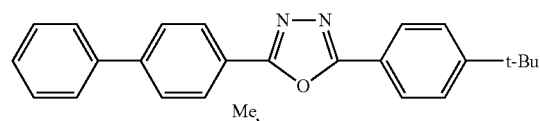
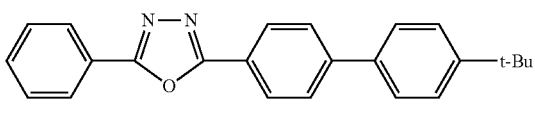
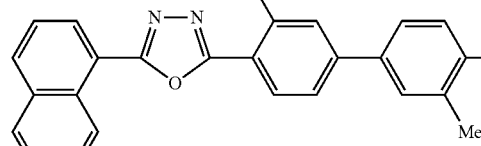
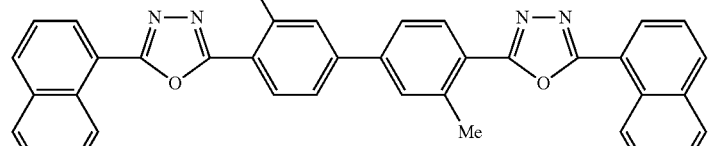
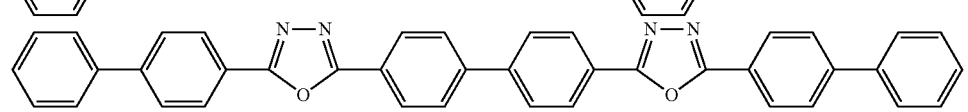
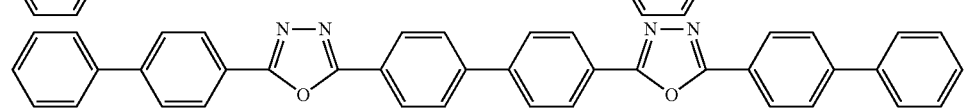
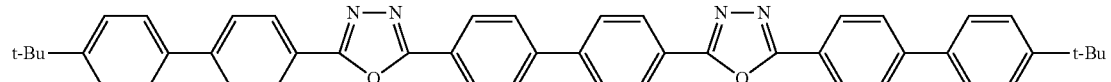
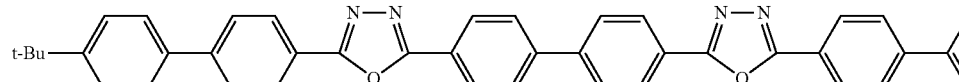
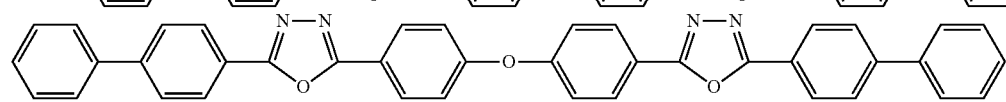
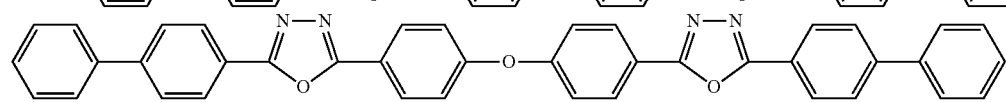

Examples of the nitrogen-containing heterocyclic derivative for use as the electron transporting compound include a nitrogen-containing compound other than a metal complex, for example, a compound having the nitrogen-containing heterocyclic group represented by any of the following formulae is preferably used.

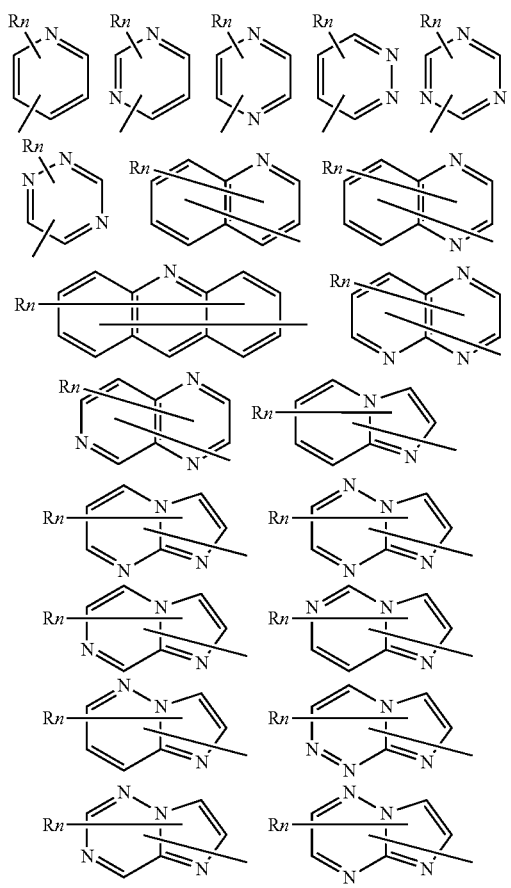

-continued

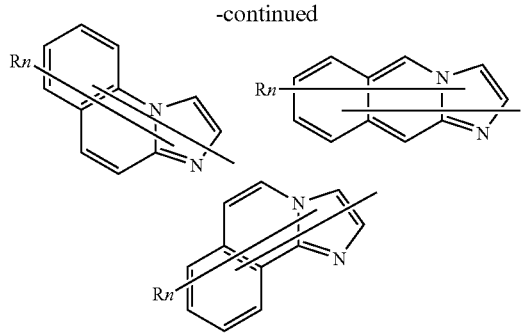

wherein, R is an aromatic hydrocarbon group or a fused aromatic hydrocarbon group each having 6 to 40 carbon atoms, an aromatic heterocyclic group or a fused aromatic heterocyclic group each having 3 to 40 carbon atoms, an alkyl group having 1 to 20 carbon atoms, or an alkoxy group having 1 to 20 carbon atoms; n is an integer of 0 to 5; and when n is an integer of 2 or more, R groups may by the same or different.

The electron transporting layer of the organic EL of the invention particularly preferably comprises at least one of the nitrogen-containing heterocyclic derivatives represented by formulae (60) to (62);

(60)

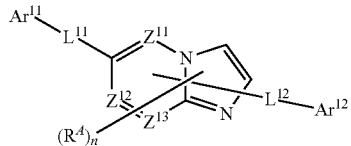

(61)

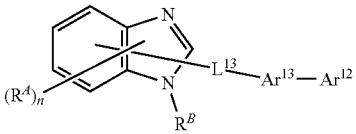

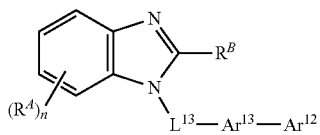

(62)

wherein:

each of $Z^{11}$, $Z^{12}$, and $Z^{13}$ is independently a nitrogen atom or a carbon atom;

each of $R^A$ and $R^B$ is independently a substituted or unsubstituted aryl group having 6 to 50, preferably 6 to 30, more preferably 6 to 20, and still more preferably 6 to 12 ring carbon atoms, a substituted or unsubstituted heterocyclic group having 5 to 50, preferably 5 to 30, more preferably 5 to 20, and still more preferably 5 to 12 ring atoms, a substituted or unsubstituted alkyl group having 1 to 20, preferably 1 to 10, and more preferably 1 to 6 carbon atoms, a substituted or unsubstituted haloalkyl group having 1 to 20, preferably 1 to 10, and more preferably 1 to 6 carbon atoms, or a substituted or unsubstituted alkoxyl group having 1 to 20, preferably 1 to 10, and more preferably 1 to 6 carbon atoms;

n is an integer of 0 to 5, when n is an integer of 2 or more, groups $R^A$ may be the same or different from each other, and adjacent two groups $R^A$ may bond to each other to form a substituted or unsubstituted hydrocarbon ring;

$Ar^{11}$ represents a substituted or unsubstituted aryl group having 6 to 50, preferably 6 to 30, more preferably 6 to 20, and still more preferably 6 to 12 ring carbon atoms or a substituted or unsubstituted heterocyclic group having 5 to 50, preferably 5 to 30, more preferably 5 to 20, and still more preferably 5 to 12 ring atoms;

$Ar^{12}$ represents a hydrogen atom, a substituted or unsubstituted alkyl group having 1 to 20, preferably 1 to 10, and more preferably 1 to 6 carbon atoms, a substituted or unsubstituted haloalkyl group having 1 to 20, preferably 1 to 10, and more preferably 1 to 6 carbon atoms, a substituted or unsubstituted alkoxyl group having 1 to 20, preferably 1 to 10, and more preferably 1 to 6 carbon atoms, a substituted or unsubstituted aryl group having 6 to 50, preferably 6 to 30, more preferably 6 to 20, and still more preferably 6 to 12 ring carbon atoms, or a substituted or unsubstituted heterocyclic group having 5 to 50, preferably 5 to 30, more preferably 5 to 20, and still more preferably 5 to 12 ring atoms;

provided that one of $Ar^{11}$ and $Ar^{12}$ is a substituted or unsubstituted fused aromatic hydrocarbon group having 10 to 50, preferably 10 to 30, more preferably 10 to 20, and still more preferably 10 to 14 ring carbon atoms or a substituted or unsubstituted fused aromatic heterocyclic group having 9 to 50, preferably 9 to 30, more preferably 9 to 20, and still more preferably 9 to 14 ring atoms;

$Ar^{13}$ represents a substituted or unsubstituted arylene group having 6 to 50, preferably 6 to 30, more preferably 6 to 20, and still more preferably 6 to 12 ring carbon atoms or a substituted or unsubstituted heteroarylene group having 5 to 50, preferably 5 to 30, more preferably 5 to 20, and still more preferably 5 to 12 ring atoms; and each of $L^1$, $L^2$, and $L^3$ is independently a single bond, a substituted or unsubstituted arylene group having 6 to 50, preferably 6 to 30, more preferably 6 to 20, and still more preferably 6 to 12 ring carbon atoms or a substituted or unsubstituted divalent fused aromatic heterocyclic group having 9 to 50, preferably 9 to 30, more preferably 9 to 20, and still more preferably 9 to 14 ring atoms.

Examples of the nitrogen-containing heterocyclic derivatives represented by formulae (60) to (62) are shown below.

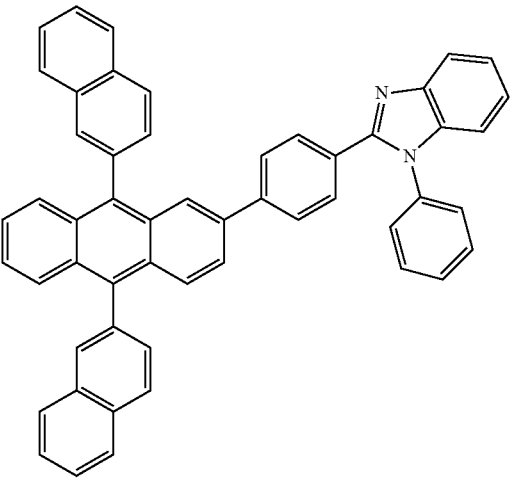

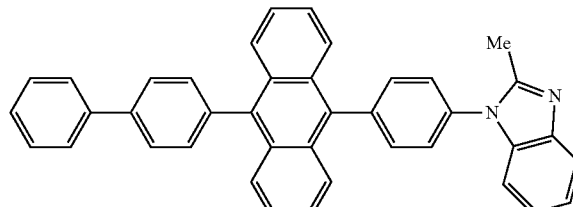

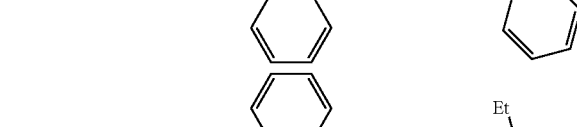

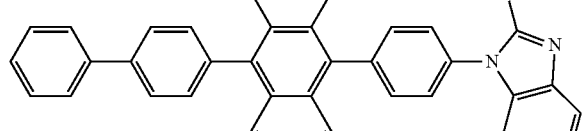

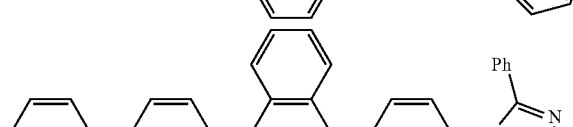

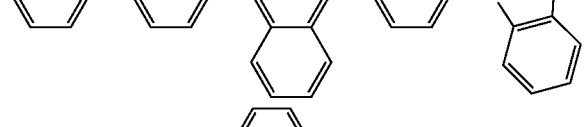

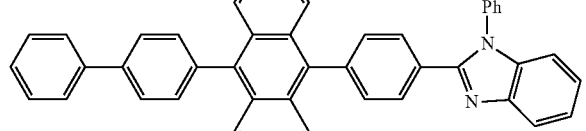

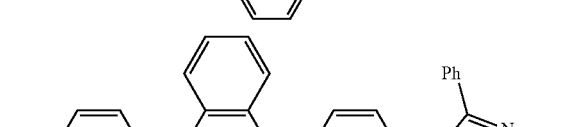

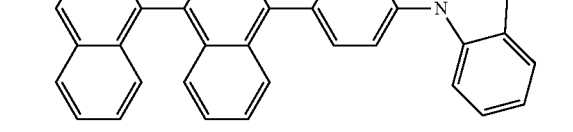

-continued

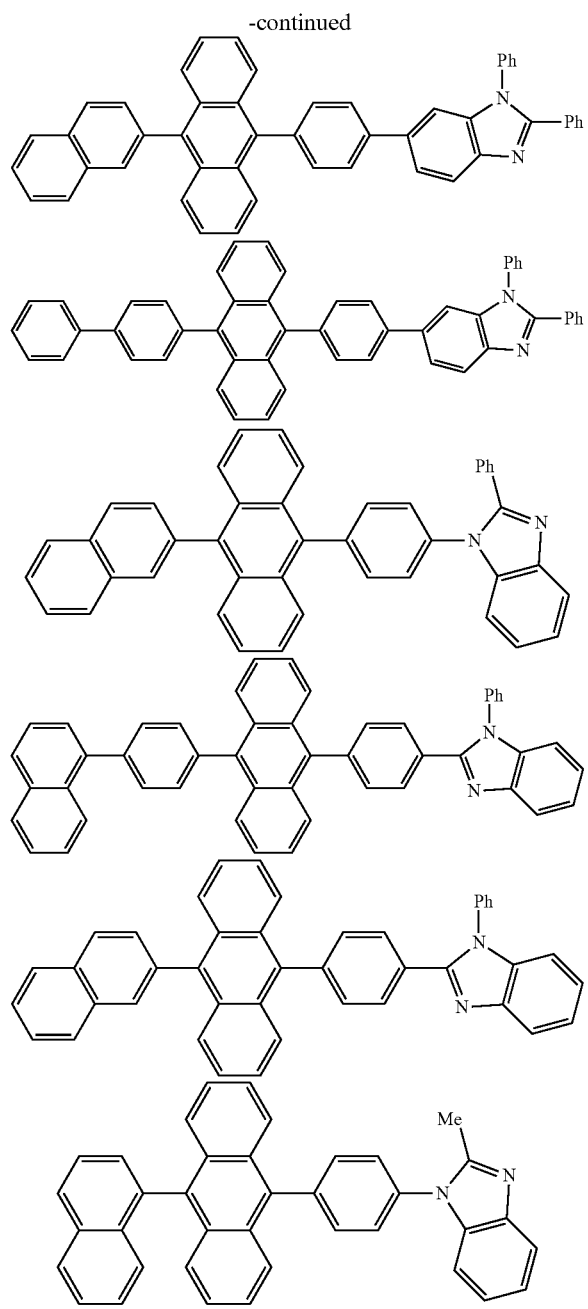

The electron transporting layer of the organic EL device of the invention may be a two-layered structure comprising a first electron transporting layer (anode side) and a second electron transporting layer (cathode side).

The thickness of the electron transporting layer is preferably 1 to 100 nm, although not particularly limited thereto. If the electron transporting layer is a two-layered structure comprising a first electron transporting layer (anode side) and a second electron transporting layer (cathode side), the thickness of the first electron transporting layer is preferably 5 to 60 nm and more preferably 10 to 40 nm, and the thickness of the second electron transporting layer is preferably 1 to 20 nm and more preferably 1 to 10 nm.

The electron injecting layer which may be formed adjacent to the electron transporting layer preferably includes an inorganic compound, such as an insulating material and a semiconductor, in addition to the nitrogen-containing ring derivative. The insulating material or semiconductor constituting the electron injecting layer effectively prevents the leak of electric current to enhance the electron injecting properties.

The insulating material is preferably at least one metal compound selected from the group consisting of an alkali metal chalcogenide, an alkaline earth metal chalcogenide, an alkali metal halide, and an alkaline earth metal halide. The alkali metal chalcogenide, etc. incorporated into the electron injecting layer further enhances the electron injecting properties. Preferred examples of the alkali metal chalcogenides include $Li_2O$, $K_2O$, $Na_2S$, $Na_2Se$, and $Na_2O$, and preferred examples of the alkaline earth metal chalcogenides include CaO, BaO, SrO, BeO, BaS, and CaSe. Preferred examples of the alkali metal halides include LiF, NaF, KF, LiCl, KCl, and NaCl. Examples of the alkaline earth metal halides include fluorides such as $CaF_2$, $BaF_2$, $SrF_2$, $MgF_2$, and $BeF_2$ and halides other than fluorides.

Examples of the semiconductor may include an oxide, a nitride or an oxynitride each containing at least one element selected from the group consisting of Ba, Ca, Sr, Yb, Al, Ga, In, Li, Na, Cd, Mg, Si, Ta, Sb and Zn. The semiconductor may be used singly or in combination of two or more. The inorganic compound forming the electron injecting layer preferably forms a microcrystalline or amorphous insulating thin film. When the electron injecting layer is formed from such an insulating thin film, the thin film is made more uniform to decrease the pixel defects such as dark spots. Examples of such an inorganic compound include an alkali metal chalcogenide, an alkaline earth metal chalcogenide, an alkali metal halide, and an alkaline earth metal halide.

The thickness of the layer including the insulating material or the semiconductor is preferably about 0.1 to 15 nm. The electron injecting layer may include the electron-donating dopant material described above.

Hole Transporting Layer

The hole transporting layer is an organic layer formed between the light emitting layer and the anode and has a function of transporting holes from the anode to the light emitting layer. When the hole transporting layer is formed by two or more layers, the layer closer to the anode may be defined as the hole injecting layer in some cases. The hole injecting layer has a function of efficiently injecting holes from the anode to the organic layer unit.

An aromatic amine compound, for example, an aromatic amine derivative represented by formula (I), is preferably used as the material for forming the hole transporting layer:

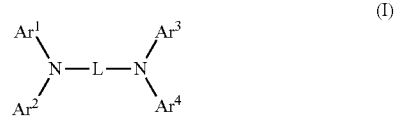

wherein:

each of $Ar^1$ to $Ar^4$ is a substituted or unsubstituted aromatic hydrocarbon group having 6 to 50, preferably 6 to 30, more preferably 6 to 20, and still more preferably 6 to 12 ring carbon atoms; a substituted or unsubstituted fused aromatic hydrocarbon group having 6 to 50, preferably 6 to 30, more preferably 6 to 20, and still more preferably 6 to 12 ring carbon atoms; a substituted or unsubstituted aromatic heterocyclic group having 5 to 50, preferably 5 to 30, more preferably 5 to 20, and still more preferably 5 to 12 ring atoms; a substituted or unsubstituted fused aromatic heterocyclic group having 5 to 50, preferably 5 to 30, more preferably 5 to 20, and still more preferably 5 to 12 ring atoms; or a group wherein the aromatic hydrocarbon group or the fused aromatic hydrocarbon group is bonded to the aromatic heterocyclic group or the fused aromatic heterocyclic group;

Ar$^1$ and Ar$^2$, or Ar$^3$ and Ar$^4$ may form a ring; and

L represents a substituted or unsubstituted aromatic hydrocarbon group having 6 to 50, preferably 6 to 30, more preferably 6 to 20, and still more preferably 6 to 12 ring carbon atoms; a substituted or unsubstituted fused aromatic hydrocarbon group having 6 to 50, preferably 6 to 30, more preferably 6 to 20, and still more preferably 6 to 12 ring carbon atoms; a substituted or unsubstituted aromatic heterocyclic group having 5 to 50, preferably 5 to 30, more preferably 5 to 20, and still more preferably 5 to 12 ring atoms; or a fused aromatic heterocyclic group having 5 to 50, preferably 5 to 30, more preferably 5 to 20, and still more preferably 5 to 12 ring atoms.

Examples of the compound represented by formula (I) are shown below.

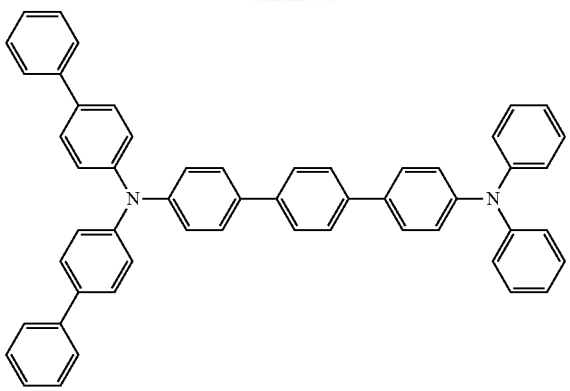

-continued

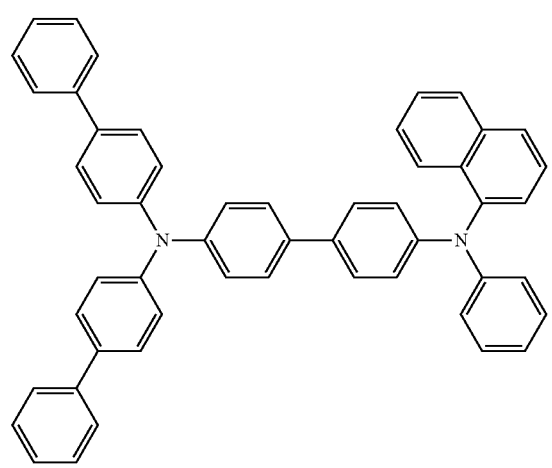

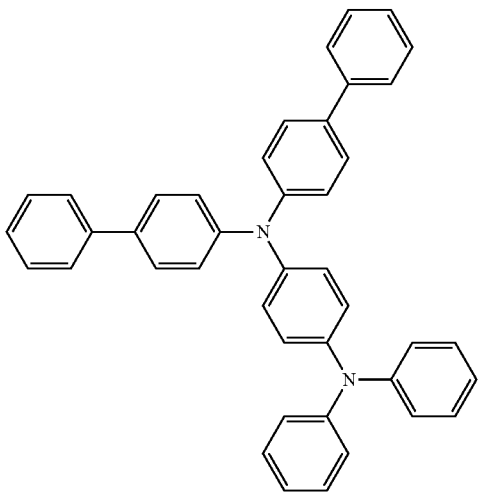

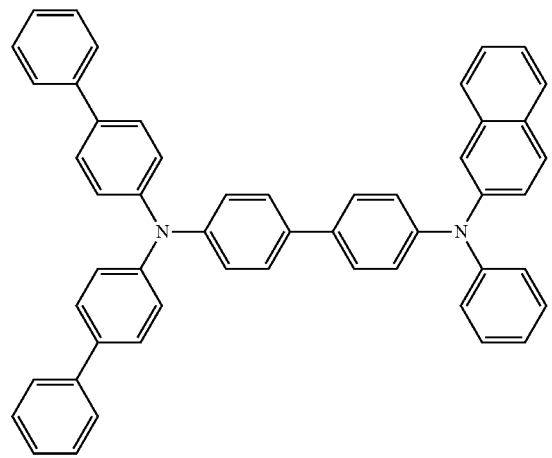

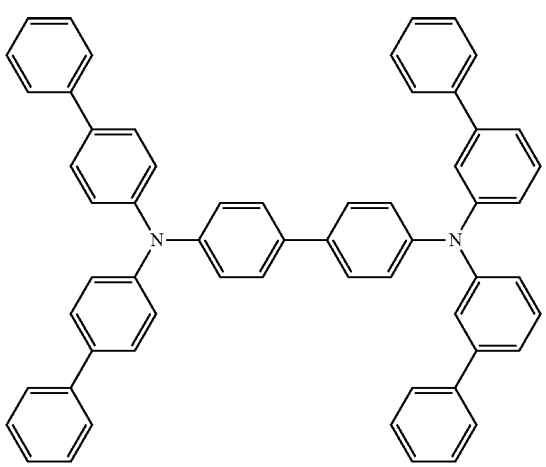

| 1399 -continued | 1400 -continued |
|---|---|
| 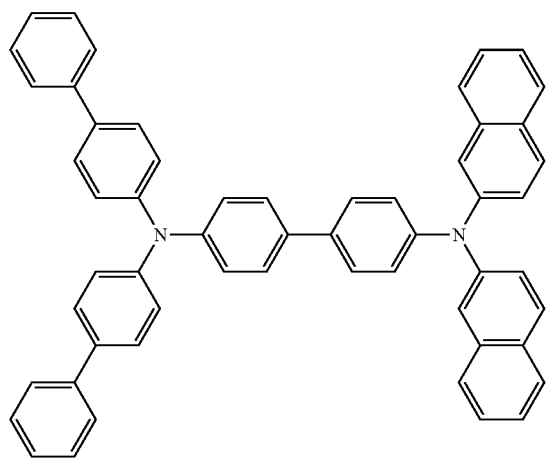 | 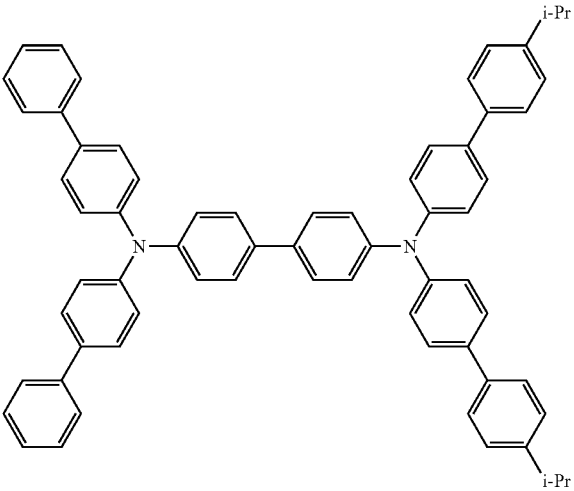 |
| 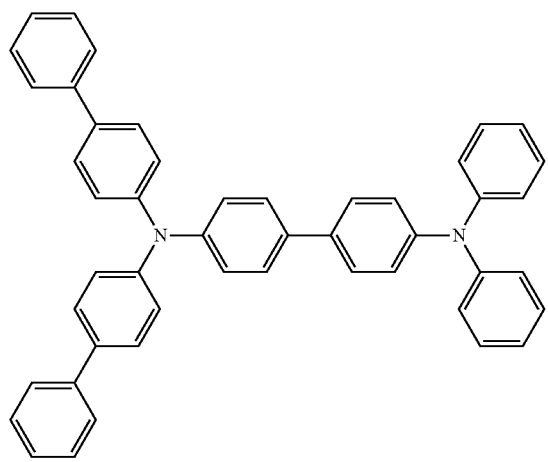 | 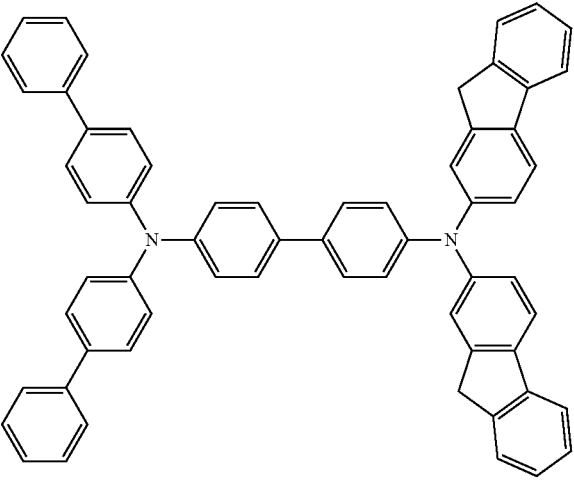 |
| 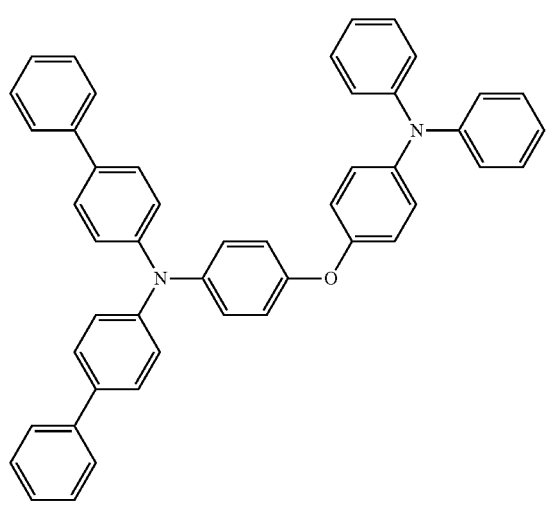 | 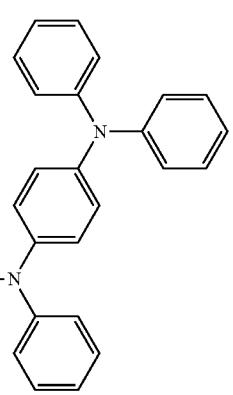 |

1401
-continued
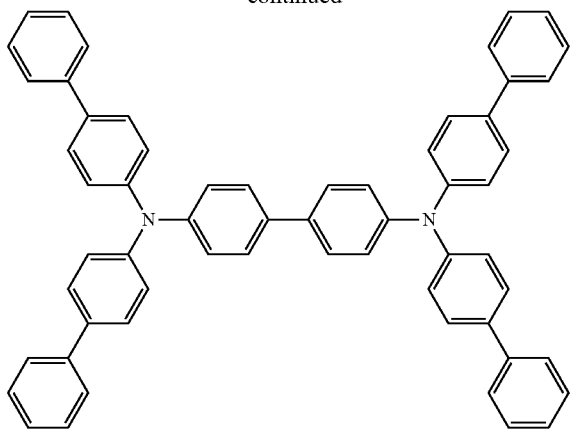
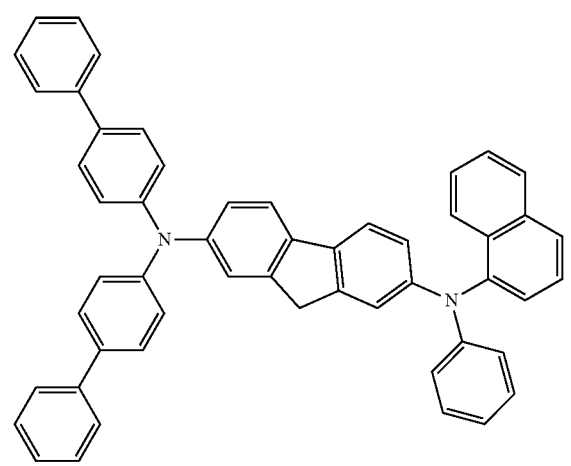
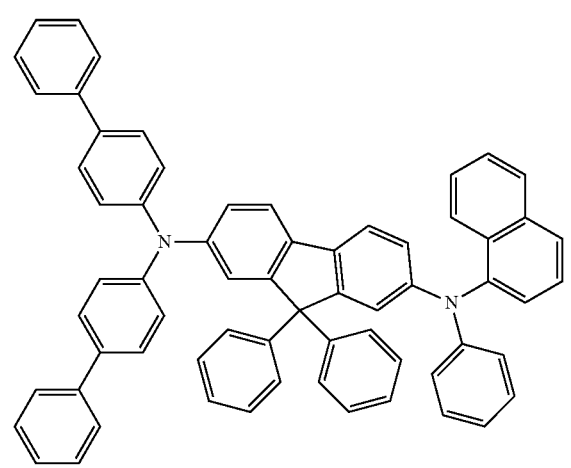
1402
-continued
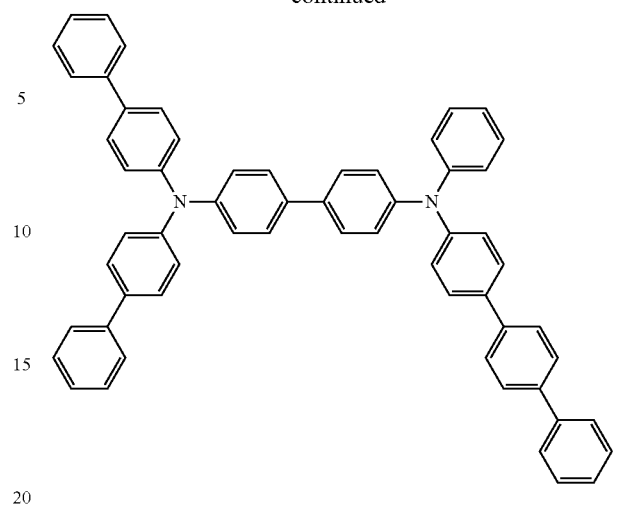
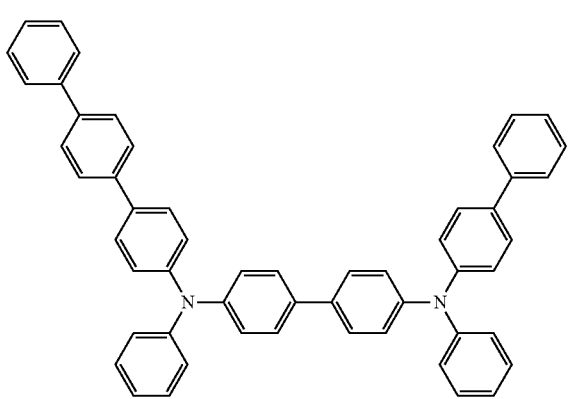
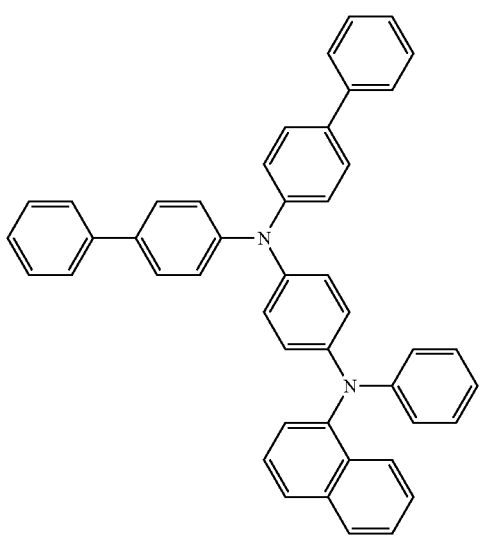

1403
-continued
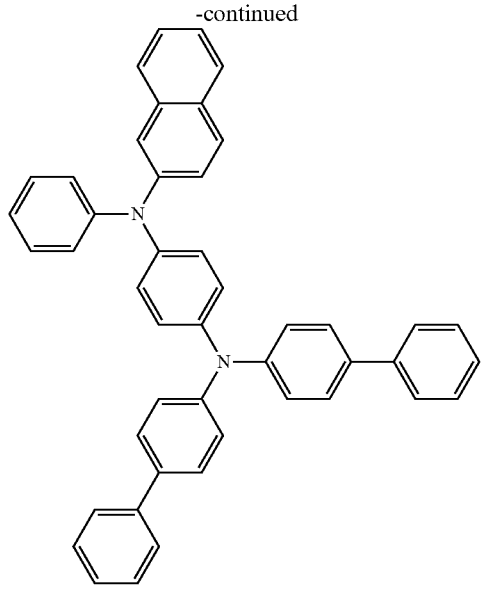
1404
-continued
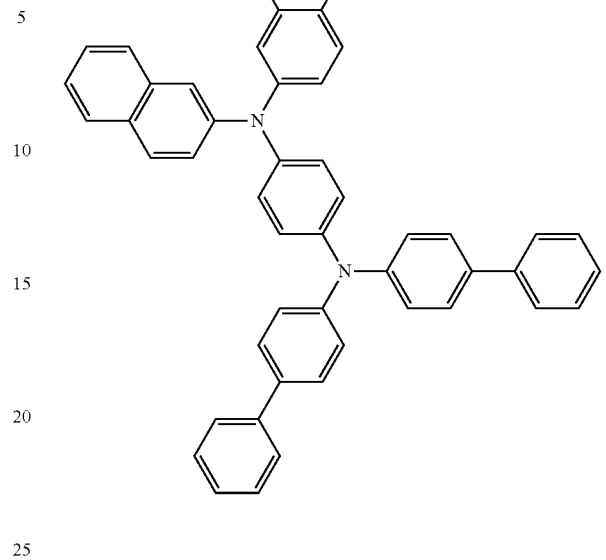
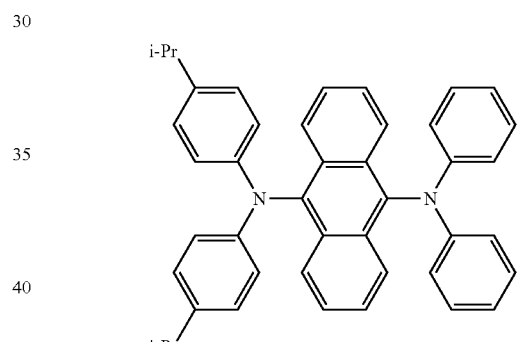
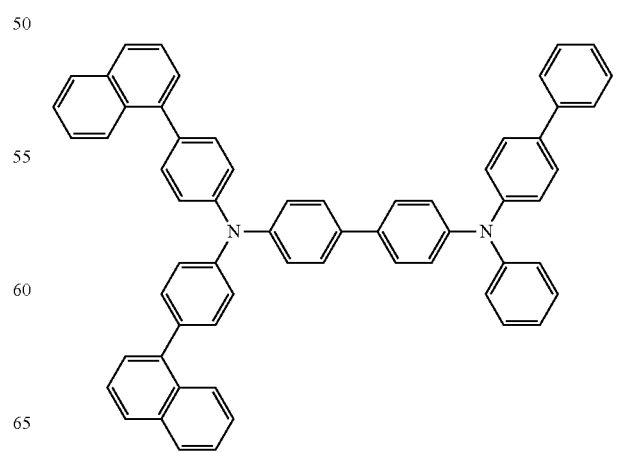

1405
-continued
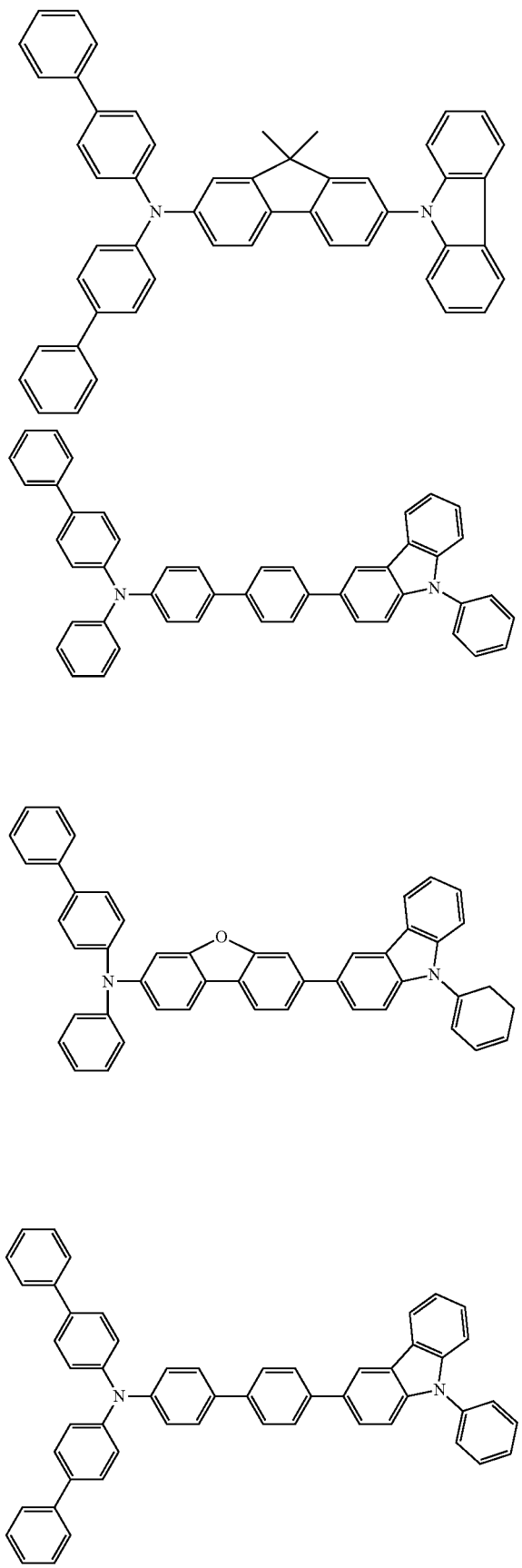
1406
-continued
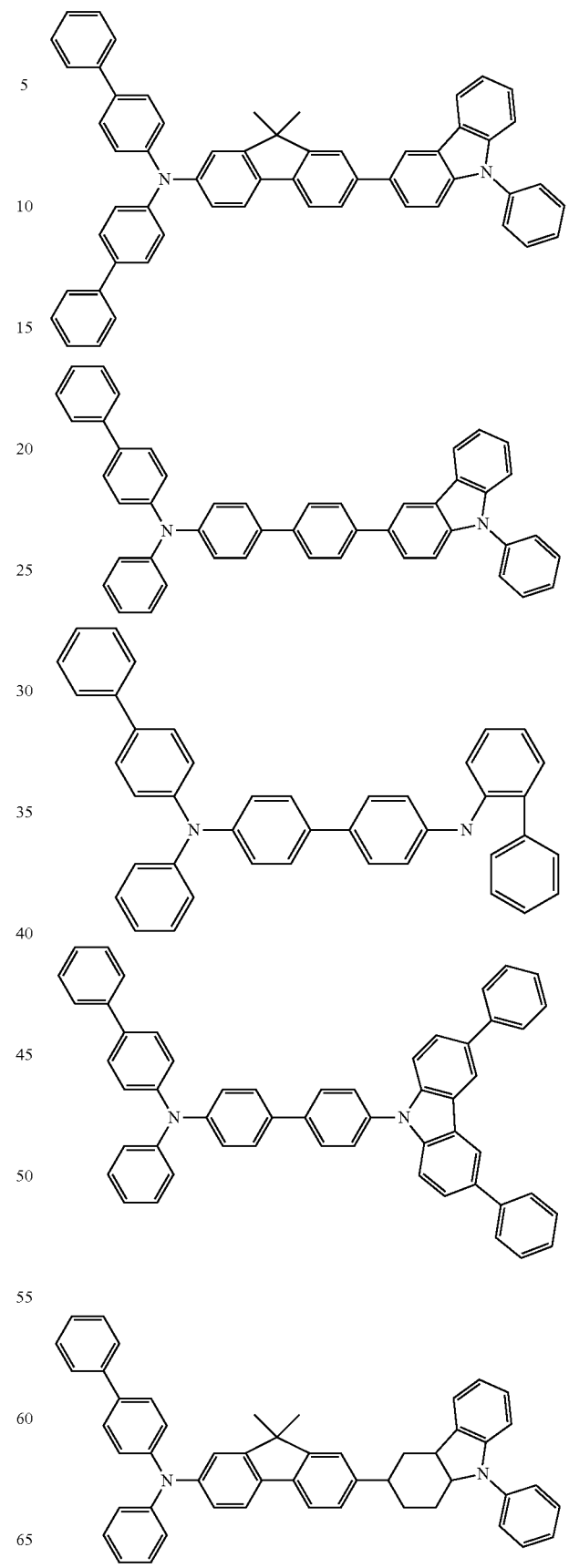

1407
-continued
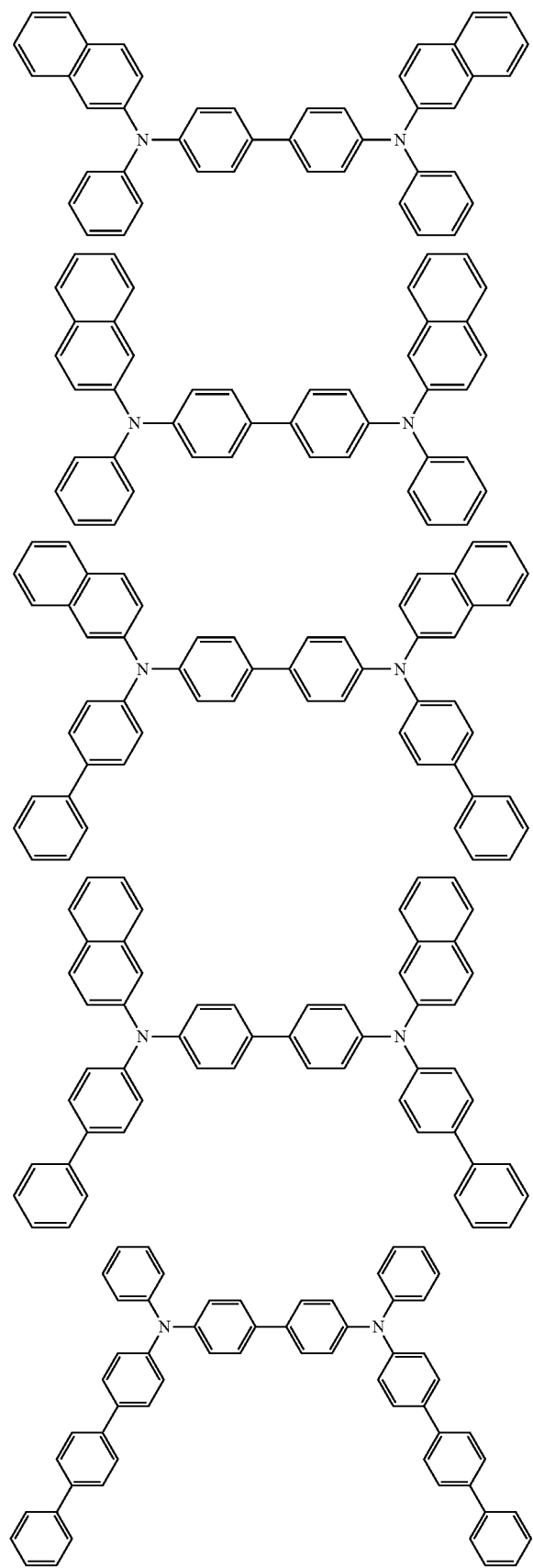
1408
-continued
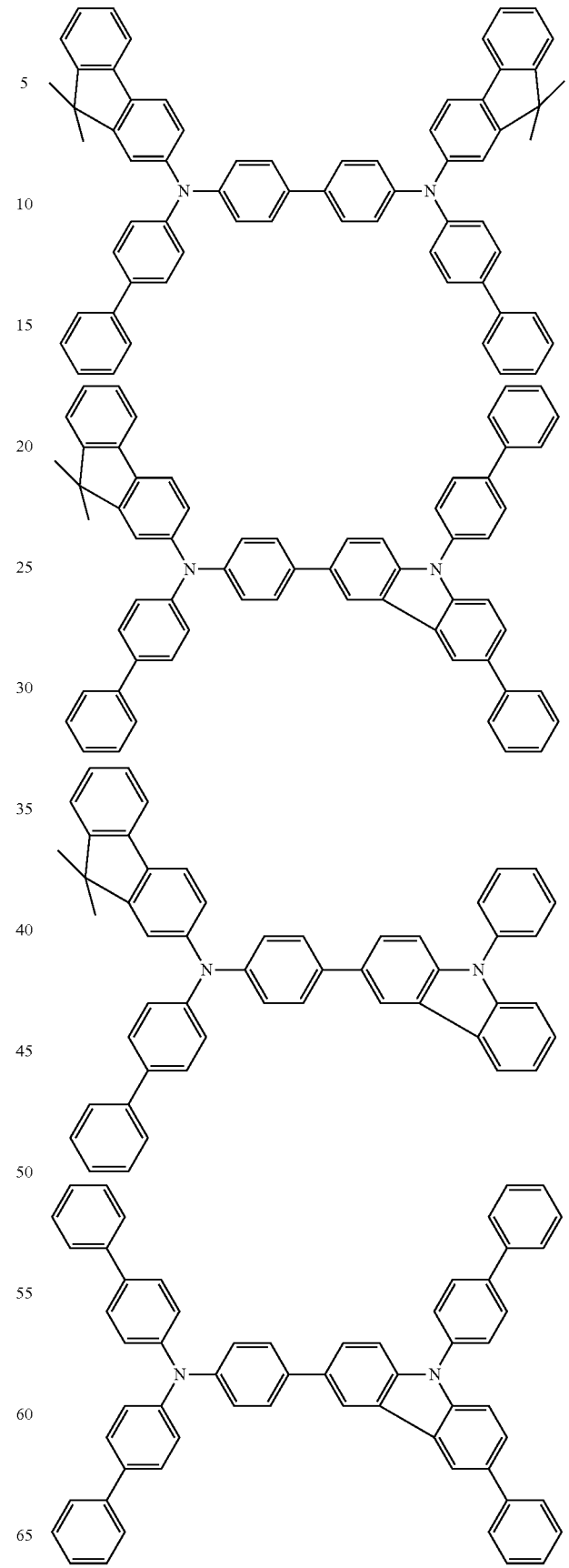

1409
-continued
1410
-continued
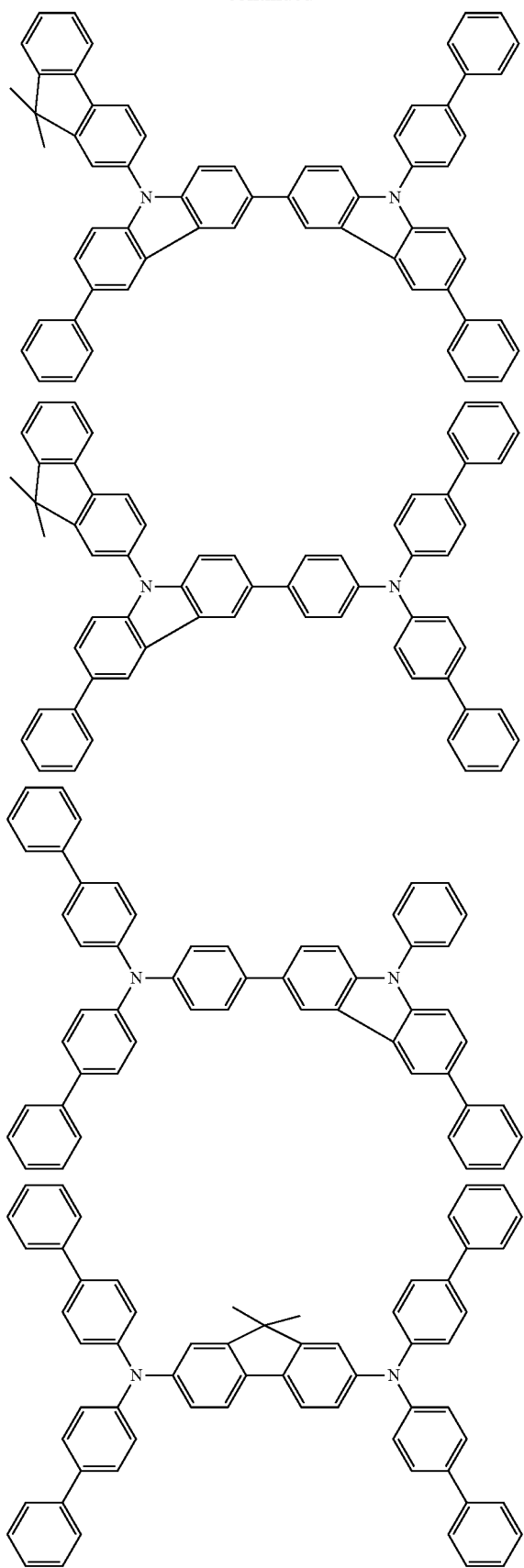
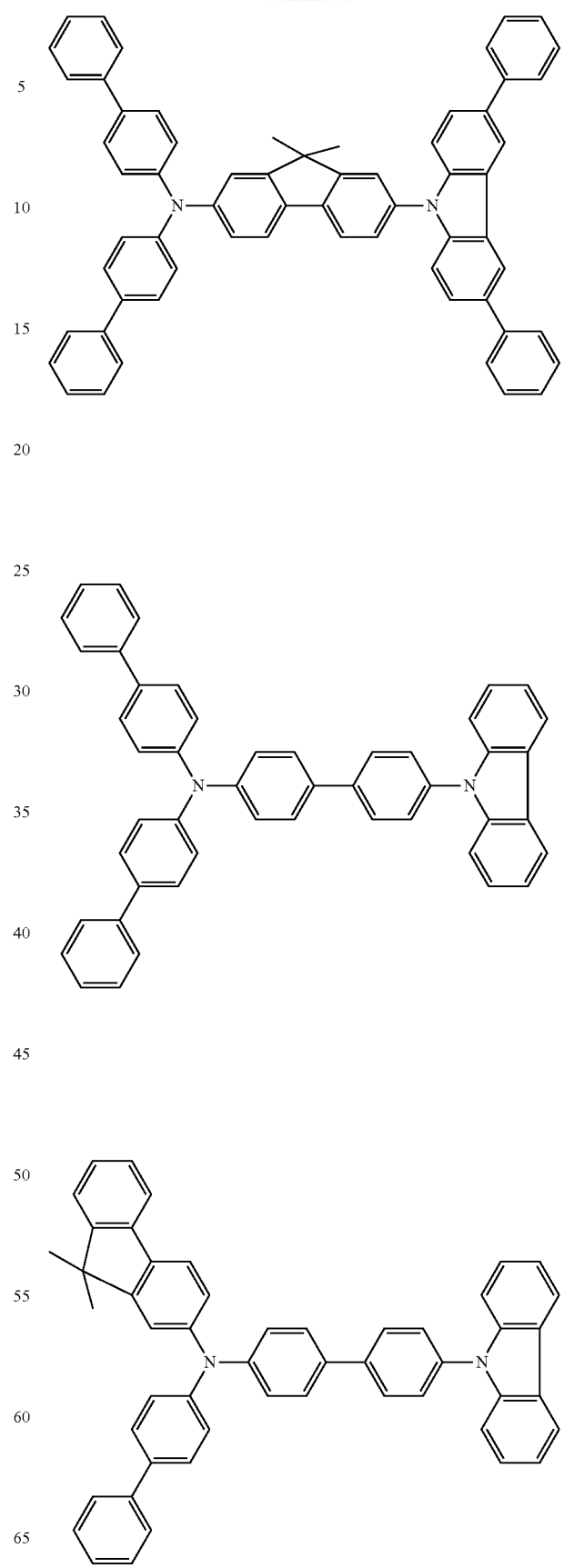

1411
-continued
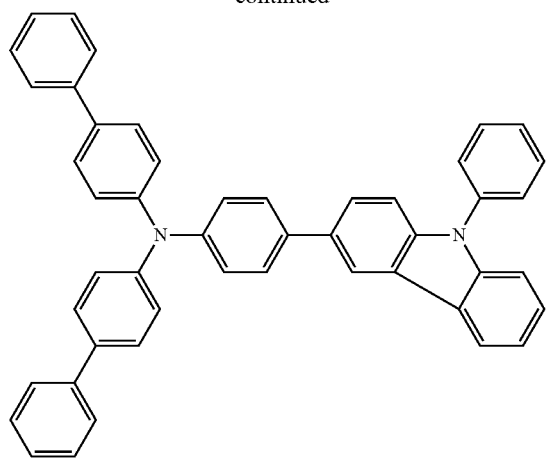
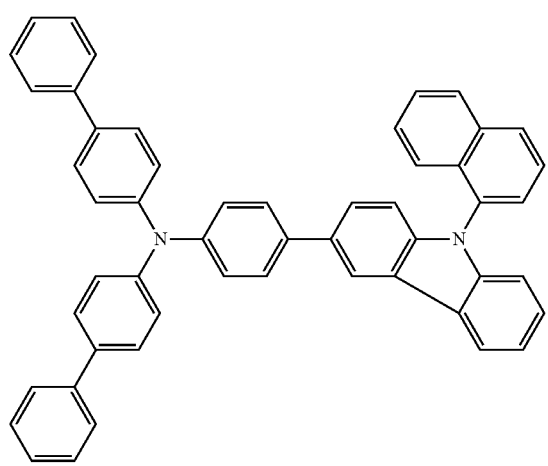
The aromatic amine represented by formula (II) is also preferably used as the material for forming the hole transporting layer:
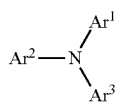 (II)
wherein $Ar^1$ to $Ar^3$ are as defined above with respect to $Ar^1$ to $Ar^4$ of formula (I). Examples of the compounds represented by formula (II) are shown below, although not limited thereto.
1412
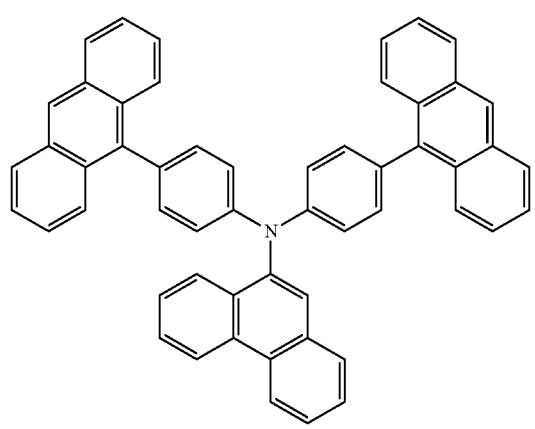

1413
-continued
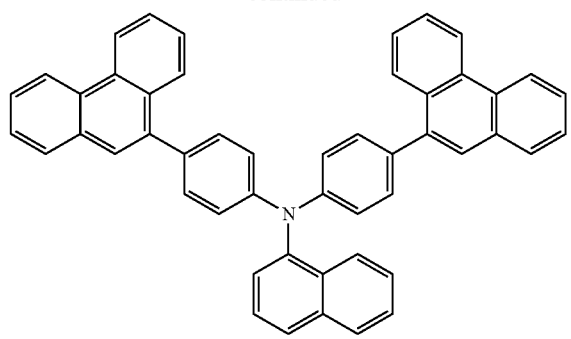
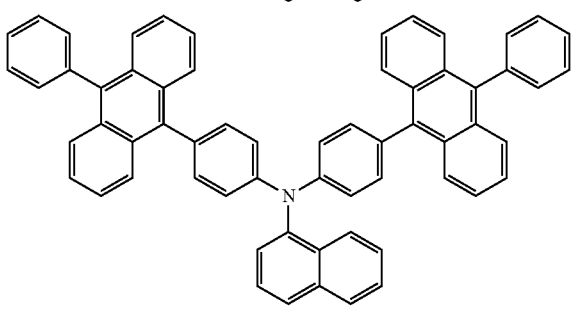
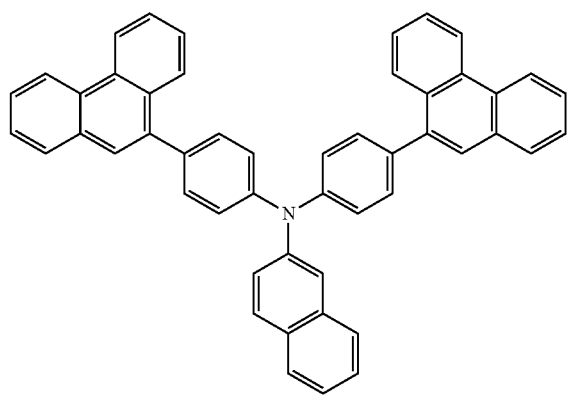
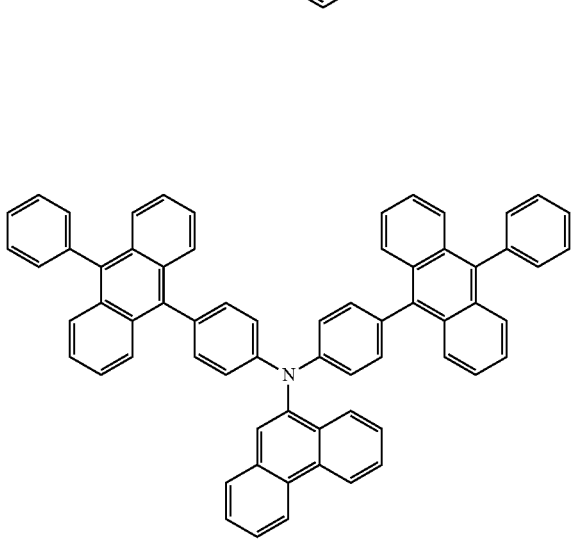
1414
-continued
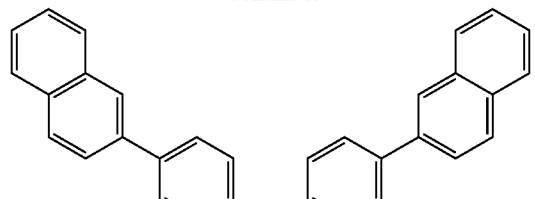
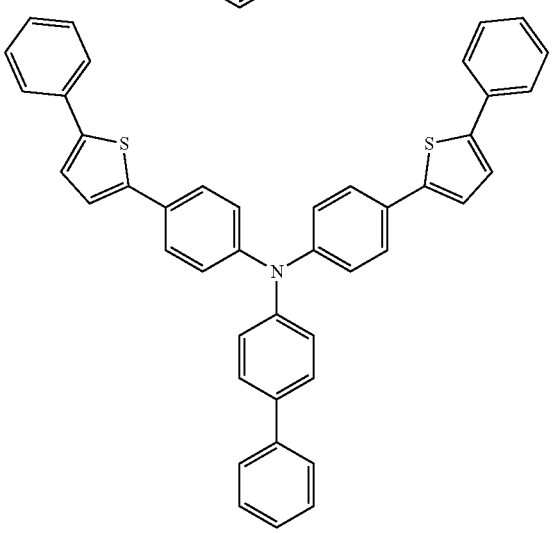
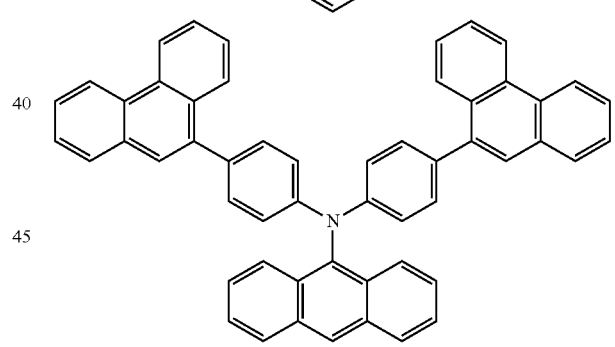
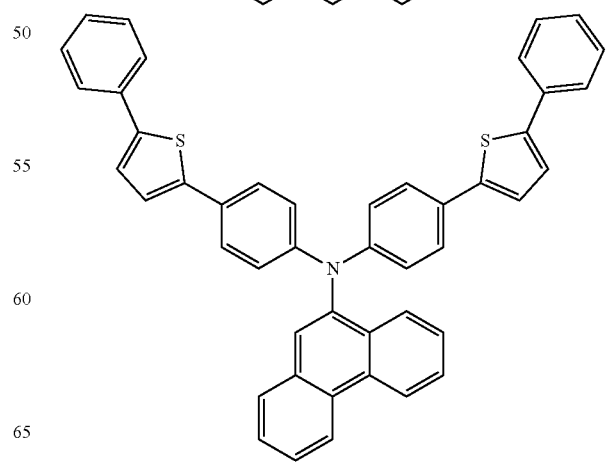

1415
-continued
1416
-continued
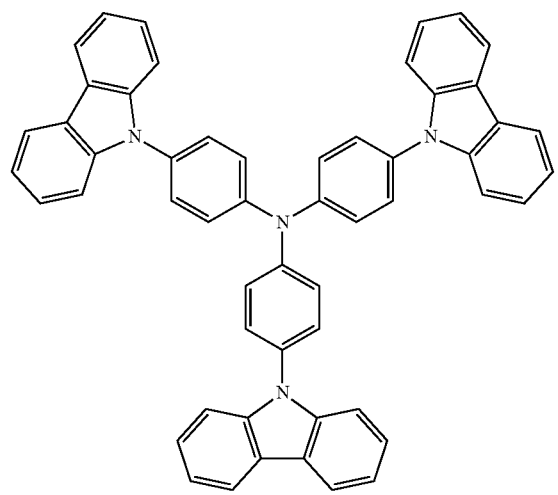
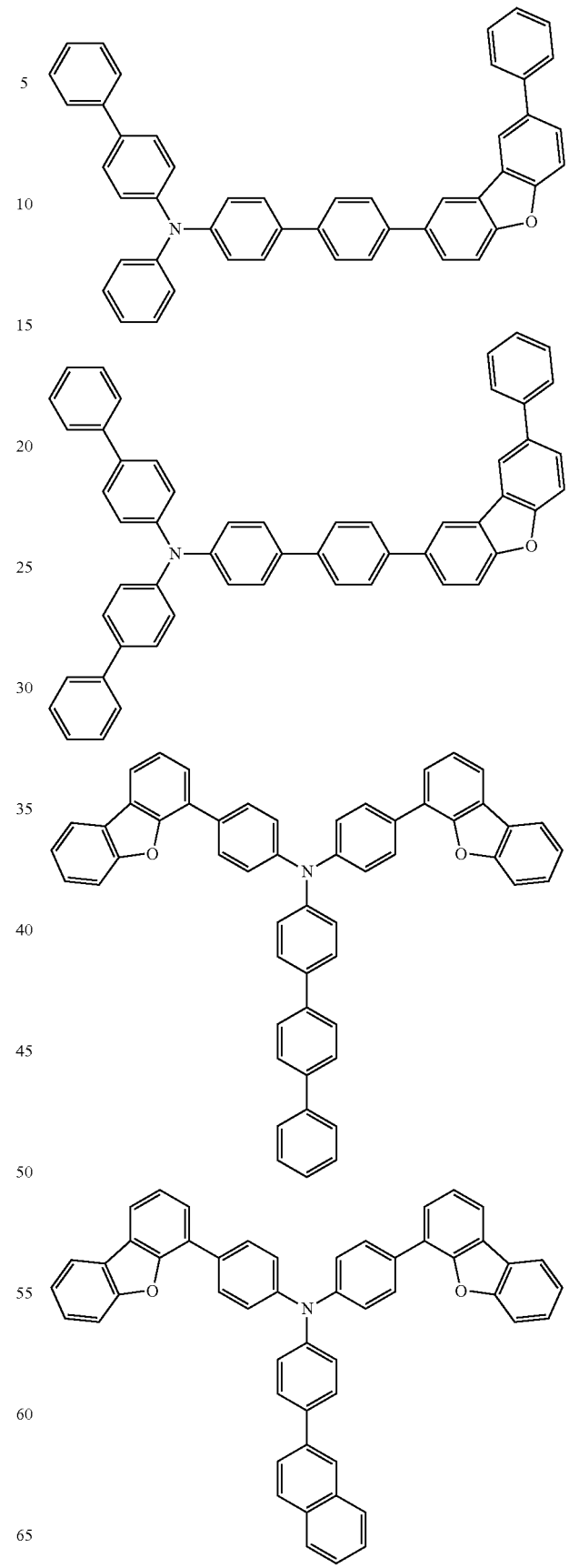

1417
-continued

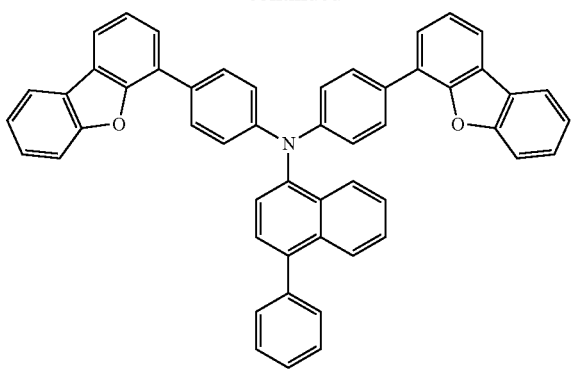

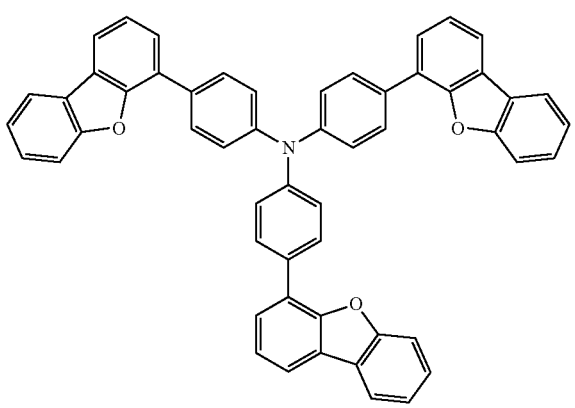

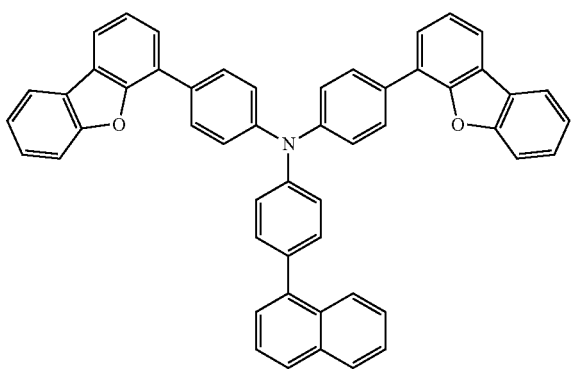

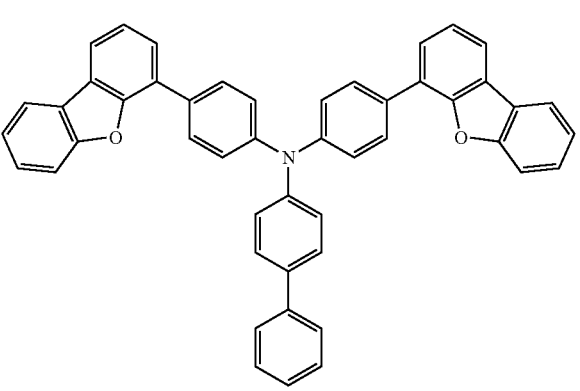

1418
-continued

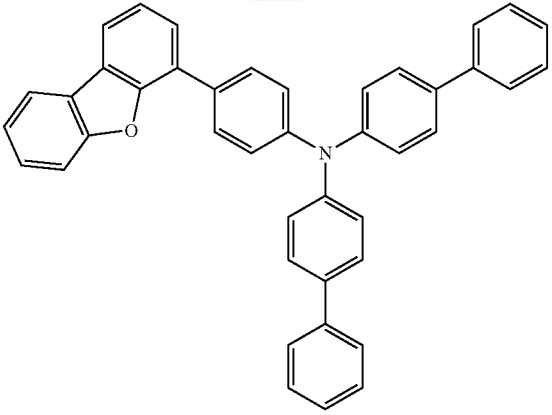

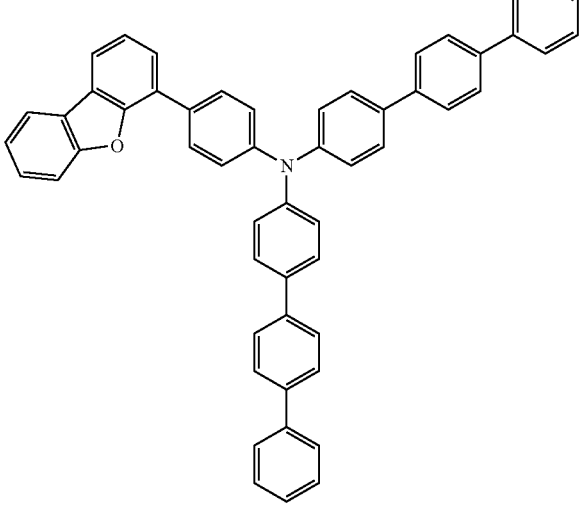

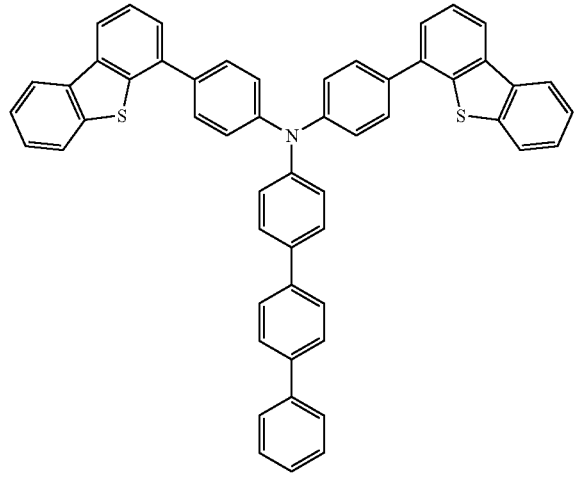

The hole transporting layer of the organic EL device of the invention may be made into a two-layered structure comprising a first hole transporting layer (anode side) and a second hole transporting layer (cathode side).

The thickness of the hole transporting layer is preferably 10 to 200 nm, although not particularly limited thereto. If the hole transporting layer is a two-layered structure comprising a first hole transporting layer (anode side) and a second hole transporting layer (cathode side), the thickness of the first hole transporting layer is preferably 50 to 150 nm and more preferably 50 to 110 nm, the thickness of the second hole transporting layer is preferably 5 to 50 nm and more preferably 5 to 30 nm.

The organic EL device of the invention may have a layer comprising an acceptor material which is attached to the anode side of the hole transporting layer or the first hole transporting layer. With such a layer, it is expected that the driving voltage is lowered and the production cost is reduced.

The acceptor material is preferably a compound represented by the following formula:

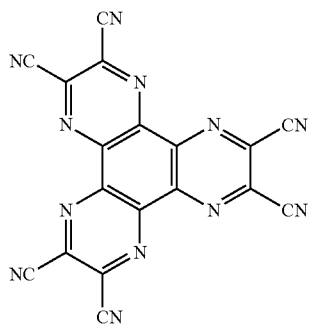 [SMILES: N#Cc1nc2c3nc(C#N)c(C#N)nc3c3nc(C#N)c(C#N)nc3c2nc1C#N]

The thickness of the layer comprising the acceptor material is preferably 5 to 20 nm, although not particularly limited thereto.

N/P Doping

The carrier injecting properties of the hole transporting layer and the electron transporting layer can be controlled by, as described in JP 3695714B, the doping (n) with a donor material or the doping (p) with an acceptor material.

A typical example of the n-doping is an electron transporting material doped with a metal, such as Li and Cs, and a typical example of the p-doping is a hole transporting material doped with an acceptor material, such as $F_4TCNQ$.

Space Layer

For example, when a fluorescent emitting layer and a phosphorescent emitting layer are laminated, a space layer may be disposed between the fluorescent emitting layer and the phosphorescent emitting layer to prevent the diffusion of excitons generated in the phosphorescent emitting layer into the fluorescent emitting layer or to control the carrier balance. The space layer may be disposed between phosphorescent emitting layers.

Since the space layer is disposed between light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described above with respect to the hole transporting layer are usable as the material for the space layer.

Blocking Layer

The organic EL device of the invention preferably comprises a blocking layer, such as an electron blocking layer, a hole blocking layer, and a triplet blocking layer, which is disposed adjacent to the light emitting layer. The electron blocking layer is a layer which prevents the diffusion of electrons from a light emitting layer to a hole transporting layer and formed between the light emitting layer and the hole transporting layer. The hole blocking layer is a layer which prevents the diffusion of holes from a light emitting layer to an electron transporting layer and formed between the light emitting layer and the electron transporting layer.

The triplet blocking layer prevents the diffusion of triplet excitons generated in the light emitting layer to adjacent layers and confines the triplet excitons in the light emitting layer, thereby preventing the deactivation of energy on molecules other than the emitting dopant of triplet excitons, for example, on molecules in the electron transporting layer.

The electron mobility of the electron injecting layer is preferably $10^{-6}$ cm$^2$/Vs or more at an electric field strength in a range of 0.04 to 0.5 MV/cm. Within the above range, the injection of electrons from the cathode to the electron transporting layer is promoted and the injection of electrons to the adjacent blocking layer and light emitting layer is also promoted, thereby enabling to drive a device at lower voltage.

Electronic Device

Since the organic EL device comprising the compound of the invention is further improved in the emission efficiency, the organic EL device is usable in an electronic device, for example, as display parts, such as organic EL panel module, display devices of television sets, mobile phones, personal computer, etc., and light emitting sources of lighting equipment and vehicle lighting equipment.

EXAMPLES

The present invention will be described in more detail with reference to the examples. However, it should be noted that the scope of the invention is not limited to the following examples.

Synthesis Example 1 (Synthesis of Aromatic Heterocyclic Derivative (E1))

(1) Synthesis of Intermediate 1

Under argon atmosphere, a solution of 1-bromonaphtharene (110.5 g, 533.6 mmol) in tetrahydrofuran (1 L) was added to magnesium (14.0 g, 576.0 mmol) dropwise. After stirring the resultant solution at 25° C. for 1 h, a tetrahydrofuran solution (100 mL) of 1-naphthoaldehyde (113.1 g, 724.2 mmol) was added dropwise at room temperature and the resultant solution was stirred at 20° C. for 1.5 h. After the reaction, a 2 N hydrochloric acid (300 mL) was added and the stirring was continued for 30 min. Then, the solution was extracted with toluene (800 mL). The collected organic layer was concentrated and the obtained solid was washed with ethanol to obtain a white solid (91.3 g), which was identified as the following intermediate 1 by FD-MS analysis (Field Desorption Mass Spectrometry) (m/e=284 for molecular weight of 284.35). The yield was 60%.

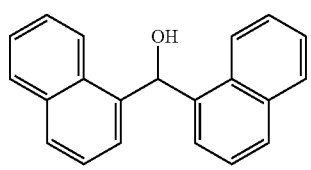

Intermediate 1

(2) Synthesis of Intermediate 2

Into phosphoric acid (1.65 L) heated to 150° C., the intermediate 1 (87.8 g, 308.8 mmol) was added little by little, and the resultant mixture was stirred for 40 h under heating. After the reaction, the reaction liquid was left to stand for cooling to room temperature, poured into iced water (1 L), and then extracted with toluene. The organic layer was concentrated and the obtained solid was purified by silica gel column chromatography to obtain a white solid (36.9 g), which was identified as the following intermediate 2 by FD-MS analysis (m/e=266 for molecular weight of 266.34). The yield was 45%.

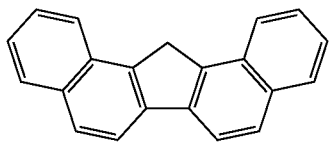

Intermediate 2

(3) Synthesis of Intermediate 3

Into a solution of intermediate 2 (15.0 g, 56.3 mmol) in pyridine (1 L), a 40% methanol solution (60 mL) of benzyltrimethylammonium hydroxide (Triton-B) was added dropwise at room temperature. After stirring for 30 min, the resultant solution was added slowly to concentrated hydrochloric acid under cooling with ice and then extracted with dichloromethane. The organic layer was concentrated and the obtained solid was purified by silica gel column chromatography to obtain a brown solid (9.3 g), which was identified as the following intermediate 3 by FD-MS analysis (m/e=280 for molecular weight of 280.32). The yield was 59%.

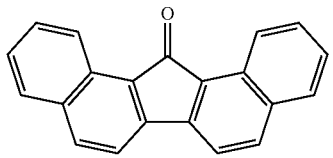

Intermediate 3

(4) Synthesis of Intermediate 4

Under argon atmosphere, a 0.5 M diethyl ether solution (60.8 mL, 30.4 mmol) of 2-biphenylmagnesium bromide was cooled to −20° C. The intermediate 3 (6.0 g, 21.4 mmol) was added to the solution little by little, while allowing the temperature to gradually rise to room temperature, and the solution was stirred at room temperature for 5 h. Then, the stirring was further continued for 5 h by refluxing under heating. After the reaction, the solution was cooled to room temperature. After adding a saturated aqueous solution of ammonium chloride, the solution was extracted with ethyl acetate. The organic layer was concentrated and the obtained solid was purified by silica gel column chromatography to obtain a white solid (6.5 g), which was identified as the following intermediate 4 by FD-MS analysis (m/e=434 for molecular weight of 434.53). The yield was 58%.

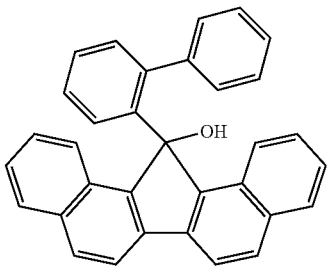

Intermediate 4

(5) Synthesis of Intermediate 5

Acetic acid (500 mL) was added to the intermediate 4 (5.0 g, 11.5 mmol), to which concentrated hydrochloric acid (10 mL) was added dropwise while stirring at 140° C. under heating. The reaction was allowed to proceed at 140° C. for 8 h. After the reaction, the reaction liquid was left to stand for cooling to room temperature and the precipitated solid was collected by filtration. The obtained solid was washed with ethanol to obtain a white solid (2.8 g), which was identified as the following intermediate 5 by FD-MS analysis (m/e=416 for molecular weight of 416.51). The yield was 58%.

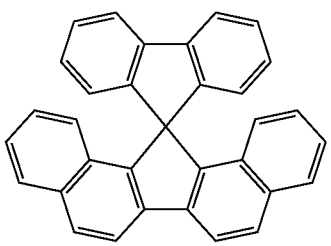

Intermediate 5

(6) Synthesis of Intermediate 6

Under argon atmosphere, into a solution of the intermediate 5 (2.8 g, 6.7 mmol) in dichloromethane (22 mL), a solution of bromine (0.90 g, 5.6 mmol) in dichloromethane (18 mL) was added dropwise under cooling with ice. The reaction was allowed to proceed overnight. After adding an aqueous solution of sodium hydrogen carbonate, the reaction mixture was extracted with dichloromethane and the solvent was evaporated off under reduced pressure. The obtained residue was purified by recrystallization to obtain a white solid (1.33 g), which was identified as the following intermediate 6 by FD-MS analysis (m/e=495 for molecular weight of 495.41). The yield was 40%.

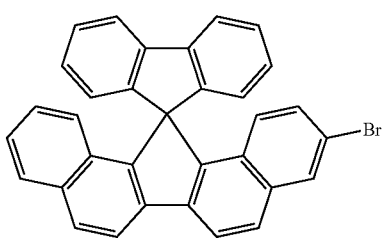

Intermediate 6

(7) Synthesis of Intermediate 7

Under argon atmosphere, into a solution of the intermediate 6 (0.99 g, 2.0 mmol) in anhydrous THF (20 mL), a 1.6 M hexane solution (3.2 mL, 2.0 mmol) of n-butyllithium was added while stirring the solution at −40° C. The solution was further stirred for one hour while heating to 0° C. Then, the solution was cooled again to −78° C. After adding a solution of trimethyl borate (0.52 g, 5.0 mmol) in dry THF (5 mL) dropwise, the solution was stirred at room temperature for 5 h. After adding a 1 N hydrochloric acid (20 mL), the stirring was continued for one hour, and then the aqueous layer was removed.

The organic layer was dried over magnesium sulfate and the solvent was evaporated off under reduced pressure. The obtained solid was washed with toluene to obtain a white solid (0.66 g). The yield was 72%.

Intermediate 7

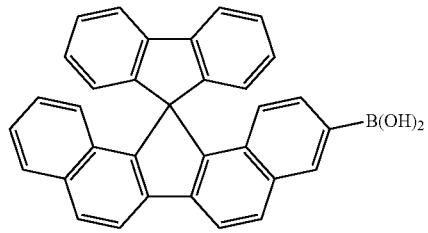

(8) Synthesis of Aromatic Heterocyclic Derivative (E1)

Under argon atmosphere, into a mixture of the intermediate 7 (0.66 g, 1.4 mmol), 2-chloro-4,6-diphenyltriazine (0.40 g, 1.5 mmol), and Pd[PPh$_3$]$_4$ (tetrakis(triphenylphosphine)palladium) (0.033 g, 0.029 mmol), toluene (5 mL), dimethoxyethane (5 mL) and a 2 M aqueous solution of Na$_2$CO$_3$ (5 mL, 10.0 mmol) were added. The resultant mixture was stirred for 10 h while refluxing under heating.

After the reaction, the reaction liquid was cooled to room temperature and extracted with dichloromethane in a separating funnel. The organic layer was dried over MgSO$_4$, filtered, and concentrated. The obtained residue was purified by silica gel column chromatography to obtain a white solid (0.66 g), which was identified as the following aromatic heterocyclic derivative (E1) by FD-MS analysis (Field Desorption Mass Spectrometry) (m/e=647 for molecular weight of 647.76). The yield was 71%.

E1

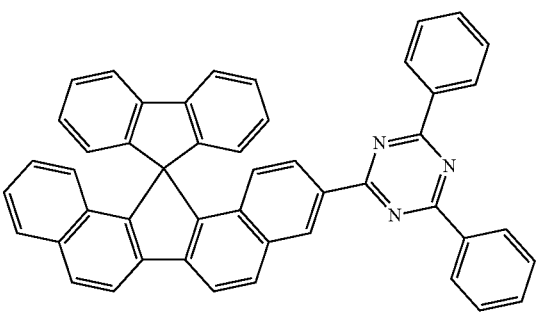

Synthesis Example 2 (Synthesis of Aromatic Amine Derivative (B1))

(1) Synthesis of Intermediate 8

Under argon atmosphere, into a solution of the intermediate 5 (2.8 g, 6.7 mmol) in dichloromethane (22 mL), a solution of bromine (1.8 g, 11.2 mmol) in dichloromethane (36 mL) was added dropwise under cooling with ice. The reaction was allowed to proceed overnight. After adding an aqueous solution of sodium hydrogen carbonate, the reaction mixture was extracted with dichloromethane and the solvent was evaporated off under reduced pressure. The obtained residue was purified by recrystallization to obtain a white solid (1.1 g), which was identified as the following intermediate 8 by FD-MS analysis (m/e=574 for molecular weight of 574.30). The yield was 29%.

Intermediate 8

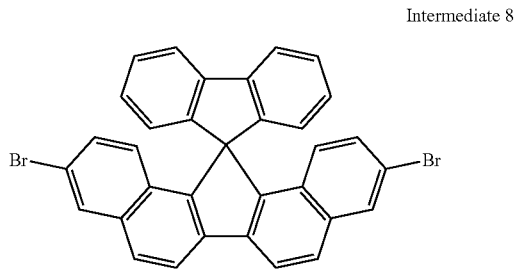 [SMILES: Brc1ccc2c3c(ccc2c1)-c1ccc2cc(Br)ccc2c1C31c2ccccc2-c2ccccc21]

(2) Synthesis of Aromatic Amine Derivative (B1)

Under argon atmosphere, into a mixture of bis(4-tert-butylphenyl)amine (1.1 g, 4.0 mmol), the intermediate 8 (1.1 g, 2.0 mmol), Pd$_2$(dba)$_3$ (0.028 g, 0.03 mmol), P(tBu)$_3$HBF$_4$ (0.017 g, 0.06 mmol), and sodium t-butoxide (0.38 g, 4.0 mmol), anhydrous xylene (10 mL) was added. The resultant mixture was refluxed for 8 h under heating.

After the reaction, the reaction liquid was cooled to 50° C. and filtered through celite/silica gel. The filtrate was concentrated. The obtained residue was purified by silica gel column chromatography to obtain a white solid. The crude product was recrystallized from toluene to obtain a white crystal (1.3 g), which was identified as the following aromatic amine derivative (B1) by FD-MS analysis (m/e=975 for molecular weight of 975.35). The yield was 65%.

B1

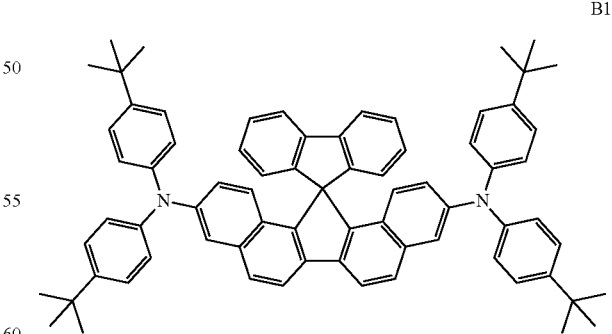

Example 1

A glass substrate of 25 mm×75 mm×1.1 mm thick having ITO transparent electrode (product of Geomatec Company) was ultrasonically cleaned in isopropyl alcohol for 5 min and then UV/ozone cleaned for 30 min. The thickness of ITO transparent electrode was 130 nm.

The cleaned glass substrate having the transparent electrode line was mounted to a substrate holder of a vacuum vapor deposition apparatus. First, the electron accepting compound HI (acceptor) was vapor-deposited on the surface having the transparent electrode line so as to cover the transparent electrode line to form a compound HI film with a thickness of 5 nm.

On the compound HI film, the aromatic amine derivative (compound HT-1) as a first hole transporting material was vapor-deposited to form a first hole transporting layer with a thickness of 100 nm.

Successively after forming the first hole transporting layer, the aromatic amine derivative (compound HT-2) as a second hole transporting material was vapor-deposited to form a second hole transporting layer with a thickness of 5 nm.

On the second hole transporting layer, the compound BH (host material) and the compound BD (fluorescent dopant material) were vapor co-deposited to form a light emitting layer with a thickness of 15 nm. The concentration of the compound BD in the light emitting layer was 3.0% by mass. The co-deposited film works as a light emitting layer.

Successively after forming the light emitting layer, the compound E1 was deposited into a thickness of 5 nm. The compound E1 film works as a first electron transporting layer.

On the first electron transporting layer, the compound ET-2 and Liq were co-deposited to form a second electron transporting layer with a thickness of 25 nm. The concentration of Liq in the second electron transporting layer was 50% by mass.

Next, Liq was vapor-deposited at a film-forming speed of 0.1 Å/min to form an electron injecting electrode (cathode) with a thickness of 1 nm. On the Liq film, metallic Al was vapor-deposited to form a metallic cathode with a thickness of 80 nm.

The organic EL device of Example 1 has the layered structure: ITO (130 nm)/HI (5 nm)/HT-1 (100 nm)/HT-2 (5 nm)/BH:BD (15 nm; 3% by mass)/E1 (5 nm)/ET-2:Liq (25 nm; 50% by mass)/Liq (1 nm)/Al (80 nm).

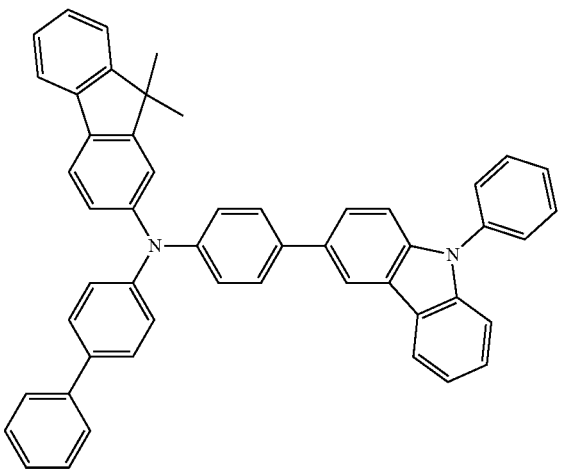

HT-1

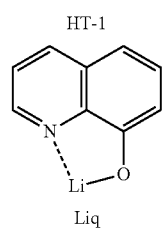

Liq

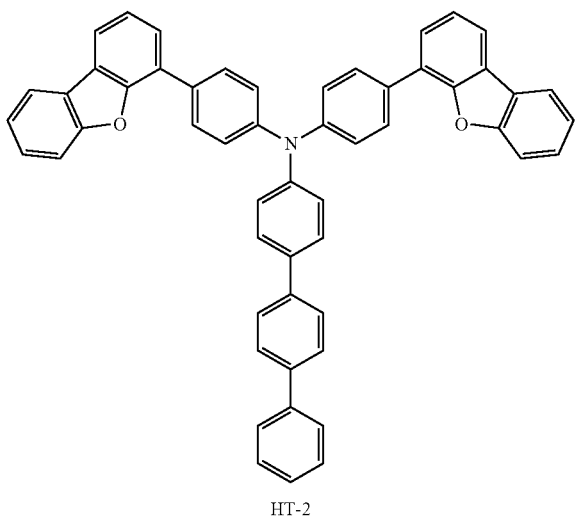

HT-2

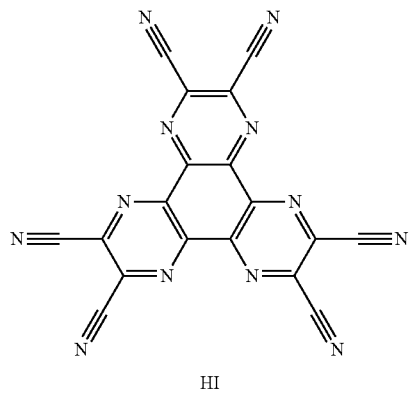

HI

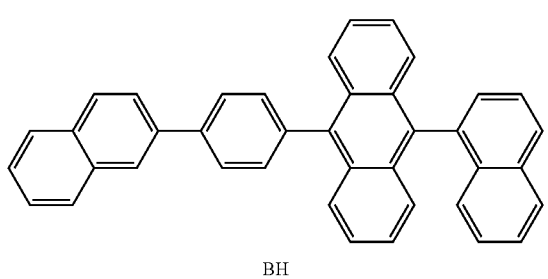

BH

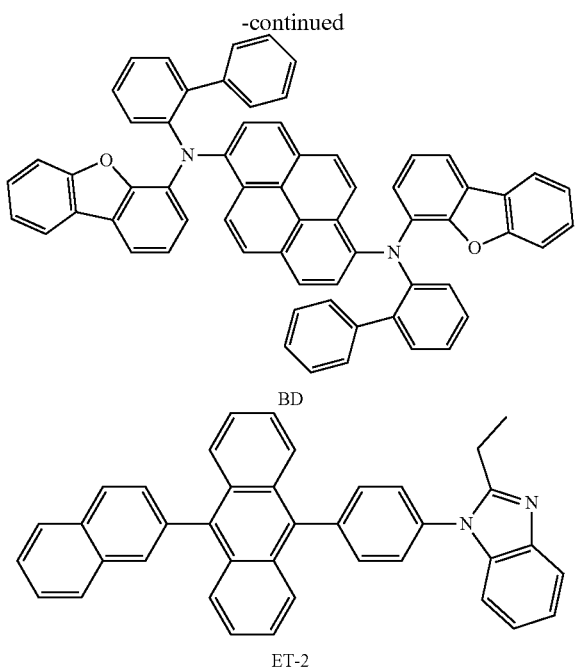

BD

ET-2

Evaluation of Device Performance

The obtained organic EL device was evaluated for the following properties. The results are shown in Table 1.

(1) Driving Voltage (V)

The voltage (unit of measure: V) when an electric current was passed between the ITO transparent electrode and the metallic Al cathode so as to obtain a current density of 10 mA/cm$^2$ was measured.

(2) External Quantum Efficiency (EQE (%))

A spectral radiance spectrum when applying a voltage to the device so as to obtain a current density of 10 mA/cm$^2$ was measured by using a spectroradiometer CS-1000 manufactured by Konica Minolta.

Assuming that Lambertian emission occurred, the external quantum efficiency (EQE) (unit of measure: %) was calculated from the obtained spectral radiance spectrum.

Comparative Examples 1 and 2

Each organic EL device was produced in the same manner as in Example 1 except for using the comparative compounds 1 or 2 in place of the compound E1 and evaluated in the same manner as in Example 1. The results are shown in Table 1.

Comparative compound 1

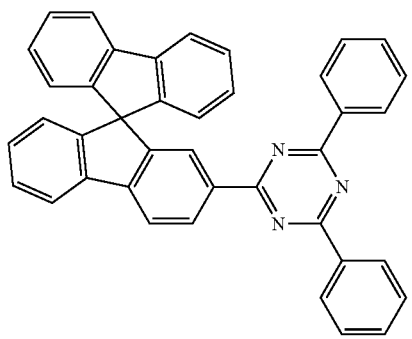

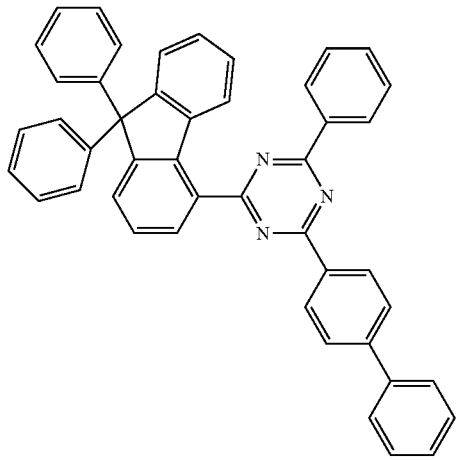

Comparative compound 2

TABLE 1

| | Material of first electron transporting layer | Current density: 10 mA/cm$^2$ | |
| --- | --- | --- | --- |
| | | Voltage (V) | EQE (%) |
| Example 1 | E1 | 3.50 | 9.7 |
| Comparative example 1 | Comparative compound 1 | 3.56 | 9.2 |
| Comparative example 2 | Comparative compound 2 | 3.70 | 8.7 |

The organic EL device having the comparative compound 1 or 2 in the electron transporting layer was operated at a low voltage and had a high efficiency among the devices known in the art. However, the organic EL device having the compound E 1 in the electron transporting layer was operated at an even lower voltage and had an even higher efficiency.

Example 2

A glass substrate of 25 mm×75 mm×1.1 mm thick having ITO transparent electrode (product of Geomatec Company) was ultrasonically cleaned in isopropyl alcohol for 5 min and then UV/ozone cleaned for 30 min. The thickness of ITO transparent electrode was 130 nm.

The cleaned glass substrate having the transparent electrode line was mounted to a substrate holder of a vacuum vapor deposition apparatus. First, the electron accepting compound HI (acceptor) was vapor-deposited on the surface having the transparent electrode line so as to cover the transparent electrode line to form a compound HI film with a thickness of 5 nm.

On the compound HI film, the aromatic amine derivative (compound HT-3) as a first hole transporting material was vapor-deposited to form a first hole transporting layer with a thickness of 100 nm.

Successively after forming the first hole transporting layer, the aromatic amine derivative (compound HT-2) as a second hole transporting material was vapor-deposited to form a second hole transporting layer with a thickness of 5 nm.

On the second hole transporting layer, the compound BH (host material) and the compound B1 (fluorescent dopant material) were vapor co-deposited to form a light emitting layer with a thickness of 25 nm. The concentration of the compound B1 in the light emitting layer was 4.0% by mass. The co-deposited film works as a light emitting layer.

Successively after forming the light emitting layer, the compound ET-3 was deposited into a thickness of 10 nm. The compound ET-3 film works as a first electron transporting layer.

On the first electron transporting layer, the compound ET-4 was vapor-deposited to form a second electron transporting layer with a thickness of 15 nm.

Next, LiF was vapor-deposited at a film-forming speed of 0.1 Å/min to form an electron injecting electrode (cathode) with a thickness of 1 nm. On the LiF film, metallic Al was vapor-deposited to form a metallic cathode with a thickness of 80 nm.

The organic EL device of Example 2 has the layered structure: ITO (130 nm)/HI (5 nm)/HT-3 (100 nm)/HT-2 (5 nm)/BH:B1 (25 nm; 4% by mass)/ET-3 (10 nm)/ET-4 (15 nm)/LiF (1 nm)/Al (80 nm).

HT-3

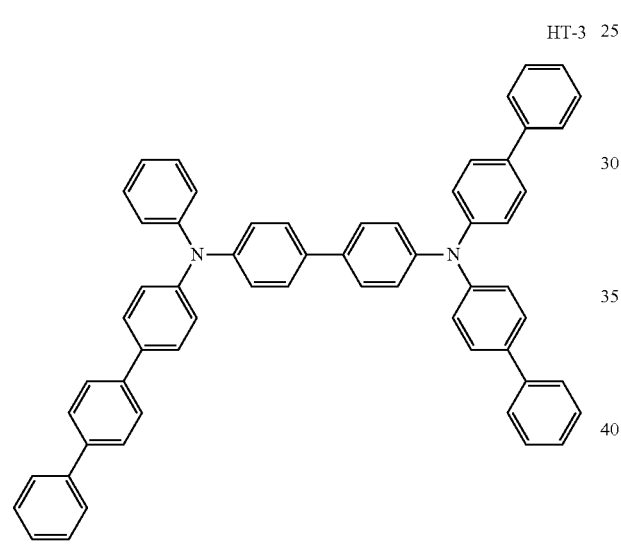

ET-3

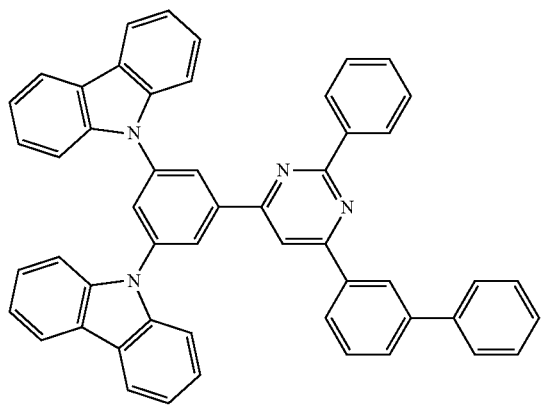

ET-4

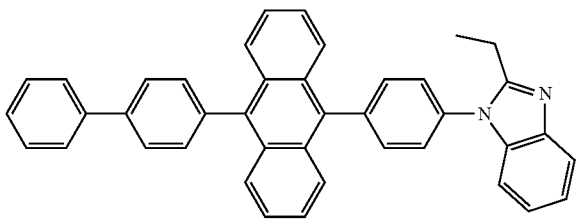

Evaluation of Device Performance

The obtained organic EL device was evaluated for the following properties. The results are shown in Table 2.

(1) External Quantum Efficiency (EQE (%))

A spectral radiance spectrum when applying a voltage to the device so as to obtain a current density of 10 mA/cm$^2$ was measured by using a spectroradiometer CS-1000 manufactured by Konica Minolta.

Assuming that Lambertian emission occurred, the external quantum efficiency (EQE) (unit of measure: %) was calculated from the obtained spectral radiance spectrum.

(2) Lifetime (LT95)

The device was continuously operated by a direct current at an initial current density of 50 mA/cm$^2$. The time taken until the luminance was reduced to 95% of the luminance when starting the test was measured. The measured time was employed as the lifetime (LT95).

Comparative Example 3

An organic EL device was produced in the same manner as in Example 2 except for using the comparative compound 3 as the dopant material in place of the compound B1 and evaluated in the same manner as in Example 1. The results are shown in Table 2.

Comparative compound 3

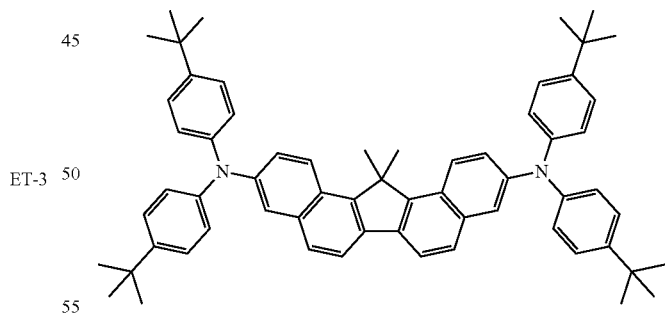

TABLE 2

| | Dopant material | Current density: 10 mA/cm$^2$ EQE (%) | Current density: 50 mA/cm$^2$ Lifetime LT95 (h) |
|---|---|---|---|
| Example 2 | B1 | 7.5 | 192 |
| Comparative example 3 | Comparative compound 3 | 4.7 | 159 |

As compared with the device using the comparative compound 3 as the dopant, the organic EL device using the compound B1 as the dopant has a higher efficiency and a longer lifetime.

REFERENCE SIGNS LIST

1: Organic electroluminescence device
2: Substrate
3: Anode
4: Cathode
5: Light emitting layer
6: Hole injecting layer/hole transporting layer
7: Electron injecting layer/electron transporting layer
10: Emission unit

The invention claimed is:
1. A compound represented by formula (2-1):

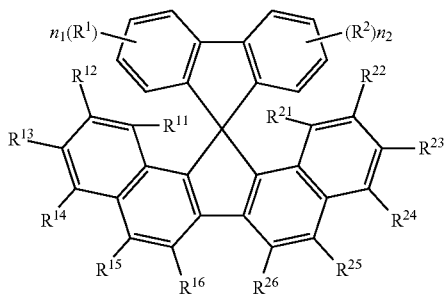

(2-1)

wherein:
each of $R^1$ and $R^2$ is independently a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a substituted or unsubstituted aryl group having 6 to 30 ring carbon atoms, a substituted or unsubstituted heteroaryl group having 5 to 30 ring carbon atoms, or a group represented by $-Si(R_{101})(R_{102})(R_{103})$;
two or more $R^1$ and/or two or more $R^2$, if present, are optionally the same or different;
each of n1 and n2 is an integer of 0 to 4;
each of $R^{11}$ to $R^{16}$ and $R^{21}$ to $R^{26}$ is independently a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a group represented by $-Si(R_{101})(R_{102})(R_{103})$, or a group represented by $-Z-R^a$;

Z is a single bond, a substituted or unsubstituted arylene group having 6 to 30 ring carbon atoms, a substituted or unsubstituted heteroarylene group having 5 to 30 ring atoms, or a divalent linking group wherein two to four groups selected from the arylene group and the heteroarylene group are linked together;

two or more Z, if present, are optionally the same or different;

$R^a$ is a group represented by $-N(R_{104})(R_{105})$, a substituted or unsubstituted aryl group having 6 to 30 ring carbon atoms, or a substituted or unsubstituted heteroaryl group having 5 to 30 ring atoms;

two or more $R^a$, if present, are optionally the same or different;

each of $R_{101}$ to $R_{105}$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms;

provided that at least one of $R^{13}$ and $R^{23}$ is $-Z-R^a$, wherein the group represented by $-Z-R^a$ is represented by formula (b):

(b)

wherein:
each of $Z^2$ is a single bond, a substituted or unsubstituted arylene group having 6 to 30 ring carbon atoms, a substituted or unsubstituted heteroarylene group having 5 to 30 ring atoms, or a divalent linking group wherein two to four groups selected from the arylene group and the heteroarylene group are linked together; and —HAr in formula (b) is selected from the following groups:

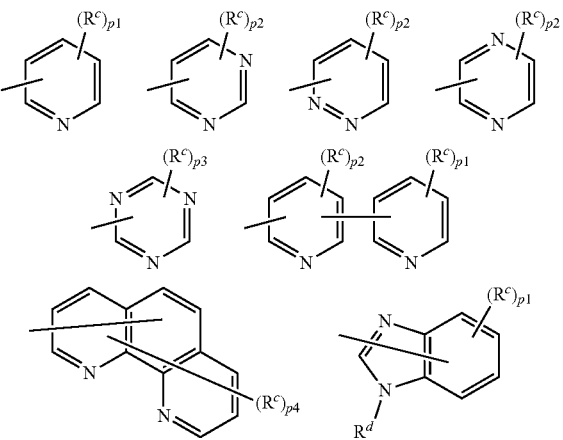

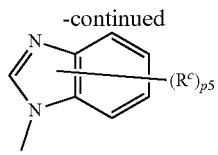

wherein:
each $R^c$ is independently a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, a substituted or unsubstituted aralkyl group having 7 to 30 carbon atoms which includes an aryl group having 6 to 30 ring carbon atoms, an amino group, a mono- or dialkylamino group having an alkyl group having 1 to 20 carbon atoms, a mono- or diarylamino group having an aryl group having 6 to 30 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a mono-, di-, or tri-substituted silyl group having a substituent selected from an alkyl group having 1 to 20 carbon atoms and an aryl group having 6 to 30 ring carbon atoms, a substituted or unsubstituted heteroaryl group having 5 to 30 ring atoms, a halogen atom, a cyano group, or a nitro group;

two or more $R^c$, if present in each group, are optionally the same or different;

$R^d$ is a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, or a substituted or unsubstituted heteroaryl group having 5 to 30 ring atoms;

each p1 is independently an integer of 0 to 4, each p2 is independently an integer of 0 to 3, p3 is an integer of 0 to 2, p4 is an integer of 0 to 7, and p5 is an integer of 0 to 5.

2. The compound according to claim 1, wherein in formula (2-1) $R^{13}$ is a group represented by formula (b), and $R^{23}$ is a group represented by formula (b).

3. A material for organic electroluminescence devices comprising the compound according to claim 1.

4. An organic electroluminescence device comprising an organic thin film layer which comprises one or more layers and is disposed between a cathode and an anode, wherein the organic thin film layer comprises a light emitting layer and at least one layer of the organic thin film layer comprises the compound according to claim 1.

5. The organic electroluminescence device according to claim 4, wherein the light emitting layer comprises the compound.

6. The organic electroluminescence device according to claim 4, wherein the at least one layer comprises the compound and an anthracene derivative represented by formula (5):

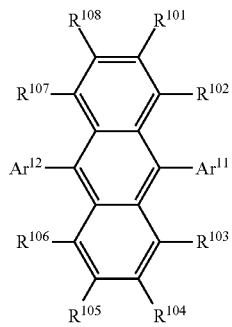

wherein
each of $Ar^{11}$ and $Ar^{12}$ is independently a substituted or unsubstituted monocyclic group having 5 to 50 ring atoms or a substituted or unsubstituted fused ring group having 8 to 50 ring atoms; and
each of $R^{101}$ to $R^{108}$ is independently a group selected from a hydrogen atom, a substituted or unsubstituted monocyclic group having 5 to 50 ring atoms, a substituted or unsubstituted fused ring group having 8 to 50 ring atoms, a group comprising a combination of the monocyclic group and the fused ring group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom, and a cyano group.

7. An organic electroluminescence device comprising an organic thin film layer which comprises one or more layers and is disposed between a cathode and an anode, wherein the organic thin film layer comprises a light emitting layer and, wherein the organic thin film layer comprises an electron transporting layer and the electron transporting layer comprises a compound represented by formula (2-1):

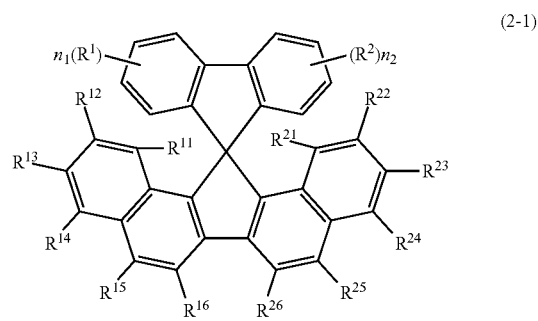

wherein:
each of $R^1$ and $R^2$ is independently a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a substituted or unsubstituted aryl group having 6 to 30 ring carbon atoms, a substituted or unsubstituted heteroaryl group having 5 to 30 ring carbon atoms, or a group represented by —Si($R_{101}$)($R_{102}$)($R_{103}$);

two or more $R^1$ and/or two or more $R^2$, if present, are optionally the same or different;

each of n1 and n2 is an integer of 0 to 4;

each of $R^{11}$ to $R^{16}$ and $R^{21}$ to $R^{26}$ is independently a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a group represented by —Si($R_{101}$)($R_{102}$)($R_{103}$), or a group represented by —Z—$R^a$;

Z is a single bond, a substituted or unsubstituted arylene group having 6 to 30 ring carbon atoms, a substituted or unsubstituted heteroarylene group having 5 to 30 ring atoms, or a divalent linking group wherein two to four groups selected from the arylene group and the heteroarylene group are linked together;

two or more Z, if present, are optionally the same or different;

$R^a$ is a group represented by —N($R_{104}$)($R_{105}$), a substituted or unsubstituted aryl group having 6 to 30 ring carbon atoms, or a substituted or unsubstituted heteroaryl group having 5 to 30 ring atoms;

two or more $R^a$, if present, are optionally the same or different;

each of $R_{101}$ to $R_{105}$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms;

provided that at least one of $R^{13}$ and $R^{23}$ is —Z—$R^a$.

8. The organic electroluminescence device according to claim 4, wherein the organic thin film layer comprises a hole transporting layer and the hole transporting layer comprises the compound.

9. An organic electroluminescence device comprising an organic thin film layer which comprises one or more layers and is disposed between a cathode and an anode, wherein the organic thin film layer comprises a light emitting layer and, wherein the organic thin film layer comprises an electron transporting layer and a blocking layer between the electron transporting layer and the light emitting layer, and the blocking layer comprises a compound represented by formula (2-1):

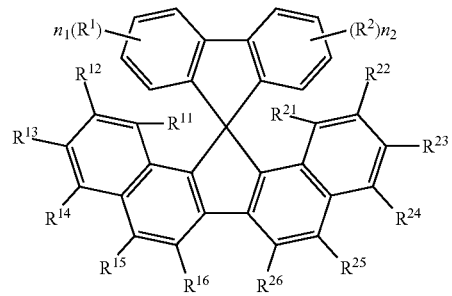

(2-1)

wherein:

each of $R^1$ and $R^2$ is independently a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a substituted or unsubstituted aryl group having 6 to 30 ring carbon atoms, a substituted or unsubstituted heteroaryl group having 5 to 30 ring carbon atoms, or a group represented by —Si($R_{101}$)($R_{102}$)($R_{103}$);

two or more $R^1$ and/or two or more $R^2$, if present, are optionally the same or different;

each of n1 and n2 is an integer of 0 to 4;

each of $R^{11}$ to $R^{16}$ and $R^{21}$ to $R^{26}$ is independently a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted fluoroalkyl group having 1 to 20 carbon atoms, a substituted or unsubstituted fluoroalkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a group represented by —Si($R_{101}$)($R_{102}$)($R_{103}$), or a group represented by —Z—$R^a$;

Z is a single bond, a substituted or unsubstituted arylene group having 6 to 30 ring carbon atoms, a substituted or unsubstituted heteroarylene group having 5 to 30 ring atoms, or a divalent linking group wherein two to four groups selected from the arylene group and the heteroarylene group are linked together;

two or more Z, if present, are optionally the same or different;

$R^a$ is a group represented by —N($R_{104}$)($R_{105}$), a substituted or unsubstituted aryl group having 6 to 30 ring carbon atoms, or a substituted or unsubstituted heteroaryl group having 5 to 30 ring atoms;

two or more $R^a$, if present, are optionally the same or different;

each of $R_{101}$ to $R_{105}$ is independently a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heteroaryl group having 5 to 50 ring atoms;

provided that at least one of $R^{13}$ and $R^{23}$ is —Z—$R^a$.

10. An electronic device comprising the organic electroluminescence device according to claim 4.

* * * * *